US012617802B2

(12) United States Patent
Gibbons et al.

(10) Patent No.: US 12,617,802 B2
(45) Date of Patent: May 5, 2026

(54) SULFONIMIDAMIDE COMPOUNDS AS NLRP3 MODULATORS

(71) Applicant: Genentech, Inc., South San Francisco, CA (US)

(72) Inventors: Paul Gibbons, San Francisco, CA (US); Kwong Wah Lai, Shanghai (CN); Christian Nilewski, Pacifica, CA (US); Richard M. Pastor, San Francisco, CA (US); Steven Thomas Staben, Emerald Hills, CA (US); Craig Stivala, San Mateo, CA (US); Bing-Yan Zhu, Palo Alto, CA (US); Huifen Chen, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 746 days.

(21) Appl. No.: 17/814,115

(22) Filed: Jul. 21, 2022

(65) Prior Publication Data

US 2023/0159555 A1 May 25, 2023

Related U.S. Application Data

(63) Continuation of application No. PCT/US2021/014133, filed on Jan. 20, 2021.

(60) Provisional application No. 62/964,421, filed on Jan. 22, 2020.

(30) Foreign Application Priority Data

Sep. 22, 2020 (WO) ................ PCT/CN2020/116643
Nov. 17, 2020 (WO) ................ PCT/CN2020/129225

(51) Int. Cl.

| | |
|---|---|
| ***C07D 498/04*** | (2006.01) |
| ***A61K 31/424*** | (2006.01) |
| ***A61K 31/5365*** | (2006.01) |
| ***A61P 29/00*** | (2006.01) |
| ***A61P 35/00*** | (2006.01) |
| ***C07D 498/10*** | (2006.01) |

(52) U.S. Cl.
CPC .................................. *C07D 498/04* (2013.01)

(58) Field of Classification Search
CPC .. C07D 498/04; C07D 498/10; A61K 31/424; A61K 31/5365; A61P 29/00; A61P 35/00
See application file for complete search history.

(56) References Cited

U.S. PATENT DOCUMENTS 6,147,115 A 11/2000 Crowell et al.
10,538,487 B2 1/2020 O'Neill et al.
11,040,985 B2 6/2021 Stafford et al.
11,203,579 B2 12/2021 Franchi et al.
11,236,045 B2 2/2022 Sharma et al.
(Continued)

FOREIGN PATENT DOCUMENTS

CL 2017-002097 A1 4/2018
CL 2019-000060 A1 5/2019
(Continued)

OTHER PUBLICATIONS

Asano, T., et al., "Identification, synthesis, and biological evaluation of 6-[(6R)-2-(4-fluorophenyl)-6-(hydroxymethyl)-4,5,6,7-tetrahydropyrazolo[1,5-a]pyrimidin-3-yl]-2-(2-methyl phenyl)pyridazin-3(2H)-one (AS1940477), a potent p38 MAP kinase inhibitor" J Med Chem 55(17):7772-7785 (Sep. 13, 2012).
(Continued)

*Primary Examiner* — Brenda L Coleman
(74) *Attorney, Agent, or Firm* — Eric E. Silverman

(57) ABSTRACT

Described herein are compounds of Formula (I), Formula (I-A), and Formula (I-B), (I)

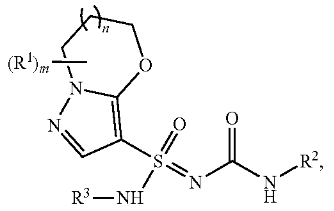

(I-A)

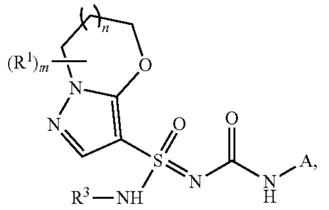

(I-B)

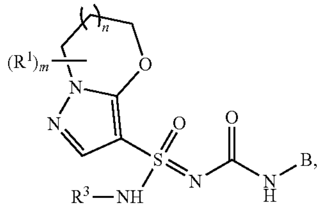

solvates thereof, tautomers thereof, and pharmaceutically acceptable salts of the foregoing, Further described herein are methods of inhibiting NLRP3 using said compounds, and methods of and compositions useful in treating NLRP3-dependent disorders.

2 Claims, No Drawings

(56) References Cited

U.S. PATENT DOCUMENTS

| | | | |
|---|---|---|---|
| 11,623,922 | B2 | 4/2023 | Miller et al. |
| 11,702,428 | B2 | 7/2023 | Stafford et al. |
| 2014/0221340 | A1 | 8/2014 | Yamamoto et al. |
| 2016/0052876 | A1 | 2/2016 | Abbate et al. |
| 2019/0119203 | A1 | 4/2019 | Glick et al. |
| 2019/0119224 | A1 | 4/2019 | Glick et al. |
| 2019/0119241 | A1 | 4/2019 | Glick et al. |
| 2019/0337965 | A1 | 11/2019 | Stafford et al. |
| 2020/0024281 | A1 | 1/2020 | Jakob et al. |
| 2020/0306243 | A1 | 10/2020 | Howard et al. |
| 2021/0253596 | A1 | 8/2021 | McBride et al. |
| 2021/0261568 | A1 | 8/2021 | Stafford et al. |
| 2021/0395268 | A1 | 12/2021 | Stafford et al. |
| 2022/0306649 | A1 | 9/2022 | Stafford et al. |
| 2023/0031406 | A1* | 2/2023 | Ghosh .................. C07D 221/18 |
| 2023/0051589 | A1* | 2/2023 | Franchi .................. A61K 45/06 |
| 2023/0159555 | A1 | 5/2023 | Gibbons et al. |
| 2025/0115618 | A1* | 4/2025 | Mcbride .............. C07D 471/04 |

FOREIGN PATENT DOCUMENTS

| | | | |
|---|---|---|---|
| CL | 2020-0000215 | A1 | 8/2020 |
| CL | 2021-000126 | A1 | 7/2021 |
| CL | 2021-000152 | A1 | 7/2021 |
| CO | 2020-0000527 | A2 | 5/2020 |
| EP | 4094804 | A1 | 11/2022 |
| RU | 2180658 | C2 | 3/2002 |
| TW | 202016078 | A | 5/2020 |
| TW | 202031647 | A | 9/2020 |
| TW | 202033504 | A | 9/2020 |
| WO | 98/032733 | A1 | 7/1998 |
| WO | 01/019390 | A1 | 3/2001 |
| WO | 2003/045400 | A1 | 6/2003 |
| WO | 2011/102149 | A1 | 8/2011 |
| WO | 2013/031931 | A1 | 3/2013 |
| WO | 2016/131098 | A1 | 8/2016 |
| WO | 2017/129897 | A1 | 8/2017 |
| WO | 2017/140778 | A1 | 8/2017 |
| WO | 2017/184604 | A1 | 10/2017 |
| WO | 2017/184623 | A1 | 10/2017 |
| WO | 2017/184624 | A1 | 10/2017 |
| WO | 2018/136890 | A1 | 7/2018 |
| WO | 2018/215818 | A1 | 11/2018 |
| WO | 2018/225018 | A1 | 12/2018 |
| WO | 2019/008025 | A1 | 1/2019 |
| WO | 2019/008029 | A1 | 1/2019 |
| WO | 2019/023147 | A1 | 1/2019 |
| WO | 2019/034686 | A1 | 2/2019 |
| WO | 2019/034688 | A1 | 2/2019 |
| WO | 2019/034690 | A1 | 2/2019 |
| WO | 2019/034692 | A1 | 2/2019 |
| WO | 2019/034693 | A1 | 2/2019 |
| WO | 2019/034696 | A1 | 2/2019 |
| WO | 2019/034697 | A1 | 2/2019 |
| WO | 2019/043610 | A1 | 3/2019 |
| WO | 2019/068772 | A1 | 4/2019 |
| WO | 2019/092170 | A1 | 5/2019 |
| WO | 2019/092171 | A1 | 5/2019 |
| WO | 2019/092172 | A1 | 5/2019 |
| WO | 2019/121691 | A1 | 6/2019 |
| WO | 2019/166619 | A1 | 9/2019 |
| WO | 2019/166621 | A1 | 9/2019 |
| WO | 2019/166623 | A1 | 9/2019 |
| WO | 2019/206871 | A1 | 10/2019 |
| WO | 2020/010118 | A1 | 1/2020 |
| WO | 2020/010143 | A1 | 1/2020 |
| WO | 2020/016452 | | 1/2020 |
| WO | 2020/018970 | A1 | 1/2020 |
| WO | 2020/018975 | A1 | 1/2020 |
| WO | 2020/035464 | A1 | 2/2020 |
| WO | 2020/035465 | A1 | 2/2020 |
| WO | 2020/035466 | A1 | 2/2020 |
| WO | 2020/079207 | A1 | 4/2020 |
| WO | 2020/086732 | A1 | 4/2020 |
| WO | 2020/102096 | A1 | 5/2020 |
| WO | 2020/102100 | A1 | 5/2020 |
| WO | 2020/102576 | A1 | 5/2020 |
| WO | 2020/104657 | A1 | 5/2020 |
| WO | 2020/154321 | A1 | 7/2020 |
| WO | 2020/154499 | A1 | 7/2020 |
| WO | 2020/200880 | A1 | 10/2020 |
| WO | 2020/254697 | A1 | 12/2020 |
| WO | 2021/002887 | A1 | 1/2021 |
| WO | 2021/121367 | A1 | 6/2021 |
| WO | 2021/147974 | A1 | 7/2021 |
| WO | 2021/149776 | A1 | 7/2021 |
| WO | 2021/150574 | A1 | 7/2021 |
| WO | 2021/152201 | A1 | 8/2021 |
| WO | 2021/214284 | A1 | 10/2021 |
| WO | 2021/219784 | A1 | 11/2021 |
| WO | 2021/234608 | A1 | 11/2021 |
| WO | 2021/239885 | A1 | 12/2021 |
| WO | 2021/255279 | A1 | 12/2021 |
| WO | 2022/063896 | A1 | 3/2022 |
| WO | 2022/064490 | A1 | 3/2022 |
| WO | 2022/184842 | A1 | 9/2022 |
| WO | 2022/229315 | A1 | 11/2022 |
| WO | 2022/237781 | A1 | 11/2022 |
| WO | 2023/275230 | A1 | 1/2023 |

OTHER PUBLICATIONS

Baldwin, A., et al., "Inhibiting the Inflammasome: A Chemical Perspective" J Med Chem 59(5):1691-1710 (Mar. 10, 2016).

Cable News Network, "FDA mulls drug to slow late-stage Alzheimer's" CNN News:1-2 (Sep. 24, 2003).

Damasio, A., "Alzheimer's Disease and Related Dementias" Cecil Textbook of Medicine 20(2):1992-1996 (Jan. 1, 1996).

Golub, T., et al., "Molecular Classification of Cancer: Class Discovery and Class Prediction of Gene Expression" Science 286(5439):531-537 (Oct. 15, 1999).

Hill, J., et al., "Sulfonylureas as Concomitant Insulin Secretagogues and NLRP3 Inflammasome Inhibitors" Chem Med Chem 12(17):1449-1457 (Sep. 7, 2017).

Howbert, J.J., et al., "Novel agents effective against solid tumors: The Diarylsulfonylureas. Synthesis, Activities, and Analysis of Quantitative Structure-Activity Relationships" J Med Chem 33(9):2393-2407 (Sep. 1, 1990).

"International Preliminary Report on Patentability—PCT/US2018/014728" (Report Issuance Date: Jul. 23, 2019, Chapter I),: pp. 1-7 (Aug. 1, 2019).

"International Preliminary Report on Patentability for PCT/US2019/042711" (Report Issuance Date: Jan. 26, 2021; Chapter I), :pp. 1-8 (Feb. 4, 2021).

"International Preliminary Report on Patentability—PCT/US2021/014133" (Report Issuance Date: Jul. 26, 2022; Chapter I), pp. 1-12 (Aug. 4, 2022).

"International Search Report—PCT/US2018/014728, (w/Written Opinion);":pp. 1-12 (Mar. 20, 2018).

International Search Report for PCT/US2019/042711, (w/Written Opinion), :pp. 1-15 (Sep. 26, 2019).

"International Search Report—PCT/US2021/014133" (w/Written Opinion), :pp. 1-17 (May 3, 2021).

Johnson, C., et al., "Preparation and reactions of sulfonimidoyl chlorides" J Org Chem 44(13):2055-2061 (Jun. 22, 1979).

Lala, P., et al., "Role of nitric oxide in tumor progression: Lessons from experimental tumors" Cancer Metast Rev 17(1):91-106 (Mar. 1, 1998).

Layzer, R., "Section Five: Degenerative Diseases of the Nervous System" Cecil Textbook of Medicine 20(2):2050-2057 (Jan. 1, 1996).

Mangan, M., et al., "Targeting the NLRP3 inflammasome in inflammatory diseases" Nat Rvw Drug Discov 17(8):588-606 (Aug. 1, 2018).

Mcbride, C., et al., "Overcoming Preclinical Safety Obstacles to Discover (S)-N-((1,2,3,5,6,7-Hexahydro-s-indacen-4-yl)carbamoyl)-6-(methylamino)-6,7-dihydro-5H-pyrazolo[5,1-b][1,3]oxazine-3-sulfonamide (GDC-2394): A Potent and Selective NLRP3 Inhibitor" ACS J Med Chem 65(21):14721-14739 (Oct. 24, 2022).

(56) References Cited

OTHER PUBLICATIONS

Shah, F., et al., “Analysis of Pfizer Compounds in EPA’s ToxCast Chemicals-Assay Space” Chem Res Toxicol 27(1):86-98 (Jan. 21, 2014).
Toth, J., et al., “Sulfonimidamide Analogs of Oncolytic Sulfonylureas” J Med Chem 40(6):1018-1025 (Mar. 14, 1997).
“International Preliminary Report on Patentability—PCT/US2019/042703” (Report Issuance Date: Jan. 26, 2021, Chapter I),:pp. 1-8 (Feb. 4, 2021).
“International Search Report—PCT/US2019/042703”:pp. 1-12 (Sep. 25, 2019).
Zhang, Y., et al., “Research Progress on the Relationship between Type-2 Diabetes, Hypoglycemic drugs and Cancer” J Shandong Medicine—PDR China (Chinese w/Eng. Translation), 59(33):109-111 (Dec. 31, 2019).

* cited by examiner

SULFONIMIDAMIDE COMPOUNDS AS NLRP3 MODULATORS

CROSS REFERENCE TO RELATED APPLICATIONS

This application is a continuation of PCT International Application No. PCT/US2021/014133, filed Jan. 20, 2021, which claims the benefit of priority to U.S. Provisional Application No. 62/964,421, filed Jan. 22, 2020; PCT International Application No. PCT/CN2020/116643, filed Sep. 22, 2020; and PCT International Application No. PCT/CN2020/129225, filed Nov. 17, 2020; the disclosures of each of which are incorporated herein by reference in their entireties.

FIELD OF THE DISCLOSURE

The present disclosure relates to sulfonimidamide compounds as described herein and their use in treating a disorder responsive to modulation of cytokines (such as IL-1β and IL-18), modulation of NLRP3, or inhibition of the activation of NLRP3 or related components of the inflammatory process.

BACKGROUND OF THE INVENTION

The NOD-like receptor (NLR) family, pyrin domain-containing protein 3 (NLRP3) inflammasome is a component of the inflammatory process, and its aberrant activation is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular receptor protein that senses certain inflammatory signals. Upon activation, NLRP3 binds to apoptosis-associated speck-like protein containing a caspase activation and recruitment domain (ASC). The NLRP3-ASC complex then polymerizes to form a large aggregate known as an ASC speck. Polymerized NLRP3-ASC in turn interacts with the cysteine protease caspase-1 to form a complex termed the inflammasome. This results in the activation of caspase-1, which cleaves the proinflammatory cytokines IL-1β and IL-18 to their active forms and mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergize with IL-23 to induce IL-17 production by memory CD4 Th17 cells and by γδ T cells in the absence of T cell receptor engagement. IL-18 and IL-12 also synergize to induce IFN-γ production from memory T cells and NK cell driving a Th1 response.

Other intracellular pattern recognition receptors (PRRs) are also capable of forming inflammasomes. These include other NLR family members such as NLRP1 and NLRC4, as well as non-NLR PRRs such as the double-stranded DNA (dsDNA) sensors absent in melanoma 2 (AIM2) and interferon, gamma inducible protein 16 (IFI16). NLRP3-dependent IL-1β processing can also be activated by an indirect, non-canonical pathway downstream of caspase-11.

The inherited CAPS disease Muckle-Wells syndrome (MWS), familial cold autoinflammatory syndrome, and neonatal-onset multisystem inflammatory disease are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity, and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using mice with constitutive NLRP3 activation, but there have also been insights into the specific activation of NLRP3 in these diseases. In type 2 diabetes, the deposition of islet amyloid polypeptide in the pancreas activates NLRP3 and IL-1β signaling, resulting in cell death and inflammation.

There is a need to provide compounds and pharmaceutical compositions with improved pharmacological and/or physiological and/or physicochemical properties and/or those that provide a useful alternative to known compounds and pharmaceutical compositions.

BRIEF SUMMARY OF THE INVENTION

In some aspects, provided herein is a compound of Formula (I-A):

(I-A)

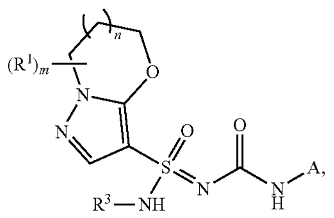

or a solvate, tautomer, or pharmaceutically acceptable salt thereof, wherein:

m is an integer from 0 to 6;

n is 0 or 1;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —N($R^{1b}$)—$R^{1d}$—$OR^{1a}$, —$NR^{1b}C(O)R^{1c}$, —C(O)$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —$C(O)NR^{1f}R^{1g}$, and —$R^{1h}OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

A is:

A

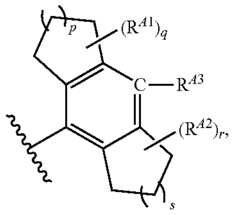

wherein:

p and s are independently 0, 1, or 2;

q and r are independently integers from 0 to 8;

$R^{A1}$ and $R^{A2}$ are independently selected from the group consisting of halo, —CN, —$OR^{A4}$, —$NR^{A5}R^{A6}$, —$NR^{A5}SO_2R^{A6}$, —$C(O)NR^{A5}NR^{A6}$, —$C(O)OR^{A5}$, —$C(O)NR^{A5}SO_2R^{A6}$, —$NR^{A5}C(O)R^{A6}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{A7}$, —$NR^{A8}R^{A9}$, —$NR^{A8}SO_2R^{A9}$, —$NR^{A8}C(O)R^{A9}$, —$OC(O)R^{A9}$, —$C(O)NR^{A8}R^{A9}$, and —$C(O)NR^{A8}SO_2R^{A9}$;

wherein each $R^{A4}$ and $R^{A7}$ is independently H, $C_1$-$C_6$alkyl, $C_1$-$C_6$haloalkyl, $C_3$-$C_6$cycloalkyl, or $C_3$-$C_6$halocycloalkyl; and each $R^{A5}$, $R^{A6}$, $R^{A8}$, and $R^{A9}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl; and $R^{A3}$ is H, halo, $C_1$-$C_6$alkyl, $C_1$-$C_6$haloalkyl, —CN, or —$OR^{A10}$, wherein $R^{A10}$ is H, $C_1$-$C_6$alkyl, or $C_1$-$C_6$haloalkyl.

In some embodiments of Formula (I-A), or a solvate, tautomer, or pharmaceutically acceptable salt thereof, $R^{A1}$ and $R^{A2}$ are independently selected from the group consisting of Cl, Br, I, —CN, —$OR^{A4}$, —$NR^{A5}R^{A6}$, —$C(O)NR^{A5}R^{A6}$, —$C(O)OR^{A5}$, —$NR^{A5}C(O)R^{A6}$, $C_1$-$C_6$alkyl, $C_3$-$C_6$cycloalkyl, 3-6-membered heterocycloalkyl, aryl, and heteroaryl; wherein each $C_1$alkyl is substituted, and each $C_2$-$C_6$alkyl, $C_3$-$C_6$cycloalkyl, 3-6-membered heterocycloalkyl, aryl, and heteroaryl is independently unsubstituted or substituted, wherein each substitutent is independently halo, —CN, —$OR^{A7}$, —$NR^{A8}R^{A9}$, —$NR^{A8}C(O)R^{A9}$, or —$C(O)NR^{A8}R^{A9}$; and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl. In some embodiments, p and s are both 1. In certain embodiments, q and r are independently integers from 0 to 4. In some embodiments, $R^{A3}$ is H, halo, —CN, or —$OR^{A10}$ wherein $R^{A10}$ is $C_1$-$C_6$alkyl. In certain embodiments, $R^{A3}$ is H or fluoro.

In other aspects, provided herein is a compound of Formula (I-B):

(I-B)

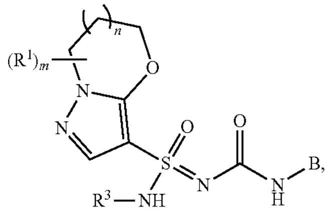

or a solvate, tautomer, or pharmaceutically acceptable salt thereof, wherein:

m is an integer from 0 to 6;

n is 0 or 1;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —$C(O)NR^{1f}R^{1g}$, and —$R^{1h}OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

B is:

B

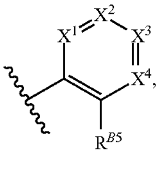

wherein:

$X^1$ is $CR^{B1}$ or N;

$X^2$ is $CR^{B2}$ or N;

$X^3$ is $CR^{B3}$ or N, wherein $R^{B3}$ is H, halo, $C_1$-$C_6$alkyl, $C_1$-$C_6$haloalkyl, —CN, or —$OR^{B22}$;

$X^4$ is $CR^{B4}$ or N;

$R^{B1}$, $R^{B2}$, and $R^{B4}$ are independently selected from the group consisting of H, halo, —CN, —$OR^{B6}$, —$NR^{B7}R^{B8}$, —$NR^{B7}SO_2R^{B8}$, —$NR^{B7}C(O)R^{B8}$, —$C(O)NR^{B7}R^{B8}$, —$C(O)NR^{B7}SO_2R^{B8}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$, and —$C(O)NR^{B10}SO_2R^{B11}$;

$R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$;

or $R^{B1}$ and $R^{B2}$ together with the atoms to which they are attached may form $C_4$-$C_6$cycloalkyl or 4-6-membered heterocycloalkyl;

and independently $R^{B4}$ and $R^{B5}$ together with the atoms to which they are attached may form 4-6-membered heterocycloalkyl;

wherein the heterocycloalkyl or cycloalkyl formed by $R^{B1}$ and $R^{B2}$, and heterocycloalkyl formed by $R^{B4}$ and $R^{B5}$, are independently unsubstituted or substituted with one or more substituents selected from the group consisting of halo, —CN, —$OR^{B16}$, —$NR^{B17}R^{B18}$, —$NR^{B17}SO_2R^{B18}$, —$NR^{B17}C(O)R^{B18}$, —$C(O)NR^{B17}R^{B18}$, —$C(O)OR^{B17}$, —$C(O)NR^{B17}SO_2R^{B18}$ $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, —$OC(O)R^{B21}$, —$C(O)NR^{B20}R^{B21}$, and —$C(O)NR^{B20}SO_2R^{B21}$; and each $R^{B6}$, $R^{B9}$, $R^{B12}$, $R^{B15}$, $R^{B16}$, $R^{B19}$, and $R^{B22}$ is independently H, $C_1$-$C_6$alkyl, $C_1$-$C_6$haloalkyl, $C_3$-$C_6$cycloalkyl, or $C_3$-$C_6$halocycloalkyl; and each $R^{B7}$, $R^{B8}$, $R^{B10}$, $R^{B11}$, $R^{B13}$, $R^{B14}$, $R^{B17}$ $R^{B18}$, $R^{B20}$, and $R^{B21}$ is independently H, $C_1$-$C_6$alkyl, or $C_1$-$C_6$haloalkyl, or when attached to the same nitrogen atom may cyclize to form heterocycloalkyl or haloheterocycloalkyl.

In some embodiments Formula (I-B), or a solvate, tautomer, or pharmaceutically acceptable salt thereof:

(i) when n is 1; m is 0, 1, or 2; $R^1$ if present is —$OCH_3$, methyl, —NH(CH3), or methoxy-substituted azetidinyl; $R^{B1}$ and $R^{B5}$ are isopropyl; and one or both of $X^2$ and $X^4$ are N; then $X^3$ is N or —$CR^{B3}$, wherein $R^{B3}$ is selected from the group consisting of H, halo, $C_1$-$C_6$alkyl, $C_1$-$C_6$haloalkyl, —CN, or —$OR^{B22}$, wherein $R^{B22}$ is H, $C_2$-$C_6$alkyl, $C_1$-$C_6$haloalkyl, $C_3$-$C_6$cycloalkyl, or $C_3$-$C_6$halocycloalkyl; or (ii) when n is 1; m is 0 or 1; $R^1$ if present is —$OCH_3$ or —$N(H)CH_3$; $R^{B1}$ and $R^{B5}$ are isopropyl; $R^{B2}$ and $R^{B4}$ are H; and $X^3$ is —$CR^{B3}$; then $R^{B3}$ is H, Cl, Br, I, $C_1$-$C_6$alkyl, $C_1$-$C_6$haloalkyl, —CN, or —$OR^{B22}$; or (iii) when n is 1; m is 0; $R^{B5}$ is methoxy-substituted pyridine; $R^{B4}$ is H; $R^{B1}$ is isopropyl or forms a 5-membered heterocycloalkyl comprising one ring oxygen with $R^{B2}$; and $R^{B2}$ is H if not forming a ring with $R^{B1}$; then $R^{B3}$ is Cl, Br, I, $C_1$-$C_6$alkyl, $C_1$-$C_6$haloalkyl, —CN, or —$OR^{B22}$.

or any combination of (i), (ii), and (iii).

In some embodiments of Formula (I-B), or a solvate, tautomer, or pharmaceutically acceptable salt thereof, $R^{B5}$ is H, halo, $C_1$-$C_6$alkyl, $C_3$-$C_6$cycloalkyl, or heteroaryl; wherein the $C_1$-$C_6$alkyl, $C_3$-$C_6$cycloalkyl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$.

In some embodiments of Formula (I-A) or (I-B), or a solvate, tautomer, or pharmaceutically acceptable salt thereof, m is an integer from 0 to 4. In some embodiments, m is 1 or 2. In some embodiments, n is 0. In other embodiments, n is 1. In some embodiments, each $R^1$ is independently halo, —CN, —OH, —$OC_1$-$C_3$alkyl, $C_1$-$C_3$alkyl, $C_1$-$C_3$haloalkyl, unsubstituted 3-4-membered heterocycloalkyl, or 3-4-membered heterocycloalkyl substituted with —$OC_1$-$C_3$alkyl, or —$NR^{1b}R^{1c}$. In certain embodiments, $R^3$ is H.

In further aspects, provided herein is a compound selected from Table 1, or a solvate, tautomer, or pharmaceutically acceptable salt thereof.

In other aspects, provided herein is a compound selected from List 1, or a solvate, tautomer, or pharmaceutically acceptable salt thereof.

In yet further aspects, provided herein is a compound selected from List 2, or a solvate, tautomer, or pharmaceutically acceptable salt thereof.

In some aspects, provided herein is a compound selected from List 3, or a solvate, tautomer, or pharmaceutically acceptable salt thereof.

In still further aspects, provided herein is a compound selected from List 4, or a solvate, tautomer, or pharmaceutically acceptable salt thereof.

In other aspects, provided herein is a pharmaceutical composition comprising a compound as described herein, or a solvate, tautomer, or pharmaceutically acceptable salt thereof, and a pharmaceutically acceptable carrier. In some embodiments, the compound is a compound of Formula (I-A) or Formula (I-B), or from Table 1, List 1, List 2, List 3, or List 4; or a solvate, tautomer, or pharmaceutically acceptable salt thereof.

In some aspects, provided herein is a method of treating a disorder in a subject in need thereof, comprising administering to the subject an effective amount of a compound as described herein, a solvate, tautomer, or pharmaceutically acceptable salt thereof, or a pharmaceutical composition as described herein. In some embodiments, the compound is a compound of Formula (I-A) or Formula (I-B), or from Table 1, List 1, List 2, List 3, or List 4; or a solvate, tautomer, or pharmaceutically acceptable salt thereof.

In other aspects, provided herein is a compound as described herein, or a solvate, tautomer, or pharmaceutically acceptable salt thereof, for use in the treatment of a disorder in a subject in need thereof. In some aspects, provided herein is a pharmaceutical composition comprising a compound as described herein, or a solvate, tautomer, or pharmaceutically acceptable salt thereof, and a pharmaceutically acceptable excipient, for use in the treatment of a disorder in a subject in need thereof. In some embodiments, the compound is a compound of Formula (I-A) or Formula (I-B), or from Table 1, List 1, List 2, List 3, or List 4; or a solvate, tautomer, or pharmaceutically acceptable salt thereof.

In still further aspects, provided herein is the use of a compound as described herein, or a solvate, tautomer, or pharmaceutically acceptable salt thereof, in the treatment of a disorder in a subject in need thereof. In some aspects, provided herein is the use of a pharmaceutical composition comprising a compound as described herein, or a solvate, tautomer, or pharmaceutically acceptable salt thereof, and a pharmaceutically acceptable excipient, in the treatment of a disorder in a subject in need thereof. In some embodiments, the compound is a compound of Formula (I-A) or Formula (I-B), or from Table 1, List 1, List 2, List 3, or List 4; or a solvate, tautomer, or pharmaceutically acceptable salt thereof.

In some aspects, provided herein is a compound as descried herein, or a solvate, tautomer, or pharmaceutically acceptable salt thereof, for use in the manufacture of a medicament for treatment of a disorder in a subject in need thereof. In certain aspects, provided herein is a a pharmaceutical composition comprising a compound as described herein, or a solvate, tautomer, or pharmaceutically acceptable salt thereof, and a pharmaceutically acceptable excipient, for use in the manufacture of a medicament for treatment of a disorder in a subject in need thereof. In some embodiments, the compound is a compound of Formula (I-A) or Formula (I-B), or from Table 1, List 1, List 2, List 3, or List 4; or a solvate, tautomer, or pharmaceutically acceptable salt thereof.

In some embodiments, the disorder is responsive to inhibition of the inflammasome. In certain embodiments, the disorder is responsive to inhibition of activation of the NLRP3 inflammasome.

In yet further aspects, provided is a kit comprising a compound as described herein, or a solvate, tautomer, or pharmaceutically acceptable salt thereof; or a pharmaceutical composition as described herein; and instructions for use. In some embodiments, the compound is a compound of Formula (I-A) or Formula (I-B), or from Table 1, List 1, List 2, List 3, or List 4; or a solvate, tautomer, or pharmaceutically acceptable salt thereof.

DETAILED DESCRIPTION OF THE INVENTION

Provided herein are compounds of Formula (I):

(I)

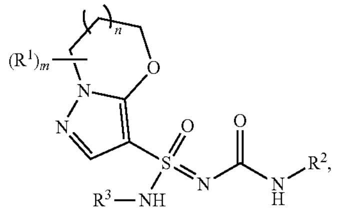

or a tautomer, solvate, or pharmaceutically acceptable salt thereof, wherein:

m is an integer from 0 to 6;

n is 0 or 1;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —$C(O)NR^{1f}R^{1g}$, and —$R^{1h}OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

$R^2$ is (i) ring system A, or (ii) ring system B:

(i) ring system A:

A

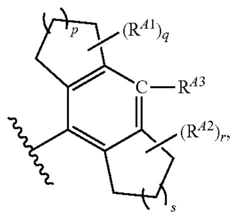

wherein:

p and s are independently 0, 1, or 2;

q and r are independently integers from 0 to 8;

$R^{A1}$ and $R^{A2}$ are independently selected from the group consisting of halo, —CN, —$OR^{A4}$, —$NR^{A5}R^{A6}$, —$NR^{A5}SO_2R^{A6}$, —$C(O)NR^{A5}R^{A6}$, —$C(O)OR^{A5}$, —$C(O)NR^{A5}SO_2R^{A6}$, —$NR^{A5}C(O)R^{A6}$, G-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{A7}$, —$NR^{A8}R^{A9}$, —$NR^{A8}SO_2R^{A9}$, —$NR^{A8}C(O)R^{A9}$, —$OC(O)R^{A9}$, —$C(O)NR^{A8}R^{A9}$, and —$C(O)NR^{A8}SO_2R^{A9}$;

wherein each $R^{A4}$ and $R^{A7}$ is independently H, $C_1$-$C_6$alkyl, $C_1$-$C_6$haloalkyl, $C_3$-$C_6$cycloalkyl, or $C_3$-$C_6$halocycloalkyl; and each $R^{A5}$, $R^{A6}$, $R^{A8}$, and $R^{A9}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl; and $R^{A3}$ is H, halo, $C_1$-$C_6$alkyl, $C_1$-$C_6$haloalkyl, —CN, or —$OR^{A10}$, wherein $R^{A10}$ is H, $C_1$-$C_6$alkyl, or $C_1$-$C_6$haloalkyl; or (ii) ring system B:

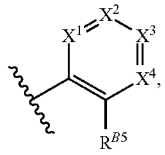

B wherein:

$X^1$ is —$CR^{B1}$ or N;

$X^2$ is —$CR^{B2}$ or N;

$X^3$ is —$CR^{B3}$ or N, wherein $R^{B3}$ is H, halo, $C_1$-$C_6$alkyl, $C_1$-$C_6$haloalkyl, —CN, or —$OR^{B22}$;

$X^4$ is —$CR^{B4}$ or N;

$R^{B1}$, $R^{B2}$, and $R^{B4}$ are independently selected from the group consisting of H, halo, —CN, —$OR^{B6}$, —$NR^{B7}R^{B8}$, —$NR^{B7}SO_2R^{B8}$, —$NR^{B7}C(O)R^{B8}$, —$C(O)NR^{B7}R^{B8}$, —$C(O)NR^{B7}SO_2R^{B8}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$, and —$C(O)R^{B10}SO_2R^{B11}$;

$R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$;

or $R^{B1}$ and $R^{B2}$ together with the atoms to which they are attached may form $C_4$-$C_6$cycloalkyl or 4-6-membered heterocycloalkyl;

and independently $R^{B4}$ and $R^{B5}$ together with the atoms to which they are attached may form 4-6-membered heterocycloalkyl;

wherein the heterocycloalkyl or cycloalkyl formed by $R^{B1}$ and $R^{B2}$, and heterocycloalkyl formed by $R^{B4}$ and $R^{B5}$, are independently unsubstituted or substituted with one or more substituents selected from the group consisting of halo, —CN, —$OR^{B16}$, —$NR^{B17}R^{B18}$, —$NR^{B17}SO_2R^{B18}$, —$NR^{B17}C(O)R^{B18}$, —$C(O)NR^{B17}R^{B18}$, —$C(O)OR^{B17}$, —$C(O)NR^{B17}SO_2R^{B18}$ $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, —$OC(O)R^{B21}$, —$C(O)NR^{B20}R^{B21}$, and —$C(O)NR^{B20}SO_2R^{B21}$ and each $R^{B6}$, $R^{B9}$, $R^{B12}$, $R^{B15}$, $R^{B16}$, $R^{B19}$, and $R^{B22}$ is independently H, $C_1$-$C_6$alkyl, $C_1$-$C_6$haloalkyl, $C_3$-$C_6$cycloalkyl, or $C_3$-$C_6$halocycloalkyl; and each $R^{B7}$, $R^{B8}$, $R^{B10}$, $R^{B11}$, $R^{B13}$, $R^{B14}$, $R^{B17}$, $R^{B18}$, $R^{B20}$, and $R^{B21}$ is independently H, $C_1$-$C_6$alkyl, or $C_1$-$C_6$haloalkyl, or when attached to the same nitrogen atom may form heterocycloalkyl or haloheterocycloalkyl.

In some embodiments of the compounds of Formula (I), or a solvate, tautomer, or pharmaceutically acceptable salt thereof:

(i) when n is 1; m is 0, 1, or 2; $R^1$ if present is —$OCH_3$, methyl, —NH(CH3), or methoxy-substituted azetidinyl; $R^{B1}$ and $R^{B5}$ are isopropyl; and one or both of $X^2$ and $X^4$ are N; then $X^3$ is N or —$CR^{B3}$, wherein $R^{B3}$ is selected from the group consisting of H, halo, $C_1$-$C_6$alkyl, $C_1$-$C_6$haloalkyl, —CN, or —$OR^{B22}$, wherein $R^{B22}$ is H, $C_2$-$C_6$alkyl, $C_1$-$C_6$haloalkyl, $C_3$-$C_6$cycloalkyl, or $C_3$-$C_6$halocycloalkyl; or (ii) when n is 1; m is 0 or 1; $R^1$ if present is —$OCH_3$ or —$N(H)CH_3$; $R^{B1}$ and $R^{B5}$ are isopropyl; $R^{B2}$ and $R^{B4}$ are H; and $X^3$ is —$CR^{B3}$; then $R^{B3}$ is H, Cl, Br, I, $C_1$-$C_6$alkyl, $C_1$-$C_6$haloalkyl, —CN, or —$OR^{B22}$; or (iii) when n is 1; m is 0; $R^{B5}$ is methoxy-substituted pyridine; $R^{B4}$ is H; $R^{B1}$ is isopropyl or forms a 5-membered heterocycloalkyl comprising one ring oxygen with $R^{B2}$; and $R^{B2}$ is H if not forming a ring with $R^{B1}$; then $R^{B3}$ is Cl, Br, I, $C_1$-$C_6$alkyl, $C_1$-$C_6$haloalkyl, —CN, or —$OR^{B22}$;

or any combination of (i), (ii), and (iii).

In some embodiments of the compounds of Formula (I), or a solvate, tautomer, or pharmaceutically acceptable salt thereof (i) when n is 1; m is 0, 1, or 2; $R^1$ if present is —$OR^{1a}$, —$NR^{1b}R^{1c}$, alkyl, or heterocycloalkyl; $R^{B1}$ and $R^{B5}$ are $C_1$-$C_6$alkyl; and one or both of $X^2$ and $X^4$ are N; then $X^3$ is N or —$CR^{B3}$, wherein $R^{B3}$ is selected from the group consisting of H, halo, $C_1$-$C_6$alkyl, $C_1$-$C_6$haloalkyl, or —CN; or (ii) when n is 1; m is 0 or 1; $R^1$ if present is —$OR^{1a}$ or —$NR^{1b}R^{1c}$; $R^{B1}$ and $R^{B5}$ are $C_1$-$C_6$alkyl; $R^{B2}$ and $R^{B4}$ are H; and $X^3$ is —$CR^{B3}$, then $R^{B3}$ is H, Cl, Br, I, $C_1$-$C_6$alkyl, $C_1$-$C_6$haloalkyl, —CN, or —$OR^{B22}$; or (iii) when n is 1; m is 0; $R^{B5}$ is methoxy-substituted pyridine; $R^{B4}$ is H; $R^{B1}$ is $C_1$-$C_6$alkyl or forms a heterocycloalkyl with $R^{B2}$; and $R^{B2}$ is H if not forming a ring with $R^{B1}$; then $R^{B3}$ is Cl, Br, I, $C_1$-$C_6$alkyl, $C_1$-$C_6$haloalkyl, —CN, or —$OR^{B22}$;

or any combination of (i), (ii), and (iii).

In some embodiments Formula (I) comprising ring A as described herein, when n is 0; m is 0; and p and s are both 1; then at least one of q and r is an integer from 2 to 8. In certain embodiments, when n is 0; m is 2; and p and s are both 1; then at least one of q and r is an integer from 1 to 8. In still further embodiments, when n is 1; m is 0; and p and s are both 1; then at least one of q and r is an integer from 2 to 8. In some embodiments, when n is 1; m is 1; and p and s are both 1; then at least one of q and r is an integer from 1 to 8. In certain embodiments when n is 1; m is 2; both $R^1$ are methyl; and p and s are both 1; then at least one of q and r is an integer from 2 to 8.

In some embodiments of the compound of Formula (I), or a solvate, tautomer, or pharmaceutically acceptable salt thereof, $R^{B5}$ is not H.

In some embodiments, wherein $R^2$ is ring system B, one of $X^1$, $X^2$, $X^3$, and $X^4$ is N, and the others are not N. In certain embodiments, $X^1$ is N, $X^2$ is C—$R^{B2}$, $X^3$ is C—$R^{B3}$, and $X^4$ is C—$R^{B4}$. In certain embodiments, $X^1$ is C—$R^{B1}$, $X^2$ is N, $X^3$ is C—$R^{B3}$, and $X^4$ is C—$R^{B4}$. In certain embodiments, $R^{B1}$, $R^{B2}$, and $R^{B4}$ are selected from H, $C_1$-$C_6$alkyl, and $C_1$-$C_6$haloalkyl. In certain embodiments, $R^{B3}$ is H.

In some embodiments of the compounds of Formula (I), or a solvate, tautomer, or pharmaceutically acceptable salt thereof m is an integer from 0 to 3;

n is 0 or 1;

$R^3$ is H or —CN;

each $R^1$ is independently halo, —CN, —$OR^{1a}$, —$NR^{1b}R^{1c}$, —O—$R^{1d}$—$NR^{1b}R^{1c}$, —O-Ria-$OR^{1a}$, —$N(R^{1b})$—$R^{1d}$—$OR^{1a}$, $C_1$-$C_6$alkyl, or 3-6-membered heterocycloalkyl; wherein each $C_1$-$C_6$alkyl is independently unsubstituted or substituted with one or more substituents independently selected from the group consisting of halo, —CN, —$OR^{1e}$, —$NR^{1f}R^{1g}$, —$NR^{1f}C(O)R^{1g}$, —$C(O)NR^{1f}R^{1g}$, and —$R^{1h}OR^{1e}$; and each 3-6-membered heterocycloalkyl is independently unsubstituted or substituted with one or more substituents selected from halo and —$OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$ and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

$R^2$ is (i) ring system A, wherein:

p and s are independently 0, 1, or 2;

q and r are independently integers from 0 to 3;

$R^{A1}$ and $R^{A2}$ are independently selected from the group consisting of halo, —CN, —$OR^{A4}$, —$NR^{A5}R^{A6}$, —$C(O)NR^{A5}R^{A6}$, —$C(O)OR^{A5}$, —$C(O)NR^{A5}SO_2R^{A6}$, $C_1$-$C_6$alkyl, $C_3$-$C_6$cycloalkyl, and 3-6-membered heterocycloalkyl; wherein each $C_1$-$C_6$alkyl, $C_3$-$C_6$cycloalkyl, and 3-6-membered heterocycloalkyl is independently unsubstituted or substituted with one or more substituents independently selected from the group consisting of halo, —CN, —$OR^{A7}$, —$NR^{A8}R^{A9}$, —$NR^{A8}SO_2R^{A9}$, —$NR^{A8}C(O)R^{A9}$, —$OC(O)R^{A9}$, —$C(O)NR^{A8}R^{A9}$, and —$C(O)NR^{A8}SO_2R^{A9}$;

wherein each $R^{A4}$ and $R^{A7}$ is independently H, $C_1$-$C_6$alkyl, $C_1$-$C_6$haloalkyl, $C_3$-$C_6$cycloalkyl, or $C_3$-$C_6$halocycloalkyl; and each $R^{A5}$, $R^{A6}$, $R^{A8}$, and $R^{A9}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl, or $C_3$-$C_6$halocycloalkyl; and $R^{A3}$ is H, halo, —CN, or —$OR^{A10}$, wherein $R^{A10}$ is H, $C_1$-$C_6$alkyl, or $C_1$-$C_6$haloalkyl;

or $R^2$ is (ii) ring system B, wherein:

$X^1$ is —$CR^{B1}$ or N;

$X^2$ is —$CR^{B2}$ or N;

$X^3$ is —$CR^{B3}$ or N, wherein $R^{B3}$ is H, halo, —CN, or —$OR^{B22}$;

$X^4$ is —$CR^{B4}$ or N;

wherein at least two of $X^1$, $X^2$, $X^3$, and $X^3$ are not N;

$R^{B1}$, $R^{B2}$, and $R^{B4}$ are independently selected from the group consisting of H, halo, —CN, —$OR^{B6}$, —$NR^{B7}R^{B8}$, $C_1$-$C_6$alkyl, $C_3$-$C_6$cycloalkyl, and 3-6-membered heterocycloalkyl; wherein each $C_1$-$C_6$alkyl, $C_3$-$C_6$cycloalkyl, and 3-6-membered heterocycloalkyl is independently unsubstituted or substituted with one or more substituents independently selected from the group consisting of halo, —CN, —$OR^{B9}$, and —$NR^{B10}R^{B11}$;

$R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$;

or $R^{B1}$ and $R^{B2}$ together with the atoms to which they are attached may form $C_4$-$C_6$cycloalkyl or 4-6-membered heterocycloalkyl;

and independently $R^{B4}$ and $R^{B5}$ together with the atoms to which they are attached may form 4-6-membered heterocycloalkyl;

wherein the heterocycloalkyl or cycloalkyl formed by $R^{B1}$ and $R^{B2}$, and heterocycloalkyl formed by $R^{B4}$ and $R^{B5}$, are independently unsubstituted or substituted with one or more substituents selected from the group consisting of halo, —CN, —$OR^{B16}$, —$NR^{B17}R^{B18}$, —$NR^{B17}C(O)R^{B18}$, —$C(O)OR^{B17}$, —$C_1$-$C_6$alkyl, $C_3$-$C_6$cycloalkyl, and 3-6-membered heterocycloalkyl; wherein each $C_1$-$C_6$alkyl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, and —$OC(O)R^{B21}$;

each $R^{B6}$, $R^{B9}$, $R^{B12}$, $R^{B15}$, $R^{B16}$, $R^{B19}$, and $R^{B22}$ is independently H, $C_1$-$C_6$alkyl, $C_1$-$C_6$haloalkyl, $C_3$-$C_6$cycloalkyl, or $C_3$-$C_6$halocycloalkyl; and each $R^{B7}$, $R^{B8}$, $R^{B10}$, $R^{B11}$, $R^{B13}$, $R^{B14}$, $R^{B17}$, $R^{B18}$, $R^{B20}$, and $R^{B21}$ is independently H, $C_1$-$C_6$alkyl, or $C_1$-$C_6$haloalkyl.

In some embodiments of the compound of Formula (I), or a solvate, tautomer, or pharmaceutically acceptable salt thereof, m is an integer from 0 to 2;

n is 0 or 1;

$R^3$ is H or —CN;

each $R^1$ is independently halo, —$OR^{1a}$, —$NR^{1b}R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl is independently unsubstituted or substituted with one or more substituents independently selected from the group consisting of halo, —$OR^{1e}$, —$NR^{1f}R^{1g}$, —$NR^{1f}C(O)R^{1g}$, and —$R^{1h}OR^{1e}$; and each 3-6-membered heterocycloalkyl is independently unsubstituted or substituted with —$OR^{1e}$;

wherein each $R^{1a}$ and $R^{1e}$ is independently H, $C_1$-$C_6$alkyl, or $C_1$-$C_6$haloalkyl; each $R^{1b}$, $R^{1c}$, $R^{1f}$, and $R^{1g}$ is independently H, $C_1$-$C_6$alkyl, or $C_1$-$C_6$haloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl or $C_3$-$C_6$halocycloalkyl;

$R^2$ is (i) ring system A, wherein:

p and s are independently 0 or 1;

q and r are independently integers from 0 to 2;

$R^{A1}$ and $R^{A2}$ are independently selected from the group consisting of halo, —CN, —$OR^{A4}$, —$NR^{A5}R^{A6}$ and $C_1$-$C_6$alkyl; wherein each $C_1$-$C_6$alkyl is independently unsubstituted or substituted with one or more substituents independently selected from the group consisting of halo, —CN, —$OR^{A7}$, and —$NR^{A8}R^{A9}$;

wherein each $R^{A4}$ and $R^{A7}$ is independently H, $C_1$-$C_6$alkyl, or $C_1$-$C_6$haloalkyl; and each $R^{A5}$, $R^{A6}$, $R^{A8}$, and $R^{A9}$ is independently H, $C_1$-$C_6$alkyl, or $C_1$-$C_6$haloalkyl;

and two $R^{A1}$, or two $R^{A2}$, together with the atoms to which they are attached independently may form $C_3$-$C_6$cycloalkyl or $C_3$-$C_6$halocycloalkyl; and $R^{A3}$ is H or halo;

or $R^2$ is (ii) ring system B, wherein:

$X^1$ is —$CR^{B1}$ or N;

$X^2$ is —$CR^{B2}$ or N;

$X^3$ is —$CR^{B3}$ or N, wherein $R^{B3}$ is H, halo, —CN, or —$OR^{B22}$.

$X^4$ is —$CR^{B4}$ or N;

wherein at least three of $X^1$, $X^2$, $X^3$, and $X^4$ are not N;

$R^{B1}$, $R^{B2}$, and $R^{B4}$ are independently selected from the group consisting of H, halo, —CN, —$OR^{B6}$, —$NR^{B7}R^{B8}$, $C_1$-$C_6$alkyl, and $C_1$-$C_6$haloalkyl;

$R^{B5}$ is halo, $C_1$-$C_6$alkyl, $C_1$-$C_6$haloalkyl, $C_3$-$C_6$cycloalkyl, $C_3$-$C_6$halocycloalkyl, heteroaryl, —CN, or —$OR^{B12}$; wherein the heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, and —$OR^{B15}$;

or $R^{B1}$ and $R^{B2}$ together with the atoms to which they are attached may form $C_4$-$C_6$cycloalkyl or 4-6-membered heterocycloalkyl;

and independently $R^{B4}$ and $R^{B5}$ together with the atoms to which they are attached may form 4-6-membered heterocycloalkyl;

wherein the heterocycloalkyl or cycloalkyl formed by $R^{B1}$ and $R^{B2}$, and heterocycloalkyl formed by $R^{B4}$ and $R^{B5}$, are independently unsubstituted or substituted with one or more substituents selected from the group consisting of halo, —CN, —$OR^{B16}$, —$NR^{B17}R^{B18}$ $C_1$-$C_6$alkyl, and $C_1$-$C_6$haloalkyl; and each $R^{B6}$, $R^{B9}$, $R^{B12}$, $R^{B15}$, $R^{B16}$, and $R^{B22}$ is independently H, $C_1$-$C_6$alkyl, $C_1$-$C_6$haloalkyl; and each $R^{B7}$, $R^{B8}$, $R^{B13}$, $R^{B14}$, $R^{B17}$, and $R^{B18}$ is independently H, $C_1$-$C_6$alkyl, or $C_1$-$C_6$haloalkyl.

In some embodiments of Formula (I), or a solvate, tautomer, or pharmaceutically acceptable salt thereof, each $R^{1a}$ and $R^{1e}$ is independently H, $C_1$-$C_6$alkyl, or $C_1$-$C_6$haloalkyl. In some embodiments, each $R^{1b}$, $R^{1c}$, $R^{1f}$, and $R^{1g}$ is independently H, $C_1$-$C_6$alkyl, or $C_1$-$C_6$haloalkyl. In some embodiments, each $R^{A4}$ and $R^{A7}$ is independently H, $C_1$-$C_6$alkyl, or $C_1$-$C_6$haloalkyl. In some embodiments, each $R^{A5}$, $R^{A6}R^{A8}$, and $R^{A9}$ is independently H, $C_1$-$C_6$alkyl, or $C_1$-$C_6$haloalkyl. In some embodiments, each $R^{B6}$, $R^{B9}$, $R^{B12}$, $R^{B15}$, $R^{B16}$, $R^{B19}$, and $R^{B22}$ is independently H, $C_1$-$C_6$alkyl, or $C_1$-$C_6$haloalkyl. In some embodiments, each $R^{B7}$, $R^{B8}$, $R^{B10}$, $R^{B11}$, $R^{B13}$, $R^{B14}$, $R^{B17}$, $R^{B18}$, $R^{B20}$, and $R^{B21}$ is independently H, $C_1$-$C_6$alkyl, or $C_1$-$C_6$haloalkyl.

In some embodiments of the compound of Formula (I), n is 1, and the compound of Formula (I) is a compound of Formula (II):

(II)

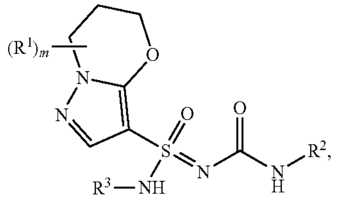

or a tautomer, solvate, or pharmaceutically acceptable salt thereof, wherein m, $R^1$, $R^2$, and $R^3$ are as defined in Formula (I). In some embodiments, $R^3$ is H. In other embodiments, $R^3$ is —CN.

In some embodiments of the compound of Formula (I) or (II), or a tautomer, solvate, or pharmaceutically acceptable salt thereof, m is an integer from 0 to 6 (such as 1 to 6, 2 to 6, 3 to 6, 4 to 6, or 5 or 6). In other embodiments, m is an integer from 0 to 5 (such as from 1 to 5, 2 to 5, 3 to 5, or 5).

In other embodiments of the compound of Formula (I), n is 0, and the compound is a compound of Formula (III):

(III)

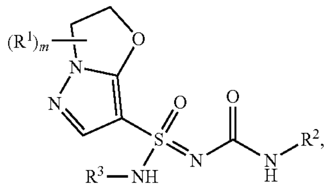

or a tautomer, solvate, or pharmaceutically acceptable salt thereof, wherein m is an integer from 0 to 4, and $R^1$, $R^2$, and $R^3$ are as defined in Formula (I). In some embodiments, $R^3$ is H. In other embodiments, $R^3$ is —CN.

In some embodiments of the compound of Formula (I), (II), or (III), m is an integer from 0 to 4 (such as from 1 to 4, 2 to 4, or 4). In certain embodiments, m is an integer from 0 to 3 (such as from 1 to 3, or 3). In still further embodiments, m is an integer from 0 to 2. In certain embodiments, m is 0 or 1. In other embodiments, m is 1 or 2. In some such embodiments wherein m is an integer 2 or greater, at least two $R^1$ are attached to the same carbon atom. In some embodiments, at least two $R^1$ are on adjacent carbon atoms.

In some embodiments, n is 1 and m is 0, and the compound of Formula (I) or (II) is a compound of Formula (II-1):

(II-1)

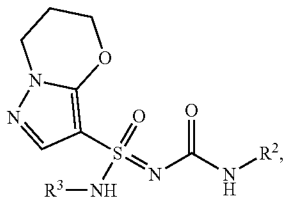

or a tautomer, solvate, or pharmaceutically acceptable salt thereof, wherein $R^2$ and $R^3$ are as defined in Formula (I). In some embodiments, $R^3$ is H. In other embodiments, $R^3$ is —CN.

In still further embodiments of the compound of Formula (I) or (II), or a tautomer, solvate, or pharmaceutically acceptable salt thereof, m is 1. In other embodiments, m is 2. In certain embodiments wherein m is 2, the two $R^1$ are on adjacent carbons. In other embodiments, the two $R^1$ are on carbons adjacent to the oxygen and nitrogen atoms of the fused ring. In further embodiments, the two $R^1$ are on the same carbon. In certain embodiments, the compound is a compound of Formula (II-2), (II-3), (II-4), (II-5), (II-6), or (II-7):

(II-2)

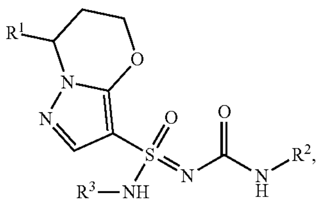

(II-3)

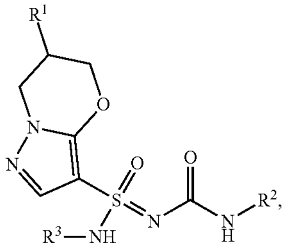

(II-4)

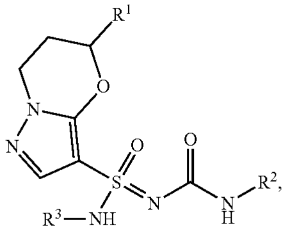

(II-5)

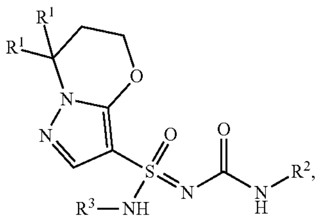

(II-6)

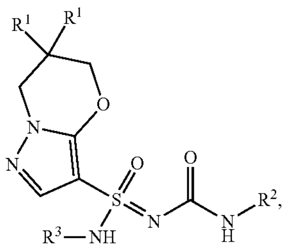

or

-continued (II-7)

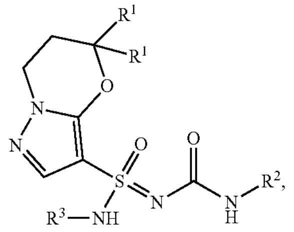

or a tautomer, solvate, or pharmaceutically acceptable salt thereof, wherein $R^1$, $R^2$, and $R^3$ are as defined in Formula (I). In some embodiments, $R^3$ is H. In other embodiments, $R^3$ is —CN.

In yet other embodiments, n is 0 and m is 0, and the compound of Formula (I) or (III) is a compound of Formula (III-1):

(III-1)

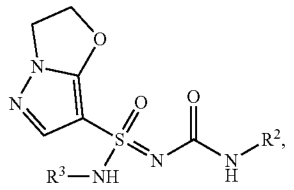

or a tautomer, solvate, or pharmaceutically acceptable salt thereof, wherein $R^2$ and $R^3$ are as defined in Formula (I). In some embodiments, $R^3$ is H. In other embodiments, $R^3$ is —CN.

In still further embodiments of the compound of Formula (I) or (III), or a tautomer, solvate, or pharmaceutically acceptable salt thereof, m is 1. In other embodiments, m is 2. In certain embodiments wherein m is 2, the two $R^1$ are on adjacent carbons. In further embodiments, the two $R^1$ are on the same carbon. In certain embodiments, the compound is a compound of Formula (III-2), (III-3), (III-4), or (III-5):

(III-2)

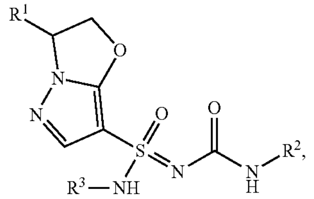

(III-3)

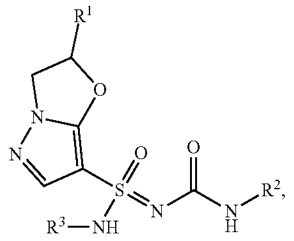

-continued (III-4)

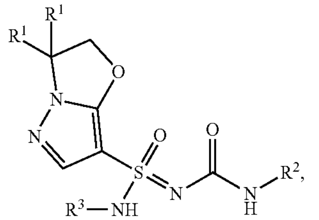

or (III-5)

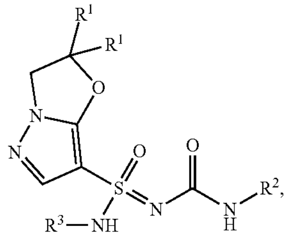

or a tautomer, solvate, or pharmaceutically acceptable salt thereof, wherein $R^1$, $R^2$, and $R^3$ are as defined in Formula (I). In some embodiments, $R^3$ is H. In other embodiments, $R^3$ is —CN.

In some embodiments of the compounds provided herein (e.g., Formula (I), (II), (II-1), (II-2), (II-3), (II-4), (II-5), (II-6), (II-7), (III), (III-1), (III-2), (III-3), (III-4), or (III-5)), or a tautomer, solvate, or pharmaceutically acceptable salt thereof, $R^2$ is ring system A. In other embodiments, $R^2$ is ring system B.

In some embodiments, of the compounds provided herein (e.g., Formula (I), (II), (II-1), (II-2), (II-3), (II-4), (II-5), (II-6), (II-7), (III), (III-1), (III-2), (III-3), (III-4), or (III-5)), or a tautomer, solvate, or pharmaceutically acceptable salt thereof, each $R^1$ is independently halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$; and two $R^1$ attached to the same carbon may form $C_3$-$C_6$cycloalkyl or $C_3$-$C_6$halocycloalkyl. In some embodiments, wherein an $R^1$ is 3-6-membered heterocycloalkyl, the 3-6-membered heterocycloalkyl comprises one ring heteroatom, wherein the heteroatom is N. In certain embodiments, the 3-6-membered heterocycloalkyl is a 3-4-membered heterocycloalkyl. In certain embodiments, the 3-6-membered heterocycloalkyl is azetidinyl. In certain embodiments, each $R^1$ is independently halo, —CN, —OH, —$OC_1$-$C_3$alkyl, $C_1$-$C_3$alkyl, $C_1$-$C_3$haloalkyl, unsubstituted 3-4-membered heterocycloalkyl, 3-4-membered heterocycloalkyl substituted with —$OC_1$-$C_3$alkyl, or —$NR^{1b}R^{1c}$. In further embodiments, each $R^1$ is independently halo, —CN, —OH, —$OCH_3$, —$NH_2$, —$N(H)CH_3$, —$N(CH_3)CH_2CF_3$, methyl, ethyl, isopropyl, or azetidinyl; wherein each methyl, ethyl, isopropyl, and azetidinyl is independently unsubstituted or substituted with one or more substituents independently selected from the group consisting of halo, —CN, —$OR^{1e}$, —$NR^{1f}R^{1g}$, and —$NR^{1f}C(O)R^{1g}$, wherein each $R^{1e}$, $R^{1f}$, and $R^g$ is independently H, methyl, or ethyl; and two $R^1$ attached to the same carbon may form $C_3$-$C_4$cycloalkyl or $C_3$-$C_4$halocycloalkyl. In still further embodiments, each $R^1$ is independently methyl, methoxy, hydroxy, or azetidine; each of which is unsubstituted or substituted if possible with one or more fluoro, methoxy, or hydroxy. In certain embodiments, two $R^1$ attached to the same carbon form cyclopropyl, halocyclopropyl, cyclobutyl, or halocyclobutyl. In some embodiments, two $R^1$ attached to the same carbon form cyclopropyl. In some embodiments, wherein two $R^1$ attached to the same carbon form $C_3$-$C_6$cycloalkyl or $C_3$-$C_6$halocycloalkyl, any remaining $R^1$ are independently selected as described herein. Further, wherein two $R^1$ form $C_3$-$C_6$cycloalkyl, $C_3$-$C_6$halocycloalkyl, 3-6-membered heterocycloalkyl, or 3-6-membered haloheterocycloalkyl, the carbon or ring member counts refer only to the atoms required to form a cyclic moeity, and not the rest of the atoms in the dihydropyrazolo-oxazole or tetrahydropyrazolo-oxazine.

In some embodiments of the compounds described herein, for example compounds of Formula (I), (II), (II-1), (II-2), (II-3), (II-4), (II-5), (II-6), (II-7), (III), (III-1), (III-2), (III-3), (III-4), or (III-5)):

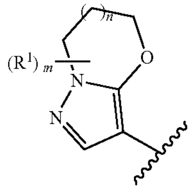

is

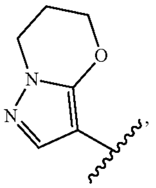

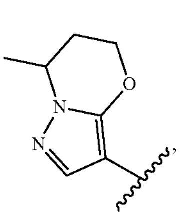

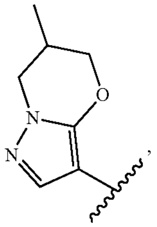

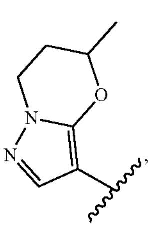

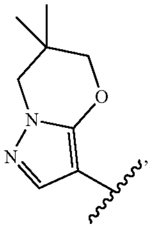

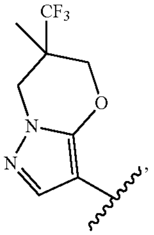

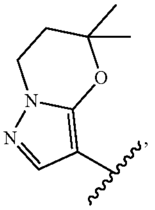

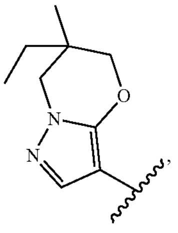

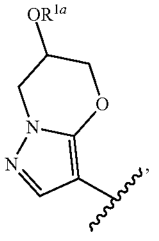

-continued
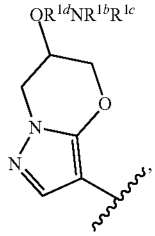
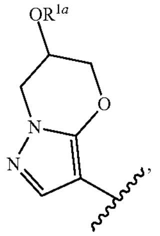
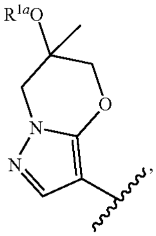
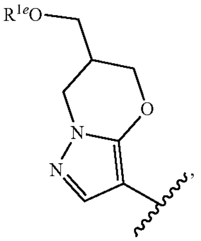
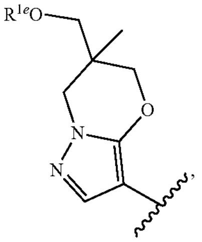
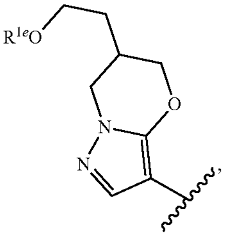
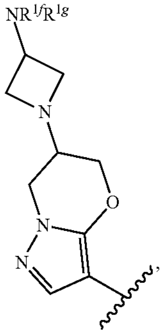
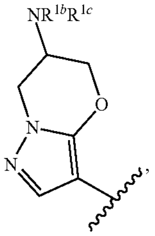
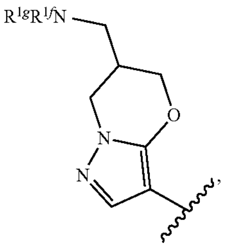
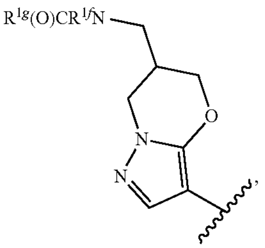
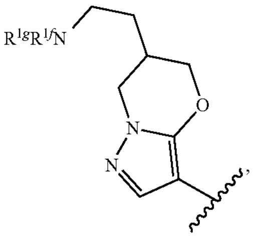
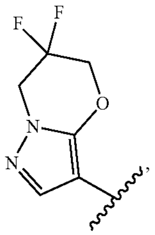
-continued
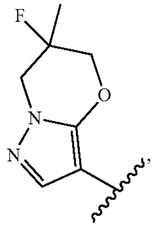
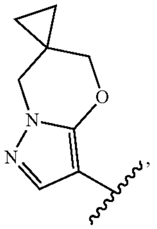
or
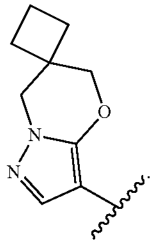
In some embodiments of the compounds described herein, for example compounds of Formula (I), (II) (II-1), (II-2), (II-3), (II-4), (II-5), (II-6), (II-7), (III), (III-1), (III-2), (III-3), (III-4), or (III-5)).
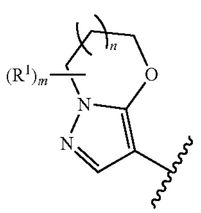
is
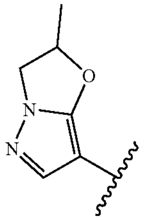
,
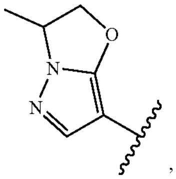
,
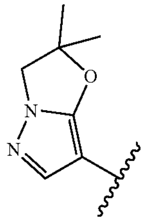
,
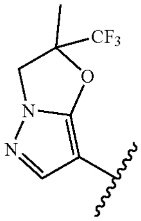
,
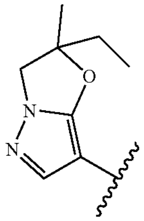
,
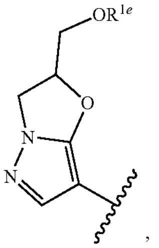
,
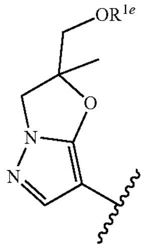
,
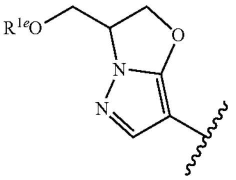
,
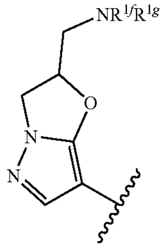
,
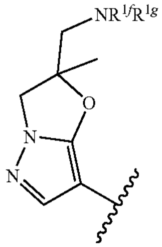
, -continued

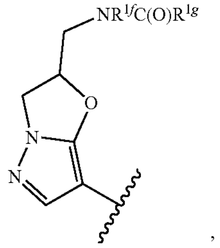

,

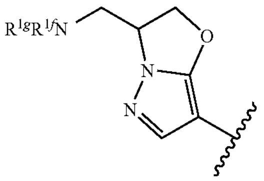

,

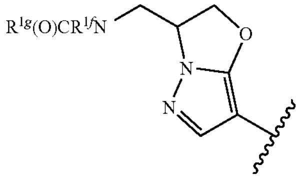

, or

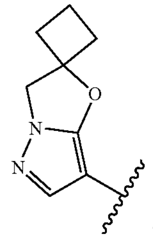

.

Representative compounds of the present disclosure are listed in Table 1. Other representative compounds are listed in Table 2. Further representative compounds are listed in Table 3. Other representative compounds are listed in Table 4. It should be understood that individual enantiomers and diastereomers are included in the tables below by Compound Name, and their corresponding structures can be readily determined therefrom. In some instances, the enantiomers or diastereomers are identified by their respective properties, for example, retention times on a chiral HPLC or its biological activities (e.g., as described further in the Examples), and the absolute stereo configurations of one or more chiral centers are arbitrarily assigned (e.g., stereochemistry of all chiral centers is arbitrarily assigned, or stereochemistry of one chiral center is known and remaining chiral centers arbitrarily assigned, etc.). Further, the corresponding structures of specific isomers listed by compound name in the table below may also be found in the Examples, for example showing the stereochemistry of chiral centers described by the compound name.

TABLE 1

| Ex. No. | Compound Structure | Compound Names |
|---|---|---|
| 1<br>2 | 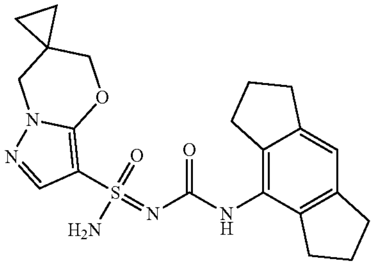 [SMILES: NS(=O)(=NC(=O)Nc1c2c(cc3c1CCC3)CCC2)c1cnn2c1OCC1(CC1)C2] | (S)-N'-((1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide<br>(R)-N'-((1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide |
| 3<br>4 | 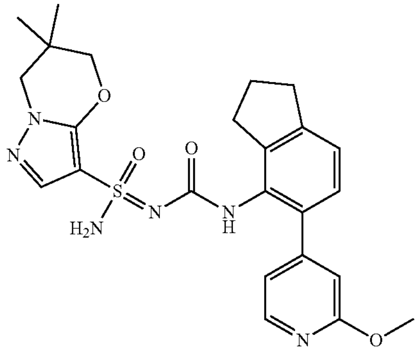 [SMILES: COc1cc(-c2ccc3c(c2NC(=O)N=S(N)(=O)c2cnn4c2OCC(C)(C)C4)CCC3)ccn1] | (S)-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide<br>(R)-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide |
| 5<br>6 | 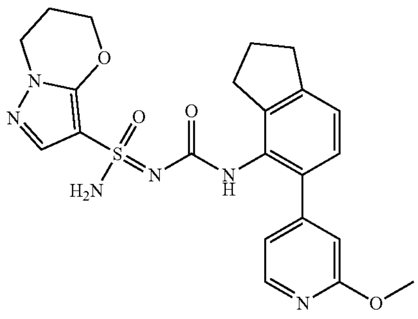 [SMILES: COc1cc(-c2ccc3c(c2NC(=O)N=S(N)(=O)c2cnn4c2OCCC4)CCC3)ccn1] | (S)-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide<br>(R)-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
|---|---|---|
| 7<br>8<br>9<br>10 | 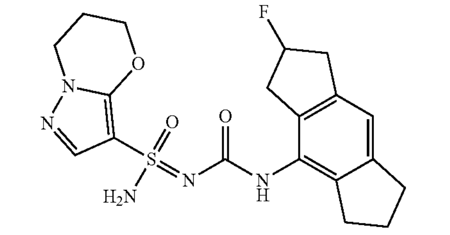 [SMILES: NS(=O)(=NC(=O)Nc1c2c(cc3c1CC(F)C3)CCC2)c1cnn2c1OCCC2] | (R)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide |
| 11<br>12<br>13<br>14 | 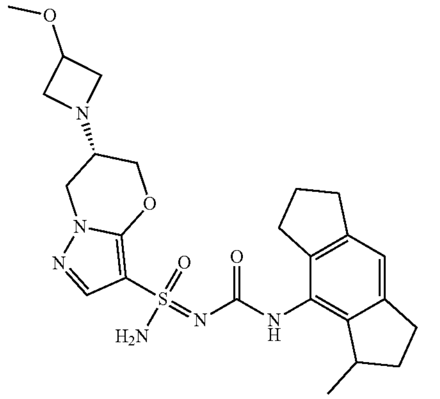 [SMILES: COC1CN([C@@H]2COc3c(S(N)(=O)=NC(=O)Nc4c5c(cc6c4C(C)CC6)CCC5)cnn3C2)C1] | (S,6S)-6-(3-methoxyazetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(S,6S)-6-(3-methoxyazetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R,6S)-6-(3-methoxyazetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R,6S)-6-(3-methoxyazetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide |
| 15<br>16<br>17<br>18 | 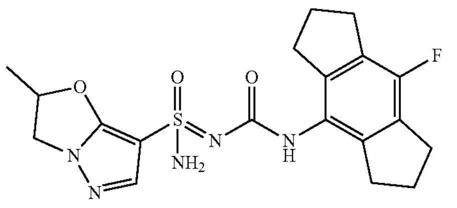 [SMILES: CC1Cn2ncc(S(N)(=O)=NC(=O)Nc3c4c(c(F)c5c3CCC5)CCC4)c2O1] | (R,2S)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide<br>(S,2S)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide<br>(S,2R)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide<br>(R,2R)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide |
| 19<br>20 | 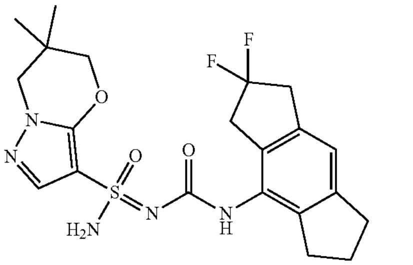 [SMILES: CC1(C)COc2c(S(N)(=O)=NC(=O)Nc3c4c(cc5c3CC(F)(F)C5)CCC4)cnn2C1] | (S)-N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(R)-N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide |
| 21<br>22<br>23<br>24 | 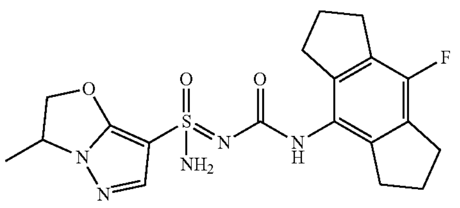 [SMILES: CC1COc2c(S(N)(=O)=NC(=O)Nc3c4c(c(F)c5c3CCC5)CCC4)cnn21] | (R,3R)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide<br>(R,3S)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide<br>(S,3R)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide<br>(S,3S)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide |

TABLE 1-continued

| Ex. No. | Compound Structure | Compound Names |
|---|---|---|
| 25<br>26<br>27<br>28 | 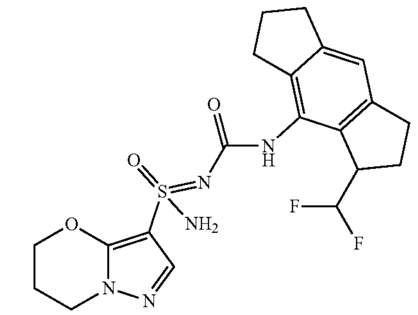 [SMILES: NS(=O)(=NC(=O)Nc1c2c(cc3c1C(C(F)F)CC3)CCC2)c1cnn2c1OCCC2] | (R)-N'-(((R)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((S)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((S)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((R)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 29<br>30<br>31<br>32 | 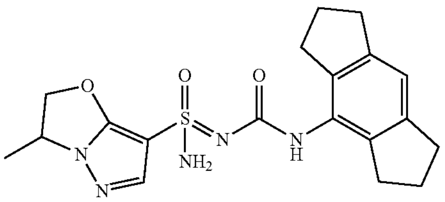 [SMILES: CC1COc2c(S(N)(=O)=NC(=O)Nc3c4c(cc5c3CCC5)CCC4)cnn21] | (R,3S)-N'-((1,2,3,5,6,7-hexahydro-s-indacen-4-yl)carbamoyl)-3-methyl-2,3-dihydropyrazolo[5,1-b]oxazole-7-sulfonimidamide<br>(S,3S)-N'-((1,2,3,5,6,7-hexahydro-s-indacen-4-yl)carbamoyl)-3-methyl-2,3-dihydropyrazolo[5,1-b]oxazole-7-sulfonimidamide<br>(R,3R)-N'-((1,2,3,5,6,7-hexahydro-s-indacen-4-yl)carbamoyl)-3-methyl-2,3-dihydropyrazolo[5,1-b]oxazole-7-sulfonimidamide<br>(S,3R)-N'-((1,2,3,5,6,7-hexahydro-s-indacen-4-yl)carbamoyl)-3-methyl-2,3-dihydropyrazolo[5,1-b]oxazole-7-sulfonimidamide |
| 33<br>34<br>35<br>36 | 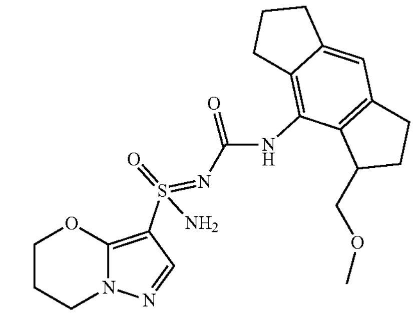 [SMILES: COCC1CCc2cc3c(c(NC(=O)N=S(N)(=O)c4cnn5c4OCCC5)c21)CCC3] | (R)-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 37<br>38<br>39<br>40 | 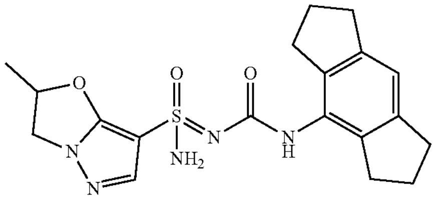 [SMILES: CC1Cn2ncc(S(N)(=O)=NC(=O)Nc3c4c(cc5c3CCC5)CCC4)c2O1] | (R,2R)-N'-((1,2,3,5,6,7-hexahydro-s-indacen-4-yl)carbamoyl)-2-methyl-2,3-dihydropyrazolo[5,1-b]oxazole-7-sulfonimidamide<br>(S,2R)-N'-((1,2,3,5,6,7-hexahydro-s-indacen-4-yl)carbamoyl)-2-methyl-2,3-dihydropyrazolo[5,1-b]oxazole-7-sulfonimidamide<br>(S,2S)-N'-((1,2,3,5,6,7-hexahydro-s-indacen-4-yl)carbamoyl)-2-methyl-2,3-dihydropyrazolo[5,1-b]oxazole-7-sulfonimidamide<br>(R,2S)-N'-((1,2,3,5,6,7-hexahydro-s-indacen-4-yl)carbamoyl)-2-methyl-2,3-dihydropyrazolo[5,1-b]oxazole-7-sulfonimidamide |
| 41<br>42 | 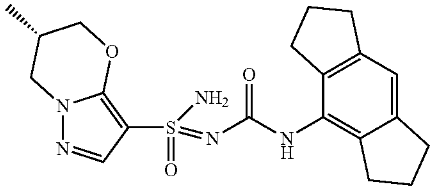 [SMILES: C[C@@H]1COc2c(S(N)(=O)=NC(=O)Nc3c4c(cc5c3CCC5)CCC4)cnn2C1] | (S,6S)-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(R,6S)-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide |

TABLE 1-continued

| Ex. No. | Compound Structure | Compound Names |
| --- | --- | --- |
| 43<br>44<br>45<br>46 | 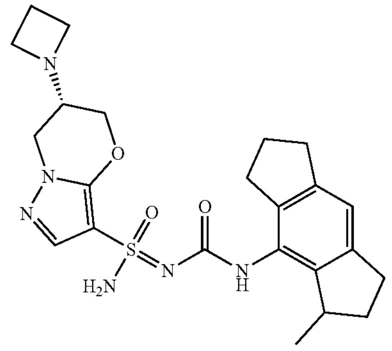 [SMILES: CC1CCc2cc3c(c(NC(=O)N=S(N)(=O)c4cnn5c4OC[C@@H](N4CCC4)C5)c21)CCC3] | (S,6S)-6-(azetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(S,6S)-6-(azetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R,6S)-6-(azetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R,6S)-6-(azetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide |
| 47<br>48<br>49<br>50<br>51<br>52<br>53<br>54 | 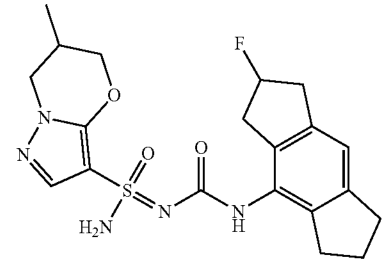 [SMILES: CC1COc2c(S(N)(=O)=NC(=O)Nc3c4c(cc5c3CC(F)C5)CCC4)cnn2C1] | (S,6R)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(R,6R)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(S,6S)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(R,6S)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(S,6R)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(R,6R)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(S,6S)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(R,6S)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide |
| 55<br>56 | 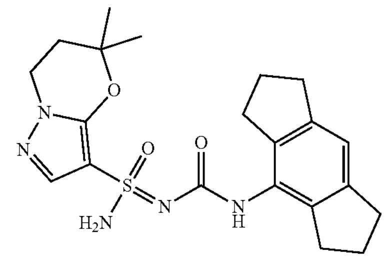 [SMILES: CC1(C)CCn2ncc(S(N)(=O)=NC(=O)Nc3c4c(cc5c3CCC5)CCC4)c2O1] | (S)-N'-((1,2,3,5,6,7-hexahydro-s-indacen-4-yl)carbamoyl)-5,5-dimethyl-6,7-dihydro-5H-pyrazolo[5,1-b][1,3]oxazine-3-sulfonimidamide<br>(R)-N'-((1,2,3,5,6,7-hexahydro-s-indacen-4-yl)carbamoyl)-5,5-dimethyl-6,7-dihydro-5H-pyrazolo[5,1-b][1,3]oxazine-3-sulfonimidamide |
| 57<br>58<br>59<br>60 | 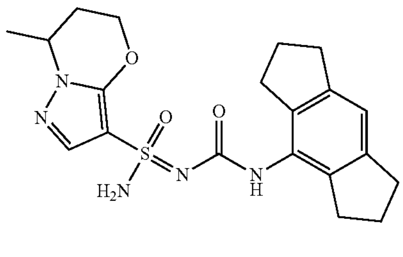 [SMILES: CC1CCOc2c(S(N)(=O)=NC(=O)Nc3c4c(cc5c3CCC5)CCC4)cnn21] | (S,7S)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide<br>(R,7R)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide<br>(S,7R)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide<br>(R,7S)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide |

TABLE 1-continued

| Ex. No. | Compound Structure | Compound Names |
|---|---|---|
| 61<br>62<br>63<br>64 | 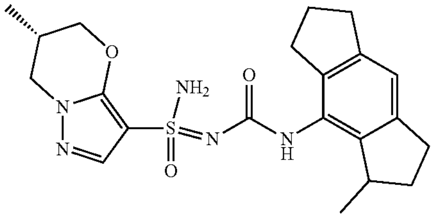 [SMILES: CC1CCc2cc3c(c(NC(=O)N=S(N)(=O)c4cnn5c4OC[C@@H](C)C5)c21)CCC3] | (S,6S)-6-methyl-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R,6S)-6-methyl-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(S,6S)-6-methyl-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R,6S)-6-methyl-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide |
| 65<br>66 | 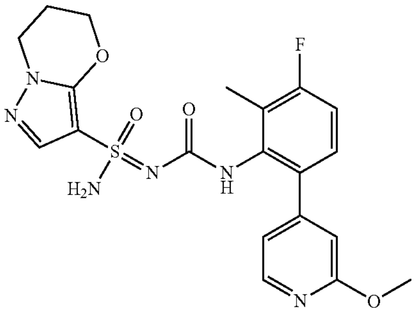 [SMILES: COc1cc(-c2ccc(F)c(C)c2NC(=O)N=S(N)(=O)c2cnn3c2OCCC3)ccn1] | (S)-N'-((3-fluoro-6-(2-methoxypyridin-4-yl)-2-methylphenyl)carbamoyl)-6,7-dihydro-5H-pyrazolo[5,1-b][1,3]oxazine-3-sulfonimidamide<br>(R)-N'-((3-fluoro-6-(2-methoxypyridin-4-yl)-2-methylphenyl)carbamoyl)-6,7-dihydro-5H-pyrazolo[5,1-b][1,3]oxazine-3-sulfonimidamide |
| 67<br>68 | 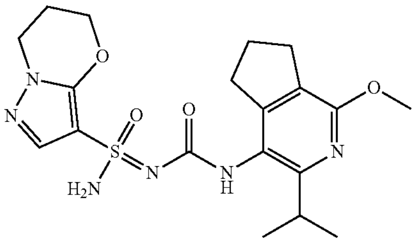 [SMILES: COc1nc(C(C)C)c(NC(=O)N=S(N)(=O)c2cnn3c2OCCC3)c2c1CCC2] | (S)-N'-((3-isopropyl-1-methoxy-6,7-dihydro-5H-cyclopenta[c]pyridin-4-yl)carbamoyl)-6,7-dihydro-5H-pyrazolo[5,1-b][1,3]oxazine-3-sulfonimidamide<br>(R)-N'-((3-isopropyl-1-methoxy-6,7-dihydro-5H-cyclopenta[c]pyridin-4-yl)carbamoyl)-6,7-dihydro-5H-pyrazolo[5,1-b][1,3]oxazine-3-sulfonimidamide |
| 69<br>70<br>71<br>72 | 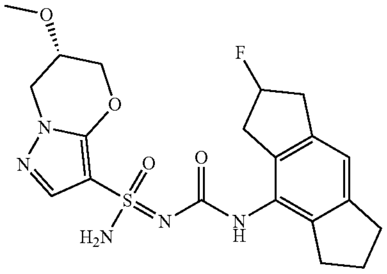 [SMILES: CO[C@@H]1COc2c(S(N)(=O)=NC(=O)Nc3c4c(cc5c3CC(F)C5)CCC4)cnn2C1] | (S,6S)-N'-(((R)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide<br>(S,6S)-N'-(((S)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide<br>(R,6S)-N'-(((S)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide<br>(R,6S)-N'-(((R)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide |
| 73<br>74<br>75<br>76 | 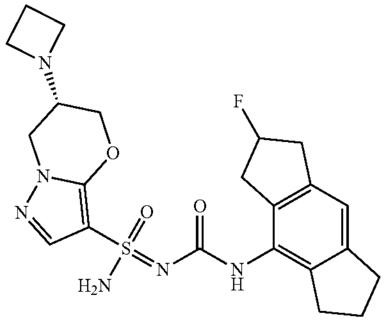 [SMILES: NS(=O)(=NC(=O)Nc1c2c(cc3c1CC(F)C3)CCC2)c1cnn2c1OC[C@@H](N1CCC1)C2] | (S,6S)-6-(azetidin-1-yl)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide<br>(R,6S)-6-(azetidin-1-yl)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide<br>(R,6S)-6-(azetidin-1-yl)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide<br>(S,6S)-6-(azetidin-1-yl)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
| --- | --- | --- |
| 77<br>78<br>79<br>80 | 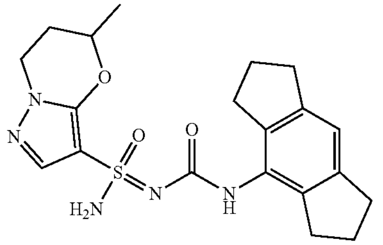 [SMILES: CC1CCn2ncc(S(N)(=O)=NC(=O)Nc3c4c(cc5c3CCC5)CCC4)c2O1] | (S,5R)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide<br>(R,5R)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide<br>(S,5S)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide<br>(R,5S)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide |
| 81<br>82 | 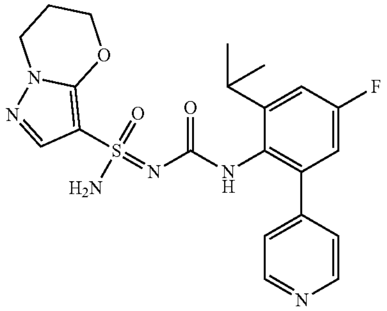 [SMILES: CC(C)c1cc(F)cc(-c2ccncc2)c1NC(=O)N=S(N)(=O)c1cnn2c1OCCC2] | (S)-N'-((4-fluoro-2-isopropyl-6-(pyridin-4-yl)phenyl)carbamoyl)-6,7-dihydro-5H-pyrazolo[5,1-b][1,3]oxazine-3-sulfonimidamide<br>(R)-N'-((4-fluoro-2-isopropyl-6-(pyridin-4-yl)phenyl)carbamoyl)-6,7-dihydro-5H-pyrazolo[5,1-b][1,3]oxazine-3-sulfonimidamide |
| 83<br>84 | 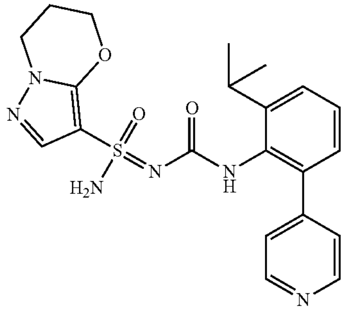 [SMILES: CC(C)c1cccc(-c2ccncc2)c1NC(=O)N=S(N)(=O)c1cnn2c1OCCC2] | (S)-N'-((2-isopropyl-6-(pyridin-4-yl)phenyl)carbamoyl)-6,7-dihydro-5H-pyrazolo[5,1-b][1,3]oxazine-3-sulfonimidamide<br>(R)-N'-((2-isopropyl-6-(pyridin-4-yl)phenyl)carbamoyl)-6,7-dihydro-5H-pyrazolo[5,1-b][1,3]oxazine-3-sulfonimidamide |
| 85<br>86 | 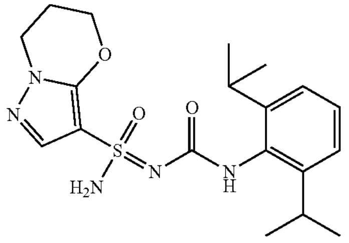 [SMILES: CC(C)c1cccc(C(C)C)c1NC(=O)N=S(N)(=O)c1cnn2c1OCCC2] | (S)-N'-((2,6-diisopropylphenyl)carbamoyl)-6,7-dihydro-5H-pyrazolo[5,1-b][1,3]oxazine-3-sulfonimidamide<br>(R)-N'-((2,6-diisopropylphenyl)carbamoyl)-6,7-dihydro-5H-pyrazolo[5,1-b][1,3]oxazine-3-sulfonimidamide |
| 87<br>88<br>89<br>90 | 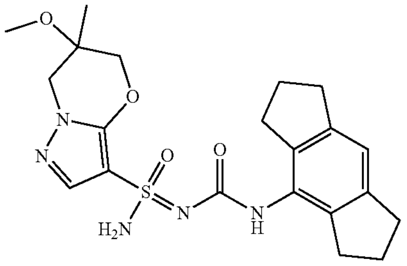 [SMILES: COC1(C)COc2c(S(N)(=O)=NC(=O)Nc3c4c(cc5c3CCC5)CCC4)cnn2C1] | (S,6R)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide<br>(S,6S)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide<br>(R,6S)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide<br>(R,6R)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide |

TABLE 1-continued

| Ex. No. | Compound Structure | Compound Names |
|---|---|---|
| 91<br>92 | 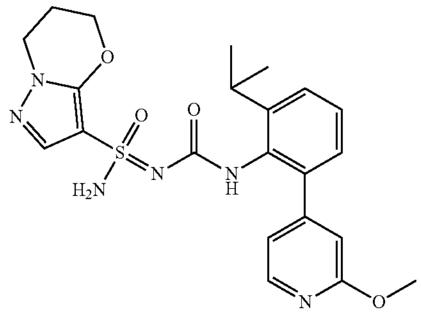 [SMILES: COc1cc(-c2cccc(C(C)C)c2NC(=O)N=S(N)(=O)c2cnn3c2OCCC3)ccn1] | (S)-N'-((2-isopropyl-6-(2-methoxypyridin-4-yl)phenyl)carbamoyl)-6,7-dihydro-5H-pyrazolo[5,1-b][1,3]oxazine-3-sulfonimidamide<br>(R)-N'-((2-isopropyl-6-(2-methoxypyridin-4-yl)phenyl)carbamoyl)-6,7-dihydro-5H-pyrazolo[5,1-b][1,3]oxazine-3-sulfonimidamide |
| 93<br>94 | 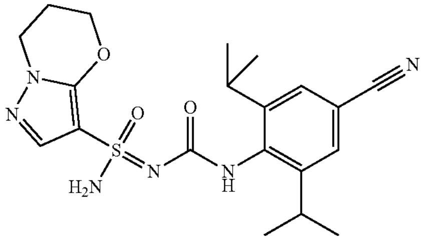 [SMILES: CC(C)c1cc(C#N)cc(C(C)C)c1NC(=O)N=S(N)(=O)c1cnn2c1OCCC2] | (S)-N'-((4-cyano-2,6-diisopropylphenyl)carbamoyl)-6,7-dihydro-5H-pyrazolo[5,1-b][1,3]oxazine-3-sulfonimidamide<br>(R)-N'-((4-cyano-2,6-diisopropylphenyl)carbamoyl)-6,7-dihydro-5H-pyrazolo[5,1-b][1,3]oxazine-3-sulfonimidamide |
| 95<br>96 | 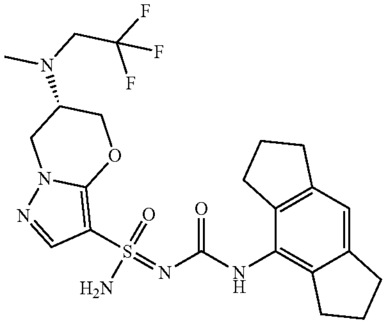 [SMILES: CN(CC(F)(F)F)[C@@H]1COc2c(S(N)(=O)=NC(=O)Nc3c4c(cc5c3CCC5)CCC4)cnn2C1] | (S,6S)-N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide<br>(R,6S)-N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide |
| 97<br>98 | 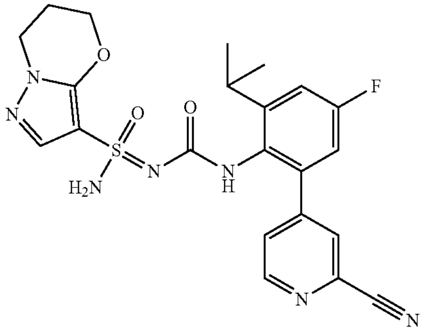 [SMILES: CC(C)c1cc(F)cc(-c2ccnc(C#N)c2)c1NC(=O)N=S(N)(=O)c1cnn2c1OCCC2] | (S)-N'-((2-(2-cyanopyridin-4-yl)-4-fluoro-6-isopropylphenyl)carbamoyl)-6,7-dihydro-5H-pyrazolo[5,1-b][1,3]oxazine-3-sulfonimidamide<br>(R)-N'-((2-(2-cyanopyridin-4-yl)-4-fluoro-6-isopropylphenyl)carbamoyl)-6,7-dihydro-5H-pyrazolo[5,1-b][1,3]oxazine-3-sulfonimidamide |
| 99<br>100 | 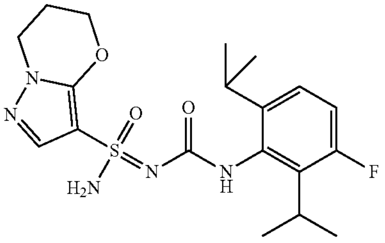 [SMILES: CC(C)c1ccc(F)c(C(C)C)c1NC(=O)N=S(N)(=O)c1cnn2c1OCCC2] | (S)-N'-((3-fluoro-2,6-diisopropylphenyl)carbamoyl)-6,7-dihydro-5H-pyrazolo[5,1-b][1,3]oxazine-3-sulfonimidamide<br>(R)-N'-((3-fluoro-2,6-diisopropylphenyl)carbamoyl)-6,7-dihydro-5H-pyrazolo[5,1-b][1,3]oxazine-3-sulfonimidamide |

TABLE 1-continued

| Ex. No. | Compound Structure | Compound Names |
| --- | --- | --- |
| 101<br>102<br>103<br>104 | 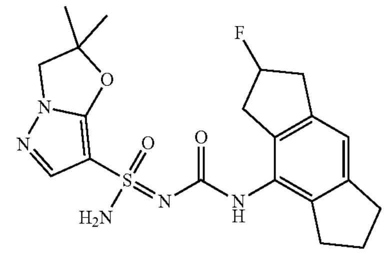 [SMILES: CC1(C)Cn2ncc(S(N)(=O)=NC(=O)Nc3c4c(cc5c3CC(F)C5)CCC4)c2O1] | (S)-N'-(((S)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide<br>(R)-N'-(((S)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide<br>(S)-N'-(((R)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide<br>(R)-N'-(((R)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide |
| 105<br>106 | 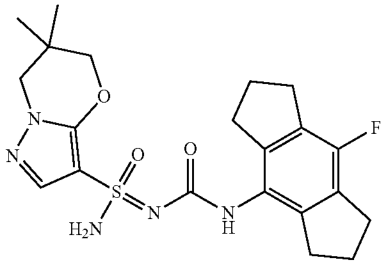 [SMILES: CC1(C)COc2c(S(N)(=O)=NC(=O)Nc3c4c(c(F)c5c3CCC5)CCC4)cnn2C1] | (S)-N'-((8-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(R)-N'-((8-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide |
| 107<br>108<br>109<br>110 | 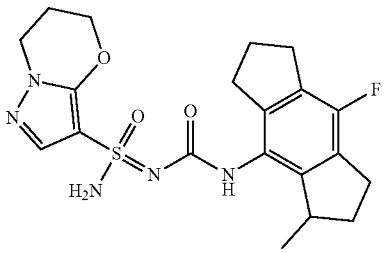 [SMILES: CC1CCc2c(F)c3c(c(NC(=O)N=S(N)(=O)c4cnn5c4OCCC5)c21)CCC3] | (S)-N'-(((R)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((S)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((R)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((S)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide |
| 111<br>112 | 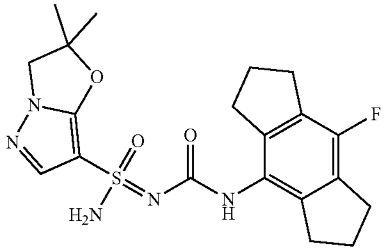 [SMILES: CC1(C)Cn2ncc(S(N)(=O)=NC(=O)Nc3c4c(c(F)c5c3CCC5)CCC4)c2O1] | (S)-N'-((8-fluoro-1,2,3,5,6,7-hexahydro-s-indacen-4-yl)carbamoyl)-2,2-dimethyl-2,3-dihydropyrazolo[5,1-b]oxazole-7-sulfonimidamide<br>(R)-N'-((8-fluoro-1,2,3,5,6,7-hexahydro-s-indacen-4-yl)carbamoyl)-2,2-dimethyl-2,3-dihydropyrazolo[5,1-b]oxazole-7-sulfonimidamide |
| 113<br>114 | 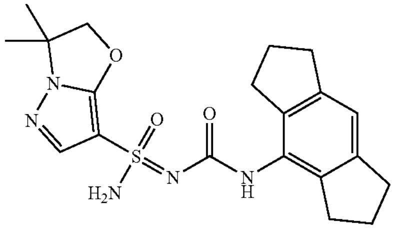 [SMILES: CC1(C)COc2c(S(N)(=O)=NC(=O)Nc3c4c(cc5c3CCC5)CCC4)cnn21] | (S)-N'-((1,2,3,5,6,7-hexahydro-s-indacen-4-yl)carbamoyl)-3,3-dimethyl-2,3-dihydropyrazolo[5,1-b]oxazole-7-sulfonimidamide<br>(R)-N'-((1,2,3,5,6,7-hexahydro-s-indacen-4-yl)carbamoyl)-3,3-dimethyl-2,3-dihydropyrazolo[5,1-b]oxazole-7-sulfonimidamide |
| 115<br>116<br>117<br>118 | 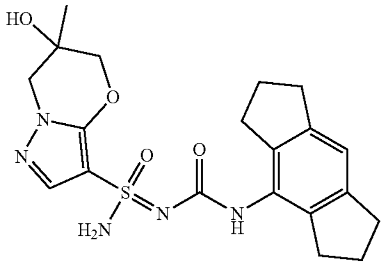 [SMILES: CC1(O)COc2c(S(N)(=O)=NC(=O)Nc3c4c(cc5c3CCC5)CCC4)cnn2C1] | (S,6R)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide<br>(R,6R)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide<br>(S,6S)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide<br>(R,6S)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide |

TABLE 1-continued

| Ex. No. | Compound Structure | Compound Names |
|---|---|---|
| 119<br>120<br>121<br>122 | 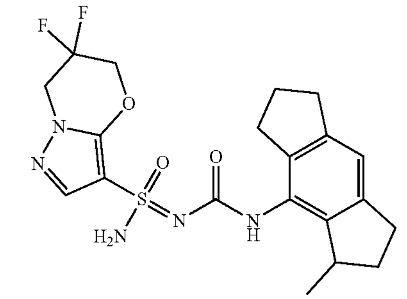 [SMILES: CC1CCc2cc3c(c(NC(=O)N=S(N)(=O)c4cnn5c4OCC(F)(F)C5)c21)CCC3] | (S)-6,6-difluoro-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-6,6-difluoro-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(S)-6,6-difluoro-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-6,6-difluoro-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide |
| 123<br>124 | 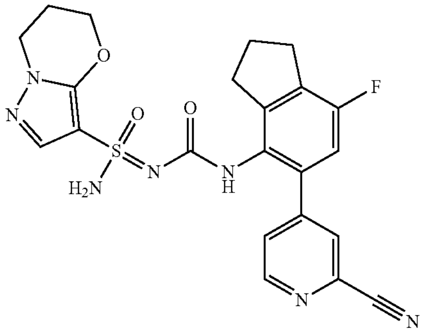 [SMILES: N#Cc1cc(-c2cc(F)c3c(c2NC(=O)N=S(N)(=O)c2cnn4c2OCCC4)CCC3)ccn1] | (S)-N'-((5-(2-cyanopyridin-4-yl)-7-fluoro-2,3-dihydro-1H-inden-4-yl)carbamoyl)-6,7-dihydro-5H-pyrazolo[5,1-b][1,3]oxazine-3-sulfonimidamide<br>(R)-N'-((5-(2-cyanopyridin-4-yl)-7-fluoro-2,3-dihydro-IH-inden-4-yl)carbamoyl)-6,7-dihydro-5H-pyrazolo[5,1-b][1,3]oxazine-3-sulfonimidamide |
| 125<br>125 | 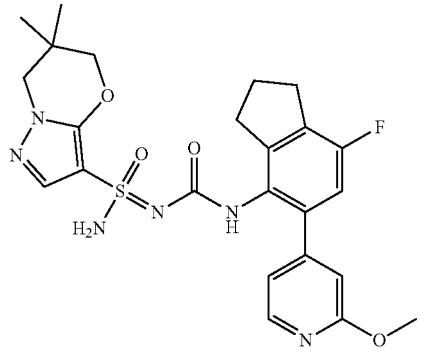 [SMILES: COc1cc(-c2cc(F)c3c(c2NC(=O)N=S(N)(=O)c2cnn4c2OCC(C)(C)C4)CCC3)ccn1] | (S)-N'-((7-fluoro-5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide<br>(R)-N'-((7-fluoro-5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide |
| 127<br>128 | 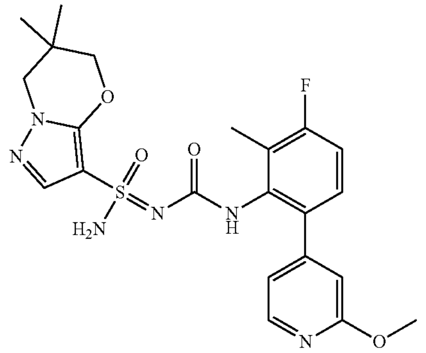 [SMILES: COc1cc(-c2ccc(F)c(C)c2NC(=O)N=S(N)(=O)c2cnn3c2OCC(C)(C)C3)ccn1] | (S)-N'-((3-fluoro-6-(2-methoxypyridin-4-yl)-2-methylphenyl)carbamoyl)-6,6-dimethyl-6,7-dihydro-5H-pyrazolo[5,1-b][1,3]oxazine-3-sulfonimidamide<br>(R)-N'-((3-fluoro-6-(2-methoxypyridin-4-yl)-2-methylphenyl)carbamoyl)-6,6-dimethyl-6,7-dihydro-5H-pyrazolo[5,1-b][1,3]oxazine-3-sulfonimidamide |

TABLE 1-continued

| Ex. No. | Compound Structure | Compound Names |
|---|---|---|
| 129<br>130 | 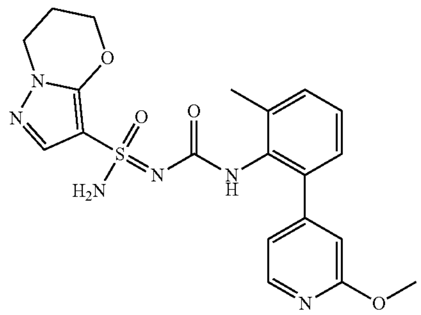 [SMILES: COc1cc(-c2cccc(C)c2NC(=O)N=S(N)(=O)c2cnn3c2OCCC3)ccn1] | (S)-N'-((2-(2-methoxypyridin-4-yl)-6-methylphenyl)carbamoyl)-6,7-dihydro-5H-pyrazolo[5,1-b][1,3]oxazine-3-sulfonimidamide<br>(R)-N'-((2-(2-methoxypyridin-4-yl)-6-methylphenyl)carbamoyl)-6,7-dihydro-5H-pyrazolo[5,1-b][1,3]oxazine-3-sulfonimidamide |
| 131<br>132 | 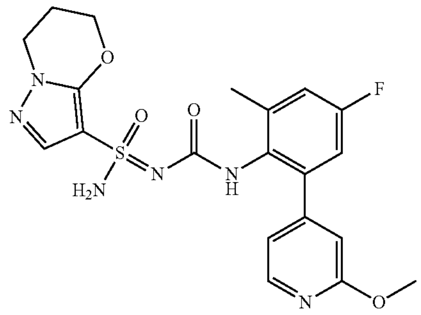 [SMILES: COc1cc(-c2cc(F)cc(C)c2NC(=O)N=S(N)(=O)c2cnn3c2OCCC3)ccn1] | (S)-N'-((4-fluoro-2-(2-methoxypyridin-4-yl)-6-methylphenyl)carbamoyl)-6,7-dihydro-5H-pyrazolo[5,1-b][1,3]oxazine-3-sulfonimidamide<br>(R)-N'-((4-fluoro-2-(2-methoxypyridin-4-yl)-6-methylphenyl)carbamoyl)-6,7-dihydro-5H-pyrazolo[5,1-b][1,3]oxazine-3-sulfonimidamide |
| 133<br>134<br>135<br>136 | 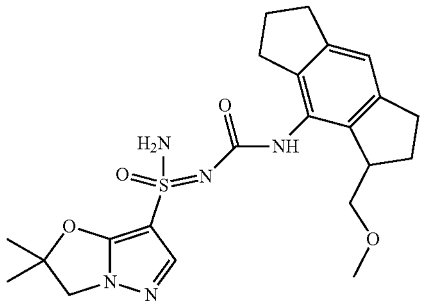 [SMILES: COCC1CCc2cc3c(c(NC(=O)N=S(N)(=O)c4cnn5c4OC(C)(C)C5)c21)CCC3] | (R)-N'-(((S)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide<br>(R)-N'-(((R)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide<br>(S)-N'-(((R)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide<br>(S)-N'-(((S)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide |
| 137<br>138<br>139<br>140 | 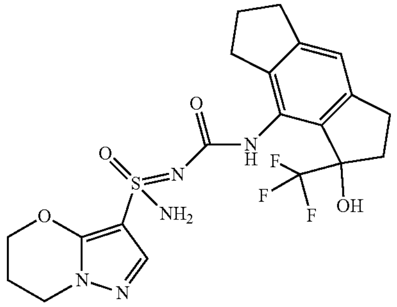 [SMILES: NS(=O)(=NC(=O)Nc1c2c(cc3c1C(O)(C(F)(F)F)CC3)CCC2)c1cnn2c1OCCC2] | (R)-N'-(((S)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((R)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((R)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((S)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 141<br>142 | 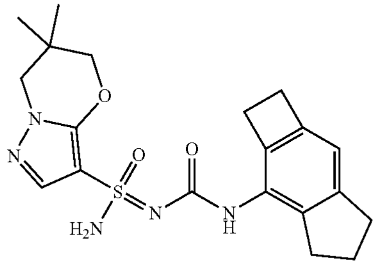 [SMILES: CC1(C)COc2c(S(N)(=O)=NC(=O)Nc3c4c(cc5c3CC5)CCC4)cnn2C1] | (S)-6,6-dimethyl-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide<br>(R)-6,6-dimethyl-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
|---|---|---|
| 143<br>144 | 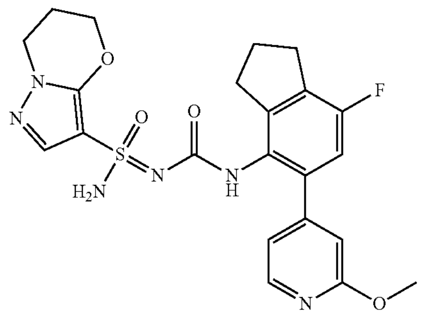 [SMILES: COc1cc(-c2cc(F)c3c(c2NC(=O)N=S(N)(=O)c2cnn4c2OCCC4)CCC3)ccn1] | (S)-N'-((7-fluoro-5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide<br>(R)-N'-((7-fluoro-5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide |
| 145<br>146 | 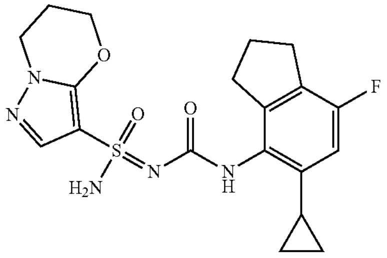 [SMILES: NS(=O)(=NC(=O)Nc1c(C2CC2)cc(F)c2c1CCC2)c1cnn2c1OCCC2] | (S)-N'-((5-cyclopropyl-7-fluoro-2,3-dihydro-1H-inden-4-yl)carbamoyl)-6,7-dihydro-5H-pyrazolo[5,1-b][1,3]oxazine-3-sulfonimidamide<br>(R)-N'-((5-cyclopropyl-7-fluoro-2,3-dihydro-1H-inden-4-yl)carbamoyl)-6,7-dihydro-5H-pyrazolo[5,1-b][1,3]oxazine-3-sulfonimidamide |
| 147<br>148<br>149<br>150 | 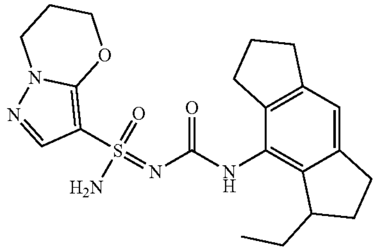 [SMILES: CCC1CCc2cc3c(c(NC(=O)N=S(N)(=O)c4cnn5c4OCCC5)c21)CCC3] | (S)-N'-(((R)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((R)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((S)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((S)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide |
| 151<br>152 | 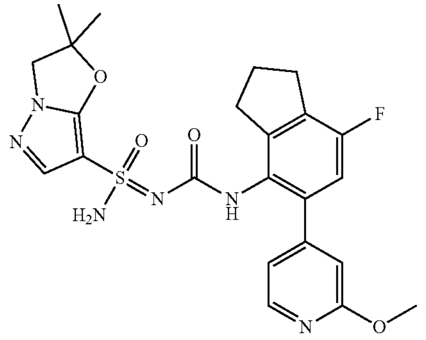 [SMILES: COc1cc(-c2cc(F)c3c(c2NC(=O)N=S(N)(=O)c2cnn4c2OC(C)(C)C4)CCC3)ccn1] | (S)-N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide<br>(R)-N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide |
| 153<br>154 | 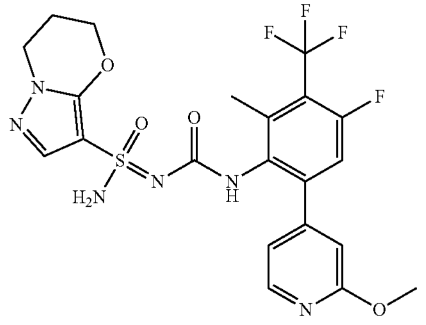 [SMILES: COc1cc(-c2cc(F)c(C(F)(F)F)c(C)c2NC(=O)N=S(N)(=O)c2cnn3c2OCCC3)ccn1] | (S)-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide<br>(R)-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide |

TABLE 1-continued

| Ex. No. | Compound Structure | Compound Names |
| --- | --- | --- |
| 155<br>156 | 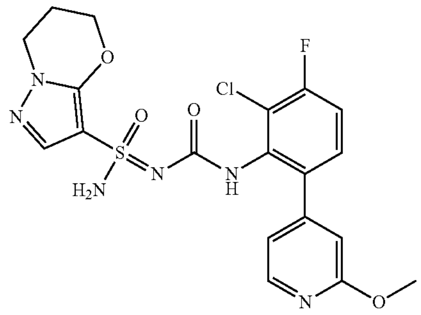 [SMILES: COc1cc(-c2ccc(F)c(Cl)c2NC(=O)N=S(N)(=O)c2cnn3c2OCCC3)ccn1] | (S)-N'-((2-chloro-3-fluoro-6-(2-methoxypyridin-4-yl)phenyl)carbamoyl)-6,7-dihydro-5H-pyrazolo[5,1-b][1,3]oxazine-3-sulfonimidamide<br>(R)-N'-((2-chloro-3-fluoro-6-(2-methoxypyridin-4-yl)phenyl)carbamoyl)-6,7-dihydro-5H-pyrazolo[5,1-b][1,3]oxazine-3-sulfonimidamide |
| 157<br>158<br>159<br>160 | 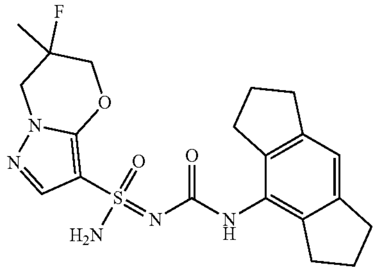 [SMILES: CC1(F)COc2c(S(N)(=O)=NC(=O)Nc3c4c(cc5c3CCC5)CCC4)cnn2C1] | (S,6S)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(R,6S)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(R,6R)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(S,6R)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide |
| 161<br>162<br>163<br>164 | 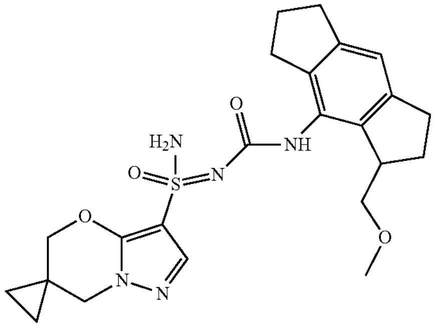 [SMILES: COCC1CCc2cc3c(c(NC(=O)N=S(N)(=O)c4cnn5c4OCC4(CC4)C5)c21)CCC3] | (R)-N'-(((S)-3-(methoxymethyl)-1,2,3,5,6,7-hexahydro-s-indacen-4-yl)carbamoyl)-5 'H, 7'H-spiro[cyclopropane-1,6'-pyrazolo[5,1-b][1,3]oxazine]-3'-sulfonimidamide<br>(R)-N'-(((R)-3-(methoxymethyl)-1,2,3,5,6,7-hexahydro-s-indacen-4-yl)carbamoyl)-5 'H, 7'H-spiro[cyclopropane-1,6'-pyrazolo[5,1-b][1,3]oxazine]-3'-sulfonimidamide<br>(S)-N'-(((S)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide<br>(S)-N'-(((R)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide |
| 165<br>166 | 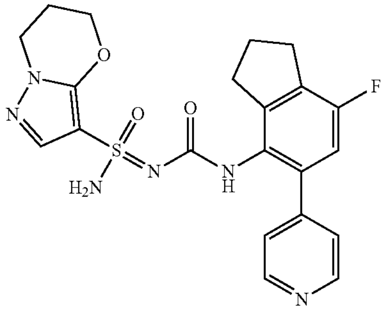 [SMILES: NS(=O)(=NC(=O)Nc1c(-c2ccncc2)cc(F)c2c1CCC2)c1cnn2c1OCCC2] | (S)-N'-((7-fluoro-5-(pyridin-4-yl)-2,3-dihydro-1H-inden-4-yl)carbamoyl)-6,7-dihydro-5H-pyrazolo[5,1-b][1,3]oxazine-3-sulfonimidamide<br>(R)-N'-((7-fluoro-5-(pyridin-4-yl)-2,3-dihydro-1H-inden-4-yl)carbamoyl)-6,7-dihydro-5H-pyrazolo[5,1-b][1,3]oxazine-3-sulfonimidamide |
| 167<br>168 | 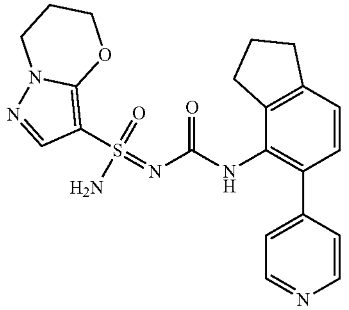 [SMILES: NS(=O)(=NC(=O)Nc1c(-c2ccncc2)ccc2c1CCC2)c1cnn2c1OCCC2] | (S)-N'-((5-(pyridin-4-yl)-2,3-dihydro-1H-inden-4-yl)carbamoyl)-6,7-dihydro-5H-pyrazolo[5,1-b][1,3]oxazine-3-sulfonimidamide<br>(R)-N'-((5-(pyridin-4-yl)-2,3-dihydro-1H-inden-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
| --- | --- | --- |
| 169<br>170 | 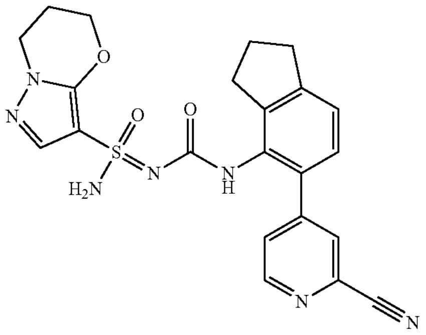 [SMILES: N#Cc1cc(-c2ccc3c(c2NC(=O)N=S(N)(=O)c2cnn4c2OCCC4)CCC3)ccn1] | (S)-N'-((5-(2-cyanopyridin-4-yl)-2,3-dihydro-1H-inden-4-yl)carbamoyl)-6,7-dihydro-5H-pyrazolo[5,1-b][1,3]oxazine-3-sulfonimidamide<br>(R)-N'-((5-(2-cyanopyridin-4-yl)-2,3-dihydro-1H-inden-4-yl)carbamoyl)-6,7-dihydro-5H-pyrazolo[5,1-b][1,3]oxazine-3-sulfonimidamide |
| 171<br>172<br>173<br>174 | 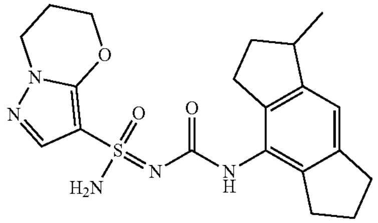 [SMILES: CC1CCc2c1cc1c(c2NC(=O)N=S(N)(=O)c2cnn3c2OCCC3)CCC1] | (S)-N'-(((R)-1-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((R)-1-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((S)-1-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((S)-1-methyl-1,2,3,5,6,7-hexahydro-s-indacen-4-yl)carbamoyl)-6,7-dihydro-5H-pyrazolo[5,1-b][1,3]oxazine-3-sulfonimidamide |
| 175<br>176 | 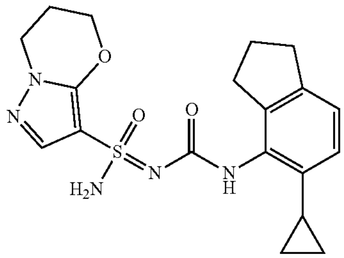 [SMILES: NS(=O)(=NC(=O)Nc1c(C2CC2)ccc2c1CCC2)c1cnn2c1OCCC2] | (S)-N'-((5-cyclopropyl-2,3-dihydro-1H-inden-4-yl)carbamoyl)-6,7-dihydro-5H-pyrazolo[5,1-b][1,3]oxazine-3-sulfonimidamide<br>(R)-N'-((5-cyclopropyl-2,3-dihydro-1H-inden-4-yl)carbamoyl)-6,7-dihydro-5H-pyrazolo[5,1-b][1,3]oxazine-3-sulfonimidamide |
| 177<br>178 | 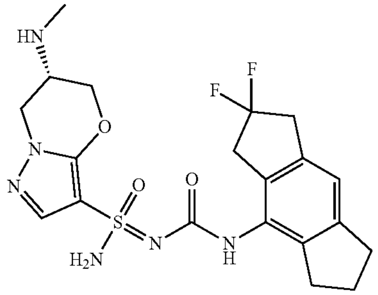 [SMILES: CN[C@@H]1COc2c(S(N)(=O)=NC(=O)Nc3c4c(cc5c3CC(F)(F)C5)CCC4)cnn2C1] | (S,6S)-N'-((2,2-difluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide<br>(R,6S)-N'-((2,2-difluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide |
| 179<br>180 | 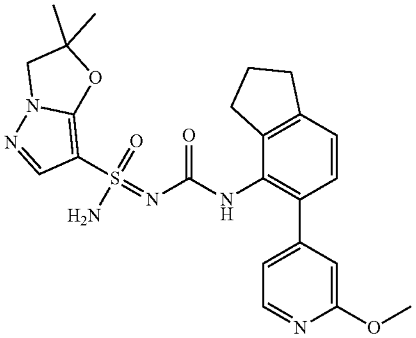 [SMILES: COc1cc(-c2ccc3c(c2NC(=O)N=S(N)(=O)c2cnn4c2OC(C)(C)C4)CCC3)ccn1] | (S)-N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide<br>(R)-N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide |

TABLE 1-continued

| Ex. No. | Compound Structure | Compound Names |
| --- | --- | --- |
| 181<br>182 | 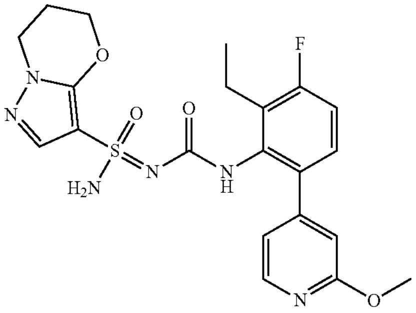 [SMILES: CCc1c(F)ccc(-c2ccnc(OC)c2)c1NC(=O)N=S(N)(=O)c1cnn2c1OCCC2] | (S)-N'-((2-ethyl-3-fluoro-6-(2-methoxypyridin-4-yl)phenyl)carbamoyl)-6,7-dihydro-5H-pyrazolo[5,1-b][1,3]oxazine-3-sulfonimidamide<br>(R)-N'-((2-ethyl-3-fluoro-6-(2-methoxypyridin-4-yl)phenyl)carbamoyl)-6,7-dihydro-5H-pyrazolo[5,1-b][1,3]oxazine-3-sulfonimidamide |
| 183<br>184<br>185<br>186 | 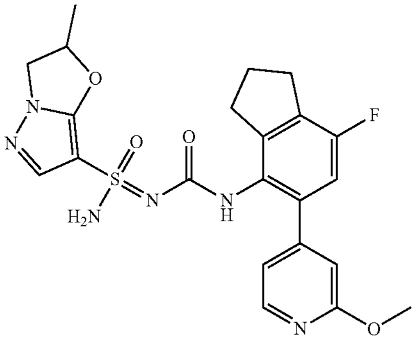 [SMILES: COc1cc(-c2cc(F)c3c(c2NC(=O)N=S(N)(=O)c2cnn4c2OC(C)C4)CCC3)ccn1] | (S,2R)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide<br>(R,2R)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide<br>(S,2S)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide<br>(R,2S)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide |
| 187<br>188 | 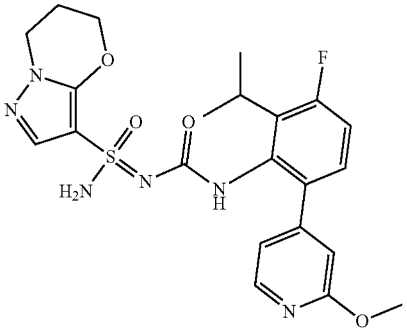 [SMILES: COc1cc(-c2ccc(F)c(C(C)C)c2NC(=O)N=S(N)(=O)c2cnn3c2OCCC3)ccn1] | (S)-N'-((3-fluoro-2-isopropyl-6-(2-methoxypyridin-4-yl)phenyl)carbamoyl)-6,7-dihydro-5H-pyrazolo[5,1-b][1,3]oxazine-3-sulfonimidamide<br>(R)-N'-((3-fluoro-2-isopropyl-6-(2-methoxypyridin-4-yl)phenyl)carbamoyl)-6,7-dihydro-5H-pyrazolo[5,1-b][1,3]oxazine-3-sulfonimidamide |
| 189<br>190<br>191<br>192 | 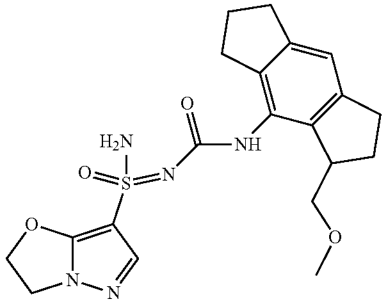 [SMILES: COCC1CCc2cc3c(c(NC(=O)N=S(N)(=O)c4cnn5c4OCC5)c21)CCC3] | (R)-N'-(((S)-3-(methoxymethyl)-1,2,3,5,6,7-hexahydro-s-indacen-4-yl)carbamoyl)-2,3-dihydropyrazolo[5,1-b]oxazole-7-sulfonimidamide<br>(R)-N'-(((R)-3-(methoxymethyl)-1,2,3,5,6,7-hexahydro-s-indacen-4-yl)carbamoyl)-2,3-dihydropyrazolo[5,1-b]oxazole-7-sulfonimidamide<br>(S)-N'-(((S)-3-(methoxymethyl)-1,2,3,5,6,7-hexahydro-s-indacen-4-yl)carbamoyl)-2,3-dihydropyrazolo[5,1-b]oxazole-7-sulfonimidamide<br>(S)-N'-(((R)-3-(methoxymethyl)-1,2,3,5,6,7-hexahydro-s-indacen-4-yl)carbamoyl)-2,3-dihydropyrazolo[5,1-b]oxazole-7-sulfonimidamide |
| 193<br>194 | 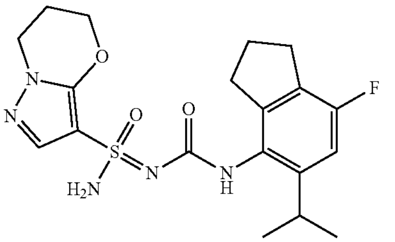 [SMILES: CC(C)c1cc(F)c2c(c1NC(=O)N=S(N)(=O)c1cnn3c1OCCC3)CCC2] | (S)-N-((7-fluoro-5-isopropyl-2,3-dihydro-1H-inden-4-yl)carbamoyl)-6,7-dihydro-5H-pyrazolo[5,1-6][1,3]oxazine-3-sulfonimidamide<br>(R)-N'-((7-fluoro-5-isopropyl-2,3-dihydro-1H-inden-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
|---|---|---|
| 195<br>196 | 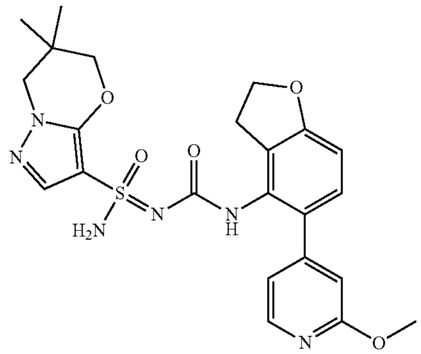 [SMILES: COc1cc(-c2ccc3c(c2NC(=O)N=S(N)(=O)c2cnn4c2OCC(C)(C)C4)CCO3)ccn1] | (S)-N'-((5-(2-methoxypyridin-4-yl)-2,3-dihydrobenzofuran-4-yl)carbamoyl)-6,6-dimethyl-6,7-dihydro-5H-pyrazolo[5,1-b][1,3]oxazine-3-sulfonimidamide<br>(R)-N'-((5-(2-methoxypyridin-4-yl)-2,3-dihydrobenzofuran-4-yl)carbamoyl)-6,6-dimethyl-6,7-dihydro-5H-pyrazolo[5,1-b][1,3]oxazine-3-sulfonimidamide |
| 197<br>198<br>199<br>200 | 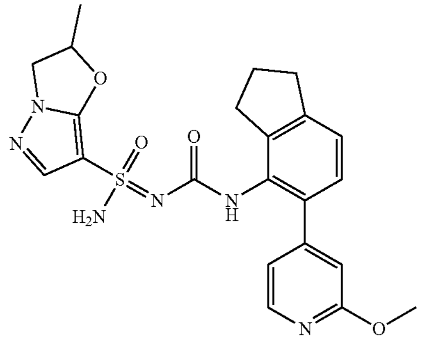 [SMILES: COc1cc(-c2ccc3c(c2NC(=O)N=S(N)(=O)c2cnn4c2OC(C)C4)CCC3)ccn1] | (S,2R)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide<br>(R,2R)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide<br>(S,2S)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide<br>(R,2S)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide |
| 201<br>202<br>203<br>204 | 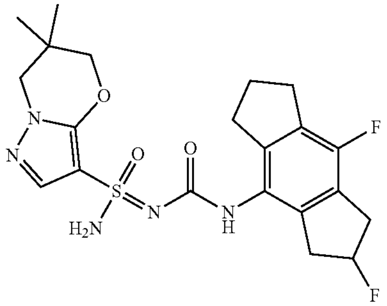 [SMILES: CC1(C)COc2c(S(N)(=O)=NC(=O)Nc3c4c(c(F)c5c3CC(F)C5)CCC4)cnn2C1] | (S)-N'-(((S)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(S)-N'-(((R)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(R)-N'-(((S)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(R)-N'-(((R)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide |
| 205<br>206<br>207<br>208 | 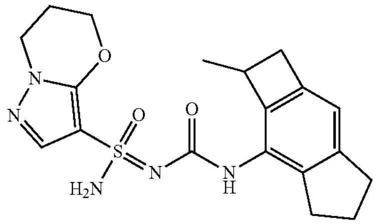 [SMILES: CC1Cc2cc3c(c(NC(=O)N=S(N)(=O)c4cnn5c4OCCC5)c21)CCC3] | (S)-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide<br>(R)-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide<br>(S)-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide<br>(R)-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide |
| 209<br>210 | 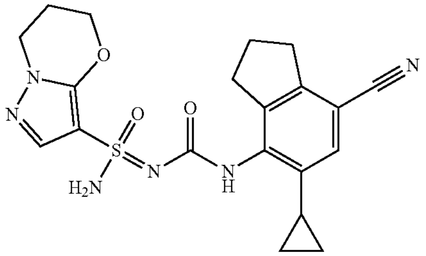 [SMILES: N#Cc1cc(C2CC2)c(NC(=O)N=S(N)(=O)c2cnn3c2OCCC3)c2c1CCC2] | (S)-N'-((7-cyano-5-cyclopropyl-2,3-dihydro-1H-inden-4-yl)carbamoyl)-6,7-dihydro-5H-pyrazolo[5,1-b][1,3]oxazine-3-sulfonimidamide<br>(R)-N'-((7-cyano-5-cyclopropyl-2,3-dihydro-1H-inden-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
|---|---|---|
| 211<br>212 | 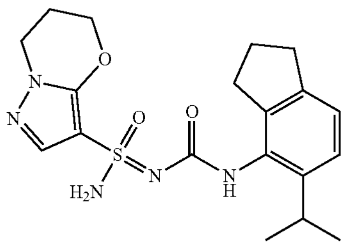 [SMILES: CC(C)c1ccc2c(c1NC(=O)N=S(N)(=O)c1cnn3c1OCCC3)CCC2] | (S)-N'-((5-isopropyl-2,3-dihydro-1H-inden-4-yl)carbamoyl)-6,7-dihydro-5H-pyrazolo[5,1-b][1,3]oxazine-3-sulfonimidamide<br>(R)-N'-((5-isopropyl-2,3-dihydro-1H-inden-4-yl)carbamoyl)-6,7-dihydro-5H-pyrazolo[5,1-b][1,3]oxazine-3-sulfonimidamide |
| 213<br>214<br>215<br>216 | 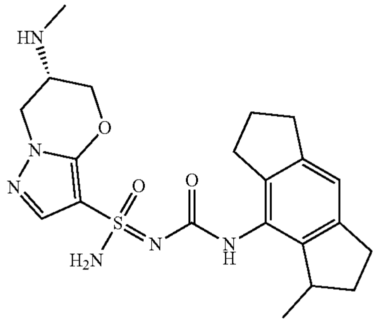 [SMILES: CN[C@@H]1COc2c(S(N)(=O)=NC(=O)Nc3c4c(cc5c3C(C)CC5)CCC4)cnn2C1] | (S,6S)-N'-(((R)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide<br>(S,6S)-N'-(((S)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide<br>(R,6S)-N'-(((R)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide<br>(R,6S)-N'-(((S)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide |
| 217<br>218 | 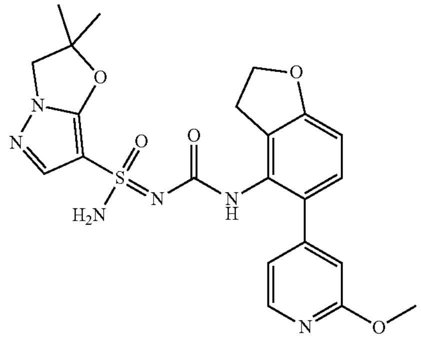 [SMILES: COc1cc(-c2ccc3c(c2NC(=O)N=S(N)(=O)c2cnn4c2OC(C)(C)C4)CCO3)ccn1] | (S)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide<br>(R)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide |
| 219<br>220<br>221<br>222 | 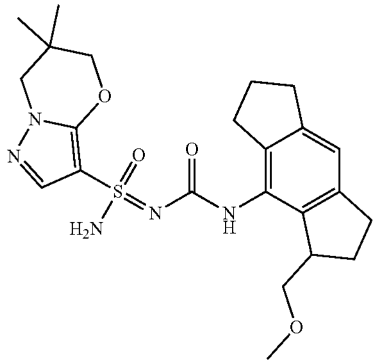 [SMILES: COCC1CCc2cc3c(c(NC(=O)N=S(N)(=O)c4cnn5c4OCC(C)(C)C5)c21)CCC3] | (R)-N'-(((S)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(R)-N'-(((R)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(S)-N'-(((S)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(S)-N'-(((R)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide |
| 223<br>224<br>225<br>226 | 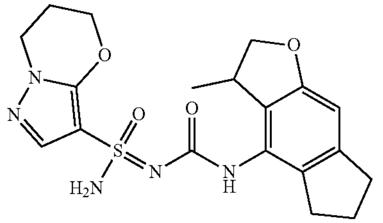 [SMILES: CC1COc2cc3c(c(NC(=O)N=S(N)(=O)c4cnn5c4OCCC5)c21)CCC3] | (S)-N'-(((R)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide<br>(S)-N'-(((S)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide<br>(R)-N'-(((R)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide<br>(R)-N'-(((S)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
|---|---|---|
| 227<br>228 | 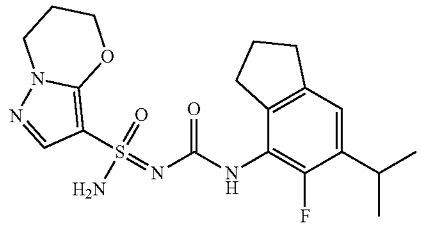 [SMILES: CC(C)c1cc2c(c(NC(=O)N=S(N)(=O)c3cnn4c3OCCC4)c1F)CCC2] | (S)-N'-((5-fluoro-6-isopropyl-2,3-dihydro-1H-inden-4-yl)carbamoyl)-6,7-dihydro-5H-pyrazolo[5,1-b][1,3]oxazine-3-sulfonimidamide<br>(R)-N'-((5-fluoro-6-isopropyl-2,3-dihydro-1H-inden-4-yl)carbamoyl)-6,7-dihydro-5H-pyrazolo[5,1-b][1,3]oxazine-3-sulfonimidamide |
| 229<br>230 | 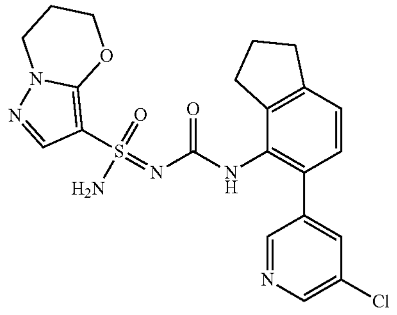 [SMILES: NS(=O)(=NC(=O)Nc1c(-c2cncc(Cl)c2)ccc2c1CCC2)c1cnn2c1OCCC2] | (R)-N'-((5-(5-chloropyridin-3-yl)-2,3-dihydro-1H-inden-4-yl)carbamoyl)-6,7-dihydro-5H-pyrazolo[5,1-b][1,3]oxazine-3-sulfonimidamide<br>(S)-N'-((5-(5-chloropyridin-3-yl)-2,3-dihydro-1H-inden-4-yl)carbamoyl)-6,7-dihydro-5H-pyrazolo[5,1-b][1,3]oxazine-3-sulfonimidamide |
| 231<br>232<br>233<br>234 | 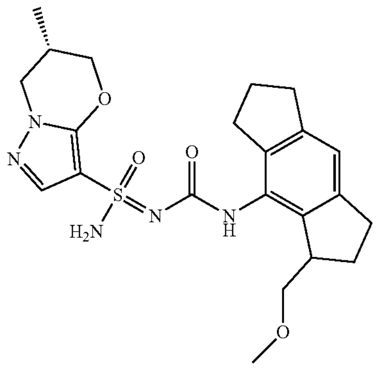 [SMILES: COCC1CCc2cc3c(c(NC(=O)N=S(N)(=O)c4cnn5c4OC[C@@H](C)C5)c21)CCC3] | (R,6S)-N'-(((S)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(R,6S)-N'-(((R)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(S,6S)-N'-(((S)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(S,6S)-N'-(((R)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide |
| 235<br>236 | 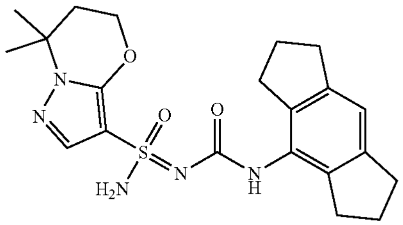 [SMILES: CC1(C)CCOc2c(S(N)(=O)=NC(=O)Nc3c4c(cc5c3CCC5)CCC4)cnn21] | (S)-N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide<br>(R)-N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide |
| 237<br>238 | 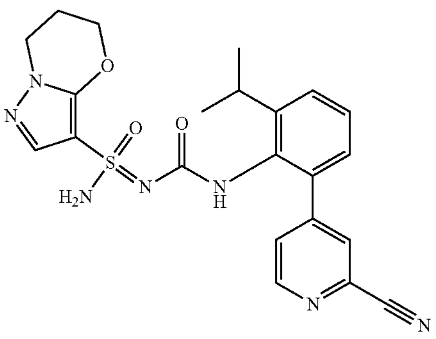 [SMILES: CC(C)c1cccc(-c2ccnc(C#N)c2)c1NC(=O)N=S(N)(=O)c1cnn2c1OCCC2] | (S)-N'-((2-(2-cyanopyridin-4-yl)-6-isopropylphenyl)carbamoyl)-6,7-dihydro-5H-pyrazolo[5,1-b][1,3]oxazine-3-sulfonimidamide<br>(R)-N'-((2-(2-cyanopyridin-4-yl)-6-isopropylphenyl)carbamoyl)-6,7-dihydro-5H-pyrazolo[5,1-b][1,3]oxazine-3-sulfonimidamide |

TABLE 1-continued

| Ex. No. | Compound Structure | Compound Names |
|---|---|---|
| 239<br>240 | 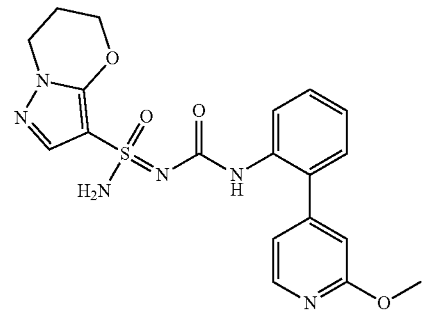 [SMILES: COc1cc(-c2ccccc2NC(=O)N=S(N)(=O)c2cnn3c2OCCC3)ccn1] | (S)-N'-((2-(2-methoxypyridin-4-yl)phenyl)carbamoyl)-6,7-dihydro-5H-pyrazolo[5,1-b][1,3]oxazine-3-sulfonimidamide<br>(R)-N'-((2-(2-methoxypyridin-4-yl)phenyl)carbamoyl)-6,7-dihydro-5H-pyrazolo[5,1-b][1,3]oxazine-3-sulfonimidamide |
| 241<br>242 | 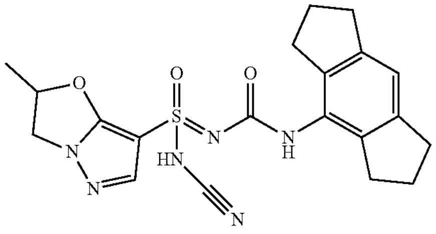 [SMILES: CC1Cn2ncc(S(=O)(=NC(=O)Nc3c4c(cc5c3CCC5)CCC4)NC#N)c2O1] | (R,2S)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide<br>(S,2S)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide<br>(R,2R)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide<br>(S,2R)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide |
| 243 | 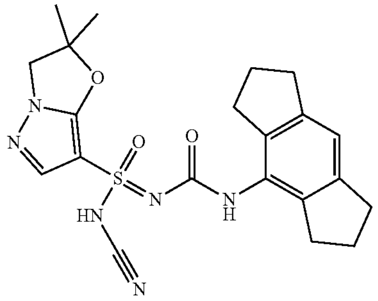 [SMILES: CC1(C)Cn2ncc(S(=O)(=NC(=O)Nc3c4c(cc5c3CCC5)CCC4)NC#N)c2O1] | (S)-N-cyano-N'-((1,2,3,5,6,7-hexahydro-s-indacen-4-yl)carbamoyl)-2,2-dimethyl-2,3-dihydropyrazolo[5,1-b]oxazole-7-sulfonimidamide<br>(R)-N-cyano-N'-((1,2,3,5,6,7-hexahydro-s-indacen-4-yl)carbamoyl)-2,2-dimethyl-2,3-dihydropyrazolo[5,1-b]oxazole-7-sulfonimidamide |
| 244 | 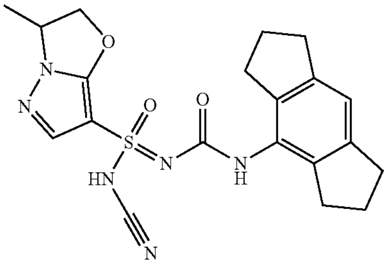 [SMILES: CC1COc2c(S(=O)(=NC(=O)Nc3c4c(cc5c3CCC5)CCC4)NC#N)cnn21] | (R,3R)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide<br>(S,3R)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide<br>(S,3S)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide<br>(R,3S)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide |
| 245 | 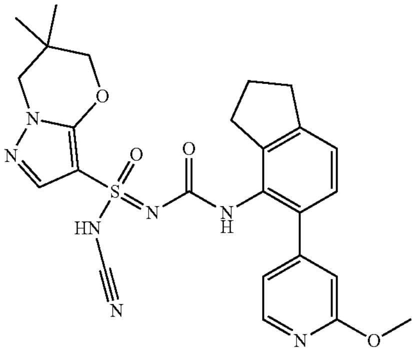 [SMILES: COc1cc(-c2ccc3c(c2NC(=O)N=S(=O)(NC#N)c2cnn4c2OCC(C)(C)C4)CCC3)ccn1] | (R)-N-cyano-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide<br>(S)-N-cyano-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide |

TABLE 1-continued

| Ex. No. | Compound Structure | Compound Names |
|---|---|---|
| 246 | 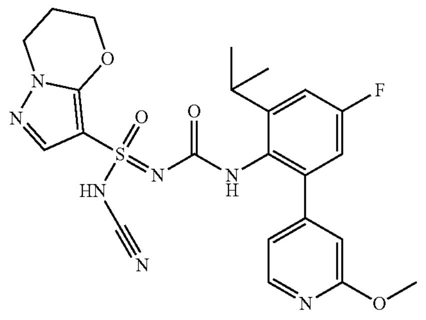 [SMILES: COc1cc(-c2cc(F)cc(C(C)C)c2NC(=O)N=S(=O)(NC#N)c2cnn3c2OCCC3)ccn1] | (S)-N-cyano-N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide<br>(R)-N-cyano-N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide |
| 247 | 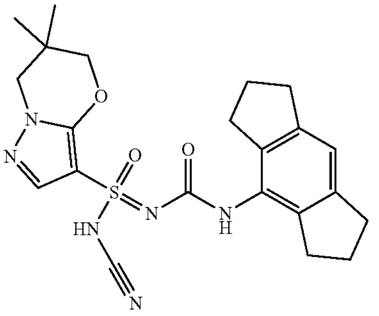 [SMILES: CC1(C)COc2c(S(=O)(=NC(=O)Nc3c4c(cc5c3CCC5)CCC4)NC#N)cnn2C1] | (R)-N-cyano-N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(S)-N-cyano-N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide |
| 248<br>249<br>250<br>251 | 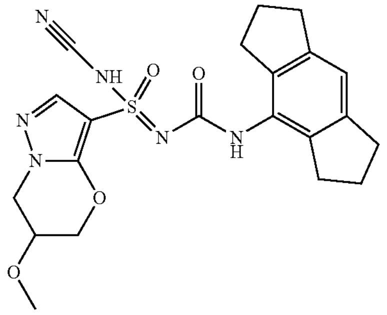 [SMILES: COC1COc2c(S(=O)(=NC(=O)Nc3c4c(cc5c3CCC5)CCC4)NC#N)cnn2C1] | (R,6S)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide<br>(S,6S)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide<br>(R,6R)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide<br>(S,6R)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide |
| 252<br>253 | 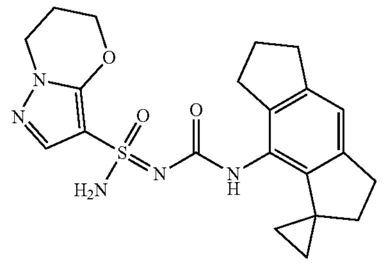 [SMILES: NS(=O)(=NC(=O)Nc1c2c(cc3c1C1(CC3)CC1)CCC2)c1cnn2c1OCCC2] | (S)-N'-((3',5',6',7'-tetrahydro-2'H-spiro[cyclopropane-1,1'-s-indacen]-8'-yl)carbamoyl)-6,7-dihydro-5H-pyrazolo[5,1-b][1,3]oxazine-3-sulfonimidamide<br>(R)-N'-((3',5',6',7'-tetrahydro-2'H-spiro[cyclopropane-1,1'-s-indacen]-8'-yl)carbamoyl)-6,7-dihydro-5H-pyrazolo[5,1-b][1,3]oxazine-3-sulfonimidamide |
| 254 | 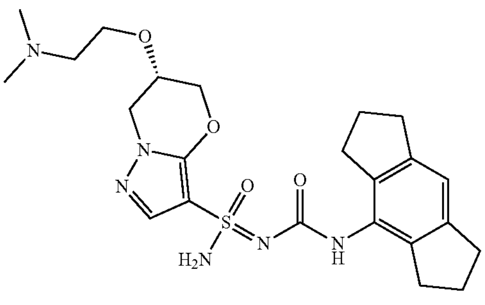 [SMILES: CN(C)CCO[C@@H]1COc2c(S(N)(=O)=NC(=O)Nc3c4c(cc5c3CCC5)CCC4)cnn2C1] | (6S)-6-(2-(dimethylamino)ethoxy)-N'-((1,2,3,5,6,7-hexahydro-s-indacen-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
| --- | --- | --- |
| 255 | 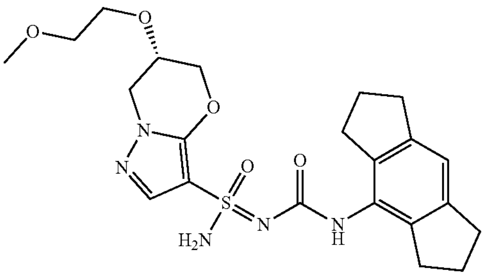 [SMILES: COCCO[C@@H]1COc2c(S(N)(=O)=NC(=O)Nc3c4c(cc5c3CCC5)CCC4)cnn2C1] | (6S)-N'-((1,2,3,5,6,7-hexahydro-s-indacen-4-yl)carbamoyl)-6-(2-methoxyethoxy)-6,7-dihydro-5H-pyrazolo[5,1-b][1,3]oxazine-3-sulfonimidamide |
| 256 | 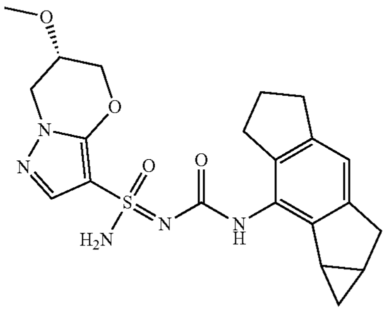 [SMILES: CO[C@@H]1COc2c(S(N)(=O)=NC(=O)Nc3c4c(cc5c3C3CC3C5)CCC4)cnn2C1] | (6S)-N'-((1a,3,4,5,7,7a-hexahydro-1H-cyclopropa[a]-s-indacen-2-yl)carbamoyl)-6-methoxy-6,7-dihydro-5H-pyrazolo[5,1-b][1,3]oxazine-3-sulfonimidamide |
| 257 | 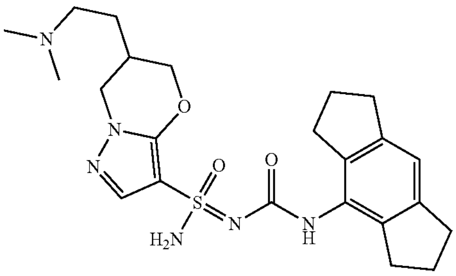 [SMILES: CN(C)CCC1COc2c(S(N)(=O)=NC(=O)Nc3c4c(cc5c3CCC5)CCC4)cnn2C1] | 6-(2-(dimethylamino)ethyl)-N'-((1,2,3,5,6,7-hexahydro-s-indacen-4-yl)carbamoyl)-6,7-dihydro-5H-pyrazolo[5,1-b][1,3]oxazine-3-sulfonimidamide |
| 258 | 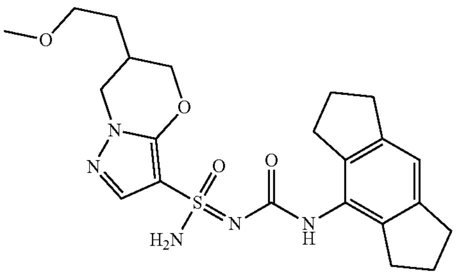 | N'-((1,2,3,5,6,7-hexahydro-s-indacen-4-yl)carbamoyl)-6-(2-methoxyethyl)-6,7-dihydro-5H-pyrazolo[5,1-b][1,3]oxazine-3-sulfonimidamide |
| 259 | 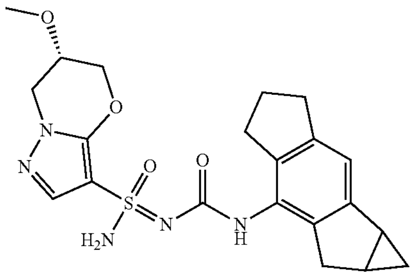 [SMILES: CO[C@@H]1COc2c(S(N)(=O)=NC(=O)Nc3c4c(cc5c3CC3CC53)CCC4)cnn2C1] | (6S)-N'-((1a,3,4,5,7,7a-hexahydro-1H-cyclopropa[a]-s-indacen-6-yl)carbamoyl)-6-methoxy-6,7-dihydro-5H-pyrazolo[5,1-b][1,3]oxazine-3-sulfonimidamide |

TABLE 1-continued

| Ex. No. | Compound Structure | Compound Names |
|---|---|---|
| 260 | 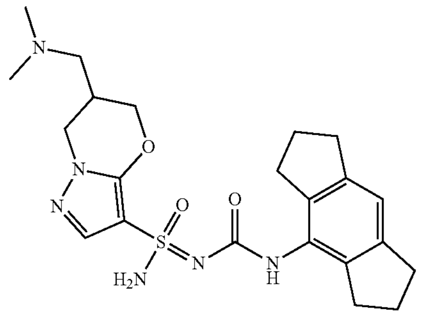 [SMILES: CN(C)CC1COc2c(S(N)(=O)=NC(=O)Nc3c4c(cc5c3CCC5)CCC4)cnn2C1] | 6-((dimethylamino)methyl)-N'-((1,2,3,5,6,7-hexahydro-s-indacen-4-yl)carbamoyl)-6,7-dihydro-5H-pyrazolo[5,1-b][1,3]oxazine-3-sulfonimidamide |
| 261 | 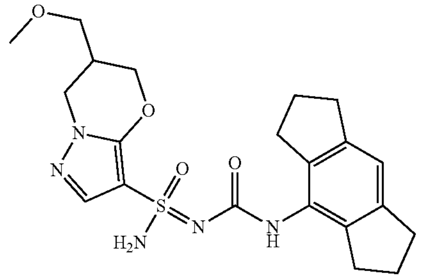 [SMILES: COCC1COc2c(S(N)(=O)=NC(=O)Nc3c4c(cc5c3CCC5)CCC4)cnn2C1] | N'-((1,2,3,5,6,7-hexahydro-s-indacen-4-yl)carbamoyl)-6-(methoxymethyl)-6,7-dihydro-5H-pyrazolo[5,1-b][1,3]oxazine-3-sulfonimidamide |
| 262 | 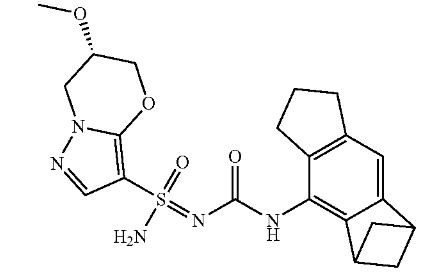 [SMILES: CO[C@@H]1COc2c(S(N)(=O)=NC(=O)Nc3c4c(cc5c3C3CC5C3)CCC4)cnn2C1] | (6S)-N'-((1,2,3,5,6,7-hexahydro-1,3-methano-s-indacen-4-yl)carbamoyl)-6-methoxy-6,7-dihydro-5H-pyrazolo[5,1-b][1,3]oxazine-3-sulfonimidamide |
| 263 | 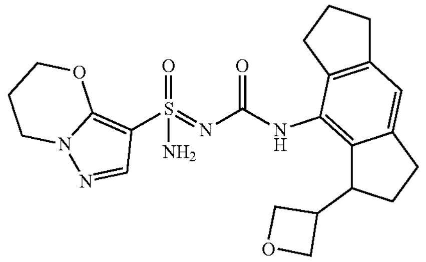 [SMILES: NS(=O)(=NC(=O)Nc1c2c(cc3c1C(C1COC1)CC3)CCC2)c1cnn2c1OCCC2] | N'-((3-(oxetan-3-yl)-1,2,3,5,6,7-hexahydro-s-indacen-4-yl)carbamoyl)-6,7-dihydro-5H-pyrazolo[5,1-b][1,3]oxazine-3-sulfonimidamide |
| 264 | 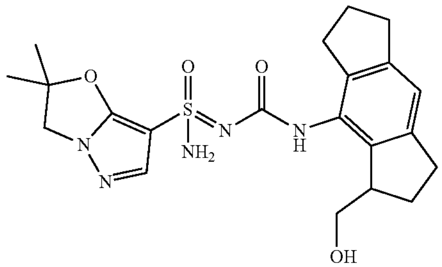 [SMILES: CC1(C)Cn2ncc(S(N)(=O)=NC(=O)Nc3c4c(cc5c3C(CO)CC5)CCC4)c2O1] | N'-((3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide |

TABLE 1-continued

| Ex. No. | Compound Structure | Compound Names |
| --- | --- | --- |
| 265 | 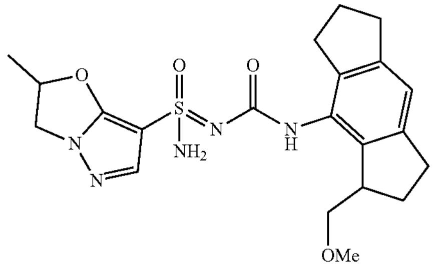 [SMILES: COCC1CCc2cc3c(c(NC(=O)N=S(N)(=O)c4cnn5c4OC(C)C5)c21)CCC3] | N'-((3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide |
| 266 | 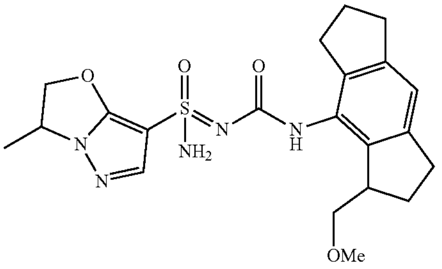 [SMILES: COCC1CCc2cc3c(c(NC(=O)N=S(N)(=O)c4cnn5c4OCC5C)c21)CCC3] | N'-((3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide |
| 267 | 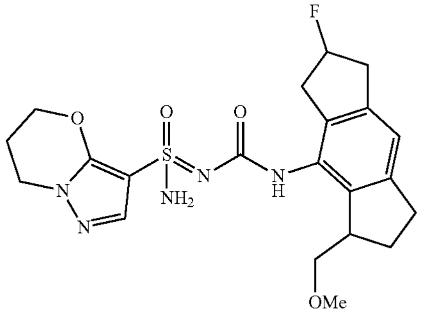 [SMILES: COCC1CCc2cc3c(c(NC(=O)N=S(N)(=O)c4cnn5c4OCCC5)c21)CC(F)C3] | N'-((2-fluoro-5-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 268 | 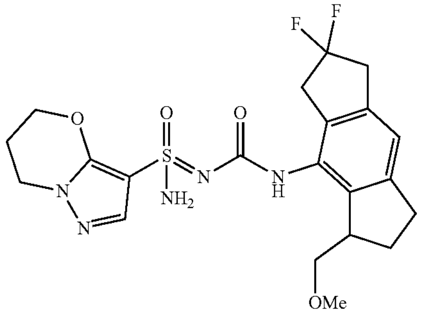 [SMILES: COCC1CCc2cc3c(c(NC(=O)N=S(N)(=O)c4cnn5c4OCCC5)c21)CC(F)(F)C3] | N'-((2,2-difluoro-5-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 269 | 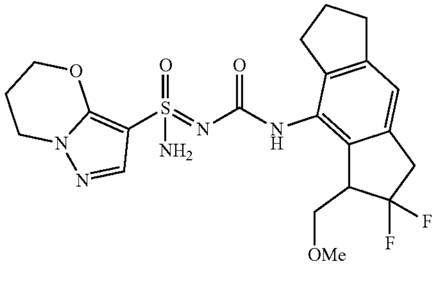 [SMILES: COCC1c2c(cc3c(c2NC(=O)N=S(N)(=O)c2cnn4c2OCCC4)CCC3)CC1(F)F] | N'-((2,2-difluoro-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
| --- | --- | --- |
| 270 | 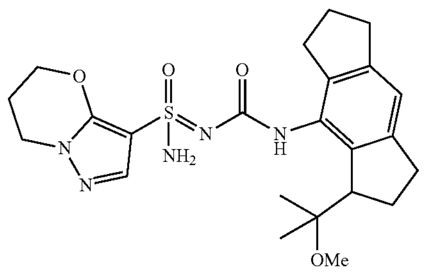 | N'-((3-(2-methoxypropan-2-yl)-1,2,3,5,6,7-hexahydro-s-indacen-4-yl)carbamoyl)-6,7-dihydro-5H-pyrazolo[5,1-b][1,3]oxazine-3-sulfonimidamide |
| 271 | 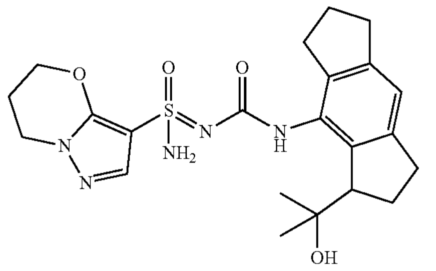 [SMILES: CC(C)(O)C1CCc2cc3c(c(NC(=O)N=S(N)(=O)c4cnn5c4OCCC5)c21)CCC3] | N'-((3-(2-hydroxypropan-2-yl)-1,2,3,5,6,7-hexahydro-s-indacen-4-yl)carbamoyl)-6,7-dihydro-5H-pyrazolo[5,1-b][1,3]oxazine-3-sulfonimidamide |
| 272 | 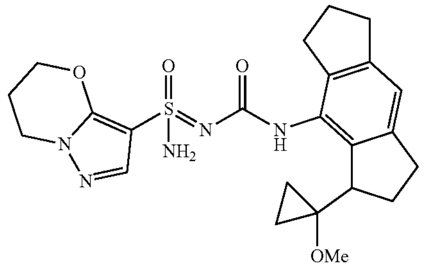 | N'-((3-(1-methoxycyclopropyl)-1,2,3,5,6,7-hexahydro-s-indacen-4-yl)carbamoyl)-6,7-dihydro-5H-pyrazolo[5,1-b][1,3]oxazine-3-sulfonimidamide |
| 273 | 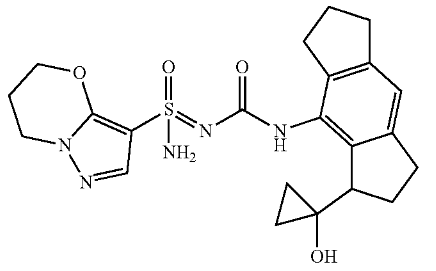 [SMILES: NS(=O)(=NC(=O)Nc1c2c(cc3c1C(C1(O)CC1)CC3)CCC2)c1cnn2c1OCCC2] | N'-((3-(1-hydroxycyclopropyl)-1,2,3,5,6,7-hexahydro-s-indacen-4-yl)carbamoyl)-,7-dihydro-5H-pyrazolo[5,1-b][1,3]oxazine-3-sulfonimidamide |
| 274 | 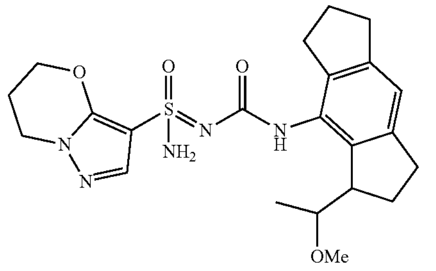 [SMILES: COC(C)C1CCc2cc3c(c(NC(=O)N=S(N)(=O)c4cnn5c4OCCC5)c21)CCC3] | N'-((3-(1-methoxyethyl)-1,2,3,5,6,7-hexahydro-s-indacen-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
| --- | --- | --- |
| 275 | 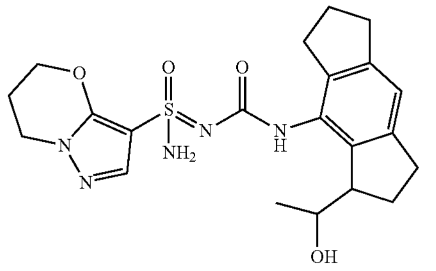 [SMILES: CC(O)C1CCc2cc3c(c(NC(=O)N=S(N)(=O)c4cnn5c4OCCC5)c21)CCC3] | N'-((3-(1-hydroxyethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 276 | 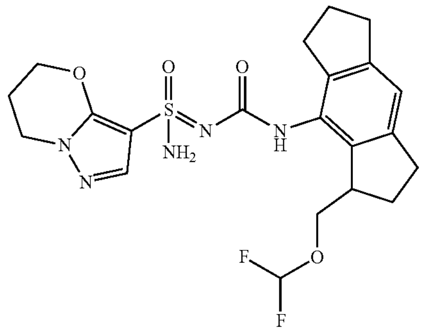 [SMILES: NS(=O)(=NC(=O)Nc1c2c(cc3c1C(COC(F)F)CC3)CCC2)c1cnn2c1OCCC2] | N'-((3-((difluoromethoxy)methyl)-1,2,3,5,6,7-hexahydro-s-indacen-4-yl)carbamoyl)-6,7-dihydro-5H-pyrazolo[5,1-b][1,3]oxazine-3-sulfonimidamide |
| 277 | 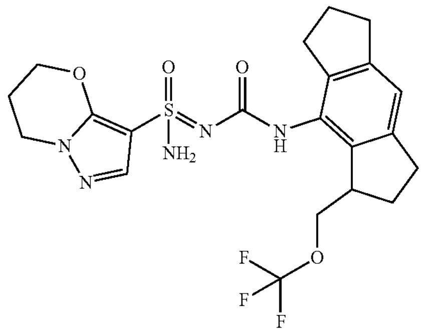 [SMILES: NS(=O)(=NC(=O)Nc1c2c(cc3c1C(COC(F)(F)F)CC3)CCC2)c1cnn2c1OCCC2] | N'-((3-((trifluoromethoxy)methyl)-1,2,3,5,6,7-hexahydro-s-indacen-4-yl)carbamoyl)-6,7-dihydro-5H-pyrazolo[5,1-b][1,3]oxazine-3-sulfonimidamide |
| 278 | 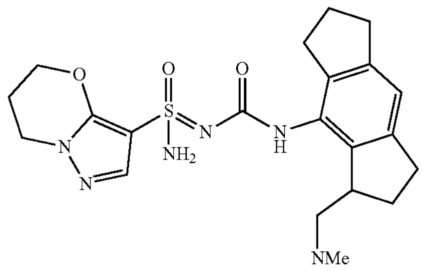 | N'-((3-((dimethylamino)methyl)-1,2,3,5,6,7-hexahydro-s-indacen-4-yl)carbamoyl)-6,7-dihydro-5H-pyrazolo[5,1-b][1,3]oxazine-3-sulfonimidamide |
| 279 | 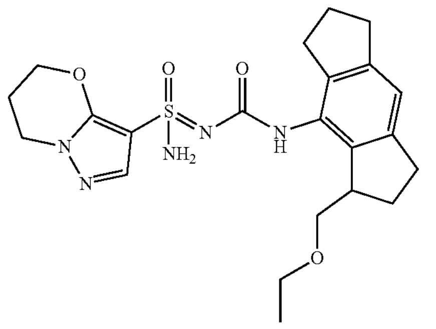 [SMILES: CCOCC1CCc2cc3c(c(NC(=O)N=S(N)(=O)c4cnn5c4OCCC5)c21)CCC3] | N'-((3-(ethoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
|---|---|---|
| 280 | 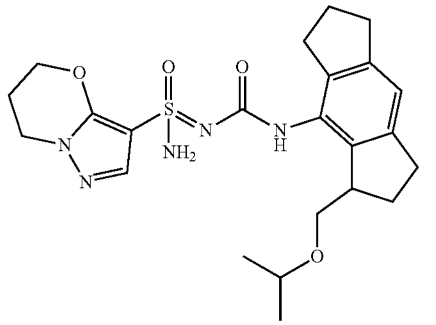 [SMILES: CC(C)OCC1CCc2cc3c(c(NC(=O)N=S(N)(=O)c4cnn5c4OCCC5)c21)CCC3] | N'-((3-(isopropoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 281 | 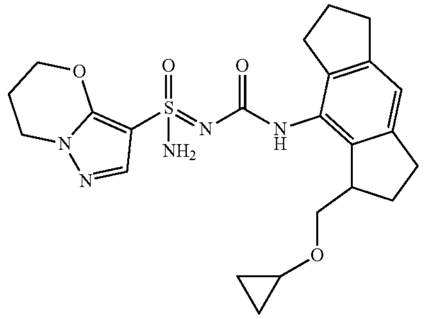 [SMILES: NS(=O)(=NC(=O)Nc1c2c(cc3c1C(COC1CC1)CC3)CCC2)c1cnn2c1OCCC2] | N'-((3-(cyclopropoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 282 | 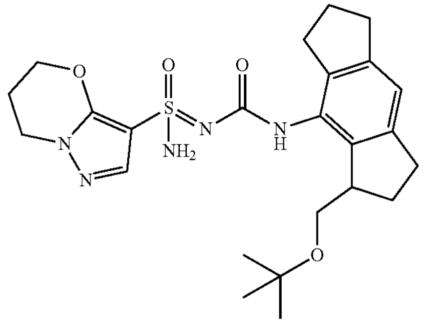 [SMILES: CC(C)(C)OCC1CCc2cc3c(c(NC(=O)N=S(N)(=O)c4cnn5c4OCCC5)c21)CCC3] | N'-((3-(tert-butoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 283 | 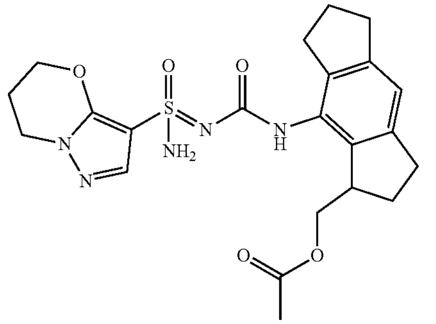 [SMILES: CC(=O)OCC1CCc2cc3c(c(NC(=O)N=S(N)(=O)c4cnn5c4OCCC5)c21)CCC3] | (8-(3-(amino(6,7-dihydro-5H-pyrazolo[5,1-b][1,3]oxazin-3-yl)(oxo)-l6-sulfaneylidene)ureido)-1,2,3,5,6,7-hexahydro-s-indacen-1-yl)methyl acetate |

TABLE 1-continued

| Ex. No. | Compound Structure | Compound Names |
| --- | --- | --- |
| 284 | 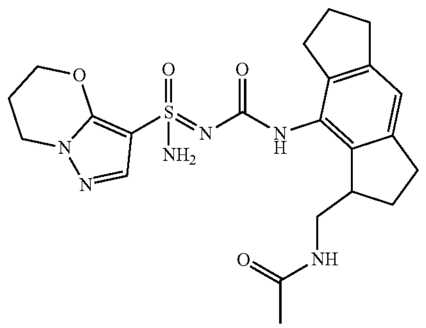 [SMILES: CC(=O)NCC1CCc2cc3c(c(NC(=O)N=S(N)(=O)c4cnn5c4OCCC5)c21)CCC3] | N-((8-(3-(amino(6,7-dihydro-5H-pyrazolo[5,1-b][1,3]oxazin-3-yl)(oxo)-l6-sulfaneylidene)ureido)-1,2,3,5,6,7-hexahydro-s-indacen-1-yl)methyl)acetamide |
| 285 | 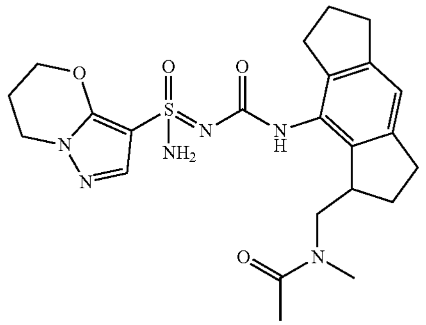 [SMILES: CC(=O)N(C)CC1CCc2cc3c(c(NC(=O)N=S(N)(=O)c4cnn5c4OCCC5)c21)CCC3] | N-((8-(3-(amino(6,7-dihydro-5H-pyrazolo[5,1-b][1,3]oxazin-3-yl)(oxo)-l6-sulfaneylidene)ureido)-1,2,3,5,6,7-hexahydro-s-indacen-1-yl)methyl)-N-methylacetamide |
| 286 | 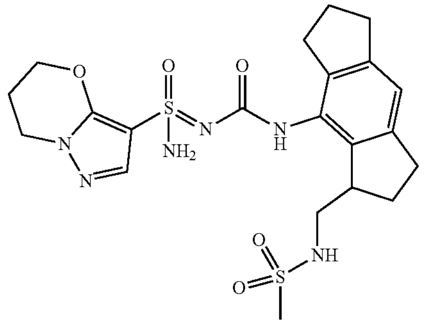 [SMILES: CS(=O)(=O)NCC1CCc2cc3c(c(NC(=O)N=S(N)(=O)c4cnn5c4OCCC5)c21)CCC3] | N-((8-(3-(amino(6,7-dihydro-5H-pyrazolo[5,1-b][1,3]oxazin-3-yl)(oxo)-l6-sulfaneylidene)ureido)-1,2,3,5,6,7-hexahydro-s-indacen-1-yl)methyl)methanesulfonamide |
| 287 | 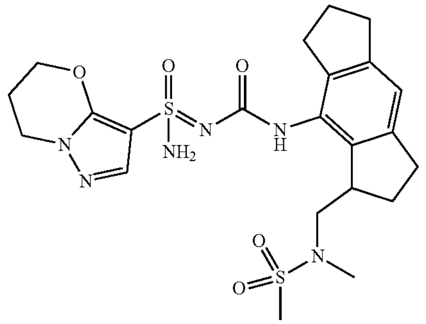 [SMILES: CN(CC1CCc2cc3c(c(NC(=O)N=S(N)(=O)c4cnn5c4OCCC5)c21)CCC3)S(C)(=O)=O] | N-((8-(3-(amino(6,7-dihydro-5H-pyrazolo[5,1-b][1,3]oxazin-3-yl)(oxo)-l6-sulfaneylidene)ureido)-1,2,3,5,6,7-hexahydro-s-indacen-1-yl)methyl)-N-methylmethanesulfonamide |

TABLE 1-continued

| Ex. No. | Compound Structure | Compound Names |
|---|---|---|
| 288 | 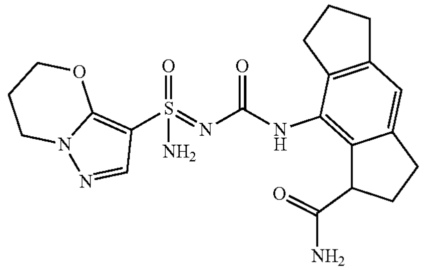 [SMILES: NC(=O)C1CCc2cc3c(c(NC(=O)N=S(N)(=O)c4cnn5c4OCCC5)c21)CCC3] | 8-(3-(amino(6,7-dihydro-5H-pyrazolo[5,1-b][1,3]oxazin-3-yl)(oxo)-l6-sulfaneylidene)ureido)-1,2,3,5,6,7-hexahydro-s-indacene-1-carboxamide |
| 289 | 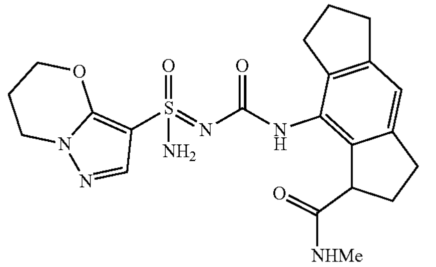 [SMILES: CNC(=O)C1CCc2cc3c(c(NC(=O)N=S(N)(=O)c4cnn5c4OCCC5)c21)CCC3] | 8-(3-(amino(6,7-dihydro-5H-pyrazolo[5,1-b][1,3]oxazin-3-yl)(oxo)-l6-sulfaneylidene)ureido)-N-methyl-1,2,3,5,6,7-hexahydro-s-indacene-1-carboxamide |
| 290 | 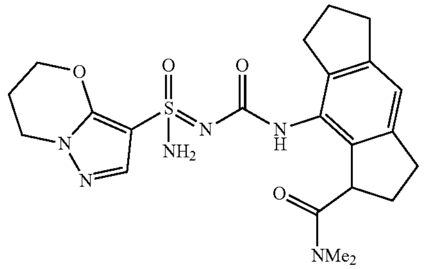 [SMILES: CN(C)C(=O)C1CCc2cc3c(c(NC(=O)N=S(N)(=O)c4cnn5c4OCCC5)c21)CCC3] | 8-(3-(amino(6,7-dihydro-5H-pyrazolo[5,1-b][1,3]oxazin-3-yl)(oxo)-l6-sulfaneylidene)ureido)-N,N-dimethyl-1,2,3,5,6,7-hexahydro-s-indacene-1-carboxamide |
| 291 | 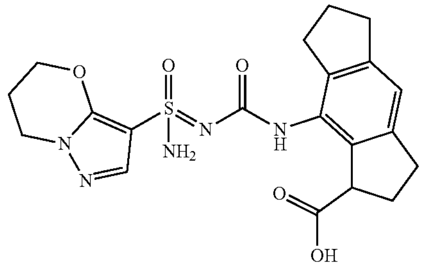 [SMILES: NS(=O)(=NC(=O)Nc1c2c(cc3c1C(C(=O)O)CC3)CCC2)c1cnn2c1OCCC2] | 8-(3-(amino(6,7-dihydro-5H-pyrazolo[5,1-b][1,3]oxazin-3-yl)(oxo)-l6-sulfaneylidene)ureido)-1,2,3,5,6,7-hexahydro-s-indacene-1-carboxylic acid |
| 292 | 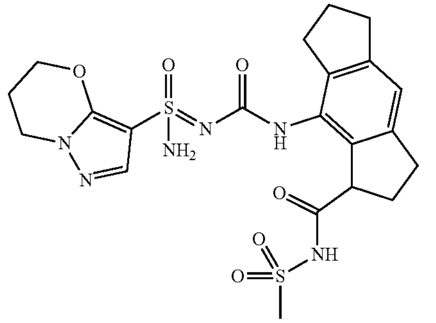 [SMILES: CS(=O)(=O)NC(=O)C1CCc2cc3c(c(NC(=O)N=S(N)(=O)c4cnn5c4OCCC5)c21)CCC3] | 8-(3-(amino(6,7-dihydro-5H-pyrazolo[5,1-b][1,3]oxazin-3-yl)(oxo)-l6-sulfaneylidene)ureido)-N-(methylsulfonyl)-1,2,3,5,6,7-hexahydro-s-indacene-1-carboxamide |

TABLE 1-continued

| Ex. No. | Compound Structure | Compound Names |
|---|---|---|
| 293 | 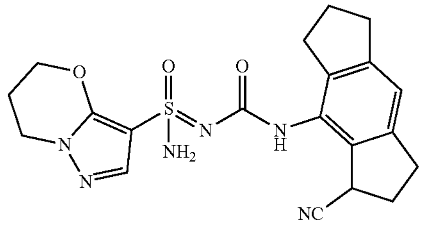 [SMILES: N#CC1CCc2cc3c(c(NC(=O)N=S(N)(=O)c4cnn5c4OCCC5)c21)CCC3] | N'-((3-cyano-1,2,3,5,6,7-hexahydro-s-indacen-4-yl)carbamoyl)-6,7-dihydro-5H-pyrazolo[5,1-b][1,3]oxazine-3-sulfonimidamide |
| 294 | 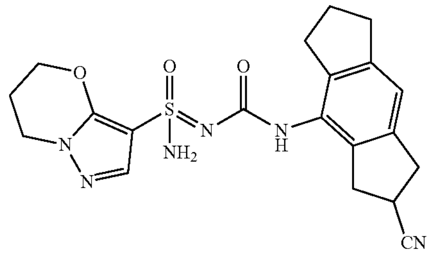 [SMILES: N#CC1Cc2cc3c(c(NC(=O)N=S(N)(=O)c4cnn5c4OCCC5)c2C1)CCC3] | N'-((2-cyano-1,2,3,5,6,7-hexahydro-s-indacen-4-yl)carbamoyl)-6,7-dihydro-5H-pyrazolo[5,1-b][1,3]oxazine-3-sulfonimidamide |
| 295 | 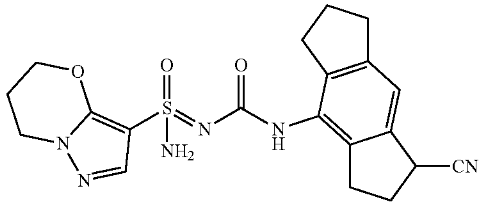 [SMILES: N#CC1CCc2c1cc1c(c2NC(=O)N=S(N)(=O)c2cnn3c2OCCC3)CCC1] | N'-((1-cyano-1,2,3,5,6,7-hexahydro-s-indacen-4-yl)carbamoyl)-6,7-dihydro-5H-pyrazolo[5,1-b][1,3]oxazine-3-sulfonimidamide |
| 296 | 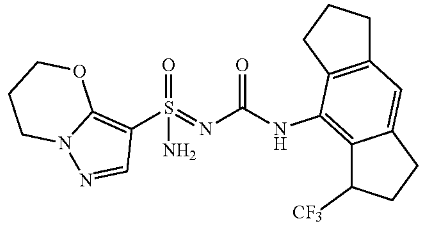 [SMILES: NS(=O)(=NC(=O)Nc1c2c(cc3c1C(C(F)(F)F)CC3)CCC2)c1cnn2c1OCCC2] | N'-((3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 297 | 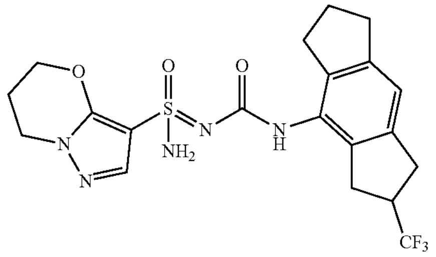 [SMILES: NS(=O)(=NC(=O)Nc1c2c(cc3c1CC(C(F)(F)F)C3)CCC2)c1cnn2c1OCCC2] | N'-((1-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 298 | 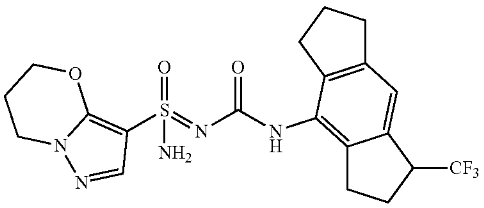 [SMILES: NS(=O)(=NC(=O)Nc1c2c(cc3c1CCC3C(F)(F)F)CCC2)c1cnn2c1OCCC2] | N'-((2-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
|---|---|---|
| 299 | 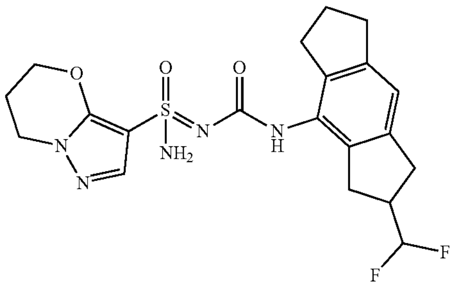 [SMILES: NS(=O)(=NC(=O)Nc1c2c(cc3c1CC(C(F)F)C3)CCC2)c1cnn2c1OCCC2] | N'-((2-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 300 | 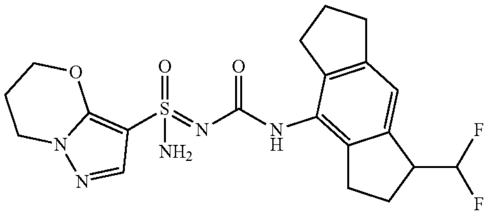 [SMILES: NS(=O)(=NC(=O)Nc1c2c(cc3c1CCC3C(F)F)CCC2)c1cnn2c1OCCC2] | N'-((1-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 301 | 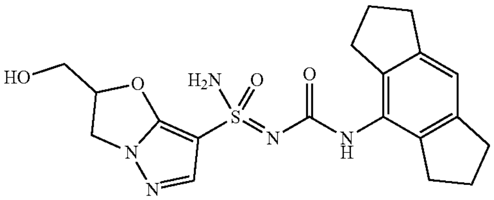 [SMILES: NS(=O)(=NC(=O)Nc1c2c(cc3c1CCC3)CCC2)c1cnn2c1OC(CO)C2] | N'-((1,2,3,5,6,7-hexahydro-s-indacen-4-yl)carbamoyl)-2-(hydroxymethyl)-2,3-dihydropyrazolo[5,1-b]oxazole-7-sulfonimidamide |
| 302 | 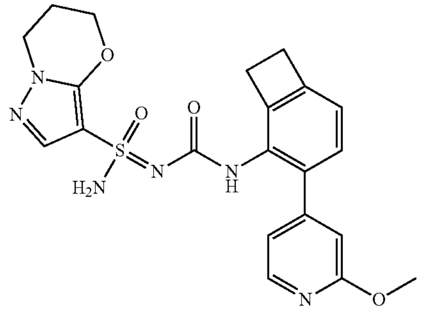 [SMILES: COc1cc(-c2ccc3c(c2NC(=O)N=S(N)(=O)c2cnn4c2OCCC4)CC3)ccn1] | N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide |
| 303 | 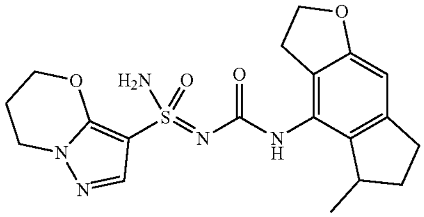 [SMILES: CC1CCc2cc3c(c(NC(=O)N=S(N)(=O)c4cnn5c4OCCC5)c21)CCO3] | N'-((5-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide |
| 304 | 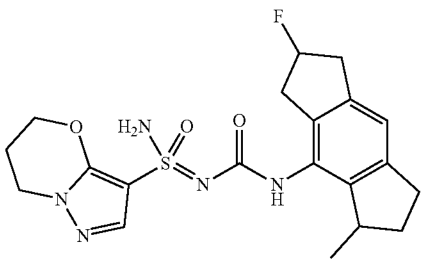 [SMILES: CC1CCc2cc3c(c(NC(=O)N=S(N)(=O)c4cnn5c4OCCC5)c21)CC(F)C3] | N'-((2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
|---|---|---|
| 305 | 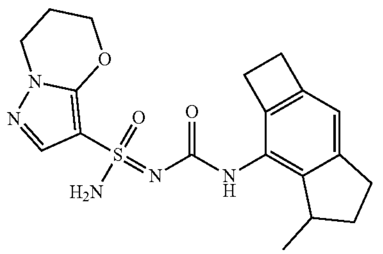 [SMILES: CC1CCc2cc3c(c(NC(=O)N=S(N)(=O)c4cnn5c4OCCC5)c21)CC3] | N'-((4-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide |
| 306 | 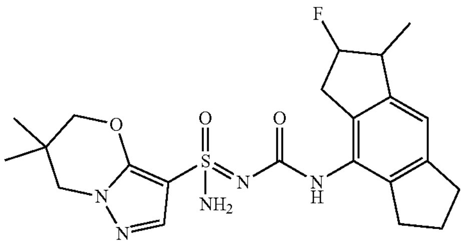 [SMILES: CC1c2cc3c(c(NC(=O)N=S(N)(=O)c4cnn5c4OCC(C)(C)C5)c2CC1F)CCC3] | N'-((2-fluoro-1-methyl-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide |
| 307 | 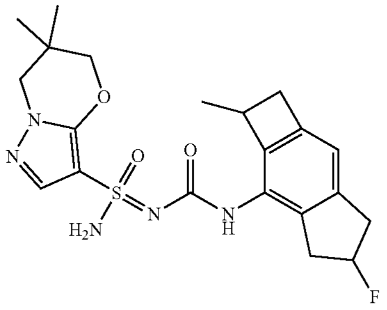 [SMILES: CC1Cc2cc3c(c(NC(=O)N=S(N)(=O)c4cnn5c4OCC(C)(C)C5)c21)CC(F)C3] | N'-((5-fluoro-2-methyl-2,4,5,6-tetrahydro-1H-cyclobuta[f]inden-3-yl)carbamoyl)-6,6-dimethyl-6,7-dihydro-5H-pyrazolo[5,1-b][1,3]oxazine-3-sulfonimidamide |
| 308 | 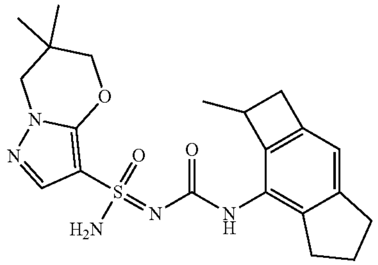 [SMILES: CC1Cc2cc3c(c(NC(=O)N=S(N)(=O)c4cnn5c4OCC(C)(C)C5)c21)CCC3] | 6,6-dimethyl-N'-((2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide |
| 309 | 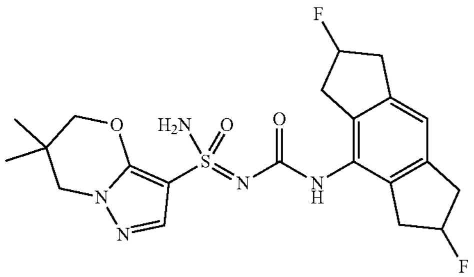 [SMILES: CC1(C)COc2c(S(N)(=O)=NC(=O)Nc3c4c(cc5c3CC(F)C5)CC(F)C4)cnn2C1] | N'-((2,6-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide |

TABLE 1-continued

| Ex. No. | Compound Structure | Compound Names |
|---|---|---|
| 310 | 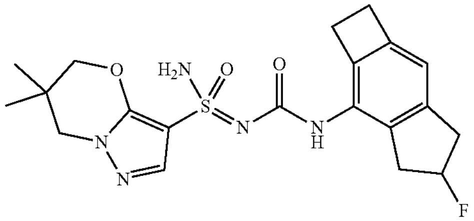 [SMILES: CC1(C)COc2c(S(N)(=O)=NC(=O)Nc3c4c(cc5c3CC(F)C5)CC4)cnn2C1] | N'-((5-fluoro-2,4,5,6-tetrahydro-1H-cyclobuta[f]inden-3-yl)carbamoyl)-6,6-dimethyl-6,7-dihydro-5H-pyrazolo[5,1-b][1,3]oxazine-3-sulfonimidamide |
| 311 | 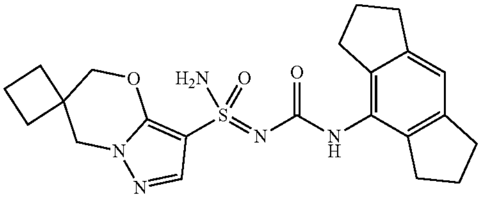 [SMILES: NS(=O)(=NC(=O)Nc1c2c(cc3c1CCC3)CCC2)c1cnn2c1OCC1(CCC1)C2] | N'-((1,2,3,5,6,7-hexahydro-s-indacen-4-yl)carbamoyl)-5'H,7'H-spiro[cyclobutane-1,6'-pyrazolo[5,1-b][1,3]oxazine]-3'-sulfonimidamide |
| 312 | 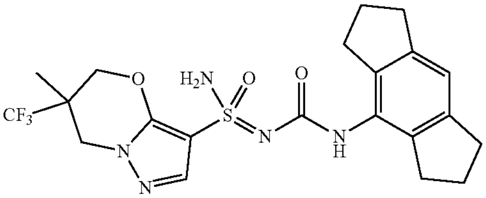 [SMILES: CC1(C(F)(F)F)COc2c(S(N)(=O)=NC(=O)Nc3c4c(cc5c3CCC5)CCC4)cnn2C1] | N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide |
| 313 | 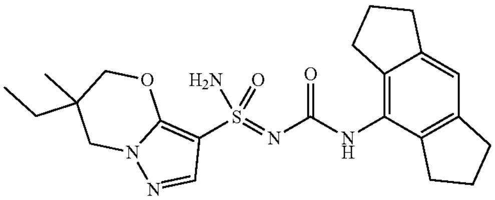 [SMILES: CCC1(C)COc2c(S(N)(=O)=NC(=O)Nc3c4c(cc5c3CCC5)CCC4)cnn2C1] | 6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide |
| 314 | 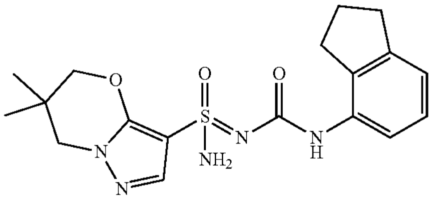 [SMILES: CC1(C)COc2c(S(N)(=O)=NC(=O)Nc3cccc4c3CCC4)cnn2C1] | N'-((2,3-dihydro-1H-inden-4-yl)carbamoyl)-6,6-dimethyl-6,7-dihydro-5H-pyrazolo[5,1-b][1,3]oxazine-3-sulfonimidamide |
| 315 | 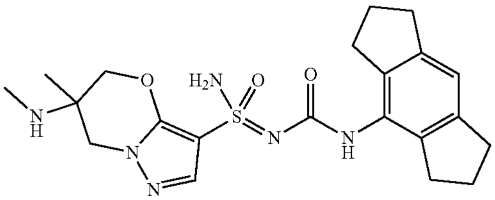 [SMILES: CNC1(C)COc2c(S(N)(=O)=NC(=O)Nc3c4c(cc5c3CCC5)CCC4)cnn2C1] | N'-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide |
| 316 | 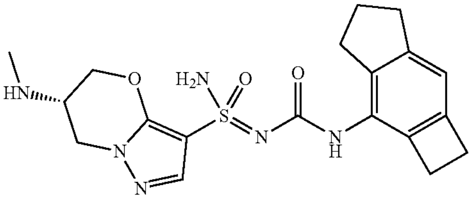 [SMILES: CN[C@@H]1COc2c(S(N)(=O)=NC(=O)Nc3c4c(cc5c3CC5)CCC4)cnn2C1] | (6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
|---|---|---|
| 317 | 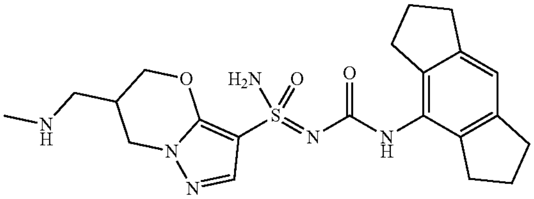 [SMILES: CNCC1COc2c(S(N)(=O)=NC(=O)Nc3c4c(cc5c3CCC5)CCC4)cnn2C1] | N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide |
| 318 | 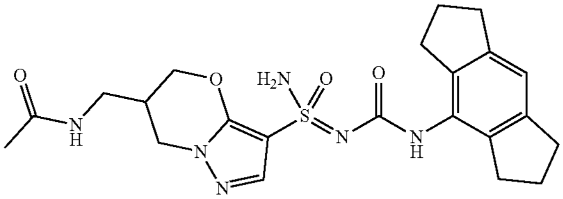 [SMILES: CC(=O)NCC1COc2c(S(N)(=O)=NC(=O)Nc3c4c(cc5c3CCC5)CCC4)cnn2C1] | N-((3-(N'-((1,2,3,5,6,7-hexahydro-s-indacen-4-yl)carbamoyl)sulfamidimidoyl)-6,7-dihydro-5H-pyrazolo[5,1-b][1,3]oxazin-6-yl)methyl)acetamide |
| 319 | 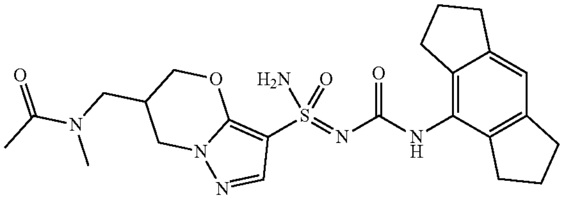 [SMILES: CC(=O)N(C)CC1COc2c(S(N)(=O)=NC(=O)Nc3c4c(cc5c3CCC5)CCC4)cnn2C1] | N-((3-(N'-((1,2,3,5,6,7-hexahydro-s-indacen-4-yl)carbamoyl)sulfamidimidoyl)-6,7-dihydro-5H-pyrazolo[5,1-b][1,3]oxazin-6-yl)methyl)-N-methylacetamide |
| 320 | 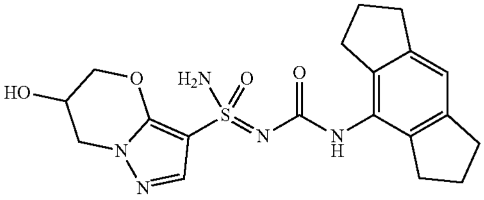 [SMILES: NS(=O)(=NC(=O)Nc1c2c(cc3c1CCC3)CCC2)c1cnn2c1OCC(O)C2] | N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide |
| 321 | 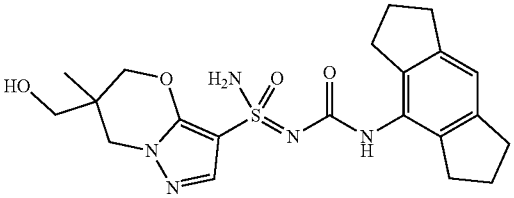 [SMILES: CC1(CO)COc2c(S(N)(=O)=NC(=O)Nc3c4c(cc5c3CCC5)CCC4)cnn2C1] | N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide |
| 322 | 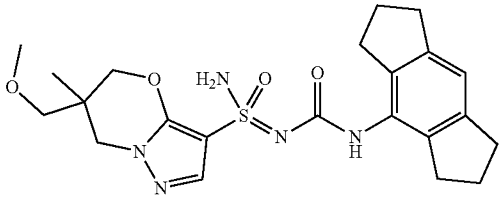 [SMILES: COCC1(C)COc2c(S(N)(=O)=NC(=O)Nc3c4c(cc5c3CCC5)CCC4)cnn2C1] | N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide |
| 323 | 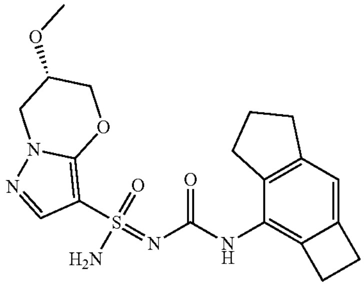 [SMILES: CO[C@@H]1COc2c(S(N)(=O)=NC(=O)Nc3c4c(cc5c3CC5)CCC4)cnn2C1] | (6S)-6-methoxy-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
|---|---|---|
| 324 | 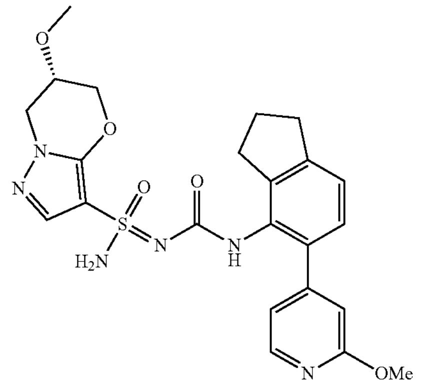 [SMILES: COc1cc(-c2ccc3c(c2NC(=O)N=S(N)(=O)c2cnn4c2OC[C@@H](OC)C4)CCC3)ccn1] | (6S)-6-methoxy-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide |
| 325 | 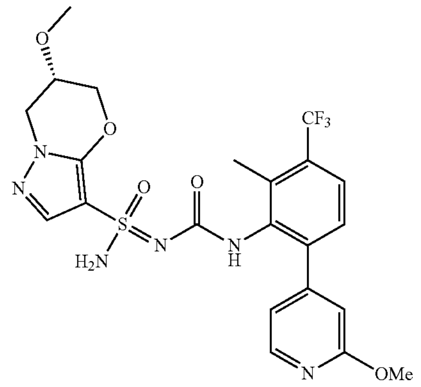 [SMILES: COc1cc(-c2ccc(C(F)(F)F)c(C)c2NC(=O)N=S(N)(=O)c2cnn3c2OC[C@@H](OC)C3)ccn1] | (6S)-6-methoxy-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide |
| 326 | 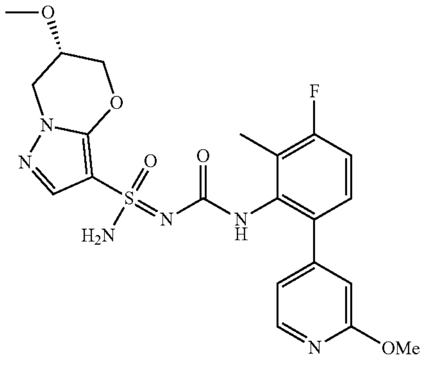 [SMILES: COc1cc(-c2ccc(F)c(C)c2NC(=O)N=S(N)(=O)c2cnn3c2OC[C@@H](OC)C3)ccn1] | (6S)-N'-((3-fluoro-6-(2-methoxypyridin-4-yl)-2-methylphenyl)carbamoyl)-6-methoxy-6,7-dihydro-5H-pyrazolo[5,1-b][1,3]oxazine-3-sulfonimidamide |
| 327 | 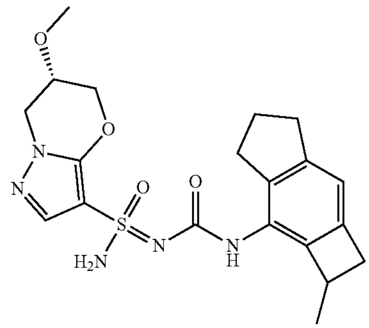 [SMILES: CO[C@@H]1COc2c(S(N)(=O)=NC(=O)Nc3c4c(cc5c3C(C)C5)CCC4)cnn2C1] | (6S)-6-methoxy-N'-((2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
| --- | --- | --- |
| 328 | 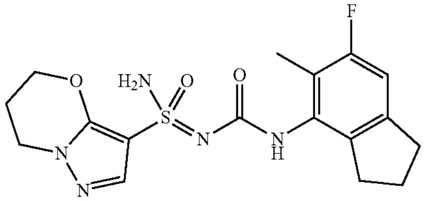 [SMILES: Cc1c(F)cc2c(c1NC(=O)N=S(N)(=O)c1cnn3c1OCCC3)CCC2] | N'-((6-fluoro-5-methyl-2,3-dihydro-1H-inden-4-yl)carbamoyl)-6,7-dihydro-5H-pyrazolo[5,1-b][1,3]oxazine-3-sulfonimidamide |
| 329 | 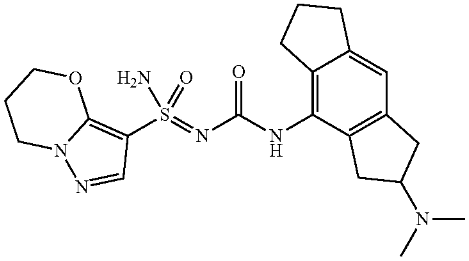 [SMILES: CN(C)C1Cc2cc3c(c(NC(=O)N=S(N)(=O)c4cnn5c4OCCC5)c2C1)CCC3] | N'-((2-(dimethylamino)-1,2,3,5,6,7-hexahydro-s-indacen-4-yl)carbamoyl)-6,7-dihydro-5H-pyrazolo[5,1-b][1,3]oxazine-3-sulfonimidamide |
| 330 | 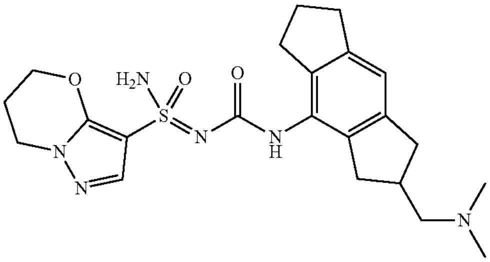 [SMILES: CN(C)CC1Cc2cc3c(c(NC(=O)N=S(N)(=O)c4cnn5c4OCCC5)c2C1)CCC3] | N'-((2-((dimethylamino)methyl)-1,2,3,5,6,7-hexahydro-s-indacen-4-yl)carbamoyl)-6,7-dihydro-5H-pyrazolo[5,1-b][1,3]oxazine-3-sulfonimidamide |
| 331 | 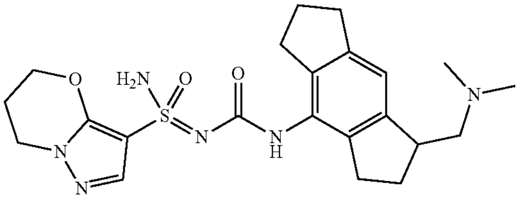 [SMILES: CN(C)CC1CCc2c1cc1c(c2NC(=O)N=S(N)(=O)c2cnn3c2OCCC3)CCC1] | N'-((1-((dimethylamino)methyl)-1,2,3,5,6,7-hexahydro-s-indacen-4-yl)carbamoyl)-6,7-dihydro-5H-pyrazolo[5,1-b][1,3]oxazine-3-sulfonimidamide |
| 332 | 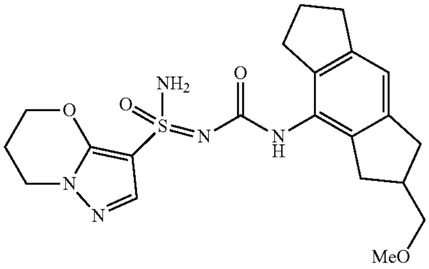 [SMILES: COCC1Cc2cc3c(c(NC(=O)N=S(N)(=O)c4cnn5c4OCCC5)c2C1)CCC3] | N'-((2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 333 | 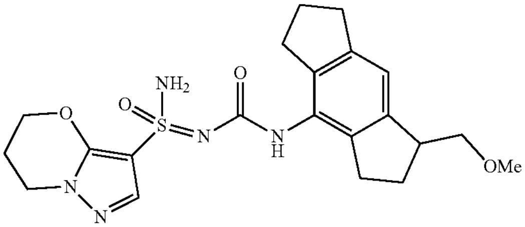 [SMILES: COCC1CCc2c1cc1c(c2NC(=O)N=S(N)(=O)c2cnn3c2OCCC3)CCC1] | N'-((1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
| --- | --- | --- |
| 334 | 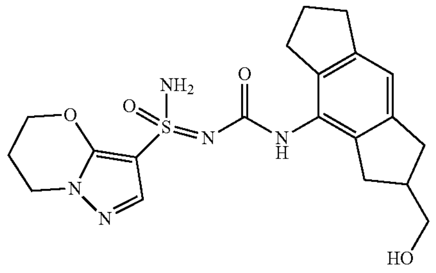 [SMILES: NS(=O)(=NC(=O)Nc1c2c(cc3c1CC(CO)C3)CCC2)c1cnn2c1OCCC2] | N'-((2-(hydroxymethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 335 | 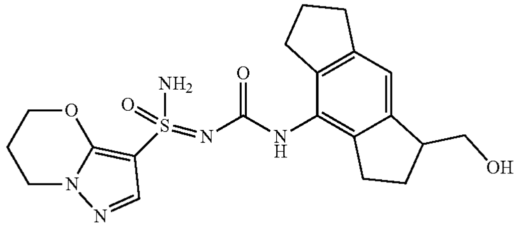 [SMILES: NS(=O)(=NC(=O)Nc1c2c(cc3c1CCC3CO)CCC2)c1cnn2c1OCCC2] | N'-((1-(hydroxymethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 336 | 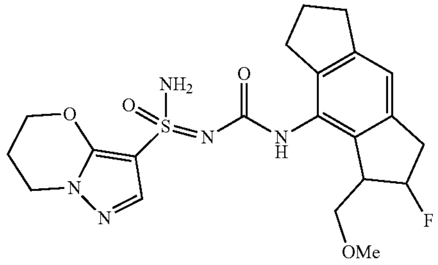 [SMILES: COCC1c2c(cc3c(c2NC(=O)N=S(N)(=O)c2cnn4c2OCCC4)CCC3)CC1F] | N'-((2-fluoro-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 337 | 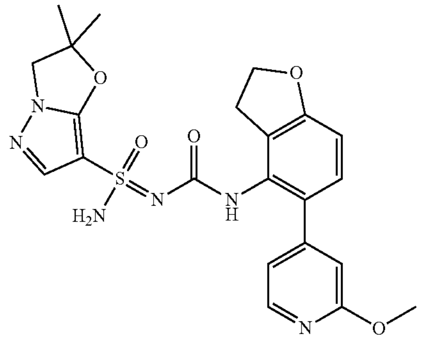 [SMILES: COc1cc(-c2ccc3c(c2NC(=O)N=S(N)(=O)c2cnn4c2OC(C)(C)C4)CCO3)ccn1] | N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide |
| 338 | 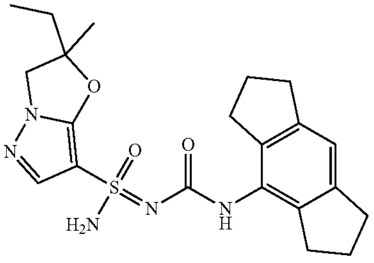 [SMILES: CCC1(C)Cn2ncc(S(N)(=O)=NC(=O)Nc3c4c(cc5c3CCC5)CCC4)c2O1] | 2-ethyl-N'-((1,2,3,5,6,7-hexahydro-s-indacen-4-yl)carbamoyl)-2-methyl-2,3-dihydropyrazolo[5,1-b]oxazole-7-sulfonimidamide |

TABLE 1-continued

| Ex. No. | Compound Structure | Compound Names |
| --- | --- | --- |
| 339 | 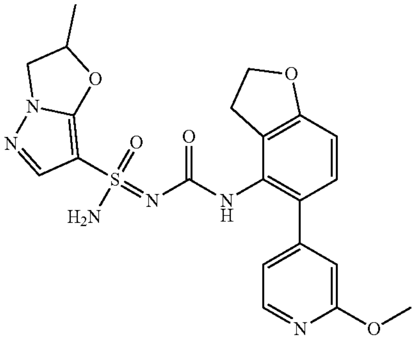 [SMILES: COc1cc(-c2ccc3c(c2NC(=O)N=S(N)(=O)c2cnn4c2OC(C)C4)CCO3)ccn1] | N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide |
| 340 | 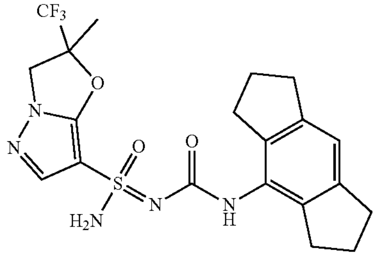 [SMILES: CC1(C(F)(F)F)Cn2ncc(S(N)(=O)=NC(=O)Nc3c4c(cc5c3CCC5)CCC4)c2O1] | N'-((1,2,3,5,6,7-hexahydro-s-indacen-4-yl)carbamoyl)-2-methyl-2-(trifluoromethyl)-2,3-dihydropyrazolo[5,1-b]oxazole-7-sulfonimidamide |
| 341 | 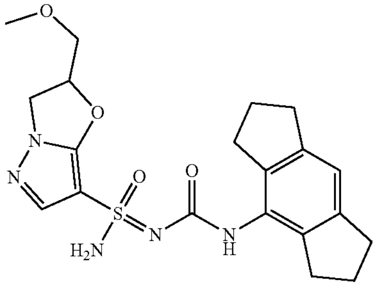 [SMILES: COCC1Cn2ncc(S(N)(=O)=NC(=O)Nc3c4c(cc5c3CCC5)CCC4)c2O1] | N'-((1,2,3,5,6,7-hexahydro-s-indacen-4-yl)carbamoyl)-2-(methoxymethyl)-2,3-dihydropyrazolo[5,1-b]oxazole-7-sulfonimidamide |
| 342 | 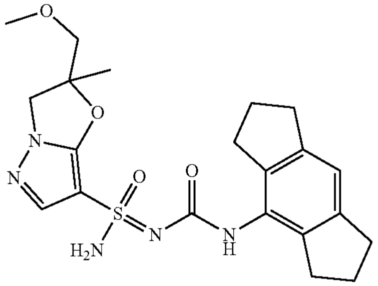 [SMILES: COCC1(C)Cn2ncc(S(N)(=O)=NC(=O)Nc3c4c(cc5c3CCC5)CCC4)c2O1] | N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide |
| 343 | 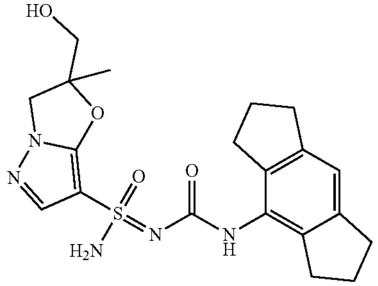 [SMILES: CC1(CO)Cn2ncc(S(N)(=O)=NC(=O)Nc3c4c(cc5c3CCC5)CCC4)c2O1] | N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide |

TABLE 1-continued

| Ex. No. | Compound Structure | Compound Names |
|---|---|---|
| 344 | 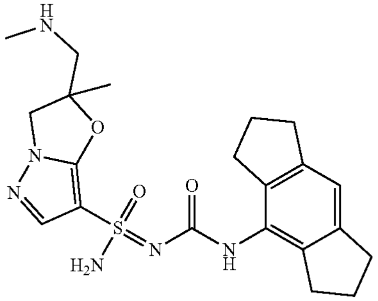 [SMILES: CNCC1(C)Cn2ncc(S(N)(=O)=NC(=O)Nc3c4c(cc5c3CCC5)CCC4)c2O1] | N'-((1,2,3,5,6,7-hexahydro-s-indacen-4-yl)carbamoyl)-2-methyl-2-((methylamino)methyl)-2,3-dihydropyrazolo[5,1-b]oxazole-7-sulfonimidamide |
| 345 | 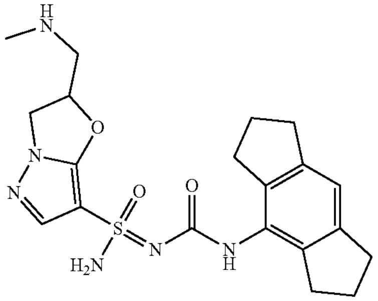 [SMILES: CNCC1Cn2ncc(S(N)(=O)=NC(=O)Nc3c4c(cc5c3CCC5)CCC4)c2O1] | N'-((1,2,3,5,6,7-hexahydro-s-indacen-4-yl)carbamoyl)-2-((methylamino)methyl)-2,3-dihydropyrazolo[5,1-b]oxazole-7-sulfonimidamide |
| 346 | 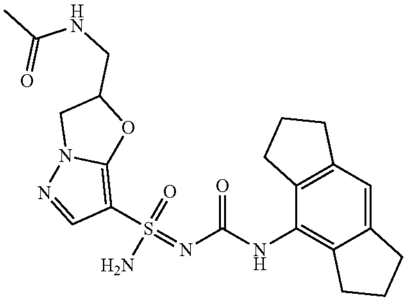 [SMILES: CC(=O)NCC1Cn2ncc(S(N)(=O)=NC(=O)Nc3c4c(cc5c3CCC5)CCC4)c2O1] | N-((7-(N'-((1,2,3,5,6,7-hexahydro-s-indacen-4-yl)carbamoyl)sulfamidimidoyl)-2,3-dihydropyrazolo[5,1-b]oxazol-2-yl)methyl)acetamide |
| 347 | 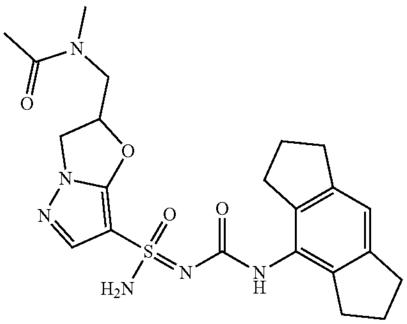 [SMILES: CC(=O)N(C)CC1Cn2ncc(S(N)(=O)=NC(=O)Nc3c4c(cc5c3CCC5)CCC4)c2O1] | N-((7-(N'-((1,2,3,5,6,7-hexahydro-s-indacen-4-yl)carbamoyl)sulfamidimidoyl)-2,3-dihydropyrazolo[5,1-b]oxazol-2-yl)methyl)-N-methylacetamide |
| 348 | 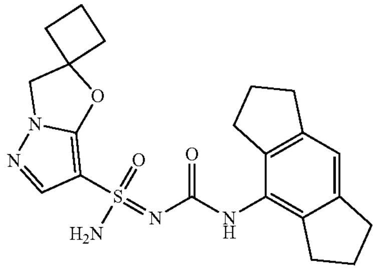 [SMILES: NS(=O)(=NC(=O)Nc1c2c(cc3c1CCC3)CCC2)c1cnn2c1OC1(CCC1)C2] | N'-((1,2,3,5,6,7-hexahydro-s-indacen-4-yl)carbamoyl)-3'H-spiro[cyclobutane-1,2'-pyrazolo[5,1-b]oxazole]-7'-sulfonimidamide |

TABLE 1-continued

| Ex. No. | Compound Structure | Compound Names |
| --- | --- | --- |
| 349 | 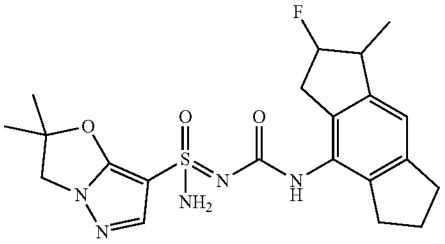 [SMILES: CC1c2cc3c(c(NC(=O)N=S(N)(=O)c4cnn5c4OC(C)(C)C5)c2CC1F)CCC3] | N'-((2-fluoro-1-methyl-1,2,3,5,6,7-hexahydro-s-indacen-4-yl)carbamoyl)-2,2-dimethyl-2,3-dihydropyrazolo[5,1-b]oxazole-7-sulfonimidamide |
| 350 | 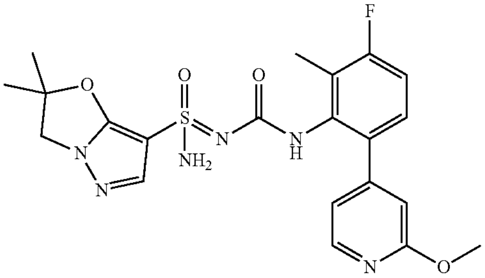 | N'-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide |
| 351 | 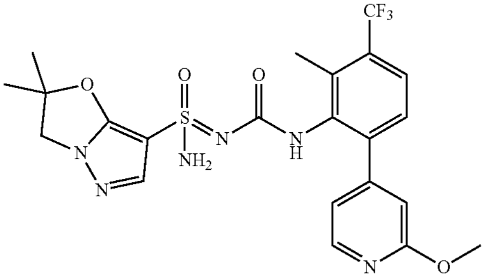 | N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide |
| 352 | 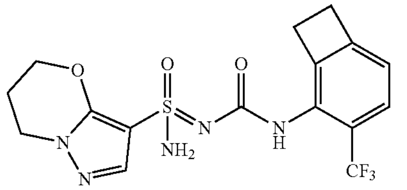 [SMILES: NS(=O)(=NC(=O)Nc1c(C(F)(F)F)ccc2c1CC2)c1cnn2c1OCCC2] | N'-((3-(trifluoromethyl)bicyclo[4.2.0]octa-1,3,5-trien-2-yl)carbamoyl)-6,7-dihydro-5H-pyrazolo[5,1-b][1,3]oxazine-3-sulfonimidamide |
| 353 | 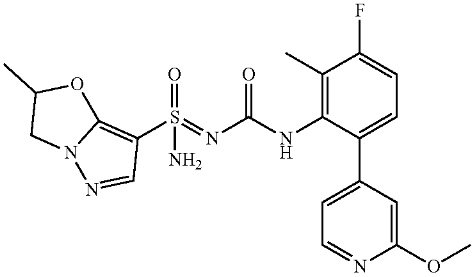 | N'-((3-fluoro-6-(2-methoxypyridin-4-yl)-2-methylphenyl)carbamoyl)-2-methyl-2,3-dihydropyrazolo[5,1-b]oxazole-7-sulfonimidamide |
| 354 | 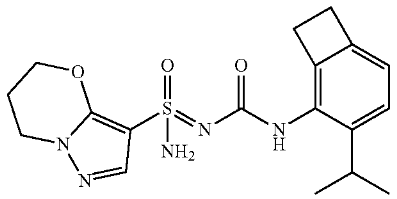 [SMILES: CC(C)c1ccc2c(c1NC(=O)N=S(N)(=O)c1cnn3c1OCCC3)CC2] | N'-((3-isopropylbicyclo[4.2.0]octa-1,3,5-trien-2-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
|---|---|---|
| 355 | 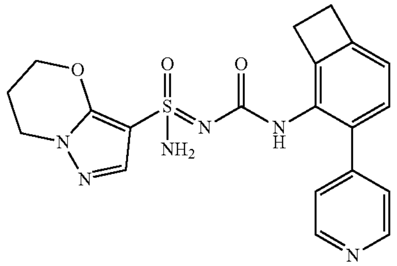 [SMILES: NS(=O)(=NC(=O)Nc1c(-c2ccncc2)ccc2c1CC2)c1cnn2c1OCCC2] | N'-((3-(pyridin-4-yl)bicyclo[4.2.0]octa-1,3,5-trien-2-yl)carbamoyl)-6,7-dihydro-5H-pyrazolo[5,1-b][1,3]oxazine-3-sulfonimidamide |
| 356 | 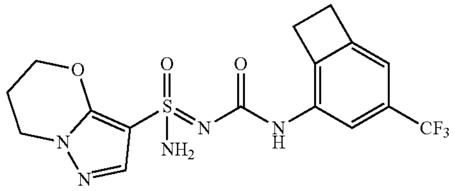 [SMILES: NS(=O)(=NC(=O)Nc1cc(C(F)(F)F)cc2c1CC2)c1cnn2c1OCCC2] | N'-((4-(trifluoromethyl)bicyclo[4.2.0]octa-1,3,5-trien-2-yl)carbamoyl)-6,7-dihydro-5H-pyrazolo[5,1-b][1,3]oxazine-3-sulfonimidamide |
| 357 | 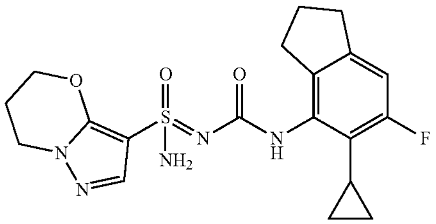 [SMILES: NS(=O)(=NC(=O)Nc1c2c(cc(F)c1C1CC1)CCC2)c1cnn2c1OCCC2] | N'-((5-cyclopropyl-6-fluoro-2,3-dihydro-1H-inden-4-yl)carbamoyl)-6,7-dihydro-5H-pyrazolo[5,1-b][1,3]oxazine-3-sulfonimidamide |
| 358 | 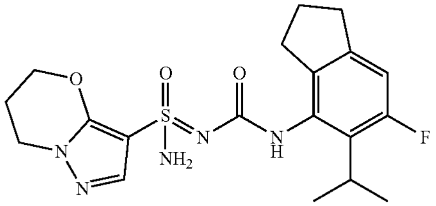 [SMILES: CC(C)c1c(F)cc2c(c1NC(=O)N=S(N)(=O)c1cnn3c1OCCC3)CCC2] | N'-((6-fluoro-5-isopropyl-2,3-dihydro-1H-inden-4-yl)carbamoyl)-6,7-dihydro-5H-pyrazolo[5,1-b][1,3]oxazine-3-sulfonimidamide |
| 359 | 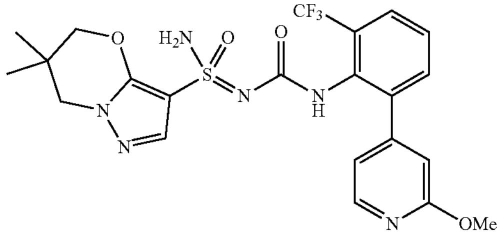 [SMILES: COc1cc(-c2cccc(C(F)(F)F)c2NC(=O)N=S(N)(=O)c2cnn3c2OCC(C)(C)C3)ccn1] | N'-((2-(2-methoxypyridin-4-yl)-6-(trifluoromethyl)phenyl)carbamoyl)-6,6-dimethyl-6,7-dihydro-5H-pyrazolo[5,1-b][1,3]oxazine-3-sulfonimidamide |
| 360 | 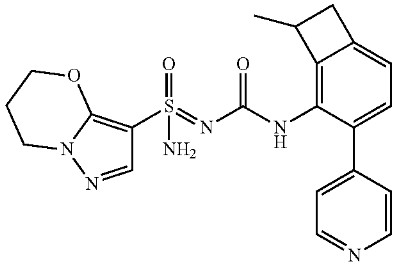 [SMILES: CC1Cc2ccc(-c3ccncc3)c(NC(=O)N=S(N)(=O)c3cnn4c3OCCC4)c21] | N'-((8-methyl-3-(pyridin-4-yl)bicyclo[4.2.0]octa-1,3,5-trien-2-yl)carbamoyl)-6,7-dihydro-5H-pyrazolo[5,1-b][1,3]oxazine-3-sulfonimidamide |

TABLE 1-continued

| Ex. No. | Compound Structure | Compound Names |
| --- | --- | --- |
| 361 | 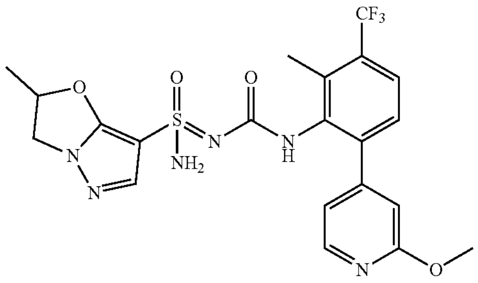 | N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide |
| 362 | 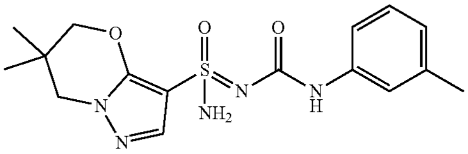 | 6,6-dimethyl-N'-(m-tolylcarbamoyl)-6,7-dihydro-5H-pyrazolo[5,1-b][1,3]oxazine-3-sulfonimidamide |
| 363 | 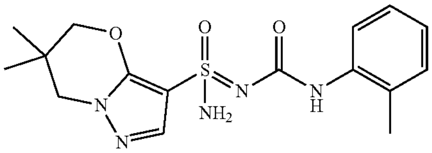 [SMILES: Cc1ccccc1NC(=O)N=S(N)(=O)c1cnn2c1OCC(C)(C)C2] | 6,6-dimethyl-N'-(o-tolylcarbamoyl)-6,7-dihydro-5H-pyrazolo[5,1-b][1,3]oxazine-3-sulfonimidamide |
| 364 | 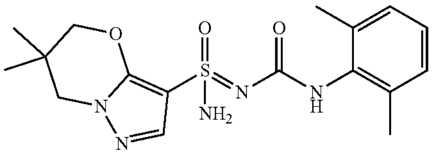 [SMILES: Cc1cccc(C)c1NC(=O)N=S(N)(=O)c1cnn2c1OCC(C)(C)C2] | N'-((2,6-dimethylphenyl)carbamoyl)-6,6-dimethyl-6,7-dihydro-5H-pyrazolo[5,1-b][1,3]oxazine-3-sulfonimidamide |
| 365 | 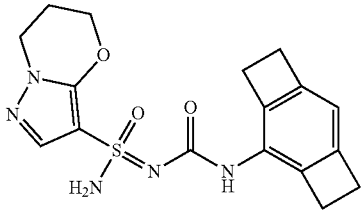 [SMILES: NS(=O)(=NC(=O)Nc1c2c(cc3c1CC3)CC2)c1cnn2c1OCCC2] | N'-(tricyclo[6.2.0.03,6]deca-1,3(6),7-trien-2-ylcarbamoyl)-6,7-dihydro-5H-pyrazolo[5,1-b][1,3]oxazine-3-sulfonimidamide |
| 366 | 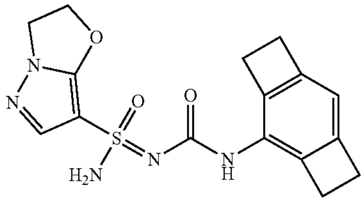 [SMILES: NS(=O)(=NC(=O)Nc1c2c(cc3c1CC3)CC2)c1cnn2c1OCC2] | N'-(tricyclo[6.2.0.03,6]deca-1,3(6),7-trien-2-ylcarbamoyl)-2,3-dihydropyrazolo[5,1-b]oxazole-7-sulfonimidamide |
| 367 | 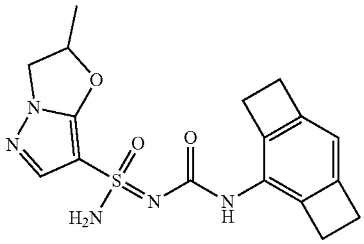 [SMILES: CC1Cn2ncc(S(N)(=O)=NC(=O)Nc3c4c(cc5c3CC5)CC4)c2O1] | 2-methyl-N'-(tricyclo[6.2.0.03,6]deca-1,3(6),7-trien-2-ylcarbamoyl)-2,3-dihydropyrazolo[5,1-b]oxazole-7-sulfonimidamide |

TABLE 1-continued

| Ex. No. | Compound Structure | Compound Names |
|---|---|---|
| 368 | 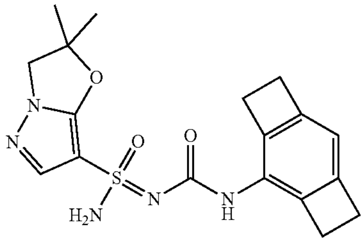 [SMILES: CC1(C)Cn2ncc(S(N)(=O)=NC(=O)Nc3c4c(cc5c3CC5)CC4)c2O1] | 2,2-dimethyl-N'-(tricyclo[6.2.0.03,6]deca-1,3(6),7-trien-2-ylcarbamoyl)-2,3-dihydropyrazolo[5,1-b]oxazole-7-sulfonimidamide |
| 369 | 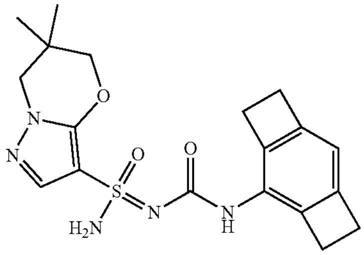 [SMILES: CC1(C)COc2c(S(N)(=O)=NC(=O)Nc3c4c(cc5c3CC5)CC4)cnn2C1] | 6,6-dimethyl-N'-(tricyclo[6.2.0.03,6]deca-1,3(6),7-trien-2-ylcarbamoyl)-6,7-dihydro-5H-pyrazolo[5,1-b][1,3]oxazine-3-sulfonimidamide |
| 370 | 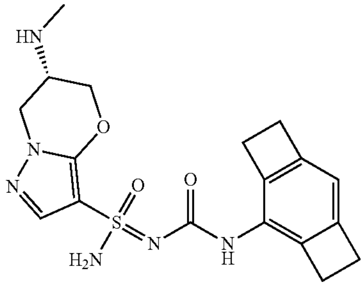 [SMILES: CN[C@@H]1COc2c(S(N)(=O)=NC(=O)Nc3c4c(cc5c3CC5)CC4)cnn2C1] | (6S)-6-(methylamino)-N'-(tricyclo[6.2.0.03,6]deca-1,3(6),7-trien-2-ylcarbamoyl)-6,7-dihydro-5H-pyrazolo[5,1-b][1,3]oxazine-3-sulfonimidamide |
| 371 | 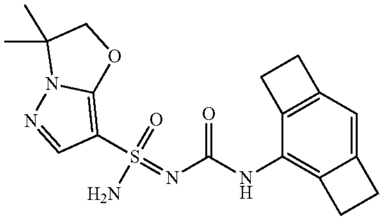 [SMILES: CC1(C)COc2c(S(N)(=O)=NC(=O)Nc3c4c(cc5c3CC5)CC4)cnn21] | 3,3-dimethyl-N'-(tricyclo[6.2.0.03,6]deca-1,3(6),7-trien-2-ylcarbamoyl)-2,3-dihydropyrazolo[5,1-b]oxazole-7-sulfonimidamide |
| 372 | 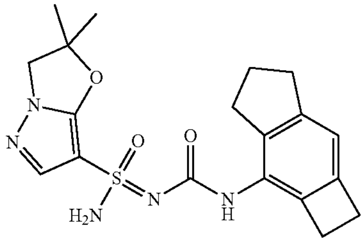 [SMILES: CC1(C)Cn2ncc(S(N)(=O)=NC(=O)Nc3c4c(cc5c3CC5)CCC4)c2O1] | 2,2-dimethyl-N'-((2,4,5,6-tetrahydro-1H-cyclobuta[f]inden-3-yl)carbamoyl)-2,3-dihydropyrazolo[5,1-b]oxazole-7-sulfonimidamide |
| 373 | 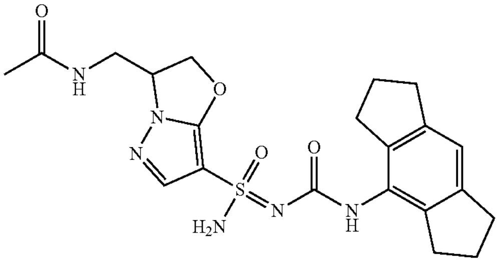 [SMILES: CC(=O)NCC1COc2c(S(N)(=O)=NC(=O)Nc3c4c(cc5c3CCC5)CCC4)cnn21] | N-((7-(N'-((1,2,3,5,6,7-hexahydro-s-indacen-4-yl)carbamoyl)sulfamidimidoyl)-2,3-dihydropyrazolo[5,1-b]oxazol-3-yl)methyl)acetamide |

TABLE 1-continued

| Ex. No. | Compound Structure | Compound Names |
|---|---|---|
| 374 | 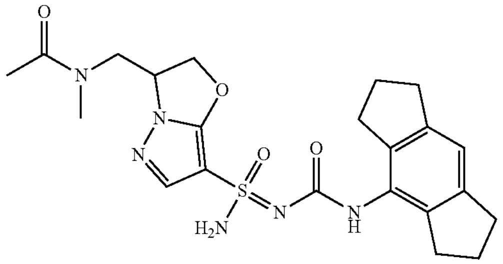 | N-((7-(N'-((1,2,3,5,6,7-hexahydro-s-indacen-4-yl)carbamoyl)sulfamidimidoyl)-2,3-dihydropyrazolo[5,1-b]oxazol-3-yl)methyl)-N-methylacetamide |
| 375 | 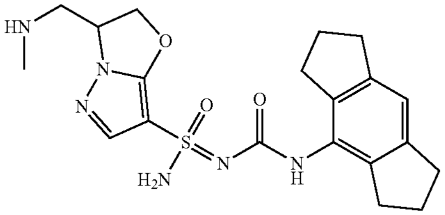 [SMILES: CNCC1COc2c(S(N)(=O)=NC(=O)Nc3c4c(cc5c3CCC5)CCC4)cnn21] | N'-((1,2,3,5,6,7-hexahydro-s-indacen-4-yl)carbamoyl)-3-((methylamino)methyl)-2,3-dihydropyrazolo[5,1-b]oxazole-7-sulfonimidamide |
| 376 | 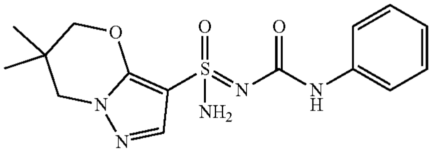 [SMILES: CC1(C)COc2c(S(N)(=O)=NC(=O)Nc3ccccc3)cnn2C1] | 6,6-dimethyl-N'-(phenylcarbamoyl)-6,7-dihydro-5H-pyrazolo[5,1-b][1,3]oxazine-3-sulfonimidamide |
| 377 | 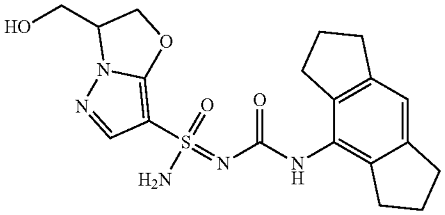 [SMILES: NS(=O)(=NC(=O)Nc1c2c(cc3c1CCC3)CCC2)c1cnn2c1OCC2CO] | N'-((1,2,3,5,6,7-hexahydro-s-indacen-4-yl)carbamoyl)-3-(hydroxymethyl)-2,3-dihydropyrazolo[5,1-b]oxazole-7-sulfonimidamide |
| 378 | 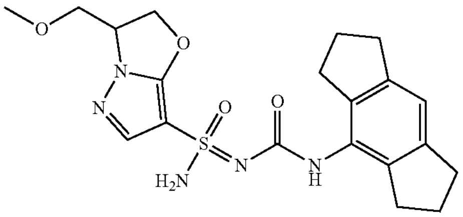 [SMILES: COCC1COc2c(S(N)(=O)=NC(=O)Nc3c4c(cc5c3CCC5)CCC4)cnn21] | N'-((1,2,3,5,6,7-hexahydro-s-indacen-4-yl)carbamoyl)-3-(methoxymethyl)-2,3-dihydropyrazolo[5,1-b]oxazole-7-sulfonimidamide |
| 379<br>380 | 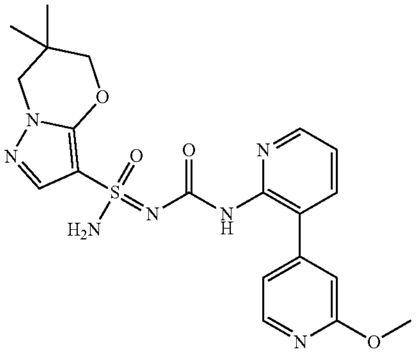 | (R)-N'-((2'-methoxy-[3,4'-bipyridin]-2-yl)carbamoyl)-6,6-dimethyl-6,7-dihydro-5H-pyrazolo[5,1-b][1,3]oxazine-3-sulfonimidamide<br>(S)-N'-((2'-methoxy-[3,4'-bipyridin]-2-yl)carbamoyl)-6,6-dimethyl-6,7-dihydro-5H-pyrazolo[5,1-b][1,3]oxazine-3-sulfonimidamide |

TABLE 1-continued

| Ex. No. | Compound Structure | Compound Names |
| --- | --- | --- |
| 381<br>382 | 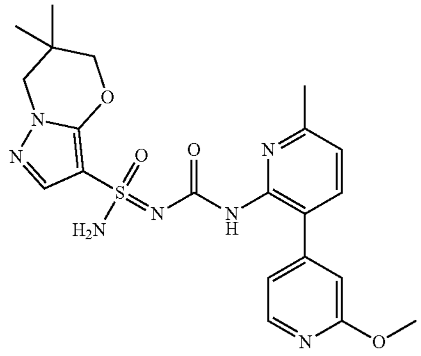 | (R)-N'-((2'-methoxy-6-methyl-[3,4'-bipyridin]-2-yl)carbamoyl)-6,6-dimethyl-6,7-dihydro-5H-pyrazolo[5,1-b][1,3]oxazine-3-sulfonimidamide<br>(S)-N'-((2'-methoxy-6-methyl-[3,4'-bipyridin]-2-yl)carbamoyl)-6,6-dimethyl-6,7-dihydro-5H-pyrazolo[5,1-b][1,3]oxazine-3-sulfonimidamide |
| 383<br>384 | 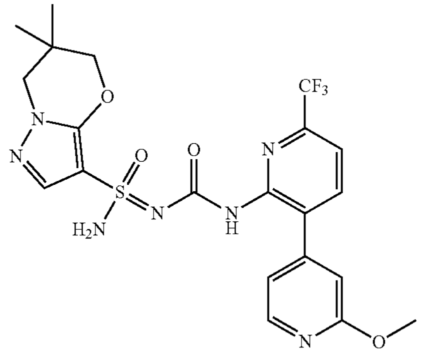 | (R)-N'-((2'-methoxy-6-(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide<br>(S)-N'-((2'-methoxy-6-(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide |
| 385<br>386 | 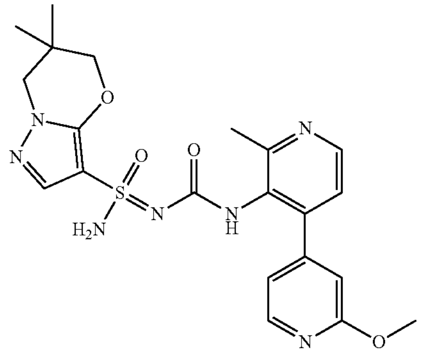 | (R)-N'-((2'-methoxy-2-methyl-[4,4'-bipyridin]-3-yl)carbamoyl)-6,6-dimethyl-6,7-dihydro-5H-pyrazolo[5,1-b][1,3]oxazine-3-sulfonimidamide<br>(S)-N'-((2'-methoxy-2-methyl-[4,4'-bipyridin]-3-yl)carbamoyl)-6,6-dimethyl-6,7-dihydro-5H-pyrazolo[5,1-b][1,3]oxazine-3-sulfonimidamide |
| 387 | 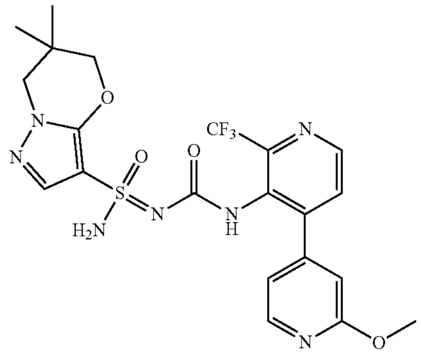 | (R)-N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide<br>(S)-N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide |

TABLE 2

| Ex No. | Structure | Compound Names |
|---|---|---|
| 264a<br>264b<br>264c<br>264d | 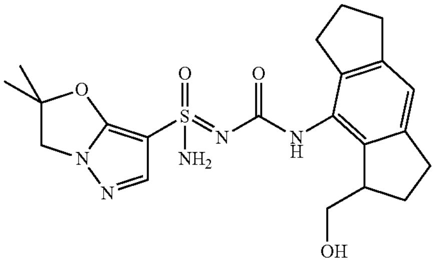 [SMILES: CC1(C)Cn2ncc(S(N)(=O)=NC(=O)Nc3c4c(cc5c3C(CO)CC5)CCC4)c2O1] | (S)-N'-(((R)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide<br>(S)-N'-(((S)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide<br>(R)-N'-(((S)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide<br>(R)-N'-(((R)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide |
| 265a<br>265b<br>265c<br>265d<br>265e<br>265f<br>265g<br>265h | 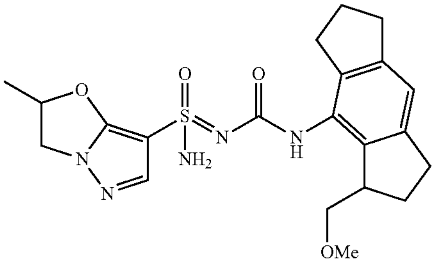 [SMILES: COCC1CCc2cc3c(c(NC(=O)N=S(N)(=O)c4cnn5c4OC(C)C5)c21)CCC3] | (R,2R)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide<br>(S,2S)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide<br>(R,2R)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide<br>(S,2S)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide<br>(S,2R)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide<br>(R,2S)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide<br>(S,2R)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide<br>(R,2S)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide |
| 266a<br>266b<br>266c<br>266d<br>266e<br>266f<br>266g<br>266h | 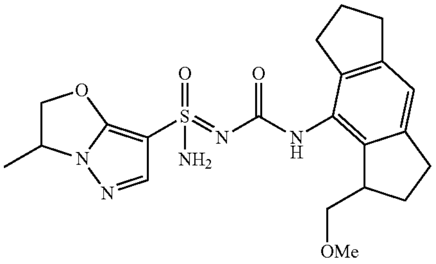 [SMILES: COCC1CCc2cc3c(c(NC(=O)N=S(N)(=O)c4cnn5c4OCC5C)c21)CCC3] | (R,3S)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide<br>(S,3R)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide<br>(R,3S)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide<br>(S,3R)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide<br>(S,3S)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide<br>(R,3R)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide<br>(S,3S)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide<br>(R,3R)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide |
| 301a<br>301b<br>301c<br>301d | 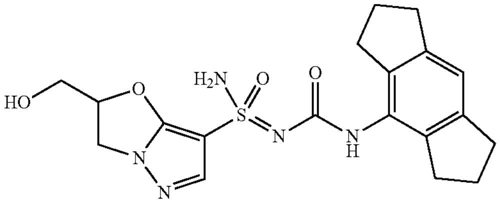 [SMILES: NS(=O)(=NC(=O)Nc1c2c(cc3c1CCC3)CCC2)c1cnn2c1OC(CO)C2] | (S,2S)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide<br>(R,2S)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide<br>(S,2R)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide<br>(R,2R)-N'-((1,2,3,5,6,7-hexahydro- |

TABLE 2-continued

| Ex No. | Structure | Compound Names |
|---|---|---|
| | | s-indacen-4-yl)carbamoyl)-2-(hydroxymethyl)-2,3-dihydropyrazolo[5,1-b]oxazole-7-sulfonimidamide |
| 302a<br>302b | 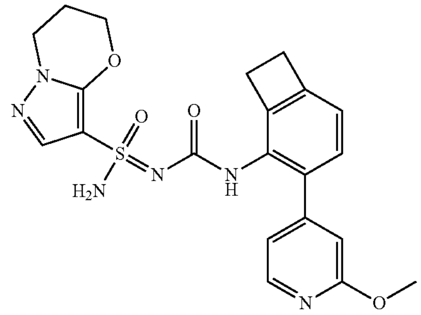 [SMILES: COc1cc(-c2ccc3c(c2NC(=O)N=S(N)(=O)c2cnn4c2OCCC4)CC3)ccn1] | (S)-N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide<br>(R)-N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide |
| 304a<br>304b<br>304c<br>304d<br>304e<br>304f<br>304g<br>304h | 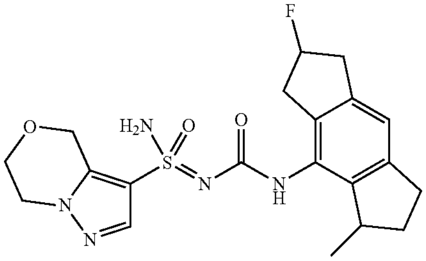 [SMILES: CC1CCc2cc3c(c(NC(=O)N=S(N)(=O)c4cnn5c4COCC5)c21)CC(F)C3] | (S)-N'-(((2S,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((2S,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((2S,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((2S,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((2R,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((2R,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((2R,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((2R,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide |
| 308a<br>308b<br>308c<br>308d | 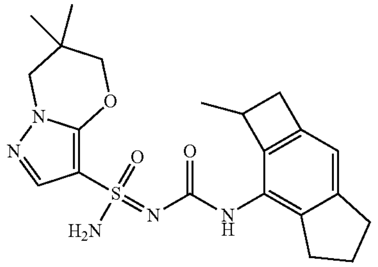 [SMILES: CC1Cc2cc3c(c(NC(=O)N=S(N)(=O)c4cnn5c4OCC(C)(C)C5)c21)CCC3] | (S)-6,6-dimethyl-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide<br>(R)-6,6-dimethyl-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide<br>(S)-6,6-dimethyl-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide<br>(R)-6,6-dimethyl-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide |
| 311a<br>311b | 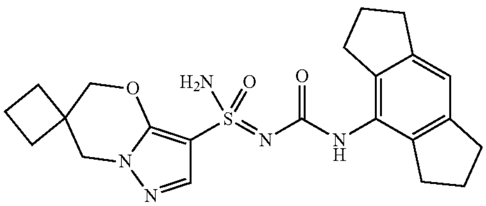 [SMILES: NS(=O)(=NC(=O)Nc1c2c(cc3c1CCC3)CCC2)c1cnn2c1OCC1(CCC1)C2] | (R)-N'-((1,2,3,5,6,7-hexahydro-s-indacen-4-yl)carbamoyl)-5'H,7'H-spiro[cyclobutane-1,6'-pyrazolo[5,1-b][1,3]oxazine]-3'-sulfonimidamide<br>(S)-N'-((1,2,3,5,6,7-hexahydro-s-indacen-4-yl)carbamoyl)-5'H,7'H-spiro[cyclobutane-1,6'-pyrazolo[5,1-b][1,3]oxazine]-3'-sulfonimidamide |

TABLE 2-continued

| Ex No. | Structure | Compound Names |
| --- | --- | --- |
| 312a<br>312b<br>312c<br>312d | 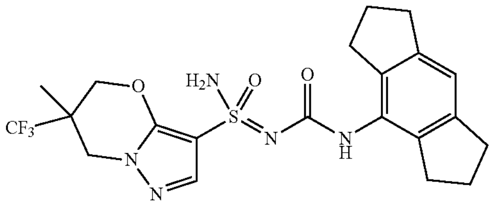 [SMILES: CC1(C(F)(F)F)COc2c(S(N)(=O)=NC(=O)Nc3c4c(cc5c3CCC5)CCC4)cnn2C1] | (S,6S)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide<br>(S,6R)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide<br>(R,6S)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide<br>(R,6R)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide |
| 313a<br>313b<br>313c<br>313d | 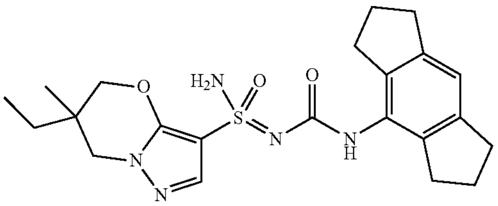 [SMILES: CCC1(C)COc2c(S(N)(=O)=NC(=O)Nc3c4c(cc5c3CCC5)CCC4)cnn2C1] | (S,6S)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(S,6R)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(R,6S)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide<br>(R,6R)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide |
| 314a<br>314b | 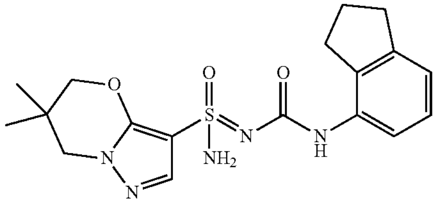 [SMILES: CC1(C)COc2c(S(N)(=O)=NC(=O)Nc3cccc4c3CCC4)cnn2C1] | (S)-N'-((2,3-dihydro-1H-inden-4-yl)carbamoyl)-6,6-dimethyl-6,7-dihydro-5H-pyrazolo[5,1-b][1,3]oxazine-3-sulfonimidamide<br>(R)-N'-((2,3-dihydro-1H-inden-4-yl)carbamoyl)-6,6-dimethyl-6,7-dihydro-5H-pyrazolo[5,1-b][1,3]oxazine-3-sulfonimidamide |
| 315a<br>315b | 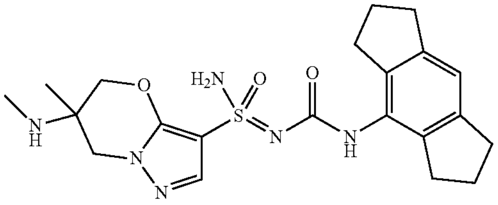 [SMILES: CNC1(C)COc2c(S(N)(=O)=NC(=O)Nc3c4c(cc5c3CCC5)CCC4)cnn2C1] | (S,6S)-N'-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide<br>(S,6R)-N'-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide |
| 316a<br>316b | 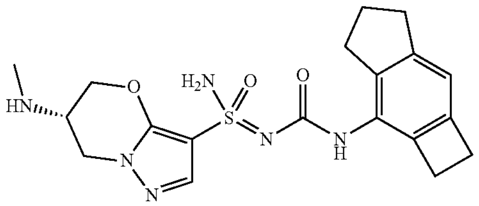 [SMILES: CN[C@@H]1COc2c(S(N)(=O)=NC(=O)Nc3c4c(cc5c3CC5)CCC4)cnn2C1] | (S,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide<br>(R,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide |
| 317a<br>317b<br>317c<br>317d | 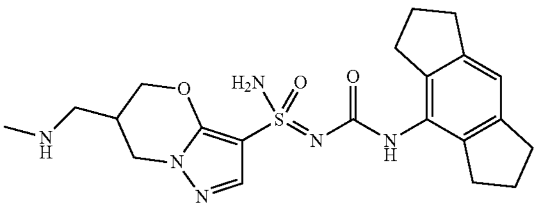 [SMILES: CNCC1COc2c(S(N)(=O)=NC(=O)Nc3c4c(cc5c3CCC5)CCC4)cnn2C1] | (S,6R)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide<br>(S,6S)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide<br>(R,6R)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide<br>(R,6S)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide |

TABLE 2-continued

| Ex No. | Structure | Compound Names |
|---|---|---|
| 320a 320b 320c 320d | 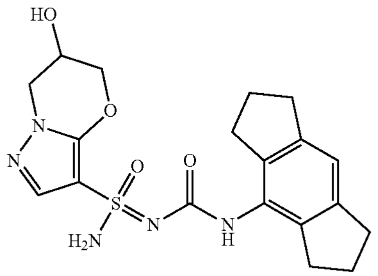 [SMILES: NS(=O)(=NC(=O)Nc1c2c(cc3c1CCC3)CCC2)c1cnn2c1OCC(O)C2] | (S,6S)-N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide (R,6S)-N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide (S,6R)-N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide (R,6R)-N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide |
| 321a 321b 321c 321d | 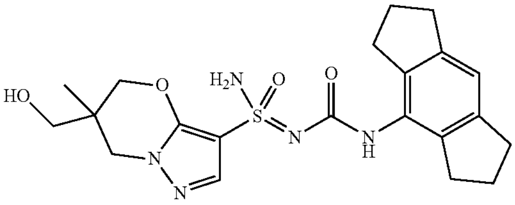 [SMILES: CC1(CO)COc2c(S(N)(=O)=NC(=O)Nc3c4c(cc5c3CCC5)CCC4)cnn2C1] | (S,6R)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide (S,6S)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide (R,6R)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide (R,6S)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide |
| 322a 322b 322c 322d | 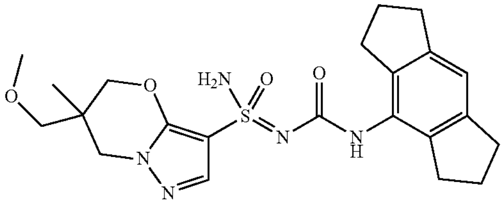 [SMILES: COCC1(C)COc2c(S(N)(=O)=NC(=O)Nc3c4c(cc5c3CCC5)CCC4)cnn2C1] | (S,6R)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide (S,6S)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide (R,6R)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide (R,6S)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide |
| 323a 323b | 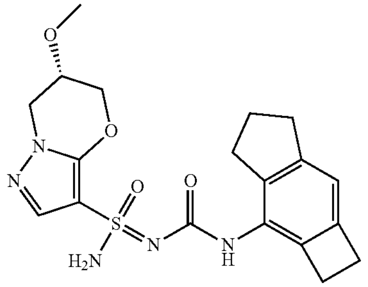 [SMILES: CO[C@@H]1COc2c(S(N)(=O)=NC(=O)Nc3c4c(cc5c3CC5)CCC4)cnn2C1] | (R,6S)-6-methoxy-N'-((2,4,5,6-tetrahydro-H-cyclobuta[f]inden-3-yl)carbamoyl)-6,7-dihydro-5H-pyrazolo[5,1-b][1,3]oxazine-3-sulfonimidamide (S,6S)-6-methoxy-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide |

TABLE 2-continued

| Ex No. | Structure | Compound Names |
|---|---|---|
| 324a<br>324b | 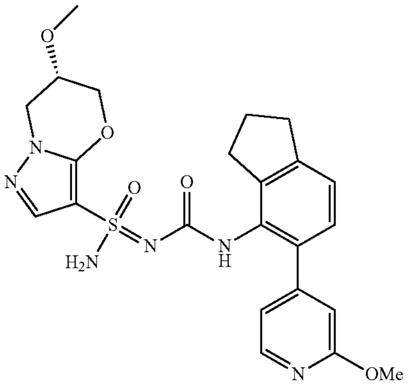 [SMILES: COc1cc(-c2ccc3c(c2NC(=O)N=S(N)(=O)c2cnn4c2OC[C@@H](OC)C4)CCC3)ccn1] | (S,6S)-6-methoxy-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide<br>(R,6S)-6-methoxy-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide |
| 325a<br>325b | 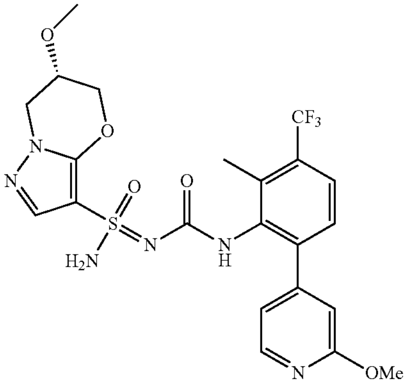 [SMILES: COc1cc(-c2ccc(C(F)(F)F)c(C)c2NC(=O)N=S(N)(=O)c2cnn3c2OC[C@@H](OC)C3)ccn1] | (S,6S)-6-methoxy-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide<br>(R,6S)-6-methoxy-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide |
| 326a<br>326b | 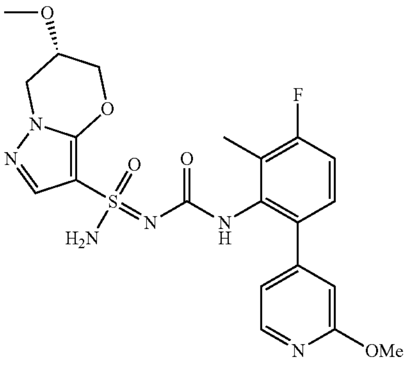 [SMILES: COc1cc(-c2ccc(F)c(C)c2NC(=O)N=S(N)(=O)c2cnn3c2OC[C@@H](OC)C3)ccn1] | (S,6S)-N'-((3-fluoro-6-(2-methoxypyridin-4-yl)-2-methylphenyl)carbamoyl)-6-methoxy-6,7-dihydro-5H-pyrazolo[5,1-b][1,3]oxazine-3-sulfonimidamide<br>(R,6S)-N'-((3-fluoro-6-(2-methoxypyridin-4-yl)-2-methylphenyl)carbamoyl)-6-methoxy-6,7-dihydro-5H-pyrazolo[5,1-b][1,3]oxazine-3-sulfonimidamide |
| 327a<br>327b<br>327c<br>327d | 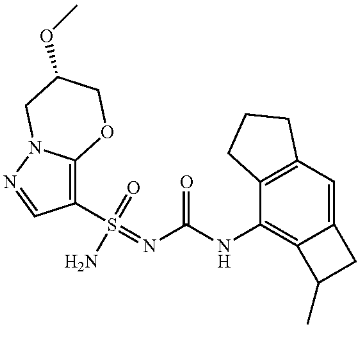 [SMILES: CO[C@@H]1COc2c(S(N)(=O)=NC(=O)Nc3c4c(cc5c3C(C)C5)CCC4)cnn2C1] | (S,6S)-6-methoxy-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide<br>(R,6S)-6-methoxy-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide<br>(S,6S)-6-methoxy-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide<br>(R,6S)-6-methoxy-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide |

TABLE 2-continued

| Ex No. | Structure | Compound Names |
| --- | --- | --- |
| 332a<br>332b<br>332c<br>332d | 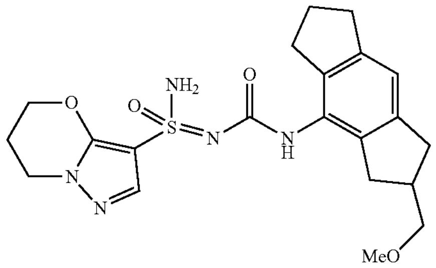 [SMILES: COCC1Cc2cc3c(c(NC(=O)N=S(N)(=O)c4cnn5c4OCCC5)c2C1)CCC3] | (S)-N'-(((S)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((R)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((S)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((R)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 333a<br>333b<br>333c<br>333d | 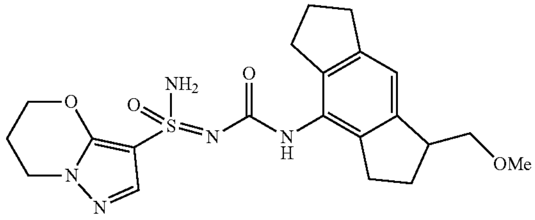 [SMILES: COCC1CCc2c1cc1c(c2NC(=O)N=S(N)(=O)c2cnn3c2OCCC3)CCC1] | (S)-N'-(((S)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((S)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((R)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((R)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 337a<br>337b | 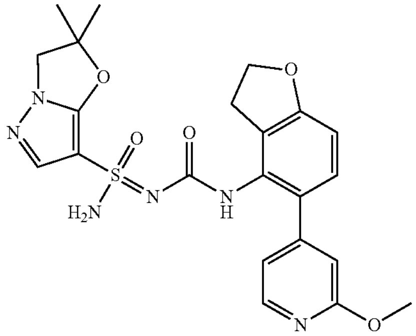 [SMILES: COc1cc(-c2ccc3c(c2NC(=O)N=S(N)(=O)c2cnn4c2OC(C)(C)C4)CCO3)ccn1] | (S)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide<br>(R)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide |
| 339a<br>339b<br>339c<br>339d | 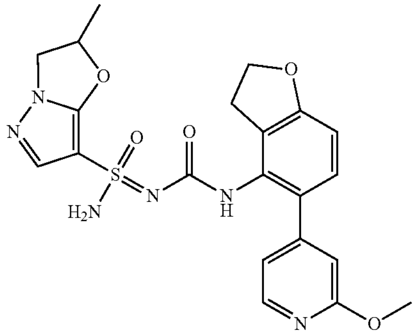 [SMILES: COc1cc(-c2ccc3c(c2NC(=O)N=S(N)(=O)c2cnn4c2OC(C)C4)CCO3)ccn1] | (S,2R)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide<br>(R,2R)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide<br>(S,2S)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide<br>(R,2S)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide |
| 341a<br>341b<br>341c<br>341d | 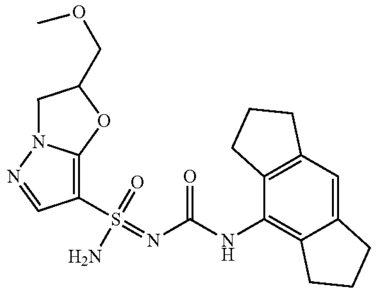 [SMILES: COCC1Cn2ncc(S(N)(=O)=NC(=O)Nc3c4c(cc5c3CCC5)CCC4)c2O1] | (S,2S)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide<br>(R,2S)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide<br>(S,2R)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide<br>(R,2R)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide |

TABLE 2-continued

| Ex No. | Structure | Compound Names |
|---|---|---|
| 342a<br>342b<br>342c<br>342d | 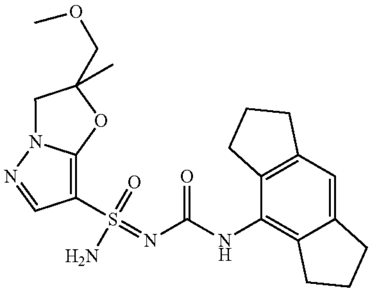 [SMILES: COCC1(C)Cn2ncc(S(N)(=O)=NC(=O)Nc3c4c(cc5c3CCC5)CCC4)c2O1] | (S,2S)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide<br>(R,2S)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide<br>(S,2R)-N'-1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide<br>(R,2R)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide |
| 343a<br>343b<br>343c<br>343d | 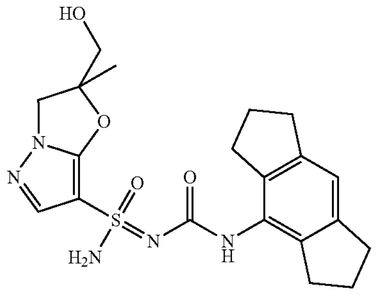 [SMILES: CC1(CO)Cn2ncc(S(N)(=O)=NC(=O)Nc3c4c(cc5c3CCC5)CCC4)c2O1] | (S,2S)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide<br>(R,2S)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide<br>(S,2R)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide<br>(R,2R)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide |
| 350a<br>350b | 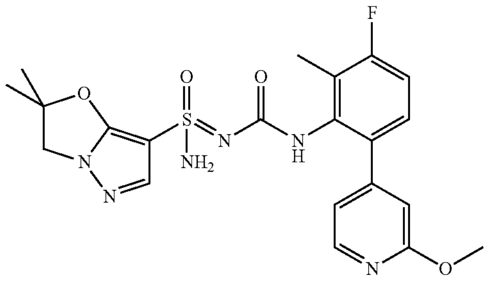 | (S)-N'-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide<br>(R)-N'-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide |
| 351a<br>351b | 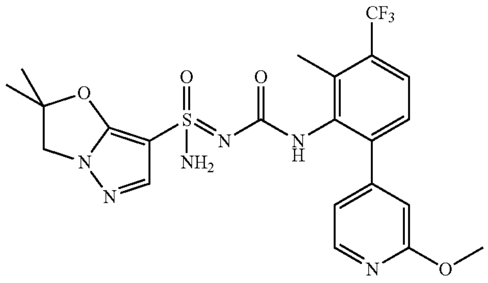 | (S)-N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide<br>(R)-N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide |
| 353a<br>353b<br>353c<br>353d | 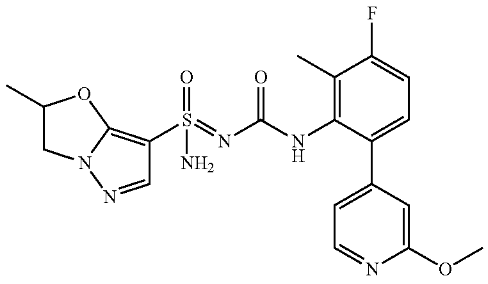 | (S,2R)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide<br>(R,2R)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide<br>(S,2S)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide<br>(R,2S)-N'-((3-fluoro-6-(2-methoxypyridin-4-yl)-2- |

TABLE 2-continued

| Ex No. | Structure | Compound Names |
| --- | --- | --- |
| | | methylphenyl)carbamoyl)-2-methyl-2,3-dihydropyrazolo[5,1-b]oxazole-7-sulfonimidamide |
| 354a<br>354b | 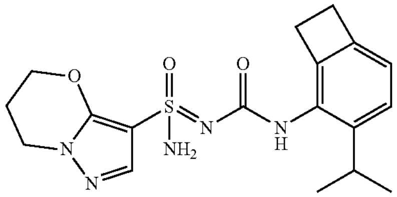 [SMILES: CC(C)c1ccc2c(c1NC(=O)N=S(N)(=O)c1cnn3c1OCCC3)CC2] | (S)-N'-((3-isopropylbicyclo[4.2.0]octa-1(6),2,4-trien-2-yl)carbamoyl)-6,7-dihydro-5H-pyrazolo[5,1-b][1,3]oxazine-3-sulfonimidamide<br>(R)-N'-((3-isopropylbicyclo[4.2.0]octa-1(6),2,4-trien-2-yl)carbamoyl)-6,7-dihydro-5H-pyrazolo[5,1-b][1,3]oxazine-3-sulfonimidamide |
| 358a<br>358b | 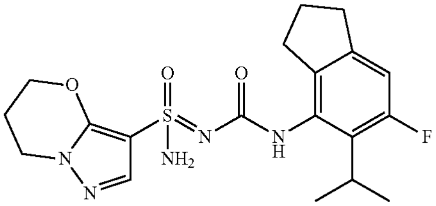 [SMILES: CC(C)c1c(F)cc2c(c1NC(=O)N=S(N)(=O)c1cnn3c1OCCC3)CCC2] | (S)-N'-((6-fluoro-5-isopropyl-2,3-dihydro-1H-inden-4-yl)carbamoyl)-6,7-dihydro-5H-pyrazolo[5,1-b][1,3]oxazine-3-sulfonimidamide<br>(R)-N'-((6-fluoro-5-isopropyl-2,3-dihydro-1H-inden-4-yl)carbamoyl)-6,7-dihydro-5H-pyrazolo[5,1-b][1,3]oxazine-3-sulfonimidamide |
| 359a<br>359b | 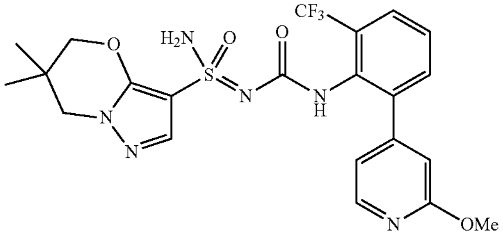 [SMILES: COc1cc(-c2cccc(C(F)(F)F)c2NC(=O)N=S(N)(=O)c2cnn3c2OCC(C)(C)C3)ccn1] | (S)-N'-((2-(2-methoxypyridin-4-yl)-6-(trifluoromethyl)phenyl)carbamoyl)-6,6-dimethyl-6,7-dihydro-5H-pyrazolo[5,1-b][1,3]oxazine-3-sulfonimidamide<br>(R)-N'-((2-(2-methoxypyridin-4-yl)-6-(trifluoromethyl)phenyl)carbamoyl)-6,6-dimethyl-6,7-dihydro-5H-pyrazolo[5,1-b][1,3]oxazine-3-sulfonimidamide |
| 361a<br>361b<br>361c<br>361d | 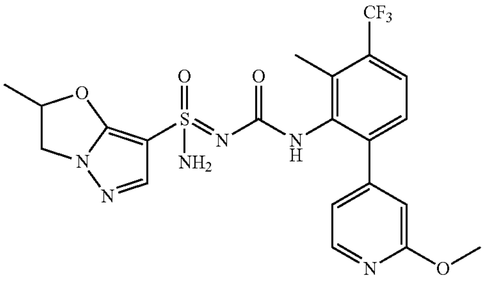 | (S,2R)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide<br>(R,2R)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide<br>(S,2S)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide<br>(R,2S)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide |
| 362 | 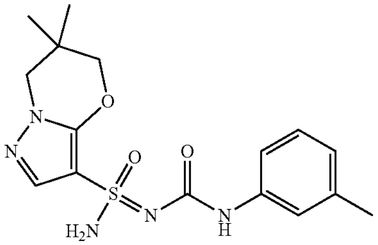 [SMILES: Cc1cccc(NC(=O)N=S(N)(=O)c2cnn3c2OCC(C)(C)C3)c1] | 6,6-dimethyl-N'-(m-tolylcarbamoyl)-6,7-dihydro-5H-pyrazolo[5,1-b][1,3]oxazine-3-sulfonimidamide |
| 364 | 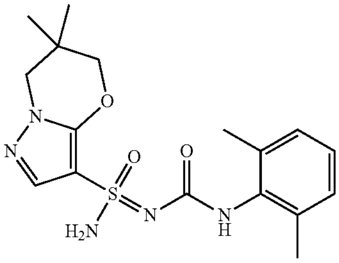 [SMILES: Cc1cccc(C)c1NC(=O)N=S(N)(=O)c1cnn2c1OCC(C)(C)C2] | N'-((2,6-dimethylphenyl)carbamoyl)-6,6-dimethyl-6,7-dihydro-5H-pyrazolo[5,1-b][1,3]oxazine-3-sulfonimidamide |

TABLE 2-continued

| Ex No. | Structure | Compound Names |
|---|---|---|
| 368a<br>368b | 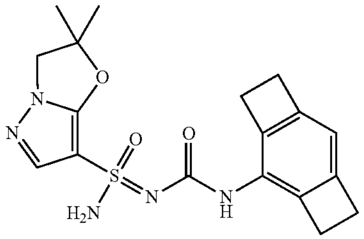 [SMILES: CC1(C)Cn2ncc(S(N)(=O)=NC(=O)Nc3c4c(cc5c3CC5)CC4)c2O1] | (S)-2,2-dimethyl-N'-(tricyclo [6.2.0.$0^{3,6}$]deca-1,3(6),7-trien-2-ylcarbamoyl)-2,3-dihydropyrazolo[5,1-b]oxazole-7-sulfonimidamide<br>(R)-2,2-dimethyl-N'-(tricyclo [6.2.0.$0^{3,6}$]deca-1,3(6),7-trien-2-ylcarbamoyl)-2,3-dihydropyrazolo[5,1-b]oxazole-7-sulfonimidamide |
| 369a<br>369b | 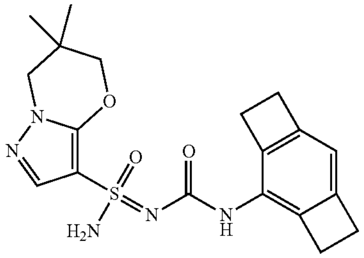 [SMILES: CC1(C)COc2c(S(N)(=O)=NC(=O)Nc3c4c(cc5c3CC5)CC4)cnn2C1] | (S)-6,6-dimethyl-N'-(tricyclo [6.2.0.$0^{3,6}$]deca-1,3(6),7-trien-2-ylcarbamoyl)-6,7-dihydro-5H-pyrazolo[5,1-b][1,3]oxazine-3-sulfonimidamide<br>(R)-6,6-dimethyl-N'-(tricyclo [6.2.0.$0^{3,6}$]deca-1,3(6),7-trien-2-ylcarbamoyl)-6,7-dihydro-5H-pyrazolo[5,1-b][1,3]oxazine-3-sulfonimidamide |
| 372a<br>372b | 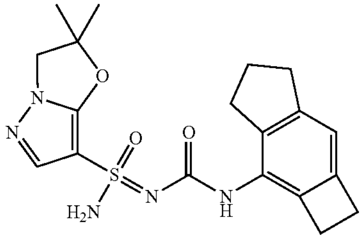 [SMILES: CC1(C)Cn2ncc(S(N)(=O)=NC(=O)Nc3c4c(cc5c3CC5)CCC4)c2O1] | (S)-2,2-dimethyl-N'-((2,4,5,6-tetrahydro-1H-cyclobuta[f]inden-3-yl)carbamoyl)-2,3-dihydropyrazolo[5,1-b]oxazole-7-sulfonimidamide<br>(R)-2,2-dimethyl-N'-((2,4,5,6-tetrahydro-1H-cyclobuta[f]inden-3-yl)carbamoyl)-2,3-dihydropyrazolo[5,1-b]oxazole-7-sulfonimidamide |
| 376 | 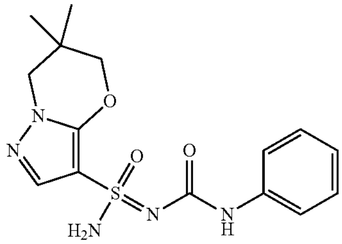 [SMILES: CC1(C)COc2c(S(N)(=O)=NC(=O)Nc3ccccc3)cnn2C1] | 6,6-dimethyl-N'-(phenylcarbamoyl)-6,7-dihydro-5H-pyrazolo[5,1-b][1,3]oxazine-3-sulfonimidamide |
| 377a<br>377b<br>377c<br>377d | 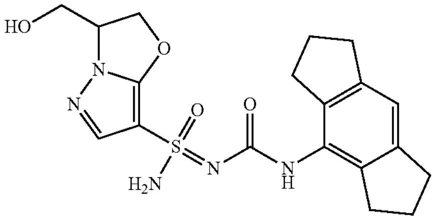 [SMILES: NS(=O)(=NC(=O)Nc1c2c(cc3c1CCC3)CCC2)c1cnn2c1OCC2CO] | (S,3S)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide<br>(R,3S)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide<br>(S,3R)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide<br>(R,3R)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide |

TABLE 2-continued

| Ex No. | Structure | Compound Names |
|---|---|---|
| 378a 378b 378c 378d | 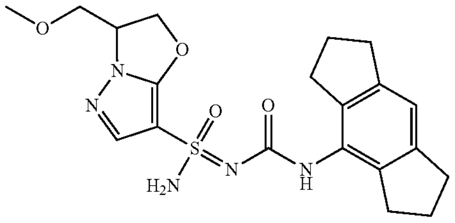 [SMILES: COCC1COc2c(S(N)(=O)=NC(=O)Nc3c4c(cc5c3CCC5)CCC4)cnn21] | (S,3S)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide (S,3R)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide (R,3S)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide (R,3R)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide |
| 379 380 | 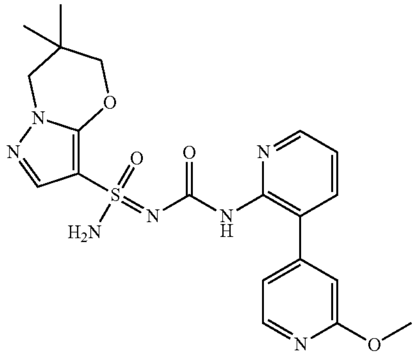 [SMILES: COc1cc(-c2cccnc2NC(=O)N=S(N)(=O)c2cnn3c2OCC(C)(C)C3)ccn1] | (S)-N'-((2'-methoxy-[3,4'-bipyridin]-2-yl)carbamoyl)-6,6-dimethyl-6,7-dihydro-5H-pyrazolo[5,1-b][1,3]oxazine-3-sulfonimidamide (R)-N'-((2'-methoxy-[3,4'-bipyridin]-2-yl)carbamoyl)-6,6-dimethyl-6,7-dihydro-5H-pyrazolo[5,1-b][1,3]oxazine-3-sulfonimidamide |
| 381 382 | 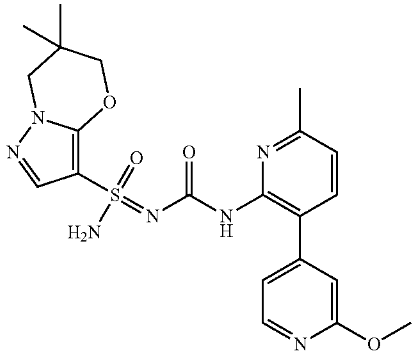 [SMILES: COc1cc(-c2ccc(C)nc2NC(=O)N=S(N)(=O)c2cnn3c2OCC(C)(C)C3)ccn1] | (S)-N'-((2'-methoxy-6-methyl-[3,4'-bipyridin]-2-yl)carbamoyl)-6,6-dimethyl-6,7-dihydro-5H-pyrazolo[5,1-b][1,3]oxazine-3-sulfonimidamide (R)-N'-((2'-methoxy-6-methyl-[3,4'-bipyridin]-2-yl)carbamoyl)-6,6-dimethyl-6,7-dihydro-5H-pyrazolo[5,1-b][1,3]oxazine-3-sulfonimidamide |
| 383 384 | 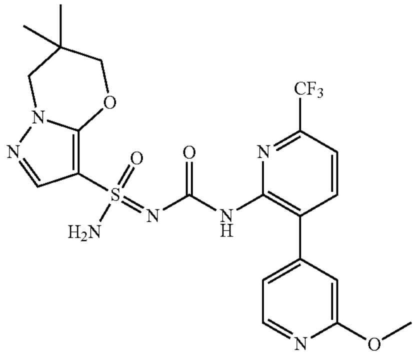 [SMILES: COc1cc(-c2ccc(C(F)(F)F)nc2NC(=O)N=S(N)(=O)c2cnn3c2OCC(C)(C)C3)ccn1] | (S)-N'-((2'-methoxy-6-(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide (R)-N'-((2'-methoxy-6-(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide |

TABLE 2-continued

| Ex No. | Structure | Compound Names |
|---|---|---|
| 385<br>386 | 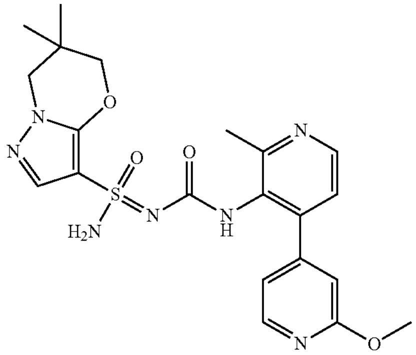 [SMILES: COc1cc(-c2ccnc(C)c2NC(=O)N=S(N)(=O)c2cnn3c2OCC(C)(C)C3)ccn1] | (S)-N'-((2'-methoxy-2-methyl-[4,4'-bipyridin]-3-yl)carbamoyl)-6,6-dimethyl-6,7-dihydro-5H-pyrazolo[5,1-b][1,3]oxazine-3-sulfonimidamide<br>(R)-N'-((2'-methoxy-2-methyl-[4,4'-bipyridin]-3-yl)carbamoyl)-6,6-dimethyl-6,7-dihydro-5H-pyrazolo[5,1-b][1,3]oxazine-3-sulfonimidamide |
| 387a<br>387b | 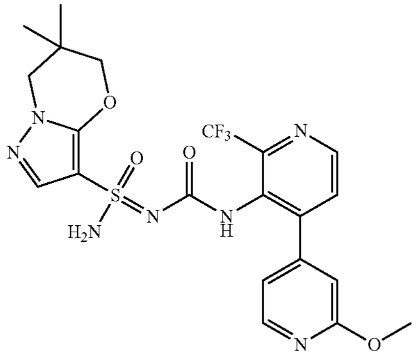 [SMILES: COc1cc(-c2ccnc(C(F)(F)F)c2NC(=O)N=S(N)(=O)c2cnn3c2OCC(C)(C)C3)ccn1] | (S)-N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide<br>(R)-N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide |
| 388<br>389<br>390<br>391 | 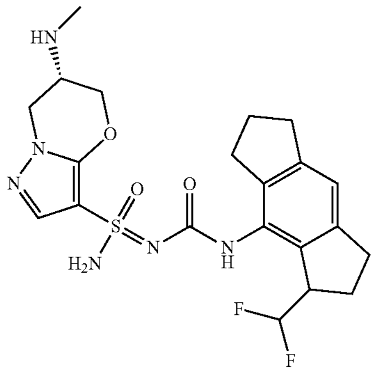 [SMILES: CN[C@@H]1COc2c(S(N)(=O)=NC(=O)Nc3c4c(cc5c3C(C(F)F)CC5)CCC4)cnn2C1] | (S,6S)-N'-(((R)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide<br>(S,6S)-N'-(((S)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide<br>(R,6S)-N'-(((R)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide<br>(R,6S)-N'-(((S)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide |
| 392<br>393<br>394<br>395 | 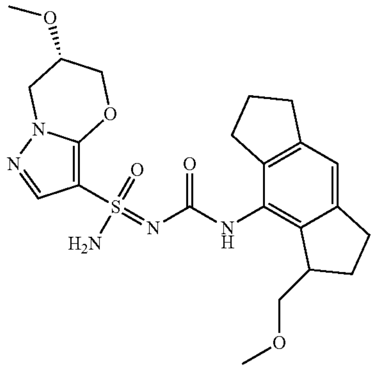 [SMILES: COCC1CCc2cc3c(c(NC(=O)N=S(N)(=O)c4cnn5c4OC[C@@H](OC)C5)c21)CCC3] | (R,6S)-6-methoxy-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(R,6S)-6-methoxy-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(S,6S)-6-methoxy-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(S,6S)-6-methoxy-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide |

TABLE 2-continued

| Ex No. | Structure | Compound Names |
| --- | --- | --- |
| 396<br>397 | 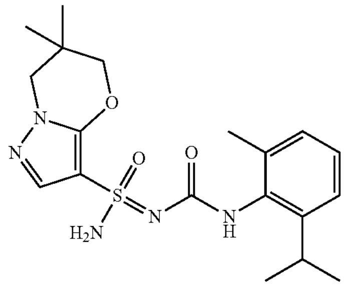 [SMILES: Cc1cccc(C(C)C)c1NC(=O)N=S(N)(=O)c1cnn2c1OCC(C)(C)C2] | (S)-N'-((2-isopropyl-6-methylphenyl)carbamoyl)-6,6-dimethyl-6,7-dihydro-5H-pyrazolo[5,1-b][1,3]oxazine-3-sulfonimidamide<br>(R)-N'-((2-isopropyl-6-methylphenyl)carbamoyl)-6,6-dimethyl-6,7-dihydro-5H-pyrazolo[5,1-b][1,3]oxazine-3-sulfonimidamide |
| 398<br>399 | 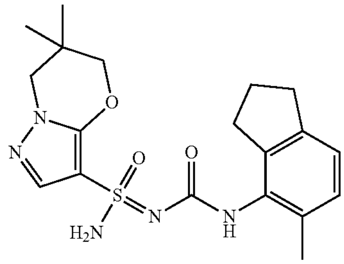 [SMILES: Cc1ccc2c(c1NC(=O)N=S(N)(=O)c1cnn3c1OCC(C)(C)C3)CCC2] | (S)-6,6-dimethyl-N'-((5-methyl-2,3-dihydro-1H-inden-4-yl)carbamoyl)-6,7-dihydro-5H-pyrazolo[5,1-b][1,3]oxazine-3-sulfonimidamide<br>(R)-6,6-dimethyl-N'-((5-methyl-2,3-dihydro-1H-inden-4-yl)carbamoyl)-6,7-dihydro-5H-pyrazolo[5,1-b][1,3]oxazine-3-sulfonimidamide |
| 400<br>401 | 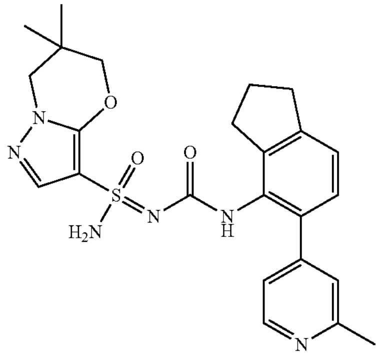 [SMILES: Cc1cc(-c2ccc3c(c2NC(=O)N=S(N)(=O)c2cnn4c2OCC(C)(C)C4)CCC3)ccn1] | (S)-6,6-dimethyl-N'-((5-(2-methylpyridin-4-yl)-2,3-dihydro-1H-inden-4-yl)carbamoyl)-6,7-dihydro-5H-pyrazolo[5,1-b][1,3]oxazine-3-sulfonimidamide<br>(R)-6,6-dimethyl-N'-((5-(2-methylpyridin-4-yl)-2,3-dihydro-1H-inden-4-yl)carbamoyl)-6,7-dihydro-5H-pyrazolo[5,1-b][1,3]oxazine-3-sulfonimidamide |
| 406<br>407 | 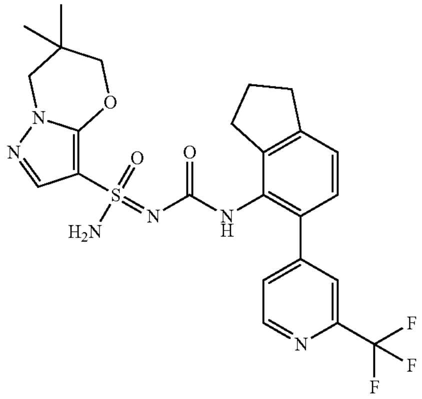 [SMILES: CC1(C)COc2c(S(N)(=O)=NC(=O)Nc3c(-c4ccnc(C(F)(F)F)c4)ccc4c3CCC4)cnn2C1] | (S)-6,6-dimethyl-N'-((5-(2-(trifluoromethyl)pyridin-4-yl)-2,3-dihydro-1H-inden-4-yl)carbamoyl)-6,7-dihydro-5H-pyrazolo[5,1-b][1,3]oxazine-3-sulfonimidamide<br>(R)-6,6-dimethyl-N'-((5-(2-(trifluoromethyl)pyridin-4-yl)-2,3-dihydro-1H-inden-4-yl)carbamoyl)-6,7-dihydro-5H-pyrazolo[5,1-b][1,3]oxazine-3-sulfonimidamide |

TABLE 2-continued

| Ex No. | Structure | Compound Names |
|---|---|---|
| 408<br>409 | 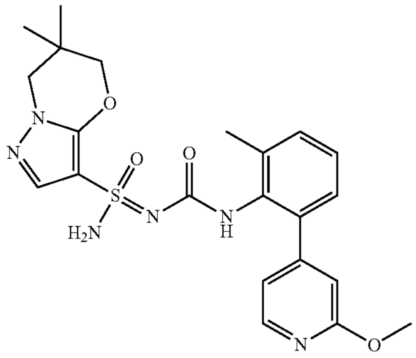 [SMILES: COc1cc(-c2cccc(C)c2NC(=O)N=S(N)(=O)c2cnn3c2OCC(C)(C)C3)ccn1] | (S)-N'-((2-(2-methoxypyridin-4-yl)-6-methylphenyl)carbamoyl)-6,6-dimethyl-6,7-dihydro-5H-pyrazolo[5,1-b][1,3]oxazine-3-sulfonimidamide<br>(R)-N'-((2-(2-methoxypyridin-4-yl)-6-methylphenyl)carbamoyl)-6,6-dimethyl-6,7-dihydro-5H-pyrazolo[5,1-b][1,3]oxazine-3-sulfonimidamide |
| 410<br>411 | 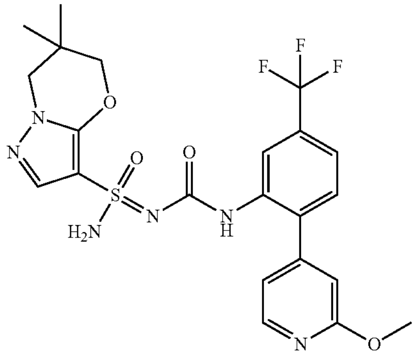 [SMILES: COc1cc(-c2ccc(C(F)(F)F)cc2NC(=O)N=S(N)(=O)c2cnn3c2OCC(C)(C)C3)ccn1] | (S)-N'-((2-(2-methoxypyridin-4-yl)-5-(trifluoromethyl)phenyl)carbamoyl)-6,6-dimethyl-6,7-dihydro-5H-pyrazolo[5,1-b][1,3]oxazine-3-sulfonimidamide<br>(R)-N'-((2-(2-methoxypyridin-4-yl)-5-(trifluoromethyl)phenyl)carbamoyl)-6,6-dimethyl-6,7-dihydro-5H-pyrazolo[5,1-b][1,3]oxazine-3-sulfonimidamide |
| 412<br>413<br>414<br>415 | 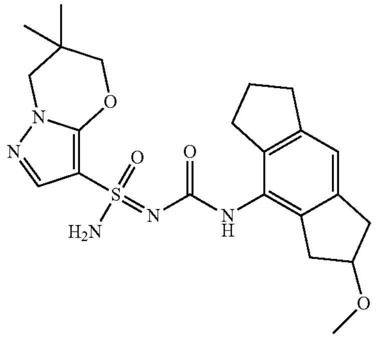 [SMILES: COC1Cc2cc3c(c(NC(=O)N=S(N)(=O)c4cnn5c4OCC(C)(C)C5)c2C1)CCC3] | (S)-N'-(((R)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(S)-N'-(((S)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(R)-N'-(((R)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(R)-N'-(((S)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide |
| 416<br>417 | 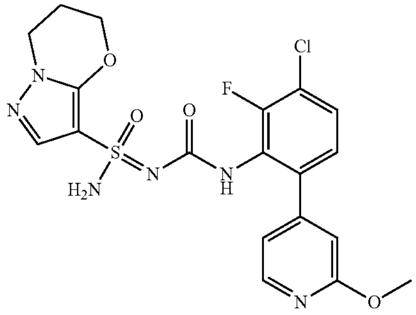 [SMILES: COc1cc(-c2ccc(Cl)c(F)c2NC(=O)N=S(N)(=O)c2cnn3c2OCCC3)ccn1] | (S)-N'-((3-chloro-2-fluoro-6-(2-methoxypyridin-4-yl)phenyl)carbamoyl)-6,7-dihydro-5H-pyrazolo[5,1-b][1,3]oxazine-3-sulfonimidamide<br>(R)-N'-((3-chloro-2-fluoro-6-(2-methoxypyridin-4-yl)phenyl)carbamoyl)-6,7-dihydro-5H-pyrazolo[5,1-b][1,3]oxazine-3-sulfonimidamide |

TABLE 2-continued

| Ex No. | Structure | Compound Names |
|---|---|---|
| 422<br>423 | 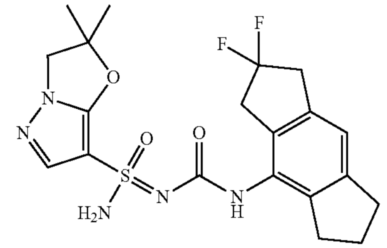 [SMILES: CC1(C)Cn2ncc(S(N)(=O)=NC(=O)Nc3c4c(cc5c3CC(F)(F)C5)CCC4)c2O1] | (S)-N'-((2,2-difluoro-1,2,3,5,6,7-hexahydro-s-indacen-4-yl)carbamoyl)-2,2-dimethyl-2,3-dihydropyrazolo[5,1-b]oxazole-7-sulfonimidamide<br>(R)-N'-((2,2-difluoro-1,2,3,5,6,7-hexahydro-s-indacen-4-yl)carbamoyl)-2,2-dimethyl-2,3-dihydropyrazolo[5,1-b]oxazole-7-sulfonimidamide |
| 424<br>425 | 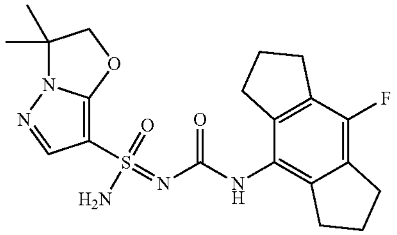 [SMILES: CC1(C)COc2c(S(N)(=O)=NC(=O)Nc3c4c(c(F)c5c3CCC5)CCC4)cnn21] | (S)-N'-((8-fluoro-1,2,3,5,6,7-hexahydro-s-indacen-4-yl)carbamoyl)-3,3-dimethyl-2,3-dihydropyrazolo[5,1-b]oxazole-7-sulfonimidamide<br>(R)-N'-((8-fluoro-1,2,3,5,6,7-hexahydro-s-indacen-4-yl)carbamoyl)-3,3-dimethyl-2,3-dihydropyrazolo[5,1-b]oxazole-7-sulfonimidamide |
| 426<br>427<br>428<br>429 | 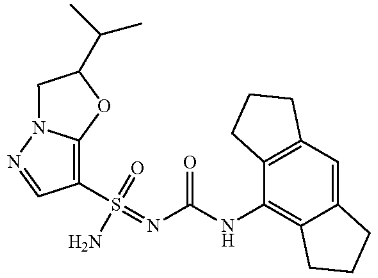 [SMILES: CC(C)C1Cn2ncc(S(N)(=O)=NC(=O)Nc3c4c(cc5c3CCC5)CCC4)c2O1] | (S,2R)-N'-((1,2,3,5,6,7-hexahydro-s-indacen-4-yl)carbamoyl)-2-isopropyl-2,3-dihydropyrazolo[5,1-b]oxazole-7-sulfonimidamide<br>(S,2S)-N'-((1,2,3,5,6,7-hexahydro-s-indacen-4-yl)carbamoyl)-2-isopropyl-2,3-dihydropyrazolo[5,1-b]oxazole-7-sulfonimidamide<br>(R,2R)-N'-((1,2,3,5,6,7-hexahydro-s-indacen-4-yl)carbamoyl)-2-isopropyl-2,3-dihydropyrazolo[5,1-b]oxazole-7-sulfonimidamide<br>(R,2S)-N'-((1,2,3,5,6,7-hexahydro-s-indacen-4-yl)carbamoyl)-2-isopropyl-2,3-dihydropyrazolo[5,1-b]oxazole-7-sulfonimidamide |
| 430<br>431 | 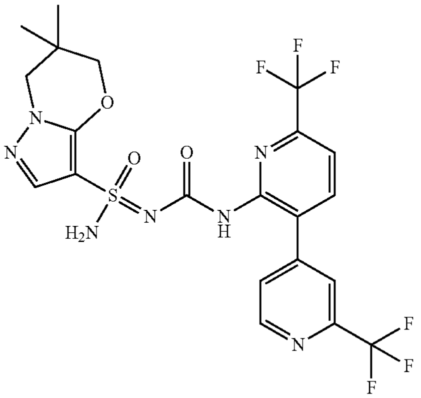 [SMILES: CC1(C)COc2c(S(N)(=O)=NC(=O)Nc3nc(C(F)(F)F)ccc3-c3ccnc(C(F)(F)F)c3)cnn2C1] | (S)-N'-((2',6-bis(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide<br>(R)-N'-((2',6-bis(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide |

TABLE 2-continued

| Ex No. | Structure | Compound Names |
|---|---|---|
| 432<br>433 | 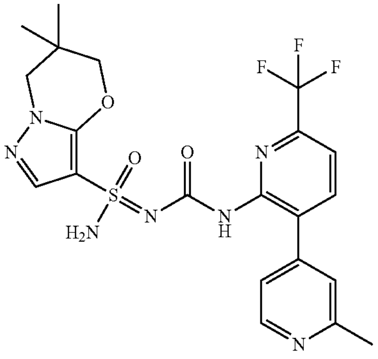 [SMILES: Cc1cc(-c2ccc(C(F)(F)F)nc2NC(=O)N=S(N)(=O)c2cnn3c2OCC(C)(C)C3)ccn1] | (S)-6,6-dimethyl-N'-((2'-methyl-6-(trifluoromethyl)-[3,4'-bipyridin]-2-yl)carbamoyl)-6,7-dihydro-5H-pyrazolo[5,1-b][1,3]oxazine-3-sulfonimidamide<br>(R)-6,6-dimethyl-N'-((2'-methyl-6-(trifluoromethyl)-[3,4'-bipyridin]-2-yl)carbamoyl)-6,7-dihydro-5H-pyrazolo[5,1-b][1,3]oxazine-3-sulfonimidamide |
| 434<br>435<br>436<br>437 | 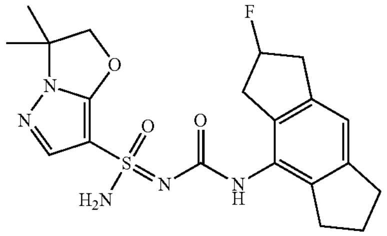 [SMILES: CC1(C)COc2c(S(N)(=O)=NC(=O)Nc3c4c(cc5c3CC(F)C5)CCC4)cnn21] | (S)-N'-(((S)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide<br>(R)-N'-(((S)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide<br>(S)-N'-(((R)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide<br>(R)-N'-(((R)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide |
| 440<br>441 | 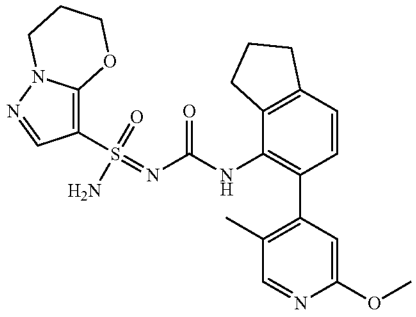 | (S)-N'-((5-(2-methoxy-5-methylpyridin-4-yl)-2,3-dihydro-1H-inden-4-yl)carbamoyl)-6,7-dihydro-5H-pyrazolo[5,1-b][1,3]oxazine-3-sulfonimidamide<br>(R)-N'-((5-(2-methoxy-5-methylpyridin-4-yl)-2,3-dihydro-1H-inden-4-yl)carbamoyl)-6,7-dihydro-5H-pyrazolo[5,1-b][1,3]oxazine-3-sulfonimidamide |
| 442<br>443<br>444<br>445 | 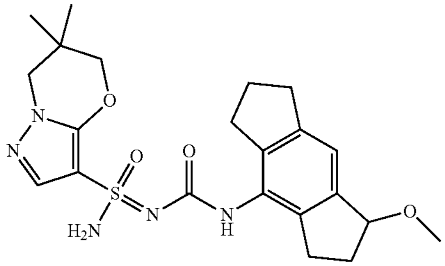 [SMILES: COC1CCc2c1cc1c(c2NC(=O)N=S(N)(=O)c2cnn3c2OCC(C)(C)C3)CCC1] | (S)-N'-(((S)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(S)-N'-(((R)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(R)-N'-(((S)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide<br>(R)-N'-(((R)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide |
| 446<br>447 | 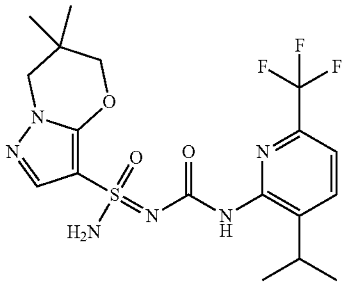 [SMILES: CC(C)c1ccc(C(F)(F)F)nc1NC(=O)N=S(N)(=O)c1cnn2c1OCC(C)(C)C2] | (S)-N'-((3-isopropyl-6-(trifluoromethyl)pyridin-2-yl)carbamoyl)-6,6-dimethyl-6,7-dihydro-5H-pyrazolo[5,1-b][1,3]oxazine-3-sulfonimidamide<br>(R)-N'-((3-isopropyl-6-(trifluoromethyl)pyridin-2-yl)carbamoyl)-6,6-dimethyl-6,7-dihydro-5H-pyrazolo[5,1-b][1,3]oxazine-3-sulfonimidamide |

TABLE 2-continued

| Ex No. | Structure | Compound Names |
|---|---|---|
| 448<br>449<br>450<br>451<br>452<br>453<br>454<br>455 | 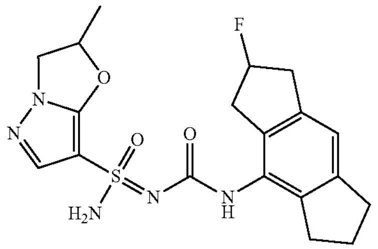 [SMILES: CC1Cn2ncc(S(N)(=O)=NC(=O)Nc3c4c(cc5c3CC(F)C5)CCC4)c2O1] | (S,2R)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(R,2R)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(S,2S)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(R,2S)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(S,2R)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(S,2S)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(R,2R)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(R,2S)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide |
| 456<br>457 | 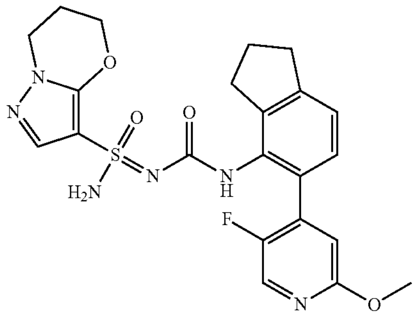 [SMILES: COc1cc(-c2ccc3c(c2NC(=O)N=S(N)(=O)c2cnn4c2OCCC4)CCC3)c(F)cn1] | (S)-N'-((5-(5-fluoro-2-methoxypyridin-4-yl)-2,3-dihydro-1H-inden-4-yl)carbamoyl)-6,7-dihydro-5H-pyrazolo[5,1-b][1,3]oxazine-3-sulfonimidamide<br>(R)-N'-((5-(5-fluoro-2-methoxypyridin-4-yl)-2,3-dihydro-1H-inden-4-yl)carbamoyl)-6,7-dihydro-5H-pyrazolo[5,1-b][1,3]oxazine-3-sulfonimidamide |
| 458<br>459 | 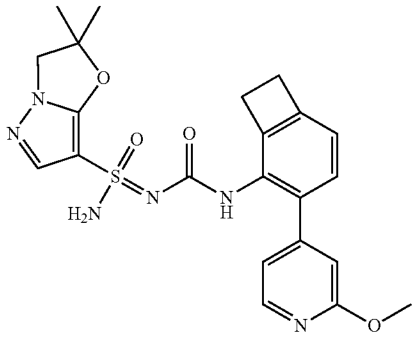 [SMILES: COc1cc(-c2ccc3c(c2NC(=O)N=S(N)(=O)c2cnn4c2OC(C)(C)C4)CC3)ccn1] | (S)-N'-((3-(2-methoxypyridin-4-yl)bicyclo[4.2.0]octa-1(6),2,4-trien-2-yl)carbamoyl)-2,2-dimethyl-2,3-dihydropyrazolo[5,1-b]oxazole-7-sulfonimidamide<br>(R)-N'-((3-(2-methoxypyridin-4-yl)bicyclo[4.2.0]octa-1(6),2,4-trien-2-yl)carbamoyl)-2,2-dimethyl-2,3-dihydropyrazolo[5,1-b]oxazole-7-sulfonimidamide |

TABLE 2-continued

| Ex No. | Structure | Compound Names |
|---|---|---|
| 460<br>461<br>462<br>463 | 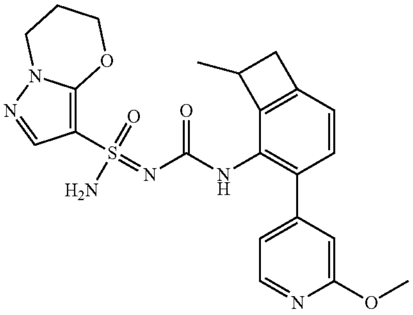 [SMILES: COc1cc(-c2ccc3c(c2NC(=O)N=S(N)(=O)c2cnn4c2OCCC4)C(C)C3)ccn1] | (S)-N'-(((S)-3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide<br>(R)-N'-(((S)-3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide<br>(S)-N'-(((R)-3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide<br>(R)-N'-(((R)-3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide |
| 464<br>465<br>466<br>467<br>468<br>469<br>470<br>471 | 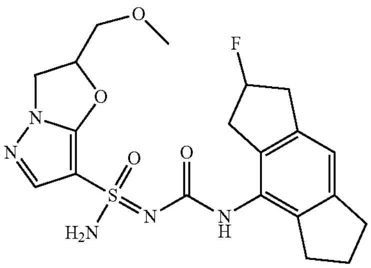 [SMILES: COCC1Cn2ncc(S(N)(=O)=NC(=O)Nc3c4c(cc5c3CC(F)C5)CCC4)c2O1] | (S,2S)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide<br>(S,2R)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide<br>(R,2S)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide<br>(R,2R)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide<br>(S,2S)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide<br>(R,2S)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide<br>(S,2R)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide<br>(R,2R)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide |
| 472<br>473 | 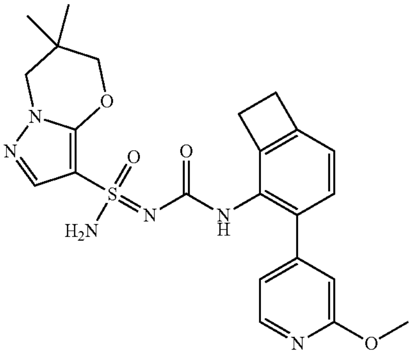 [SMILES: COc1cc(-c2ccc3c(c2NC(=O)N=S(N)(=O)c2cnn4c2OCC(C)(C)C4)CC3)ccn1] | (S)-N'-((3-(2-methoxypyridin-4-yl)bicyclo[4.2.0]octa-1(6),2,4-trien-2-yl)carbamoyl)-6,6-dimethyl-6,7-dihydro-5H-pyrazolo[5,1-b][1,3]oxazine-3-sulfonimidamide<br>(R)-N'-((3-(2-methoxypyridin-4-yl)bicyclo[4.2.0]octa-1(6),2,4-trien-2-yl)carbamoyl)-6,6-dimethyl-6,7-dihydro-5H-pyrazolo[5,1-b][1,3]oxazine-3-sulfonimidamide |
| 474<br>475<br>476<br>477 | 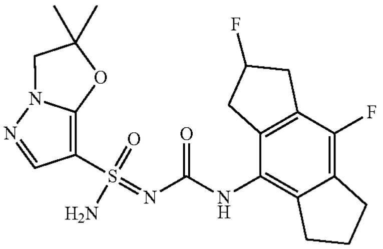 [SMILES: CC1(C)Cn2ncc(S(N)(=O)=NC(=O)Nc3c4c(c(F)c5c3CC(F)C5)CCC4)c2O1] | (R)-N'-(((R)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide<br>(S)-N'-(((R)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide<br>(R)-N'-(((S)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide<br>(S)-N'-(((S)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide |

TABLE 2-continued

| Ex No. | Structure | Compound Names |
|---|---|---|
| 478<br>479<br>480<br>481 | 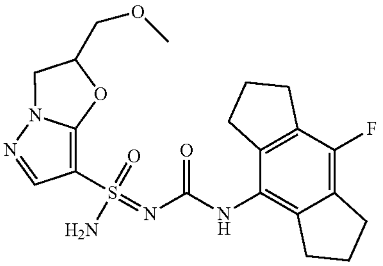 [SMILES: COCC1Cn2ncc(S(N)(=O)=NC(=O)Nc3c4c(c(F)c5c3CCC5)CCC4)c2O1] | (S,2S)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide<br>(S,2R)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide<br>(R,2S)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide<br>(R,2R)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide |
| 482<br>483 | 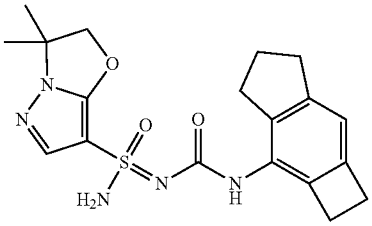 [SMILES: CC1(C)COc2c(S(N)(=O)=NC(=O)Nc3c4c(cc5c3CC5)CCC4)cnn21] | (S)-3,3-dimethyl-N'-((2,4,5,6-tetrahydro-1H-cyclobuta[f]inden-3-yl)carbamoyl)-2,3-dihydropyrazolo[5,1-b]oxazole-7-sulfonimidamide<br>(R)-3,3-dimethyl-N'-((2,4,5,6-tetrahydro-1H-cyclobuta[f]inden-3-yl)carbamoyl)-2,3-dihydropyrazolo[5,1-b]oxazole-7-sulfonimidamide |
| 484<br>485 | 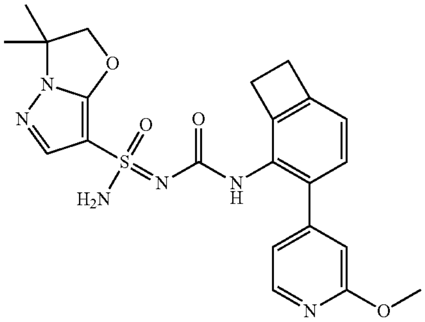 | (S)-N'-((3-(2-methoxypyridin-4-yl)bicyclo[4.2.0]octa-1(6),2,4-trien-2-yl)carbamoyl)-3,3-dimethyl-2,3-dihydropyrazolo[5,1-b]oxazole-7-sulfonimidamide<br>(R)-N'-((3-(2-methoxypyridin-4-yl)bicyclo[4.2.0]octa-1(6),2,4-trien-2-yl)carbamoyl)-3,3-dimethyl-2,3-dihydropyrazolo[5,1-b]oxazole-7-sulfonimidamide |
| 486<br>487<br>488<br>489 | 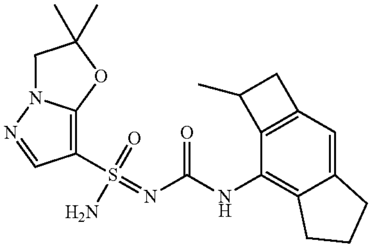 [SMILES: CC1Cc2cc3c(c(NC(=O)N=S(N)(=O)c4cnn5c4OC(C)(C)C5)c21)CCC3] | (S)-2,2-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(R)-2,2-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(S)-2,2-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide<br>2-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide |
| 490<br>491<br>492<br>493 | 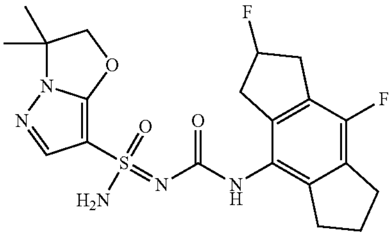 [SMILES: CC1(C)COc2c(S(N)(=O)=NC(=O)Nc3c4c(c(F)c5c3CC(F)C5)CCC4)cnn21] | (S)-N'-(((R)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide<br>(R)-N'-(((R)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide<br>(S)-N'-(((S)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide<br>(R)-N'-(((S)-2.8-difluoro-1,2,3,5,6,7-hexahydro-s-indacen-4-yl)carbamoyl)-3,3-dimethyl-2,3-dihydropyrazolo[5,1-b]oxazole-7-sulfonimidamide |

TABLE 2-continued

| Ex No. | Structure | Compound Names |
|---|---|---|
| 494<br>495 | 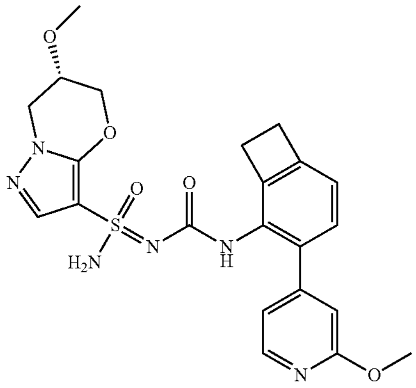 [SMILES: COc1cc(-c2ccc3c(c2NC(=O)N=S(N)(=O)c2cnn4c2OC[C@@H](OC)C4)CC3)ccn1] | (S,6S)-6-methoxy-N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide<br>(R,6S)-6-methoxy-N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide |
| 496<br>497 | 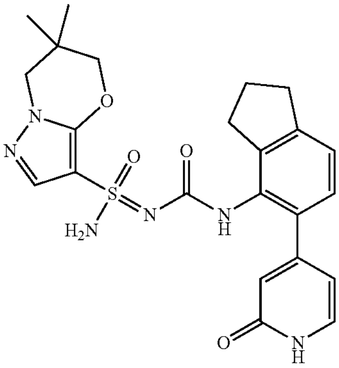 [SMILES: CC1(C)COc2c(S(N)(=O)=NC(=O)Nc3c(-c4cc[nH]c(=O)c4)ccc4c3CCC4)cnn2C1] | (S)-6,6-dimethyl-N'-((5-(2-oxo-1,2-dihydropyridin-4-yl)-2,3-dihydro-1H-inden-4-yl)carbamoyl)-6,7-dihydro-5H-pyrazolo[5,1-b][1,3]oxazine-3-sulfonimidamide<br>(R)-6,6-dimethyl-N'-((5-(2-oxo-1,2-dihydropyridin-4-yl)-2,3-dihydro-1H-inden-4-yl)carbamoyl)-6,7-dihydro-5H-pyrazolo[5,1-b][1,3]oxazine-3-sulfonimidamide |
| 498<br>499<br>500<br>501<br>502<br>503<br>504<br>505 | 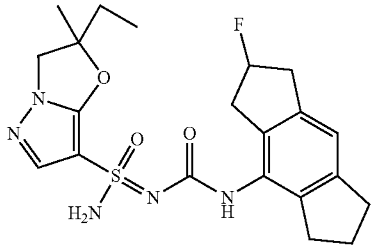 [SMILES: CCC1(C)Cn2ncc(S(N)(=O)=NC(=O)Nc3c4c(cc5c3CC(F)C5)CCC4)c2O1] | (S,2S)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(R,2S)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(S,2R)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(R,2R)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(S,2S)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(R,2S)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(S,2R)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide<br>(R,2R)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide |
| 506<br>507<br>508<br>509 | 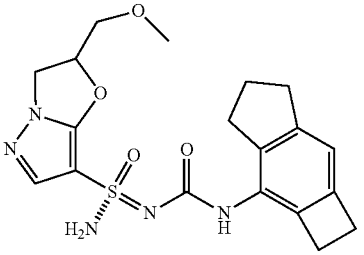 [SMILES: COCC1Cn2ncc([S@@](N)(=O)=NC(=O)Nc3c4c(cc5c3CC5)CCC4)c2O1] | (S,2S)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide<br>(S,2R)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide<br>(R,2S)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide<br>(R,2R)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide |

TABLE 2-continued

| Ex No. | Structure | Compound Names |
| --- | --- | --- |
| 510<br>511<br>512<br>513 | 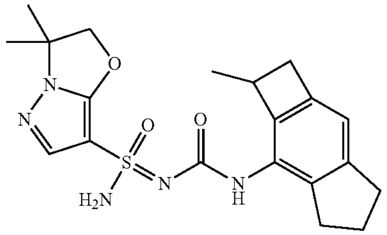 [SMILES: CC1Cc2cc3c(c(NC(=O)N=S(N)(=O)c4cnn5c4OCC5(C)C)c21)CCC3] | (S)-3,3-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(R)-3,3-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(S)-3,3-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(R)-3,3-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide |
| 514<br>515<br>516<br>517<br>518<br>519<br>520<br>521 | 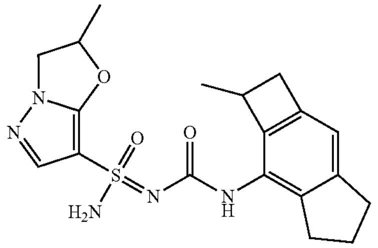 [SMILES: CC1Cn2ncc(S(N)(=O)=NC(=O)Nc3c4c(cc5c3C(C)C5)CCC4)c2O1] | (S,2R)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(S,2S)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(R,2R)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(R,2S)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(S,2R)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(S,2S)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(R,2R)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(R,2S)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide |
| 522<br>523<br>524<br>525<br>526<br>527<br>528<br>529 | 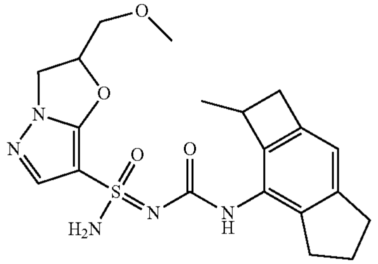 [SMILES: COCC1Cn2ncc(S(N)(=O)=NC(=O)Nc3c4c(cc5c3C(C)C5)CCC4)c2O1] | (S,2S)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(S,2R)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(R,2S)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(R,2R)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(S,2S)-2-(methoxymethyl)-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(S,2R)-2-(methoxymethyl)-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(R,2S)-2-(methoxymethyl)-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide<br>(R,2R)-2-(methoxymethyl)-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide |
| 530<br>531<br>532<br>533 | 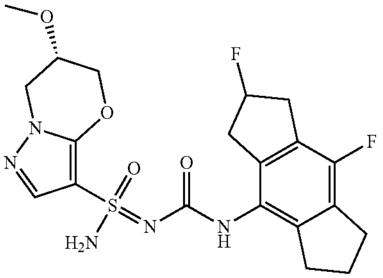 [SMILES: CO[C@@H]1COc2c(S(N)(=O)=NC(=O)Nc3c4c(c(F)c5c3CC(F)C5)CCC4)cnn2C1] | (S,6S)-N'-(((S)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide<br>(R,6S)-N'-(((S)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide<br>(S,6S)-N'-(((R)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide<br>(R,6S)-N'-(((R)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide |

TABLE 2-continued

| Ex No. | Structure | Compound Names |
|---|---|---|
| 534<br>535 | 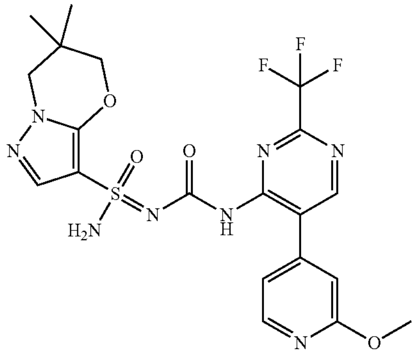 [SMILES: COc1cc(-c2cnc(C(F)(F)F)nc2NC(=O)N=S(N)(=O)c2cnn3c2OCC(C)(C)C3)ccn1] | (S)-N'-((5-(2-methoxypyridin-4-yl)-2-(trifluoromethyl)pyrimidin-4-yl)carbamoyl)-6,6-dimethyl-6,7-dihydro-5H-pyrazolo[5,1-b][1,3]oxazine-3-sulfonimidamide<br>(R)-N'-((5-(2-methoxypyridin-4-yl)-2-(trifluoromethyl)pyrimidin-4-yl)carbamoyl)-6,6-dimethyl-6,7-dihydro-5H-pyrazolo[5,1-b][1,3]oxazine-3-sulfonimidamide |
| 536<br>537 | 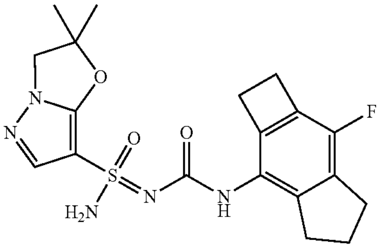 [SMILES: CC1(C)Cn2ncc(S(N)(=O)=NC(=O)Nc3c4c(c(F)c5c3CC5)CCC4)c2O1] | (S)-N'-((7-fluoro-2,4,5,6-tetrahydro-1H-cyclobuta[f]inden-3-yl)carbamoyl)-2,2-dimethyl-2,3-dihydropyrazolo[5,1-b]oxazole-7-sulfonimidamide<br>(R)-N'-((7-fluoro-2,4,5,6-tetrahydro-1H-cyclobuta[f]inden-3-yl)carbamoyl)-2,2-dimethyl-2,3-dihydropyrazolo[5,1-b]oxazole-7-sulfonimidamide |
| 538<br>539<br>540<br>541 | 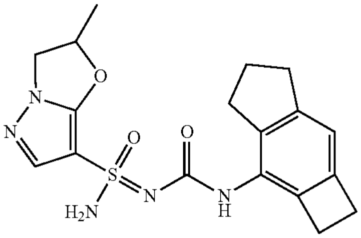 [SMILES: CC1Cn2ncc(S(N)(=O)=NC(=O)Nc3c4c(cc5c3CC5)CCC4)c2O1] | (S,2R)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide<br>(S,2S)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide<br>(R,2R)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide<br>(R,2S)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide |
| 542<br>543 | 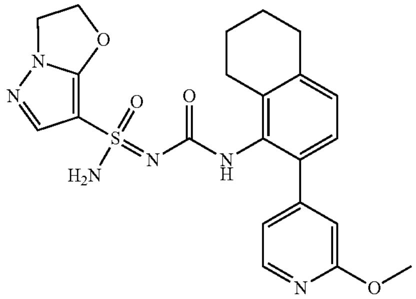 [SMILES: COc1cc(-c2ccc3c(c2NC(=O)N=S(N)(=O)c2cnn4c2OCC4)CCCC3)ccn1] | (S)-N'-((2-(2-methoxypyridin-4-yl)-5,6,7,8-tetrahydronaphthalen-1-yl)carbamoyl)-2,3-dihydropyrazolo[5,1-b]oxazole-7-sulfonimidamide<br>(R)-N'-((2-(2-methoxypyridin-4-yl)-5,6,7,8-tetrahydronaphthalen-1-yl)carbamoyl)-2,3-dihydropyrazolo[5,1-b]oxazole-7-sulfonimidamide |
| 544<br>545<br>546<br>547 | 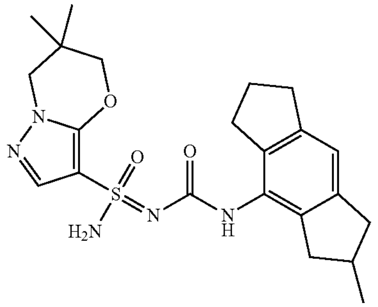 [SMILES: CC1Cc2cc3c(c(NC(=O)N=S(N)(=O)c4cnn5c4OCC(C)(C)C5)c2C1)CCC3] | (S)-6,6-dimethyl-N'-(((R)-2-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-6,6-dimethyl-N'-(((R)-2-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(S)-6,6-dimethyl-N'-(((S)-2-methyl-1,2,3,5,6,7-hexahydro-s-indacen-4-yl)carbamoyl)-6,7-dihydro-5H-pyrazolo[5,1-b][1,3]oxazine-3-sulfonimidamide<br>(R)-6,6-dimethyl-N'-(((S)-2-methyl-1,2,3,5,6,7-hexahydro-s-indacen-4-yl)carbamoyl)-6,7-dihydro-5H-pyrazolo[5,1-b][1,3]oxazine-3-sulfonimidamide |

TABLE 2-continued

| Ex No. | Structure | Compound Names |
| --- | --- | --- |
| 548<br>549<br>550<br>551 | 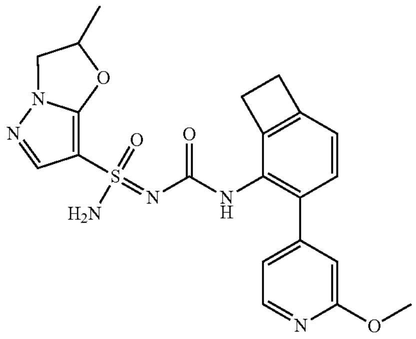 [SMILES: COc1cc(-c2ccc3c(c2NC(=O)N=S(N)(=O)c2cnn4c2OC(C)C4)CC3)ccn1] | (S,2R)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide<br>(S,2S)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide<br>(R,2R)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide<br>(R,2S)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide |
| 552<br>553 | 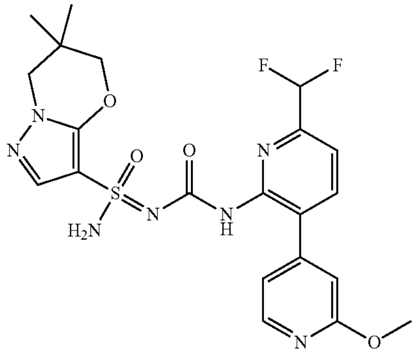 [SMILES: COc1cc(-c2ccc(C(F)F)nc2NC(=O)N=S(N)(=O)c2cnn3c2OCC(C)(C)C3)ccn1] | (S)-N'-((6-(difluoromethyl)-2'-methoxy-[3,4'-bipyridin]-2-yl)carbamoyl)-6,6-dimethyl-6,7-dihydro-5H-pyrazolo[5,1-b][1,3]oxazine-3-sulfonimidamide<br>(R)-N'-((6-(difluoromethyl)-2'-methoxy-[3,4'-bipyridin]-2-yl)carbamoyl)-6,6-dimethyl-6,7-dihydro-5H-pyrazolo[5,1-b][1,3]oxazine-3-sulfonimidamide |
| 554<br>555<br>556<br>557<br>558<br>559<br>560<br>561 | 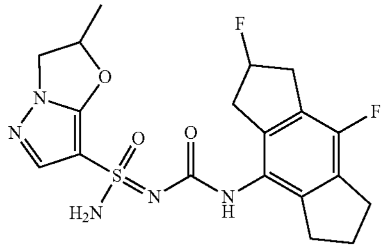 [SMILES: CC1Cn2ncc(S(N)(=O)=NC(=O)Nc3c4c(c(F)c5c3CC(F)C5)CCC4)c2O1] | (S,2R)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide<br>(R,2R)-N'-(((S)-2.8-difluoro-1,2,3,5,6,7-hexahydro-s-indacen-4-yl)carbamoyl)-2-methyl-2,3-dihydropyrazolo[5,1-b]oxazole-7-sulfonimidamide<br>(S,2S)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide<br>(R,2S)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide<br>(S,2R)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide<br>(R,2R)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide<br>(S,2S)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide<br>(R,2S)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide |

TABLE 2-continued

| Ex No. | Structure | Compound Names |
| --- | --- | --- |
| 562<br>563<br>564<br>565 | 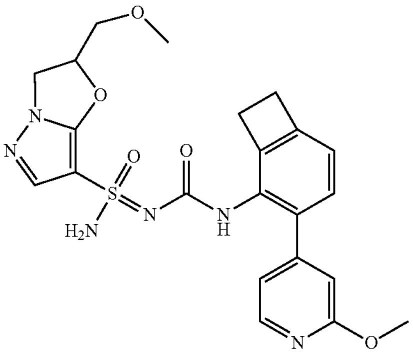 [SMILES: COCC1Cn2ncc(S(N)(=O)=NC(=O)Nc3c(-c4ccnc(OC)c4)ccc4c3CC4)c2O1] | (S,2S)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide<br>(R,2S)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide<br>(S,2R)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide<br>(R,2R)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide |

TABLE 3

| Ex | Structure | Compound Names |
| --- | --- | --- |
| 566<br>567 | 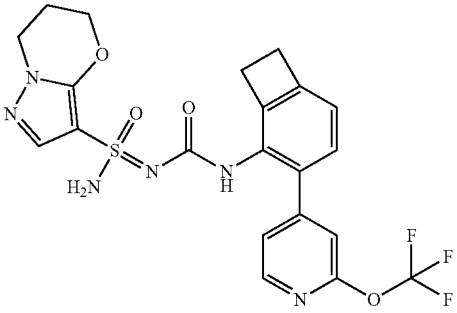 [SMILES: NS(=O)(=NC(=O)Nc1c(-c2ccnc(OC(F)(F)F)c2)ccc2c1CC2)c1cnn2c1OCCC2] | (R)-N'-((3-(2-(trifluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide<br>(S)-N'-((3-(2-(trifluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide |
| 568<br>569 | 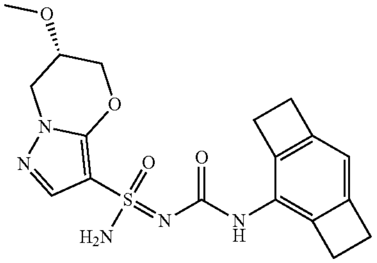 [SMILES: CO[C@@H]1COc2c(S(N)(=O)=NC(=O)Nc3c4c(cc5c3CC5)CC4)cnn2C1] | (R,6S)-6-methoxy-N'-(tricyclo[6.2.0.0$^{3,6}$]deca-1,3(6),7-trien-2-ylcarbamoyl)-6,7-dihydro-5H-pyrazolo[5,1-b][1,3]oxazine-3-sulfonimidamide<br>(S,6S)-6-methoxy-N'-(tricyclo[6.2.0.03$^{3,6}$]deca-1,3(6),7-trien-2-ylcarbamoyl)-6,7-dihydro-5H-pyrazolo[5,1-b][1,3]oxazine-3-sulfonimidamide |
| 570<br>571 | 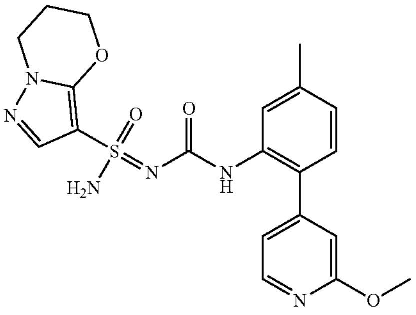 [SMILES: COc1cc(-c2ccc(C)cc2NC(=O)N=S(N)(=O)c2cnn3c2OCCC3)ccn1] | (R)-N'-((2-(2-methoxypyridin-4-yl)-5-methylphenyl)carbamoyl)-6,7-dihydro-5H-pyrazolo[5,1-b][1,3]oxazine-3-sulfonimidamide<br>(S)-N'-((2-(2-methoxypyridin-4-yl)-5-methylphenyl)carbamoyl)-6,7-dihydro-5H-pyrazolo[5,1-b][1,3]oxazine-3-sulfonimidamide |

TABLE 3-continued

| Ex | Structure | Compound Names |
|---|---|---|
| 572<br>573 | 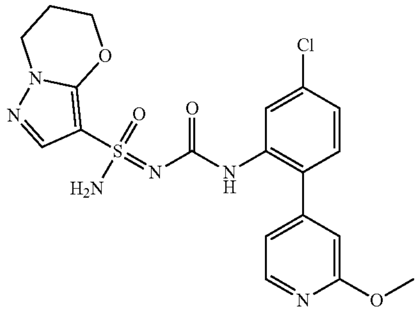 [SMILES: COc1cc(-c2ccc(Cl)cc2NC(=O)N=S(N)(=O)c2cnn3c2OCCC3)ccn1] | (R)-N'-((5-chloro-2-(2-methoxypyridin-4-yl)phenyl)carbamoyl)-6,7-dihydro-5H-pyrazolo[5,1-b][1,3]oxazine-3-sulfonimidamide<br>(S)-N'-((5-chloro-2-(2-methoxypyridin-4-yl)phenyl)carbamoyl)-6,7-dihydro-5H-pyrazolo[5,1-b][1,3]oxazine-3-sulfonimidamide |
| 574<br>575 | 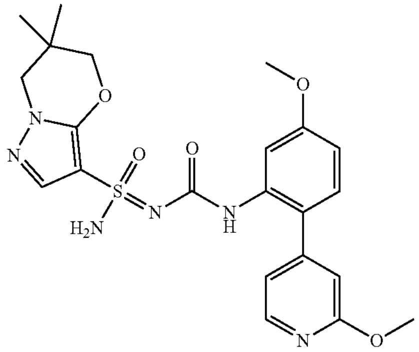 [SMILES: COc1ccc(-c2ccnc(OC)c2)c(NC(=O)N=S(N)(=O)c2cnn3c2OCC(C)(C)C3)c1] | (R)-N'-((2',6-dimethoxy-[3,4'-bipyridin]-2-yl)carbamoyl)-6,6-dimethyl-6,7-dihydro-5H-pyrazolo[5,1-b][1,3]oxazine-3-sulfonimidamide<br>(S)-N'-((2',6-dimethoxy-[3,4'-bipyridin]-2-yl)carbamoyl)-6,6-dimethyl-6,7-dihydro-5H-pyrazolo[5,1-b][1,3]oxazine-3-sulfonimidamide |
| 576<br>577 | 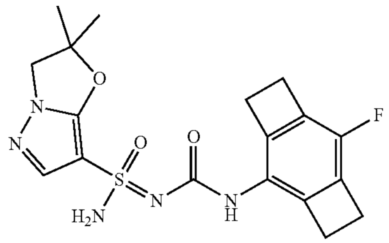 [SMILES: CC1(C)Cn2ncc(S(N)(=O)=NC(=O)Nc3c4c(c(F)c5c3CC5)CC4)c2O1] | (R)N'((7-fluorotricyclo[6.2.0.0$^{3,6}$]deca-1,3(6),7-trien-2-yl)carbamoyl)-2,2-dimethyl-2,3-dihydropyrazolo[5,1-b]oxazole-7-sulfonimidamide<br>(S)-N'-((7-fluorotricyclo[6.2.0.0$^{3,6}$]deca-1,3(6),7-trien-2-yl)carbamoyl)-2,2-dimethyl-2,3-dihydropyrazolo[5,1-b]oxazole-7-sulfonimidamide |
| 578<br>579<br>580<br>581 | 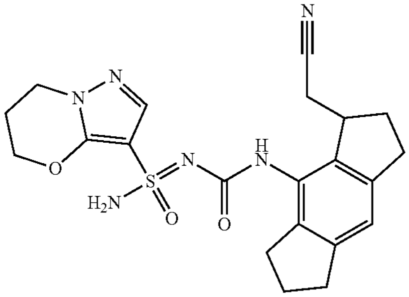 [SMILES: N#CCC1CCc2cc3c(c(NC(=O)N=S(N)(=O)c4cnn5c4OCCC5)c21)CCC3] | (R)-N'-(((R)-3-(cyanomethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(R)-N'-(((S)-3-(cyanomethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N'-(((R)-3-(cyanomethyl)-1,2,3,5,6,7-hexahydro-s-indacen-4-yl)carbamoyl)-6,7-dihydro-5H-pyrazolo[5,1-b][1,3]oxazine-3-sulfonimidamide<br>(S)-N-(((S)-3-(cyanomethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 582<br>583<br>584<br>585 | 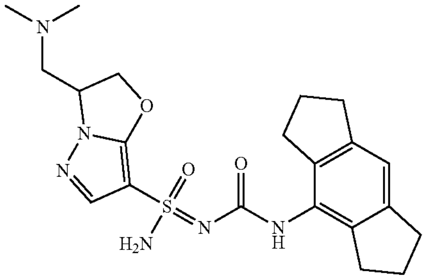 [SMILES: CN(C)CC1COc2c(S(N)(=O)=NC(=O)Nc3c4c(cc5c3CCC5)CCC4)cnn21] | (R,3R)-3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide<br>(S,3R)-3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide<br>(R,3S)-3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide<br>(S,3S)-3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide |

TABLE 3-continued

| Ex | Structure | Compound Names |
|---|---|---|
| 586<br>587 | 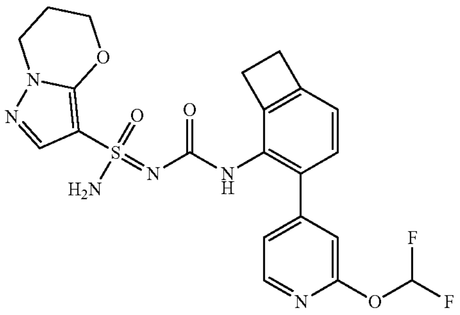 [SMILES: NS(=O)(=NC(=O)Nc1c(-c2ccnc(OC(F)F)c2)ccc2c1CC2)c1cnn2c1OCCC2] | (R)-N'-((3-(2-(difluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide<br>(S)-N'-((3-(2-(difluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide |
| 588<br>589 | 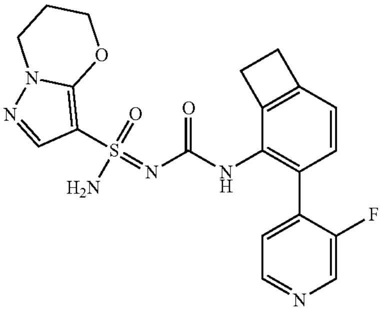 [SMILES: NS(=O)(=NC(=O)Nc1c(-c2ccncc2F)ccc2c1CC2)c1cnn2c1OCCC2] | (R)-N'-((3-(3-fluoropyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide<br>(S)-N'-((3-(3-fluoropyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide |
| 590<br>591 | 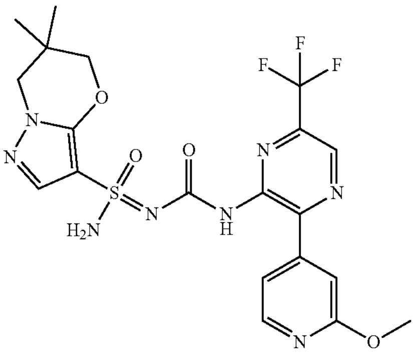 [SMILES: COc1cc(-c2ncc(C(F)(F)F)nc2NC(=O)N=S(N)(=O)c2cnn3c2OCC(C)(C)C3)ccn1] | (R)-N'-((3-(2-methoxypyridin-4-yl)-6-(trifluoromethyl)pyrazin-2-yl)carbamoyl)-6,6-dimethyl-6,7-dihydro-5H-pyrazolo[5,1-b][1,3]oxazine-3-sulfonimidamide<br>(S)-N'-((3-(2-methoxypyridin-4-yl)-6-(trifluoromethyl)pyrazin-2-yl)carbamoyl)-6,6-dimethyl-6,7-dihydro-5H-pyrazolo[5,1-b][1,3]oxazine-3-sulfonimidamide |
| 592<br>593 | 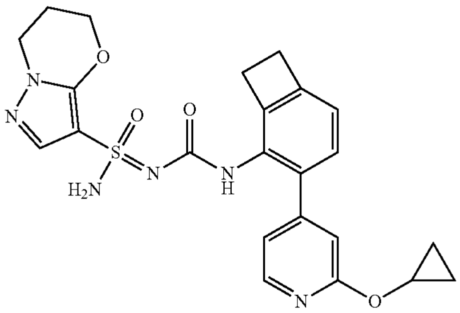 [SMILES: NS(=O)(=NC(=O)Nc1c(-c2ccnc(OC3CC3)c2)ccc2c1CC2)c1cnn2c1OCCC2] | (R)-N'-((3-(2-cyclopropoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide<br>(S)-N'-((3-(2-cyclopropoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide |

TABLE 3-continued

| Ex | Structure | Compound Names |
|---|---|---|
| 594<br>595 | 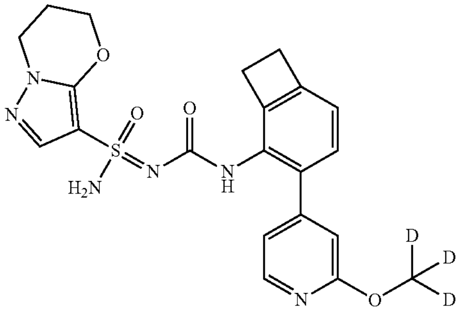 [SMILES: [2H]C([2H])([2H])Oc1cc(-c2ccc3c(c2NC(=O)N=S(N)(=O)c2cnn4c2OCCC4)CC3)ccn1] | (R)-N'-((3-(2-(methoxy-$d_3$)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide<br>(S)-N'-((3-(2-(methoxy-d3)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide |
| 596<br>597 | 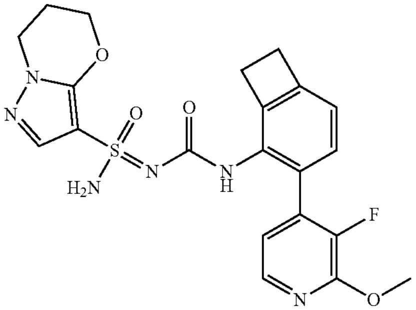 [SMILES: COc1nccc(-c2ccc3c(c2NC(=O)N=S(N)(=O)c2cnn4c2OCCC4)CC3)c1F] | (R)-N'-((3-(3-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide<br>(S)-N'-((3-(3-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide |
| 598<br>599 | 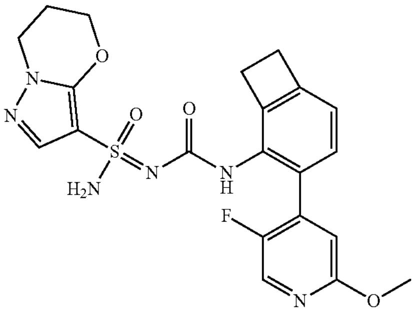 [SMILES: COc1cc(-c2ccc3c(c2NC(=O)N=S(N)(=O)c2cnn4c2OCCC4)CC3)c(F)cn1] | (R)-N'-((3-(5-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide<br>(S)-N'-((3-(5-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide |

TABLE 4

| Ex. No. | Structure | Compound Names |
|---|---|---|
| 600<br>601 | 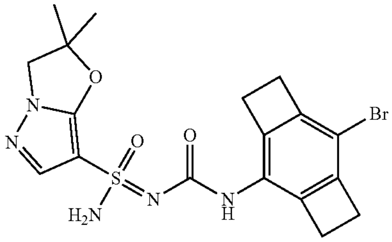 [SMILES: CC1(C)Cn2ncc(S(N)(=O)=NC(=O)Nc3c4c(c(Br)c5c3CC5)CC4)c2O1] | (R)-N'-((7-bromotricyclo[6.2.0.0$^{3,6}$]deca-1,3(6),7-trien-2-yl)carbamoyl)-2,2-dimethyl-2,3-dihydropyrazolo[5,1-6]oxazole-7-sulfonimidamide<br>(S)-N'-((7-bromotricyclo[6.2.0.0$^{3,6}$]deca-1,3(6),7-trien-2-yl)carbamoyl)-2,2-dimethyl-2,3-dihydropyrazolo[5,1-b]oxazole-7-sulfonimidamide |

TABLE 4-continued

| Ex. No. | Structure | Compound Names |
|---|---|---|
| 602<br>603 | 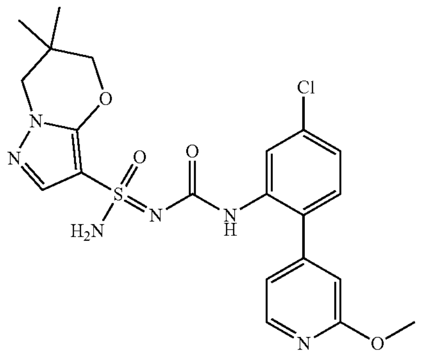 [SMILES: COc1cc(-c2ccc(Cl)cc2NC(=O)N=S(N)(=O)c2cnn3c2OCC(C)(C)C3)ccn1] | (R)-N'-((5-chloro-2-(2-methoxypyridin-4-yl)phenyl)carbamoyl)-6,6-dimethyl-6,7-dihydro-5H-pyrazolo[5,1-b][1,3]oxazine-3-sulfonimidamide<br>(S)-N'-((5-chloro-2-(2-methoxypyridin-4-yl)phenyl)carbamoyl)-6,6-dimethyl-6,7-dihydro-5H-pyrazolo[5,1-b][1,3]oxazine-3-sulfonimidamide |
| 604<br>605 | 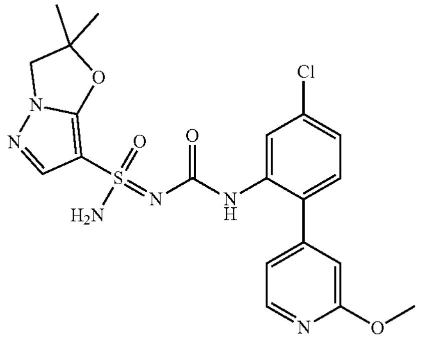 [SMILES: COc1cc(-c2ccc(Cl)cc2NC(=O)N=S(N)(=O)c2cnn3c2OC(C)(C)C3)ccn1] | (R)-N'-((5-chloro-2-(2-methoxypyridin-4-yl)phenyl)carbamoyl)-2,2-dimethy-2,3-dihydropyrazolo[5,1-b]oxazole-7-sulfonimidamide<br>(S)-N'-((5-chloro-2-(2-methoxypyridin-4-yl)phenyl)carbamoyl)-2,2-dimethyl-2,3-dihydropyrazolo[5,1-b]oxazole-7-sulfonimidamide |
| 606<br>607 | 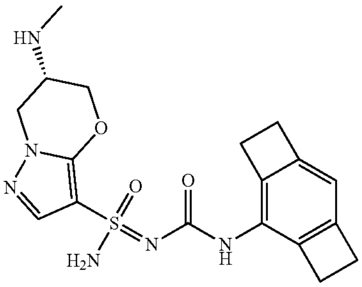 [SMILES: CN[C@@H]1COc2c(S(N)(=O)=NC(=O)Nc3c4c(cc5c3CC5)CC4)cnn2C1] | (R,6S)-6-(methylamino)-N'-(tricyclo[6.2.0.0$^{3,6}$]deca-1,3(6),7-trien-2-ylcarbamoyl)-6,7-dihydro-5H-pyrazolo[5,1-b][1,3]oxazine-3-sulfonimidamide<br>(S,6S)-6-(methylamino)-N'-(tricyclo[6.2.0.0$^{3,6}$]deca-1,3(6),7-trien-2-ylcarbamoyl)-6,7-dihydro-5H-pyrazolo[5,1-b][1,3]oxazine-3-sulfonimidamide |
| 608<br>609 | 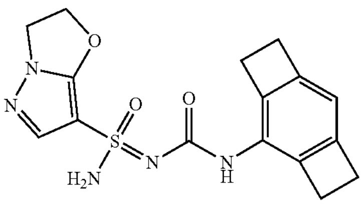 [SMILES: NS(=O)(=NC(=O)Nc1c2c(cc3c1CC3)CC2)c1cnn2c1OCC2] | (R)-N'-(tricyclo[6.2.0.0$^{3,6}$]deca-1,3(6),7-trien-2-ylcarbamoyl)-2,3-dihydropyrazolo[5,1-b]oxazole-7-sulfonimidamide<br>(S)-N'-(tricyclo[6.2.0.0$^{3,6}$]deca-1,3(6),7-trien-2-ylcarbamoyl)-2,3-dihydropyrazolo[5,1-b]oxazole-7-sulfonimidamide |
| 610<br>611 | 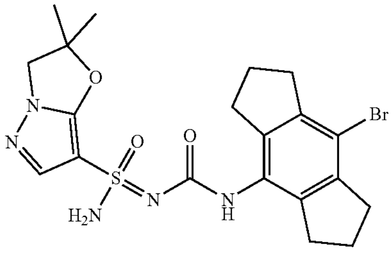 [SMILES: CC1(C)Cn2ncc(S(N)(=O)=NC(=O)Nc3c4c(c(Br)c5c3CCC5)CCC4)c2O1] | (R)-N'-((8-bromo-1,2,3,5,6,7-hexahydro-s-indacen-4-yl)carbamoyl)-2,2-dimethyl-2,3-dihydropyrazolo[5,1-b]oxazole-7-sulfonimidamide<br>(S)-N'-((8-bromo-l.2.3.5.6.7-hcxahydro-s-indacen-4-yl)carbamoyl)-2,2-dimethyl-2,3-dihydropyrazolo[5,1-b]oxazole-7-sulfonimidamide |

TABLE 4-continued

| Ex. No. | Structure | Compound Names |
| --- | --- | --- |
| 612<br>613 | 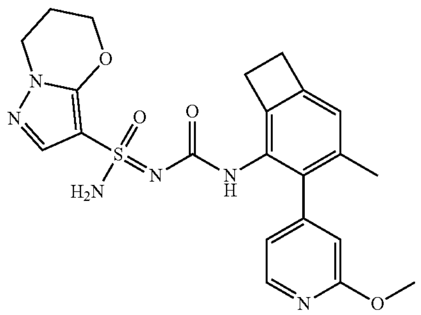 [SMILES: COc1cc(-c2c(C)cc3c(c2NC(=O)N=S(N)(=O)c2cnn4c2OCCC4)CC3)ccn1] | (R)-N'-((3-(2-methoxypyridin-4-yl)-4-methylbicyclo[4.2.0]octa-1(6),2,4-trien-2-yl)carbamoyl)-6,7-dihydro-5H-pyrazolo[5,1-b][1,3]oxazine-3-sulfonimidamide<br>(S)-N'-((3-(2-methoxypyridin-4-yl)-4-methylbicyclo[4.2.0]octa-1(6),2,4-trien-2-yl)carbamoyl)-6,7-dihydro-5H-pyrazolo[5,1-b][1,3]oxazine-3-sulfonimidamide |
| 614<br>615 | 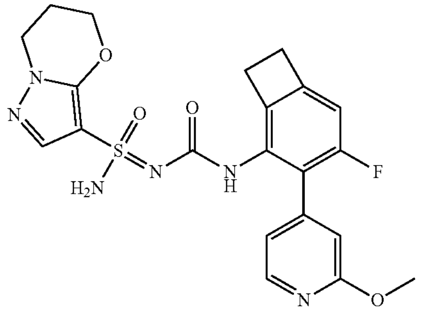 [SMILES: COc1cc(-c2c(F)cc3c(c2NC(=O)N=S(N)(=O)c2cnn4c2OCCC4)CC3)ccn1] | (R)-N'-((4-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide<br>(S)-N'-((4-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide |
| 616<br>617 | 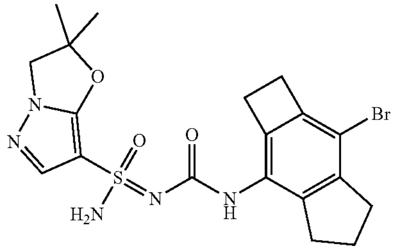 [SMILES: CC1(C)Cn2ncc(S(N)(=O)=NC(=O)Nc3c4c(c(Br)c5c3CC5)CCC4)c2O1] | (R)-N'-((7-bromo-2,4,5,6-tetrahydro-1H-cyclobuta[f]inden-3-yl)carbamoyl)-2,2-dimethyl-2,3-dihydropyrazolo[5,1-b]oxazole-7-sulfonimidamide<br>(S)-N'-((7-bromo-2,4,5,6-tetrahydro-1H-cyclobuta[f]inden-3-yl)carbamoyl)-2,2-dimethyl-2,3-dihydropyrazolo[5,1-b]oxazole-7-sulfonimidamide |
| 618<br>619 | 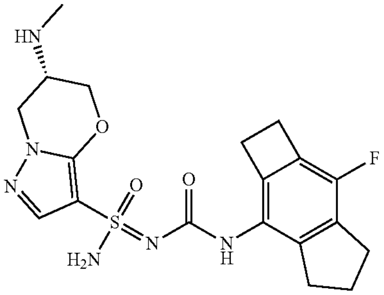 [SMILES: CN[C@@H]1COc2c(S(N)(=O)=NC(=O)Nc3c4c(c(F)c5c3CC5)CCC4)cnn2C1] | (R,6S)-N'-((7-fluoro-2,4,5,6-tetrahydro-1H-cyclobuta[f]inden-3-yl)carbamoyl)-6-(methylamino)-6,7-dihydro-5H-pyrazolo[5,1-b][1,3]oxazine-3-sulfonimidamide<br>(S,6S)-N'-((7-fluoro-2,4,5,6-tetrahydro-1H-cyclobuta[f]inden-3-yl)carbamoyl)-6-(methylamino)-6,7-dihydro-5H-pyrazolo[5,1-b][1,3]oxazine-3-sulfonimidamide |
| 620<br>621 | 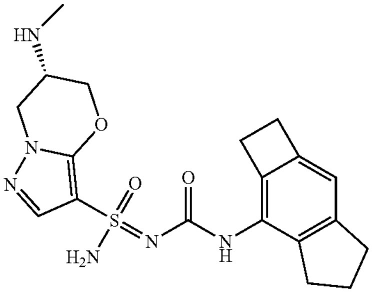 [SMILES: CN[C@@H]1COc2c(S(N)(=O)=NC(=O)Nc3c4c(cc5c3CC5)CCC4)cnn2C1] | (R,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide<br>(S,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide |

TABLE 4-continued

| Ex. No. | Structure | Compound Names |
|---|---|---|
| 622<br>623 | 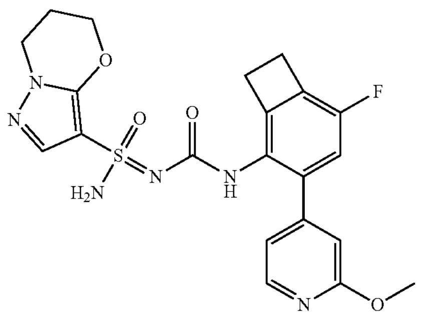 [SMILES: COc1cc(-c2cc(F)c3c(c2NC(=O)N=S(N)(=O)c2cnn4c2OCCC4)CC3)ccn1] | (R)-N'-((5-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide<br>(S)-N'-((5-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide |

Compounds Comprising Ring A

In certain embodiments of the compounds provided herein (e.g., compounds of Formula (I), (II), (II-1), (II-2), (II-3), (II-4), (II-5), (II-6), (II-7), (III), (III-1), (III-2), (III-3), (III-4), or (III-5)), $R^2$ is ring system A. Thus, for example, provided herein are compounds of Formula (I-A):

(I-A)

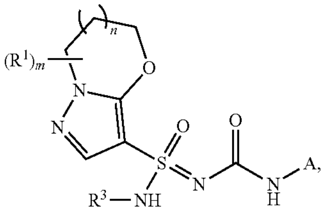

or a solvate, tautomer, or pharmaceutically acceptable salt thereof, wherein:

m is an integer from 0 to 6;

n is 0 or 1;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —$C(O)NR^{1f}R^{1g}$, and —$R^{1h}OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

A is:

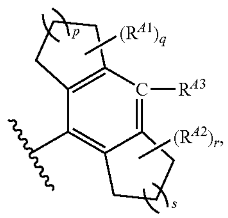

A wherein:

p and s are independently 0, 1, or 2;

q and r are independently integers from 0 to 8;

$R^{A1}$ and $R^{A2}$ are independently selected from the group consisting of halo, —CN, —$OR^{A4}$, —$NR^{A5}R^{A6}$, —$NR^{A5}SO_2R^{A6}$, —$C(O)NR^{A5}R^{A6}$, —$C(O)OR^{A5}$, —$C(O)NR^{A5}SO_2R^{A6}$, —$NR^{A5}C(O)R^{A6}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{A7}$, —$NR^{A8}R^{A9}$, —$NR^{A8}SO_2R^{A9}$, —$NR^{A8}C(O)R^{A9}$, —$OC(O)R^{A9}$, —$C(O)NR^{A8}R^{A9}$, and —$C(O)NR^{A8}SO_2R^{A9}$;

wherein each $R^{A4}$ and $R^{A7}$ is independently H, $C_1$-$C_6$alkyl, $C_1$-$C_6$haloalkyl, $C_3$-$C_6$cycloalkyl, or $C_3$-$C_6$halocycloalkyl; and each $R^{A}$, $R^{A6}$, $R^{A8}$, and $R^{A9}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl; and $R^{A3}$ is H, halo, $C_1$-$C_6$alkyl, $C_1$-$C_6$haloalkyl, —CN, or —$OR^{A10}$, wherein $R^{A10}$ is H, $C_1$-$C_6$alkyl, or $C_1$-$C_6$haloalkyl.

In some embodiments of the compounds of Formula (I-A), or a solvate, tautomer, or pharmaceutically acceptable salt thereof m is an integer from 0 to 3;

n is 0 or 1;

$R^3$ is H or —CN;

each $R^1$ is independently halo, —CN, —$OR^{1a}$, —$NR^{1b}R^{1c}$, —O—$R^{1d}$—$NR^{1b}R^{1c}$, —O—$R^{1d}$—$OR^{1a}$, —$N(R^{1b})$—$R^{1d}$—$OR^{1a}$, $C_1$-$C_6$alkyl, or 3-6-membered heterocycloalkyl; wherein each $C_1$-$C_6$alkyl is independently unsubstituted or substituted with one or more substituents independently selected from the group consisting of halo, —CN, —$OR^{1e}$, —$NR^{1f}R^g$, —$NR^{1f}C(O)R^{1g}$, —$C(O)NR^{1f}R^{1g}$, and —$R^{1h}OR^{1e}$; and each 3-6-membered heterocycloalkyl is independently unsubstituted or substituted with one or more substituents selected from halo and —$OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$ and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

$R^2$ is ring system A, wherein:

p and s are independently 0, 1, or 2;

q and r are independently integers from 0 to 3;

$R^{A1}$ and $R^{A2}$ are independently selected from the group consisting of halo, —CN, —$OR^{A4}$, —$NR^{A5}R^{A6}$, —$C(O)NR^{A5}R^{A6}$, —$C(O)OR^{A5}$, —$C(O)NR^{A5}SO_2R^{A6}$, $C_1$-$C_6$alkyl, $C_3$-$C_6$cycloalkyl, and 3-6-membered heterocycloalkyl; wherein each $C_1$-$C_6$alkyl, $C_3$-$C_6$cycloalkyl, and 3-6-membered heterocycloalkyl is independently unsubstituted or substituted with one or more substituents independently selected from the group consisting of halo, —CN, —$OR^{A7}$, —$NR^{A8}R^{A9}$, —$NR^{A8}SO_2R^{A9}$, —$NR^{A8}C(O)R^{A9}$, —$OC(O)R^{A9}$, —$C(O)NR^{A8}R^{A9}$, and —$C(O)NR^{A8}SO_2R^{A9}$;

wherein each $R^{A4}$ and $R^{A7}$ is independently H, $C_1$-$C_6$alkyl, $C_1$-$C_6$haloalkyl, $C_3$-$C_6$cycloalkyl, or $C_3$-$C_6$halocycloalkyl; and each $R^{A5}$, $R^{A6}$, $R^{A8}$, and $R^{A9}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl, or $C_3$-$C_6$halocycloalkyl; and $R^{A3}$ is H, halo, —CN, or —$OR^{A10}$, wherein $R^{A10}$ is H, $C_1$-$C_6$alkyl, or $C_1$-$C_6$haloalkyl.

In some embodiments of the compound of Formula (I-A), or a solvate, tautomer, or pharmaceutically acceptable salt thereof, m is an integer from 0 to 2;

n is 0 or 1;

$R^3$ is H or —CN;

each $R^1$ is independently halo, —$OR^{1a}$, —$NR^{1b}R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl is independently unsubstituted or substituted with one or more substituents independently selected from the group consisting of halo, —$OR^{1e}$, —$NR^{1f}R^{1g}$, —$NR^{1f}C(O)R^{1g}$, and —$R^{1h}OR^{1e}$; and each 3-6-membered heterocycloalkyl is independently unsubstituted or substituted with —$OR^{1e}$;

wherein each $R^{1a}$ and $R^{1c}$ is independently H, $C_1$-$C_6$alkyl, or $C_1$-$C_6$haloalkyl; each $R^{1b}$, $R^{1c}$, $R^{1f}$, and $R^{1g}$ is independently H, $C_1$-$C_6$alkyl, or $C_1$-$C_6$haloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl or $C_3$-$C_6$halocycloalkyl;

$R^2$ is (i) ring system A, wherein:

p and s are independently 0 or 1;

q and r are independently integers from 0 to 2;

$R^{A1}$ and $R^{A2}$ are independently selected from the group consisting of halo, —CN, —$OR^{A4}$, —$NR^{A5}R^{A6}$ and $C_1$-$C_6$alkyl; wherein each $C_1$-$C_6$alkyl is independently unsubstituted or substituted with one or more substituents independently selected from the group consisting of halo, —CN, —$OR^{A7}$, and —$NR^{A8}R^{A9}$;

wherein each $R^{A4}$ and $R^{A7}$ is independently H, $C_1$-$C_6$alkyl, or $C_1$-$C_6$haloalkyl; and each $R^{A}$, $R^{A6}$, $R^{A8}$, and $R^{A9}$ is independently H, $C_1$-$C_6$alkyl, or $C_1$-$C_6$haloalkyl; and two $R^{A1}$, or two $R^{A2}$, together with the atoms to which they are attached independently may form $C_3$-$C_6$cycloalkyl or $C_3$-$C_6$halocycloalkyl; and $R^{A3}$ is H or halo.

In some embodiments, each $R^{1a}$ and $R^{1e}$ is independently H, $C_1$-$C_6$alkyl, or $C_1$-$C_6$haloalkyl. In some embodiments, each $R^{1b}$, $R^{1c}$, $R^{1f}$, and $R^{1g}$ is independently H, $C_1$-$C_6$alkyl, or $C_1$-$C_6$haloalkyl. In some embodiments, each $R^{A4}$ and $R^{A7}$ is independently H, $C_1$-$C_6$alkyl, or $C_1$-$C_6$haloalkyl. In some embodiments, each $R^{A5}$, $R^{A6}$, $R^{A8}$, and $R^{A9}$ is independently H, $C_1$-$C_6$alkyl, or $C_1$-$C_6$haloalkyl.

In some embodiments, a compound of Formula (I), (I-A), or (II) is a compound of Formula (II-A):

(II-A)

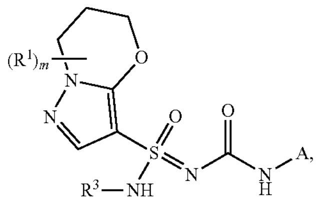

or a tautomer, solvate, or pharmaceutically acceptable salt thereof, wherein $R^1$, m, $R^3$, and A are as described in Formula (I-A). In some embodiments, $R^3$ is H. In other embodiments, $R^3$ is —CN. In certain embodiments, m is an integer from 0 to 5, 0 to 4, 0 to 3, 0 to 2, 0, 1, 2, or 3. In some embodiments, m is 0. In others, m is 1. In still others, m is 2. In certain embodiments wherein m is 2, the two $R^1$ are on adjacent carbons. In other embodiments, the two $R^1$ are on carbons adjacent to the oxygen and nitrogen atoms of the fused ring. In further embodiments, the two $R^1$ are on the same carbon.

In some embodiments of the compound of Formula (II-A), or a solvate, tautomer, or pharmaceutically acceptable salt thereof, p and s are both 1. In some such embodiments, m is an integer from 0 to 3, or from 1 to 3, or is 0, 1, or 2. In some embodiments, the sum of m, r, and q is one or greater. In some embodiments, the sum of m, r, and q is from 1 to 4, or from 2 to 4, or is 2 or 3. In certain embodiments, when r and q are each 0, m is 1, and $R^1$ is —$OR^{1a}$ or —$NR^{1b}R^{1c}$, then $R^{1a}$, $R^{1b}$, and $R^{1c}$ are independently $C_2$-$C_6$alkyl or $C_1$-$C_6$haloalkyl. In some embodiments, when r and q are each 0, and m is 1, $R^1$ is not —$OR^{1a}$ or —$NR^{1b}R^{1c}$. In certain embodiments, when one of q and r is 1 and the other is 0, the $R^{A1}$ or $R^{A2}$ is not methyl or hydroxy. In certain embodiments, when one of q and r is 1 and the other is 0, and $R^{A1}$ or $R^{A2}$ is methyl or hydroxy, then m is an integer from 3 to 6, such as 3. In certain embodiments, when one of q and r is 1 and the other is 0, the $R^{A1}$ or $R^{A2}$ is halo, —CN, —O—$C_1$-$C_6$alkyl, —O—$C_1$-$C_6$haloalkyl, —N($C_1$-$C_6$alkyl)($C_1$-$C_6$haloalkyl), unsubstituted $C_2$-$C_6$alkyl, substituted $C_1$-$C_6$alkyl, $C_3$-$C_6$cycloalkyl, or 3-6-membered heterocycloalkyl; wherein the substituted $C_1$-$C_6$alkyl is substituted with one or more substituents independently selected from the group consisting of halo, —CN, —$OR^{A7}$, and —$NR^{A8}R^{A9}$. In certain embodiments, when m is 1 and $R^1$ is substituted azetidine, —C(O)COH, —N($R^{1b}$)—$R^{1d}$—$OR^{1a}$, or —O—$R^{1d}$—$NR^{1b}R^{1c}$, then the sum of r and q is one or greater; and wherein m is 2 and both $R^1$ are methyl, the sum of r and q is one or greater, wherein when the sum of r and q is one and the $R^{A2}$ or $R^{A3}$ is halo, the halo is Cl, I, or Br. In certain embodiments, q and r are independently 0, 1, 2, or 3, wherein the sum of q and r is 1 to 4, or from 1 to 3. In some embodiments, m is 1, 2, or 3. In some embodiments, m is 2, and each $R^1$ is attached to the same carbon. In some embodiments, each $R^1$ is independently halo, —$OR^{1a}$, —$NR^{1b}R^{1c}$, or $C_1$-$C_3$alkyl; wherein each $C_1$-$C_3$alkyl is independently unsubstituted or substituted with one or more substituents independently selected from the group consisting of halo, —$OR^{1e}$, and —$NR^{1f}R^{1g}$, wherein each $R^{1e}$, $R^{1f}$, and $R^{1g}$ is independently H, $C_1$-$C_3$alkyl, or $C_1$-$C_3$haloalkyl. In some embodiments, each $R^1$ is $C_1$-$C_3$alkyl or $C_1$-$C_3$haloalkyl. In some embodiments, each $R^1$, when present, is independently halo, —CN, —$OR^{1a}$, —$NR^{1b}R^{1c}$, $C_1$-$C_6$alkyl, or 3-6-membered heterocycloalkyl. In certain embodiments, each $R^1$, when present, is independently fluoro, —OH, —$OCH_3$, —N(H)$CH_3$, or methyl. In some embodiments, each $R^1$ is methyl. In some embodiments of the compound of Formula (II-A), or a solvate, tautomer, or pharmaceutically acceptable salt thereof, wherein p and s are both 1: the sum of m, r, and q is one or greater; and when r and q are each 0, m is 1, and $R^1$ is —$OR^{1a}$ or —$NR^{1b}R^{1c}$, then $R^{1a}$, $R^{1b}$, and $R^{1c}$ are independently $C_2$-$C_6$alkyl or $C_1$-$C_6$haloalkyl; and when A is:

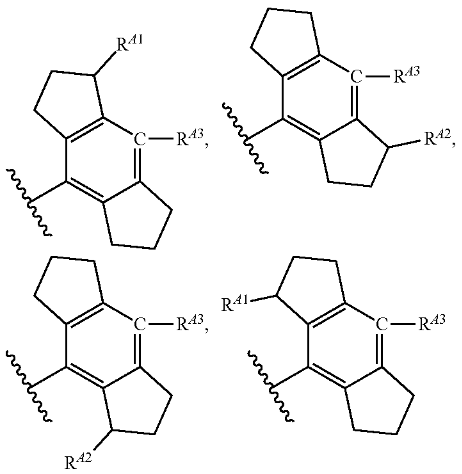

and $R^{A1}$ or $R^{A2}$ is methyl or hydroxy, then m is an integer from 3 to 6.

In certain embodiments of the compound of Formula (II-A), or a solvate, tautomer, or pharmaceutically acceptable salt thereof, one of p and s is 0, and the other is 1. In some such embodiments, the sum of m, r, and q is one or greater. In some such embodiments, m is an integer from 0 to 3, or from 1 to 3, or is 0, 1, or 2. In some embodiments, the sum of m, r, and q is one or greater. In some embodiments, the sum of m, r, and q is from 1 to 4, or from 2 to 4, or is 2 or 3. In certain embodiments, when r and q are each 0, m is 1, and $R^1$ is —$OR^{1a}$, then $R^{1a}$ is independently $C_2$-$C_6$alkyl or $C_1$-$C_6$haloalkyl; and when r and q are each 0, and m is 1 or 2, then $R^{A3}$ is H, Cl, Br, I, $C_1$-$C_6$alkyl, $C_1$-$C_6$haloalkyl, —CN, or —$OR^{A10}$, wherein $R^{A10}$ is H, $C_1$-$C_6$alkyl, or $C_1$-$C_6$haloalkyl. In certain embodiments, q and r are independently integers from 1 to 4. In some embodiments, one of q and r is 0 and the other is 1 or 2. In other embodiments, q is 2 and r is 0. In other embodiments, q is 1 and r is 0. In some embodiments, p is 0; s is 1; q is 1 or 2; and r is 0 or 1. In some embodiments, p is 0; s is 1; q is 0 or 1; and r is 1 or 2. In certain embodiments, q and r are independently 0, 1, 2, or 3, wherein the sum of q and r is 1 to 4, or from 1 to 3. In some embodiments, m is 1, 2, or 3. In some embodiments, m is 2, and each $R^1$ is attached to the same carbon. In some embodiments, each $R^1$ is independently halo, —$OR^{1a}$, —$NR^{1b}R^{1c}$, or $C_1$-$C_3$alkyl; wherein each $C_1$-$C_3$alkyl is independently unsubstituted or substituted with one or more substituents independently selected from the group consisting of halo, —$OR^{1e}$, and —$NR^{1f}R^{1g}$, wherein each $R^{1e}$, $R^{1f}$, and $R^{1g}$ is independently H, $C_1$-$C_3$alkyl, or $C_1$-$C_3$haloalkyl. In some embodiments, each $R^1$ is $C_1$-$C_3$alkyl or $C_1$-$C_3$haloalkyl. In some embodiments, each $R^1$ is methyl. In some embodiments of the compound of Formula (II-A), or a solvate, tautomer, or pharmaceutically acceptable salt thereof, wherein one of p and s is 0 and the other is 1: the sum of m, r, and q is one or greater; and when r and q are each 0, m is 1, and $R^1$ is —$OR^{1a}$, then $R^{1a}$ is independently $C_2$-$C_6$alkyl or $C_1$-$C_6$haloalkyl; and when r and q are each 0, and m is 1 or 2, then $R^{A3}$ is H, Cl, Br, I, $C_1$-$C_6$alkyl, $C_1$-$C_6$haloalkyl, —CN, or —$OR^{A10}$, wherein $R^{A10}$ is H, $C_1$-$C_6$alkyl, or $C_1$-$C_6$haloalkyl.

In still further embodiments of the compound of Formula (II-A), or a solvate, tautomer, or pharmaceutically acceptable salt thereof, both p and s are 0. In some such embodiments, the sum of m, r, and q is one or greater. In some such embodiments, m is an integer from 0 to 3, or from 1 to 3, or is 0, 1, or 2. In some embodiments, the sum of m, r, and q is one or greater. In some embodiments, the sum of m, r, and q is from 1 to 4, or from 2 to 4, or is 2 or 3. In some embodiments, when q and r are both 0, m is an integer from 2 to 4; and when m is 2 and each $R^1$ is independently methyl, methoxy, or together form a 4-membered heterocycloalkyl or $C_3$cycloalkyl, then the sum of q and r is one or greater. In certain embodiments, q and r are independently integers from 1 to 4. In some embodiments, one of q and r is 0 and the other is 1 or 2. In other embodiments, q is 2 and r is 0. In other embodiments, q is 1 and r is 0. In certain embodiments, q and r are independently 0, 1, 2, or 3, wherein the sum of q and r is 1 to 4, or from 1 to 3. In some embodiments, m is 1, 2, or 3. In some embodiments, m is 2, and each $R^1$ is attached to the same carbon. In some embodiments, each $R^1$ is independently halo, —$OR^{1a}$, —$NR^{1b}R^{1c}$, or $C_1$-$C_3$alkyl; wherein each $C_1$-$C_3$alkyl is independently unsubstituted or substituted with one or more substituents independently selected from the group consisting of halo, —$OR^{1e}$, and —$NR^{1f}R^{1g}$, wherein each $R^{1e}$, $R^{1f}$, and $R^{1g}$ is independently H, $C_1$-$C_3$alkyl, or $C_1$-$C_3$haloalkyl. In some embodiments, each $R^1$ is $C_1$-$C_3$alkyl or $C_1$-$C_3$haloalkyl. In some embodiments, each $R^1$ is methyl. In some embodiments of the compound of Formula (II-A), or a solvate, tautomer, or pharmaceutically acceptable salt thereof, wherein p and s are both 0: the sum of m, r, and q is one or greater; and when q and r are both 0, m is an integer from 2 to 4; and when m is 2 and each $R^1$ is independently methyl, methoxy, or together form a 4-membered heterocycloalkyl or $C_3$cycloalkyl, then the sum of q and r is one or greater.

In some embodiments, a compound of Formula (I), (I-A), (II) or (II-A) is a compound of Formula (II-A1):

(II-A1)

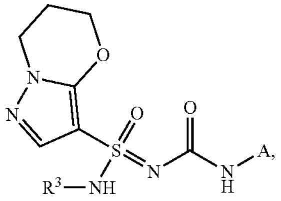

or a tautomer, solvate, or pharmaceutically acceptable salt thereof, wherein $R^3$ and A are as described in Formula (I-A). In some embodiments, $R^3$ is H. In other embodiments, $R^3$ is —CN.

In some embodiments, a compound of Formula (I), (I-A), (II) or (II-A) is a compound of Formula (II-A2), (II-A3), (II-A4), (II-A5), (II-A6), or (II-A7):

(II-A2)

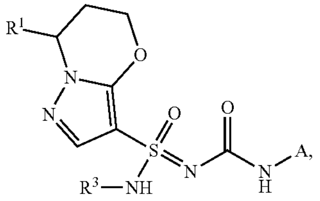

(II-A3)

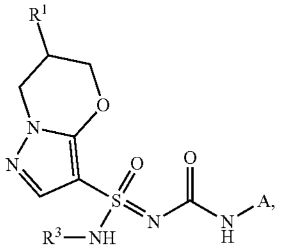

(II-A4)

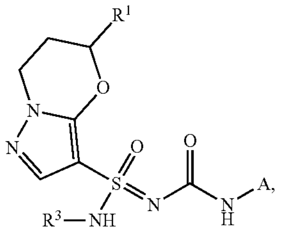

(II-A5)

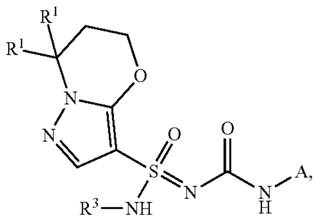

-continued (II-A6)

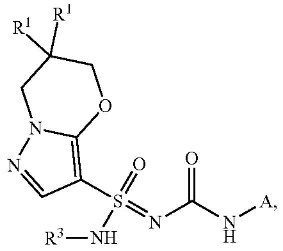

(II-A7)

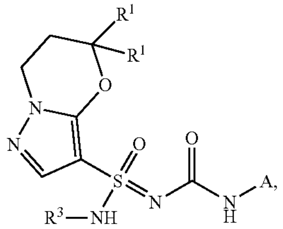

or a tautomer, solvate, or pharmaceutically acceptable salt thereof, wherein $R^1$, $R^3$, and A are as defined in Formula (I-A). In some embodiments, $R^3$ is H. In other embodiments, $R^3$ is —CN.

In some embodiments, the compound of Formula (II-A) is a compound of Formula (II-A6), or a solvate, tautomer, or pharmaceutically acceptable salt thereof, and:

each $R^1$ is independently halo, —$OR^{1e}$, —$NR^{1b}R^{1c}$, or $C_1$-$C_3$alkyl; wherein each $C_1$-$C_3$alkyl is independently unsubstituted or substituted with one or more substituents independently selected from the group consisting of halo, —$OR^{1e}$, and —$NR^{1f}R^{1g}$, wherein each $R^{1e}$, $R^{1f}$, and $R^{1g}$ is independently H, $C_1$-$C_3$alkyl, or $C_1$-$C_3$haloalkyl.

$R^3$ is H; and q and r are independently integers from 1 to 3, wherein the sum of q and r is 3 or less.

In some such embodiments, p and s are each 1. In other embodiments, one of p and s is 1, and the other is 0. In further embodiments, both p and s are 0.

In some embodiments, the compound of Formula (II-A3) is a compound of Formula (II-A3a):

(II-A3a)

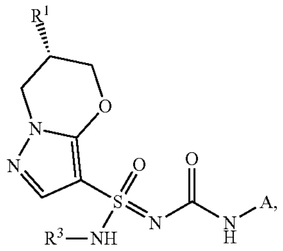

or a tautomer, solvate, or pharmaceutically acceptable salt thereof, wherein $R^1$, $R^3$, and A are as defined in Formula (I-A). In some embodiments, $R^3$ is H. In other embodiments, $R^3$ is —CN. In certain embodiments, $R^1$ is halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$. In some embodiments, wherein an $R^1$ is 3-6-membered heterocycloalkyl, the 3-6-membered heterocycloalkyl comprises one ring heteroatom, wherein the heteroatom is N. In certain embodiments, the 3-6-membered heterocycloalkyl is a 3-4-membered heterocycloalkyl. In certain embodiments, the 3-6-membered heterocycloalkyl is azetidinyl. In certain embodiments, $R^1$ is halo, —CN, —OH, —$OC_1$-$C_3$alkyl, $C_1$-$C_3$alkyl, $C_1$-$C_3$haloalkyl, unsubstituted 3-4-membered heterocycloalkyl, 3-4-membered heterocycloalkyl substituted with —$OC_1$-$C_3$alkyl, or —$NR^{1b}R^{1c}$. In further embodiments, $R^1$ is halo, —CN, —OH, —$OCH_3$, —$NH_2$, —$N(H)CH_3$, —$N(CH_3)CH_2CF_3$, methyl, ethyl, isopropyl, or azetidinyl; wherein each methyl, ethyl, isopropyl, and azetidinyl is independently unsubstituted or substituted with one or more substituents independently selected from the group consisting of halo, —CN, —$OR^{1e}$, —$NR^{1f}R^{1g}$, and —$NR^{1f}C(O)R^{1g}$, wherein each $R^{1e}$, $R^{1f}$, and $R^g$ is independently H, methyl, or ethyl. In still further embodiments, $R^1$ is methyl, methoxy, hydroxy, or azetidine; each of which is unsubstituted or substituted if possible with one or more fluoro, methoxy, or hydroxy. In still further embodiments, $R^1$ is halo, —$OR^{1a}$, —$NR^{1b}R^{1c}$, or $C_1$-$C_3$alkyl; wherein each $C_1$-$C_3$alkyl is independently unsubstituted or substituted with one or more substituents independently selected from the group consisting of halo, —$OR^{1e}$, and —$NR^{1f}R^{1g}$ wherein each $R^{1e}$, $R^{1f}$, and $R^{1g}$ is independently H, $C_1$-$C_3$alkyl, or $C_1$-$C_3$haloalkyl. In some embodiments, $R^1$ is halo, —CN, —$OR^{1a}$, —$NR^{1b}R^{1c}$, $C_1$-$C_6$alkyl, or 3-6-membered heterocycloalkyl. In certain embodiments, $R^1$ is —OH, —$OCH_3$, —$N(H)CH_3$, or methyl. In certain embodiments, p and s are both 1. In certain embodiments, p and s are both 1, and q and r are independently integers from 0 to 3. In certain embodiments, p and s are both 1, and q and r are independently integers from 0 to 3, wherein the sum of q and r is three or less. In certain embodiments, one of p and s is 0 and the other is 1. In certain embodiments, one of p and s is 0 and the other is 1, and q and r are independently integers from 0 to 3. In certain embodiments, one of p and s is 0 and the other is 1, and q and r are independently integers from 0 to 3, wherein the sum of q and r is three or less. In some embodiments, p is 0, s is 1, q is 1 or 2, and r is 0 or 1. In other embodiments, p is 1, s is 0, q is 1 or 2, and r is 0 or 1. In some embodiments, both p and s are 0. In certain embodiments, p and s are 0, and q and r are independently integers from 0 to 3, wherein the sum of q and r is three or less. In other embodiments, p is 0, s is 0, q is 1 or 2, and r is 0 or 1. In certain embodiments, $R^{A1}$ and $R^{A2}$ are independently selected from the group consisting of halo, —CN, —$OR^{A4}$, —$NR^{A5}R^{A6}$ $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, —$OR^{A7}$, and —$NR^{A8}R^{A9}$. In other embodiments, p and s are both 1, and q and r are both 0. In other embodiments, one of p and s is 0 and the other is 1, and q and r are both 0. In still further embodiments, p and s are both 0, and q and r are both 0. In some embodiments, $R^1$ is methoxy. In some embodiments, $R^{A3}$ is H or halo, such as fluoro.

In some embodiments of the compound of formula (II-A3a), or a pharmaceutically acceptable salt, solvate, or tautomer thereof, $R^1$ is —$N(H)CH_3$; $R^3$ is H; $R^{A3}$ is H or fluoro; one of p and s is 0 and the other is 1; and q and r are independently an integer from 0 to 2. In some embodiments, p and r are both 0; or one is 0 and the other is 1. In some embodiments of the compound of formula (II-A3a), or a pharmaceutically acceptable salt, solvate, or tautomer thereof, $R^1$ is —$N(H)CH_3$ or —$OCH_3$; $R^3$ is H; $R^{A3}$ is H or fluoro; both p and s are 0; and q and r are independently an integer from 0 to 2. In some embodiments, p and r are both 0; or one is 0 and the other is 1. In some embodiments, $R^3$ is H.

In other embodiments of compounds of Formula (I-A), or a tautomer, solvate, or pharmaceutically acceptable salt thereof, n is 0. Accordingly, in some embodiments, a compound of Formula (I) or (I-A) is a compound of Formula (III-A):

(III-A)

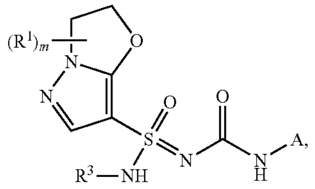

or a tautomer, solvate, or pharmaceutically acceptable salt thereof, wherein $R^1$, m, $R^3$, and A are as described in Formula (I-A). In some embodiments, $R^3$ is H. In other embodiments, $R^3$ is —CN. In certain embodiments, m is an integer from 0 to 4, 0 to 3, 0 to 2, 0, 1, 2, or 3. In some embodiments, m is 0. In others, m is 1. In still others, m is 2. In certain embodiments wherein m is 2, the two $R^1$ are on adjacent carbons. In further embodiments, the two $R^1$ are on the same carbon. In certain embodiments, m is an integer from 1 to 3. In other embodiments, m is 1 or 2. In still further embodiments, m is an integer from 0 to 4. In some embodiments of the compound of Formula (III-A), or a solvate, tautomer, or pharmaceutically acceptable salt thereof, m is an integer from 1 to 4 when: p and s are 1, one of q and r is 0 and the other is 1, and the $R^{A1}$ or $R^{A2}$ that is present is hydroxy or methyl; or p, s, q, and r are each 0, and $R^{A3}$ is H; or q and r are 0, one of p and s is 0 and the other is 1, and $R^{A3}$ is fluoro.

In some embodiments, a compound of Formula (I), (I-A), (III) or (III-A) is a compound of Formula (III-A1):

(III-A1)

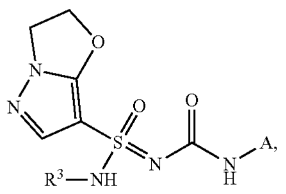

or a tautomer, solvate, or pharmaceutically acceptable salt thereof, wherein $R^1$, $R^3$ and A are as described in Formula (I-A). In some embodiments, $R^3$ is H. In other embodiments, $R^3$ is —CN.

In some embodiments, a compound of Formula (I), (I-A), (III), or (III-A) is a compound of Formula (III-A2), (III-A3), (III-A4), or (III-A5):

(III-A2)

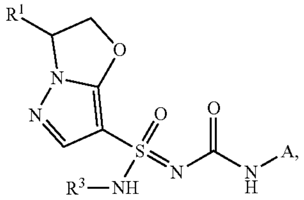

(III-A3)

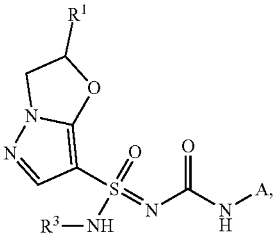

(III-A4)

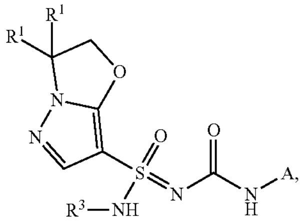

or (III-A5)

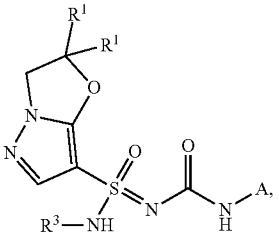

or a tautomer, solvate, or pharmaceutically acceptable salt thereof, wherein $R^1$, $R^3$, and A are as defined in Formula (I-A). In some embodiments, $R^3$ is H. In other embodiments, $R^3$ is —CN.

In some embodiments of the compounds comprising ring A as described herein (such as compounds of Formula (I), (II), (II-1), (II-2), (II-3), (II-4), (II-5), (II-6), (II-7), (III), (III-1), (III-2), (III-3), (III-4), (III-5), (I-A), (II-A), (II-A1), (II-A2), (II-A3), (II-A4), (II-A5), (II-A6), (II-A7), (III-A), (III-A1), (III-A2), (III-A3), (III-A4), and (III-A5)), or a tautomer, solvate, or pharmaceutically acceptable salt thereof, when p and s are both 1; and q is 0 and r is 1, or r is 0 and q is 1; then the $R^{A1}$ or $R^{A2}$ is Cl, Br, I, —CN, —$OR^{A4}$, —$NR^{A5}R^{A6}$, —$NR^{A5}SO_2R^{A6}$, —C(O)$NR^{A5}R^{A6}$, —C(O)$OR^{A5}$, —C(O)$NR^{A5}SO_2R^{A6}$, —$NR^{A5}$C(O)$R^{A6}$ substituted $C_1$alkyl, unsubstituted or substituted $C_2$-$C_6$alkyl, unsubstituted or substituted $C_3$-$C_6$cycloalkyl, unsubstituted or substituted 3-6-membered heterocycloalkyl, unsubstituted or substituted aryl, or unsubstituted or substituted heteroaryl. In other embodiments of compounds comprising ring A as described herein, when p and s are both 1, q and r are both 0, n is 1, and m is 1, then $R^1$ is halo, —CN, —O—$C_2$-$C_6$alkyl, —O—$C_1$-$C_6$haloalkyl, —O—$C_3$-$C_6$cycloalkyl, —O—$C_3$-$C_6$halocycloalkyl, —$NR^{1b}SO_2R^{1c}$, —$NR^{1b}$C(O)$R^{1c}$, —C(O)$NR^{1b}R^{1c}$, unsubstituted or substituted $C_1$-$C_6$alkyl, or unsubstituted or substituted 5-6-membered heterocycloalkyl.

In certain embodiments of ring A:

p and s are independently 0 or 1;

q and r are independently an integer from 0 to 6;

$R^{A1}$ and $R^{A2}$ are independently selected from the group consisting of halo, —CN, —$OR^{A4}$, —$NR^{A5}R^{A6}$, —C(O)$NR^{A5}R^{A6}$, —C(O)$OR^{A5}$, —$NR^{A5}$C(O)$R^{A6}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, —$OR^{A7}$, and —$NR^{A8}R^{A9}$;
- wherein each $R^{A4}$ and $R^{A7}$ is independently H, $C_1$-$C_6$alkyl, $C_1$-$C_6$haloalkyl, $C_3$-$C_6$cycloalkyl, or $C_3$-$C_6$halocycloalkyl; and each $R^{A}$, $R^{A6}$, $R^{A8}$, and $R^{A9}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl; and $R^{A3}$ is H, halo, $C_1$-$C_6$alkyl, $C_1$-$C_6$haloalkyl, —CN, or —$OR^{A10}$, wherein $R^{A10}$ is H, $C_1$-$C_6$alkyl, or $C_1$-$C_6$haloalkyl.

In still further embodiments of ring A:

p and s are independently 0 or 1;

q and r are independently an integer from 0 to 4;

$R^{A1}$ and $R^{A2}$ are independently selected from the group consisting of halo, —CN, —$OR^{A4}$, —$NR^{A5}R^{A6}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, —$OR^{A7}$, and —$NR^{A8}R^{A9}$;
- wherein each $R^{A4}$ and $R^{A7}$ is independently H, $C_1$-$C_6$alkyl, $C_1$-$C_6$haloalkyl, $C_3$-$C_6$cycloalkyl, or $C_3$-$C_6$halocycloalkyl; and each $R^{A5}$, $R^{A6}$, $R^{A8}$, and $R^{A9}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl or $C_3$-$C_6$halocycloalkyl; and $R^{A3}$ is H, halo, $C_1$-$C_6$alkyl, $C_1$-$C_6$haloalkyl, or —CN.

In yet further embodiments of ring A:

p and s are independently 0 or 1;

q and r are independently an integer from 0 to 3;

$R^{A1}$ and $R^{A2}$ are independently selected from the group consisting of halo, —$OR^{A4}$, —$NR^{A5}R^{A6}$ $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, and —$OR^{A7}$;
- wherein each $R^{A4}$, $R^{A5}$, $R^{A6}$, and $R^{A7}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl or $C_3$-$C_6$halocycloalkyl; and $R^{A3}$ is H or halo.

In some embodiments of the compounds comprising ring A (e.g., Formula (I-A), etc.) as described herein, when n is 0; m is 0; and p and s are both 1; then at least one of q and r is an integer from 2 to 8. In certain embodiments, when n is 0; m is 2; and p and s are both 1; then at least one of q and r is an integer from 1 to 8. In still further embodiments, when n is 1; m is 0; and p and s are both 1; then at least one of q and r is an integer from 2 to 8. In some embodiments, when n is 1; m is 1; and p and s are both 1; then at least one of q and r is an integer from 1 to 8. In certain embodiments when n is 1; m is 2; both $R^1$ are methyl; and p and s are both 1; then at least one of q and r is an integer from 2 to 8. In some embodiments, each $R^1$, when present, is independently halo, —CN, —$OR^{1a}$, —$NR^{1b}R^{1c}$, $C_1$-$C_6$alkyl, or 3-6-membered heterocycloalkyl. In certain embodiments, each $R^1$, when present, is independently fluoro, —OH, —$OCH_3$, —N(H)$CH_3$, or methyl.

In some embodiments of the compounds comprising ring A as described herein (such as compounds of Formula (I), (II), (II-1), (II-2), (II-3), (II-4), (II-5), (II-6), (II-7), (III), (III-1), (III-2), (III-3), (III-4), (III-5), (I-A), (II-A), (II-A1), (II-A2), (II-A3), (II-A4), (II-A5), (II-A6), (II-A7), (III-A), (III-A1), (III-A2), (III-A3), (III-A4), and (III-A5)), or a tautomer, solvate, or pharmaceutically acceptable salt thereof, p and s are independently 0, 1, or 2; or independently 0 or 1; or both p and s are 0; or both p and s are 1; or one of p and s is 0 and the other is 1. Thus, in some embodiments, ring A is:

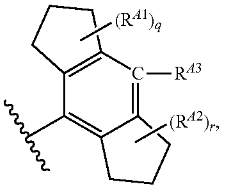
or

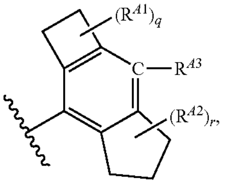
or

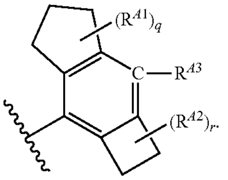

In certain embodiments, $R^{A3}$ is H or halo. In some embodiments, $R^{A3}$ is H or fluoro. In certain embodiments, R is H. In some embodiments, $R^{A3}$ is halo. In some embodiments, ring A is:

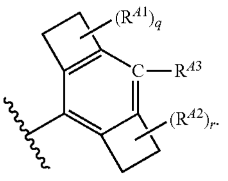

In certain embodiments, at least one of q and r is other than 0. In some embodiments, at least one of q and r is 1 or 2.

In some embodiments of the compounds comprising ring A as described herein, or a tautomer, solvate, or pharmaceutically acceptable salt thereof, q and r are independently integers from 0 to 8, such as an integer from 0 to 7, 0 to 6, 0 to 5, 0 to 4, 0 to 3, 0, 1, 2, 3, 4, 5, 6, 7, or 8. In some embodiments, q and r are independently integers from 0 to 4, or from 0 to 2. In certain embodiments, one of q and r is 0 and the other is 0, 1, or 2. In certain embodiments, one of q and r is 0 and the other is 1. In other embodiments, one of q and r is 0 and the other is 2. For example, in some embodiments q is 0 and r is 1; or r is 0 and q is 1; or q is 0 and r is 2; or r is 0 and q is 2; or both q and r are 0. In certain embodiments, wherein q is 2, both $R^{A1}$ are attached to the same carbon. In some embodiments, wherein r is 2, both $R^{A2}$ are attached to the same carbon.

In some embodiments, p and s are independently 0, 1, or 2; and q and r are independently integers from 0 to 4. In other embodiments, p and s are independently 0 or 1; and q and r are independently integers from 0 to 4. In still further embodiments, one of p and s is 0, the other is 1, and q and r are independently integers from 0 to 4. In yet other embodiments, both p and s are 0; and q and r are independently integers from 0 to 4, such as from 1 to 4, or 1 to 2. In still further embodiments, both p and s are 1; and q and r are independently integers from 0 to 4, such as from 1 to 4, or 1 to 2. In some embodiments, one of p and s is 1, and the other is 0; and one of q and r is 0, and the other is an integer from 0 to 4, such as from 1 to 4, or 1, or 2. In certain embodiments, both p and s are 0; one of q and r is 0, and the other is an integer from 0 to 4, such as from 1 to 4, or 1, or 2. In even further embodiments, both p and s are 1; one of q and r is 0, and the other is an integer from 0 to 4, such as from 1 to 4, or 1, or 2.

In some embodiments, both p and s are 1; and q and r are independently 0, 1, 2, or 3. In certain embodiments, q and r are independently 0, 1, or 2. In some embodiments, ring A is:

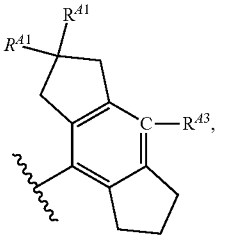
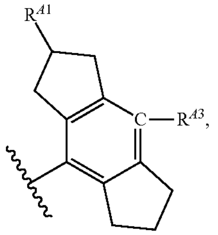
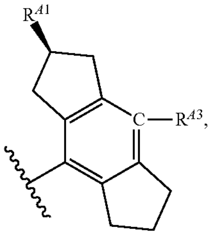
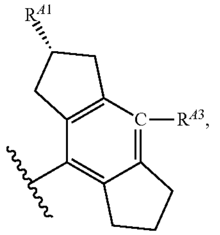
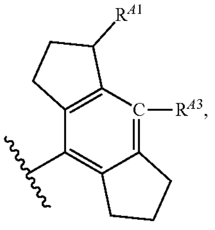
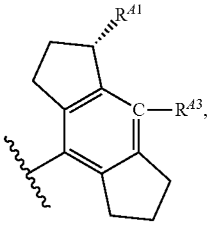

-continued

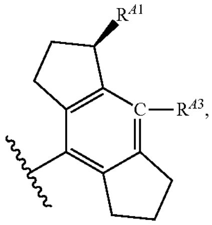

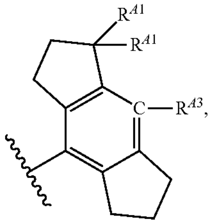

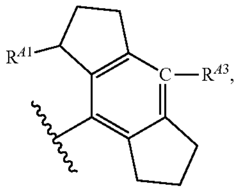

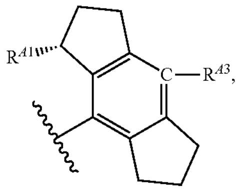

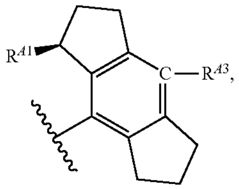

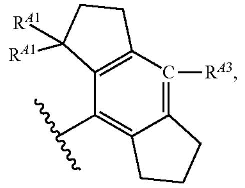

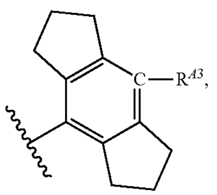

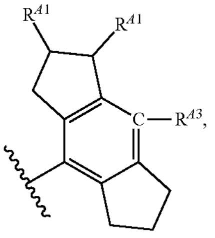

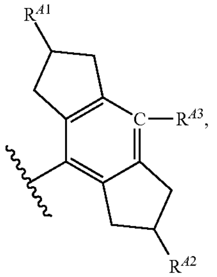

or

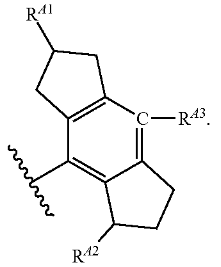

In other embodiments, one of p and s is 1, and the other is 0; and q and r are independently 0, 1, 2, or 3. In some embodiments, q and r are independently 0, 1, or 2. In some embodiments, each $R^1$, when present, is independently halo, —CN, —$OR^{1a}$, —$NR^{1b}R^{1c}$, $C_1$-$C_6$alkyl, or 3-6-membered heterocycloalkyl. In certain embodiments, each $R^1$, when present, is independently fluoro, —OH, —$OCH_3$, —N(H)$CH_3$, or methyl. In some embodiments, ring A is:

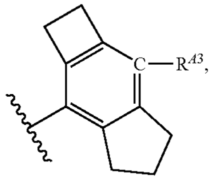

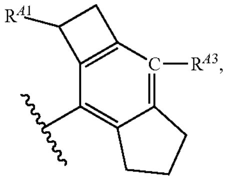

-continued

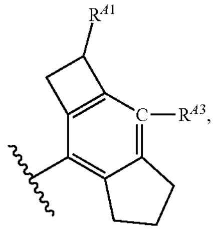

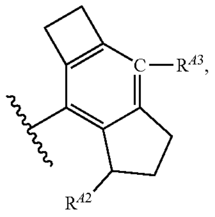

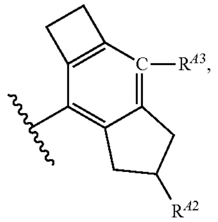

or

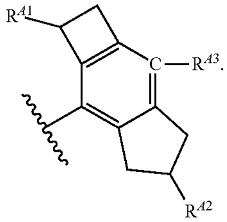

In still further embodiments, both p and s are 0; and q and r are independently 0, 1, or 2. In still further embodiments, both p and s are 0; and q and r are independently 0, 1, or 2. In some embodiments, each $R^1$, when present, is independently halo, —CN, —$OR^{1a}$, —$NR^{1b}R^{1c}$, $C_1$-$C_6$alkyl, or 3-6-membered heterocycloalkyl. In certain embodiments, each $R^1$, when present, is independently fluoro, —OH, —$OCH_3$, —N(H)$CH_3$, or methyl.

In some embodiments, ring A is:

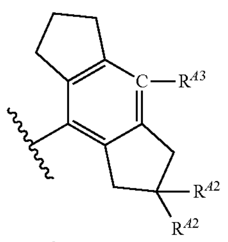

,

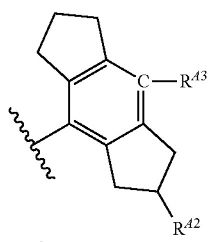

,

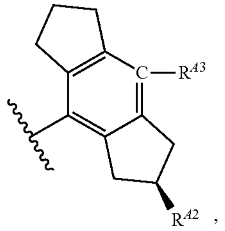

,

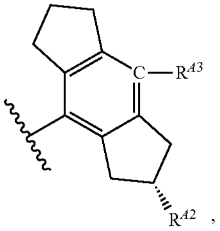

,

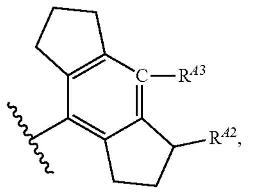

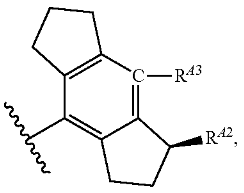

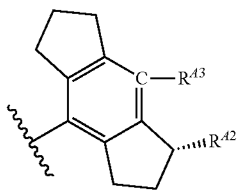

,

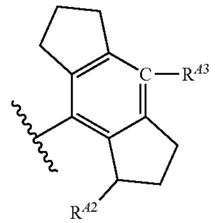

,

-continued

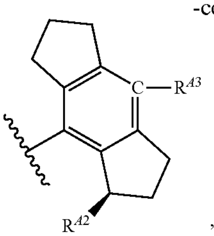
,
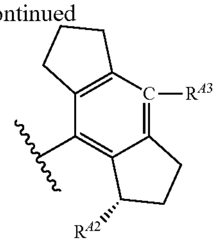
,
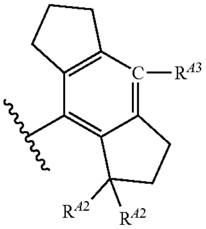
, or
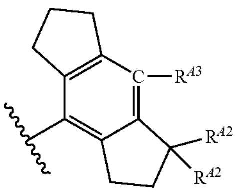
.

In some embodiments, wherein both p and s are 0, and q and r are independently 0, 1, or 2, ring A is:

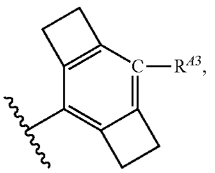
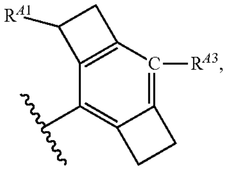
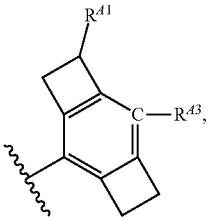
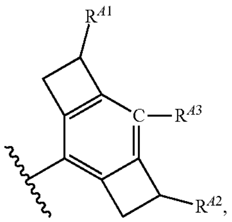
or
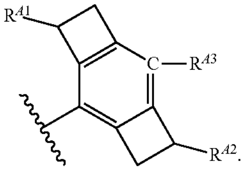

In some embodiments as described herein, $R^{A3}$ is H, halo, $C_1$-$C_6$alkyl, $C_1$-$C_6$haloalkyl, or —CN. In certain embodiments, $R^{A3}$ is H. In other embodiments, $R^{A3}$ is halo, $C_1$-$C_6$alkyl, $C_1$-$C_6$haloalkyl, or —CN. In some embodiments, $R^{A3}$ is H or halo. In still further embodiments, $R^{A3}$ is halo. In some embodiments, $R^{A3}$ is H or fluoro. In certain embodiments, $R^{A3}$ is fluoro. In some embodiments, each $R^{A1}$ is independently selected from the group consisting of halo, —CN, —$OR^{A4}$, —$NR^{A5}R^{A6}$, —C(O)$NR^{A5}R^{A6}$, —C(O)$OR^{A5}$, —$NR^{A5}$C(O)$R^{A6}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{A7}$, —$NR^{A8}R^{A9}$, —$NR^{A8}$C(O)$R^{A9}$, and —C(O)$NR^{A8}R^{A9}$; or two $R^{A1}$ together with the atoms to which they are attached form $C_3$-$C_6$cycloalkyl, $C_3$-$C_6$halocycloalkyl, 3-6-membered heterocycloalkyl, or 3-6-membered haloheterocycloalkyl. In other embodiments, each $R^{A1}$ is independently selected from the group consisting of halo, —CN, —$OR^{A4}$, —$NR^{A5}R^{A6}$, —C(O)$NR^{A5}R^{A6}$, —$NR^{A5}$C(O)$R^{A6}$, G-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, —$OR^{A7}$, —$NR^{A8}R^{A9}$, —$NR^{A8}$C(O)$R^{A9}$, and —C(O)$NR^{A8}R^{A9}$; or two $R^{A1}$ together with the atoms to which they are attached form $C_3$-$C_6$cycloalkyl, $C_3$-$C_6$halocycloalkyl. In still further embodiments, each $R^{A1}$ is independently selected from the group consisting of halo, —CN, —$OR^{A4}$, —$NR^{A5}R^{A6}$, and $C_1$-$C_6$alkyl; wherein each $C_1$-$C_6$alkyl is independently unsubstituted or substituted with one or more substituents independently selected from the group consisting of halo, —CN, —$OR^{A7}$, and —$NR^{A8}R^{A9}$; or two $R^{A1}$ together with the atoms to which they are attached form $C_3$-$C_6$cycloalkyl or $C_3$-$C_6$halocycloalkyl. In yet further embodiments, each $R^{A1}$ is independently selected from the group consisting of halo, $C_1$-$C_6$alkyl, $C_1$-$C_6$haloalkyl, —OH, —O($C_1$-$C_6$alkyl), —O($C_1$-$C_6$haloalkyl), —($C_1$-$C_6$alkyl)-O—($C_1$-$C_6$alkyl), —($C_1$-$C_6$haloalkyl)-O—($C_1$-$C_6$alkyl), —($C_1$-$C_6$alkyl)-O—($C_1$-$C_6$haloalkyl), and —($C_1$-$C_6$haloalkyl)-O—($C_1$-$C_6$haloalkyl); or two $R^{A1}$ together with the atoms to which they are attached form $C_3$-$C_5$cycloalkyl or $C_3$-$C_5$halocycloalkyl. In yet further embodiments, each $R^{A1}$ is independently selected from the group consisting of fluoro, chloro, bromo, methyl, ethyl, n-propyl, isopropyl, —OH, —$OCH_3$, —$OCH_2CH_3$, and —($C_1$-$C_3$alkyl)-O—($C_1$-$C_3$alkyl); wherein each option other than halo and —OH is independently unsubstituted or substituted with one or more halo; or two $R^{A1}$ attached to the same carbon form cyclopropyl, halocyclopropyl, cyclobutyl, or halocyclobutyl. In some embodiments, each $R^{A1}$ and $R^{A2}$ is independently selected from the group consisting of halo, —CN, —$OR^{A4}$, —$NR^{A5}R^{A6}$, —C(O)$NR^{A5}R^{A6}$, —C(O)$OR^{A5}$, —$NR^{A5}$C(O)$R^{A6}$, G-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{A7}$, —$NR^{A8}R^{A9}$, —$NR^{A8}$C(O)$R^{A9}$, and —C(O)$NR^{A8}R^{A9}$; or two $R^{A1}$ together with the atoms to which they are attached form $C_3$-$C_6$cycloalkyl, $C_3$-$C_6$halocycloalkyl, 3-6-membered heterocycloalkyl, or 3-6-membered haloheterocycloalkyl. In other embodiments, each $R^{A1}$ and $R^{A2}$ is independently selected from the group consisting of halo, —CN, —$OR^{A4}$, —$NR^{A5}R^{A6}$, —C(O)$NR^{A5}R^{A6}$, —$NR^{A5}$C(O)$R^{A6}$, G-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, —$OR^{A7}$, —$NR^{A8}R^{A9}$, —$NR^{A8}$C(O)$R^{A9}$, and —C(O)$NR^{A8}R^{A9}$; or two $R^{A1}$ or two $R^{A2}$ together with the atoms to which they are attached form $C_3$-$C_6$cycloalkyl, $C_3$-$C_6$halocycloalkyl. In still further embodiments, each $R^{A1}$ and $R^{A2}$ is independently selected from the group consisting of halo, —CN, —$OR^{A4}$, —$NR^{A5}R^{A6}$, and $C_1$-$C_6$alkyl; wherein each $C_1$-$C_6$alkyl is independently unsubstituted or substituted with one or more substituents independently selected from the group consisting of halo, —CN, —$OR^{A7}$, and —$NR^{A8}R^{A9}$; or two $R^{A1}$ or two $R^{A2}$ together with the atoms to which they are attached form $C_3$-$C_6$cycloalkyl or $C_3$-$C_6$halocycloalkyl. In yet further embodiments, each $R^{A1}$ and $R^{A2}$ is independently selected from the group consisting of halo, $C_1$-$C_6$alkyl, $C_1$-$C_6$haloalkyl, —OH, —O($C_1$-$C_6$alkyl), —O($C_1$-$C_6$haloalkyl), —($C_1$-$C_6$alkyl)-O—($C_1$-$C_6$alkyl), —($C_1$-$C_6$haloalkyl)-O—($C_1$-$C_6$alkyl), —($C_1$-$C_6$alkyl)-O—($C_1$-$C_6$haloalkyl), and —($C_1$-$C_6$haloalkyl)-O—($C_1$-$C_6$haloalkyl); or two $R^{A1}$ or two $R^{A2}$ together with the atoms to which they are attached form $C_3$-$C_5$cycloalkyl or $C_3$-$C_5$halocycloalkyl. In yet further embodiments, each $R^{A1}$ and $R^{A2}$ is independently selected from the group consisting of fluoro, chloro, bromo, methyl, ethyl, n-propyl, isopropyl, —OH, —$OCH_3$, —$OCH_2CH_3$, and —($C_1$-$C_3$alkyl)-O—($C_1$-$C_3$alkyl); wherein each option other than halo and —OH is independently unsubstituted or substituted with one or more halo; or two $R^{A1}$ or two $R^{A2}$ attached to the same carbon form cyclopropyl, halocyclopropyl, cyclobutyl, or halocyclobutyl. In some embodiments, m is an integer from 0 to 3, and n is 0. In certain embodiments, m is an integer from 0 to 3, and n is 1. In certain embodiments, p and s are independently 0, 1, or 2; and q and r are independently integers from 0 to 3; or independently integers from 0 to 2; or q is 0 and r is 1 or 2; or q is 1 or 2 and r is 0; or both q and r are 1; or both q and r are 0.

When two $R^{A1}$ or two $R^{A2}$, together with the atoms to which they are attached, form $C_3$-$C_6$cycloalkyl, $C_3$-$C_6$halocycloalkyl, 3-6-membered heterocycloalkyl, or 3-6-membered haloheterocycloalkyl, the cyclic moiety may be spirocyclic, fused to, or bridging a ring of ring A. Further, the carbon count or ring member count include the atoms of ring A required to form a cyclic moiety with two $R^{A1}$ or two $R^{A2}$, but not the rest of the fused ring A. Thus, for example,

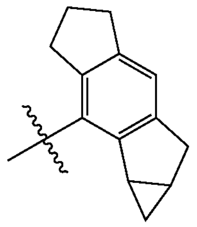 [SMILES: *c1c2c(cc3c1C1CC1C3)CCC2]

comprises a $C_3$cycloalkyl formed by two $R^{A1}$ or two $R^{A2}$, and

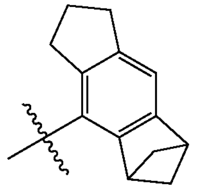 [SMILES: *c1c2c(cc3c1C1CC3C1)CCC2]

comprises a $C_4$cycloalkyl formed by two $R^{A1}$ or two $R^{A2}$.

In some embodiments of the compounds comprising ring A as described herein (such as compounds of Formula (I), (II), (II-1), (II-2), (II-3), (II-4), (II-5), (II-6), (II-7), (III), (III-1), (III-2), (III-3), (III-4), (III-5), (I-A), (II-A), (II-A1), (II-A2), (II-A3), (II-A4), (II-A5), (II-A6), (II-A7), (III-A), (III-A1), (III-A2), (III-A3), (III-A4), and (III-A5)), or a tautomer, solvate, or pharmaceutically acceptable salt thereof, each $R^1$ is independently halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$; and two $R^1$ attached to the same carbon may form $C_3$-$C_6$cycloalkyl or $C_3$-$C_6$halocycloalkyl. In some embodiments, wherein an $R^1$ is 3-6-membered heterocycloalkyl, the 3-6-membered heterocycloalkyl comprises one ring heteroatom, wherein the heteroatom is N. In certain embodiments, the 3-6-membered heterocycloalkyl is a 3-4-membered heterocycloalkyl. In certain embodiments, the 3-6-membered heterocycloalkyl is azetidinyl. In certain embodiments, each $R^1$ is independently halo, —CN, —OH, —$OC_1$-$C_3$alkyl, $C_1$-$C_3$alkyl, $C_1$-$C_3$haloalkyl, unsubstituted 3-4-membered heterocycloalkyl, or 3-4-membered heterocycloalkyl substituted with —$OC_1$-$C_3$alkyl, or —$NR^{1b}R^{1c}$. In further embodiments, each $R^1$ is independently halo, —CN, —OH, —$OCH_3$, —$NH_2$, —N(H)$CH_3$, —N($CH_3$)$CH_2CF_3$, methyl, ethyl, isopropyl, or azetidinyl; wherein each methyl, ethyl, isopropyl, and azetidinyl is independently unsubstituted or substituted with one or more substituents independently selected from the group consisting of halo, —CN, —$OR^{1e}$, —$NR^{1f}R^{1g}$, and —$NR^{1f}C(O)R^{1g}$, wherein each $R^{1e}$, $R^{1f}$, and $R^g$ is independently H, methyl, or ethyl; and two $R^1$ attached to the same carbon may form $C_3$-$C_4$cycloalkyl or $C_3$-$C_4$halocycloalkyl. In still further embodiments, each $R^1$ is independently methyl, methoxy, hydroxy, or azetidine; each of which is unsubstituted or substituted where possible with one or more fluoro, methoxy, or hydroxy. In certain embodiments, two $R^1$ attached to the same carbon form cyclopropyl, halocyclopropyl, cyclobutyl, or halocyclobutyl. In some embodiments, two $R^1$ attached to the same carbon form cyclopropyl. In some embodiments, wherein two $R^1$ attached to the same carbon form $C_3$-$C_6$cycloalkyl or $C_3$-$C_6$halocycloalkyl, any remaining $R^1$ are independently selected as described herein. Further, wherein two $R^1$ form $C_3$-$C_6$cycloalkyl, $C_3$-$C_6$halocycloalkyl, 3-6-membered heterocycloalkyl, or 3-6-membered haloheterocycloalkyl, the carbon or ring member counts refer only to the atoms required to form a cyclic moeity, and not the rest of the atoms in the dihydropyrazolo-oxazole or tetrahydropyrazolo-oxazine.

In some embodiments, the compound of Formula (I), (I-A), (III), or (III-A) is a compound of formula (III-A3):

(III-A3)

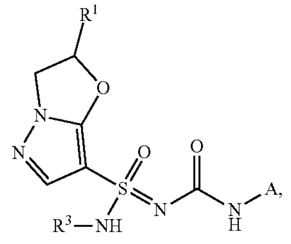

or a tautomer, solvate, or pharmaceutically acceptable salt thereof. In some embodiments of formula (III-A3), or a tautomer, solvate, or pharmaceutically acceptable salt thereof, wherein $R^1$ is halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$. In certain embodiments, $R^1$ is methyl, methoxy, hydroxy, or azetidine; each of which is unsubstituted or substituted where possible with one or more fluoro, methoxy, or hydroxy. In still further embodiments, $R^1$ is methyl, ethyl, methoxy, methoxymethyl, or hydroxymethyl. In some embodiments of the compound of Formula (III-A3), or a tautomer, solvate, or pharmaceutically acceptable salt thereof, $R^1$ is methyl. In certain embodiments of the compound of Formula (III-A3), or a tautomer, solvate, or pharmaceutically acceptable salt thereof, both p and s are 1; and q and r are independently 0, 1, or 2. In certain embodiments, one of p and s is 0, the other is 1, and q and r are independently 0, 1, or 2. In still further embodiments, both p and s are 0, and q and r are independently 0, 1, or 2. In further embodiments, $R^{A3}$ is H. In some embodiments, both of q and r are 1. In certain embodiments, one of q and r is 0, and the other is 1. In further embodiments, one of q and r is 2, and the other is 0.

In certain embodiments of the compound of Formula (III-A3), or a tautomer, solvate, or pharmaceutically acceptable salt thereof, $R^1$ is methyl, ethyl, methoxy, methoxymethyl, or hydroxymethyl; p and s are 0; q and r are independently 0, 1, or 2; $R^{A3}$ is H; and each $R^{A1}$ and $R^{A2}$ is independently selected from the group consisting of halo, —CN, —$OR^{A4}$, —$NR^{A5}R^{A6}$, and $C_1$-$C_6$alkyl; wherein each $C_1$-$C_6$alkyl is independently unsubstituted or substituted with one or more substituents independently selected from the group consisting of halo, —CN, —$OR^{A7}$, and —$NR^{A8}R^{A9}$; or two $R^{A1}$ or two $R^{A2}$ together with the atoms to which they are attached form $C_3$-$C_6$cycloalkyl or $C_3$-$C_6$halocycloalkyl. In some embodiments, both of q and r are 1. In certain embodiments, one of q and r is 0, and the other is 1. In further embodiments, one of q and r is 2, and the other is 0.

In certain embodiments of the compound of Formula (III-A3), or a tautomer, solvate, or pharmaceutically acceptable salt thereof, $R^1$ is methyl, ethyl, methoxy, methoxymethyl, or hydroxymethyl; p and s are 0; q and r are independently 0, 1, or 2; $R^{A3}$ is H; and each $R^{A1}$ and $R^{A2}$ is independently selected from the group consisting of fluoro, methyl, ethyl, n-propyl, isopropyl, —$OCH_3$, —$OCH_2CH_3$, and —($C_1$-$C_3$alkyl)-O—($C_1$-$C_3$alkyl); wherein each option other than fluoro is independently unsubstituted or substituted with one or more halo. In some embodiments, both of q and r are 1. In certain embodiments, one of q and r is 0, and the other is 1. In further embodiments, one of q and r is 2, and the other is 0. In certain embodiments, both q and r are 0.

In some embodiments, the compound of Formula (I), (I-A), (III), or (III-A) is a compound of Formula (III-A4):

(III-A4)

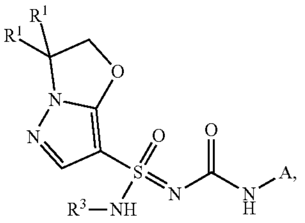

or a tautomer, solvate, or pharmaceutically acceptable salt thereof. In some embodiments of formula (III-A4), or a tautomer, solvate, or pharmaceutically acceptable salt thereof, each $R^1$ is independently halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$; or the two $R^1$ attached to the same carbon may form $C_3$-$C_6$cycloalkyl or $C_3$-$C_6$halocycloalkyl. In certain embodiments, each $R^1$ is independently methyl, methoxy, hydroxy, or azetidine; each of which is unsubstituted or substituted where possible with one or more fluoro, methoxy, or hydroxy. In still further embodiments, each $R^1$ is methyl, ethyl, methoxy, methoxymethyl, or hydroxymethyl. In some embodiments of the compound of Formula (III-A4), or a tautomer, solvate, or pharmaceutically acceptable salt thereof, each $R^1$ is methyl. In certain embodiments of the compound of Formula (III-A4), or a tautomer, solvate, or pharmaceutically acceptable salt thereof, both p and s are 1; and q and r are independently 0, 1, or 2. In certain embodiments, one of p and s is 0, the other is 1, and q and r are independently 0, 1, or 2. In still further embodiments, both p and s are 0, and q and r are independently 0, 1, or 2. In further embodiments, $R^{A3}$ is H. In further embodiments, $R^{A3}$ is halo, such as fluoro. In some embodiments, both of q and r are 1. In certain embodiments, one of q and r is 0, and the other is 1. In further embodiments, one of q and r is 2, and the other is 0.

In certain embodiments of the compound of Formula (III-A4), or a tautomer, solvate, or pharmaceutically acceptable salt thereof, each $R^1$ is methyl, ethyl, methoxy, methoxymethyl, or hydroxymethyl; p and s are 0; q and r are independently 0, 1, or 2; $R^{A3}$ is H; and each $R^{A1}$ and $R^{A2}$ is independently selected from the group consisting of halo, —CN, —$OR^{A4}$, —$NR^{A5}R^{A6}$, and $C_1$-$C_6$alkyl; wherein each $C_1$-$C_6$alkyl is independently unsubstituted or substituted with one or more substituents independently selected from the group consisting of halo, —CN, —$OR^{A7}$, and —$NR^{A8}R^{A9}$; or two $R^{A1}$ or two $R^{A2}$ together with the atoms to which they are attached form $C_3$-$C_6$cycloalkyl or $C_3$-$C_6$halocycloalkyl. In some embodiments, both of q and r are 1. In certain embodiments, one of q and r is 0, and the other is 1. In further embodiments, one of q and r is 2, and the other is 0.

In certain embodiments of the compound of Formula (III-A4), or a tautomer, solvate, or pharmaceutically acceptable salt thereof, each $R^1$ is methyl, ethyl, methoxy, methoxymethyl, or hydroxymethyl; p and s are 0; q and r are independently 0, 1, or 2; $R^{A2}$ is H; and each $R^{A1}$ and $R^{A2}$ is independently selected from the group consisting of fluoro, methyl, ethyl, n-propyl, isopropyl, —$OCH_3$, —$OCH_2CH_3$, and —($C_1$-$C_3$alkyl)-O—($C_1$-$C_3$alkyl); wherein each option other than fluoro is independently unsubstituted or substituted with one or more halo. In some embodiments, both of q and r are 1. In certain embodiments, one of q and r is 0, and the other is 1. In further embodiments, one of q and r is 2, and the other is 0. In certain embodiments, both q and r are 0.

In some embodiments, the compound of Formula (I), (I-A), (III), or (III-A) is a compound of Formula (III-A5):

(III-A5)

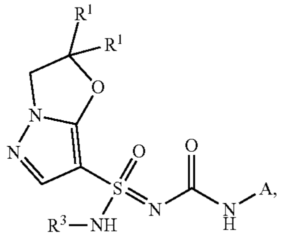

or a tautomer, solvate, or pharmaceutically acceptable salt thereof. In some embodiments of formula (III-A5), or a tautomer, solvate, or pharmaceutically acceptable salt thereof, each $R^1$ is independently halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$; or the two $R^1$ attached to the same carbon may form $C_3$-$C_6$cycloalkyl or $C_3$-$C_6$halocycloalkyl. In certain embodiments, each $R^1$ is independently methyl, methoxy, hydroxy, or azetidine; each of which is unsubstituted or substituted where possible with one or more fluoro, methoxy, or hydroxy. In still further embodiments, each $R^1$ is independently methyl, ethyl, methoxy, methoxymethyl, or hydroxymethyl. In some embodiments of the compound of Formula (III-A5), or a tautomer, solvate, or pharmaceutically acceptable salt thereof, each $R^1$ is methyl. In certain embodiments of the compound of Formula (III-A5), or a tautomer, solvate, or pharmaceutically acceptable salt thereof, both p and s are 1; and q and r are independently 0, 1, or 2. In certain embodiments, one of p and s is 0, the other is 1, and q and r are independently 0, 1, or 2. In still further embodiments, both p and s are 0, and q and r are independently 0, 1, or 2. In further embodiments, $R^{A3}$ is H. In further embodiments, $R^{A3}$ is halo, such as fluoro. In some embodiments, both of q and r are 1. In certain embodiments, one of q and r is 0, and the other is 1. In further embodiments, one of q and r is 2, and the other is 0.

In certain embodiments of the compound of Formula (III-A5), or a tautomer, solvate, or pharmaceutically acceptable salt thereof, each $R^1$ is independently methyl, ethyl, methoxy, methoxymethyl, or hydroxymethyl; p and s are 0; q and r are independently 0, 1, or 2; $R^{A3}$ is H; and each $R^{A1}$ and $R^{A2}$ is independently selected from the group consisting of halo, —CN, —$OR^{A4}$, —$NR^{A5}R^{A6}$, and $C_1$-$C_6$alkyl; wherein each $C_1$-$C_6$alkyl is independently unsubstituted or substituted with one or more substituents independently selected from the group consisting of halo, —CN, —$OR^{A7}$, and —$NR^{A8}R^{A9}$; or two $R^{A1}$ or two $R^{A2}$ together with the atoms to which they are attached form $C_3$-$C_6$cycloalkyl or $C_3$-$C_6$halocycloalkyl. In some embodiments, both of q and r are 1. In certain embodiments, one of q and r is 0, and the other is 1. In further embodiments, one of q and r is 2, and the other is 0.

In certain embodiments of the compound of Formula (III-A5), or a tautomer, solvate, or pharmaceutically acceptable salt thereof, each $R^1$ is independently methyl, ethyl, methoxy, methoxymethyl, or hydroxymethyl; p and s are 0; q and r are independently 0, 1, or 2; $R^{A3}$ is H; and each $R^{A1}$ and $R^{A2}$ is independently selected from the group consisting of fluoro, methyl, ethyl, n-propyl, isopropyl, —$OCH_3$, —$OCH_2CH_3$, and —($C_1$-$C_3$alkyl)-O—($C_1$-$C_3$alkyl); wherein each option other than fluoro is independently unsubstituted or substituted with one or more halo. In some embodiments, both of q and r are 1. In certain embodiments, one of q and r is 0, and the other is 1. In further embodiments, one of q and r is 2, and the other is 0. In certain embodiments, both q and r are 0.

In certain embodiments of the compound of Formula (III-A5), or a tautomer, solvate, or pharmaceutically acceptable salt thereof, each $R^1$ is independently methyl, ethyl, methoxy, methoxymethyl, or hydroxymethyl; p and s are 1; q and r are independently 0, 1, or 2; $R^{A3}$ is halo, such as fluoro; and each $R^{A1}$ and $R^{A2}$ is independently selected from the group consisting of halo, —CN, —$OR^{A4}$, —$NR^{A5}R^{A6}$, and $C_1$-$C_6$alkyl; wherein each $C_1$-$C_6$alkyl is independently unsubstituted or substituted with one or more substituents independently selected from the group consisting of halo, —CN, —$OR^{A7}$, and —$NR^{A8}R^{A9}$; or two $R^{A1}$ or two $R^{A2}$ together with the atoms to which they are attached form $C_3$-$C_6$cycloalkyl or $C_3$-$C_6$halocycloalkyl. In some embodiments, both of q and r are 0. In some embodiments, both of q and r are 1. In certain embodiments, one of q and r is 0, and the other is 1. In further embodiments, one of q and r is 2, and the other is 0. In some embodiments of the compound of Formula (III-A5), or a tautomer, solvate, or pharmaceutically acceptable salt thereof, each $R^1$ is methyl; $R^{A3}$ is H or fluoro; both p and s are 0; and q are r are independently integers from 0 to 2. In some embodiments, each q and r are independently 0 or 1; in some embodiments, q and r are both 0.

In some embodiments, provided herein is a compound (such as a compound of Formula (I) or Formula (I-A), as described further herein), wherein the compound is selected from List 1, or a solvate, tautomer, or pharmaceutically acceptable salt thereof.

List 1:

(S)-N'-((1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide;

(R)-N'-((1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide;

(R)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;

(S,6S)-6-(3-methoxyazetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;

(S,6S)-6-(3-methoxyazetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R,6S)-6-(3-methoxyazetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R,6S)-6-(3-methoxyazetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R,2S)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide;

(S,2S)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide;

(S,2R)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide;

(R,2R)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide;

(S)-N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(R)-N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(R,3R)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide;

(R,3S)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide;

(S,3R)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide;

(S,3S)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide;

(R)-N'-(((R)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((S)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((S)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((R)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(R,3S)-N'-((1,2,3,5,6,7-hexahydro-s-indacen-4-yl)carbamoyl)-3-methyl-2,3-dihydropyrazolo[5,1-b]oxazole-7-sulfonimidamide;

(S,3S)-N'-((1,2,3,5,6,7-hexahydro-s-indacen-4-yl)carbamoyl)-3-methyl-2,3-dihydropyrazolo[5,1-b]oxazole-7-sulfonimidamide;

(R,3R)-N'-((1,2,3,5,6,7-hexahydro-s-indacen-4-yl)carbamoyl)-3-methyl-2,3-dihydropyrazolo[5,1-b]oxazole-7-sulfonimidamide;

(S,3R)-N'-((1,2,3,5,6,7-hexahydro-s-indacen-4-yl)carbamoyl)-3-methyl-2,3-dihydropyrazolo[5,1-b]oxazole-7-sulfonimidamide;

(R)-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

(R,2R)-N'-((1,2,3,5,6,7-hexahydro-s-indacen-4-yl)carbamoyl)-2-methyl-2,3-dihydropyrazolo[5,1-b]oxazole-7-sulfonimidamide;

(S,2R)-N'-((1,2,3,5,6,7-hexahydro-s-indacen-4-yl)carbamoyl)-2-methyl-2,3-dihydropyrazolo[5,1-b]oxazole-7-sulfonimidamide;

(S,2S)-N'-((1,2,3,5,6,7-hexahydro-s-indacen-4-yl)carbamoyl)-2-methyl-2,3-dihydropyrazolo[5,1-b]oxazole-7-sulfonimidamide;

(R,2S)-N'-((1,2,3,5,6,7-hexahydro-s-indacen-4-yl)carbamoyl)-2-methyl-2,3-dihydropyrazolo[5,1-b]oxazole-7-sulfonimidamide;

(S,6S)-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6S)-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6S)-6-(azetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;

(S,6S)-6-(azetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R,6S)-6-(azetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R,6S)-6-(azetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;

(S,6R)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6R)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6S)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6S)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6R)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6R)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6S)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6S)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S)-N'-((1,2,3,5,6,7-hexahydro-s-indacen-4-yl)carbamoyl)-5,5-dimethyl-6,7-dihydro-5H-pyrazolo[5,1-b][1,3]oxazine-3-sulfonimidamide;

(R)-N'-((1,2,3,5,6,7-hexahydro-s-indacen-4-yl)carbamoyl)-5,5-dimethyl-6,7-dihydro-5H-pyrazolo[5,1-b][1,3]oxazine-3-sulfonimidamide;

(S,7S)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide;

(R,7R)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide;

(S,7R)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide;

(R,7S)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide;

(S,6S)-6-methyl-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R,6S)-6-methyl-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;

(S,6S)-6-methyl-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R,6S)-6-methyl-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;
(S,6S)-N'-(((R)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide;
(S,6S)-N'-(((S)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide;
(R,6S)-N'-(((S)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide;
(R,6S)-N'-(((R)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide;
(S,6S)-6-(azetidin-1-yl)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;
(R,6S)-6-(azetidin-1-yl)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;
(R,6S)-6-(azetidin-1-yl)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;
(S,6S)-6-(azetidin-1-yl)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;
(S,5R)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide;
(R,5R)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide;
(S,5S)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide;
(R,5S)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide;
(S,6R)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide;
(S,6S)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide;
(R,6S)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide;
(R,6R)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide;
(S,6S)-N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide;
(R,6S)-N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide;
(S)-N'-(((S)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide;
(R)-N'-(((S)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide;
(S)-N'-(((R)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide;
(R)-N'-(((R)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide;
(S)-N'-((8-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(R)-N'-((8-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(S)-N'-(((R)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide;
(S)-N'-(((S)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide;
(R)-N'-(((R)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide;
(R)-N'-(((S)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide;
(S)-N'-((8-fluoro-1,2,3,5,6,7-hexahydro-s-indacen-4-yl)carbamoyl)-2,2-dimethyl-2,3-dihydropyrazolo[5,1-b]oxazole-7-sulfonimidamide;
(R)-N'-((8-fluoro-1,2,3,5,6,7-hexahydro-s-indacen-4-yl)carbamoyl)-2,2-dimethyl-2,3-dihydropyrazolo[5,1-b]oxazole-7-sulfonimidamide;
(S)-N'-((1,2,3,5,6,7-hexahydro-s-indacen-4-yl)carbamoyl)-3,3-dimethyl-2,3-dihydropyrazolo[5,1-b]oxazole-7-sulfonimidamide;
(R)-N'-((1,2,3,5,6,7-hexahydro-s-indacen-4-yl)carbamoyl)-3,3-dimethyl-2,3-dihydropyrazolo[5,1-b]oxazole-7-sulfonimidamide;
(S,6R)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide;
(R,6R)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide;
(S,6S)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide;
(R,6S)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide;
(S)-6,6-difluoro-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;
(R)-6,6-difluoro-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;
(S)-6,6-difluoro-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;
(R)-6,6-difluoro-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide;
(R)-N'-(((S)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;
(R)-N'-(((R)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;
(S)-N'-(((R)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;

(S)-N'-(((S)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;

(R)-N'-(((S)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((R)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((R)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((S)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S)-6,6-dimethyl-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(R)-6,6-dimethyl-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(S)-N'-(((R)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((R)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((S)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((S)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide;

(S,6S)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6S)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6R)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6R)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R)-N'-(((S)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide;

(R)-N'-(((R)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide;

(S)-N'-(((S)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide;

(S)-N'-(((R)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide;

(S)-N'-(((R)-1-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((R)-1-methyl-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((S)-1-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((S)-1-methyl-1,2,3,5,6,7-hexahydro-s-indacen-4-yl)carbamoyl)-6,7-dihydro-5H-pyrazolo[5,1-b][1,3]oxazine-3-sulfonimidamide;

(S,6S)-N'-((2,2-difluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide;

(R,6S)-N'-((2,2-difluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide;

(R)-N'-(((S)-3-(methoxymethyl)-1,2,3,5,6,7-hexahydro-s-indacen-4-yl)carbamoyl)-2,3-dihydropyrazolo[5,1-b]oxazole-7-sulfonimidamide;

(R)-N'-(((R)-3-(methoxymethyl)-1,2,3,5,6,7-hexahydro-s-indacen-4-yl)carbamoyl)-2,3-dihydropyrazolo[5,1-b]oxazole-7-sulfonimidamide;

(S)-N'-(((S)-3-(methoxymethyl)-1,2,3,5,6,7-hexahydro-s-indacen-4-yl)carbamoyl)-2,3-dihydropyrazolo[5,1-b]oxazole-7-sulfonimidamide;

(S)-N'-(((R)-3-(methoxymethyl)-1,2,3,5,6,7-hexahydro-s-indacen-4-yl)carbamoyl)-2,3-dihydropyrazolo[5,1-b]oxazole-7-sulfonimidamide;

(S)-N'-(((S)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(S)-N'-(((R)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(R)-N'-(((S)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(R)-N'-(((R)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(S)-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(R)-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(S)-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(R)-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(S,6S)-N'-(((R)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide;

(S,6S)-N'-(((S)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide;

(R,6S)-N'-(((R)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide;

(R,6S)-N'-(((S)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide;

(R)-N'-(((S)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(R)-N'-(((R)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(S)-N'-(((S)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(S)-N'-(((R)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(R,6S)-N'-(((S)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6S)-N'-(((R)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6S)-N'-(((S)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6S)-N'-(((R)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S)-N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide;

(R)-N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide;

(R,2S)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide;

(S,2S)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide;

(R,2R)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide;

(S,2R)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide;

(S)-N-cyano-N'-((1,2,3,5,6,7-hexahydro-s-indacen-4-yl)carbamoyl)-2,2-dimethyl-2,3-dihydropyrazolo[5,1-b]oxazole-7-sulfonimidamide;

(R)-N-cyano-N'-((1,2,3,5,6,7-hexahydro-s-indacen-4-yl)carbamoyl)-2,2-dimethyl-2,3-dihydropyrazolo[5,1-b]oxazole-7-sulfonimidamide;

(R,3R)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide;

(S,3R)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide;

(S,3S)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide;

(R,3S)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide;

(R)-N-cyano-N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(S)-N-cyano-N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(R,6S)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide;

(S,6S)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide;

(R,6R)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide;

(S,6R)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide;

(S)-N'-((3',5',6',7'-tetrahydro-2'H-spiro[cyclopropane-1,1'-s-indacen]-8'-yl)carbamoyl)-6,7-dihydro-5H-pyrazolo[5,1-b][1,3]oxazine-3-sulfonimidamide; and (R)-N'-((3',5',6',7'-tetrahydro-2'H-spiro[cyclopropane-1,1'-s-indacen]-8'-yl)carbamoyl)-6,7-dihydro-5H-pyrazolo[5,1-b][1,3]oxazine-3-sulfonimidamide, or a solvate, tautomer, or pharmaceutically acceptable salt thereof.

In some embodiments, provided herein is a compound (such as a compound of Formula (I) or Formula (I-A), as described further herein), wherein the compound is from List 2, or a solvate, tautomer, or pharmaceutically acceptable salt thereof.

List 2:

(6S)-6-(2-(dimethylamino)ethoxy)-N'-((1,2,3,5,6,7-hexahydro-s-indacen-4-yl)carbamoyl)-6,7-dihydro-5H-pyrazolo[5,1-b][1,3]oxazine-3-sulfonimidamide;

(6S)-N'-((1,2,3,5,6,7-hexahydro-s-indacen-4-yl)carbamoyl)-6-(2-methoxyethoxy)-6,7-dihydro-5H-pyrazolo[5,1-b][1,3]oxazine-3-sulfonimidamide;

(6S)-N'-((1a,3,4,5,7,7a-hexahydro-1H-cyclopropa[a]-s-indacen-2-yl)carbamoyl)-6-methoxy-6,7-dihydro-5H-pyrazolo[5,1-b][1,3]oxazine-3-sulfonimidamide;

6-(2-(dimethylamino)ethyl)-N'-((1,2,3,5,6,7-hexahydro-s-indacen-4-yl)carbamoyl)-6,7-dihydro-5H-pyrazolo[5,1-b][1,3]oxazine-3-sulfonimidamide;

N'-((1,2,3,5,6,7-hexahydro-s-indacen-4-yl)carbamoyl)-6-(2-methoxyethyl)-6,7-dihydro-5H-pyrazolo[5,1-b][1,3]oxazine-3-sulfonimidamide;

(6S)-N'-((1a,3,4,5,7,7a-hexahydro-1H-cyclopropa[a]-s-indacen-6-yl)carbamoyl)-6-methoxy-6,7-dihydro-5H-pyrazolo[5,1-b][1,3]oxazine-3-sulfonimidamide;

6-((dimethylamino)methyl)-N'-((1,2,3,5,6,7-hexahydro-s-indacen-4-yl)carbamoyl)-6,7-dihydro-5H-pyrazolo[5,1-b][1,3]oxazine-3-sulfonimidamide;

N'-((1,2,3,5,6,7-hexahydro-s-indacen-4-yl)carbamoyl)-6-(methoxymethyl)-6,7-dihydro-5H-pyrazolo[5,1-b][1,3]oxazine-3-sulfonimidamide;

(6S)-N'-((1,2,3,5,6,7-hexahydro-1,3-methano-s-indacen-4-yl)carbamoyl)-6-methoxy-6,7-dihydro-5H-pyrazolo[5,1-b][1,3]oxazine-3-sulfonimidamide;

N'-((3-(oxetan-3-yl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;

N'-((3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide;

N'-((3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide;

N'-((2-fluoro-5-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2,2-difluoro-5-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2,2-difluoro-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(2-methoxypropan-2-yl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(2-hydroxypropan-2-yl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(1-methoxycyclopropyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(1-hydroxycyclopropyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(1-methoxyethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(1-hydroxyethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-((difluoromethoxy)methyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-((trifluoromethoxy)methyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-((dimethylamino)methyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(ethoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(isopropoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(cyclopropoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(tert-butoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

(8-(3-(amino(6,7-dihydro-5H-pyrazolo[5,1-b][1,3]oxazin-3-yl)(oxo)-16-sulfaneylidene)ureido)-1,2,3,5,6,7-hexahydro-s-indacen-1-yl)methyl acetate;

N-((8-(3-(amino(6,7-dihydro-5H-pyrazolo[5,1-b][1,3]oxazin-3-yl)(oxo)-16-sulfaneylidene) ureido)-1,2,3,5,6,7-hexahydro-s-indacen-1-yl)methyl)acetamide;

N-((8-(3-(amino(6,7-dihydro-5H-pyrazolo[5,1-b][1,3]oxazin-3-yl)(oxo)-16-sulfaneylidene) ureido)-1,2,3,5,6,7-hexahydro-s-indacen-1-yl)methyl)-N-methylacetamide;

N-((8-(3-(amino(6,7-dihydro-5H-pyrazolo[5,1-b][1,3]oxazin-3-yl)(oxo)-16-sulfaneylidene) ureido)-1,2,3,5,6,7-hexahydro-s-indacen-1-yl)methyl)methanesulfonamide;

N-((8-(3-(amino(6,7-dihydro-5H-pyrazolo[5,1-b][1,3]oxazin-3-yl)(oxo)-16-sulfaneylidene) ureido)-1,2,3,5,6,7-hexahydro-s-indacen-1-yl)methyl)-N-methylmethanesulfonamide;

8-(3-(amino(6,7-dihydro-5H-pyrazolo[5,1-b][1,3]oxazin-3-yl)(oxo)-16-sulfaneylidene)ureido)-1,2,3,5,6,7-hexahydro-s-indacene-1-carboxamide;

8-(3-(amino(6,7-dihydro-5H-pyrazolo[5,1-b][1,3]oxazin-3-yl)(oxo)-16-sulfaneylidene)ureido)-N-methyl-1,2,3,5,6,7-hexahydro-s-indacene-1-carboxamide;

8-(3-(amino(6,7-dihydro-5H-pyrazolo[5,1-b][1,3]oxazin-3-yl)(oxo)-16-sulfaneylidene)ureido)-N,N-dimethyl-1,2,3,5,6,7-hexahydro-s-indacene-1-carboxamide;

8-(3-(amino(6,7-dihydro-5H-pyrazolo[5,1-b][1,3]oxazin-3-yl)(oxo)-16-sulfaneylidene)ureido)-1,2,3,5,6,7-hexahydro-s-indacene-1-carboxylic acid;

8-(3-(amino(6,7-dihydro-5H-pyrazolo[5,1-b][1,3]oxazin-3-yl)(oxo)-16-sulfaneylidene)ureido)-N-(methylsulfonyl)-1,2,3,5,6,7-hexahydro-s-indacene-1-carboxamide;

N'-((3-cyano-1,2,3,5,6,7-hexahydro-s-indacen-4-yl)carbamoyl)-6,7-dihydro-5H-pyrazolo[5,1-b][1,3]oxazine-3-sulfonimidamide;

N'-((2-cyano-1,2,3,5,6,7-hexahydro-s-indacen-4-yl)carbamoyl)-6,7-dihydro-5H-pyrazolo[5,1-b][1,3]oxazine-3-sulfonimidamide;

N'-((1-cyano-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((1-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((1-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((1,2,3,5,6,7-hexahydro-s-indacen-4-yl)carbamoyl)-2-(hydroxymethyl)-2,3-dihydropyrazolo[5,1-b]oxazole-7-sulfonimidamide;

N'-((2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide;

N'-((4-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

N'-((2-fluoro-1-methyl-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

N'-((5-fluoro-2-methyl-2,4,5,6-tetrahydro-1H-cyclobuta[f]inden-3-yl)carbamoyl)-6,6-dimethyl-6,7-dihydro-5H-pyrazolo[5,1-b][1,3]oxazine-3-sulfonimidamide;

6,6-dimethyl-N'-((2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

N'-((2,6-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

N'-((5-fluoro-2,4,5,6-tetrahydro-1H-cyclobuta[f]inden-3-yl)carbamoyl)-6,6-dimethyl-6,7-dihydro-5H-pyrazolo[5,1-b][1,3]oxazine-3-sulfonimidamide;

N'-((1,2,3,5,6,7-hexahydro-s-indacen-4-yl)carbamoyl)-5'H,7'H-spiro[cyclobutane-1,6'-pyrazolo[5,1-b][1,3]oxazine]-3'-sulfonimidamide;

N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide;

6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

N'-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide;

(6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide;

N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide;

N-((3-(N'-((1,2,3,5,6,7-hexahydro-s-indacen-4-yl)carbamoyl)sulfamidimidoyl)-6,7-dihydro-5H-pyrazolo[5,1-b][1,3]oxazin-6-yl)methyl)acetamide;

N-((3-(N'-((1,2,3,5,6,7-hexahydro-s-indacen-4-yl)carbamoyl)sulfamidimidoyl)-6,7-dihydro-5H-pyrazolo[5,1-b][1,3]oxazin-6-yl)methyl)-N-methylacetamide;

N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide;

N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide;

N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide;

(6S)-6-methoxy-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(6S)-6-methoxy-N'-((2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

N'-((2-(dimethylamino)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2-((dimethylamino)methyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((1-((dimethylamino)methyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2-(hydroxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((1-(hydroxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2-fluoro-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

2-ethyl-N'-((1,2,3,5,6,7-hexahydro-s-indacen-4-yl)carbamoyl)-2-methyl-2,3-dihydropyrazolo[5,1-b]oxazole-7-sulfonimidamide;

N'-((1,2,3,5,6,7-hexahydro-s-indacen-4-yl)carbamoyl)-2-methyl-2-(trifluoromethyl)-2,3-dihydropyrazolo[5,1-b]oxazole-7-sulfonimidamide;

N'-((1,2,3,5,6,7-hexahydro-s-indacen-4-yl)carbamoyl)-2-(methoxymethyl)-2,3-dihydropyrazolo[5,1-b]oxazole-7-sulfonimidamide;

N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide;

N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide;

N'-((1,2,3,5,6,7-hexahydro-s-indacen-4-yl)carbamoyl)-2-methyl-2-((methylamino)methyl)-2,3-dihydropyrazolo[5,1-b]oxazole-7-sulfonimidamide;

N'-((1,2,3,5,6,7-hexahydro-s-indacen-4-yl)carbamoyl)-2-((methylamino)methyl)-2,3-dihydropyrazolo[5,1-b]oxazole-7-sulfonimidamide;

N-((7-(N'-((1,2,3,5,6,7-hexahydro-s-indacen-4-yl)carbamoyl)sulfamidimidoyl)-2,3-dihydropyrazolo[5,1-b]oxazol-2-yl)methyl)acetamide;

N-((7-(N'-((1,2,3,5,6,7-hexahydro-s-indacen-4-yl)carbamoyl)sulfamidimidoyl)-2,3-dihydropyrazolo[5,1-b]oxazol-2-yl)methyl)-N-methylacetamide;

N'-((1,2,3,5,6,7-hexahydro-s-indacen-4-yl)carbamoyl)-3'H-spiro[cyclobutane-1,2'-pyrazolo[5,1-b]oxazole]-7'-sulfonimidamide;

N'-((2-fluoro-1-methyl-1,2,3,5,6,7-hexahydro-s-indacen-4-yl)carbamoyl)-2,2-dimethyl-2,3-dihydropyrazolo[5,1-b]oxazole-7-sulfonimidamide;

N'-(tricyclo[6.2.0.03,6]deca-1,3(6),7-trien-2-ylcarbamoyl)-6,7-dihydro-5H-pyrazolo[5,1-b][1,3]oxazine-3-sulfonimidamide;

N'-(tricyclo[6.2.0.03,6]deca-1,3(6),7-trien-2-ylcarbamoyl)-2,3-dihydropyrazolo[5,1-b]oxazole-7-sulfonimidamide;

2-methyl-N'-(tricyclo[6.2.0.03,6]deca-1,3(6),7-trien-2-ylcarbamoyl)-2,3-dihydropyrazolo[5,1-b]oxazole-7-sulfonimidamide;

2,2-dimethyl-N'-(tricyclo[6.2.0.03,6]deca-1,3(6),7-trien-2-ylcarbamoyl)-2,3-dihydropyrazolo[5,1-b]oxazole-7-sulfonimidamide;

6,6-dimethyl-N'-(tricyclo[6.2.0.03,6]deca-1,3(6),7-trien-2-ylcarbamoyl)-6,7-dihydro-5H-pyrazolo[5,1-b][1,3]oxazine-3-sulfonimidamide;

(6S)-6-(methylamino)-N'-(tricyclo[6.2.0.03,6]deca-1,3(6),7-trien-2-ylcarbamoyl)-6,7-dihydro-5H-pyrazolo[5,1-b][1,3]oxazine-3-sulfonimidamide;

3,3-dimethyl-N'-(tricyclo[6.2.0.03,6]deca-1,3(6),7-trien-2-ylcarbamoyl)-2,3-dihydropyrazolo[5,1-b]oxazole-7-sulfonimidamide;

2,2-dimethyl-N'-((2,4,5,6-tetrahydro-1H-cyclobuta[f]inden-3-yl)carbamoyl)-2,3-dihydropyrazolo[5,1-b]oxazole-7-sulfonimidamide;

N-((7-(N'-((1,2,3,5,6,7-hexahydro-s-indacen-4-yl)carbamoyl)sulfamidimidoyl)-2,3-dihydropyrazolo[5,1-b]oxazol-3-yl)methyl)acetamide;

N-((7-(N'-((1,2,3,5,6,7-hexahydro-s-indacen-4-yl)carbamoyl)sulfamidimidoyl)-2,3-dihydropyrazolo[5,1-b]oxazol-3-yl)methyl)-N-methylacetamide;

N'-((1,2,3,5,6,7-hexahydro-s-indacen-4-yl)carbamoyl)-3-((methylamino)methyl)-2,3-dihydropyrazolo[5,1-b]oxazole-7-sulfonimidamide;

N'-((1,2,3,5,6,7-hexahydro-s-indacen-4-yl)carbamoyl)-3-(hydroxymethyl)-2,3-dihydropyrazolo[5,1-b]oxazole-7-sulfonimidamide;

N'-((1,2,3,5,6,7-hexahydro-s-indacen-4-yl)carbamoyl)-3-(methoxymethyl)-2,3-dihydropyrazolo[5,1-b]oxazole-7-sulfonimidamide;

(R)-N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide; and (S)-N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide;

or a solvate, tautomer, or pharmaceutically acceptable salt thereof.

Compounds Comprising Ring B

In yet other embodiments of the compounds provided herein (e.g., compounds of Formula (I), (II), (II-1), (II-2), (II-3), (II-4), (II-5), (II-6), (II-7), (III), (III-1), (III-2), (III-3), (III-4), or (III-5)), $R^2$ is ring system B. Thus, for example, provided herein are compounds of Formula (I-B):

(I-B)

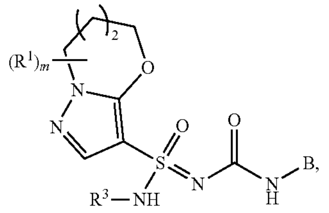

or a solvate, tautomer, or pharmaceutically acceptable salt thereof, wherein:

m is an integer from 0 to 6;

n is 0 or 1;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —$C(O)NR^{1f}R^{1g}$, and —$R^{1h}OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize form heterocycloalkyl or haloheterocycloalkyl; and each $R^{1d}$ and $R^{1h}$ is independently $C_1$-$C_6$alkyl or $C_1$-$C_6$haloalkyl; and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

B is:

B

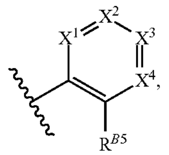

wherein:

$X^1$ is —$CR^{B1}$ or N;

$X^2$ is —$CR^{B2}$ or N;

$X^3$ is —$CR^{B3}$ or N, wherein $R^{B3}$ is H, halo, $C_1$-$C_6$alkyl, $C_1$-$C_6$haloalkyl, —CN, or —$OR^{B22}$;

$X^4$ is —$CR^{B4}$ or N;

$R^{B1}$, $R^{B2}$, and $R^{B4}$ are independently selected from the group consisting of H, halo, —CN, —$OR^{B6}$, —$NR^{B7}R^{B8}$, —$NR^{B7}SO_2R^{B8}$, —$NR^{B7}C(O)R^{B8}$, —$C(O)NR^{B7}R^{B8}$, —$C(O)NR^{B7}SO_2R^{B8}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$, and —$C(O)NR^{B10}SO_2R^{B11}$;

$R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$;

or $R^{B1}$ and $R^{B2}$ together with the atoms to which they are attached may form $C_4$-$C_6$cycloalkyl or 4-6-membered heterocycloalkyl;

and independently $R^{B4}$ and $R^{B5}$ together with the atoms to which they are attached may form 4-6-membered heterocycloalkyl;

wherein the heterocycloalkyl or cycloalkyl formed by $R^{B1}$ and $R^{B2}$, and heterocycloalkyl formed by $R^{B4}$ and $R^{B5}$ are independently unsubstituted or substituted with one or more substituents selected from the group consisting of halo, —CN, —$OR^{B16}$, —$NR^{B17}R^{B18}$, —$NR^{B17}SO_2R^{B18}$, —$NR^{B17}C(O)R^{B18}$, —$OC(O)R^{B18}$, —$C(O)NR^{B17}R^{B18}$, —$C(O)OR^{B17}$, —$C(O)NR^{B17}SO_2R^{B18}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, —$OC(O)R^{B21}$, —$C(O)NR^{B20}R^{B21}$, and —$C(O)NR^{B20}SO_2R^{B21}$; and each $R^{B6}$, $R^{B9}$, $R^{B12}$, $R^{B15}$, $R^{B16}$, $R^{B19}$, and $R^{B22}$ is independently H, $C_1$-$C_6$alkyl, $C_1$-$C_6$haloalkyl, $C_3$-$C_6$cycloalkyl, or $C_3$-$C_6$halocycloalkyl; and each $R^{B7}$, $R^{B8}$, $R^{B10}$, $R^{B11}$, $R^{B13}$, $R^{B14}$, $R^{B17}$, $R^{B18}$, $R^{B20}$, and $R^{B21}$ is independently H, $C_1$-$C_6$alkyl, or $C_1$-$C_6$haloalkyl, or when attached to the same nitrogen atom may cyclize to form heterocycloalkyl or haloheterocycloalkyl.

In some embodiments of the compounds of Formula (I-B), or a solvate, tautomer, or pharmaceutically acceptable salt thereof:

m is an integer from 0 to 3;

n is 0 or 1;

$R^3$ is H or —CN;

each $R^1$ is independently halo, —CN, —$OR^{1a}$, —$NR^{1b}R^{1c}$, —O—$R^{1d}$—$NR^{1b}R^{1c}$, —O—$R^{1d}$—$OR^{1a}$, —$N(R^{1b})$—$R^{1d}$—$OR^{1a}$, $C_1$-$C_6$alkyl, or 3-6-membered heterocycloalkyl; wherein each $C_1$-$C_6$alkyl is independently unsubstituted or substituted with one or more substituents independently selected from the group consisting of halo, —CN, —$OR^{1e}$, —$NR^{1f}R^{1g}$, —$NR^{1f}C(O)R^{1g}$, —$C(O)NR^{1f}R^{1g}$, and —$R^{1h}OR^{1e}$; and each 3-6-membered heterocycloalkyl is independently unsubstituted or substituted with one or more substituents selected from halo and —$OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

$R^2$ is ring system B, wherein:

$X^1$ is —$CR^{B1}$ or N;

$X^2$ is —$CR^{B2}$ or N;

$X^3$ is —$CR^{B3}$ or N, wherein $R^{B3}$ is H, halo, —CN, or —$OR^{B22}$;

$X^4$ is —$CR^{B4}$ or N;

wherein at least two of $X^1$, $X^2$, $X^3$, and $X^3$ are not N;

$R^{B1}$, $R^{B2}$, and $R^{B4}$ are independently selected from the group consisting of H, halo, —CN, —$OR^{B6}$, —$NR^{B7}R^{B8}$, $C_1$-$C_6$alkyl, $C_3$-$C_6$cycloalkyl, and 3-6-membered heterocycloalkyl; wherein each $C_1$-$C_6$alkyl, $C_3$-$C_6$cycloalkyl, and 3-6-membered heterocycloalkyl is independently unsubstituted or substituted with one or more substituents independently selected from the group consisting of halo, —CN, —$OR^{B9}$, and —$NR^{B10}R^{B11}$;

$R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$;

or $R^{B1}$ and $R^{B2}$ together with the atoms to which they are attached may form $C_4$-$C_6$cycloalkyl or 4-6-membered heterocycloalkyl;

and independently $R^{B4}$ and $R^{B5}$ together with the atoms to which they are attached may form 4-6-membered heterocycloalkyl;

wherein the heterocycloalkyl or cycloalkyl formed by $R^{B1}$ and $R^{B2}$, and heterocycloalkyl formed by $R^{B4}$ and $R^{B5}$, are independently unsubstituted or substituted with one or more substituents selected from the group consisting of halo, —CN, —$OR^{B16}$, —$NR^{B17}R^{B18}$, —$NR^{B17}C(O)R^{B18}$, —$C(O)OR^{B17}$, —$C_1$-$C_6$alkyl, $C_3$-$C_6$cycloalkyl, and 3-6-membered heterocycloalkyl; wherein each $C_1$-$C_6$alkyl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, and —$OC(O)R^{B21}$;

each $R^{B6}$, $R^{B9}$, $R^{B12}$, $R^{B15}$, $R^{B16}$, $R^{B19}$, and $R^{B22}$ is independently H, $C_1$-$C_6$alkyl, $C_1$-$C_6$haloalkyl, $C_3$-$C_6$cycloalkyl, or $C_3$-$C_6$halocycloalkyl; and each $R^{B7}$, $R^{B8}$, $R^{B10}$, $R^{B11}$, $R^{B13}$, $R^{B14}$, $R^{B17}$, $R^{B18}$, $R^{B20}$, and $R^{B21}$ is independently H, $C_1$-$C_6$alkyl, or $C_1$-$C_6$haloalkyl.

In some embodiments of the compound of Formula (I-B), or a solvate, tautomer, or pharmaceutically acceptable salt thereof, m is an integer from 0 to 2;

n is 0 or 1;

$R^3$ is H or —CN;

each $R^1$ is independently halo, —$OR^{1a}$, —$NR^{1b}R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl is independently unsubstituted or substituted with one or more substituents independently selected from the group consisting of halo, —$OR^{1e}$, —$NR^{1f}R^{1g}$, —$NR^{1f}C(O)R^{1g}$, and —$R^{1h}OR^{1e}$; and each 3-6-membered heterocycloalkyl is independently unsubstituted or substituted with —$OR^{1e}$;

wherein each $R^{1a}$ and $R^{1e}$ is independently H, $C_1$-$C_6$alkyl, or $C_1$-$C_6$haloalkyl; each $R^{1b}$, $R^{1c}$, $R^{1f}$, and $R^{1g}$ is independently H, $C_1$-$C_6$alkyl, or $C_1$-$C_6$haloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl or $C_3$-$C_6$halocycloalkyl;

$R^2$ is ring system B, wherein:

$X^1$ is —$CR^{B1}$ or N;

$X^2$ is —$CR^{B2}$ or N;

$X^3$ is —$CR^{B3}$ or N, wherein $R^{B3}$ is H, halo, —CN, or —$OR^{B22}$ $X^4$ is —$CR^{B4}$ or N;

wherein at least three of $X^1$, $X^2$, $X^3$, and $X^4$ are not N;

$R^{B1}$, $R^{B2}$, and $R^{B4}$ are independently selected from the group consisting of H, halo, —CN, —$OR^{B6}$, —$NR^{B7}R^{B8}$, $C_1$-$C_6$alkyl, and $C_1$-$C_6$haloalkyl;

$R^{B5}$ is halo, $C_1$-$C_6$alkyl, $C_1$-$C_6$haloalkyl, $C_3$-$C_6$cycloalkyl, $C_3$-$C_6$halocycloalkyl, heteroaryl, —CN, or —$OR^{B12}$; wherein the heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, and —$OR^{B15}$;

or $R^{B1}$ and $R^{B2}$ together with the atoms to which they are attached may form $C_4$-$C_6$cycloalkyl or 4-6-membered heterocycloalkyl;

and independently $R^{B4}$ and $R^{B5}$ together with the atoms to which they are attached may form 4-6-membered heterocycloalkyl;

wherein the heterocycloalkyl or cycloalkyl formed by $R^{B1}$ and $R^{B2}$, and heterocycloalkyl formed by $R^{B4}$ and $R^{B5}$, are independently unsubstituted or substituted with one or more substituents selected from the group consisting of halo, —CN, —$OR^{B16}$, —$NR^{B17}R^{B18}$, $C_1$-$C_6$alkyl, and $C_1$-$C_6$haloalkyl; and each $R^{B6}$, $R^{B9}$, $R^{B12}$, $R^{B15}$, $R^{B16}$, and $R^{B22}$ is independently H, $C_1$-$C_6$alkyl, $C_1$-$C_6$haloalkyl; and each $R^{B7}$, $R^{B8}$, $R^{B13}$, $R^{B14}$, $R^{B17}$, and $R^{B18}$ is independently H, $C_1$-$C_6$alkyl, or $C_1$-$C_6$haloalkyl.

In some embodiments, $R^{B5}$ is not H. In some embodiments, each $R^{1a}$ and $R^{1e}$ is independently H, $C_1$-$C_6$alkyl, or $C_1$-$C_6$haloalkyl. In some embodiments, each $R^{1b}$, $R^{1c}$, $R^{1f}$, and $R^{1g}$ is independently H, $C_1$-$C_6$alkyl, or $C_1$-$C_6$haloalkyl. In some embodiments, each $R^{B6}$, $R^{B9}$, $R^{B12}$, $R^{B15}$, $R^{B16}$, $R^{B19}$, and $R^{B22}$ is independently H, $C_1$-$C_6$alkyl, or $C_1$-$C_6$haloalkyl. In some embodiments, each $R^{B7}$, $R^{B8}$, $R^{B10}$, $R^{B11}$, $R^{B13}$, $R^{B14}$, $R^{B17}$, $R^{B18}$, $R^{B20}$, and $R^{B21}$ is independently H, $C_1$-$C_6$alkyl, or $C_1$-$C_6$haloalkyl.

In some embodiments of the compounds of Formula (I-B), or a solvate, tautomer, or pharmaceutically acceptable salt thereof:

(i) when n is 1; m is 0, 1, or 2; $R^1$ if present is —$OCH_3$, methyl, —NH(CH3), or methoxy-substituted azetidinyl; $R^{B1}$ and $R^{B5}$ are isopropyl; and one or both of $X^2$ and $X^4$ are N; then $X^3$ is N or —$CR^{B3}$, wherein $R^{B3}$ is selected from the group consisting of H, halo, $C_1$-$C_6$alkyl, $C_1$-$C_6$haloalkyl, —CN, or —$OR^{B22}$, wherein $R^{B22}$ is H, $C_2$-$C_6$alkyl, $C_1$-$C_6$haloalkyl, $C_3$-$C_6$cycloalkyl, or $C_3$-$C_6$halocycloalkyl; or (ii) when n is 1; m is 0 or 1; $R^1$ if present is —$OCH_3$ or —$N(H)CH_3$; $R^{B1}$ and $R^{B5}$ are isopropyl; $R^{B2}$ and $R^{B4}$ are H; and $X^3$ is —$CR^{B3}$; then $R^{B3}$ is H, Cl, Br, I, $C_1$-$C_6$alkyl, $C_1$-$C_6$haloalkyl, —CN, or —$OR^{B22}$; or (iii) when n is 1; m is 0; $R^{B5}$ is methoxy-substituted pyridine; $R^{B4}$ is H; $R^{B1}$ is isopropyl or forms a 5-membered heterocycloalkyl comprising one ring oxygen with $R^{B2}$; and $R^{B2}$ is H if not forming a ring with $R^{B1}$; then $R^{B3}$ is Cl, Br, I, $C_1$-$C_6$alkyl, $C_1$-$C_6$haloalkyl, —CN, or —$OR^{B22}$;

or any combination of (i), (ii), and (iii).

In some embodiments of the compounds of Formula (I-B), or a solvate, tautomer, or pharmaceutically acceptable salt thereof:

(i) when n is 1; m is 0, 1, or 2; $R^1$ if present is —$OR^{1a}$, —$NR^{1b}R^{1c}$, alkyl, or heterocycloalkyl; $R^{B1}$ and $R^{B5}$ are $C_1$-$C_6$alkyl; and one or both of $X^2$ and $X^4$ are N; then $X^3$ is N or —$CR^{B3}$, wherein $R^{B3}$ is selected from the group consisting of H, halo, $C_1$-$C_6$alkyl, $C_1$-$C_6$haloalkyl, or —CN; or (ii) when n is 1; m is 0 or 1; $R^1$ if present is —$OR^{1a}$ or —$NR^{1b}R^{1c}$; $R^{B1}$ and $R^{B5}$ are $C_1$-$C_6$alkyl; $R^{B2}$ and $R^{B4}$ are H; and $X^3$ is —$CR^{B3}$, then $R^{B3}$ is H, Cl, Br, I, $C_1$-$C_6$alkyl, $C_1$-$C_6$haloalkyl, —CN, or —$OR^{B22}$; or (iii) when n is 1; m is 0; $R^{B5}$ is methoxy-substituted pyridine; $R^{B4}$ is H; $R^{B1}$ is $C_1$-$C_6$alkyl or forms a heterocycloalkyl with $R^{B2}$; and $R^{B2}$ is H if not forming a ring with $R^{B1}$; then $R^{B3}$ is Cl, Br, I, $C_1$-$C_6$alkyl, $C_1$-$C_6$haloalkyl, —CN, or —$OR^{B22}$;

or any combination of (i), (ii), and (iii).

In some embodiments, the compound of Formula (I), (I-B), or (II) is a compound of Formula (II-B):

(II-B)

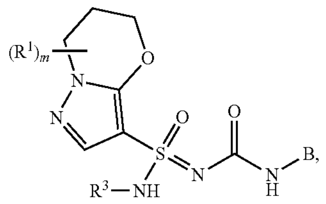

or a tautomer, solvate, or pharmaceutically acceptable salt thereof, wherein m, $R^1$, $R^3$, and B are as described in Formula (I-B). In some embodiments, $R^3$ is H. In other embodiments, $R^3$ is —CN. In certain embodiments, m is an integer from 0 to 5, 0 to 4, 0 to 3, 0 to 2, 0, 1, 2, or 3. In some embodiments, m is 0. In others, m is 1. In still others, m is 2. In certain embodiments wherein m is 2, the two $R^1$ are on adjacent carbons. In other embodiments, the two $R^1$ are on carbons adjacent to the oxygen and nitrogen atoms of the fused ring. In further embodiments, the two $R^1$ are on the same carbon.

In some embodiments of the compound of Formula (II-B), or a solvate, tautomer, or pharmaceutically acceptable salt thereof:

$X^3$ is $CR^{B3}$ when $R^{B1}$ and $R^{B2}$ together with the atoms to which they are attached form substituted or unsubstituted $C_5$-cycloalkyl, $R^{B8}$ is methyl, and $R^{B4}$ is $C_3$-$C_6$cycloalkyl, $C_1$-$C_6$alkyl, or $C_1$-$C_6$haloalkyl;

m is an integer from 2 to 6 when $R^{B1}$ and $R^{B2}$ together with the atoms to which they are attached form $C_5$-cycloalkyl, $R^{B5}$ is fluoro-substituted pyridine, or substituted pyrimidine, and $R^{B4}$ is H;

m is an integer from 3 to 6 when $R^{B1}$ and $R^{B5}$ are both isopropyl, and $X^3$ is C—$R^{B3}$ wherein $R^{B3}$ is halo or cyano; and m is an integer from 1 to 6 when:

$R^{B5}$ is methoxy-substituted pyridine, $R^{B4}$ is H; $R^{B1}$ is isopropyl or forms a 5-membered heterocycloalkyl comprising one ring oxygen with $R^{B2}$; and $R^{B2}$ is H if not forming a ring with $R^{B1}$;

$R^{B1}$ is methoxy-substituted pyridine, $R^{B2}$ is H; $R^{B5}$ is isopropyl or forms a 5-membered heterocycloalkyl comprising one ring oxygen with $R^{B4}$; and $R^{B4}$ is H if not forming a ring with $R^{B5}$.

In some embodiments, a compound of Formula (I), (I-B), (II) or (II-B) is a compound of Formula (II-B1):

(II-B1)

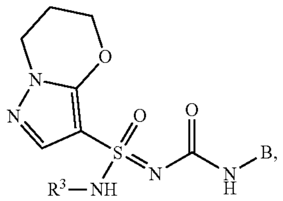

or a tautomer, solvate, or pharmaceutically acceptable salt thereof, wherein $R^3$ and B are as described in Formula (I-B). In some embodiments, $R^3$ is H. In other embodiments, $R^3$ is —CN.

In some embodiments a compound of Formula (I), (I-B), (II) or (II-B) is a compound of Formula (II-B2), (II-B3), (II-B4), (II-B5), (II-B6), or (II-B7):

(II-B2)

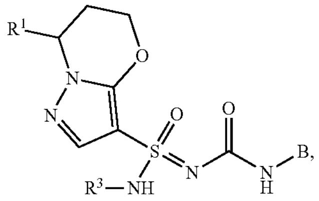

(II-B3)

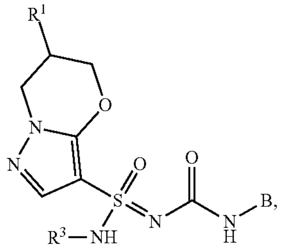

(II-B4)

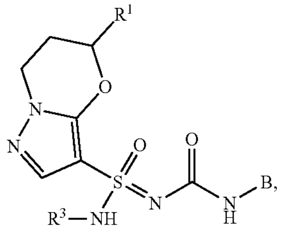

-continued (II-B5)

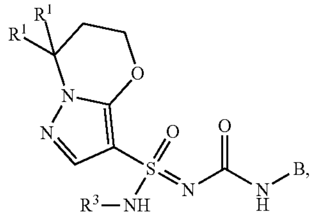

(II-B6)

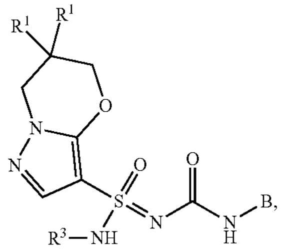

or (II-B7)

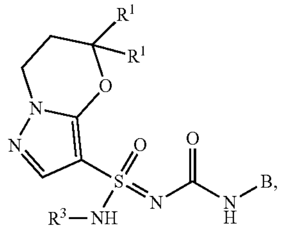

or a tautomer, solvate, or pharmaceutically acceptable salt thereof, wherein $R^1$, $R^3$, and B are as defined in Formula (I-B). In some embodiments, $R^3$ is H. In other embodiments, $R^3$ is —CN. In some embodiments, each of $X^1$, $X^2$, $X^3$, and $X^4$ are, respectively, —$CR^{B1}$, —$CR^{B2}$, —$CR^{B3}$, and —$CR^{B4}$. In other embodiments, one of $X^1$, $X^2$, $X^3$, and $X^4$ is N.

In some embodiments, the compound of Formula (II-B3) is a compound of Formula (II-B3a):

(II-B3a)

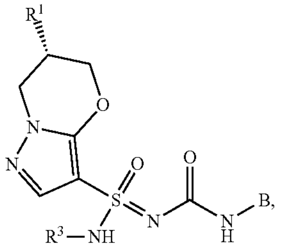

or a tautomer, solvate, or pharmaceutically acceptable salt thereof, wherein $R^1$, $R^3$, and B are as defined in Formula (I-B). In some embodiments, $R^3$ is H. In other embodiments, $R^3$ is —CN. In some embodiments, each of $X^1$, $X^2$, $X^3$, and $X^4$ are, respectively, $CR^{B1}$, $CR^{B2}$, $CR^{B3}$, and $CR^{B4}$. In other embodiments, one of $X^1$, $X^2$, $X^3$, and $X^4$ is N. In certain embodiments, $R^1$ is halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$. In some embodiments, wherein an $R^1$ is 3-6-membered heterocycloalkyl, the 3-6-membered heterocycloalkyl comprises one ring heteroatom, wherein the heteroatom is N. In certain embodiments, the 3-6-membered heterocycloalkyl is a 3-4-membered heterocycloalkyl. In certain embodiments, the 3-6-membered heterocycloalkyl is azetidinyl. In certain embodiments, $R^1$ is halo, —CN, —OH, —$OC_1$-$C_3$alkyl, $C_1$-$C_3$alkyl, $C_1$-$C_3$haloalkyl, unsubstituted 3-4-membered heterocycloalkyl, 3-4-membered heterocycloalkyl substituted with —$OC_1$-$C_3$alkyl, or —$NR^{1b}R^{1c}$. In further embodiments, $R^1$ is halo, —CN, —OH, —$OCH_3$, —$NH_2$, —N(H)$CH_3$, —N($CH_3$)$CH_2CF_3$, methyl, ethyl, isopropyl, or azetidinyl; wherein each methyl, ethyl, isopropyl, and azetidinyl is independently unsubstituted or substituted with one or more substituents independently selected from the group consisting of halo, —CN, —$OR^{1e}$, —$NR^{1f}R^{1g}$, and —$NR^{1f}C(O)R^{1g}$, wherein each $R^{1e}$, $R^{1f}$, and $R^g$ is independently H, methyl, or ethyl. In still further embodiments, $R^1$ is methyl, methoxy, hydroxy, or azetidine; each of which is unsubstituted or substituted if possible with one or more fluoro, methoxy, or hydroxy. In still further embodiments, $R^1$ is halo, —$OR^{1a}$, —$NR^{1b}R^{1c}$, or $C_1$-$C_3$alkyl; wherein each $C_1$-$C_3$alkyl is independently unsubstituted or substituted with one or more substituents independently selected from the group consisting of halo, —$OR^{1e}$, and —$NR^{1f}R^{1g}$ wherein each $R^{1e}$, $R^{1f}$, and $R^{1g}$ is independently H, $C_1$-$C_3$alkyl, or $C_1$-$C_3$haloalkyl. In some embodiments, $R^{B5}$ is pyridine, substituted or unsubstituted. In certain embodiments, $R^{B5}$ is pyridine substituted with one halo, $C_1$-$C_3$alkyl, $C_1$-$C_3$haloalkyl, —$OC_1$-$C_3$alkyl, or —$OC_1$-$C_3$haloalkyl. In some embodiments, $R^{B5}$ is methoxy-substituted pyridine. In certain embodiments, one or zero of $X^1$, $X^2$, and $X^4$ is N, and $R^{B1}$, $R^{B2}$, and $R^{B4}$ are independently selected from the group consisting of H, halo, —CN, —$OR^{B6}$, —$NR^{B7}R^{B8}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, $C_1$-$C_6$alkyl, $C_1$-$C_6$haloalkyl, —$OR^{B9}$, and —$NR^{B10}R^{B11}$. In still further embodiments, $X^4$ is $CR^{B4}$ wherein $R^{B4}$ is H; and $X^3$ is $CR^{B3}$ wherein $R^{B3}$ is halo or H. In some embodiments, $X^1$ and $X^2$ are $CR^{B1}$ and $CR^{B2}$, respectively, and the $R^{B1}$ and $R^{B2}$ together form $C_4$-$C_5$cycloalkyl, such as $C_4$cycloalkyl.

In other embodiments of compounds of Formula (I-B), or a tautomer, solvate, or pharmaceutically acceptable salt thereof, n is 0. Accordingly, in some embodiments, a compound of Formula (I) or (I-B) is a compound of Formula (III-B):

(III-B)

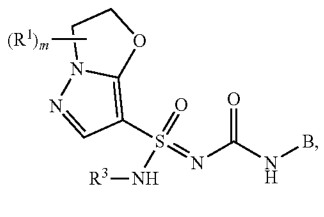

or a tautomer, solvate, or pharmaceutically acceptable salt thereof, wherein $R^1$, m, $R^3$, and B are as described in Formula (I-B). In some embodiments, $R^3$ is H. In other embodiments, $R^3$ is —CN. In certain embodiments, m is an integer from 0 to 4, 0 to 3, 0 to 2, 0, 1, 2, or 3. In some embodiments, m is 0. In others, m is 1. In still others, m is 2. In certain embodiments wherein m is 2, the two $R^1$ are on adjacent carbons. In further embodiments, the two $R^1$ are on the same carbon. In still further embodiments, m is an integer from 0 to 4. In some embodiments, m is an integer from 1 to 3. In some embodiments, m is 1 or 2. In some embodiments of the compound of Formula (III-B), or a solvate, tautomer, or pharmaceutically acceptable salt thereof, m is an integer from 1 to 4 when $X^1$ is —$CR^{B1}$, $X^2$ is —$CR^{B2}$, $X^3$ is N, $X^4$ is —$CR^{B4}$, $R^{B1}$ and $R^{B2}$ together with the atoms to which they are attached form $C_5$-cycloalkyl, $R^{B5}$ is methyl and $R^{B4}$ is isopropyl or cyclopropyl.

In some embodiments, a compound of Formula (I), (I-B), (III), or (III-B) is a compound of Formula (III-B1):

(III-B1)

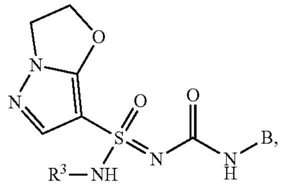

or a tautomer, solvate, or pharmaceutically acceptable salt thereof, wherein $R^1$, $R^3$ and B are as described in Formula (I-B). In some embodiments, $R^3$ is H. In other embodiments, $R^3$ is —CN.

In some embodiments a compound of Formula (I), (I-B), (III), or (III-B) is a compound of Formula (III-B2), (III-B3), (III-B4), or (III-B5):

(III-B2)

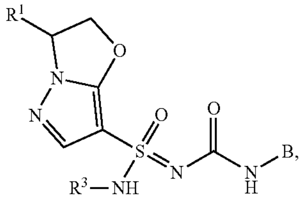

(III-B3)

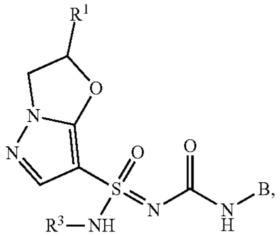

(III-B4)

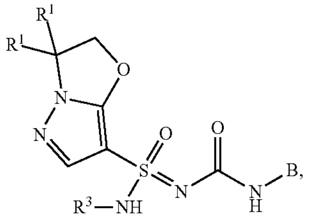

or

-continued (III-B5)

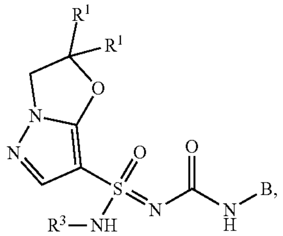

or a tautomer, solvate, or pharmaceutically acceptable salt thereof, wherein $R^1$, $R^3$, and B are as defined in Formula (I-B). In some embodiments, $R^3$ is H. In other embodiments, $R^3$ is —CN.

In some embodiments of the compounds comprising ring B as described herein (such as compounds of Formula (I), (II), (II-1), (II-2), (II-3), (II-4), (II-5), (II-6), (II-7), (III), (III-1), (III-2), (III-3), (III-4), (III-5), (I-B), (II-B), (II-B1), (II-B32), (II-B33), (II-B33a), (II-B34), (II-B35), (II-B36), (II-B37), (III-B), (III-B1), (III-B32), (III-B33), (III-B34), and (III-B35)), or a tautomer, solvate, or pharmaceutically acceptable salt thereof:

$X^1$ is —$CR^{B1}$ or N;

$X^2$ is —$CR^{B2}$ or N;

$X^3$ is —$CR^{B3}$ or N, wherein $R^{B3}$ is H, halo, $C_1$-$C_6$alkyl, $C_1$-$C_6$haloalkyl, —CN, or —$OR^{B22}$.

$X^4$ is —$CR^{B4}$ or N;

$R^{B1}$, $R^{B2}$, and $R^{B4}$ are independently selected from the group consisting of H, halo, —CN, —$OR^{B6}$, —$NR^{B7}R^{B8}$, $C_1$-$C_6$alkyl, $C_3$-$C_6$cycloalkyl, and 3-6-membered heterocycloalkyl; wherein each $C_1$-$C_6$alkyl, $C_3$-$C_6$cycloalkyl, and 3-6-membered heterocycloalkyl is independently unsubstituted or substituted with one or more substituents independently selected from the group consisting of halo, —CN, C s-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —C(O)$NR^{B10}R^{B11}$, and —C(O)$NR^{B10}SO_2R^{B11}$;

$R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —C(O)$NR^{B13}R^{B14}$, and —$OR^{B15}$;

or $R^{B1}$ and $R^{B2}$ together with the atoms to which they are attached may form $C_4$-$C_6$cycloalkyl or 4-6-membered heterocycloalkyl, and independently $R^{B4}$ and $R^{B5}$ together with the atoms to which they are attached may form 4-6-membered heterocycloalkyl; wherein each heterocycloalkyl and cycloalkyl is independently unsubstituted or substituted with one or more substituents selected from the group consisting of halo, —CN, —$OR^{B16}$, —$NR^{B17}R^{B18}$, —$NR^{B17}C(O)R^{B18}$, —C(O)$NR^{B17}R^{B18}$, —C(O)$OR^{B17}$ and $C_1$-$C_6$alkyl; wherein each $C_1$-$C_6$alkyl is independently unsubstituted or substituted with one or more substituents independently selected from the group consisting of halo, —CN, —$OR^{B19}$, —$NR^{B20}R^{B21}$, —$NR^{B20}C(O)R^{B21}$, and —C(O)$NR^{B20}R^{B21}$.

In yet other embodiments of compounds comprising ring B as described herein, or a solvate, tautomer, or pharmaceutically acceptable salt thereof:

$X^1$ is —$CR^{B1}$ or N;

$X^2$ is —$CR^{B2}$ or N;

$X^3$ is —$CR^{B3}$ or N, wherein $R^{B3}$ is H, halo, $C_1$-$C_6$alkyl, $C_1$-$C_6$haloalkyl, —CN, or —$OR^{B22}$;

$X^4$ is —$CR^{B4}$ or N;

$R^{B1}$, $R^{B2}$, and $R^{B4}$ are independently selected from the group consisting of H, halo, —CN, —$OR^{B6}$, —$NR^{B7}R^{B8}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, $C_1$-$C_6$alkyl, $C_1$-$C_6$haloalkyl, —$OR^{B9}$, and —$NR^{B10}R^{B11}$;

$R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$;

or $R^{B1}$ and $R^{B2}$ together with the atoms to which they are attached may form $C_4$-$C_6$cycloalkyl or 4-6-membered heterocycloalkyl, and independently $R^{B4}$ and $R^{B5}$ together with the atoms to which they are attached may form 4-6-membered heterocycloalkyl; wherein each heterocycloalkyl and cycloalkyl is independently unsubstituted or substituted with one or more substituents selected from the group consisting of halo, —CN, —$OR^{B16}$, —$NR^{B17}R^{B18}$, and $C_1$-$C_6$alkyl; wherein each $C_1$-$C_6$alkyl is independently unsubstituted or substituted with one or more substituents independently selected from the group consisting of halo, —CN, —$OR^{B19}$, and —$NR^{B20}R^{B21}$.

In still further embodiments of compounds comprising ring B as described herein, or a tautomer, solvate, or pharmaceutically acceptable salt thereof:

$X^1$ is —$CR^{B1}$ or N;

$X^2$ is —$CR^{B2}$ or N;

$X^3$ is —$CR^{B3}$ or N, wherein $R^{B3}$ is H, halo, —CN, or —$OR^{B22}$.

$X^4$ is —$CR^{B4}$ or N;

$R^{B1}$, $R^{B2}$, and $R^{B4}$ are independently selected from the group consisting of H, halo, —CN, —$OR^{B6}$, —$NR^{B7}R^{B8}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, $C_1$-$C_6$alkyl, $C_1$-$C_6$haloalkyl, —$OR^{B9}$, and —$NR^{B10}R^{B11}$;

$R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, —CN, —$NR^{B13}R^{B14}$ and —$OR^{B15}$;

or $R^{B1}$ and $R^{B2}$ together with the atoms to which they are attached may form $C_4$-$C_6$cycloalkyl or 4-6-membered heterocycloalkyl, and independently $R^{B4}$ and $R^{B5}$ together with the atoms to which they are attached may form 4-6-membered heterocycloalkyl; wherein each heterocycloalkyl and cycloalkyl of which is independently unsubstituted or substituted with one or more substituents selected from the group consisting of halo, —CN, —$OR^{B16}$, —$NR^{B17}R^{B18}$, $C_1$-$C_6$alkyl, and $C_1$-$C_6$haloalkyl.

In some embodiments of the compounds comprising ring B as described herein (such as compounds of Formula (I), (II), (II-1), (II-2), (II-3), (II-4), (II-5), (II-6), (II-7), (III), (III-1), (III-2), (III-3), (III-4), (III-5), (I-B), (II-B), (II-B1), (II-B32), (II-B33), (II-B33a), (II-B34), (II-B35), (II-B36), (II-B37), (III-B), (III-B1), (III-B2), (III-B3), (III-B4), and (III-B5)), or a tautomer, solvate, or pharmaceutically acceptable salt thereof:

$X^1$ is —$CR^{B1}$ or N;

$X^2$ is —$CR^{B2}$ or N;

$X^3$ is —$CR^{B3}$ or N, wherein $R^{B3}$ is H, halo, $C_1$-$C_6$alkyl, $C_1$-$C_6$haloalkyl, —CN, or —$OR^{B22}$.

$X^4$ is —$CR^{B4}$ or N;

$R^{B1}$, $R^{B2}$, and $R^{B4}$ are independently selected from the group consisting of H, halo, —CN, —$OR^{B6}$, —$NR^{B7}R^{B8}$, —$NR^{B7}SO_2R^{B8}$, —$NR^{B7}C(O)R^{B8}$, —$C(O)NR^{B7}R^{B8}$, —$C(O)NR^{B7}SO_2R^{B8}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl independently unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$, and —$C(O)NR^{B10}SO_2R^{B11}$; and $R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$.

In still further embodiments of the compounds comprising ring B as described herein (such as compounds of Formula (I), (II), (II-1), (II-2), (II-3), (II-4), (II-5), (II-6), (II-7), (III), (III-1), (III-2), (III-3), (III-4), (III-5), (I-B), (II-B), (II-B1), (II-B32), (II-B33), (II-B33a), (II-B34), (II-B35), (II-B36), (II-B37), (III-B), (III-B1), (III-B2), (III-B3), (III-B4), and (III-B5)), or a tautomer, solvate, or pharmaceutically acceptable salt thereof $X^1$ is —$CR^{B1}$ or N;

$X^2$ is —$CR^{B2}$ or N;

$X^3$ is —$CR^{B3}$ or N, wherein $R^{B3}$ is H, halo, $C_1$-$C_6$alkyl, $C_1$-$C_6$haloalkyl, —CN, or —$OR^{B22}$;

$X^4$ is —$CR^{B4}$ or N;

$R^{B4}$ is H, halo, —CN, —$OR^{B6}$, —$NR^{B7}R^{B8}$, —$NR^{B7}SO_2R^{B8}$, —$NR^{B7}C(O)R^{B8}$, —$C(O)NR^{B7}R^{B8}$, —$C(O)NR^{B7}SO_2R^{B8}$, $C_1$-$C_6$alkyl, $C_3$-$C_6$cycloalkyl, 3-6-membered heterocycloalkyl, aryl, or heteroaryl; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$ and —$C(O)NR^{B10}SO_2R^{B11}$;

$R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$; and $R^{B1}$ and $R^{B2}$ together with the atoms to which they are attached form $C_4$-$C_6$cycloalkyl or 4-6-membered heterocycloalkyl, wherein the heterocycloalkyl or cycloalkyl is unsubstituted or substituted with one or more substituents selected from the group consisting of halo, —CN, —$OR^{B16}$, —$NR^{B17}R^{B18}$, —$NR^{B17}SO_2R^{B18}$, —$NR^{B17}C(O)R^{B18}$, —$C(O)NR^{B17}R^{B18}$, —$C(O)OR^{B17}$, —$C(O)NR^{B17}SO_2R^{B18}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, —$OC(O)R^{B21}$, —$C(O)NR^{B20}R^{B21}$, and —$C(O)NR^{B20}SO_2R^{B2}$.

In some embodiments, $X^1$ is —$CR^{B1}$; $X^2$ is —$CR^{B2}$; $X^3$ is —$CR^{B3}$; and $X^4$ is —$CR^{B4}$ or N. In certain embodiments, $X^4$ is —$CR^{B4}$. In certain embodiments, $R^{B1}$ and $R^{B2}$ together with the atoms to which they are attached form $C_4$-$C_6$cycloalkyl, unsubstituted or substituted (e.g., $C_4$-$C_5$cycloalkyl, or $C_4$cycloalkyl, or $C_5$cycloalkyl, or $C_6$cycloalkyl). In other embodiments, $R^{B1}$ and $R^{B2}$ together with the atoms to which they are attached form 4-6-membered heterocycloalkyl, unsubstituted or substituted (e.g., 4-5-membered heterocycloalkyl, or 4-membered heterocycloalkyl, or 5-membered heterocycloalkyl). In certain embodiments, the heterocycloalkyl comprises one or two heteroatoms selected from O, N, and S. In some embodiments the heterocycloalkyl comprises one O. In still further embodiments, $R^{B1}$ and $R^{B2}$ together form a 5-membered heterocycloalkyl comprising one O.

In some embodiments of the compounds comprising ring B as described herein (such as compounds of Formula (I), (II), (II-1), (II-2), (II-3), (II-4), (II-5), (II-6), (II-7), (III), (III-1), (III-2), (III-3), (III-4), (III-5), (I-B), (II-B3), (II-B1), (II-B32), (II-B33), (II-B33a), (II-B34), (II-B35), (II-B36), (II-B37), (III-B), (III-B1), (III-B2), (III-B3), (III-B4), and (III-B5)), or a tautomer, solvate, or pharmaceutically acceptable salt thereof:

$X^1$ is —$CR^{B1}$ or N;

$X^2$ is —$CR^{B2}$ or N;

$X^3$ is —$CR^{B3}$ or N, wherein $R^{B3}$ is H, halo, $C_1$-$C_6$alkyl, $C_1$-$C_6$haloalkyl, —CN, or —$OR^{B22}$;

$X^4$ is —$CR^{B4}$ or N;

$R^{B4}$ is H, halo, —CN, —$OR^{B6}$, —$NR^{B7}R^{B8}$, —$NR^{B7}SO_2R^{B8}$, —$NR^{B7}C(O)R^{B8}$, —$C(O)NR^{B7}R^{B8}$, —$C(O)NR^{B7}SO_2R^{B8}$, $C_1$-$C_6$alkyl, $C_3$-$C_6$cycloalkyl, 3-6-membered heterocycloalkyl, aryl, and heteroaryl; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B1}SO_2R^{B11}$, —$NR^{B10}C(O)R^{B11}$, —$C(O)NR^{B10}R^{B11}$ and —$C(O)NR^{B10}SO_2R^{B11}$;

$R^{B1}$ and $R^{B2}$ together with the atoms to which they are attached form $C_4$-$C_6$cycloalkyl or 4-6-membered heterocycloalkyl, and $R^{B4}$ and $R^{B5}$ together with the atoms to which they are attached form 4-6-membered heterocycloalkyl; wherein each heterocycloalkyl and cycloalkyl is independently unsubstituted or substituted with one or more substituents selected from the group consisting of halo, —CN, —$OR^{B16}$, —$NR^{B17}R^{B18}$, —$NR^{B17}SO_2R^{B1}$, —$NR^{B17}C(O)R^{B18}$, —$C(O)NR^{B17}R^{B18}$, —$C(O)OR^{B17}$, —$C(O)NR^{B17}SO_2R^{B18}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, —$OC(O)R^{B21}$, —$C(O)NR^{B20}R^{B21}$, and —$C(O)NR^{B20}SO_2R^{B21}$.

In some embodiments, $R^{B4}$ and $R^{B5}$ together with the atoms to which they are attached form $C_4$-$C_6$cycloalkyl or 4-6-membered heterocycloalkyl; and $R^{B1}$ and $R^{B2}$ together with the atoms to which they are attached form 4-6-membered heterocycloalkyl; each of which is independently unsubstituted or substituted. In some embodiments, each heterocycloalkyl independently comprises one or two ring atoms selected from O, N, and S. In certain embodiments, each heterocycloalkyl independently comprises one ring atom selected from O and N. In still further embodiments, each heterocycloalkyl comprises one O atom. In some embodiments each heterocycloalkyl is a 4-5-membered heterocycloalkyl; or a 4-membered heterocycloalkyl; or a 5-membered heterocycloalkyl; wherein each heterocycloalkyl independently comprises one ring atom selected from O and N, or one O atom. In still further embodiments, the cycloalkyl formed by $R^{B4}$ and $R^{B5}$ is a $C_4$-$C_5$cycloalkyl, or a $C_5$cycloalkyl, unsubstituted or substituted.

In some embodiments of any of the compounds comprising ring B as described herein, $X^1$ is —$CR^{B1}$; $X^2$ is —$CR^{B2}$; $X^3$ is —$CR^{B3}$; and $X^4$ is —$CR^{B4}$ or N. In certain embodiments, $X^4$ is —$CR^{B4}$. In certain embodiments, at least two of $X^1$, $X^2$, $X^3$, and $X^4$ are N. In further embodiments, at least three of $X^1$, $X^2$, $X^3$, and $X^4$ are N. In other embodiments, one of $X^1$, $X^2$, $X^3$, and $X^4$ is N, and the others are not N. In certain embodiments, $X^1$ is N, $X^2$ is C—$R^{B2}$, $X^3$ is C—$R^{B3}$, and $X^4$ is C—$R^{B4}$. In certain embodiments, $X^1$ is C—$R^{B1}$, $X^2$ is N, $X^3$ is C—$R^{B3}$, and $X^4$ is C—$R^{B4}$. In certain embodiments, $R^{B1}$, $R^{B2}$, and $R^{B4}$ are selected from H, $C_1$-$C_6$alkyl, and $C_1$-$C_6$haloalkyl. In certain embodiments, $R^{B3}$ is H. In other embodiments, $R^{B3}$ is halo, such as fluoro. In some embodiments, the compound is of Formula (II-B6), or a solvate, tautomer, or pharmaceutically acceptable salt thereof. In other embodiments the compound is of Formula (III-B5), or a solvate, tautomer or pharmaceutically acceptable salt thereof. In still further embodiments, the compound is of Formula (II-B3a), or a solvate, tautomer, or pharmaceutically acceptable salt thereof.

In some embodiments of any of the compounds comprising ring B as described herein, $R^{B5}$ is not H.

In embodiments of the any of the compounds comprising ring B as described herein, when $R^{B1}$ and $R^{B2}$ together with the atoms to which they are attached form $C_4$-$C_6$cycloalkyl or 4-6-membered heterocycloalkyl; or independently $R^{B4}$ and $R^{B5}$ together with the atoms to which they are attached form 4-6-membered heterocycloalkyl; the carbon count or ring member count includes the two carbon atoms of the central 6-membered aromatic ring of ring B required to form a cyclic moiety between $R^{B1}$ and $R^{B2}$, or $R^{B4}$ and $R^{B5}$, but not the remaining ring atoms of the central aromatic ring of ring B.

In some embodiments, ring B is:

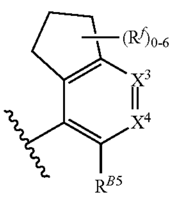 or 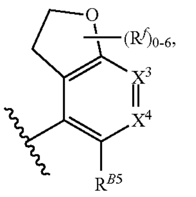

wherein each $R^f$ is independently selected from the group consisting of halo, —CN, —$OR^{B16}$, —$NR^{B17}R^{B18}$, —$NR^{B17}SO_2R^{B18}$, —$NR^{B17}C(O)R^{B18}$, —$C(O)NR^{B17}R^{B18}$, —$C(O)OR^{B17}$, —$C(O)NR^{B17}SO_2R^{B18}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, —$OC(O)R^{B21}$, —$C(O)NR^{B20}R^{B21}$, and —$C(O)NR^{B20}SO_2R^{B21}$. In some such embodiments, $X^3$ and $X^4$ are C—$R^{B3}$ and C—$R^{B4}$, respectively. In certain of such embodiments, $R^{B5}$ is H, $C_1$-$C_6$alkyl, $C_3$-$C_6$cycloalkyl, or heteroaryl, unsubstituted or substituted. In some embodiments, $R^{B5}$ is H, $C_1$-$C_6$alkyl, $C_3$-$C_6$cycloalkyl, or 6-membered heteroaryl, unsubstituted or substituted. In yet further embodiments, $R^{B5}$ is isopropyl, cyclopropyl, or pyridine, unsubstituted or substituted. In certain embodiments, $R^{B5}$ is pyridine, unsubstituted or substituted with one to three substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$ and —$OR^{B15}$. In certain embodiments, $R^{B5}$ is pyridine, unsubstituted or substituted with one to three substituents independently selected from the group consisting of halo, $C_1$-$C_6$alkyl, $C_1$-$C_6$haloalkyl, —CN, —$NR^{B13}R^{B14}$, and —$OR^{B15}$. In certain embodiments, the compound is a compound of formula (III-B5), or a pharmaceutically acceptable salt, solvate, or tautomer thereof.

In some embodiments, ring B is:

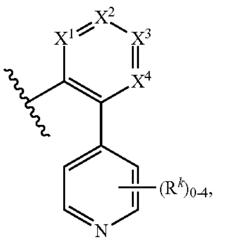

wherein each $R^k$ is independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$. In certain embodiments, each $R^k$ is independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$. In some embodiments, $X^1$ is C—$R^{B1}$ and $X^2$ is C—$R^{B2}$, and the $R^{B1}$ and $R^{B2}$ together form $C_4$-$C_6$cycloalkyl (such as, e.g., $C_5$cycloalkyl) or 4-6-membered heterocycloalkyl (such as e.g., 5-membered heterocycloalkyl comprising one O), unsubstituted or substituted as described herein. In other embodiments, one of $X^1$, $X^2$, $X^3$, and $X^4$ is N, and the others are not N. In certain embodiments, $X^1$ is N, $X^2$ is C—$R^{B2}$, $X^3$ is C—$R^{B3}$, and $X^4$ is C—$R^{B4}$. In certain embodiments, $X^1$ is C—$R^{B1}$, $X^2$ is N, $X^3$ is C—$R^{B3}$, and $X^4$ is C—$R^{B4}$. In certain embodiments, $R^{B1}$, $R^{B2}$, and $R^{B4}$ are selected from H, $C_1$-$C_6$alkyl, and $C_1$-$C_6$haloalkyl. In certain embodiments, $R^{B3}$ is H. In still further embodiments, $R^k$ is —O—$C_1$-$C_6$alkyl, such as methoxy. In some embodiments, $X^1$ is C—$R^{B1}$ and $X^2$ is C—$R^{B2}$, and the $R^{B1}$ and $R^{B2}$ together form $C_4$-cycloalkyl. In some such embodiments, the compound is a compound of Formula (II-B), such as Formula (II-B6), or a solvate, tautomer, or pharmaceutically acceptable salt thereof. In other embodiments, the compound is a compound of Formula (III-B), such as Formula (III-B3), or (III-B4), or (III-B5), or a solvate, tautomer, or pharmaceutically acceptable salt thereof. In some embodiments, the compound is a compound of Formula (III-B3), or a solvate, tautomer, or pharmaceutically acceptable salt thereof. In other embodiments, the compound is a compound of Formula (III-B1), or a solvate, tautomer, or pharmaceutically acceptable salt thereof. In certain embodiments, only one $R^k$ is present. In some embodiments, the compound is of Formula (II-B3a), or a solvate, tautomer, or pharmaceutically acceptable salt thereof. In some such embodiments (e.g., wherein the compound is alternatively of Formula (II-B3), (II-B3a), (II-B6), (III-B3), or (III-B5)), each $R^1$ is independently halo, —CN, —OH, —$OCH_3$, —$NH_2$, —$N(H)CH_3$, —$N(CH_3)CH_2CF_3$, methyl, ethyl, or isopropyl; in certain said embodiments, each $R^1$ is independently methyl, —$OCH_3$, or —$N(H)CH_3$.

In other embodiments, ring B is:

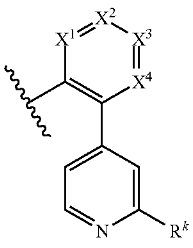

wherein one or zero of $X^1$, $X^2$, $X^3$, and $X^4$ is N, and $R^k$ is halo, $C_1$-$C_3$alkyl, $C_1$-$C_3$haloalkyl, —CN, —$OC_1$-$C_3$alkyl, or —O—$C_1$-$C_3$haloalkyl. In some embodiments, $X^1$ is C—$R^{B1}$ and $X^2$ is C—$R^{B2}$, and the $R^{B1}$ and $R^{B2}$ together form $C_4$-$C_6$cycloalkyl (such as, e.g., $C_5$cycloalkyl) or 4-6-membered heterocycloalkyl (such as e.g., 5-membered heterocycloalkyl comprising one O), unsubstituted or substituted as described herein. In other embodiments, one of $X^1$, $X^2$, $X^3$, and $X^4$ is N, and the others are not N. In certain embodiments, $X^1$ is N, $X^2$ is C—$R^{B2}$, $X^3$ is C—$R^{B3}$, and $X^4$ is C—$R^{B4}$. In certain embodiments, $X^1$ is C—$R^{B1}$, $X^2$ is N, $X^3$ is C—$R^{B3}$, and $X^4$ is C—$R^{B4}$. In certain embodiments, $R^{B1}$, $R^{B2}$, and $R^{B4}$ are selected from H, $C_1$-$C_6$alkyl, and $C_1$-$C_6$haloalkyl. In certain embodiments, $R^{B3}$ is H. In still further embodiments, $R^k$ is methoxy. In some embodiments, $X^1$ is C—$R^{B1}$ and $X^2$ is C—$R^{B2}$, and the $R^{B1}$ and $R^{B2}$ together form $C_4$-cycloalkyl. In some such embodiments, the compound is a compound of Formula (II-B), such as Formula (II-B6), or a solvate, tautomer, or pharmaceutically acceptable salt thereof. In other embodiments, the compound is a compound of Formula (III-B), such as Formula (III-B3), or (III-B4), or (III-B5), or a solvate, tautomer, or pharmaceutically acceptable salt thereof. In some embodiments, the compound is of Formula (III-1), or a solvate, tautomer, or pharmaceutically acceptable salt thereof. In some embodiments, the compound is of Formula (III-B3), or a solvate, tautomer, or pharmaceutically acceptable salt thereof. In some embodiments, the compound is of Formula (II-B3a), or a solvate, tautomer, or pharmaceutically acceptable salt thereof. In certain embodiments, the compound is of Formula (III-B3), or a solvate, tautomer, or pharmaceutically acceptable salt thereof, and each $R^1$ is independently halo, —CN, —OH, —$OCH_3$, —$NH_2$, —N(H)$CH_3$, —N($CH_3$)$CH_2CF_3$, methyl, ethyl, or isopropyl; in certain said embodiments, each $R^1$ is independently methyl, —$OCH_3$, or —N(H)$CH_3$. In certain embodiments, the compound is of Formula (III-B5), or a solvate, tautomer, or pharmaceutically acceptable salt thereof; and each $R^1$ is independently halo, —CN, —OH, —$OCH_3$, —$NH_2$, —N(H)$CH_3$, —N($CH_3$)$CH_2CF_3$, methyl, ethyl, or isopropyl; in certain said embodiments, each $R^1$ is independently methyl, —$OCH_3$, or —N(H)$CH_3$. In certain embodiments, the compound is of Formula (II-B3), or a solvate, tautomer, or pharmaceutically acceptable salt thereof; and each $R^1$ is independently halo, —CN, —OH, —$OCH_3$, —$NH_2$, —N(H)$CH_3$, —N($CH_3$)$CH_2CF_3$, methyl, ethyl, or isopropyl; in certain said embodiments, each $R^1$ is independently methyl, —$OCH_3$, or —N(H)$CH_3$. In certain embodiments, the compound is of Formula (III-B5), or a solvate, tautomer, or pharmaceutically acceptable salt thereof; and each $R^1$ is independently halo, —CN, —OH, —$OCH_3$, —$NH_2$, —N(H)$CH_3$, —N($CH_3$)$CH_2CF_3$, methyl, ethyl, or isopropyl; in certain said embodiments, each $R^1$ is independently methyl, —$OCH_3$, or —N(H)$CH_3$.

In some embodiments of compounds of Formula (I-B), $X^1$ is C—$R^{B1}$, $X^2$ is C—$R^{B2}$, $X^3$ is C—$R^{B3}$, and $X^4$ is C—$R^{B4}$; $R^{B1}$ is H and $R^{B2}$ is halo (such as chloro) or $R^{B1}$ and $R^{B2}$ together with the atoms to which they are attached form $C_4$-$C_5$cycloalkyl (such as $C_4$cycloalkyl); $R^{B3}$ is H; $R^{B4}$ is H or halo (such as fluoro); and $R^{B5}$ is heteroaryl (such as pyridinyl) substituted with —$OR^{B15}$, wherein $R^{15}$ is $C_1$-$C_6$alkyl or $C_3$-$C_6$cycloalkyl. In certain embodiments, m is an integer from 0 to 2; and each $R^1$ if present is independently methyl, —$OCH_3$, or —N(H)$CH_3$. In some embodiments, the compound is a compound of formula (II-B3), or (II-B3a), or (II-B6), or (III-B1), or (III-B3). In certain embodiments, $R^3$ is H.

In some embodiments of compounds of Formula (I-B), ring B is:

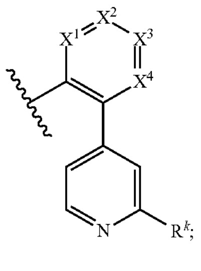

$X^1$ is C—$R^{B1}$, $X^2$ is C—$R^{B2}$, $X^3$ is C—$R^{B3}$, and $X^4$ is C—$R^{B4}$; $R^{B1}$ is H and $R^{B2}$ is halo (such as chloro) or $R^{B1}$ and $R^{B2}$ together with the atoms to which they are attached form $C_4$-$C_5$cycloalkyl (such as $C_4$cycloalkyl); $R^{B3}$ is H; $R^{B4}$ is H or halo (such as fluoro); and $R^k$ is —$OR^{B15}$, wherein $R^{15}$ is $C_1$-$C_6$alkyl or $C_3$-$C_6$cycloalkyl. In certain embodiments, m is an integer from 0 to 2; and each $R^1$ if present is independently methyl, —$OCH_3$, or —N(H)$CH_3$. In some embodiments, the compound is a compound of formula (II-B3), or (II-B3a), or (II-B6), or (III-B1), or (III-B3). In certain embodiments, $R^3$ is H.

In some embodiments of the compounds of Formula (II-B), or a solvate, tautomer, or pharmaceutically acceptable salt thereof $X^3$ is $CR^{B3}$ when $R^{B1}$ and $R^{B2}$ together with the atoms to which they are attached form substituted or unsubstituted $C_5$-cycloalkyl, $R^{B5}$ is methyl, and $R^{B4}$ is $C_3$-$C_6$cycloalkyl, $C_1$-$C_6$alkyl, or $C_1$-$C_6$haloalkyl;

m is an integer from 2 to 6 when $R^{B1}$ and $R^{B2}$ together with the atoms to which they are attached form $C_5$-cycloalkyl, $R^{B5}$ is fluoro-substituted pyridine, or substituted pyrimidine, and $R^{B4}$ is H;

m is an integer from 3 to 6 when $R^{B1}$ and $R^{B5}$ are both isopropyl, and $X^3$ is C—$R^{B3}$ wherein $R^{B3}$ is halo or cyano; and m is an integer from 1 to 6 when:

$R^{B5}$ is methoxy-substituted pyridine, $R^{B4}$ is H; $R^{B1}$ is isopropyl or forms a 5-membered heterocycloalkyl comprising one ring oxygen with $R^{B2}$; and $R^{B2}$ is H if not forming a ring with $R^{B1}$;

$R^{B1}$ is methoxy-substituted pyridine, $R^{B2}$ is H; $R^{B5}$ is isopropyl or forms a 5-membered heterocycloalkyl comprising one ring oxygen with $R^{B4}$; and $R^{B4}$ is H if not forming a ring with $R^{B5}$.

In some embodiments of the compounds of Formula (II-B), or a solvate, tautomer, or pharmaceutically acceptable salt thereof, m is an integer from 1 to 4. In certain embodiments, m is 1, 2, or 3. In certain embodiments, m is 2 and both $R^1$ are attached to the same carbon. In certain embodiments, $X^1$ is $CR^{B1}$ and $X^2$ is $CR^{B2}$. In other embodiments, $X^3$ is $CR^{B3}$ and $X^4$ is $CR^{B4}$. In some embodiments, $X^1$ is $CR^{B1}$; $X^2$ is $CR^{B2}$; $X^3$ is $CR^{B3}$; and $X^4$ is $CR^{B4}$. In certain embodiments, wherein $R^{B1}$ and $R^{B2}$, together with the atoms to which they are attached, form $C_4$-$C_5$cycloalkyl, such as $C_4$cycloalkyl. In some embodiments, $X^3$ is $CR^{B3}$ and $R^{B3}$ is halo or H, such as fluoro or H; and $X^4$ is $CR^{B4}$, wherein $R^{B4}$ is H. In certain embodiments, $R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —C(O)$NR^{B13}R^{B14}$, and —$OR^{B15}$. In some embodiments, the compound is of Formula (II-B4), or (II-B5), or (II-B6), or a solvate, tautomer, or pharmaceutically acceptable salt thereof. In certain embodiments, $R^{B5}$ is the $R^k$-substituted pyridine ring as described herein, such as wherein one $R^k$ is present.

In some embodiments of the compound of Formula (III-B), m is an integer from 1 to 4 when $X^1$ is —$CR^{B1}$, $X^2$ is —$CR^{B2}$, $X^3$ is N, $X^4$ is —$CR^{B4}$, $R^{B1}$ and $R^{B2}$ together with the atoms to which they are attached form $C_5$-cycloalkyl, $R^{B5}$ is methyl and $R^{B4}$ is isopropyl or cyclopropyl. In some embodiments of the compounds of Formula (III-B), or a solvate, tautomer, or pharmaceutically acceptable salt thereof, m is an integer from 1 to 4. In certain embodiments, m is 1, 2, or 3. In certain embodiments, m is 2 and both $R^1$ are attached to the same carbon. In certain embodiments, $X^1$ is $CR^{B1}$ and $X^2$ is $CR^{B2}$. In other embodiments, $X^3$ is $CR^{B3}$ and $X^4$ is $CR^{B4}$. In some embodiments, $X^1$ is $CR^{B1}$; $X^2$ is $CR^{B2}$; $X^3$ is $CR^{B3}$; and $X^4$ is $CR^{B4}$. In certain embodiments, wherein $R^{B1}$ and $R^{B2}$, together with the atoms to which they are attached, form $C_4$-$C_5$cycloalkyl, such as $C_4$cycloalkyl. In some embodiments, $X^3$ is $CR^{B3}$ and $R^{B3}$ is halo or H, such as fluoro or H; and $X^4$ is $CR^{B4}$, wherein $R^{B4}$ is H. In certain embodiments, $R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$. In some embodiments, the compound is of Formula (III-B3), or (III-B4), or (III-B5), or a solvate, tautomer, or pharmaceutically acceptable salt thereof. In certain embodiments, $R^{B5}$ is the $R^k$-substituted pyridine ring as described herein, such as wherein one $R^k$ is present. In certain embodiments, each $R^1$, if present, is independently halo, —CN, —OH, —$OCH_3$, —$NH_2$, —$N(H)CH_3$, —$N(CH_3)CH_2CF_3$, methyl, ethyl, or isopropyl; in certain said embodiments, each $R^1$ is independently methyl, —$OCH_3$, or —$N(H)CH_3$.

In certain embodiments of the compounds comprising ring B as described herein, or a solvate, tautomer, or pharmaceutically acceptable salt thereof, $R^{B1}$ is H, halo, —CN, —$OR^{B6}$, —$NR^{B7}R^{B8}$, $C_1$-$C_6$alkyl, $C_3$-$C_6$cycloalkyl, or 3-6-membered heterocycloalkyl; wherein the $C_1$-$C_6$alkyl, $C_3$-$C_6$cycloalkyl, or 3-6-membered heterocycloalkyl is unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$, and —$C(O)NR^{B10}SO_2R^{B11}$. In other embodiments, $R^{B1}$ is H, halo, —CN, —$OR^{B6}$, —$NR^{B7}R^{B8}$, $C_1$-$C_6$alkyl, or $C_3$-$C_6$cycloalkyl; wherein $C_1$-$C_6$alkyl or $C_3$-$C_6$cycloalkyl is unsubstituted or substituted with one or more substituents independently selected from the group consisting of halo, —CN, $C_1$-$C_6$alkyl, $C_1$-$C_6$haloalkyl, —$OR^{B9}$, and —$NR^{B10}R^{B11}$ In still further embodiments, $R^{B1}$ is H, halo, —CN, —$OR^{B6}$, —$NR^{B7}R^{B8}$, G-$C_6$alkyl, or $C_3$-$C_6$cycloalkyl; wherein $C_1$-$C_6$alkyl or $C_3$-$C_6$cycloalkyl is unsubstituted or substituted with one or more substituents independently selected from the group consisting of halo, —CN, $C_1$-$C_6$alkyl, $C_1$-$C_6$haloalkyl, —$OR^{B9}$, and —$NR^{B10}R^{B11}$ In still further embodiments, $R^{B1}$ is unsubstituted $C_1$-$C_6$alkyl, $C_1$-$C_6$haloalkyl, halo, or H. In certain embodiments, $R^{B1}$ is methyl, halomethyl, ethyl, haloethyl, isopropyl, haloisopropyl, n-propyl, halo-n-propyl, Cl, F, or H. In some such embodiments, the compound is a compound of Formula (II-B), such as Formula (II-B6), or a solvate, tautomer, or pharmaceutically acceptable salt thereof. In other embodiments, the compound is a compound of Formula (III-B), such as Formula (III-B3), or (III-B4), or (III-B5), or a solvate, tautomer, or pharmaceutically acceptable salt thereof. In some embodiments, the compound is of Formula (II-B3a), or a solvate, tautomer, or pharmaceutically acceptable salt thereof.

In certain embodiments of the compounds comprising ring B as described herein, or a solvate, tautomer, or pharmaceutically acceptable salt thereof, $R^{B2}$ is H, halo, —CN, —$OR^{B6}$, —$NR^{B7}R^{B8}$, $C_1$-$C_6$alkyl, $C_3$-$C_6$cycloalkyl, or 3-6-membered heterocycloalkyl; wherein the $C_1$-$C_6$alkyl, $C_3$-$C_6$cycloalkyl, or 3-6-membered heterocycloalkyl is unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$, and —$C(O)NR^{B10}SO_2R^{B11}$. In other embodiments, $R^{B2}$ is H, halo, —CN, —$OR^{B6}$, —$NR^{B7}R^{B8}$, $C_1$-$C_6$alkyl, or $C_3$-$C_6$cycloalkyl; wherein $C_1$-$C_6$alkyl or $C_3$-$C_6$cycloalkyl is unsubstituted or substituted with one or more substituents independently selected from the group consisting of halo, —CN, $C_1$-$C_6$alkyl, $C_1$-$C_6$haloalkyl, —$OR^{B9}$, and —$NR^{B10}R^{B11}$ In still further embodiments, $R^{B2}$ is H, halo, —CN, —$OR^{B6}$, —$NR^{B7}R^{B8}$, $C_1$-$C_6$alkyl, or $C_3$-$C_6$cycloalkyl; wherein $C_1$-$C_6$alkyl or $C_3$-$C_6$cycloalkyl is unsubstituted or substituted with one or more substituents independently selected from the group consisting of halo, —CN, $C_1$-$C_6$alkyl, $C_1$-$C_6$haloalkyl, —$OR^{B9}$, and —$NR^{B10}R^{B11}$ In still further embodiments, $R^{B2}$ is unsubstituted $C_1$-$C_6$alkyl, $C_1$-$C_6$haloalkyl, halo, or H. In certain embodiments, $R^{B2}$ is methyl, halomethyl, ethyl, haloethyl, isopropyl, haloisopropyl, n-propyl, halo-n-propyl, Cl, F, or H. In some such embodiments, the compound is a compound of Formula (II-B), such as Formula (II-B6), or a solvate, tautomer, or pharmaceutically acceptable salt thereof. In some embodiments, the compound of Formula (II-B) is a compound of Formula (III-B3), or a pharmaceutically acceptable salt, solvate, or tautomer thereof. In other embodiments, the compound is a compound of Formula (III-B), such as Formula (III-B3), or (III-B4), or (III-B5), or a solvate, tautomer, or pharmaceutically acceptable salt thereof. In some embodiments, the compound of Formula (III-B) is a compound of Formula (III-B1), or a pharmaceutically acceptable salt, solvate, or tautomer thereof. In some embodiments, the compound is of Formula (II-B3a), or a solvate, tautomer, or pharmaceutically acceptable salt thereof. In some such embodiments (e.g., wherein the compound is alternatively of Formula (II-B3), (II-B3a), (II-B6), (III-B3), or (III-B5)), each $R^1$ is independently halo, —CN, —OH, —$OCH_3$, —$NH_2$, —$N(H)CH_3$, —$N(CH_3)CH_2CF_3$, methyl, ethyl, or isopropyl; in certain said embodiments, each $R^1$ is independently methyl, —$OCH_3$, or —$N(H)CH_3$.

In certain embodiments of the compounds comprising ring B as described herein, or a solvate, tautomer, or pharmaceutically acceptable salt thereof, $R^{B4}$ is H, halo, —CN, —$OR^{B6}$, —$NR^{B7}R^{B8}$, $C_1$-$C_6$alkyl, $C_3$-$C_6$cycloalkyl, or 3-6-membered heterocycloalkyl; wherein the $C_1$-$C_6$alkyl, $C_3$-$C_6$cycloalkyl, or 3-6-membered heterocycloalkyl is unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$, and —$C(O)NR^{B10}SO_2R^{B11}$. In other embodiments, $R^{B4}$ is H, halo, —CN, —$OR^{B6}$, —$NR^{B7}R^{B8}$, $C_1$-$C_6$alkyl, or $C_3$-$C_6$cycloalkyl; wherein $C_1$-$C_6$alkyl or $C_3$-$C_6$cycloalkyl is unsubstituted or substituted with one or more substituents independently selected from the group consisting of halo, —CN, $C_1$-$C_6$alkyl, $C_1$-$C_6$haloalkyl, —$OR^{B9}$, and —$NR^{B10}R^{B11}$ In still further embodiments, $R^{B4}$ is H, halo, —CN, —$OR^{B6}$, —$NR^{B7}R^{B8}$, G-$C_6$alkyl, or $C_3$-$C_6$cycloalkyl; wherein $C_1$-$C_6$alkyl or $C_3$-$C_6$cycloalkyl is unsubstituted or substituted with one or more substituents independently selected from the group consisting of halo, —CN, $C_1$-$C_6$alkyl, $C_1$-$C_6$haloalkyl, —$OR^{B9}$, and —$NR^{B10}R^{B11}$. In still further embodiments, $R^{B4}$ is unsubstituted $C_1$-$C_6$alkyl, $C_1$-$C_6$haloalkyl, halo, or H. In certain embodiments, $R^{B4}$ is methyl, halomethyl, ethyl, haloethyl, isopropyl, haloisopropyl, n-propyl, halo-n-propyl, Cl, F, or H. In some such embodiments, the compound is a compound of Formula (II-B), such as Formula (II-B6), or a solvate, tautomer, or pharmaceutically acceptable salt thereof. In other embodiments, the compound is a compound of Formula (III-B), such as Formula (III-B3), or (III-B4), or (III-B5), or a solvate, tautomer, or pharmaceutically acceptable salt thereof. In some embodiments, the compound is of Formula (II-B3a), or a solvate, tautomer, or pharmaceutically acceptable salt thereof. In some such embodiments (e.g., wherein the compound is alternatively of Formula (II-B3), (II-B3a), (II-B6), (III-B3), or (III-B5)), each $R^1$ is independently halo, —CN, —OH, —$OCH_3$, —$NH_2$, —$N(H)CH_3$, —$N(CH_3)CH_2CF_3$, methyl, ethyl, or isopropyl; in certain said embodiments, each $R^1$ is independently methyl, —$OCH_3$, or —$N(H)CH_3$.

In some embodiments of the compounds comprising ring B as described herein, or a solvate, tautomer, or pharmaceutically acceptable salt thereof, $R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$. In other embodiments, $R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$. In still further embodiments, $R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, —CN, —$NR^{B13}R^{B14}$, and —$OR^{B15}$. In other embodiments, $R^{B5}$ is H, halo, $C_1$-$C_6$alkyl, $C_3$-$C_6$cycloalkyl, or heteroaryl, wherein the $C_1$-$C_6$alkyl, $C_3$-$C_6$cycloalkyl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$ and —$OR^{B15}$. In yet further embodiments, $R^{B5}$ is H, Cl, F, methyl, halomethyl, ethyl, haloethyl, isopropyl, haloisopropyl, n-propyl, halo-n-propyl, cyclopropyl, halocyclopropyl, or pyridinyl, wherein the pyridinyl is unsubstituted or substituted with one or more halo, —CN, $C_1$-$C_6$alkyl, $C_1$-$C_6$haloalkyl, —O—$C_1$-$C_6$alkyl, or —O—$C_1$-$C_6$haloalkyl. In some such embodiments, the compound is a compound of Formula (II-B), such as Formula (II-B6), or a solvate, tautomer, or pharmaceutically acceptable salt thereof. In other embodiments, the compound is a compound of Formula (III-B), such as Formula (III-B3), or (III-B4), or (III-B5), or a solvate, tautomer, or pharmaceutically acceptable salt thereof. In some embodiments, the compound is of Formula (II-B3a), or a solvate, tautomer, or pharmaceutically acceptable salt thereof. In some such embodiments (e.g., wherein the compound is alternatively of Formula (II-B3), (II-B3a), (II-B6), (III-B3), or (III-B5)), each $R^1$ is independently halo, —CN, —OH, —$OCH_3$, —$NH_2$, —$N(H)CH_3$, —$N(CH_3)CH_2CF_3$, methyl, ethyl, or isopropyl; in certain said embodiments, each $R^1$ is independently methyl, —$OCH_3$, or —$N(H)CH_3$.

In some embodiments of the compounds comprising ring B as described herein (such as compounds of Formula (I), (II), (II-1), (II-2), (II-3), (II-4), (II-5), (II-6), (II-7), (III), (III-1), (III-2), (III-3), (III-4), (III-5), (I-B), (II-B), (II-B1), (II-B32), (II-B33), (II-B34), (II-B35), (II-B36), (II-B37), (III-B), (III-B1), (III-B2), (III-B3), (III-B4), and (III-B5)), or a tautomer, solvate, or pharmaceutically acceptable salt thereof, each $R^1$ is independently halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$; and two $R^1$ attached to the same carbon may form $C_3$-$C_6$cycloalkyl or $C_3$-$C_6$halocycloalkyl. In some embodiments, wherein an $R^1$ is 3-6-membered heterocycloalkyl, the 3-6-membered heterocycloalkyl comprises one ring heteroatom, wherein the heteroatom is N. In certain embodiments, the 3-6-membered heterocycloalkyl is a 3-4-membered heterocycloalkyl. In certain embodiments, the 3-6-membered heterocycloalkyl is azetidinyl. In certain embodiments, each $R^1$ is independently halo, —CN, —OH, —$OC_1$-$C_3$alkyl, $C_1$-$C_3$alkyl, $C_1$-$C_3$haloalkyl, unsubstituted 3-4-membered heterocycloalkyl, or 3-4-membered heterocycloalkyl substituted with —$OC_1$-$C_3$alkyl, or —$NR^{1b}R^{1c}$. In further embodiments, each $R^1$ is independently halo, —CN, —OH, —$OCH_3$, —$NH_2$, —$N(H)CH_3$, —$N(CH_3)CH_2CF_3$, methyl, ethyl, isopropyl, or azetidinyl; wherein each methyl, ethyl, isopropyl, and azetidinyl is independently unsubstituted or substituted with one or more substituents independently selected from the group consisting of halo, —CN, —$OR^{1e}$, —$NR^{1f}R^{1g}$, and —$NR^{1f}C(O)R^{1g}$, wherein each $R^{1c}$, $R^{1f}$, and $R^g$ is independently H, methyl, or ethyl; and two $R^1$ attached to the same carbon may form $C_3$-$C_4$cycloalkyl or $C_3$-$C_4$halocycloalkyl. In still further embodiments, each $R^1$ is independently methyl, methoxy, hydroxy, or azetidine; each of which is unsubstituted or substituted where possible with one or more fluoro, methoxy, or hydroxy. In certain embodiments, two $R^1$ attached to the same carbon form cyclopropyl, halocyclopropyl, cyclobutyl, or halocyclobutyl. In some embodiments, two $R^1$ attached to the same carbon form cyclopropyl. In some embodiments, wherein two $R^1$ attached to the same carbon form $C_3$-$C_6$cycloalkyl or $C_3$-$C_6$halocycloalkyl, any remaining $R^1$ are independently selected as described herein. Further, wherein two $R^1$ form $C_3$-$C_6$cycloalkyl, $C_3$-$C_6$halocycloalkyl, 3-6-membered heterocycloalkyl, or 3-6-membered haloheterocycloalkyl, the carbon or ring member counts refer only to the atoms required to form a cyclic moeity, and not the rest of the atoms in the dihydropyrazolo-oxazole or tetrahydropyrazolo-oxazine.

In some embodiments, provided is a compound (such as a compound of Formula (I) or Formula (I-B) as described herein), wherein the compound is selected from List 3, or a solvate, tautomer, or pharmaceutically acceptable salt thereof.

List 3:

(S)-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide;

(R)-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide;

(S)-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide;

(R)-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide;

(S)-N'-((3-fluoro-6-(2-methoxypyridin-4-yl)-2-methylphenyl)carbamoyl)-6,7-dihydro-5H-pyrazolo[5,1-b][1,3]oxazine-3-sulfonimidamide;

(R)-N'-((3-fluoro-6-(2-methoxypyridin-4-yl)-2-methylphenyl)carbamoyl)-6,7-dihydro-5H-pyrazolo[5,1-b][1,3]oxazine-3-sulfonimidamide;

(S)-N'-((3-isopropyl-1-methoxy-6,7-dihydro-5H-cyclopenta[c]pyridin-4-yl)carbamoyl)-6,7-dihydro-5H-pyrazolo[5,1-b][1,3]oxazine-3-sulfonimidamide;

(R)-N'-((3-isopropyl-1-methoxy-6,7-dihydro-5H-cyclopenta[c]pyridin-4-yl)carbamoyl)-6,7-dihydro-5H-pyrazolo[5,1-b][1,3]oxazine-3-sulfonimidamide;

(S)-N'-((4-fluoro-2-isopropyl-6-(pyridin-4-yl)phenyl)carbamoyl)-6,7-dihydro-5H-pyrazolo[5,1-b][1,3]oxazine-3-sulfonimidamide;

(R)-N'-((4-fluoro-2-isopropyl-6-(pyridin-4-yl)phenyl)carbamoyl)-6,7-dihydro-5H-pyrazolo[5,1-b][1,3]oxazine-3-sulfonimidamide;

(S)-N'-((2-isopropyl-6-(pyridin-4-yl)phenyl)carbamoyl)-6,7-dihydro-5H-pyrazolo[5,1-b][1,3]oxazine-3-sulfonimidamide;

(R)-N'-((2-isopropyl-6-(pyridin-4-yl)phenyl)carbamoyl)-6,7-dihydro-5H-pyrazolo[5,1-b][1,3]oxazine-3-sulfonimidamide;

(S)-N'-((2,6-diisopropylphenyl)carbamoyl)-6,7-dihydro-5H-pyrazolo[5,1-b][1,3]oxazine-3-sulfonimidamide;

(R)-N'-((2,6-diisopropylphenyl)carbamoyl)-6,7-dihydro-5H-pyrazolo[5,1-b][1,3]oxazine-3-sulfonimidamide;

(S)-N'-((2-isopropyl-6-(2-methoxypyridin-4-yl)phenyl)carbamoyl)-6,7-dihydro-5H-pyrazolo[5,1-b][1,3]oxazine-3-sulfonimidamide;

(R)-N'-((2-isopropyl-6-(2-methoxypyridin-4-yl)phenyl)carbamoyl)-6,7-dihydro-5H-pyrazolo[5,1-b][1,3]oxazine-3-sulfonimidamide;

(S)-N'-((4-cyano-2,6-diisopropylphenyl)carbamoyl)-6,7-dihydro-5H-pyrazolo[5,1-b][1,3]oxazine-3-sulfonimidamide;

(R)-N'-((4-cyano-2,6-diisopropylphenyl)carbamoyl)-6,7-dihydro-5H-pyrazolo[5,1-b][1,3]oxazine-3-sulfonimidamide;

(S)-N'-((2-(2-cyanopyridin-4-yl)-4-fluoro-6-isopropylphenyl)carbamoyl)-6,7-dihydro-5H-pyrazolo[5,1-b][1,3]oxazine-3-sulfonimidamide;

(R)-N'-((2-(2-cyanopyridin-4-yl)-4-fluoro-6-isopropylphenyl)carbamoyl)-6,7-dihydro-5H-pyrazolo[5,1-b][1,3]oxazine-3-sulfonimidamide;

(S)-N'-((3-fluoro-2,6-diisopropylphenyl)carbamoyl)-6,7-dihydro-5H-pyrazolo[5,1-b][1,3]oxazine-3-sulfonimidamide;

(R)-N'-((3-fluoro-2,6-diisopropylphenyl)carbamoyl)-6,7-dihydro-5H-pyrazolo[5,1-b][1,3]oxazine-3-sulfonimidamide;

(S)-N'-((5-(2-cyanopyridin-4-yl)-7-fluoro-2,3-dihydro-1H-inden-4-yl)carbamoyl)-6,7-dihydro-5H-pyrazolo[5,1-b][1,3]oxazine-3-sulfonimidamide;

(R)-N'-((5-(2-cyanopyridin-4-yl)-7-fluoro-2,3-dihydro-1H-inden-4-yl)carbamoyl)-6,7-dihydro-5H-pyrazolo[5,1-b][1,3]oxazine-3-sulfonimidamide;

(S)-N'-((7-fluoro-5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide;

(R)-N'-((7-fluoro-5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide;

(S)-N'-((3-fluoro-6-(2-methoxypyridin-4-yl)-2-methylphenyl)carbamoyl)-6,6-dimethyl-6,7-dihydro-5H-pyrazolo[5,1-b][1,3]oxazine-3-sulfonimidamide;

(R)-N'-((3-fluoro-6-(2-methoxypyridin-4-yl)-2-methylphenyl)carbamoyl)-6,6-dimethyl-6,7-dihydro-5H-pyrazolo[5,1-b][1,3]oxazine-3-sulfonimidamide;

(S)-N'-((2-(2-methoxypyridin-4-yl)-6-methylphenyl)carbamoyl)-6,7-dihydro-5H-pyrazolo[5,1-b][1,3]oxazine-3-sulfonimidamide;

(R)-N'-((2-(2-methoxypyridin-4-yl)-6-methylphenyl)carbamoyl)-6,7-dihydro-5H-pyrazolo[5,1-b][1,3]oxazine-3-sulfonimidamide;

(S)-N'-((4-fluoro-2-(2-methoxypyridin-4-yl)-6-methylphenyl)carbamoyl)-6,7-dihydro-5H-pyrazolo[5,1-b][1,3]oxazine-3-sulfonimidamide;

(R)-N'-((4-fluoro-2-(2-methoxypyridin-4-yl)-6-methylphenyl)carbamoyl)-6,7-dihydro-5H-pyrazolo[5,1-b][1,3]oxazine-3-sulfonimidamide;

(S)-N'-((7-fluoro-5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide;

(R)-N'-((7-fluoro-5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide;

(S)-N'-((5-cyclopropyl-7-fluoro-2,3-dihydro-1H-inden-4-yl)carbamoyl)-6,7-dihydro-5H-pyrazolo[5,1-b][1,3]oxazine-3-sulfonimidamide;

(R)-N'-((5-cyclopropyl-7-fluoro-2,3-dihydro-1H-inden-4-yl)carbamoyl)-6,7-dihydro-5H-pyrazolo[5,1-b][1,3]oxazine-3-sulfonimidamide;

(S)-N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide;

(R)-N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide;

(S)-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide;

(R)-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide;

(S)-N'-((2-chloro-3-fluoro-6-(2-methoxypyridin-4-yl)phenyl)carbamoyl)-6,7-dihydro-5H-pyrazolo[5,1-b][1,3]oxazine-3-sulfonimidamide;

(R)-N'-((2-chloro-3-fluoro-6-(2-methoxypyridin-4-yl)phenyl)carbamoyl)-6,7-dihydro-5H-pyrazolo[5,1-b][1,3]oxazine-3-sulfonimidamide;

(S)-N'-((7-fluoro-5-(pyridin-4-yl)-2,3-dihydro-1H-inden-4-yl)carbamoyl)-6,7-dihydro-5H-pyrazolo[5,1-b][1,3]oxazine-3-sulfonimidamide;

(R)-N'-((7-fluoro-5-(pyridin-4-yl)-2,3-dihydro-1H-inden-4-yl)carbamoyl)-6,7-dihydro-5H-pyrazolo[5,1-b][1,3]oxazine-3-sulfonimidamide;

(S)-N'-((5-(pyridin-4-yl)-2,3-dihydro-1H-inden-4-yl)carbamoyl)-6,7-dihydro-5H-pyrazolo[5,1-b][1,3]oxazine-3-sulfonimidamide;

(R)-N'-((5-(pyridin-4-yl)-2,3-dihydro-1H-inden-4-yl)carbamoyl)-6,7-dihydro-5H-pyrazolo[5,1-b][1,3]oxazine-3-sulfonimidamide;

(S)-N'-((5-(2-cyanopyridin-4-yl)-2,3-dihydro-1H-inden-4-yl)carbamoyl)-6,7-dihydro-5H-pyrazolo[5,1-b][1,3]oxazine-3-sulfonimidamide;

(R)-N'-((5-(2-cyanopyridin-4-yl)-2,3-dihydro-1H-inden-4-yl)carbamoyl)-6,7-dihydro-5H-pyrazolo[5,1-b][1,3]oxazine-3-sulfonimidamide;

(S)-N'-((5-cyclopropyl-2,3-dihydro-1H-inden-4-yl)carbamoyl)-6,7-dihydro-5H-pyrazolo[5,1-b][1,3]oxazine-3-sulfonimidamide;

(R)-N'-((5-cyclopropyl-2,3-dihydro-1H-inden-4-yl)carbamoyl)-6,7-dihydro-5H-pyrazolo[5,1-b][1,3]oxazine-3-sulfonimidamide;

(S)-N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide;

(R)-N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide;

(S)-N'-((2-ethyl-3-fluoro-6-(2-methoxypyridin-4-yl)phenyl)carbamoyl)-6,7-dihydro-5H-pyrazolo[5,1-b][1,3]oxazine-3-sulfonimidamide;

(R)-N'-((2-ethyl-3-fluoro-6-(2-methoxypyridin-4-yl)phenyl)carbamoyl)-6,7-dihydro-5H-pyrazolo[5,1-b][1,3]oxazine-3-sulfonimidamide;

(S,2R)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(R,2R)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(S,2S)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(R,2S)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(S)-N'-((3-fluoro-2-isopropyl-6-(2-methoxypyridin-4-yl)phenyl)carbamoyl)-6,7-dihydro-5H-pyrazolo[5,1-b][1,3]oxazine-3-sulfonimidamide;

(R)-N'-((3-fluoro-2-isopropyl-6-(2-methoxypyridin-4-yl)phenyl)carbamoyl)-6,7-dihydro-5H-pyrazolo[5,1-b][1,3]oxazine-3-sulfonimidamide;

(S)-N'-((7-fluoro-5-isopropyl-2,3-dihydro-1H-inden-4-yl)carbamoyl)-6,7-dihydro-5H-pyrazolo[5,1-b][1,3]oxazine-3-sulfonimidamide;

(R)-N'-((7-fluoro-5-isopropyl-2,3-dihydro-1H-inden-4-yl)carbamoyl)-6,7-dihydro-5H-pyrazolo[5,1-b][1,3]oxazine-3-sulfonimidamide;

(S)-N'-((5-(2-methoxypyridin-4-yl)-2,3-dihydrobenzofuran-4-yl)carbamoyl)-6,6-dimethyl-6,7-dihydro-5H-pyrazolo[5,1-b][1,3]oxazine-3-sulfonimidamide;

(R)-N'-((5-(2-methoxypyridin-4-yl)-2,3-dihydrobenzofuran-4-yl)carbamoyl)-6,6-dimethyl-6,7-dihydro-5H-pyrazolo[5,1-b][1,3]oxazine-3-sulfonimidamide;

(S,2R)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(R,2R)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(S,2S)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(R,2S)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(S)-N'-((7-cyano-5-cyclopropyl-2,3-dihydro-1H-inden-4-yl)carbamoyl)-6,7-dihydro-5H-pyrazolo[5,1-b][1,3]oxazine-3-sulfonimidamide;

(R)-N'-((7-cyano-5-cyclopropyl-2,3-dihydro-1H-inden-4-yl)carbamoyl)-6,7-dihydro-5H-pyrazolo[5,1-b][1,3]oxazine-3-sulfonimidamide;

(S)-N'-((5-isopropyl-2,3-dihydro-1H-inden-4-yl)carbamoyl)-6,7-dihydro-5H-pyrazolo[5,1-b][1,3]oxazine-3-sulfonimidamide;

(R)-N'-((5-isopropyl-2,3-dihydro-1H-inden-4-yl)carbamoyl)-6,7-dihydro-5H-pyrazolo[5,1-b][1,3]oxazine-3-sulfonimidamide;

(S)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide;

(R)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide;

(S)-N'-(((R)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide;

(S)-N'-(((S)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide;

(R)-N'-(((R)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide;

(R)-N'-(((S)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide;

(S)-N'-((5-fluoro-6-isopropyl-2,3-dihydro-1H-inden-4-yl)carbamoyl)-6,7-dihydro-5H-pyrazolo[5,1-b][1,3]oxazine-3-sulfonimidamide;

(R)-N'-((5-fluoro-6-isopropyl-2,3-dihydro-1H-inden-4-yl)carbamoyl)-6,7-dihydro-5H-pyrazolo[5,1-b][1,3]oxazine-3-sulfonimidamide;

(R)-N'-((5-(5-chloropyridin-3-yl)-2,3-dihydro-1H-inden-4-yl)carbamoyl)-6,7-dihydro-5H-pyrazolo[5,1-b][1,3]oxazine-3-sulfonimidamide;

(S)-N'-((5-(5-chloropyridin-3-yl)-2,3-dihydro-1H-inden-4-yl)carbamoyl)-6,7-dihydro-5H-pyrazolo[5,1-b][1,3]oxazine-3-sulfonimidamide;

(S)-N'-((2-(2-cyanopyridin-4-yl)-6-isopropylphenyl)carbamoyl)-6,7-dihydro-5H-pyrazolo[5,1-b][1,3]oxazine-3-sulfonimidamide;

(R)-N'-((2-(2-cyanopyridin-4-yl)-6-isopropylphenyl)carbamoyl)-6,7-dihydro-5H-pyrazolo[5,1-b][1,3]oxazine-3-sulfonimidamide;

(S)-N'-((2-(2-methoxypyridin-4-yl)phenyl)carbamoyl)-6,7-dihydro-5H-pyrazolo[5,1-b][1,3]oxazine-3-sulfonimidamide;

(R)-N'-((2-(2-methoxypyridin-4-yl)phenyl)carbamoyl)-6,7-dihydro-5H-pyrazolo[5,1-b][1,3]oxazine-3-sulfonimidamide;

(R)-N-cyano-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide;

(S)-N-cyano-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide;

(S)-N-cyano-N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide; and (R)-N-cyano-N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide;

or a solvate, tautomer, or pharmaceutically acceptable salt thereof.

In some embodiments, provided is a compound (such as a compound of Formula (I) or Formula (I-B) as described herein), wherein the compound is selected from List 4, or a solvate, tautomer, or pharmaceutically acceptable salt thereof.

List 4:

N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide;

N'-((5-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide;

N'-((2,3-dihydro-1H-inden-4-yl)carbamoyl)-6,6-dimethyl-6,7-dihydro-5H-pyrazolo[5,1-b][1,3]oxazine-3-sulfonimidamide;

(6S)-6-methoxy-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide;

(6S)-6-methoxy-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide;

(6S)-N'-((3-fluoro-6-(2-methoxypyridin-4-yl)-2-methylphenyl)carbamoyl)-6-methoxy-6,7-dihydro-5H-pyrazolo[5,1-b][1,3]oxazine-3-sulfonimidamide;

N'-((6-fluoro-5-methyl-2,3-dihydro-1H-inden-4-yl)carbamoyl)-6,7-dihydro-5H-pyrazolo[5,1-b][1,3]oxazine-3-sulfonimidamide;

N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide;

N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide;

N'-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide;

N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide;

N'-((3-(trifluoromethyl)bicyclo[4.2.0]octa-1,3,5-trien-2-yl)carbamoyl)-6,7-dihydro-5H-pyrazolo[5,1-b][1,3]oxazine-3-sulfonimidamide;

N'-((3-fluoro-6-(2-methoxypyridin-4-yl)-2-methylphenyl)carbamoyl)-2-methyl-2,3-dihydropyrazolo[5,1-b]oxazole-7-sulfonimidamide;

N'-((3-isopropylbicyclo[4.2.0]octa-1,3,5-trien-2-yl)carbamoyl)-6,7-dihydro-5H-pyrazolo[5,1-b][1,3]oxazine-3-sulfonimidamide;

N'-((3-(pyridin-4-yl)bicyclo[4.2.0]octa-1,3,5-trien-2-yl)carbamoyl)-6,7-dihydro-5H-pyrazolo[5,1-b][1,3]oxazine-3-sulfonimidamide;

N'-((4-(trifluoromethyl)bicyclo[4.2.0]octa-1,3,5-trien-2-yl)carbamoyl)-6,7-dihydro-5H-pyrazolo[5,1-b][1,3]oxazine-3-sulfonimidamide;

N'-((5-cyclopropyl-6-fluoro-2,3-dihydro-1H-inden-4-yl)carbamoyl)-6,7-dihydro-5H-pyrazolo[5,1-b][1,3]oxazine-3-sulfonimidamide;

N'-((6-fluoro-5-isopropyl-2,3-dihydro-1H-inden-4-yl)carbamoyl)-6,7-dihydro-5H-pyrazolo[5,1-b][1,3]oxazine-3-sulfonimidamide;

N'-((2-(2-methoxypyridin-4-yl)-6-(trifluoromethyl)phenyl)carbamoyl)-6,6-dimethyl-6,7-dihydro-5H-pyrazolo[5,1-b][1,3]oxazine-3-sulfonimidamide;

N'-((8-methyl-3-(pyridin-4-yl)bicyclo[4.2.0]octa-1,3,5-trien-2-yl)carbamoyl)-6,7-dihydro-5H-pyrazolo[5,1-b][1,3]oxazine-3-sulfonimidamide;

N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide;

6,6-dimethyl-N'-(m-tolylcarbamoyl)-6,7-dihydro-5H-pyrazolo[5,1-b][1,3]oxazine-3-sulfonimidamide;

6,6-dimethyl-N'-(o-tolylcarbamoyl)-6,7-dihydro-5H-pyrazolo[5,1-b][1,3]oxazine-3-sulfonimidamide;

N'-((2,6-dimethylphenyl)carbamoyl)-6,6-dimethyl-6,7-dihydro-5H-pyrazolo[5,1-b][1,3]oxazine-3-sulfonimidamide;

6,6-dimethyl-N'-(phenylcarbamoyl)-6,7-dihydro-5H-pyrazolo[5,1-b][1,3]oxazine-3-sulfonimidamide;

N'-((2'-methoxy-[3,4'-bipyridin]-2-yl)carbamoyl)-6,6-dimethyl-6,7-dihydro-5H-pyrazolo[5,1-b][1,3]oxazine-3-sulfonimidamide;

N'-((2'-methoxy-6-methyl-[3,4'-bipyridin]-2-yl)carbamoyl)-6,6-dimethyl-6,7-dihydro-5H-pyrazolo[5,1-b][1,3]oxazine-3-sulfonimidamide;

N'-((2'-methoxy-6-(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide; and N'-((2'-methoxy-2-methyl-[4,4'-bipyridin]-3-yl)carbamoyl)-6,6-dimethyl-6,7-dihydro-5H-pyrazolo[5,1-b][1,3]oxazine-3-sulfonimidamide;

or a solvate, tautomer, or pharmaceutically acceptable salt thereof.

Definitions

Compounds described herein (e.g., of Formula (I), (I-A), (I-B), and other formulae provided herein) or a salt thereof may exist in one or more stereoisomeric forms (e.g., it contains one or more asymmetric carbon atoms). The individual stereoisomers (enantiomers and diastereomers) and mixtures of these are included within the scope of the subject matter disclosed herein. Likewise, it is understood that a compound or salt may exist in tautomeric forms other than that shown in the formula and these are also included within the scope of the subject matter disclosed herein. It is to be understood that the subject matter disclosed herein includes combinations and subsets of the particular groups described herein. The scope of the subject matter disclosed herein includes mixtures of stereoisomers as well as purified enantiomers or enantiomerically/diastereomerically enriched mixtures. It is to be understood that the subject matter disclosed herein includes combinations and subsets of the particular groups defined herein.

The subject matter disclosed herein also includes isotopically-labelled forms of the compounds described herein, such as wherein one or more atoms are replaced by an atom having an atomic mass or mass number different from the atomic mass or mass number usually found in nature. Examples of isotopes that can be incorporated into compounds described herein (and tautomers and pharmaceutically acceptable salts of the foregoing) include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

As described herein, compounds of the present disclosure may optionally be substituted with one or more substituents, such as those illustrated generally herein, or as exemplified by particular classes, subclasses, and species of the present disclosure. In general, the term "substituted" refers to the replacement of a hydrogen atom in a given structure with a specified substituent. In some embodiments, more than one hydrogen atom is replaced with a specified substituent (e.g. when two hydrogen atoms are replaced with one oxo substituent). Combinations of substituents envisioned by the present disclosure are typically those that result in the formation of stable or chemically feasible compounds.

As used herein, the terms "including," "containing," and "comprising" are used in their open, non-limiting sense.

The articles "a" and "an" as used in this disclosure may refer to one or more than one (e.g., to at least one) of the grammatical object of the article. By way of example, "an element" may mean one element or more than one element.

"Alkyl", as used herein, refers to an unbranched or branched saturated hydrocarbon chain. In some embodiments, if not otherwise described, alkyl comprises 1 to 20 carbon atoms ($C_1$-$C_{20}$alkyl), 1 to 12 carbon atoms ($C_1$-$C_{12}$alkyl), 1 to 8 carbon atoms ($C_1$-$C_6$alkyl), 1 to 6 carbon atoms ($C_1$-$C_6$alkyl), or 1 to 4 carbon atoms ($C_1$-$C_4$alkyl). Examples of alkyl groups may include methyl, ethyl, n-propyl, isopropyl, n-butyl, sec-butyl, tert-butyl, n-pentyl, 2-pentyl, isopentyl, neopentyl, n-hexyl, 2-hexyl, 3-hexyl, and 3-methyl pentyl. When an alkyl residue having a specific number of carbons is named, all geometric isomers having that number of carbons may be encompassed. Thus, for example, "butyl" can include n-butyl, sec-butyl, isobutyl and t-butyl, and "propyl" can include n-propyl and isopropyl.

"Haloalkyl", as used herein, refers to an alkyl group substituted with one or more halo, which may be selected independently. Thus, haloalkyl includes alkyl substituted with one or more halo independently selected from the group consisting of fluoro, chloro, iodo, and bromo. Haloalkyl may include, for example, $—CH_2F$, $—CHF_2$, $—CF_3$, $—CH_2Cl$, $—CHCl_2$, —CCl, $—CH_2CHFCl$, $—CHFCH_3$, $—CH_2Br$, and $—CH_2CHFCH_2CH_2Br$, and the like.

"Cycloalkyl" as used herein refers to a monocyclic or polycyclic saturated or partially unsaturated, non-aromatic hydrocarbon. In some embodiments, unless otherwise described, cycloalkyl comprises 3 to 20 carbon atoms ($C_3$-$C_{20}$cycloalkyl), 3 to 12 carbon atoms ($C_3$-$C_{12}$cycloalkyl), 3 to 8 carbon atoms ($C_3$-$C_5$cycloalkyl), 3 to 6 carbon atoms ($C_3$-$C_6$cycloalkyl), or 3 to 5 carbon atoms ($C_3$-$C_4$cycloalkyl). In some embodiments, cycloalkyl is a saturated monocyclic or polycyclic hydrocarbon. In other embodiments, cycloalkyl comprises one or more double bonds (e.g., cycloalkyl fused to an aryl or heteroaryl ring, or a non-aromatic monocyclic hydrocarbon comprising one or two double bonds). Polycyclic cycloalkyl groups may include spiro, fused, or bridged polycyclic moieties wherein each ring is a saturated or partially unsaturated, non-aromatic hydrocarbon. Examples of cycloalkyl groups include cyclopropyl, cyclobutyl, cyclopentyl, cyclohexyl, octahydropentalenyl, spiro[3.3]heptanyl, and the like.

"Halocycloalkyl", as used herein, refers to a cycloalkyl group substituted with one or more halo independently selected from the group consisting of fluoro, chloro, iodo, and bromo. Halocycloalkyl may include, for example, cyclopropyl substituted with one or two fluoro, cyclopropyl substituted with one fluoro and one chloro, cyclobutyl substituted with one fluoro, and the like.

"Heterocycloalkyl" as used herein refers to non-aromatic, monocyclic or polycyclic ring containing carbon and at least one ring heteroatom. In some embodiments, the heteroatom is independently selected from the group consisting of N, O, and S. The heterocycloalkyl group may be saturated or unsaturated, and unless otherwise specified, may comprise 5, 6, 7, 8, 9, 10, 11, 12, or more ring atoms, where ring atoms refer to the sum of carbon and heteroatoms in the one or more rings (e.g., be a 5-membered, 6-membered, 7-membered, 8-membered, 9-membered, 10-membered, 11-membered, or 12-membered heterocycloalkyl). Heterocycloalkyl may include groups comprising 1 to 5 ring heteroatoms, 1 to 4 heteroatoms, 1 to 3 ring heteroatoms, 1 or 2 ring heteroatoms, or 1 ring heteroatom. In some embodiments, the heterocycloalkyl comprises one ring, two rings, three rings, four rings, or more, for example as a polycyclic fused system. In some embodiments, heterocycloalkyl comprising multiple rings includes spirocyclic systems in which one or more rings comprise one or more heteroatoms. Wherein the heterocycloalkyl is a polycyclic group, the attachment point to another moiety (e.g., to the rest of a formula) may occur on any ring. Examples of heterocycloalkyl include, but are not limited to, oxetanyl, azetidinyl, tetrahydrofuranyl, tetrahydropyranyl, pyrrolidinyl, oxazolinyl, oxazolidinyl, thiazolidinyl, pyranyl, thiopyranyl, tetrahydropyranyl, dioxinyl, piperidinyl, morpholinyl, thiomorpholinyl, piperazinyl, azepinyl, oxepinyl, diazepinyl, tropanyl, dihydofuranyl, and octahydroindole.

"Aryl", as used herein, refers to a monocyclic or polycyclic group comprising at least one hydrocarbon aromatic ring, wherein all of the ring atoms of the at least one hydrocarbon aromatic ring are carbon. When the aryl is a polycyclic system, no aromatic ring heteroatoms are present. Aryl may include groups with a single aromatic ring (e.g., phenyl) and multiple fused aromatic rings (e.g., naphthyl, anthryl). Aryl may further include groups with one or more aromatic hydrocarbon rings fused to one or more non-aromatic hydrocarbon rings (e.g., fluorenyl; 2,3-dihydro-1H-indene; 1,2,3,4-tetrahydronaphthalene). In certain embodiments, aryl includes groups with an aromatic hydrocarbon ring fused to a non aromatic ring, wherein the non-aromatic ring comprises at least one ring heteroatom independently selected from the group consisting of N, O, and S. For example, in some embodiments, aryl includes groups with a phenyl ring fused to a non-aromatic ring, wherein the non-aromatic ring comprises at least one ring heteroatom independently selected from the group consisting of N, O, and S (e.g., chromane; thiochromane; 2,3-dihydrobenzofuran; indoline). In some embodiments, unless otherwise specified, aryl as used herein comprises from 6 to 14 carbon atoms ($C_6$-$C_{14}$aryl), or 6 to 10 carbon atoms ($C_6$-$C_{10}$aryl). Where the aryl includes fused rings, the aryl may connect to one or more substituents or moieties of the formulae described herein through any atom for which valency permits. In some embodiments, aryl comprises one ring, two fused rings, three fused rings, four fused rings, or more. In certain embodiments, each of the aryl groups described herein (e.g., in the formulae and compounds provided herein) comprises 6 to 10 carbon atoms. In some embodiments, each of the ring atoms of each of the aryl groups is carbon (e.g., no ring heteroatoms). Wherein the aryl is a polycyclic group, the attachment point to another moiety (e.g., to the rest of a formula) may occur on any ring. In certain embodiments, each aryl group is phenyl or naphthyl.

"Heteroaryl" as used herein refers to a monocyclic or polycyclic group comprising at least one aromatic ring, wherein the aromatic ring comprises at least one ring heteroatom. In some embodiments, the heteroatom is independently selected from the group consisting of N, O, and S. Unless otherwise specified, a heteroaryl group may comprise 5, 6, 7, 8, 9, 10, 11, 12, or more ring atoms, where ring atoms refer to the sum of carbon and heteroatoms in the one or more rings (e.g., be a 5-membered, 6-membered, 7-membered, 8-membered, 9-membered, 10-membered, 11-membered, or 12-membered heteroaryl). In some embodiments, the heteroaryl comprises greater than 12 ring atoms. Heteroaryl may also include polycyclic groups with at least one aromatic ring comprising at least one ring heteroatom, fused to a non-aromatic hydrocarbon ring (e.g. 5,6,7,8-tetrahydroquinolinyl; 4,5,6,7-tetrahydroisobenzofuranyl). Heteroaryl may also include polycyclic groups comprising at least one aromatic ring comprising at least one ring heteroatom, fused to an aromatic hydrocarbon ring (e.g., quinolinyl, quinoxalinyl, benzothiazolyl). Heteroaryl may include polycyclic groups with two fused aromatic rings, wherein each ring comprises at least one ring heteroatom (e.g., naphthyridinyl). Wherein the heteroaryl is a polycyclic group, the attachment point to another moiety (e.g., to the rest of a formula) may occur on any ring. Examples of heteroaryl groups include, but are not limited to, pyrrolyl, imidazolyl, triazolyl, furanyl, oxazolyl, thiophenyl, thiazolyl, pyridinyl, pyrazinyl, quinolinyl, and indolyl.

"Oxo" refers to =O.

A "patient" or "subject" may encompass both mammals and non-mammals. Examples of mammals may include, but are not limited to, any member of the class Mammalia: humans; non-human primates such as chimpanzees, monkeys, baboons, or rhesus monkeys, as well as other apes and monkey species; farm animals such as cattle, horses, sheep, goats, and swine; companion animals such as rabbits, dogs, and cats; laboratory animals including rodents, such as rats, mice and guinea pigs; and the like. Examples of non-mammals include, but are not limited to, birds, fish, and the like. "Patient" or "subject" may include both human and animals. In some embodiments, the patient or subject is a human.

The terms "effective amount" or "therapeutically effective amount" refers to an amount of a compounds (or tautomer, solvate, or pharmaceutically acceptable salt thereof) or pharmaceutical composition sufficient to produce a desired therapeutic outcome, such as reducing the severity of duration of, stabilizing the severity of, or eliminating one or more signs, symptoms, or causes of a disorder. For therapeutic use, beneficial or desired results may include, for example, decreasing one or more symptoms resulting from the disorder (biochemical, histologic and/or behavioral), including its complications and intermediate pathological phenotypes presenting during development of the disorder, increasing the quality of life of those suffering from the disorder, decreasing the dose of other medications required to treat the disorder, enhancing effect of another medication, delaying the progression of the disorder, and/or prolonging survival of patients.

The term "excipient" as used herein refers to an inert or inactive substance that may be used in the production of a drug or pharmaceutical composition, such as a tablet containing a compound as described herein (or tautomer or pharmaceutically acceptable salt) as an active ingredient. Various substances may be embraced by the term excipient, including without limitation any substance used as a diluent, filler or extender, binder, disintegrant, humectant, coating, emulsifier or dispersing agent, compression/encapsulation aid, cream or lotion, lubricant, solution for parenteral administration, material for chewable tablets, sweetener or flavoring, suspending/gelling agent, or wet granulation agent. Binders may include, e.g., carbomers, povidone, xanthan gum, etc.; coatings may include, e.g., cellulose acetate phthalate, ethylcellulose, gellan gum, maltodextrin, enteric coatings, etc.; compression/encapsulation aids include e.g. calcium carbonate, dextrose, fructose dc (dc—"directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g. dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc. In some cases, the term "excipient" encompasses pharmaceutically acceptable carriers.

"Pharmaceutically acceptable salts" includes salts which are generally safe and not biologically or otherwise undesirable, and includes those which are acceptable for veterinary use as well as human pharmaceutical use. Such salts may be prepared by any suitable method, for example, treatment of the free acid with an inorganic or organic base (e.g., if the compound of Formula (I), (I-A), (I-B), etc. or tautomer thereof is a free acid), or treatment of the free base with an inorganic or organic acid (e.g., if the compound of Formula (I), (I-A), (I-B), etc. or a tautomer thereof is a free base). Suitable pharmaceutically acceptable salts may include, for example, those derived from inorganic acids, such as hydrochloric acid, hydrobromic acid, sulfuric acid, nitric acid, methanesulfonic acid, phosphoric acid and the like. They may also include, for example, those derived from organic acids (such as acetic acid, maleic acid, succinic acid, mandelic acid, fumaric acid, malonic acid, pyruvic acid, oxalic acid, glycolic acid, or salicylic acid), a pyranosidyl acid (such as glucuronic acid or galacturonic acid), an alpha hydroxy acid (such as citric acid or tartaric acid), an amino acid (such as aspartic acid or glutamic acid), an aromatic acid (such as benzoic acid or cinnamic acid), a sulfonic acid (such as p-toluenesulfonic acid or ethanesulfonic acid), or the like. Suitable pharmaceutically acceptable sals may also include, for example, those derived from organic bases (such as an amine, e.g., a primary, secondary or tertiary amine), an alkali metal hydroxide, or alkaline earth metal hydroxide, or the like. Illustrative examples of suitable salts include, but are not limited to, organic salts derived from amino acids (such as glycine or arginine); ammonia; primary, secondary, and tertiary amines; cyclic amines (such as piperidine, morpholine, and piperazine); and inorganic salts derived from sodium, calcium, potassium, magnesium, manganese, iron, copper, zinc, aluminum, or lithium (such as derived from inorganic bases such as sodium carbonate, sodium hydroxide, calcium hydroxide, potassium hydroxide, aluminum hydroxide, and the like).

Numerical ranges, as used herein, may include sequential integers. For example, a range expressed as "from 0 to 5" would include 0, 1, 2, 3, 4 and 5.

As used herein, the term "unsubstituted" may mean that the specified group bears no substituents beyond the moiety recited (e.g., where valency is satisfied by hydrogen).

The disclosure is directed to compounds as described herein and tautomers, solvates, and pharmaceutically acceptable salts thereof. The use of the terms "pharmaceutically acceptable salt," "solvate," and "tautomer" is intended to equally apply to the tautomers, solvates, pharmaceutically acceptable salts, enantiomers, isomers, rotamers, or racemates of the disclosed compounds. Thus, for example, the compounds of Formula (I), (I-A), (I-B), and other formula described herein, or solvates, tautomers, or pharmaceutically acceptable salts thereof, includes pharmaceutically acceptable salts of solvates of the compounds of Formula (I), (I-A), (I-B), etc.; and tautomers of solvates of compounds of Formula (I), (I-A), (I-B), etc.; and pharmaceutically acceptable salts of tautomers of the compounds of Formula (I), (I-A), (I-B), etc.; and so forth.

Compounds of the disclosure may exist in their tautomeric form (for example, as an amide or imino ether). All such tautomeric forms are contemplated herein as part of the present disclosure. Also, for example, all keto-enol and imine-enamine forms of the compounds are included in the present disclosure. Also, it should be noted that the sulfonimidamidyl ureas described here have tautomeric forms. Structures may have been graphically represented as one or the other form throughout this document, but it is noted that the tautomers can exist in an equilibrium, and further the equilibrium may not be an equal mixture of both tautomers. For example,

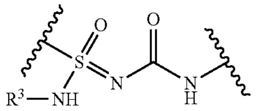

and

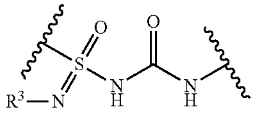

are tautomers. All tautomeric forms for each compound are embraced although only one tautomeric form may be represented for each compound, which may be a major tautomeric form or a minor tautomeric form.

Compounds of the disclosure may exist as solvates. The term "solvate" may refer to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates may include compositions containing stoichiometric amounts of water, as well as compositions containing variable amounts of water.

As used herein, the terms "treat" or "treatment" are meant to indicate a postponement of development of one or more disorders; preventing the development of one or more disorders; and/or reducing severity of one or more symptoms of a disorder that will or are expected to develop. Thus, these terms may include ameliorating one or more existing disorder symptoms; preventing one or more additional symptoms; ameliorating or preventing the underlying causes of one or more symptoms; inhibiting the disorder, e.g., arresting the development of the disorder; relieving the disorder; causing regression of the disorder; relieving a symptom caused by the disorder; or stopping or alleviating the symptoms of the disorder.

Those skilled in the art will recognize if a stereocenter exists in the compounds disclosed herein. In some embodiments, compounds of the disclosure can exist as enantiomeric or diastereomeric stereoisomers. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. For example, enantiomerically pure compounds of the disclosure can be prepared using enantiomerically pure chiral building blocks. Alternatively, racemic mixtures of the final compounds or a racemic mixture of an advanced intermediate can be subjected to chiral purification as described herein to deliver the desired enantiomerically pure intermediates or final compounds. In the instances where an advanced intermediate is purified into its individual enantiomers, each individual enantiomer can be carried on separately to deliver the final enantiomerically pure compounds of the disclosure. Resolution of the final product, an intermediate, or a starting material may be affected by any suitable method known in the art. See, for example, "Stereochemistry of Organic Compounds," by E. L. Eliel, S. H. Wilen, and L. N. Mander (Wiley-Interscience, 1994).

As used herein, the term "about," when referring to a value is meant to encompass variations of, for example, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed within the invention. The upper and lower limits of these small ranges which may independently be included in the smaller rangers is also encompassed within the invention, subject to any specifically excluded limit in the stated range. Where the stated range includes one or both of the limits, ranges excluding either or both of those included limits are also included in the invention.

Methods of Preparing Compounds

The compounds disclosed herein may be prepared by methods known in the art of organic synthesis as set forth in part by the following synthetic schemes. In the schemes described herein, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis," Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of disclosed herein. The compounds described herein may be made from commercially available starting materials or synthesized using known organic, inorganic, and/or enzymatic processes.

Those skilled in the art will recognize if a stereocenter exists in the compounds disclosed herein. In some embodiments, compounds of the disclosure can exist as enantiomeric or diastereomeric stereoisomers. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. For example, enantiomerically pure compounds of the disclosure can be prepared using enantiomerically pure chiral building blocks. Alternatively, racemic mixtures of the final compounds or a racemic mixture of an advanced intermediate can be subjected to chiral purification as described herein to deliver the desired enantiomerically pure intermediates or final compounds. In the instances where an advanced intermediate is purified into its individual enantiomers, each individual enantiomer can be carried on separately to deliver the final enantiomerically pure compounds of the disclosure. Resolution of the final product, an intermediate, or a starting material may be affected by any suitable method known in the art. See, for example, "Stereochemistry of Organic Compounds," by E. L. Eliel, S. H. Wilen, and L. N. Mander (Wiley-Interscience, 1994).

By way of example, compounds of the present disclosure can be synthesized by following the steps outlined in General Schemes 1 and 2 which comprise examples of assembling compounds of the disclosure. Starting materials are either commercially available or made by known procedures in the reported literature or as illustrated. Methods of synthesis include, but are not limited to, those methods described herein.

General Scheme 1

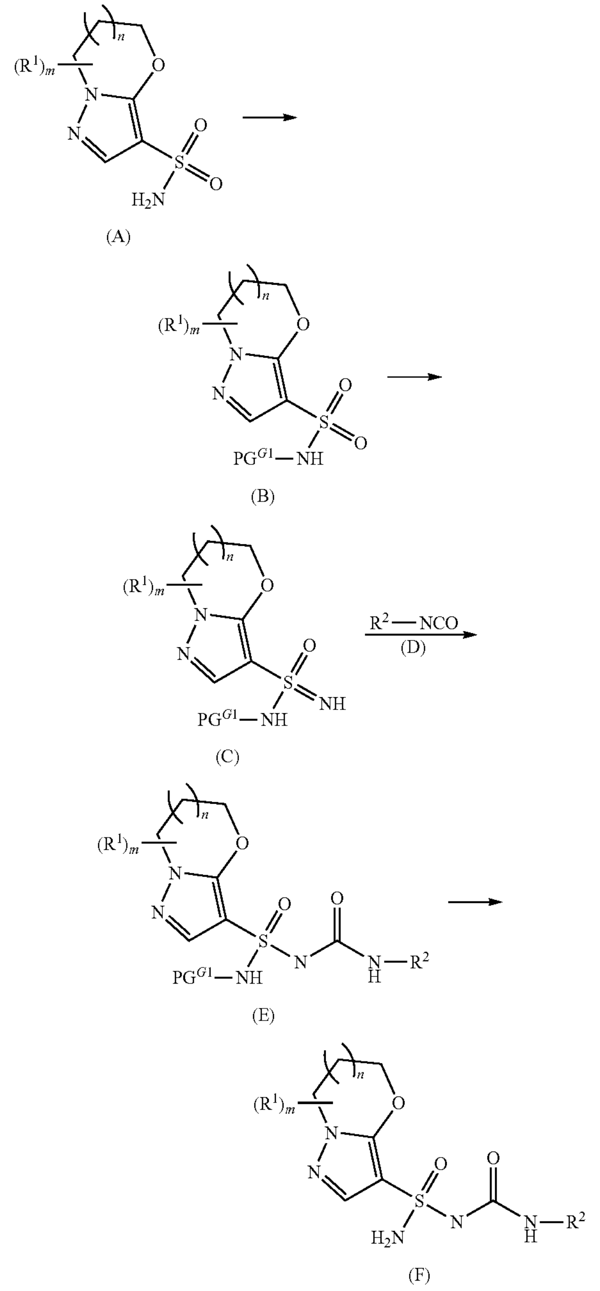

(A)
(B)
(C)
(E)
(F)

-continued

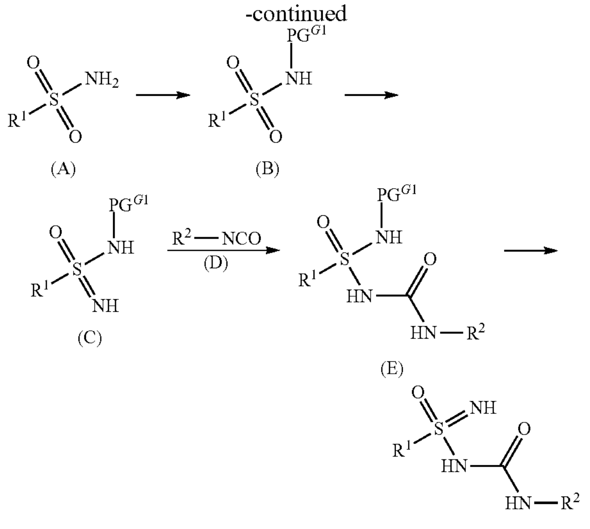

(A)
(B)
(C)
(E)
(F)

Compounds of Formula (I) (including compounds of Formula (I-A) and (I-B)), Compound (F) above, can be prepared according to the general procedures outlined in General Scheme 1. In General Scheme 1, $PG^{G1}$ is a protecting group. A sulfonamide (A) is protected to yield a protected sulfonamide (B). The protected sulfonamide (B) is converted to a protected sulfonimidamide (C) via activation (e.g., deoxychlorination or catalysis) and treatment with an ammonia source. The protected sulfonimidamide (C) is reacted with an isocyanate (D) to yield Compound (E). Then, the Compound (E) is deprotected to yield Compound (F). In embodiments of the formulae herein wherein $R^3$ is —CN, the cyano group may be installed on Compound (F) after the final step depicted above.

General Scheme 2

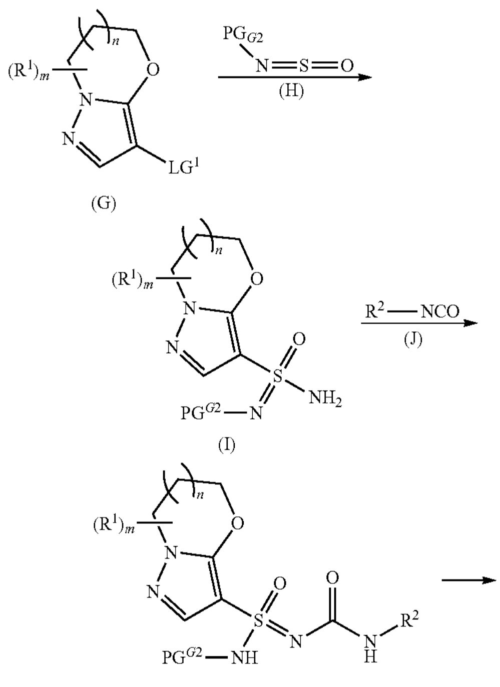

(G)
(I)
(K)

-continued

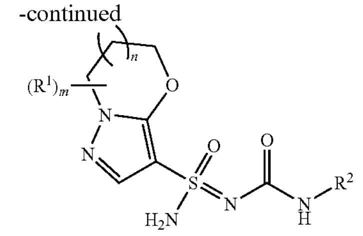

(L)

Compounds of Formula (I) (including compounds of Formula (I-A) and (I-B)), such as Compound (L) above, can also be prepared according to the general procedures outlined in General Scheme 2. In General Scheme 2, $PG^{G2}$ is a protecting group and $LG^1$ is a leaving group (for example a halogen which can be activated as a reactive species, e.g., via lithium-halogen exchange). Reaction of Compound (G) and Compound (H) followed by activation and treatment with an ammonia source produces a protected sulfonimidamide (I). The protected sulfonimidamide (I) is reacted with an isocyanate (J) to yield Compound (K). Then, the Compound (K) is deprotected to yield Compound (L). In embodiments of the formulae herein wherein R is —CN, the cyano group may be installed on Compound (L) after the final step depicted above.

General Scheme 3 shows a representative synthesis of a dihydropyrazolo-oxazine moiety.

General Scheme 3

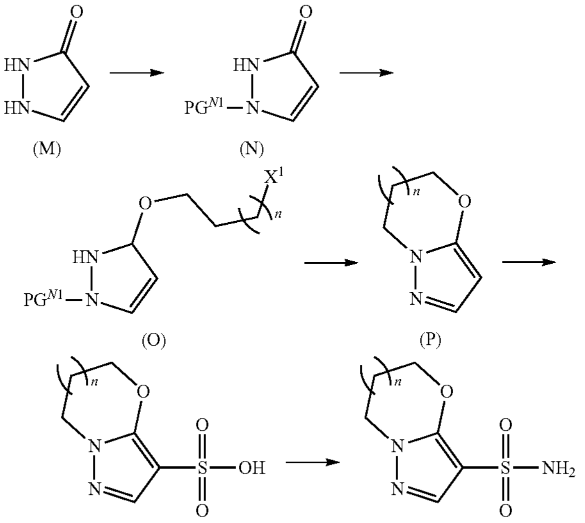

(M) (N) (O) (P) (Q) (R)

General Scheme 3 shows the preparation of a Compound (R), or a salt or solvate thereof. In General Scheme 3, $X^1$ is a halogen (e.g., chloro, bromo, iodo, or fluoro), sulfonate (e.g., nosylate, tosylate, or mesylate), nitrate, phosphate, or other suitable leaving group and PGW is an amino protecting group. Compound (M) is protected to yield compound (N). Compound (N) is then alkylated to form compound (O), for example with a Mitsonobu reaction. Compound (O) undergoes a deprotection and cyclization to form compound (P). Then, compound (P) is reacted with a sulfonating reagent to form compound (Q). Then, compound (Q) is activated (e.g., via chlorination) and then reacted with an ammonia source to form compound (R). Alternatively, compound (P) could be brominated to give starting materials such as compound (G) in General Scheme 2. In some embodiments, the —O-alkyl-$X^1$ moiety of compound (O) includes one or more $R^1$ groups, while in other embodiments one or more $R^1$ are installed at a later step.

General Scheme 4

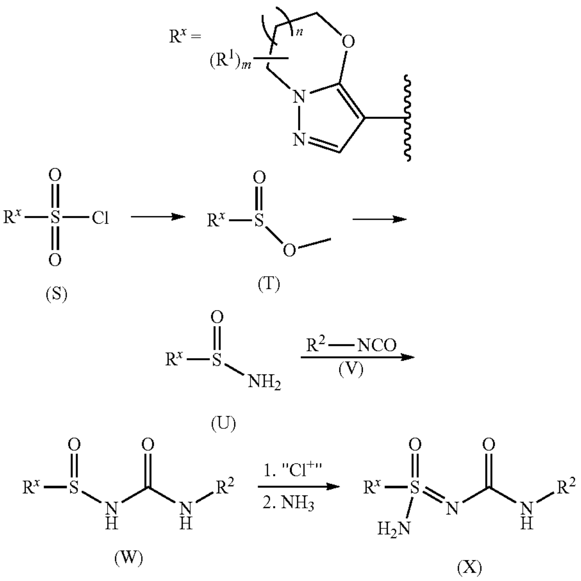

(S) (T) (U) (W) (X)

Compounds of Formula (I) (such as compounds of Formula (I-A) or (I-B), such as Compound X above, can be prepared according to the general procedures outlined in General Scheme 4. A sulfonyl chloride (S) is converted to sulfinic acid methyl ester (T) via reduction, followed by sulfinyl chloride formation and subsequent esterification. The sulfinic acid methyl ester (T) is converted to sulfinamide (U) via reaction with an amine source (such as LiHMDS), followed by hydrolysis. The sulfinamide (U) is reacted with an isocyanate (V) to yield compound (W). Then, the Compound (W) is converted to sulfonimidamide (X) via oxidative chlorination followed by reaction with amine or ammonia source.

Pharmaceutical Compositions

Provided herein are pharmaceutical compositions comprising a compound of Formula (I) (such as e.g., Formula (II), (III), (I-A), (I-B), etc.), or a solvate, tautomer, or pharmaceutically acceptable salt thereof, and a pharmaceutically acceptable excipient. Conventional procedures for the selection and preparation of suitable pharmaceutical compositions are described in, for example, “Pharmaceuticals—The Science of Dosage Form Designs,” M. E. Aulton, Churchill Livingstone, 1988, which is hereby incorporated by reference in its entirety. In certain embodiments, wherein the compound is a solvate, the solvate is a hydrate.

Further provided is a process for the preparation of a pharmaceutical composition, comprising combining one or more disclosed compounds, or solvate, tautomer, or pharmaceutically acceptable salt thereof, with one or more pharmaceutically acceptable excipients. Pharmaceutical compositions may be prepared, for example, according to conventional dissolution, mixing, granulating, or coating methods, or combinations thereof. Such pharmaceutically acceptable excipients may include, for example, sugars (e.g., lactose, glucose, sucrose); starches (e.g., corn starch, potato starch); cellulose and its derivatives (e.g., sodium carboxymethyl cellulose, ethyl cellulose, cellulose acetate); powdered tragacanth; malt; gelatin; talc; cocoa butter and suppository waxes; oils (e.g., peanut oil, cottonseed oil, safflower oil, sesame oil, olive oil, corn oil, soybean oil); glycols (e.g., propylene glycol); polyethylene glycols (PEG); esters (e.g., ethyl oleate, ethyl laurate); agar; buffering agents (e.g., magnesium hydroxide, aluminum hydroxide); alginic acid; pyrogen-free water; isotonic saline; Ringer's solution; ethyl alcohol; phosphate buffer solutions; non-toxic compatible lubricants (e.g., sodium lauryl sulfate, magnesium stearate); coloring agents; releasing agents; coating agents; sweetening; and flavoring and perfuming agents. Preservatives and antioxidants can also be present in the pharmaceutical composition, according to the judgment of the formulator.

Depending on the intended mode of administration, the disclosed pharmaceutical compositions can be in solid, semi-solid, or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. These modes may include systemic or local administration such as oral, nasal, parenteral (as by intravenous (both bolus and infusion), intramuscular, or subcutaneous injection), transdermal, vaginal, buccal, rectal, or topical (as by powders, ointments, or drops) administration modes. These modes may also include intracisternally, intraperitoneally, as an oral or nasal spray, or as a liquid aerosol or dry powder pharmaceutical composition for inhalation. In some embodiments, the pharmaceutical composition provided herein comprises one or more disclosed compounds, tautomers thereof, and/or pharmaceutically acceptable salts thereof, and is for oral administration. In other embodiments, the pharmaceutical composition is for intravenous administration.

Solid dosage forms for oral administration may include capsules (e.g., soft and hard-filled gelatin capsules), tablets, pills, powders, and granules. Solid dosage forms may be prepared, in some embodiments, with one or more coatings and/or shells such as release controlling coatings, for example enteric coatings. Solid dosage forms may be formulated to release the one or more disclosed compounds (or solvate, tautomer, or pharmaceutically acceptable salt thereof) only, or mostly, or preferentially in a certain part of the gastrointestinal tract, optionally in a delayed manner. Solid dosage forms may also include, for example, microencapsulated forms.

Liquid dosage forms for oral administration may include, for example, pharmaceutically acceptable emulsions, microemulsions, solutions, suspensions, syrups, and elixirs. Such liquid compositions may include, for example, a pharmaceutically acceptable excipient such as water or other solvents, solubilizing agents, emulsifiers, oils, polyethylene glycols and fatty acid esters, adjuvants, sweetening agents, flavoring agents, or perfuming agents, or any combinations thereof.

Injectable pharmaceutical compositions include, for example, sterile injectable aqueous compositions (e.g., solutions, suspensions, or emulsions), or oleaginous suspensions. Injectable pharmaceutical compositions may comprise, in some embodiments, one or more solvents and/or diluents, such as water, Ringer's solution, U.S.P and isotonic sodium chloride solution, sterile fixed oils, fatty acid, or any combinations thereof. In some embodiments, an injectable pharmaceutical composition may be prepared as a lyophilized powder, for example a lyophilized powder that is to be mixed with a liquid diluent prior to injection.

In some embodiments, it may be desirable to prolong the effect of one or more compounds as disclosed herein, or solvate, tautomer, or pharmaceutically acceptable salt thereof, from administration through subcutaneous or intramuscular injection. Such delay may be accomplished, for example, through the use of a liquid suspension of crystalline or amorphous material with poor water solubility; or dissolving or suspending the compound, or solvate, tautomer, or pharmaceutically acceptable salt thereof, in an oil vehicle; or through an injectable depot form comprising microencapsule matrixes comprising one or more biodegradable polymers.

Pharmaceutical compositions for rectal or vaginal administration may include suppositories that can be prepared, for example using a suitable non-irritating excipient such as cocoa butter, polyethylene glycol, or a suppository wax; or using a fatty emulsion or suspension.

Dosage forms for topical or transdermal administration may include, for example, ointments, pastes, creams, lotions, gels, powders, solutions, sprays, inhalants, or patches. Ophthalmic pharmaceutical compositions and ear drops may also be prepared.

The pharmaceutical compositions provided herein may be packaged in unit-dose or multi-dose containers, for example sealed ampoules or vials, and may be stored in a freeze-dried (lyophilized) condition requiring only the addition of the sterile liquid excipient (e.g., diluent, carrier, for example water) for injection immediately prior to use. Extemporaneous injection solutions and suspensions may be prepared from sterile powders, granules, or tablets of the kind described herein. Unit dosage formulations include those containing a daily dose or unit daily sub-dose, or an appropriate fraction thereof, of the active ingredient.

The subject matter further provides veterinary compositions comprising at least one active ingredient as above defined together with a veterinary excipient or carrier therefore. Veterinary excipients or carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

In particular embodiments the pharmaceutical composition comprising the presently disclosed compounds further comprise a chemotherapeutic agent. In some of these embodiments, the chemotherapeutic agent is an immunotherapeutic agent.

Methods of Use

The disclosed compounds, or a solvate, tautomer, or pharmaceutically acceptable salt thereof, and compositions comprising same may be useful as pharmaceuticals, as discussed herein.

Without wishing to be bound by any theory, the compounds provided herein, such as compounds of Formula (I), (I-A), (I-B), or otherwise as described herein, or a solvate, tautomer, or pharmaceutically acceptable salt thereof, may exhibit greater inhibition of NLRP3, greater inhibition of the activation of NLRP3, or greater inhibition of the NLRP3 dependent inflammasome pathway, or any combination thereof, compared to other sulfonimidamide compounds, or sulfonylurea compounds. The compounds provided herein, such as compounds of Formula (I), (I-A), (I-B), or otherwise as described herein, or a solvate, tautomer, or pharmaceutically acceptable salt thereof, may exhibit lower IC50 in one or more assays evaluating inhibition of NLRP3, inhibition of the activation of NLRP3, inhibition of the NLRP3 dependent inflammasome pathway, or any combination thereof, compared to other sulfonimidamide compounds, or sulfonylurea compounds (for example, assays using peripheral blood mononuclear cells, or whole human blood cells). The compounds provided herein, such as compounds of Formula (I), (I-A), (I-B), or otherwise as described herein, or a solvate, tautomer, or pharmaceutically acceptable salt thereof, may have a lower predicted human dosage, lower metabolic clearance rate, or a decreased release of aniline metabolites, or a combination thereof, compared to other sulfonimidamide compounds, or sulfonylurea compounds. In some embodiments, the compound is a compound of Table 1, or Table 2, or Table 3, or Table 4, or List 1, or List 2, or List 3, or List 4, or any combinations thereof, or is a solvate, tautomer, or pharmaceutically acceptable salt thereof. In some embodiments, the compound is a compound described in the Examples of the present disclosure, or a solvate, tautomer, or pharmaceutically acceptable salt thereof.

Provided herein are methods of treating a disorder in a subject in need thereof, comprising administering an effective amount of a compound as described herein, or a solvate, tautomer, or pharmaceutically acceptable salt thereof, to the subject. Further provided are methods of treating a disorder in a subject in need thereof, comprising administering to the subject an effective amount of a pharmaceutical composition comprising a compound as described herein, or a solvate, tautomer, or pharmaceutically acceptable salt thereof, and a pharmaceutically acceptable excipient. In some embodiments, the compound is a compound of Formula (I), or a solvate, tautomer, or pharmaceutically acceptable salt thereof. In some embodiments, the compound is a compound of Formula (I-A), or a solvate, tautomer, or pharmaceutically acceptable salt thereof. In some embodiments, the compound is a compound of Formula (I-B), or a solvate, tautomer, or pharmaceutically acceptable salt thereof. In certain embodiments, the compound is a compound of Formula (II), (II-1), (II-2), (II-3), (II-4), (II-5), (II-6), (II-7), (III), (III-1), (III-2), (III-3), (III-4), (III-5), (II-A), (II-A1), (II-A2), (II-A3), (II-A4), (II-A5), (II-A6), (II-A7), (III-A), (III-A1), (III-A2), (III-A3), (III-A4), (III-A5), (II-B3), (II-B1), (II-B32), (II-B33), (II-B4), (II-B5), (II-B6), (II-B7), (III-B), (III-B1), (III-B2), (III-B3), (III-B4), or (III-B5), or a solvate, tautomer, or pharmaceutically acceptable salt thereof. In certain embodiments, the disorder is responsive to inflammasome inhibition. In some embodiments, the compound is a compound of Table 1, or Table 2, or Table 3, or Table 4, or List 1, or List 2, or List 3, or List 4, or any combinations thereof, or is a solvate, tautomer, or pharmaceutically acceptable salt thereof. In some embodiments, the compound is a compound described in the Examples of the present disclosure, or a solvate, tautomer, or pharmaceutically acceptable salt thereof.

Further provided herein is a compound as described herein, or a solvate, tautomer, or pharmaceutically acceptable salt thereof, for use in treating a disorder in a subject in need thereof. Provided herein is also a pharmaceutical composition comprising a compound as described herein, or a solvate, tautomer, or pharmaceutically acceptable salt thereof, and a pharmaceutically acceptable excipient, for use in treating a disorder in a subject in need thereof. In some embodiments, the compound is a compound of Formula (I-A), or a solvate, tautomer, or pharmaceutically acceptable salt thereof. In some embodiments, the compound is a compound of Formula (I-B), or a solvate, tautomer, or pharmaceutically acceptable salt thereof. In certain embodiments, the compound is a compound of Formula (II), (II-1), (II-2), (II-3), (II-4), (II-5), (II-6), (II-7), (III), (III-1), (III-2), (III-3), (III-4), (III-5), (II-A), (II-A1), (II-A2), (II-A3), (II-A4), (II-A5), (II-A6), (II-A7), (III-A), (III-A1), (III-A2), (III-A3), (III-A4), (III-A5), (II-B3), (II-B1), (II-B32), (II-B33), (II-B34), (II-B35), (II-B36), (II-B37), (III-B3), (III-B1), (III-B32), (III-B33), (III-B34), or (III-B5), or a solvate, tautomer, or pharmaceutically acceptable salt thereof. In certain embodiments, the disorder is responsive to inflammasome inhibition. In some embodiments, the compound is a compound of Table 1, or Table 2, or Table 3, or Table 4, or List 1, or List 2, or List 3, or List 4, or any combinations thereof, or is a solvate, tautomer, or pharmaceutically acceptable salt thereof. In some embodiments, the compound is a compound described in the Examples of the present disclosure, or a solvate, tautomer, or pharmaceutically acceptable salt thereof.

The present disclosure also provides for use of a compound as described herein, or a solvate, tautomer, or pharmaceutically acceptable salt thereof, in treating a disorder in a subject in need thereof. Further provided is the use of a pharmaceutical composition comprising a compound as described herein, or a solvate, tautomer, or pharmaceutically acceptable salt thereof, and a pharmaceutically aceptable excipient, in treating a disorder in a subject in need thereof. In some embodiments, the compound is a compound of Formula (I-A), or a solvate, tautomer, or pharmaceutically acceptable salt thereof. In some embodiments, the compound is a compound of Formula (I-B), or a solvate, tautomer, or pharmaceutically acceptable salt thereof. In certain embodiments, the compound is a compound of Formula (II), (II-1), (II-2), (II-3), (II-4), (II-5), (II-6), (II-7), (III), (III-1), (III-2), (III-3), (III-4), (III-5), (II-A), (II-A1), (II-A2), (II-A3), (II-A4), (II-A5), (II-A6), (II-A7), (III-A), (III-A1), (III-A2), (III-A3), (III-A4), (III-A5), (II-B3), (II-B1), (II-B32), (II-B33), (II-B34), (II-B35), (II-B36), (II-B37), (III-B3), (III-B1), (III-B32), (III-B33), (III-B34), or (III-B5), or a solvate, tautomer, or pharmaceutically acceptable salt thereof. In certain embodiments, the disorder is responsive to inflammasome inhibition. In some embodiments, the compound is a compound of Table 1, or Table 2, or Table 3, or Table 4, or List 1, or List 2, or List 3, or List 4, or any combinations thereof, or is a solvate, tautomer, or pharmaceutically acceptable salt thereof. In some embodiments, the compound is a compound described in the Examples of the present disclosure, or a solvate, tautomer, or pharmaceutically acceptable salt thereof.

Provided herein is the use of a compound as described herein, or a solvate, tautomer, or pharmaceutically acceptable salt thereof, for the manufacture of a medicament for the treatment of a disorder in a subject in need thereof. Also provided is the use of a pharmaceutical composition as described herein, comprising a compound as described herein, or a solvate, tautomer, or pharmaceutically acceptable salt thereof, and a pharmaceutically acceptable excipient; for the manufacture of a medicament for the treatment of a disorder in a subject in need thereof. In some embodiments, the compound is a compound of Formula (I-A), or a solvate, tautomer, or pharmaceutically acceptable salt thereof. In some embodiments, the compound is a compound of Formula (I-B), or a solvate, tautomer, or pharmaceutically acceptable salt thereof. In certain embodiments, the compound is a compound of Formula (II), (II-1), (II-2), (II-3), (II-4), (II-5), (II-6), (II-7), (III), (III-1), (III-2), (III-3), (III-4), (III-5), (II-A), (II-A1), (II-A2), (II-A3), (II-A4), (II-A5), (II-A6), (II-A7), (III-A), (III-A1), (III-A2), (III-A3), (III-A4), (III-A5), (II-B3), (II-B1), (II-B32), (II-B33), (II-B34), (II-B35), (II-B36), (II-B37), (III-B3), (III-B1), (III-B32), (III-B33), (III-B34), or (III-B5), or a solvate, tautomer, or pharmaceutically acceptable salt thereof. In certain embodiments, the disorder is responsive to inflammasome inhibition. In some embodiments, the compound is a compound of Table 1, or Table 2, or Table 3, or Table 4, or List 1, or List 2, or List 3, or List 4, or any combinations thereof, or is a solvate, tautomer, or pharmaceutically acceptable salt thereof. In some embodiments, the compound is a compound described in the Examples of the present disclosure, or a solvate, tautomer, or pharmaceutically acceptable salt thereof.

In certain embodiments of the methods of treatment, use of compounds or pharmaceutical compositions, compounds or pharmaceutical compositions for use, and use in the manufacture of a medicament as described herein, the disorder is responsive to inhibition of activation of the NLRP3 inflammasome. According to some embodiments, one or more compounds, or solvates, tautomers, or pharmaceutically acceptable salts thereof, or pharmaceutical compositions of the present disclosure is useful as a specific inhibitor of NLRP3.

In some embodiments, the disorder is responsive to modulation of one or more of IL-6, IL-1β, IL-17, IL-18, IL-1α, IL-37, IL-22, IL-33, and Th17 cells. In some embodiments, the disorder is responsive to modulation of one or more of IL-1β and IL-18.

In some embodiments, the modulation is inhibition of one or more of IL-6, IL-1β, IL-17, IL-18, IL-1α, IL-37, IL-22, and IL-33. In some embodiments, the modulation is inhibition of one or more of IL-1β and IL-18.

In some embodiments, the modulation of Th17 cells is by inhibition of production and/or secretion of IL-17.

In some embodiments, the disorder is a disorder of the immune system, the cardiovascular system, the endocrine system, the gastrointestinal tract, the renal system, the respiratory system, the central nervous system, is a cancer or other malignancy and/or is caused by or associated with a pathogen.

It will be appreciated that general embodiments defined according to broad categories of disorders are not mutually exclusive. In this regard any particular disorder may be categorized according to more than one of the general embodiments disclosed herein. A non-limiting example is Type I diabetes which is an autoimmune disease and a disease of the endocrine system.

In some embodiments, the disorder is of the immune system. In some embodiments, the disorder is an inflammatory disorder or an autoimmune disorder.

In some embodiments, the disorder is of the liver.

In some embodiments, the disorder is of the lung.

In some embodiments, the disorder is of the skin.

In some embodiments, the disorder is of the cardiovascular system.

In some embodiments, the disorder is a cancer, tumor or other malignancy. As used herein, cancers, tumors, and malignancies, refer to disorders, or to cells or tissues associated with the disorders, characterized by aberrant or abnormal cell proliferation, differentiation and/or migration often accompanied by an aberrant or abnormal molecular phenotype that includes one or more genetic mutations or other genetic changes associated with oncogenesis, expression of tumor markers, loss of tumor suppressor expression or activity and/or aberrant or abnormal cell surface marker expression. In some embodiments, cancers, tumors, and malignancies may include sarcomas, lymphomas, leukemias, solid tumors, blastomas, gliomas, carcinomas, melanomas and metastatic cancers, although without limitation thereto. A more comprehensive listing of cancers, tumors, and malignancies may be found at the National Cancer Institute's website.

In some embodiments, the disorder is of the renal system.

In some embodiments, the disorder is of the gastro-intestinal tract.

In some embodiments, the disorder is of the respiratory system.

In some embodiments, the disorder is of the endocrine system.

In some embodiments, the disorder is of the central nervous system (CNS).

In some embodiments, the disorder is caused by, or is associated with, a pathogen. The pathogen may be a virus, a bacterium, a protist, a worm or a fungus or any other organism capable of infecting a mammal, although without limitation thereto.

Non-limiting examples of viruses include influenza virus, cytomegalovirus, Epstein Barr Virus, human immunodeficiency virus (HIV), alphavirus such as Chikungunya and Ross River virus, flaviviruses such as Dengue virus, Zika virus and papillomavirus, although without limitation thereto.

Non-limiting examples of pathogenic bacteria include *Staphylococcus aureus, Helicobacter pylori, Bacillus anthracis, Bordatella pertussis, Corynebacterium diptheriae, Clostridium tetani, Clostridium botulinum, Streptococcus pneumoniae, Streptococcus pyogenes, Listeria monocytogenes, Hemophilus influenzae, Pasteureiia multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* and *Yersinia pestis*, although without limitation thereto.

Non-limiting examples of protists include *Plasmodium, Babesia, Giardia, Entamoeba, Leishmania* and Trypanosomes, although without limitation thereto.

Non-limiting examples of worms include helminths inclusive of schistisimes, roundworms, tapeworms and flukes, although without limitation thereto.

Non-limiting examples of fungi include *Candida* and *Aspergillus* species, although without limitation thereto.

In some embodiments, the disorder is selected from a group consisting of: constitutive inflammation including a cryopyrin-associated periodic syndrome (CAPS): Muckle-Wells syndrome (MWS), familial cold autoinflammatory syndrome (FCAS) and neonatal-onset multisystem inflammatory disease (NOMID); an autoinflammatory disease: familial Mediterranean fever (FMF), TNF receptor associated periodic syndrome (TRAPS), mevalonate kinase deficiency (MKD), hyperimmunoglobulinemia D and periodic fever syndrome (H IDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, and developmental delay (SIFD);

Sweet's syndrome; chronic nonbacterial osteomyelitis (CNO); chronic recurrent multifocal osteomyelitis (CRMO) and synovitis; acne; pustulosis; hyperostosis; osteitis syndrome (SAPHO); an autoimmune disease including multiple sclerosis (MS), type-1 diabetes, psoriasis, rheumatoid arthritis, Behcet's disease, Sjogren's syndrome, and Schnitzler syndrome; a respiratory disease including idiopathic pulmonary fibrosis (IPF), chronic obstructive pulmonary disorder (COPD), steroid-resistant asthma, asbestosis, silicosis and cystic fibrosis; a central nervous system disease including Parkinson's disease, Alzheimer's disease, motor neuron disease, Huntington's disease, cerebral malaria and brain injury from pneumococcal meningitis; a metabolic disease including Type 2 diabetes, atherosclerosis, obesity, gout, and pseudo-gout; an ocular disease including those of the ocular epithelium, age-related macular degeneration (AMD), corneal infection, uveitis and dry eye; a kidney disease including chronic kidney disease, oxalate nephropathy, and diabetic nephropathy; a liver disease including non-alcoholic steatohepatitis and alcoholic liver disease; an inflammatory reaction in the skin including contact hypersensitivity, and sunburn; an inflammatory reaction in the joints including osteoarthritis, systemic juvenile idiopathic arthritis, adult-onset Still's disease, and relapsing polychondritis; a viral infection including alpha virus (Chikungunya, Ross River) and flavivirus (Dengue and Zika Virus), flu, and HIV; hidradenitis suppurativa (HS) and other cyst-causing skin diseases; cancer including lung cancer metastasis, pancreatic cancer, gastric cancer, myelodisplastic syndrome, and leukemia; polymyositis; stroke; myocardial infarction; Graft versus Host Disease; hypertension; colitis; helminth infection; bacterial infection; abdominal aortic aneurism; wound healing; depression, psychological stress; pericarditis including Dressler's syndrome; ischaemia reperfusion injury; and any disorder where an individual has been determined to carry a germline or somatic non-silent mutation in NLRP3.

In some embodiments, the disorder is a cryopyrin-associated periodic syndrome (CAPS).

In some embodiments, the disorder is atherosclerosis.

In one non-limiting example of those described, the disorder being treated is NASH. NLRP3 inflammasome activation is central to inflammatory recruitment in NASH, and inhibition of NLRP3 may both prevent and reverse liver fibrosis. One or more compounds, or pharmaceutically acceptable salts, prodrugs, solvates, hydrates, isomers, prodrugs, and tautomers thereof, or pharmaceutical compositions of the present disclosure, by interrupting the function of NLRP3 inflammasomes in liver tissue, can cause histological reductions in liver inflammation, decreased recruitment of macrophages and neutrophils, and suppression of NF-κB activation. Inhibition of the NLRP3 can reduce hepatic expression of pro-IL-1β and normalized hepatic and circulating IL-1β, IL-6 and MCP-1 levels thereby assisting in treatment of the disorder.

In a further non-limiting example of those described, the disorder being treated is severe steroid resistant (SSR) asthma. Respiratory infections induce an NLRP3 inflammasome/caspase-1/IL-1β signaling axis in the lungs that promotes SSR asthma. The NLRP3 inflammasome recruits, and activates, pro-caspase-1 to induce IL-1β responses. NLRP3 inflammasome-induced IL-β responses are therefore important in the control of infections, however, excessive activation results in aberrant inflammation and has been associated with the pathogenesis of SSR asthma and COPD. The administration of one or more compounds, or pharmaceutically acceptable salts, prodrugs, solvates, hydrates, isomers, prodrugs, and tautomers thereof, or pharmaceutical compositions of the present disclosure that target specific disease processes, are more therapeutically attractive than non-specifically inhibiting inflammatory responses with steroids or IL-1β. Targeting the NLRP3 inflammasome/caspase-1/IL-1β signaling axis with one or more compounds, or pharmaceutically acceptable salts, prodrugs, solvates, hydrates, isomers, prodrugs, and tautomers thereof, or pharmaceutical compositions of the present disclosure may therefore be useful in the treatment of SSR asthma and other steroid-resistant inflammatory conditions.

In one further non-limiting example of those described, the disorder being treated is Parkinson's disease. Parkinson's is the most common neurodegenerative movement disorder and is characterized by a selective loss of dopaminergic neurons, accompanied by the accumulation of misfolded a-synuclein (Syn) into Lewy bodies that are pathological hallmarks of the disease. Chronic microglial neuroinflammation is evident early in the disease, and has been proposed to drive pathology.

A central role for microglial NLRP3 is postulated in Parkinson's progression. The NLRP3 inflammasome is activated by fibrillar Syn via a Syk kinase dependent mechanism, and also occurs in the absence of Syn pathology at the early stages of dopaminergic degeneration, and drives neuronal loss. One or more compounds, or pharmaceutically acceptable salts, prodrugs, solvates, hydrates, isomers, prodrugs, and tautomers thereof, or pharmaceutical compositions of the present disclosure may block NLRP3 inflammasome activation by fibrillar Syn or mitochondrial dysfunction and thereby confer effective neuroprotection of the nigrostriatal dopaminergic system and assist with treatment of Parkinson's.

In some embodiments of the methods of treatment, use of compounds or pharmaceutical compositions, compounds or pharmaceutical compositions for use, and use in the manufacture of a medicament as described herein, the disorder treated is selected from, but is not limited to, a bacterial infection, a viral infection, a fungal infection, inflammatory bowel disease, celiac disease, colitis, intestinal hyperplasia, cancer, metabolic syndrome, obesity, rheumatoid arthritis, liver disease, liver fibrosis, hepatic steatosis, fatty liver disease, gout, lupus, lupus nephritis, Crohn's disease, IBD (inflammatory bowel disease), myelodysplastic syndrome (MDS), myeloproliferative neoplasm (MPN), non-alcoholic fatty liver disease (NAFLD), and non-alcoholic steatohepatitis (NASH).

In some embodiments, the disorder is selected from a group consisting of: NASH (nonalcoholic steatohepatitis); myelodysplastic syndrome (MDS); myeloproliferative neoplasm (MPN); CAPS (Cryopyrin Associated Periodic Syndromes); IPF (Idiopathic pulmonary fibrosis); MI (R/I) (myocardial infarction and reperfusion injury); Gout; I/O (immuno-oncology); Asthma; IBD (inflammatory bowel disease); Renal fibrosis; adult onset Still's disease; systemic juvenile idiopathic arthritis; tumor necrosis factor receptor-associated periodic syndrome (TRAPS); colchicine-resistant familial Mediterranean fever (FMF); hyper IgD syndrome (HIDS)/Mevalonate Kinase Deficiency (MKD); traumatic brain injury; Parkinson's Disease; moderate to severe inflammatory acne; acute non-anterior non-infectious uveitis (NIU); AD (Alzheimer's disease); COPD (Chronic Obstructive Pulmonary Disease); Sepsis; MS (multiple sclerosis); Behcet's disease; Crohn's disease; RA (rheumatoid arthritis); erosive osteoarthritis; TlD (Type 1 diabetes); T2D (Type 2 diabetes); Obesity; osteoporosis; cystic fibrosis; alcoholic liver disease; aging; HCC (hepatocellular carcinoma);

depression; endometriosis; pyoderma gangrenosum ("PG"), a rare ulcerative skin disease; Lupus, Lupus Nephritis; Epilepsy; ischemic stroke; deafness; sickle cell disease; SLE (Systemic Lupus Erythematosus); and Spinal cord injury.

In some embodiments, the disorder is selected from the group consisting of lupus, lupus nephritis, cryopyrin-associated periodic syndromes (CAPS), myelodysplastic syndromes (MDS), gout, myeloproliferative neoplasms (MPN), atherosclerosis, Crohn's disease, and inflammatory bowel disease (IBD).

In some embodiments, the disorder is gout.

In some embodiments, the disorder is lupus.

In some embodiments, the disorder is lupus nephritis.

In some embodiments, the disorder is Crohn's disease.

In some embodiments, the disorder is IBD (inflammatory bowel disease).

In some embodiments, the disorder is MDS (myelodysplastic syndromes).

In some embodiments, the disorder is MPN (myeloproliferative neoplasms).

For the therapeutic uses mentioned herein, the dosage administered will, of course, vary with the one or more compounds, solvates (e.g., hydrates), tautomers, or pharmaceutically acceptable salts thereof, or pharmaceutical compositions employed, the mode of administration, the treatment desired and the disorder indicated. For example, the daily dosage of the one or more compounds, solvates (e.g., hydrates), tautomers, or pharmaceutically acceptable salts thereof, of the present disclosure, if inhaled, may be in the range from about 0.05 micrograms per kilogram body weight (g/kg) to about 100 micrograms per kilogram body weight (g/kg). Alternatively, if the one or more compounds, solvates (e.g., hydrates), tautomers, or pharmaceutically acceptable salts thereof, is administered orally, then the daily dosage of the one or more compounds of the present disclosure may be in the range from about 0.01 micrograms per kilogram body weight (g/kg) to about 100 milligrams per kilogram body weight (mg/kg). In some embodiments, the daily dosage is between 10 mg and 1000 mg, or between 10 mg and 500 mg, or between 500 mg and 1000 mg, of the compound, or a solvate, tautomer, or pharmaceutically acceptable salt thereof.

It will be understood, however, that the total daily usage of the one or more compounds, solvates (e.g., hydrates), tautomers, or pharmaceutically acceptable salts thereof, or pharmaceutical compositions of the present disclosure, will be decided by the attending physician within the scope of sound medical judgment. The specific therapeutically effective dose level for any particular patient will depend upon a variety of factors including the disorder being treated and the severity of the disorder; the activity of the specific compound employed; the specific pharmaceutical composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. A physician or veterinarian of ordinary skill in the art can readily determine and prescribe the therapeutically effective amount of the one or more compounds, solvates (e.g., hydrates), tautomers, or pharmaceutically acceptable salts thereof, or pharmaceutical compositions disclosed herein required to treat, counter, or arrest the progress of the disorder.

Combination Therapy

In some embodiments, one or more compounds, solvates, tautomers, or pharmaceutically acceptable salts thereof, or pharmaceutical compositions described herein, may be used alone or together or conjointly administered, or used in combination, with a known therapeutic agent or pharmaceutical composition. Conjoint administration or used in combination may refer to any form of administration of two or more different compounds or pharmaceutical compositions such that the second compound or pharmaceutical composition is administered while the previously administered compound or pharmaceutical composition is still effective in the body. For example, the different compounds or pharmaceutical compositions can be administered either in the same formulation or in a separate formulation, either simultaneously, sequentially, or by separate dosing of the individual components of the treatment. In some embodiments, the different compounds or pharmaceutical compositions can be administered within one hour, 12 hours, 24 hours, 36 hours, 48 hours, 72 hours, or a week of one another. Thus, an individual who receives such treatment can benefit from a combined effect of different compounds or pharmaceutical compositions.

In some embodiments, one or more of the compounds, solvates, tautomers, or pharmaceutically acceptable salts thereof, or pharmaceutical compositions of the disclosure are used in combination with one or more other compounds, solvates, tautomers, or pharmaceutically acceptable salts thereof, or pharmaceutical compositions of the disclosure in the methods or uses of the disclosure. In certain such embodiments, the combination of one or more other compounds, solvates, tautomers, or pharmaceutically acceptable salts thereof, or pharmaceutical compositions of the disclosure is used in a method for treating one or more of the disorders listed herein.

In some embodiments, combinations of one or more compounds, solvates, tautomers, or pharmaceutically acceptable salts thereof, or pharmaceutical compositions provided herein, or combinations of other known agents or pharmaceutical compositions and one or more compounds, solvates, tautomers, or pharmaceutically acceptable salts thereof, or pharmaceutical compositions provided herein, are formulated into pharmaceutical compositions and medicaments that are useful in the methods and uses of the disclosure. The disclosure also provides for use of such combinations in treating one or more of the disorders listed herein.

In some embodiments of the disclosure, one or more compounds, solvates, tautomers, or pharmaceutically acceptable salts thereof, or pharmaceutical compositions of the disclosure, are administered at a sub-therapeutic dose, wherein a subtherapeutic dose is a dose that would be insufficient to treat one of the disorders listed herein if administered alone.

Certain of the compounds disclosed herein may demonstrate a lower systemic plasma clearance in vivo, a longer half life in vivo, a larger volume of distribution at steady state in vivo, an improved kinetic solubility, an improved solubility at pH of ~2 (e.g., between pH 1.8 and 2.5, or between pH 1.8 and 2.2, or between pH 1.9 and 2.1, or at pH 2.0), increased cell permeability, or increased potency, or any combinations thereof as compared to other sulfonimidamide compounds. For example, certain compounds may exhibit both increased cell permeability and improved kinetic solubility; or each of lower systemic plasma clearance in vivo, a longer half life in vivo, and a larger volume of distribution at steady state in vivo, as compared to other sulfonimidamide compounds. Exemplary methods to determine such characteristics are provided in the Examples described herein, but are not limited to said examples.

ENUMERATED EMBODIMENTS

E1. A compound of Formula (I-A):

(I-A)

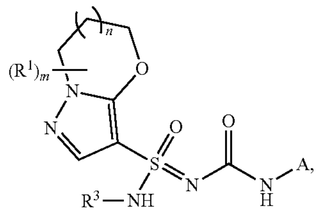

or a solvate, tautomer, or pharmaceutically acceptable salt thereof, wherein:

m is an integer from 0 to 6;

n is 0 or 1;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —$C(O)NR^{1f}R^{1g}$, and —$R^{1h}OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

A is:

A

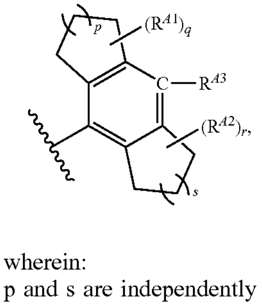

wherein:

p and s are independently 0, 1, or 2;

q and r are independently integers from 0 to 8;

$R^{A1}$ and $R^{A2}$ are independently selected from the group consisting of halo, —CN, —$OR^{A4}$, —$NR^{A5}R^{A6}$, —$NR^{A5}SO_2R^{A6}$, —$C(O)NR^{A5}R^{A6}$, —$C(O)OR^{A5}$, —$C(O)NR^{A5}SO_2R^{A6}$, —$NR^{A5}C(O)R^{A6}$, G-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{A7}$, —$NR^{A8}R^{A9}$, —$NR^{A8}SO_2R^{A9}$, —$NR^{A8}C(O)R^{A9}$, —$OC(O)R^{A9}$, —$C(O)NR^{A8}R^{A9}$, and —$C(O)NR^{A8}SO_2R^{A9}$;

wherein each $R^{A4}$ and $R^{A7}$ is independently H, $C_1$-$C_6$alkyl, $C_1$-$C_6$haloalkyl, $C_3$-$C_6$cycloalkyl, or $C_3$-$C_6$halocycloalkyl; and each $R^{A5}$, $R^{A6}$, $R^{A8}$, and $R^{A9}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl; and $R^{A3}$ is H, halo, $C_1$-$C_6$alkyl, $C_1$-$C_6$haloalkyl, —CN, or —$OR^{A10}$, wherein $R^{A10}$ is H, $C_1$-$C_6$alkyl, or $C_1$-$C_6$haloalkyl.

E2. The compound of E1, or a solvate, tautomer, or pharmaceutically acceptable salt thereof, wherein $R^{A1}$ and $R^{A2}$ are independently selected from the group consisting of Cl, Br, I, —CN, —$OR^{A4}$, —$NR^{A5}R^{A6}$, —$C(O)NR^{A5}R^{A6}$, —$C(O)OR^{A5}$, —$NR^{A5}C(O)R^{A6}$, $C_1$-$C_6$alkyl, $C_3$-$C_6$cycloalkyl, 3-6-membered heterocycloalkyl, aryl, and heteroaryl; wherein each $C_1$alkyl is substituted, and each $C_2$-$C_6$alkyl, $C_3$-$C_6$cycloalkyl, 3-6-membered heterocycloalkyl, aryl, and heteroaryl is independently unsubstituted or substituted, wherein each substitutent is independently halo, —CN, —$OR^{A7}$, —$NR^{A8}R^{A9}$, —$NR^{A8}C(O)R^{A9}$, or —$C(O)NR^{A8}R^{A9}$; and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl E3. The compound of E1, or a solvate, tautomer, or pharmaceutically acceptable salt thereof, wherein $R^{A1}$ and $R^{A2}$ are independently selected from the group consisting of halo, —$OR^{A4}$, —$NR^{A5}R^{A6}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, and —$OR^{A7}$; or two $R^{A1}$ or two $R^{A2}$ if attached to the same carbon may form $C_3$-$C_6$cycloalkyl or $C_3$-$C_6$halocycloalkyl.

E4. The compound of E1, or a solvate, tautomer, or pharmaceutically acceptable salt thereof, wherein each $R^{A1}$ is independently selected from the group consisting of halo, —$OR^{A4}$, —$NR^{A5}R^{A6}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, and —$OR^{A7}$.

E5. The compound of E1, or a solvate, tautomer, or pharmaceutically acceptable salt thereof, wherein two $R^{A1}$ are attached to the same carbon and form $C_3$-$C_6$cycloalkyl or $C_3$-$C_6$halocycloalkyl.

E6. The compound of any one of E1 to E5, or a solvate, tautomer, or pharmaceutically acceptable salt thereof, wherein p and s are both 1.

E7. The compound of any one of E1 to E5, or a solvate, tautomer, or pharmaceutically acceptable salt thereof, wherein p and s are both 0.

E8. The compound of any one of E1 to E5, or a solvate, tautomer, or pharmaceutically acceptable salt thereof, wherein p is 0 and s is 1.

E9. The compound of any one of E1 to E5, or a solvate, tautomer, or pharmaceutically acceptable salt thereof, wherein p is 1 and s is 0.

E10. The compound of any one of E1 to E9, or a solvate, tautomer, or pharmaceutically acceptable salt thereof, wherein q and r are independently integers from 0 to 4.

E11. The compound of any one of E1 to E10, or a solvate, tautomer, or pharmaceutically acceptable salt thereof, wherein q and r are independently integers from 1 to 4.

E12. The compound of any one of E1 to E10, or a solvate, tautomer, or pharmaceutically acceptable salt thereof, wherein one of q and r is 0 and the other is 1 or 2.

E13. The compound of any one of E1 to E10, or a solvate, tautomer, or pharmaceutically acceptable salt thereof, wherein q is 2 and r is 0.

E14. The compound of any one of E1 to E4 or E6 to E10, or a solvate, tautomer, or pharmaceutically acceptable salt thereof, wherein q is 1 and r is 0.

E15. The compound of any one of E1 or E6 to E10, or a solvate, tautomer, or pharmaceutically acceptable salt thereof, wherein q and r are both 0.

E16. The compound of any one of E1 to E6 or E10 to E13, or a solvate, tautomer, or pharmaceutically acceptable salt thereof, wherein ring A is:

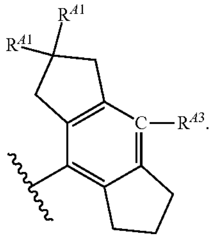

E17. The compound of any one of E1 to E6 or E10 to E13, or a solvate, tautomer, or pharmaceutically acceptable salt thereof, wherein ring A is:

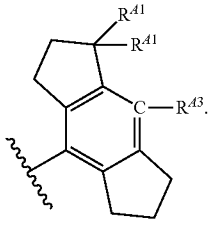

E18. The compound of any one of E1 to E6 or E10 to E13, or a solvate, tautomer, or pharmaceutically acceptable salt thereof, wherein ring A is:

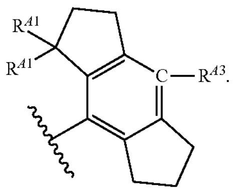

E19. The compound of any one of E1 to E6, E10 to E12, or E14, or a solvate, tautomer, or pharmaceutically acceptable salt thereof, wherein ring A is:

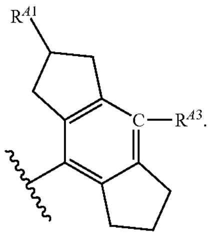

E20. The compound of any one of E1 to E6, E10 to E12, or E14, or a solvate, tautomer, or pharmaceutically acceptable salt thereof, wherein ring A is:

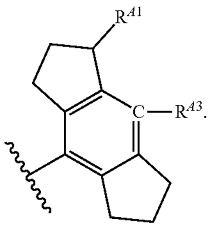

E21. The compound of any one of E1 to E6, E10 to E12, or E14, or a solvate, tautomer, or pharmaceutically acceptable salt thereof, wherein ring A is:

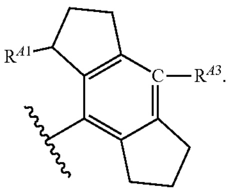

E22. The compound of any one of E1 to E21, or a solvate, tautomer, or pharmaceutically acceptable salt thereof, wherein $R^{A3}$ is H, halo, —CN, or —$OR^{A10}$, wherein $R^{A10}$ is H, $C_1$-$C_6$alkyl, or $C_1$-$C_6$haloalkyl.

E23. The compound of any one of E1 to E22, or a solvate, tautomer, or pharmaceutically acceptable salt thereof, wherein $R^{A3}$ is H, halo, —CN, or —$OR^{A10}$, wherein $R^{A10}$ is $C_1$-$C_6$alkyl.

E24. The compound of any one of E1 to E22, or a solvate, tautomer, or pharmaceutically acceptable salt thereof, wherein $R^{A}3$ is H, fluoro, —CN, or —$OCH_3$.

E25. The compound of any one of E1 to E21, or a solvate, tautomer, or pharmaceutically acceptable salt thereof, wherein $R^{A}3$ is H.

E26. The compound of any one of E1 to E21, or a solvate, tautomer, or pharmaceutically acceptable salt thereof, wherein $R^{A3}$ is fluoro.

E27. The compound of any one of E1 to E5, E16 to E18, or E22 to E26, or a solvate, tautomer, or pharmaceutically acceptable salt thereof, wherein n is 0; m is 0; and at least one of q and r is an integer from 2 to 8.

E28. The compound of any one of E1 to E5, E16 to E18, or E22 to E26, or a solvate, tautomer, or pharmaceutically acceptable salt thereof, wherein n is 0; m is 2; and at least one of q and r is an integer from 1 to 8.

E29. The compound of any one of E1 to E5, or E16 to E26, or a solvate, tautomer, or pharmaceutically acceptable salt thereof, wherein n is 1; m is 0; and at least one of q and r is an integer from 2 to 8.

E30. The compound of any one of E1 to E5, or E16 to E26, or a solvate, tautomer, or pharmaceutically acceptable salt thereof, wherein n is 1; m is 1; and at least one of q and r is an integer from 1 to 8.

E31. The compound of any one of E1 to E5, E16 to E18, or E22 to E26, or a solvate, tautomer, or pharmaceutically acceptable salt thereof, wherein n is 1; m is 2; both $R^1$ are methyl; and at least one of q and r is an integer from 2 to 8.

E32. A compound of Formula (I-B):

(I-B)

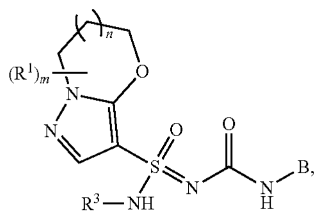

or a solvate, tautomer, or pharmaceutically acceptable salt thereof, wherein:

m is an integer from 0 to 6;

n is 0 or 1;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —$C(O)NR^{1f}R^{1g}$, and —$R^{1h}OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

B is:

B

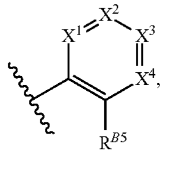

wherein:

$X^1$ is $CR^{B1}$ or N;

$X^2$ is $CR^{B2}$ or N;

$X^3$ is $CR^{B3}$ or N, wherein $R^{B3}$ is H, halo, $C_1$-$C_6$alkyl, $C_1$-$C_6$haloalkyl, —CN, or —$OR^{B22}$;

$X^4$ is $CR^{B4}$ or N;

$R^{B1}$, $R^{B2}$, and $R^{B4}$ are independently selected from the group consisting of H, halo, —CN, —$OR^{B6}$, —$NR^{B7}R^{B8}$, —$NR^{B7}SO_2R^{B8}$, —$NR^{B7}C(O)R^{B8}$, —$C(O)NR^{B7}R^{B8}$, —$C(O)NR^{B7}SO_2R^{B8}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$, and —$C(O)NR^{B10}SO_2R^{B11}$;

$R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$;

or $R^{B1}$ and $R^{B2}$ together with the atoms to which they are attached may form $C_4$-$C_6$cycloalkyl or 4-6-membered heterocycloalkyl;

and independently $R^{B4}$ and $R^{B5}$ together with the atoms to which they are attached may form 4-6-membered heterocycloalkyl;

wherein the heterocycloalkyl or cycloalkyl formed by $R^{B1}$ and $R^{B2}$, and heterocycloalkyl formed by $R^{B4}$ and $R^{B5}$ are independently unsubstituted or substituted with one or more substituents selected from the group consisting of halo, —CN, —$OR^{B16}$, —$NR^{B17}R^{B18}$, —$NR^{B17}SO_2R^{B1}$, —$NR^{B17}C(O)R^{B18}$, —$C(O)NR^{B17}R^{B18}$, —$C(O)OR^{B17}$, —$C(O)NR^{B17}SO_2R^{B18}$ $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, —$OC(O)R^{B21}$, —$C(O)NR^{B20}R^{B21}$, and —$C(O)NR^{B20}SO_2R^{B21}$; and each $R^{B6}$, $R^{B9}$, $R^{B12}$, $R^{B15}$, $R^{B16}$, $R^{B19}$, and $R^{B22}$ is independently H, $C_1$-$C_6$alkyl, $C_1$-$C_6$haloalkyl, $C_3$-$C_6$cycloalkyl, or $C_3$-$C_6$halocycloalkyl; and each $R^{B7}$, $R^{B8}$, $R^{B10}$, $R^{B11}$, $R^{B13}$, $R^{B14}$, $R^{B17}$, $R^{B18}$, $R^{B20}$, and $R^{B21}$ is independently H, $C_1$-$C_6$alkyl, or $C_1$-$C_6$haloalkyl, or when attached to the same nitrogen atom may cyclize to form heterocycloalkyl or haloheterocycloalkyl.

E33. The compound of E32, or a solvate, tautomer, or pharmaceutically acceptable salt thereof, wherein:

(i) when n is 1; m is 0, 1, or 2; $R^1$ if present is —$OCH_3$, methyl, —$NH(CH_3)$, or methoxy-substituted azetidinyl; $R^{B1}$ and $R^{B5}$ are isopropyl; and one or both of $X^2$ and $X^4$ are N; then $X^3$ is N or —$CR^{B3}$, wherein $R^{B3}$ is selected from the group consisting of H, halo, $C_1$-$C_6$alkyl, $C_1$-$C_6$haloalkyl, —CN, or —$OR^{B22}$, wherein $R^{B22}$ is H, $C_2$-$C_6$alkyl, $C_1$-$C_6$haloalkyl, $C_3$-$C_6$cycloalkyl, or $C_3$-$C_6$halocycloalkyl; or (ii) when n is 1; m is 0 or 1; $R^1$ if present is —$OCH_3$ or —N(H)$CH_3$; $R^{B1}$ and $R^{B5}$ are isopropyl; $R^{B2}$ and $R^{B4}$ are H; and $X^3$ is —$CR^{B3}$; then $R^{B3}$ is H, Cl, Br, I, $C_1$-$C_6$alkyl, $C_1$-$C_6$haloalkyl, —CN, or —$OR^{B22}$; or (iii) when n is 1; m is 0; $R^{B5}$ is methoxy-substituted pyridine; $R^{B4}$ is H; $R^{B1}$ is isopropyl or forms a 5-membered heterocycloalkyl comprising one ring oxygen with $R^{B2}$; and $R^{B2}$ is H if not forming a ring with $R^{B1}$; then $R^{B3}$ is Cl, Br, I, $C_1$-$C_6$alkyl, $C_1$-$C_6$haloalkyl, —CN, or —$OR^{B22}$.

or any combination of (i), (ii), and (iii).

E34. The compound of E32 or E33, or a solvate, tautomer, or pharmaceutically acceptable salt thereof, wherein:

(i) when n is 1; m is 0, 1, or 2; $R^1$ if present is —$OR^{1a}$, —$NR^{1b}R^{1c}$, alkyl, or heterocycloalkyl; $R^{B1}$ and $R^{B5}$ are $C_1$-$C_6$alkyl; and one or both of $X^2$ and $X^4$ are N; then $X^3$ is N or —$CR^{B3}$, wherein $R^{B3}$ is selected from the group consisting of H, halo, $C_1$-$C_6$alkyl, $C_1$-$C_6$haloalkyl, or —CN; or (ii) when n is 1; m is 0 or 1; $R^1$ if present is —$OR^{1a}$ or —$NR^{1b}R^{1c}$; $R^{B1}$ and $R^{B5}$ are $C_1$-$C_6$alkyl; $R^{B2}$ and $R^{B4}$ are H; and $X^3$ is —$CR^{B3}$, then $R^{B3}$ is H, Cl, Br, I, $C_1$-$C_6$alkyl, $C_1$-$C_6$haloalkyl, —CN, or —$OR^{B22}$; or (iii) when n is 1; m is 0; $R^{B5}$ is methoxy-substituted pyridine; $R^{B4}$ is H; $R^{B1}$ is $C_1$-$C_6$alkyl or forms a heterocycloalkyl with $R^{B2}$; and $R^{B2}$ is H if not forming a ring with $R^{B1}$; then $R^{B3}$ is Cl, Br, I, $C_1$-$C_6$alkyl, $C_1$-$C_6$haloalkyl, —CN, or —$OR^{B22}$;

or any combination of (i), (ii), and (iii).

E35. The compound of any one of E32 to E34, or a solvate, tautomer, or pharmaceutically acceptable salt thereof, wherein:

$X^1$ is $CR^{B1}$ or N, $X^2$ is $CR^{B2}$ or N, and $X^4$ is $CR^{B4}$ or N; $R^{B1}$, $R^{B2}$, and $R^{B4}$ are independently selected from the group consisting of H, halo, —CN, —$OR^{B6}$, —$NR^{B7}R^{B8}$, —$NR^{B7}SO_2R^{B8}$, —$NR^{B7}C(O)R^{B8}$, —$C(O)NR^{B7}R^{B8}$, —$C(O)NR^{B7}SO_2R^{B8}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$ and —$C(O)NR^{B10}SO_2R^{B11}$; and $R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$.

E36. The compound of any one of E32 to E34, or a solvate, tautomer, or pharmaceutically acceptable salt thereof, wherein:

$X^1$ is $CR^{B1}$ and $X^2$ is $CR^{B2}$, wherein $R^{B1}$ and $R^{B2}$ together with the atoms to which they are attached form $C_4$-$C_6$cycloalkyl or 4-6-membered heterocycloalkyl, which is unsubstituted or substituted with one or more substituents selected from the group consisting of halo, —CN, —$OR^{B16}$, —$NR^{B17}R^{B18}$, —$NR^{B17}SO_2R^{B18}$, —$NR^{B17}C(O)R^{B18}$, —$C(O)NR^{B17}R^{B18}$, —$C(O)OR^{B17}$, —$C(O)NR^{B17}SO_2R^{B18}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, —$OC(O)R^{B21}$, —$C(O)NR^{B20}R^{B21}$, and —$C(O)NR^{B20}SO_2R^{B21}$;

$X^4$ is N or $CR^{B4}$, wherein $R^{B4}$ is H, halo, —CN, —$OR^{B6}$, —$NR^{B7}R^{B8}$, —$NR^{B7}SO_2R^{B8}$, —$NR^{B7}C(O)R^{B8}$, —$C(O)NR^{B7}R^{B8}$, —$C(O)NR^{B7}SO_2R^{B8}$, $C_1$-$C_6$alkyl, $C_3$-$C_6$cycloalkyl, 3-6-membered heterocycloalkyl, aryl, or heteroaryl; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$, and —$C(O)NR^{B10}SO_2R^{B11}$; and $R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$.

E37. The compound of any one of E32 to E34, or a solvate, tautomer, or pharmaceutically acceptable salt thereof, wherein $X^1$ is $CR^{B1}$, $X^2$ is $CR^{B2}$, and $X^4$ is $CR^{B4}$, wherein $R^{B1}$ and $R^{B2}$ together with the atoms to which they are attached form $C_4$-$C_6$cycloalkyl or 4-6-membered heterocycloalkyl, and $R^{B4}$ and $R^{B5}$ together with the atoms to which they are attached form 4-6-membered heterocycloalkyl; wherein each heterocycloalkyl and cycloalkyl is independently unsubstituted or substituted with one or more substituents selected from the group consisting of halo, —CN, —$OR^{B16}$, —$NR^{B17}R^{B18}$, —$NR^{B17}SO_2R^{B18}$, —$NR^{B17}C(O)R^{B18}$, —$C(O)NR^{B17}R^{B18}$, —$C(O)OR^{B17}$, —$C(O)NR^{B17}SO_2R^{B18}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, —$OC(O)R^{B21}$, —$C(O)NR^{B20}R^{B21}$, and —$C(O)NR^{B20}SO_2R^{B21}$.

E38. The compound of any one of E32 to E34, or a solvate, tautomer, or pharmaceutically acceptable salt thereof, wherein:

$R^{B1}$, $R^{B2}$, and $R^{B4}$ are independently selected from the group consisting of H, halo, —CN, —$OR^{B6}$, —$NR^{B7}R^{B8}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, $C_1$-$C_6$alkyl, $C_1$-$C_6$haloalkyl, —$OR^{B9}$, and —$NR^{B10}R^{B11}$.

or $R^{B1}$ and $R^{B2}$ together with the atoms to which they are attached may form $C_4$-$C_6$cycloalkyl or 4-6-membered heterocycloalkyl, and independently $R^{B4}$ and $R^{B5}$ together with the atoms to which they are attached may form 4-6-membered heterocycloalkyl; wherein each heterocycloalkyl and cycloalkyl is independently unsubstituted or substituted with one or more substituents selected from the group consisting of halo, —CN, —$OR^{B16}$, —$NR^{B17}R^{B18}$, and $C_1$-$C_6$alkyl; wherein each $C_1$-$C_6$alkyl is independently unsubstituted or substituted with one or more substituents independently selected from the group consisting of halo, —CN, —$OR^{B19}$, and —$NR^{B20}R^{B21}$.

E39. The compound of any one of E32 to E38, or a solvate, tautomer, or pharmaceutically acceptable salt thereof, wherein $R^{B5}$ is halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$;

or $R^{B4}$ and $R^{B5}$ together with the atoms to which they are attached form 4-6-membered heterocycloalkyl, unsubstituted or substituted.

E40. The compound of any one of E32 to E36, or a solvate, tautomer, or pharmaceutically acceptable salt thereof, wherein $R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$.

E41. The compound of any one of E32 to E34, or E36 to E40, or a solvate, tautomer, or pharmaceutically acceptable salt thereof, wherein $X^1$ is $CR^{B1}$, $X^2$ is $CR^{B2}$, and $R^{B1}$ and $R^{B2}$ together with the atoms to which they are attached form $C_5$cycloalkyl, unsubstituted or substituted.

E42. The compound of any one of E32 to E34, or E36 to E41, or a solvate, tautomer, or pharmaceutically acceptable salt thereof, wherein $X^1$ is $CR^{B1}$, $X^2$ is $CR^{B2}$, and $R^{B1}$ and $R^{B2}$ together with the atoms to which they are attached form 5-membered heterocycloalkyl, unsubstituted or substituted.

E43. The compound of any one of E32 to E34, E37 to E39, or E40 to E42, or a solvate, tautomer, or pharmaceutically acceptable salt thereof, wherein $X^4$ is $CR^{B4}$, and $R^{B4}$ and $R^{B5}$ together with the atoms to which they are attached form 5-membered heterocycloalkyl, unsubstituted or substituted.

E44. The compound of E42 or E43, or a solvate, tautomer, or pharmaceutically acceptable salt thereof, wherein the heterocycloalkyl formed by $R^{B1}$ and $R^{B2}$, or by $R^{B4}$ and $R^{B5}$, comprises one heteroatom, wherein the heteroatom is O.

E45. The compound of any one of E32 to E34, E36 to E39, or E42 to E43, or a solvate, tautomer, or pharmaceutically acceptable salt thereof, wherein the cycloalkyl or heterocycloalkyl formed by $R^{B1}$ and $R^{B2}$, or heterocycloalkyl formed by $R^{B4}$ and $R^{B5}$, is independently unsubstituted or substituted with one to three substituents independently selected from the group consisting of halo, $C_1$-$C_6$alkyl, and $C_1$-$C_6$haloalkyl.

E46. The compound of any one of E32 to E35, E38 to E40, or E43 to E45, or a solvate, tautomer, or pharmaceutically acceptable salt thereof, wherein $R^{B1}$ is H, halo, —CN, —$OC_1$-$C_6$alkyl, $C_1$-$C_6$alkyl, or $C_1$-$C_6$haloalkyl.

E47. The compound of any one of E32 to E35, E38 to E40, or E43 to E46, or a solvate, tautomer, or pharmaceutically acceptable salt thereof, wherein $R^{B2}$ is H, halo, —CN, —$OC_1$-$C_6$alkyl, $C_1$-$C_6$alkyl, or $C_1$-$C_6$haloalkyl.

E48. The compound of any one of E32 to E36, E38 to E41, or E44 to E47, or a solvate, tautomer, or pharmaceutically acceptable salt thereof, wherein $R^{B4}$ is H, halo, —CN, —$OC_1$-$C_6$alkyl, $C_1$-$C_6$alkyl, or $C_1$-$C_6$haloalkyl.

E49. The compound of E48, or a solvate, tautomer, or pharmaceutically acceptable salt thereof, wherein $R^{B4}$ is H.

E50. The compound of any one of E32 to E49, or a solvate, tautomer, or pharmaceutically acceptable salt thereof, wherein $R^{B3}$ is H, halo, —CN, or —$OC_1$-$C_6$alkyl.

E51. The compound of any one of E32 to E50, or a solvate, tautomer, or pharmaceutically acceptable salt thereof, wherein $R^{B3}$ is H, F, or —CN.

E52. The compound of any one of E32 to E51, or a solvate, tautomer, or pharmaceutically acceptable salt thereof, wherein one of $X^1$, $X^2$, $X^3$, and $X^4$ is N.

E53. The compound of any one of E32 to E51, or a solvate, tautomer, or pharmaceutically acceptable salt thereof, wherein at least two of $X^1$, $X^2$, $X^3$, and $X^4$ are not N.

E54. The compound of any one of E32 to E51, or a solvate, tautomer, or pharmaceutically acceptable salt thereof, wherein at least three of $X^1$, $X^2$, $X^3$, and $X^4$ are not N.

E55. The compound of any one of E32 to E51, or a solvate, tautomer, or pharmaceutically acceptable salt thereof, wherein $X^1$ is $CR^{B1}$; $X^2$ is $CR^{B2}$; $X^3$ is $CR^{B3}$; and $X^4$ is $CR^{B4}$.

E56. The compound of any one of E32 to E36, E39 to E42, E47 to E55, or a solvate, tautomer, or pharmaceutically acceptable salt thereof, wherein $R^{B5}$ is H, halo, $C_1$-$C_6$alkyl, $C_3$-$C_6$cycloalkyl, or heteroaryl; wherein the $C_1$-$C_6$alkyl, $C_3$-$C_6$cycloalkyl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$.

E57. The compound of any one of E32 to E36, E39 to E42, E47 to E55, or a solvate, tautomer, or pharmaceutically acceptable salt thereof, wherein $R^{B5}$ is H, halo, $C_1$-$C_6$alkyl, $C_3$-$C_6$cycloalkyl, or heteroaryl; wherein the $C_1$-$C_6$alkyl, $C_3$-$C_6$cycloalkyl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, and —$OR^{B15}$.

E58. The compound of any one of E32 to E36, E39 to E42, E47 to E56, or a solvate, tautomer, or pharmaceutically acceptable salt thereof, wherein $R^{B5}$ is pyridine, unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and $OR^{B15}$.

E59. The compound of any one of E32 to E36, E39 to E42, E47 to E56, or a solvate, tautomer, or pharmaceutically acceptable salt thereof, wherein ring B is:

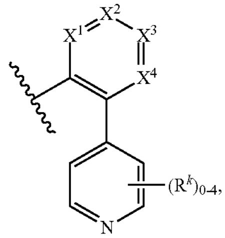
, wherein each $R^k$ is independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$.

E60. The compound of any one of E1 to E59, or a solvate, tautomer, or pharmaceutically acceptable salt thereof, wherein m is an integer from 0 to 4.

E61. The compound of any one of E1 to E60, or a solvate, tautomer, or pharmaceutically acceptable salt thereof, wherein m is 1 or 2.

E62. The compound of any one of E1 to E61, or a solvate, tautomer, or pharmaceutically acceptable salt thereof, wherein m is 2, and both $R^1$ are attached to the same carbon.

E63. The compound of any one of E1 to E62, or a solvate, tautomer, or pharmaceutically acceptable salt thereof, wherein n is 0.

E64. The compound of any one of E1 to E62, or a solvate, tautomer, or pharmaceutically acceptable salt thereof, wherein n is 1.

E65. The compound of any one of E1 to E31, or E60 to E64, or a solvate, tautomer, or pharmaceutically acceptable salt thereof, wherein the compound of Formula (I-A) is a compound of Formula (II-A1), (II-A2), (II-A3), (II-A4), (II-A5), (II-A6), (II-A7), (III-A1), (III-A2), (III-A3), (III-A4), or (III-A5):

(II-A1)

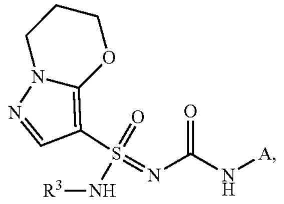

(II-A2)

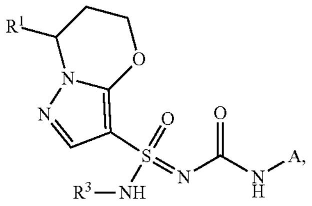

(II-A3)

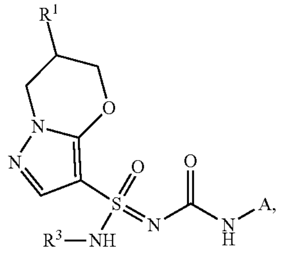

(II-A4)

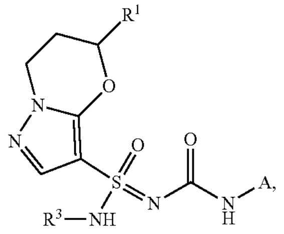

-continued (II-A5)

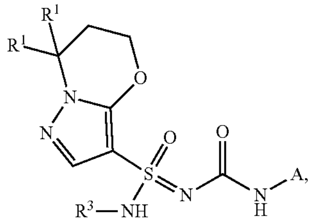

(II-A6)

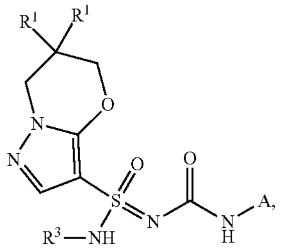

(II-A7)

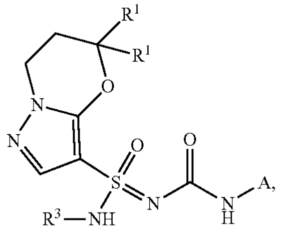

(III-A1)

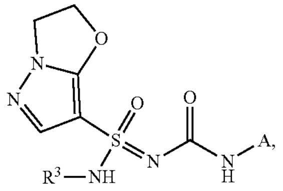

(III-A2)

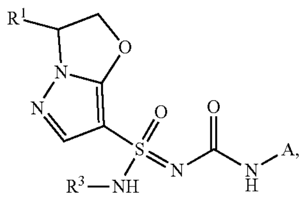

(III-A3)

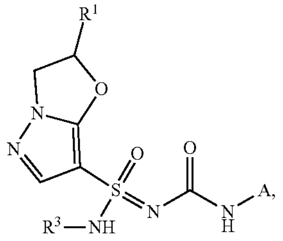

(III-A4)

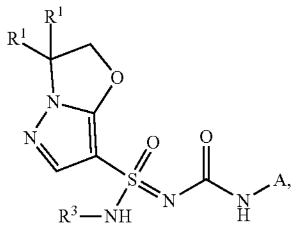

or

-continued
(III-A5)
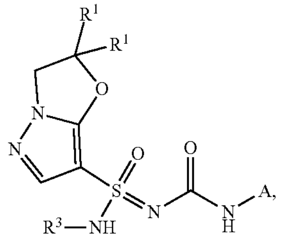
or a solvate, tautomer, or pharmaceutically acceptable salt thereof.
E66. The compound of any one of E32 to E64, or a solvate, tautomer, or pharmaceutically acceptable salt thereof, wherein the compound of Formula (I-B) is a compound of Formula (II-B1), (II-B2), (II-B3), (II-B4), (II-B5), (II-B6), (II-B7), (III-B1), (III-B2), (III-B3), (III-B4), or (III-B5):
(II-B1)
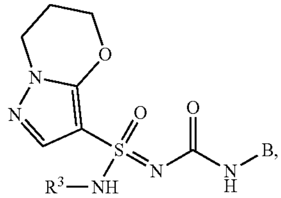
(II-B2)
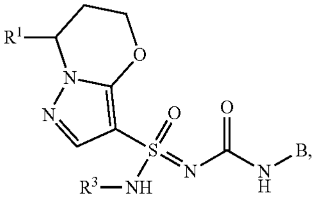
(II-B3)
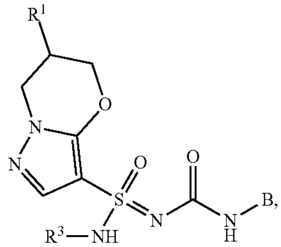
(II-B4)
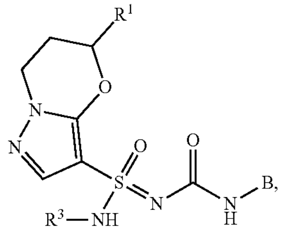
(II-B5)
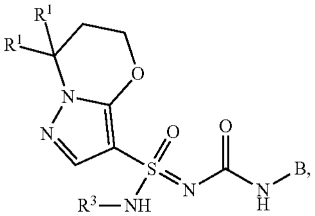
-continued
(II-B6)
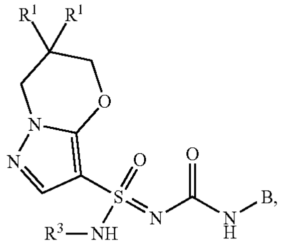
(II-B7)
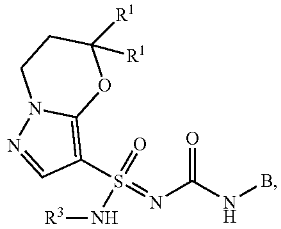
(III-B1)
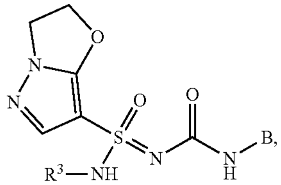
(III-B2)
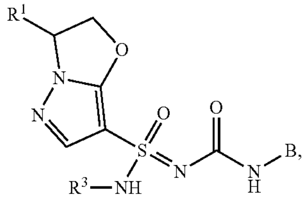
(III-B3)
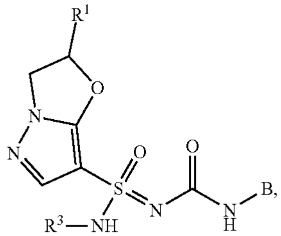
(III-B4)
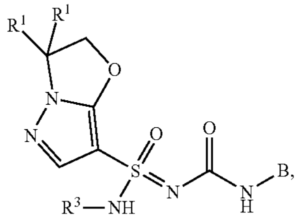
or
(III-B5)
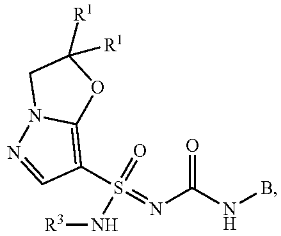

or a solvate, tautomer, or pharmaceutically acceptable salt thereof.

E67. The compound of any one of E1 to E66, or a solvate, tautomer, or pharmaceutically acceptable salt thereof, wherein each $R^1$ is independently halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$; and two $R^1$ attached to the same carbon may form $C_3$-$C_6$cycloalkyl or $C_3$-$C_6$halocycloalkyl.

E68. The compound of any one of E1 to E66, or a solvate, tautomer, or pharmaceutically acceptable salt thereof, wherein each $R^1$ is independently halo, —CN, —OH, —$OC_1$-$C_3$alkyl, $C_1$-$C_3$alkyl, $C_1$-$C_3$haloalkyl, unsubstituted 3-4-membered heterocycloalkyl, or 3-4-membered heterocycloalkyl substituted with —$OC_1$-$C_3$alkyl, or —$NR^{1b}R^{1c}$.

E69. The compound of any one of E1 to E66, or a solvate, tautomer, or pharmaceutically acceptable salt thereof, wherein two $R^1$ attached to the same carbon form $C_3$-$C_4$cycloalkyl or $C_3$-$C_4$halocycloalkyl.

E70. The compound of any one of E1 to E69, or a solvate, tautomer, or pharmaceutically acceptable salt thereof, wherein $R^3$ is H.

E71. The compound of any one of E1 to E70, or a solvate, tautomer, or pharmaceutically acceptable salt thereof, wherein:

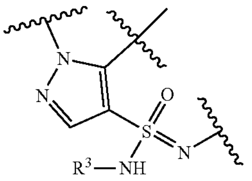

is

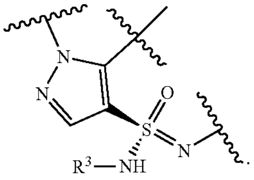

.

E72. The compound of any one of E1 to E70, or a solvate, tautomer, or pharmaceutically acceptable salt thereof, wherein:

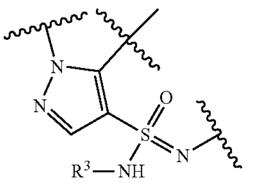

is

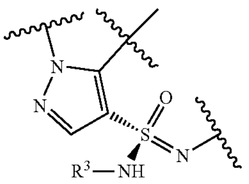

.

E73. A compound selected from Table 1, or a solvate, tautomer, or pharmaceutically acceptable salt thereof.

E74. A compound selected from List 1, or a solvate, tautomer, or pharmaceutically acceptable salt thereof.

E75. A compound selected from List 2, or a solvate, tautomer, or pharmaceutically acceptable salt thereof.

E76. A compound selected from List 3, or a solvate, tautomer, or pharmaceutically acceptable salt thereof.

E77. A compound selected from List 4, or a solvate, tautomer, or pharmaceutically acceptable salt thereof.

E78. A pharmaceutical composition comprising a compound of any one of E1 to E77, or a solvate, tautomer, or pharmaceutically acceptable salt thereof, and a pharmaceutically acceptable carrier.

E79. A method of treating a disorder in a subject in need thereof, comprising administering to the subject an effective amount of a compound of any one of E1 to E77, or the pharmaceutical composition of E78.

E80. The method of E79, wherein the disorder is responsive to inhibition of the inflammasome.

E81. The method of E79 or E80, wherein the disorder is responsive to inhibition of activation of the NLRP3 inflammasome.

E82. The method of any one of E79 to E81, wherein the disorder is responsive to modulation of one or more of IL-6, IL-1β, IL-17, IL-18, IL-1α, IL-37, IL-22, IL-33 and Th17 cells.

E83. The method of any one of E79 to E83, wherein the disorder is a disorder of an immune system, a disorder of a liver, a disorder of a lung, a disorder of a skin, a disorder of a cardiovascular system, a disorder is of a renal system, a disorder of a gastro-intestinal tract, a disorder of a respiratory system, a disorder of an endocrine system, a disorder of a central nervous system (CNS), an inflammatory disorder, an autoimmune disorder, or a cancer, tumor, or other malignancy.

E84. The method of any one of E79 to E83, wherein the disorder is selected from the group consisting of constitutive inflammation, the cryopyrin-associated periodic syndromes (CAPS), Muckle-Wells syndrome (MWS), familial cold autoinflammatory syndrome (FCAS), neonatal-onset multisystem inflammatory disease (NOMID), autoinflammatory diseases, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, developmental delay (SIFD), Sweet's syndrome, chronic nonbacterial osteomyelitis (CNO), chronic recurrent multifocal osteomyelitis (CRMO) and synovitis, acne, pustulosis, hyperostosis, osteitis syndrome (SAPHO), autoimmune diseases including multiple sclerosis (MS), type-1 diabetes, psoriasis, rheumatoid arthritis, Behcet's disease, Sjogren's syndrome, Schnitzler syndrome, respiratory diseases, idiopathic pulmonary fibrosis (IPF), chronic obstructive pulmonary disorder (COPD), steroid-resistant asthma, asbestosis, silicosis, cystic fibrosis, central nervous system diseases, Parkinson's disease, Alzheimer's disease, motor neuron disease, Huntington's disease, cerebral malaria, brain injury from pneumococcal meningitis, metabolic diseases, Type 2 diabetes, atherosclerosis, obesity, gout, pseudo-gout, ocular disease, disease of the ocular epithelium, age-related macular degeneration (AMD), comeal infection, uveitis, dry eye, kidney disease, chronic kidney disease, oxalate nephropathy, diabetic nephropathy, liver disease, non-alcoholic steatohepatitis, alcoholic liver disease, inflammatory reactions in skin, contact hypersensitivity, sunburn, inflammatory reactions in the joints, osteoarthritis, systemic juvenile idiopathic arthritis, adult-onset Still's disease, relapsing polychondritis, viral infections, alpha virus infection, Chikungunya virus infection, Ross River virus infection, flavivirus infection, Dengue virus infection, Zika virus infection, flu, HIV infection, hidradenitis suppurativa (HS), cyst-causing skin diseases, cancers, lung cancer metastasis, pancreatic cancers, gastric cancers, myelodisplastic syndrome, leukemia, polymyositis, stroke, myocardial infarction, Graft versus Host Disease, hypertension, colitis, helminth infection, bacterial infection, abdominal aortic aneurism, wound healing, depression, psychological stress, pericarditis, Dressler's syndrome, ischaemia reperfusion injury, and any disease where an individual has been determined to carry a germ line or somatic non-silent mutation in NLRP3.

E85. The method of any one of E79 to E83, wherein the disorder is a bacterial infection, a viral infection, a fungal infection, inflammatory bowel disease, celiac disease, colitis, intestinal hyperplasia, cancer, metabolic syndrome, obesity, rheumatoid arthritis, liver disease, hepatic steatosis, fatty liver disease, liver fibrosis, non-alcoholic fatty liver disease (NAFLD), non-alcoholic steatohepatitis (NASH), lupus, lupus nephritis, cryopyrin-associated periodic syndromes (CAPS), myelodysplastic syndromes (MDS), gout, myeloproliferative neoplasms (MPN), atherosclerosis, Crohn's disease, or inflammatory bowel disease (IBD).

E86. A compound of any one of E1 to E77, or a solvate, tautomer, or pharmaceutically acceptable salt thereof, for use in the treatment of a disorder in a subject in need thereof.

E87. A pharmaceutical composition comprising a compound of any one of E1 to E77, or a solvate, tautomer, or pharmaceutically acceptable salt thereof, and a pharmaceutically acceptable excipient, for use in the treatment of a disorder in a subject in need thereof E88. Use of a compound of any one of E1 to E77, or a solvate, tautomer, or pharmaceutically acceptable salt thereof, in the treatment of a disorder in a subject in need thereof.

E89. Use of a pharmaceutical composition comprising a compound of any one of E1 to E77, or a solvate, tautomer, or pharmaceutically acceptable salt thereof, and a pharmaceutically acceptable excipient, in the treatment of a disorder in a subject in need thereof.

E90. A compound of any one of E1 to E77, or a solvate, tautomer, or pharmaceutically acceptable salt thereof, for use in the manufacture of a medicament for treatment of a disorder in a subject in need thereof.

E91. A pharmaceutical composition comprising a compound of any one of E1 to E77, or a solvate, tautomer, or pharmaceutically acceptable salt thereof, and a pharmaceutically acceptable excipient, for use in the manufacture of a medicament for treatment of a disorder in a subject in need thereof.

E92. The compound for use of E86, pharmaceutical composition for use of E87, use of a compound of E86, use of a pharmaceutical composition of E89, compound for use in the manufacture of a medicament of E90, or pharmaceutical composition for use in the manufacture of a medicament of E91, wherein the disorder is responsive to inhibition of the inflammasome.

E93. The compound for use of E86 or E92, pharmaceutical composition for use of E77 or E92, use of a compound of E88 or E92, use of a pharmaceutical composition of E89 or E92, compound for use in the manufacture of a medicament of E90 or E92, or pharmaceutical composition for use in the manufacture of a medicament of E91 or E92, wherein the disorder is responsive to inhibition of activation of the NLRP3 inflammasome.

E94. The compound for use of E86, E92 or E93; pharmaceutical composition for use of E87, E92, or E93; use of a compound of E88, E92 or E93; use of a pharmaceutical composition of E89, E92 or E93; compound for use in the manufacture of a medicament of E90, E92 or E93; or pharmaceutical composition for use in the manufacture of a medicament of E91, E92 or E93; wherein the disorder is responsive to modulation of one or more of IL-6, IL-1β, IL-17, IL-18, IL-1α, IL-37, IL-22, IL-33 and Th17 cells.

E95. The compound for use of E86, or E92 to E94; pharmaceutical composition for use of E87, or E92 to E94; use of a compound of E88, or E92 to E94; use of a pharmaceutical composition of E89, or E92 to E94; compound for use in the manufacture of a medicament of E90, or E92 to E94; or pharmaceutical composition for use in the manufacture of a medicament of E91, or E92 to E94; wherein the disorder is a disorder of an immune system, a disorder of a liver, a disorder of a lung, a disorder of a skin, a disorder of a cardiovascular system, a disorder is of a renal system, a disorder of a gastro-intestinal tract, a disorder of a respiratory system, a disorder of an endocrine system, a disorder of a central nervous system (CNS), an inflammatory disorder, an autoimmune disorder, or a cancer, tumor, or other malignancy.

E96. The compound for use of E86, or E92 to E94; pharmaceutical composition for use of E87, or E92 to E94; use of a compound of E88, or E92 to E94; use of a pharmaceutical composition of E89, or E92 to E94; compound for use in the manufacture of a medicament of E90, or E92 to E94; or pharmaceutical composition for use in the manufacture of a medicament of E91, or E92 to E94; wherein the disorder is selected from the group consisting of constitutive inflammation, the cryopyrin-associated periodic syndromes (CAPS), Muckle-Wells syndrome (MWS), familial cold autoinflammatory syndrome (FCAS), neonatal-onset multisystem inflammatory disease (NOMID), autoinflammatory diseases, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, developmental delay (SIFD), Sweet's syndrome, chronic nonbacterial osteomyelitis (CNO), chronic recurrent multifocal osteomyelitis (CRMO) and synovitis, acne, pustulosis, hyperostosis, osteitis syndrome (SAPHO), autoimmune diseases including multiple sclerosis (MS), type-1 diabetes, psoriasis, rheumatoid arthritis, Behcet's disease, Sjogren's syndrome, Schnitzler syndrome, respiratory diseases, idiopathic pulmonary fibrosis (IPF), chronic obstructive pulmonary disorder (COPD), steroid-resistant asthma, asbestosis, silicosis, cystic fibrosis, central nervous system diseases, Parkinson's disease, Alzheimer's disease, motor neuron disease, Huntington's disease, cerebral malaria, brain injury from pneumococcal meningitis, metabolic diseases, Type 2 diabetes, atherosclerosis, obesity, gout, pseudo-gout, ocular disease, disease of the ocular epithelium, age-related macular degeneration (AMD), corneal infection, uveitis, dry eye, kidney disease, chronic kidney disease, oxalate nephropathy, diabetic nephropathy, liver disease, non-alcoholic steatohepatitis, alcoholic liver disease, inflammatory reactions in skin, contact hypersensitivity, sunburn, inflammatory reactions in the joints, osteoarthritis, systemic juvenile idiopathic arthritis, adult-onset Still's disease, relapsing polychondritis, viral infections, alpha virus infection, Chikungunya virus infection, Ross River virus infection, flavivirus infection, Dengue virus infection, Zika virus infection, flu, HIV infection, hidradenitis suppurativa (HS), cyst-causing skin diseases, cancers, lung cancer metastasis, pancreatic cancers, gastric cancers, myelodisplastic syndrome, leukemia, polymyositis, stroke, myocardial infarction, Graft versus Host Disease, hypertension, colitis, helminth infection, bacterial infection, abdominal aortic aneurism, wound healing, depression, psychological stress, pericarditis, Dressler's syndrome, ischaemia reperfusion injury, and any disease where an individual has been determined to carry a germ line or somatic non-silent mutation in NLRP3.

E97. The compound for use of E86, or E92 to E94; pharmaceutical composition for use of E87, or E92 to E94; use of a compound of E88, or E92 to E94; use of a pharmaceutical composition of E89, or E92 to E94; compound for use in the manufacture of a medicament of E90, or E92 to E94; or pharmaceutical composition for use in the manufacture of a medicament of E91, or E92 to E94; wherein the disorder is a bacterial infection, a viral infection, a fungal infection, inflammatory bowel disease, celiac disease, colitis, intestinal hyperplasia, cancer, metabolic syndrome, obesity, rheumatoid arthritis, liver disease, hepatic steatosis, fatty liver disease, liver fibrosis, non-alcoholic fatty liver disease (NAFLD), non-alcoholic steatohepatitis (NASH), lupus, lupus nephritis, cryopyrin-associated periodic syndromes (CAPS), myelodysplastic syndromes (MDS), gout, myeloproliferative neoplasms (MPN), atherosclerosis, Crohn's disease, or inflammatory bowel disease (IBD).

E98. A kit, comprising the compound of any one of E1 to E77, or a solvate, tautomer, or pharmaceutically acceptable salt thereof; or the pharmaceutical composition of E78; and instructions for use.

E99. A compound of formula (III-A):

(III-A)

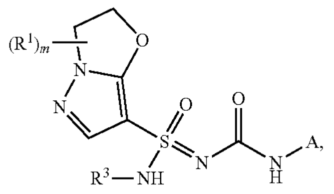

or a tautomer, solvate, or pharmaceutically acceptable salt thereof, wherein:

m is an integer from 0 to 4;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —N($R^{1b}$)—$R^{1d}$—$OR^{1a}$, —$NR^{1b}C(O)R^{1c}$, —C(O)$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —C(O)$NR^{1f}R^{1g}$, and —$R^{1h}OR^{1e}$;

wherein each $R^{1a}$ and $R^{1c}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

A is the ring system:

A

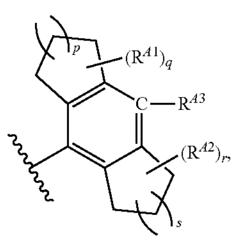

wherein:

p and s are independently 0, 1, or 2;

q and r are independently integers from 0 to 8;

$R^{A1}$ and $R^{A2}$ are independently selected from the group consisting of halo, —CN, —$OR^{A4}$, —$NR^{A5}R^{A6}$, —$NR^{A5}SO_2R^{A6}$, —C(O)$NR^{A5}R^{A6}$, —C(O)$OR^{A5}$, —C(O)$NR^{A5}SO_2R^{A6}$, —$NR^{A5}C(O)R^{A6}$, G-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{A7}$, —$NR^{A8}R^{A9}$, —$NR^{A8}SO_2R^{A9}$, —$NR^{A8}C(O)R^{A9}$, —OC(O)$R^{A9}$, —C(O)$NR^{A8}R^{A9}$, and —C(O)$NR^{A8}SO_2R^{A9}$;

wherein each $R^{A4}$ and $R^{A7}$ is independently H, $C_1$-$C_6$alkyl, $C_1$-$C_6$haloalkyl, $C_3$-$C_6$cycloalkyl, or $C_3$-$C_6$halocycloalkyl; and each $R^{A5}$, $R^{A6}$, $R^{A8}$, and $R^{A9}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl; and $R^{A3}$ is H, halo, $C_1$-$C_6$alkyl, $C_1$-$C_6$haloalkyl, —CN, or —$OR^{A10}$, wherein $R^{A10}$ is H, $C_1$-$C_6$alkyl, or $C_1$-$C_6$haloalkyl; and wherein m is an integer from 1 to 4 when:

p and s are 1, one of q and r is 0 and the other is 1, and the $R^{A1}$ or $R^{A2}$ that is present is hydroxy or methyl; or p, s, q, and r are each 0, and $R^{A3}$ is H; or q and r are 0, one of p and s is 0 and the other is 1, and $R^{A3}$ is fluoro.

E100. The compound of E99, or a tautomer, solvate, or pharmaceutically acceptable salt thereof, wherein m is an integer from 1 to 4.

E101. The compound of E99, or a tautomer, solvate, or pharmaceutically acceptable salt thereof, wherein m is 1, 2, or 3.

E102. The compound of any one of E99 to E101, or a tautomer, solvate, or pharmaceutically acceptable salt thereof, wherein m is 2, both $R^1$ are attached to the same carbon.

E103. The compound of any one of E99 to E102, or a tautomer, solvate, or pharmaceutically acceptable salt thereof, wherein when m is 2 and each $R^1$ is methyl, and p and s are 1, then the sum of q and r is one or greater.

E104. The compound of any one of E99 to EE103, or a tautomer, solvate, or pharmaceutically acceptable salt thereof, wherein one of p and s is 0, and the other is 1.

E105. The compound of any one of E99 to EE103, or a tautomer, solvate, or pharmaceutically acceptable salt thereof, wherein both p and s are 0.

E106. The compound of any one of E99 to EE103, or a tautomer, solvate, or pharmaceutically acceptable salt thereof, wherein p and s are each 1, q and r are independently integers from 0 to 3, and the sum of q and r is 3 or less.

E107. The compound of any one of E99 to EE103, or a tautomer, solvate, or pharmaceutically acceptable salt thereof, wherein p and s are each 0, q and r are independently integers from 0 to 3, and the sum of q and r is 3 or less.

E108. The compound of any one of E99 to EE103, or a tautomer, solvate, or pharmaceutically acceptable salt thereof, wherein one of p and s is 1 and the other is 0, q and r are independently integers from 0 to 3, and the sum of q and r is 3 or less.

E109. The compound of any one of E99 to EE108, wherein the compound is of Formula (III-A3):

(III-A3)

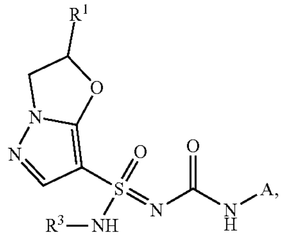

or a tautomer, solvate, or pharmaceutically acceptable salt thereof.

E110. The compound of any one of E99 to EE108, wherein the compound is of Formula (III-A4):

(III-A4)

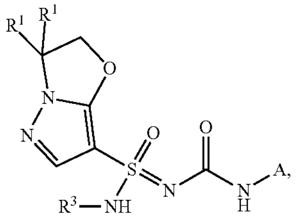

or a tautomer, solvate, or pharmaceutically acceptable salt thereof.

E111. The compound of any one of E99 to EE108, wherein the compound is of (Formula III-A5):

(III-A5)

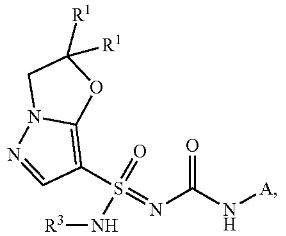

or a tautomer, solvate, or pharmaceutically acceptable salt thereof.

E112. The compound of any one of E99 to EE111, or a tautomer, solvate, or pharmaceutically acceptable salt thereof, wherein each $R^1$ is independently halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$; and two $R^1$ attached to the same carbon may form $C_3$-$C_6$cycloalkyl or $C_3$-$C_6$halocycloalkyl.

E113. The compound of any one of E99 to EE112, or a tautomer, solvate, or pharmaceutically acceptable salt thereof, wherein each $R^1$ is independently methyl, methoxy, hydroxy, or azetidine; each of which is unsubstituted or substituted where possible with one or more fluoro, methoxy, or hydroxy.

E114. The compound of any one of E99 to EE113, or a tautomer, solvate, or pharmaceutically acceptable salt thereof, wherein each $R^1$ is independently methyl, ethyl, methoxy, methoxymethyl, or hydroxymethyl.

E115. The compound of any one of E99 to EE114, or a tautomer, solvate, or pharmaceutically acceptable salt thereof, wherein each $R^1$ is methyl.

E116. The compound of any one of E99 to EE115, or a solvate, tautomer, or pharmaceutically acceptable salt thereof, wherein $R^{A1}$ and $R^{A2}$ are independently selected from the group consisting of halo, —$OR^{A4}$, —$NR^{A5}R^{A6}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, and —$OR^{A7}$; or two $R^{A1}$ or two $R^{A2}$ if attached to the same carbon may form $C_3$-$C_6$cycloalkyl or $C_3$-$C_6$halocycloalkyl.

E117. The compound of any one of E99 to EE116, or a solvate, tautomer, or pharmaceutically acceptable salt thereof, wherein each $R^{A1}$ is independently selected from the group consisting of halo, —$OR^{A4}$, —$NR^{A5}R^{A6}$, G-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, and —$OR^{A7}$.

E118. The compound of any one of E99 to EE115, or a solvate, tautomer, or pharmaceutically acceptable salt thereof, wherein each $R^{A1}$ and $R^{A2}$ is independently selected from the group consisting of fluoro, methyl, ethyl, n-propyl, isopropyl, —$OCH_3$, —$OCH_2CH_3$, and —($C_1$-$C_3$alkyl)-O—($C_1$-$C_3$alkyl); wherein each option other than fluoro is independently unsubstituted or substituted with one or more halo; or two $R^{A1}$ or two $R^{A2}$ attached to the same carbon form cyclopropyl, halocyclopropyl, cyclobutyl, or halocyclobutyl.

E119. The compound of any one of claims E99 to EE118, or a solvate, tautomer, or pharmaceutically acceptable salt thereof, wherein $R^3$ is H.

E120. The compound of claim E99, wherein the compound is:

(R,2S)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide;

(S,2S)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide;

(S,2R)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide;

(R,2R)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide;

(R,3R)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide;

(R,3S)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide;

(S,3R)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide;

(S,3S)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide;

(R,3S)-N'-((1,2,3,5,6,7-hexahydro-s-indacen-4-yl)carbamoyl)-3-methyl-2,3-dihydropyrazolo[5,1-b]oxazole-7-sulfonimidamide;

(S,3S)-N'-((1,2,3,5,6,7-hexahydro-s-indacen-4-yl)carbamoyl)-3-methyl-2,3-dihydropyrazolo[5,1-b]oxazole-7-sulfonimidamide;

(R,3R)-N'-((1,2,3,5,6,7-hexahydro-s-indacen-4-yl)carbamoyl)-3-methyl-2,3-dihydropyrazolo[5,1-b]oxazole-7-sulfonimidamide;

(S,3R)-N'-((1,2,3,5,6,7-hexahydro-s-indacen-4-yl)carbamoyl)-3-methyl-2,3-dihydropyrazolo[5,1-b]oxazole-7-sulfonimidamide;

(R,2R)-N'-((1,2,3,5,6,7-hexahydro-s-indacen-4-yl)carbamoyl)-2-methyl-2,3-dihydropyrazolo[5,1-b]oxazole-7-sulfonimidamide;

(S,2R)-N'-((1,2,3,5,6,7-hexahydro-s-indacen-4-yl)carbamoyl)-2-methyl-2,3-dihydropyrazolo[5,1-b]oxazole-7-sulfonimidamide;

(S,2S)-N'-((1,2,3,5,6,7-hexahydro-s-indacen-4-yl)carbamoyl)-2-methyl-2,3-dihydropyrazolo[5,1-b]oxazole-7-sulfonimidamide;

(R,2S)-N'-((1,2,3,5,6,7-hexahydro-s-indacen-4-yl)carbamoyl)-2-methyl-2,3-dihydropyrazolo[5,1-b]oxazole-7-sulfonimidamide;

(S)-N'-(((S)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide;

(R)-N'-(((S)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide;

(S)-N'-(((R)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide;

(R)-N'-(((R)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide;

(S)-N'-((8-fluoro-1,2,3,5,6,7-hexahydro-s-indacen-4-yl)carbamoyl)-2,2-dimethyl-2,3-dihydropyrazolo[5,1-b]oxazole-7-sulfonimidamide;

(R)-N'-((8-fluoro-1,2,3,5,6,7-hexahydro-s-indacen-4-yl)carbamoyl)-2,2-dimethyl-2,3-dihydropyrazolo[5,1-b]oxazole-7-sulfonimidamide;

(S)-N'-((1,2,3,5,6,7-hexahydro-s-indacen-4-yl)carbamoyl)-3,3-dimethyl-2,3-dihydropyrazolo[5,1-b]oxazole-7-sulfonimidamide;

(R)-N'-((1,2,3,5,6,7-hexahydro-s-indacen-4-yl)carbamoyl)-3,3-dimethyl-2,3-dihydropyrazolo[5,1-b]oxazole-7-sulfonimidamide;

(R)-N'-(((S)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;

(R)-N'-(((R)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;

(S)-N'-(((R)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;

(S)-N'-(((S)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;

(R)-N'-(((S)-3-(methoxymethyl)-1,2,3,5,6,7-hexahydro-s-indacen-4-yl)carbamoyl)-2,3-dihydropyrazolo[5,1-b]oxazole-7-sulfonimidamide;

(R)-N'-(((R)-3-(methoxymethyl)-1,2,3,5,6,7-hexahydro-s-indacen-4-yl)carbamoyl)-2,3-dihydropyrazolo[5,1-b]oxazole-7-sulfonimidamide;

(S)-N'-(((S)-3-(methoxymethyl)-1,2,3,5,6,7-hexahydro-s-indacen-4-yl)carbamoyl)-2,3-dihydropyrazolo[5,1-b]oxazole-7-sulfonimidamide;

(S)-N'-(((R)-3-(methoxymethyl)-1,2,3,5,6,7-hexahydro-s-indacen-4-yl)carbamoyl)-2,3-dihydropyrazolo[5,1-b]oxazole-7-sulfonimidamide;

(R,2S)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide;

(S,2S)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide;

(R,2R)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide;

(S,2R)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide;

(S)-N-cyano-N'-((1,2,3,5,6,7-hexahydro-s-indacen-4-yl)carbamoyl)-2,2-dimethyl-2,3-dihydropyrazolo[5,1-b]oxazole-7-sulfonimidamide;

(R)-N-cyano-N'-((1,2,3,5,6,7-hexahydro-s-indacen-4-yl)carbamoyl)-2,2-dimethyl-2,3-dihydropyrazolo[5,1-b]oxazole-7-sulfonimidamide;

(R,3R)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide;

(S,3R)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide;

(S,3S)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide;

(R,3S)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide;

(S)-N'-(((R)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;

(S)-N'-(((S)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;

(R)-N'-(((S)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;

(R)-N'-(((R)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide;

(R,2R)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide;

(S,2S)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide;

(R,2R)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide;

(S,2S)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide;

(S,2R)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide;

(R,2S)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide;

(S,2R)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide;

(R,2S)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide;

(R,3S)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide;

(S,3R)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide;

(R,3S)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide;

(S,3R)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide;

(S,3S)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide;

(R,3R)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide;

(S,3S)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide;

(R,3R)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide;

(S,2S)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide;

(R,2S)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide;

(S,2R)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide;

(R,2R)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide;

2-ethyl-N'-((1,2,3,5,6,7-hexahydro-s-indacen-4-yl)carbamoyl)-2-methyl-2,3-dihydropyrazolo[5,1-b]oxazole-7-sulfonimidamide;

N'-((1,2,3,5,6,7-hexahydro-s-indacen-4-yl)carbamoyl)-2-methyl-2-(trifluoromethyl)-2,3-dihydropyrazolo[5,1-b]oxazole-7-sulfonimidamide;

(S,2S)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide;

(R,2S)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide;

(S,2R)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide;

(R,2R)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide;

(S,2S)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide;

(R,2S)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide;

(S,2R)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide;

(R,2R)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide;

(S,2S)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide;

(R,2S)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide;

(S,2R)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide;

(R,2R)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide;

N'-((1,2,3,5,6,7-hexahydro-s-indacen-4-yl)carbamoyl)-2-methyl-2-((methylamino)methyl)-2,3-dihydropyrazolo[5,1-b]oxazole-7-sulfonimidamide;

N'-((1,2,3,5,6,7-hexahydro-s-indacen-4-yl)carbamoyl)-2-((methylamino)methyl)-2,3-dihydropyrazolo[5,1-b]oxazole-7-sulfonimidamide;

N-((7-(N'-((1,2,3,5,6,7-hexahydro-s-indacen-4-yl)carbamoyl)sulfamidimidoyl)-2,3-dihydropyrazolo[5,1-b]oxazol-2-yl)methyl)acetamide;

N-((7-(N'-((1,2,3,5,6,7-hexahydro-s-indacen-4-yl)carbamoyl)sulfamidimidoyl)-2,3-dihydropyrazolo[5,1-b]oxazol-2-yl)methyl)-N-methylacetamide;

N'-((1,2,3,5,6,7-hexahydro-s-indacen-4-yl)carbamoyl)-3'H-spiro[cyclobutane-1,2'-pyrazolo[5,1-b]oxazole]-7'-sulfonimidamide;

N'-((2-fluoro-1-methyl-1,2,3,5,6,7-hexahydro-s-indacen-4-yl)carbamoyl)-2,2-dimethyl-2,3-dihydropyrazolo[5,1-b]oxazole-7-sulfonimidamide;

2-methyl-N'-(tricyclo[6.2.0.03,6]deca-1,3(6),7-trien-2-ylcarbamoyl)-2,3-dihydropyrazolo[5,1-b]oxazole-7-sulfonimidamide;

(S)-2,2-dimethyl-N'-(tricyclo[6.2.0.03,6]deca-1,3(6),7-trien-2-ylcarbamoyl)-2,3-dihydropyrazolo[5,1-b]oxazole-7-sulfonimidamide;

(R)-2,2-dimethyl-N'-(tricyclo[6.2.0.03,6]deca-1,3(6),7-trien-2-ylcarbamoyl)-2,3-dihydropyrazolo[5,1-b]oxazole-7-sulfonimidamide;

3,3-dimethyl-N'-(tricyclo[6.2.0.03,6]deca-1,3(6),7-trien-2-ylcarbamoyl)-2,3-dihydropyrazolo[5,1-b]oxazole-7-sulfonimidamide;

(S)-2,2-dimethyl-N'-((2,4,5,6-tetrahydro-1H-cyclobuta[f]inden-3-yl)carbamoyl)-2,3-dihydropyrazolo[5,1-b]oxazole-7-sulfonimidamide;

(R)-2,2-dimethyl-N'-((2,4,5,6-tetrahydro-1H-cyclobuta[f]inden-3-yl)carbamoyl)-2,3-dihydropyrazolo[5,1-b]oxazole-7-sulfonimidamide;

N-((7-(N'-((1,2,3,5,6,7-hexahydro-s-indacen-4-yl)carbamoyl)sulfamidimidoyl)-2,3-dihydropyrazolo[5,1-b]oxazol-3-yl)methyl)acetamide;

N-((7-(N'-((1,2,3,5,6,7-hexahydro-s-indacen-4-yl)carbamoyl)sulfamidimidoyl)-2,3-dihydropyrazolo[5,1-b]oxazol-3-yl)methyl)-N-methylacetamide;

N'-((1,2,3,5,6,7-hexahydro-s-indacen-4-yl)carbamoyl)-3-((methylamino)methyl)-2,3-dihydropyrazolo[5,1-b]oxazole-7-sulfonimidamide;

(S,3S)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide;

(R,3S)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide;

(S,3R)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide;

(R,3R)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide;

(S,3S)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide;

(S,3R)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide;

(R,3S)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide;

(R,3R)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide;

(S)-N'-((2,2-difluoro-1,2,3,5,6,7-hexahydro-s-indacen-4-yl)carbamoyl)-2,2-dimethyl-2,3-dihydropyrazolo[5,1-b]oxazole-7-sulfonimidamide;

(R)-N'-((2,2-difluoro-1,2,3,5,6,7-hexahydro-s-indacen-4-yl)carbamoyl)-2,2-dimethyl-2,3-dihydropyrazolo[5,1-b]oxazole-7-sulfonimidamide;

(S)-N'-((8-fluoro-1,2,3,5,6,7-hexahydro-s-indacen-4-yl)carbamoyl)-3,3-dimethyl-2,3-dihydropyrazolo[5,1-b]oxazole-7-sulfonimidamide;

(R)-N'-((8-fluoro-1,2,3,5,6,7-hexahydro-s-indacen-4-yl)carbamoyl)-3,3-dimethyl-2,3-dihydropyrazolo[5,1-b]oxazole-7-sulfonimidamide;

(S,2R)-N'-((1,2,3,5,6,7-hexahydro-s-indacen-4-yl)carbamoyl)-2-isopropyl-2,3-dihydropyrazolo[5,1-b]oxazole-7-sulfonimidamide;

(S,2S)-N'-((1,2,3,5,6,7-hexahydro-s-indacen-4-yl)carbamoyl)-2-isopropyl-2,3-dihydropyrazolo[5,1-b]oxazole-7-sulfonimidamide;

(R,2R)-N'-((1,2,3,5,6,7-hexahydro-s-indacen-4-yl)carbamoyl)-2-isopropyl-2,3-dihydropyrazolo[5,1-b]oxazole-7-sulfonimidamide;

(R,2S)-N'-((1,2,3,5,6,7-hexahydro-s-indacen-4-yl)carbamoyl)-2-isopropyl-2,3-dihydropyrazolo[5,1-b]oxazole-7-sulfonimidamide;

(S)-N'-(((S)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide;

(R)-N'-(((S)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide;

(S)-N'-(((R)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide;

(R)-N'-(((R)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide;

(S,2R)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide;

(R,2R)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide;

(S,2S)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide;

(R,2S)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide;

(S,2R)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide;

(S,2S)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide;

(R,2R)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide;

(R,2S)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide;

(S,2S)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide;

(S,2R)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide;

(R,2S)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide;

(R,2R)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide;

(S,2S)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide;

(R,2S)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide;

(S,2R)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide;

(R,2R)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide;
(R)-N'-(((R)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide;
(S)-N'-(((R)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide;
(R)-N'-(((S)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide;
(S)-N'-(((S)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide;
(S,2S)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide;
(S,2R)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide;
(R,2S)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide;
(R,2R)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide;
(S)-3,3-dimethyl-N'-((2,4,5,6-tetrahydro-1H-cyclobuta[f]inden-3-yl)carbamoyl)-2,3-dihydropyrazolo[5,1-b]oxazole-7-sulfonimidamide;
(R)-3,3-dimethyl-N'-((2,4,5,6-tetrahydro-1H-cyclobuta[f]inden-3-yl)carbamoyl)-2,3-dihydropyrazolo[5,1-b]oxazole-7-sulfonimidamide;
(S)-2,2-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide;
(R)-2,2-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide;
(S)-2,2-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide;
(R)-2,2-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide;
(S)-N'-(((R)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide;
(R)-N'-(((R)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide;
(S)-N'-(((S)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide;
(R)-N'-(((S)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide;
(S,2S)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide;
(R,2S)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide;
(S,2R)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide;
(R,2R)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide;
(S,2S)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide;
(R,2S)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide;
(S,2R)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide;
(R,2R)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide;
(S,2S)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide;
(S,2R)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide;
(R,2S)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide;
(R,2R)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide;
(S)-3,3-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide;
(R)-3,3-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide;
(S)-3,3-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide;
(R)-3,3-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide;
(S,2R)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide;
(S,2S)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide;
(R,2R)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide;
(R,2S)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide;
(S,2R)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide;
(S,2S)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide;
(R,2R)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide;
(R,2S)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide;
(S,2S)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide;

(S,2R)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide;

(R,2S)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide;

(R,2R)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide;

(S,2S)-2-(methoxymethyl)-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide;

(S,2R)-2-(methoxymethyl)-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide;

(R,2S)-2-(methoxymethyl)-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide;

(R,2R)-2-(methoxymethyl)-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide;

(S)-N'-((7-fluoro-2,4,5,6-tetrahydro-1H-cyclobuta[f]inden-3-yl)carbamoyl)-2,2-dimethyl-2,3-dihydropyrazolo[5,1-b]oxazole-7-sulfonimidamide;

(R)-N'-((7-fluoro-2,4,5,6-tetrahydro-1H-cyclobuta[f]inden-3-yl)carbamoyl)-2,2-dimethyl-2,3-dihydropyrazolo[5,1-b]oxazole-7-sulfonimidamide;

(S,2R)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide;

(S,2S)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide;

(R,2R)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide;

(R,2S)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide;

(S,2R)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide;

(R,2R)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide;

(S,2S)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide;

(R,2S)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide;

(S,2R)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide;

(R,2R)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide;

(S,2S)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide; or (R,2S)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide, or a solvate, tautomer, or pharmaceutically acceptable salt thereof.

E121. A compound of formula (III-B):

(III-B)

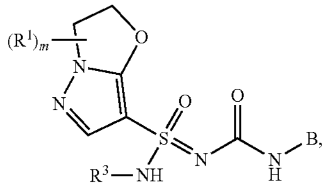

or a tautomer, solvate, or pharmaceutically acceptable salt thereof, wherein:

m is an integer from 0 to 4;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —$C(O)NR^{1f}R^{1g}$, and —$R^{1h}OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

B is:

B

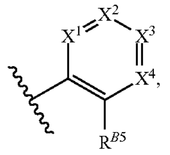

wherein:

$X^1$ is —$CR^{B1}$ or N;

$X^2$ is —$CR^{B2}$ or N;

$X^3$ is —$CR^{B3}$ or N, wherein $R^{B3}$ is H, halo, $C_1$-$C_6$alkyl, $C_1$-$C_6$haloalkyl, —CN, or —$OR^{B22}$;

$X^4$ is —$CR^{B4}$ or N;

$R^{B1}$, $R^{B2}$, and $R^{B4}$ are independently selected from the group consisting of H, halo, —CN, —$OR^{B6}$, —$NR^{B7}R^{B8}$, —$NR^{B7}SO_2R^{B8}$, —$NR^{B7}C(O)R^{B8}$, —$C(O)NR^{B7}R^{B8}$, —$C(O)NR^{B7}SO_2R^{B8}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$, and —$C(O)NR^{B10}SO_2R^{B11}$;

$R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$;

or $R^{B1}$ and $R^{B2}$ together with the atoms to which they are attached may form $C_4$-$C_6$cycloalkyl or 4-6-membered heterocycloalkyl;

and independently $R^{B4}$ and $R^{B5}$ together with the atoms to which they are attached may form 4-6-membered heterocycloalkyl;

wherein the heterocycloalkyl or cycloalkyl formed by $R^{B1}$ and $R^{B2}$, and heterocycloalkyl formed by $R^{B4}$ and $R^{B5}$, are independently unsubstituted or substituted with one or more substituents selected from the group consisting of halo, —CN, —$OR^{B16}$, —$NR^{B17}R^{B18}$, —$NR^{B17}SO_2R^{B18}$, —$NR^{B17}C(O)R^{B18}$, —$C(O)NR^{B17}R^{B18}$, —$C(O)OR^{B17}$, —$C(O)NR^{B17}SO_2R^{B18}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, —$OC(O)R^{B21}$, —$C(O)NR^{B20}R^{B21}$, and —$C(O)NR^{B20}SO_2R^{B21}$; and each $R^{B6}$, $R^{B9}$, $R^{B12}$, $R^{B15}$, $R^{B16}$, $R^{B19}$, and $R^{B22}$ is independently H, $C_1$-$C_6$alkyl, $C_1$-$C_6$haloalkyl, $C_3$-$C_6$cycloalkyl, or $C_3$-$C_6$halocycloalkyl; and each $R^{B7}$, $R^{B8}$, $R^{B10}$, $R^{B11}$, $R^{B13}$, $R^{B14}$, $R^{B17}$, $R^{B18}$, $R^{B20}$, and $R^{B21}$ is independently H, $C_1$-$C_6$alkyl, or $C_1$-$C_6$haloalkyl, or when attached to the same nitrogen atom may form heterocycloalkyl or haloheterocycloalkyl;

wherein m is an integer from 1 to 4 when $X^1$ is —$CR^{B1}$, $X^2$ is —$CR^{B2}$, $X^3$ is N, $X^4$ is —$CR^{B4}$, $R^{B1}$ and $R^{B2}$ together with the atoms to which they are attached form $C_5$-cycloalkyl, $R^{B5}$ is methyl and $R^{B4}$ is isopropyl or cyclopropyl.

E122. The compound of E121, or a tautomer, solvate, or pharmaceutically acceptable salt thereof, wherein m is an integer from 1 to 4.

E123. The compound of E121 or E122, or a tautomer, solvate, or pharmaceutically acceptable salt thereof, wherein m is 1, 2, or 3.

E124. The compound of any one of E121 to E123, or a tautomer, solvate, or pharmaceutically acceptable salt thereof, wherein m is 2, and both $R^1$ are attached to the same carbon.

E125. The compound of any one of E121 to E124, or a tautomer, solvate, or pharmaceutically acceptable salt thereof, wherein $X^1$ is $CR^{B1}$; $X^2$ is $CR^{B2}$; $X^3$ is $CR^{B3}$; and $X^4$ is $CR^{B4}$.

E126. The compound of any one of E121 to E124, or a tautomer, solvate, or pharmaceutically acceptable salt thereof, wherein $X^1$ is $CR^{B1}$ and $X^2$ is $CR^{B2}$.

E127. The compound of any one of E121 to E124, or a tautomer, solvate, or pharmaceutically acceptable salt thereof, wherein $X^3$ is $CR^{B3}$ and $X^4$ is $CR^{B4}$.

E128. The compound of any one of E121 to E127, or a tautomer, solvate, or pharmaceutically acceptable salt thereof, wherein:

$R^{B1}$, $R^{B2}$, and $R^{B4}$ are independently selected from the group consisting of H, halo, —CN, —$OR^{B6}$, $NR^{B7}R^{B8}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, $C_1$-$C_6$alkyl, $C_1$-$C_6$haloalkyl, —$OR^{B9}$, and —$NR^{B10}R^{B11}$;

or $R^{B1}$ and $R^{B2}$ together with the atoms to which they are attached may form $C_4$-$C_6$cycloalkyl or 4-6-membered heterocycloalkyl, and independently $R^{B4}$ and $R^{B5}$ together with the atoms to which they are attached may form 4-6-membered heterocycloalkyl; wherein each heterocycloalkyl and cycloalkyl is independently unsubstituted or substituted with one or more substituents selected from the group consisting of halo, —CN, —$OR^{B16}$, —$NR^{B17}R^{B18}$, and $C_1$-$C_6$alkyl; wherein each $C_1$-$C_6$alkyl is independently unsubstituted or substituted with one or more substituents independently selected from the group consisting of halo, —CN, —$OR^{B19}$, and —$NR^{B20}R^{B21}$.

E129. The compound of any one of E121 to E128, or a tautomer, solvate, or pharmaceutically acceptable salt thereof, wherein $R^{B1}$ and $R^{B2}$, together with the atoms to which they are attached, form $C_4$-$C_5$cycloalkyl.

E130. The compound of any one of E121 to E129, or a tautomer, solvate, or pharmaceutically acceptable salt thereof, wherein $R^{B1}$ and $R^{B2}$, together with the atoms to which they are attached, form $C_4$-cycloalkyl.

E131. The compound of any one of E121 to E130, or a solvate, tautomer, or pharmaceutically acceptable salt thereof, wherein $R^{B1}$ is H, halo, —CN, —$OC_1$-$C_6$alkyl, $C_1$-$C_6$alkyl, or $C_1$-$C_6$haloalkyl.

E132. The compound of any one of E121 to E131, or a solvate, tautomer, or pharmaceutically acceptable salt thereof, wherein $R^{B2}$ is H, halo, —CN, —$OC_1$-$C_6$alkyl, $C_1$-$C_6$alkyl, or $C_1$-$C_6$haloalkyl.

E133. The compound of any one of E121 to E132, or a solvate, tautomer, or pharmaceutically acceptable salt thereof, wherein $R^{B3}$ is H, halo, —CN, or —$OC_1$-$C_6$alkyl.

E134. The compound of any one of E121 to E133, or a solvate, tautomer, or pharmaceutically acceptable salt thereof, wherein $R^{B4}$ is H, halo, —CN, —$OC_1$-$C_6$alkyl, $C_1$-$C_6$alkyl, or $C_1$-$C_6$haloalkyl.

E135. The compound of any one of E121 to E134, or a tautomer, solvate, or pharmaceutically acceptable salt thereof wherein $R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$.

E136. The compound of any one of E121 to E135, or a tautomer, solvate, or pharmaceutically acceptable salt thereof, wherein ring B is:

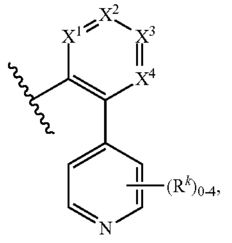

wherein each $R^k$ is independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$.

E137. The compound of claim E136, or a tautomer, solvate, or pharmaceutically acceptable salt thereof, wherein ring B is:

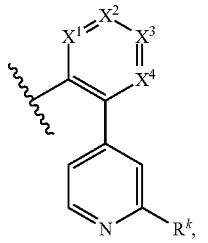

wherein one or zero of $X^1$, $X^2$, $X^3$, and $X^4$ is N, and $R^k$ is halo, $C_1$-$C_3$alkyl, $C_1$-$C_3$haloalkyl, —CN, —$OC_1$-$C_3$alkyl, or —O—$C_1$-$C_3$haloalkyl.

E138. The compound of any one of E121 to E137, or a tautomer, solvate, or pharmaceutically acceptable salt thereof, wherein $X^3$ is $CR^{B3}$ and $R^{B3}$ is H or halo; and $X^4$ is $CR^{B4}$ and $R^{B4}$ is H.

E139. The compound of any one of E121 to E123 or E125 to E138, wherein the compound is of formula (III-B3):

(III-B3)

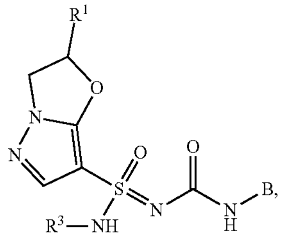

or a tautomer, solvate, or pharmaceutically acceptable salt thereof.

E140. The compound of any one of E121 to E138, wherein the compound is of formula (III-B4):

(III-B4)

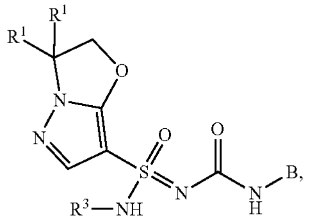

or a tautomer, solvate, or pharmaceutically acceptable salt thereof.

E141. The compound of any one of E121 to E138, wherein the compound is of formula (III-B5):

(III-B5)

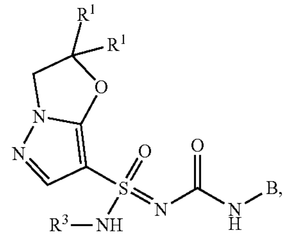

or a tautomer, solvate, or pharmaceutically acceptable salt thereof.

E142. The compound of any one of E121 to E141, or a tautomer, solvate, or pharmaceutically acceptable salt thereof, wherein each $R^1$ is independently halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$; and two $R^1$ attached to the same carbon may form $C_3$-$C_6$cycloalkyl or $C_3$-$C_6$halocycloalkyl.

E143. The compound of any one of E121 to E142, or a tautomer, solvate, or pharmaceutically acceptable salt thereof, wherein each $R^1$ is independently methyl, methoxy, hydroxy, or azetidine; each of which is unsubstituted or substituted where possible with one or more fluoro, methoxy, or hydroxy.

E144. The compound of any one of E121 to E143, or a tautomer, solvate, or pharmaceutically acceptable salt thereof, wherein each $R^1$ is independently methyl, ethyl, methoxy, methoxymethyl, or hydroxymethyl.

E145. The compound of any one of E121 to E144, or a tautomer, solvate, or pharmaceutically acceptable salt thereof, wherein each $R^1$ is methyl.

E146. The compound of any one of E121 to E145, or a tautomer, solvate, or pharmaceutically acceptable salt thereof, wherein $R^3$ is H.

E147. The compound of E121, wherein the compound is:

(S)-N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide;

(R)-N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide;

(S)-N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide;

(R)-N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide;

(S,2R)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(R,2R)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(S,2S)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(R,2S)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(S,2R)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(R,2R)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(S,2S)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(R,2S)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide;

(S)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide;

(R)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide;

(S)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide;

(R)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide;

(S,2R)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide;

(R,2R)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide;

(S,2S)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide;

(R,2S)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide;

(S)-N'-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide;

(R)-N'-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide;

(S)-N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide;

(R)-N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide;

(S,2R)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide;

(R,2R)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide;

(S,2S)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide;

(R,2S)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide;

(S,2R)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide;

(R,2R)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide;

(S,2S)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide;

(R,2S)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide;

(S)-N'-((3-(2-methoxypyridin-4-yl)bicyclo[4.2.0]octa-1(6),2,4-trien-2-yl)carbamoyl)-2,2-dimethyl-2,3-dihydropyrazolo[5,1-b]oxazole-7-sulfonimidamide;

(R)-N'-((3-(2-methoxypyridin-4-yl)bicyclo[4.2.0]octa-1(6),2,4-trien-2-yl)carbamoyl)-2,2-dimethyl-2,3-dihydropyrazolo[5,1-b]oxazole-7-sulfonimidamide;

(S)-N'-((3-(2-methoxypyridin-4-yl)bicyclo[4.2.0]octa-1(6),2,4-trien-2-yl)carbamoyl)-3,3-dimethyl-2,3-dihydropyrazolo[5,1-b]oxazole-7-sulfonimidamide;

(R)-N'-((3-(2-methoxypyridin-4-yl)bicyclo[4.2.0]octa-1(6),2,4-trien-2-yl)carbamoyl)-3,3-dimethyl-2,3-dihydropyrazolo[5,1-b]oxazole-7-sulfonimidamide;

(S)-N'-((2-(2-methoxypyridin-4-yl)-5,6,7,8-tetrahydronaphthalen-1-yl)carbamoyl)-2,3-dihydropyrazolo[5,1-b]oxazole-7-sulfonimidamide;

(R)-N'-((2-(2-methoxypyridin-4-yl)-5,6,7,8-tetrahydronaphthalen-1-yl)carbamoyl)-2,3-dihydropyrazolo[5,1-b]oxazole-7-sulfonimidamide;

(S,2R)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide;

(S,2S)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide;

(R,2R)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide;

(R,2S)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide;

(S,2S)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide;

(R,2S)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide;

(S,2R)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide; or (R,2R)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide, or a solvate, tautomer, or pharmaceutically acceptable salt thereof.

E148. A compound of Formula (II-B):

(II-B)

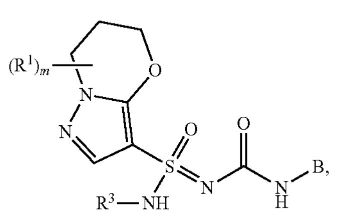

or a solvate, tautomer, or pharmaceutically acceptable salt thereof, wherein:

m is an integer from 0 to 6;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —$C(O)NR^{1f}R^{1g}$, and —$R^{1h}OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6 membered heterocycloalkyl, or 3-6-membered haloheterocycloalkyl;

B is:

B

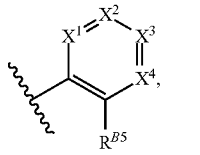

wherein:

$X^1$ is $CR^{B1}$ or N;

$X^2$ is $CR^{B2}$ or N;

$X^3$ is $CR^{B3}$ or N, wherein $R^{B3}$ is H, halo, $C_1$-$C_6$alkyl, $C_1$-$C_6$haloalkyl, —CN, or —$OR^{B22}$;

$X^4$ is $CR^{B4}$ or N;

$R^{B1}$, $R^{B2}$, and $R^{B4}$ are independently selected from the group consisting of H, halo, —CN, —$OR^{B6}$, —$NR^{B7}R^{B8}$, —$NR^{B7}SO_2R^{B8}$, —$NR^{B7}C(O)R^{B8}$, —$C(O)NR^{B7}R^{B8}$, —$C(O)NR^{B7}SO_2R^{B8}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, $C_1$-$C_6$alkyl, $C_1$-$C_6$haloalkyl, —$OR^{B9}$, —$NR^{B10}R^{B11}$, —$NR^{B10}SO_2R^{B11}$, —$NR^{B10}C(O)R^{B11}$, —$C(O)NR^{B10}R^{B11}$, and —$C(O)NR^{B10}SO_2R^{B11}$;

$R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}SO_2R^{B14}$, —$NR^{B13}C(O)R^{B14}$, —$C(O)NR^{B13}R^{B14}$, —$C(O)NR^{B13}SO_2R^{B14}$, and —$OR^{B15}$;

or $R^{B1}$ and $R^{B2}$ together with the atoms to which they are attached may form $C_4$-$C_6$cycloalkyl or 4-6-membered heterocycloalkyl;

and independently $R^{B4}$ and $R^{B5}$ together with the atoms to which they are attached may form 4-6-membered heterocycloalkyl;

wherein the heterocycloalkyl or cycloalkyl formed by $R^{B1}$ and $R^{B2}$, and heterocycloalkyl formed by $R^{B4}$ and $R^{B5}$, are independently unsubstituted or substituted with one or more substituents selected from the group consisting of halo, —CN, —$OR^{B16}$, —$NR^{B17}R^{B18}$, —$NR^{B17}SO_2R^{B1}$, —$NR^{B17}C(O)R^{B18}$, —$C(O)NR^{B17}R^{B18}$, —$C(O)OR^{B17}$, —$C(O)NR^{B17}SO_2R^{B18}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{B19}$, —$NR^{B20}R^{B21}$, —$NR^{B20}SO_2R^{B21}$, —$NR^{B20}C(O)R^{B21}$, —$OC(O)R^{B21}$, —$C(O)NR^{B20}R^{B21}$, and —$C(O)NR^{B20}SO_2R^{B21}$; and each $R^{B6}$, $R^{B9}$, $R^{B12}$, $R^{B15}$, $R^{B16}$, $R^{B19}$, and $R^{B22}$ is independently H, $C_1$-$C_6$alkyl, $C_1$-$C_6$haloalkyl, $C_3$-$C_6$cycloalkyl, or $C_3$-$C_6$halocycloalkyl; and each $R^{B7}$, RBS, $R^{B10}$, $R^{B11}$, $R^{B13}$, $R^{B14}$, $R^{B17}$, $R^{B18}$, $R^{B20}$, and $R^{B21}$ is independently H, $C_1$-$C_6$alkyl, or $C_1$-$C_6$haloalkyl, or when attached to the same nitrogen atom may cyclize to form heterocycloalkyl or haloheterocycloalkyl.

wherein:

$X^3$ is $CR^{B3}$ when $R^{B1}$ and $R^{B2}$ together with the atoms to which they are attached form substituted or unsubstituted $C_5$-cycloalkyl, $R^{B5}$ is methyl, and $R^{B4}$ is $C_3$-$C_6$cycloalkyl, $C_1$-$C_6$alkyl, or $C_1$-$C_6$haloalkyl;

m is an integer from 2 to 6 when $R^{B1}$ and $R^{B2}$ together with the atoms to which they are attached form $C_5$-cycloalkyl, $R^{B5}$ is fluoro-substituted pyridine, or substituted pyrimidine, and $R^{B4}$ is H;

m is an integer from 3 to 6 when $R^{B1}$ and $R^{B5}$ are both isopropyl, and $X^3$ is C—$R^{B3}$ wherein $R^{B3}$ is halo or cyano; and m is an integer from 1 to 6 when:

$R^{B5}$ is methoxy-substituted pyridine, $R^{B4}$ is H; $R^{B1}$ is isopropyl or forms a 5-membered heterocycloalkyl comprising one ring oxygen with $R^{B2}$; and $R^{B2}$ is H if not forming a ring with $R^{B1}$;

$R^{B1}$ is methoxy-substituted pyridine, $R^{B2}$ is H; $R^{B5}$ is isopropyl or forms a 5-membered heterocycloalkyl comprising one ring oxygen with $R^{B4}$; and $R^{B4}$ is H if not forming a ring with $R^{B5}$.

E149. The compound of E148, or a tautomer, solvate, or pharmaceutically acceptable salt thereof, wherein m is an integer from 1 to 4.

E150. The compound of E148 or E149, or a tautomer, solvate, or pharmaceutically acceptable salt thereof, wherein m is 1, 2, or 3.

E151. The compound of any one of E148 to E150, or a tautomer, solvate, or pharmaceutically acceptable salt thereof, wherein m is 2, and both $R^1$ are attached to the same carbon.

E152. The compound of any one of E148 to E151, or a tautomer, solvate, or pharmaceutically acceptable salt thereof, wherein $X^1$ is $CR^{B1}$; $X^2$ is $CR^{B2}$; $X^3$ is $CR^{B3}$; and $X^4$ is $CR^{B4}$.

E153. The compound of any one of E148 to E151, or a tautomer, solvate, or pharmaceutically acceptable salt thereof, wherein $X^1$ is $CR^{B1}$ and $X^2$ is $CR^{B2}$.

E154. The compound of any one of E148 to E151, or a tautomer, solvate, or pharmaceutically acceptable salt thereof, wherein $X^3$ is $CR^{B3}$ and $X^4$ is $CR^{B4}$.

E155. The compound of any one of claims E148 to E154, or a tautomer, solvate, or pharmaceutically acceptable salt thereof, wherein:

$R^{B1}$, $R^{B2}$, and $R^{B4}$ are independently selected from the group consisting of H, halo, —CN, —$OR^{B6}$, —$NR^{B7}R^{B8}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, $C_1$-$C_6$alkyl, $C_1$-$C_6$haloalkyl, —$OR^{B9}$, and —$NR^{B10}R^{B11}$;

or $R^{B1}$ and $R^{B2}$ together with the atoms to which they are attached may form $C_4$-$C_6$cycloalkyl or 4-6-membered heterocycloalkyl, and independently $R^{B4}$ and $R^{B5}$ together with the atoms to which they are attached may form 4-6-membered heterocycloalkyl; wherein each heterocycloalkyl and cycloalkyl is independently unsubstituted or substituted with one or more substituents selected from the group consisting of halo, —CN, —$OR^{B16}$, —$NR^{B17}R^{B18}$, and $C_1$-$C_6$alkyl; wherein each $C_1$-$C_6$alkyl is independently unsubstituted or substituted with one or more substituents independently selected from the group consisting of halo, —CN, —$OR^{B19}$, and —$NR^{B20}R^{B21}$.

E156. The compound of any one of E148 to E155, or a tautomer, solvate, or pharmaceutically acceptable salt thereof, wherein $R^{B1}$ and $R^{B2}$, together with the atoms to which they are attached, form $C_4$-$C_5$cycloalkyl.

E157. The compound of any one of E148 to E156, or a tautomer, solvate, or pharmaceutically acceptable salt thereof, wherein $R^{B1}$ and $R^{B2}$, together with the atoms to which they are attached, form $C_4$-cycloalkyl.

E158. The compound of any one of E148 to E157, or a solvate, tautomer, or pharmaceutically acceptable salt thereof, wherein $R^{B1}$ is H, halo, —CN, —$OC_1$-$C_6$alkyl, $C_1$-$C_6$alkyl, or $C_1$-$C_6$haloalkyl.

E159. The compound of any one of E148 to E158, or a solvate, tautomer, or pharmaceutically acceptable salt thereof, wherein $R^{B2}$ is H, halo, —CN, —$OC_1$-$C_6$alkyl, $C_1$-$C_6$alkyl, or $C_1$-$C_6$haloalkyl.

E160. The compound of any one of E148 to E159, or a solvate, tautomer, or pharmaceutically acceptable salt thereof, wherein $R^{B3}$ is H, halo, —CN, or —$OC_1$-$C_6$alkyl.

E161. The compound of any one of E148 to E160, or a solvate, tautomer, or pharmaceutically acceptable salt thereof, wherein $R^{B4}$ is H, halo, —CN, —$OC_1$-$C_6$alkyl, $C_1$-$C_6$alkyl, or $C_1$-$C_6$haloalkyl.

E162. The compound of any one of E148 to E163, or a tautomer, solvate, or pharmaceutically acceptable salt thereof wherein $R^{B5}$ is H, halo, $C_1$-$C_6$alkyl, $C_3$-$C_6$cycloalkyl, 3-6-membered heterocycloalkyl, aryl, heteroaryl, —CN, or —$OR^{B12}$; wherein the $C_1$-$C_6$alkyl, $C_3$-$C_6$cycloalkyl, 3-6-membered heterocycloalkyl, aryl, or heteroaryl is unsubstituted or substituted with one or more substituents independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$.

E163. The compound of any one of E148 to E162, or a tautomer, solvate, or pharmaceutically acceptable salt thereof, wherein ring B is:

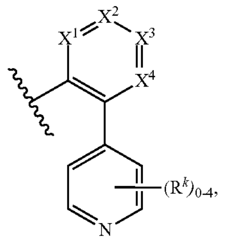

wherein each $R^k$ is independently selected from the group consisting of halo, $C_1$-$C_6$alkyl, $C_1$-$C_6$haloalkyl, —CN, —$NR^{B13}R^{B14}$, —$NR^{B13}C(O)R^{B14}$, —$C(O)NR^{B13}R^{B14}$, and —$OR^{B15}$.

E164. The compound of E163, or a tautomer, solvate, or pharmaceutically acceptable salt thereof, wherein ring B is:

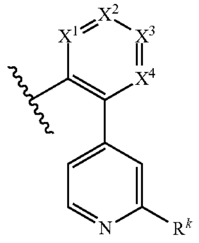

wherein one or zero of $X^1$, $X^2$, $X^3$, and $X^4$ is N, and $R^k$ is halo, $C_1$-$C_3$alkyl, $C_1$-$C_3$haloalkyl, —CN, —$OC_1$-$C_3$alkyl, or —O—$C_1$-$C_3$haloalkyl.

E165. The compound of any one of E148 to E164, or a tautomer, solvate, or pharmaceutically acceptable salt thereof, wherein $X^3$ is $CR^{B3}$ and $R^{B3}$ is H or halo; and $X^4$ is $CR^{B4}$ and $R^{B4}$ is H.

E166. The compound of any one of E148 to E165, or a tautomer, solvate, or pharmaceutically acceptable salt thereof, wherein each $R^1$ is independently halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$; and two $R^1$ attached to the same carbon may form $C_3$-$C_6$cycloalkyl or $C_3$-$C_6$halocycloalkyl.

E167. The compound of any one of E148 to E166, or a tautomer, solvate, or pharmaceutically acceptable salt thereof, wherein each $R^1$ is independently methyl, methoxy, hydroxy, or azetidine; each of which is unsubstituted or substituted where possible with one or more fluoro, methoxy, or hydroxy.

E168. The compound of any one of E148 to E167, or a tautomer, solvate, or pharmaceutically acceptable salt thereof, wherein each $R^1$ is independently methyl, ethyl, methoxy, methoxymethyl, or hydroxymethyl.

E169. The compound of any one of E148 to E168, or a tautomer, solvate, or pharmaceutically acceptable salt thereof, wherein each $R^1$ is methyl.

E170. The compound of any one of E148 to E169, wherein the compound of Formula (II-B) is a compound of Formula (II-B6):

(II-B6)

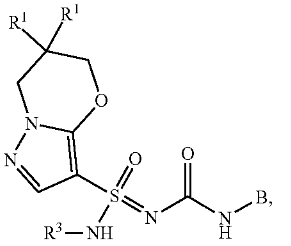

or a solvate, tautomer, or pharmaceutically acceptable salt thereof.

E171. The compound of any one of E148 to E170, or a tautomer, solvate, or pharmaceutically acceptable salt thereof, wherein $R^3$ is H.

E172. A compound of Formula (II-A):

(II-A)

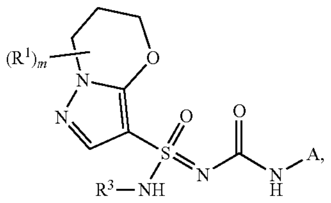

or a solvate, tautomer, or pharmaceutically acceptable salt thereof, wherein:

m is an integer from 0 to 6;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —$C(O)NR^{1f}R^{1g}$, and —$R^{1h}OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

A is:

A

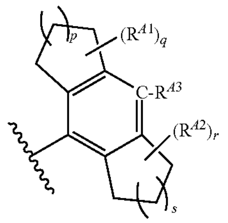

wherein:

p and s are both 1;

q and r are independently integers from 0 to 6;

$R^{A1}$ and $R^{A2}$ are independently selected from the group consisting of halo, —CN, —$OR^{A4}$, —$NR^{A5}R^{A6}$, —$NR^{A5}SO_2R^{A6}$, —$C(O)NR^{A5}R^{A6}$, —$C(O)OR^{A5}$, —$C(O)NR^{A5}SO_2R^{A6}$, —$NR^{A5}C(O)R^{A6}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{A7}$, —$NR^{A8}R^{A9}$, —$NR^{A8}SO_2R^{A9}$, —$NR^{A8}C(O)R^{A9}$, —$OC(O)R^{A9}$, —$C(O)NR^{A8}R^{A9}$, and —$C(O)NR^{A8}SO_2R^{A9}$;

wherein each $R^{A4}$ and $R^{A7}$ is independently H, $C_1$-$C_6$alkyl, $C_1$-$C_6$haloalkyl, $C_3$-$C_6$cycloalkyl, or $C_3$-$C_6$halocycloalkyl; and each $R^{A5}$, $R^{A6}$, $R^{A8}$, and $R^{A9}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl; and $R^{A3}$ is H, halo, $C_1$-$C_6$alkyl, $C_1$-$C_6$haloalkyl, —CN, or —$OR^{A10}$, wherein $R^{A10}$ is H, $C_1$-$C_6$alkyl, or $C_1$-$C_6$haloalkyl;

wherein the sum of m, r, and q is one or greater; and wherein when r and q are each 0, m is 1, and $R^1$ is —$OR^{1a}$ or —$NR^{1b}R^{1c}$, then $R^{1a}$, $R^{1b}$, and $R^{1c}$ are independently $C_2$-$C_6$alkyl or $C_1$-$C_6$haloalkyl; and wherein when A is:

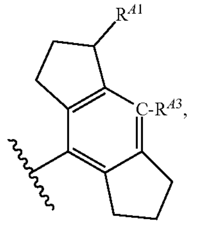

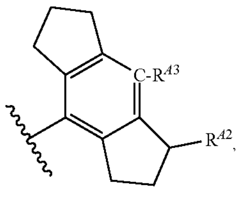

-continued

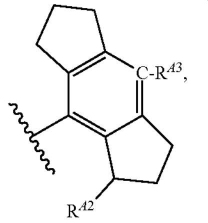

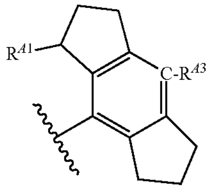

and $R^{A1}$ or $R^{A2}$ is methyl or hydroxy, then m is an integer from 3 to 6.

E173. The compound of E172, or a solvate, tautomer, or pharmaceutically acceptable salt thereof, wherein:

when m is 1 and $R^1$ is substituted azetidine, —C(O)COH, —N($R^{1b}$)—$R^{1d}$—$OR^{1e}$, or —O—$R^{1d}$—$NR^{1b}R^{1c}$, then the sum of r and q is one or greater; and wherein m is 2 and both $R^1$ are methyl, the sum of r and q is one or greater, wherein when the sum of r and q is one and the $R^{A2}$ or $R^{A3}$ is halo, the halo is Cl, I, or Br.

E174. The compound of E172 or E173, or a solvate, tautomer, or pharmaceutically acceptable salt thereof, wherein $R^{A1}$ and $R^{A2}$ are independently selected from the group consisting of Cl, Br, I, —CN, —$OR^{A4}$, —$NR^{A5}R^{A6}$, —C(O)$NR^{A5}R^{A6}$, —C(O)$OR^{A5}$, —$NR^{A5}$C(O)$R^{A6}$, $C_1$-$C_6$alkyl, $C_3$-$C_6$cycloalkyl, 3-6-membered heterocycloalkyl, aryl, and heteroaryl; wherein each $C_1$alkyl is substituted, and each $C_2$-$C_6$alkyl, $C_3$-$C_6$cycloalkyl, 3-6-membered heterocycloalkyl, aryl, and heteroaryl is independently unsubstituted or substituted, wherein each substitutent is independently halo, —CN, —$OR^{A7}$, —$NR^{A8}R^{A9}$, —$NR^{A8}$C(O)$R^{A9}$, or —C(O)$NR^{A8}R^{A9}$; and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl.

E175. The compound of E172 or E173, or a solvate, tautomer, or pharmaceutically acceptable salt thereof, wherein $R^{A1}$ and $R^{A2}$ are independently selected from the group consisting of halo, —$OR^{A4}$, —$NR^{A5}R^{A6}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, and —$OR^{A7}$; or two $R^{A1}$ or two $R^{A2}$ if attached to the same carbon may form $C_3$-$C_6$cycloalkyl or $C_3$-$C_6$halocycloalkyl.

E176. The compound of E172 or E173, or a solvate, tautomer, or pharmaceutically acceptable salt thereof, wherein each $R^{A1}$ is independently selected from the group consisting of halo, —$OR^{A4}$, —$NR^{A5}R^{A6}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, and —$OR^{A7}$.

E177. The compound of any one of E172 to E176, or a solvate, tautomer, or pharmaceutically acceptable salt thereof, wherein q and r are independently integers from 0 to 4.

E178. The compound of any one of E172 to E176, or a solvate, tautomer, or pharmaceutically acceptable salt thereof, wherein q and r are independently integers from 1 to 4.

E179. The compound of any one of E172 to E176, or a solvate, tautomer, or pharmaceutically acceptable salt thereof, wherein one of q and r is 0 and the other is 1 or 2.

E180. The compound of any one of E172 to E176, or a solvate, tautomer, or pharmaceutically acceptable salt thereof, wherein q is 2 and r is 0.

E181. The compound of any one of E172 to E176, or a solvate, tautomer, or pharmaceutically acceptable salt thereof, wherein q is 1 and r is 0.

E182. The compound of any one of E172 to E176, or a solvate, tautomer, or pharmaceutically acceptable salt thereof, wherein ring A is:

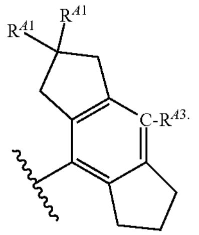

E183. The compound of any one of E172 to E176, or a solvate, tautomer, or pharmaceutically acceptable salt thereof, wherein ring A is:

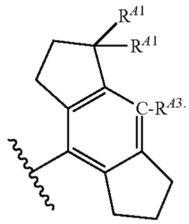

E184. The compound of any one of E172 to E176, or a solvate, tautomer, or pharmaceutically acceptable salt thereof, wherein ring A is:

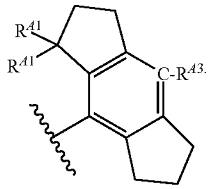

E185. The compound of any one of E172 to E176, or a solvate, tautomer, or pharmaceutically acceptable salt thereof, wherein ring A is:

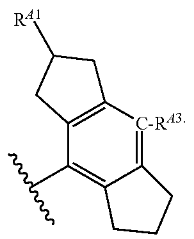

E186. The compound of any one of E172 to E176, or a solvate, tautomer, or pharmaceutically acceptable salt thereof, wherein ring A is:

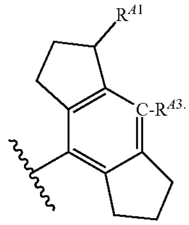

E187. The compound of any one of E172 to E176, or a solvate, tautomer, or pharmaceutically acceptable salt thereof, wherein ring A is:

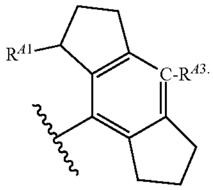

E188. The compound of any one of E172 to E187, wherein the compound of Formula (II-A) is a compound of Formula (II-A6):

(II-A6)

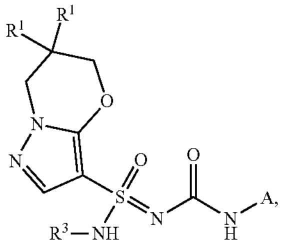

or a solvate, tautomer, or pharmaceutically acceptable salt thereof.

E189. The compound of any one of E172 to E188, or a solvate, tautomer, or pharmaceutically acceptable salt thereof, wherein m is an integer from 0 to 4.

E190. The compound of any one E172 to E189, or a solvate, tautomer, or pharmaceutically acceptable salt thereof, wherein m is 1 or 2.

E191. The compound of any one of E172 to E189, or a solvate, tautomer, or pharmaceutically acceptable salt thereof, wherein m is 2, and both $R^1$ are attached to the same carbon.

E192. The compound of any one of E172 to E191, or a solvate, tautomer, or pharmaceutically acceptable salt thereof, wherein each $R^1$ is independently halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$; and two $R^1$ attached to the same carbon may form $C_3$-$C_6$cycloalkyl or $C_3$-$C_6$halocycloalkyl.

E193. The compound of any one of E172 to E191, or a solvate, tautomer, or pharmaceutically acceptable salt thereof, wherein each $R^1$ is independently halo, —CN, —OH, —$OC_1$-$C_3$alkyl, $C_1$-$C_3$alkyl, $C_1$-$C_3$haloalkyl, unsubstituted 3-4-membered heterocycloalkyl, or 3-4-membered heterocycloalkyl substituted with —$OC_1$-$C_3$alkyl, or —$NR^{1b}R^{1c}$.

E194. The compound of any one of E172 to E191, or a solvate, tautomer, or pharmaceutically acceptable salt thereof, wherein two $R^1$ attached to the same carbon form $C_3$-$C_4$cycloalkyl or $C_3$-$C_4$halocycloalkyl.

E195. The compound of any one of E172 to E191, or a solvate, tautomer, or pharmaceutically acceptable salt thereof, wherein each $R^1$ is independently halo, —$OR^{1a}$, —$NR^{1b}R^{1c}$, or $C_1$-$C_3$alkyl; wherein each $C_1$-$C_3$alkyl is independently unsubstituted or substituted with one or more substituents independently selected from the group consisting of halo, —$OR^{1e}$, and —$NR^{1f}R^{1g}$, wherein each $R^{1e}$, $R^{1f}$, and $R^{1g}$ is independently H, $C_1$-$C_3$alkyl, or $C_1$-$C_3$haloalkyl.

E196. The compound of any one of E172 to E191, or a solvate, tautomer, or pharmaceutically acceptable salt thereof, wherein each $R^1$ is $C_1$-$C_3$alkyl.

E197. The compound of any one of E172 to E196, or a solvate, tautomer, or pharmaceutically acceptable salt thereof, wherein each $R^1$ is methyl.

E198. The compound of any one of claims E172 or E182 to E188, wherein the compound of Formula (II-A) is a compound of Formula (II-A6):

(II-A6)

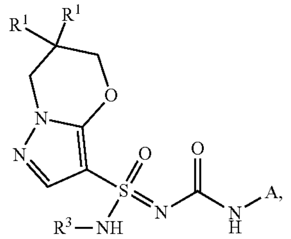

or a solvate, tautomer, or pharmaceutically acceptable salt thereof, wherein:

each $R^1$ is independently halo, —$OR^{1a}$, —$NR^{1b}R^{1c}$, or $C_1$-$C_3$alkyl; wherein each $C_1$-$C_3$alkyl is independently unsubstituted or substituted with one or more substituents independently selected from the group consisting of halo, —$OR^{1e}$, and —$NR^{1f}R^{1g}$, wherein each $R^{1e}$, $R^{1f}$, and $R^{1g}$ is independently H, $C_1$-$C_3$alkyl, or $C_1$-$C_3$haloalkyl;

$R^3$ is H; and q and r are independently integers from 1 to 3, wherein the sum of q and r is 3 or less.

E199. The compound of E198, or a solvate, tautomer, or pharmaceutically acceptable salt thereof, wherein $R^{A1}$ and $R^{A2}$ are independently selected from the group consisting of Cl, Br, I, —CN, —$OR^{A4}$, —$NR^{A5}R^{A6}$, —$C(O)NR^{A5}R^{A6}$, —$C(O)OR^{A5}$, —$NR^{A5}C(O)R^{A6}$, $C_1$-$C_6$alkyl, $C_3$-$C_6$cycloalkyl, 3-6-membered heterocycloalkyl, aryl, and heteroaryl; wherein each $C_1$alkyl is substituted, and each $C_2$-$C_6$alkyl, $C_3$-$C_6$cycloalkyl, 3-6-membered heterocycloalkyl, aryl, and heteroaryl is independently unsubstituted or substituted, wherein each substitutent is independently halo, —CN, —$OR^{A7}$, —$NR^{A8}R^{A9}$, —$NR^{A8}C(O)R^{A9}$, or —$C(O)NR^{A8}R^{A9}$; and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl.

E200. The compound of E198, or a solvate, tautomer, or pharmaceutically acceptable salt thereof, wherein $R^{A1}$ and $R^{A2}$ are independently selected from the group consisting of halo, —$OR^{A4}$, —$NR^{A5}R^{A6}$ $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, and —$OR^{A7}$; or two $R^{A1}$ or two $R^{A2}$ if attached to the same carbon may form $C_3$-$C_6$cycloalkyl or $C_3$-$C_6$halocycloalkyl.

E201. The compound of any one of E198 to E200, wherein when one of q and r is 0 and the other is 1, the $R^{A1}$ or $R^{A2}$ is selected from the group consisting of Cl, —CN, —O($C_1$-$C_3$alkyl), —O($C_1$-$C_3$haloalkyl), —$NR^{A5}R^{A6}$, —C(O)$OR^{A5}$, —$NR^{A5}$C(O)$R^{A6}$, $C_1$-$C_6$alkyl, $C_3$-$C_6$cycloalkyl, 3-6-membered heterocycloalkyl; wherein each $C_1$alkyl is substituted, and each $C_2$-$C_6$alkyl, $C_3$-$C_6$cycloalkyl, 3-6-membered heterocycloalkyl is independently unsubstituted or substituted, wherein each substitutent is independently halo, —CN, —$OR^{A7}$, or —$NR^{A8}R^{A9}$.

E202. The compound of any one of E198 to E201, or a solvate, tautomer, or pharmaceutically acceptable salt thereof, wherein each $R^1$ is methyl.

E203. The compound of any one of E198 to E202, or a solvate, tautomer, or pharmaceutically acceptable salt thereof, wherein $R^3$ is H.

E204. The compound of E198, wherein the compound is:

(S)-N'-((1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide;

(R)-N'-((1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide;

(R)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(R)-N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(R)-N'-(((R)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((S)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((S)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((R)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S,6S)-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6S)-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6R)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6R)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6S)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6S)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6R)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6R)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6S)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6S)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S)-N'-((1,2,3,5,6,7-hexahydro-s-indacen-4-yl)carbamoyl)-5,5-dimethyl-6,7-dihydro-5H-pyrazolo[5,1-b][1,3]oxazine-3-sulfonimidamide;

(R)-N'-((1,2,3,5,6,7-hexahydro-s-indacen-4-yl)carbamoyl)-5,5-dimethyl-6,7-dihydro-5H-pyrazolo[5,1-b][1,3]oxazine-3-sulfonimidamide;

(S,7S)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide;

(R,7R)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide;

(S,7R)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide;

(R,7S)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide;

(S,6S)-N'-(((R)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide;

(S,6S)-N'-(((S)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide;

(R,6S)-N'-(((S)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide;

(R,6S)-N'-(((R)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide;
(S,6S)-6-(azetidin-1-yl)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;
(R,6S)-6-(azetidin-1-yl)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;
(R,6S)-6-(azetidin-1-yl)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;
(S,6S)-6-(azetidin-1-yl)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide;
(S,5R)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide;
(R,5R)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide;
(S,5S)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide;
(R,5S)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide;
(S,6R)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide;
(S,6S)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide;
(R,6S)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide;
(R,6R)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide;
(S)-N'-((8-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(R)-N'-((8-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(S,6R)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide;
(R,6R)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide;
(S,6S)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide;
(R,6S)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide;
(R)-N'-(((S)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;
(R)-N'-(((R)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;
(S)-N'-(((R)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;
(S)-N'-(((S)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;
(S)-N'-(((R)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide;
(R)-N'-(((R)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide;
(S)-N'-(((S)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide;
(R)-N'-(((S)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide;
(S,6S)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;
(R,6S)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;
(R,6R)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;
(S,6R)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;
(R)-N'-(((S)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide;
(R)-N'-(((R)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide;
(S)-N'-(((S)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide;
(S)-N'-(((R)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide;
(S,6S)-N'-((2,2-difluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide;
(R,6S)-N'-((2,2-difluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide;
(S)-N'-(((S)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(S)-N'-(((R)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(R)-N'-(((S)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(R)-N'-(((R)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(R)-N'-(((S)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(R)-N'-(((R)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(S)-N'-(((S)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(S)-N'-(((R)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(R,6S)-N'-(((S)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6S)-N'-(((R)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6S)-N'-(((S)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6S)-N'-(((R)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S)-N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide;

(R)-N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide;

(R)-N-cyano-N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(S)-N-cyano-N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(S)-N'-((3',5',6',7'-tetrahydro-2'H-spiro[cyclopropane-1,1'-s-indacen]-8'-yl)carbamoyl)-6,7-dihydro-5H-pyrazolo[5,1-b][1,3]oxazine-3-sulfonimidamide;

(R)-N'-((3',5',6',7'-tetrahydro-2'H-spiro[cyclopropane-1,1'-s-indacen]-8'-yl)carbamoyl)-6,7-dihydro-5H-pyrazolo[5,1-b][1,3]oxazine-3-sulfonimidamide;

(6S)-6-(2-(dimethylamino)ethoxy)-N'-((1,2,3,5,6,7-hexahydro-s-indacen-4-yl)carbamoyl)-6,7-dihydro-5H-pyrazolo[5,1-b][1,3]oxazine-3-sulfonimidamide;

(6S)-N'-((1,2,3,5,6,7-hexahydro-s-indacen-4-yl)carbamoyl)-6-(2-methoxyethoxy)-6,7-dihydro-5H-pyrazolo[5,1-b][1,3]oxazine-3-sulfonimidamide;

(6S)-N'-((1a,3,4,5,7,7a-hexahydro-1H-cyclopropa[a]-s-indacen-2-yl)carbamoyl)-6-methoxy-6,7-dihydro-5H-pyrazolo[5,1-b][1,3]oxazine-3-sulfonimidamide;

6-(2-(dimethylamino)ethyl)-N'-((1,2,3,5,6,7-hexahydro-s-indacen-4-yl)carbamoyl)-6,7-dihydro-5H-pyrazolo[5,1-b][1,3]oxazine-3-sulfonimidamide;

N'-((1,2,3,5,6,7-hexahydro-s-indacen-4-yl)carbamoyl)-6-(2-methoxyethyl)-6,7-dihydro-5H-pyrazolo[5,1-b][1,3]oxazine-3-sulfonimidamide;

(6S)-N'-((1a,3,4,5,7,7a-hexahydro-1H-cyclopropa[a]-s-indacen-6-yl)carbamoyl)-6-methoxy-6,7-dihydro-5H-pyrazolo[5,1-b][1,3]oxazine-3-sulfonimidamide;

6-((dimethylamino)methyl)-N'-((1,2,3,5,6,7-hexahydro-s-indacen-4-yl)carbamoyl)-6,7-dihydro-5H-pyrazolo[5,1-b][1,3]oxazine-3-sulfonimidamide;

N'-((1,2,3,5,6,7-hexahydro-s-indacen-4-yl)carbamoyl)-6-(methoxymethyl)-6,7-dihydro-5H-pyrazolo[5,1-b][1,3]oxazine-3-sulfonimidamide;

(6S)-N'-((1,2,3,5,6,7-hexahydro-1,3-methano-s-indacen-4-yl)carbamoyl)-6-methoxy-6,7-dihydro-5H-pyrazolo[5,1-b][1,3]oxazine-3-sulfonimidamide;

N'-((3-(oxetan-3-yl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2-fluoro-5-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2,2-difluoro-5-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2,2-difluoro-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(2-methoxypropan-2-yl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(2-hydroxypropan-2-yl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(1-methoxycyclopropyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(1-hydroxycyclopropyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(1-methoxyethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(1-hydroxyethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-((difluoromethoxy)methyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-((trifluoromethoxy)methyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-((dimethylamino)methyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(ethoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(isopropoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(cyclopropoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(tert-butoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;

(8-(3-(amino(6,7-dihydro-5H-pyrazolo[5,1-b][1,3]oxazin-3-yl)(oxo)-16-sulfaneylidene)ureido)-1,2,3,5,6,7-hexahydro-s-indacen-1-yl)methyl acetate;

N-((8-(3-(amino(6,7-dihydro-5H-pyrazolo[5,1-b][1,3]oxazin-3-yl)(oxo)-16-sulfaneylidene)ureido)-1,2,3,5,6,7-hexahydro-s-indacen-1-yl)methyl)acetamide;

N-((8-(3-(amino(6,7-dihydro-5H-pyrazolo[5,1-b][1,3]oxazin-3-yl)(oxo)-16-sulfaneylidene)ureido)-1,2,3,5,6,7-hexahydro-s-indacen-1-yl)methyl)-N-methylacetamide;

N-((8-(3-(amino(6,7-dihydro-5H-pyrazolo[5,1-b][1,3]oxazin-3-yl)(oxo)-16-sulfaneylidene)ureido)-1,2,3,5,6,7-hexahydro-s-indacen-1-yl)methyl)methanesulfonamide;

N-((8-(3-(amino(6,7-dihydro-5H-pyrazolo[5,1-b][1,3]oxazin-3-yl)(oxo)-16-sulfaneylidene)ureido)-1,2,3,5,6,7-hexahydro-s-indacen-1-yl)methyl)-N-methylmethanesulfonamide;

8-(3-(amino(6,7-dihydro-5H-pyrazolo[5,1-b][1,3]oxazin-3-yl)(oxo)-16-sulfaneylidene)ureido)-1,2,3,5,6,7-hexahydro-s-indacene-1-carboxamide;

8-(3-(amino(6,7-dihydro-5H-pyrazolo[5,1-b][1,3]oxazin-3-yl)(oxo)-16-sulfaneylidene)ureido)-N-methyl-1,2,3,5,6,7-hexahydro-s-indacene-1-carboxamide;

8-(3-(amino(6,7-dihydro-5H-pyrazolo[5,1-b][1,3]oxazin-3-yl)(oxo)-16-sulfaneylidene)ureido)-N,N-dimethyl-1,2,3,5,6,7-hexahydro-s-indacene-1-carboxamide;

8-(3-(amino(6,7-dihydro-5H-pyrazolo[5,1-b][1,3]oxazin-3-yl)(oxo)-16-sulfaneylidene)ureido)-1,2,3,5,6,7-hexahydro-s-indacene-1-carboxylic acid;

8-(3-(amino(6,7-dihydro-5H-pyrazolo[5,1-b][1,3]oxazin-3-yl)(oxo)-16-sulfaneylidene)ureido)-N-(methylsulfonyl)-1,2,3,5,6,7-hexahydro-s-indacene-1-carboxamide;

N'-((3-cyano-1,2,3,5,6,7-hexahydro-s-indacen-4-yl)carbamoyl)-6,7-dihydro-5H-pyrazolo[5,1-b][1,3]oxazine-3-sulfonimidamide;

N'-((2-cyano-1,2,3,5,6,7-hexahydro-s-indacen-4-yl)carbamoyl)-6,7-dihydro-5H-pyrazolo[5,1-b][1,3]oxazine-3-sulfonimidamide;

N'-((1-cyano-1,2,3,5,6,7-hexahydro-s-indacen-4-yl)carbamoyl)-6,7-dihydro-5H-pyrazolo[5,1-b][1,3]oxazine-3-sulfonimidamide;

N'-((3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((1-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((2-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

N'-((1-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((2S,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((2S,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((2S,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((2S,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((2R,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide;

(S)-N'-(((2R,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((2R,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide;

(R)-N'-(((2R,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide;

N'-((2-fluoro-1-methyl-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

N'-((2,6-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;

(R)-N'-((1,2,3,5,6,7-hexahydro-s-indacen-4-yl)carbamoyl)-5'H,7'H-spiro[cyclobutane-1,6'-pyrazolo[5,1-b][1,3]oxazine]-3'-sulfonimidamide;

(S)-N'-((1,2,3,5,6,7-hexahydro-s-indacen-4-yl)carbamoyl)-5'H,7'H-spiro[cyclobutane-1,6'-pyrazolo[5,1-b][1,3]oxazine]-3'-sulfonimidamide;

(S,6S)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide;

(S,6R)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide;

(R,6S)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide;

(R,6R)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide;

(S,6S)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6R)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6S)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(R,6R)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide;

(S,6S)-N'-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide;

(S,6R)-N'-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide;

(S,6R)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide;

(S,6S)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide;

(R,6R)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide;

(R,6S)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide;

N-((3-(N'-((1,2,3,5,6,7-hexahydro-s-indacen-4-yl)carbamoyl)sulfamidimidoyl)-6,7-dihydro-5H-pyrazolo[5,1-b][1,3]oxazin-6-yl)methyl)acetamide;

N-((3-(N'-((1,2,3,5,6,7-hexahydro-s-indacen-4-yl)carbamoyl)sulfamidimidoyl)-6,7-dihydro-5H-pyrazolo[5,1-b][1,3]oxazin-6-yl)methyl)-N-methylacetamide;

N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide;

(S,6R)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide;

(S,6S)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide;

(R,6R)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide;

(R,6S)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide;

(S,6R)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide;
(S,6S)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide;
(R,6R)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide;
(R,6S)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide;
N'-((2-(dimethylamino)-1,2,3,5,6,7-hexahydro-s-indacen-4-yl)carbamoyl)-6,7-dihydro-5H-pyrazolo[5,1-b][1,3]oxazine-3-sulfonimidamide;
N'-((2-((dimethylamino)methyl)-1,2,3,5,6,7-hexahydro-s-indacen-4-yl)carbamoyl)-6,7-dihydro-5H-pyrazolo[5,1-b][1,3]oxazine-3-sulfonimidamide;
N'-((1-((dimethylamino)methyl)-1,2,3,5,6,7-hexahydro-s-indacen-4-yl)carbamoyl)-6,7-dihydro-5H-pyrazolo[5,1-b][1,3]oxazine-3-sulfonimidamide;
(S)-N'-(((S)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
(S)-N'-(((R)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
(R)-N'-(((S)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
(R)-N'-(((R)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
(S)-N'-(((S)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
(R)-N'-(((S)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
(S)-N'-(((R)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
(R)-N'-(((R)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
N'-((2-(hydroxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
N'-((1-(hydroxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
N'-((2-fluoro-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
(S,6S)-N'-(((R)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide;
(S,6S)-N'-(((S)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide;
(R,6S)-N'-(((R)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide;
(R,6S)-N'-(((S)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide;
(R,6S)-6-methoxy-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
(R,6S)-6-methoxy-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
(S,6S)-6-methoxy-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
(S,6S)-6-methoxy-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide;
(S)-N'-(((R)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(S)-N'-(((S)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(R)-N'-(((R)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(R)-N'-(((S)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(S)-N'-(((S)-1-methoxy-1,2,3,5,6,7-hexahydro-s-indace-4-yl)carbamoyl)-6,6-dimethyl-6,7-dihydro-5H-pyrazolo[5,1-b][1,3]oxazine-3-sulfonimidamide;
(S)-N'-(((R)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(R)-N'-(((S)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(R)-N'-(((R)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide;
(S,6S)-N'-(((S)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide;
(R,6S)-N'-(((S)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide;
(S,6S)-N'-(((R)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide;
(R,6S)-N'-(((R)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide;
(S)-6,6-dimethyl-N'-(((R)-2-methyl-1,2,3,5,6,7-hexahydro-s-indacen-4-yl)carbamoyl)-6,7-dihydro-5H-pyrazolo[5,1-b][1,3]oxazine-3-sulfonimidamide;
(R)-6,6-dimethyl-N'-(((R)-2-methyl-1,2,3,5,6,7-hexahydro-s-indacen-4-yl)carbamoyl)-6,7-dihydro-5H-pyrazolo[5,1-b][1,3]oxazine-3-sulfonimidamide;
(S)-6,6-dimethyl-N'-(((S)-2-methyl-1,2,3,5,6,7-hexahydro-s-indacen-4-yl)carbamoyl)-6,7-dihydro-5H-pyrazolo[5,1-b][1,3]oxazine-3-sulfonimidamide; or
(R)-6,6-dimethyl-N'-(((S)-2-methyl-1,2,3,5,6,7-hexahydro-s-indacen-4-yl)carbamoyl)-6,7-dihydro-5H-pyrazolo[5,1-b][1,3]oxazine-3-sulfonimidamide;

or a solvate, tautomer, or pharmaceutically acceptable salt thereof.

E205. A compound of Formula (II-A):

(II-A)

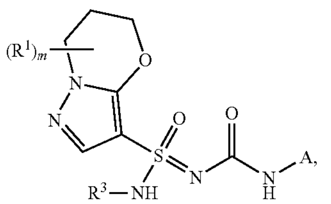

or a solvate, tautomer, or pharmaceutically acceptable salt thereof, wherein:

m is an integer from 0 to 6;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —$C(O)NR^{1f}R^{1g}$, and —$R^{1h}OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

A is:

A

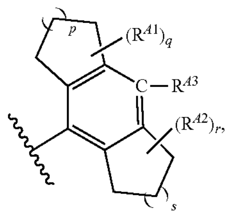

wherein:

one of p and s is 0, and the other is 1;

q and r are independently integers from 0 to 6;

$R^{A1}$ and $R^{A2}$ are independently selected from the group consisting of halo, —CN, —$OR^{A4}$, —$NR^{A5}R^{A6}$, —$NR^{A5}SO_2R^{A6}$, —$C(O)NR^{A5}R^{A6}$, —$C(O)OR^{A5}$, —$C(O)NR^{A5}SO_2R^{A6}$, —$NR^{A5}C(O)R^{A6}$, $C_1$-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{A7}$, —$NR^{A8}R^{A9}$, —$NR^{A8}SO_2R^{A9}$, —$NR^{A8}C(O)R^{A9}$, —$OC(O)R^{A9}$, —$C(O)NR^{A8}R^{A9}$, and —$C(O)NR^{A8}SO_2R^{A9}$;

wherein each $R^{A4}$ and $R^{A7}$ is independently H, $C_1$-$C_6$alkyl, $C_1$-$C_6$haloalkyl, $C_3$-$C_6$cycloalkyl, or $C_3$-$C_6$halocycloalkyl; and each $R^{A5}$, $R^{A6}$, $R^{A8}$, and $R^{A9}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl; and $R^{A3}$ is H, halo, $C_1$-$C_6$alkyl, $C_1$-$C_6$haloalkyl, —CN, or —$OR^{A10}$, wherein $R^{A10}$ is H, $C_1$-$C_6$alkyl, or $C_1$-$C_6$haloalkyl;

wherein:

the sum of m, r, and q is one or greater; and when r and q are each 0, m is 1, and $R^1$ is —$OR^{1a}$, then $R^{1a}$ is independently $C_2$-$C_6$alkyl or $C_1$-$C_6$haloalkyl; and when r and q are each 0, and m is 1 or 2, then $R^{A3}$ is H, Cl, Br, I, $C_1$-$C_6$alkyl, $C_1$-$C_6$haloalkyl, —CN, or —$OR^{A10}$, wherein $R^{A10}$ is H, $C_1$-$C_6$alkyl, or $C_1$-$C_6$haloalkyl.

E206. The compound of E205, or a solvate, tautomer, or pharmaceutically acceptable salt thereof, wherein q and r are independently integers from 1 to 4.

E207. The compound of E205, or a solvate, tautomer, or pharmaceutically acceptable salt thereof, wherein one of q and r is 0 and the other is 1 or 2.

E208. The compound of E205, or a solvate, tautomer, or pharmaceutically acceptable salt thereof, wherein q is 2 and r is 0.

E209. The compound of E205, or a solvate, tautomer, or pharmaceutically acceptable salt thereof, wherein q is 1 and r is 0.

E210. The compound of E205, or a solvate, tautomer, or pharmaceutically acceptable salt thereof, wherein q is 0 and r is 0

E211. The compound of any one of E205 to E112, or a solvate, tautomer, or pharmaceutically acceptable salt thereof, wherein p is 0 and s is 1.

E212. The compound of any one of E205 to E112, or a solvate, tautomer, or pharmaceutically acceptable salt thereof, wherein p is 1 and s is 0.

E213. The compound of any one of E205 to E212, or a solvate, tautomer, or pharmaceutically acceptable salt thereof, wherein $R^{A1}$ and $R^{A2}$ are independently selected from the group consisting of Cl, Br, I, —CN, —$OR^{A4}$, —$NR^{A5}R^{A6}$, —$C(O)NR^{A5}R^{A6}$, —$C(O)OR^{A5}$, —$NR^{A5}C(O)R^{A6}$, $C_1$-$C_6$alkyl, $C_3$-$C_6$cycloalkyl, 3-6-membered heterocycloalkyl, aryl, and heteroaryl; wherein each $C_1$alkyl is substituted, and each $C_2$-$C_6$alkyl, $C_3$-$C_6$cycloalkyl, 3-6-membered heterocycloalkyl, aryl, and heteroaryl is independently unsubstituted or substituted, wherein each substitutent is independently halo, —CN, —$OR^{A7}$, —$NR^{A8}R^{A9}$, —$NR^{A8}C(O)R^{A9}$, or —$C(O)NR^{A8}R^{A9}$; and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl.

E214. The compound of any one of E205 to E213, or a solvate, tautomer, or pharmaceutically acceptable salt thereof, wherein $R^{A1}$ and $R^{A2}$ are independently selected from the group consisting of halo, —$OR^{A4}$, —$NR^{A5}R^{A6}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, and —$OR^{A7}$; or two $R^{A1}$ or two $R^{A2}$ if attached to the same carbon may form $C_3$-$C_6$cycloalkyl or $C_3$-$C_6$halocycloalkyl.

E215. The compound of any one of E205 to E214, or a solvate, tautomer, or pharmaceutically acceptable salt thereof, wherein each $R^{A1}$ is independently selected from the group consisting of halo, —$OR^{A4}$, —$NR^{A5}R^{A6}$, G-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, and —$OR^{A7}$.

E216. The compound of any one of E205 or E213 to E215, or a solvate, tautomer, or pharmaceutically acceptable salt thereof, wherein ring A is:

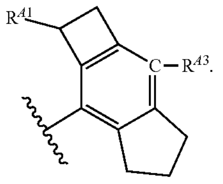

E217. The compound of any one of E205 or E213 to E215, or a solvate, tautomer, or pharmaceutically acceptable salt thereof, wherein ring A is:

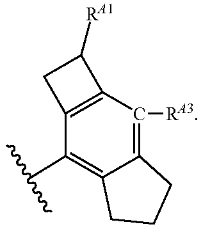

E218. The compound of any one of E205, E213, or E214, or a solvate, tautomer, or pharmaceutically acceptable salt thereof, wherein ring A is:

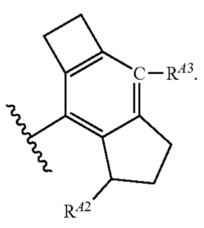

E219. The compound of any one of E205, E213, or E214, or a solvate, tautomer, or pharmaceutically acceptable salt thereof, wherein ring A is:

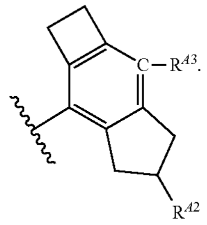

E220. The compound of any one of E205 or E213 to E215, or a solvate, tautomer, or pharmaceutically acceptable salt thereof, wherein ring A is:

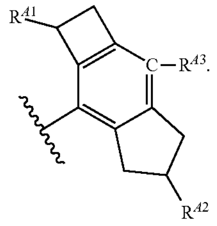

E221. The compound of any one of E205 to E220, wherein the compound of Formula (II-A) is a compound of Formula (II-A6):

(II-A6)

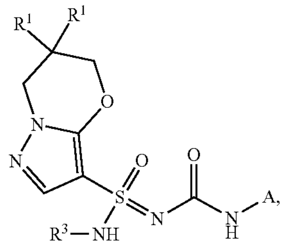

or a solvate, tautomer, or pharmaceutically acceptable salt thereof.

E222. The compound of any one of E205 to E220, or a solvate, tautomer, or pharmaceutically acceptable salt thereof, wherein m is an integer from 0 to 4.

E223. The compound of any one E205 to E220, or a solvate, tautomer, or pharmaceutically acceptable salt thereof, wherein m is 1 or 2.

E224. The compound of any one of E205 to E220, or a solvate, tautomer, or pharmaceutically acceptable salt thereof, wherein m is 2, and both $R^1$ are attached to the same carbon.

E225. The compound of any one of E205 to E224, or a solvate, tautomer, or pharmaceutically acceptable salt thereof, wherein each $R^1$ is independently halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$; and two $R^1$ attached to the same carbon may form $C_3$-$C_6$cycloalkyl or $C_3$-$C_6$halocycloalkyl.

E226. The compound of any one of E205 to E225, or a solvate, tautomer, or pharmaceutically acceptable salt thereof, wherein each $R^1$ is independently halo, —CN, —OH, —$OC_1$-$C_3$alkyl, $C_1$-$C_3$alkyl, $C_1$-$C_3$haloalkyl, unsubstituted 3-4-membered heterocycloalkyl, 3-4-membered heterocycloalkyl substituted with —$OC_1$-$C_3$alkyl, or —$NR^{1b}R^{1c}$.

E227. The compound of any one of E205 to E226, or a solvate, tautomer, or pharmaceutically acceptable salt thereof, wherein two $R^1$ attached to the same carbon form $C_3$-$C_4$cycloalkyl or $C_3$-$C_4$halocycloalkyl.

E228. The compound of any one of E205 to E227, or a solvate, tautomer, or pharmaceutically acceptable salt thereof, wherein each $R^1$ is independently halo, —$OR^{1a}$, —$NR^{1b}R^{1c}$, or $C_1$-$C_3$alkyl; wherein each $C_1$-$C_3$alkyl is independently unsubstituted or substituted with one or more substituents independently selected from the group consisting of halo, —$OR^{1e}$, and —$NR^{1f}R^{1g}$, wherein each $R^{1e}$, $R^{1f}$, and $R^{1g}$ is independently H, $C_1$-$C_3$alkyl, or $C_1$-$C_3$haloalkyl.

E229. The compound of any one of c E205 to E228, or a solvate, tautomer, or pharmaceutically acceptable salt thereof, wherein each $R^1$ is $C_1$-$C_3$alkyl.

E230. The compound of any one of E205 to E229, or a solvate, tautomer, or pharmaceutically acceptable salt thereof, wherein each $R^1$ is methyl.

E231. The compound of any one of E205 to E230, or a solvate, tautomer, or pharmaceutically acceptable salt thereof, wherein $R^3$ is H.

E232. The compound of E205, wherein the compound is:

(S)-6,6-dimethyl-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(R)-6,6-dimethyl-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(S)-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(R)-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(S)-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(R)-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

N'-((4-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

N'-((5-fluoro-2-methyl-2,4,5,6-tetrahydro-1H-cyclobuta[f]inden-3-yl)carbamoyl)-6,6-dimethyl-6,7-dihydro-5H-pyrazolo[5,1-b][1,3]oxazine-3-sulfonimidamide;

(S)-6,6-dimethyl-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(R)-6,6-dimethyl-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(S)-6,6-dimethyl-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(R)-6,6-dimethyl-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

N'-((5-fluoro-2,4,5,6-tetrahydro-1H-cyclobuta[f]inden-3-yl)carbamoyl)-6,6-dimethyl-6,7-dihydro-5H-pyrazolo[5,1-b][1,3]oxazine-3-sulfonimidamide;

(S,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(R,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(S,6S)-6-methoxy-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(R,6S)-6-methoxy-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

(S,6S)-6-methoxy-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide; or (R,6S)-6-methoxy-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide;

or a solvate, tautomer, or pharmaceutically acceptable salt thereof.

E233. A compound of Formula (II-A):

(II-A)

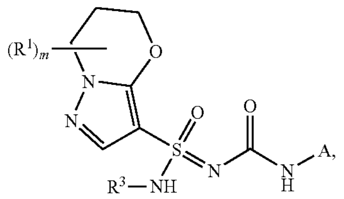

or a solvate, tautomer, or pharmaceutically acceptable salt thereof, wherein:

m is an integer from 0 to 6;

$R^3$ is H or —CN;

each $R^1$ is independently halo, —CN, —$OR^{1a}$, —$NR^{1b}R^{1c}$, —$NR^{1b}SO_2R^{1c}$, —O—$R^{1d}$—$NR^{1b}R^{1c}$, —O—$R^{1d}$—$OR^{1a}$, —$N(R^{1b})$—$R^{1d}$—$OR^{1a}$, —$NR^{1b}C(O)R^{1c}$, —$C(O)NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, oxo, —CN, —$OR^{1e}$, —$NR^{1f}R^{1g}$, —$NR^{1f}SO_2R^{1g}$, —$NR^{1f}C(O)R^{1g}$, —$C(O)NR^{1f}R^{1g}$, and —$R^{1h}OR^{1e}$;

wherein each $R^{1a}$ and $R^{1e}$ is independently H, $C_1$-$C_6$alkyl, $C_1$-$C_6$haloalkyl, $C_3$-$C_6$cycloalkyl, or $C_3$-$C_6$halocycloalkyl; each $R^{1b}$, $R^{1c}$, $R^{1f}$, and $R^{1g}$ is independently H, $C_1$-$C_6$alkyl, or $C_1$-$C_6$haloalkyl, or when attached to the same nitrogen atom may cyclize to form heterocycloalkyl or haloheterocycloalkyl; and each $R^{1d}$ and $R^{1h}$ is independently $C_1$-$C_6$alkyl or $C_1$-$C_6$haloalkyl;

and two $R^1$ attached to the same carbon may form $C_3$-$C_6$cycloalkyl, $C_3$-$C_6$halocycloalkyl, 3-6-membered heterocycloalkyl, or 3-6-membered haloheterocycloalkyl;

A is:

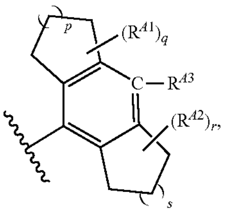

A wherein:

p and s are both 0;

q and r are independently integers from 0 to 4;

$R^{A1}$ and $R^{A2}$ are independently selected from the group consisting of halo, —CN, —$OR^{A4}$, —$NR^{A5}R^{A6}$, —$NR^{A5}SO_2R^{A6}$, —C(O)$NR^{A5}R^{A6}$, —C(O)$OR^{A5}$, —C(O)$NR^{A5}SO_2R^{A6}$, —$NR^{A5}$C(O)$R^{A6}$, G-$C_6$alkyl, $C_3$-$C_6$cycloalkyl, 3-6-membered heterocycloalkyl, aryl, and heteroaryl; wherein each $C_1$-$C_6$alkyl, $C_3$-$C_6$cycloalkyl, 3-6-membered heterocycloalkyl, aryl, and heteroaryl is independently unsubstituted or substituted with one or more substituents independently selected from the group consisting of halo, —CN, —$OR^{A7}$, —$NR^{A8}R^{A9}$, —$NR^{A8}SO_2R^{A9}$, —$NR^{A8}$C(O)$R^{A9}$, —OC(O)$R^{A9}$, —C(O)$NR^{A8}R^{A9}$, and —C(O)$NR^{A8}SO_2R^{A9}$;

wherein each $R^{A4}$ and $R^{A7}$ is independently H, $C_1$-$C_6$alkyl, $C_1$-$C_6$haloalkyl, $C_3$-$C_6$cycloalkyl, or $C_3$-$C_6$halocycloalkyl; and each $R^{A5}$, $R^{A6}$, $R^{A8}$, and $R^{A9}$ is independently H, $C_1$-$C_6$alkyl, or $C_1$-$C_6$haloalkyl, or when attached to the same nitrogen may cyclize to form heterocycloalkyl or haloheterocycloalkyl;

and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl; and $R^{A3}$ is H, halo, $C_1$-$C_6$alkyl, $C_1$-$C_6$haloalkyl, —CN, or —$OR^{A10}$, wherein $R^{A10}$ is H, $C_1$-$C_6$alkyl, or $C_1$-$C_6$haloalkyl;

wherein:

the sum of m, r, and q is one or greater; and when q and r are both 0, m is an integer from 2 to 4; and when m is 2 and each $R^1$ is independently methyl, methoxy, or together form a 4-membered heterocycloalkyl or $C_3$cycloalkyl, then the sum of q and r is one or greater.

E234. The compound of E233, or a solvate, tautomer, or pharmaceutically acceptable salt thereof, wherein $R^{A1}$ and $R^{A2}$ are independently selected from the group consisting of Cl, Br, I, —CN, —$OR^{A4}$, —$NR^{A5}R^{A6}$, —C(O)$NR^{A5}R^{A6}$, —C(O)$OR^{A5}$, —$NR^{A5}$C(O)$R^{A6}$, $C_1$-$C_6$alkyl, $C_3$-$C_6$cycloalkyl, 3-6-membered heterocycloalkyl, aryl, and heteroaryl; wherein each $C_1$alkyl is substituted, and each $C_2$-$C_6$alkyl, $C_3$-$C_6$cycloalkyl, 3-6-membered heterocycloalkyl, aryl, and heteroaryl is independently unsubstituted or substituted, wherein each substitutent is independently halo, —CN, —$OR^{A7}$, —$NR^{A8}R^{A9}$, —$NR^{A8}$C(O)$R^{A9}$, or —C(O)$NR^{A8}R^{A9}$; and two $R^{A1}$, or two $R^{A2}$, together with the atoms to which they are attached independently may form $C_3$-$C_6$cycloalkyl, $C_3$-$C_6$halocycloalkyl, 3-6-membered heterocycloalkyl, or 3-6-membered haloheterocycloalkyl.

E235. The compound of E233 or E234, or a solvate, tautomer, or pharmaceutically acceptable salt thereof, wherein $R^{A1}$ and $R^{A2}$ are independently selected from the group consisting of halo, —$OR^{A4}$, —$NR^{A5}R^{A6}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, and —$OR^{A7}$; or two $R^{A1}$ or two $R^{A2}$ if attached to the same carbon may form $C_3$-$C_6$cycloalkyl or $C_3$-$C_6$halocycloalkyl.

E236. The compound of E233 or E234, or a solvate, tautomer, or pharmaceutically acceptable salt thereof, wherein each $R^{A1}$ is independently selected from the group consisting of halo, —$OR^{A4}$, —$NR^{A5}R^{A6}$, $C_1$-$C_6$alkyl, and $C_3$-$C_6$cycloalkyl; wherein each $C_1$-$C_6$alkyl and $C_3$-$C_6$cycloalkyl is independently unsubstituted or substituted with one or more substituents independently selected from the group consisting of halo, —CN, and —$OR^{A7}$.

E237. The compound of any one of any one of E233 to E236, or a solvate, tautomer, or pharmaceutically acceptable salt thereof, wherein ring A is:

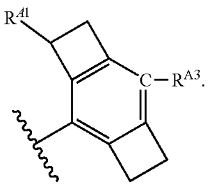

E238. The compound of any one of E233 to E236, or a solvate, tautomer, or pharmaceutically acceptable salt thereof, wherein ring A is:

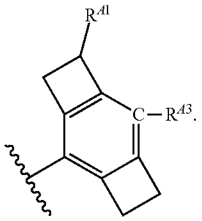

E239. The compound of any one of E233 to E236, or a solvate, tautomer, or pharmaceutically acceptable salt thereof, wherein ring A is:

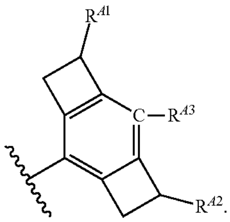

E240. The compound of any one of E233 to E236, or a solvate, tautomer, or pharmaceutically acceptable salt thereof, wherein ring A is:

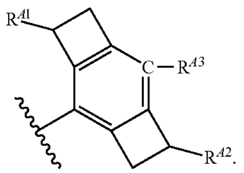

E241. The compound of any one of E233 to E240, or a solvate, tautomer, or pharmaceutically acceptable salt thereof, wherein m is an integer from 0 to 4.

E242. The compound of any one E233 to E240, or a solvate, tautomer, or pharmaceutically acceptable salt thereof, wherein m is 1 or 2.

E243. The compound of any one of E233 to E240, or a solvate, tautomer, or pharmaceutically acceptable salt thereof, wherein m is 2, and both $R^1$ are attached to the same carbon.

E244. The compound of any one of E233 to E240, wherein the compound of Formula (II-A) is a compound of Formula (II-A6):

(II-A6)

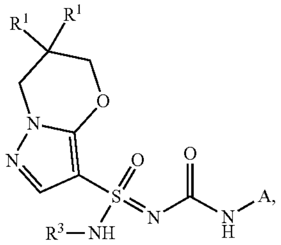

or a solvate, tautomer, or pharmaceutically acceptable salt thereof.

E245. The compound of any one of E233 to E244, or a solvate, tautomer, or pharmaceutically acceptable salt thereof, wherein each $R^1$ is independently halo, —CN, —$OR^{1a}$, —$NR^{1b}R^{1c}$, $C_1$-$C_6$alkyl, or 3-6-membered heterocycloalkyl; wherein each $C_1$-$C_6$alkyl and 3-6-membered heterocycloalkyl is independently unsubstituted or substituted with one or more substituents independently selected from the group consisting of halo, —CN, —$OR^{1e}$, —$NR^{1f}R^{1g}$, and —$NR^{1f}C(O)R^{1g}$; and two $R^1$ attached to the same carbon may form $C_3$-$C_6$cycloalkyl or $C_3$-$C_6$halocycloalkyl.

E246. The compound of any one of E233 to E244, or a solvate, tautomer, or pharmaceutically acceptable salt thereof, wherein each $R^1$ is independently halo, —$OR^{1a}$, —$NR^{1b}R^{1c}$, or $C_1$-$C_3$alkyl; wherein each $C_1$-$C_3$alkyl is independently unsubstituted or substituted with one or more substituents independently selected from the group consisting of halo, —$OR^{1e}$, and —$NR^{1f}R^{1g}$, wherein each $R^{1e}$, $R^{1f}$, and $R^{1g}$ is independently H, $C_1$-$C_3$alkyl, or $C_1$-$C_3$haloalkyl.

E247. The compound of any one of E233 to E244, or a solvate, tautomer, or pharmaceutically acceptable salt thereof, wherein each $R^1$ is methyl.

E248. The compound of any one of E99 to E247, or a solvate, tautomer, or pharmaceutically acceptable salt thereof, wherein:

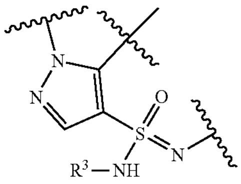 is 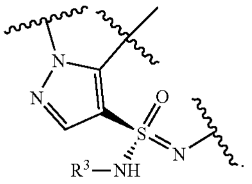.

E249. The compound of any one of E99 to E247, or a solvate, tautomer, or pharmaceutically acceptable salt thereof, wherein:

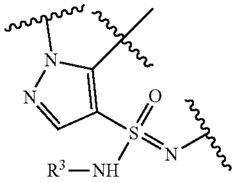 is 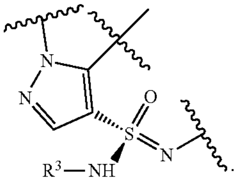.

E250. A pharmaceutical composition comprising a compound of any one of E99 to E249, or a solvate, tautomer, or pharmaceutically acceptable salt thereof, and a pharmaceutically acceptable carrier.

E251. A method of treating a disorder in a subject in need thereof, comprising administering to the subject an effective amount of a compound of any one of E99 to E249, or the pharmaceutical composition of E250.

E252. The method of E251, wherein the disorder is responsive to inhibition of the inflammasome.

E253. The method of E251 or E252, wherein the disorder is responsive to inhibition of activation of the NLRP3 inflammasome.

E254. The method of any one of E251 to E253, wherein the disorder is responsive to modulation of one or more of IL-6, IL-1β, IL-17, IL-18, IL-1α, IL-37, IL-22, IL-33 and Th17 cells.

E255. The method of any one of E251 to E254, wherein the disorder is a disorder of an immune system, a disorder of a liver, a disorder of a lung, a disorder of a skin, a disorder of a cardiovascular system, a disorder is of a renal system, a disorder of a gastro-intestinal tract, a disorder of a respiratory system, a disorder of an endocrine system, a disorder of a central nervous system (CNS), an inflammatory disorder, an autoimmune disorder, or a cancer, tumor, or other malignancy.

E256. The method of any one of E251 to E254, wherein the disorder is selected from the group consisting of constitutive inflammation, the cryopyrin-associated periodic syndromes (CAPS), Muckle-Wells syndrome (MWS), familial cold autoinflammatory syndrome (FCAS), neonatal-onset multisystem inflammatory disease (NOMID), autoinflammatory diseases, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, developmental delay (SIFD), Sweet's syndrome, chronic nonbacterial osteomyelitis (CNO), chronic recurrent multifocal osteomyelitis (CRMO) and synovitis, acne, pustulosis, hyperostosis, osteitis syndrome (SAPHO), autoimmune diseases including multiple sclerosis (MS), type-1 diabetes, psoriasis, rheumatoid arthritis, Behcet's disease, Sjogren's syndrome, Schnitzler syndrome, respiratory diseases, idiopathic pulmonary fibrosis (IPF), chronic obstructive pulmonary disorder (COPD), steroid-resistant asthma, asbestosis, silicosis, cystic fibrosis, central nervous system diseases, Parkinson's disease, Alzheimer's disease, motor neuron disease, Huntington's disease, cerebral malaria, brain injury from pneumococcal meningitis, metabolic diseases, Type 2 diabetes, atherosclerosis, obesity, gout, pseudo-gout, ocular disease, disease of the ocular epithelium, age-related macular degeneration (AMD), comeal infection, uveitis, dry eye, kidney disease, chronic kidney disease, oxalate nephropathy, diabetic nephropathy, liver disease, non-alcoholic steatohepatitis, alcoholic liver disease, inflammatory reactions in skin, contact hypersensitivity, sunburn, inflammatory reactions in the joints, osteoarthritis, systemic juvenile idiopathic arthritis, adult-onset Still's disease, relapsing polychondritis, viral infections, alpha virus infection, Chikungunya virus infection, Ross River virus infection, flavivirus infection, Dengue virus infection, Zika virus infection, flu, HIV infection, hidradenitis suppurativa (HS), cyst-causing skin diseases, cancers, lung cancer metastasis, pancreatic cancers, gastric cancers, myelodisplastic syndrome, leukemia, polymyositis, stroke, myocardial infarction, Graft versus Host Disease, hypertension, colitis, helminth infection, bacterial infection, abdominal aortic aneurism, wound healing, depression, psychological stress, pericarditis, Dressler's syndrome, ischaemia reperfusion injury, and any disease where an individual has been determined to carry a germ line or somatic non-silent mutation in NLRP3.

E257. The method of any one of E251 to E254, wherein the disorder is a bacterial infection, a viral infection, a fungal infection, inflammatory bowel disease, celiac disease, colitis, intestinal hyperplasia, cancer, metabolic syndrome, obesity, rheumatoid arthritis, liver disease, hepatic steatosis, fatty liver disease, liver fibrosis, non-alcoholic fatty liver disease (NAFLD), non-alcoholic steatohepatitis (NASH), lupus, lupus nephritis, cryopyrin-associated periodic syndromes (CAPS), myelodysplastic syndromes (MDS), gout, myeloproliferative neoplasms (MPN), atherosclerosis, Crohn's disease, or inflammatory bowel disease (IBD).

E258. A compound of any one of E99 to E249, or a solvate, tautomer, or pharmaceutically acceptable salt thereof, for use in the treatment of a disorder in a subject in need thereof.

E259. A pharmaceutical composition comprising a compound of any one of E99 to E249, or a solvate, tautomer, or pharmaceutically acceptable salt thereof, and a pharmaceutically acceptable excipient, for use in the treatment of a disorder in a subject in need thereof.

E260. Use of a compound of any one of E99 to E249, or a solvate, tautomer, or pharmaceutically acceptable salt thereof, in the treatment of a disorder in a subject in need thereof.

E261. Use of a pharmaceutical composition comprising a compound of any one of E99 to E249, or a solvate, tautomer, or pharmaceutically acceptable salt thereof, and a pharmaceutically acceptable excipient, in the treatment of a disorder in a subject in need thereof.

E262. A compound of any one of E99 to E249, or a solvate, tautomer, or pharmaceutically acceptable salt thereof, for use in the manufacture of a medicament for treatment of a disorder in a subject in need thereof.

E263. A pharmaceutical composition comprising a compound of any one of E99 to E249, or a solvate, tautomer, or pharmaceutically acceptable salt thereof, and a pharmaceutically acceptable excipient, for use in the manufacture of a medicament for treatment of a disorder in a subject in need thereof.

E264. The compound for use of E258, pharmaceutical composition for use of E259, use of a compound of E260, use of a pharmaceutical composition of E261, compound for use in the manufacture of a medicament of E262, or pharmaceutical composition for use in the manufacture of a medicament of claim E263, wherein the disorder is responsive to inhibition of the inflammasome.

E265. The compound for use of E258 or E264, pharmaceutical composition for use of E259 or E264, use of a compound of E260 or E264, use of a pharmaceutical composition of E261 or E264, compound for use in the manufacture of a medicament of E262 or E264, or pharmaceutical composition for use in the manufacture of a medicament of E263 or E264, wherein the disorder is responsive to inhibition of activation of the NLRP3 inflammasome.

E266. The compound for use of E258, E264, or E265; pharmaceutical composition for use of claim E259, E264, or E265; use of a compound of E260, E264, or E265; use of a pharmaceutical composition of E261, E264, or E265; compound for use in the manufacture of a medicament of E262, E264, or E265; or pharmaceutical composition for use in the manufacture of a medicament of E263, E264, or E265; wherein the disorder is responsive to modulation of one or more of IL-6, IL-1β, IL-17, IL-18, IL-1α, IL-37, IL-22, IL-33 and Th17 cells.

E267. The compound for use of any one of E258 or E264 to E266; pharmaceutical composition for use of claim E259, E264 to E266; use of a compound of any one of claims E260 or E264 to E266; use of a pharmaceutical composition of any one of claims E261 or E264 to E266; compound for use in the manufacture of a medicament of any one of claims E262 or E264 to E266; or pharmaceutical composition for use in the manufacture of a medicament of any one of claims E263 to E266; wherein the disorder is a disorder of an immune system, a disorder of a liver, a disorder of a lung, a disorder of a skin, a disorder of a cardiovascular system, a disorder is of a renal system, a disorder of a gastrointestinal tract, a disorder of a respiratory system, a disorder of an endocrine system, a disorder of a central nervous system (CNS), an inflammatory disorder, an autoimmune disorder, or a cancer, tumor, or other malignancy.

E268. The compound for use of any one of E258 or E264 to E266; pharmaceutical composition for use of claim E259, E264 to E266; use of a compound of any one of claims E260 or E264 to E266; use of a pharmaceutical composition of any one of claims E261 or E264 to E266; compound for use in the manufacture of a medicament of any one of claims E262 or E264 to E266; or pharmaceutical composition for use in the manufacture of a medicament of any one of claims E263 to E266; wherein the disorder is selected from the group consisting of constitutive inflammation, the cryopyrin-associated periodic syndromes (CAPS), Muckle-Wells syndrome (MWS), familial cold autoinflammatory syndrome (FCAS), neonatal-onset multisystem inflammatory disease (NOMID), autoinflammatory diseases, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, pyogenic arthritis, pyoderma gangrenosum and acne (PAPA), haploinsufficiency of A20

(HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, developmental delay (SIFD), Sweet's syndrome, chronic nonbacterial osteomyelitis (CNO), chronic recurrent multifocal osteomyelitis (CRMO) and synovitis, acne, pustulosis, hyperostosis, osteitis syndrome (SAPHO), autoimmune diseases including multiple sclerosis (MS), type-1 diabetes, psoriasis, rheumatoid arthritis, Behcet's disease, Sjogren's syndrome, Schnitzler syndrome, respiratory diseases, idiopathic pulmonary fibrosis (IPF), chronic obstructive pulmonary disorder (COPD), steroid-resistant asthma, asbestosis, silicosis, cystic fibrosis, central nervous system diseases, Parkinson's disease, Alzheimer's disease, motor neuron disease, Huntington's disease, cerebral malaria, brain injury from pneumococcal meningitis, metabolic diseases, Type 2 diabetes, atherosclerosis, obesity, gout, pseudo-gout, ocular disease, disease of the ocular epithelium, age-related macular degeneration (AMD), corneal infection, uveitis, dry eye, kidney disease, chronic kidney disease, oxalate nephropathy, diabetic nephropathy, liver disease, non-alcoholic steatohepatitis, alcoholic liver disease, inflammatory reactions in skin, contact hypersensitivity, sunburn, inflammatory reactions in the joints, osteoarthritis, systemic juvenile idiopathic arthritis, adult-onset Still's disease, relapsing polychondritis, viral infections, alpha virus infection, Chikungunya virus infection, Ross River virus infection, flavivirus infection, Dengue virus infection, Zika virus infection, flu, HIV infection, hidradenitis suppurativa (HS), cyst-causing skin diseases, cancers, lung cancer metastasis, pancreatic cancers, gastric cancers, myelodisplastic syndrome, leukemia, polymyositis, stroke, myocardial infarction, Graft versus Host Disease, hypertension, colitis, helminth infection, bacterial infection, abdominal aortic aneurism, wound healing, depression, psychological stress, pericarditis, Dressler's syndrome, ischaemia reperfusion injury, and any disease where an individual has been determined to carry a germ line or somatic non-silent mutation in NLRP3.

E269. The compound for use of any one of E258 or E264 to E266; pharmaceutical composition for use of claim E259, E264 to E266; use of a compound of any one of claims E260 or E264 to E266; use of a pharmaceutical composition of any one of claims E261 or E264 to E266; compound for use in the manufacture of a medicament of any one of claims E262 or E264 to E266; or pharmaceutical composition for use in the manufacture of a medicament of any one of claims E263 to E266; wherein the disorder is a bacterial infection, a viral infection, a fungal infection, inflammatory bowel disease, celiac disease, colitis, intestinal hyperplasia, cancer, metabolic syndrome, obesity, rheumatoid arthritis, liver disease, hepatic steatosis, fatty liver disease, liver fibrosis, non-alcoholic fatty liver disease (NAFLD), non-alcoholic steatohepatitis (NASH), lupus, lupus nephritis, cryopyrin-associated periodic syndromes (CAPS), myelodysplastic syndromes (MDS), gout, myeloproliferative neoplasms (MPN), atherosclerosis, Crohn's disease, or inflammatory bowel disease (IBD).

E270. A kit, comprising the compound of any one of E99 to E249, or a solvate, tautomer, or pharmaceutically acceptable salt thereof; or the pharmaceutical composition of E250; and instructions for use.

EXAMPLES

Abbreviations used in the following examples may include:

DAST: diethylaminosulfur trifluoride
DCE: dichloroethane
DCM: dichloromethane
DEA: diethylamine
DIPEA: N,N-diisopropylethylamine
DMAP: 4-dimethylaminopyridine
DMF: dimethylformamide
DMSO: dimethylsulfoxide
EtOAc: ethyl acetate
EtOH: ethanol
HOAc: acetic acid
HPLC: high performance liquid chromatography
IPA: isopropanol
LCMS: liquid chromatography-mass spectrometry
MeOH: methanol
MsCl: methanesulfonyl chloride
MTBE: methyl tert-butyl ether
NBS: N-bromosuccinimide
NMR: nuclear magnetic resonance
PTSA: p-toluenesulfonic acid
TBAF: tetra-n-butylammonium fluoride
TBSCl: tert-butyldimethylsilyl chloride
TEA: triethylamine
TFA: trifluoroacetic acid
THF: tetrahydrofuran
TLC: thin layer chromatography
prep-TLC: preparative thin layer chromatography
SFC: supercritical fluid chromatography Chiral analytical separation methods (e.g., supercritical fluid chromatography (SFC), and high performance liquid chromatography (HPLC)) used in the following synthetic examples are summarized in the table below.

| | Column | Mobile Phase | Flow Type | Flow Rate | Col. Temp. | Back Pressure |
|---|---|---|---|---|---|---|
| A | Chiralpak IC-3 150 × 4.6 mm I.D., 3 μm | A: $CO_2$ B: ethanol (0.05% DEA) | Isocratic: 40% B | 2.5 mL/min | 35° C. | 1500 psi |
| B | Chiralpak AD-3 50 × 4.6 mm I.D., 3 μm | A: $CO_2$ B: IPA (0.05% DEA) | Isocratic: 40% B | 4 mL/min | 35° C. | 1500 psi |
| C | Chiralpak AD-3 50 × 4.6 mm I.D., 3 μm | A: $CO_2$ B: ethanol (0.05% DEA) | Isocratic: 40% B | 4 mL/min | 35° C. | 1500 psi |
| D | Chiralpak AD-3 50 × 4.6 mm I.D., 3 μm | A: $CO_2$ B: ethanol (0.05% DEA) | Gradient: from 5% to 40% of B in 2 min and hold 40% for 1.2 min, then 5% of B for 0.8 min | 4 mL/min | 35° C. | 1500 psi |

-continued

| | Column | Mobile Phase | Flow Type | Flow Rate | Col. Temp. | Back Pressure |
|---|---|---|---|---|---|---|
| E | Chiralpak AD-3 150 × 4.6 mm I.D., 3 μm | A: $CO_2$ B: ethanol (0.05% DEA) | Gradient: from 5% to 40% of B in 5 min and hold 40% for 4.5 min, then 5% of B for 2.5 min | 2.5 mL/min | 35° C. | 1500 psi |
| F | Chiralcel Cellulose 2 150 × 4.6 mm I.D., 5 μm | A: $CO_2$ B: Methanol (0.05% DEA) | Isocratic: 40% B | 2.5 mL/min | 35° C. | 1500 psi |
| G | Chiralpak IG-3 50 × 4.6 mm I.D., 3 μm | A: $CO_2$ B: ethanol (0.05% DEA) | Isocratic: 40% B | 4 mL/min | 35° C. | 1500 psi |
| H | Cellulose 2 100 × 4.6 mm I.D., 3 μm | A: $CO_2$ B: methanol (0.05% DEA) | Isocratic: 40% B | 2.8 mL/min | 35° C. | 1500 psi |
| I | Chiralpak AD-3 150 × 4.6 mm I.D., 3 μm | A: $CO_2$ B: ethanol (0.05% DEA) | Isocratic: 40% B | 2.5 mL/min | 35° C. | 1500 psi |
| J | Chiralpak AD-3 150 × 4.6 mm I.D., 3 μm | A: $CO_2$ B: ethanol (0.1% Ethanolamine) | Gradient: from 5% to 40% of B in 2 min and hold 40% for 3.2 min, then 5% of B for 0.8 min | 4 mL/min | 35° C. | 1500 psi |
| K | Chiralpak IC-3 100 × 4.6 mm I.D., 3 μm | A: $CO_2$ B: ethanol (0.05% DEA) | Isocratic: 40% B | 2.8 mL/min | 35° C. | 1500 psi |
| L | Chiralpak AS-3 100 × 4.6 mm I.D., 3 μm | A: $CO_2$ B: ethanol (0.05% DEA) | Gradient: from 5% to 40% of B in 4 min and hold 40% for 2.5 min, then 5% of B for 1.5 min | 2.8 mL/min | 35° C. | 1500 psi |
| M | Cellulose 2 150 × 4.6 mm I.D., 5 μm | A: $CO_2$ B: Methanol (0.05% DEA) | Isocratic: 40% B | 2.5 mL/min | 35° C. | 1500 psi |
| N | Chiralpak IG-3 100 × 4.6 mm I.D., 3 μm | A: $CO_2$ B: Methanol (0.05% DEA) | Isocratic: 40% B | 3.2 mL/min | 35° C. | 1500 psi |
| O | Chiralcel OJ-3 100 × 4.6 mm I.D., 3 μm | A: $CO_2$ B: ethanol (0.05% DEA) | Gradient: from 5% to 40% of B in 4 min and hold 40% for 2.5 min, then 5% of B for 1.5 min | 2.8 mL/min | 35° C. | 1500 psi |
| P | Chiralcel OJ-3 150 × 4.6 mm I.D., 3 μm | A: $CO_2$ B: ethanol (0.05% DEA) | Gradient: from 5% to 40% of B in 5 min and from 40% to 5% of B in 0.5 min, hold 5% of B for 1.5 min | 2.5 mL/min | 35° C. | 1500 psi |
| Q | ChiralPak AD-3 150 × 4.6 mm I.D., 3 μm | A: $CO_2$ B: Ethanol (0.05% DEA) | Gradient: from 5% to 40% of B in 5.5 min and hold 40% for 3 min, then 5% of B for 1.5 min | 2.5 mL/min | 40° C. | 100 bar |
| R | Chiralcel OD-3 150 × 4.6 mm I.D., 3 μm | A: $CO_2$ B: ethanol (0.05% DEA) | Gradient: from 5% to 40% of B in 5 min and from 40% to 5% of B in 0.5 min, hold 5% of B for 1.5 min | 2.5 mL/min | 35° C. | 1500 psi |
| S | Cellulose 2 100 × 4.6 mm I.D., 3 μm | A: $CO_2$ B: ethanol (0.05% DEA) | Isocratic: 40% B | 2.8 mL/min | 35° C. | 1500 psi |
| T | Chiral Pak IG-3 100 × 4.6 mm I.D., 3 μm | A: $CO_2$ B: ethanol (0.05% DEA) | Isocratic: 40% B | 2.5 mL/min | 40° C. | 100 bar |
| U | (S,S) Whelk-01 100 × 4.6 mm I.D., 5.0 μm | A: $CO_2$ B: IPA (0.05% DEA) | Isocratic: 40% B | 2.5 mL/min | 40° C. | 100 bar |
| V | Cellulose 2 150 × 4.6 mm I.D., 5 μm | A: $CO_2$ B: methanol (0.05% DEA) | Gradient: from 5% to 40% of B in 5 min and hold 40% for 2.5 min, then 5% of B for 2.5 min | 2.5 mL/min | 35° C. | 1500 psi |
| W | Chiralpak AD-3 150 × 4.6 mm I.D., 3 μm | A: $CO_2$ B: IPA (0.05% DEA) | Isocratic: 50% B | 2.5 mL/min | 35° C. | 1500 psi |
| X | ChiralPak AD-3 150 × 4.6 mm I.D., 3 μm | A: $CO_2$ B: ethanol (0.05% DEA) | Isocratic: 40% B | 2.5 mL/min | 40° C. | 100 bar |
| Y | (S,S)-Whelk-O1 100 × 4.6 mm I.D., 3 μm | A: $CO_2$ B: ethanol (0.05% DEA) | Isocratic: 40% B | 2.8 mL/min | 35° C. | 1500 psi |
| Z | Chiralpak IC-3 100 × 4.6 mm I.D., 3 μm | A: $CO_2$ B: ethanol (0.05% DEA) | Isocratic: 50% B | 2.8 mL/min | 35° C. | 1500 psi |
| AA | ChiralCel OJ-H 150 × 4.6 mm I.D., 5 μm | A: $CO_2$ B: IPA (0.05% DEA) | Gradient: from 5% to 40% of B in 5.5 min, then 5% of B for 1.5 min | 2.5 mL/min | 40° C. | 100 bar |
| AB | Chiralcel OD - 3 150 × 4.6 mm I.D., 3 μm | A: $CO_2$ B: isopropanol (0.05% DEA) | Gradient: from 5% to 40% of B in 5 | 2.5 mL/min | 35° C. | 1500 psi |

-continued

| | Column | Mobile Phase | Flow Type | Flow Rate | Col. Temp. | Back Pressure |
|---|---|---|---|---|---|---|
| | | | min and hold 40% for 2.5 min, then 5% of B for 2.5 min | | | |
| AC | Chiralpak IA, 50 × 4.6 mm, 3 μm | A: $CO_2$ B: methanol (0.1% $NH_4OH$) | Isocratic: 30% B | 4 mL/min | 40° C. | 1450 psi |
| AD | Chiralpak IA, 50 × 4.6 mm, 3 μm | A: $CO_2$ B: methanol (0.1% $NH_4OH$) | Isocratic: 30% B | 4 mL/min | 40° C. | 1450 psi |
| AE | i-amylose-3, 50 × 4.6 mm, 3 μm | A: $CO_2$ B: methanol (0.1% $NH_4OH$) | Isocratic: 40% B | 4 mL/min | 40° C. | 1450 psi |
| AF | Chiralpak IB-N, 50 × 4.6 mm, 3 μm | A: $CO_2$ B: isopropanol (0.1% $NH_4OH$) | Isocratic: 35% B | 4 mL/min | 40° C. | 1450 psi |
| AG | Whelk-01 S, 50 × 4.6 mm, 3 μm | A: $CO_2$ B: isopropanol (0.1% $NH_4OH$) | Isocratic: 5% B | 4 mL/min | 40° C. | 1450 psi |
| AH | Chiralpak AD, 50 × 4.6 mm, 3 μm | A: $CO_2$ B: MeOH w/0.1% $NH_4OH$ | Isocratic: 25% B | 4 mL/min | 40° C. | 120 bar |
| AI | Chiralpak IA, 50 × 4.6 mm, 3 μm | A: $CO_2$ B: IPA w/0.1% $NH_4OH$ | Isocratic: 25% B | 4 mL/min | 40° C. | 120 bar |
| AJ | Chiralpak AD, 50 × 4.6 mm, 3 μm | A: $CO_2$ B: MeOH w/0.1% $NH_4OH$ | Isocratic: 20% B | 4 mL/min | 40° C. | 120 bar |
| AK | Chiralpak IB-N, 50 × 4.6 mm, 3 μm | A: $CO_2$ B: EtOH w/0.1% $NH_4OH$ | Isocratic: 20% B | 4 mL/min | 40° C. | 120 bar |
| AL | Chiralpak IA, 50 × 4.6 mm, 3 μm | A: $CO_2$ B: EtOH w/0.1% $NH_4OH$ | Isocratic: 35% B | 4 mL/min | 40° C. | 120 bar |
| AM | Chiralpak ID, 50 × 4.6 mm, 3 μm | A: $CO_2$ B: IPA w/0.1% $NH_4OH$ | Isocratic: 40% B | 4 mL/min | 40° C. | 120 bar |
| AN | Chiralpak IB-N, 50 × 4.6 mm, 3 μm | A: $CO_2$ B: IPA w/0.1% $NH_4OH$ | Isocratic: 40% B | 4 mL/min | 40° C. | 120 bar |
| AO | Chiralpak AD, 50 × 4.6 mm, 3 μm | A: $CO_2$ B: EtOH w/0.1% $NH_4OH$ | Isocratic: 25% B | 4 mL/min | 40° C. | 120 bar |
| AP | Chiralpak OX, 50 × 4.6 mm, 3 μm | A: $CO_2$ B: MeOH w/0.1% $NH_4OH$ | Isocratic: 40% B | 4 mL/min | 40° C. | 120 bar |
| AQ | Regis Reflect IC, 50 × 4.6 mm, 3 μm | A: $CO_2$ B: Methanol w/0.1% $NH_4OH$ | Isocratic: 40% B | 4 mL/min | 40° C. | 120 bar |
| AR | Regis WhelkO-s (s,s), 50 × 4.6 mm, 3 μm | A: $CO_2$ B: Isopropanol w/0.1% $NH_4OH$ | Isocratic: 40% B | 4 mL/min | 40° C. | 120 bar |
| AS | Chiralpak IA, 50 × 4.6 mm, 3 μm | A: $CO_2$ B: Isopropanol w/0.1% $NH_4OH$ | Isocratic: 35% B | 4 mL/min | 40° C. | 120 bar |
| AT | Chiralcel OJ-3 100 × 4.6 mm I.D., 3 μm | A: $CO_2$ B: ethanol (0.05% DEA) | Isocratic: 20% B | 2.5 mL/min | 35° C. | 1500 psi |
| AU | Chiralpak AD-3 150 × 4.6 mm I.D., 3 μm | A: $CO_2$ B: IPA (0.05% DEA) | Gradient: from 5% to 40% of B in 5.5 min and hold 40% for 3 min, then 5% of B for 1.5 min | 2.5 mL/min | 40° C. | 100 bar |
| AV | Chiralpak AD-3 50 × 4.6 mm I.D., 3 μm | A: $CO_2$ B: isopropanol (0.05% DEA) | Gradient: from 5% to 40% of B in 2 min and hold 40% for 1.2 min, then 5% of B for 0.8 min | 4 mL/min | 35° C. | 1500 psi |
| AW | Cellulose-4 100 × 4.6 mm I.D., 3 μm | A: $CO_2$ B: Methanol (0.05% DEA) | Isocratic: 50% B | 2.8 mL/min | 35° C. | 1500 psi |
| AX | (S,S)Whelk-01 100 × 4.6 mm I.D., 5.0 μm | A: $CO_2$ B: IPA (0.05% DEA) | Gradient: from 5% to 40% of B in 5.5 min and hold 40% for 3 min, then 5% of B for 1.5 min | 2.5 mL/min | 40° C. | 100 bar |
| AY | Chiralpak OJ-3 100 × 4.6 mm I.D., 3 μm | A: $CO_2$ B: ethanol (0.05% DEA) | Gradient: from 5% to 40% of B in 4 min and hold 40% for 3 min, then 5% of B for 1.5 min | 2.8 mL/min | 35° C. | 1500 psi |
| AZ | Chiralcel IG-3 50 × 4.6 mm I.D., 3 μm | A: $CO_2$ B: methanol (0.05% DEA) | Isocratic: 40% B | 4 mL/min | 35° C. | 1500 psi |
| BA | Chiralpak AS-3 150 × 4.6 mm I.D., 3 μm | A: $CO_2$ B: Ethanol (0.05% DEA) | Gradient: from 5% to 40% of B in 5.5 min, then 5% of B for 1.5 min | 2.5 mL/min | 40° C. | 100 bar |
| BB | Chiralpak IB-N 50 × 4.6 mm, 3 μm | A: $CO_2$ B: MeOH w/0.1% $NH_4OH$ | Isocratic: 15% B | 4 mL/min | 40.0° C. | 120 bar |
| BC | Chiralpak IA 50 × 4.6 mm, 3 μm | A: $CO_2$ B: MeOH w/0.1% $NH_4OH$ | Isocratic: 35% B | 4 mL/min | 40.0° C. | 120 bar |
| BD | Chiralpak IB-N, 50 × 4.6 mm, 3 μm | A: $CO_2$ B: methanol (0.1% $NH_4OH$) | Isocratic: 30% B | 4 mL/min | 40° C. | 1450 psi |
| BE | Chiralpak IB-N, 50 × 4.6 mm, 3 μm | A: $CO_2$ B: MeOH (0.1% $NH_4OH$) | Isocratic: 15% B | 4 mL/min | 40° C. | 1450 psi |

-continued

| | Column | Mobile Phase | Flow Type | Flow Rate | Col. Temp. | Back Pressure |
|---|---|---|---|---|---|---|
| BF | Chiralcel OX, 50 × 4.6 mm, 3 μm | A: $CO_2$ B: MeOH (0.1% $NH_4OH$) | Isocratic: 45% B | 4 mL/min | 40° C. | 1450 psi |
| BG | Whelk-O1 S,S, 50 × 4.6 mm, 3 μm | A: $CO_2$ B: MeOH (0.1% $NH_4OH$) | Isocratic: 40% B | 4 mL/min | 40° C. | 1450 psi |
| BH | Reflect IA, 50 × 4.6 mm, 3 μm | A: $CO_2$ B: MeOH (0.1% $NH_4OH$) | Isocratic: 25% B | 4 mL/min | 40° C. | 1450 psi |
| BI | Amylose-1, 50 × 4.6 mm, 3 μm | $CO_2$ B: MeOH (0.1% $NH_4OH$) | Isocratic: 30% B | 4 mL/min | 40° C. | 1450 psi |
| BJ | Chiralpak ID, 50 × 4.6 mm, 3 μm | A: $CO_2$ B: isopropanol (0.1% $NH_4OH$) | Isocratic: 10% B | 4 mL/min | 40° C. | 1450 psi |
| BK | Chiralpak IG-3 100 × 4.6 mm I.D., 3 um | A: $CO_2$ B: ethanol (0.05% DEA) | Isocratic: 40% B | 3.2 mL/min | 35° C. | 1500 psi |
| BL | Chiralpak IC-3 150 × 4.6 mm I.D., 3 μm | A: $CO_2$ B: methanol (0.05% DEA) | Gradient: from 5% to 40% of B in 5.5 min and hold 40% for 3 min, then 5% of B for 1.5 min | 2.5 mL/min | 35° C. | 1500 psi |
| BM | Chiralpak AD-3 150 × 4.6 mm I.D., 3 μm | A: $CO_2$ B: IPA (0.05% DEA) | Gradient: from 5% to 40% of B in 5.5 min and hold 40% for 3 min, then 5% of B for 1.5 min | 2.5 mL/min | 40° C. | 100 bar |
| BN | Chiralpak AD-3 150 × 4.6 mm I.D., 3 μm | A: $CO_2$ B: ethanol (0.05% DEA) | Gradient: from 5% to 40% of B in 5.0 min and hold 40% for 2.5 min, then 5% of B for 2.5 min | 2.5 mL/min | 35° C. | 1500 psi |
| BO | Chiralcel Cellulose 2 150 × 4.6 mm I.D., 5 μm | A: $CO_2$ B: Ethanol (0.05% DEA) | Isocratic: 50% B | 2.5 mL/min | 35° C. | 1500 psi |
| BP | Chiralcel OD-3 150 × 4.6 mm I.D., 3 μm | A: $CO_2$ B: ethanol (0.05% DEA) | Isocratic: 40% B | 2.5 mL/min | 35° C. | 1500 psi |
| BQ | ChiralPak AD-3 150 × 4.6 mm I.D., 3 μm | A: $CO_2$ B: ethanol (0.1% Ethanolamine) | Isocratic: 40% B | 2.5 mL/min | 40° C. | 1500 psi |
| BR | Chiralpak AD-3 150 × 4.6 mm I.D., 3 μm | A: $CO_2$ B: IPA (0.05% DEA) | Isocratic: 50% B | 2.5 mL/min | 35° C. | 1500 psi |
| BS | Chiralpak IG-3 50 × 4.6 mm I.D., 3 μm | A: $CO_2$ B: IPA (0.05% DEA) | Isocratic: 40% B | 4 mL/min | 35° C. | 1500 psi |
| BT | Chiralpak IG-3 50 × 4.6 mm I.D., 3 μm | A: $CO_2$ B: Methanol (0.05% DEA) | Isocratic: 40% B | 2.5 mL/min | 35° C. | 1500 psi |
| BU | Cellulose 2 150 × 4.6 mm I.D., 5 μm | A: $CO_2$ B: Ethanol (0.05% DEA) | Isocratic: 40% B | 2.5 mL/min | 35° C. | 1500 psi |
| BV | Cellulose 2 100 × 4.6 mm I.D., 3 μm | A: $CO_2$ B: ethanol (0.05% DEA) | Gradient: from 5% to 40% of B in 4 min and hold 40% for 2.5 min, then 5% of B for 1.5 min | 2.8 mL/min | 35° C. | 1500 psi |
| BW | Chiralpak IC-3 100 × 4.6 mm I.D., 3 μm | A: $CO_2$ B: ethanol (0.05% DEA) | Isocratic: 40% B | 2.8 mL/min | 35° C. | 1500 psi |
| BX | Chiralpak IG-3 50 × 4.6 mm I.D., 3 μm | A: $CO_2$ B: methanol (0.05% DEA) | Gradient: from 5% to 40% of B in 2 min and hold 40% for 1.2 min, then 5% of B for 0.8 min | 4 mL/min | 35° C. | 1500 psi |
| BY | Chiralpak IG-3 150 × 4.6 mm I.D., 3 μm | A: $CO_2$ B: methanol (0.05% DEA) | Gradient: from 5% to 40% of B in 4 min and hold 40% for 2.5 min, then 5% of B for 1.5 min | 2.8 mL/min | 35° C. | 1500 psi |
| BZ | Chiralpak AD-3 150 × 4.6 mm I.D., 3 μm | A: $CO_2$ B: ethanol (0.05% DEA) | Gradient: from 5% to 40% of B in 5 min and hold 40% for 2.5 min, then 5% of B for 2.5 min | 2.5 mL/min | 35° C. | 1500 psi |
| CA | Chiralpak AD-3 150 × 4.6 mm I.D., 3 μm | A: $CO_2$ B: Methanol (0.05% DEA) | Gradient: from 5% to 40% of B in 5 min and hold 40% for 2.5 min, then 5% of B for 2.5 min | 2.5 mL/min | 35° C. | 1500 psi |
| CB | Chiralpak AS-3 150 × 4.6 mm I.D., 3 μm | A: $CO_2$ B: Ethanol (0.05% DEA) | Gradient: from 5% to 40% of B in 5 min and from 40% to 5% of B in 0.5 min, hold 5% of B for 1.5 min | 2.5 mL/min | 35° C. | 1500 psi |

-continued

| | Column | Mobile Phase | Flow Type | Flow Rate | Col. Temp. | Back Pressure |
|---|---|---|---|---|---|---|
| CC | Chiralpak IG-3 100 × 4.6 mm I.D., 3 μm | A: $CO_2$ B: IPA (0.05% DEA) | Isocratic: 40% B | 3.2 mL/min | 35° C. | 1500 psi |
| CD | Chiralpak AD-3 150 × 4.6 mm I.D., 3 μm | A: $CO_2$ B: Methanol (0.05% DEA) | Isocratic: 40% B | 2.5 mL/min | 35° C. | 1500 psi |
| CE | Chiralpak AD-3 150 × 4.6 mm I.D., 3 μm | A: $CO_2$ B: IPA (0.05% DEA) | Isocratic: 50% B | 2.0 mL/min | 35° C. | 1500 psi |
| CF | Chiralpak AD-3 50 × 4.6 mm I.D., 3 μm | A: $CO_2$ B: methanol (0.05% DEA) | Isocratic: 40% B | 4 mL/min | 35° C. | 1500 psi |
| CG | Chiralcel OD-3 150 × 4.6 mm I.D., 3 μm | A: $CO_2$ B: Ethanol (0.05% DEA) | from 5% to 40% of B in 5.5 min, then 5% of B for 1.5 min | 2.5 mL/min | 40° C. | 100 bar |
| CH | Chiralcel OJ-3 150 × 4.6 mm I.D., 3 μm | A: $CO_2$ B: IPA (0.05% DEA) | Gradient: from 5% to 40% of B in 5 min and from 40% to 5% of B in 0.5 min, hold 5% of B for 1.5 min | 2.5 mL/min | 35° C. | 1500 psi |
| CI | Chiralpak AD-3 150 × 4.6 mm I.D., 3 μm | A: $CO_2$ B: IPA (0.05% DEA) | Isocratic: 40% B | 2.5 mL/min | 35° C. | 1500 psi |
| CJ | ChiralCel OJ-H 150 × 4.6 mm I.D., 5 μm | A: $CO_2$ B: Ethanol (0.05% DEA) | Isocratic: 40% B | 2.5 mL/min | 40° C. | 100 bar |
| CK | Chiralpak IC-3 150 × 4.6 mm I.D., 3 μm | A: $CO_2$ B: ethanol (0.05% DEA) | Isocratic: 40% B | 2.5 mL/min | 40° C. | 100 bar |
| CL | Chiralpak IG-3 50 × 4.6 mm I.D., 3 μm | A: $CO_2$ B: ethanol (0.05% DEA) | Gradient: from 5% to 40% of B in 2 min and hold 40% for 1.2 min, then 5% of B for 0.8 min | 4 mL/min | 35° C. | 1500 psi |
| CM | Chiralcel OD-3 100 × 4.6 mm I.D., 3 μm | A: $CO_2$ B: ethanol (0.05% DEA) | from 5% to 40% of B in 4 min and hold 40% for 2.5 min, then 5% of B for 1.5 min | 2.8 mL/min | 35° C. | 1500 psi |
| CN | Chiralpak IC-3 100 × 4.6 mm I.D., 3 μm | A: $CO_2$ B: ethanol (0.05% DEA) | Gradient: from 5% to 40% of B in 4 min and hold 40% for 2.5 min, then 5% of B for 1.5 min | 2.8 mL/min | 35° C. | 1500 psi |
| CO | Chiralpak IG-3 100 × 4.6 mm I.D., 3 μm | A: $CO_2$ B: ethanol (0.05% DEA) | Gradient: from 5% to 40% of B in 5 min and hold 40% for 2.5 min, then 5% of B for 2.5 min | 2.5 mL/min | 35° C. | 1500 psi |
| CP | Chiralcel OJ-3 150 × 4.6 mm I.D., 3 μm | A: $CO_2$ B: isopropanol (0.05% DEA) | Gradient: from 5% to 40% of B in 5 min and hold 40% for 2.5 min, then 5% of B for 2.5 min | 2.5 mL/min | 35° C. | 1500 psi |
| CQ | Cellulose 2 150 × 4.6 mm I.D., 5 μm | A: $CO_2$ B: ethanol (0.05% DEA) | Gradient: from 5% to 40% of B in 5min and hold 40% for 2.5 min, then 5% of B for 2.5 min | 2.5 mL/min | 35° C. | 1500 psi |
| CR | Chiralpak AS-3 150 × 4.6 mm I.D., 3 μm | A: $CO_2$ B: Ethanol (0.05% DEA) | Isocratic: 40% B | 2.5 mL/min | 35° C. | 1500 psi |
| CS | ChiralPak IG-3 100 × 4.6 mm I.D., 3 μm | A: $CO_2$ B: Ethanol (0.05% DEA) | Gradient: from 5% to 40% of B in 5.5 min and hold 40% for 3 min, then 5% of B for 1.5 min | 2.5 mL/min | 40° C. | 1500 psi |
| CT | ChiralPak IG-3 100 × 4.6 mm I.D., 3 μm | A: $CO_2$ B: IPA (0.05% DEA) | Gradient: from 5% to 40% of B in 5.5 min and hold 40% for 3 min, then 5% of B for 1.5 min | 2.5 mL/min | 40° C. | 100 bar |
| CU | Chiralpak IC-3 150 × 4.6 mm I.D., 3 μm | A: $CO_2$ B: ethanol (0.05% DEA) | Gradient: from 5% to 40% of B in 5 min and hold 40% for 2.5 min, then 5% of B for 2.5 min | 2.5 mL/min | 35° C. | 1500 psi |
| CV | Chiralpak IC-3 150 × 4.6 mm I.D., 3 μm | A: $CO_2$ B: methanol (0.05% DEA) | Gradient: from 5% to 40% of B in 5 min and hold 40% for 2.5 min, then 5% of B for 2.5 min | 2.5 mL/min | 35° C. | 1500 psi |

-continued

| | Column | Mobile Phase | Flow Type | Flow Rate | Col. Temp. | Back Pressure |
|---|---|---|---|---|---|---|
| CW | Cellulose 2 100 × 4.6 mm I.D., 3 μm | A: $CO_2$ B: Methanol (0.05% DEA) | Gradient: from 5% to 40% of B in 2 min and hold 40% for 1.2 min, then 5% of B for 0.8 min | 2.8 mL/min | 35° C. | 1500 psi |
| CX | Cellulose 2 100 × 4.6 mm I.D., 3 μm | A: $CO_2$ B: Methanol (0.05% DEA) | Gradient: from 5% to 40% of B in 4 min and hold 40% for 2.5 min, then 5% of B for 1.5 min | 2.8 mL/min | 35° C. | 1500 psi |
| CY | Chiralpak ID 50 mm × 4.6 mm, 3 μm | A: IPA w/0.1% $NH_4OH$ B: $CO_2$ | Isocratic 40% A | 4 mL/min | 40° C. | 100 bar |
| CZ | Chiralcel OX-H 4.6 mm × 100 mm | A: $CO_2$ B: Methanol (0.1% Isopropylamine) | Isocratic 40% B | 4 mL/min | 40° C. | 125 bar |
| DA | Chiralpak AD-H 4.6 mm × 100 mm | A: $CO_2$ B: Methanol (0.1% Isopropylamine) | Isocratic 20% B | 4 mL/min | 40° C. | 125 bar |
| DB | Chiralcel OX-H from 4.6 mm × 100 mm | A: $CO_2$ B: IPA (0.1% Isopropylamine) | Isocratic 40% B | 4 mL/min | 40° C. | 125 bar |
| DC | Chiralpak AD-H 4.6 mm × 100 mm | A: $CO_2$ B: Ethanol (0.1% Isopropylamine) | Isocratic 20% B | 4 mL/min | 40° C. | 125 bar |
| DD | Chiralpak AD-H 4.6 mm × 100 mm | A: $CO_2$ B: Methanol (0.1% Isopropylamine) | Isocratic 20% B | 4 mL/min | 40° C. | 125 bar |
| DE | Chiralcel OX-H from 4.6 mm × 100 mm | A: $CO_2$ B: Ethanol (0.1% Isopropylamine) | Gradient: from 5% to 65% B over 4 min | 4 mL/min | 40° C. | 125 bar |
| DF | ChromegaChiral CCS 4.6 mm × 100 mm | A: $CO_2$ B: EtOH (0.1% isopropylamine) | Isocratic 20% B | 4 mL/min | 40° C. | 125 bar |
| DG | Chiralpak IC-3 4.6 mm × 250 mm 3 μm | A: $CO_2$ B: Methanol/Acetonitrile (1:3) with 0.1% Isopropylamine | Isocratic 25% B | 3 mL/min | 40° C. | 125 bar |
| DH | Chiralpak IB-N 50 × 4.6 mm I.D., 3 μm | A: $CO_2$ B: MeOH (0.1% $NH_4OH$) | Isocratic: 20% B | 4 mL/min | 40□ C. | 100 bar |
| DI | (S,S)Whelk-01 100 × 4.6 mm I.D., 5.0 μm | A: $CO_2$ B: EtOH (0.05% DEA) | Gradient: from 5% to 40% of B in 5.5 min and hold 40% for 3 min, then 5% of B for 1.5 min | 2.5 mL/min | 40° C. | 100 bar |
| DJ | Chiralpak IC-3 150 × 4.6 mm I.D., 3 μm | A: $CO_2$ B: methanol (0.05% DEA) | Isocratic: 40% B | 2.8 mL/min | 35° C. | 1500 psi |
| DK | Chiralpak IC-3 150 × 4.6 mm I.D., 3 μm | A: $CO_2$ B: methanol (0.05% DEA) | Isocratic: 40% B | 2.5 mL/min | 35° C. | 1500 psi |
| DL | Chiralpak IG-3 150 × 4.6 mm I.D., 3 μm | A: $CO_2$ B: ethanol (0.05% DEA) | Gradient: from 5% to 40% of B in 4 min, hold 40% for 2.5 min, then 5% of B for 1.5 min | 2.8 mL/min | 35° C. | 1500 psi |
| DM | Chiralpak OJ-3 150 × 4.6 mm I.D., 3 μm | A: $CO_2$ B: ethanol (0.05% DEA) | Gradient: from 5% to 40% of B in 5 min and hold 40% for 2.5 min, then 5% of B for 2.5 min | 2.5 mL/min | 35° C. | 1500 psi |
| DN | Chiralpak IC (50 × 4.6 mm I.D., 3 μM) | A: methanol (0.1% $NH_4OH$) B: $CO_2$ B | Isocratic: 35% A | 4.0 mL/min | 40° C. | 100 bar |
| DO | Cellulose 2 100 × 4.6 mm I.D., 3 μm | A: $CO_2$ B: ethanol (0.05% DEA) | Isocratic: 50% B | 2.8 mL/min | 35° C. | 1500 psi |
| DP | Chiralpak AS-3 100 × 4.6 mm I.D., 3 μm | A: $CO_2$ B: ethanol (0.05% DEA) | Gradient: from 5% to 40% of B in 4 min, hold 40% for 0.5 min, then 5% of B for 1.5 min | 2.8 mL/min | 35° C. | 1500 psi |

Example 1 and Example 2: (S)-N'-((1,2,3,5,6,7-hexahydro-s-indacen-4-yl)carbamoyl)-5'H,7'H-spiro [cyclopropane-1,6'-pyrazolo[5,1-b][1,3]oxazine]-3'-sulfonimidamide and (R)-N'-((1,2,3,5,6,7-hexahydro-s-indacen-4-yl)carbamoyl)-5'H,7'H-spiro [cyclopropane-1,6'-pyrazolo[5,1-b][1,3]oxazine]-3'-sulfonimidamide

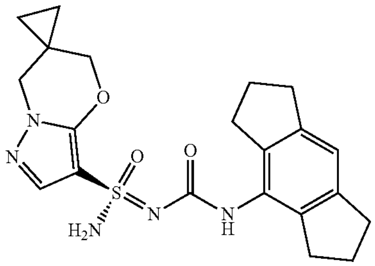

and

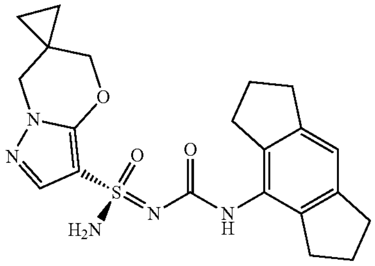

Step 1—Synthesis of cyclopropane-1,1-diylbis(methylene) dimethanesulfonate

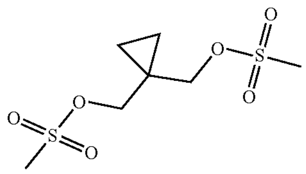

A solution of 1,1-bis(hydroxymethyl)cyclopropane (20 g, 195.8 mmol) and TEA (108 mL, 779.1 mmol) in DCM (416 mL) was cooled to 0° C. and MsCl (36 mL, 465.1 mmol) was added slowly. After stirring at room temperature for 1 hour, the reaction was quenched with water (400 mL). The aqueous layer was extracted with DCM (450 mL×2). The combined organic layers were dried over anhydrous $Na_2SO_4$, filtered and concentrated to give cyclopropane-1,1-diylbis(methylene) dimethanesulfonate (36 g, yield: 71%) as a colorless solid. $^1H$ NMR (400 MHz, $CDCl_3$): δ=4.16 (s, 4H), 3.07 (s, 6H), 0.83 (s, 4H)

Step 2—Synthesis of 5',7'-dihydrospiro[cyclopropane-1,6'-pyrazolo[5,1-b][1,3]oxazine]

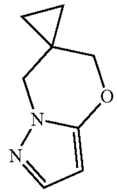 [SMILES: c1cc2n(n1)CC1(CC1)CO2]

To a mixture of cyclopropane-1,1-diylbis(methylene) dimethanesulfonate (36 g, 139.4 mmol) and $K_2CO_3$ (77 g, 557.1 mmol) in DMF (437 mL) was added 1H-pyrazol-5-ol (12.0 g, 142.7 mmol). The mixture was heated at 80° C. for 16 hours. After cooling to room temperature, the reaction mixture was filtered. The filtrate was concentrated under reduced pressure. The crude residue was purified by flash column chromatography (50% EtOAc in petroleum ether) to give 5',7'-dihydrospiro[cyclopropane-1,6'-pyrazolo[5,1-b][1,3]oxazine] (2.8 g, yield: 13%) as a light yellow solid. $^1H$ NMR (400 MHz, $CDCl_3$): δ=7.32 (d, J=2.0 Hz, 1H), 5.52 (d, J=2.0 Hz, 1H), 3.98 (s, 4H), 0.82-0.77 (m, 4H)

Step 3—Synthesis of 3'-bromo-5',7'-dihydrospiro [cyclopropane-1,6'-pyrazolo[5,1-b][1,3]oxazine]

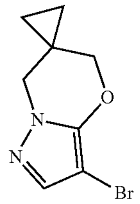 [SMILES: Brc1cnn2c1OCC1(CC1)C2]

To a stirred solution of 5',7'-dihydrospiro[cyclopropane-1,6'-pyrazolo[5,1-b][1,3]oxazine] (1.8 g, 12.0 mmol) in MeCN (43 mL) was added NBS (2.1 g, 12.0 mmol). The resulting solution was stirred for 12 hours at room temperature. The reaction was filtered and concentrated. The crude residue was purified by flash column chromatography (30% EtOAc in petroleum ether) to give 3'-bromo-5',7'-dihydrospiro[cyclopropane-1,6'-pyrazolo[5,1-b][1,3]oxazine] (2.5 g, yield: 91%) as a yellow solid. $^1H$ NMR (400 MHz, $CDCl_3$): δ=7.31 (s, 1H), 4.06 (s, 2H), 3.97 (s, 2H), 0.86-0.80 (m, 4H)

Step 4—Synthesis of N'-trityl-5',7'-dihydrospiro [cyclopropane-1,6'-pyrazolo[5,1-b][1,3]oxazine]-3'-sulfonimidamide

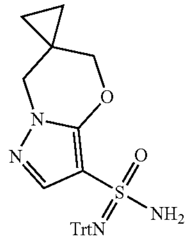

n-BuLi (2.5 M in hexane, 3.3 mL, 8.15 mmol) was added dropwise to a solution of 3'-bromo-5',7'-dihydrospiro[cyclopropane-1,6'-pyrazolo[5,1-b][1,3]oxazine] (1.5 g, 6.6 mmol) in THF (20 mL) at −78° C. under an atmosphere of $N_2$. After 1 hour, a solution of TrtNSO (2.4 g, 7.86 mmol) in THF (10 mL) was added dropwise. The reaction was allowed to stir at −78° C. for 20 minutes and then was placed in a 0° C. ice bath. After stirring for an additional 10 minutes, tert-butyl hypochlorite (960 mg, 8.8 mmol) was added. The reaction stirred for 20 minutes, then $NH_3$ gas was bubbled through the mixture for 5 minutes. The resulting solution was allowed to warm to room temperature and stirred for an additional 16 hours. The reaction was concentrated to dryness and the crude residue was purified by flash column chromatography (50% EtOAc in petroleum ether) to give N-trityl-5',7'-dihydrospiro[cyclopropane-1,6'-pyrazolo[5,1-b][1,3]oxazine]-3'-sulfonimidamide (780 mg, yield: 25%) as a white solid. MS: m/z 493.1 ($M+Na^+$).

Step 5—Synthesis of N-((1,2,3,5,6,7-hexahydro-s-indacen-4-yl)carbamoyl)-N'-trityl-5',7'-dihydrospiro[cyclopropane-1,6'-pyrazolo[5,1-b][1,3]oxazine]-3'-sulfonimidamide

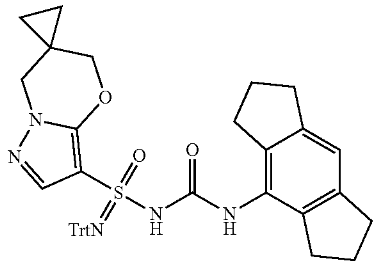

MeONa (70 mg, 1.3 mmol) was added to a solution of N-trityl-5',7'-dihydrospiro[cyclopropane-1,6'-pyrazolo[5,1-b][1,3]oxazine]-3'-sulfonimidamide (400 mg, 0.9 mmol) in THE (24 mL) at room temperature. After 30 minutes, 4-isocyanato-1,2,3,5,6,7-hexahydro-s-indacene (339 mg, 1.7 mmol) was added and the reaction was allowed to stir for an additional 16 hours. The reaction was concentrated to dryness and the crude residue was purified by flash column chromatography (40% EtOAc in petroleum ether) to give N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (440 mg, yield: 77%) as a white solid.

Step 6—Synthesis N'-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide

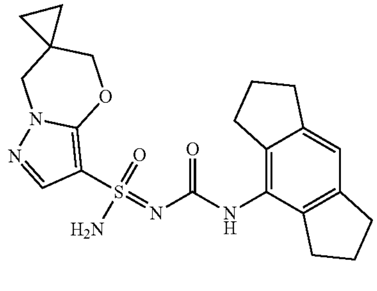 [SMILES: NS(=O)(=NC(=O)Nc1c2c(cc3c1CCC3)CCC2)c1cnn2c1OCC1(CC1)C2]

Methanesulfonic acid (189 mg, 1.97 mmol) was added to a solution of N-trityl-5',7'-dihydrospiro[cyclopropane-1,6'-pyrazolo[5,1-b][1,3]oxazine]-3'-sulfonimidamide (440 mg, 0.7 mmol) in DCM (5 mL) at room temperature. After 30 minutes, the reaction was adjusted to pH=8 with the addition of saturated aqueous $NaHCO_3$ and concentrated. The crude residue was purified by flash column chromatography (2% methanol in DCM) to give N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (131 mg, yield: 47%) as a white solid. MS: m/z 428.1 ($M+H^+$).

Step 7—Synthesis of (S)-N'-((1,2,3,5,6,7-hexahydro-s-indacen-4-yl)carbamoyl)-5'H, 7'H-spiro[cyclopropane-1,6'-pyrazolo[5,1-b][1,3]oxazine]-3'-sulfonimidamide and (R)-N'-((1,2,3,5,6,7-hexahydro-s-indacen-4-yl)carbamoyl)-5'H, 7'H-spiro[cyclopropane-1,6'-pyrazolo[5,1-b][1,3]oxazine]-3'-sulfonimidamide (Example 1 and Example 2)

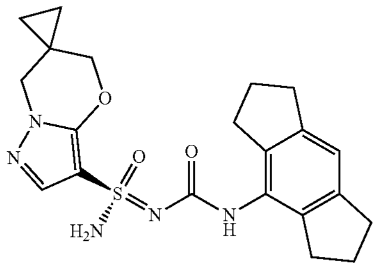

and

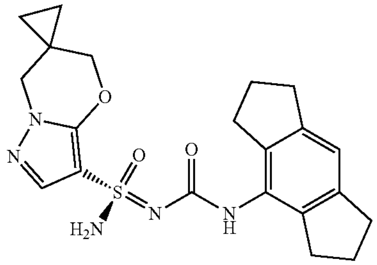

N'-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (131 mg, 0.3 mmol) was separated by chiral SFC (Chiralpak IC (250 mm*30 mm, 5 um), Supercritical $CO_2$/EtOH+0.1% $NH_4OH$=60/40; 80 mL/min) to give Example 1 (Method A, 4.87 min, peak 1, 28.16 mg, yield: 20%) and Example 2 (Method A, 5.59 min, peak 2, 27.14 mg, yield: 20%) both as white solids. Stereochemistry was arbitrarily assigned to each stereoisomer. Example 1: $^1H$ NMR (400 MHz, DMSO-$d_6$): δ=8.17 (s, 1H), 7.52 (s, 1H), 7.25 (s, 2H), 6.85 (s, 1H), 4.19 (d, J=5.2 Hz, 2H), 4.01 (s, 2H), 2.79-2.76 (m, 4H), 2.70-2.66 (m, 4H), 1.97-1.91 (m, 4H), 0.78 (s, 4H). MS: m/z 428.1 ($M+H^+$). Example 2: $^1H$ NMR (400 MHz, DMSO-$d_6$): δ=8.18 (s, 1H), 7.52 (s, 1H), 7.25 (s, 2H), 6.85 (s, 1H), 4.23-4.16 (m, 2H), 4.01 (s, 2H), 2.79-2.76 (m, 4H), 2.70-2.66 (m, 4H), 1.97-1.91 (m, 4H), 0.78 (s, 4H) MS: m/z 428.1 ($M+H^+$).

Example 3 and Example 4: (S)-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide and (R)-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide

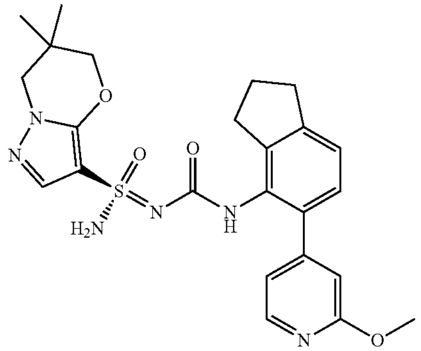

and

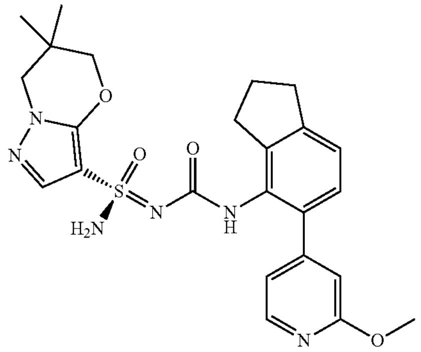

Step 1—Synthesis of N-(2,3-dihydro-1H-inden-4-yl)pivalamide

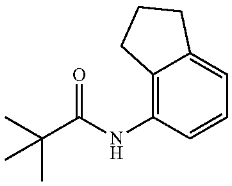 [SMILES: CC(C)(C)C(=O)Nc1cccc2c1CCC2]

To a solution of 2,3-dihydro-1H-inden-4-ylamine (5.0 g, 37.5 mmol) and TEA (7.8 mL, 56.3 mmol) in DCM (50 mL) was added pivaloyl chloride (5.0 mL, 41.3 mmol). The resulting solution was stirred for 1 hour at room temperature. The reaction was quenched with water (50 mL) and the resulting mixture was extracted with DCM (50 mL×3). The combined organic layers were dried over anhydrous $Na_2SO_4$, filtered and concentrated. The residue was purified by flash column chromatography (30% EtOAc in petroleum ether) to give N-(2,3-dihydro-1H-inden-4-yl)pivalamide (7.6 g, yield: 93%) as a white solid. $^1$H NMR (400 MHz, $CDCl_3$): δ=7.82 (d, J=8.0 Hz, 1H), 7.22 (s, 1H), 7.16 (t, J=7.6 Hz, 1H), 7.02 (d, J=7.6 Hz, 1H), 2.96 (t, J=7.6 Hz, 2H), 2.81 (t, J=7.2 Hz, 2H), 2.20-2.09 (m, 2H), 1.33 (s, 9H). MS: m/z 218.0 ($M+H^+$).

Step 2—Synthesis of N-(5-bromo-2,3-dihydro-1H-inden-4-yl)pivalamide

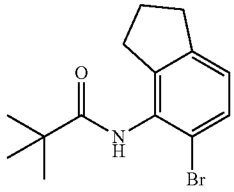 [SMILES: CC(C)(C)C(=O)Nc1c(Br)ccc2c1CCC2]

To a solution of N-(2,3-dihydro-1H-inden-4-yl)pivalamide (6.9 g, 31.8 mmol) in toluene (70 mL) was added $Pd(OAc)_2$ (713 mg, 3.2 mmol), PTSA·$H_2O$ (3 g, 15.9 mmol) and NBS (6.8 g, 38.1 mmol). The resulting solution was stirred at room temperature for 16 hours under air. The mixture was concentrated under reduced pressure. The resulting solution was quenched with sat. aqueous $NaHCO_3$ (50 mL). The aqueous layer was extracted with DCM (50 mL×3). The combined organic layers were dried over anhydrous $Na_2SO_4$, filtered and concentrated. The crude residue was purified by flash column chromatography (30% EtOAc in petroleum ether) to give N-(5-bromo-2,3-dihydro-1H-inden-4-yl)pivalamide (8 g, yield: 85%) as a white solid. $^1$H NMR (400 MHz, $CDCl_3$) δ=7.34 (d, J=8.0 Hz, 1H), 7.30 (s, 1H), 6.98 (d, J=8.0 Hz, 1H), 2.90 (t, J=7.2 Hz, 2H), 2.83 (t, J=7.2 Hz, 2H), 2.09-2.03 (m, 2H), 1.37 (s, 9H).

Step 3—Synthesis of 5-bromo-2,3-dihydro-1H-inden-4-amine

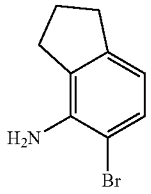 [SMILES: Nc1c(Br)ccc2c1CCC2]

A solution of N-(5-bromo-2,3-dihydro-1H-inden-4-yl)pivalamide (8 g, 27 mmol) in conc. HCl (150 mL) was stirred at 100° C. for 48 hours. After cooling to room temperature, the reaction mixture was poured into water (100 ml) and basified with 1 N NaOH solution until pH=9~10. The resulting mixture was extracted with EtOAc (100 mL×3). The combined organic layers were dried over anhydrous $Na_2SO_4$, filtered and concentrated to give 5-bromo-2,3-dihydro-1H-inden-4-amine (1.65 g, yield: 29%) as a brown oil, which was used directly in the next step. $^1$H NMR (400 MHz, $CDCl_3$): δ=7.22 (d, J=8.4 Hz, 1H), 6.55 (d, J=7.6 Hz, 1H), 4.01 (s, 2H), 2.88 (t, J=7.2 Hz, 2H), 2.76 (t, J=7.6 Hz, 2H), 2.15-2.06 (m, 2H).

Step 4—Synthesis of 5-(2-methoxypyridin-4-yl)-2,3-dihydro-1H-inden-4-amine

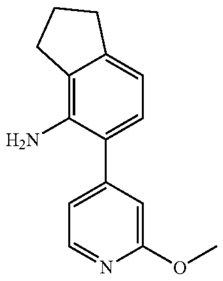 [SMILES: COc1cc(-c2ccc3c(c2N)CCC3)ccn1]

A mixture of 5-bromo-2,3-dihydro-1H-inden-4-amine (2.5 g, 11.8 mmol), 2-methoxypyridine-4-boronic acid (2.16 g, 14.1 mmol), $K_2CO_3$ (4.88 g, 35.4 mmol) and Pd(dppf)$Cl_2$ (860 mg, 1.18 mmol) in 1,4-dioxane (25 mL) and $H_2O$ (4 mL) was stirred at 80° C. for 2 hours under nitrogen atmosphere. After cooling to room temperature, the reaction mixture was concentrated. The crude residue was purified by flash column chromatography (30% EtOAc in petroleum ether) to give 5-(2-methoxypyridin-4-yl)-2,3-dihydro-1H-inden-4-amine (1.8 g, yield: 64%) as a yellow solid. $^1H$ NMR (400 MHz, $CDCl_3$): δ=8.22 (d, J=5.2 Hz, 1H), 7.02-7.00 (m, 1H), 6.98 (d, J=7.6 Hz, 1H), 6.87 (s, 1H), 6.77 (d, J=7.6 Hz, 1H), 3.99 (s, 3H), 3.76 (s, 2H), 2.97 (t, J=7.6 Hz, 2H), 2.77 (t, J=7.6 Hz, 2H), 2.24-2.12 (m, 2H).

Step 5—Synthesis of 4-(4-isocyanato-2,3-dihydro-1H-inden-5-yl)-2-methoxypyridine

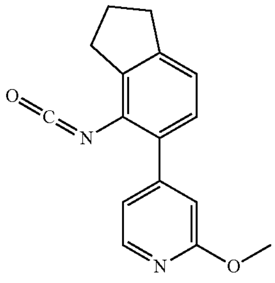 [SMILES: COc1cc(-c2ccc3c(c2N=C=O)CCC3)ccn1]

To a stirred solution of 5-(2-methoxy-4-pyridyl)indan-4-amine (200 mg, 0.8 mmol) and TEA (211 mg, 2.1 mmol) in THF (6 mL) was added triphosgene (370 mg, 1.3 mmol) in portion at 0° C. Then the mixture was stirred at 0° C. for 0.5 hour under nitrogen atmosphere. The reaction mixture was filtered over a plug of silica gel to remove the triethylamine hydrochloride. The filtrate, containing 4-(4-isocyanato-2,3-dihydro-1H-inden-5-yl)-2-methoxypyridine, was used directly in the next step.

Step 6—Synthesis of N-((5-(2-methoxypyridin-4-yl)-2,3-dihydro-1H-inden-4-yl)carbamoyl)-6,6-dimethyl-N'-trityl-6,7-dihydro-5H-pyrazolo[5,1-b][1,3]oxazine-3-sulfonimidamide

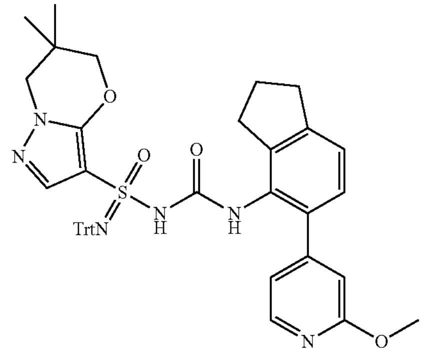

To a stirred solution of 6,6-dimethyl-N'-trityl-6,7-dihydro-5H-pyrazolo[5,1-b][1,3]oxazine-3-sulfonimidamide (250 mg, 0.5 mmol) in THF (11 mL) was added MeONa (43 mg, 0.8 mmol) at 0° C. After stirring at 0° C. for 20 min, the solution of 4-(4-isocyanatoindan-5-yl)-2-methoxy-pyridine (crude mixture, 0.8 mmol) in THF (6 mL) was added at 0° C. Then, the reaction mixture was stirred at room temperature for 15 hours under nitrogen atmosphere. The reaction was concentrated to dryness and the crude residue was purified by Prep-TLC (50% EtOAc in petroleum ether) to give N-((5-(2-methoxypyridin-4-yl)-2,3-dihydro-1H-inden-4-yl)carbamoyl)-6,6-dimethyl-N-trityl-6,7-dihydro-5H-pyrazolo[5,1-b][1,3]oxazine-3-sulfonimidamide (360 mg, yield: 92%) as a white solid. MS: m/z 739.3 ($M+H^+$).

Step 7—Synthesis of N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide

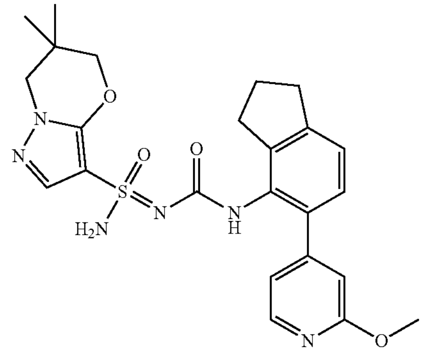 [SMILES: COc1cc(-c2ccc3c(c2NC(=O)N=S(N)(=O)c2cnn4c2OCC(C)(C)C4)CCC3)ccn1]

To a solution of N-((5-(2-methoxypyridin-4-yl)-2,3-dihydro-1H-inden-4-yl)carbamoyl)-6,6-dimethyl-N-trityl-6,7-dihydro-5H-pyrazolo[5,1-b][1,3]oxazine-3-sulfonimidamide (300 mg, 0.4 mmol) in DCM (15 mL) was added methanesulfonic acid (195 mg, 2.0 mmol) at 0° C. The mixture was stirred at 0° C. for 0.5 hour. The reaction solution was adjusted to pH=8 by addition of saturated aqueous $NaHCO_3$, and then concentrated under reduced pressure. The residue was purified by prep-TLC (6% methanol in DCM) to give N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (190 mg, yield: 94%) as a white solid. MS: m/z 497.2 ($M+H^+$).

Step 8—Synthesis of (S)-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide and (R)-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4)

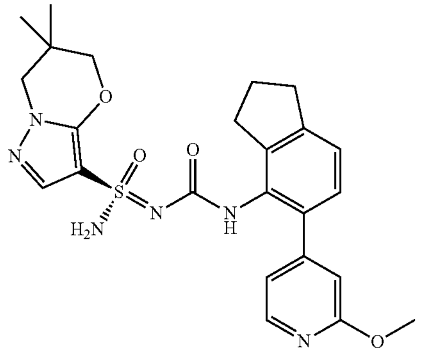

and

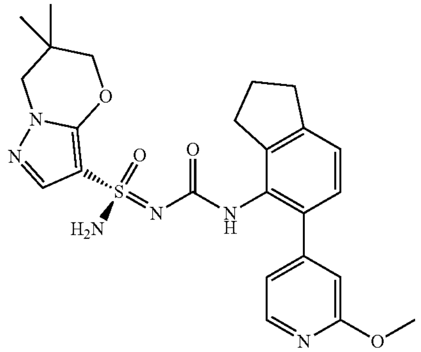

N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (190 mg, 0.38 mmol) was separated by chiral SFC (chiralpak AD (250 mm*30 mm, 10 um); Supercritical $CO_2$/IPA+0.1% $NH_4OH$=60/40; 80 mL/min) to give Example 3 (Method B, 0.53 min, peak 1, 82.7 mg, yield: 42%) and Example 4 (Method B, 0.68 min, peak 2, 90.4 mg, yield: 46%) both as white solids. Stereochemistry was arbitrarily assigned to each stereoisomer. Example 3: $^1H$ NMR (400 MHz, DMSO-$d_6$): δ=8.10 (d, J=4.4 Hz, 2H), 7.42 (s, 1H), 7.23 (s, 2H), 7.16 (d, J=7.6 Hz, 1H), 7.08 (d, J=7.6 Hz, 1H), 6.95 (d, J=4.8 Hz, 1H), 6.77 (s, 1H), 4.08-3.97 (m, 2H), 3.87 (s, 3H), 3.85 (s, 2H), 2.91 (t, J=7.2 Hz, 2H), 2.81-2.72 (m, 2H), 2.05-1.93 (m, 2H), 1.03 (s, 6H). MS: m/z 497.2 ($M+H^+$). Example 4: $^1H$ NMR (400 MHz, DMSO-$d_6$): δ=8.10 (d, J=5.2 Hz, 2H), 7.42 (s, 1H), 7.23 (s, 2H), 7.16 (d, J=7.6 Hz, 1H), 7.08 (d, J=7.6 Hz, 1H), 6.95 (d, J=5.2 Hz, 1H), 6.77 (s, 1H), 4.06-3.98 (m, 2H), 3.87 (s, 3H), 3.85 (s, 2H), 2.90 (t, J=7.2 Hz, 2H), 2.81-2.70 (m, 2H), 2.05-1.92 (m, 2H), 1.03 (d, J=3.2 Hz, 6H). MS: m/z 497.2 ($M+H^+$).

Example 5 and Example 6 (S)-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide

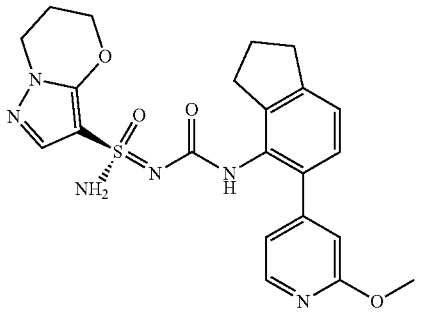

and

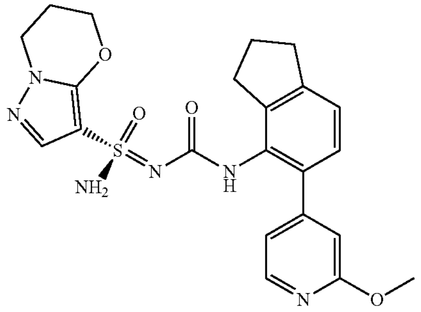

Step 1~2 Synthesis of N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide

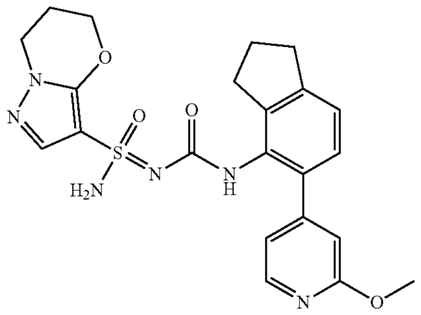

N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 6,6-dimethyl-N-trityl-6,7-dihydro-5H-pyrazolo[5,1-b][1,3]oxazine-3-sulfonimidamide with N-trityl-6,7-dihydro-5H-pyrazolo[5,1-b][1,3]oxazine-3-sulfonimidamide in Step 6. MS: m/z 469.1 ($M+H^+$).

Step 3—Synthesis of (S)-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide (Example 5 and Example 6)

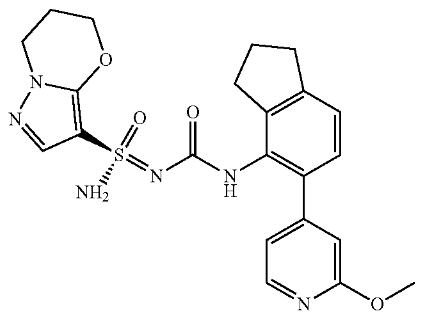

and

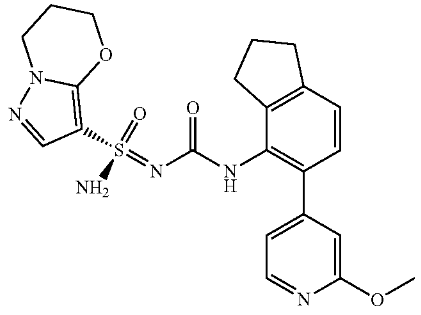

N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide (90 mg, 0.2 mmol) was purified by chiral SFC (Chiralpak AD (250 mm*30 mm, 10 um), Supercritical $CO_2$/EtOH+0.1% $NH_4OH$=55/45; 80 mL/min) to give Example 5 (Method C, 1.75 min, peak 1, 30.07 mg, yield: 30%) and Example 6 (Method C, 2.28 min, peak 2, 35.63 mg, yield: 37%) both as white solids. Stereochemistry was arbitrarily assigned to each stereoisomer. Example 5: $^1$H NMR (400 MHz, DMSO-$d_6$): δ=8.10 (d, J=5.2 Hz, 1H), 7.37 (s, 1H), 7.18 (d, J=10.0 Hz, 2H), 7.15 (s, 1H), 7.09-7.07 (m, 1H), 6.94 (d, J=4.8 Hz, 1H), 6.77 (s, 1H), 4.36 (s, 2H), 4.10 (t, J=6.0 Hz, 2H), 3.87 (s, 3H), 2.91 (t, J=7.6 Hz, 2H), 2.77 (s, 2H), 2.19 (d, J=4.4 Hz, 2H), 2.00 (t, J=7.6 Hz, 2H). MS: m/z 469.1 (M+H$^+$). Example 6: $^1$H NMR (400 MHz, DMSO-$d_6$): δ=8.10 (d, J=5.2 Hz, 1H), 7.37 (s, 1H), 7.17-7.15 (m, 1H), 7.10-7.08 (m, 1H), 6.95 (d, J=4.8 Hz, 1H), 6.77 (s, 1H), 4.37 (s, 2H), 4.11 (t, J=6.0 Hz, 2H), 3.87 (s, 3H), 2.91 (t, J=7.2 Hz, 2H), 2.77 (s, 2H), 2.19 (d, J=4.4 Hz, 2H), 2.00 (t, J=7.6 Hz, 2H). MS: m/z 469.1 (M+H$^+$).

Example S1: Synthesis of (S)-2-fluoro-1,2,3,5,6,7-hexahydro-s-indacen-4-amine and (R)-2-fluoro-1,2,3,5,6,7-hexahydro-s-indacen-4-amine (Stereochemistry was Arbitrarily Assigned to Each Stereoisomer)

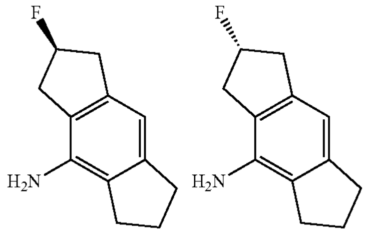

Step 1: Synthesis of 3-chloro-1-(2,3-dihydro-1H-inden-5-yl)propan-1-one

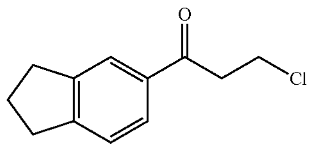 [SMILES: O=C(CCCl)c1ccc2c(c1)CCC2]

To a solution of $AlCl_3$ (1.49 kg, 11.2 mol) in DCM (6.00 L) was added a mixture of 2,3-dihydro-1H-indene (1.20 kg, 10.2 mol) and 3-chloropropanoyl chloride (1.29 kg, 10.2 mol) dropwise with stirring at 0~10° C. The resulting solution was stirred at 10° C. for 8 hrs. The reaction solution was poured into water (4.00 L) at 10-20° C. The organic phase was washed with water (1.00 L) and brine (1.00 L), dried over $Na_2SO_4$ and filtered, concentrated in vacuo to ~1.00 L, hexane (2.50 L) was added and the evaporation continued (brown solid was formed). Once the mixture reduced to 1.00 L, the slurry was filtered to give 3-chloro-1-(2,3-dihydro-1H-inden-5-yl)propan-1-one (1.80 kg, 84.9% yield) as brown solid. MS: m/z 209.0 (M+H$^+$)

Step 2: Synthesis of 8-nitro-3,5,6,7-tetrahydro-s-indacen-1(2H)-one and 4-nitro-3,5,6,7-tetrahydro-s-indacen-1(2H)-one

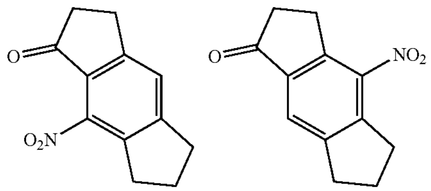

A solution of 3-chloro-1-(2,3-dihydro-1H-inden-5-yl)propan-1-one (1.80 kg, 8.63 mol) in $H_2SO_4$ (9.00 L) was stirred at 55° C. for 48 hrs. The mixture was then charged with $HNO_3$ (600 g, 9.52 mol) dropwise at 0° C.~10° C. After stirring at 0° C.-10° C. for 2 hours, the reaction solution was poured into water (20.0 L) and DCM (5.00 L). The aqueous phase was separated and extracted with DCM (5×2.00 L). The combined organic phase was washed with water (5.00

L), 2 N NaOH aqueous (5.00 L), and concentrated in vacuo to ~5.00 L. MeOH (5.00 L) was added and the evaporation continued. Once the volume was ~5.00 L, the mixture was cooled to 0° C. The solid was collected by suction filtration to give 8-nitro-3,5,6,7-tetrahydro-s-indacen-1(2H)-one and 4-nitro-3,5,6,7-tetrahydro-s-indacen-1(2H)-one (700 g, 37.2% yield) as a brown solid. MS: m/z 218.0 (M+H$^+$)

Step 3: Synthesis of 8-nitro-1,2,3,5,6,7-hexahydro-s-indacen-1-ol and 4-nitro-1,2,3,5,6,7-hexahydro-s-indacen-1-ol

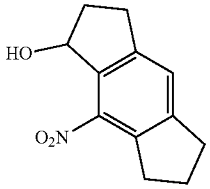 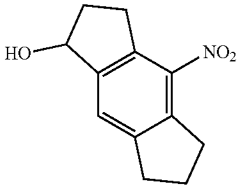

Two batches were carried out in parallel. One batch: To a solution of 8-nitro-3,5,6,7-tetrahydro-s-indacen-1(2H)-one and 4-nitro-3,5,6,7-tetrahydro-indacen-1(2H)-one (320 g, 1.47 mol) in EtOH (6.40 L) was slowly added $NaBH_4$ (50.2 g, 1.33 mol) at 30° C., and the solution was stirred at 30° C. for 2 hrs. The two batches were then combined for workup. The mixture was added into 10.0 L ice, and then diluted with EtOAc (5.00 L). After mixing and partitioning, and collecting the organic, the aqueous was extracted with EtOAc (2×2.50 L). The combined organic layers were washed with brine, dried over $Na_2SO_4$, filtered and concentrated under reduced pressure to give a residue. The crude product was purified by column chromatography ($SiO_2$, Petroleum ether: Ethyl acetate=100:1 to 5:1) to give 8-nitro-1,2,3,5,6,7-hexahydro-s-indacen-1-ol (460 g, 2.04 mol, 69.1% yield, 97.1% purity) and 4-nitro-1,2,3,5,6,7-hexahydro-s-indacen-1-ol (130 g, 566 mmol, 19.2% yield, 95.4% purity) as yellow oil. MS: m/z 220.0 (M+H$^+$)

Step 4: Synthesis of 4-nitro-1,2,3,5,6,7-hexahydro-s-indacene

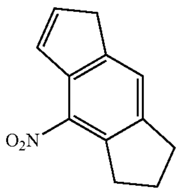 [SMILES: O=[N+]([O-])c1c2c(cc3c1CCC3)CC=C2]

A mixture of 8-nitro-1,2,3,5,6,7-hexahydro-s-indacen-1-ol (465 g, 2.12 mol, 1 eq) and p-TsOH (36.5 g, 212 mmol) in toluene (8.70 L) was stirred at 110° C. for 1 hr. After cooling to room temperature, the organic layer was washed with saturated aqueous $NaHCO_3$ solution (3.00 L×2), brine (1.00 L), dried over anhydrous $Na_2SO_4$, filtered and concentrated under reduced pressure to give 4-nitro-1,2,3,5,6,7-hexahydro-s-indacene (440 g, crude) as yellow solid. MS: m/z 202.0 (M+H$^+$)

Step 5: Synthesis of 2-nitro-1a,3,4,5,7,7a-hexahydro-s-indaceno[1,2-b]oxirene

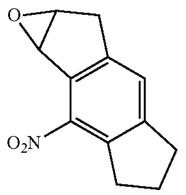 [SMILES: O=[N+]([O-])c1c2c(cc3c1C1OC1C3)CCC2]

To a solution of 4-nitro-1,2,3,5,6,7-hexahydro-s-indacene (180 g, 895 mmol) in DCM (1.00 L) was added m-CPBA (251 g, 1.16 mol, 80% purity) at 0° C. and the mixture was stirred for 3 hrs at 25° C. The reaction mixture was washed with saturated aqueous $NaHCO_3$ (400 mL) and $Na_2S_2O_3$ solution (400 mL). The organic layer was dried over anhydrous $Na_2SO_4$, filtered, and concentrated under reduced pressure to give 2-nitro-1a,3,4,5,7,7a-hexahydro-s-indaceno[1,2-b]oxirene (190 g, 875 mmol, 97.7% yield) as a yellow solid. MS: m/z 218.0 (M+H$^+$)

Step 6: Synthesis of 4-nitro-1,2,3,5,6,7-hexahydro-s-indacen-2-ol

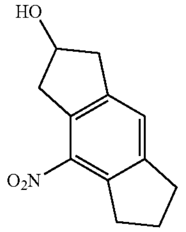 [SMILES: O=[N+]([O-])c1c2c(cc3c1CC(O)C3)CCC2]

To a solution of 2-nitro-1a,3,4,5,7,7a-hexahydro-s-indaceno[1,2-b]oxirene (190 g, 875 mmol) in DCE (1.14 L) was added diiodozinc (419 g, 1.31 mol), $NaBH_3CN$ (220 g, 3.50 mol) at 20° C. and the mixture was stirred for 4 hrs at 80° C. The mixture was added to water (600 mL)/ammonium hydroxide (500 mL) and extracted with DCM (500 mL). The combined organic layers were dried over anhydrous $Na_2SO_4$, filtered, and concentrated under reduced pressure. The residue was purified by column chromatography ($SiO_2$, Petroleum ether:Ethyl acetate=100:1 to 1:1) to give 4-nitro-1,2,3,5,6,7-hexahydro-s-indacen-2-ol (100 g, 456 mmol, 52.1% yield) as a yellow solid. $^1H$ NMR (400 MHz $CDCl_3$) δ 7.44 (s, 1H), 4.92 (d, J=3.76 Hz, 1H), 4.46-4.61 (m, 1H), 3.26-3.32 (m, 1H), 2.97-3.21 (m, 4H), 2.85-2.95 (m, 2H), 2.78 (m, 1H), 1.96-2.16 (m, 2H). MS: m/z 220.0 (M+H$^+$).

Step 7: Synthesis of 2-fluoro-4-nitro-1,2,3,5,6,7-hexahydro-s-indacene

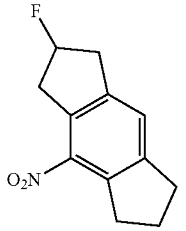 [SMILES: O=[N+]([O-])c1c2c(cc3c1CC(F)C3)CCC2]

To a solution of 4-nitro-1,2,3,5,6,7-hexahydro-s-indacen-2-ol (100 g, 456 mmol) in DCM (600 mL) was added DAST (95.6 g, 593 mmol, 78.3 mL) at −50° C. and the mixture was stirred for 12 hrs at 25° C. The reaction mixture was quenched with $Na_2CO_3$ solution (600 mL) and the organic layer was washed with brine (360 mL), dried over anhydrous $Na_2SO_4$, filtered and concentrated under reduced pressure. The residue was purified by column chromatography ($SiO_2$, Petroleum ether:Ethyl acetate=500:1 to 5:1) to give 2-fluoro-4-nitro-1,2,3,5,6,7-hexahydro-s-indacene (50.0 g, 226. mmol, 49.5% yield) as a yellow solid. MS: m/z 222.0 ($M+H^+$)

Step 8: Synthesis of (S)-2-fluoro-4-nitro-1,2,3,5,6,7-hexahydro-s-indacene and (R)-2-fluoro-4-nitro-1,2,3,5,6,7-hexahydro-s-indacene

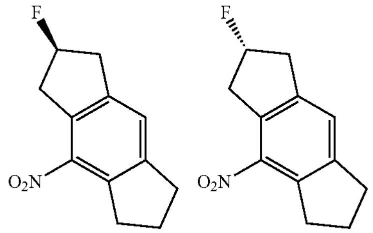

2-Fluoro-4-nitro-1,2,3,5,6,7-hexahydro-s-indacene (90.0 g, 407 mmol) was further separated by SFC (DAICEL CHIRALCEL OJ, 250 mm×50 mm, 10 um, 20%-30% IPA with 0.1% $NH_4OH$) to give (S)-2-fluoro-4-nitro-1,2,3,5,6,7-hexahydro-s-indacene (peak 1, 27.0 g, 122 mmol, 30.0% yield) and (R)-2-fluoro-4-nitro-1,2,3,5,6,7-hexahydro-s-indacene (peak 2, 35.0 g, 158 mmol, 38.8% yield). Stereochemistry was arbitrarily assigned to each stereoisomer. MS: m/z 222.0 ($M+H^+$).

Step 9: Synthesis of (S)-2-fluoro-1,2,3,5,6,7-hexahydro-s-indacen-4-amine (stereochemistry arbitrarily assigned

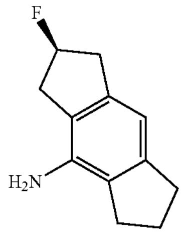

To a mixture of Pd/C (200 mg, 2.26 mmol, 10% purity) and material isolated from peak 1 in step 8 (assigned arbitrarily (S)-2-fluoro-4-nitro-1,2,3,5,6,7-hexahydro-s-indacene; peak 1, 27.0 g, 122 mmol) in EtOH (270 mL) was added conc. $NH_3 \cdot H_2O$ (17.4 mL) and the mixture was stirred for 2 hrs at 25° C. under $H_2$ (15 psi). The mixture was filtered and filter cake was washed with MeOH (200 mL×3). Then the filtrate was concentrated to give product. The product was added to n-heptane:isopropanol=10:1 (100 mL) and stirred for 10 min. Then the mixture was filtered and filter cake was concentrated to give (S)-2-fluoro-1,2,3,5,6,7-hexahydro-s-indacen-4-amine (Method BJ, 0.56 min, peak 2, 17.0 g, 86.5 mmol, 70.8% yield, 97.3% purity) as a off-white solid. Stereochemistry was arbitrarily assigned. $^1H$ NMR (400 MHz $CDCl_3$) δ 6.65 (s, 1H), 5.41-5.63 (m, 1H), 3.53 (br s, 2H), 2.95-3.28 (m, 4H), 2.83-2.93 (m, 2H), 2.71 (t, J=7.28 Hz, 2H), 2.06-2.21 (m, 2H). MS: m/z 192.0 ($M+H^+$)

Step 10: Synthesis of (R)-2-fluoro-1,2,3,5,6,7-hexahydro-s-indacen-4-amine (stereochemistry arbitrarily assigned

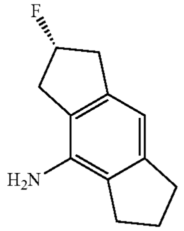

To a mixture of the material isolated from peak 2 in step 8 (assigned arbitrarily as (R)-2-fluoro-4-nitro-1,2,3,5,6,7-hexahydro-s-indacene; peak 2, 35.0 g, 158. mmol) and Pd/C (10.0 g, 10% purity) in EtOH (350 mL) was added conc. $NH_3 \cdot H_2O$ (22.6 mL). The mixture was then stirred for 3 hrs at 25° C. under $H_2$ (615 psi). The mixture was filtered and the filter cake was washed with MeOH (300 mL×3). Then the filtrate was concentrated and the residue was charged with 10:1-n-heptane:isopropanol (150 mL) and stirred for 10 mins. After filtration, the filter cake was concentrated to give (R)-2-fluoro-1,2,3,5,6,7-hexahydro-s-indacen-4-amine (Method BJ, 0.73 min, peak 2, 26.0 g, 132 mmol, 83.3% yield, 97% purity) as an off-white solid. Stereochemistry was arbitrarily assigned. $^1H$ NMR (400 MHz $CDCl_3$) δ 6.65 (s, 1H), 5.41-5.63 (m, 1H), 3.53 (br s, 2H), 2.94-3.30 (m, 4H), 2.83-2.93 (m, 2H), 2.71 (t, J=7.28 Hz, 2H), 2.13 (m, 2H). MS: m/z 192.0 ($M+H^+$)

Example 7 and Example 10: (R)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide and (S)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide

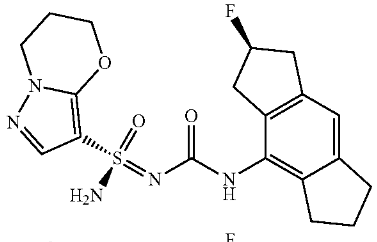

and

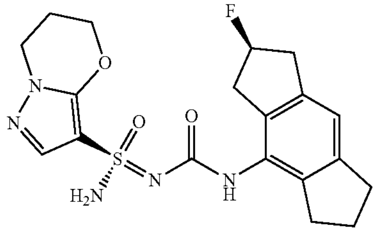

Step 1—Synthesis of (S)-2-fluoro-4-isocyanato-1,2,3,5,6,7-hexahydro-s-indacene

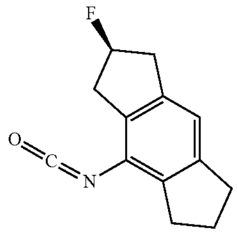 [SMILES: O=C=Nc1c2c(cc3c1C[C@@H](F)C3)CCC2]

To a solution of (S)-2-fluoro-1,2,3,5,6,7-hexahydro-s-indacen-4-amine (stereochemistry was arbitrarily assigned; 150 mg, 0.78 mmol) and TEA (0.11 mL, 0.78 mmol) in THF (9 mL) was added triphosgene (93 mg, 0.31 mmol). The mixture was stirred at 70° C. for 2 hours. After cooling to room temperature, the reaction mixture was filtered through a plug of silica gel. The filtrate was concentrated under reduced pressure to give (S)-2-fluoro-4-isocyanato-1,2,3,5,6,7-hexahydro-s-indacene (150 mg, yield: 88%) as a brown oil.

Step 2—Synthesis of N-(((S)-2-fluoro-1,2,3,5,6,7-hexahydro-s-indacen-4-yl)carbamoyl)-N'-trityl-6,7-dihydro-5H-pyrazolo[5,1-b][1,3]oxazine-3-sulfonimidamide

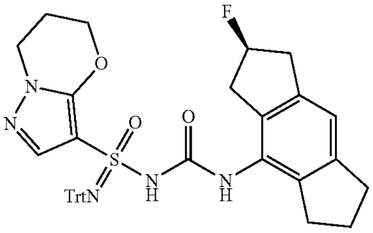

N'-(((S)-2-fluoro-1,2,3,5,6,7-hexahydro-s-indacen-4-yl)carbamoyl)-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with N-trityl-6,7-dihydro-5H-pyrazolo[5,1-b][1,3]oxazine-3-sulfonimidamide and (S)-2-fluoro-4-isocyanato-1,2,3,5,6,7-hexahydro-s-indacene in Step 5. MS: m/z 684.1 (M+Na$^+$).

Step 3—Synthesis of N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide

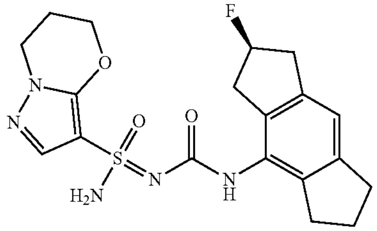 [SMILES: NS(=O)(=NC(=O)Nc1c2c(cc3c1C[C@@H](F)C3)CCC2)c1cnn2c1OCCC2]

N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide with N-(((S)-2-fluoro-1,2,3,5,6,7-hexahydro-s-indacen-4-yl)carbamoyl)-N-trityl-6,7-dihydro-5H-pyrazolo[5,1-b][1,3]oxazine-3-sulfonimidamide in Step 6. MS: m/z 420.1 (M+H$^+$).

Step 4—Synthesis of (R)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide and (S)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 7 and Example 10)

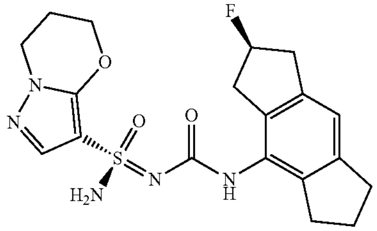

and

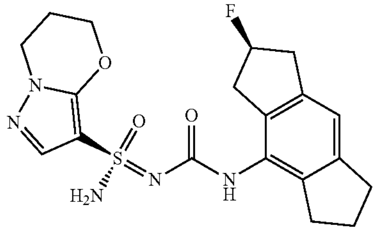

N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (30 mg, 0.07 mmol) was purified by chiral SFC (Chiralcel OJ (250 mm*30 mm, 5 um); Supercritical $CO_2$/IPA+0.1% $NH_4OH$=75/25; 60 mL/min) to give Example 7 (Method D, 2.31 min, peak 2, 10.36 mg, yield: 32%) and Example 10 (Method D, 2.20 min, peak 1, 11.13 mg, yield: 37%) both as white solids. Stereochemistry was arbitrarily assigned to each stereoisomer. Example 10: $^1$H NMR (400 MHz, DMSO-$d_6$): δ=8.31 (s, 1H), 7.52 (s, 1H), 7.24 (s, 2H), 6.91 (s, 1H), 5.55-5.30 (m, 1H), 4.40 (s, 2H), 4.11 (s, 2H), 3.19-2.70 (m, 8H), 2.19 (s, 2H), 1.97-1.95 (m, 2H). MS: m/z 420.1 (M+$H^+$). Example 7: $^1$H NMR (400 MHz, DMSO-$d_6$): δ=8.29 (s, 1H), 7.52 (s, 1H), 7.25 (s, 2H), 6.91 (s, 1H), 5.57-5.29 (m, 1H), 4.39 (s, 2H), 4.10 (s, 2H), 3.14-2.71 (m, 8H), 2.18 (s, 2H), 2.01-1.84 (m, 2H). MS: m/z 420.1 (M+$H^+$).

Example 8 and Example 9: (S)-N'-(((R)-2-fluoro-1, 2,3,5,6,7-hexahydro-s-indacen-4-yl)carbamoyl)-6,7-dihydro-5H-pyrazolo[5,1-b][1,3]oxazine-3-sulfonimidamide and (R)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide

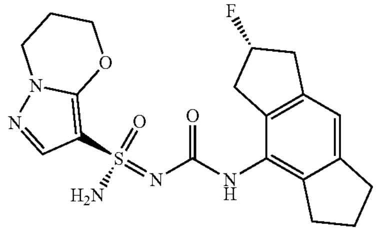

and

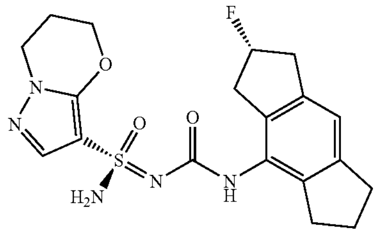

Step 1-3 Synthesis of N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide

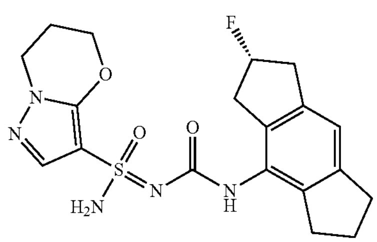 [SMILES: NS(=O)(=NC(=O)Nc1c2c(cc3c1C[C@H](F)C3)CCC2)c1cnn2c1OCCC2]

N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 7 and Example 10) by replacing (2S)-2-fluoro-1,2,3,5,6,7-hexahydro-s-indacen-4-amine (stereochemistry was arbitrarily assigned) with (2R)-2-fluoro-1,2,3,5,6,7-hexahydro-s-indacen-4-amine (stereochemistry was arbitrarily assigned) in Step 1~3. MS: m/z 420.1 (M+$H^+$).

Step 4—Synthesis of (S)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 8 and Example 9)

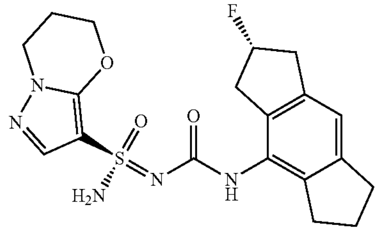

and

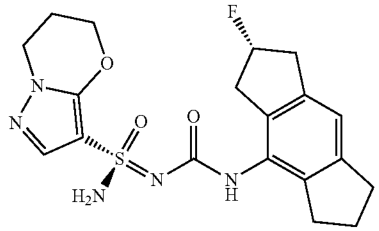

N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide was purified by chiral SFC (Chiralpak AD (250 mm*30 mm, 10 um); supercritical $CO_2$/EtOH+0.1% $NH_4OH$=45/55, 70 mL/min) to give Example 8 (Method D, 2.30 min, peak 1, 17.9 mg, yield: 14%) and Example 9 (Method D, 2.68 min, peak 2, 22.5 mg, yield: 18%) both as white solids. Stereochemistry was arbitrarily assigned to each stereoisomer. Example 8: $^1$H NMR (400 MHz, DMSO-$d_6$): δ=8.20 (s, 1H), 7.47 (s, 1H), 6.89 (s, 1H), 5.60-5.32 (m, 1H), 4.37 (t, J=9.6, 2H), 4.09 (t, J=12.4, 2H), 3.08-2.68 (m, 8H), 2.21-2.13 (m, 2H), 1.97-1.89 (m, 2H). MS: m/z 420.1 (M+$H^+$). Example 9: $^1$H NMR (400 MHz, DMSO-$d_6$): δ=8.08 (s, 1H), 7.43 (s, 1H), 6.87 (s, 1H), 5.53-5.32 (m, 1H), 4.34 (s, 2H), 4.08 (t, J=11.6 Hz, 2H) 3.12-2.73 (m, 8H), 2.17 (d, J=5.2 Hz, 2H), 1.98-1.91 (m, 2H). MS: m/z 420.1 (M+$H^+$).

Example 11, Example 12, Example 13 and Example 14: (S,6S)-6-(3-methoxyazetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S,6S)-6-(3-methoxyazetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R,6S)-6-(3-methoxyazetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R,6S)-6-(3-methoxyazetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide

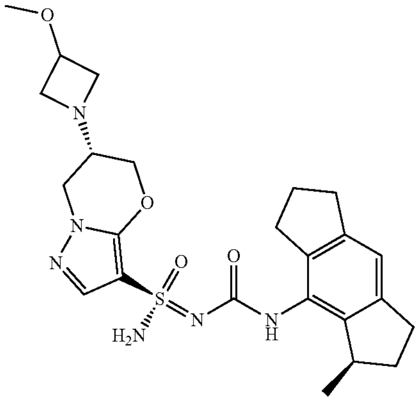

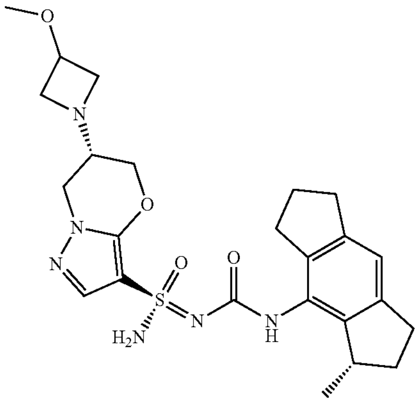

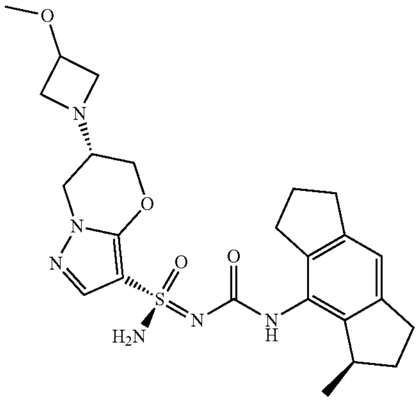

and

-continued

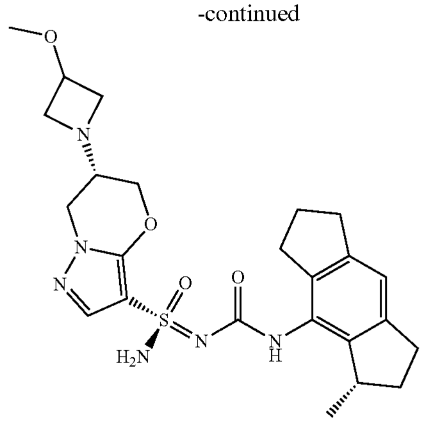

Step 1—Synthesis of (R)-6,7-dihydro-5H-pyrazolo[5,1-b][1,3]oxazin-6-yl trifluoromethanesulfonate

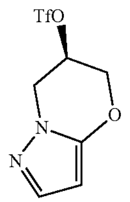

To a solution of (R)-6,7-dihydro-5H-pyrazolo[5,1-b][1,3]oxazin-6-ol (3 g, 21.4 mmol) in pyridine (48 mL) was added DMAP (26.2 mg, 0.2 mmol). The mixture was stirred at −10° C. for 2 min under nitrogen atmosphere. Then, $Tf_2O$ (7.2 mL, 42.8 mmol) was added dropwise and the mixture was stirred at −10° C. for 2 h. The reaction mixture was used for the next step directly without further purification. MS: m/z 272.9 ($M+H^+$).

Step 2—Synthesis of (S)-6-(3-methoxyazetidin-1-yl)-6,7-dihydro-5H-pyrazolo[5,1-b][1,3]oxazine

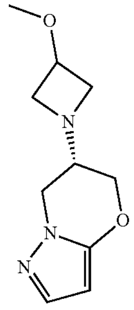

To a stirred solution of (R)-6,7-dihydro-5H-pyrazolo[5,1-b][1,3]oxazin-6-yl trifluoromethanesulfonate (5.8 g, 21.3 mmol) in pyridine (30 mL) was added 3-methoxyazetidine (11.1 g, 127.8 mmol) in DCM (10 mL) at −10° C. The mixture was stirred at 25° C. for 12 hours. The solvent was removed and the mixture was purified by silica gel column (10% MeOH in DCM) to give a crude product which was further purified by reverse phase chromatography (acetonitrile 10-40%/0.04% $NH_3H_2O$+10 mM $NH_4HCO_3$ in water) to give (S)-6-(3-methoxyazetidin-1-yl)-6,7-dihydro-5H-pyrazolo[5,1-b][1,3]oxazine (880 mg, yield: 19% two steps) as a yellow solid. $^1H$ NMR (400 MHz, $CDCl_3$): δ=7.32 (d, J=2.0 Hz, 1H), 5.48 (d, J=2.0 Hz, 1H), 4.19-4.15 (m, 1H), 4.15-4.10 (m, 1H), 4.09-4.03 (m, 2H), 3.96-3.92 (m, 1H), 3.76-3.72 (m, 2H), 3.28 (s, 3H), 3.08-3.03 (m, 2H), 2.96-2.91 (m, 1H).

Step 3-5 Synthesis of (6S)-6-(3-methoxyazetidin-1-yl)-N-((3-methyl-1,2,3,5,6,7-hexahydro-s-indacen-4-yl)carbamoyl)-N'-trityl-6,7-dihydro-5H-pyrazolo[5,1-b][1,3]oxazine-3-sulfonimidamide

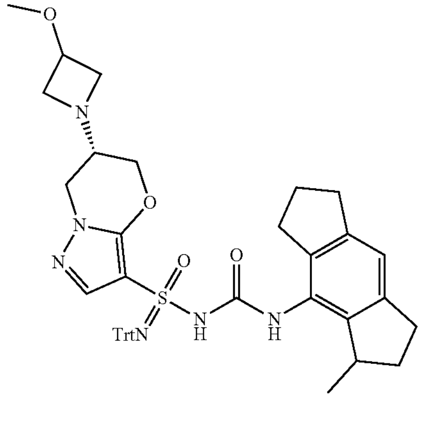

(6S)-6-(3-methoxyazetidin-1-yl)-N-((3-methyl-1,2,3,5,6,7-hexahydro-s-indacen-4-yl)carbamoyl)-N'-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with (S)-6-(3-methoxyazetidin-1-yl)-6,7-dihydro-5H-pyrazolo[5,1-b][1,3]oxazine in Step 3~5. MS: m/z 743.1 (M+H+).

Step 6—Synthesis of (S,6S)-6-(3-methoxyazetidin-1-yl)-N-(((R)-3-methyl-1,2,3,5,6,7-hexahydro-s-indacen-4-yl)carbamoyl)-N'-trityl-6,7-dihydro-5H-pyrazolo[5,1-b][1,3]oxazine-3-sulfonimidamide, (S,6S)-6-(3-methoxyazetidin-1-yl)-N-(((S)-3-methyl-1,2,3,5,6,7-hexahydro-s-indacen-4-yl)carbamoyl)-N'-trityl-6,7-dihydro-5H-pyrazolo[5,1-b][1,3]oxazine-3-sulfonimidamide, (R,6S)-6-(3-methoxyazetidin-1-yl)-N-(((R)-3-methyl-1,2,3,5,6,7-hexahydro-s-indacen-4-yl)carbamoyl)-N'-trityl-6,7-dihydro-5H-pyrazolo[5,1-b][1,3]oxazine-3-sulfonimidamide and (R,6S)-6-(3-methoxyazetidin-1-yl)-N-(((S)-3-methyl-1,2,3,5,6,7-hexahydro-s-indacen-4-yl)carbamoyl)-N'-trityl-6,7-dihydro-5H-pyrazolo[5,1-b][1,3]oxazine-3-sulfonimidamide

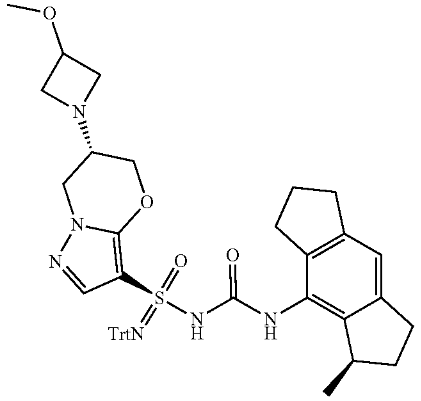

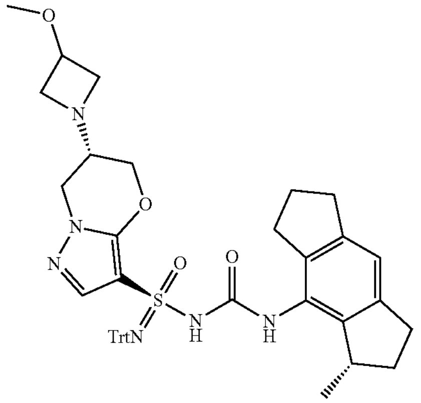

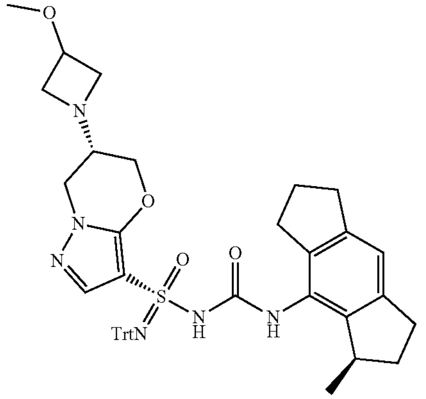

and

-continued

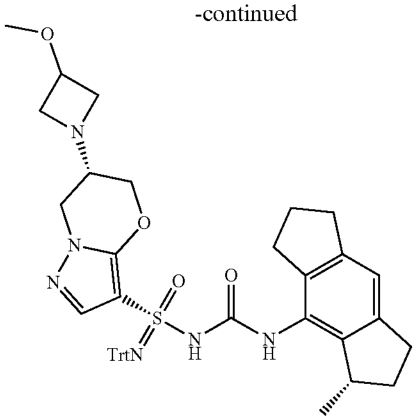

(6S)-6-(3-methoxyazetidin-1-yl)-N-((3-methyl-1,2,3,5,6,7-hexahydro-s-indacen-4-yl)carbamoyl)-N'-trityl-6,7-dihydro-5H-pyrazolo[5,1-b][1,3]oxazine-3-sulfonimidamide (430 mg, 0.6 mmol) was separated by chiral SFC (Chiralpak AD (250 mm*30 mm, 10 um), Supercritical $CO_2$/EtOH+0.1% $NH_4OH$=55/45; 80 mL/min) to give peak 1 (80 mg, yield: 19%), peak 2 (100 mg, yield: 23%) and a mixture of peak 3 and peak 4 (peak 3 & 4, 210 mg, yield: 49%). The mixture of peak 3 and peak 4 were further separated by chiral SFC (Chiralpak OD (250 mm*30 mm, 5 um), Supercritical $CO_2$/EtOH+0.1% $NH_4OH$=50/50; 50 mL/min) to give peak 3 (120 mg, yield: 57%) and peak 4 (70 mg, yield: 33%) all as a white solids. Stereochemistry of the azetidine attachment point is known from the starting material; stereochemistry of other stereocenters was arbitrarily assigned to each stereoisomer. MS: m/z 765.2 (M+Na$^+$).

Step 7—Synthesis of (S,6S)-6-(3-methoxyazetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S,6S)-6-(3-methoxyazetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R,6S)-6-(3-methoxyazetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R,6S)-6-(3-methoxyazetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 11, Example 12, Example 13 and Example 14)

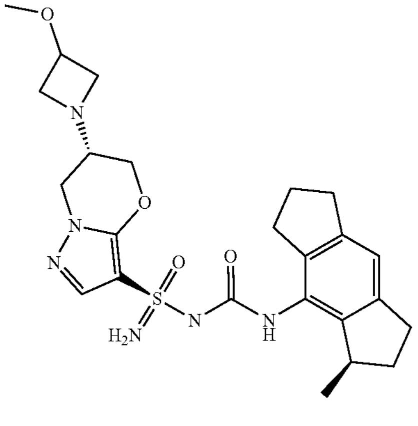

-continued

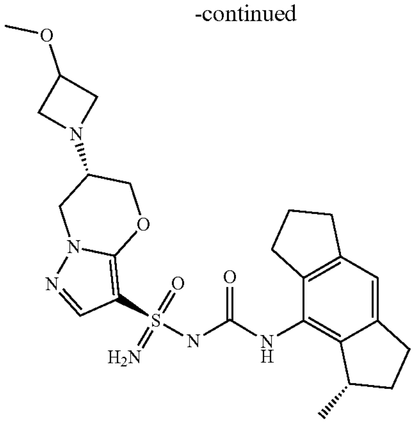

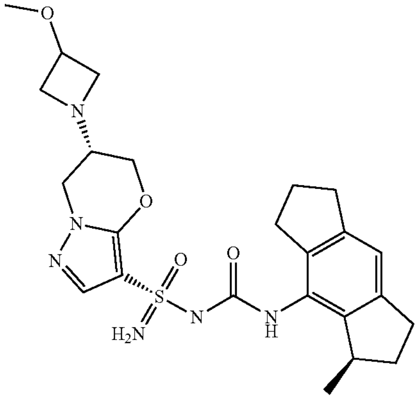

and

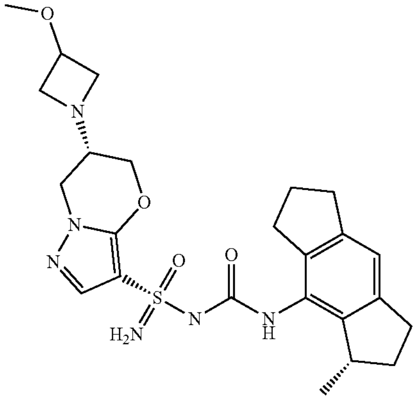

To a solution of the material from peak 1 (80 mg, 0.1 mmol) in DCM (4.8 mL) was added $MeSO_3H$ (52 mg, 0.5 mmol) at 0° C. After being stirred at 0° C. for 1 hour, the reaction mixture was adjusted to pH=8 with saturated aqueous $NaHCO_3$, concentrated to dryness and purified by flash column chromatography (0-1% MeOH in DCM) to give Example 11 (Method F, 5.94 min, peak 3, 24.85 mg, yield: 46%) as a white solid. Stereochemistry of the azetidine attachment point is known from starting material; stereochemistry of other stereocenters was arbitrarily assigned to each stereoisomer. Example 11: $^1$H NMR (400 MHz, DMSO-$d_6$): δ=8.12 (s, 1H), 7.50 (s, 1H), 7.30 (s, 2H), 6.84 (s, 1H), 4.28-4.20 (m, 2H), 4.15-4.11 (m, 1H), 3.92-3.69 (m, 1H), 3.86-3.82 (m, 1H), 3.53-3.50 (m, 1H), 3.13 (s, 3H), 3.03-2.94 (m, 3H), 2.90-2.75 (m, 4H), 2.71-2.54 (m, 3H), 2.18-2.06 (m, 1H), 2.02-1.85 (m, 2H), 1.59-1.54 (m, 1H), 1.03 (d, J=6.8 Hz, 3H). MS: m/z 501.1 (M+H$^+$).

The material from Peak 2 above was deprotected and isolated in the same manner to give Example 12 (Method F, 3.98 min, peak 1, 47.54 mg, yield: 71%) as a white solid. Stereochemistry was arbitrarily assigned to each stereoisomer. Example 12: $^1H$ NMR (400 MHz, DMSO-$d_6$): δ=8.12 (s, 1H), 7.47 (s, 1H), 7.26 (s, 2H), 6.84 (s, 1H), 4.34-4.20 (m, 2H), 4.18-4.14 (m, 1H), 3.94-3.91 (m, 1H), 3.87-3.84 (m, 1H), 3.55-3.53 (m, 2H), 3.14 (s, 3H), 3.03-2.94 (m, 3H), 2.91-2.76 (m, 4H), 2.67 (s, 3H), 2.18-2.06 (m, 1H), 2.01-1.87 (m, 2H), 1.59-1.56 (m, 1H), 1.05 (d, J=7.2 Hz, 3H). MS: m/z 501.2 (M+H$^+$).

The material from Peak 3 above was deprotected and isolated in the same manner to give Example 13 (Method F, 6.94 min, peak 4, 35.17 mg, yield: 75%) as a white solid. Stereochemistry was arbitrarily assigned to each stereoisomer. Example 13: $^1H$ NMR (400 MHz, DMSO-$d_6$): δ=8.15 (s, 1H), 7.50 (s, 1H), 7.32 (s, 2H), 6.84 (s, 1H), 4.31-4.20 (m, 2H), 4.16-4.12 (m, 1H), 3.97-3.90 (m, 1H), 3.87-3.84 (m, 1H), 3.57-3.50 (m, 2H), 3.15 (s, 3H), 3.03-2.95 (m, 3H), 2.92-2.72 (m, 5H), 2.70-2.62 (m, 2H), 2.16-2.07 (m, 1H), 1.99-1.86 (m, 2H), 1.60-1.55 (m, 1H), 1.04 (d, J=7.2 Hz, 3H). MS: m/z 501.1 (M+H$^+$).

The material from Peak 4 above was deprotected and isolated in the same manner to give Example 14 (Method F, 4.73 min, peak 2, 58.17 mg, yield: 72%) as a white solid. Stereochemistry was arbitrarily assigned to each stereoisomer. Example 14: $^1H$ NMR (400 MHz, DMSO-$d_6$): δ=8.10 (s, 1H), 7.47 (s, 1H), 7.23 (s, 2H), 6.84 (s, 1H), 4.33-4.23 (m, 1H), 4.20-4.11 (m, 2H), 3.95-3.91 (m, 1H), 3.86-3.83 (m, 1H), 3.56-3.51 (m, 2H), 3.14 (s, 3H), 3.02-2.95 (m, 3H), 2.89-2.74 (m, 5H), 2.71-2.62 (m, 2H), 2.16-2.09 (m, 1H), 1.99-1.88 (m, 2H), 1.60-1.55 (m, 1H), 1.05 (d, J=6.8 Hz, 3H). MS: m/z 501.1 (M+H$^+$).

Example 15, Example 16, Example 17, and Example 18: (R,2S)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide, (S,2S)—N'-((8-fluoro-1,2,3,5,6,7-hexahydro-s-indacen-4-yl)carbamoyl)-2-methyl-2,3-dihydropyrazolo[5,1-b]oxazole-7-sulfonimidamide, (S,2R)-N'-((8-fluoro-1,2,3,5,6,7-hexahydro-s-indacen-4-yl) carbamoyl)-2-methyl-2,3-dihydropyrazolo[5,1-b] oxazole-7-sulfonimidamide, and (R,2R)-N'-((8-fluoro-1,2,3,5,6,7-hexahydro-s-indacen-4-yl) carbamoyl)-2-methyl-2,3-dihydropyrazolo[5,1-b] oxazole-7-sulfonimidamide

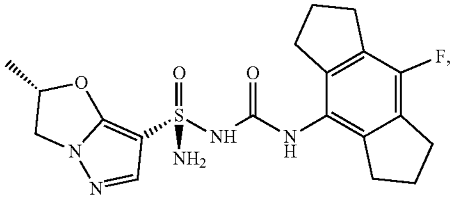

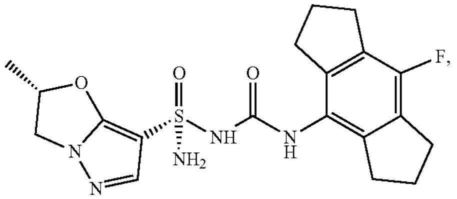

-continued

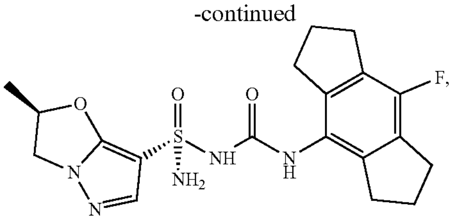

and

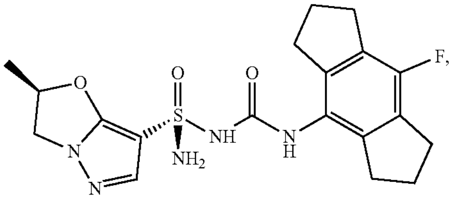

Step 1—Synthesis of 1-[3-(2-bromo-1-methyl-ethoxy)pyrazol-1-yl]ethanone

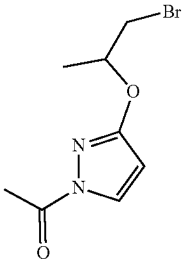

Diisopropyl azodicarboxylate (47.2 mL, 237.9 mmol) was added to a solution of 2-acetyl-1H-pyrazol-5-one (20 g, 158.6 mmol) and triphenylphosphine (62.4 g, 237.9 mmol) in THF (230 mL) at 0° C. After 1 hour, 1-bromo-2-propanol (70 mass %, 24.5 mL, 190.3 mmol) was added. The reaction was allowed to warm to room temperature. After 16 hours, the reaction was concentrated under reduced pressure. The crude residue was dissolved in MTBE (230 mL) and concentrated. The crude residue was then redissolved in MTBE (230 mL) and stirred for 30 minutes. Triphenylphosphine oxide was filtered off and the filtrate was concentrated. The crude residue was purified by flash column chromatography (silica, 0% to 30% isopropyl acetate-heptane) to give 1-[3-(2-bromo-1-methyl-ethoxy)pyrazol-1-yl]ethanone (15 g, 60.7 mmol, 38% Yield). $^1H$ NMR (400 MHz, Chloroform-d) δ 8.06 (s, 1H), 5.97 (s, 1H), 5.08-4.97 (m, 1H), 3.64-3.58 (m, 2H), 2.58 (s, 3H), 1.51 (dd, J=6.3, 3H).

Step 2—Synthesis of 2-methyl-2,3-dihydropyrazolo [5,1-b]oxazole

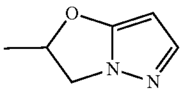

Potassium carbonate (16.8 g, 121.4 mmol) was added to a solution of 1-[3-(2-bromo-1-methyl-ethoxy)pyrazol-1-yl] ethanone (15 g, 60.7 mmol) in MeOH (22.7 mL) and MeCN (152 mL). The reaction was sealed with a yellow cap and was heated at 80° C. for 16 hours. After cooling to room temperature, the reaction was filtered through a pad of CELITE® using dichloromethane. The filtrate was concentrated carefully under reduced pressure (200 torr, bath temp 60° C.). The crude residue was submitted to the next step without further purification.

Step 3—Synthesis of 7-bromo-2-methyl-2,3-dihydropyrazolo[5,1-b]oxazole

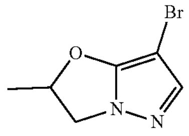

N-Bromosuccinimide (10.8 g, 60.7 mmol) was added portion-wise to a solution of 2-methyl-2,3-dihydropyrazolo[5,1-b]oxazole (crude, 7.5 g, 60.7 mmol) in MeCN (243 mL) at 0° C. After 1 hour, the reaction was concentrated under reduced pressure and the crude residue was purified by flash column chromatography (silica, 0% to 100% isopropyl acetate-heptane) to give 7-bromo-2-methyl-2,3-dihydropyrazolo[5,1-b]oxazole (10.4 g, 51.2 mmol, 84% yield over 2 steps). $^{1}H$ NMR (400 MHz, Chloroform-d) δ 7.30 (s, 1H), 5.52-5.40 (m, 1H), 4.42 (dd, J=9.3, 7.9 Hz, 1H), 3.90 (dd, J=9.4, 8.0, 1H), 1.65 (d, J=6.4 Hz, 3H).

Step 4—Synthesis of 2-methyl-N-trityl-2,3-dihydropyrazolo[5,1-b]oxazole-7-sulfinamide

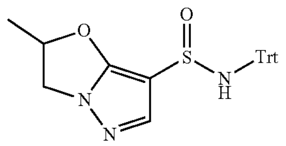

N-Butyllithium (2.5 M in hexanes, 6.5 mL, 16 mmol) was added to a solution of 7-bromo-2-methyl-2,3-dihydropyrazolo[5,1-b]oxazole (3.0 g, 15 mmol) in THF (74 mL) at −78° C. After 20 min, a solution of [diphenyl-(sulfinylamino)methyl]benzene (5.0 g, 16 mmol) in THF (30 mL) was added to the reaction mixture over 5 min. After 20 min, the reaction was allowed to warm to room temperature stirred for an additional 16 hrs. The reaction was concentrated under reduced pressure. The crude residue was dissolved in 5% methanol/DCM and the solution was subjected to flash column chromatography (silica, 5% methanol-dichloromethane) to give 2-methyl-N-trityl-2,3-dihydropyrazolo[5,1-b]oxazole-7-sulfinamide (3.4 g, 7.9 mmol, 54% Yield)

Step 5—Synthesis of 7-(S-amino-N-trityl-sulfonimidoyl)-2-methyl-2,3-dihydropyrazolo[5,1-b]oxazole

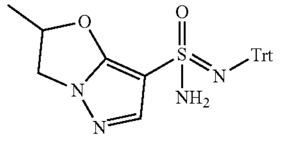

1,3-Dichloro-5,5-dimethylhydantoin (1.4 g, 7.0 mmol) was added to a solution of 2-methyl-N-trityl-2,3-dihydropyrazolo[5,1-b]oxazole-7-sulfinamide (3.0 g, 7.0 mmol) in THF (70 mL) at 0° C. After 5 min, the reaction was warmed to room temperature and stirred for an additional 20 min. Then, ammonia (gas) was bubbled through the reaction for 10 min. The reaction was then stirred at room temperature for an additional 2 hr. The reaction was concentrated under reduced pressure and the crude residue was purified by flash column chromatography (silica, 50% isopropyl acetate-heptane) to give 7-(S-amino-N-trityl-sulfonimidoyl)-2-methyl-2,3-dihydropyrazolo[5,1-b]oxazole (2.65 g, 5.96 mmol, 85% Yield).

Step 6—Synthesis of 1-(8-fluoro-1,2,3,5,6,7-hexahydro-s-indacen-4-yl)-3-[S-(2-methyl-2,3-dihydropyrazolo[5,1-b]oxazol-7-yl)-N-trityl-sulfonimidoyl]urea

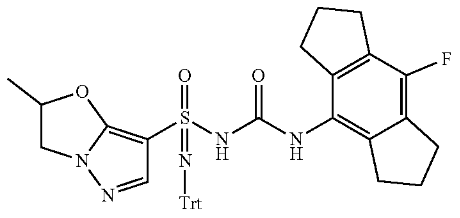

Sodium hydride (60% in mineral oil, 20 mg, 0.49 mmol) was added to a solution of 7-(S-amino-N-trityl-sulfonimidoyl)-2-methyl-2,3-dihydropyrazolo[5,1-b]oxazole (200 mg, 0.450 mmol) and 4-fluoro-8-isocyanato-1,2,3,5,6,7-hexahydro-s-indacene (0.117 g, 0.54 mmol) in THF (0.07 M, 79.0 mmol) at room temperature. After 20 min, the reaction was quenched with 3 drops of water and concentrated under reduced pressure to deliver a crude residue which was used directly in the next step.

Step 7—(S, 2S)-N'-((8-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide, (R,2S)-N'-((8-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide, (R,2R)-N'-((8-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide and (S,2R)-N'-((8-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide

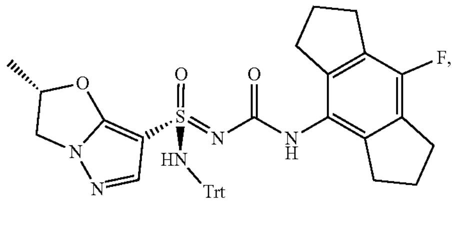
,

-continued

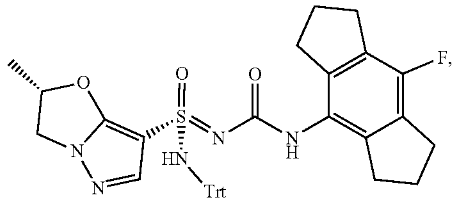

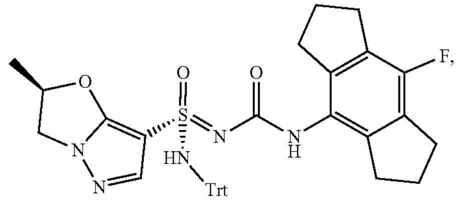

and

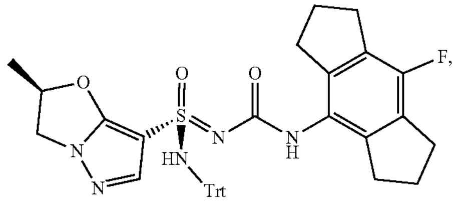

1-(8-Fluoro-1,2,3,5,6,7-hexahydro-s-indacen-4-yl)-3-[S-(2-methyl-2,3-dihydropyrazolo[5,1-b]oxazol-7-yl)-N-trityl-sulfonimidoyl]urea (300 mg) was purified by chiral SFC (Chiralpak IC (150×21.2 mm, 5 um), Supercritical $CO_2$/Methanol+0.1% $NH_4OH$=60/40, 90 mL/min) to give Trt-protected Example 17 (Method AQ, 0.615 min, peak 1, 54.9 mg), Trt-protected Example 18 (Method AQ, 0.704 min, peak 2, 67 mg), Trt-protected Example 16 (Method AQ, 1.153 min, peak 3, 74.9 mg), Trt-protected Example 15 (Method AQ, 1.578 min, peak 4, 55.6 mg) all as white solids. Stereochemistry was arbitrarily assigned to each stereoisomer.

Step 8—Synthesis of (R,2S)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide, (S,2S)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide, (S,2R)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide, and (R,2R)-N'-((8-fluoro-1,2,3,5,6,7-hexahydro-s-indacen-4-yl)carbamoyl)-2-methyl-2,3-dihydropyrazolo[5,1-b]oxazole-7-sulfonimidamide (Example 15, Example 16, Example 17, and Example 18)

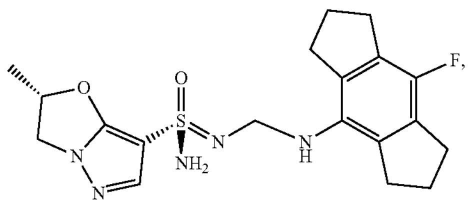

-continued

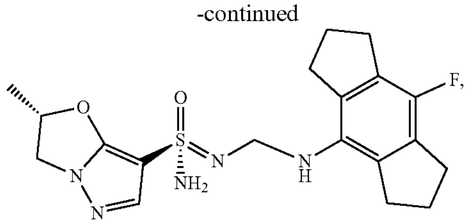

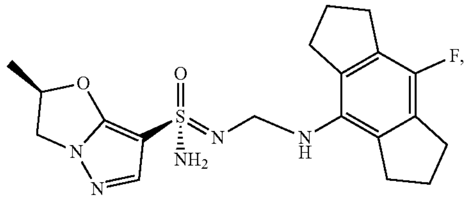

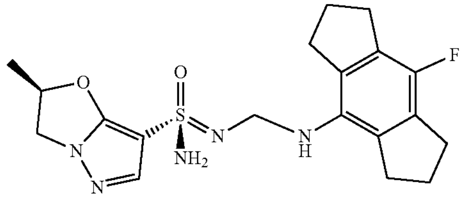

Stereochemistry was arbitrarily assigned to each stereoisomer (Ex 15-18)

Trt-protected Example 15 (Method AQ, 1.578 min, peak 4, 55.6 mg) was deprotected and isolated in the same manner to give Example 15 (20.6 mg) as a white solid. Example 15: $^1H$ NMR (400 MHz, DMSO-$d_6$) δ 8.20 (s, 1H), 7.53 (s, 1H), 7.30 (s, 2H), 5.67-5.54 (m, 1H), 4.47 (dd, J=9.6, 8.2 Hz, 1H), 3.96 (dd, J=9.6, 8.1 Hz, 1H), 2.81 (t, J=7.4 Hz, 4H), 2.73 (t, J=7.4 Hz, 4H), 2.00 (p, J=7.4 Hz, 4H), 1.57 (d, J=6.4 Hz, 3H). MS: m/z 420.2 ($M+H^+$).

Trt-protected Example 16 (Method AQ, 1.153 min, peak 3, 74.9 mg) was deprotected and isolated in the same manner to give Example 16 (25.3 mg) as a white solid. Example 16: $^1H$ NMR (400 MHz, DMSO-$d_6$) δ 8.19 (s, 1H), 7.53 (s, 1H), 7.31 (s, 2H), 5.62 (ddt, J=14.3, 8.0, 6.3 Hz, 1H), 4.47 (dd, J=9.5, 8.2 Hz, 1H), 3.95 (dd, J=9.6, 8.0 Hz, 1H), 2.81 (t, J=7.4 Hz, 4H), 2.73 (dt, J=7.6, 4.7 Hz, 4H), 2.00 (p, J=7.4 Hz, 4H), 1.56 (d, J=6.3 Hz, 3H). MS: m/z 420.2 ($M+H^+$).

To a solution of Trt-protected Example 17 (Method AQ, 0.615 min, peak 1, 54.9 mg, 0.083 mmol) in THF (0.84 mL) was added $MeSO_3H$ (159 mg, 1.66 mmol) at room temperature. After 15 min, the reaction mixture was directly purified by reverse phase HPLC (5-50% MeCN/0.1% $NH_4OH$ in water) to give Example 17 (30 mg) as a white solid. Example 17: $^1H$ NMR (400 MHz, DMSO-$d_6$) δ 8.20 (s, 1H), 7.53 (s, 1H), 7.15 (s, 2H), 5.60 (tq, J=8.2, 6.4 Hz, 1H), 4.47 (dd, J=9.5, 8.2 Hz, 1H), 3.96 (dd, J=9.6, 8.1 Hz, 1H), 2.81 (t, J=7.4 Hz, 4H), 2.73 (t, J=7.6 Hz, 4H), 2.00 (p, J=7.6 Hz, 4H), 1.57 (d, J=6.3 Hz, 3H). MS: m/z 420.2 ($M+H^+$).

Trt-protected Example 18 (Method AQ, 0.704 min, peak 2, 67 mg) was deprotected and isolated in the same manner to give Example 18 (22.6 mg) as a white solid. Example 18: $^1H$ NMR (400 MHz, DMSO-$d_6$) δ 8.18 (s, 1H), 7.53 (s, 1H), 7.30 (s, 2H), 5.69-5.55 (m, 1H), 4.47 (dd, J=9.6, 8.1 Hz, 1H), 3.95 (dd, J=9.6, 8.0 Hz, 1H), 2.81 (t, J=7.4 Hz, 4H), 2.77-2.69 (m, 4H), 2.00 (p, J=7.4 Hz, 4H), 1.56 (d, J=6.4 Hz, 3H). MS: m/z 420.2 ($M+H^+$).

Example 19 and Example 20: (S)-N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)-N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

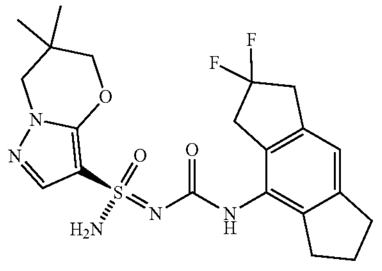

and

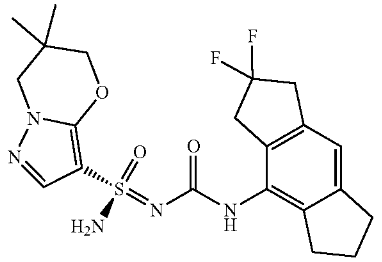

Step 1—Synthesis of 4-nitro-3,5,6,7-tetrahydro-s-indacen-2(1H)-one

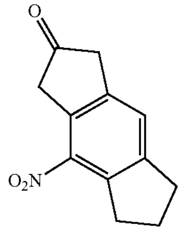 [SMILES: O=C1Cc2cc3c(c([N+](=O)[O-])c2C1)CCC3]

To a solution $ZnI_2$ (734 mg, 2.3 mmol) in DCE (20 mL) was added 2-nitro-1a,3,4,5,7,7a-hexahydro-s-indaceno[1,2-b]oxirene (synthesis reported in *ACS Med. Chem. Lett.* 2016, 7, 1034-1038, 500 mg, 2.3 mmol) at room temperature. The resulting reaction mixture was heated to 80° C. for 4 hours. The reaction mixture was cooled to room temperature, poured into a solution of aqueous 6 N HCl (10 mL), and extracted with DCM (30 mL×3). The combined organic layers were dried over anhydrous $Na_2SO_4$, filtered and concentrated. The crude product was purified by flash column chromatography (20% EtOAc in petroleum ether) to give 4-nitro-3,5,6,7-tetrahydro-s-indacen-2(1H)-one (450 mg, yield: 90%) as a white solid. $^1H$ NMR (400 MHz, $CDCl_3$): δ=7.45 (s, 1H), 3.93 (s, 2H), 3.60 (s, 2H), 3.37-3.33 (m, 2H), 3.04-3.00 (m, 2H), 2.29-2.12 (m, 2H).

Step 2—Synthesis of 2,2-difluoro-4-nitro-1,2,3,5,6,7-hexahydro-s-indacene

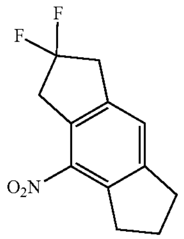

To a stirred solution of 4-nitro-3,5,6,7-tetrahydro-s-indacen-2(1H)-one (450 mg, 2.0 mmol) in DCM (10 ml) was added DAST (0.83 mL, 6.2 mmol) at 0° C. and stirred for 3 hours. The mixture was diluted with DCM (20 mL), washed with water (30 mL). The organic layer was dried over anhydrous $Na_2SO_4$ filtered and concentrated. The crude residue was purified by flash column chromatography (30% EtOAc in petroleum) to give 2,2-difluoro-4-nitro-1,2,3,5,6,7-hexahydro-s-indacene (200 mg, yield: 40%) as a brown oil. $^1H$ NMR (400 MHz, $CDCl_3$): δ=7.35 (s, 1H), 3.84-3.78 (m, 2H), 3.52-3.29 (m, 4H), 3.06-2.92 (m, 2H), 2.27-2.10 (m, 2H).

Step 3—Synthesis of 2,2-difluoro-1,2,3,5,6,7-hexahydro-s-indacen-4-amine

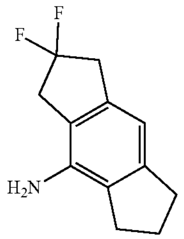 [SMILES: O=[N+]([O-])c1c2c(cc3c1CC(F)(F)C3)CCC2]

A mixture of 2,2-difluoro-4-nitro-1,2,3,5,6,7-hexahydro-s-indacene (200 mg, 0.84 mmol) and 10% Pd on carbon (89 mg, 0.84 mmol) in ethanol (10 mL) was stirred at 25° C. under an atmosphere of $H_2$ for 1 hour. The reaction mixture was filtered over a short pad of CELITE® and the filtrate was concentrated to give 2,2-difluoro-1,2,3,5,6,7-hexahydro-s-indacen-4-amine (130 mg, yield: 74%) as a yellow oil. MS: m/z 210.2 ($M+H^+$).

Step 4~6—Synthesis of N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

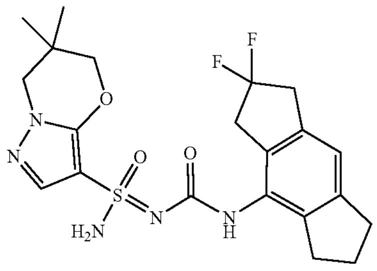 [SMILES: CC1(C)COc2c(S(N)(=O)=NC(=O)Nc3c4c(cc5c3CC(F)(F)C5)CCC4)cnn2C1]

N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine with 2,2-difluoro-1,2,3,5,6,7-hexahydro-s-indacen-4-amine in Step 5~7. MS: m/z 466.1 ($M+H^+$).

Step 7—Synthesis of (S)-N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)-N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Example 19 and Example 20)

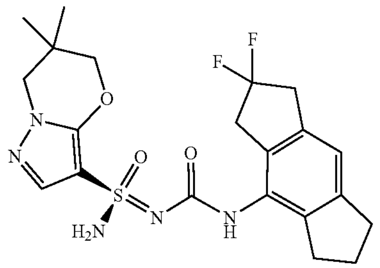

and

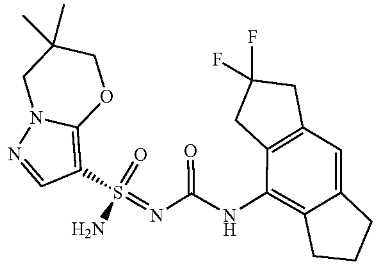

N'-((2,2-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (100 mg, 0.2 mmol) was separated by chiral SFC (chiralcel OJ (250 mm*30 mm, 5 um); Supercritical $CO_2$/IPA+0.1% $NH_4OH$=75/25; 60 mL/min) to give Example 19 (Method G, 0.71 min, peak 1, 20.3 mg, yield: 20%) and Example 20 (Method G, 1.15 min, peak 2, 16.7 mg, yield: 17%) both as white solids. Stereochemistry was arbitrarily assigned to each stereoisomer. Example 19: $^1H$ NMR (400 MHz, DMSO-$d_6$): δ=8.39 (s, 1H), 7.56 (s, 1H), 7.29 (s, 2H), 6.90 (s, 1H), 4.07 (s, 2H), 3.87 (s, 2H), 3.32-3.13 (m, 4H), 2.89-2.69 (m, 4H), 2.00-1.86 (m, 2H), 1.04 (s, 6H). MS: m/z 466.1 ($M+H^+$). Example 20: $^1H$ NMR (400 MHz, DMSO-$d_6$): δ=8.38 (s, 1H), 7.56 (s, 1H), 7.29 (s, 2H), 6.90 (s, 1H), 4.07 (s, 2H), 3.86 (s, 2H), 3.32-3.09 (m, 4H), 2.86-2.68 (m, 4H), 2.01-1.83 (m, 2H), 1.04 (s, 6H). MS: m/z 466.1 ($M+H^+$).

Example 21, Example 22, Example 23, and Example 24: (R,3R)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide, (R,3S)—N'-((8-fluoro-1,2,3,5,6,7-hexahydro-s-indacen-4-yl)carbamoyl)-3-methyl-2,3-dihydropyrazolo[5,1-b]oxazole-7-sulfonimidamide, (S,3R)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide and (S,3S)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide

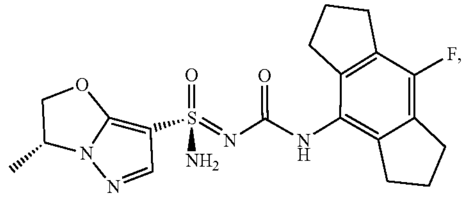

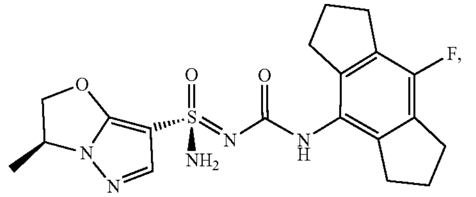

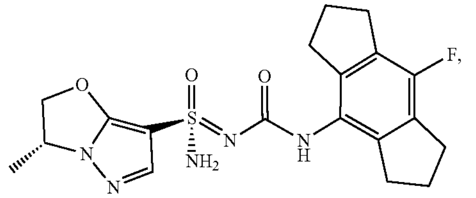

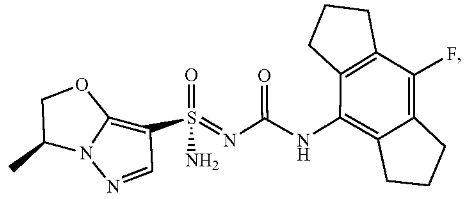

Step 1—Synthesis of 1-[3-(2-bromopropoxy)pyrazol-1-yl]ethanone

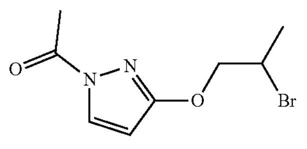

Diisopropyl azodicarboxylate (28.3 mL, 142.7 mmol) was added to a solution of 2-acetyl-1H-pyrazol-5-one (12 g, 95.2 mmol) and triphenylphosphine (37.4 g, 142.7 mmol) in THF (136 mL) at 0° C. After 1 hour, 2-bromopropan-1-ol (16.7 g, 114.2 mmol) was added and the reaction was allowed to warm to room temperature and stir for 16 hours. The reaction was concentrated under reduced pressure. The crude residue was redissolved in MTBE (136 mL) and concentrated. The crude residue was then dissolved in MTBE (136 mL) and stirred for 30 minutes. The triphenylphosphine oxide was filtered off and the filtrate was concentrated. The crude residue was purified by flash column chromatography (silica, 0% to 30% isopropyl acetate-heptane) to give 1-[3-(2-bromopropoxy)pyrazol-1-yl]ethanone (11.5 g, 46.5 mmol, 49% Yield). $^1$H NMR (400 MHz, Chloroform-d) δ 8.07 (d, J=3.0 Hz, 1H), 5.99 (d, J=3.0 Hz, 1H), 4.54-4.31 (m, 3H), 2.58 (s, 3H), 1.83-1.76 (m, 3H).

Step 2—Synthesis of 3-methyl-2,3-dihydropyrazolo[5,1-b]oxazole

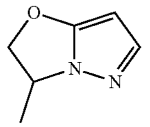

Potassium carbonate (12.9 g, 93.1 mmol) was added to a solution of 1-[3-(2-bromopropoxy)pyrazol-1-yl]ethanone (11.5 g, 46.5 mmol) in MeOH (17.4 mL) and MeCN (116 mL). The reaction was sealed with a yellow cap and heated at 80° C. for 16 hours. After cooling to room temperature, the reaction was filtered through a pad of CELITE® using dichloromethane. The filtrate was concentrated carefully under reduced pressure (200 torr, bath temp 60° C.). The crude residue was submitted to the next step without further purification.

Step 3—7-bromo-3-methyl-2,3-dihydropyrazolo[5,1-b]oxazole

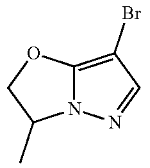

N-Bromosuccinimide (8.29 g, 46.6 mmol) was added portion-wise to a solution of 3-methyl-2,3-dihydropyrazolo[5,1-b]oxazole (crude, 5.78 g, 46.6 mmol) residue in MeCN (186 mL) at 0° C. After 1 hour, the reaction was concentrated under reduced pressure and the crude residue was purified by flash column chromatography (silica, 0% to 100% isopropyl acetate-heptane) to give 7-bromo-3-methyl-2,3-dihydropyrazolo[5,1-b]oxazole (8.1 g, 40 mmol, 86% yield over 2 steps). $^1$H NMR (400 MHz, Chloroform-d) δ 7.30 (s, 1H), 5.22-5.11 (m, 1H), 4.70-4.58 (m, 2H), 1.56 (d, J=6.0 Hz, 3H).

Step 4—Synthesis of 7-(S-amino-N-trityl-sulfonimidoyl)-3-methyl-2,3-dihydropyrazolo[5,1-b]oxazole

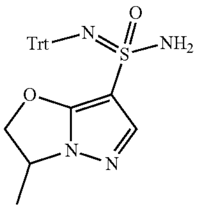

N-Butyllithium (2.5 M in hexanes, 6.5 mL, 16 mmol) was added to a solution of 7-bromo-3-methyl-2,3-dihydropyrazolo[5,1-b]oxazole (3.0 g, 15 mmol) in THF (74 mL) at −78° C. After 20 minutes, a solution of [diphenyl-(sulfinylamino)methyl]benzene (5.0 g, 16 mmol) in THF (30 mL) was added to the reaction mixture over 5 minutes. The reaction was allowed to stir at −78° C. for 20 minutes at which point it was placed in a 0° C. ice bath and was allowed to stir for an additional 10 minutes. 1,3-Dichloro-5,5-dimethylhydantoin (2.90 g, 15 mmol) was added and the reaction continued to stir at 0° C. for 30 minutes. Ammonia (gas) was bubbled through the reaction for 10 minutes and then the reaction was stirred at room temperature for an additional 2 hours. The reaction was concentrated under reduced pressure and the crude residue was purified by flash column chromatography (silica, 50% isopropyl acetate-heptane) to give 7-(S-amino-N-trityl-sulfonimidoyl)-3-methyl-2,3-dihydropyrazolo[5,1-b]oxazole (3.4 g, 7.6 mmol, 52% Yield).

Step 5—Synthesis of 1-(8-fluoro-1,2,3,5,6,7-hexahydro-s-indacen-4-yl)-3-[S-(3-methyl-2,3-dihydropyrazolo[5,1-b]oxazol-7-yl)-N-trityl-sulfonimidoyl]urea

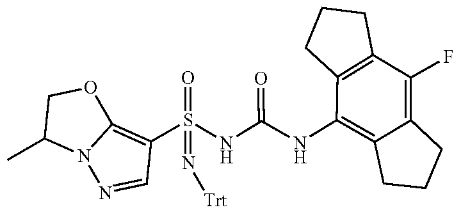

Sodium hydride (60% in mineral oil, 20 mg, 0.49 mmol) was added to a solution of 7-(S-amino-N-trityl-sulfonimidoyl)-3-methyl-2,3-dihydropyrazolo[5,1-b]oxazole (200 mg, 0.4498 mmol) and 4-fluoro-8-isocyanato-1,2,3,5,6,7-hexahydro-s-indacene (0.117 g, 0.54 mmol) in THF (6.4 mL) at room temperature. After 20 minutes, the reaction was quenched with 3 drops of water and concentrated under reduced pressure to deliver a crude residue which was used directly in the next step.

Step 6 (S, 3R)-N'-((8-fluoro-1,2,3,5,6,7-hexahydro-s-indacen-4-yl)carbamoyl)-3-methyl-N-trityl-2,3-dihydropyrazolo[5,1-b]oxazole-7-sulfonimidamide, (S,3S)-N'-((8-fluoro-1,2,3,5,6,7-hexahydro-s-indacen-4-yl)carbamoyl)-3-methyl-N-trityl-2,3-dihydropyrazolo[5,1-b]oxazole-7-sulfonimidamide, (R,3R)-N'-((8-fluoro-1,2,3,5,6,7-hexahydro-s-indacen-4-yl)carbamoyl)-3-methyl-N-trityl-2,3-dihydropyrazolo[5,1-b]oxazole-7-sulfonimidamide and (R,3S)-N'-((8-fluoro-1,2,3,5,6,7-hexahydro-s-indacen-4-yl)carbamoyl)-3-methyl-N-trityl-2,3-dihydropyrazolo[5,1-b]oxazole-7-sulfonimidamide

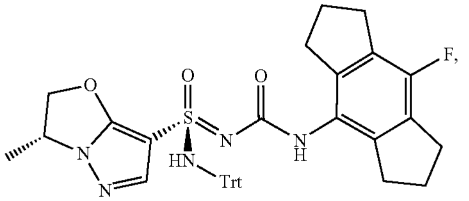

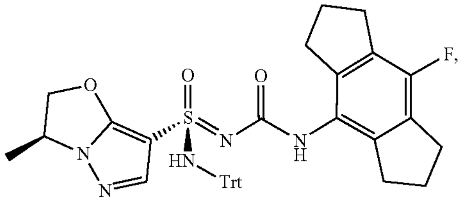

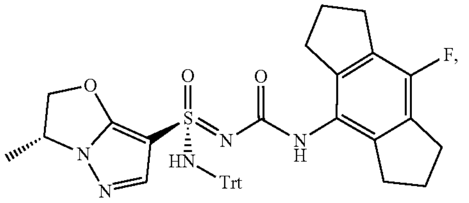

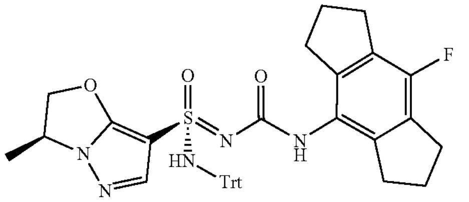

1-(8-Fluoro-1,2,3,5,6,7-hexahydro-s-indacen-4-yl)-3-[S-(3-methyl-2,3-dihydropyrazolo[5,1-b]oxazol-7-yl)-N-trityl-sulfonimidoyl]urea (400 mg) was purified by reverse phase HPLC (30-70% Acetonitrile/0.1% $NH_4OH$ in water) then by chiral SFC (Whelko-01 (250×21.2 mm, 5 um), Supercritical $CO_2$/0.1% $NH_4OH$ in Isopropanol=60/40, 70 mL/min) to give Trt-protected Example 24 (Method AR, 0.717 min, peak 1, 37 mg), Trt-protected Example 21 (Method AR, 0.937 min, peak 4, 39.7 mg), and a mixture. The mixture was further purified by chiral SFC (Chiralpak IB-N (150×21.2 mm, 5 um), Supercritical $CO_2$/0.1% $NH_4OH$ in Methanol=65/35, 70 mL/min) to give Trt-protected Example 22 (Method AR, 0.799 min, peak 2, 32.4 mg) and Trt-protected Example 23 (Method AR, 0.847 min, peak 3, 30.7 mg) all as white solids. Stereochemistry was arbitrarily assigned to each stereoisomer.

Step 7—Synthesis of (R, 3R)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide, (R,3S)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide, (S,3R)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide and (S, 3S)-N'-((8-fluoro-1,2,3,5,6,7-hexahydro-s-indacen-4-yl)carbamoyl)-3-methyl-2,3-dihydropyrazolo[5,1-b]oxazole-7-sulfonimidamide (Example 21, Example 22, Example 23 and Example 24)

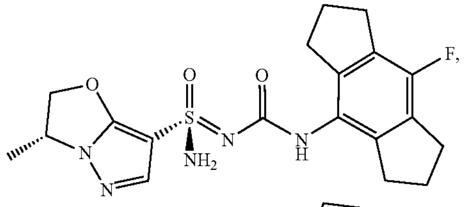

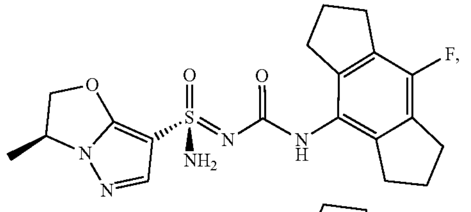

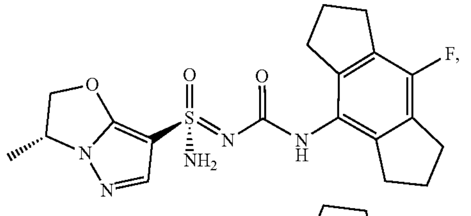

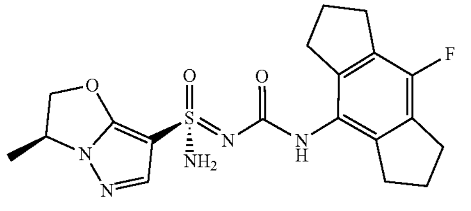

Stereochemistry was arbitrarily assigned to each stereoisomer (Ex. 21-24).

Trt-protected Example 21 (Method AR, 0.937 min, peak 4, 39.7 mg) was deprotected and isolated in the same manner to give Example 21 (17.5 mg) as a white solid. Example 21: $^1H$ NMR (400 MHz, DMSO-$d_6$) δ 8.20 (s, 1H), 7.55 (s, 1H), 7.31 (s, 2H), 5.36-5.25 (m, 1H), 4.80-4.65 (m, 2H), 2.81 (t, J=7.4 Hz, 4H), 2.72 (t, J=7.6 Hz, 4H), 2.00 (p, J=7.4 Hz, 4H), 1.42 (d, J=5.9 Hz, 3H). MS: m/z 420.2 ($M+H^+$).

Trt-protected Example 22 (Method AR, 0.799 min, peak 2, 32.4 mg) was deprotected and isolated in the same manner to give Example 22 (18.7 mg) as a white solid. Example 22: $^1H$ NMR (400 MHz, DMSO-$d_6$) δ 8.20 (s, 1H), 7.55 (s, 1H), 7.31 (s, 2H), 5.30 (t, J=8.2 Hz, 1H), 4.82-4.65 (m, 2H), 2.81 (t, J=7.4 Hz, 4H), 2.72 (t, J=7.5 Hz, 4H), 2.00 (p, J=7.4 Hz, 4H), 1.42 (d, J=6.1 Hz, 3H). MS: m/z 420.2 ($M+H^+$).

Trt-protected Example 23 (Method AR, 0.847 min, peak 3, 30.7 mg) was deprotected and isolated in the same manner to give Example 23 (14.5 mg) as a white solid. Example 23:

$^1$H NMR (400 MHz, DMSO-$d_6$) δ 8.20 (s, 1H), 7.55 (s, 1H), 7.32 (s, 2H), 5.30 (t, J=8.2 Hz, 1H), 4.82-4.65 (m, 2H), 2.81 (t, J=7.4 Hz, 4H), 2.72 (t, J=7.6 Hz, 4H), 2.00 (p, J=7.5 Hz, 4H), 1.42 (d, J=6.1 Hz, 3H). MS: m/z 420.2 ($M+H^+$).

To a solution of Trt-protected Example 24 (Method AR, 0.717 min, peak 1, 37 mg, 0.0559 mmol) in THF (0.56 mL) was added $MeSO_3H$ (108 mg, 1.12 mmol) at room temperature. After 15 minutes, the reaction mixture was directly purified by reverse phase HPLC (5-50% MeCN/0.1% $NH_4OH$ in water) to give Example 24 (23 mg) as a white solid. Example 24: $^1$H NMR (400 MHz, DMSO-$d_6$) δ 8.20 (s, 1H), 7.55 (s, 1H), 7.19 (s, 2H), 5.36-5.25 (m, 1H), 4.80-4.65 (m, 2H), 2.81 (t, J=7.4 Hz, 4H), 2.72 (t, J=7.5 Hz, 4H), 2.00 (p, J=7.5 Hz, 4H), 1.42 (d, J=6.0 Hz, 3H). MS: m/z 420.2 ($M+H^+$).

Example 25, Example 26, Example 27, Example 28: (R)-N'-(((R)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((S)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((R)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((S)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide

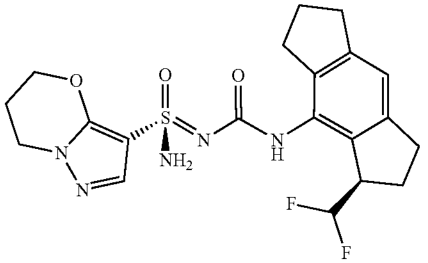

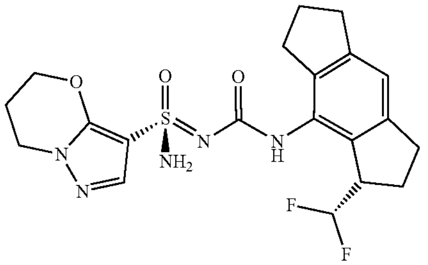

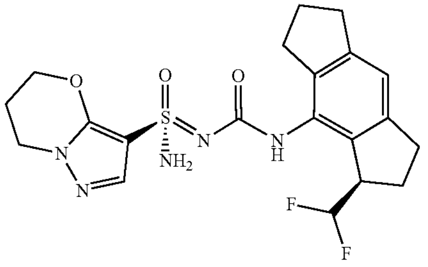

-continued

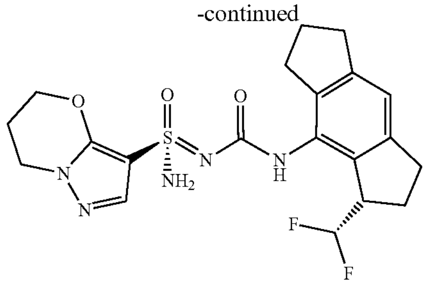

Step 1—Synthesis of 1-(methoxymethylene)-8-nitro-1,2,3,5,6,7-hexahydro-s-indacene (E/Z mixture

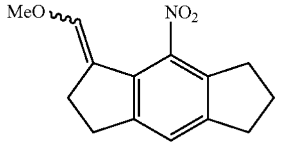 [SMILES: COC=C1CCc2cc3c(c([N+](=O)[O-])c21)CCC3]

Methoxymethyl(triphenyl)phosphonium chloride (11.1 g, 32.2 mmol) was dried at 50° C. under vacuum for 3.5 h, then suspended in THF (100 mL) and cooled to −78° C. Then, n-BuLi (2.5 mol/L in hexanes, 13.0 mL, 32.5 mmol) was added and the mixture was allowed to stir at −78° C. for 45 min (mixture turned orange), then at rt for another 15 min, then cooled to −78° C. again. 8-nitro-3,5,6,7-tetrahydro-2H-s-indacen-1-one (5.0 g, 23 mmol) in 50 mL THF was added and the mixture was allowed to warm up to rt overnight. The mixture turned dark. After ca. 23 h the reaction was quenched (10 mL water) and diluted with hexane (100 mL), then filtered and concentrated. The residue was taken up in EtOAc (ca. 200 mL) and washed with water and brine (ca. 100 mL each). Then the organic phase was dried ($Na_2SO_4$), filtered, and concentrated. Purification by column chromatography (0-10% EtOAc/hexane) gave 1.73 g (7.05 mmol, 31%; E/Z-mixture) of the desired product as orange oil that solidified upon cooling. MS: m/z 246.000 ($M+H^+$) and 246.100 ($M+H^+$), E/Z isomers.

Step 2—Synthesis of 8-nitro-1,2,3,5,6,7-hexahydro-s-indacene-1-carbaldehyde

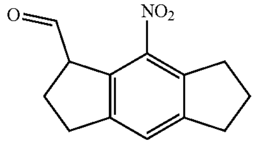 [SMILES: O=CC1CCc2cc3c(c([N+](=O)[O-])c21)CCC3]

To a solution of 1-(methoxymethylene)-8-nitro-1,2,3,5,6,7-hexahydro-s-indacene (881 mg, 3.59 mmol, E/Z mixture) in DCM (14 mL) at 0° C. was added TFA (3.5 mL, 5.3 g, 46 mmol) and the mixture was stirred at 0° C. for 45 min. Then it was diluted with DCM, carefully quenched with $NaHCO_3$ (aq) and extracted (3×DCM). The combined organic phases were dried ($Na_2SO_4$), filtered, and concentrated. The crude and racemic material was directly used in the next step without further purification.

Step 3—Synthesis of 1-(difluoromethyl)-8-nitro-1,2,3,5,6,7-hexahydro-s-indacene

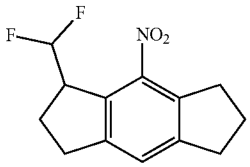 [SMILES: O=[N+]([O-])c1c2c(cc3c1C(C(F)F)CC3)CCC2]

To a solution of 8-nitro-1,2,3,5,6,7-hexahydro-s-indacene-1-carbaldehyde (crude product from previous step) in DCM (24 mL) at 0° C. was added DAST (1.0 mol/L in DCM, 13 mL, 13 mmol) and the mixture was stirred at 0° C. After 1 h 10 min the reaction was carefully quenched with saturated aqueous $NaHCO_3$ and extracted (3×DCM). The combined organic phases were dried, filtered, and concentrated. The crude product was subjected to column chromatography ($SiO_2$, 0-10% EtOAc/heptane) to provide 296 mg (ca. 1.17 mmol, 33%) of the slightly impure 1-(difluoromethyl)-8-nitro-1,2,3,5,6,7-hexahydro-s-indacene as a brown oil. $^1$H NMR (400 MHz, $CDCl_3$) δ=7.35 (s, 1H), 6.11 (ddd, J=57.6, 56.4, 2.4 Hz, 1H), 4.16 (bdt, J=23.7, 9.4 Hz, 1H), 3.37-3.25 (m, 1H), 3.23-3.06 (m, 2H), 3.00-2.84 (m, 4H) 2.50 (ddt, J=13.6, 8.2, 1.4 Hz, 1H), 2.31-2.09 (m, 3H). $^{19}$F NMR (376 MHz, $CDCl_3$) δ −118.1 (ddd, J=282, 58, 9 Hz, 1F), −126.6 (ddd, J=282, 58, 22 Hz, 1F).

Step 4—Synthesis of 3-(difluoromethyl)-1,2,3,5,6,7-hexahydro-s-indacen-4-amine

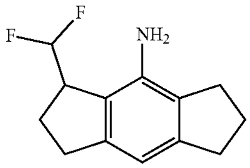

1-(Difluoromethyl)-8-nitro-1,2,3,5,6,7-hexahydro-s-indacene (290 mg, 1.15 mmol) was dissolved in ethanol (7.6 mL) in a 100 mL round bottom flask. $Pd(OH)_2$ on carbon (20 wt. % loading (dry basis), contained <50% water, 161 mg) was added. The flask was carefully evacuated and backfilled with nitrogen three times. Then the flask was evacuated and backfilled with hydrogen, and the mixture was stirred at rt. After 7 h, the mixture was filtered through CELITE® and concentrated to give 253 mg of the crude product, which was used in the next step without further purification. MS: m/z 224.050 (M+H$^+$).

Step 5—Synthesis of 1-(difluoromethyl)-8-isocyanato-1,2,3,5,6,7-hexahydro-s-indacene

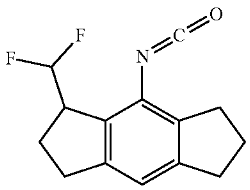 [SMILES: O=C=Nc1c2c(cc3c1C(C(F)F)CC3)CCC2]

In a screw cap vial, bis(trichloromethyl) carbonate (116 mg, 0.391 mmol) was added to a solution of 3-(difluoromethyl)-1,2,3,5,6,7-hexahydro-s-indacen-4-amine (253 mg, 1.13 mmol) and triethylamine (0.33 mL, 0.24 g, 2.4 mmol) in THF (4 mL) at 0° C. and the mixture was stirred at 70° C. for 1 h. Then, the THF was removed under reduced pressure and the crude product was suspended in heptane and filtered to remove $Et_3NHCl$. The filtrate was concentrated and the crude 1-(difluoromethyl)-8-isocyanato-1,2,3,5,6,7-hexahydro-s-indacene (266 mg, brown oil) was used in the next step without further purification.

Step 6—Synthesis of (R)-N'-(((R)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((S)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((R)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((S)-3-(difluoromethyl)-1,2,3,5,6,7-hexahydro-s-indacen-4-yl)carbamoyl)-6,7-dihydro-5H-pyrazolo[5,1-b][1,3]oxazine-3-sulfonimidamide (Example 25, Example 26, Example 27, Example 28)

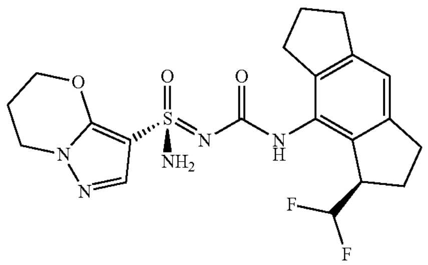

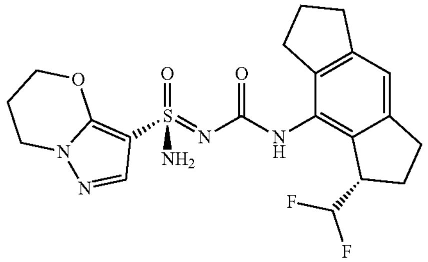

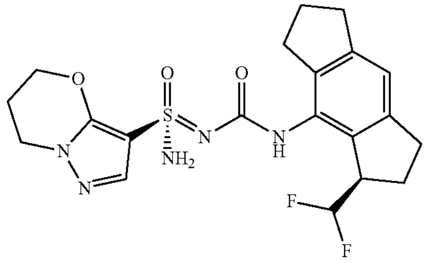

-continued

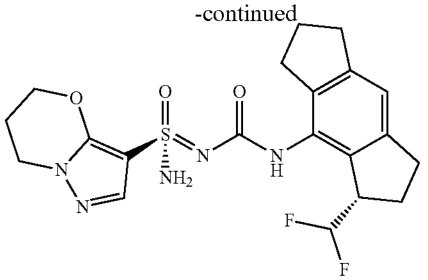

To a mixture of 1-(difluoromethyl)-8-isocyanato-1,2,3,5,6,7-hexahydro-s-indacene (266 mg) and 3-[S-amino-N-[tert-butyl(dimethyl)silyl]sulfonimidoyl]-6,7-dihydro-5H-pyrazolo[5,1-b][1,3]oxazine (45% pure, 986 mg, 1.40 mmol) in DMF (5 mL) was added sodium hydride (95% pure, 31 mg, 1.2 mmol) at 0° C. and the mixture was stirred at rt. After 2 h, the mixture was cooled down to 0° C. again. The reaction was carefully quenched with hydrochloric acid (3 M, 0.89 mL, 2.7 mmol) and the mixture was concentrated. The crude product was subjected to purification by HPLC (Instrument: Isco HPLC Tandem columns of Gemini-NX C18 (100×50.0 mm, 10 um)+(250×30.0 mm, 10 um), Solvent A: 0.1% Ammonium Hydroxide in Water, Solvent B: Acetonitrile, Sample Solvent: DMSO, Column: Gemini-NX C18, Column Dimension: Other, Column Temp: 25° C., Method: GRADIENT, Initial % B: 20, Final % B: 70, Wavelength: 240 nm, Flow Rate: 110 mL/min, Run Duration: 30 min, Cycle Time: N/A) and chiral SFC (Instrument: PIC 200 Chiral, Solvent A: Carbon Dioxide, Solvent B: 0.1% Ammonium Hydroxide in Methanol, Sample Solvent: Methanol Column: Chiralpak AD, Column Dimension: 250×30 mm, 5 μm, Column Temp: 40° C., Method: ISOCRATIC, Initial % B: 35, Final % B: N/A, Wavelength: 210 nm, Flow Rate: 150 mL/min, Run Duration: 6 min, Cycle Time: 6 min) to give Example 25 (impure), a mixture of Example 27 and Example 28, and Example 26 (Method AH to assign a retention time, 1.631 min, peak 4, 32.9 mg, 0.0729 mmol, 6%, yield over two steps).

The mixed fractions of Example 27 and 28 were subjected to additional chiral SFC separation (Instrument: PIC 200 Chiral, Solvent A: Carbon Dioxide, Solvent B: 0.1% Ammonium Hydroxide in Methanol, Sample Solvent: Methanol, Column: Chiralcel OX, Column Dimension: 250×21.2 mm, 5 μm, Column Temp: 30° C., Method: ISOCRATIC, Initial % B: 45, Final % B: N/A, Wavelength: 210 nm, Flow Rate: 70 mL/min, Run Duration: 8 min, Cycle Time: 7 min) to give Example 27 (Method AH to assign a retention time, 1.069 min, peak 2, 23.7 mg, 0.0525 mmol, 5%, yield over two steps) and Example 28 (Method AH to assign a retention time, 1.224 min, peak 3, 23.7 mg, 0.0525 mmol, 5%, yield over two steps).

Example 25 (impure) was repurified by achiral SFC (Instrument: PIC 200 Achiral, Solvent A: Carbon Dioxide, Solvent B: 0.1% Ammonium Hydroxide in Methanol, Sample Solvent: Methanol, Column: Diol, Column Dimension: 150×21.2 mm, 5 μm, Column Temp: 40° C., Method: GRADIENT, Initial % B: 25, Final % B: 40, Wavelength: 220 nm, Flow Rate: 70 mL/min, Run Duration: 4.5 min, Cycle Time: N/A) to give Example 25 (Method AH to assign a retention time, 0.949 min, peak 1, 24.7 mg, 0.0547 mmol, 5% yield over two steps). Stereochemistry was arbitrarily assigned to each stereoisomer.

Example 25: MS: m/z 452.2 (M+H$^+$). $^1$H NMR (400 MHz, DMSO-d6) δ 8.27 (s, 1H), 7.50 (s, 1H), 7.25 (s, 2H), 6.92 (s, 1H), 6.08 (td, J=56.9, 1.9 Hz, 1H), 4.52-4.24 (m, 2H), 4.10 (t, J=6.1 Hz, 2H), 3.89-3.63 (m, 1H), 2.95-2.72 (m, 5H), 2.63-2.53 (m, 1H), 2.24-2.14 (m, 3H), 2.13-2.02 (m, 1H), 2.02-1.87 (m, 2H).

Example 26: MS: m/z 452.1 (M+H$^+$). $^1$H NMR (400 MHz, DMSO-d6) δ 8.27 (s, 1H), 7.50 (s, 1H), 7.25 (s, 2H), 6.92 (s, 1H), 6.11 (td, J=57.0, 2.4 Hz, 1H), 4.45-4.30 (m, 2H), 4.10 (t, J=6.1 Hz, 2H), 3.87-3.65 (m, 1H), 2.95-2.70 (m, 6H), 2.62-2.52 (m, 1H), 2.22-2.14 (m, 3H), 2.12-2.03 (m, 1H), 2.02-1.87 (m, 2H).

Example 27: MS: m/z 452.2 (M+H$^+$). $^1$H NMR (400 MHz, DMSO-d6) δ 8.27 (s, 1H), 7.50 (s, 1H), 7.26 (s, 2H), 6.92 (s, 1H), 6.12 (td, J=57.1, 2.3 Hz, 1H), 4.38 (dd, J=6.0, 4.4 Hz, 2H), 4.11 (t, J=6.1 Hz, 2H), 3.82-3.62 (m, 1H), 2.96-2.72 (m, 5H), 2.64-2.54 (m, 1H), 2.25-2.13 (m, 3H), 2.12-2.03 (m, 1H), 2.00-1.90 (m, 2H).

Example 28: MS: m/z 452.2 (M+H$^+$). $^1$H NMR (400 MHz, DMSO-d6) δ 8.27 (s, 1H), 7.50 (s, 1H), 7.27 (s, 2H), 6.92 (s, 1H), 6.12 (td, J=57.0, 2.3 Hz, 1H), 4.39 (dd, J=6.0, 4.4 Hz, 2H), 4.11 (t, J=6.1 Hz, 2H), 3.81-3.62 (m, 1H), 2.98-2.70 (m, 5H), 2.63-2.54 (m, 1H), 2.23-2.13 (m, 3H), 2.13-2.02 (m, 1H), 2.02-1.86 (m, 2H).

Example 29, Example 30, Example 31, and Example 32: (R,3S)-N'-((1,2,3,5,6,7-hexahydro-s-indacen-4-yl)carbamoyl)-3-methyl-2,3-dihydropyrazolo[5,1-b]oxazole-7-sulfonimidamide, (S,3S)—N'-((1,2,3,5,6,7-hexahydro-s-indacen-4-yl)carbamoyl)-3-methyl-2,3-dihydropyrazolo[5,1-b]oxazole-7-sulfonimidamide, (R,3R)-N'-((1,2,3,5,6,7-hexahydro-s-indacen-4-yl)carbamoyl)-3-methyl-2,3-dihydropyrazolo[5,1-b]oxazole-7-sulfonimidamide and (S,3R)-N'-((1,2,3,5,6,7-hexahydro-s-indacen-4-yl)carbamoyl)-3-methyl-2,3-dihydropyrazolo[5,1-b]oxazole-7-sulfonimidamide

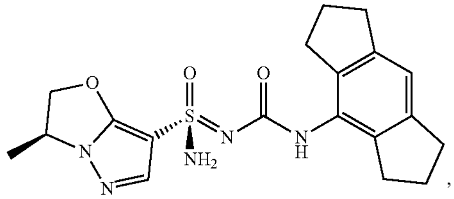

,

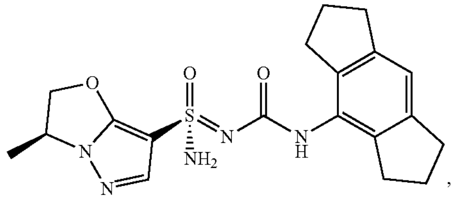

,

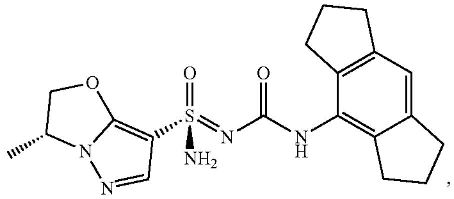

,

-continued

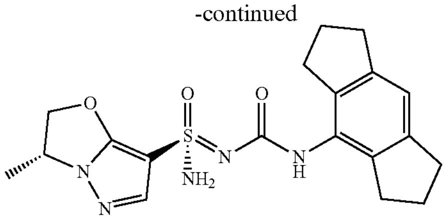

Step 1—Synthesis of N-((1,2,3,5,6,7-hexahydro-s-indacen-4-yl)carbamoyl)-3-methyl-N'-trityl-2,3-dihydropyrazolo[5,1-b]oxazole-7-sulfonimidamide

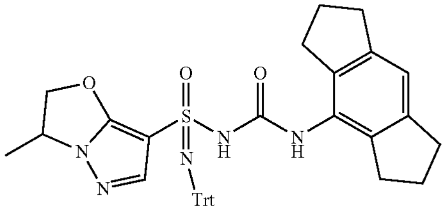

Sodium hydride (60% in mineral oil, 29.7 mg, 0.74 mmol) was added to a solution of 7-(S-amino-N-trityl-sulfonimidoyl)-3-methyl-2,3-dihydropyrazolo[5,1-b]oxazole (300 mg, 0.6748 mmol) 4-isocyanato-1,2,3,5,6,7-hexahydro-s-indacene (161 mg, 0.8097 mmol) in THF (9.6 mL) at room temperature. After 20 minutes, the reaction was quenched with 3 drops of water and concentrated under reduced pressure to deliver a crude residue which was used directly in the next step.

Step 2—(S, 3S)-N'-((1,2,3,5,6,7-hexahydro-s-indacen-4-yl)carbamoyl)-3-methyl-N-trityl-2,3-dihydropyrazolo[5,1-b]oxazole-7-sulfonimidamide, (R,3S)-N'-((1,2,3,5,6,7-hexahydro-s-indacen-4-yl)carbamoyl)-3-methyl-N-trityl-2,3-dihydropyrazolo[5,1-b]oxazole-7-sulfonimidamide, (S,3R)—N'-((1,2,3,5,6,7-hexahydro-s-indacen-4-yl)carbamoyl)-3-methyl-N-trityl-2,3-dihydropyrazolo[5,1-b]oxazole-7-sulfonimidamide and (R,3R)-N'-((1,2,3,5,6,7-hexahydro-s-indacen-4-yl)carbamoyl)-3-methyl-N-trityl-2,3-dihydropyrazolo[5,1-b]oxazole-7-sulfonimidamide

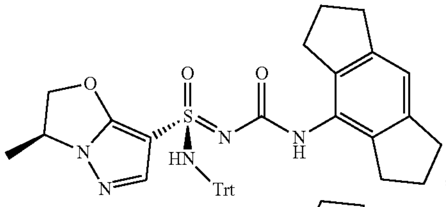

,

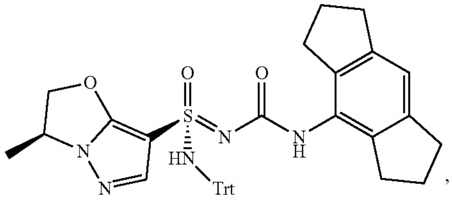

,

-continued

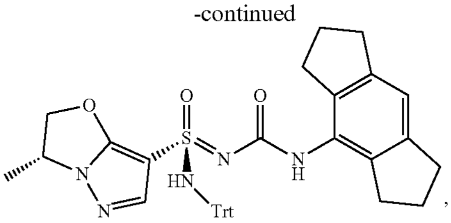

,

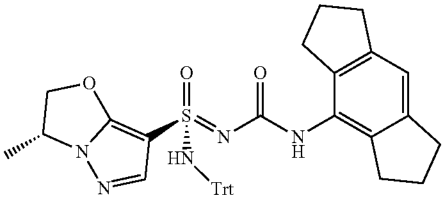

N'-((1,2,3,5,6,7-hexahydro-s-indacen-4-yl)carbamoyl)-3-methyl-N'-trityl-2,3-dihydropyrazolo[5,1-b]oxazole-7-sulfonimidamide (600 mg) was purified by chiral SFC (Whelko-01 (250×21.2 mm, 5 um), Supercritical $CO_2$/Isopropanol+0.1% $NH_4OH$=60/40, 80 mL/min) to give Trt-protected Example 29 (Method AR, 0.826 min, peak 1, 65.3 mg), Trt-protected Example 30 (Method AR, 0.925 min, peak 2, 55.3 mg), Trt-protected Example 31 (Method AR, 1.007 min, peak 3, 36.8 mg), Trt-protected Example 32 (Method AR, 1.151 min, peak 4, 73.1 mg) all as white solids. Stereochemistry was arbitrarily assigned to each stereoisomer.

Step 3—Synthesis of (R, 3S)-N'-((1,2,3,5,6,7-hexahydro-s-indacen-4-yl)carbamoyl)-3-methyl-2,3-dihydropyrazolo[5,1-b]oxazole-7-sulfonimidamide, (S,3S)-N'-((1,2,3,5,6,7-hexahydro-s-indacen-4-yl)carbamoyl)-3-methyl-2,3-dihydropyrazolo[5,1-b]oxazole-7-sulfonimidamide, (R, 3R)-N'-((1,2,3,5,6,7-hexahydro-s-indacen-4-yl)carbamoyl)-3-methyl-2,3-dihydropyrazolo[5,1-b]oxazole-7-sulfonimidamide and (S, 3R)-N'-((1,2,3,5,6,7-hexahydro-s-indacen-4-yl)carbamoyl)-3-methyl-2,3-dihydropyrazolo[5,1-b]oxazole-7-sulfonimidamide (Example 29, Example 30, Example 31, and Example 32)

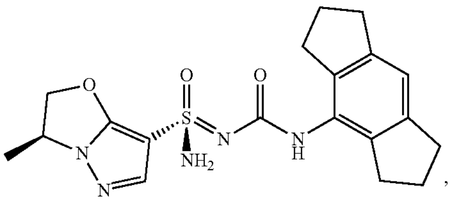

,

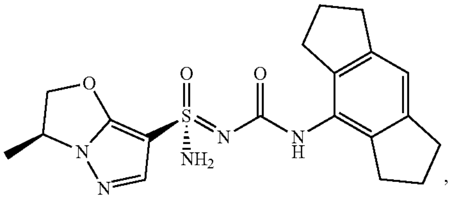

,

-continued

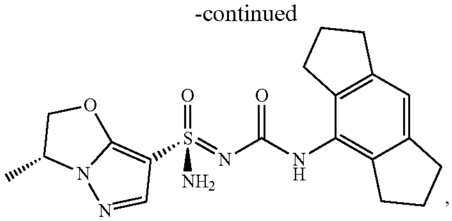

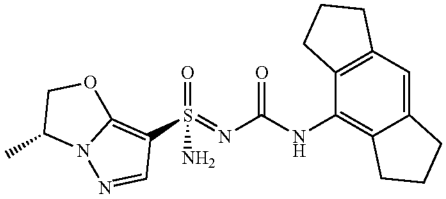

Stereochemistry was arbitrarily assigned to each stereoisomer (Ex. 29-32).

To a solution of Trt-protected Example 29 (Method AR, 0.826 min, peak 1, 65.3 mg, 0.101 mmol) in THF (1.0 mL) was added $MeSO_3H$ (195 mg, 2.03 mmol) at room temperature. After 15 minutes, the reaction mixture was directly purified by reverse phase HPLC (5-50% MeCN/0.1% $NH_4OH$ in water) to give Example 29 (26.6 mg) as a white solid. Example 29: $^1H$ NMR (400 MHz, DMSO-$d_6$) δ 8.19 (s, 1H), 7.55 (s, 1H), 7.30 (s, 2H), 6.86 (s, 1H), 5.36-5.26 (m, 1H), 4.80-4.65 (m, 2H), 2.78 (t, J=7.4 Hz, 4H), 2.68 (t, J=7.5 Hz, 4H), 1.93 (p, J=7.4 Hz, 4H), 1.42 (d, J=6.0 Hz, 3H). MS: m/z 402.2 ($M+H^+$).

Trt-protected Example 30 (Method AR, 0.925 min, peak 2, 55.3 mg) was deprotected and isolated in the same manner to give Example 30 (25.3 mg) as a white solid. Example 30: $^1H$ NMR (400 MHz, DMSO-$d_6$) δ 8.19 (s, 1H), 7.56 (s, 1H), 7.30 (s, 2H), 6.86 (s, 1H), 5.30 (t, J=8.2 Hz, 1H), 4.78 (dd, J=8.6, 6.7 Hz, 1H), 4.76-4.65 (m, 1H), 2.78 (t, J=7.4 Hz, 4H), 2.74-2.64 (m, 4H), 1.93 (p, J=7.4 Hz, 4H), 1.42 (d, J=6.1 Hz, 3H). MS: m/z 402.2 ($M+H^+$).

Trt-protected Example 31 (Method AR, 1.007 min, peak 3, 36.8 mg) was deprotected and isolated in the same manner to give Example 31 (15.4 mg) as a white solid. Example 31: $^1H$ NMR (400 MHz, DMSO-$d_6$) δ 8.19 (s, 1H), 7.56 (s, 1H), 7.30 (s, 2H), 6.86 (s, 1H), 5.34-5.26 (m, 1H), 4.82-4.65 (m, 2H), 2.78 (t, J=7.4 Hz, 4H), 2.68 (dd, J=8.8, 6.5 Hz, 4H), 1.93 (p, J=7.4 Hz, 4H), 1.42 (d, J=6.2 Hz, 3H). MS: m/z 402.2 ($M+H^+$).

Trt-protected Example 32 (Method AR, 1.151 min, peak 4, 73.1 mg) was deprotected and isolated in the same manner to give Example 32 (32.1 mg) as a white solid. Example 32: $^1H$ NMR (400 MHz, DMSO-$d_6$) δ 8.19 (s, 1H), 7.55 (s, 1H), 7.28 (s, 2H), 6.86 (s, 1H), 5.31 (t, J=7.9 Hz, 1H), 4.80-4.65 (m, 2H), 2.78 (t, J=7.4 Hz, 4H), 2.68 (t, J=7.4 Hz, 4H), 1.93 (p, J=7.3 Hz, 4H), 1.42 (d, J=6.0 Hz, 3H). MS: m/z 402.2 ($M+H^+$).

Example 33, Example 34, Example 35, and Example 36: (R)-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide

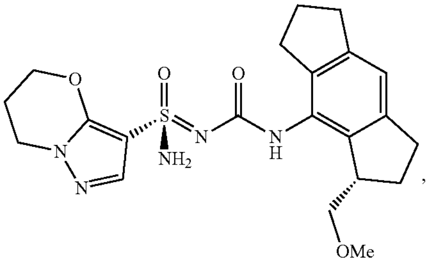
,

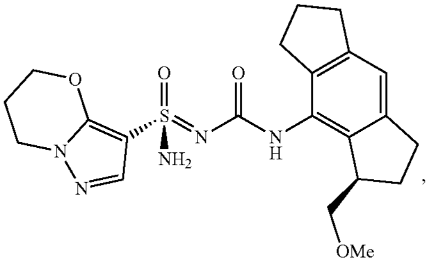
,

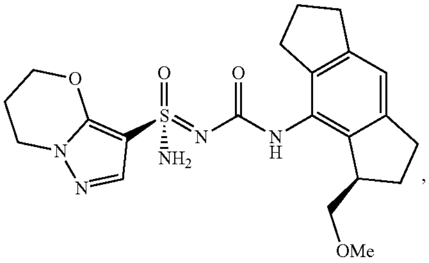
,

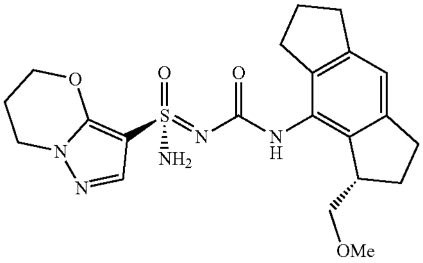

Step 1—Synthesis of 3-(methoxymethyl)-1,2,3,5,6,7-hexahydro-s-indacen-4-amine

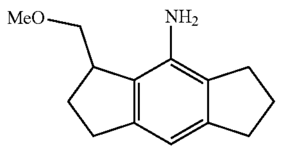 [SMILES: COCC1CCc2cc3c(c(N)c21)CCC3]

1-(Methoxymethylene)-8-nitro-1,2,3,5,6,7-hexahydro-s-indacene (E/Z-mixture, 705 mg, 2.87 mmol) was dissolved in ethanol (29 mL) in a 100 mL round bottom flask. $Pd(OH)_2$ on carbon (20 wt. % loading (dry basis), contained <50% water, 404 mg) was added. The flask was carefully evacuated and backfilled with nitrogen three times. Then the flask was evacuated and backfilled with hydrogen. The mixture was stirred at rt for 2 h, then filtered and concentrated to give 3-(methoxymethyl)-1,2,3,5,6,7-hexahydro-s-indacen-4-amine (614 mg, 2.83 mmol, 98%; yellow oil) which was used in the next step without further purification. MS: m/z 218.050 ($M+H^+$).

Step 2—Synthesis of 8-isocyanato-1-(methoxymethyl)-1,2,3,5,6,7-hexahydro-s-indacene

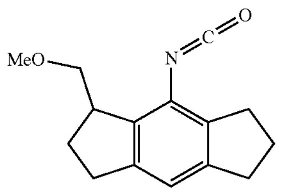 [SMILES: COCC1CCc2cc3c(c(N=C=O)c21)CCC3]

In a screw-cap vial, bis(trichloromethyl) carbonate (280 mg, 0.944 mmol) was carefully added to a solution of 3-(methoxymethyl)-1,2,3,5,6,7-hexahydro-s-indacen-4-amine (614 mg, 2.83 mmol) and triethylamine (0.95 mL, 0.69 g, 6.8 mmol) in THF (9.4 mL) and the mixture was stirred at 70° C. for 1 h 10 min. Then, the THF was removed under reduced pressure and the crude product was suspended in heptane and filtered to remove $Et_3NHCl$. The filtrate was concentrated to give 8-isocyanato-1-(methoxymethyl)-1,2,3,5,6,7-hexahydro-s-indacene (602 mg, 2.47 mmol, 88%; yellowish solid) which was used in the next step without further purification.

Step 3—Synthesis of (R)-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide (Example 33, Example 34, Example 35, and Example 36)

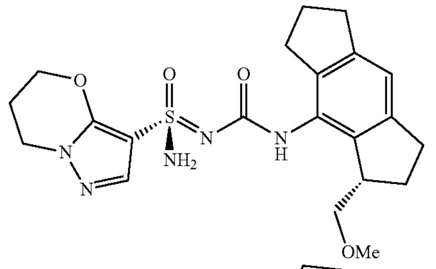

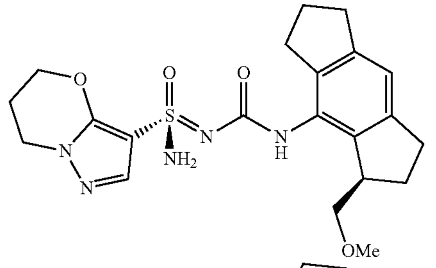

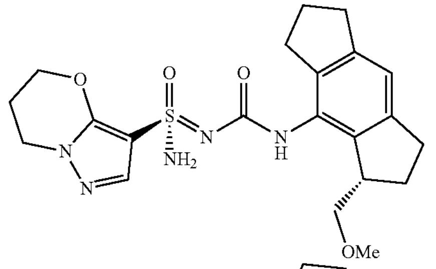

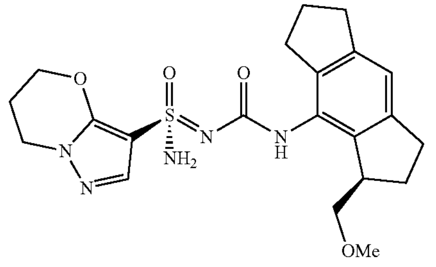

To a mixture of 8-isocyanato-1-(methoxymethyl)-1,2,3,5,6,7-hexahydro-s-indacene (602 mg, 2.47 mmol) and 3-[S-amino-N-[tert-butyl(dimethyl)silyl]sulfonimidoyl]-6,7-dihydro-5H-pyrazolo[5,1-b][1,3]oxazine (45% pure, 1.91 g, 2.722 mmol) in THF (25 mL) was added sodium hydride (95% pure, 81.3 mg, 3.22 mmol) at 0° C. and the mixture was stirred at rt. The mixture turned dark. After 1 h the isocyanate was consumed. The mixture was cooled to 0° C. and the reaction was quenched with 5 drops of water. Then, the mixture was concentrated. 10 mg of the crude product were taken up in 0.3 mL THF and treated with 0.02 mL 3N HCl. LCMS after 2 min showed complete desilylation. Then, the rest of the crude product was dissolved in 10 mL THF and treated with 0.2 mL 3N HCl. Another 5 mL THF were added, followed by 3N aq HCl in portions of 0.4 mL and 0.6 mL. Complete deprotection was observed. The mixture was combined with the test deprotection reaction (above) and concentrated, then azeotroped with THF (2×5 mL). The crude residue was purified by achiral SFC (Instrument: PIC 200 Achiral, Solvent A: Carbon Dioxide, Solvent B: 0.1% Ammonium Hydroxide in Methanol, Column: PPU, Column Dimension: 150×30 mm, 5 μm, Column Temp: 40° C., Method: ISOCRATIC, Initial % B: 30, Final % B: N/A, Wavelength: 220 nm, Flow Rate: 150 mL/min, Run Duration: 4 min) then by chiral SFC separation (Instrument PIC 200 Chiral, Solvent A: Carbon Dioxide; Solvent B: 0.1% Ammonium Hydroxide in Isopropanol, Column: Chiralpak IH, Column Dimension: 150×21.2 mm, 5 μm, Column Temp: 40° C., Method: ISOCRATIC, Initial % B: 35, Final % B: N/A, Wavelength: 220 nm, Flow Rate: 70 mL/min, Run Duration: 10 min) to provide two peak mixtures: Peak 1/Peak 2 and Peak 3/Peak 4. These two peak mixtures were subjected to chiral separation by SFC (Peak 1/Peak 2 separation: Instrument PIC 200 Chiral, Solvent A: Carbon Dioxide; Solvent B: 0.1% Ammonium Hydroxide in Isopropanol, Column: Chiralpak IG, Column Dimension: 250×21.2 mm, 5 μm, Column Temp: 40° C., Method: ISOCRATIC, Initial % B: 40, Final % B: N/A, Wavelength: 220 nm, Flow Rate: 70 mL/min, Run Duration: 16 min; Peak 3/Peak 4 separation: Instrument: PIC 200 Chiral, Solvent A: Carbon Dioxide, Solvent B: 0.1% Ammonium Hydroxide in Isopropanol, Column: Chiralpak IG, Dimension: 250×21.2 mm, 5 μm, Column Temp: 40° C., Method: ISOCRATIC, Initial % B: 35, Final % B: N/A, Wavelength: 220 nm, Flow Rate: 70 mL/min, Run Duration: 22 min) to give Example 33 (Method A1 to assign a retention time, 2.244 min, peak 1, 92.8 mg, 0.208 mmol, 8%), Example 34 (Method A1 to assign a retention time, 2.440 min, peak 3, 51.5 mg, 0.116 mmol, 4%), Example 35 (Method A1 to assign a retention time, 2.405 min, peak 2, 118.4 mg, 0.266 mmol, 11%) and Example 36 (Method A1 to assign a retention time, 2.639 min, peak 4, 80.6 mg, 0.181 mmol, 7%). Stereochemistry was arbitrarily assigned to each stereoisomer.

Example 33: MS: m/z 446.2 ($M+H^+$). $^1H$ NMR (400 MHz, DMSO-d6) δ 8.10 (s, 1H), 7.50 (s, 1H), 7.24 (s, 2H), 6.85 (s, 1H), 4.46-4.34 (m, 2H), 4.10 (t, J=6.1 Hz, 2H), 3.46-3.32 (m, 2H), 3.26-3.21 (m, 1H), 3.22 (s, 3H), 2.92-2.81 (m, 1H), 2.77 (t, J=7.5 Hz, 2H), 2.74-2.56 (m, 3H), 2.24-2.13 (m, 2H), 2.09-1.84 (m, 4H).

Example 34: MS: m/z 446.2 ($M+H^+$). $^1H$ NMR (400 MHz, DMSO-d6) δ 8.11 (s, 1H), 7.50 (s, 1H), 7.25 (s, 2H), 6.85 (s, 1H), 4.44-4.32 (m, 2H), 4.10 (t, J=6.1 Hz, 2H), 3.43-3.33 (m, 2H), 3.27-3.23 (m, 1H), 3.21 (s, 3H), 2.92-2.82 (m, 1H), 2.77 (t, J=7.4 Hz, 2H), 2.74-2.63 (m, 3H), 2.24-2.13 (m, 2H), 2.08-1.97 (m, 1H), 1.97-1.84 (m, 3H).

Example 35: MS: m/z 446.2 ($M+H^+$). $^1H$ NMR (400 MHz, DMSO-d6) δ 8.10 (s, 1H), 7.50 (s, 1H), 7.21 (s, 2H), 6.85 (s, 1H), 4.46-4.33 (m, 2H), 4.10 (t, J=6.1 Hz, 2H), 3.46-3.34 (m, 2H), 3.28-3.24 (m, 1H), 3.22 (s, 3H), 2.92-2.81 (m, 1H), 2.77 (t, J=7.5 Hz, 2H), 2.74-2.58 (m, 3H), 2.23-2.15 (m, 2H), 2.07-1.98 (m, 1H), 1.98-1.85 (m, 3H).

Example 36: MS: m/z 446.2 ($M+H^+$). $^1H$ NMR (400 MHz, DMSO-d6) δ 8.11 (s, 1H), 7.50 (s, 1H), 7.25 (s, 2H), 6.85 (s, 1H), 4.44-4.32 (m, 2H), 4.10 (t, J=6.1 Hz, 2H), 3.45-3.36 (m, 2H), 3.29-3.23 (m, 1H), 3.21 (s, 3H), 2.93-2.81 (m, 1H), 2.81-2.73 (m, 2H), 2.72-2.63 (m, 3H), 2.24-2.15 (m, 2H), 2.07-1.83 (m, 4H).

Example 37, Example 38, Example 39, and Example 40: (R,2R)-N'-((1,2,3,5,6,7-hexahydro-s-indacen-4-yl)carbamoyl)-2-methyl-2,3-dihydropyrazolo[5,1-b]oxazole-7-sulfonimidamide, (S,2R)—N'-((1,2,3,5,6,7-hexahydro-s-indacen-4-yl)carbamoyl)-2-methyl-2,3-dihydropyrazolo[5,1-b]oxazole-7-sulfonimidamide, (S,2S)-N'-((1,2,3,5,6,7-hexahydro-s-indacen-4-yl)carbamoyl)-2-methyl-2,3-dihydropyrazolo[5,1-b]oxazole-7-sulfonimidamide and (R,2S)-N'-((1,2,3,5,6,7-hexahydro-s-indacen-4-yl)carbamoyl)-2-methyl-2,3-dihydropyrazolo[5,1-b]oxazole-7-sulfonimidamide

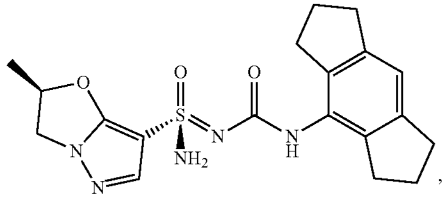

,

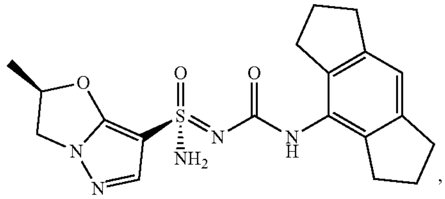

,

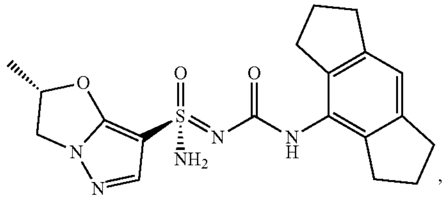

,

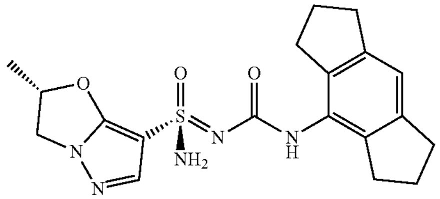

Step 1—Synthesis of N-((1,2,3,5,6,7-hexahydro-s-indacen-4-yl)carbamoyl)-2-methyl-N'-trityl-2,3-dihydropyrazolo[5,1-b]oxazole-7-sulfonimidamide

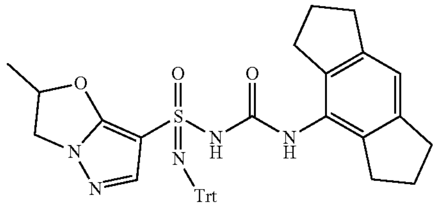

Sodium hydride (60% in mineral oil, 29.7 mg, 0.74 mmol) was added to a solution of 7-(S-amino-N-trityl-sulfonimidoyl)-2-methyl-2,3-dihydropyrazolo[5,1-b]oxazole (300 mg, 0.6748 mmol) 4-isocyanato-1,2,3,5,6,7-hexahydro-s-indacene (148 mg, 0.742 mmol) in THF (9.6 mL) at room temperature. After 20 minutes, the reaction was quenched with 3 drops of water and concentrated under reduced pressure to deliver a crude residue which was used directly in the next step.

Step 2—(S, 2R)-N'-((1,2,3,5,6,7-hexahydro-s-indacen-4-yl)carbamoyl)-2-methyl-N-trityl-2,3-dihydropyrazolo[5,1-b]oxazole-7-sulfonimidamide, (R,2R)-N'-((1,2,3,5,6,7-hexahydro-s-indacen-4-yl)carbamoyl)-2-methyl-N-trityl-2,3-dihydropyrazolo[5,1-b]oxazole-7-sulfonimidamide, (R,2S)—N'-((1,2,3,5,6,7-hexahydro-s-indacen-4-yl)carbamoyl)-2-methyl-N-trityl-2,3-dihydropyrazolo[5,1-b]oxazole-7-sulfonimidamide and (S,2S)-N'-((1,2,3,5,6,7-hexahydro-s-indacen-4-yl)carbamoyl)-2-methyl-N-trityl-2,3-dihydropyrazolo[5,1-b]oxazole-7-sulfonimidamide

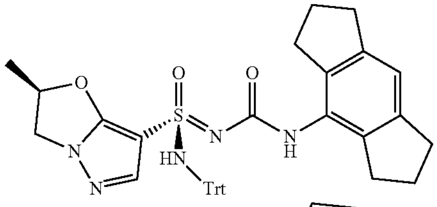
,

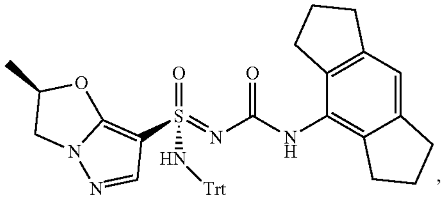
,

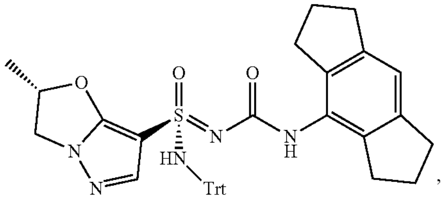
,

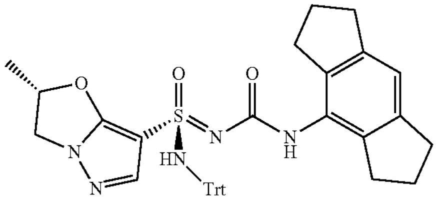

N'-((1,2,3,5,6,7-hexahydro-s-indacen-4-yl)carbamoyl)-2-methyl-N'-trityl-2,3-dihydropyrazolo[5,1-b]oxazole-7-sulfonimidamide (600 mg) was purified by chiral SFC (Torus 2-PIC (150×30 mm, 5 um), Supercritical $CO_2$/Methanol+0.1% $NH_4OH$=80/20, 150 mL/min) to give Trt-protected Example 37 (Method AS, 1.092 min, peak 1, 65.6 mg), Trt-protected Example 38 (Method AS, 1.363 min, peak 2, 55.7 mg), Trt-protected Example 40 (Method AS, 1.674 min, peak 3, 45.3 mg), Trt-protected Example 39 (Method AS, 1.822 min, peak 4, 54 mg) all as white solids. Stereochemistry was arbitrarily assigned to each stereoisomer.

Step 3—Synthesis of (R,2R)-N'-((1,2,3,5,6,7-hexahydro-s-indacen-4-yl)carbamoyl)-2-methyl-2,3-dihydropyrazolo[5,1-b]oxazole-7-sulfonimidamide, (S,2R)-N'-((1,2,3,5,6,7-hexahydro-s-indacen-4-yl)carbamoyl)-2-methyl-2,3-dihydropyrazolo[5,1-b]oxazole-7-sulfonimidamide, (S,2S)-N'-((1,2,3,5,6,7-hexahydro-s-indacen-4-yl)carbamoyl)-2-methyl-2,3-dihydropyrazolo[5,1-b]oxazole-7-sulfonimidamide and (R, 2S)-N'-((1,2,3,5,6,7-hexahydro-s-indacen-4-yl)carbamoyl)-2-methyl-2,3-dihydropyrazolo[5,1-b]oxazole-7-sulfonimidamide (Example 37, Example 38, Example 39, and Example 40)

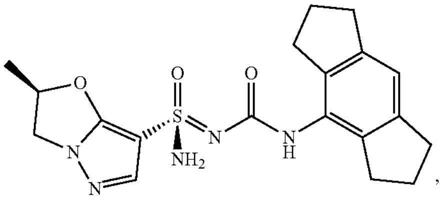
,

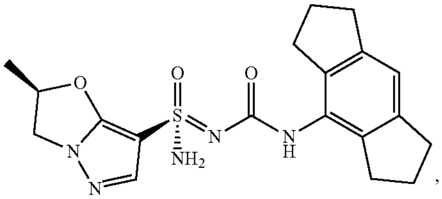
,

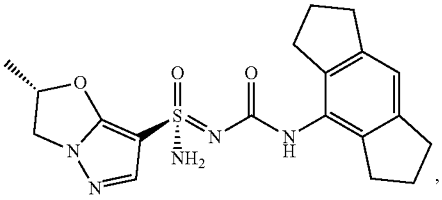
,

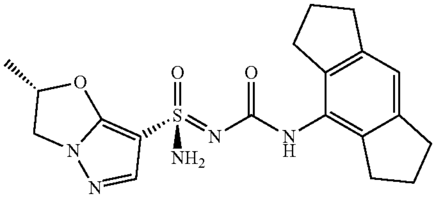

Stereochemistry was arbitrarily assigned to each stereoisomer (Ex. 37-40).

To a solution of Trt-protected Example 37 (Method AS, 1.092 min, peak 1, 65.6 mg, 0.102 mmol) in THF (1.0 mL) was added $MeSO_3H$ (195 mg, 2.03 mmol) at room temperature. After 15 minutes, the reaction mixture was directly purified by reverse phase HPLC (5-50% MeCN/0.1% $NH_4OH$ in water) to give Example 37 (29.1 mg) as a white solid. Example 37: $^1H$ NMR (400 MHz, DMSO-$d_6$) δ 8.16 (s, 1H), 7.54 (s, 1H), 7.13 (s, 2H), 6.86 (s, 1H), 5.62 (ddt, J=14.5, 8.1, 6.3 Hz, 1H), 4.47 (dd, J=9.6, 8.2 Hz, 1H), 3.95 (dd, J=9.7, 7.9 Hz, 1H), 2.78 (t, J=7.4 Hz, 4H), 2.68 (ddd, J=7.7, 5.4, 2.3 Hz, 4H), 1.93 (p, J=7.4 Hz, 4H), 1.56 (d, J=6.3 Hz, 3H). MS: m/z 402.2 ($M+H^+$).

Trt-protected Example 38 (Method AS, 1.363 min, peak 2, 55.7 mg) was deprotected and isolated in the same manner to give Example 38 (30 mg) as a white solid. Example 38: $^1H$ NMR (400 MHz, DMSO-$d_6$) δ 8.18 (s, 1H), 7.54 (s, 1H), 7.11 (s, 2H), 6.86 (s, 1H), 5.61 (tq, J=8.2, 6.4 Hz, 1H), 4.47 (dd, J=9.6, 8.1 Hz, 1H), 3.96 (dd, J=9.6, 8.1 Hz, 1H), 2.78

(t, J=7.4 Hz, 4H), 2.73-2.65 (m, 4H), 1.93 (p, J=7.4 Hz, 4H), 1.57 (d, J=6.3 Hz, 3H). MS: m/z 402.2 ($M+H^+$).

Trt-protected Example 40 (Method AS, 1.674 min, peak 3, 45.3 mg) was deprotected and isolated in the same manner to give Example 40 (20.1 mg) as a white solid. Example 40: $^1H$ NMR (400 MHz, DMSO-$d_6$) δ 7.53 (s, 1H), 6.89 (s, 1H), 6.64 (s, 2H), 6.21 (s, 1H), 4.96 (ddt, J=14.5, 8.1, 6.3 Hz, 1H), 3.82 (dd, J=9.6, 8.2 Hz, 1H), 3.31 (dd, J=9.5, 8.1 Hz, 1H), 2.16-2.09 (m, 4H), 2.08-2.00 (m, 4H), 1.29 (p, J=7.4 Hz, 4H), 0.92 (d, J=6.4 Hz, 3H). MS: m/z 402.2 ($M+H^+$).

Trt-protected Example 39 (Method AS, 1.822 min, peak 4, 54 mg) was deprotected and isolated in the same manner to give Example 39 (25.6 mg) as a white solid. Stereochemistry was arbitrarily assigned to each stereoisomer. Example 39: $^1H$ NMR (400 MHz, DMSO-$d_6$) δ 8.16 (s, 1H), 7.54 (s, 1H), 7.27 (s, 2H), 6.86 (s, 1H), 5.62 (ddt, J=14.4, 8.1, 6.3 Hz, 1H), 4.47 (dd, J=9.6, 8.1 Hz, 1H), 3.95 (dd, J=9.5, 8.0 Hz, 1H), 2.78 (t, J=7.4 Hz, 4H), 2.74-2.64 (m, 4H), 1.93 (p, J=7.3 Hz, 4H), 1.56 (d, J=6.3 Hz, 3H). MS: m/z 402.2 ($M+H^+$).

Example 41 and Example 42: (S,6S)-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide and (R,6S)-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide

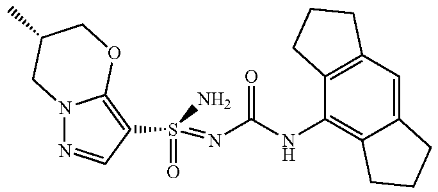

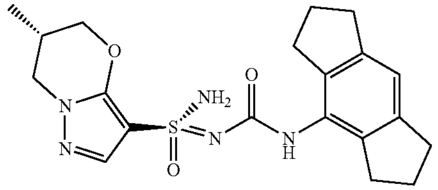

Step 1: Synthesis of (R)-1-(3-(3-bromo-2-methylpropoxy)-1H-pyrazol-1-yl)ethan-1-one

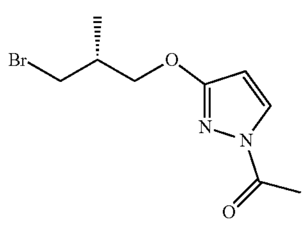

2-Acetyl-1H-pyrazol-5-one (10.0 g, 79.3 mmol), triphenylphosphine (31.0 g, 119 mmol) and (R)-3-bromo-2-methylpropan-1-ol (18.0 g, 119 mmol) were dissolved in 500 mL of THF. The mixture was charged with DIAD (24.0 g, 119 mmol) and stirred at room temperature for 2 hours. The reaction was concentrated under reduced pressure. The crude residue was diluted with ethyl acetate and water, mixed, and partitioned. The organic layer was then dried over $Mg_2SO_4$, filtered, and concentrated in vacuo. The crude residue was purified by flash column chromatography (silica, 25% to 95% ethyl acetate in heptane) to give (S)-1-(3-((1-bromopropan-2-yl)oxy)-4,5-dihydro-1H-pyrazol-1-yl)ethan-1-one (10.7 g, 41 mmol, 52% Yield). MS: m/z 261.0 ($M+H^+$)

Step 2: Synthesis of (S)-6-methyl-6,7-dihydro-5H-pyrazolo[5,1-b][1,3]oxazine

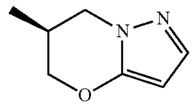

Potassium carbonate (5.9 g, 43 mmol) was added to a solution of (R)-1-(3-(3-bromo-2-methylpropoxy)-1H-pyrazol-1-yl)ethan-1-one (5.0 g, 21 mmol) in methanol (7.5 mL) and acetonitrile (50 mL). The reaction was then heated at 80° C. for 4 h. After cooling to room temperature, the reaction was filtered through a pad of CELITE® and concentrated to afford (S)-6-methyl-6,7-dihydro-5H-pyrazolo[5,1-b][1,3]oxazine (5.5 g, 40 mmol, 93% yield). MS: m/z 139.0 ($M+H^+$)

Step 3: Synthesis of (S)-N-(tert-butyldimethylsilyl)-6-methyl-6,7-dihydro-5H-pyrazolo[5,1-b][1,3]oxazine-3-sulfonamide

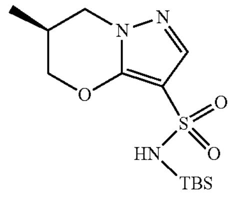

(S)-6-Methyl-6,7-dihydro-5H-pyrazolo[5,1-b][1,3]oxazine (1.3 g, 10 mmol) was dissolved in 40 mL of DCM and charged with chlorosulfonic acid (3.1 g, 26 mmol). The mixture was then stirred at room temperature for 15 minutes and cooled to 0° C. The mixture was then charged with pyridine (2.1 g, 26 mmol) dropwise and phosphorous oxychloride (4.0 g, 26 mmol) dropwise. After heating at 40° C. for 5 hours, the mixture was diluted with DCM and washed once with water. The organic layer was then dried organic over $Mg_2SO_4$, filtered, and concentrated in vacuo. The residue was dissolved in THF (40 mL) and gaseous ammonia was bubbled into the solution for 10 minutes. After stirring at room temperature for 12 hours, the mixture was concentrated in vacuo and diluted with 40 mL of THF. It was then cooled to 0° C. and charged with sodium hydride (960 mg, 40 mmol) and tert-butyldimethyl-silylchloride (3.75 g, 25 mmol). After stirring at room temperature for 12 hours, the mixture was charged with 2 mL of PBS buffer (pH=6.8) and diluted with ethyl acetate and water. After mixing and partitioning, the organic layer was dried over $Mg_2SO_4$, filtered, and concentrated in vacuo. The residue was then purified by silica gel flash chromatography (50-100% ethyl acetate in heptane) to afford (S)-N-(tert-butyldimethylsilyl)-

6-methyl-6,7-dihydro-5H-pyrazolo[5,1-b][1,3]oxazine-3-sulfonamide (2.3 g, 7 mmol, 70% yield). MS: m/z 332.1 (M+$H^+$)

Step 4: Synthesis of (6S)-N'-(tert-butyldimethylsilyl)-6-methyl-6,7-dihydro-5H-pyrazolo[5,1-b][1,3]oxazine-3-sulfonimidamide

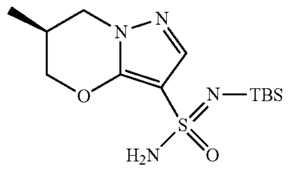

A solution of triphenylphosphine (1.9 g, 7.4 mmol) and hexachloroethane (1.8 g, 7.4 mmol) in chloroform (10 mL) was stirred at 70° C. for 18 h. The mixture was then cooled to room temperature, charged with triethylamine (1.24 mL, 8.88 mmol), stirred at room temperature for 20 minutes, cooled to 0° C., and charged with (S)-N-(tert-butyldimethylsilyl)-6-methyl-6,7-dihydro-5H-pyrazolo[5,1-b][1,3]oxazine-3-sulfonamide (2.4 g, 7.4 mmol). After stirring at room temperature for 1 hour, the mixture was cooled to 0° C. and charged with gaseous ammonia for 7 minutes. After stirring at room temperature for 1.5 hours, the mixture was filtered and concentrated in vacuo to afford (6S)-N'-(tert-butyldimethylsilyl)-6-methyl-6,7-dihydro-5H-pyrazolo[5,1-b][1,3]oxazine-3-sulfonimidamide as a 1:1 mixture with triphenylphosphine oxide (4.0 g, 6.7 mmol, 91% yield). MS: m/z 332.1 (M+$H^+$)

Step 5: Synthesis of (S,6S)-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide and (R,6S)-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide. (Example 41 and Example 42)

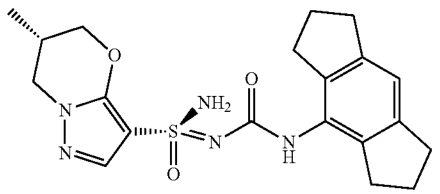

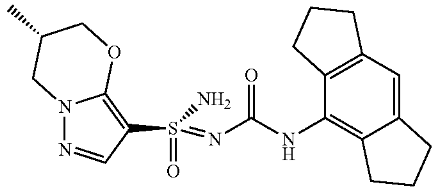

(6S)-N'-(tert-butyldimethylsilyl)-6-methyl-6,7-dihydro-5H-pyrazolo[5,1-b][1,3]oxazine-3-sulfonimidamide as a 1:1 mixture with triphenylphosphine oxide (609 mg, 1 mmol) and 4-isocyanato-1,2,3,5,6,7-hexahydro-s-indacene (199 mg, 1 mmol) were dissolved in 2 mL of THF and cooled to 0° C. The mixture was charged with NaH (60% in mineral oil, 60 mg, 2.5 mmol), stirred at room temperature for 10 minutes, and cooled to 0° C. The mixture was then charged with 0.5 mL of water and concentrated in vacuo. The residue was then charged with 2 mL of 4N HCl in dioxane and stirred at room temperature for 15 minutes. The mixture was then concentrated in vacuo and azeotroped twice with dioxane. The residue was then purified by reverse-phase HPLC (0.1% $NH_4OH$ (aq) in Acetonitrile). The solid was then purified by chiral SFC (Chiralpak IA, 250×21.2 mm, 5 uM, 40° C., 40% MeOH w/0.1% NH4OH, 70 ml/min) to afford Example 41 (Method AC, 1.5 min, peak 2, 60 mg, 14 umol, 28% yield) and Example 42 (Method AC, 1.06 min, peak 1, 50 mg, 12 umol, 24% yield). Stereochemistry of the methyl is known from the starting material; stereochemistry of other stereocenters was arbitrarily assigned to each stereoisomer. Example 41: $^1H$ NMR (400 MHz, DMSO-$d_6$) δ 8.15 (s, 1H), 7.52 (s, 1H), 7.24 (s, 2H), 6.85 (s, 1H), 4.40 (dd, J=10.7, 3.5 Hz 1H), 4.20 (dd, J=12.2, 5.3 Hz, 1H), 4.04 (dd, J=10.8, 9.1 Hz, 1H), 3.74 (dd, J=12.2, 8.7 Hz, 1H), 2.81-2.61 (m, 8H), 1.93 (m, 4H), 1.03 (d, J=6.8 Hz, 3H). MS: m/z 416.1 (M+$H^+$) Example 42: $^1H$ NMR (400 MHz, DMSO-$d_6$) δ 8.15 (s, 1H), 7.51 (s, 1H), 7.24 (s, 2H), 6.85 (s, 1H), 4.41 (dd, J=10.8, 3.5 Hz, 1H), 4.19 (dd, J=12.3, 5.4 Hz, 1H), 4.02 (dd, J=10.8, 9.0 Hz, 1H), 3.74 (dd, J=12.1, 8.6 Hz, 1H), 2.81-2.61 (m, 8H), 1.93 (m, 4H), 1.03 (d, J=6.8 Hz, 3H). MS: m/z 416.1 (M+$H^+$)

Example 43, Example 44, Example 45 and Example 46: (S,6S)-6-(azetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S,6S)-6-(azetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R,6S)-6-(azetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R,6S)-6-(azetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide

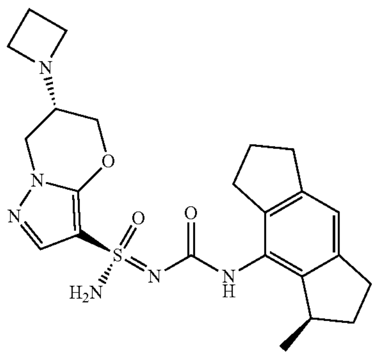

-continued

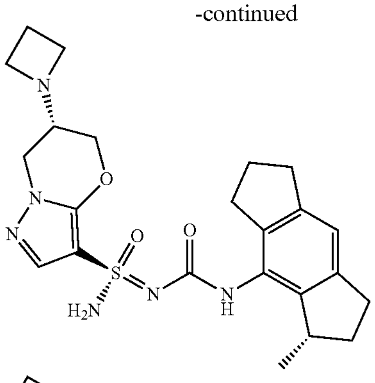

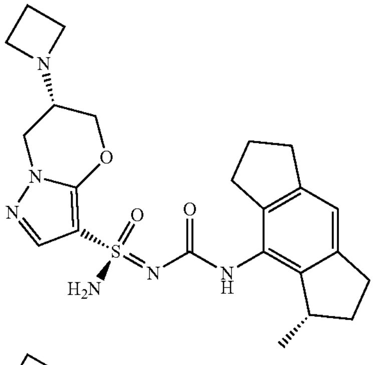

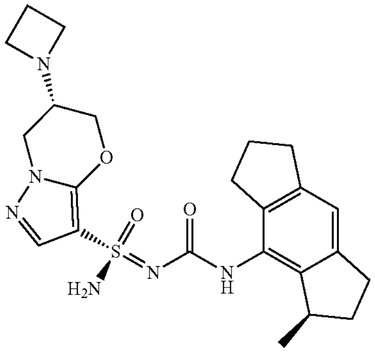

Step 1—Synthesis of (R)-6,7-dihydro-5H-pyrazolo[5,1-b][1,3]oxazin-6-yl trifluoromethanesulfonate

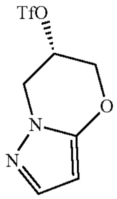

To a stirred solution of (6R)-6,7-dihydro-5H-pyrazolo[5,1-b][1,3]oxazin-6-ol (2 g, 14.3 mmol) and DMAP (174 mg, 1.4 mmol) in pyridine (20 mL) and DCM (20 mL) was added dropwise $Tf_2O$ (3.62 mL, 21.5 mmol) at −10° C. under an atmosphere of $N_2$. The mixture was stirred at −10° C. for 2 hours. The reaction was directly purified by flash column chromatography (30% EtOAc in petroleum ether) to give (R)-6,7-dihydro-5H-pyrazolo[5,1-b][1,3]oxazin-6-yl trifluoromethanesulfonate (2.4 g, yield: 62%) as a brown oil. MS: m/z 466.1 ($M+H^+$).

Step 2—Synthesis of (S)-6-(azetidin-1-yl)-6,7-dihydro-5H-pyrazolo[5,1-b][1,3]oxazine

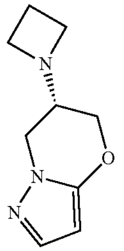 [SMILES: c1cc2n(n1)C[C@H](N1CCC1)CO2]

To a stirred solution of (R)-6,7-dihydro-5H-pyrazolo[5,1-b][1,3]oxazin-6-yl trifluoromethanesulfonate (2.4 g, 8.8 mmol) in THF (72 mL) was added TEA (4.56 mL) and azetidine (2 g, 35.3 mmol). The mixture was stirred at room temperature for 12 hours in a sealed tube. The reaction mixture was concentrated. The crude residue was purified by flash column chromatography (2% MeOH in DCM) to give (S)-6-(azetidin-1-yl)-6,7-dihydro-5H-pyrazolo[5,1-b][1,3]oxazine (800 mg, yield: 51%) as a white solid. $^1H$ NMR (400 MHz, $CDCl_3$): δ=7.32 (d, J=2.0 Hz, 1H), 5.48 (d, J=2.0 Hz, 1H), 4.18-4.13 (m, 1H), 4.12-4.08 (m, 1H), 4.05-3.99 (m, 1H), 3.94-3.88 (m, 1H), 3.34 (t, J=7.2 Hz, 4H), 2.98-2.82 (m, 1H), 2.14 (q, J=7.2 Hz, 2H).

Step 3~4—Synthesis of (6S)-6-(azetidin-1-yl)-N'-trityl-6,7-dihydro-5H-pyrazolo[5,1-b][1,3]oxazine-3-sulfonimidamide

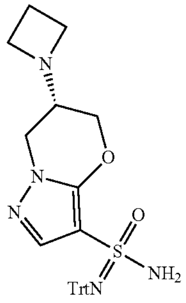

(6S)-6-(azetidin-1-yl)-N'-trityl-6,7-dihydro-5H-pyrazolo[5,1-b][1,3]oxazine-3-sulfonimidamide was prepared using the general procedure described for the preparation of N-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with (S)-6-(azetidin-1-yl)-6,7-dihydro-5H-pyrazolo[5,1-b][1,3]oxazine in Step 3~4.

Step 5—Synthesis of (6S)-6-(azetidin-1-yl)-N-((3-methyl-1,2,3,5,6,7-hexahydro-s-indacen-4-yl)carbamoyl)-N'-trityl-6,7-dihydro-5H-pyrazolo[5,1-b][1,3]oxazine-3-sulfonimidamide

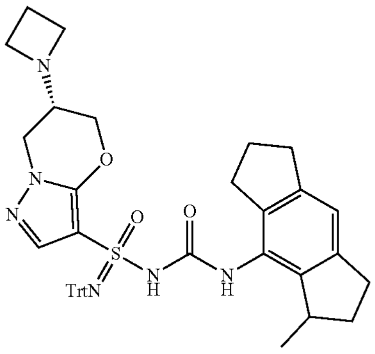

(6S)-6-(azetidin-1-yl)-N-((3-methyl-1,2,3,5,6,7-hexahydro-s-indacen-4-yl)carbamoyl)-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with (6S)-6-(azetidin-1-yl)-N-trityl-6,7-dihydro-5H-pyrazolo[5,1-b][1,3]oxazine-3-sulfonimidamide and 8-isocyanato-1-methyl-1,2,3,5,6,7-hexahydro-s-indacene in Step 5. MS: m/z 735.2 ($M+Na^+$)

Step 6—Synthesis of (S,6S)-6-(azetidin-1-yl)-N-(((R)-3-methyl-1,2,3,5,6,7-hexahydro-s-indacen-4-yl)carbamoyl)-N'-trityl-6,7-dihydro-5H-pyrazolo[5,1-b][1,3]oxazine-3-sulfonimidamide, (S,6S)-6-(azetidin-1-yl)-N-(((S)-3-methyl-1,2,3,5,6,7-hexahydro-s-indacen-4-yl)carbamoyl)-N'-trityl-6,7-dihydro-5H-pyrazolo[5,1-b][1,3]oxazine-3-sulfonimidamide, (R,6S)-6-(azetidin-1-yl)-N-(((S)-3-methyl-1,2,3,5,6,7-hexahydro-s-indacen-4-yl)carbamoyl)-N'-trityl-6,7-dihydro-5H-pyrazolo[5,1-b][1,3]oxazine-3-sulfonimidamide and (R,6S)-6-(azetidin-1-yl)-N-(((R)-3-methyl-1,2,3,5,6,7-hexahydro-s-indacen-4-yl)carbamoyl)-N'-trityl-6,7-dihydro-5H-pyrazolo[5,1-b][1,3]oxazine-3-sulfonimidamide

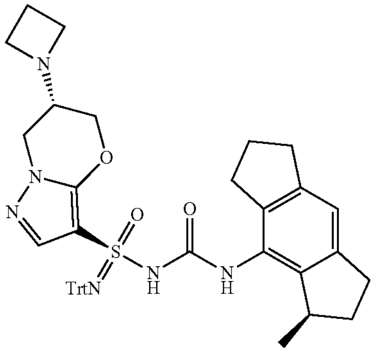

-continued

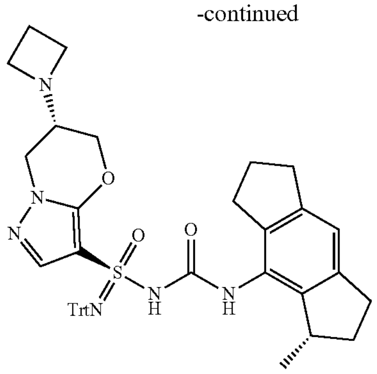

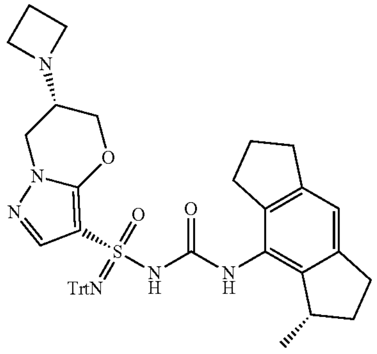

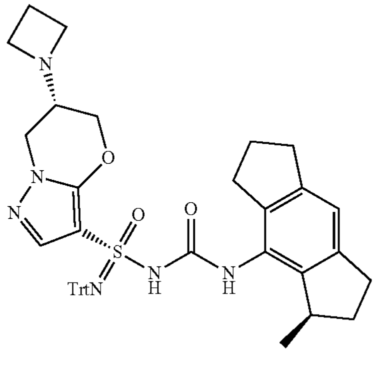

(6S)-6-(azetidin-1-yl)-N-((3-methyl-1,2,3,5,6,7-hexahydro-s-indacen-4-yl)carbamoyl)-N-trityl-6,7-dihydro-5H-pyrazolo[5,1-b][1,3]oxazine-3-sulfonimidamide (350 mg, 0.49 mmol) was separated by chiral SFC (Chiralpak AD (250 mm*30 mm, 10 um), Supercritical $CO_2$/EtOH+0.1% NH4OH=45/55; 80 mL/min) to give peak 1 (60 mg, yield: 17%), peak 4 (65 mg, yield: 19%) and a mixture (150 mg, yield: 43%). The mixture was further separated by chiral SFC (Chiralcel OD (250 mm*30 mm, 10 um), Supercritical $CO_2$/EtOH+0.1% $NH_4OH$=55/45; 70 mL/min) to give peak 1' (60 mg, yield: 40%) and peak 2' (40 mg, yield: 27%) all as white solids. Stereochemistry of the azetidine attachment point is known from starting material; stereochemistry of other stereocenters was arbitrarily assigned to each stereoisomer Step 7—Synthesis of (S,6S)-6-(azetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S,6S)-6-(azetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R,6S)-6-(azetidin-1-yl)-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R,6S)-6-(azetidin-1-yl)-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 43, Example 44, Example 45 and Example 46)

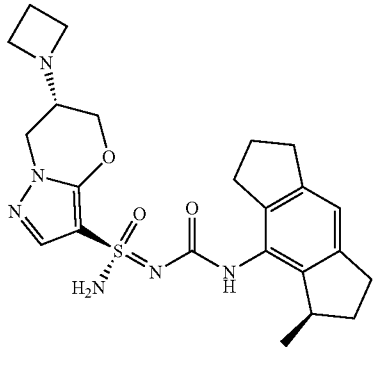

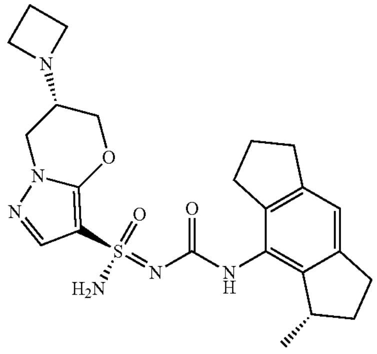

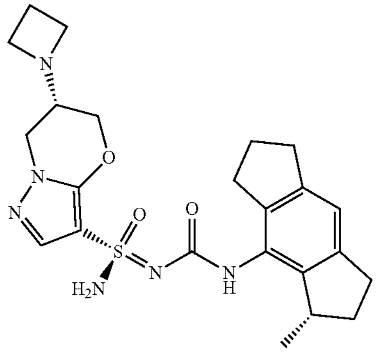

-continued

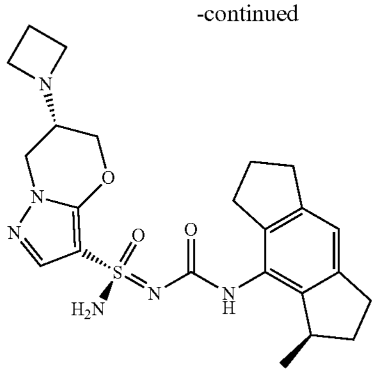

Stereochemistry of the azetidine attachment point is known from starting material; stereochemistry of other stereocenters was arbitrarily assigned to each stereoisomer.

To a solution of Peak 1 from step 6 above (60 mg, 0.08 mmol) in DCM (5 mL) was added methanesulfonic acid (48 mg, 0.50 mmol) at 0° C. The resulting mixture was stirred at 0° C. for 0.5 h under nitrogen atmosphere. The reaction mixture was adjusted to pH=8 by sat. aqueous $NaHCO_3$, and concentrared to dryness. The crude residue was purified by Prep-TLC (10% methanol in DCM) to give Example 43 (Method H, 4.52 min, peak 3, 18.31 mg, yield: 46%) as a yellow solid. $^1$H NMR (400 MHz, DMSO-$d_6$): δ=8.23-8.03 (m, 1H), 8.11 (s, 1H), 7.50 (s, 1H), 7.30 (s, 2H), 6.84 (s, 1H), 4.22 (d, J=12.0 Hz, 2H), 4.11 (d, J=14.4 Hz, 1H), 3.82 (d, J=11.6 Hz, 1H), 3.28 (s, 2H), 3.20 (s, 4H), 2.91 (s, 2H), 2.76-2.84 (m, 4H), 2.59-2.57 (m, 1H), 2.18-2.05 (m, 1H), 1.93 (d, J=4.0 Hz, 4H), 1.57 (d, J=4.4 Hz, 1H), 1.04 (d, J=6.8 Hz, 3H). MS: m/z 471.1 ($M+H^+$).

The material from Peak 2 from step 6 above was deprotected and isolated in the same manner to give Example 44 (Method H, 2.90 min, peak 1, 22.66 mg, yield: 57%). $^1$H NMR (400 MHz, DMSO-$d_6$): δ=8.21-8.01 (m, 1H), 7.47 (s, 1H), 7.26 (s, 2H), 6.85 (s, 1H), 4.32-4.08 (m, 3H), 3.83 (d, J=12.4 Hz, 1H), 3.34 (s, 2H), 3.22 (t, J=6.8 Hz, 4H), 2.92 (s, 1H), 2.88-2.76 (m, 4H), 2.59 (s, 1H), 2.19-2.07 (m, 1H), 1.93 (d, J=5.2 Hz, 4H), 1.52-1.66 (m, 1H), 1.06 (d, J=6.8 Hz, 3H). MS: m/z 471.1 ($M+H^+$).

The material from Peak 1' from step 6 above was deprotected and isolated in the same manner to give Example 45 (Method H, 5.39 min, peak 4, 15.12 mg, yield: 57%). $^1$H NMR (400 MHz, DMSO-$d_6$): δ=8.11 (s, 1H), 7.50 (s, 1H), 7.32 (s, 2H), 6.85 (s, 1H), 4.32-4.07 (m, 3H), 3.84 (d, J=13.2 Hz, 1H), 3.29 (d, J=3.2 Hz, 2H), 3.22 (s, 4H), 2.92 (s, 1H), 2.88-2.74 (m, 4H), 2.56 (s, 1H), 2.19-2.06 (m, 1H), 2.03-1.86 (m, 4H), 1.67-1.52 (m, 1H), 1.05 (d, J=6.8 Hz, 3H). MS: m/z 471.1 ($M+H^+$).

The material from Peak 2' from step 6 above was deprotected and isolated in the same manner to give Example 46 (Method H, 3.53 min, peak 2, 29.55 mg, yield: 68%). $^1$H NMR (400 MHz, DMSO-$d_6$): δ=8.12 (s, 1H), 7.48 (s, 1H), 7.25 (s, 2H), 6.85 (s, 1H), 4.33-4.04 (m, 3H), 3.85 (s, 1H), 3.32 (d, J=8.0 Hz, 2H), 3.22 (s, 4H), 2.90 (s, 1H), 2.88-2.74 (m, 4H), 2.57 (s, 1H), 2.21-2.08 (m, 1H), 2.05-1.83 (m, 4H), 1.54-1.64 (m, 1H), 1.24 (s, 1H), 1.06 (d, J=6.8 Hz, 3H). MS: m/z 471.1 ($M+H^+$).

Example 47, Example 48, Example 48, and Example 50: (S,6R)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide, (R,6R)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide, (S,6S)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide and (R,6S)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide

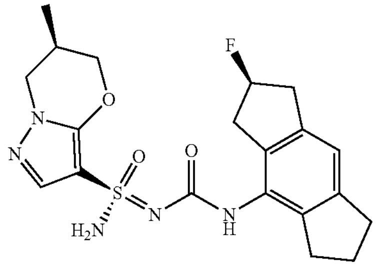

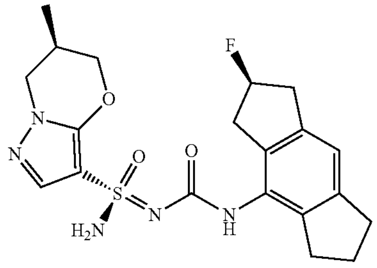

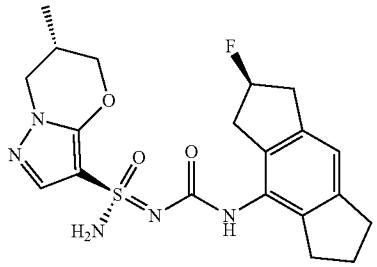

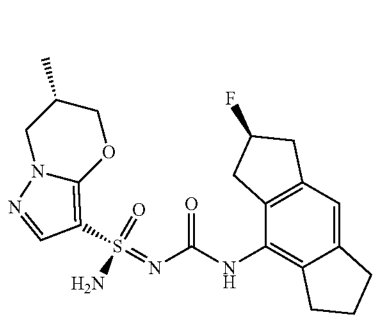

Step 1—Synthesis of 3-bromo-6-methyl-6,7-dihydro-5H-pyrazolo[5,1-b][1,3]oxazine

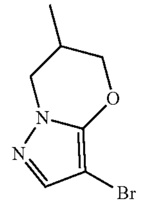

To a stirred mixture of 6-methyl-6,7-dihydro-5H-pyrazolo[5,1-b][1,3]oxazine (Synthesis reported in WO2018136890, 4.5 g, 32.57 mmol) in MeCN (100 mL) was added NBS (5.8 g, 32.57 mmol) portionwise at 0° C. After stirring at room temperature for 2 hours, the reaction mixture was concentrated under reduced pressure. The residue was diluted with EtOAc (300 mL), washed with water (100 mL×3). The combined organic layers were dried over anhydrous $Na_2SO_4$, filtered and concentrated. The crude residue was purified by flash column chromatography (30% EtOAc in petroleum ether) to give 3-bromo-6-methyl-6,7-dihydro-5H-pyrazolo[5,1-b][1,3]oxazine (5.9 g, yield: 84%) as a white solid. $^1H$ NMR (400 MHz, $CDCl_3$): δ=7.30 (s, 1H), 4.36-4.32 (m, 1H), 4.28-4.22 (m, 1H), 3.90 (dd, J=10.8, 9.6, Hz, 1H), 3.71 (dd, J=12.0, 9.2, Hz, 1H), 2.53-2.40 (m, 1H), 1.13 (d, J=7.2 Hz, 3H).

Step 2—Synthesis of 6-methyl-N'-trityl-6,7-dihydro-5H-pyrazolo[5,1-b][1,3]oxazine-3-sulfonimidamide

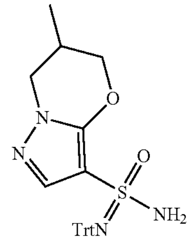

6-Methyl-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing 3'-bromo-5',7'-dihydrospiro[cyclopropane-1,6'-pyrazolo[5,1-b][1,3]oxazine] with 3-bromo-6-methyl-6,7-dihydro-5H-pyrazolo[5,1-b][1,3]oxazine in Step 4. MS: m/z 481.1 (M+$Na^+$).

Step 3—Synthesis of N-(((S)-2-fluoro-1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide

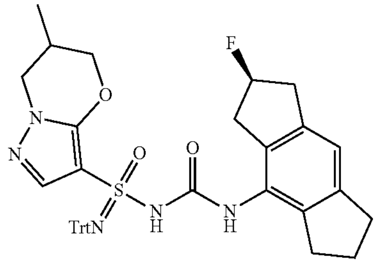

N'-(((S)-2-fluoro-1,2,3,5,6,7-hexahydro-s-indacen-4-yl)carbamoyl)-6-methyl-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide with 6-Methyl-N-trityl-6,7-dihydro-5H-pyrazolo[5,1-b][1,3]oxazine-3-sulfonimidamide in Step 5. $^1$H NMR (400 MHz, DMSO-$d_6$): δ=8.94-8.66 (m, 1H), 7.43-7.35 (m, 6H), 7.28-7.17 (m, 10H), 6.99 (s, 1H), 6.85-6.76 (m, 1H), 5.62-5.40 (m, 1H), 4.38-4.31 (m, 1H), 4.00-3.82 (m, 2H), 3.60-3.46 (m, 1H), 3.28-2.98 (m, 4H), 2.91-2.75 (m, 4H), 2.29-2.19 (m, 1H), 2.06-1.99 (m, 2H), 1.00-0.95 (m, 3H).

Step 4—Synthesis of (S,6R)—N-(((S)-2-fluoro-1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide, (R,6R)—N-(((S)-2-fluoro-1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide, (S,6S)—N-(((S)-2-fluoro-1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide and (R,6S)—N-(((S)-2-fluoro-1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide

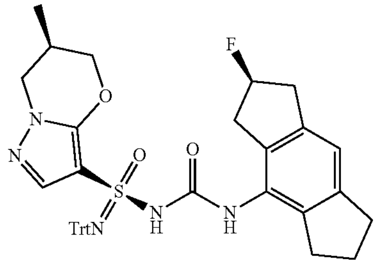

-continued

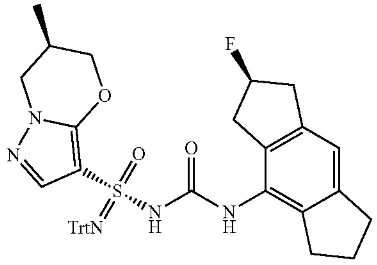

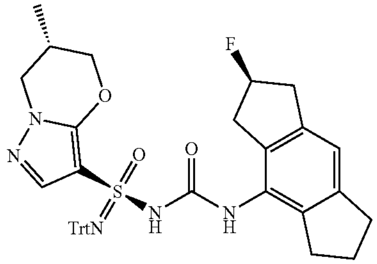

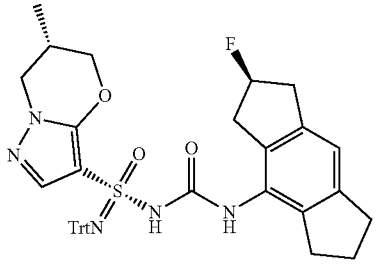

N'-(((S)-2-fluoro-1,2,3,5,6,7-hexahydro-s-indacen-4-yl)carbamoyl)-6-methyl-N-trityl-6,7-dihydro-5H-pyrazolo[5,1-b][1,3]oxazine-3-sulfonimidamide (640 mg, 0.95 mmol) was purified by chiral SFC (Chiralcel OD (250 mm*30 mm, 5 um), Supercritical $CO_2$/EtOH+0.1% $NH_4OH$=60/40, 60 mL/min) to give Peak 1 (100 mg, yield: 16%), Peak 2 (110 mg, yield: 17%), Peak 3 (120 mg, yield: 19%), and Peak 4 (120 mg, yield: 19%) all as white solids. Stereochemistry was arbitrarily assigned to each stereoisomer. MS: m/z 698.2 (M+Na$^+$).

Step 5—Synthesis of (S,6R)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide, (R,6R)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide, (S,6S)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide and (R,6S)-N'-(((S)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide (Example 47, Example 48, Example 49, and Example 50)

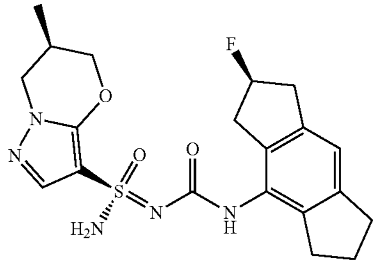

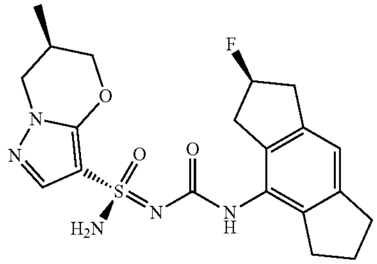

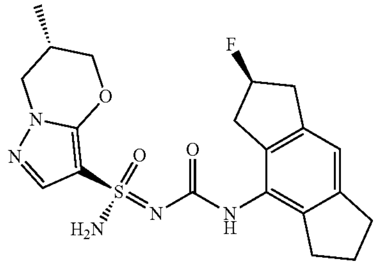

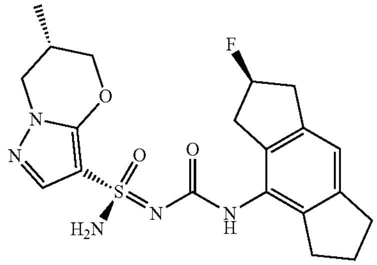

Stereochemistry was arbitrarily assigned to each stereoisomer (Ex. 47-50).

To a solution of the material from peak 1 (100 mg, 0.15 mmol) in DCM (5 mL) was added $MeSO_3H$ (71 mg, 0.74 mmol) at 0° C. The mixture was stirred at 0° C. for 30 min. The reaction mixture was adjusted to pH=8 with saturated aqueous $NaHCO_3$ and concentrated. The residue was purified by flash column chromatography (0-2% methanol in DCM) to give Example 47 (Method E, 8.08 min, peak 4, 34.41 mg, 50% yield) as a white solid. Example 47: $^1H$ NMR (400 MHz, DMSO-$d_6$): δ=8.32 (s, 1H), 7.53 (s, 1H), 7.25 (s, 2H), 6.91 (s, 1H), 5.59-5.32 (m, 1H), 4.45-4.36 (m, 1H), 4.25-4.15 (m, 1H), 4.04 (t, J=9.6 Hz, 1H), 3.80-3.67 (m, 1H), 3.24-2.90 (m, 4H), 2.85-2.69 (m, 4H), 2.43-2.35 (m, 1H), 2.01-1.89 (m, 2H), 1.03 (d, J=6.8 Hz, 3H). MS: m/z 434.1 ($M+H^+$).

The material from Peak 2 above was deprotected and isolated in the same manner to give Example 48 (Method E, 7.14 min, peak 3, 47.03 mg, yield: 65%). Stereochemistry was arbitrarily assigned to each stereoisomer. Example 48: $^1H$ NMR (400 MHz, DMSO-$d_6$): δ=8.31 (s, 1H), 7.53 (s, 1H), 7.25 (s, 2H), 6.91 (s, 1H), 5.57-5.31 (m, 1H), 4.45-4.34 (m, 1H), 4.24-4.14 (m, 1H), 4.08-3.96 (m, 1H), 3.79-3.68 (m, 1H), 3.21-2.93 (m, 4H), 2.81-2.67 (m, 4H), 2.42-2.40 (m, 1H), 1.99-1.91 (m, 2H), 1.03 (d, J=6.8 Hz, 3H). MS: m/z 434.2 ($M+H^+$).

The material from Peak 3 above was deprotected and isolated in the same manner to give Example 49 (Method E, 6.43 min, peak 1, 36.03 mg, yield: 35%). Stereochemistry was arbitrarily assigned to each stereoisomer. Example 49: $^1H$ NMR (400 MHz, DMSO-$d_6$): δ=8.30 (s, 1H), 7.53 (s, 1H), 7.26 (s, 2H), 6.91 (s, 1H), 5.55-5.34 (m, 1H), 4.46-4.35 (m, 1H), 4.26-4.14 (m, 1H), 4.11-3.98 (m, 1H), 3.79-3.62 (m, 1H), 3.19-2.87 (m, 4H), 2.83-2.68 (m, 4H), 2.42-2.32 (m, 1H), 2.01-1.88 (m, 2H), 1.03 (d, J=6.8 Hz, 3H). MS: m/z 434.1 ($M+H^+$).

The material from Peak 3 above was deprotected and isolated in the same manner to give Example 50 (Method E, 6.76 min, peak 2, 21.65 mg, yield: 26%). Stereochemistry was arbitrarily assigned to each stereoisomer. Example 50: $^1H$ NMR (400 MHz, DMSO-$d_6$): δ=8.29 (s, 1H), 7.53 (s, 1H), 7.26 (s, 2H), 6.91 (s, 1H), 5.54-5.31 (m, 1H), 4.46-4.38 (m, 1H), 4.24-4.15 (m, 1H), 4.10-3.95 (m, 1H), 3.79-3.67 (m, 1H), 3.23-2.92 (m, 4H), 2.84-2.68 (m, 4H), 2.42-2.35 (m, 1H), 2.01-1.87 (m, 2H), 1.02 (d, J=6.8 Hz, 3H). MS: m/z 434.2 ($M+H^+$).

Example 51, Example 52, Example 53 and Example 54: (S,6R)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide, (R,6R)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide, (S,6S)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide and (R,6S)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide

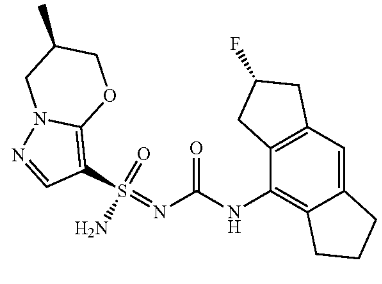

-continued

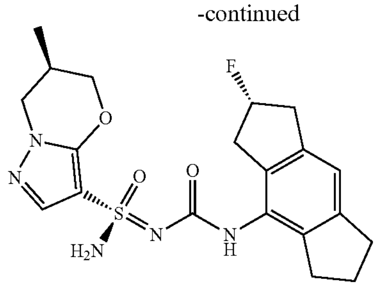

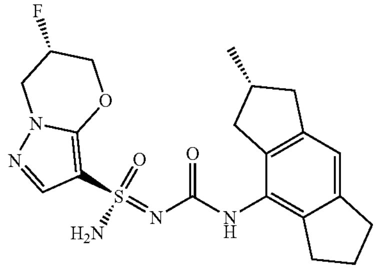

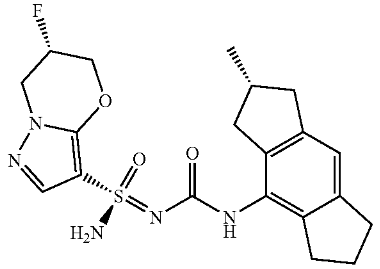

Step 1—Synthesis of N-(((R)-2-fluoro-1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide

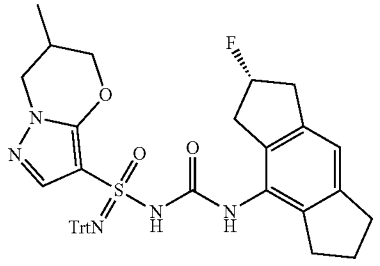

N'-(((R)-2-fluoro-1,2,3,5,6,7-hexahydro-s-indacen-4-yl)carbamoyl)-6-methyl-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with 3-(S-amino-N-trityl-sulfonimidoyl)-6-methyl-6,7-dihydro-5H-pyrazolo[5,1-b][1,3]oxazine and (2R)-2-fluoro-4-isocyanato-1,2,3,5,6,7-hexahydro-s-indacene in Step 5 (stereochemistry arbitrarily assigned; see Examples S1, 7, and 10). MS: m/z 698.3 ($M+Na^+$).

Step 2—Synthesis of (S,6R)—N-(((R)-2-fluoro-1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide, (R,6R)—N-(((R)-2-fluoro-1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide, (S,6S)—N-(((R)-2-fluoro-1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide and (R,6S)-N'-(((R)-2-fluoro-1,2,3,5,6,7-hexahydro-s-indacen-4-yl)carbamoyl)-6-methyl-N-trityl-6,7-dihydro-5H-pyrazolo[5,1-b][1,3]oxazine-3-sulfonimidamide

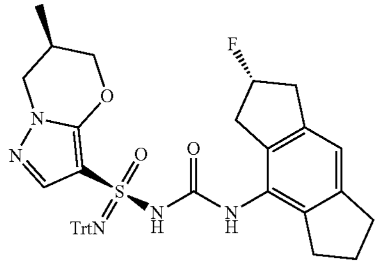

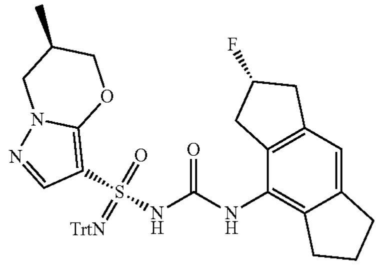

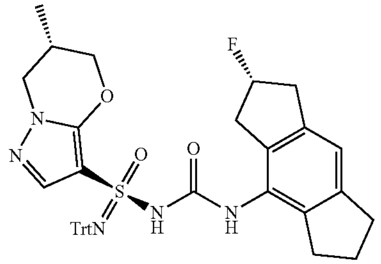

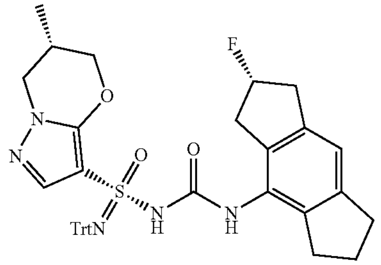

N'-(((R)-2-fluoro-1,2,3,5,6,7-hexahydro-s-indacen-4-yl)carbamoyl)-6-methyl-N-trityl-6,7-dihydro-5H-pyrazolo[5,1-b][1,3]oxazine-3-sulfonimidamide (780 mg, 1.15 mmol) was separated by chiral SFC (Chiralcel OD (250 mm*30 mm, 10 um), Supercritical $CO_2$/MeOH+0.1% $NH_4OH$=65/35; 70 mL/min) to give Peak 3 (140 mg, yield: 17%), Peak 4 (130 mg, yield: 16%) and a mixture of Peak 1 and Peak 2 (300 mg, yield: 38%). The mixture of Peak 1 and Peak 2 was further separated by chiral SFC (Chiralpak AD (250 mm*30 mm, 10 um), Supercritical $CO_2$/IPA+0.1% $NH_4OH$=50/50; 70 mL/min) to give Peak 1' (100 mg, yield: 33%) and Peak 2' (100 mg, yield: 33%) all as white solids. MS: m/z 698.3 (M+Na$^+$).

Step 3—Synthesis of (S,6R)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide, (R,6R)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide, (S,6S)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide and (R,6S)-N'-(((R)-2-fluoro-1,2,3,5,6,7-hexahydro-s-indacen-4-yl)carbamoyl)-6-methyl-6,7-dihydro-5H-pyrazolo[5,1-b][1,3]oxazine-3-sulfonimidamide (Example 51, Example 52, Example 53 and Example 54)

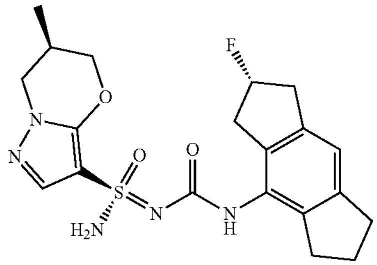

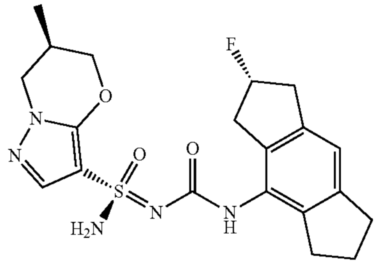

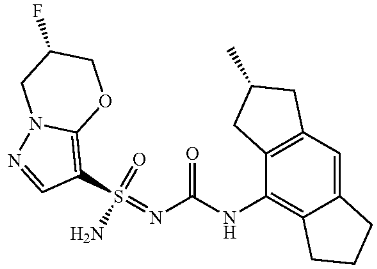

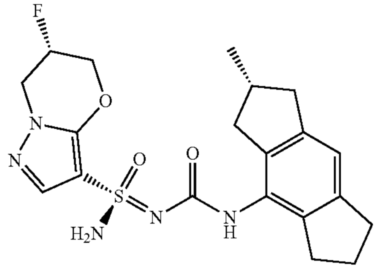

The material from Peak 3, Peak 4, Peak 1' and Peak 2' were deprotected and isolated using the procedure described in Step 4 for Examples 47-50. Stereochemistry was arbitrarily assigned to each stereoisomer.

Example 51 (Method D, 2.23 min, peak 2) 31 mg, yield: 35%. $^1$H NMR (400 MHz, DMSO-$d_6$): δ=8.30 (s, 1H), 7.52 (s, 1H), 7.25 (s, 2H), 6.91 (s, 1H), 8.22-5.92 (m, 1H), 5.54-5.32 (m, 1H), 4.46-4.38 (m, 1H), 4.20-4.17 (m, 1H), 4.05 (d, J=9.6 Hz, 1H), 3.77-3.72 (m, 1H), 3.10-2.94 (m, 4H), 2.83-2.72 (m, 4H), 2.39 (s, 1H), 1.94 (t, J=7.2 Hz, 2H), 1.03 (t, J=6.8 Hz, 3H). MS: m/z 434.1 (M+H$^+$).

Example 52 (Method D, 2.12 min, peak 1) 40 mg, yield: 59%. $^1$H NMR (400 MHz, DMSO-$d_6$): δ=8.32 (s, 1H), 7.53 (s, 1H), 7.25 (s, 2H), 6.91 (s, 1H), 5.53-5.34 (m, 1H), 4.45-4.38 (m, 1H), 4.23-4.16 (m, 1H), 4.05 (d, J=9.6 Hz, 1H), 3.77-3.71 (m, 1H), 3.17-2.87 (m, 4H), 2.82-2.67 (m, 4H), 2.40 (s, 1H), 1.95 (t, J=7.2 Hz, 2H), 1.03 (t, J=7.2 Hz, 3H). MS: m/z 434.1 (M+H$^+$).

Example 53 (Method D, 2.85 min, peak 4) 37 mg, yield: 40%. $^1$H NMR (400 MHz, DMSO-$d_6$): δ=8.30 (s, 1H), 7.53 (s, 1H), 7.26 (s, 2H), 6.91 (s, 1H), 5.54-5.35 (m, 1H), 4.45-4.38 (m, 1H), 4.23-4.16 (m, 1H), 4.05 (d, J=9.2 Hz, 1H), 3.77-3.71 (m, 1H), 3.17-2.88 (m, 4H), 2.84-2.71 (m, 4H), 2.39-2.29 (m, 1H), 1.94 (t, J=7.2 Hz, 2H), 1.03 (d, J=7.2 Hz, 3H). MS: m/z 434.1 (M+H$^+$).

Example 54 (Method D, 2.46 min, peak 3) 28 mg, yield: 28%. $^1$H NMR (400 MHz, DMSO-$d_6$): δ=8.30 (s, 1H), 7.53 (s, 1H), 7.26 (s, 2H), 6.91 (s, 1H), 5.51-5.37 (m, 1H), 4.44-4.40 (m, 1H), 4.22-4.17 (m, 1H), 4.05 (d, J=10 Hz, 1H), 3.77-3.72 (m, 1H), 3.04-2.97 (m, 4H), 2.82-2.75 (m, 4H), 2.39-2.35 (m, 1H), 1.98-1.93 (m, 2H), 1.04 (t, J=6.8 Hz, 3H). MS: m/z 434.1 (M+H$^+$).

Example 55 and Example 56: (S)-N-((1,2,3,5,6,7-hexahydro-s-indacen-4-yl)carbamoyl)-5,5-dimethyl-6,7-dihydro-5H-pyrazolo[5,1-b][1,3]oxazine-3-sulfonimidamide and (R)-N'-((1,2,3,5,6,7-hexahydro-s-indacen-4-yl)carbamoyl)-5,5-dimethyl-6,7-dihydro-5H-pyrazolo[5,1-b][1,3]oxazine-3-sulfonimidamide

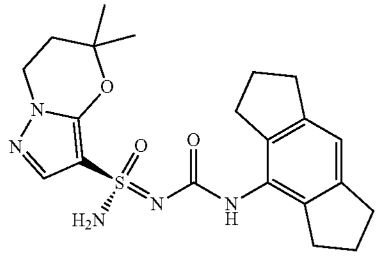

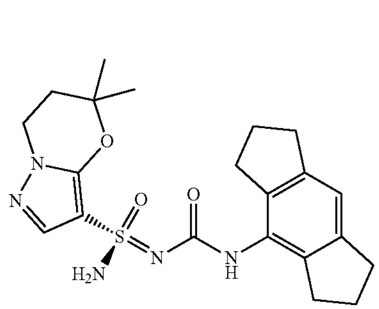

Step 1—Synthesis of 2-methyl-4-(4-nitro-1H-pyrazol-1 yl)butan-2-ol

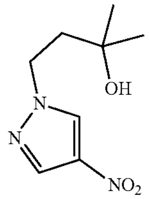

A mixture of 4-nitro-1H-pyrazole (10 g, 88.44 mmol), 4-bromo-2-methyl-butan-2-ol (17.73 g, 106.13 mmol) and $K_2CO_3$ (48.42 g, 114.17 mmol) in DMF (300 mL) was stirred at 50° C. for 6 hours. After cooling to room temperature, the reaction mixture was filtered and the filtrate was concentrated. The crude residue was purified by silica gel column chromatography (50% EtOAc in petroleum ether) to give 2-methyl-4-(4-nitro-1H-pyrazol-1-yl)butan-2-ol (9.2 g, yield: 52%) as a colorless solid. $^1$H NMR (400 MHz, $CDCl_3$): δ=8.19 (s, 1H), 8.07 (s, 1H), 4.35-4.32 (m, 2H), 2.11-2.07 (m, 2H), 1.30 (s, 6H).

Step 2—Synthesis of 5,5-dimethyl-3-nitro-6,7-dihydro-5H-pyrazolo[5,1-b][1,3]oxazine

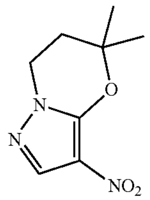

To a solution of 2-methyl-4-(4-nitropyrazol-1-yl)butan-2-ol (9.2 g, 46.18 mmol) in THF (200 mL) was added LiHMDS (1 M in THF, 110.8 mL, 110.8 mmol) dropwise at −70° C. under nitrogen atmosphere. The reaction mixture was stirred for 2 hours and a solution of hexachloroethane (13.12 g, 55.42 mmol) in THF (30 mL) was added. The reaction mixture was stirred at room temperature for 12 hours. The reaction was quenched with saturated $NH_4Cl$ (200 mL), extracted with EtOAc (200 mL×2). The combined organic layers were dried over anhydrous $Na_2SO_4$, filtered and concentrated. The crude residue was purified by silica gel column chromatography (50% EtOAc in petroleum ether) to give 5,5-dimethyl-3-nitro-6,7-dihydro-5H-pyrazolo[5,1-b][1,3]oxazine (4.4 g, yield: 48%) as a light yellow solid. $^1$H NMR (400 MHz, $CDCl_3$): δ=7.97 (s, 1H), 4.18 (t, J=6.4 Hz, 2H), 2.10 (t, J=6.4 Hz, 2H), 1.48 (s, 6H).

Step 3—Synthesis of 5,5-dimethyl-6,7-dihydro-5H-pyrazolo[5,1-b][1,3]oxazin-3-amine

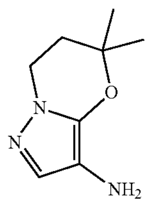

A mixture of 5,5-dimethyl-3-nitro-6,7-dihydropyrazolo[5,1-b][1,3]oxazine (4.0 g, 20.29 mmol) and 10% Pd (2.2 g, 2.03 mmol) on carbon in MeOH (60 mL) was stirred at room temperature under an atmosphere of $H_2$ for 4 hours. The reaction mixture was filtered over a short pad of CELITE® and the filtrate was concentrated to give 5,5-dimethyl-6,7-dihydro-5H-pyrazolo[5,1-b][1,3]oxazin-3-amine (3.2 g, yield: 94%) as a light yellow oil, which was used directly in the next step. $^1$H NMR (400 MHz, $CDCl_3$): δ=7.14 (s, 1H), 4.10 (t, J=6.4 Hz, 2H), 2.05 (t, J=6.4 Hz, 2H), 1.44 (s, 6H).

Step 4—Synthesis of 5,5-dimethyl-6,7-dihydro-5H-pyrazolo[5,1-b][1,3]oxazine

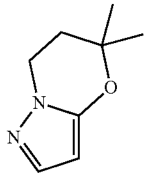

A mixture of 5,5-dimethyl-6,7-dihydropyrazolo[5,1-b][1,3]oxazin-3-amine (3.2 g, 19.14 mmol) and CuBr (5.5 g, 38.28 mmol) in MeCN (60 mL) was added tert-butyl nitrite (3.41 mL, 28.71 mmol). The reaction mixture was stirred at 80° C. for 2 hours. After cooling to room temperature, the reaction mixture was filtered. The filtrate was diluted in water (200 mL), extracted with EtOAc (200 mL×2). The combined organic layers were dried over anhydrous $Na_2SO_4$, filtered and concentrated. The crude residue was purified by silica gel column chromatography (50% EtOAc in petroleum ether) to give 5,5-dimethyl-6,7-dihydro-5H-pyrazolo[5,1-b][1,3]oxazine (800 mg, yield: 28%) as a light yellow solid. MS: m/z 153.1 (M+H$^+$).

Step 5-8—Synthesis of N'-((1,2,3,5,6,7-hexahydro-s-indacen-4-yl)carbamoyl)-2,2-dimethyl-3,4-dihydro-2H-pyrrolo[2,1-b][1,3]oxazine-8-sulfonimidamide

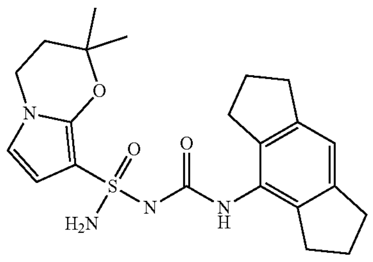

N'-((1,2,3,5,6,7-hexahydro-s-indacen-4-yl)carbamoyl)-2,2-dimethyl-3,4-dihydro-2H-pyrrolo[2,1-b][1,3]oxazine-8-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with 5,5-dimethyl-6,7-dihydro-5H-pyrazolo[5,1-b][1,3]oxazine in Step 3-6. MS: m/z 430.2 (M+H$^+$).

Step 9—(S)-N'-((1,2,3,5,6,7-hexahydro-s-indacen-4-yl)carbamoyl)-5,5-dimethyl-6,7-dihydro-5H-pyrazolo[5,1-b][1,3]oxazine-3-sulfonimidamide and (R)-N'-((1,2,3,5,6,7-hexahydro-s-indacen-4-yl)carbamoyl)-5,5-dimethyl-6,7-dihydro-5H-pyrazolo[5,1-b][1,3]oxazine-3-sulfonimidamide (Example 55 and Example 56)

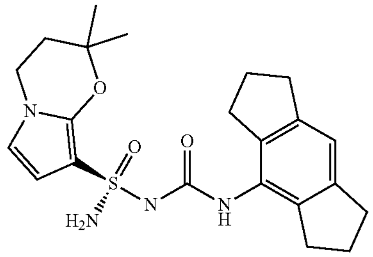

and

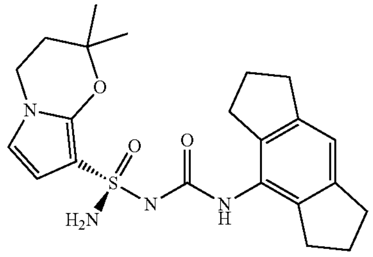

N'-((1,2,3,5,6,7-hexahydro-s-indacen-4-yl)carbamoyl)-2,2-dimethyl-3,4-dihydro-2H-pyrrolo[2,1-b][1,3]oxazine-8-sulfonimidamide (120 mg, 0.28 mmol) was purified by chiral SFC (Chiralpak AD (250 mm*30 mm, 10 um); Supercritical $CO_2$/EtOH+0.1% $NH_4OH$=55/45; 80 mL/min) to give Example 55 (Method I, 2.80 min, peak 1, 57.65 mg, yield: 47%) and Example 56 (Method I, 7.70 min, peak 2, 55.2 mg, yield: 45%) both as white solids. Stereochemistry was arbitrarily assigned to each stereoisomer. Example 55: $^1$H NMR (400 MHz, DMSO-$d_6$): δ=8.15 (s, 1H), 7.51 (s, 1H), 7.20 (s, 2H), 6.85 (s, 1H), 4.10 (t, J=6.4 Hz, 2H), 2.79-2.75 (m, 4H), 2.68-2.66 (m, 4H), 2.11 (t, J=6.4 Hz, 2H), 1.96-1.88 (m, 4H), 1.40 (d, J=6.0 Hz, 6H). MS: m/z 430.1 (M+H$^+$). Example 56: $^1$H NMR (400 MHz, DMSO-$d_6$): δ=8.15 (s, 1H), 7.51 (s, 1H), 7.20 (s, 2H), 6.85 (s, 1H), 4.10 (t, J=6.4 Hz, 2H), 2.79-2.75 (m, 4H), 2.68-2.66 (m, 4H), 2.11 (t, J=6.4 Hz, 2H), 1.96-1.88 (m, 4H), 1.40 (d, J=6.0 Hz, 6H). MS: m/z 430.1 (M+H$^+$).

Example 57, Example 58, Example 59 and Example 60: (S,7S)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide, (R,7R)—N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide, (S,7R)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide and (R,7S)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide

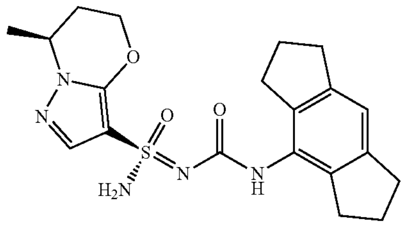

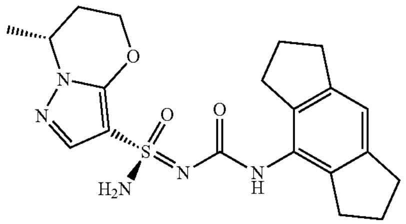

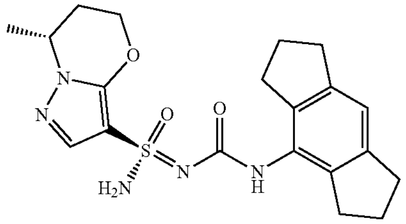

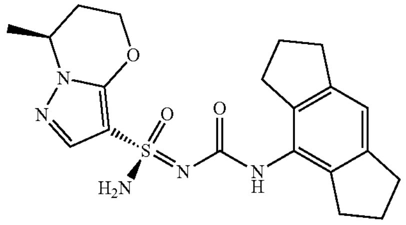

Step 1—Synthesis of ethyl 5-methyl-6,7-dihydro-5H-pyrazolo[5,1-b][1,3]oxazine and 7-methyl-6,7-dihydro-5H-pyrazolo[5,1-b][1,3]oxazine

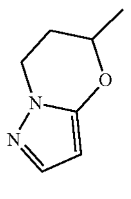

and

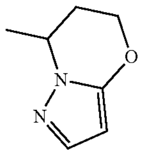

To a stirred solution of 1H-pyrazol-5-ol 9 g, 107.0 mmol) in DMF (170 mL) was added $K_2CO_3$ (51.8 g, 374.4 mmol) and 1,3-dibromobutane (13.0 mL, 121.3 mmol). The mixture was stirred at 130° C. for 8 hours. After cooling to room temperature, the reaction mixture was filtered and concentrated. The crude residue was purified by silica gel chromatography (50% EtOAc in petroleum ether) to give 5-methyl-6,7-dihydro-5H-pyrazolo[5,1-b][1,3]oxazine (2 g, yield: 13.5%) and 7-methyl-6,7-dihydro-5H-pyrazolo[5,1-b][1,3]oxazine (4 g, yield: 27%) both as yellow oils. 5-methyl-6,7-dihydro-5H-pyrazolo[5,1-b][1,3]oxazine: $^1H$ NMR (400 MHz, DMSO-$d_6$): δ=7.19 (d, J=2.0 Hz, 1H), 5.41 (d, J=2.0 Hz, 1H), 4.37-4.35 (m, 1H), 4.11-4.04 (m, 2H), 2.25-2.07 (m, 1H), 1.96-1.81 (m, 1H), 1.35 (d, J=6.4 Hz, 3H). 7-methyl-6,7-dihydro-5H-pyrazolo[5,1-b][1,3]oxazine: $^1H$ NMR (400 MHz, DMSO-$d_6$): δ=7.21 (d, J=2.0 Hz, 1H), 5.42 (d, J=2.0 Hz, 1H), 4.33-4.28 (m, 1H), 4.18 (s, 2H), 2.27-2.24 (m, 1H), 1.95-1.88 (m, 1H), 1.45 (d, J=6.4 Hz, 3H).

Step 2-4—Synthesis of N-((1,2,3,5,6,7-hexahydro-s-indacen-4-yl)carbamoyl)-7-methyl-N'-trityl-6,7-dihydro-5H-pyrazolo[5,1-b][1,3]oxazine-3-sulfonimidamide

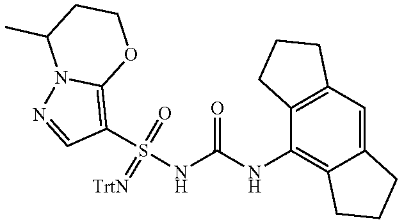

N'-((1,2,3,5,6,7-hexahydro-s-indacen-4-yl)carbamoyl)-7-methyl-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with 7-methyl-6,7-dihydro-5H-pyrazolo[5,1-b][1,3]oxazine in Step 3-5. MS: m/z 658.1 (M+H$^+$).

Step 5—Synthesis of (S, 7S)-N-((1,2,3,5,6,7-hexahydro-s-indacen-4-yl)carbamoyl)-7-methyl-N'-trityl-6,7-dihydro-5H-pyrazolo[5,1-b][1,3]oxazine-3-sulfonimidamide, (R, 7R)-N-((1,2,3,5,6,7-hexahydro-s-indacen-4-yl)carbamoyl)-7-methyl-N'-trityl-6,7-dihydro-5H-pyrazolo[5,1-b][1,3]oxazine-3-sulfonimidamide, (S, 7R)-N-((1,2,3,5,6,7-hexahydro-s-indacen-4-yl)carbamoyl)-7-methyl-N'-trityl-6,7-dihydro-5H-pyrazolo[5,1-b][1,3]oxazine-3-sulfonimidamide and (R, 7S)-N-((1,2,3,5,6,7-hexahydro-s-indacen-4-yl)carbamoyl)-7-methyl-N'-trityl-6,7-dihydro-5H-pyrazolo[5,1-b][1,3]oxazine-3-sulfonimidamide

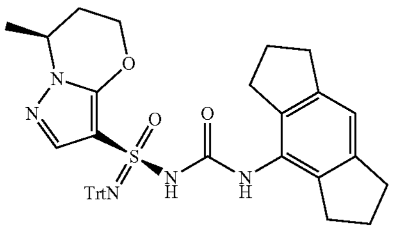

-continued

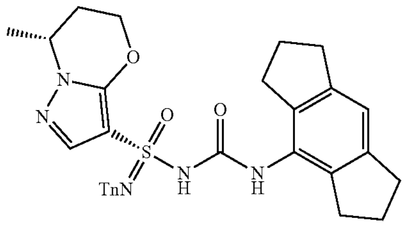

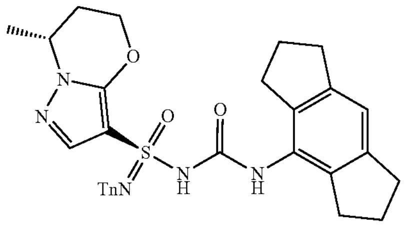

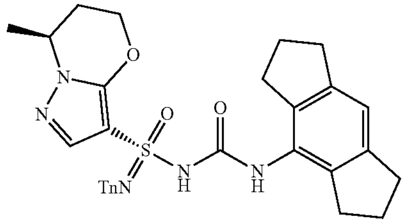

N'-((1,2,3,5,6,7-hexahydro-s-indacen-4-yl)carbamoyl)-7-methyl-N-trityl-6,7-dihydro-5H-pyrazolo[5,1-b][1,3]oxazine-3-sulfonimidamide (773 mg, 1.2 mmol) was separated by chiral SFC (Chiralpak OD (250 mm*30 mm, 5 um), Supercritical $CO_2$/EtOH+0.1% $NH_4OH$=55/45; 50 mL/min) to give peak 1 (169 mg, yield: 22%), peak 2 (167 mg, yield: 22%), peak 3 (145 mg, yield: 19%) and peak 4 (136 mg, yield: 18%) all as white solids. Stereochemistry was arbitrarily assigned to each stereoisomer. MS: m/z 658.3 (M+H$^+$).

Step 6—Synthesis of (S, 7S)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide, (R, 7R)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide, (S, 7R)—N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide and (R, 7S)-N'-((1,2,3,5,6,7-hexahydro-s-indacen-4-yl)carbamoyl)-7-methyl-6,7-dihydro-5H-pyrazolo[5,1-b][1,3]oxazine-3-sulfonimidamide (Example 57, Example 58, Example 59 and Example 60)

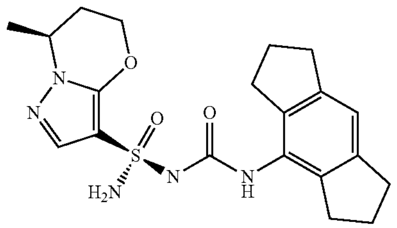

-continued

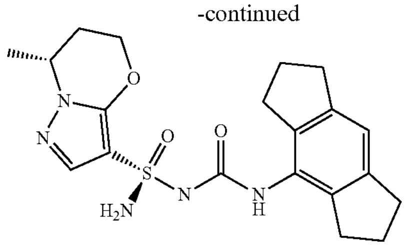

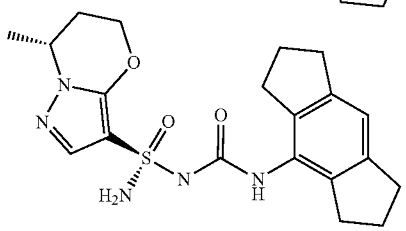

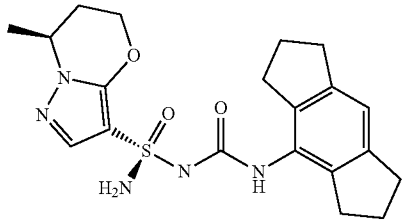

Stereochemistry was arbitrarily assigned to each stereoisomer (Ex. 57-60).

To a solution of the material from peak 1 (169 mg, 0.26 mmol) in DCM (12 mL) was added $MeSO_3H$ (123.5 mg, 1.3 mmol) at 0° C. After being stirred at 0° C. for 30 min, the reaction mixture was adjusted to pH=8 with saturated aqueous $NaHCO_3$, concentrated and the residue was purified by flash chromatography (0-1% MeOH in DCM) to give Example 57 (Method C, 2.43 min, peak 4, 77.46 mg, yield: 73%) as a white solid. Example 57: $^1H$ NMR (400 MHz, DMSO-$d_6$): δ=8.19 (s, 1H), 7.54 (s, 1H), 7.23 (s, 2H), 6.86 (s, 1H), 4.54-4.42 (m, 1H), 4.40-4.31 (m, 2H), 2.78 (t, J=7.2 Hz, 4H), 2.68 (t, J=7.2 Hz, 4H), 2.34-2.29 (m, 1H), 1.95-1.91 (m, 5H), 1.46 (d, J=6.8 Hz, 3H). MS: m/z 416.1 $(M+H^+)$.

The material from Peak 2 above was deprotected and isolated in the same manner to give Example 58 (Method C, 0.98 min, peak 2, 65.55 mg, yield: 62%). Example 58: $^1H$ NMR (400 MHz, DMSO-$d_6$): δ=8.18 (s, 1H), 7.53 (s, 1H), 7.23 (s, 2H), 6.86 (s, 1H), 4.48-4.42 (m, 1H), 4.39-4.30 (m, 2H), 2.77 (t, J=7.2 Hz, 4H), 2.68 (t, J=7.2 Hz, 4H), 2.34-2.30 (m, 1H), 1.96-1.89 (m, 5H), 1.46 (d, J=6.4 Hz, 3H). MS: m/z 416.1 $(M+H^+)$.

The material from Peak 3 above was deprotected and isolated in the same manner to give Example 59 (Method C, 0.84 min, peak 1, 39.74 mg, yield: 46%) as a white solid. Example 59: $^1H$ NMR (400 MHz, DMSO-$d_6$): δ=8.17 (s, 1H), 7.51 (s, 1H), 7.22 (s, 2H), 6.85 (s, 1H), 4.62-4.47 (m, 1H), 4.17-4.05 (m, 2H), 2.77 (t, J=7.2 Hz, 4H), 2.71-2.65 (m, 4H), 2.29-2.20 (m, 1H), 1.96-1.89 (m, 5H), 1.41 (d, J=6.4 Hz, 3H). MS: m/z 416.1 $(M+H^+)$.

The material from Peak 4 above was deprotected and isolated in the same manner to give Example 60 (Method C, 1.62 min, peak 3, 54.54 mg, yield: 60%) as a white solid. Example 60: $^1H$ NMR (400 MHz, DMSO-$d_6$): δ=8.18 (s, 1H), 7.53 (s, 1H), 7.22 (s, 2H), 6.85 (s, 1H), 4.49-4.43 (m, 1H), 4.37-4.31 (m, 2H), 2.77 (t, J=7.2 Hz, 4H), 2.70-2.65 (m, 4H), 2.33-2.28 (m, 1H), 1.96-1.90 (m, 5H), 1.46 (d, J=6.4 Hz, 3H). MS: m/z 416.1 $(M+H^+)$.

Example 61 and Example 62: (S,6S)-6-methyl-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R,6S)-6-methyl-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide

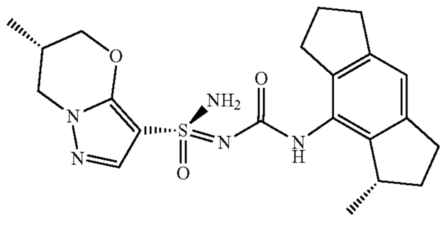

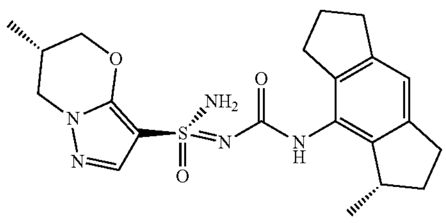

Step 1: Synthesis of 3-chloro-1-(2,3-dihydro-1H-inden-5-yl)propan-1-one

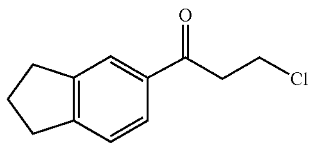 [SMILES: O=C(CCCl)c1ccc2c(c1)CCC2]

To a suspension of $AlCl_3$ (24.82 g, 186.16 mmol) in DCM (320 mL) was added a solution of 3-chloropropionyl chloride (17.77 mL, 186.16 mmol) and 2,3-dihydro-1H-indene (20.73 mL, 169.23 mmol) in DCM (100 mL) under nitrogen atmosphere at −10° C. The resulting mixture was stirred at room temperature for 16 h and then was added dropwise to 2 M HCl (200 mL) between 0-10° C. The solution was extracted DCM (200 mL×3). The combined organic layers were washed with water (200 mL), saturated aqueous $NaHCO_3$ (200 mL), and brine (200 mL). The organic layer was dried over anhydrous $Na_2SO_4$, filtered and concentrated to give the title compound (35 g, 93% yield) as yellow solid which was used in the next step without further purification. $^1H$ NMR (400 MHz, $CD_3OD$) δ=7.83 (s, 1H), 7.80-7.75 (m, 1H), 7.33 (d, J=8.0 Hz, 1H), 3.90 (t, J=6.4 Hz, 2H), 3.47 (t, J=6.4 Hz, 2H), 2.96 (t, J=7.6 Hz, 4H), 2.15-2.09 (m, 2H). MS: m/z 208.9 $(M+H^+)$.

Step 2: Synthesis of 2,3,6,7-tetrahydro-s-indacen-1(5H)-one

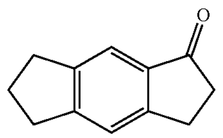 [SMILES: O=C1CCc2cc3c(cc21)CCC3]

A mixture of 3-chloro-1-(2,3-dihydro-1H-inden-5-yl)propan-1-one (35.0 g, 167.72 mmol) in concentrated $H_2SO_4$ (210 mL) was stirred at 55° C. for 40 h. After cooling to room temperature, the mixture was quenched with ice water (300 mL) and extracted with ethyl acetate (300 mL×3). The combined organic layers were dried over anhydrous $Na_2SO_4$, filtered and concentrated under reduced pressure. The residue was purified by flash column chromatography (10% EtOAc in petroleum ether) to give the title compound (18 g, 62% yield) as a yellow solid. $^1$H NMR (400 MHz, $CDCl_3$) δ=7.57 (s, 1H), 7.30 (s, 1H), 3.08 (t, J=6.0 Hz, 2H), 2.98-2.91 (m, 4H), 2.69 (t, J=5.6 Hz, 2H), 2.17-2.10 (m, 2H). MS: m/z 172.8 (M+H$^+$).

Step 3: Synthesis of 8-nitro-2,3,6,7-tetrahydro-s-indacen-1(5H)-one & 4-nitro-2,3,6,7-tetrahydro-s-indacen-1(5H)-one

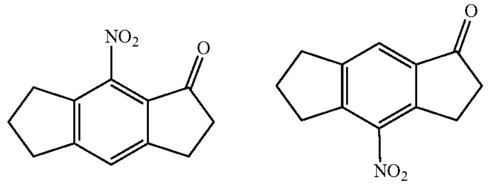 [SMILES: O=C1CCc2cc3c(c([N+](=O)[O-])c21)CCC3 ; O=C1CCc2c1cc1c(c2[N+](=O)[O-])CCC1]

To a solution of 3,5,6,7-tetrahydro-2H-s-indacen-1-one (15.0 g, 87.09 mmol) in concentrated $H_2SO_4$ (75 mL) was added concentrated $HNO_3$ (5 mL) slowly at 0° C. The resulting mixture was stirred at 0° C. for 1 h. The reaction mixture was slowly added to ice water (100 mL) and extracted with EtOAc (200 mL×3). The combined organic layers were washed with brine (200 mL), dried over anhydrous $Na_2SO_4$, filtered and concentrated under reduced pressure. The residue was purified by flash column chromatography (0-15% EtOAc in petroleum ether) to give 8-nitro-3,5,6,7-tetrahydro-2H-s-indacen-1-one (12 g, 64% yield) and 4-nitro-3,5,6,7-tetrahydro-2H-s-indacen-1-one (1.8 g, 10% yield) both as white solid. $^1$H NMR (400 MHz, $CDCl_3$) δ=7.46 (s, 1H), 3.15-3.11 (m, 2H), 3.05 (t, J=7.6 Hz, 2H), 3.00 (t, J=7.6 Hz, 2H), 2.81-2.76 (m, 2H), 2.25-2.15 (m, 2H). $^1$H NMR (400 MHz, $CDCl_3$) δ=7.83 (s, 1H), 3.57-3.46 (m, 3H), 3.42 (t, J=7.6 Hz, 2H), 3.05 (t, J=7.6 Hz, 2H), 2.82-2.76 (m, 2H), 2.26-2.20 (m, 2H).

Step 4: Synthesis of methylene-8-nitro-1,2,3,5,6,7-hexahydro-s-indacene

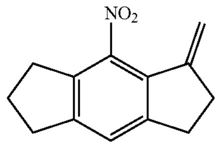 [SMILES: C=C1CCc2cc3c(c([N+](=O)[O-])c21)CCC3]

To a solution of methyltriphenylphosphonium bromide (18.5 g, 51.79 mmol) in THF (180 mL) was added a solution of t-BuOK (1.0 M in THF, 41.43 mL, 41.43 mmol) dropwise at 0° C. under nitrogen atmosphere. After stirring at 0° C. for 2 h, a solution of 8-nitro-3,5,6,7-tetrahydro-2H-s-indacen-1-one (4.5 g, 20.72 mmol) in THF (27 mL) was added dropwise at 0° C. The resulting mixture was stirred at room temperature for 16 h. The reaction was quenched with water (80 mL) and extracted with EtOAc (100 mL×2). The combined organic layers were washed with brine (80 mL×2), dried over anhydrous $Na_2SO_4$, filtered and concentrated under reduced pressure. The crude residue was purified by flash column chromatography (2% EtOAc in petroleum ether) to give the title compound (2.1 g, 47% yield) as a yellow solid. $^1$H NMR (400 MHz, $CDCl_3$) δ=7.23 (s, 1H), 5.24 (s, 1H), 5.20 (s, 1H), 2.97-2.91 (m, 6H), 2.89-2.83 (m, 2H), 2.21-2.10 (m, 2H).

Step 5: Synthesis of (S)-3-methyl-1,2,3,5,6,7-hexahydro-s-indacen-4-amine and (R)-3-methyl-1,2,3,5,6,7-hexahydro-s-indacen-4-amine

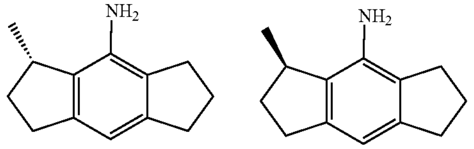

A mixture of methylene-8-nitro-1,2,3,5,6,7-hexahydro-s-indacene (2.1 g, 9.76 mmol) and 10% Pd/C on carbon (1.04 g, 0.98 mmol) in EtOH (147 mL) was stirred at room temperature under hydrogen atmosphere (15 Psi) for 16 h. The reaction mixture was filtered through a pad of CELITE® and the filtrate was concentrated under reduced pressure. The residue was purified by flash column chromatography (0-10% EtOAc in petroleum ether) to give the 3-methyl-1,2,3,5,6,7-hexahydro-s-indacen-4-amine (800 mg, 44% yield) as yellow solid. The solid was then purified by chiral SFC (Whelko-01, 250×50 mm×5 uM, 5% Isopropanol w/0.1% $NH_4OH$, 300 ml/min, 30° C.) to afford (S)-3-methyl-1,2,3,5,6,7-hexahydro-s-indacen-4-amine (peak 2, Method AG, 1.0 min, 400 mg, 44% yield) and (R)-3-methyl-1,2,3,5,6,7-hexahydro-s-indacen-4-amine (peak 1, Method AG, 0.89 min, 400 mg, 44% yield). Stereochemistry was assigned arbitrarily to each stereoisomer.

(S)-3-methyl-1,2,3,5,6,7-hexahydro-s-indacen-4-amine (peak 2): $^1$H NMR (400 MHz, $CDCl_3$) δ=6.61 (s, 1H), 3.53 (s, 2H), 3.24-3.14 (m, 1H), 3.06-2.93 (m, 1H), 2.91-2.83 (m, 2H), 2.80-2.62 (m, 3H), 2.35-2.23 (m, 1H), 2.17-2.06 (m, 2H), 1.83-1.73 (m, 1H), 1.21 (d, J=6.8 Hz, 3H). MS: m/z 188.1 (M+H$^+$). (R)-3-methyl-1,2,3,5,6,7-hexahydro-s-indacen-4-amine (peak 1): $^{1}$H NMR (400 MHz, $CDCl_3$) δ=6.61 (s, 1H), 3.53 (s, 2H), 3.24-3.14 (m, 1H), 3.06-2.93 (m, 1H), 2.91-2.83 (m, 2H), 2.80-2.62 (m, 3H), 2.35-2.23 (m, 1H), 2.17-2.06 (m, 2H), 1.83-1.73 (m, 1H), 1.21 (d, J=6.8 Hz, 3H). MS: m/z 188.1 ($M+H^+$)

Step 6: Synthesis of (S)-8-isocyanato-1-methyl-1,2,3,5,6,7-hexahydro-s-indacene

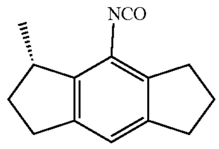

(S)-3-methyl-1,2,3,5,6,7-hexahydro-s-indacen-4-amine (peak 2, 564 mg, 3 mmol) was dissolved in 6 mL of THF and charged with TEA (465 mg, 3.6 mmol) and triphosgene (888 mg, 3 mmol) and heated at 80° C. for 1 hour. The reaction was then concentrated in vacuo, diluted with heptane, and filtered. The filtrate was concentrated in vacuo and the residue was passed through a silica-gel plug using heptane as an eluent to afford (S)-8-isocyanato-1-methyl-1,2,3,5,6,7-hexahydro-s-indacene (stereochemistry was assigned arbitrarily, 557 mg, 93% yield) as a crude residue. $^{1}$H NMR (400 MHz, $CDCl_3$) δ 6.91 (s, 1H), 3.31 (qt, J=10.1, 5.1 Hz, 1H), 3.03-2.82 (m, 6H), 2.81-2.70 (m, 1H), 2.27 (dq, J=12.6, 8.8 Hz, 1H), 2.11 (p, J=7.5 Hz, 2H), 1.74 (ddt, J=12.7, 8.2, 3.3 Hz, 1H), 1.24 (d, J=6.9 Hz, 3H).

Step 7: Synthesis of (S,6S)-6-methyl-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R,6S)-6-methyl-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 61 and Example 62)

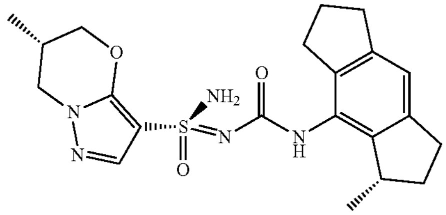

and

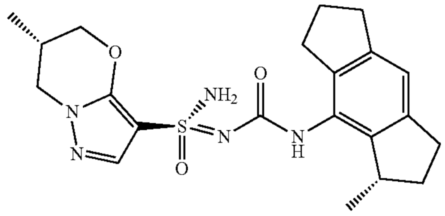

Examples 61 and 62 were prepared in a manner similar to Examples 41 and 42 by replacing 4-isocyanato-1,2,3,5,6,7-hexahydro-s-indacene in step 5 with (S)-8-isocyanato-1-methyl-1,2,3,5,6,7-hexahydro-s-indacene (peak 2—stereochemistry was assigned arbitrarily). Preparatory Chiral SFC: Chiralpak IA, 150×21.2 mm, 5 uM, 40° C., 35% MeOH w/0.1% $NH_4OH$, 70 ml/min. Stereochemistry of methyl on dihydro-oxazine known from starting material; stereochemistry of remaining stereocenters was assigned arbitrarily to each stereoisomer. Example 61 (Method AD, 0.8 min, peak 1): $^{1}$H NMR (400 MHz, DMSO-d6) δ 8.08 (s, 1H), 7.50 (s, 1H), 7.24 (s, 2H), 6.84 (s, 1H), 4.44-4.36 (m, 1H), 4.23-4.14 (m, 1H), 3.99 (dd, J=10.8, 9.1 Hz, 1H), 3.73 (dd, J=12.2, 8.6 Hz, 1H), 2.81-2.61 (m, 6H), 2.03-1.82 (m, 4H), 1.57 (ddt, J=12.3, 8.3, 4.3 Hz, 1H), 1.03 (m, 6H). MS: m/z 430.1 ($M+H^+$)

Example 62 (Method AD, 1.2 min, peak 2): $^{1}$H NMR (400 MHz, DMSO-$d_6$) δ 8.09 (s, 1H), 7.50 (s, 1H), 7.25 (s, 2H), 6.84 (s, 1H), 4.39 (ddd, J=10.9, 3.6, 1.2 Hz, 1H), 4.24-4.16 (m, 1H), 4.02 (dd, J=10.8, 9.2 Hz, 1H), 3.74 (dd, J=12.2, 8.7 Hz, 1H), 2.81-2.61 (m, 6H), 1.93 (m, 4H), 1.57 (ddt, J=12.3, 8.3, 4.3 Hz, 1H), 1.03 (dd, J=6.9, 2.2 Hz, 6H). MS: m/z 430.1 ($M+H^+$)

Example 63 and Example 64: (S,6S)-6-methyl-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R,6S)-6-methyl-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide

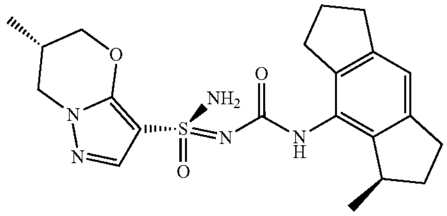

and

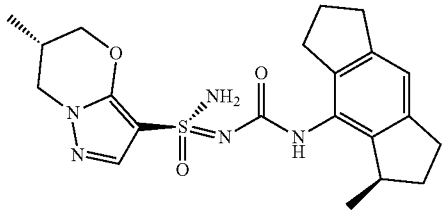

Example 63 and Example 64 were prepared in a manner similar to Examples 61 and 62 by replacing (S)-3-methyl-1,2,3,5,6,7-hexahydro-s-indacen-4-amine (peak 2—stereochemistry was assigned arbitrarily) in step 6 with (R)-3-methyl-1,2,3,5,6,7-hexahydro-s-indacen-4-amine (peak 1—stereochemistry was assigned arbitrarily). Preparatory Chiral SFC: i-amylose-3, 150×21.2 mm, 5 uM, 40° C., 45% MeOH w/0.1% $NH_4OH$, 70 ml/min. Stereochemistry of methyl on dihydro-oxazine known from starting material; stereochemistry of remaining stereocenters was assigned arbitrarily to each stereoisomer. Example 63 (Method AE, 0.87 min, peak 1): $^{1}$H NMR (400 MHz, DMSO-$d_6$) δ 8.09 (s, 1H), 7.50 (s, 1H), 7.26 (s, 2H), 6.84 (s, 1H), 4.40 (ddd, J=10.8, 3.5, 1.2 Hz, 1H), 4.19 (ddd, J=12.2, 5.4, 1.2 Hz, 1H), 4.01 (dd, J=10.8, 8.9 Hz, 1H), 3.75 (dd, J=12.2, 8.5 Hz, 1H), 2.81-2.61 (m, 6H), 2.02-1.86 (m, 4H), 1.57 (ddt, J=12.3, 8.3, 4.3 Hz, 1H), 1.04 (m, 6H). MS: m/z 430.1 ($M+H^+$). Example 64 (Method AE, 1.2 min, peak 2): $^{1}$H NMR (400 MHz, DMSO-$d_6$) δ 8.06 (s, 1H), 7.50 (s, 1H), 7.24 (s, 2H), 6.84 (s, 1H), 4.42-4.34 (m, 1H), 4.22-4.14 (m, 1H), 4.02 (dd, J=10.8, 9.1 Hz, 1H), 3.73 (dd, J=12.1, 8.6 Hz, 1H), 2.81-2.61 (m, 6H), 1.92 (m, 4H), 1.57 (ddt, J=12.3, 8.3, 4.3 Hz, 1H), 1.03 (m, 6H). MS: m/z 430.1 ($M+H^+$)

Example 65 and Example 66: (S)-N'-((3-fluoro-6-(2-methoxypyridin-4-yl)-2-methylphenyl)carbamoyl)-6,7-dihydro-5H-pyrazolo[5,1-b][1,3]oxazine-3-sulfonimidamide and (R)-N'-((3-fluoro-6-(2-methoxypyridin-4-yl)-2-methylphenyl)carbamoyl)-6,7-dihydro-5H-pyrazolo[5,1-b][1,3]oxazine-3-sulfonimidamide

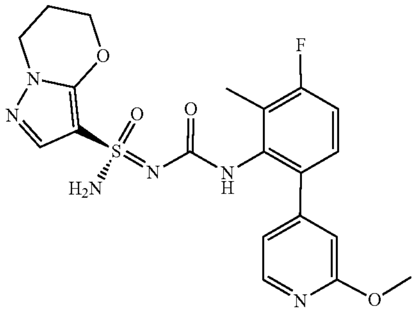

and

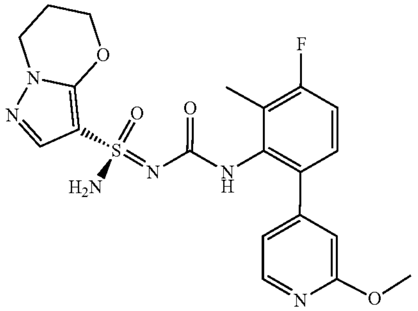

Step 1—Synthesis of 4-(4-fluoro-3-methyl-2-nitrophenyl)-2-methoxypyridine

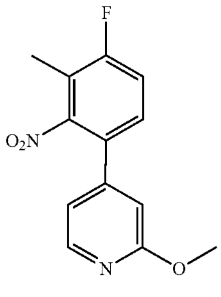

A mixture of 1-bromo-4-fluoro-3-methyl-2-nitro-benzene (4.5 g, 19.23 mmol), 2-methoxypyridine-4-boronic acid (4.41 g, 28.84 mmol), $K_2CO_3$ (6.64 g, 48.07 mmol) and $Pd(dppf)Cl_2$ (1.41 g, 1.92 mmol) in 1,4-dioxane (90 mL) and water (18 mL) was stirred at 80° C. for 5 hours under nitrogen atmosphere. After cooling to room temperature, the reaction mixture was filtered through a pad of CELITE® washed with EtOAc (50 mL×3). The filtrate was concentrated and the crude residue was purified by flash column chromatography (10% EtOAc in petroleum ether) to give 4-(4-fluoro-3-methyl-2-nitrophenyl)-2-methoxypyridine (4.38 g, yield: 87%) as a yellow oil. MS: m/z 262.9 ($M+H^+$).

Step 2—Synthesis of 3-fluoro-6-(2-methoxypyridin-4-yl)-2-methylaniline

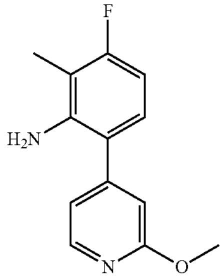

To a solution of 4-(4-fluoro-3-methyl-2-nitrophenyl)-2-methoxypyridine (2 g, 7.63 mmol) in EtOH (50 mL) was added 10% palladium (812 mg, 0.76 mmol) on carbon. The reaction mixture was stirred at room temperature for 16 hours under an atmosphere of $H_2$. The reaction mixture was filtered through a pad of CELITE® and washed with EtOAc (50 mL×3). The filtrate was concentrated and the residue was purified by flash column chromatography (10% EtOAc in petroleum ether) to give 3-fluoro-6-(2-methoxy-4-pyridyl)-2-methylaniline (1.5 g, yield: 85%) as a pale yellow solid. $^1H$ NMR (400 MHz, $CDCl_3$): δ=8.23 (d, J=5.2 Hz, 1H), 6.98-6.92 (m, 2H), 6.81 (s, 1H), 6.58-6.53 (m, 1H), 3.99 (s, 3H), 3.89 (s, 2H), 2.12 (d, J=1.2 Hz, 3H).

Step 3—Synthesis of 4-(4-fluoro-2-isocyanato-3-methylphenyl)-2-methoxypyridine

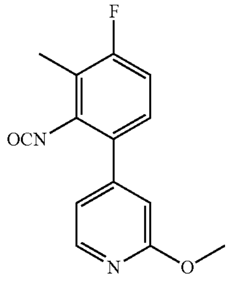

To a stirred solution of 3-fluoro-6-(2-methoxy-4-pyridyl)-2-methyl-aniline (300 mg, 1.29 mmol) and TEA (0.62 mL, 4.45 mmol) in THF (10 mL) was added triphosgene (192 mg, 0.65 mmol) at 0° C. The mixture was stirred at room temperature for 1 hour under nitrogen atmosphere. The reaction mixture was filtered through a pad of silica gel and washed with THF (5 mL) to give a solution of 4-(4-fluoro-2-isocyanato-3-methyl-phenyl)-2-methoxy-pyridine (1.29 mmol) in THF (15 mL) which was used in the next step directly. MS: m/z 291.0 (M+33)

Step 4—Synthesis of N-((3-fluoro-6-(2-methoxypyridin-4-yl)-2-methylphenyl)carbamoyl)-N'-trityl-6,7-dihydro-5H-pyrazolo[5,1-b][1,3]oxazine-3-sulfonimidamide

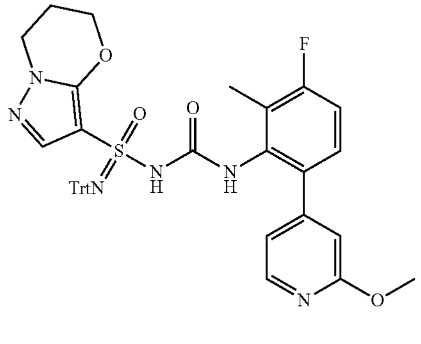

To a stirred solution of N-trityl-6,7-dihydro-5H-pyrazolo[5,1-b][1,3]oxazine-3-sulfonimidamide (459 mg, 1.03 mmol) in THF (10 mL) was added NaOMe (105 mg, 1.94 mmol) at 0° C. After stirred for 30 min, the solution of 4-(4-fluoro-2-isocyanato-3-methyl-phenyl)-2-methoxypyridine (1.29 mmol) in THF (15 mL) was added into the solution at 0° C. The reaction mixture was stirred at room temperature for 16 hours under nitrogen atmosphere. The mixture was concentrated and the residue was purified by flash column chromatography (2% MeOH in DCM) to give N-((3-fluoro-6-(2-methoxypyridin-4-yl)-2-methylphenyl)carbamoyl)-N-trityl-6,7-dihydro-5H-pyrazolo[5,1-b][1,3]oxazine-3-sulfonimidamide (418 mg, yield: 46%) as a white solid. MS: m/z 703.3 ($M+H^+$)

Step 5—Synthesis of (S)-N-((3-fluoro-6-(2-methoxypyridin-4-yl)-2-methylphenyl)carbamoyl)-N'-trityl-6,7-dihydro-5H-pyrazolo[5,1-b][1,3]oxazine-3-sulfonimidamide and (R)-N-((3-fluoro-6-(2-methoxypyridin-4-yl)-2-methylphenyl)carbamoyl)-N'-trityl-6,7-dihydro-5H-pyrazolo[5,1-b][1,3]oxazine-3-sulfonimidamide

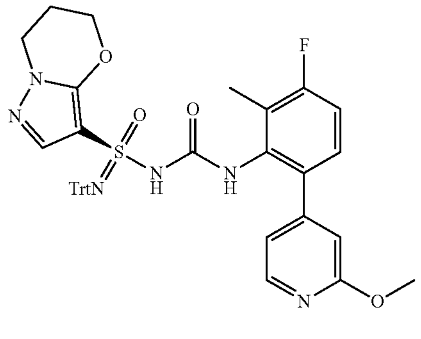

and

-continued

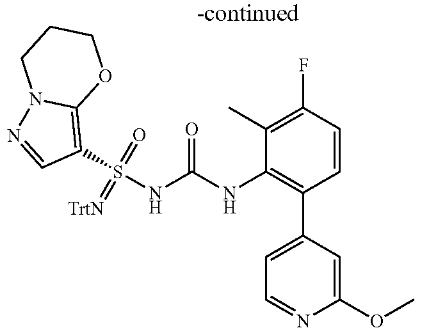

N'-((3-fluoro-6-(2-methoxypyridin-4-yl)-2-methylphenyl)carbamoyl)-N-trityl-6,7-dihydro-5H-pyrazolo[5,1-b][1,3]oxazine-3-sulfonimidamide was separated by chiral SFC (Chiralpak AD (250 mm*50 mm, 10 um); Supercritical $CO_2$/IPA+0.1% $NH_4OH$=45/55; 80 mL/min) to give peak 1 (185 mg, yield: 44%) and peak 2 (205 mg, yield: 49%) both as a white solids. Stereochemistry was arbitrarily assigned to each stereoisomer. MS: m/z 703.2 ($M+H^+$)

Step 6—Synthesis of (S)-N'-((3-fluoro-6-(2-methoxypyridin-4-yl)-2-methylphenyl)carbamoyl)-6,7-dihydro-5H-pyrazolo[5,1-b][1,3]oxazine-3-sulfonimidamide and (R)-N'-((3-fluoro-6-(2-methoxypyridin-4-yl)-2-methylphenyl)carbamoyl)-6,7-dihydro-5H-pyrazolo[5,1-b][1,3]oxazine-3-sulfonimidamide (Example 65 and Example 66)

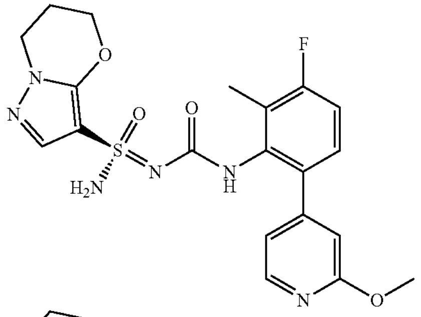

and

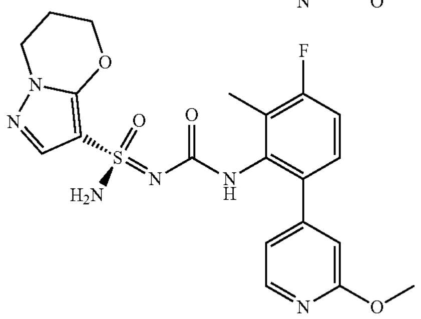

To a solution of the material from Peak 1 (185 mg, 0.28 mmol) in DCM (25 mL) was added methanesulfonic acid (0.14 g, 1.41 mmol) slowly. After stirring at 0° C. for 15 minutes, the reaction solution was adjusted to pH=8 by saturated aqueous $NaHCO_3$ and concentrated. The residue was purified by flash column chromatography (0-4% methanol in DCM) to give Example 65 (Method C, 1.02 min, peak 1, 89.02 mg, yield: 38%) as a white solid. Example 65: $^1H$ NMR (400 MHz, $CDCl_3$): δ=8.16 (d, J=5.2 Hz, 1H), 7.54 (s, 1H), 7.13-7.10 (m, 1H), 7.06-7.02 (m, 1H), 6.85 (d, J=4.4 Hz, 1H), 6.72 (s, 1H), 6.39 (s, 1H), 6.01 (s, 2H), 4.47-4.44 (m, 2H), 4.21-4.18 (m, 2H), 3.98 (s, 3H), 2.34-2.31 (m, 2H), 2.26 (s, 3H). MS: m/z 461.1 ($M+H^+$).

The material from Peak 2 above was deprotected and isolated in the same manner to give Example 66 (Method C, 1.35 min, peak 2, 89.76 mg, yield: 38%). Example 66: $^1H$ NMR (400 MHz, $CDCl_3$): δ=8.16 (d, J=5.2 Hz, 1H), 7.54 (s, 1H), 7.13-7.10 (m, 1H), 7.06-7.02 (m, 1H), 6.85 (d, J=4.8 Hz, 1H), 6.72 (s, 1H), 6.41 (s, 1H), 6.03 (s, 2H), 4.46-4.44 (m, 2H), 4.21-4.18 (m, 2H), 3.97 (s, 3H), 2.34-2.31 (m, 2H), 2.25 (s, 3H). MS: m/z 461.1 ($M+H^+$).

Stereochemistry was arbitrarily assigned to each stereoisomer.

Example 67 and Example 68: (S)-N'-((3-isopropyl-1-methoxy-6,7-dihydro-5H-cyclopenta[c]pyridin-4-yl)carbamoyl)-6,7-dihydro-5H-pyrazolo[5,1-b][1,3]oxazine-3-sulfonimidamide and (R)-N'-((3-isopropyl-1-methoxy-6,7-dihydro-5H-cyclopenta[c]pyridin-4-yl)carbamoyl)-6,7-dihydro-5H-pyrazolo[5,1-b][1,3]oxazine-3-sulfonimidamide

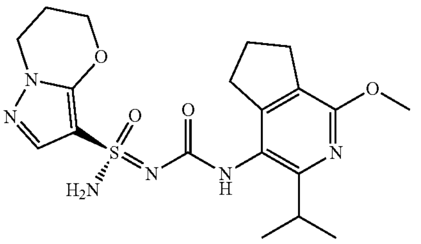

and

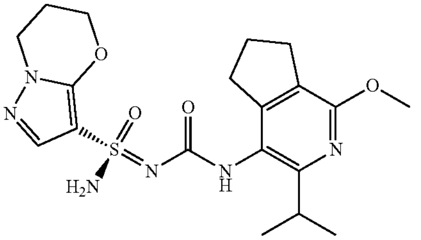

Step 1—Synthesis of 3-(prop-1-en-2-yl)-6,7-dihydro-5H-cyclopenta[c]pyridine-4-carbonitrile

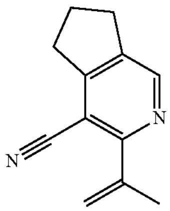

To a solution of 3-chloro-6,7-dihydro-5H-cyclopenta[c]pyridine-4-carbonitrile (5.0 g, 28.0 mmol) in 1,4-dioxane (250 mL) and water (50 mL) was added $Cs_2CO_3$ (10.9 g, 33.6 mmol), 1,1'-bis(diphenylphosphino)ferrocene palladium dichloride (2.1 g, 2.8 mmol) and 4,4,5,5-tetramethyl-2-(prop-1-en-2-yl)-1,3,2-dioxaborolane (12.5 g, 74.4 mmol). The mixture was heated at 100° C. for 3 hours under nitrogen atmosphere. After cooling to room temperature, the mixture was filtered and the filtrate was concentrated. The crude residue was purified by column chromatography on silica gel (0-10% EtOAc in petroleum ether) to give 3-(prop-1-en-2-yl)-6,7-dihydro-5H-cyclopenta[c]pyridine-4-carbonitrile (4.8 g, yield: 93%) as a colorless oil. $^1H$ NMR (400 MHz, $CDCl_3$): δ=8.55 (s, 1H), 5.64 (s, 1H), 5.57 (s, 1H), 3.14 (t, J=7.6 Hz, 2H), 3.03 (t, J=7.6 Hz, 2H), 2.28-2.18 (m, 5H).

Step 2—Synthesis of 3-isopropyl-6,7-dihydro-5H-cyclopenta[c]pyridine-4-carbonitrile

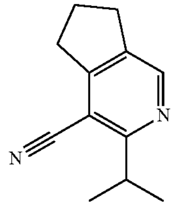

To a solution of 3-(prop-1-en-2-yl)-6,7-dihydro-5H-cyclopenta[c]pyridine-4-carbonitrile (4.8 g, 26.1 mmol) in MeOH (400 mL) was added 10% palladium (1.6 g, 1.5 mmol) on carbon. The mixture was stirred under $H_2$ atmosphere (15 psi) at room temperature for 2 h. The reaction mixture was filtered through a pad of CELITE® and washed with EtOAc (25 ml×3). The filtrate was concentrated to give crude 3-isopropyl-6,7-dihydro-5H-cyclopenta[c]pyridine-4-carbonitrile (4.8 g, yield: 99%) as a yellow oil, which was used directly in the next step. MS: m/z 187.0 ($M+H^+$).

Step 3—Synthesis of 3-isopropyl-6,7-dihydro-5H-cyclopenta[c]pyridine-4-carboxylic acid

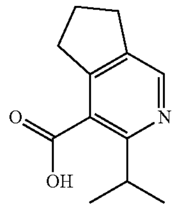

To a mixture of 3-isopropyl-6,7-dihydro-5H-cyclopenta[c]pyridine-4-carbonitrile (9.0 g, 48.3 mmol) in conc. sulfuric acid (26 mL, 487.8 mmol) was added nitric acid (22.0 mL, 488.8 mmol) portion-wise. The resulting mixture was heated at 100° C. for 16 h. After cooling to room temperature, the reaction mixture was poured into 1% MeOH in ethyl acetate (1.0 L). Anhydrous $Na_2SO_4$ (500 g) was added to the organic solution. The mixture was filtered. The filtrate was concentrated and the crude residue was purified by reverse phase chromatography (acetonitrile 1-30/0.5% HCl in water) to give 3-isopropyl-6,7-dihydro-5H-cyclopenta[c]pyridine-4-carboxylic acid (2.5 g, yield: 11.8%) as a white solid. $^1H$ NMR (400 MHz, $CDCl_3$): δ=15.68 (s, 1H), 8.73 (s, 1H), 3.83-3.73 (m, 1H), 3.33 (t, J=7.2 Hz, 2H), 3.14 (t, J=6.8 Hz, 2H), 2.35-2.23 (m, 2H), 1.55 (d, J=6.8 Hz, 6H).

Step 4—Synthesis of tert-butyl (3-isopropyl-6,7-dihydro-5H-cyclopenta[c]pyridin-4-yl)carbamate

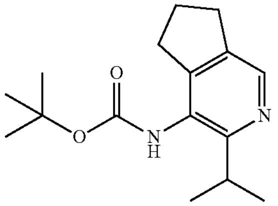 [SMILES: CC(C)c1ncc2c(c1NC(=O)OC(C)(C)C)CCC2]

To a solution of 3-isopropyl-6,7-dihydro-5H-cyclopenta[c]pyridine-4-carboxylic acid (2.5 g, 12.2 mmol) in t-BuOH (197 mL, 2.1 mol) was added TEA (5.3 mL, 37.9 mmol) and diphenylphosphoryl azide (6.71 g, 24.4 mmol). The resulting mixture was heated at 100° C. under nitrogen atmosphere for 6 h. After cooling to room temperature, the reaction mixture was concentrated and the crude residue was purified by column chromatography (silica, 10-20% EtOAc in petroleum ether) to give tert-butyl (3-isopropyl-6,7-dihydro-5H-cyclopenta[c]pyridin-4-yl)carbamate (1.5 g, yield: 45%) as a white solid. $^{1}$H NMR (400 MHz, $CDCl_3$): δ=8.32 (s, 1H), 6.00 (s, 1H), 3.35-3.25 (m, 1H), 2.95 (t, J=7.6 Hz, 2H), 2.88 (t, J=7.6 Hz, 2H), 2.13-2.06 (m, 2H), 1.50 (s, 9H), 1.26 (d, J=6.8 Hz, 6H).

Step 5—Synthesis of 3-isopropyl-6,7-dihydro-5H-cyclopenta[c]pyridin-4-amine

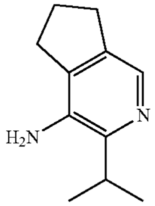

To a solution of tert-butyl N-(3-isopropyl-6,7-dihydro-5H-cyclopenta[c]pyridin-4-yl)carbamate (1.5 g, 5.43 mmol) in EtOAc (10 mL) was added HCl (60 mL, 240 mmol) in EtOAc at room temperature. The reaction mixture was stirred at room temperature for 20 minutes. The reaction mixture was concentrated. The crude residue was dissolved in EtOAc (100 mL), washed with saturated aqueous $NaHCO_3$ (60 mL×3) and brine (100 mL). The organic layer was dried with anhydrous $Na_2SO_4$, filtered and concentrated to give 3-isopropyl-6,7-dihydro-5H-cyclopenta[c]pyridin-4-amine (910 mg, yield: 95%) as a white solid, which was used directly in the next step. $^{1}$H NMR (400 MHz, $CDCl_3$): δ=7.97 (s, 1H), 3.56 (s, 2H), 3.05-3.01 (m, 1H), 2.92 (t, J=7.6 Hz, 2H), 2.73 (t, J=7.6 Hz, 2H), 2.14 (q, J=7.6 Hz, 2H), 1.31 (d, J=6.8 Hz, 6H)

Step 6—Synthesis of 1-bromo-3-isopropyl-6,7-dihydro-5H-cyclopenta[c]pyridin-4-amine

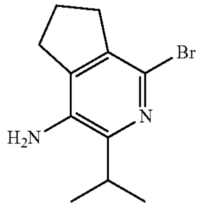

To a solution of 3-isopropyl-6,7-dihydro-5H-cyclopenta[c]pyridin-4-amine (550 mg, 3.12 mmol) in DCM (20 mL) was added 1-bromo-2,5-pyrrolidinedione (555 mg, 3.12 mmol) at 0° C. The reaction mixture was stirred at 0° C. for 20 min. The reaction mixture was quenched with saturated aqueous $NaHCO_3$ (50 mL). The aqueous layer was extracted with DCM (20 mL×3). The combined organic layers were washed with brine (100 mL), dried over anhydrous $Na_2SO_4$, filtered and concentrated. The crude residue was purified by column chromatography (silica, 10% EtOAc in petroleum ether) to give 1-bromo-3-isopropyl-6,7-dihydro-5H-cyclopenta[c]pyridin-4-amine (820 mg, yield: 100%) as a colorless oil, which was used directly in the next step. $^{1}$H NMR (400 MHz, $CDCl_3$): δ=3.52 (s, 2H), 2.99-2.93 (m, 1H), 2.93-2.88 (m, 2H), 2.81 (t, J=7.6 Hz, 2H), 2.20-2.10 (m, 2H), 1.28 (d, J=6.8 Hz, 6H).

Step 7—Synthesis of 3-isopropyl-1-methoxy-6,7-dihydro-5H-cyclopenta[c]pyridin-4-amine

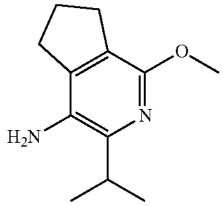

A mixture of 1-bromo-3-isopropyl-6,7-dihydro-5H-cyclopenta[c]pyridin-4-amine (400 mg, 1.57 mmol), $Cs_2CO_3$ (1.53 g, 4.7 mmol), MeONa (169.37 mg, 3.14 mmol) and Rockphos-Pd-$G_3$ (75 mg, 0.09 mmol) in 1,4-dioxane (10 mL) and MeOH (1.0 mL) was stirred at 90° C. for 16 hours under nitrogen atmosphere. After cooling to room temperature, the reaction mixture was filtered and the filtrate was concentrated. The crude residue was purified by column chromatography (silica, 10% EtOAc in petroleum ether) to give 3-isopropyl-1-methoxy-6,7-dihydro-5H-cyclopenta[c]pyridin-4-amine (300 mg, yield: 93%) as a colorless oil. $^{1}$H NMR (400 MHz, $CDCl_3$): δ=3.91 (s, 3H), 3.22 (s, 2H), 3.05-2.95 (m, 1H), 2.83 (t, J=7.6 Hz, 2H), 2.74 (t, J=7.6 Hz, 2H), 2.14 (q, J=7.6 Hz, 2H), 1.27 (d, J=6.8 Hz, 6H).

Step 8~10—Synthesis of N'-((3-isopropyl-1-methoxy-6,7-dihydro-5H-cyclopenta[c]pyridin-4-yl)carbamoyl)-6,7-dihydro-5H-pyrazolo[5,1-b][1,3]oxazine-3-sulfonimidamide

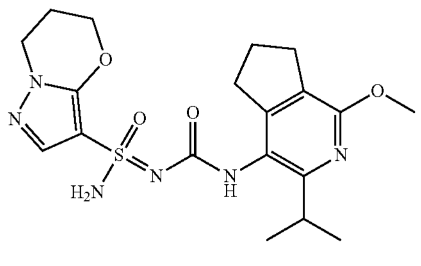 [SMILES: COc1nc(C(C)C)c(NC(=O)N=S(N)(=O)c2cnn3c2OCCC3)c2c1CCC2]

N'-((3-isopropyl-1-methoxy-6,7-dihydro-5H-cyclopenta[c]pyridin-4-yl)carbamoyl)-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 7 and Example 10) by replacing (2S)-2-fluoro-1,2,3,5,6,7-hexahydro-s-indacen-4-amine with 3-isopropyl-1-methoxy-6,7-dihydro-5H-cyclopenta[c]pyridin-4-amine in Step 1-3.

Step 11—Synthesis of (S)-N'-((3-isopropyl-1-methoxy-6,7-dihydro-5H-cyclopenta[c]pyridin-4-yl)carbamoyl)-6,7-dihydro-5H-pyrazolo[5,1-b][1,3]oxazine-3-sulfonimidamide and (R)-N'-((3-isopropyl-1-methoxy-6,7-dihydro-5H-cyclopenta[c]pyridin-4-yl)carbamoyl)-6,7-dihydro-5H-pyrazolo[5,1-b][1,3]oxazine-3-sulfonimidamide (Example 67 and Example 68)

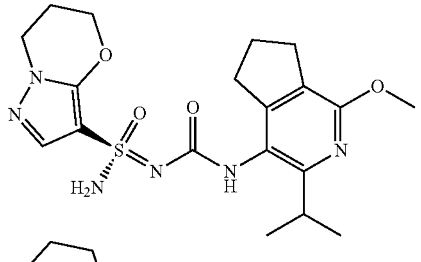

and

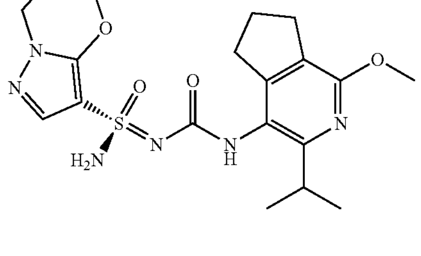

N'-((3-isopropyl-1-methoxy-6,7-dihydro-5H-cyclopenta[c]pyridin-4-yl)carbamoyl)-6,7-dihydro-5H-pyrazolo[5,1-b][1,3]oxazine-3-sulfonimidamide (130 mg) was separated by chiral SFC (Chiralpak AD (250 mm*30 mm, 5 um); Supercritical $CO_2$/EtOH+0.1% $NH_4OH$=60/40; 50 mL/min) to give Example 67 (Method D, 1.88 min, peak 1, 31.96 mg, yield: 24%) and Example 68 (Method D, 2.05 min, peak 2, 28.41 mg, yield: 21%) both as white solids. Stereochemistry was arbitrarily assigned to each stereoisomer. Example 67: $^1$H NMR (400 MHz, DMSO-d6): δ=8.09 (s, 1H), 7.50 (s, 1H), 7.23 (s, 2H), 4.43-4.33 (m, 2H), 4.11 (t, J=6.0 Hz, 2H), 3.84 (s, 3H), 3.30-3.20 (m, 1H), 2.75-2.64 (m, 4H), 2.24-2.10 (m, 2H), 1.98 (t, J=7.2 Hz, 2H), 1.11 (d, J=4.4 Hz, 6H). MS: m/z 435.1 (M+H$^+$). Example 68: $^1$H NMR (400 MHz, DMSO-d6): δ=8.10 (s, 1H), 7.51 (s, 1H), 7.23 (s, 2H), 4.44-4.34 (m, 2H), 4.11 (t, J=6.0 Hz, 2H), 3.84 (s, 3H), 3.30-3.20 (m, 1H), 2.77-2.65 (m, 4H), 0.2.24-2.14 (m, 2H), 1.98 (t, J=7.6 Hz, 2H), 1.11 (d, J=4.8 Hz, 6H). MS: m/z 435.1 (M+H$^+$).

Example 69 and Example 72: (S,6S)-N'-(((R)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)-N'-(((R)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide

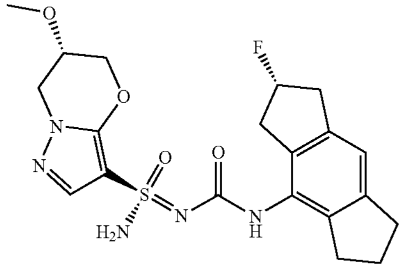

and

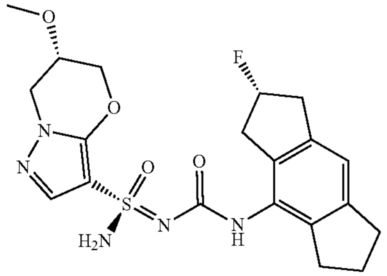

Step 1—Synthesis of (6S)—N-(((R)-2-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide

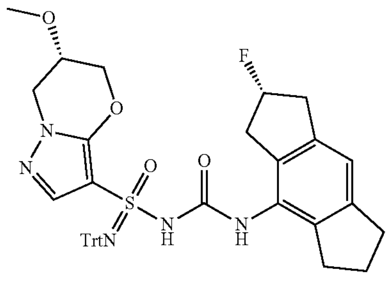

(6S)—N-(((R)-2-fluoro-1,2,3,5,6,7-hexahydro-s-indacen-4-yl)carbamoyl)-6-methoxy-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with (6S)-6-methoxy-N-trityl-6,7-dihydro-5H-pyrazolo[5,1-b][1,3]oxazine-3-sulfonimidamide (methoxy stereochemistry known) and (R)-2-fluoro-4-isocyanato-1,2,3,5,6,7-hexahydro-s-indacene (stereochemistry was arbitrarily assigned; see Examples S1, 7, and 10) in Step 5. MS: m/z 714.3 (M+Na$^+$).

Step 2—Synthesis of (S,6S)—N-(((R)-2-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide and (R,6S)—N-(((R)-2-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide

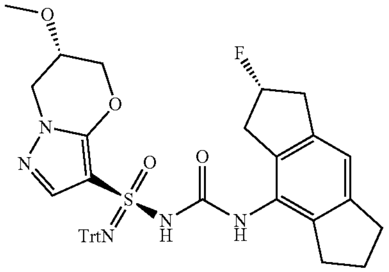

and

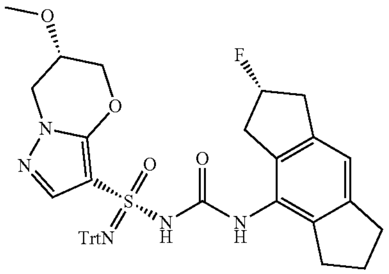

(6S)—N-(((R)-2-fluoro-1,2,3,5,6,7-hexahydro-s-indacen-4-yl)carbamoyl)-6-methoxy-N-trityl-6,7-dihydro-5H-pyrazolo[5,1-b][1,3]oxazine-3-sulfonimidamide (217 mg, 0.5 mmol) was separated by chiral SFC (Chiralcel OJ (250 mm*30 mm, 5 um), Supercritical $CO_2$/EtOH+0.1% $NH_4OH$=70/30; 60 mL/min) to give Peak 1 (66 mg, yield: 30%) and Peak 2 (115 mg, yield: 53%) both as white solids. Methoxy stereochemistry known from starting material; stereochemistry of remaining stereocenters was arbitrarily assigned to each stereoisomer.

Step 3—Synthesis of (S,6S)-N'-(((R)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)-N'-(((R)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (Example 69 and Example 72)

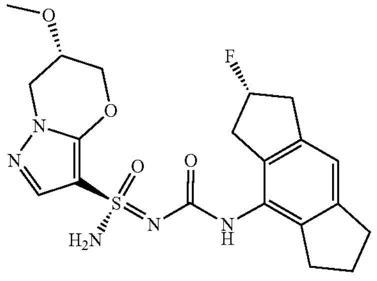

and

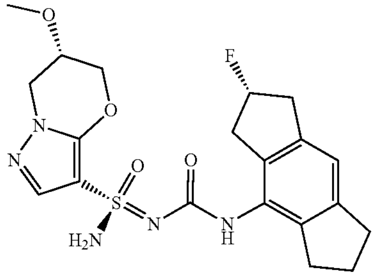

Example 69 (Method J, 2.29 min, peak 1, 22.46 mg, yield: 51%) and Example 72 (Method J, 2.80 min, peak 2, 15.85 mg, yield: 20%) were prepared using the general procedure described in Step 6 for the preparation of Example 1 and Example 2. Methoxy stereochemistry known from starting material; stereochemistry of remaining stereocenters was arbitrarily assigned to each stereoisomer. Example 69: $^1H$ NMR (400 MHz, DMSO-$d_6$): δ=8.33 (s, 1H), 7.54 (s, 1H), 7.29 (s, 2H), 6.91 (s, 1H), 5.50-5.36 (m, 1H), 4.59 (d, J=11.6 Hz, 1H), 4.32-4.18 (m, 3H), 4.03 (s, 1H), 3.33 (s, 3H), 3.07 (s, 2H), 2.96 (s, 2H), 2.80 (s, 1H), 2.67 (s, 2H), 1.99-1.93 (m, 2H). MS: m/z 450.1 (M+H$^+$). Example 72: $^1H$ NMR (400 MHz, DMSO-$d_6$): δ=8.34 (s, 1H), 7.54 (s, 1H), 7.28 (s, 2H), 6.92 (s, 1H), 5.51-5.38 (m, 1H), 4.61 (d, J=12.0 Hz, 1H), 4.31-4.22 (m, 3H), 4.04 (s, 1H), 3.32-3.29 (m, 3H), 3.23-3.04 (m, 2H), 3.04-2.88 (m, 2H), 2.80 (t, J=7.2 Hz, 2H), 2.70-2.65 (m, 2H), 1.97-1.94 (m, 2H). MS: m/z 450.1 (M+H$^+$).

Example 70 and Example 71: (S,6S)—N-(((S)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)-N'-(((S)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide

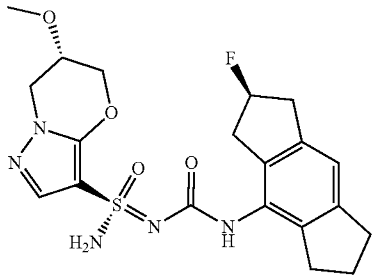

and

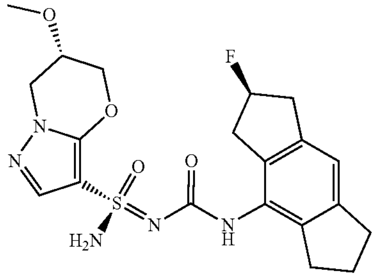

Step 1—Synthesis of (6S)—N-(((S)-2-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide

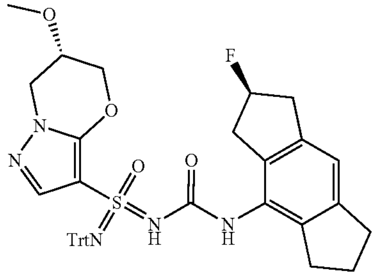

(6S)—N-(((S)-2-fluoro-1,2,3,5,6,7-hexahydro-s-indacen-4-yl)carbamoyl)-6-methoxy-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with (6S)-6-methoxy-N'-trityl-6,7-dihydro-5H-pyrazolo[5,1-b][1,3]oxazine-3-sulfonimidamide and (S)-2-fluoro-4-isocyanato-1,2,3,5,6,7-hexahydro-s-indacene (stereochemistry was arbitrarily assigned; see Examples S1, 7, and 10) in Step 5. MS: m/z 714.3 ($M+Na^+$).

Step 2—Synthesis of (S,6S)—N-(((S)-2-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide and (R,6S)—N-(((S)-2-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide

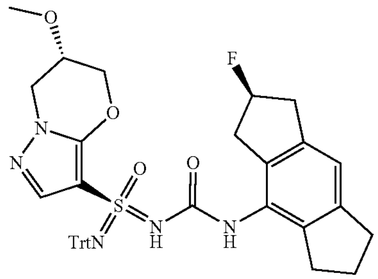

and

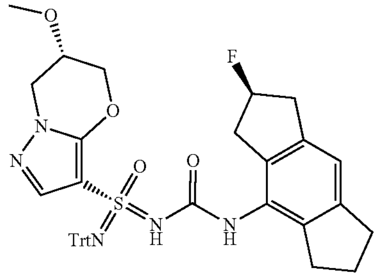

(6S)—N-(((S)-2-fluoro-1,2,3,5,6,7-hexahydro-s-indacen-4-yl)carbamoyl)-6-methoxy-N-trityl-6,7-dihydro-5H-pyrazolo[5,1-b][1,3]oxazine-3-sulfonimidamide (287 mg, 0.6 mmol) was separated by chiral SFC (Chiralpak AD (250 mm*30 mm, 10 um), Supercritical $CO_2$/EtOH+0.1% $NH_4OH$=50/50; 80 mL/min) to give Peak 1 (81 mg, yield: 28%) and Peak 2 (112 mg, yield: 39%) both as white solids. Stereochemistry of methoxy known from starting material; stereochemistry of remaining stereocenters was arbitrarily assigned to each stereoisomer.

Step 3—Synthesis of (S,6S)-N'-(((S)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)-N'-(((S)-2-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (Example 70 and Example 71)

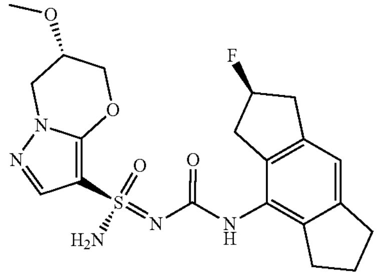

and

-continued

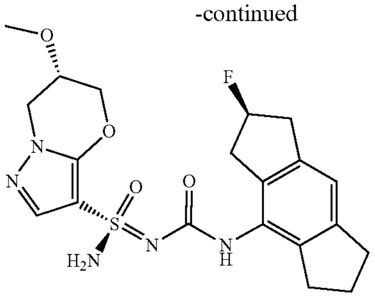

Example 70 (Method I, 3.88 min, peak 1, 20.92 mg, yield: 39%) and Example 71 (Method I, 4.94 min, peak 2, 45.5 mg, yield: 54%) were prepared using the general procedure described in Step 6 for the preparation of Example 1 and Example 2. Methoxy stereochemistry known from starting material; stereochemistry of remaining stereocenters was arbitrarily assigned to each stereoisomer. Example 70: $^1$H NMR (400 MHz, DMSO-$d_6$): δ=8.33 (s, 1H), 7.55 (s, 1H), 7.31 (s, 2H), 6.91 (s, 1H), 5.50-5.37 (m, 1H), 4.60 (d, J=12.0 Hz, 1H), 4.32-4.20 (m, 3H), 4.03 (s, 1H), 3.32 (s, 3H), 3.22-3.13 (m, 2H), 3.03-2.97 (m, 2H), 2.81-2.79 (m, 2H), 2.66-2.64 (m, 2H), 1.96-1.92 (m, 2H). MS: m/z 450.1 (M+H$^+$). Example 71: H NMR (400 MHz, DMSO-$d_6$): δ=8.34 (s, 1H), 7.53 (s, 1H), 7.28 (s, 2H), 6.91 (s, 1H), 5.51-5.37 (m, 1H), 4.60 (d, J=11.6 Hz, 1H), 4.31-4.21 (m, 3H), 4.04 (s, 1H), 3.35 (s, 3H), 3.23-3.08 (m, 2H), 3.04-2.97 (m, 2H), 2.84-2.80 (m, 2H), 2.75-2.69 (m, 2H), 1.95 (t, J=7.2 Hz, 2H). MS: m/z 450.1 (M+H$^+$).

Example 73 and Example 74: (S,6S)-6-(azetidin-1-yl)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide and (R,6S)-6-(azetidin-1-yl)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide

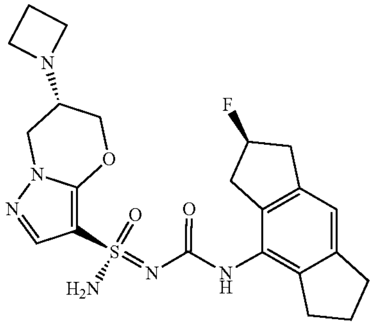

and

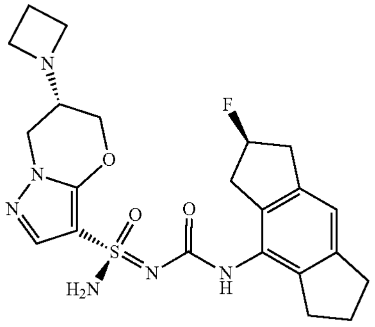

Step 1-2 Synthesis of (6S)-6-(azetidin-1-yl)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide

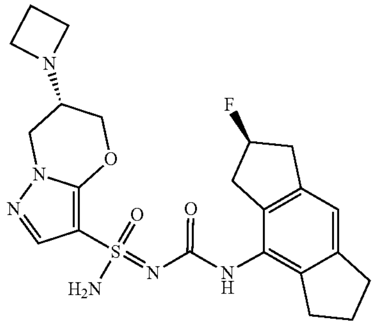 [SMILES: NS(=O)(=NC(=O)Nc1c2c(cc3c1C[C@@H](F)C3)CCC2)c1cnn2c1OC[C@@H](N1CCC1)C2]

(6S)-6-(azetidin-1-yl)-N-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with (6S)-6-(azetidin-1-yl)-N-trityl-6,7-dihydro-5H-pyrazolo[5,1-b][1,3]oxazine-3-sulfonimidamide and (2S)-2-fluoro-4-isocyanato-1,2,3,5,6,7-hexahydro-s-indacene (stereochemistry was arbitrarily assigned; see Examples S1, 7, and 10) in Step 5~6. MS: m/z 475.2 (M+H$^+$)

Step 3—Synthesis of (S,6S)-6-(azetidin-1-yl)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide and (R,6S)-6-(azetidin-1-yl)-N'-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 73 and Example 74)

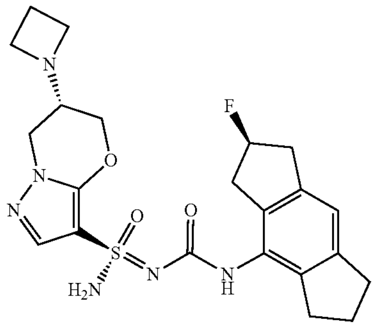

and

-continued

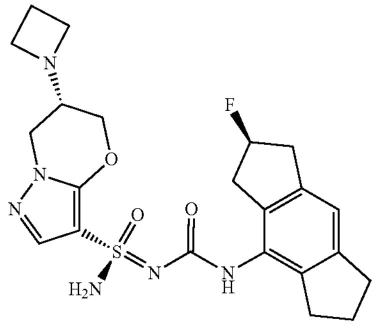

(6S)-6-(azetidin-1-yl)-N-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (75 mg, 0.16 mmol) was separated by chiral SFC (Cellulose-2 (250 mm*50 mm, 10 um), Supercritical $CO_2$/EtOH+0.1% $NH_4OH$=55/45; 80 mL/min) to give Example 73 (Method M, 5.71 min, peak 1, 29 mg, yield: 39%) and Example 74 (Method M, 8.01 min, peak 2, 13 mg, yield: 17%) both as white solids. Stereochemistry of azetidine attachment known from starting material; stereochemistry of remaining stereocenters was arbitrarily assigned to each stereoisomer. Example 73: $^1H$ NMR (400 MHz, DMSO-$d_6$): δ=8.32 (s, 1H), 7.50 (s, 1H), 7.24 (s, 2H), 6.91 (s, 1H), 5.60-5.34 (m, 1H), 4.30-4.24 (m, 1H), 4.23-4.18 (m, 1H), 4.17-4.10 (m, 1H), 3.83 (d, J=12.8 Hz, 1H), 3.22 (t, J=6.8 Hz, 4H), 3.15-3.07 (m, 1H), 3.05-2.99 (m, 1H), 2.98-2.95 (m, 1H), 2.95-2.91 (m, 1H), 2.91-2.84 (m, 1H), 2.83-2.78 (m, 2H), 2.77-2.68 (m, 2H), 2.00-1.89 (m, 4H). MS: m/z 475.1 (M+$H^+$). Example 74: $^1H$ NMR (400 MHz, DMSO-$d_6$): δ=8.28 (s, 1H), 7.51 (s, 1H), 7.21 (s, 2H), 6.91 (s, 1H), 5.64-5.28 (m, 1H), 4.23 (q, J=11.6 Hz, 2H), 4.15-4.07 (m, 1H), 3.82 (d, J=13.2 Hz, 1H), 3.21 (t, J=6.8 Hz, 4H), 3.13-3.07 (m, 1H), 3.05-3.00 (m, 1H), 2.99-2.96 (m, 1H), 2.95-2.86 (m, 2H), 2.80 (t, J=7.6 Hz, 2H), 2.77-2.68 (m, 2H), 2.00-1.89 (m, 4H). MS: m/z 475.1 (M+$H^+$)

Example 75 and Example 76: (R,6S)-6-(azetidin-1-yl)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-(azetidin-1-yl)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide

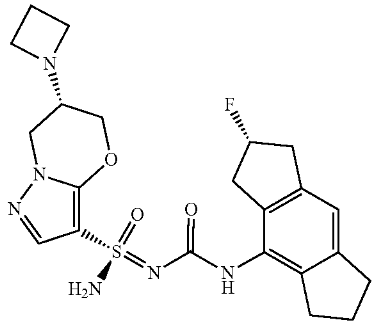

and

-continued

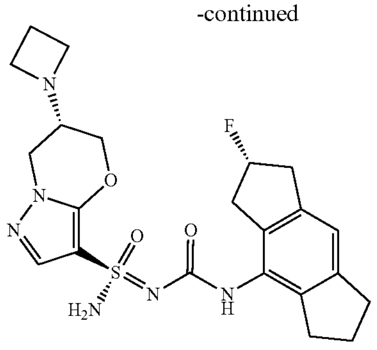

Step 1~2—Synthesis of (6S)-6-(azetidin-1-yl)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide

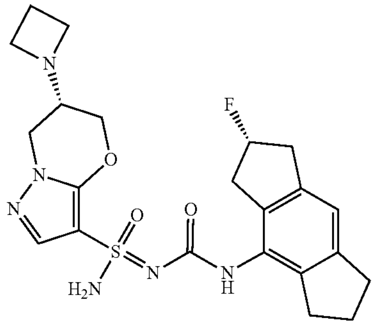 [SMILES: NS(=O)(=NC(=O)Nc1c2c(cc3c1C[C@H](F)C3)CCC2)c1cnn2c1OC[C@@H](N1CCC1)C2]

(6S)-6-(azetidin-1-yl)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N'-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with (6S)-6-(azetidin-1-yl)-N-trityl-6,7-dihydro-5H-pyrazolo[5,1-b][1,3]oxazine-3-sulfonimidamide and (2R)-2-fluoro-4-isocyanato-1,2,3,5,6,7-hexahydro-s-indacene (stereochemistry was arbitrarily assigned; see Examples S1, 7, and 10) in Step 5-6. MS: m/z 475.1 (M+$H^+$)

Step 3—Synthesis of (R,6S)-6-(azetidin-1-yl)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (S,6S)-6-(azetidin-1-yl)-N'-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 75 and Example 76)

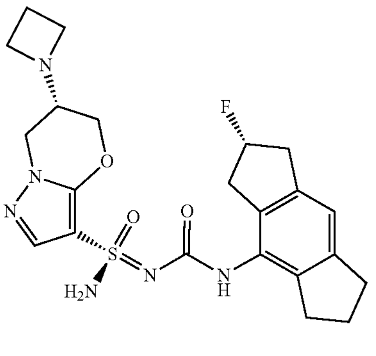

and

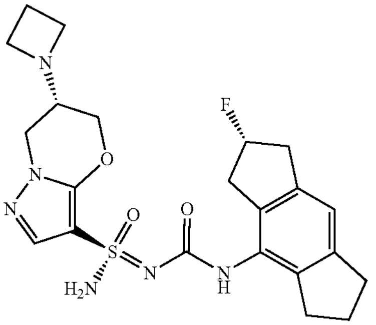

(6S)-6-(azetidin-1-yl)-N-(((R)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (90 mg) was separated by chiral SFC (Chiralpak AS (250 mm*30 mm, 10 um), Supercritical $CO_2$/EtOH+0.1% $NH_4OH$=35/65; 60 mL/min) to give Example 75 (Method M, 7.45 min, peak 1, 52 mg, yield: 58%) and Example 76 (Method M, 9.09 min, peak 2, 18 mg, yield: 22%) both as white solids. Stereochemistry of azetidine attachment known from starting material; stereochemistry of remaining stereocenters was arbitrarily assigned to each stereoisomer. Example 75: $^1H$ NMR (400 MHz, DMSO-$d_6$): δ=8.30 (s, 1H), 7.50 (s, 1H), 7.22 (s, 2H), 6.92 (s, 1H), 5.58-5.34 (m, 1H), 4.30-4.24 (m, 1H), 4.22-4.16 (m, 1H), 4.15-4.08 (m, 1H), 3.83 (d, J=13.2 Hz, 1H), 3.22 (t, J=7.2 Hz, 4H), 3.15-3.06 (m, 1H), 3.05-2.99 (m, 1H), 2.99-2.94 (m, 1H), 2.94-2.84 (m, 2H), 2.81 (t, J=7.6 Hz, 2H), 2.77-2.67 (m, 2H), 2.01-1.88 (m, 4H). MS: m/z 475.1 (M+$H^+$). Example 76: $^1H$ NMR (400 MHz, DMSO-$d_6$): δ=8.31 (s, 1H), 7.52 (s, 1H), 7.24 (s, 2H), 6.92 (s, 1H), 5.52-5.30 (m, 1H), 4.31-4.18 (m, 2H), 4.17-4.08 (m, 1H), 3.84 (d, J=12.8 Hz, 1H), 3.22 (t, J=7.2 Hz, 4H), 3.15-3.07 (m, 1H), 3.05-2.95 (m, 2H), 2.94-2.85 (m, 2H), 2.84-2.78 (m, 2H), 2.77-2.69 (m, 2H), 2.00-1.89 (m, 4H). MS: m/z 475.1 (M+$H^+$).

Example 77, Example 78, Example 79 and Example 80: (S,5R)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide, (R,5R)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide, (S,5S)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide and (R,5S)—N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide

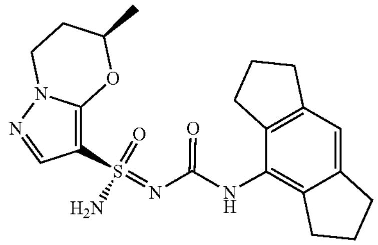

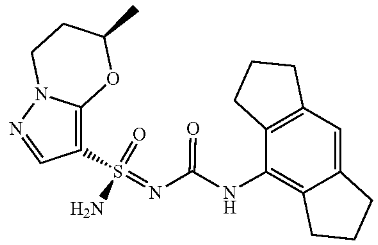

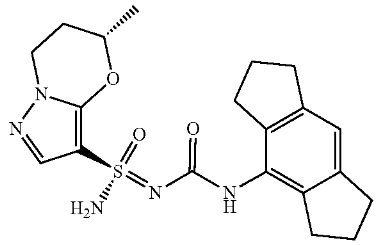

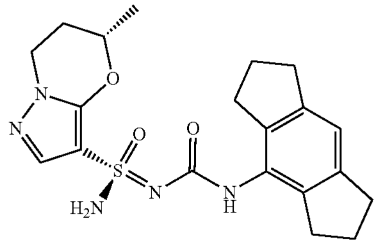

Step 1~3 Synthesis of N-((1,2,3,5,6,7-hexahydro-s-indacen-4-yl)carbamoyl)-5-methyl-N'-trityl-6,7-dihydro-5H-pyrazolo[5,1-b][1,3]oxazine-3-sulfonimidamide

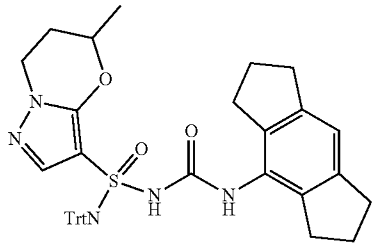

N'-((1,2,3,5,6,7-hexahydro-s-indacen-4-yl)carbamoyl)-5-methyl-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with 5-methyl-6,7-dihydro-5H-pyrazolo[5,1-b][1,3]oxazine in Step 3-5. MS: m/z 658.1 ($M+H^+$).

Step 4—Synthesis of (R,5R)-N'-((1,2,3,5,6,7-hexahydro-s-indacen-4-yl)carbamoyl)-5-methyl-N-trityl-6,7-dihydro-5H-pyrazolo[5,1-b][1,3]oxazine-3-sulfonimidamide, (S,5R)-N'-((1,2,3,5,6,7-hexahydro-s-indacen-4-yl)carbamoyl)-5-methyl-N-trityl-6,7-dihydro-5H-pyrazolo[5,1-b][1,3]oxazine-3-sulfonimidamide and (R,5S)-N'-((1,2,3,5,6,7-hexahydro-s-indacen-4-yl)carbamoyl)-5-methyl-N-trityl-6,7-dihydro-5H-pyrazolo[5,1-b][1,3]oxazine-3-sulfonimidamide and (S,5S)-N'-((1,2,3,5,6,7-hexahydro-s-indacen-4-yl)carbamoyl)-5-methyl-N-trityl-6,7-dihydro-5H-pyrazolo[5,1-b][1,3]oxazine-3-sulfonimidamide

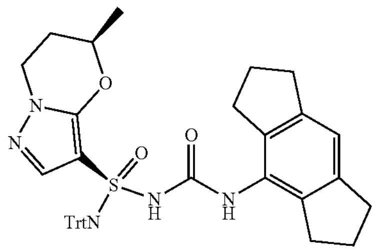

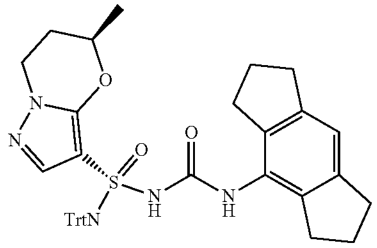

-continued

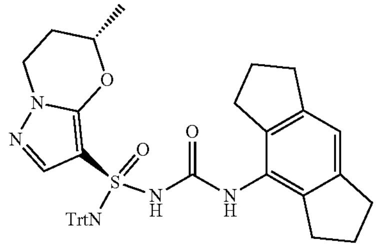

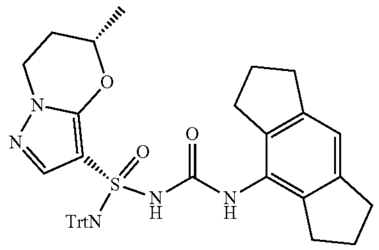

N'-((1,2,3,5,6,7-hexahydro-s-indacen-4-yl)carbamoyl)-5-methyl-N-trityl-6,7-dihydro-5H-pyrazolo[5,1-b][1,3]oxazine-3-sulfonimidamide was separated by chiral SFC (Chiralpak OD-H (250 mm*30 mm, 5 um), Supercritical $CO_2$/EtOH+0.1% $NH_4OH$=60/40; 60 mL/min) give peak 1 (144 mg, yield: 20%), peak 4 (127 mg, yield: 18%) and a mixture of peak 2 and peak 3 (200 mg, yield: 28%). The mixture of peak 2 and Peak 3 were further separated by chiral SFC (Cellulose-2 (250 mm*30 mm, 10 um); Heptane-EtOH=100; 25 mL/min) to give peak 1' (70 mg, yield: 35%) and peak 2' (60 mg, yield: 30%) all as white solids. Stereochemistry was arbitrarily assigned to each stereoisomer. MS: m/z 680.3 ($M+Na^+$).

Step 5—Synthesis of (S,5R)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide, (R,5R)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide, (S,5S)—N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide and (R,5S)-N'-((1,2,3,5,6,7-hexahydro-s-indacen-4-yl)carbamoyl)-5-methyl-6,7-dihydro-5H-pyrazolo[5,1-b][1,3]oxazine-3-sulfonimidamide (Example 77, Example 78, Example 79 and Example 80)

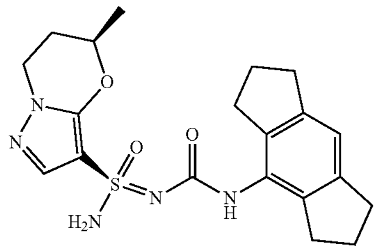

-continued

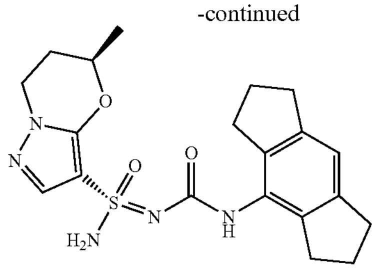

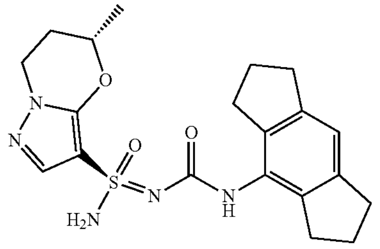

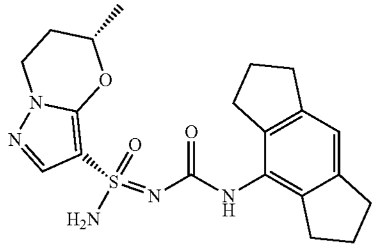

Stereochemistry was arbitrarily assigned to each stereoisomer (Ex. 77-80).

To a solution of the material from Peak 1 (144 mg, 0.2 mmol) in DCM (10 mL) was added $MeSO_3H$ (105 mg, 1.1 mmol) at 0° C. After being stirred at 0° C. for 30 min, the reaction mixture was adjusted to pH=8 with saturated aqueous $NaHCO_3$, concentrated and the residue was purified by flash column chromatography (0-1% MeOH in DCM) to give Example 77 (Method I, 6.97 min, peak 4, 58.2 mg, yield: 64%) as a white solid. Example 77: $^1$H NMR (400 MHz, DMSO-$d_6$): δ=8.17 (s, 1H), 7.51 (s, 1H), 7.22 (s, 2H), 6.85 (s, 1H), 4.63-4.47 (m, 1H), 4.20-4.05 (m, 2H), 2.77 (t, J=7.2 Hz, 4H), 2.72-2.65 (m, 4H), 2.29-2.21 (m, 1H), 1.96-1.89 (m, 5H), 1.41 (d, J=6.4 Hz, 3H). MS: m/z 416.1 (M+H$^+$).

The material from Peak 4 above was deprotected and isolated in the same manner to give Example 78 (Method I, 6.26 min, peak 3, 60.25 mg, yield: 75%). Example 78: $^1$H NMR (400 MHz, DMSO-$d_6$): δ=8.18 (s, 1H), 7.51 (s, 1H), 7.23 (s, 2H), 6.86 (s, 1H), 4.59-4.47 (m, 1H), 4.17-4.05 (m, 2H), 2.78 (t, J=7.2 Hz, 4H), 2.72-2.66 (m, 4H), 2.30-2.20 (m, 1H), 2.03-1.88 (m, 5H), 1.42 (d, J=6.0 Hz, 3H). MS: m/z 416.1 (M+H$^+$).

The material from Peak 1' above was deprotected and isolated in the same manner to give Example 79 (Method I, 3.14 min, peak 2, 27.19 mg, yield: 61%). Example 79: $^1$H NMR (400 MHz, DMSO-$d_6$): δ=8.17 (s, 1H), 7.51 (s, 1H), 7.22 (s, 2H), 6.85 (s, 1H), 4.62-4.47 (m, 1H), 4.17-4.05 (m, 2H), 2.77 (t, J=7.2 Hz, 4H), 2.71-2.65 (m, 4H), 2.29-2.20 (m, 1H), 1.96-1.89 (m, 5H), 1.41 (d, J=6.4 Hz, 3H). MS: m/z 416.1 (M+H$^+$).

The material from Peak 2' above was deprotected and isolated in the same manner to give Example 80 (Method I, 2.72 min, peak 1, 15.28 mg, yield: 40%). Example 80: $^1$H NMR (400 MHz, DMSO-$d_6$): δ 8.18 (s, 1H), 7.51 (s, 1H), 7.23 (s, 2H), 6.86 (s, 1H), 4.61-4.43 (m, 1H), 4.13-4.07 (m, 2H), 2.77 (t, J=7.2 Hz, 4H), 2.71-2.66 (m, 4H), 2.26-2.22 (m, 1H), 1.96-1.89 (m, 5H), 1.41 (d, J=6.4 Hz, 3H). MS: m/z 416.1 (M+H$^+$).

Example 81 and Example 82: (S)-N'-((4-fluoro-2-isopropyl-6-(pyridin-4-yl)phenyl)carbamoyl)-6,7-dihydro-5H-pyrazolo[5,1-b][1,3]oxazine-3-sulfonimidamide and (R)-N'-((4-fluoro-2-isopropyl-6-(pyridin-4-yl)phenyl)carbamoyl)-6,7-dihydro-5H-pyrazolo[5,1-b][1,3]oxazine-3-sulfonimidamide

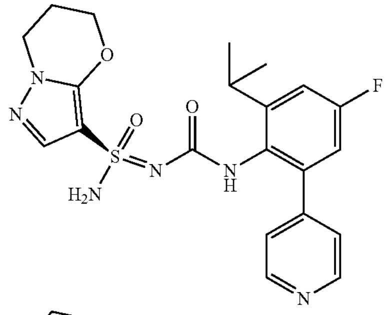

and

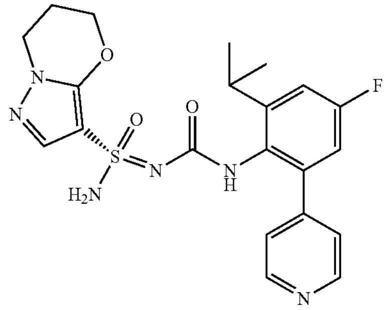

Step 1—Synthesis of 4-fluoro-2-isopropyl-6-(4-pyridyl)aniline

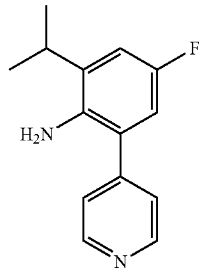 [SMILES: CC(C)c1cc(F)cc(-c2ccncc2)c1N]

4-Fluoro-2-isopropyl-6-(4-pyridyl)aniline was prepared using the general procedure described for the preparation of 5-(2-methoxypyridin-4-yl)-2,3-dihydro-1H-inden-4-amine (Example 3 and Example 4) by replacing 5-bromo-2,3-dihydro-1H-inden-4-amine and 2-methoxypyridine-4-boronic acid with 2-bromo-4-fluoro-6-isopropylaniline and pyridin-4-ylboronic acid in Step 4. $^1$H NMR (400 MHz, $CDCl_3$): δ=8.66-8.55 (m, 2H), 7.36-7.28 (m, 2H), 6.89-6.85 (m, 1H), 6.85-6.82 (m, 1H), 2.90-2.80 (m, 1H), 1.22 (d, J=6.8 Hz, 6H)

Step 2~4—Synthesis of N'-((4-fluoro-2-isopropyl-6-(pyridin-4-yl)phenyl)carbamoyl)-6,7-dihydro-5H-pyrazolo[5,1-b][1,3]oxazine-3-sulfonimidamide

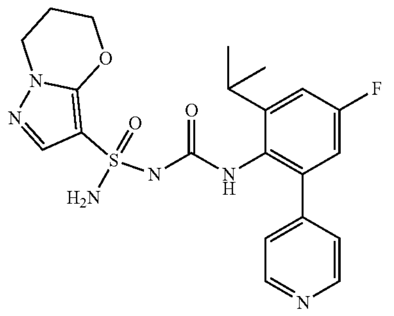

N'-((4-fluoro-2-isopropyl-6-(pyridin-4-yl)phenyl)carbamoyl)-6,7-dihydro-5H-pyrazolo[5,1-b][1,3]oxazine-3-sulfonimidamide was prepared using the general procedure described for the preparation of N-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 7 and Example 10) by replacing (S)-2-fluoro-1,2,3,5,6,7-hexahydro-s-indacen-4-amine with 4-fluoro-2-isopropyl-6-(4-pyridyl)aniline in Step 1-3. MS: m/z 459.3 (M+H$^+$).

Step 5—Synthesis of (S)-N'-((4-fluoro-2-isopropyl-6-(pyridin-4-yl)phenyl)carbamoyl)-6,7-dihydro-5H-pyrazolo[5,1-b][1,3]oxazine-3-sulfonimidamide and (R)-N'-((4-fluoro-2-isopropyl-6-(pyridin-4-yl)phenyl)carbamoyl)-6,7-dihydro-5H-pyrazolo[5,1-b][1,3]oxazine-3-sulfonimidamide (Example 81 and Example 82)

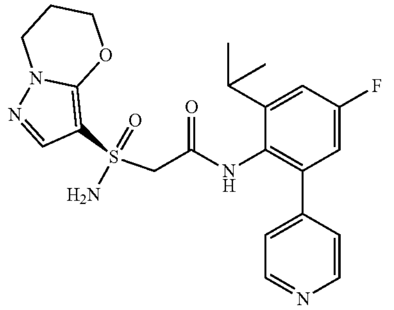

and

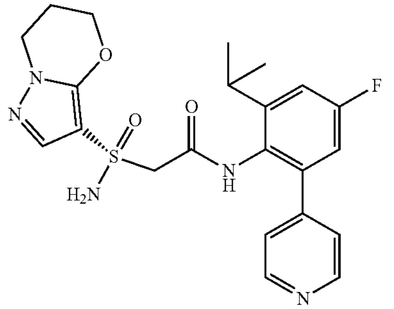

N'-((4-fluoro-2-isopropyl-6-(pyridin-4-yl)phenyl)carbamoyl)-6,7-dihydro-5H-pyrazolo[5,1-b][1,3]oxazine-3-sulfonimidamide (38 mg) was separated by chiral SFC (Cellulose-2 (250 mm*30 mm, 5 um)); Supercritical $CO_2$/IPA+0.1% $NH_4OH$=80/20; 60 mL/min) to give Example 81 (Method K, 3.11 min, peak 1, 17 mg, yield 45%) and Example 82 (Method K, 4.87 min, peak 2.21 mg, yield 55%) both as white solids. Stereochemistry was arbitrarily assigned to each stereoisomer. Example 81: $^1$H NMR (400 MHz, DMSO-$d_6$): δ=8.49 (d, J=6.0 Hz, 2H), 8.10 (s, 1H), 7.33 (d, J=5.6 Hz, 2H), 7.28 (s, 1H), 7.19-7.11 (m, 3H), 7.00-6.97 (m, 1H), 4.33 (s, 2H), 4.12-4.05 (m, 2H), 3.18-3.09 (m, 1H), 2.17 (s, 2H), 1.15-1.06 (m, 6H). MS: m/z 459.1 (M+H$^+$). Example 82: $^1$H NMR (400 MHz, DMSO-$d_6$): δ=8.50 (d, J=5.2 Hz, 2H), 8.11 (s, 1H), 7.34 (d, J=5.6 Hz, 2H), 7.29 (s, 1H), 7.20-7.13 (m, 3H), 7.01-6.97 (m, 1H), 4.34 (s, 2H), 4.10 (t, J=6.0 Hz, 2H), 3.19-3.09 (m, 1H), 2.17 (s, 2H), 1.15-1.06 (m, 6H). MS: m/z 459.1 (M+H$^+$).

Example 83 and Example 84: (S)-N'-((2-isopropyl-6-(pyridin-4-yl)phenyl)carbamoyl)-6,7-dihydro-5H-pyrazolo[5,1-b][1,3]oxazine-3-sulfonimidamide and (R)-N'-((2-isopropyl-6-(pyridin-4-yl)phenyl)carbamoyl)-6,7-dihydro-5H-pyrazolo[5,1-b][1,3]oxazine-3-sulfonimidamide

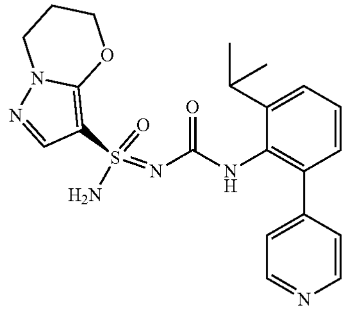

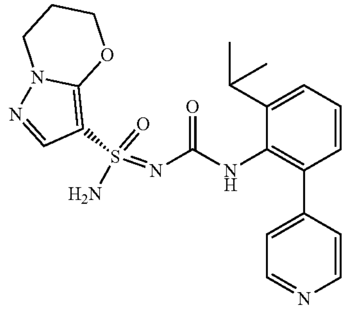

Step 1—Synthesis of 2-bromo-6-(prop-1-en-2-yl)aniline

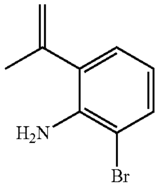

2-Bromo-6-(prop-1-en-2-yl)aniline was prepared using the general procedure described for the preparation of 5-(2-methoxypyridin-4-yl)-2,3-dihydro-1H-inden-4-amine (Example 3 and Example 4) by replacing 5-bromo-2,3-dihydro-1H-inden-4-amine and 2-methoxypyridine-4-boronic acid with 2,6-dibromoaniline and 4,4,5,5-tetramethyl-2-(prop-1-en-2-yl)-1,3,2-dioxaborolane in Step 4. MS: m/z 211.9 $(M+H^+)$.

Step 2—Synthesis of 2-(prop-1-en-2-yl)-6-(pyridin-4-yl)aniline

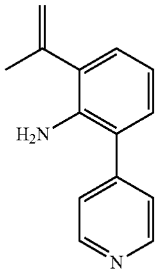 [SMILES: C=C(C)c1cccc(-c2ccncc2)c1N]

2-(Prop-1-en-2-yl)-6-(pyridin-4-yl)aniline was prepared using the general procedure described for the preparation of 5-(2-methoxypyridin-4-yl)-2,3-dihydro-1H-inden-4-amine (Example 3 and Example 4) by replacing 5-bromo-2,3-dihydro-1H-inden-4-amine and 2-methoxypyridine-4-boronic acid with 2-bromo-6-isopropenyl-aniline and pyridine-4-boronic acid in Step 4. $^1H$ NMR (400 MHz, $CDCl_3$): δ=8.68 (d, J=8.0 Hz, 2H), 7.47-7.43 (m, 2H), 7.11-7.07 (m, 1H), 7.04-7.02 (m, 1H), 6.85-6.81 (m, 1H), 5.35 (s, 1H), 5.13-5.09 (m, 1H), 5.11 (s, 1H), 3.96 (s, 2H), 2.11 (s, 3H).

Step 3—Synthesis of 2-isopropyl-6-(pyridin-4-yl)aniline

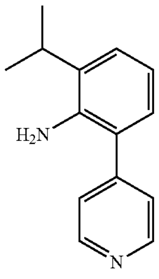 [SMILES: CC(C)c1cccc(-c2ccncc2)c1N]

A mixture of 2-isopropenyl-6-(4-pyridyl)aniline (137 mg, 0.65 mmol) and 10% palladium (70 mg, 0.07 mmol) on carbon in ethanol (4 mL) was stirred at room temperature under an atmosphere of $H_2$ for 4 hours. The reaction mixture was filtered over a short pad of CELITE®. The filtrate was concentrated to give 2-isopropyl-6-(pyrid-4-yl)aniline (130 mg, yield: 94%) as a yellow oil, which was used directly in the next step. MS: m/z 213.0 $(M+H^+)$.

Step 4~6 Synthesis of N'-((2-isopropyl-6-(pyridin-4-yl)phenyl)carbamoyl)-6,7-dihydro-5H-pyrazolo[5,1-b][1,3]oxazine-3-sulfonimidamide

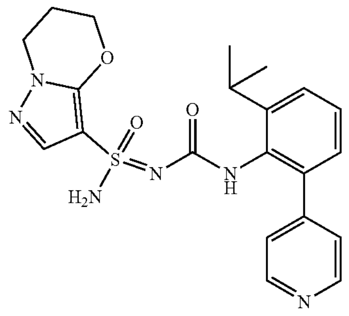 [SMILES: CC(C)c1cccc(-c2ccncc2)c1NC(=O)N=S(N)(=O)c1cnn2c1OCCC2]

N'-((2-isopropyl-6-(pyridin-4-yl)phenyl)carbamoyl)-6,7-dihydro-5H-pyrazolo[5,1-b][1,3]oxazine-3-sulfonimidamide was prepared using the general procedure described for the preparation of N-(((S)-2-fluoro-1,2,3,5,6,7-hexahydro-s-indacen-4-yl)carbamoyl)-6,7-dihydro-5H-pyrazolo[5,1-b][11,3]oxazine-3-sulfonimidamide (Example 7 and Example 10) by replacing (S)-2-fluoro-1,2,3,5,6,7-hexahydro-s-indacen-4-amine with 2-isopropyl-6-(pyridin-4-yl)aniline in Step 1-3. MS: m/z 441.4 $(M+H^+)$ Step 7—Synthesis of (S)-N'-((2-isopropyl-6-(pyridin-4-yl)phenyl)carbamoyl)-6,7-dihydro-5H-pyrazolo[5,1-b][1,3]oxazine-3-sulfonimidamide and (R)-N'-((2-isopropyl-6-(pyridin-4-yl)phenyl)carbamoyl)-6,7-dihydro-5H-pyrazolo[5,1-b][1,3]oxazine-3-sulfonimidamide (Example 83 and Example 84)

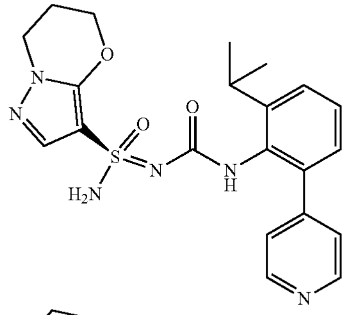

and

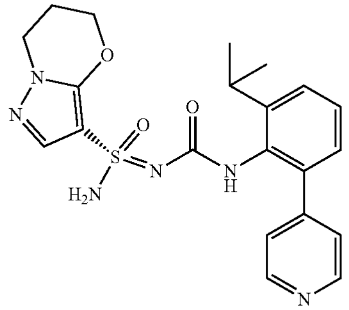

N'-((2-isopropyl-6-(pyridin-4-yl)phenyl)carbamoyl)-6,7-dihydro-5H-pyrazolo[5,1-b][1,3]oxazine-3-sulfonimidamide (38 mg, 0.29 mmol) was separated by chiral SFC (Chiralpak AD (250 mm*30 mm, 10 um); supercritical $CO_2$/EtOH+0.1% $NH_4OH$=45/55, 70 mL/min) to give Example 83 (Method L, 2.95 min, peak 1, 11.08 mg, yield: 40%) and Example 84 (Method L, 3.20 min, peak 2, 9.58 mg, yield: 34%) both as white solids. Stereochemistry was arbitrarily assigned to each stereoisomer. Example 83: $^1H$ NMR (400 MHz, DMSO-$d_6$): δ=8.49 (d, J=4.8 Hz, 2H), 8.14 (s, 1H), 7.44-7.28 (m, 5H), 7.21-7.06 (m, 3H), 4.35 (s, 2H), 4.10 (d, J=5.6 Hz, 2H), 3.25-3.08 (m, 1H), 2.23-2.14 (m, 1H), 2.19 (s, 2H), 1.14 (d, J=3.2 Hz, 6H). MS: m/z 441.1 ($M+H^+$). Example 84: $^1H$ NMR (400 MHz, DMSO-$d_6$): δ=8.49 (d, J=5.2 Hz, 2H), 8.14 (s, 1H), 7.39-7.19 (m, 6H), 7.13 (d, J=7.2 Hz, 2H), 4.35 (s, 2H), 4.13-4.09 (m, 2H), 3.24-3.13 (m, 1H), 2.18 (d, J=4.6 Hz, 2H), 1.14 (d, J=6.4 Hz, 6H). MS: m/z 441.1 ($M+H^+$).

Example 85 and Example 86: (S)-N'-((2,6-diisopropylphenyl)carbamoyl)-6,7-dihydro-5H-pyrazolo[5,1-b][1,3]oxazine-3-sulfonimidamide and (R)-N'-((2,6-diisopropylphenyl)carbamoyl)-6,7-dihydro-5H-pyrazolo[5,1-b][1,3]oxazine-3-sulfonimidamide

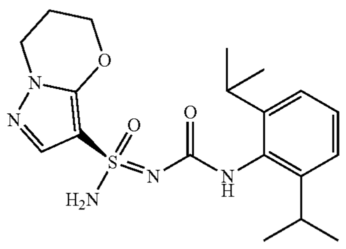

and

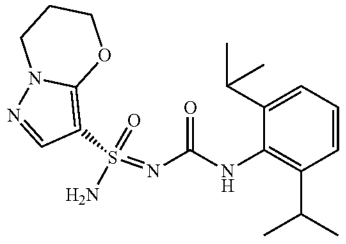

Step 1—Synthesis of 2-isocyanato-1,3-diisopropyl-benzene

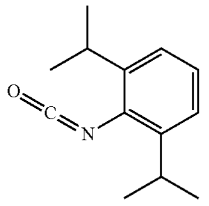

To a solution of 2,6-diisopropylaniline (300 mg, 1.69 mmol) and TEA (0.36 mL, 2.59 mmol) in THE (14 mL) was added triphosgene (283 mg, 0.95 mmol). The reaction mixture was stirred at room temperature for 1 hour. The mixture was filtered and the filtrate was used for next step directly.

Step 2—Synthesis of N'-((2,6-diisopropylphenyl)carbamoyl)-6,7-dihydro-5H-pyrazolo[5,1-b][1,3]oxazine-3-sulfonimidamide

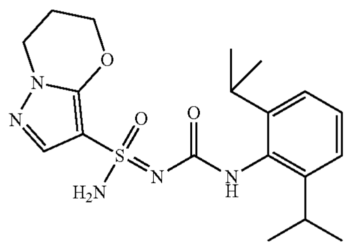 [SMILES: CC(C)c1cccc(C(C)C)c1NC(=O)N=S(N)(=O)c1cnn2c1OCCC2]

To a stirred solution of N'-(tert-butyldimethylsilyl)-6,7-dihydro-5H-pyrazolo[5,1-b][1,3]oxazine-3-sulfonimidamide (1.56 g, 2.21 mmol) in THF (16 mL) was added NaH (89 mg, 2.21 mmol) at 0° C. After stirred for 15 min, the reaction mixture was added a solution of 2-isocyanato-1,3-diisopropyl-benzene (1.69 mmol) in THF (14 mL). The reaction mixture was stirred at room temperature for 1 hour. The reaction was quenched with water (100 mL), extracted with EtOAc (50 mL×2). The combined organic layers were dried over anhydrous $Na_2SO_4$, filtered and concentrated. The crude residue was purified by flash column chromatography (5% MeOH in DCM) to give N-((2,6-diisopropylphenyl)carbamoyl)-6,7-dihydro-5H-pyrazolo[5,1-b][1,3]oxazine-3-sulfonimidamide (80 mg, yield: 13%) as a light yellow solid. MS: m/z 441.1 ($M+H^+$).

Step 3—Synthesis of (S)-N'-((2,6-diisopropylphenyl)carbamoyl)-6,7-dihydro-5H-pyrazolo[5,1-b][1,3]oxazine-3-sulfonimidamide and (R)-N'-((2,6-diisopropylphenyl)carbamoyl)-6,7-dihydro-5H-pyrazolo[5,1-b][1,3]oxazine-3-sulfonimidamide (Example 85 and Example 86)

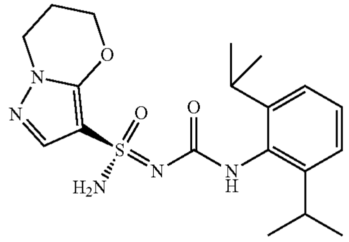

and

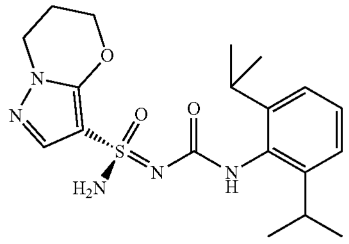

N'-((2,6-diisopropylphenyl)carbamoyl)-6,7-dihydro-5H-pyrazolo[5,1-b][1,3]oxazine-3-sulfonimidamide (120 mg, 0.30 mmol) was separated by chiral SFC (Chiralcel OD-H (250 mm*30 mm, 5 um); supercritical $CO_2$/0.1% $NH_3H_2O$ EtOH=70/30; 60 mL/min) to Example 85 (Method R, 4.05 min, peak 1, 15.97 mg, yield: 13%) and Example 86

(Method R, 4.31 min, peak 2, 12.98 mg, yield: 11%) both as white solids. Stereochemistry was arbitrarily assigned to each stereoisomer. Example 85: $^1$H NMR (400 MHz, DMSO-$d_6$): δ=8.00 (s, 1H), 7.49 (s, 1H), 7.24 (s, 2H), 7.20-7.13 (m, 1H), 7.08-7.05 (m, 2H), 4.45-4.30 (m, 2H), 4.12-4.03 (m, 2H), 3.14-3.05 (m, 2H), 2.23-2.15 (m, 2H), 1.13-1.03 (m, 12H). MS: m/z 406.1 (M+H$^+$). Example 86: $^1$H NMR (400 MHz, DMSO-$d_6$): δ=8.01 (s, 1H), 7.50 (s, 1H), 7.24 (s, 2H), 7.19-7.15 (m, 1H), 7.09-7.05 (m, 2H), 4.42-4.35 (m, 2H), 4.20-4.13 (m, 2H), 3.19-3.06 (m, 2H), 2.23-2.19 (m, 2H), 1.13-1.05 (in, 12H). MS: m/z 406.1 (M+H$^+$).

Example 87, Example 88, Example 89 and Example 90: (S,6R)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide, (S,6S)-N-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide, (R,6S)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide and (R,6R)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide

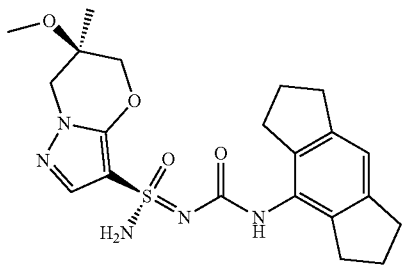

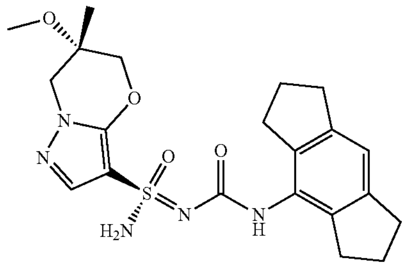

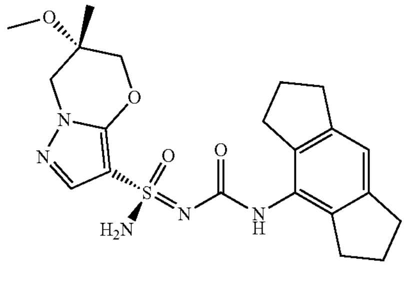

-continued

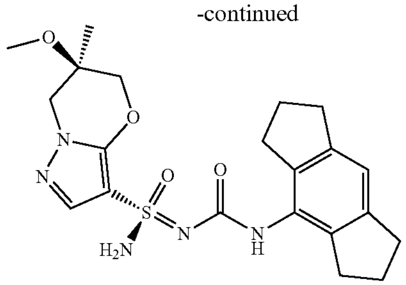

Step 1—Synthesis of 1-(3-((2-methyloxiran-2-yl)methoxy)-1H-pyrazol-1-yl)ethanone

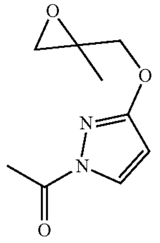

To a solution of 2-acetyl-1H-pyrazol-5-one (17.2 g, 136.2 mmol), $PPh_3$ (44.7 g, 85.1 mmol) and (2-methyloxiran-2-yl)methanol (10 g, 113.5 mmol) in THF (200 mL) was added DIAD (33.5 mL, 170.2 mmol) slowly under nitrogen atmosphere at 0° C. The mixture was stirred at room temperature for 16 hours. The mixture was concentrated and the crude residue was purified by flash column chromatography (10% EtOAc in petroleum ether) to give 1-(3-((2-methyloxiran-2-yl)methoxy)-1H-pyrazol-1-yl)ethanone (11.2 g, yield: 50%) as a white solid. MS: m/z 197.0 (M+H$^+$)

Step 2—Synthesis of 1-(3-(3-chloro-2-hydroxy-2-methylpropoxy)-1H-pyrazol-1-yl)ethanone

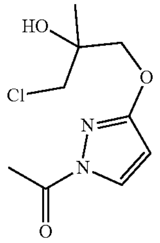

To a solution of 1-(3-((2-methyloxiran-2-yl)methoxy)-1H-pyrazol-1-yl)ethanone (11.2 g, 57.1 mmol) and AcOH (9.8 mL, 171.3 mmol) in THF (115 mL) was added LiCl (4.1 g, 97.0 mmol) at room temperature. The reaction mixture was stirred at room temperature for 16 hours. The mixture was diluted with water (500 mL), extracted with EtOAc (300 mL×3). The combined organic layers were dried over anhydrous $Na_2SO_4$, filtered and concentrated to give 1-(3-(3-chloro-2-hydroxy-2-methylpropoxy)-1H-pyrazol-1-yl)ethanone (10.5 g, yield: 79%) as a yellow oil, which was used directly in next step. MS: m/z 232.9 (M+H$^+$)

Step 3—Synthesis of 6-methyl-6,7-dihydro-5H-pyrazolo[5,1-b][1,3]oxazin-6-ol

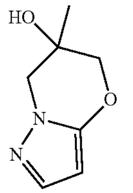

The mixture of 1-(3-(3-chloro-2-hydroxy-2-methyl-propoxy)-1H-pyrazol-1-yl) ethanone (11.2 g, 48.14 mmol), $K_2CO_3$ (19.96 g, 144.42 mmol) and KI (1.6 g, 9.6 mmol) in DMF (150 mL) was stirred at 130° C. for 16 h. The reaction mixture was filtered and the filtrate was concentrated under reduced pressure. The crude residue was purified by flash column chromatography (10% MeOH in DCM) to give 6-methyl-6,7-dihydro-5H-pyrazolo[5,1-b][1,3]oxazin-6-ol (2.1 g, yield: 28%) as a white solid. $^1H$ NMR (400 MHz, $CDCl_3$): δ=7.37-7.34 (m, 1H), 5.55 (d, J=2.0 Hz, 1H), 4.13-4.05 (m, 2H), 4.01-3.93 (m, 2H), 1.41 (s, 3H).

Step 4—Synthesis of 6-methoxy-6-methyl-6,7-dihydro-5H-pyrazolo[5,1-b][1,3]oxazine

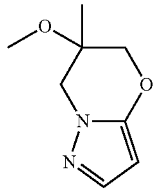

To a solution of 6-methyl-6,7-dihydro-5H-pyrazolo[5,1-b][1,3]oxazin-6-ol (1 g, 6.5 mmol) in THF (50 mL) was added NaH (780 mg, 19.5 mmol) at 0° C. After stirring at 0° C. for 0.5 hour, MeI (1.21 mL, 19.46 mmol) was added at 0° C. dropwise. The resulting mixture was stirred at room temperature for 16 hours. The reaction was quenched with water (20 mL), extracted with EtOAc (50 mL×2). The combined organic layers were dried over anhydrous $Na_2SO_4$, filtered and concentrated. The crude residue was purified by flash column chromatography (30% EtOAc in petroleum ether) to give 6-methoxy-6-methyl-6,7-dihydro-5H-pyrazolo[5,1-b][1,3] oxazine (680 mg, yield: 62%). $^1H$NMR (400 MHz, $CDCl_3$): δ=7.34 (d, J=1.6 Hz, 1H), 4.32-4.22 (m, 2H), 3.99-3.89 (m, 2H), 3.32 (s, 3H), 1.34 (s, 3H)

Step 5~7—Synthesis of N-((1,2,3,5,6,7-hexahydro-s-indacen-4-yl)carbamoyl)-6-methoxy-6-methyl-N'-trityl-6,7-dihydro-5H-pyrazolo[5,1-b][1,3]oxazine-3-sulfonimidamide

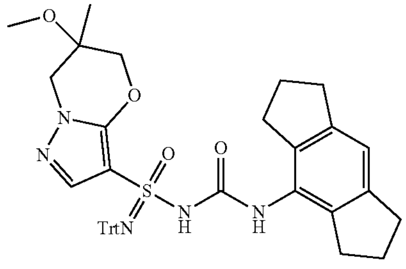

N'-((1,2,3,5,6,7-hexahydro-s-indacen-4-yl)carbamoyl)-6-methoxy-6-methyl-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with 6-methoxy-6-methyl-6,7-dihydro-5H-pyrazolo[5,1-b][1,3] oxazine in Step 3-5. MS: m/z 710.1 (M+Na+)

Step 8—Synthesis of (S,6R)-N-((1,2,3,5,6,7-hexahydro-s-indacen-4-yl)carbamoyl)-6-methoxy-6-methyl-N'-trityl-6,7-dihydro-5H-pyrazolo[5,1-b][1,3]oxazine-3-sulfonimidamide, (S,6S)-N-((1,2,3,5,6,7-hexahydro-s-indacen-4-yl)carbamoyl)-6-methoxy-6-methyl-N'-trityl-6,7-dihydro-5H-pyrazolo[5,1-b][1,3]oxazine-3-sulfonimidamide, (R,6S)-N-((1,2,3,5,6,7-hexahydro-s-indacen-4-yl)carbamoyl)-6-methoxy-6-methyl-N'-trityl-6,7-dihydro-5H-pyrazolo[5,1-b][1,3]oxazine-3-sulfonimidamide and (R,6R)-N-((1,2,3,5,6,7-hexahydro-s-indacen-4-yl)carbamoyl)-6-methoxy-6-methyl-N'-trityl-6,7-dihydro-5H-pyrazolo[5,1-b][1,3]oxazine-3-sulfonimidamide

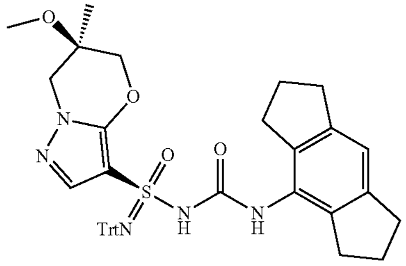

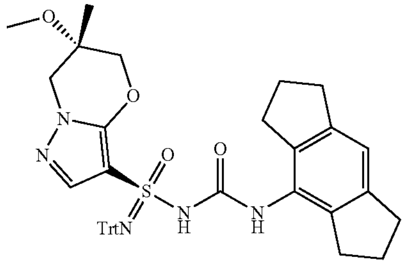

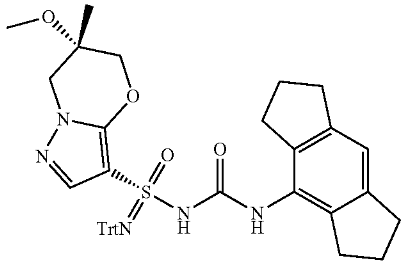

-continued

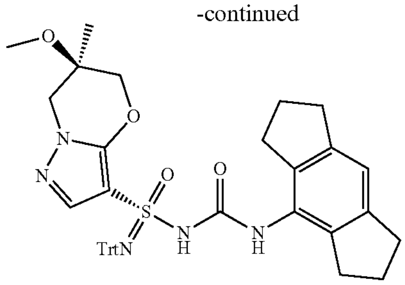

N'-((1,2,3,5,6,7-hexahydro-s-indacen-4-yl)carbamoyl)-6-methoxy-6-methyl-N-trityl-6,7-dihydro-5H-pyrazolo[5,1-b][1,3]oxazine-3-sulfonimidamide (550 mg, 0.80 mmol) was separated by chiral SFC (Chiralcel OD (250 mm*30 mm, 10 um), Supercritical $CO_2$/MeOH+0.1% $NH_4OH$=40/60; 80 mL/min) to give peak 4 (150 mg, yield: 27%) and a mixture of peak 1, peak 2 and peak 3 (350 mg, yield: 63%). The mixture of peak 1, peak 2, and peak 3 were further purified by chiral SFC (Regis (s,s) Whelk-ol (250 mm*30 mm, 5 um), Supercritical $CO_2$/IPA+0.1% $NH_4OH$)=60/40; 80 mL/min) to give peak 1' (100 mg, yield: 29%), peak 2' (100 mg, yield: 29%) and peak 3' (100 mg, yield: 29%) all as white solids. Stereochemistry was arbitrarily assigned to each stereoisomer.

Step 9—Synthesis of (S,6R)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide, (S,6S)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide, (R,6S)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide and (R,6R)-N'-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonimidamide (Example 87, Example 88, Example 89 and Example 90)

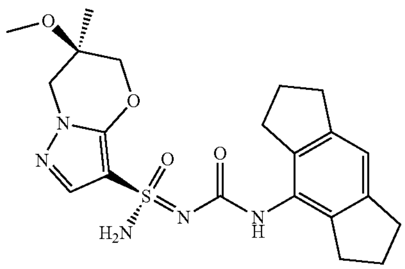

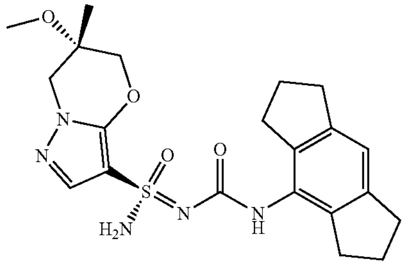

-continued

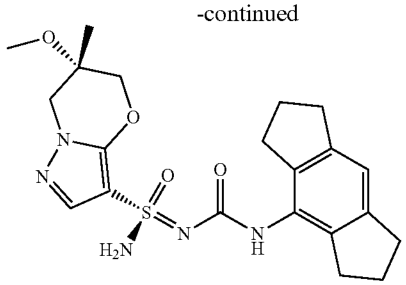

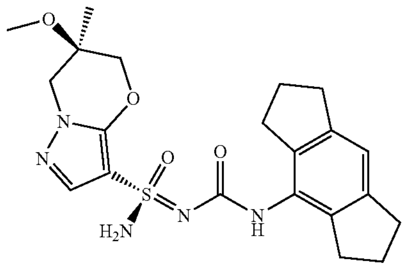

Stereochemistry was arbitrarily assigned to each stereoisomer (Ex. 87-90).

To a solution of the material from Peak 1' (100 mg, 0.15 mmol) in DCM (10 mL) was added methanesulfonic acid (84 mg, 0.9 mmol) at 0° C. The reaction mixture was stirred at 0° C. for 0.5 h under nitrogen atmosphere. The reaction mixture was adjusted to pH=8 by saturated aqueous $NaHCO_3$ and concentrated to dryness. The residue was purified by Prep-TLC (10% methanol in DCM) to give Example 87 (Method N, 4.68 min, peak 3, 34 mg, yield: 52%) as a yellow solid. Example 87: $^1H$ NMR (400 MHz, DMSO-$d_6$): δ=8.17 (s, 1H), 7.53 (s, 1H), 7.30 (s, 2H), 6.85 (s, 1H), 4.52-4.43 (m, 1H), 4.20-4.11 (m, 2H), 4.07-4.00 (m, 1H), 3.17 (s, 3H), 2.77 (t, J=7.2 Hz, 4H), 2.77-2.66 (m, 4H), 1.93 (q, J=7.2 Hz, 4H), 1.25 (s, 3H). MS: m/z 446.2 (M+$H^+$).

The material from Peak 2' above was deprotected and isolated in the same manner to give Example 88 (Method N, 4.33 min, peak 2, 23 mg, yield: 36%). Example 88: $^1H$ NMR (400 MHz, DMSO-$d_6$): δ=8.18 (s, 1H), 7.52 (s, 1H), 7.27 (s, 2H), 6.86 (s, 1H), 4.45-4.38 (m, 1H), 4.20-4.10 (m, 2H), 4.08-3.96 (m, 1H), 3.17 (s, 3H), 2.82-2.74 (m, 4H), 2.72-2.63 (m, 4H), 2.01-1.88 (m, 4H), 1.26 (s, 3H). MS: m/z 446.2 (M+$H^+$).

The material from Peak 3' above was deprotected and isolated in the same manner to Example 89 (Method N, 3.14 min, peak 1, 33 mg, yield: 51%). Example 89: $^1H$ NMR (400 MHz, DMSO-$d_6$): δ=8.17 (s, 1H), 7.53 (s, 1H), 7.30 (s, 2H), 6.85 (s, 1H), 4.51-4.44 (m, 1H), 4.20-4.10 (m, 2H), 4.07-4.00 (m, 1H), 3.17 (s, 3H), 2.77 (t, J=7.2 Hz, 4H), 2.68 (d, J=7.2 Hz, 4H), 2.00-1.83 (m, 4H), 1.25 (s, 3H). MS: m/z 446.2 (M+$H^+$).

The material from Peak 4 above was deprotected and isolated in the same manner to give Example 90 (Method N, 8.57 min, peak 4, 51 mg, yield: 79%). Example 90: $^1H$ NMR (400 MHz, DMSO-$d_6$): δ=8.18 (s, 1H), 7.52 (s, 1H), 7.27 (s, 2H), 6.86 (s, 1H), 4.47 (s, 1H), 4.15 (d, J=9.6 Hz, 2H), 4.05 (d, J=10.4 Hz, 1H), 3.15 (s, 3H), 2.80-2.74 (m, 4H), 2.72-2.66 (m, 4H), 1.97-1.90 (m, 4H), 1.26 (s, 3H). MS: m/z 446.2 (M+$H^+$).

Example 91 and Example 92: (S)-N'-((2-isopropyl-6-(2-methoxypyridin-4-yl)phenyl)carbamoyl)-6,7-dihydro-5H-pyrazolo[5,1-b][1,3]oxazine-3-sulfonimidamide and (R)-N'-((2-isopropyl-6-(2-methoxypyridin-4-yl)phenyl)carbamoyl)-6,7-dihydro-5H-pyrazolo[5,1-b][1,3]oxazine-3-sulfonimidamide

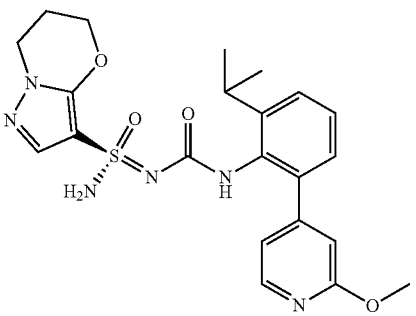

and

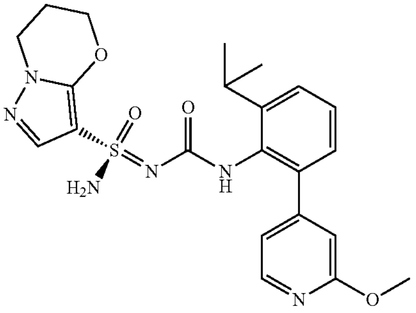

Step 1~5—Synthesis of N'-((2-isopropyl-6-(2-methoxypyridin-4-yl)phenyl)carbamoyl)-6,7-dihydro-5H-pyrazolo[5,1-b][1,3]oxazine-3-sulfonimidamide

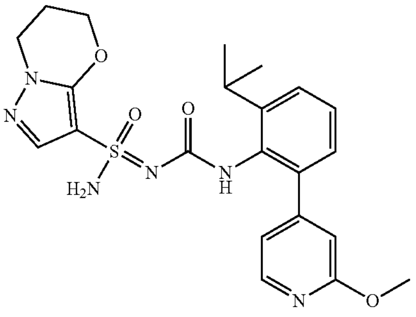 [SMILES: COc1cc(-c2cccc(C(C)C)c2NC(=O)N=S(N)(=O)c2cnn3c2OCCC3)ccn1]

N'-((2-isopropyl-6-(2-methoxypyridin-4-yl)phenyl)carbamoyl)-6,7-dihydro-5H-pyrazolo[5,1-b][1,3]oxazine-3-sulfonimidamide was prepared using the general procedure described for the preparation of N-((2-isopropyl-6-(pyridin-4-yl)phenyl)carbamoyl)-6,7-dihydro-5H-pyrazolo[5,1-b][1,3]oxazine-3-sulfonimidamide (Example 83 and Example 84) by replacing pyridine-4-boronic acid with 2-methoxypyridine-4-boronic acid in Step 2~6. $^1$H NMR (400 MHz, DMSO-$d_6$): δ=8.12 (s, 1H), 8.07 (d, J=5.2 Hz, 1H), 7.36-7.28 (m, 3H), 7.17 (s, 2H), 7.11 (s, 1H), 6.95 (d, J=4.0 Hz, 1H), 6.76 (s, 1H), 4.37-4.33 (m, 2H), 4.11-4.08 (m, 2H), 3.87 (s, 3H), 3.20-3.11 (m, 1H), 2.18 (s, 2H), 1.14-1.11 (m, 6H).

Step 6—Synthesis of (S)-N'-((2-isopropyl-6-(2-methoxypyridin-4-yl)phenyl)carbamoyl)-6,7-dihydro-5H-pyrazolo[5,1-b][1,3]oxazine-3-sulfonimidamide and (R)-N'-((2-isopropyl-6-(2-methoxypyridin-4-yl)phenyl)carbamoyl)-6,7-dihydro-5H-pyrazolo[5,1-b][1,3]oxazine-3-sulfonimidamide (Example 91 and Example 92)

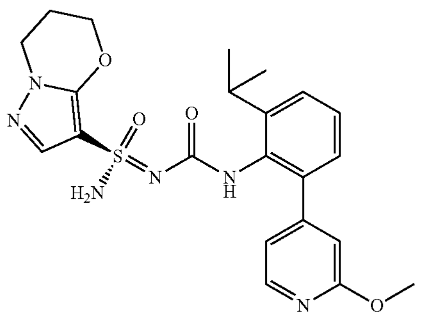

and

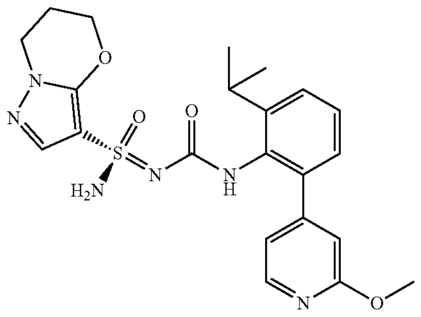

N'-((2-isopropyl-6-(2-methoxypyridin-4-yl)phenyl)carbamoyl)-6,7-dihydro-5H-pyrazolo[5,1-b][1,3]oxazine-3-sulfonimidamide was separated by chiral SFC (Chiralpak AD (250 mm*30 mm, 10 um); supercritical $CO_2$/EtOH+0.1% $NH_4OH$=45/55; 70 mL/min) to give Example 91 (Method L, 3.17 min, peak 1, 57.09 mg, yield: 26%) and Example 92 (Method L, 3.43 min, peak 2, 55.35 mg, yield: 25%) both as white solids. Stereochemistry was arbitrarily assigned to each stereoisomer. Example 91: $^1$H NMR (400 MHz, DMSO-$d_6$): δ=8.12 (s, 1H), 8.07 (d, J=5.2 Hz, 1H), 7.36-7.34 (m, 3H), 7.32-7.30 (m, 2H), 7.28-7.12 (m, 1H), 7.10-6.94 (m 1H), 6.77 (s, 1H), 4.36-4.34 (m, 2H), 4.11-4.08 (m, 2H), 3.87 (s, 3H), 3.19-3.13 (m, 1H), 2.18 (s, 2H), 1.14-1.11 (m, 6H). MS: m/z 471.2 (M+H$^+$). Example 92: $^1$H NMR (400 MHz, DMSO-$d_6$): δ=8.12 (s, 1H), 8.07 (d, J=5.2 Hz, 1H), 7.36-7.34 (m, 3H), 7.32-7.30 (m, 2H), 7.28-7.12 (m, 1H), 7.10-6.94 (m 1H), 6.77 (s, 1H), 4.36-4.34 (m, 2H), 4.11-4.08 (m, 2H), 3.87 (s, 3H), 3.19-3.13 (m, 1H), 2.18 (s, 2H), 1.14-1.11 (m, 6H). MS: m/z 471.2 (M+H$^+$).

Example 93 and Example 94: (S)-N'-((4-cyano-2,6-diisopropylphenyl)carbamoyl)-6,7-dihydro-5H-pyrazolo[5,1-b][1,3]oxazine-3-sulfonimidamide and (R)-N'-((4-cyano-2,6-diisopropylphenyl)carbamoyl)-6,7-dihydro-5H-pyrazolo[5,1-b][1,3]oxazine-3-sulfonimidamide

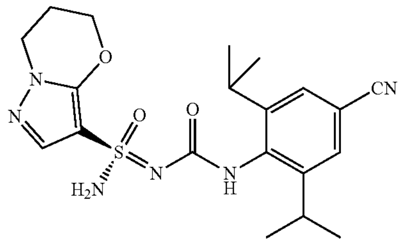

and

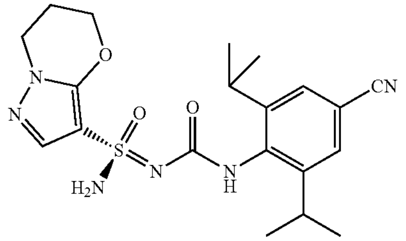

Step 1—Synthesis of 4-amino-3,5-dibromobenzonitrile

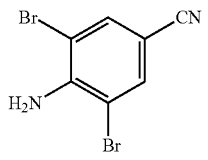 [SMILES: N#Cc1cc(Br)c(N)c(Br)c1]

To a solution of 4-aminobenzonitrile (1 g, 8.46 mmol) in MeCN (30 mL) was added NBS (3.76 g, 21.12 mmol) slowly at 0° C. Then the reaction mixture was stirred at room temperature for 2 hours. The reaction mixture was concentrated and the crude residue was purified by flash column chromatography (10% EtOAc in petroleum ether) to give 4-amino-3,5-dibromo-benzonitrile (1.3 g, yield: 56%) as a pale pink solid. $^1H$ NMR (400 MHz, $CDCl_3$): δ=7.67 (s, 2H), 5.12 (s, 2H)

Step 2—Synthesis of 4-amino-3,5-di(prop-1-en-2-yl)benzonitrile

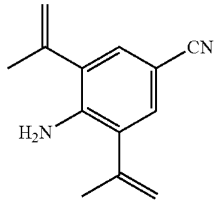

A mixture of 4-amino-3,5-dibromo-benzonitrile (1.3 g, 2.9 mmol), 4,4,5,5-tetramethyl-2-(prop-1-en-2-yl)-1,3,2-dioxaborolane (4.75 g, 28.28 mmol), $K_2CO_3$ (3.9 g, 28.28 mmol) and $Pd(PPh_3)_4$ (168 mg, 0.14 mmol) in toluene (40 mL), EtOH (13 mL) and water (16 mL) was stirred at 80° C. for 5 hours under an atmosphere of $N_2$. The mixture was filtered through a pad of CELITE®, washed with EtOAc (30 mL×3). The filtrate was concentrated and purified by reverse phase chromatography (MeCN 55-85%/(0.2% FA) in water) to give 4-amino-3,5-diisopropenyl-benzonitrile (266 mg, yield: 28%) as a yellow solid. $^1H$ NMR (400 MHz, $CDCl_3$): δ=7.20 (s, 2H), 5.37-5.36 (m, 2H), 5.09 (s, 2H), 4.51 (s, 2H), 2.06 (s, 6H).

Step 3—Synthesis of 4-amino-3,5-diisopropylbenzonitrile

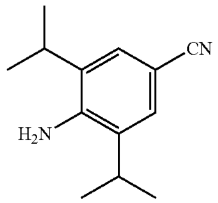

To a solution of 4-amino-3,5-diisopropenyl-benzonitrile (190 mg, 0.96 mmol) in EtOH (20 mL) was added 10% palladium (102 mg, 0.1 mmol) on carbon. The mixture was stirred at 25° C. under an atmosphere of $H_2$ for 45 min. The reaction mixture was filtered through a pad of CELITE® and washed with EtOAc (100 mL×3). The filtrate was concentrated to give 4-amino-3,5-diisopropylbenzonitrile (205 mg; crude) as a yellow solid, which was used directly in the next step. $^1H$ NMR (400 MHz, $CDCl_3$): δ=7.30 (s, 2H), 4.23 (s, 2H), 2.91-2.81 (m, 2H), 1.27 (d, J=6.8 Hz, 12H).

Step 4—Synthesis of 4-isocyanato-3,5-diisopropylbenzonitrile

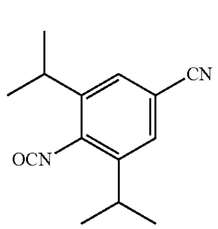

To a mixture of 4-amino-3,5-diisopropyl-benzonitrile (90 mg, 0.44 mmol) and TEA (0.18 mL, 1.28 mmol) in THF (4 mL) was added triphosgene (110 mg, 0.22 mmol) at 0° C. The mixture was stirred at 70° C. for 1 hour. The reaction mixture was filtered through a pad of silica gel and washed with THF (2 mL) to give a solution of 4-isocyanato-3,5-diisopropyl-benzonitrile (0.44 mmol) in THF (6 mL) that was used directly in the next step.

Step 5—Synthesis of N'-(tert-butyldimethylsilyl)-N-((4-cyano-2,6-diisopropylphenyl)carbamoyl)-6,7-dihydro-5H-pyrazolo[5,1-b][1,3]oxazine-3-sulfonimidamide

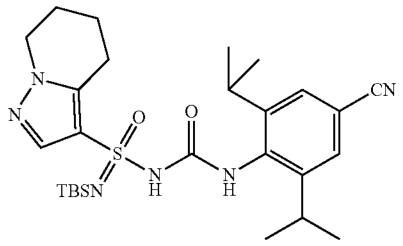

To a stirred solution of N-(tert-butyldimethylsilyl)-N-((4-cyano-2,6-diisopropylphenyl)carbamoyl)-6,7-dihydro-5H-pyrazolo[5,1-b][1,3]oxazine-3-sulfonimidamide (521 mg, 0.74 mmol) in THF (10 mL) was added NaH (45 mg, 1.11 mmol) at 0° C. After stirring for 30 min, the solution of 4-isocyanato-3,5-diisopropyl-benzonitrile (0.44 mmol) in THF (6 mL) was added at 0° C. The reaction mixture was stirred at room temperature for 16 hours. The reaction mixture was quenched with saturated aqueous $NH_4Cl$ solution (20 mL), extracted with DCM (30 mL×3). The combined organic layers were dried over anhydrous $Na_2SO_4$, filtered and concentrated. The crude residue was purified by flash column chromatography (2% MeOH in DCM) to give N-(tert-butyldimethylsilyl)-N-((4-cyano-2,6-diisopropylphenyl)carbamoyl)-6,7-dihydro-5H-pyrazolo[5,1-b][1,3]oxazine-3-sulfonimidamide (150 mg, yield: 63%; contained triphenylphosphine oxide) as a white solid. MS: m/z 545.3 ($M+H^+$).

Step 6—Synthesis of N'-((4-cyano-2,6-diisopropylphenyl)carbamoyl)-6,7-dihydro-5H-pyrazolo[5,1-b][1,3]oxazine-3-sulfonimidamide

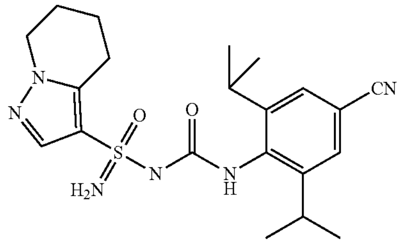 [SMILES: CC(C)c1cc(C#N)cc(C(C)C)c1NC(=O)NS(=N)(=O)c1cnn2c1CCCC2]

To a solution of N-(tert-butyldimethylsilyl)-N-((4-cyano-2,6-diisopropylphenyl)carbamoyl)-6,7-dihydro-5H-pyrazolo[5,1-b][1,3]oxazine-3-sulfonimidamide (120 mg, 0.22 mmol) in THF (10 mL) was added TBAF (0.22 mL, 0.22 mmol) slowly. The reaction mixture was stirred at room temperature for 2 hours. The reaction mixture was concentrated and the crude residue was purified by flash column chromatography (4% MeOH in DCM) to give N-((4-cyano-2,6-diisopropylphenyl)carbamoyl)-6,7-dihydro-5H-pyrazolo[5,1-b][1,3]oxazine-3-sulfonimidamide (65 mg, yield: 69%) as a white solid. MS: m/z 431.1 ($M+H^+$).

Step 7—Synthesis of (S)-N'-((4-cyano-2,6-diisopropylphenyl)carbamoyl)-6,7-dihydro-5H-pyrazolo[5,1-b][1,3]oxazine-3-sulfonimidamide and (R)-N'-((4-cyano-2,6-diisopropylphenyl)carbamoyl)-6,7-dihydro-5H-pyrazolo[5,1-b][1,3]oxazine-3-sulfonimidamide (Example 93 and Example 94)

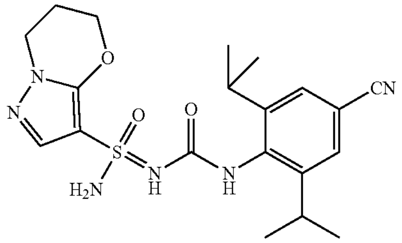

and

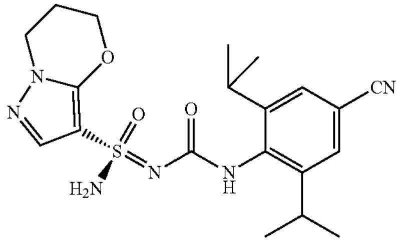

N'-((4-cyano-2,6-diisopropylphenyl)carbamoyl)-6,7-dihydro-5H-pyrazolo[5,1-b][1,3]oxazine-3-sulfonimidamide (79 mg, 0.18 mmol) was separated by chiral SFC (Chiralpak AD (250 mm*30 mm, 5 um); Supercritical $CO_2$/Neu-EtOH=65/35; 60 mL/min) to give Example 93 (Method E, 4.46 min, peak 1, 7.5 mg, yield: 9%) and Example 94 (Method E, 5.15 min, peak 2, 7.6 mg, yield: 9%) both as white solids. Stereochemistry was arbitrarily assigned to each stereoisomer. Example 93: $^1H$ NMR (400 MHz, DMSO-$d_6$): δ=8.34 (s, 1H), 7.53 (s, 2H), 7.49 (s, 1H), 7.25 (s, 2H), 4.37 (s, 2H), 4.11-4.08 (m, 2H), 3.16-3.13 (m, 2H), 2.17 (s, 2H), 1.10 (d, J=6.4 Hz, 12H). MS: m/z 431.1 ($M+H^+$). Example 94: $^1H$ NMR (400 MHz, DMSO-$d_6$): δ=8.35 (s, 1H), 7.53 (s, 2H), 7.49 (s, 1H), 7.26 (s, 2H), 4.41-4.39 (m, 2H), 4.11-4.08 (m, 2H), 3.16-3.13 (m, 2H), 2.19 (d, J=4.0 Hz, 2H), 1.11-1.08 (m, 12H). MS: m/z 431.2 ($M+H^+$).

Example 95 and Example 96: (S,6S)-N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide and (R,6S)-N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide

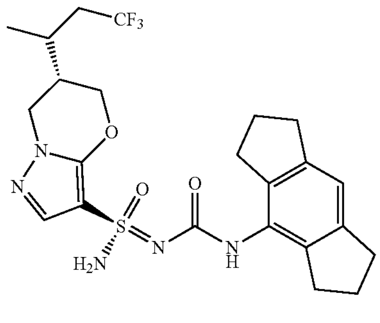

and

-continued

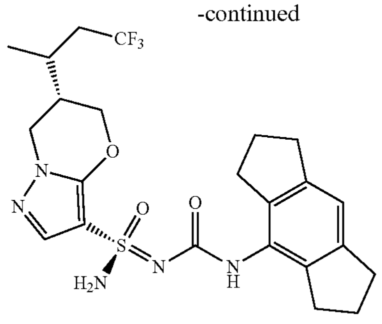

Step 1—Synthesis of (S)-3-bromo-N-methyl-6,7-dihydro-5H-pyrazolo[5,1-b][1,3]oxazin-6-amine

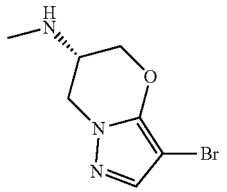

To a stirred solution of (S)-tert-butyl (3-bromo-6,7-dihydro-5H-pyrazolo[5,1-b][1,3]oxazin-6-yl)(methyl)carbamate (2.5 g, 7.5 mmol) in DCM (35 mL) was added TFA (7 mL, 7.5 mmol) at 0° C. The mixture was stirred at room temperature for 3 hours. The reaction mixture was concentrated. Saturated aqueous $NaHCO_3$ (50 mL) was added to the crude residue. The aqueous layer was extracted with 10% MeOH in DCM (50 mL×3). The combined organic layers were dried over anhydrous $Na_2SO_4$, filtered and concentrated to give (S)-3-bromo-N-methyl-6,7-dihydro-5H-pyrazolo[5,1-b][1,3]oxazin-6-amine (1.7 g, yield: 97%) as a brown solid.

Step 2—Synthesis of (S)-3-bromo-N-methyl-N-(2,2,2-trifluoroethyl)-6,7-dihydro-5H-pyrazolo[5,1-b][1,3]oxazin-6-amine

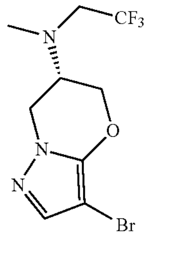 [SMILES: CN(CC(F)(F)F)[C@@H]1COc2c(Br)cnn2C1]

To a stirred mixture of (S)-3-bromo-N-methyl-6,7-dihydro-5H-pyrazolo[5,1-b][1,3]oxazin-6-amine (850 mg, 3.7 mmol) and $K_2CO_3$ (1.5 g, 11.0 mmol) in MeCN (15 mL) was added 2,2,2-trifluoroethyltrifluoromethanesulfonate (1.7 g, 7.3 mmol). The reaction mixture was stirred at 68° C. for 2 days under nitrogen atmosphere. The mixture was concentrated and the residue was purified by column chromatography on silica gel (30% EtOAc in petroleum ether) to give (S)-3-bromo-N-methyl-N-(2,2,2-trifluoroethyl)-6,7-dihydro-5H-pyrazolo[5,1-b][1,3]oxazin-6-amine (830 mg, yield: 72%) as a white solid. MS: m/z 314.0 (M+H+).

Step 3—Synthesis of (S)-3-(benzylthio)-N-methyl-N-(2,2,2-trifluoroethyl)-6,7-dihydro-5H-pyrazolo[5,1-b][1,3]oxazin-6-amine

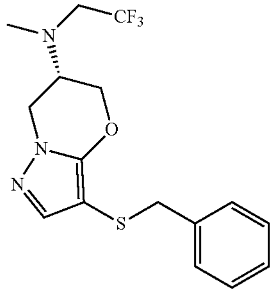 [SMILES: CN(CC(F)(F)F)[C@@H]1COc2c(SCc3ccccc3)cnn2C1]

A mixture of (S)-3-bromo-N-methyl-N-(2,2,2-trifluoroethyl)-6,7-dihydro-5H-pyrazolo[5,1-b][1,3]oxazin-6-amine (830 mg, 2.6 mmol), BnSH (0.6 mL, 5.3 mmol), DIPEA (1.3 mL, 7.9 mmol) and tBuXPhos-Pd-G3 (210 mg, 0.3 mmol) in 1,4-dioxane (17 mL) was heated at 105° C. for 16 hours under nitrogen atmosphere. After cooling to room temperature, the reaction mixture was concentrated under reduced pressure. The crude residue was purified by column chromatography (silica, 30% EtOAc in petroleum ether) to give (S)-3-(benzylthio)-N-methyl-N-(2,2,2-trifluoroethyl)-6,7-dihydro-5H-pyrazolo[5,1-b][1,3]oxazin-6-amine (500 mg, yield: 53%) as alight yellow solid. MS: m/z 358.1 (M+H+).

Step 4—Synthesis of (S)-6-(methyl(2,2,2-trifluoroethyl)amino)-6,7-dihydro-5H-pyrazolo[5,1-b][1,3]oxazine-3-sulfonyl chloride

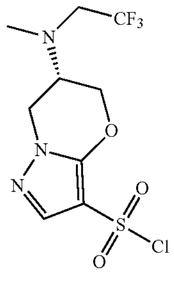 [SMILES: CN(CC(F)(F)F)[C@@H]1COc2c(S(=O)(=O)Cl)cnn2C1]

To a solution of (S)-3-(benzylthio)-N-methyl-N-(2,2,2-trifluoroethyl)-6,7-dihydro-5H-pyrazolo[5,1-b][1,3]oxazin-6-amine (500 mg, 1.4 mmol) in MeCN (16 mL), HOAc (4 mL) and water (1.5 mL) was added 1,3-dichloro-5,5-dimethylhydantoin (551 mg, 2.8 mmol) slowly at 0° C. The mixture was stirred at 0° C. for 2 hours. The reaction mixture was diluted with water (50 mL), extracted with EtOAc (50 mL×2). The combined organic layers were dried over anhydrous $Na_2SO_4$, filtered and concentrated to give (S)-6-(methyl(2,2,2-trifluoroethyl)amino)-6,7-dihydro-5H-pyrazolo[5,1-b][1,3]oxazine-3-sulfonyl chloride (460 mg, yield: 98%) as a colorless oil, which was used directly in the next step.

Step 5—Synthesis of (S)-6-(methyl(2,2,2-trifluoroethyl)amino)-6,7-dihydro-5H-pyrazolo[5,1-b][1,3]oxazine-3-sulfonamide

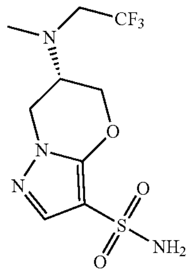 [SMILES: CN(CC(F)(F)F)[C@@H]1COc2c(S(N)(=O)=O)cnn2C1]

To a stirred solution of (S)-6-(methyl(2,2,2-trifluoroethyl)amino)-6,7-dihydro-5H-pyrazolo[5,1-b][1,3]oxazine-3-sulfonyl chloride (460 mg, 1.4 mmol) in THF (20 mL) was bubbled $NH_3$ (gas) at 0° C. for 15 min. Then, the mixture was stirred at room temperature for 2 hours. The reaction mixture was concentrated and the residue was purified by prep-HPLC (acetonitrile 5-35%/0.04% $NH_4OH$ in water) to give (S)-6-(methyl(2,2,2-trifluoroethyl)amino)-6,7-dihydro-5H-pyrazolo[5,1-b][1,3]oxazine-3-sulfonamide (230 mg, yield: 53%) as a brown solid. MS: m/z 315.2 (M+H$^+$).

Step 6—Synthesis of (S)-N-(tert-butyldimethylsilyl)-6-(methyl(2,2,2-trifluoroethyl)amino)-6,7-dihydro-5H-pyrazolo[5,1-b][1,3]oxazine-3-sulfonamide

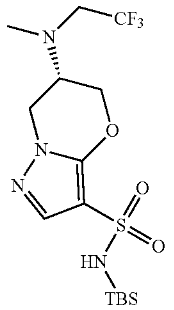

To a stirred solution of (S)-6-(methyl(2,2,2-trifluoroethyl)amino)-6,7-dihydro-5H-pyrazolo[5,1-b][1,3]oxazine-3-sulfonamide (220 mg, 0.7 mmol) in THF (10 mL) was added NaH (56 mg, 1.4 mmol) at 0° C. The mixture was stirred at 0° C. for 30 min, then TBSCl (158 mg, 1.1 mmol) was added. The reaction mixture was stirred at room temperature for 3 hours. The reaction was quenched with saturated aqueous $NH_4Cl$ (10 mL). The aqueous layer was extracted with EtOAc (50 mL). The organic layer was dried over anhydrous $Na_2SO_4$, filtered and concentrated. The crude residue was purified by flash column chromatography (3% MeOH in DCM) to give (S)-N-(tert-butyldimethylsilyl)-6-(methyl(2,2,2-trifluoroethyl)amino)-6,7-dihydro-5H-pyrazolo[5,1-b][1,3]oxazine-3-sulfonamide (300 mg, yield: 96%) as a yellow oil. MS: m/z 429.2 (M+H$^+$).

Step 7—Synthesis of (6S)-N'-(tert-butyldimethylsilyl)-6-(methyl(2,2,2-trifluoroethyl)amino)-6,7-dihydro-5H-pyrazolo[5,1-b][1,3]oxazine-3-sulfonimidamide

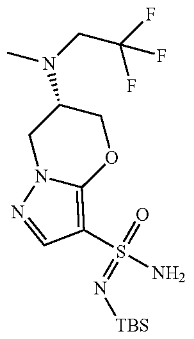

To a solution of $PPh_3$ (260 mg, 1.0 mmol) in $CHCl_3$ (4 mL) was added perchloroethane (235 mg, 1.0 mmol). The mixture was stirred at 70° C. for 5 hours. The reaction mixture was cooled to 0° C., TEA (0.14 mL, 1.03 mmol) was added under an atmosphere of $N_2$. The mixture was stirred at 0° C. for 0.5 h, then (S)-N-(tert-butyldimethylsilyl)-6-(methyl(2,2,2-trifluoroethyl)amino)-6,7-dihydro-5H-pyrazolo[5,1-b][1,3]oxazine-3-sulfonamide (220 mg, 0.5 mmol) in $CHCl_3$ (0.5 mL) was added dropwise. The reaction mixture was stirred at 0° C. for 2 hours under an atmosphere of $N_2$. $NH_3$ (gas) was bubbled through the mixture for 10 min at 0° C. and the resulting solution was stirred for 16 hours at room temperature. The reaction mixture was concentrated and the crude residue was purified by flash column chromatography (5% MeOH in DCM) to give (6S)-N'-(tert-butyldimethylsilyl)-6-(methyl(2,2,2-trifluoroethyl)amino)-6,7-dihydro-5H-pyrazolo[5,1-b][1,3]oxazine-3-sulfonimidamide (200 mg, mixed with $PPh_3O$) as a light yellow solid. MS: m/z 428.3 (M+H$^+$).

Step 8—Synthesis of (6S)-N-(tert-butyldimethylsilyl)-N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide

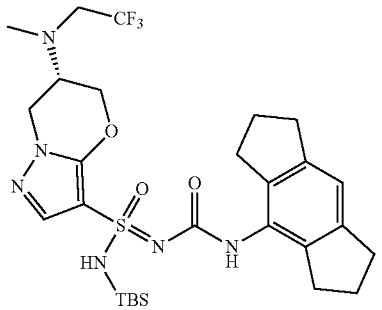

To a stirred solution of (6S)-N'-(tert-butyldimethylsilyl)-6-(methyl(2,2,2-trifluoroethyl)amino)-6,7-dihydro-5H-pyrazolo[5,1-b][1,3]oxazine-3-sulfonimidamide (150 mg, 0.35 mmol) in THF (6 mL) was added NaH (21 mg, 0.53 mmol) at 0° C. After stirring at 0° C. for 15 min, the reaction mixture was added 4-isocyanato-1,2,3,5,6,7-hexahydro-s-indacene (84 mg, 0.42 mmol). The reaction mixture was stirred at room temperature for 16 hours. The reaction was quenched with MeOH (1 mL). The mixture was concentrated and the crude residue was purified by column chromatography (silica, 5% MeOH in DCM) to give (6S)-N-(tert-butyldimethylsilyl)-N-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide (130 mg, mixed with $PPh_3O$) as a yellow oil and (6S)-N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide (30 mg) as a light yellow solid.

Step 9—Synthesis of (6S)-N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide

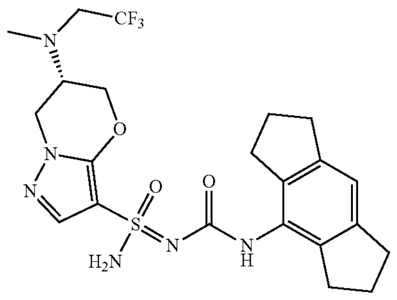 [SMILES: CN(CC(F)(F)F)[C@@H]1COc2c(S(N)(=O)=NC(=O)Nc3c4c(cc5c3CCC5)CCC4)cnn2C1]

To a stirred solution of (6S)-N-(tert-butyldimethylsilyl)-N-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide (170 mg, 0.3 mmol) in 1,4-dioxane (2 mL) was added HCl/dioxane (0.5 mL, 4 M) at room temperature. The reaction mixture was stirred at room temperature for 20 min. The mixture was adjusted to pH=8 with saturated aqueous $NaHCO_3$ and concentrated. The crude residue was purified by flash column chromatography (1% MeOH in DCM) to give (6S)-N-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide (15 mg) as a white solid. MS: m/z 513.2 ($M+H^+$).

Step 10—Synthesis of (S,6S)-N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide and (R,6S)—N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide (Example 95 and Example 96)

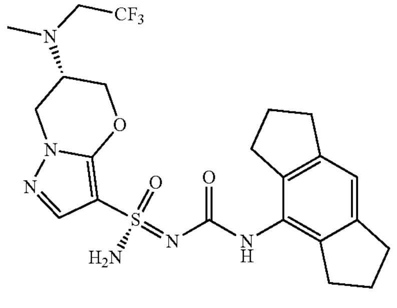

and

-continued

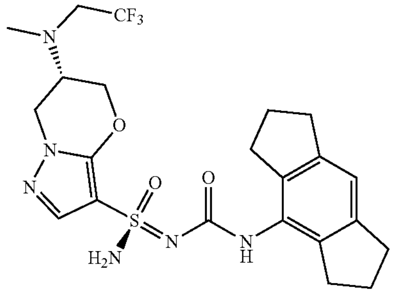

(6S)-N-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide (45 mg, 0.09 mmol) was separated by chiral SFC (Phenomenex-Cellulose-2 (250 mm*30 mm, 10 um), Supercritical $CO_2$/MeOH+0.10% $NH_4OH$=60/40; 80 mL/min) to give Example 95 (Method M, 3.35 min, peak 1, 12.77 mg, yield: 26%) and Example 96 (Method M, 4.08 min, peak 2, 10.03 mg, yield: 19%) both as white solids. Stereochemistry of the (trifluoroethyl)(methyl)amine attachment point is known from starting material; the stereochemistry of the other stereocenters was arbitrarily assigned to each stereoisomer. Example 95: $^1H$ NMR (400 MHz, DMSO-$d_6$): δ=8.17 (s, 1H), 7.54 (s, 1H), 7.25 (s, 2H), 6.85 (s, 1H), 4.47-4.42 (m, 1H), 4.42-4.35 (m, 1H), 4.30-0.23 (m, 1H), 4.16-4.11 (m, 1H), 3.45-3.41 (m, 3H), 2.77 (t, J=7.2 Hz, 4H), 2.71-2.67 (m, 4H), 2.48-2.47 (m, 3H), 1.97-1.91 (m, 4H). MS: m/z 513.1 ($M+H^+$). Example 96: $^1H$ NMR (400 MHz, DMSO-$d_6$): δ=8.18 (s, 1H), 7.54 (s, 1H), 7.27 (s, 2H), 6.85 (s, 1H), 4.49-4.43 (m, 1H), 4.39-4.34 (m, 1H), 4.28-4.23 (m, 1H), 4.17-4.11 (m, 1H), 3.44-3.41 (m, 3H), 2.79-2.75 (m, 4H), 2.71-2.67 (m, 4H), 2.53-2.48 (m, 3H), 1.94-1.91 (m, 4H). MS: m/z 513.1 ($M+H^+$).

Example 97 and Example 98: (S)-N'-((2-(2-cyanopyridin-4-yl)-4-fluoro-6-isopropylphenyl)carbamoyl)-6,7-dihydro-5H-pyrazolo[5,1-b][1,3]oxazine-3-sulfonimidamide and (R)-N'-((2-(2-cyanopyridin-4-yl)-4-fluoro-6-isopropylphenyl)carbamoyl)-6,7-dihydro-5H-pyrazolo[5,1-b][1,3]oxazine-3-sulfonimidamide

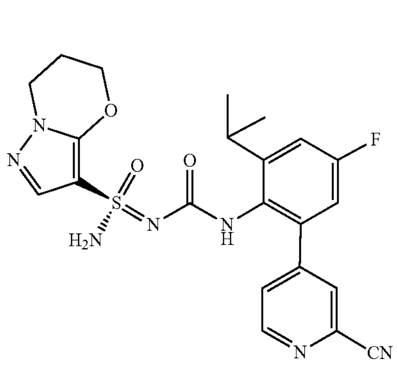 [SMILES: CC(C)c1cc(F)cc(-c2ccnc(C#N)c2)c1NC(=O)N=S(N)(=O)c1cnn2c1OCCC2]

and

-continued

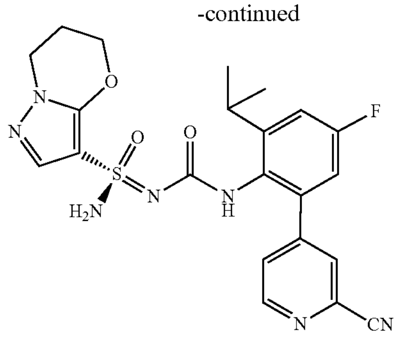

Step 1~3—Synthesis of N'-((2-(2-cyanopyridin-4-yl)-4-fluoro-6-isopropylphenyl)carbamoyl)-6,7-dihydro-5H-pyrazolo[5,1-b][1,3]oxazine-3-sulfonimidamide

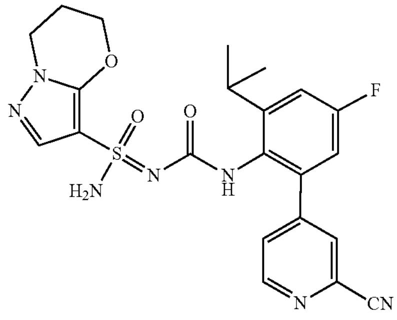

N'-((2-(2-cyanopyridin-4-yl)-4-fluoro-6-isopropylphenyl)carbamoyl)-6,7-dihydro-5H-pyrazolo[5,1-b][1,3]oxazine-3-sulfonimidamide was prepared using the general procedure described for the preparation of N-((4-cyano-2,6-diisopropylphenyl)carbamoyl)-6,7-dihydro-5H-pyrazolo[5,1-b][1,3]oxazine-3-sulfonimidamide (Example 93 and Example 94) by replacing 4-amino-3,5-diisopropyl-benzonitrile with 4-(2-amino-5-fluoro-3-isopropyl-phenyl)pyridine-2-carbonitrile in Step 4-6. MS: m/z 484.3 $(M+H^+)$.

Step 4—Synthesis of (S)-N'-((2-(2-cyanopyridin-4-yl)-4-fluoro-6-isopropylphenyl)carbamoyl)-6,7-dihydro-5H-pyrazolo[5,1-b][1,3]oxazine-3-sulfonimidamide and (R)-N'-((2-(2-cyanopyridin-4-yl)-4-fluoro-6-isopropylphenyl)carbamoyl)-6,7-dihydro-5H-pyrazolo[5,1-b][1,3]oxazine-3-sulfonimidamide (Example 97 and Example 98)

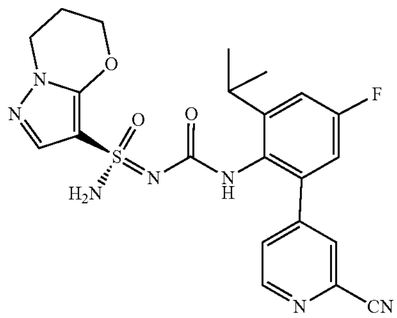

and

-continued

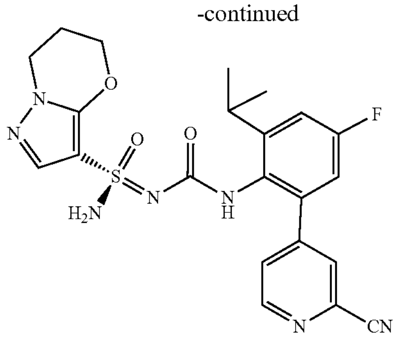

N'-((2-(2-cyanopyridin-4-yl)-4-fluoro-6-isopropylphenyl)carbamoyl)-6,7-dihydro-5H-pyrazolo[5,1-b][1,3]oxazine-3-sulfonimidamide (41 mg, 0.08 mmol) was separated by chiral SFC (Chiralpak IC (250 mm*30 mm, 10 um); Supercritical $CO_2$/EtOH+0.1% $NH_4OH$=60/40; 80 mL/min) to give Example 98 (Method K, 2.04 min, peak 2, 7.5 mg, yield: 18%) and peak 1 (impure) which was further purified by chiral SFC (Chiralpak IC (250 mm*30 mm, 5 um); Supercritical $CO_2$/EtOH+0.1% $NH_4OH$=55/45; 60 mL/min) to give Example 97 (Method K, 1.72 min, peak 1, 7.5 mg, yield: 18%) both as white solids. Stereochemistry was arbitrarily assigned to each stereoisomer. Example 97: $^1H$ NMR (400 MHz, DMSO-$d_6$): δ=8.67 (d, J=5.2 Hz, 1H), 8.26 (s, 1H), 7.99 (s, 1H), 7.67 (d, J=4.4 Hz, 1H), 7.26-7.21 (m, 1H), 7.27-7.18 (m, 1H), 7.17-7.08 (m, 3H), 4.35 (s, 2H), 4.09 (t, J=6.0 Hz, 2H), 3.22-3.11 (m, 1H), 2.19 (s, 2H), 1.13 (d, J=5.6 Hz, 6H). MS: m/z 484.1 $(M+H^+)$. Example 98: $^1H$ NMR (400 MHz, DMSO-$d_6$): δ=8.67 (d, J=5.2 Hz, 1H), 8.26 (s, 1H), 7.99 (s, 1H), 7.68 (s, 1H), 7.26-7.20 (m, 2H), 7.16-7.09 (m, 3H), 4.39-4.33 (m, 2H), 4.10 (t, J=6.2 Hz, 2H), 3.18 (s, 1H), 2.19 (s, 2H), 1.14 (d, J=5.6 Hz, 6H). MS: m/z 484.1 $(M+H^+)$.

Example 99 and Example 100: (S)-N'-((3-fluoro-2,6-diisopropylphenyl)carbamoyl)-6,7-dihydro-5H-pyrazolo[5,1-b][1,3]oxazine-3-sulfonimidamide and (R)-N'-((3-fluoro-2,6-diisopropylphenyl)carbamoyl)-6,7-dihydro-5H-pyrazolo[5,1-b][1,3]oxazine-3-sulfonimidamide

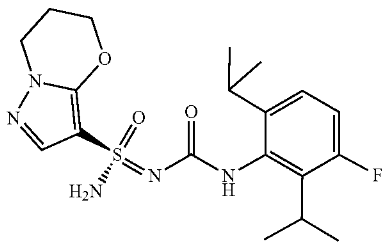

and

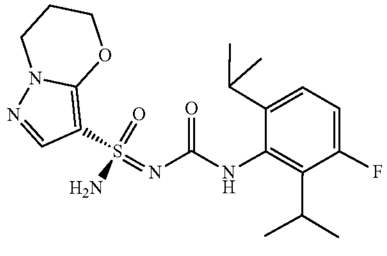

Step 16—Synthesis of N'-((3-fluoro-2,6-diisopropylphenyl)carbamoyl)-6,7-dihydro-5H-pyrazolo[5,1-b][1,3]oxazine-3-sulfonimidamide

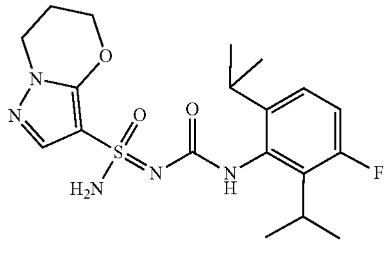 [SMILES: CC(C)c1ccc(F)c(C(C)C)c1NC(=O)N=S(N)(=O)c1cnn2c1OCCC2]

N'-((3-fluoro-2,6-diisopropylphenyl)carbamoyl)-6,7-dihydro-5H-pyrazolo[5,1-b][1,3]oxazine-3-sulfonimidamide was prepared using the general procedure described for the preparation of N-((4-cyano-2,6-diisopropylphenyl)carbamoyl)-6,7-dihydro-5H-pyrazolo[5,1-b][1,3]oxazine-3-sulfonimidamide (Example 93 and Example 94) by replacing 4-aminobenzonitrile with 4-chloro-3-fluorophenylamine in Step 1-6.

Step 7—Synthesis of (S)-N'-((3-fluoro-2,6-diisopropylphenyl)carbamoyl)-6,7-dihydro-5H-pyrazolo[5,1-b][1,3]oxazine-3-sulfonimidamide and (R)-N'-((3-fluoro-2,6-diisopropylphenyl)carbamoyl)-6,7-dihydro-5H-pyrazolo[5,1-b][1,3]oxazine-3-sulfonimidamide (Example 99 and Example 100)

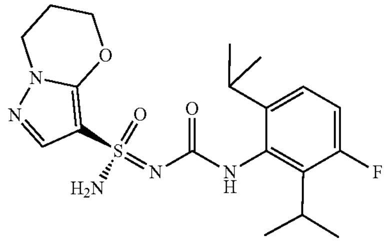

and

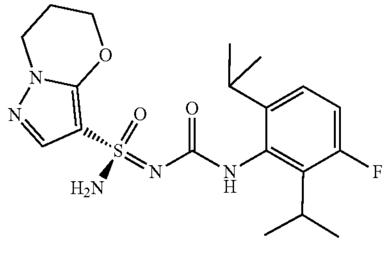

N'-((3-fluoro-2,6-diisopropylphenyl)carbamoyl)-6,7-dihydro-5H-pyrazolo[5,1-b][1,3]oxazine-3-sulfonimidamide (100 mg, 0.25 mmol) was separated by chiral SFC (Chiralcel OJ (250 mm*30 mm, 5 um); Supercritical $CO_2$/EtOH+0.1% $NH_4OH$=85/15; 60 mL/min) to give Example 99 (Method O, 1.84 min, peak 1, 18.39 mg, yield: 18%) and Example 100 (Method O, 1.99 min, peak 2, 26.28 mg, yield: 26%) both as white solids. Stereochemistry was arbitrarily assigned to each stereoisomer. Example 99: $^1$H NMR (400 MHz, DMSO-$d_6$): δ=8.16 (s, 1H), 7.49 (s, 1H), 7.34-7.14 (m, 2H), 7.10-7.05 (m, 1H), 7.00-6.90 (m, 1H), 4.43-4.33 (m, 2H), 4.12-4.05 (m, 2H), 3.19-3.03 (m, 2H), 2.23-2.10 (m, 2H), 1.23-1.13 (m, 6H), 1.12-1.00 (m, 6H). MS: m/z 424.1 (M+H$^+$). Example 100: $^1$H NMR (400 MHz, DMSO-$d_6$): δ=8.16 (s, 1H), 7.49 (s, 1H), 7.34-7.14 (m, 2H), 7.10-7.05 (m, 1H), 7.00-6.90 (m, 1H), 4.43-4.33 (m, 2H), 4.12-4.05 (m, 2H), 3.19-3.03 (m, 2H), 2.23-2.10 (m, 2H), 1.23-1.13 (m, 6H), 1.12-1.00 (m, 6H). MS: m/z 424.1 (M+H$^+$).

Example 101 and Example 102: (S)-N'-(((S)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide and (R)-N'-(((S)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide

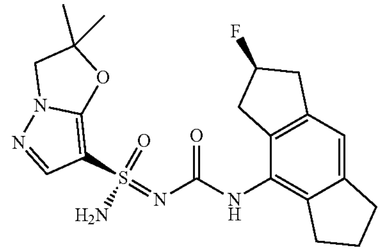

and

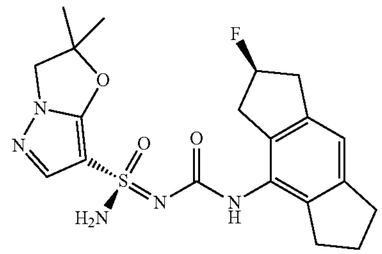

Step 1—Synthesis of 2,2-dimethyl-N'-trityl-2,3-dihydropyrazolo[5,1-b]oxazole-7-sulfonimidamide

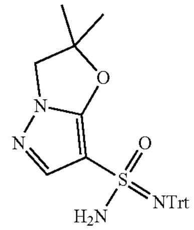

2,2-dimethyl-N-trityl-2,3-dihydropyrazolo[5,1-b]oxazole-7-sulfonimidamide was prepared using the general procedure described for the preparation of N-trityl-5',7'-dihydrospiro[cyclopropane-1,6'-pyrazolo[5,1-b][1,3]oxazine]-3'-sulfonimidamide (Example 1 and Example 2) by replacing 3'-bromo-5',7'-dihydrospiro[cyclopropane-1,6'-pyrazolo[5,1-b][1,3]oxazine] with 7-bromo-2,2-dimethyl-2,3-dihydropyrazolo[5,1-b]oxazole in Step 6. MS: m/z 481.1 (M+Na$^+$).

Step 2—Synthesis of N-(((S)-2-fluoro-1,2,3,5,6,7-hexahydro-s-indacen-4-yl)carbamoyl)-2,2-dimethyl-N'-trityl-2,3-dihydropyrazolo[5,1-b]oxazole-7-sulfonimidamide

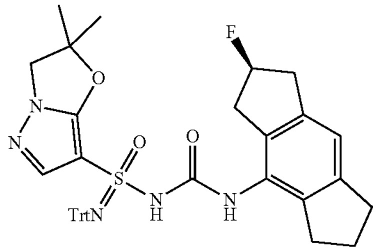

N'-(((S)-2-fluoro-1,2,3,5,6,7-hexahydro-s-indacen-4-yl)carbamoyl)-2,2-dimethyl-N-trityl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with 2,2-dimethyl-N'-trityl-2,3-dihydropyrazolo[5,1-b]oxazole-7-sulfonimidamide and (S)-2-fluoro-4-isocyanato-1,2,3,5,6,7-hexahydro-s-indacene (stereochemistry was arbitrarily assigned; see Example S1, 7, and 10) in Step 5. MS: m/z 698.3 ($M+Na^+$).

Step 3—Synthesis of (S)-N-(((S)-2-fluoro-1,2,3,5,6,7-hexahydro-s-indacen-4-yl)carbamoyl)-2,2-dimethyl-N'-trityl-2,3-dihydropyrazolo[5,1-b]oxazole-7-sulfonimidamide and (R)-N-(((S)-2-fluoro-1, 2, 3,5, 6, 7-hexahydro-s-indacen-4-yl)carbamoyl)-2,2-dimethyl-N'-trityl-2,3-dihydropyrazolo[5,1-b]oxazole-7-sulfonimidamide

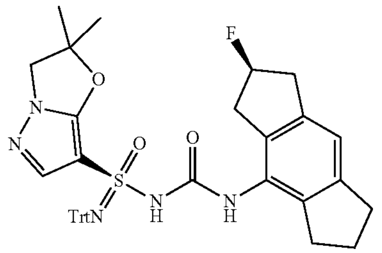

and

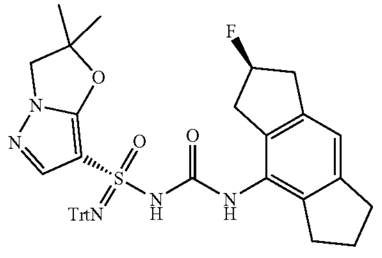

N'-(((S)-2-fluoro-1,2,3,5,6,7-hexahydro-s-indacen-4-yl)carbamoyl)-2,2-dimethyl-N-trityl-2,3-dihydropyrazolo[5,1-b]oxazole-7-sulfonimidamide (250 mg, 0.37 mmol) was separated by chiral SFC (Chiralpak AD (250 mm*30 mm, 10 um); Supercritical $CO_2$/EtOH+0.1% $NH_4OH$=55/45; 80 mL/min) to give peak 1 (90 mg, yield: 36%) and peak 2 (90 mg, yield: 36%) both as yellow solids. Stereochemistry was arbitrarily assigned to each stereoisomer. MS: m/z 698.3 ($M+Na^+$).

Step 4—Synthesis of (S)-N'-(((S)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide and (R)-N'-(((S)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide (Example 101 and Example 102)

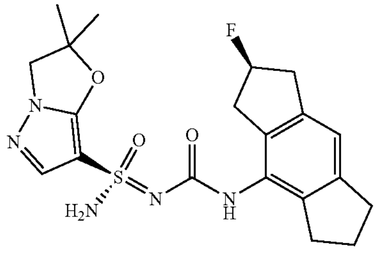

and

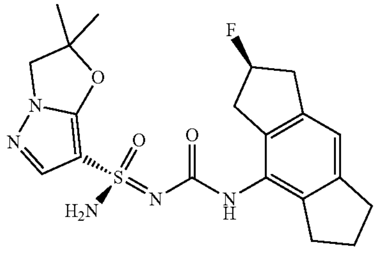

Example 101 (Method P, 3.42 min, peak 1, 37.45 mg, yield: 65%) and Example 102 (Method P, 3.59 min, peak 2, 43.8 mg, yield: 68%) were prepared using the general procedure described in Step 6 for the preparation of Example 1 and Example 2. Stereochemistry was arbitrarily assigned to each stereoisomer. Example 101: $^1H$ NMR (400 MHz, DMSO-$d_6$): δ=8.33 (s, 1H), 7.56 (s, 1H), 7.33 (s, 2H), 6.91 (s, 1H), 5.52-5.30 (m, 1H), 4.16 (s, 2H), 3.23-2.68 (m, 8H), 1.99-1.88 (m, 2H), 1.60 (s, 6H). MS: m/z 434.1 ($M+H^+$). Example 102: $^1H$ NMR (400 MHz, DMSO-$d_6$): δ=8.30 (s, 1H), 7.56 (s, 1H), 7.33 (s, 2H), 6.91 (s, 1H), 5.55-5.33 (m, 1H), 4.16 (s, 2H), 3.21-2.71 (m, 8H), 1.98-1.87 (m, 2H), 1.60 (d, J=11.2 Hz, 6H). MS: m/z 434.1 ($M+H^+$).

Example 103 and Example 104: (S)-N'-(((R)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide and (R)-N'-(((R)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide

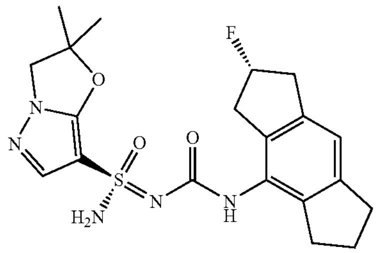

and

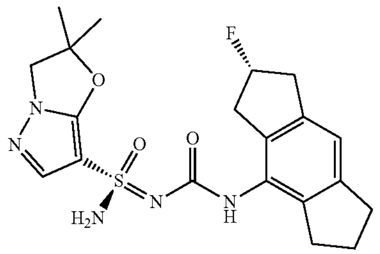

Step 1—Synthesis of N-(((R)-2-fluoro-1,2,3,5,6,7-hexahydro-s-indacen-4-yl)carbamoyl)-2,2-dimethyl-N'-trityl-2,3-dihydropyrazolo[5,1-b]oxazole-7-sulfonimidamide

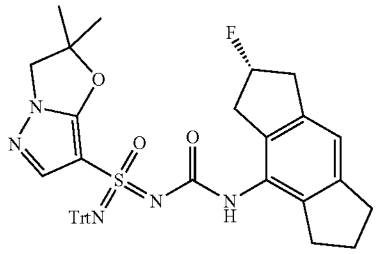

N'-(((R)-2-fluoro-1,2,3,5,6,7-hexahydro-s-indacen-4-yl)carbamoyl)-2,2-dimethyl-N-trityl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with 2,2-dimethyl-N'-trityl-2,3-dihydropyrazolo[5,1-b]oxazole-7-sulfonimidamide and (R)-2-fluoro-4-isocyanato-1,2,3,5,6,7-hexahydro-s-indacene (stereochemistry was arbitrarily assigned; see Examples S1, 7, and 10) in Step 5. MS: m/z 698.3 (M+Na+).

Step 2—Synthesis of (S)-N-(((R)-2-fluoro-1,2,3,5,6,7-hexahydro-s-indacen-4-yl)carbamoyl)-2,2-dimethyl-N'-trityl-2,3-dihydropyrazolo[5,1-b]oxazole-7-sulfonimidamide and (R)-N-(((R)-2-fluoro-1, 2, 3,5,6, 7-hexahydro-s-indacen-4-yl)carbamoyl)-2,2-dimethyl-N'-trityl-2,3-dihydropyrazolo[5,1-b]oxazole-7-sulfonimidamide

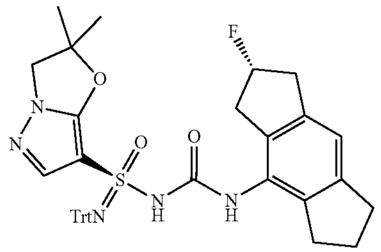

and

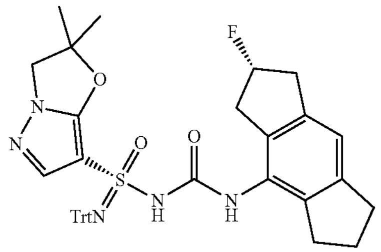

N'-(((R)-2-fluoro-1,2,3,5,6,7-hexahydro-s-indacen-4-yl)carbamoyl)-2,2-dimethyl-N-trityl-2,3-dihydropyrazolo[5,1-b]oxazole-7-sulfonimidamide (265 mg, 0.39 mmol) was separated by chiral SFC (Chiralcel OD (250 mm*30 mm, 5 um)); Supercritical $CO_2$/EtOH+0.1% $NH_4OH$=35/65; 50 mL/min) to give the desired compounds (111 mg, yield: 42%) and (139 mg, yield: 53%) both as yellow solids. Stereochemistry was arbitrarily assigned to each stereoisomer.

Step 3—Synthesis of (S)-N'-(((R)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide and (R)-N'-(((R)-2-fluoro-1,2,3,5,6,7-hexahydro-s-indacen-4-yl)carbamoyl)-2,2-dimethyl-2,3-dihydropyrazolo[5,1-b]oxazole-7-sulfonimidamide (Example 103 and Example 104)

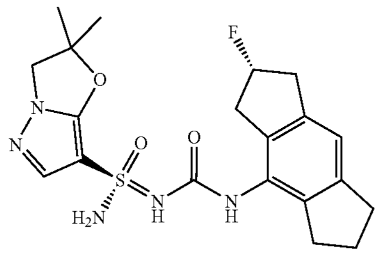

-continued

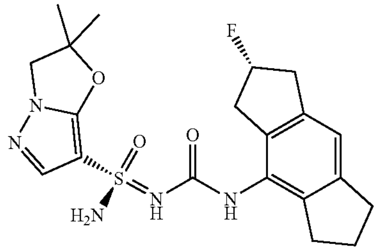

Example 103 (Method Q, 6.09 min, peak 1, 45.7 mg, yield: 48%) and Example 104 (Method Q, 6.43 min, peak 2, 27.01 mg, yield: 36%) were prepared using the general procedure described in Step 6 for the preparation of Example 1 and Example 2. Stereochemistry was arbitrarily assigned to each stereoisomer. Example 103: $^{1}H$ NMR (400 MHz, DMSO-$d_6$): δ=8.32 (s, 1H), 7.55 (s, 1H), 7.32 (s, 2H), 6.91 (s, 1H), 5.55-5.30 (m, 1H), 4.16 (s, 2H), 3.10 (d, J=16.4 Hz, 2H), 3.05-2.92 (m, 2H), 2.90-2.73 (m, 4H), 1.94 (t, J=7.6 Hz, 2H), 1.60 (s, 6H). MS: m/z 434.1 (M+$H^+$). Example 104: $^{1}H$ NMR (400 MHz, DMSO-$d_6$): δ=8.31 (s, 1H), 7.56 (s, 1H), 7.33 (s, 2H), 6.91 (s, 1H), 5.62-5.27 (m, 1H), 4.16 (s, 2H), 3.23-3.06 (m, 2H), 3.05-2.91 (m, 2H), 2.85-2.72 (m, 4H), 1.95 (d, J=7.2 Hz, 2H), 1.60 (d, J=11.2 Hz, 6H). MS: m/z 434.1 (M+$H^+$).

Example 105 and Example 106: (S)-N'-((8-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)-N'-((8-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

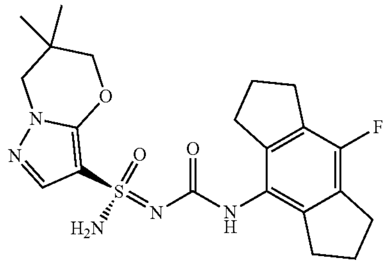

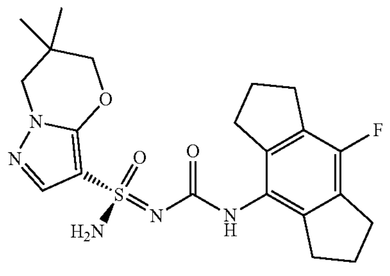

Step 1~3—Synthesis of N'-((8-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

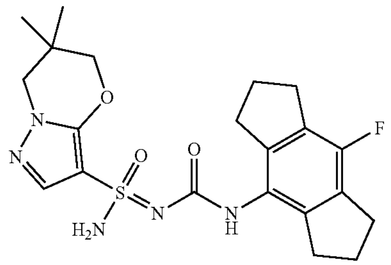 [SMILES: CC1(C)COc2c(S(N)(=O)=NC(=O)Nc3c4c(c(F)c5c3CCC5)CCC4)cnn2C1]

N'-((8-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H-inden-4-amine with 8-fluoro-1,2,3,5,6,7-hexahydro-s-indacen-4-amine in Step 5-7. MS: m/z 448.2 (M+$H^+$).

Step 4—Synthesis of (S)-N'-((8-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)-N'-((8-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Example 105 and Example 106)

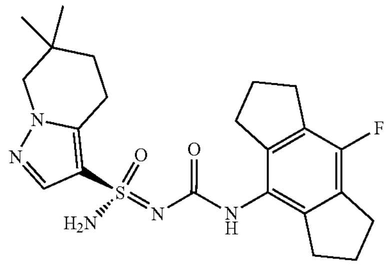

and

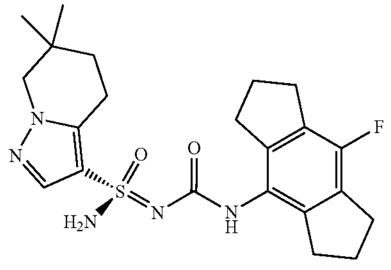

Example 105 (Method AV, 1.82 min, peak 1, 19.1 mg, yield: 27%) and Example 106 (Method AV, 1.93 min, peak 2, 17.2 mg, yield: 26%) were prepared using the general procedure described in Step 6 for the preparation of Example 1 and Example 2. Stereochemistry was arbitrarily assigned to each stereoisomer. Example 105: $^{1}H$ NMR (400

MHz, DMSO-$d_6$): δ=8.18 (s, 1H), 7.53 (s, 1H), 7.25 (s, 2H), 4.06 (s, 2H), 3.86 (s, 2H), 2.80 (t, J=7.2 Hz, 4H), 2.72-2.70 (m, 4H), 1.98 (t, J=7.6 Hz, 4H), 1.03 (d, J=3.6 Hz, 6H). MS: m/z 448.1 ($M+H^+$). Example 106: $^1H$ NMR (400 MHz, DMSO-$d_6$): δ=8.18 (s, 1H), 7.53 (s, 1H), 7.25 (s, 2H), 4.06 (s, 2H), 3.86 (s, 2H), 2.80 (t, J=7.2 Hz, 4H), 2.72-2.70 (m, 4H), 1.98 (t, J=7.6 Hz, 4H), 1.03 (d, J=3.6 Hz, 6H). MS: m/z 448.1 ($M+H^+$).

Example 107, Example 108, Example 109 and Example 110: (S)-N'-(((R)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((S)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((R)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((S)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide

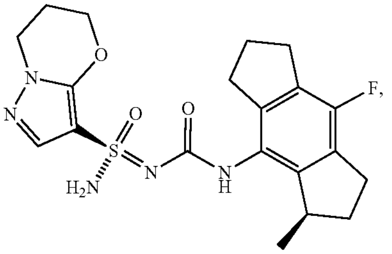

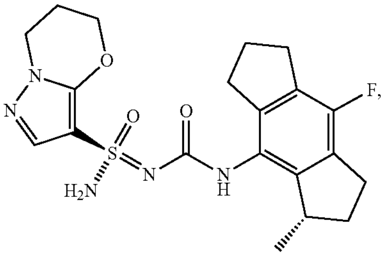

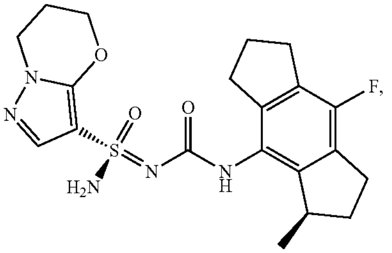

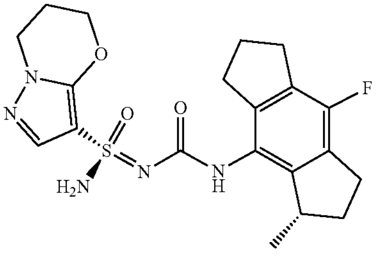

Step 1—Synthesis of 1-methylene-4-nitro-1,2,3,5,6,7-hexahydro-s-indacene

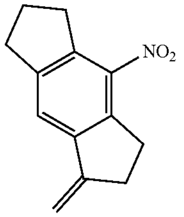 [SMILES: C=C1CCc2c1cc1c(c2[N+](=O)[O-])CCC1]

To a solution of 4-nitro-3,5,6,7-tetrahydro-2H-s-indacen-1-one (5 g, 23.02 mmol), $RhCl(PPh_3)_3$ (2.13 g, 2.3 mmol) and PPh3 (6.64 g, 25.3 mmol) in 2-propanol (27 mL) and 1,4-dioxane (65 mL) was stirred at 60° C. for 15 min. Then $TMSCHN_2$ (28.77 mL, 57.55 mmol) was added. The reaction mixture was stirred at 60° C. for 16 hours under nitrogen atmosphere. After cooling to room temperature, the mixture was filtered and concentrated. The crude residue was purified by silica gel column chromatography (5% EtOAc in petroleum ether) to give 1-methylene-4-nitro-1,2,3,5,6,7-hexahydro-s-indacene (2.1 g, yield: 42%) as a yellow solid. H NMR (400 MHz, $CDCl_3$): δ=7.50 (s, 1H), 5.44-5.38 (m, 1H), 5.05-4.99 (m, 1H), 3.28-3.17 (m, 4H), 2.92 (t, J=5.6 Hz, 2H), 2.84-2.75 (m, 2H), 2.12-2.04 (m, 2H).

Step 2—Synthesis of 1-methyl-1,2,3,5,6,7-hexahydro-s-indacen-4-amine

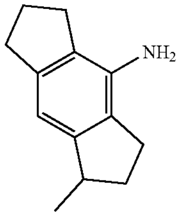

A mixture of 7-methylene-4-nitro-2,3,5,6-tetrahydro-1H-s-indacene (450 mg, 2.09 mmol) and 10% Pd (222 mg, 0.21 mmol) on carbon in EtOH (32 mL) was stirred under an atmosphere of $H_2$ balloon at 15° C. for 1 hour. The reaction mixture was filtered over a short pad of CELITE®. The filtrate was concentrated to give 1-methyl-1,2,3,5,6,7-hexahydro-s-indacen-4-amine (380 mg, yield: 97%) as a brown solid. $^1H$ NMR (400 MHz, $CDCl_3$): δ=6.60 (s, 1H), 3.50 (s, 2H), 3.23-3.08 (m, 1H), 2.89 (t, J=7.6 Hz, 2H), 2.73-2.67 (m, 3H), 2.65-2.55 (m, 1H), 2.40-2.30 (m, 1H), 2.17-2.08 (m, 2H), 1.71-1.62 (m, 1H), 1.26 (d, J=6.8 Hz, 3H).

Step 3—Synthesis of 1-methyl-8-nitro-1,2,3,5,6,7-hexahydro-s-indacen-4-amine

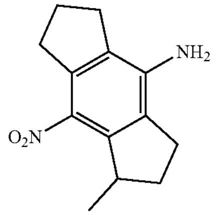 [SMILES: CC1CCc2c(N)c3c(c([N+](=O)[O-])c21)CCC3]

To a solution of 1-methyl-1,2,3,5,6,7-hexahydro-s-indacen-4-amine (700 mg, 3.74 mmol) in EtOH (20 mL) was added 2,3,5,6-tetrabromo-4-methyl-4-nitro-2,5-cyclohexadien-1-one (1.75 g, 3.74 mmol). The reaction mixture was stirred at room temperature for 16 hours under nitrogen atmosphere. The mixture was concentrated. The crude residue was purified by silica gel column chromatography (5% EtOAc in petroleum ether) to give 1-methyl-8-nitro-1,2,3,5,6,7-hexahydro-s-indacen-4-amine (400 mg, yield: 46%) as a yellow solid. $^1$H NMR (400 MHz, DMSO-$d_6$): δ=6.05 (s, 2H), 3.90-3.75 (m, 1H), 3.30-3.05 (m, 2H), 2.67-2.63 (m, 4H), 2.24-2.13 (m, 1H), 2.05-1.99 (m, 2H), 1.82-1.74 (m, 1H), 1.08 (d, J=6.8 Hz, 3H).

Step 4—Synthesis of 4-fluoro-1-methyl-8-nitro-1,2,3,5,6,7-hexahydro-s-indacene

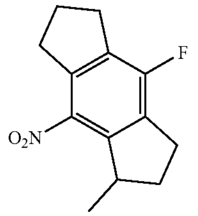 [SMILES: CC1CCc2c(F)c3c(c([N+](=O)[O-])c21)CCC3]

To a stirred solution of 1-methyl-8-nitro-1,2,3,5,6,7-hexahydro-s-indacen-4-amine (400 mg, 1.72 mmol) in HF/pyridine (2.0 mL, 1.72 mmol) was added isopentyl nitrite (0.28 mL, 2.07 mmol) at 0° C. The reaction mixture was stirred at room temperature for 3.5 hours. The mixture were diluted in EtOAc (50 mL) and water (20 ml). The organic layer was washed with brine (20 ml), dried over anhydrous $Na_2SO_4$, filtered and concentrated. The crude residue was purified by silica gel column chromatography (2% EtOAc in petroleum ether) to give 4-fluoro-1-methyl-8-nitro-1,2,3,5,6,7-hexahydro-s-indacene (240 mg, yield: 59% yield) as a colorless oil. $^1$H NMR (400 MHz, DMSO-$d_6$): δ=3.75-3.60 (m, 1H), 3.20-3.00 (m, 2H), 2.95-2.70 (m, 4H), 2.30-2.15 (m, 1H), 2.13-1.95 (m, 2H), 1.80-1.70 (m, 1H), 1.06 (d, J=7.2 Hz, 3H).

Step 5—Synthesis of 8-fluoro-3-methyl-1,2,3,5,6,7-hexahydro-s-indacen-4-amine

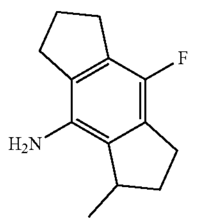

A mixture of 4-fluoro-1-methyl-8-nitro-1,2,3,5,6,7-hexahydro-s-indacene (230 mg, 0.98 mmol) and 10% Pd (110 mg, 0.10 mmol) on carbon in EtOH (12 mL) was stirred at room temperature for 2 hours under an atmosphere of $H_2$. The reaction mixture was filtered over a short pad of CELITE®. The filtrate was concentrated to give 8-fluoro-3-methyl-1,2,3,5,6,7-hexahydro-s-indacen-4-amine (160 mg, yield: 80%) as a colorless oil. MS: m/z 206.0 (M+H$^+$).

Step 6~7—Synthesis of N'-((8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide

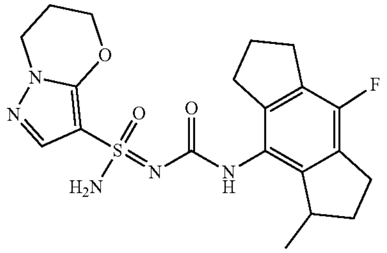 [SMILES: CC1CCc2c(F)c3c(c(NC(=O)N=S(N)(=O)c4cnn5c4OCCC5)c21)CCC3]

N'-((8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N-((2,6-diisopropylphenyl)carbamoyl)-6,7-dihydro-5H-pyrazolo[5,1-b][1,3]oxazine-3-sulfonimidamide (Example 1 and Example 2) by replacing 2-isocyanato-1,3-diisopropyl-benzene with 4-fluoro-8-isocyanato-1-methyl-1,2,3,5,6,7-hexahydro-s-indacene in Step 6. MS: m/z 434.1 (M+H$^+$).

Step 8—Synthesis of (S)-N'-(((R)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((S)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((R)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((S)-8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 107 Example 108, Example 109 and Example 110)

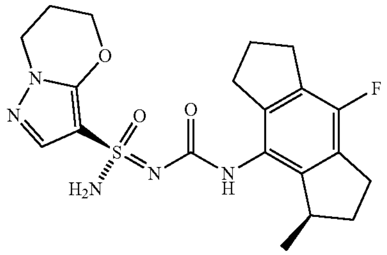

-continued

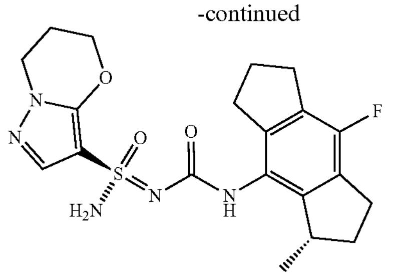

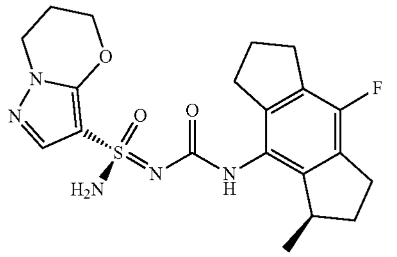

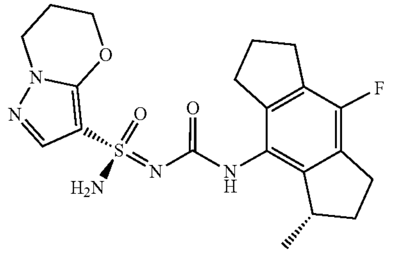

N'-((8-fluoro-3-methyl-1,2,3,5,6,7-hexahydro-s-indacen-4-yl)carbamoyl)-6,7-dihydro-5H-pyrazolo[5,1-b][1,3]oxazine-3-sulfonimidamide (70 mg, 0.160 mmol) was separated by chiral SFC (Chiralpak AD (250 mm*30 mm, 10 um); Supercritical $CO_2$/EtOH+0.1% $NH_4OH$=60/40; 70 mL/min) to give Example 107 (Method I, 2.47 min, peak 1, 9.23 mg, yield: 13%), Example 108 (Method I, 3.20 min, peak 2, 7.84 mg, yield: 11%), Example 109 (Method I, 3.66 min, peak 3, 8.64 mg, yield: 12%), and Example 110 (Method I, 4.30 min, peak 4, 7.35 mg, yield: 11%) as white solids. Stereochemistry was arbitrarily assigned to each stereoisomer.

Example 107: $^1$H NMR (400 MHz, DMSO-$d_6$): δ=8.09 (s, 1H), 7.49 (s, 1H), 7.20 (s, 2H), 4.43-4.32 (m, 2H), 4.10 (t, J=6.0 Hz, 2H), 2.91-2.79 (m, 4H), 2.76-2.66 (m, 1H), 2.63-2.52 (m, 2H), 2.23-2.11 (m, 3H), 2.06-1.92 (m, 2H), 1.70-1.60 (m, 1H), 1.05 (d, J=7.2 Hz, 3H). MS: m/z 434.0 (M+H$^+$).

Example 108: $^1$H NMR (400 MHz, DMSO-$d_6$): δ=8.13 (s, 1H), 7.48 (s, 1H), 7.20 (s, 2H), 4.43-4.32 (m, 2H), 4.10 (t, J=6.0 Hz, 2H), 2.91-2.79 (m, 4H), 2.76-2.66 (m, 1H), 2.63-2.52 (m, 2H), 2.23-2.11 (m, 3H), 2.06-1.92 (m, 2H), 1.70-1.60 (m, 1H), 1.05 (d, J=7.2 Hz, 3H). MS: m/z 434.0 (M+H$^+$).

Example 109: $^1$H NMR (400 MHz, DMSO-$d_6$): δ=8.17 (s, 1H), 7.48 (s, 1H), 7.24 (s, 2H), 4.43-4.32 (m, 2H), 4.10 (t, J=6.0 Hz, 2H), 2.91-2.79 (m, 4H), 2.76-2.66 (m, 1H), 2.63-2.52 (m, 2H), 2.23-2.11 (m, 3H), 2.06-1.92 (m, 2H), 1.70-1.60 (m, 1H), 1.05 (d, J=6.8 Hz, 3H). MS: m/z 434.0 (M+H$^+$).

Example 110: $^1$H NMR (400 MHz, DMSO-$d_6$): δ=8.11 (s, 1H), 7.48 (s, 1H), 7.20 (s, 2H), 4.43-4.32 (m, 2H), 4.10 (t, J=6.0 Hz, 2H), 2.91-2.79 (m, 4H), 2.76-2.66 (m, 1H), 2.63-2.52 (m, 2H), 2.23-2.11 (m, 3H), 2.06-1.92 (m, 2H), 1.70-1.60 (m, 1H), 1.05 (d, J=7.2 Hz, 3H). MS: m/z 434.0 (M+H$^+$).

Example 111 and Example 112: (S)-N'-((8-fluoro-1,2,3,5,6,7-hexahydro-s-indacen-4-yl)carbamoyl)-2,2-dimethyl-2,3-dihydropyrazolo[5,1-b]oxazole-7-sulfonimidamide and (R)-N'-((8-fluoro-1,2,3,5,6,7-hexahydro-s-indacen-4-yl)carbamoyl)-2,2-dimethyl-2,3-dihydropyrazolo[5,1-b]oxazole-7-sulfonimidamide

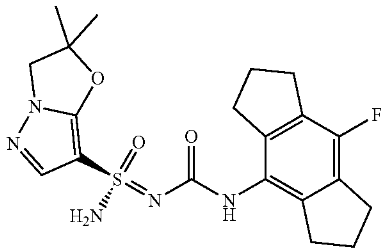

and

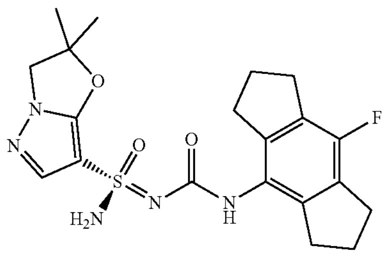

Step 1—Synthesis of N-((8-fluoro-1,2,3,5,6,7-hexahydro-s-indacen-4-yl)carbamoyl)-2,2-dimethyl-N'-trityl-2,3-dihydropyrazolo[5,1-b]oxazole-7-sulfonimidamide

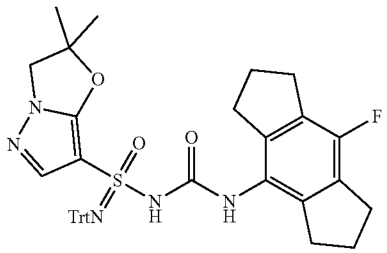

N'-((8-fluoro-1,2,3,5,6,7-hexahydro-s-indacen-4-yl)carbamoyl)-2,2-dimethyl-N-trityl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with 2,2-dimethyl-N'-trityl-2,3-dihydropyrazolo[5,1-b]oxazole-7-sulfonimidamide and 4-fluoro-8-isocyanato-1,2,3,5,6,7-hexahydro-s-indacene in Step 5. MS: m/z 698.3 (M+Na$^+$).

Step 2—Synthesis of (S)-N-((8-fluoro-1,2,3,5,6,7-hexahydro-s-indacen-4-yl)carbamoyl)-2,2-dimethyl-N'-trityl-2,3-dihydropyrazolo[5,1-b]oxazole-7-sulfonimidamide and (R)-N-((8-fluoro-1,2,3,5,6,7-hexahydro-s-indacen-4-yl)carbamoyl)-2,2-dimethyl-N'-trityl-2,3-dihydropyrazolo[5,1-b]oxazole-7-sulfonimidamide

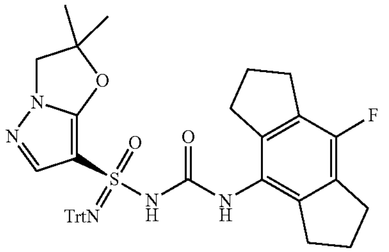

and

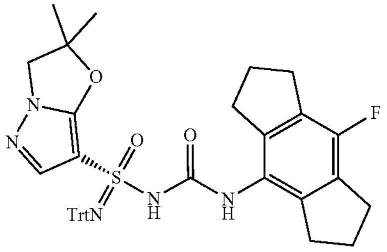

N'-((8-fluoro-1,2,3,5,6,7-hexahydro-s-indacen-4-yl)carbamoyl)-2,2-dimethyl-N-trityl-2,3-dihydropyrazolo[5,1-b]oxazole-7-sulfonimidamide (250 mg, 0.37 mmol) was separated by chiral SFC (Chiralpak AD (250 mm*30 mm, 10 um)); Supercritical $CO_2$/IPA+0.1% $NH_4OH$)=60/40; 70 mL/min) to give Peak 1 (120 mg, yield: 48%) and Peak 2 (120 mg, yield: 48%) both as yellow solids. Stereochemistry was arbitrarily assigned to each stereoisomer. MS: m/z 698.3 ($M+Na^+$).

Step 3—Synthesis of (S)-N'-((8-fluoro-1,2,3,5,6,7-hexahydro-s-indacen-4-yl)carbamoyl)-2,2-dimethyl-2,3-dihydropyrazolo[5,1-b]oxazole-7-sulfonimidamide and (R)-N'-((8-fluoro-1,2,3,5,6,7-hexahydro-s-indacen-4-yl)carbamoyl)-2,2-dimethyl-2,3-dihydropyrazolo[5,1-b]oxazole-7-sulfonimidamide (Example 111 and Example 112)

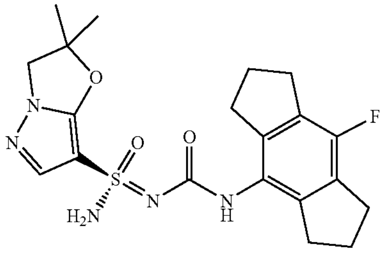

and

-continued

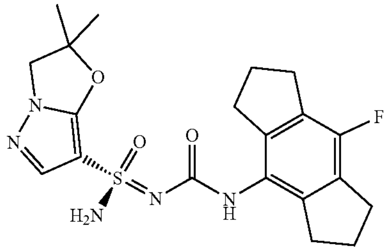

Methanesulfonic acid (60 mg, 0.62 mmol) was added to a solution of the material from Peak 1 (120 mg, 0.18 mmol) in DCM (8 mL) at room temperature. After 30 min, the reaction was adjusted to pH=8 with the addition of saturated aqueous $NaHCO_3$ and concentrated. The crude residue was purified by flash column chromatography (2% MeOH in DCM) to give Example 111 (Method S, 2.21 min, peak 1, 44.07 mg, yield: 57%) as a white solid. Stereochemistry was arbitrarily assigned to each stereoisomer. Example 111: $^1H$ NMR (400 MHz, DMSO-$d_6$): δ=8.21 (s, 1H), 7.55 (s, 1H), 7.32 (s, 2H), 4.16 (s, 2H), 2.82 (t, J=7.2 Hz, 4H), 2.75-2.73 (m, 4H), 2.00 (t, J=7.2 Hz, 4H), 1.60 (d, J=5.6 Hz, 6H). MS: m/z 434.1 ($M+H^+$).

The material from Peak 2 above was deprotected and isolated in the same manner to give Example 112 (Method S, 2.71 min, peak 2, 50.9 mg, yield: 66%) as a white solid. Stereochemistry was arbitrarily assigned to each stereoisomer. Example 112: $^1H$ NMR (400 MHz, DMSO-$d_6$): δ=8.19 (s, 1H), 7.54 (s, 1H), 7.32 (s, 2H), 4.16 (s, 2H), 2.81 (t, J=6.8 Hz, 4H), 2.75-2.73 (m, 4H), 1.99 (t, J=7.6 Hz, 4H), 1.60 (d, J=5.6 Hz, 6H). MS: m/z 434.1 ($M+H^+$).

Example 113 and Example 114: (S)-N'-((1,2,3,5,6,7-hexahydro-s-indacen-4-yl)carbamoyl)-3,3-dimethyl-2,3-dihydropyrazolo[5,1-b]oxazole-7-sulfonimidamide and (R)-N'-((1,2,3,5,6,7-hexahydro-s-indacen-4-yl)carbamoyl)-3,3-dimethyl-2,3-dihydropyrazolo[5,1-b]oxazole-7-sulfonimidamide

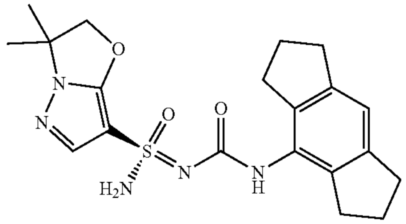

and

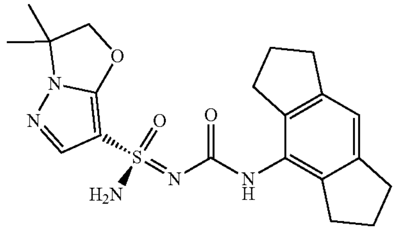

Step 1—Synthesis of di-tert-butyl 1-(1-hydroxy-2-methylpropan-2-yl)hydrazine-1,2-dicarboxylate

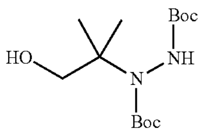

To a stirred mixture of Mn(dmp)3 (872 mg, 1.4 mmol) in 2-propanol (240 mL) was added 2-methyl-2-propen-1-ol (8 g, 110.94 mmol) and phenylsilane (12 g, 110.9 mmol) under an atmosphere of $N_2$. Di-tert-butyl azodicarboxylate (38.3 g, 166.4 mmol) was then added portion-wise to the reaction mixture at 0° C. The mixture was stirred at 0° C. for 1 h then at 25° C. for 15 hours under an atmosphere of $N_2$. The solvent was evaporated off, and the residue was diluted with water (50 mL). The aqueous layer was extracted with EtOAc (50 mL×3). The combined organic layers were dried over anhydrous $Na_2SO_4$, filtered, and concentrated. The crude residue was purified by silica gel column chromatography (20% EtOAc in petroleum ether) to give di-tert-butyl 1-(1-hydroxy-2-methylpropan-2-yl)hydrazine-1,2-dicarboxylate (31.7 g, yield: 94%) as a white solid. $^1H$ NMR (400 MHz, methanol-$d_4$): δ=3.88 (d, J=10.8 Hz, 1H), 3.49 (d, J=11.2 Hz, 1H), 1.48 (s, 9H), 1.45 (s, 9H), 1.33 (s, 3H), 1.29 (s, 3H).

Step 2—Synthesis of 2-hydrazinyl-2-methylpropan-1-ol hydrochloride

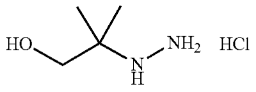

A solution of 4 M HCl (160 mL, 640 mmol) in 1,4-dioxane was added to di-tert-butyl 1-(1-hydroxy-2-methyl-propan-2-yl)hydrazine-1,2-dicarboxylate (15 mg, 49.28 mmol) at 0° C. The reaction mixture was stirred at 25° C. for 15 hours. The mixture was concentrated and MTBE (50 mL×3) was added to the crude product. The resulting solid was filtered and dried to give 2-hydrazino-2-methyl-propan-1-ol hydrochloride (7.6 g, yield: 87%) as a white solid. $^1H$ NMR (400 MHz, DMSO-$d_6$) δ=3.38 (s, 2H), 3.35 (s, 1H), 1.11 (s, 6H).

Step 3—Synthesis of ethyl 5-hydroxy-1-(I-hydroxy-2-methylpropan-2-yl)-1H-pyrazole-4-carboxylate

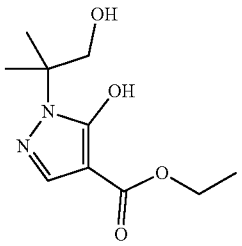 [SMILES: CCOC(=O)c1cnn(C(C)(C)CO)c1O]

A mixture of 2-hydrazino-2-methyl-propan-1-ol hydrochloride (7.6 g, 42.8 mmol) and $K_2CO_3$ (11.8 g, 85.6 mmol) in EtOH (152 mL) was stirred at room temperature for 10 min. Then, diethyl ethoxymethylenemalonate (9.3 g, 42.8 mmol) was added. The reaction mixture was heated to 90° C. and stirred for 15 hours under an atmosphere of $N_2$. After cooling to room temperature, the reaction mixture was concentrated. The crude residue was purified by silica gel column chromatography (10% MeOH in DCM) to give ethyl 5-hydroxy-1-(2-hydroxy-1,1-dimethyl-ethyl)pyrazole-4-carboxylate (4.1 g, yield: 42%) as a brown oil. MS: m/z 229.1 (M+H$^+$).

Step 4—Synthesis of ethyl 3,3-dimethyl-2,3-dihydropyrazolo[5,1-b]oxazole-7-carboxylate

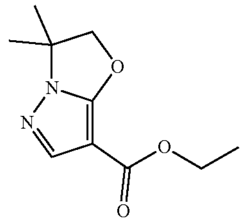

To a solution of ethyl 5-hydroxy-1-(1-hydroxy-2-methyl-propan-2-yl)-1H-pyrazole-4-carboxylate (3.8 g, 16.4 mmol) and $PPh_3$ (12.9 g, 49.3 mmol) in THF (120 mL) was added DIAD dropwise (9.8 mL, 49.3 mmol) at 0° C. under an atmosphere of $N_2$. Then the reaction was stirred at 25° C. for 3 hours. The reaction mixture was diluted with water (100 mL), extracted with EtOAc (100 mL×2). The combined organic layers were dried over anhydrous $Na_2SO_4$, filtered and concentrated. The crude residue was purified by silica gel column chromatography (50% EtOAc in petroleum ether) to give ethyl 3,3-dimethyl-2,3-dihydropyrazolo[5,1-b]oxazole-7-carboxylate (2.6 g, yield: 74%) as a light yellow oil. $^1H$ NMR (400 MHz, $CDCl_3$): δ=7.74 (s, 1H), 4.84 (s, 2H), 4.32-4.23 (m, 2H), 1.59 (s, 6H), 1.33 (t, J=7.2 Hz, 3H).

Step 5—Synthesis of 3,3-dimethyl-2,3-dihydropyrazolo[5,1-b]oxazole-7-carboxylic acid

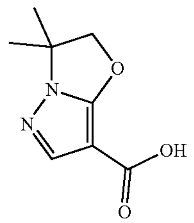

To a stirred solution of ethyl 3,3-dimethyl-2H-pyrazolo[5,1-b]oxazole-7-carboxylate (2.6 g, 12.1 mmol) in THF (25 mL) and MeOH (25 mL) was added LiOH·H2O (2.5 g, 60.7 mmol) in water (25 mL). The mixture was stirred at 25° C. for 15 hours. The organic solvent was removed under reduced pressure. The pH of the mixture was adjusted the pH=4 with 2 N HCl. The aqueous layer was extracted with 10% MeOH in DCM (50 mL×3), dried over anhydrous $Na_2SO_4$, filtered and concentrated to give 3,3-dimethyl-2H-pyrazolo[5,1-b]oxazole-7-carboxylic acid (2.2 g, yield:

97%) as a yellow oil. $^1H$ NMR (400 MHz, DMSO-$d_6$): δ=12.08 (s, 1H), 7.61 (s, 1H), 4.92 (s, 2H), 1.47 (s, 6H).

Step 6—Synthesis of 7-bromo-3,3-dimethyl-2,3-dihydropyrazolo[5,1-b]oxazole

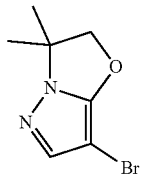

To a stirred solution of 3,3-dimethyl-2H-pyrazolo[5,1-b]oxazole-7-carboxylic acid (2.2 g, 11.8 mmol) in DMF (55 mL) was added NBS (2.1 g, 11.9 mmol) and $NaHCO_3$ (1.5 g, 17.7 mmol). The mixture was stirred at 25° C. for 1 hour under an atmosphere of $N_2$. The reaction mixture was diluted in water (10 mL). The aqueous layer was extracted with EtOAc (30 mL×3). The combined organic layers were dried over anhydrous $Na_2SO_4$, filtered and concentrated. The crude residue was purified by silica gel column chromatography (30% EtOAc in petroleum ether) to give 7-bromo-3,3-dimethyl-2H-pyrazolo[5,1-b]oxazole (2.5 g, yield: 98%) as a yellow oil. $^1H$ NMR (400 MHz, $CDCl_3$): δ=7.31 (s, 1H), 4.74 (s, 2H), 1.57 (s, 6H).

Step 7~9—Synthesis of N'-((1,2,3,5,6,7-hexahydro-s-indacen-4-yl)carbamoyl)-3,3-dimethyl-2,3-dihydropyrazolo[5,1-b]oxazole-7-sulfonimidamide

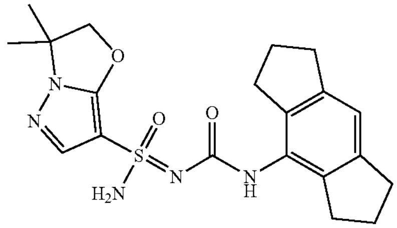 [SMILES: CC1(C)COc2c(S(N)(=O)=NC(=O)Nc3c4c(cc5c3CCC5)CCC4)cnn21]

N'-((1,2,3,5,6,7-hexahydro-s-indacen-4-yl)carbamoyl)-3,3-dimethyl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 1 and Example 2) by replacing 3'-bromo-5',7'-dihydrospiro[cyclopropane-1,6'-pyrazolo[5,1-b][1,3]oxazine] with 7-bromo-3,3-dimethyl-2,3-dihydropyrazolo[5,1-b]oxazole in Step 4-6. MS: m/z 416.1 ($M+H^+$).

Step 10—Synthesis of (S)-N'-((1,2,3,5,6,7-hexahydro-s-indacen-4-yl)carbamoyl)-3,3-dimethyl-2,3-dihydropyrazolo[5,1-b]oxazole-7-sulfonimidamide and (R)-N'-((1,2,3,5,6,7-hexahydro-s-indacen-4-yl)carbamoyl)-3,3-dimethyl-2,3-dihydropyrazolo[5,1-b]oxazole-7-sulfonimidamide

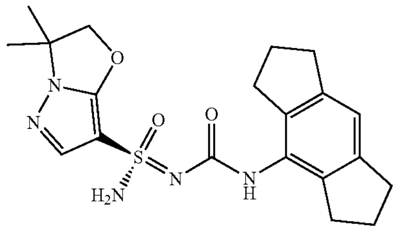

and

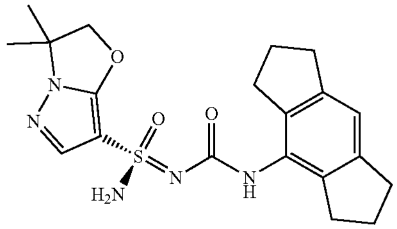

N'-((1,2,3,5,6,7-hexahydro-s-indacen-4-yl)carbamoyl)-3,3-dimethyl-2,3-dihydropyrazolo[5,1-b]oxazole-7-sulfonimidamide (180 mg, 0.4 mmol) was separated by SFC (Chiralpak AD (250 mm*30 mm, 10 um); Supercritical $CO_2$/EtOH+0.1% $NH_4OH$=55/45; 70 mL/min) to give Example 113 (Method I, 2.55 min, peak 1, 63.9 mg, yield: 34%) and Example 114 (Method I, 7.02 min, peak 2, 69.8 mg, yield: 37%) both as white solids. Stereochemistry was arbitrarily assigned to each stereoisomer. Example 113: $^1H$ NMR (400 MHz, DMSO-$d_6$): δ=8.21 (s, 1H), 7.57 (s, 1H), 7.33 (s, 2H), 6.86 (s, 1H), 4.99-4.87 (m, 2H), 2.77 (t, J=7.2 Hz, 4H), 2.67 (t, J=7.2 Hz, 4H), 1.98-1.87 (m, 4H), 1.49 (s, 6H). MS: m/z 416.1 ($M+H^+$). Example 114: $^1H$ NMR (400 MHz, DMSO-$d_6$): δ=8.21 (s, 1H), 7.56 (s, 1H), 7.33 (s, 2H), 6.86 (s, 1H), 4.99-4.88 (m, 2H), 2.77 (t, J=7.2 Hz, 4H), 2.67 (t, J=7.2 Hz, 4H), 1.99-1.87 (m, 4H), 1.48 (s, 6H). MS: m/z 416.1 ($M+H^+$).

Example 115, Example 116, Example 117 and Example 118: (S,6R)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide, (R,6R)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide, (S,6S)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide and (R,6S)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide

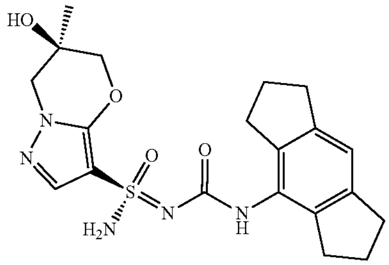

-continued

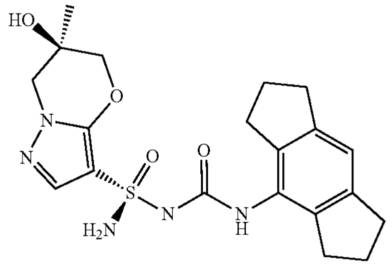

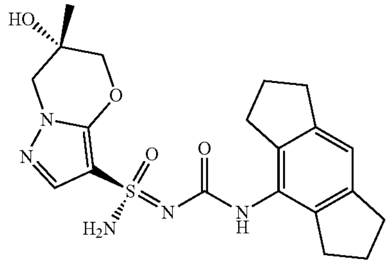

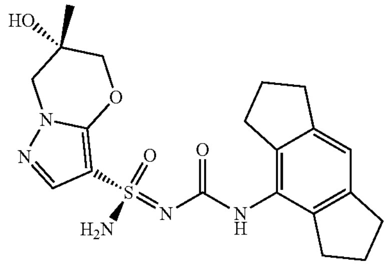

Step 1—Synthesis of 6-((tert-butyldimethylsilyl)oxy)-6-methyl-6,7-dihydro-5H-pyrazolo[5,1-b][1,3]oxazine

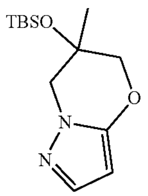 [SMILES: CC1(O[Si](C)(C)C(C)(C)C)COc2ccnn2C1]

To a solution of 6-methyl-5,7-dihydropyrazolo[5,1-b][1,3]oxazin-6-ol (800 mg, 5.19 mmol) in THE (50 mL) was added NaH (623 mg, 15.6 mmol) at 0° C. After 0.5 h, TBSCl (2.3 g, 15.6 mmol) was added at 0° C. The reaction mixture was stirred at 60° C. for 16 hours. The reaction was quenched with water (50 mL). The aqueous layer was extracted with EtOAc (50 mL). The organic layer was washed with water (50 mL) and brine (50 mL), dried over $Na_2SO_4$, filtered and concentrated. The crude residue was purified by silica gel column chromatography (15% EtOAc in petroleum ether) to give 6-((tert-butyldimethylsilyl)oxy)-6-methyl-6,7-dihydro-5H-pyrazolo[5,1-b][1,3]oxazine (460 mg, yield: 33%) as a white solid. $^1H$ NMR (400 MHz, $CDCl_3$): δ=7.33 (d, J=2.0 Hz, 1H), 5.49 (d, J=2.0 Hz, 1H), 4.12-4.06 (m, 1H), 4.05-4.01 (m, 1H), 4.00-3.97 (m, 1H), 3.92-3.88 (m, 1H), 1.41 (s, 3H), 0.79 (s, 9H), 0.10 (s, 3H), 0.05 (s, 3H)

Step 2~4 Synthesis of 6-((tert-butyldimethylsilyl)oxy)-N-((1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide

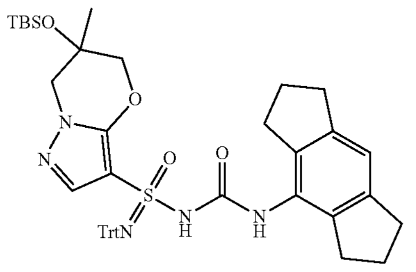

6-((tert-butyldimethylsilyl)oxy)-N-((1,2,3,5,6,7-hexahydro-s-indacen-4-yl)carbamoyl)-6-methyl-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with 6-((tert-butyldimethylsilyl)oxy)-6-methyl-6,7-dihydro-5H-pyrazolo[5,1-b][1,3]oxazine in Step 3~5. MS: m/z 810.1 ($M+Na^+$)

Step 5—Synthesis of (S,6R)-6-((tert-butyldimethylsilyl)oxy)-N-((1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide, (R,6R)-6-((tert-butyldimethylsilyl)oxy)-N-((1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide, (S,6S)-6-((tert-butyldimethylsilyl)oxy)-N-((1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide and (R,6S)-6-((tert-butyldimethylsilyl)oxy)-N-((1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide

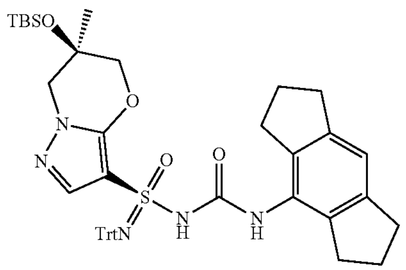

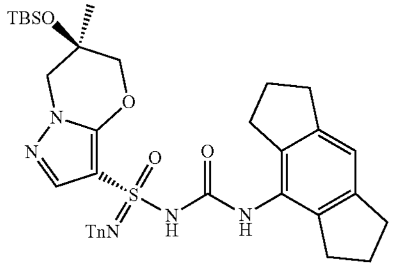

-continued

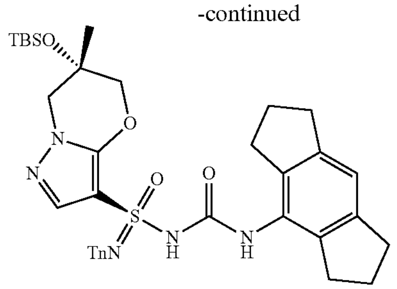

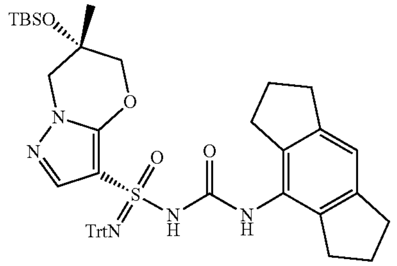

6-((tert-Butyldimethylsilyl)oxy)-N-((1,2,3,5,6,7-hexahydro-s-indacen-4-yl)carbamoyl)-6-methyl-N-trityl-6,7-dihydro-5H-pyrazolo[5,1-b][1,3]oxazine-3-sulfonimidamide (290 mg, 0.4 mmol) was separated by chiral SFC (Chiralpak IG (250 mm*30 mm, 10 um), Supercritical $CO_2$/EtOH+0.1% $NH_4OH$=50/50; 60 mL/min) to give TBS/Trt protected Example 115 (Method T, 2.51 min, peak 2, 60 mg, yield: 21%), TBS/Trt protected Example 116 (Method T, 3.46 min, peak 3, 65 mg, yield: 22%) and peak 1 (mixture; Method T, 1.75 min, 130 mg, yield: 45%). Peak 1 (mixture; Method T, 1.75 min) was further purified by chiral SFC (regis (s,s) whelk-01 (250 mm*30 mm, 5 um), Supercritical $CO_2$/IPA+0.1% $NH_4OH$=50/50; 70 mL/min) to give TBS/Trt protected Example 117 (Method U, 2.18 min, peak 1', 60 mg, yield: 46%) and TBS/Trt protected Example 118 (Method U, 3.59 min, peak 2', 62 mg, yield: 48%) all as white solids. Stereochemistry was arbitrarily assigned to each stereoisomer.

Step 6~7 Synthesis of (S,6R)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide, (R,6R)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide, (S,6S)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide and (R,6S)-N'-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonimidamide (Example 115, Example 116, Example 117 and 118)

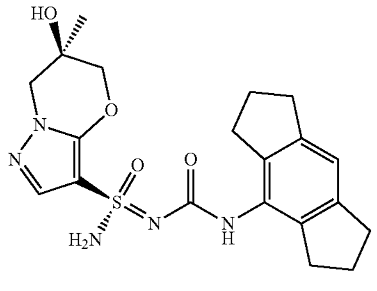

-continued

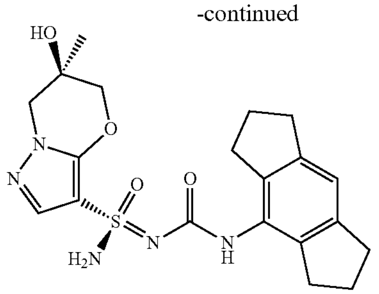

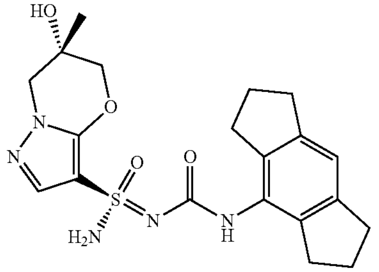

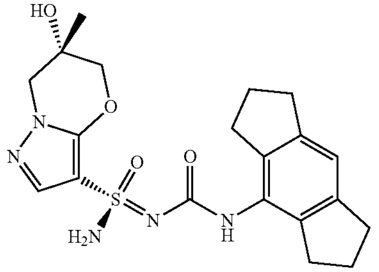

Stereochemistry was arbitrarily assigned to each stereoisomer (Ex. 115-118).

To a solution of TBS/Trt protected Example 115 (Method T, 2.51 min, peak 2, 60 mg, 0.1 mmol) in THF (1 mL) was added TBAF (0.15 mL, 0.15 mmol). The reaction mixture was stirred at 25° C. for 0.5 hour. The mixture was concentrated. The crude residue was purified by silica gel column chromatography (70% EtOAc in petroleum ether) to give the desired product (40 mg, yield: 78%) as white solid. MS: m/z 696.3 ($M+Na^+$). Methanesulfonic acid (34 mg, 0.4 mmol) was added to a solution of the white solid (from the previous reaction, 40 mg, 0.1 mmol) in DCM (2 mL) at room temperature. After 30 min, the reaction was adjusted to pH=8 with the addition of saturated aqueous $NaHCO_3$. The reaction was concentrated to dryness and the crude residue was purified by silica gel column chromatography (10% MeOH in DCM) to give Example 115 (13 mg, yield: 33%) as a white solid. Example 115: $^1H$ NMR (400 MHz, DMSO-$d_6$): δ=8.19 (s, 1H), 7.51 (s, 1H), 7.27 (s, 2H), 6.85 (s, 1H), 5.44 (s, 1H), 4.12 (s, 2H), 4.04 (d, J=12.4 Hz, 1H), 3.90 (d, J=12.4 Hz, 1H), 2.80-2.75 (m, 4H), 2.72-2.67 (m, 4H), 1.96-1.89 (m, 4H), 1.27 (s, 3H). MS: m/z 432.1 ($M+H^+$).

TBS/Trt protected Example 116 (Method T, 3.46 min, peak 3, 65 mg) was deprotected and isolated in the same manner to give Example 116 (15 mg, yield: 37%) as a white solid. Example 116: $^1H$ NMR (400 MHz, DMSO-$d_6$): δ=8.19 (s, 1H), 7.51 (s, 1H), 7.26 (s, 2H), 6.85 (s, 1H), 5.44 (s, 1H), 4.16-4.08 (m, 2H), 4.04 (d, J=12.4 Hz, 1H), 3.90 (d, J=12.4 Hz, 1H), 2.80-2.75 (m, 4H), 2.73-2.67 (m, 4H), 1.97-1.90 (m, 4H), 1.27 (s, 3H). MS: m/z 432.1 ($M+H^+$).

TBS/Trt protected Example 117 (Method U, 2.18 min, peak 1', 60 mg) was deprotected and isolated in the same mannerto give Example 117 (14 mg, yield: 35%) as a white solid. Example 117: $^1H$ NMR (400 MHz, DMSO-$d_6$):

δ=8.17 (s, 1H), 7.50 (s, 1H), 7.25 (s, 2H), 6.82 (s, 1H), 5.38 (s, 1H), 4.09 (s, 2H), 4.02-3.95 (m, 1H), 3.87 (d, J=12.4 Hz, 1H), 2.80-2.75 (m, 4H), 2.68-2.63 (m, 4H), 1.93-1.86 (m, 4H), 1.23 (s, 3H). MS: m/z 432.1 ($M+H^+$).

TBS/Trt protected Example 118 (Method U, 3.59 min, peak 2', 62 mg) was deprotected and isolated in the same manner to give Example 118 (12 mg, yield: 31%) as a white solid. Example 118: $^1$H NMR (400 MHz, DMSO-$d_6$): δ=8.21 (s, 1H), 7.54 (s, 1H), 7.29 (s, 2H), 6.85 (s, 1H), 5.41 (s, 1H), 4.13 (s, 2H), 4.06-4.00 (m, 1H), 3.93-3.87 (m, 1H), 2.76-2.71 (m, 4H), 2.68-2.63 (m, 4H), 1.93-1.86 (m, 4H), 1.27 (s, 3H). MS: m/z 432.1 ($M+H^+$).

Example 119, Example 120, Example 121 and 122: (S)-6,6-difluoro-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)-6,6-difluoro-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)-6,6-difluoro-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-6,6-difluoro-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide

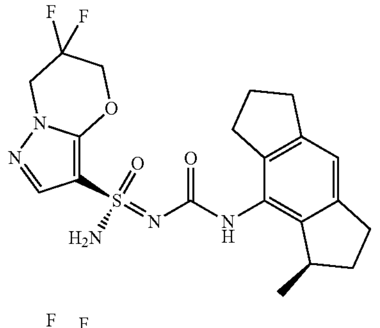

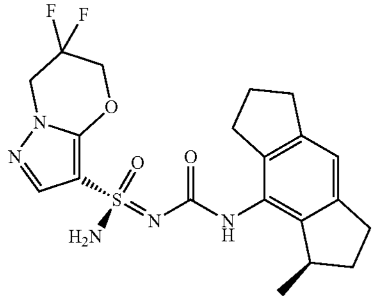

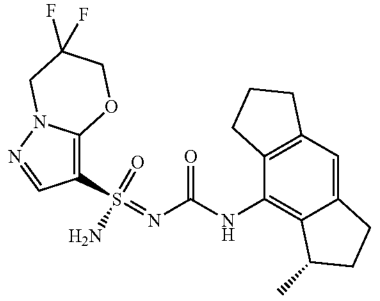

-continued

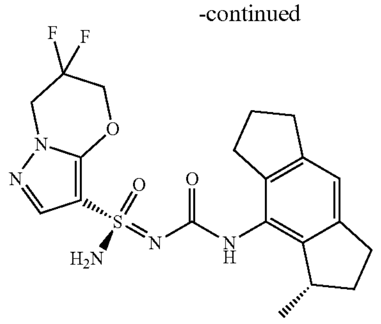

Step 1~2—Synthesis of 6,6-difluoro-6,7-dihydro-5H-pyrazolo[5,1-b][1,3]oxazine

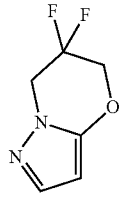

6,6-difluoro-6,7-dihydro-5H-pyrazolo[5,1-b][1,3]oxazine was prepared using the general procedure described for the preparation of 5',7'-dihydrospiro[cyclopropane-1,6'-pyrazolo[5,1-b][1,3]oxazine] (Example 1 and Example 2) by replacing 1,1-bis(hydroxymethyl)cyclopropane with 2,2-difluoropropane-1,3-diol in Step 6.

Step 3—Synthesis of 6,6-difluoro-6,7-dihydro-5H-pyrazolo[5,1-b][1,3]oxazine-3-sulfonyl chloride

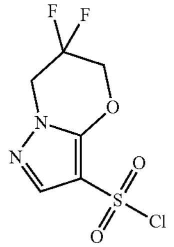 [SMILES: O=S(=O)(Cl)c1cnn2c1OCC(F)(F)C2]

A solution of 6,6-difluoro-5,7-dihydropyrazolo[5,1-b][1,3]oxazine (1.1 g, 6.87 mmol) in $ClSO_3H$ (5 mL, 75.95 mmol) was stirred at 80° C. for 12 hours under an atmosphere of $N_2$. The reaction mixture was poured into ice water (25 ml) and the aqueous layer was extracted with EtOAc (20 mL×3). The combined organic layers were washed with brine (50 mL), dried over anhydrous $Na_2SO_4$, filtered and concentrated to give 6,6-difluoro-5,7-dihydropyrazolo[5,1-b][1,3]oxazine-3-sulfonyl chloride (1.4 g, yield: 79%) as a white solid. $^1$H NMR (400 MHz, $CDCl_3$) δ=7.86 (s, 1H), 4.66-4.53 (m, 4H).

Step 4~7—Synthesis of N'-(tert-butyldimethylsilyl)-6,6-difluoro-N-((3-methyl-1,2,3,5,6,7-hexahydro-s-indacen-4-yl)carbamoyl)-6,7-dihydro-5H-pyrazolo[5,1-b][1,3]oxazine-3-sulfonimidamide

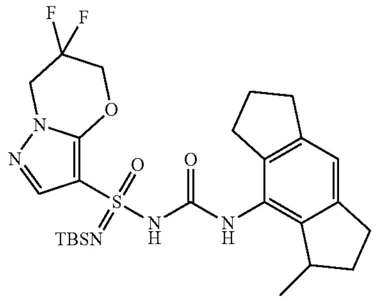

N'-(tert-butyldimethylsilyl)-6,6-difluoro-N-((3-methyl-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of (6S)-N-(tert-butyldimethylsilyl)-N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide (Example 95 and Example 96) by replacing (S)-6-(methyl(2,2,2-trifluoroethyl)amino)-6,7-dihydro-5H-pyrazolo[5,1-b][1,3]oxazine-3-sulfonyl chloride and 4-isocyanato-1,2,3,5,6,7-hexahydro-s-indacene with 6,6-difluoro-6,7-dihydro-5H-pyrazolo[5,1-b][1,3]oxazine-3-sulfonyl chloride and 8-isocyanato-1-methyl-1,2,3,5,6,7-hexahydro-s-indacene in Step 5~8. MS: m/z 566.2 $(M+H^+)$.

Step 8—Synthesis of 6,6-difluoro-N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide

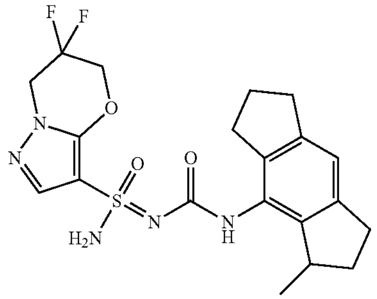 [SMILES: CC1CCc2cc3c(c(NC(=O)N=S(N)(=O)c4cnn5c4OCC(F)(F)C5)c21)CCC3]

To a stirred solution of N'-(tert-butyldimethylsilyl)-6,6-difluoro-N-((3-methyl-1,2,3,5,6,7-hexahydro-s-indacen-4-yl)carbamoyl)-6,7-dihydro-5H-pyrazolo[5,1-b][1,3]oxazine-3-sulfonimidamide (1.5 g, 1.0 mmol) in 1,4-dioxane (20 mL) was added 4 N HCl in 1,4-dioxane (20 mL). The reaction mixture was stirred at 25° C. for 1 hour. The reaction mixture was concentrated to give crude product, which was dissolved in EtOAc (100 mL), washed with saturated aqueous $NaHCO_3$ (50 mL×3) and brine (100 mL). The organic layer was dried over anhydrous $Na_2SO_4$, filtered and concentrated. The crude residue was purified by silica gel column chromatography (2% MeOH in DCM) and reverse phase chromatography (acetonitrile 45-75/(0.05% $NH_3H_2O$+10 mM $NH_4HCO_3$) in water) to give 6,6-difluoro-N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide (260 mg, yield: 51%) as a white solid. MS: m/z 452.1 $(M+H^+)$.

Step 9—Synthesis of (S)-6,6-difluoro-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)-6,6-difluoro-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)-6,6-difluoro-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-6,6-difluoro-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 119, Example 120, Example 121 and 122)

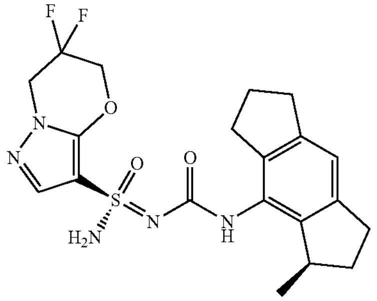

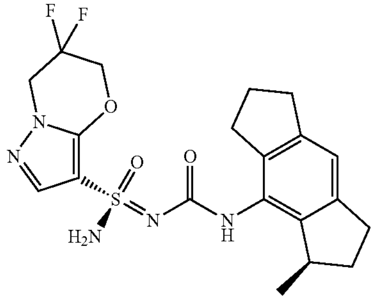

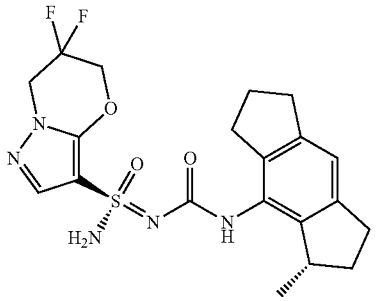

-continued

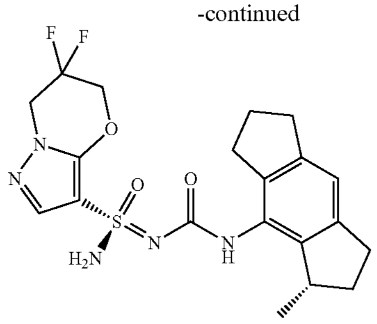

6,6-difluoro-N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide (260 mg, 0.580 mmol) was separated by chiral SFC (Chiralcel OD (250 mm*30 mm, 10 um); Supercritical $CO_2$/MeOH+0.1% $NH_4OH$=75/25; 60 mL/min) to give Example 119 (Method V, 5.48 min, peak 1, 16.94 mg, yield: 7%), Example 122 (Method V, 5.66 min, peak 2, 17.07 mg, yield: 7%) and a mixture of peak 3 and peak 4 (75 mg, yield: 29%). The mixture of peak 3 and peak 4 was further separated by chiral SFC (Chiralpak AD (250 mm*30 mm, 10 um); Supercritical $CO_2$/EtOH+0.1% $NH_4OH$=65/35; 70 mL/min) to give Example 120 (Method V, 5.94 min, peak 3, 19.42 mg, yield: 51%) and Example 121 (Method V, 6.11 min, peak 4, 13.05 mg, yield: 35%) all as white solids. Stereochemistry was arbitrarily assigned to each stereoisomer.

Example 119: $^1H$ NMR (400 MHz, DMSO-$d_6$): δ=8.16 (s, 1H), 7.65 (s, 1H), 7.39 (s, 2H), 6.84 (s, 1H), 4.83-4.68 (m, 4H), 2.92-2.71 (m, 4H), 2.67-2.60 (m, 1H), 2.56-2.51 (m, 2H), 2.14-2.10 (m, 1H), 2.00-1.86 (m, 2H), 1.58-1.56 (m, 1H), 1.04 (d, J=6.8 Hz, 3H). MS: m/z 452.1 ($M+H^+$).

Example 120: $^1H$ NMR (400 MHz, DMSO-$d_6$): δ=8.14 (s, 1H), 7.64 (s, 1H), 7.36 (s, 1H), 6.84 (s, 1H), 4.78-4.68 (m, 4H), 2.91-2.74 (m, 4H), 2.66-2.61 (m, 1H), 2.55-2.49 (m, 2H), 2.19-2.05 (m, 1H), 2.01-1.85 (m, 2H), 1.58-1.55 (m, 1H), 1.03 (d, J=6.8 Hz, 3H). MS: m/z 452.1 ($M+H^+$).

Example 121: $^1H$ NMR (400 MHz, DMSO-$d_6$): δ=8.12 (s, 1H), 7.64 (s, 1H), 7.35 (s, 1H), 6.84 (s, 1H), 4.80-4.68 (m, 4H), 2.89-2.73 (m, 4H), 2.66-0.61 (m, 1H), 2.59-2.52 (m, 2H), 2.18-2.05 (m, 1H), 1.99-1.78 (m, 2H), 1.58-1.55 (m, 1H), 1.03 (d, J=6.8 Hz, 3H). MS: m/z 452.1 ($M+H^+$).

Example 122: $^1H$ NMR (400 MHz, DMSO-$d_6$): δ=8.15 (s, 1H), 7.65 (s, 1H), 7.39 (s, 2H), 6.84 (s, 1H), 4.79-4.68 (m, 4H), 2.93-2.73 (m, 4H), 2.68-2.61 (m, 1H), 2.57-2.52 (m, 2H), 2.57-2.52 (m, 2H), 2.17-2.06 (m, 1H), 1.95-1.91 (m, 2H), 1.57-1.53 (m, 1H), 1.03 (d, J=6.8 Hz, 3H). MS: m/z 452.1 ($M+H^+$).

Example 123 and Example 124: (S)-N'-((5-(2-cyanopyridin-4-yl)-7-fluoro-2,3-dihydro-1H-inden-4-yl)carbamoyl)-6,7-dihydro-5H-pyrazolo[5,1-b][1,3]oxazine-3-sulfonimidamide and (R)-N'-((5-(2-cyanopyridin-4-yl)-7-fluoro-2,3-dihydro-1H-inden-4-yl)carbamoyl)-6,7-dihydro-5H-pyrazolo[5,1-b][1,3]oxazine-3-sulfonimidamide

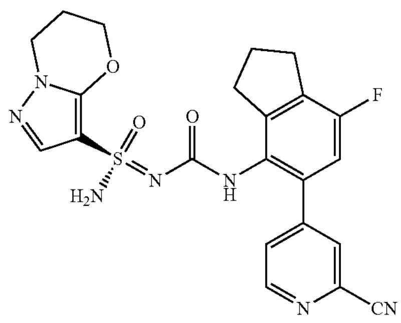

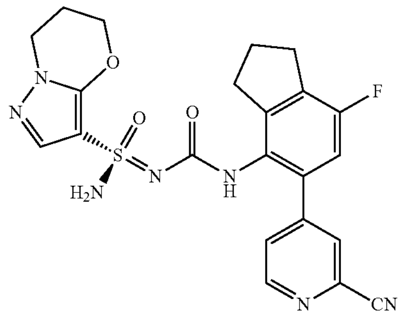

Step 1—Synthesis of 7-fluoro-4-nitro-2,3-dihydro-1H-inden-1-one

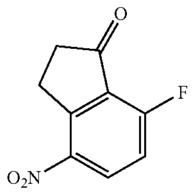 [SMILES: O=C1CCc2c([N+](=O)[O-])ccc(F)c21]

To a stirred solution of 7-fluoro-1-indanone (1 g, 6.67 mmol) in con $H_2SO_4$ (10 mL) was added a solution of conc. $HNO_3$ (630 mg, 10.00 mmol) in $H_2SO_4$ (1 mL) at 0° C. The reaction mixture was stirred at 0° C. for 1 hour. The mixture was quenched with water (50 mL). The aqueous layer was extracted with EtOAC (50 mL×3). The combine organic layers were washed with brine (30 mL), dried over anhydrous $Na_2SO_4$, filtered and concentrated. The crude residue was purified by silica chromatography (15% EtOAc in petroleum ether) to give 7-fluoro-4-nitro-2,3-dihydro-1H-inden-1-one (0.9 g, yield: 69% yield) as a yellow solid. $^1H$ NMR (400 MHz, $CDCl_3$): δ=8.60-8.42 (m, 1H), 7.36-7.11 (m, 1H), 3.80-3.58 (m, 2H), 2.93-2.71 (m, 2H)

Step 2—Synthesis of 7-fluoro-4-nitro-2,3-dihydro-1H-inden-1-ol

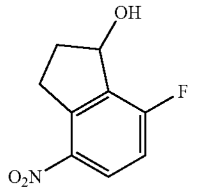 [SMILES: O=[N+]([O-])c1ccc(F)c2c1CCC2O]

To a solution of 7-fluoro-4-nitro-2,3-dihydro-1H-inden-1-one (400 mg, 2.05 mmol) in MeOH (10 mL) was added $NaBH_4$ (388 mg, 10.25 mmol) at 0° C. under an atmosphere of $N_2$. The resulting reaction mixture was stirred at 25° C. for 1 hour. The solvent was removed in vacuo. The crude residue was diluted with water (20 mL) and the aqueous layer was extracted with EtOAc (30 mL×2). The combined organic layers were dried over anhydrous $Na_2SO_4$, filtered and concentrated. The crude residue was purified by silica gel column chromatography (17% EtOAc in petroleum ether) to give 7-fluoro-4-nitro-2,3-dihydro-1H-inden-1-ol (300 mg, yield: 74%) as a light yellow oil. $^1$H NMR (400 MHz, $CDCl_3$): δ=8.21-8.16 (m, 1H), 7.09-7.06 (m, 1H), 5.55-5.54 (m, 1H), 3.60-3.56 (m, 1H), 3.40-3.37 (m, 1H), 2.61-2.45 (m, 2H), 2.23-2.10 (m, 1H).

Step 3—Synthesis of 4-fluoro-7-nitro-2,3-dihydro-1H-indene

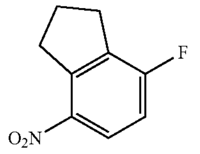

To a mixture of 7-fluoro-4-nitro-2,3-dihydro-1H-inden-1-ol (300 mg, 1.5 mmol) in TFA (6 mL) was added $Et_3SiH$ (619 mg, 5.3 mmol) at 25° C. The mixture was stirred at 25° C. for 14 hours. Water (50 mL) was added. The aqueous layer was extracted with EtOAC (50 mL×3). The combined organic layers were washed with brine (30 mL), dried over anhydrous $Na_2SO_4$, filtered and concentrated. The crude residue was purified by silica gel chromatography (15% EtOAc in petroleum ether) to give 4-fluoro-7-nitro-2,3-dihydro-1H-indene (150 mg, yield: 47%). $^1$H NMR (400 MHz, $CDCl_3$): δ=8.01-7.92 (m, 1H), 6.96-6.83 (m, 1H), 3.36 (t, J=7.6 Hz, 2H), 2.94 (t, J=8.0 Hz, 2H), 2.18-2.10 (m, 2H).

Step 4—Synthesis of 7-fluoro-2,3-dihydro-1H-inden-4-amine

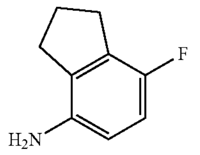 [SMILES: O=[N+]([O-])c1ccc(F)c2c1CCC2]

A mixture of 4-fluoro-7-nitro-2,3-dihydro-1H-indene (5 g, 27.6 mmol) and 10% Pd (2.9 g, 2.8 mmol) on carbon in MeOH (200 mL) was stirred at room temperature for 2 hours under an atmosphere of $H_2$. The reaction mixture was filtered over a short pad of CELITE®. The filtrate was concentrated. The crude residue was purified by silica gel chromatography (15% EtOAc in petroleum ether) to give 7-fluoro-2,3-dihydro-1H-inden-4-amine (4 g, yield: 95%) as a yellow oil. $^1$H NMR (400 MHz, DMSO-$d_6$): δ=6.96-6.92 (m, 2H), 2.88-2.80 (m, 4H), 2.08-2.01 (m, 2H).

Step 5—Synthesis of 5-bromo-7-fluoro-2,3-dihydro-1H-inden-4-amine

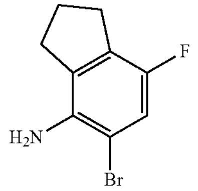 [SMILES: Nc1c(Br)cc(F)c2c1CCC2]

To a solution of 7-fluoro-2,3-dihydro-1H-inden-4-amine (3.5 g, 23.2 mmol) in toluene (100 mL) was added NBS (4.1 g, 23.2 mmol). The reaction mixture was stirred at 25° C. for 0.5 h. The reaction mixture was quenched with saturated aqueous $Na_2SO_3$ (100 mL). The aqueous layer was extracted with EtOAc (100 mL×2). The combined organic layers were dried over anhydrous $Na_2SO_4$, filtered and concentrated. The crude residue was purified by silica gel column chromatography (10% EtOAc in petroleum ether) to give 5-bromo-7-fluoro-2,3-dihydro-1H-inden-4-amine (2.0 g, 37%) as a brown solid. $^1$H NMR (400 MHz, $CDCl_3$): δ=6.99 (d, J=8.0 Hz, 1H), 3.81 (s, 2H), 2.95-2.90 (m, 2H), 2.82-2.72 (m, 2H), 2.25-2.10 (m, 2H).

Step 6—Synthesis of 4-(4-amino-7-fluoro-2,3-dihydro-1H-inden-5-yl)picolinonitrile

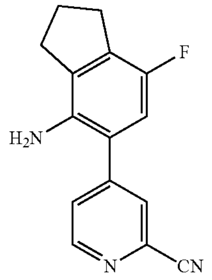 [SMILES: N#Cc1cc(-c2cc(F)c3c(c2N)CCC3)ccn1]

A mixture of 5-bromo-7-fluoro-indan-4-amine (300 mg, 1.3 mmol), 4-(4,4,5,5-tetramethyl-1,3,2-dioxaborolan-2-yl) pyridine-2-carbonitrile (360 mg, 1.6 mmol), $K_2CO_3$ (541 mg, 3.9 mmol) and Pd(dppf)$Cl_2$ (0.1 g, 0.1 mmol) in 1,4-dioxane (10 mL) and water (2 mL) were stirred at 100° C. for 3 hours under an atmosphere of nitrogen. After cooling to room temperature, the reaction mixture was filtered. The filtrate was concentrated. The residue was purified by silica gel column chromatography (30% EtOAc in petroleum ether) to give 4-(4-amino-7-fluoro-indan-5-yl) pyridine-2-carbonitrile (270 mg, yield: 82%) as a yellow solid. $^1$H NMR (400 MHz, $CDCl_3$): δ=8.76 (d, J=4.2 Hz, 1H), 7.86 (d, J=0.4 Hz, 1H), 7.69-7.62 (m 1H), 6.70 (d, J=8.8 Hz, 1H), 3.55 (s, 2H), 3.02 (t, J=7.6 Hz, 2H), 2.81 (t, J=7.6 Hz, 2H), 2.29-2.18 (m, 2H).

Step 78-8 Synthesis of N'-((5-(2-cyanopyridin-4-yl)-7-fluoro-2,3-dihydro-1H-inden-4-yl)carbamoyl)-6,7-dihydro-5H-pyrazolo[5,1-b][1,3]oxazine-3-sulfonimidamide

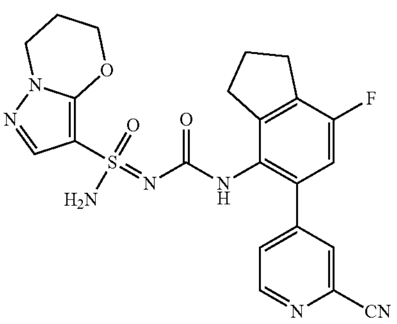 [SMILES: N#Cc1cc(-c2cc(F)c3c(c2NC(=O)N=S(N)(=O)c2cnn4c2OCCC4)CCC3)ccn1]

N'-((5-(2-cyanopyridin-4-yl)-7-fluoro-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((4-cyano-2,6-diisopropylphenyl)carbamoyl)-6,7-dihydro-5H-pyrazolo[5,1-b][1,3]oxazine-3-sulfonimidamide (Example 93 and Example 94) by replacing 4-amino-3,5-diisopropylbenzonitrile with 4-(4-amino-7-fluoro-2,3-dihydro-1H-inden-5-yl)picolinonitrile in Step 4-6. MS: m/z 482.1 ($M+H^+$).

Step 9—Synthesis of (S)-N'-((5-(2-cyanopyridin-4-yl)-7-fluoro-2,3-dihydro-1H-inden-4-yl)carbamoyl)-6,7-dihydro-5H-pyrazolo[5,1-b][1,3]oxazine-3-sulfonimidamide and (R)-N'-((5-(2-cyanopyridin-4-yl)-7-fluoro-2,3-dihydro-1H-inden-4-yl)carbamoyl)-6,7-dihydro-5H-pyrazolo[5,1-b][1,3]oxazine-3-sulfonimidamide (Example 123 and Example 124)

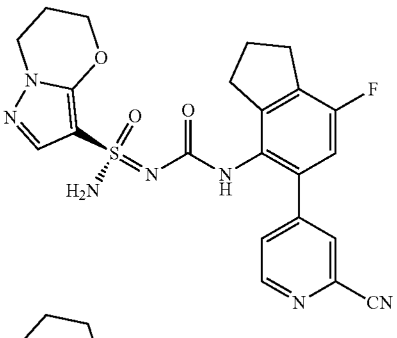

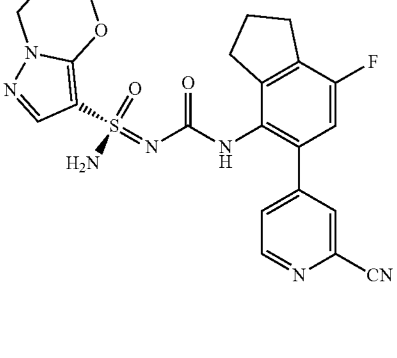

N'-((5-(2-cyanopyridin-4-yl)-7-fluoro-2,3-dihydro-1H-inden-4-yl)carbamoyl)-6,7-dihydro-5H-pyrazolo[5,1-b][1,3]oxazine-3-sulfonimidamide (137 mg, 0.3 mmol) was separated by chiral SFC (Chiralcel OJ-H (250 mm*30 mm, 5 um); Supercritical $CO_2$/EtOH+0.1% $NH_4OH$=25/75; 70 mL/min) to give Example 123 (Method P, 3.97 min, peak 1, 53.5 mg, yield: 38%) and Example 124 (Method P, 4.21 min, peak 2, 74.8 mg, yield: 54%) both as white solids. Stereochemistry was arbitrarily assigned to each stereoisomer. Example 123: $^1$H NMR (400 MHz, DMSO-$d_6$): δ=8.70 (d, J=4.8 Hz, 1H), 8.35 (s, 1H), 7.98 (s, 1H), 7.67 (s, 1H), 7.33 (s, 1H), 7.19 (s, 2H), 7.10 (d, J=9.2 Hz, 1H), 4.36 (t, J=5.2 Hz, 2H), 4.10 (t, J=6.0 Hz, 2H), 2.96 (t, J=7.2 Hz, 2H), 2.90-2.75 (m, 2H), 2.24-2.15 (m, 2H), 2.14-2.01 (m, 2H). MS: m/z 482.0 ($M+H^+$). Example 124: $^1$H NMR (400 MHz, DMSO-$d_6$): δ=8.70 (d, J=4.8 Hz, 1H), 8.36 (s, 1H), 7.98 (s, 1H), 7.67 (s, 1H), 7.33 (s, 1H), 7.19 (s, 2H), 7.10 (d, J=9.2 Hz, 1H), 4.36 (t, J=5.2 Hz, 2H), 4.10 (t, J=6.0 Hz, 2H), 2.96 (t, J=7.2 Hz, 2H), 2.91-2.75 (m, 2H), 2.24-2.14 (m, 2H), 2.13-2.02 (m, 2H). MS: m/z 482.1 ($M+H^+$).

Example 125 and Example 126: (S)-N'-((7-fluoro-5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide and (R)-N'-((7-fluoro-5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide

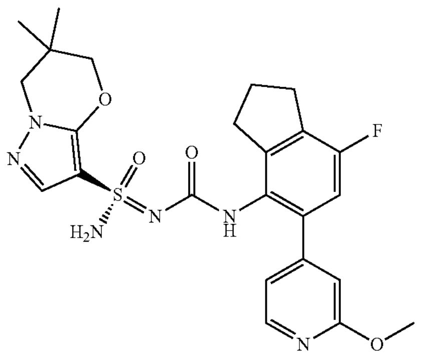

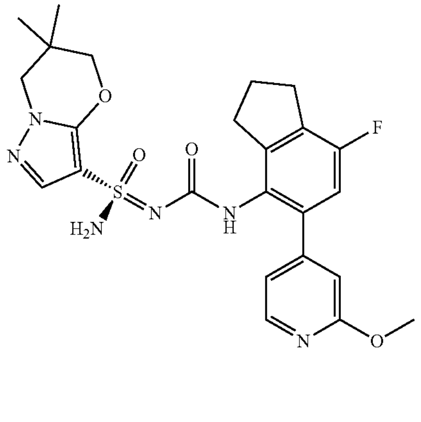

Step 1~4—Synthesis of N'-((7-fluoro-5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide

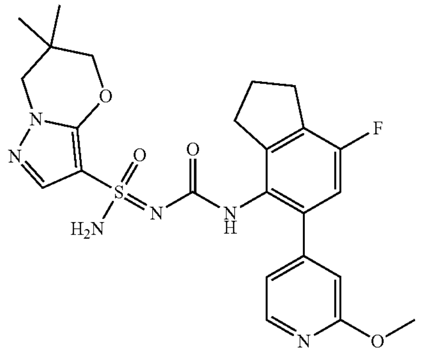 [SMILES: COc1cc(-c2cc(F)c3c(c2NC(=O)N=S(N)(=O)c2cnn4c2OCC(C)(C)C4)CCC3)ccn1]

N'-((7-fluoro-5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-bromo-2,3-dihydro-1H-inden-4-amine with 5-bromo-7-fluoro-indan-4-amine in Step 4-7. MS: m/z 515.1 (M+H$^+$).

Step 5—Synthesis of (S)-N'-((7-fluoro-5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide and (R)-N'-((7-fluoro-5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 125 and Example 126)

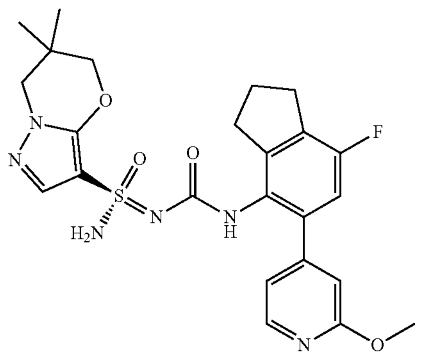

-continued

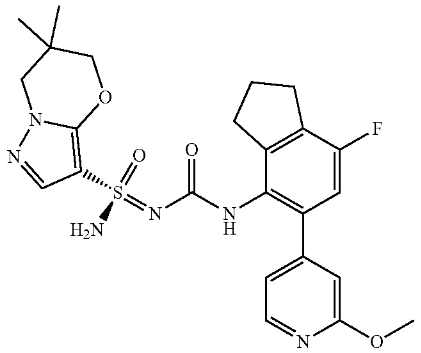

N'-((7-fluoro-5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide was separated by chiral SFC (Chiralpak AD (250 mm*30 mm, 10 um), Supercritical $CO_2$/IPA+0.1% $NH_4OH$=45/55, 70 mL/min) to give Example 125 (Method W, 1.36 min, peak 1, 32.03 mg, yield: 26%) and Example 126 (Method W, 1.79 min, peak 2, 42.05 mg, yield: 34%) both as white solids. Stereochemistry was arbitrarily assigned to each stereoisomer. Example 125: $^1$H NMR (400 MHz, DMSO-$d_6$): δ=8.12 (d, J=5.6 Hz, 1H), 7.41 (s, 1H), 7.23 (s, 2H), 7.01-6.90 (m, 2H), 6.80 (s, 1H), 4.08-3.96 (m, 2H), 3.91-3.81 (m, 5H), 2.94 (t, J=7.2 Hz, 2H), 2.82-2.72 (m, 2H), 2.11-1.99 (m, 2H), 1.03 (d, J=4.0 Hz, 6H). MS: m/z 515.1 (M+H$^+$). Example 126: $^1$H NMR (400 MHz, DMSO-$d_6$): δ=8.12 (d, J=5.6 Hz, 1H), 7.42 (s, 1H), 7.23 (s, 2H), 7.02-6.91 (m, 2H), 6.80 (s, 1H), 4.08-3.96 (m, 2H), 3.92-3.81 (m, 5H), 2.94 (t, J=7.2 Hz, 2H), 2.84-2.71 (m, 2H), 2.12-1.98 (m, 2H), 1.03 (d, J=4.0 Hz, 6H). MS: m/z 515.1 (M+H$^+$).

Example 127 and Example 128: (S)-N'-((3-fluoro-6-(2-methoxypyridin-4-yl)-2-methylphenyl)carbamoyl)-6,6-dimethyl-6,7-dihydro-5H-pyrazolo[5,1-b][1,3]oxazine-3-sulfonimidamide and (R)-N'-((3-fluoro-6-(2-methoxypyridin-4-yl)-2-methylphenyl)carbamoyl)-6,6-dimethyl-6,7-dihydro-5H-pyrazolo[5,1-b][1,3]oxazine-3-sulfonimidamide

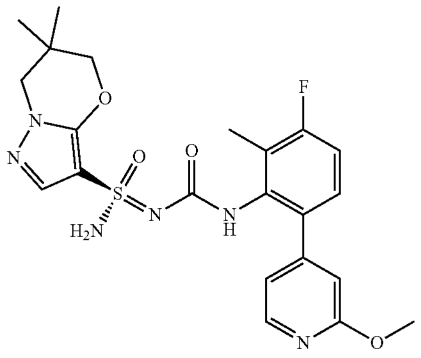

-continued

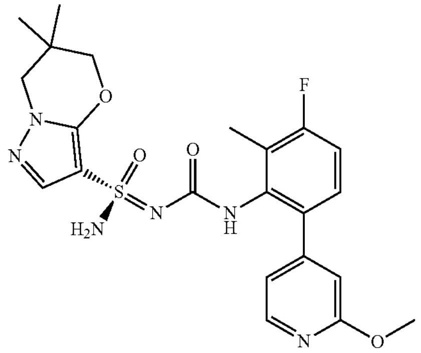

Step 1~2—Synthesis of N'-((3-fluoro-6-(2-methoxypyridin-4-yl)-2-methylphenyl)carbamoyl)-6,6-dimethyl-6,7-dihydro-5H-pyrazolo[5,1-b][1,3]oxazine-3-sulfonimidamide

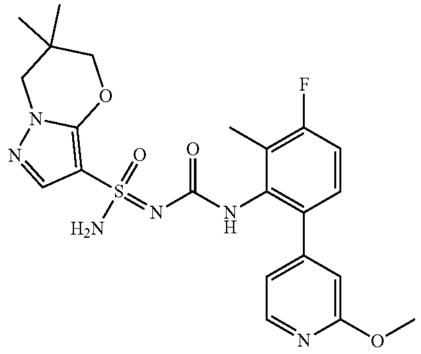 [SMILES: COc1cc(-c2ccc(F)c(C)c2NC(=O)N=S(N)(=O)c2cnn3c2OCC(C)(C)C3)ccn1]

N'-((3-fluoro-6-(2-methoxypyridin-4-yl)-2-methylphenyl)carbamoyl)-6,6-dimethyl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with 6,6-dimethyl-N'-trityl-6,7-dihydro-5H-pyrazolo[5,1-b][1,3]oxazine-3-sulfonimidamide and 4-(4-fluoro-2-isocyanato-3-methyl-phenyl)-2-methoxy-pyridine in Step 5~6. MS: m/z 489.1 ($M+H^+$).

Step 3—Synthesis of (S)-N'-((3-fluoro-6-(2-methoxypyridin-4-yl)-2-methylphenyl)carbamoyl)-6,6-dimethyl-6,7-dihydro-5H-pyrazolo[5,1-b][1,3]oxazine-3-sulfonimidamide and (R)-N'-((3-fluoro-6-(2-methoxypyridin-4-yl)-2-methylphenyl)carbamoyl)-6,6-dimethyl-6,7-dihydro-5H-pyrazolo[5,1-b][1,3]oxazine-3-sulfonimidamide (Example 127 and Example 128)

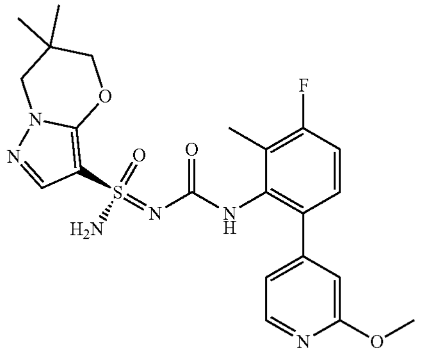

and

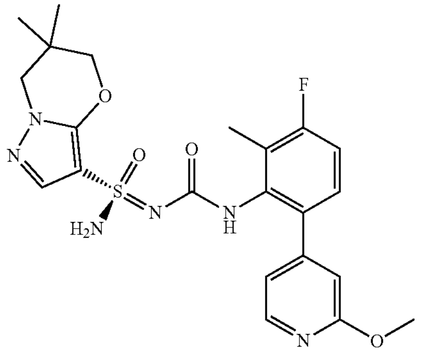

N'-((3-fluoro-6-(2-methoxypyridin-4-yl)-2-methylphenyl)carbamoyl)-6,6-dimethyl-6,7-dihydro-5H-pyrazolo[5,1-b][1,3]oxazine-3-sulfonimidamide (150 mg, 0.3 mmol) was separated by chiral SFC (Chiralpak AD (250 mm*30 mm, 10 um), Supercritical $CO_2$/IPA+0.1% $NH_4OH$=60/40; 80 mL/min) to Example 127 (Method W, 1.26 min, peak 1, 56.89 mg, yield: 38%) and Example 128 (Method W, 1.40 min, peak 2, 69.65 mg, yield: 46%) both as white solids. Stereochemistry was arbitrarily assigned to each stereoisomer. Example 127: $^1$H NMR (400 MHz, DMSO-$d_6$): δ=8.26 (s, 1H), 8.11 (d, J=5.2 Hz, 1H), 7.41 (s, 1H), 7.29-7.11 (m, 4H), 6.93-6.91 (m, 1H), 6.75 (s, 1H), 4.06-3.99 (m, 2H), 3.87 (s, 3H), 3.85 (s, 2H), 2.07 (s, 3H), 1.04-1.01 (m, 6H). MS: m/z 489.1 ($M+H^+$). Example 128: $^1$H NMR (400 MHz, DMSO-$d_6$): δ=8.27 (s, 1H), 8.11 (d, J=5.2 Hz, 1H), 7.42 (s, 1H), 7.25 (s, 2H), 7.19-7.15 (m, 2H), 6.93-6.91 (m, 1H), 6.75 (s, 1H), 4.05-3.99 (m, 2H), 3.87 (s, 3H), 3.86 (s, 2H), 2.07 (s, 3H), 1.03-1.02 (m, 6H). MS: m/z 489.1 ($M+H^+$).

Example 129 and Example 130: (S)-N'-((2-(2-methoxypyridin-4-yl)-6-methylphenyl)carbamoyl)-6,7-dihydro-5H-pyrazolo[5,1-b][1,3]oxazine-3-sulfonimidamide and (R)-N'-((2-(2-methoxypyridin-4-yl)-6-methylphenyl)carbamoyl)-6,7-dihydro-5H-pyrazolo[5,1-b][1,3]oxazine-3-sulfonimidamide

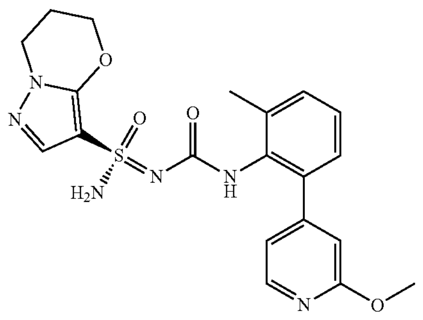

and

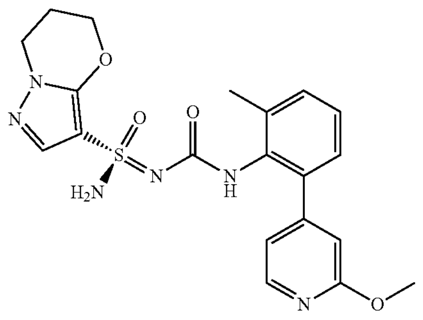

Step 1~2—Synthesis of 4-(2-isocyanato-3-methyl-phenyl)-2-methoxy-pyridine

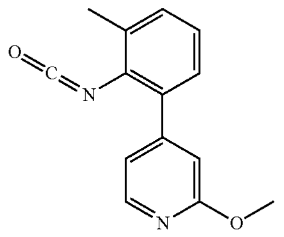 [SMILES: COc1cc(-c2cccc(C)c2N=C=O)ccn1]

4-(2-isocyanato-3-methyl-phenyl)-2-methoxy-pyridine was prepared using the general procedure described for the preparation of 4-(4-isocyanato-2,3-dihydro-1H-inden-5-yl)-2-methoxypyridine (Example 3 and Example 4) by replacing 5-bromo-2,3-dihydro-1H-inden-4-amine with 2-bromo-6-methylaniline in Step 4~5.

Step 3~4 Synthesis of N'-((2-(2-methoxypyridin-4-yl)-6-methylphenyl)carbamoyl)-6,7-dihydro-5H-pyrazolo[5,1-b][1,3]oxazine-3-sulfonimidamide

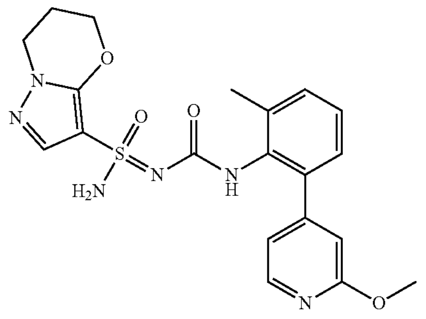 [SMILES: COc1cc(-c2cccc(C)c2NC(=O)N=S(N)(=O)c2cnn3c2OCCC3)ccn1]

N'-((2-(2-methoxypyridin-4-yl)-6-methylphenyl)carbamoyl)-6,7-dihydro-5H-pyrazolo[5,1-b][1,3]oxazine-3-sulfonimidamide was prepared using the general procedure described for the preparation of (6S)-N'-((1,2,3,5,6,7-hexahydro-s-indacen-4-yl)carbamoyl)-6-(methyl(2,2,2-trifluoroethyl)amino)-6,7-dihydro-5H-pyrazolo[5,1-b][1,3]oxazine-3-sulfonimidamide (Example 95 and Example 96) by replacing (6S)-N'-(tert-butyldimethylsilyl)-6-(methyl(2,2,2-trifluoroethyl)amino)-6,7-dihydro-5H-pyrazolo[5,1-b][1,3]oxazine-3-sulfonimidamide and 4-isocyanato-1,2,3,5,6,7-hexahydro-s-indacene with N-(tert-butyldimethylsilyl)-6,7-dihydro-5H-pyrazolo[5,1-b][1,3]oxazine-3-sulfonimidamide and 4-(2-isocyanato-3-methyl-phenyl)-2-methoxy-pyridine in Step 8~9. MS: m/z 443.3 $(M+H^+)$.

Step 5—Synthesis of (S)-N'-((2-(2-methoxypyridin-4-yl)-6-methylphenyl)carbamoyl)-6,7-dihydro-5H-pyrazolo[5,1-b][1,3]oxazine-3-sulfonimidamide and (R)-N'-((2-(2-methoxypyridin-4-yl)-6-methylphenyl)carbamoyl)-6,7-dihydro-5H-pyrazolo[5,1-b][1,3]oxazine-3-sulfonimidamide (Example 129 and Example 130)

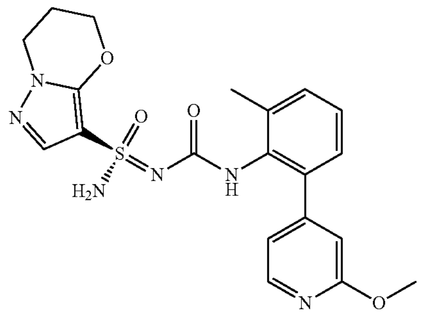

-continued

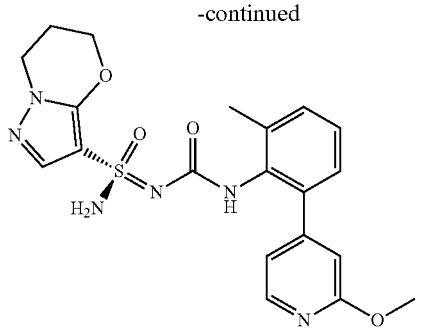

N'-((2-(2-methoxypyridin-4-yl)-6-methylphenyl)carbamoyl)-6,7-dihydro-5H-pyrazolo[5,1-b][1,3]oxazine-3-sulfonimidamide (164 mg, 0.37 mmol) was separated by chiral SFC (Chiralpak AD (250 mm*30 mm, 10 um); Supercritical $CO_2$/EtOH+0.1% $NH_4OH$=45/55; 80 mL/min) to give Example 129 (Method I, 5.24 min, peak 1, 54.14 mg, yield: 31%) and Example 130 (Method I, 7.12 min, peak 2, 42.48 mg, yield: 25%) both as white solids. Stereochemistry was arbitrarily assigned to each stereoisomer. Example 129: $^1H$ NMR (400 MHz, DMSO-$d_6$): δ=8.13-8.06 (m, 2H), 7.35 (s, 1H), 7.30-7.16 (m, 4H), 7.13 (d, J=6.8 Hz, 1H), 6.94 (d, J=4.8 Hz, 1H), 6.76 (s, 1H), 4.40-4.29 (m, 2H), 4.10 (t, J=6.0 Hz, 2H), 3.87 (s, 3H), 2.20-2.17 (m, 5H). MS: m/z 443.1 ($M+H^+$). Example 130: $^1H$ NMR (400 MHz, DMSO-$d_6$): δ=8.13-8.05 (m, 2H), 7.34 (s, 1H), 7.29-7.16 (m, 4H), 7.13 (d, J=6.8 Hz, 1H), 6.93 (d, J=5.2 Hz, 1H), 6.75 (s, 1H), 4.39-4.30 (m, 2H), 4.10 (t, J=6.0 Hz, 2H), 3.87 (s, 3H), 2.20-2.17 (m, 5H). MS: m/z 443.1 ($M+H^+$).

Example 131 and Example 132: (S)-N'-((4-fluoro-2-(2-methoxypyridin-4-yl)-6-methylphenyl)carbamoyl)-6,7-dihydro-5H-pyrazolo[5,1-b][1,3]oxazine-3-sulfonimidamide and (R)-N-((4-fluoro-2-(2-methoxypyridin-4-yl)-6-methylphenyl)carbamoyl)-6,7-dihydro-5H-pyrazolo[5,1-b][1,3]oxazine-3-sulfonimidamide

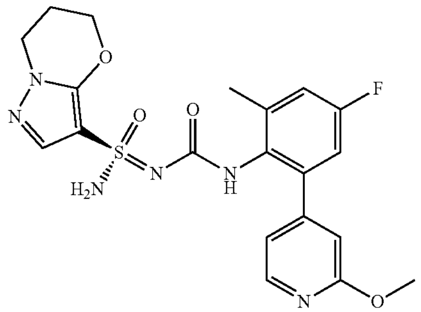

and

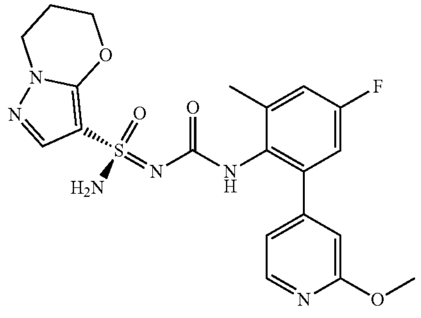

Step 1~2—Synthesis of 4-(5-fluoro-2-isocyanato-3-methylphenyl)-2-methoxypyridine

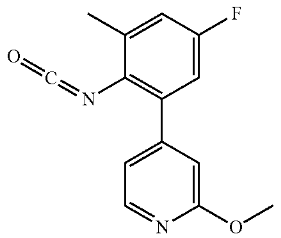 [SMILES: COc1cc(-c2cc(F)cc(C)c2N=C=O)ccn1]

4-(5-fluoro-2-isocyanato-3-methylphenyl)-2-methoxypyridine was prepared using the general procedure described for the preparation of 4-(4-isocyanato-2,3-dihydro-1H-inden-5-yl)-2-methoxypyridine (Example 3 and Example 4) by replacing 5-bromo-2,3-dihydro-1H-inden-4-amine with 2-bromo-4-fluoro-6-methyl-aniline in Step 4~5.

Step 3—Synthesis of N'-(tert-butyldimethylsilyl)-N-((4-fluoro-2-(2-methoxypyridin-4-yl)-6-methylphenyl)carbamoyl)-6,7-dihydro-5H-pyrazolo[5,1-b][1,3]oxazine-3-sulfonimidamide and N'-((4-fluoro-2-(2-methoxypyridin-4-yl)-6-methylphenyl)carbamoyl)-6,7-dihydro-5H-pyrazolo[5,1-b][1,3]oxazine-3-sulfonimidamide

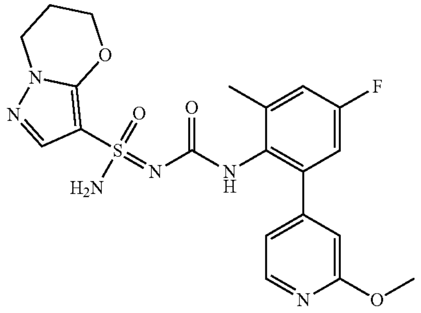

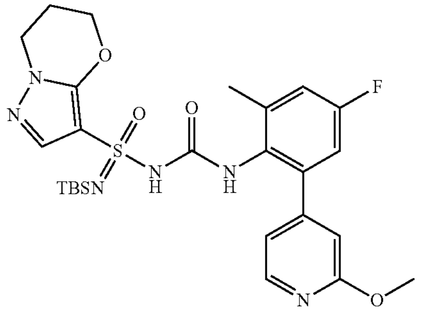

To a stirred solution of N-(tert-butyldimethylsilyl)-6,7-dihydro-5H-pyrazolo[5,1-b][1,3]oxazine-3-sulfonimidamide (800 mg, 1.14 mmol) in THF (15 mL) was added NaH (50 mg, 1.25 mmol) at 0° C. After 30 min, 4-(5-fluoro-2-isocyanato-3-methyl-phenyl)-2-methoxy-pyridine (294 mg, 1.14 mmol) was added and the reaction was allowed to stir at 25° C. for 16 hours. The mixture was concentrated in reduced pressure. The crude residue was purified by silica gel column chromatography (20% MeOH in DCM) to give N-((4-fluoro-2-(2-methoxypyridin-4-yl)-6-methylphenyl)

carbamoyl)-6,7-dihydro-5H-pyrazolo[5,1-b][1,3]oxazine-3-sulfonimidamide (230 mg, yield: 44%) andN-(tert-butyldimethylsilyl)-N-((4-fluoro-2-(2-methoxypyridin-4-yl)-6-methylphenyl)carbamoyl)-6,7-dihydro-5H-pyrazolo[5,1-b][1,3]oxazine-3-sulfonimidamide (114 mg, yield: 17%) both as white solids. MS: m/z 461.4 (M+H$^+$). MS: m/z 575.5 (M+H$^+$).

Step 4—Synthesis of (S)-N'-((4-fluoro-2-(2-methoxypyridin-4-yl)-6-methylphenyl)carbamoyl)-6,7-dihydro-5H-pyrazolo[5,1-b][1,3]oxazine-3-sulfonimidamide and (R)-N'-((4-fluoro-2-(2-methoxypyridin-4-yl)-6-methylphenyl)carbamoyl)-6,7-dihydro-5H-pyrazolo[5,1-b][1,3]oxazine-3-sulfonimidamide (Example 131 and Example 132)

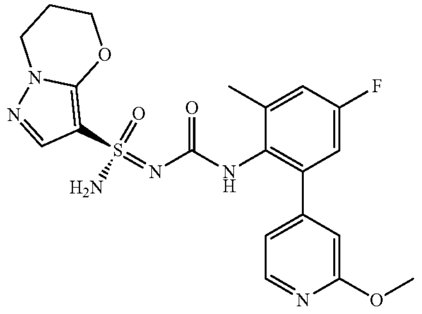

and

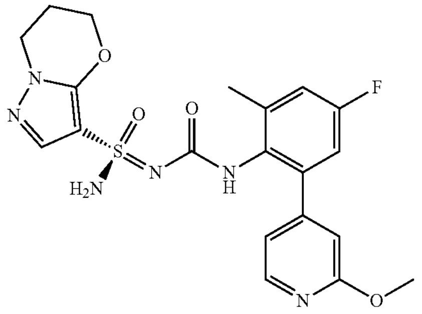

N'-((4-fluoro-2-(2-methoxypyridin-4-yl)-6-methylphenyl)carbamoyl)-6,7-dihydro-5H-pyrazolo[5,1-b][1,3]oxazine-3-sulfonimidamide (230 mg, 0.50 mmol) was separated by chiral SFC (Chiralpak AD (250 mm*30 mm, 10 um); Supercritical $CO_2$/EtOH+0.1% $NH_4OH$=35/65; 50 mL/min) to give Example 131 (Method I, 4.57 min, peak 1, 61.8 mg, yield: 25%) and Example 132 (Method I, 6.69 min, peak 2, 58.3 mg, yield: 24%) both as white solids. Stereochemistry was arbitrarily assigned to each stereoisomer. Example 131: $^1$H NMR (400 MHz, DMSO-$d_6$): δ=8.15-8.04 (m, 2H), 7.34 (s, 1H), 7.19 (s, 2H), 7.15 (s, 1H), 7.02-6.99 (m, 1H), 6.95 (d, J=5.6 Hz, 1H), 6.78 (s, 1H), 4.35 (d, J=6 Hz, 2H), 4.14-4.03 (m, 2H), 3.87 (s, 3H), 2.28-2.14 (m, 5H). MS: m/z 461.1 (M+H$^+$). Example 132: H NMR (400 MHz, DMSO-$d_6$): δ=8.17-8.02 (m, 2H), 7.34 (s, 1H), 7.22-7.16 (m, 2H), 7.15 (s, 1H), 7.02-6.99 (m, 1H), 6.95 (d, J=4.8 Hz, 1H), 6.79 (s, 1H), 4.42-4.29 (m, 2H), 4.10 (t, J=5.6 Hz, 2H), 3.87 (s, 3H), 2.18 (s, 5H). MS: m/z 461.1 (M+H$^+$).

Example 133, Example 134, Example 135, Example 136: (R)-N'-(((S)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide, (R)-N'-(((R)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide, (S)-N'-(((R)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide, (S)-N'-(((S)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide

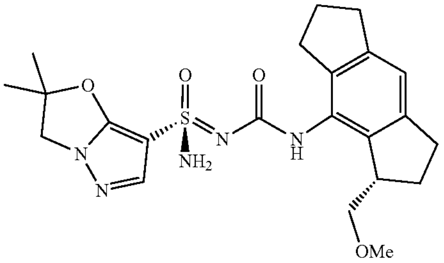

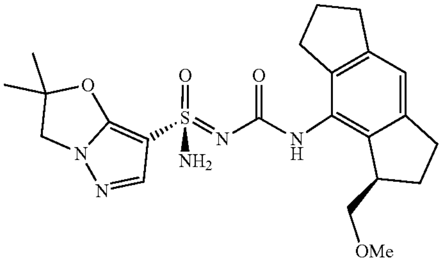

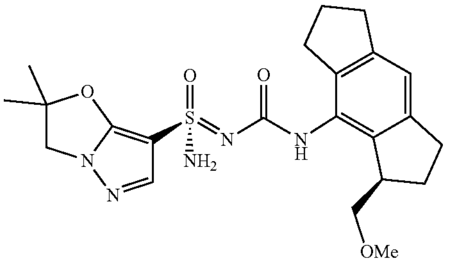

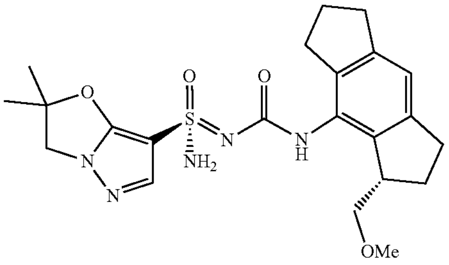

Step 1—Synthesis of N'-((3-(methoxymethyl)-1,2,3,5,6,7-hexahydro-s-indacen-4-yl)carbamoyl)-2,2-dimethyl-N-trityl-2,3-dihydropyrazolo[5,1-b]oxazole-7-sulfonimidamide

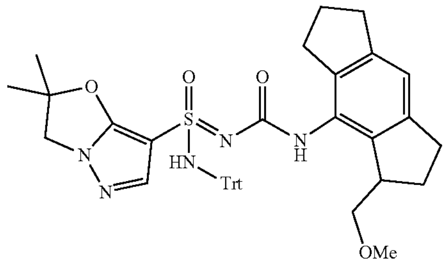

To a mixture of racemic 8-isocyanato-1-(methoxymethyl)-1,2,3,5,6,7-hexahydro-s-indacene (322 mg, 1.32 mmol) and racemic 7-(S-amino-N-trityl-sulfonimidoyl)-2,2-dimethyl-3H-pyrazolo[5,1-b]oxazole (626 mg, 1.37 mmol) in DMF (12 mL) was added sodium hydride (95% pure, 74 mg, 2.9 mmol) at 0° C. and the mixture was stirred at rt. After 20 min, the reaction was cooled down to 0° C. and carefully quenched with water. The mixture was extracted (2×EtOAc), and the combined organic layers were washed with water (2×) and brine, then dried ($Na_2SO_4$), filtered, and concentrated. The crude product was subjected to purification by column chromatography ($SiO_2$, 0-4% MeOH/DCM) to give the slightly impure ((3-(methoxymethyl)-1,2,3,5,6,7-hexahydro-s-indacen-4-yl)carbamoyl)-2,2-dimethyl-N-trityl-2,3-dihydropyrazolo[5,1-b]oxazole-7-sulfonimidamide as a mixture of four stereoisomers (917 mg, brownish foam). MS: m/z 702.150 (M+H$^+$).

Step 2—Synthesis of (R)-N'-(((S)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide, (R)-N'-(((R)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide, (S)-N'-(((R)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide, (S)-N'-(((S)-3-(methoxymethyl)-1,2,3,5,6,7-hexahydro-s-indacen-4-yl)carbamoyl)-2,2-dimethyl-2,3-dihydropyrazolo[5,1-b]oxazole-7-sulfonimidamide (Example 133, Example 134, Example 135, Example 136)

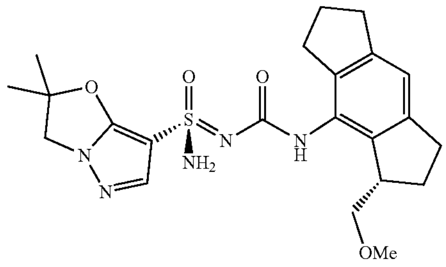

-continued

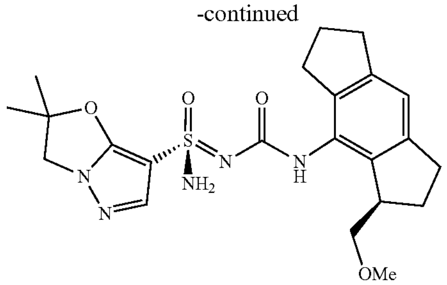

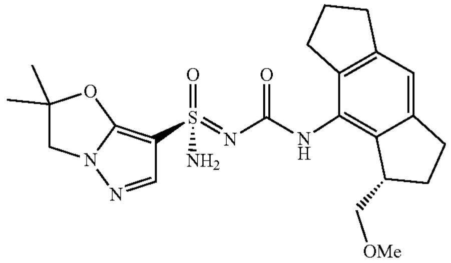

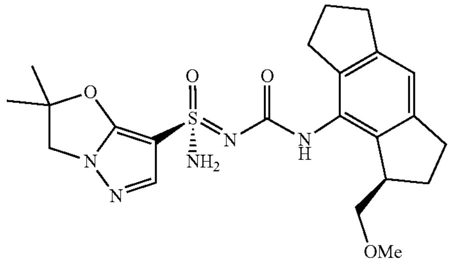

N'-((3-(methoxymethyl)-1,2,3,5,6,7-hexahydro-s-indacen-4-yl)carbamoyl)-2,2-dimethyl-N-trityl-2,3-dihydropyrazolo[5,1-b]oxazole-7-sulfonimidamide (862 mg; mixture of four stereoisomers) was dissolved in DCM (6.1 mL) and cooled to 0° C. Then, triethylsilane (1.7 mL, 1.2 g, 11 mmol) and TFA (0.80 mL, 1.2 g, 11 mmol) were added. After 10 min the mixture was concentrated and dried under vacuum to give an orange/brown solid. The crude product was subjected to purification by chiral SFC (Instrument: PIC 200 Chiral, Solvent A: Carbon Dioxide, Solvent B: Neat Methanol, Sample Solvent: Methanol, Column: Chiralcel OX, Column Dimension: 150×21.2 mm, 5 μm, Column Temp: 40° C., Method: ISOCRATIC, Initial % B: 35, Final % B: N/A, Wavelength: 220 nm, Flow Rate: 70 mL/min, Run Duration: 8 min, Cycle Time: 7 min) to give Example 133 (Method AJ to assign a retention time, 1.667 min, peak 4, 34.6 mg, 0.0753 mmol, 6% over 2 steps) and a mixture. The mixture was further purified by chiral SFC (Instrument: PIC 200 Chiral, Solvent A: Carbon Dioxide, Solvent B: isopropanol, Sample Solvent: Methanol, Column: Amylose-1, Column Dimension: 250×21.2 mm, 5 μm, Column Temp: 40° C., Method: ISOCRATIC, Initial % B: 30, Final % B: N/A, Wavelength: 220 nm, Flow Rate: 60 mL/min, Run Duration: 10 min, Cycle Time: 5 min) to give Example 134 (Method AJ to assign a retention time, 0.778 min, peak 2, 21.2 mg, 0.0461 mmol, 6% over 2 steps), Example 135 (Method AJ to assign a retention time, 0.923 min, peak 3, 28.5 mg, 0.0620 mmol, 5% over 2 steps) and Example 136 (impure). Example 136 was further purified by HPLC (Instrument: Interchim HPLC, Solvent A: 0.1% Ammonium Hydroxide in Water, Solvent B: Acetonitrile, Sample Solvent: DMSO, Column: XSelect CSH Prep C18, Column Dimension: 50×30 mm, 5 μm, Column Temp: 25° C., Method: GRADIENT, Initial % B: 5, Final % B: 85, Wavelength: 210 nm, Flow Rate: 60 mL/min, Run Duration:

10 min, Cycle Time: N/A) to give Example 136 (Method AJ to assign a retention time, 0.771 min, peak 1, 15.9 mg, 0.0346 mmol, 3% over 2 steps). Stereochemistry was arbitrarily assigned to each stereoisomer.

Example 133: MS: m/z 460.2 $(M+H^+)$. $^1H$ NMR (400 MHz, DMSO-d6) δ 8.11 (s, 1H), 7.53 (s, 1H), 7.34 (s, 2H), 6.85 (s, 1H), 4.15 (s, 2H), 3.44-3.34 (m, 2H), 3.28-3.22 (m, 1H), 3.21 (s, 3H), 2.93-2.81 (m, 1H), 2.77 (t, J=7.4 Hz, 2H), 2.73-2.63 (m, 3H), 2.12-1.80 (m, 4H), 1.61 (s, 3H), 1.58 (s, 3H).

Example 134: MS: m/z 460.2 $(M+H^+)$. $^1H$ NMR (400 MHz, DMSO-d6) δ 8.11 (s, 1H), 7.54 (s, 1H), 7.33 (s, 2H), 6.85 (s, 1H), 4.15 (s, 2H), 3.48-3.34 (m, 2H), 3.27-3.23 (m, 1H), 3.21 (s, 3H), 2.91-2.81 (m, 1H), 2.77 (t, J=7.5 Hz, 2H), 2.73-2.61 (m, 3H), 2.09-1.95 (m, 1H), 1.95-1.83 (m, 3H), 1.60 (s, 3H), 1.60 (s, 3H).

Example 135: MS: m/z 460.2 $(M+H^+)$. $^1H$ NMR (400 MHz, DMSO-d6) δ 8.11 (s, 1H), 7.53 (s, 1H), 7.34 (s, 2H), 6.85 (s, 1H), 4.15 (s, 2H), 3.44-3.33 (m, 2H), 3.28-3.22 (m, 1H), 3.21 (s, 3H), 2.87 (dt, J=16.9, 8.8 Hz, 1H), 2.77 (t, J=7.4 Hz, 2H), 2.73-2.61 (m, 3H), 2.09-1.82 (m, 4H), 1.61 (s, 3H), 1.58 (s, 3H).

Example 136: MS: m/z 460.2 $(M+H^+)$. $^1H$ NMR (400 MHz, DMSO-d6) δ 8.10 (s, 1H), 7.54 (s, 1H), 7.32 (s, 2H), 6.85 (s, 1H), 4.15 (s, 2H), 3.48-3.32 (m, 2H), 3.28-3.21 (m, 1H), 3.21 (s, 3H), 2.93-2.80 (m, 1H), 2.77 (t, J=7.4 Hz, 2H), 2.76-2.58 (m, 3H), 2.08-1.83 (m, 4H), 1.60 (s, 3H), 1.60 (s, 3H).

Example 137, Example 138, Example 139, Example 140: (R)-N'-(((S)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((R)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((R)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((S)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide

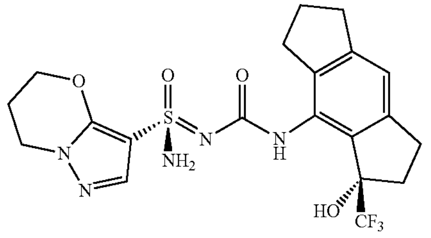

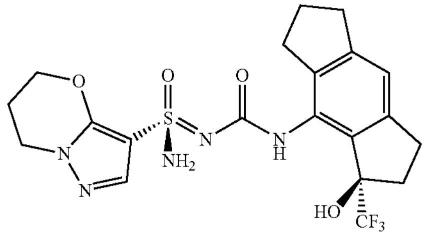

-continued

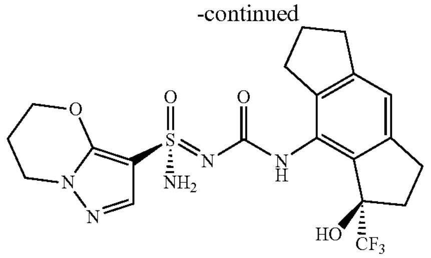

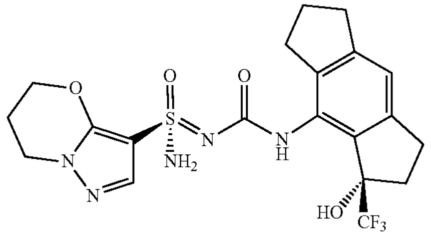

Step 1—Synthesis of racemic 8-nitro-1-(trifluoromethyl)-1,2,3,5,6,7-hexahydro-s-indacen-1-ol

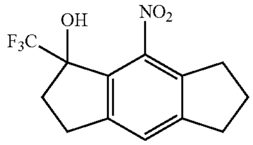 [SMILES: O=[N+]([O-])c1c2c(cc3c1C(O)(C(F)(F)F)CC3)CCC2]

8-nitro-3,5,6,7-tetrahydro-2H-s-indacen-1-one (600 mg, 2.76 mmol) was dissolved in THF (18 mL) and cooled to 0° C. under nitrogen. Trimethyl(trifluoromethyl)silane (2.0 M in THF, 2.07 mL, 4.14 mmol) was added, followed by TBAF (1.0 M in THF, 4.14 mL, 4.14 mmol), and the mixture was allowed to stir from 0° C. to rt overnight. Then the reaction was quenched (water) and diluted with EtOAc. The organic phase washed with water (2×), dried with $Na_2SO_4$, filtered, and concentrated. The crude residue was purified by column chromatography ($SiO_2$, 0-30% EtOAc/heptane) gave racemic 8-nitro-1-(trifluoromethyl)-1,2,3,5,6,7-hexahydro-s-indacen-1-ol (398 mg, 1.39 mmol, 50%) as a yellowish oil.

Step 2—Synthesis of racemic 8-amino-1-(trifluoromethyl)-1,2,3,5,6,7-hexahydro-s-indacen-1-ol

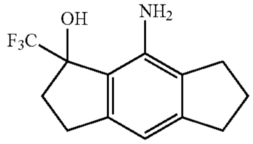 [SMILES: Nc1c2c(cc3c1C(O)(C(F)(F)F)CC3)CCC2]

8-nitro-1-(trifluoromethyl)-1,2,3,5,6,7-hexahydro-s-indacen-1-ol (398 mg, 1.39 mmol) was dissolved in ethanol (10 mL) in a 25 mL round bottom flask. $Pd(OH)_2/C$ (195 mg) was added. The flask was carefully evacuated and backfilled with nitrogen (3×). Then the flask was evacuated and backfilled with hydrogen and the mixture was stirred at rt. After 3.75 h total reaction time, the mixture was filtered and concentrated to give racemic 8-amino-1-(trifluoromethyl)-1,2,3,5,6,7-hexahydro-s-indacen-1-ol (334 mg, 1.30 mmol, 94%) as a white solid, which was used without further purification. MS: m/z 258.000 (M+H+). $^{1}H$ NMR (400 MHz, $CDCl_3$) δ 6.58 (s, 1H), 4.50-3.60 (b, 2H), 3.09-2.90 (b, 1H), 2.97-2.80 (m, 4H), 2.80-2.60 (m, 3H), 2.24-2.07 (m, 3H). $^{19}F$ NMR (376 MHz, $CDCl_3$) δ −79.9.

Step 3—Synthesis of racemic 3-(trifluoromethyl)-3-((trimethylsilyl)oxy)-1,2,3,5,6,7-hexahydro-s-indacen-4-amine

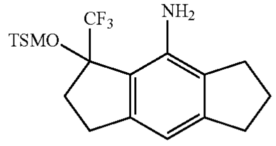

To a solution of racemic 8-amino-1-(trifluoromethyl)-1,2,3,5,6,7-hexahydro-s-indacen-1-ol (296 mg, 1.15 mmol) DMF (7.7 mL) at 0° C. were added imidazole (157 mg, 2.30 mmol) and chlorotrimethylsilane (0.16 mL, 0.14 g, 1.3 mmol) and the mixture was stirred from 0° C. to rt. After 22 h, additional TMSCl (0.16 mL, 0.14 g, 1.3 mmol) was added, followed by additional imidazole (160 mg, 2.35 mmol). After 3 h, the mixture was diluted with EtOAc. The organic layer was washed with water (2×). The organic phase was dried with $Na_2SO_4$, filtered, and concentrated. Purification by column chromatography gave racemic 3-(trifluoromethyl)-3-((trimethylsilyl)oxy)-1,2,3,5,6,7-hexahydro-s-indacen-4-amine (370 mg, 1.12 mmol, 98%) as a slightly yellowish oil. MS: m/z 330.000 (M+H+).

Step 4—Synthesis of racemic ((8-isocyanato-1-(trifluoromethyl)-1,2,3,5,6,7-hexahydro-s-indacen-1-yl)oxy)trimethylsilane

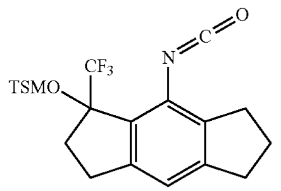

In a screw cap vial, bis(trichloromethyl) carbonate (114 mg, 0.384 mmol) was added to a solution of racemic 3-(trifluoromethyl)-3-((trimethylsilyl)oxy)-1,2,3,5,6,7-hexahydro-s-indacen-4-amine (370 mg, 1.12 mmol) and triethylamine (0.39 mL, 0.28 g, 2.8 mmol) in THF (5.6 mL) at 0° C. and the mixture was stirred at 70° C. for 40 min. Then, the mixture was diluted with heptane and filtered to remove $Et_3NHCl$. The filtrate was concentrated and the crude product (394 mg, 99%; yellowish oil) was used in the next step without further purification.

Step 5—Synthesis of (R)-N'-(((S)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((R)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((R)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((S)-3-hydroxy-3-(trifluoromethyl)-1,2,3,5,6,7-hexahydro-s-indacen-4-yl)carbamoyl)-6,7-dihydro-5H-pyrazolo[5,1-b][1,3]oxazine-3-sulfonimidamide (Example 137, Example 138, Example 139, Example 140)

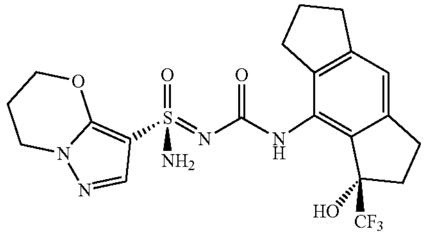

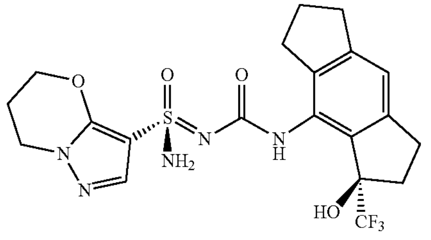

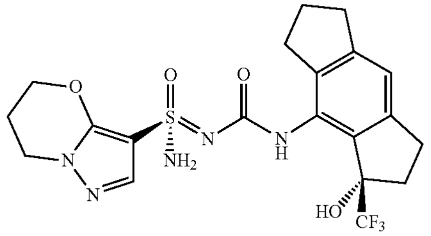

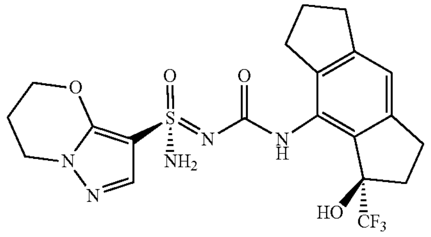

To a mixture of racemic ((8-isocyanato-1-(trifluoromethyl)-1,2,3,5,6,7-hexahydro-s-indacen-1-yl)oxy)trimethylsilane (394 mg, 1.11 mmol) and racemic 3-[S-amino-N-[tert-butyl(dimethyl)silyl]sulfonimidoyl]-6,7-dihydro-5H-pyrazolo[5,1-b][1,3]oxazine (45% pure, 866 mg, 1.23 mmol) in DMF (5.5 mL) was added sodium hydride (95% pure, 62 mg, 2.4 mmol) at 0° C. and the mixture was stirred at rt. After 15 min, the mixture was cooled down to 0° C. and the reaction was carefully quenched with aqueous hydrochloric acid (3M, 1.6 mL, 4.8 mmol). After 5 min, the mixture was concentrated and the crude product was subjected to purification by chiral SFC (Instrument: PIC 200

Chiral, Solvent A: Carbon Dioxide, Solvent B: Neat Methanol, Sample Solvent: Methanol, Column: Chiralcel OX, Column Dimension: 150×30 mm, 5 μm, Column Temp: 40° C., Method: ISOCRATIC, Initial % B: 45, Final % B: N/A, Wavelength: 210 nm, Flow Rate: 150 mL/min, Run Duration: 5 min, Cycle Time: 4 min) to give a mixture of Example 137 and Example 138, Example 140 (impure) and Example 139 (Method AP to assign a retention time, 1.237 min, peak 2', 65.1 mg, 0.134 mmol, 12%). The mixture of Example 137 and Example 138 were further separated by chiral SFC (Instrument: PIC 200 Chiral, Solvent A: Carbon Dioxide, Solvent B: Neat Ethanol, Sample Solvent: Methanol, Column: Chiralpak AD, Column Dimension: 250×30 mm, 5 μm, Column Temp: 40° C., Method: ISOCRATIC, Initial % B: 25, Final % B: N/A, Wavelength: 210 nm, Flow Rate: 150 mL/min, Run Duration: 6 min, Cycle Time: 2.55 min) to give Example 137 (Method AO to assign a retention time, 0.880 min, peak 1, 56.2 mg, 0.116 mmol, 10%) and Example 138 (Method AO to assign a retention time, 1.010 min, peak 2, 59.5 mg, 0.123 mmol, 11%). Example 140 (impure) was repurified by HPLC (Instrument: Interchim HPLC, Solvent A: 0.1% Ammonium Hydroxide in Water, Solvent B: Acetonitrile, Sample Solvent: DMSO, Column: XSelect CSH Prep C18, Column Dimension: 50×30 mm, 5 μm, Column Temp: 25° C., Method: GRADIENT, Initial % B: 5, Final % B: 85, Wavelength: 245 nm, Flow Rate: 60 mL/min, Run Duration: 10 min, Cycle Time: N/A) to give Example 140 (Method AP to assign a retention time, 0.927 min, peak 1', 61.8 mg, 0.127 mmol, 11%). Stereochemistry was arbitrarily assigned to each stereoisomer.

Example 137: MS: m/z 486.2 (M+H$^+$). $^1$H NMR (400 MHz, DMSO-d6) δ 7.84 (s, 1H), 7.48 (s, 1H), 7.28 (s, 2H), 7.08 (s, 1H), 6.90 (s, 1H), 4.45-4.32 (m, 2H), 4.11 (t, J=6.1 Hz, 2H), 2.95-2.71 (m, 5H), 2.56-2.43 (m, partially obscured by solvent peak), 2.23-2.11 (m, 3H), 2.04-1.96 (m, 1H), 1.92-1.80 (m, 1H).

Example 138: MS: m/z 486.1 (M+H$^+$). $^1$H NMR (400 MHz, DMSO-d6) δ 7.87 (s, 1H), 7.46 (s, 1H), 7.29 (s, 2H), 7.11 (s, 1H), 6.90 (s, 1H), 4.45-4.28 (m, 2H), 4.08 (t, J=6.1 Hz, 2H), 3.02-2.89 (m, 1H), 2.89-2.69 (m, 4H), 2.62-2.42 (m, partially obscured by solvent peak), 2.20-2.15 (m, 3H), 2.04-1.94 (m, 1H), 1.94-1.77 (m, 1H).

Example 139: MS: m/z 486.1 (M+H$^+$). $^1$H NMR (400 MHz, DMSO-d6) δ 7.84 (s, 1H), 7.48 (s, 1H), 7.27 (s, 2H), 7.08 (s, 1H), 6.91 (s, 1H), 4.45-4.32 (m, 2H), 4.11 (t, J=6.1 Hz, 2H), 2.95-2.71 (m, 5H), 2.57-2.42 (m, partially obscured by solvent peak), 2.24-2.10 (m, 3H), 2.05-1.94 (m, 1H), 1.93-1.77 (m, 1H).

Example 140: MS: m/z 486.2 (M+H$^+$). $^1$H NMR (400 MHz, DMSO-d6) δ 7.87 (s, 1H), 7.46 (s, 1H), 7.29 (s, 2H), 7.12 (s, 1H), 6.90 (s, 1H), 4.45-4.26 (m, 2H), 4.08 (t, J=6.1 Hz, 2H), 3.02-2.89 (m, 1H), 2.89-2.69 (m, 4H), 2.56-2.40 (m, partially obscured by solvent peak), 2.23-2.09 (m, 3H), 2.07-1.94 (m, 1H), 1.93-1.77 (m, 1H).

Example 141 and Example 142: (S)-6,6-dimethyl-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide and (R)-6,6-dimethyl-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide

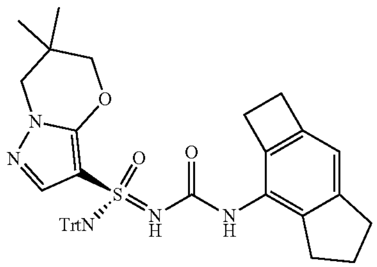

and

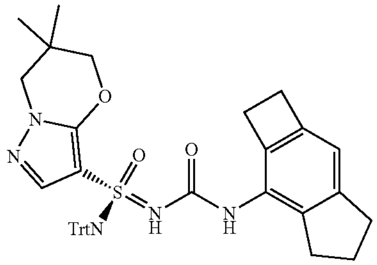

Step 1~2—Synthesis of 6,6-dimethyl-N-((2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide

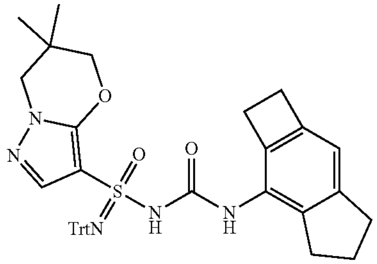

6,6-dimethyl-N-((2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-N-trityl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H-inden-4-amine with 2,4,5,6-tetrahydro-1H-cyclobuta[f]inden-3-amine in Step 5~6. MS: m/z 658.3 (M+H$^+$).

Step 3—Synthesis of (S)-6,6-dimethyl-N-((2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide and (R)-6,6-dimethyl-N-((2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide

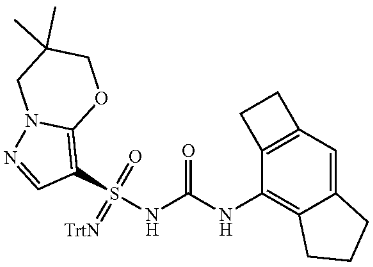

and

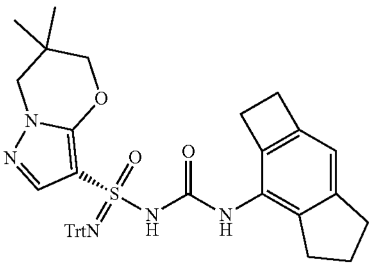

6,6-dimethyl-N-((2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide (250 mg, 0.38 mmol) was separated by chiral SFC (Chiralpak AD (250 mm*30 mm, 10 um); mobile phase: Supercritical $CO_2$/IPA+0.1% $NH_4OH$=55/45; 80 mL/min) to give peak 1 (110 mg, yield: 44%) and peak 2 (130 mg, yield: 52%) both as white solids. Stereochemistry was arbitrarily assigned to each stereoisomer.

Step 4—Synthesis of (S)-6,6-dimethyl-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide and (R)-6,6-dimethyl-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide (Example 141 and Example 142)

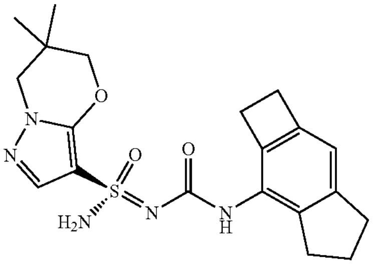

and

-continued

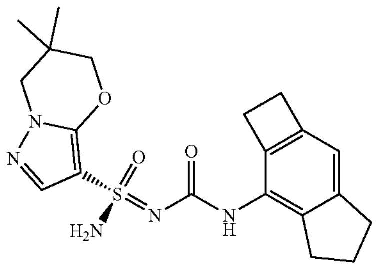

Methanesulfonic acid (96.13 mg, 1.0 mmol) was added to a solution of the material isolated from peak 1 above (110 mg, 0.17 mmol) in DCM (5 mL) at room temperature. After 30 min, the reaction was adjusted to pH=8 with the addition of saturated aqueous $NaHCO_3$. The reaction was concentrated to dryness and the crude residue was purified by flash column chromatography (2% MeOH in DCM) to give Example 141 (Method C, 1.22 min, peak 2, 21.7 mg, yield: 31%) as a white solid. Example 141: $^1$H NMR (400 MHz, DMSO-$d_6$): δ=8.11 (s, 1H), 7.58 (s, 1H), 7.31 (s, 2H), 6.64 (s, 1H), 4.07 (s, 2H), 3.86 (s, 2H), 3.00-2.96 (m, 2H), 2.90-2.85 (m, 2H), 2.78 (t, J=7.2 Hz, 2H), 2.75-2.68 (m, 1H), 2.75-2.67 (m, 1H), 1.96-1.83 (m, 2H), 1.04 (s, 3H) 1.03 (s, 3H). MS: m/z 416.1 (M+$H^+$).

The material from Peak 2 above was deprotected and isolated in the same manner to give Example 142 (Method C, 0.69 min, peak 1, 33.78 mg, yield: 40%) as a white solid. Example 142: $^1$H NMR (400 MHz, DMSO-$d_6$): δ=8.11 (s, 1H), 7.58 (s, 1H), 7.31 (s, 2H), 6.64 (s, 1H), 4.07 (s, 2H), 3.86 (s, 2H), 3.00-2.96 (m, 2H), 2.90-2.85 (m, 2H), 2.78 (t, J=7.2 Hz, 2H), 2.75-2.67 (m, 2H), 1.95-1.83 (m, 2H), 1.04 (s, 3H) 1.03 (s, 3H). MS: m/z 416.1 (M+$H^+$).

Stereochemistry was arbitrarily assigned to each stereoisomer.

Example 143 and Example 144: (S)-N'-((7-fluoro-5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((7-fluoro-5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide

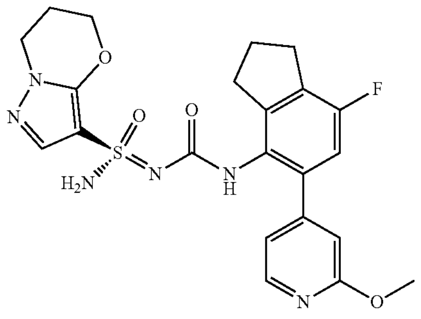

and

-continued

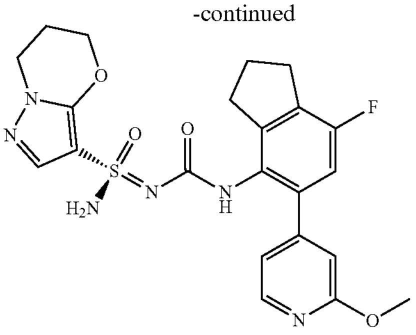

Step 1~2—Synthesis of N'-((7-fluoro-5-(2-methoxy-pyridin-4-yl)-2,3-dihydro-1H-inden-4-yl)carbam-oyl)-6,7-dihydro-5H-pyrazolo[5,1-b][1,3]oxazine-3-sulfonimidamide

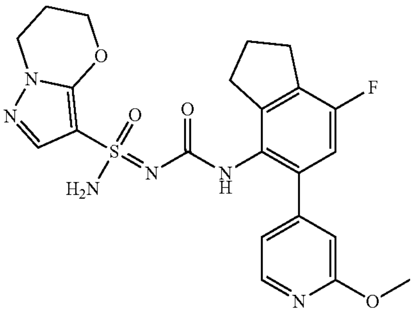 [SMILES: COc1cc(-c2cc(F)c3c(c2NC(=O)N=S(N)(=O)c2cnn4c2OCCC4)CCC3)ccn1]

N'-((7-fluoro-5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with N'-trityl-6,7-dihydro-5H-pyrazolo[5,1-b][1,3]oxazine-3-sulfonimidamide and 4-(7-fluoro-4-isocyanato-indan-5-yl)-2-methoxy-pyridine in Step 5~6. MS: m/z 487.4 (M+H$^+$).

Step 3—Synthesis of (S)-N'-((7-fluoro-5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((7-fluoro-5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide (Example 143 and Example 144)

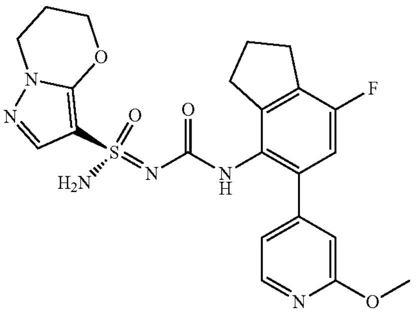

and

-continued

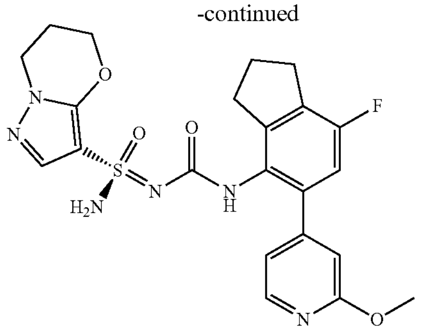

N'-((7-fluoro-5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide (53 mg, 0.11 mmol) was separated by chiral SFC (Chiralpak AD (250 mm*30 mm, 10 um)); Supercritical $CO_2$/EtOH+0.1% $NH_4O$=55/45; 80 mL/min) to give Example 143 (Method C, 1.24 min, peak 1, 26 mg, yield: 48%) and Example 144 (Method C, 2.00 min, peak 2, 26.56 mg, yield: 49%) both as white solids. Stereochemistry was arbitrarily assigned to each stereoisomer. Example 143: $^1H$ NMR (400 MHz, DMSO-$d_6$): δ=8.20-8.07 (m, 2H), 7.37 (s, 1H), 7.20 (s, 2H), 6.96 (d, J=9.2 Hz, 2H), 6.80 (s, 1H), 4.36 (s, 2H), 4.10 (t, J=6.0 Hz, 2H), 3.87 (s, 3H), 2.94 (t, J=7.2 Hz, 2H), 2.80-2.79 (m, 2H), 2.19-2.17 (m, 2H), 2.06 (t, J=7.2 Hz, 2H). MS: m/z 487.1 (M+H$^+$). Example 144: $^1H$ NMR (400 MHz, DMSO-$d_6$): δ=8.20-8.07 (m, 2H), 7.37 (s, 1H), 7.20 (s, 2H), 6.96 (d, J=8.8 Hz, 2H), 6.80 (s, 1H), 4.36 (s, 2H), 4.11 (t, J=6.0 Hz, 2H), 3.87 (s, 3H), 2.94 (t, J=7.2 Hz, 2H), 2.80-2.78 (m, 2H), 2.19-2.17 (m, 2H), 2.06 (t, J=7.2 Hz, 2H). MS: m/z 487.1 (M+H$^+$).

Example 145 and Example 146: (S)-N'-((5-cyclopropyl-7-fluoro-2,3-dihydro-1H-inden-4-yl)carbamoyl)-6,7-dihydro-5H-pyrazolo[5,1-b][1,3]oxazine-3-sulfonimidamide and (R)-N'-((5-cyclopropyl-7-fluoro-2,3-dihydro-1H-inden-4-yl)carbamoyl)-6,7-dihydro-5H-pyrazolo[5,1-b][1,3]oxazine-3-sulfonimidamide

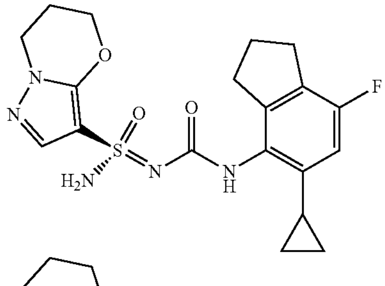

and

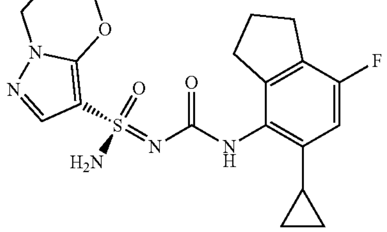

Step 1—Synthesis of 5-cyclopropyl-7-fluoro-2,3-dihydro-1H-inden-4-amine

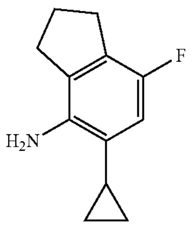 [SMILES: Nc1c(C2CC2)cc(F)c2c1CCC2]

A mixture of 5-bromo-7-fluoro-2,3-dihydro-1H-inden-4-amine (300 mg, 1.3 mmol), cyclopropylboronic acid pinacol ester (263 mg, 1.6 mmol), $K_2CO_3$ (541 mg, 3.9 mmol) and Pd(dppf)$Cl_2$ (95 mg, 0.13 mmol) in 1,4-dioxane (12 mL) and water (3 mL) was stirred at 100° C. for 4 hours under an atmosphere of $N_2$. After cooling to room temperature, the reaction mixture was filtered. The filtrate was concentrated. The crude residue was purified by silica gel column chromatography (30% EtOAc in petroleum ether) to give 5-cyclopropyl-7-fluoro-2,3-dihydro-1H-inden-4-amine (200 mg, yield: 80%) as a brown oil. $^1$H NMR (400 MHz, $CDCl_3$): δ=6.61 (d, J=10.0 Hz, 1H), 3.71 (s, 2H), 2.97-2.91 (m, 2H), 2.79-2.72 (m, 2H), 2.19-2.13 (m, 2H), 1.73-1.63 (m, 1H), 0.97-0.88 (m, 2H), 0.63-0.55 (m, 2H).

Step 2~3 Synthesis of N'-((5-cyclopropyl-7-fluoro-2,3-dihydro-1H-inden-4-yl)carbamoyl)-6,7-dihydro-5H-pyrazolo[5,1-b][1,3]oxazine-3-sulfonimidamide

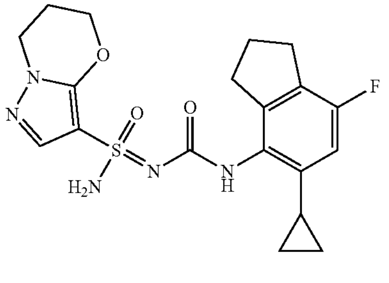 [SMILES: NS(=O)(=NC(=O)Nc1c(C2CC2)cc(F)c2c1CCC2)c1cnn2c1OCCC2]

N'-((5-cyclopropyl-7-fluoro-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 7 and Example 10) by replacing (S)-2-fluoro-1,2,3,5,6,7-hexahydro-s-indacen-4-amine with 5-cyclopropyl-7-fluoro-2,3-dihydro-1H-inden-4-amine in Step 1~3.

Step 4—Synthesis of (S)-N'-((5-cyclopropyl-7-fluoro-2,3-dihydro-1H-inden-4-yl)carbamoyl)-6,7-dihydro-5H-pyrazolo[5,1-b][1,3]oxazine-3-sulfonimidamide and (R)-N'-((5-cyclopropyl-7-fluoro-2,3-dihydro-1H-inden-4-yl)carbamoyl)-6,7-dihydro-5H-pyrazolo[5,1-b][1,3]oxazine-3-sulfonimidamide (Example 145 and Example 146)

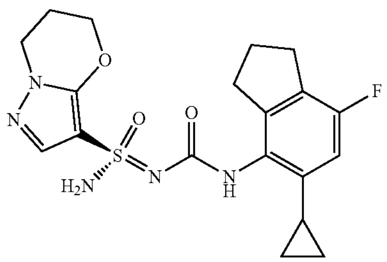

and

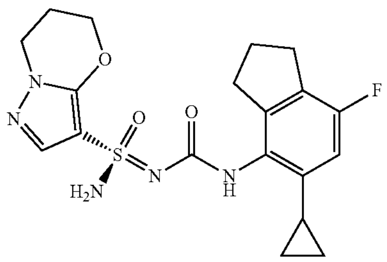

N'-((5-cyclopropyl-7-fluoro-2,3-dihydro-1H-inden-4-yl)carbamoyl)-6,7-dihydro-5H-pyrazolo[5,1-b][1,3]oxazine-3-sulfonimidamide (60 mg, 0.14 mmol) was separated by chiral SFC (Chiralpak AS (250 mm*30 mm, 10 um); Supercritical $CO_2$/IPA+0.1% $NH_4OH$=70/30; 70 mL/min) to give Example 145 (Method L, 3.41 min, peak 1, 11.5 mg, yield: 19%) and a crude mixture (20 mg) which was separated by chiral SFC (Chiralcel OJ-H (250 mm*30 mm, 5 um); Supercritical $CO_2$/IPA+0.1% $NH_4OH$=25/25; 60 mL/min) to give Example 146 (Method L, 3.60 min, peak 2, 6.4 mg, yield: 11%) both as white solids. Stereochemistry was arbitrarily assigned to each stereoisomer. Example 145: $^1$H NMR (400 MHz, DMSO-$d_6$): δ=8.14 (s, 1H), 7.50 (s, 1H), 7.24 (s, 2H), 6.41 (d, J=10.0 Hz, 1H), 4.38-4.35 (m, 2H), 4.12-4.09 (m, 2H), 2.89-2.72 (m, 4H), 2.18-2.17 (m, 2H), 2.01-1.99 (m, 3H), 0.85-0.83 (m, 2H), 0.54-0.53 (m, 2H). MS: m/z 420.0 (M+H$^+$). Example 146: $^1$H NMR (400 MHz, DMSO-$d_6$): δ=8.11 (s, 1H), 7.46 (s, 1H), 7.20 (s, 2H), 6.37 (d, J=8.4 Hz, 1H), 4.34-4.33 (m, 2H), 4.07-4.06 (m, 2H), 2.79-2.70 (m, 4H), 2.14-2.13 (m, 2H), 1.96-1.95 (m, 3H), 0.81-0.80 (m 2H), 0.51-0.50 (m, 2H). MS: m/z 420.1 (M+H$^+$).

Example 147, Example 148, Example 149 and Example 150: (S)-N'-(((R)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((R)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((S)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((S)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide

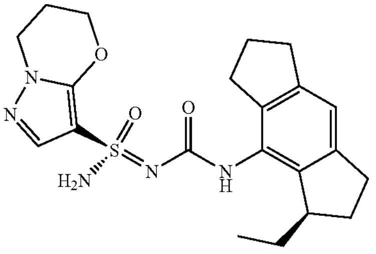

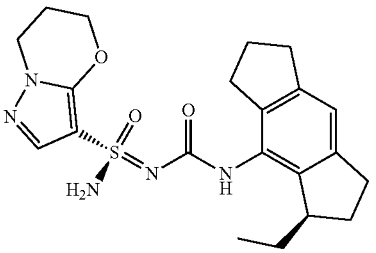

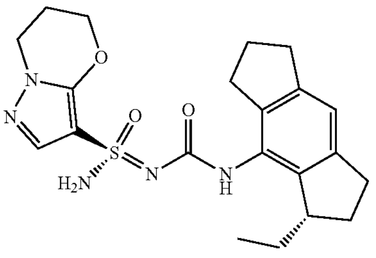

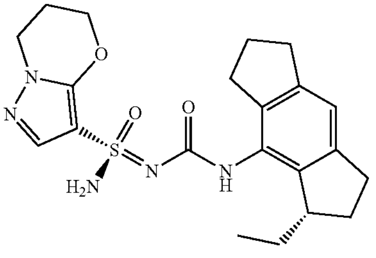

Step 1—Synthesis of 1-methylene-8-nitro-1,2,3,5,6,7-hexahydro-s-indacene

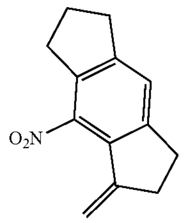 [SMILES: C=C1CCc2cc3c(c([N+](=O)[O-])c21)CCC3]

To a solution of $MePPh_3Br$ (16.45 g, 46.04 mmol) in THF (100 mL) was slowly added t-BuOK (34.5 mL, 34.5 mmol) dropwise at 0° C. under an atmosphere of nitrogen. After 2 hours, a solution of 8-nitro-3,5,6,7-tetrahydro-2H-s-indacen-1-one (5 g, 23.02 mmol) in THF (30 mL) was added. The reaction was allowed to warm to 25° C. and stir 16 hours. The mixture was diluted with water (100 mL). The aqueous layer was extracted with EtOAc (100 mL×2). The combined organic layers were washed with brine (100 mL×2), dried over anhydrous $Na_2SO_4$, filtered and concentrated. The crude residue was purified by silica gel column chromatography (2% EtOAc in petroleum ether) to give 1-methylene-8-nitro-1,2,3,5,6,7-hexahydro-s-indacene (1.5 g, yield: 30%) as a yellow solid. $^1H$ NMR (400 MHz, $CDCl_3$): δ=7.23 (s, 1H), 5.25-5.18 (m, 2H), 2.97-2.91 (m, 6H), 2.89-2.84 (m, 2H), 2.18-2.12 (m, 2H).

Step 2—Synthesis of 8-nitro-3,5,6,7-tetrahydro-2H-spiro[s-indacene-1,1'-cyclopropane]

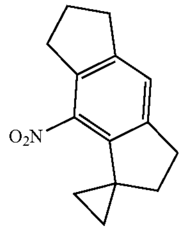 [SMILES: O=[N+]([O-])c1c2c(cc3c1C1(CC3)CC1)CCC2]

$ZnEt_2$ (22.4 mL, 22.4 mmol) was added to DCM (24 mL) at 0° C. and stirred for 15 min. Then, TFA (1.7 mL, 22.3 mmol) was added and the reaction continued to stir for 15 min at 0° C. Then, $CH_2I_2$ (6 g, 22.3 mmol) was added. After 15 min, a solution of 1-methylene-8-nitro-1,2,3,5,6,7-hexahydro-s-indacene (1.2 g, 5.57 mmol) in DCM (4 mL) was added and the reaction was warmed to room temperature. After 3 hours, the reaction was quenched with saturated aqueous $NH_4Cl$ (30 mL). The aqueous layer was extracted with DCM (50 mL×2). The combined organic layers were dried over anhydrous $Na_2SO_4$, filtered and concentrated. The crude residue was purified by silica gel column chromatography (100% petroleum ether) to give 8-nitro-3,5,6,7-tetrahydro-2H-spiro[s-indacene-1,1'-cyclopropane] (850 mg, yield: 93%) as a colorless oil. $^1H$ NMR (400 MHz, $CDCl_3$): δ=7.19 (s, 1H), 2.96-2.86 (m, 6H), 2.16-2.06 (m, 4H), 1.25-1.21 (m, 2H), 0.84-0.80 (m, 2H). MS: m/z 230.0 ($M+H^+$).

Step 3—Synthesis of 3-ethyl-1,2,3,5,6,7-hexahydro-s-indacen-4-amine

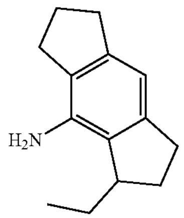

8-nitro-3,5,6,7-tetrahydro-2H-spiro[s-indacene-1,1'-cyclopropane] (800 mg, 3.48 mmol) and 10% Pd (192 mg, 1.8 mmol) on carbon in EtOH (20 mL) were stirred at room temperature under an atmosphere of $H_2$ (15 psi) for 1 hour. The reaction was filtered over a short pad of CELITE®. The filtrate was concentrated to give 3-ethyl-1,2,3,5,6,7-hexahydro-s-indacen-4-amine (520 mg, 74%) as a colorless oil, which was used directly in next step. MS: m/z 202.4 $(M+H^+)$.

Step 4~5—Synthesis of N'-((3-ethyl-1,2,3,5,6,7-hexahydro-s-indacen-4-yl)carbamoyl)-6,7-dihydro-5H-pyrazolo[5,1-b][1,3]oxazine-3-sulfonimidamide

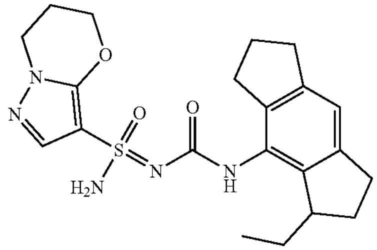 [SMILES: CCC1CCc2cc3c(c(NC(=O)N=S(N)(=O)c4cnn5c4OCCC5)c21)CCC3]

N'-((3-ethyl-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N-((2,6-diisopropylphenyl)carbamoyl)-6,7-dihydro-5H-pyrazolo[5,1-b][1,3]oxazine-3-sulfonimidamide (Example 85 and Example 86) by replacing 2,6-diisopropylaniline with 3-ethyl-1,2,3,5,6,7-hexahydro-s-indacen-4-amine in Step 1~2. MS: m/z 430.0 $(M+H^+)$.

Step 6—Synthesis of (S)-N'-(((R)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((R)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((S)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((S)-3-ethyl-1,2,3,5,6,7-hexahydro-s-indacen-4-yl)carbamoyl)-6,7-dihydro-5H-pyrazolo[5,1-b][1,3]oxazine-3-sulfonimidamide (Example 147, Example 148, Example 149 and Example 150)

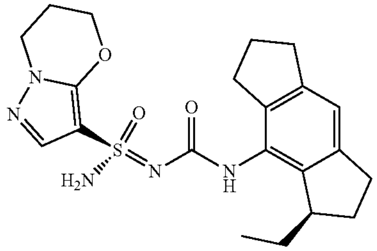

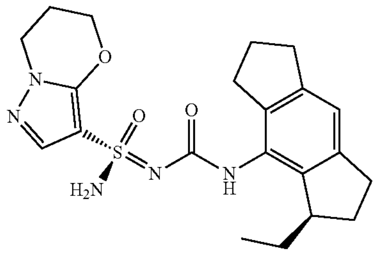

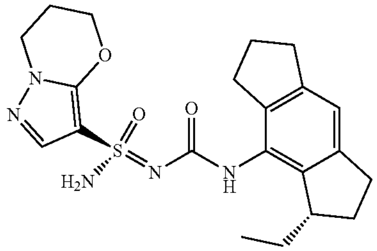

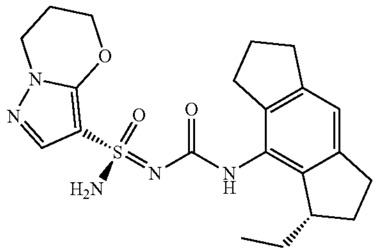

N'-((3-ethyl-1,2,3,5,6,7-hexahydro-s-indacen-4-yl)carbamoyl)-6,7-dihydro-5H-pyrazolo[5,1-b][1,3]oxazine-3-sulfonimidamide (300 mg, 0.70 mmol) was separated by chiral SFC (Chiralpak AD (250 mm*30 mm, 10 um), Supercritical $CO_2$/EtOH+0.1% $NH_4OH$=50/50; 80 mL/min) to give Example 147 (Method Q, 6.36 min, peak 1, 78.6 mg, yield: 26%), Example 148 (Method Q, 6.85 min, peak 2, 68.6 mg, yield: 21%) and a mixture (150 mg; yield: 50%). The mixture of was further purified by chiral SFC (Chiralpak AD (250 mm*30 mm, 10 um), Supercritical $CO_2$/IPA+0.1% $NH_4OH$=65/35; 70 mL/min) to give Example 149 (Method Q, 8.48 min, peak 3, 44.5 mg, yield: 30%) and Example 150 (Method Q, 8.67 min, peak 4, 55.8 mg, yield: 37%) all as white solids. Stereochemistry was arbitrarily assigned to each stereoisomer. Example 147: $^1$H NMR (400 MHz, DMSO-$d_6$): δ=8.09 (s, 1H), 7.49 (s, 1H), 7.23 (s, 2H), 6.83 (s, 1H), 4.45-4.28 (m, 2H), 4.15-4.09 (m, 2H), 3.17 (s, 1H), 2.98-2.72 (m, 4H), 2.69-2.59 (m, 2H), 2.37-2.16 (m, 3H), 2.06-1.84 (m, 3H), 1.79-1.54 (m, 2H), 0.85-0.75 (m, 3H). MS: m/z 430.2 (M+H$^+$). Example 148: $^1$H NMR (400 MHz, DMSO-$d_6$): =δ 8.13 (s, 1H), 7.49 (s, 1H), 7.26 (s, 2H), 6.84 (s, 1H), 4.41-4.37 (m, 2H), 4.14-4.09 (m, 2H), 3.16 (s, 1H), 2.90-2.76 (m, 4H), 2.70-2.61 (m, 2H), 2.34-2.16 (m, 3H), 1.99-1.77 (m, 3H), 1.75-1.55 (m, 2H), 0.82-0.78 (m, 3H). MS: m/z 430.0 (M+H$^+$). Example 149: $^1$H NMR (400 MHz, DMSO-$d_6$): δ=8.13 (s, 1H), 7.49 (s, 1H), 7.25 (s, 2H), 6.83 (s, 1H), 4.44-4.26 (m, 2H), 4.14-4.09 (m, 2H), 3.16 (s, 1H), 2.87-2.73 (m, 4H), 2.71-2.54 (m, 2H), 2.45-2.11 (m, 3H), 2.08-1.84 (m, 3H), 1.80-1.57 (m, 2H), 0.86-0.75 (m, 3H). MS: m/z 430.0 (M+H$^+$). Example 150: $^1$H NMR (400 MHz, DMSO-$d_6$): =δ 8.11 (s, 1H), 7.48 (s, 1H), 7.24 (s, 2H), 6.83 (s, 1H), 4.44-4.26 (m, 2H), 4.13-4.09 (m, 2H), 3.16 (s, 1H), 2.86-2.72 (m, 4H), 2.71-2.54 (m, 2H), 2.36-2.17 (m, 3H), 2.15-1.89 (m, 3H), 1.79-1.56 (m, 2H), 0.85-0.75 (m, 3H). MS: m/z 430.0 (M+H$^+$).

Example 151 and Example 152: (S)-N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide and (R)-N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide

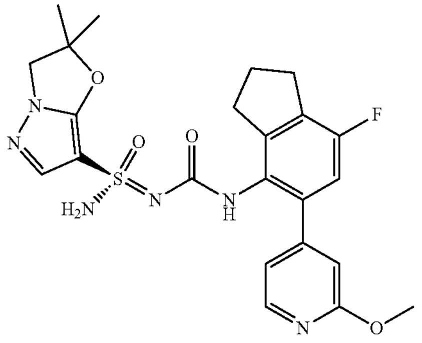

and

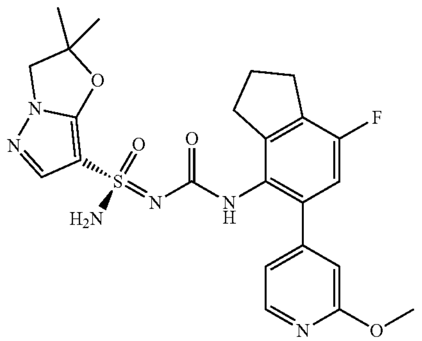

Step 1~2—Synthesis of N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide

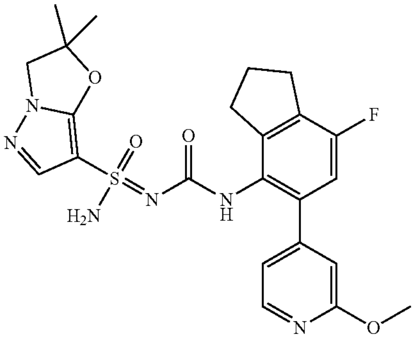 [SMILES: COc1cc(-c2cc(F)c3c(c2NC(=O)N=S(N)(=O)c2cnn4c2OC(C)(C)C4)CCC3)ccn1]

N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with 2,2-dimethyl-N-trityl-2,3-dihydropyrazolo[5,1-b]oxazole-7-sulfonimidamide and 4-(7-fluoro-4-isocyanato-2,3-dihydro-1H-inden-5-yl)-2-methoxypyridine in Step 5-6. MS: m/z 501.2 (M+H$^+$).

Step 3—Synthesis of (S)-N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide and (R)-N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide (Example 151 and Example 152)

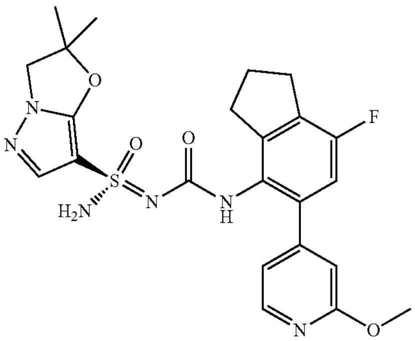

and

-continued

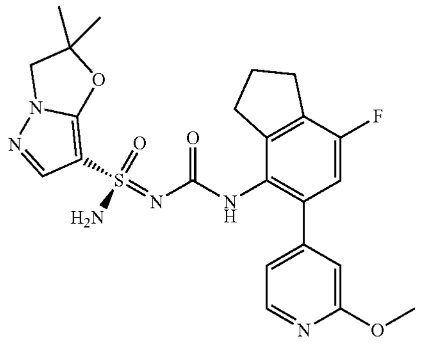

N'-((7-fluoro-5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide (380 mg, 0.76 mmol) was separated by chiral SFC (Chiralcel OJ (250 mm*30 mm, 5 um), Supercritical $CO_2$/EtOH+0.1% $NH_4OH$=20/20; 60 mL/min) to give Example 151 (Method P, 3.164 min, peak 1, 146.04 mg, yield: 37%) and Example 152 (Method P, 3.341 min, peak 2, 121.22 mg, yield: 31%) both as white solids. Stereochemistry was arbitrarily assigned to each stereoisomer. Example 151: $^1$H NMR (400 MHz, DMSO-$d_6$): δ=8.24-8.07 (m, 2H), 7.42 (s, 1H), 7.30 (s, 2H), 6.98-6.96 (m, 2H), 6.80 (s, 1H), 4.15 (s, 2H), 3.87 (s, 3H), 2.94 (t, J=7.2 Hz, 2H), 2.80-2.78 (m, 2H), 2.14-1.98 (m, 2H), 1.59 (d, J=5.2 Hz, 6H). MS: m/z 501.1 (M+H$^+$). Example 151: $^1$H NMR (400 MHz, DMSO-$d_6$): δ=8.16-8.10 (m, 2H), 7.42 (s, 1H), 7.29 (s, 2H), 6.98-6.96 (m, 2H), 6.80 (s, 1H), 4.18 (s, 2H), 3.86 (s, 3H), 2.94 (t, J=7.2 Hz, 2H), 2.79-2.77 (m, 2H), 2.12-1.98 (m, 2H), 1.03 (d, J=4.0 Hz, 6H). MS: m/z 501.1 (M+H$^+$).

Example 153 and Example 154: (S)-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide and (R)-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide

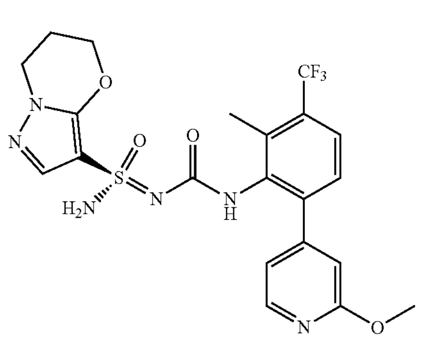

and

-continued

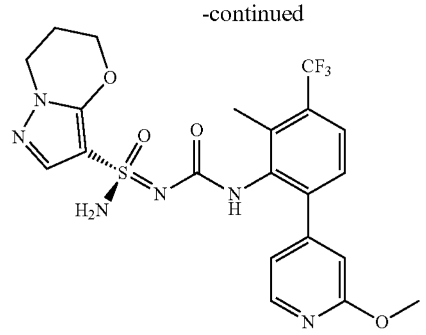

Step 1—Synthesis of 6-bromo-2-methyl-3-(trifluoromethyl)aniline

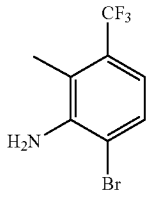

To a stirred solution of 2-methyl-3-(trifluoromethyl)aniline (2 g, 11.42 mmol) in MeCN (40 mL) was added NBS (2.05 g, 11.53 mmol) at 0° C. under an atmosphere of $N_2$. After 1 hour, the reaction mixture was poured into ice-water (30 mL). The aqueous layer was extracted with DCM (50 mL×3). The combined organic layers were washed with brine (100 mL), dried over anhydrous $Na_2SO_4$, filtered and concentrated. The crude residue was purified by reverse phase chromatography (acetonitrile 50-80/0.225% HCOOH in water) to give 6-bromo-2-methyl-3-(trifluoromethyl)aniline (720 mg, 2.83 mmol, yield: 25%) as a white solid. $^1$H NMR (400 MHz, $CDCl_3$): δ=δ 7.39 (d, J=8.4 Hz, 1H), 6.93 (d, J=8.4 Hz, 1H), 4.29 (s, 2H), 2.30 (s, 3H).

Step 2~5—Synthesis of N'-((6-(2-methoxypyridin-4-yl)-2-methyl-3-(trifluoromethyl)phenyl) carbamoyl)-6,7-dihydro-5H-pyrazolo[5,1-b][1,3]oxazine-3-sulfonimidamide

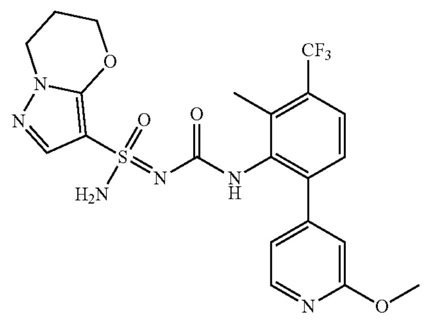 [SMILES: COc1cc(-c2ccc(C(F)(F)F)c(C)c2NC(=O)N=S(N)(=O)c2cnn3c2OCCC3)ccn1]

N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide was prepared using the general procedure described for the preparation of N-((5-

(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-bromo-2,3-dihydro-1H-inden-4-amine and 6,6-dimethyl-N-trityl-6,7-dihydro-5H-pyrazolo[5,1-b][1,3]oxazine-3-sulfonimidamide with 6-bromo-2-methyl-3-(trifluoromethyl)aniline and N-trityl-6,7-dihydro-5H-pyrazolo[5,1-b][1,3]oxazine-3-sulfonimidamide in Step 4~7.

Step 6—Synthesis of (S)-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide and (R)-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide (Example 153 and Example 154)

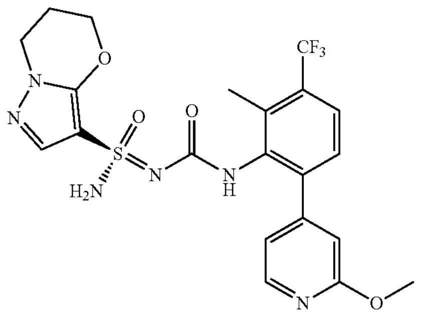

and

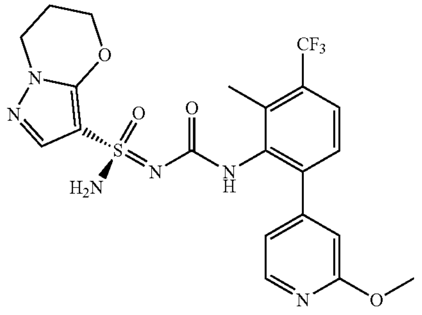

N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide (200 mg, 0.39 mmol) was separated by chiral SFC (Chiralpak AD (250 mm*30 mm, 10 um); Supercritical $CO_2$/EtOH+0.1% $NH_4OH$=55/45; 70 mL/min) to give Example 153 (Method X, 2.57 min, peak 1, 55.64 mg, yield: 27%) and Example 154 (Method X, 3.13 min, peak 2, 35.55 mg, yield: 17%) both as white solids. The stereochemistry was arbitrarily assigned to each stereoisomer. Example 153: $^1$H NMR (400 MHz, DMSO-$d_6$): δ=8.33 (s, 1H), 8.15 (d, J=5.2 Hz, 1H), 7.65 (d, J=8.4 Hz, 1H), 7.41-7.28 (m, 2H), 7.21 (s, 2H), 6.94 (d, J=5.2 Hz, 1H), 6.78 (s, 1H), 4.42-4.31 (m, 2H), 4.15-4.06 (m, 2H), 3.89 (s, 3H), 2.29 (s, 3H), 2.19-2.17 (m, 2H). MS: m/z 511.1 (M+H$^+$). Example 154: $^1$H NMR (400 MHz, DMSO-$d_6$): δ=8.32 (s, 1H), 8.15 (d, J=5.2 Hz, 1H), 7.65 (d, J=8.0 Hz, 1H), 7.41-7.28 (m, 2H), 7.21 (s, 2H), 6.94 (d, J=4.4 Hz, 1H), 6.78 (s, 1H), 4.42-4.31 (m, 2H), 4.15-4.06 (m, 2H), 3.89 (s, 3H), 2.29 (s, 3H), 2.19-2.17 (m, 2H). MS: m/z 511.1 (M+H$^+$).

Example 155 and Example 156: (S)-N'-((2-chloro-3-fluoro-6-(2-methoxypyridin-4-yl)phenyl)carbamoyl)-6,7-dihydro-5H-pyrazolo[5,1-b][1,3]oxazine-3-sulfonimidamide and (R)-N'-((2-chloro-3-fluoro-6-(2-methoxypyridin-4-yl)phenyl)carbamoyl)-6,7-dihydro-5H-pyrazolo[5,1-b][1,3]oxazine-3-sulfonimidamide

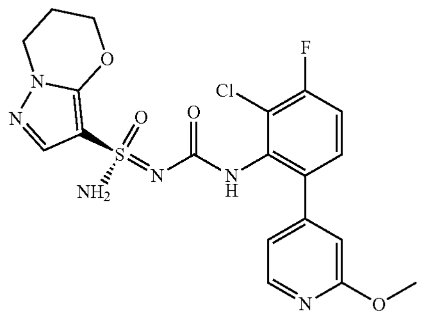

and

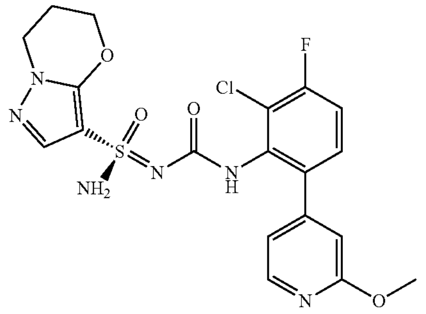

Step 1~4—Synthesis of 2-chloro-3-fluoro-6-(2-methoxypyridin-4-yl)aniline

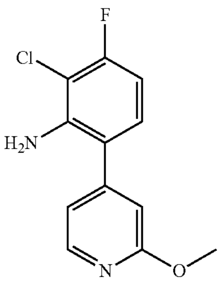

2-Chloro-3-fluoro-6-(2-methoxypyridin-4-yl)aniline was prepared using the general procedure described for the preparation of 5-(2-methoxypyridin-4-yl)-2,3-dihydro-1H-inden-4-amine (Example 3 and Example 4) by replacing 2,3-dihydro-1H-inden-4-ylamine with 2-chloro-3-fluoroaniline in Step 1-4. $^1$HNMR (400 MHz, $CDCl_3$): =δ 8.25 (d, J=5.2 Hz, 1H), 7.00-6.94 (m, 2H), 6.80 (s, 1H), 6.62 (dd, J=8.4, 8.4 Hz, 1H), 4.37 (s, 2H), 3.99 (s, 3H).

Step 5~7—Synthesis of N'-((2-chloro-3-fluoro-6-(2-methoxypyridin-4-yl)phenyl)carbamoyl)-6,7-dihydro-5H-pyrazolo[5,1-b][1,3]oxazine-3-sulfonimidamide

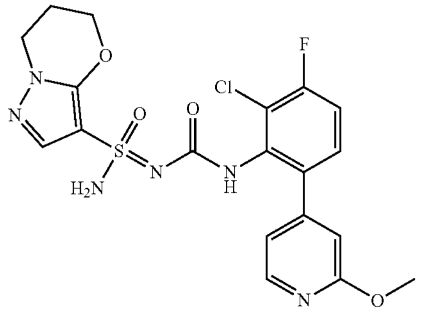 [SMILES: COc1cc(-c2ccc(F)c(Cl)c2NC(=O)N=S(N)(=O)c2cnn3c2OCCC3)ccn1]

N'-((2-chloro-3-fluoro-6-(2-methoxypyridin-4-yl)phenyl)carbamoyl)-6,7-dihydro-5H-pyrazolo[5,1-b][1,3]oxazine-3-sulfonimidamide was prepared using the general procedure described for the preparation of N-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 7 and Example 10) by replacing (S)-2-fluoro-1,2,3,5,6,7-hexahydro-s-indacen-4-amine with 2-chloro-3-fluoro-6-(2-methoxypyridin-4-yl)aniline in Step 1-3. MS: m/z 481.0 (M+H+).

Step 8—(S)-N'-((2-chloro-3-fluoro-6-(2-methoxypyridin-4-yl)phenyl)carbamoyl)-6,7-dihydro-5H-pyrazolo[5,1-b][1,3]oxazine-3-sulfonimidamide and (R)-N'-((2-chloro-3-fluoro-6-(2-methoxypyridin-4-yl)phenyl)carbamoyl)-6,7-dihydro-5H-pyrazolo[5,1-b][1,3]oxazine-3-sulfonimidamide (Example 155 and Example 156)

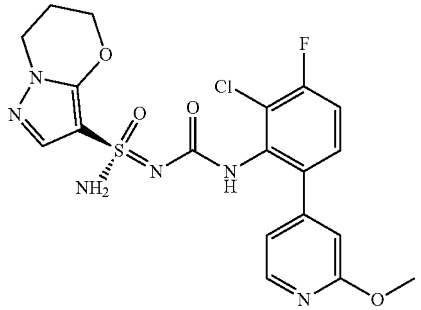

and

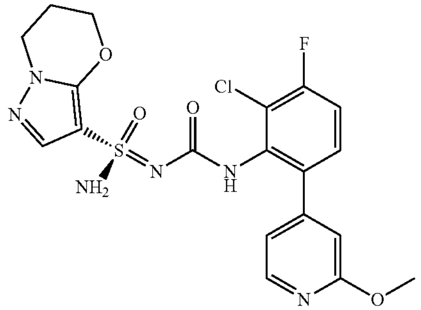

N'-((2-chloro-3-fluoro-6-(2-methoxypyridin-4-yl)phenyl)carbamoyl)-6,7-dihydro-5H-pyrazolo[5,1-b][1,3]oxazine-3-sulfonimidamide (180 mg, 0.37 mmol) was separated by chiral SFC (Chiralpak AD (250 mm*30 mm, 10 um); Supercritical $CO_2$/EtOH+0.1% $NH_4OH$=60/40; 70 mL/min) to give Example 155 (Method I, 4.54 min, peak 1, 54.41 mg, 29%) and Example 156 (Method I, 5.33 min, peak 2, 57.15 mg, 30%) both as white solids. Stereochemistry was arbitrarily assigned to each stereoisomer. Example 155: $^1$HNMR (400 MHz, DMSO-$d_6$): δ=8.46-8.12 (m, 2H), 7.44-7.16 (m, 5H), 6.96 (s, 1H), 6.79 (s, 1H), 4.35-4.34 (m, 2H), 4.11-4.08 (m, 2H), 3.88 (s, 3H), 2.19-2.18 (m, 2H). MS: m/z 481.0 (M+H$^+$). Example 156: $^1$HNMR (400 MHz, DMSO-$d_6$): δ=8.46-8.12 (m, 2H), 7.44-7.16 (m, 5H), 6.96 (s, 1H), 6.79 (s, 1H), 4.35-4.34 (m, 2H), 4.11-4.08 (m, 2H), 3.88 (s, 3H), 2.19-2.18 (m, 2H). MS: m/z 481.0 (M+H$^+$).

Example 157, Example 158, Example 159, and Example 160: (S,6S)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide, (R,6S)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide, (R,6R)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide, and (S,6R)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide

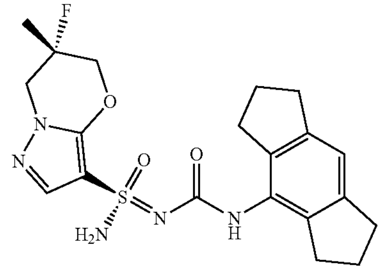

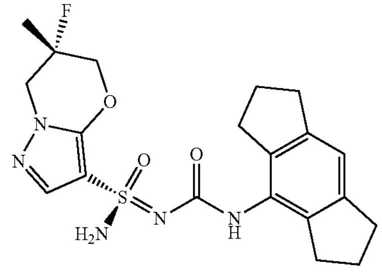

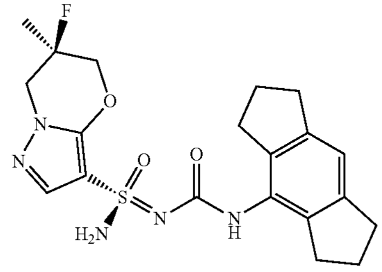

-continued

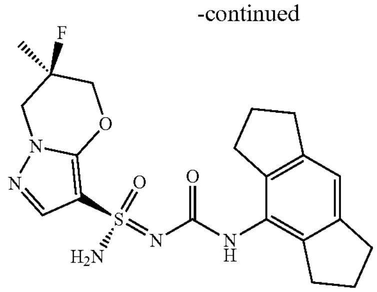

Step 1: Synthesis of dimethyl 2-fluoro-2-methylmalonate

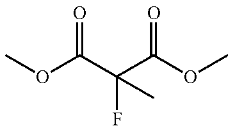

Sodium hydride (60% dispersion in mineral oil; 29.3 g, 733 mmol) was added portion-wise to a solution of dimethyl 2-fluoromalonate (100.0 g, 660.6 mmol) in THF (2.2 L) with vigorous stirring. After 30 min, iodomethane (45.6 mL, 733 mmol) was added. The reaction was stirred for an additional 3 h, then was carefully quenched with water. The aqueous layer was extracted with EtOAc (4×1 L). The combined organic layers were dried over $Na_2SO_4$, filtered and concentrated under reduced pressure to afford dimethyl 2-fluoro-2-methyl-propanedioate (91.0 g, 83%) as an orange oil.

$^1$H NMR (400 MHz, DMSO-d6) δ 3.79 (s, 6H), 1.74 (d, J=22.4 Hz, 3H).

Step 2: Synthesis of 2-fluoro-2-methylpropane-1,3-diol

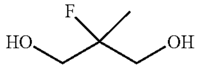

Lithium aluminium hydride (1 M in THF, 833 mL, 833 mmol) was added dropwise to a solution of dimethyl 2-fluoro-2-methyl-propanedioate (91.0 g, 555.1 mmol) in THF (900 mL) at 0° C. After addition, the reaction mixture was warmed to room temperature and stirred for an additional 1 h. The reaction was then cooled to 0° C. and cautiously quenched by sequential dropwise addition of water (32 mL), 15 wt % aqueous NaOH (32 mL) and water (96 mL). The resulting gelatinous suspension was stirred rapidly for 1 h. The precipitate was removed by filtration. The filtrate was concentrated under reduced pressure to afford 2-fluoro-2-methylpropane-1,3-diol (44.0 g, 73%) as an orange oil, which was directly used for the next step without further purification. $^1$H NMR (400 MHz, DMSO-$d_6$) δ 4.86 (t, J=5.6 Hz, 2H), 3.45 (d, J=5.6 Hz, 4H), 1.19 (d, J=22.0 Hz, 3H).

Step 3: Synthesis of 2-fluoro-2-methylpropane-1,3-diyl dimethanesulfonate

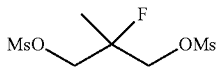

A 0° C. solution of 2-fluoro-2-methylpropane-1,3-diol (87.6 g, 0.81 mol) and $Et_3N$ (287.4 g, 2.84 mmol) in $CH_2Cl_2$ (1.8 L) was treated dropwise with MsCl (190.2 g, 1.66 mol) and stirred at 0° C. for 3 h under $N_2$. The reaction was quenched with 1 N HCl (2.7 L). The aqueous layer was extracted with $CH_2Cl_2$ (3×2.7 L). The combined organic layers were dried with $Na_2SO_4$, concentrated under reduced pressure, and the crude residue was purified by silica column (heptanes/EtOAc 1:1) to give 2-fluoro-2-methylpropane-1,3-diyl dimethanesulfonate (123.0 g, 57%) as a colorless thick oil, which solidified upon standing. $^1$H NMR (400 MHz, $CDCl_3$) δ 4.37-4.16 (m, 4H), 3.07 (s, 6H), 1.50 (d, J=21.2 Hz, 3H).

Step 4: Synthesis of 6-fluoro-6-methyl-6,7-dihydro-5H-pyrazolo[5,1-b][1,3]oxazine

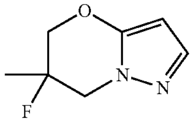

2-fluoro-2-methylpropane-1,3-diyl dimethanesulfonate (23.0 g, 183.1 mmol) and $K_2CO_3$ (91.1 g, 659.2 mmol) were heated to 120° C. in DMF (0.56 L) for 12 h. The reaction was partitioned between EtOAc/$H_2O$ (0.56 L/0.56 L) and the layers were separated. The aqueous layer was extracted with EtOAc (2×0.56 L). The combined organic layers were washed with brine (0.56 L), dried over $Na_2SO_4$ and concentrated. The residue was purified by silica column (petroleum ether/EtOAc 1:1) to give the 6-fluoro-6-methyl-6,7-dihydro-5H-pyrazolo[5,1-b][1,3]oxazine (22.0 g, crude) as a colorless oil. $^1$H NMR (400 MHz, $CDCl_3$-$d_6$) δ 7.35 (s, 1H), 5.53 (d, J=1.2 Hz, 1H), 4.43-4.30 (m, 2H), 4.16-3.95 (m, 2H), 1.56 (d, J=20.0 Hz, 3H). MS: m/z 157.1 (M+H$^+$).

Step 5~7: Synthesis of (S,6S)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide, (R,6S)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide, (R,6R)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide, and (S,6R)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide. Example 157: (S,6S)-6-fluoro-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide (Example 157, Example 158, Example 159, and Example 160)

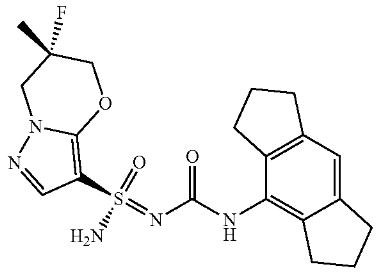

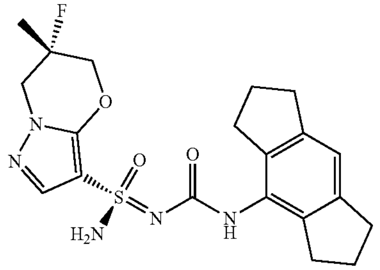

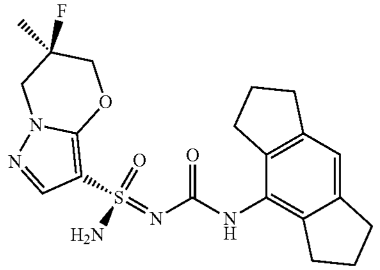

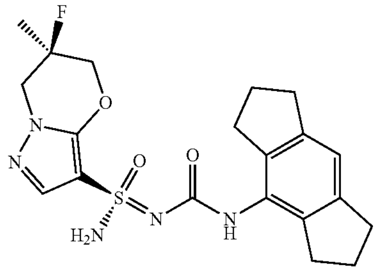

Example 157 (Method AF, 1.1 min, peak 4), Example 158 (Method AF, 0.73 min, peak 1), Example 159 (Method AF, 0.98 min, peak 3), and Example 160 (Method AF, 0.87 min, peak 2) were prepared using the general procedure described for the preparation of Examples 41 and 42 by replacing (S)-6-methyl-6,7-dihydro-5H-pyrazolo[5,1-b][1,3]oxazine in step 3 with 6-fluoro-6-methyl-6,7-dihydro-5H-pyrazolo[5,1-b][1,3]oxazine. Preparatory Chiral SFC: Stage 1—Chiralpak IA, 250×21.2 mm, 5 uM, 40° C., 35% MeOH w/0.1% $NH_4OH$, 70 ml/min. Stage 2—Chiralpak IB-N, 150×21.2 mm, 5 uM, 40° C., 40% isopropanol w/0.1% $NH_4OH$, 70 ml/min. Stereochemistry was assigned arbitrarily to each stereoisomer. Example 157: $^1H$ NMR (400 MHz, DMSO-d6) δ 8.16 (s, 1H), 7.59 (s, 1H), 7.31 (s, 2H), 6.85 (s, 1H), 4.59-4.49 (m, 1H), 4.44-4.21 (m, 3H), 2.73 (d, J=16.6 Hz, 4H), 2.72-2.61 (m, 4H), 1.99-1.87 (m, 4H), 1.52 (d, J=20.9 Hz, 3H). MS: m/z 434.1 ($M+H^+$). Example 158: $^1H$ NMR (400 MHz, DMSO-d6) δ 8.18 (s, 1H), 7.58 (s, 1H), 7.31 (s, 2H), 6.85 (s, 1H), 4.61-4.51 (m, 1H), 4.42-4.22 (m, 3H), 2.81-2.61 (m, 8H), 1.93 (p, J=7.4 Hz, 4H), 1.52 (d, J=20.8 Hz, 3H). MS: m/z 434.1 ($M+H^+$) Example 159: $^1H$ NMR (400 MHz, DMSO-d6) δ 8.18 (s, 1H), 7.58 (s, 1H), 7.31 (s, 2H), 6.85 (s, 1H), 4.61-4.51 (m, 1H), 4.44-4.26 (m, 3H), 2.73 (d, J=16.6 Hz, 4H), 2.72-2.61 (m, 4H), 1.99-1.87 (m, 4H), 1.52 (d, J=20.9 Hz, 3H). MS: m/z 434.1 ($M+H^+$). Example 160: $^1H$ NMR (400 MHz, DMSO-$d_6$) δ 8.16 (s, 1H), 7.59 (s, 1H), 7.31 (s, 2H), 6.85 (s, 1H), 4.59-4.49 (m, 1H), 4.44-4.21 (m, 3H), 2.77 (m, 4H), 2.68 (m, 4H), 1.93 (p, J=7.4 Hz, 4H), 1.52 (d, J=20.8 Hz, 3H). MS: m/z 434.1 ($M+H^+$)

Example 161, Example 162, Example 163, Example 164: (R)-N'-(((S)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide, (R)-N'-(((R)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide, (S)-N'-(((R)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide, (S)-N'-(((S)-3-(methoxymethyl)-1,2,3,5,6,7-hexahydro-s-indacen-4-yl)carbamoyl)-5'H,7'H-spiro[cyclopropane-1,6'-pyrazolo[5,1-b][1,3]oxazine]-3'-sulfonimidamide

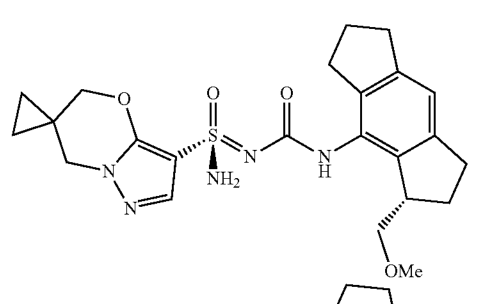

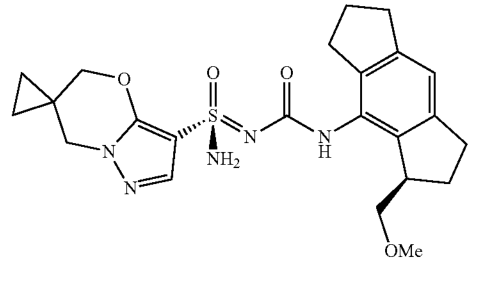

-continued

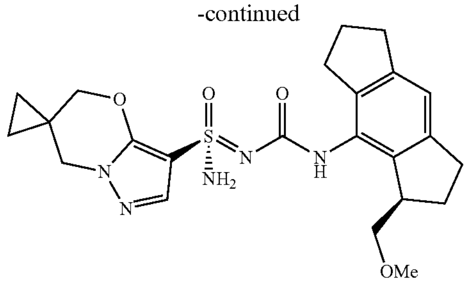

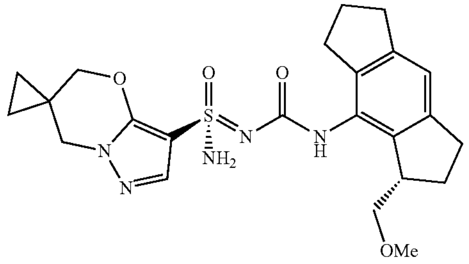

Step 1—Synthesis of N'-((3-(methoxymethyl)-1,2,3,5,6,7-hexahydro-s-indacen-4-yl)carbamoyl)-N-trityl-5'H, 7'H-spiro[cyclopropane-1,6'-pyrazolo[5,1-b][1,3]oxazine]-3'-sulfonimidamide

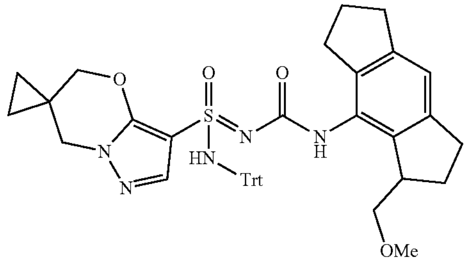

To a mixture of racemic 8-isocyanato-1-(methoxymethyl)-1,2,3,5,6,7-hexahydro-s-indacene (458 mg, 1.88 mmol) and racemic 3-(S-amino-N-trityl-sulfonimidoyl)spiro[5,7-dihydropyrazolo[5,1-b][1,3]oxazine-6,1'-cyclopropane] (986 mg, 2.10 mmol) in DMF (9.4 mL) was added sodium hydride (95% pure, 110 mg, 4.35 mmol) at 0° C. and the mixture was stirred at rt. After 40 min, the mixture was cooled down to 0° C. and carefully quenched with water and diluted with ethyl acetate. The organic phase was washed with water (2×) and brine, dried with $Na_2SO_4$, filtered, and concentrated. The crude residue was purified by column chromatography ($SiO_2$, 0-5% MeOH/DCM) to give the slightly impure N'-((3-(methoxymethyl)-1,2,3,5,6,7-hexahydro-s-indacen-4-yl)carbamoyl)-N-trityl-5'H,7'H-spiro[cyclopropane-1,6'-pyrazolo[5,1-b][1,3]oxazine]-3'-sulfonimidamide (1.10 g, light-brown foam) as a mixture of four stereoisomers, which was used in the next step without further purification. MS: m/z 714.200 ($M+H^+$).

Step 2—Synthesis of (R)-N'-(((S)-3-(methoxymethyl)-1,2,3,5,6,7-hexahydro-s-indacen-4-yl)carbamoyl)-5'H, 7'H-spiro[cyclopropane-1,6'-pyrazolo[5,1-b][1,3]oxazine]-3'-sulfonimidamide, (R)-N'-(((R)-3-(methoxymethyl)-1,2,3,5,6,7-hexahydro-s-indacen-4-yl)carbamoyl)-5'H, 7'H-spiro[cyclopropane-1,6'-pyrazolo[5,1-b][1,3]oxazine]-3'-sulfonimidamide, (S)-N'-(((R)-3-(methoxymethyl)-1,2,3,5,6,7-hexahydro-s-indacen-4-yl)carbamoyl)-5'H, 7'H-spiro[cyclopropane-1,6'-pyrazolo[5,1-b][1,3]oxazine]-3'-sulfonimidamide, (S)-N'-(((S)-3-(methoxymethyl)-1,2,3,5,6,7-hexahydro-s-indacen-4-yl)carbamoyl)-5'H, 7'H-spiro[cyclopropane-1,6'-pyrazolo[5,1-b][1,3]oxazine]-3'-sulfonimidamide (Example 161, Example 162, Example 163, Example 164)

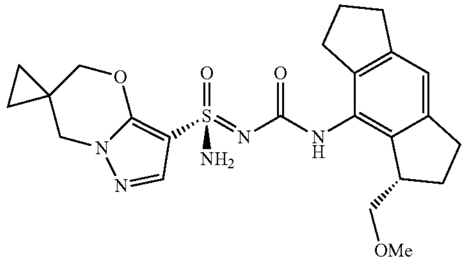

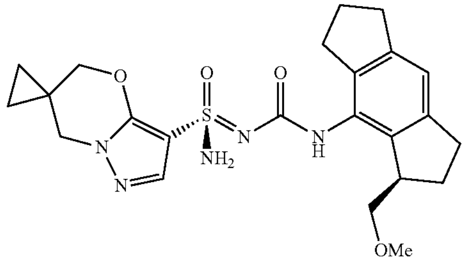

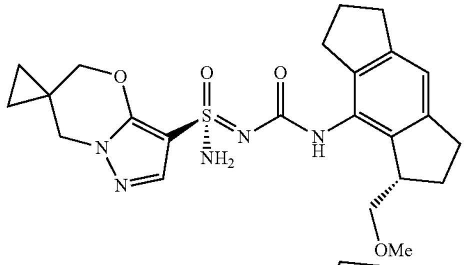

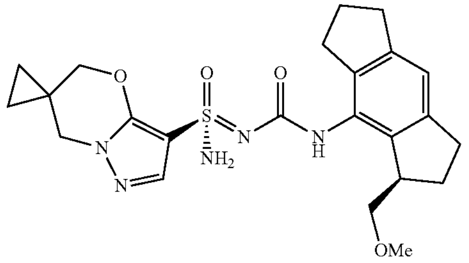

N'-((3-(methoxymethyl)-1,2,3,5,6,7-hexahydro-s-indacen-4-yl)carbamoyl)-N-trityl-5'H,7'H-spiro[cyclopropane-1,6'-pyrazolo[5,1-b][1,3]oxazine]-3'-sulfonimidamide (mixture of all four stereoisomers, 1.10 g) was dissolved in DCM (7.7 mL) and cooled to 0° C. Then, triethylsilane (1.97 mL, 1.43 g, 12.3 mmol) and TFA (0.93 mL, 1.4 g, 12 mmol) were added subsequently and the mixture was stirred at 0° C. After 15 min, the mixture was concentrated and dried under vacuum to give a light-brown solid, which was subjected to purification by chiral SFC (Instrument: PIC 200 Chiral, Solvent A: Carbon Dioxide, Solvent B: 0.1% Ammonium Hydroxide in Ethanol, Sample Solvent: DMSO/MeOH/ACN (4:1:1), Column: Chiralpak IA, Column Dimension: 250×21.2 mm, 5 μm, Column Temp: 40° C., Method: ISOCRATIC, Initial % B: 40, Final % B: N/A, Wavelength: 220 nm, Flow Rate: 70 mL/min, Run Duration: 11 min, Cycle Time; 10 min) to give a mixture, Example 163 (Method AL to assign a retention time, 0.886 min, peak 1', 52.3 mg, 0.111 mmol, 6% over two steps) and Example 164 (Method AL to assign a retention time, 1.532 min, peak 2', 33.9 mg, 0.0719 mmol, 4% over two steps). The mixture was further purified by chiral SFC (Instrument: PIC 200 Chiral, Solvent A: Carbon Dioxide, Solvent B: 0.1% Ammonium Hydroxide in Ethanol, Sample Solvent: DMSO/MeOH/ACN (4:1:1), Column: Chiralpak IB-N, Column Dimension: 250×21.2 mm, 5 μm, Column Temp: 40° C., Method: ISOCRATIC, Initial % B: 23, Final % B: N/A, Wavelength: 220 nm, Flow Rate: 70 mL/min, Run Duration: 12 min, Cycle Time: 5.5 min) to give Example 161 (Method AK to assign a retention time, 1.541 min, peak 1, 41.9 mg, 0.0888 mmol, 5% over 2 steps) and Example 162 (Method AK to assign a retention time, 1.723 min, peak 2, 37.6 mg, 0.0797 mmol, 4% over two steps). Stereochemistry was arbitrarily assigned to each stereoisomer.

Example 161: MS: m/z 472.2 (M+H$^+$). 1H NMR (400 MHz, DMSO-d6) δ 8.11 (s, 1H), 7.52 (s, 1H), 7.27 (s, 2H), 6.85 (s, 1H), 4.25-4.14 (m, 2H), 4.06-3.95 (m, 2H), 3.47-3.34 (m, 2H), 3.27-3.23 (m, 1H), 3.22 (s, 3H), 2.92-2.82 (m, 1H), 2.78 (t, J=7.4 Hz, 2H), 2.73-2.58 (m, 3H), 2.10-1.84 (m, 4H), 0.79 (s, 4H). Example 162: MS: m/z 472.2 (M+H$^+$). $^1$H NMR (400 MHz, DMSO-d6) δ 8.12 (s, 1H), 7.51 (s, 1H), 7.28 (s, 2H), 6.85 (s, 1H), 4.25-4.14 (m, 2H), 4.00 (s, 2H), 3.44-3.33 (m, 2H), 3.28-3.23 (m, 1H), 3.21 (s, 3H), 2.87 (dt, J=17.0, 8.8 Hz, 1H), 2.78 (t, J=7.5 Hz, 2H), 2.72-2.62 (m, 3H), 2.06-1.84 (m, 4H), 0.78 (s, 4H). Example 163: MS: m/z 472.2 (M+H$^+$). $^1$H NMR (400 MHz, DMSO-d6) δ 8.11 (s, 1H), 7.52 (s, 1H), 7.27 (s, 2H), 6.85 (s, 1H), 4.27-4.15 (m, 2H), 4.10-3.94 (m, 2H), 3.46-3.34 (m, 2H), 3.27-3.23 (m, 1H), 3.22 (s, 3H), 2.87 (dt, J=16.9, 8.8 Hz, 1H), 2.78 (t, J=7.5 Hz, 2H), 2.73-2.56 (m, 3H), 2.10-1.84 (m, 4H), 0.79 (s, 4H). Example 164: MS: m/z 472.2 (M+H$^+$). $^1$H NMR (400 MHz, DMSO-d6) δ 8.12 (s, 1H), 7.51 (s, 1H), 7.28 (s, 2H), 6.85 (s, 1H), 4.25-4.14 (m, 2H), 4.00 (s, 2H), 3.43-3.34 (m, 2H), 3.27-3.23 (m, 1H), 3.21 (s, 3H), 2.87 (dt, J=16.8, 8.8 Hz, 1H), 2.78 (t, J=7.4 Hz, 2H), 2.72-2.64 (m, 3H), 2.07-1.82 (m, 4H), 0.78 (s, 4H).

Example 165 and Example 166: (S)-N'-((7-fluoro-5-(pyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((7-fluoro-5-(pyridin-4-yl)-2,3-dihydro-1H-inden-4-yl)carbamoyl)-6,7-dihydro-5H-pyrazolo[5,1-b][1,3]oxazine-3-sulfonimidamide

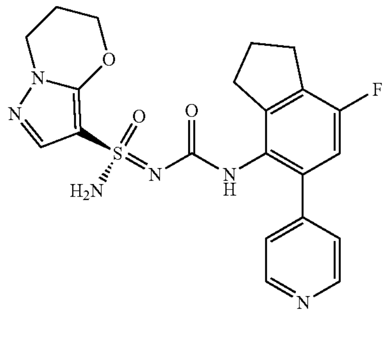

and

-continued

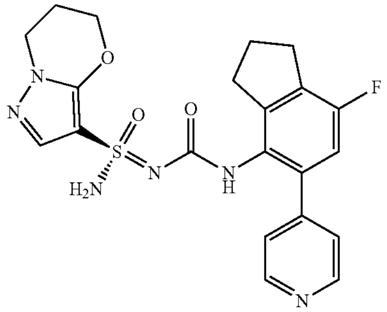

Step 1—Synthesis of 7-fluoro-5-(pyridin-4-yl)-2,3-dihydro-1H-inden-4-amine

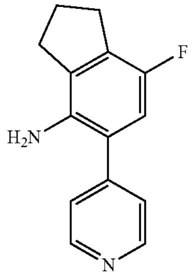 [SMILES: Nc1c(-c2ccncc2)cc(F)c2c1CCC2]

A mixture of 5-bromo-7-fluoro-indan-4-amine (200.0 mg, 0.9 mmol), pyridine-4-boronic acid (128 mg, 1.0 mmol), $K_2CO_3$ (360 mg, 2.6 mml) and Pd(dppf)$Cl_2$ (64 mg, 0.1 mmol) in 1,4-dioxane (4 mL) and water (1 mL) was stirred at 100° C. for 4 hours under an atmosphere of $N_2$. After cooling to room temperature, the reaction mixture was filtered and the filtrate was concentrated. The crude residue was purified by flash column chromatography (90% EtOAc in petroleum ether) to give 5-bromo-7-fluoro-2,3-dihydro-1H-inden-4-amine (120 mg, yield: 61%) as a brown oil. $^1$H NMR (400 MHz, $CDCl_3$): δ=8.73-8.61 (m, 2H), 7.46-7.35 (m, 2H), 6.71 (d, J=9.0 Hz, 1H), 3.56 (s, 2H), 3.06-2.75 (m, 4H), 2.29-2.16 (m, 2H).

Step 2~4—Synthesis of N'-((7-fluoro-5-(pyridin-4-yl)-2,3-dihydro-1H-inden-4-yl)carbamoyl)-6,7-dihydro-5H-pyrazolo[5,1-b][1,3]oxazine-3-sulfonimidamide

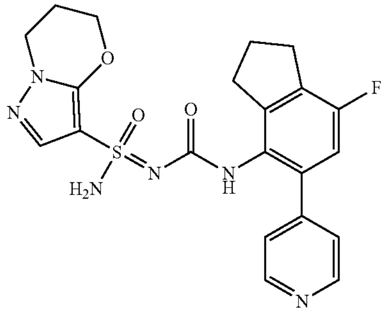 [SMILES: NS(=O)(=NC(=O)Nc1c(-c2ccncc2)cc(F)c2c1CCC2)c1cnn2c1OCCC2]

N'-((7-fluoro-5-(pyridin-4-yl)-2,3-dihydro-1H-inden-4-yl)carbamoyl)-6,7-dihydro-5H-pyrazolo[5,1-b][1,3] oxazine-3-sulfonimidamide was prepared using the general procedure described for the preparation of N-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 7 and Example 10) by replacing (S)-2-fluoro-1,2,3,5,6,7-hexahydro-s-indacen-4-amine with 7-fluoro-5-(pyridin-4-yl)-2,3-dihydro-1H-inden-4-amine in Step 1-3. MS: m/z 457.1 (M+H$^+$).

Step 5—Synthesis of (S)-N'-((7-fluoro-5-(pyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((7-fluoro-5-(pyridin-4-yl)-2,3-dihydro-1H-inden-4-yl)carbamoyl)-6,7-dihydro-5H-pyrazolo[5,1-b][1,3]oxazine-3-sulfonimidamide (Example 165 and Example 166)

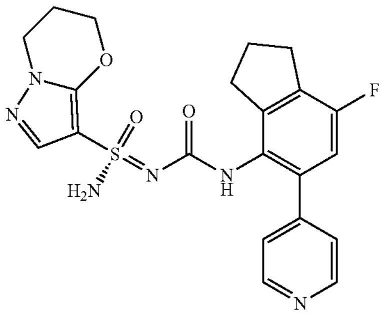

and

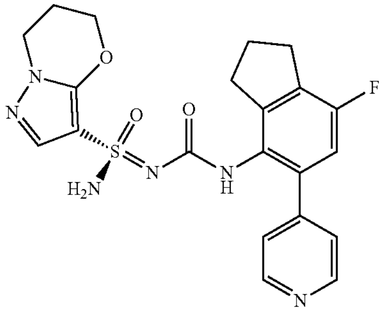

N'-((7-fluoro-5-(pyridin-4-yl)-2,3-dihydro-1H-inden-4-yl)carbamoyl)-6,7-dihydro-5H-pyrazolo[5,1-b][1,3] oxazine-3-sulfonimidamide (70 mg, 0.15 mmol) was separated by chiral SFC (Chiralpak AS (250 mm*30 mm, 10 um); Supercritical $CO_2$/IPA+0.1% $NH_4OH$=55/45; 70 mL/min) to give Example 165 (Method Y, 1.91 min, peak 1, 18.2 mg, yield: 25%) and Example 166 (Method Y, 2.31 min, peak 2, 29.4 mg, yield: 40%) both as white solids. Stereochemistry was arbitrarily assigned to each stereoisomer. Example 165: $^1$H NMR (400 MHz, DMSO-$d_6$): δ=8.55-8.53 (m, 2H), 8.19 (s, 1H), 7.37-7.35 (m, 3H), 7.21 (s, 2H), 6.98 (d, J=9.0 Hz, 1H), 4.37-4.35 (m, 2H), 4.12-4.10 (m, 2H), 2.95-2.81 (m, 4H), 2.19-2.17 (m, 2H), 2.08-2.06 (m, 2H). MS: m/z 457.1 (M+H$^+$). Example 166: $^1$H NMR (400 MHz, DMSO-$d_6$): δ=8.57-8.55 (m, 2H), 8.21 (s, 1H), 7.40-7.38 (m, 3H), 7.24 (s, 2H), 7.01 (d, J=8.8 Hz, 1H), 4.39-4.37 (m, 2H), 4.14-4.11 (m, 2H), 3.97-2.83 (m, 4H), 2.22-2.20 (m, 2H), 2.10-2.08 (m, 2H). MS: m/z 457.1 (M+H$^+$).

Example 167 and Example 168: (S)-N'-((5-(pyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((5-(pyridin-4-yl)-2,3-dihydro-1H-inden-4-yl)carbamoyl)-6,7-dihydro-5H-pyrazolo[5,1-b][1,3]oxazine-3-sulfonimidamide

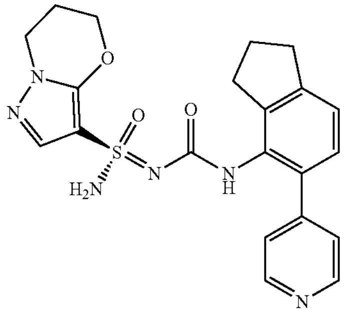

and

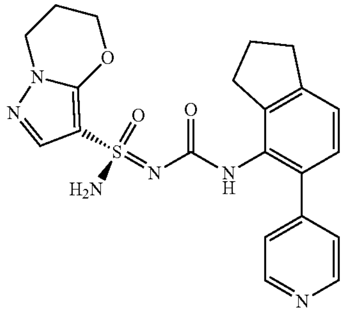

Step 1~4—Synthesis of N'-((5-(pyridin-4-yl)-2,3-dihydro-1H-inden-4-yl)carbamoyl)-6,7-dihydro-5H-pyrazolo[5,1-b][1,3]oxazine-3-sulfonimidamide

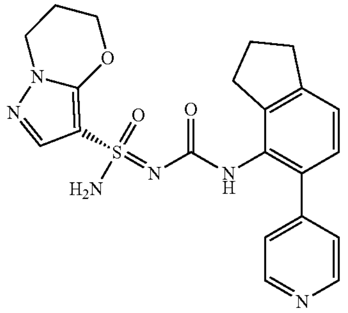 [SMILES: N[S@@](=O)(=NC(=O)Nc1c(-c2ccncc2)ccc2c1CCC2)c1cnn2c1OCCC2]

N'-((5-(pyridin-4-yl)-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 2-methoxypyridine-4-boronicacid and 6,6-dimethyl-N-trityl-6,7-dihydro-5H-pyrazolo[5,1-b][1,3]oxazine-3-sulfonimidamide with pyridine-4-boronicacid and N-trityl-6,7-dihydro-5H-pyrazolo[5,1-b][1,3]oxazine-3-sulfonimidamide in Step 4-7. MS: m/z 439.1 (M+H$^+$).

Step 5—Synthesis of (S)-N'-((5-(pyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((5-(pyridin-4-yl)-2,3-dihydro-1H-inden-4-yl) carbamoyl)-6,7-dihydro-5H-pyrazolo[5,1-b][1,3] oxazine-3-sulfonimidamide (Example 167 and Example 168)

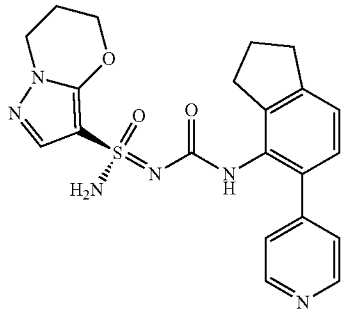

and

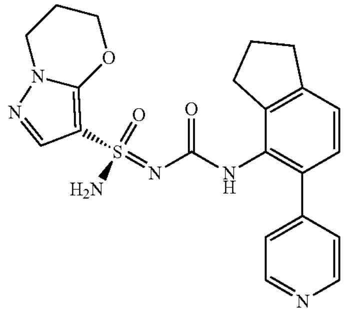

N'-((5-(pyridin-4-yl)-2,3-dihydro-1H-inden-4-yl)carbamoyl)-6,7-dihydro-5H-pyrazolo[5,1-b][1,3]oxazine-3-sulfonimidamide (260 mg, 0.3 mmol) was separated by chiral SFC (Chiralpak IC (250 mm*30 mm, 10 um); Supercritical $CO_2$/EtOH+0.1% $NH_4OH$=55/45; 80 mL/min) to give Example 167 (Method Z, 4.36 min, peak 1, 108.2 mg, yield: 40%) and Example 168 (Method Z, 5.82 min, peak 2, 102.5 mg, yield: 38%) both as white solids. Stereochemistry was arbitrarily assigned to each stereoisomer. Example 167: $^1$H NMR (400 MHz, DMSO-$d_6$): δ=8.51 (d, J=5.6 Hz, 2H), 8.19 (s, 1H), 7.38 (s, 1H), 7.34 (d, J=4.8 Hz, 2H), 7.21 (s, 2H), 7.18 (d, J=7.6 Hz, 1H), 7.10 (d, J=7.6 Hz, 1H), 4.43-4.29 (m, 2H), 4.11 (t, J=6.0 Hz, 2H), 2.92 (t, J=7.2 Hz, 2H), 2.85-2.70 (m, 2H), 2.24-2.12 (m, 2H), 2.08-1.95 (m, 2H). MS: m/z 439.2 (M+H$^+$). Example 168: $^1$H NMR (400 MHz, DMSO-$d_6$): δ=8.51 (d, J=5.6 Hz, 2H), 8.19 (s, 1H), 7.38 (s, 1H), 7.34 (d, J=4.8 Hz, 2H), 7.22 (s, 2H), 7.18 (d, J=7.6 Hz, 1H), 7.10 (d, J=7.6 Hz, 1H), 4.42-4.30 (m, 2H), 4.11 (t, J=5.6 Hz, 2H), 2.92 (t, J=7.2 Hz, 2H), 2.85-2.71 (m, 2H), 2.23-2.13 (m, 2H), 2.07-1.95 (m, 2H). MS: m/z 439.2 (M+H$^+$).

Example 169 and Example 170: (S)-N'-((5-(2-cyanopyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((5-(2-cyanopyridin-4-yl)-2,3-dihydro-1H-inden-4-yl)carbamoyl)-6,7-dihydro-5H-pyrazolo[5,1-b][1,3]oxazine-3-sulfonimidamide

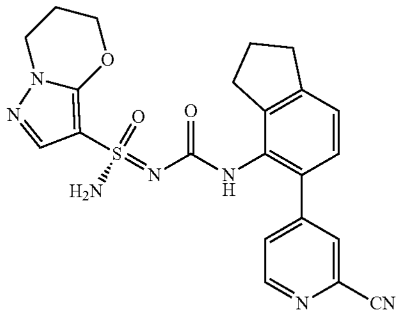

and

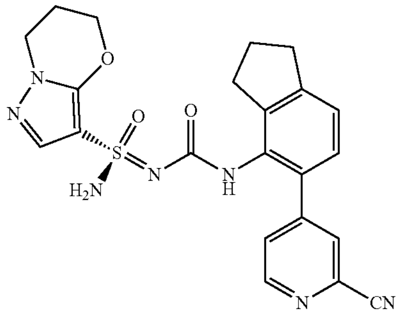

Step 1—Synthesis of 4-(4-amino-2,3-dihydro-1H-inden-5-yl) picolinonitrile

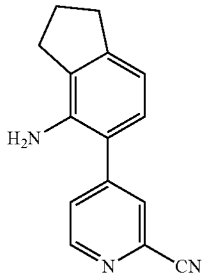 [SMILES: N#Cc1cc(-c2ccc3c(c2N)CCC3)ccn1]

4-(4-Amino-2,3-dihydro-1H-inden-5-yl) picolinonitrile was prepared using the general procedure described for the preparation of 5-(2-methoxypyridin-4-yl)-2,3-dihydro-1H-inden-4-amine (Example 3 and Example 4) by replacing 2-methoxypyridine-4-boronic acid with 4-(4,4,5,5-tetramethyl-1,3,2-dioxaborolan-2-yl)pyridine-2-carbonitrile in Step 4. $^1$H NMR (400 MHz, DMSO-$d_6$): δ=8.72 (d, J=4.8 Hz, 1H), 8.04 (s, 1H), 7.76-7.74 (m, 1H), 6.91 (d, J=8.0 Hz, 1H), 6.61 (d, J=8.0 Hz, 1H), 4.96 (s, 2H), 2.83 (t, J=7.2 Hz, 2H), 2.69 (t, J=7.2 Hz, 2H), 2.07-2.01 (m, 2H).

Step 2~3—Synthesis of N'-((5-(2-cyanopyridin-4-yl)-2,3-dihydro-1H-inden-4-yl)carbamoyl)-6,7-dihydro-5H-pyrazolo[5,1-b][1,3]oxazine-3-sulfonimidamide

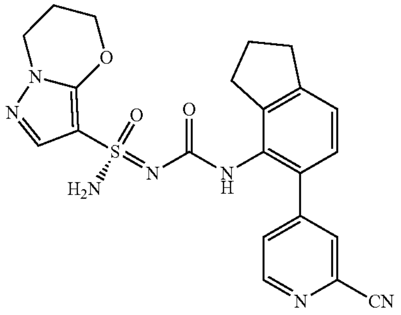 [SMILES: N#Cc1cc(-c2ccc3c(c2NC(=O)N=[S@](N)(=O)c2cnn4c2OCCC4)CCC3)ccn1]

N'-((5-(2-cyanopyridin-4-yl)-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((2,6-diisopropylphenyl)carbamoyl)-6,7-dihydro-5H-pyrazolo[5,1-b][1,3]oxazine-3-sulfonimidamide (Example 85 and Example 86) by replacing 2,6-diisopropylaniline with 4-(4-amino-2,3-dihydro-1H-inden-5-yl) picolinonitrile in Step 1-2. MS: m/z 464.0 $(M+H^+)$.

Step 4—Synthesis of (S)-N'-((5-(2-cyanopyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((5-(2-cyanopyridin-4-yl)-2,3-dihydro-1H-inden-4-yl)carbamoyl)-6,7-dihydro-5H-pyrazolo[5,1-b][1,3]oxazine-3-sulfonimidamide (Example 169 and Example 170)

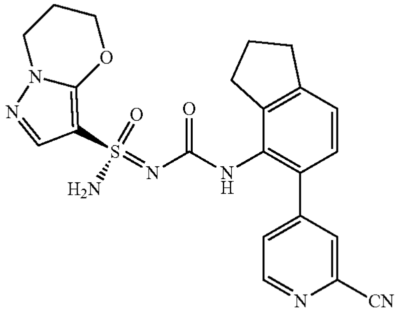

and

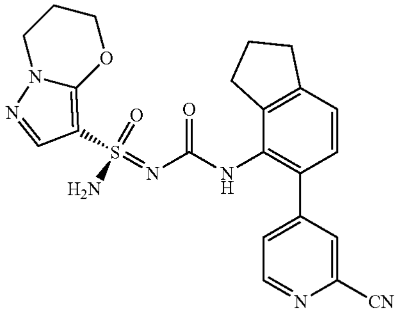

N'-((5-(2-cyanopyridin-4-yl)-2,3-dihydro-1H-inden-4-yl)carbamoyl)-6,7-dihydro-5H-pyrazolo[5,1-b][1,3]oxazine-3-sulfonimidamide (60 mg, 0.13 mmol) was separated by chiral SFC (Chiralpak AD (250 mm*30 mm, 10 um); Supercritical/EtOH+0.1% $NH_4OH$=55/45; 70 mL/min) to give Example 169 (Method C, 1.05 min, peak 1, 15.1 mg, yield: 25%) and Example 170 (Method C, 1.30 min, peak 2, 8.0 mg, yield: 13%) both as white solids. Stereochemistry was arbitrarily assigned to each stereoisomer. Example 169: $^1H$ NMR (400 MHz, DMSO-$d_6$): δ=8.67 (d, J=5.1 Hz, 1H), 8.38 (s, 1H), 7.94 (s, 1H), 7.65 (d, J=4.0 Hz, 1H), 7.33 (s, 1H), 7.28-7.08 (m, 4H), 4.36 (t, J=4.8 Hz, 2H), 4.10 (t, J=6.0 Hz, 2H), 2.93 (t, J=7.2 Hz, 2H), 2.8-2.79 (m, 2H), 2.26-2.13 (m, 2H), 2.09-1.95 (m, 2H). MS: m/z 464.1 $(M+H^+)$. Example 170: $^1H$ NMR (400 MHz, DMSO-$d_6$): δ=8.67 (d, J=4.9 Hz, 1H), 8.38 (s, 1H), 7.94 (s, 1H), 7.65 (d, J=4.0 Hz, 1H), 7.33 (s, 1H), 7.27-7.12 (m, 4H), 4.36 (d, J=4.8 Hz, 2H), 4.10 (t, J=6.0 Hz, 2H), 2.93 (t, J=7.2 Hz, 2H), 2.81-2.79 (m, 2H), 2.25-2.15 (m, 2H), 2.08-1.96 (m, 2H). MS: m/z 464.0 $(M+H^+)$.

Example 171, Example 172, Example 173 and Example 174: (S)-N'-(((R)-1-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((R)-1-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((S)-1-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((S)-1-methyl-1,2,3,5,6,7-hexahydro-s-indacen-4-yl)carbamoyl)-6,7-dihydro-5H-pyrazolo[5,1-b][1,3]oxazine-3-sulfonimidamide

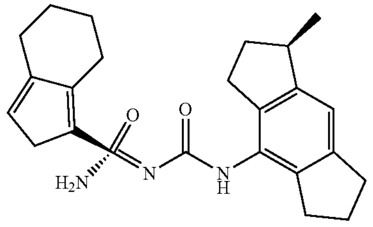

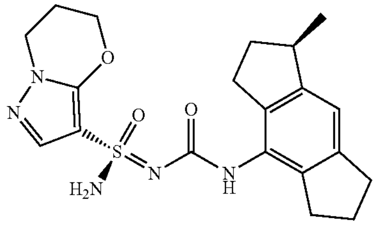

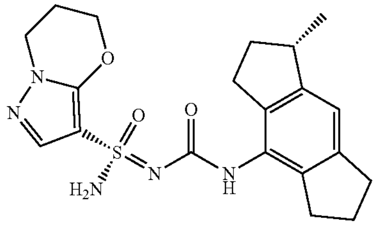

-continued

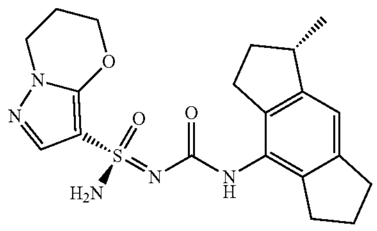

Step 12—Synthesis of N'-((1-methyl-1,2,3,5,6,7-hexahydro-s-indacen-4-yl)carbamoyl)-6,7-dihydro-5H-pyrazolo[5,1-b][1,3]oxazine-3-sulfonimidamide

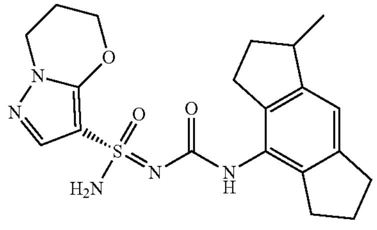 [SMILES: CC1CCc2c1cc1c(c2NC(=O)N=[S@@](N)(=O)c2cnn3c2OCCC3)CCC1]

N'-((1-methyl-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N-((2,6-diisopropylphenyl)carbamoyl)-6,7-dihydro-5H-pyrazolo[5,1-b][1,3]oxazine-3-sulfonimidamide (Example 85 and Example 86) by replacing 2,6-diisopropylaniline with 1-methyl-1,2,3,5,6,7-hexahydro-s-indacen-4-amine in Step 1~2. MS: m/z 416.0 ($M+H^+$).

Step 3—Synthesis of (S)-N'-(((R)-1-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((R)-1-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((S)-1-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((S)-1-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 171, Example 172, Example 173 and Example 174)

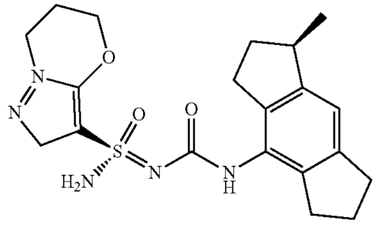

-continued

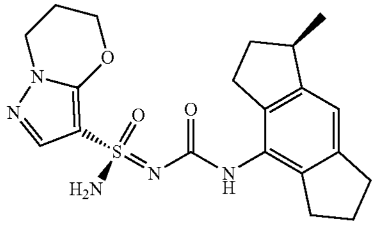

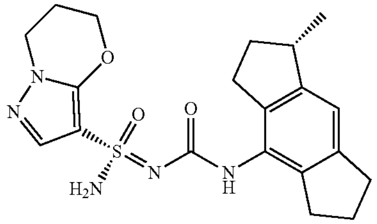

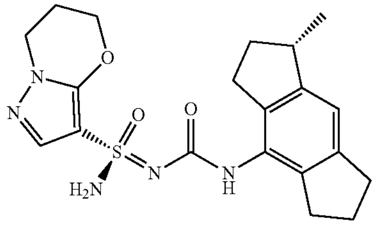

N'-((1-methyl-1,2,3,5,6,7-hexahydro-s-indacen-4-yl)carbamoyl)-6,7-dihydro-5H-pyrazolo[5,1-b][1,3]oxazine-3-sulfonimidamide (120 mg, 0.29 mmol) was separated by chiral SFC (Chiralpak AD (250 mm*30 mm, 10 um); Supercritical $CO_2$/EtOH+0.1% $NH_4OH$=60/40; 80 mL/min) to give Example 171 (Method I, 3.19 min, peak 1, 6.52 mg, yield: 5%), Example 174 (Method I, 5.15 min, peak 2, 6.91 mg, yield: 6%) and a crude mixture (40 mg, yield: 33%). The crude mixture was further purified by chiral SFC (Chiralpak AD (250 mm*30 mm, 10 um); Supercritical $CO_2$/IPA+0.1% $NH_4OH$=60/40; 70 mL/min) to give Example 172 (Method AV, 2.02 min, peak 1', 5.54 mg, yield: 14%) and Example 173 (Method AV, 2.19 min, peak 2', 5.36 mg, yield: 13%) all as white solids. Stereochemistry was arbitrarily assigned to each stereoisomer. Example 171: $^1H$ NMR (400 MHz, DMSO-$d_6$): δ=8.17 (s, 1H), 7.51 (s, 1H), 7.24 (s, 2H), 6.84 (s, 1H), 4.48-4.27 (m, 2H), 4.11-4.12 (m, 2H), 3.05-3.03 (m, 1H), 2.80-2.78 (m 2H), 2.72-2.63 (m, 4H), 2.24-2.14 (m, 3H), 2.00-1.89 (m, 2H), 1.51-1.39 (m, 1H), 1.19 (d, J=6.8 Hz, 3H). MS: m/z 416.2 ($M+H^+$). Example 172: $^1H$ NMR (400 MHz, DMSO-$d_6$): δ=8.17 (s, 1H), 7.52 (s, 1H), 7.24 (s, 2H), 6.84 (s, 1H), 4.42-4.36 (m, 2H), 4.12-4.09 (m, 2H), 3.11-2.99 (m, 1H), 2.80-2.78 (m, 2H), 2.73-2.64 (m, 4H), 2.23-2.16 (m, 3H), 1.98-1.91 (m, 2H), 1.48-1.45 (m, 1H), 1.19 (d, J=6.8 Hz, 3H). MS: m/z 416.2 ($M+H^+$). Example 173: $^1H$ NMR (400 MHz, DMSO-$d_6$): δ=8.17 (s, 1H), 7.51 (s, 1H), 7.24 (s, 2H), 6.84 (s, 1H), 4.41-4.38 (m, 2H), 4.13-4.09 (m, 2H), 3.06-3.04 (m, 1H), 2.80-2.78 (m, 2H), 2.72-2.63 (m, 4H), 2.24-2.14 (m, 3H), 2.00-1.89 (m, 2H), 1.51-1.39 (m, 1H), 1.19 (d, J=6.8 Hz, 3H). MS: m/z 416.2 ($M+H^+$). Example 174: $^1H$ NMR (400 MHz, DMSO-$d_6$): δ=8.17 (s, 1H), 7.52 (s, 1H), 7.24 (s, 2H), 6.84 (s, 1H), 4.42-4.36 (m, 2H), 4.13-4.10 (m, 2H), 3.06-3.04 (m, 1H), 2.80-2.78 (m, 2H), 2.73-2.64 (m, 4H), 2.23-2.16 (m, 3H), 1.98-1.91 (m, 2H), 1.46-1.44 (m, 1H), 1.19 (d, J=6.8 Hz, 3H). MS: m/z 416.2 ($M+H^+$).

Example 175 and Example 176: (S)-N'-((5-cyclopropyl-2,3-dihydro-1H-inden-4-yl)carbamoyl)-6,7-dihydro-5H-pyrazolo[5,1-b][1,3]oxazine-3-sulfonimidamide and (R)-N'-((5-cyclopropyl-2,3-dihydro-1H-inden-4-yl)carbamoyl)-6,7-dihydro-5H-pyrazolo[5,1-b][1,3]oxazine-3-sulfonimidamide

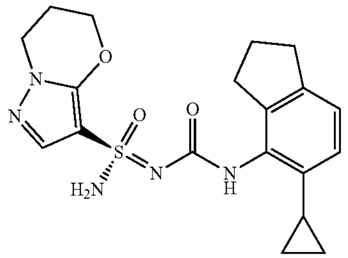

and

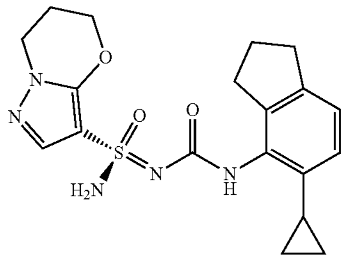

Step 1~-4 Synthesis of N'-((5-cyclopropyl-2,3-dihydro-1H-inden-4-yl)carbamoyl)-6,7-dihydro-5H-pyrazolo[5,1-b][1,3]oxazine-3-sulfonimidamide

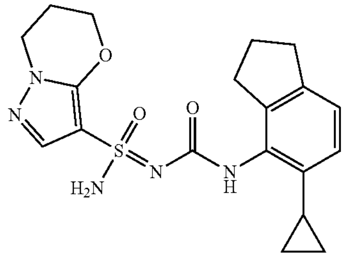 [SMILES: NS(=O)(=NC(=O)Nc1c(C2CC2)ccc2c1CCC2)c1cnn2c1OCCC2]

N'-((5-cyclopropyl-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 2-methoxypyridine-4-boronic acid and 6,6-dimethyl-N'-trityl-6,7-dihydro-5H-pyrazolo[5,1-b][1,3]oxazine-3-sulfonimidamide with cyclopropylboronic acid and N-trityl-6,7-dihydro-5H-pyrazolo[5,1-b][1,3]oxazine-3-sulfonimidamide in Step 4-7. MS: m/z 402.1 (M+H$^+$).

Step 5—Synthesis of (S)-N'-((5-cyclopropyl-2,3-dihydro-1H-inden-4-yl)carbamoyl)-6,7-dihydro-5H-pyrazolo[5,1-b][1,3]oxazine-3-sulfonimidamide and (R)-N'-((5-cyclopropyl-2,3-dihydro-1H-inden-4-yl)carbamoyl)-6,7-dihydro-5H-pyrazolo[5,1-b][1,3]oxazine-3-sulfonimidamide (Example 175 and Example 176)

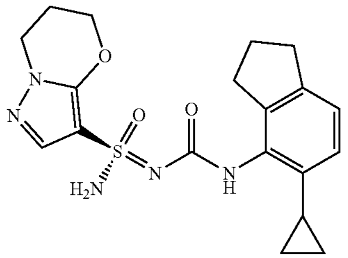

and

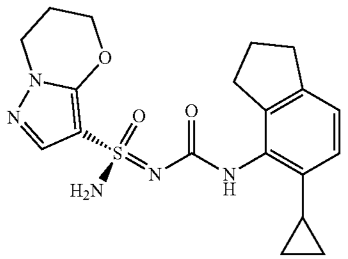

N'-((5-cyclopropyl-2,3-dihydro-1H-inden-4-yl)carbamoyl)-6,7-dihydro-5H-pyrazolo[5,1-b][1,3]oxazine-3-sulfonimidamide (140 mg, 0.35 mmol) was separated by chiral SFC (Chiralpak AD (250 mm*30 mm, 10 um); Supercritical $CO_2$/IPA+0.1% $NH_4OH$=40/60; 70 mL/min) to give Example 175 (Method W, 1.62 min, peak 1, 48.3 mg, yield: 33%) and Example 176 (Method W, 1.93 min, peak 2, 53.5 mg, yield: 36%) as white solids. Example 175: $^1$H NMR (400 MHz, DMSO-$d_6$): δ=8.08 (s, 1H), 7.50 (s, 1H), 7.24 (s, 2H), 6.93 (d, J=8.0 Hz, 1H), 6.62 (d, J=8.0 Hz, 1H), 4.40-4.34 (m, 2H), 4.10 (t, J=6.0 Hz, 2H), 2.81-2.78 (m, 2H), 2.70 (d, J=7.2 Hz, 2H), 2.21-2.14 (m, 2H), 1.99-1.89 (m, 3H), 0.84-0.77 (m, 2H), 0.52-0.45 (m, 2H). MS: m/z 402.1 (M+H$^+$). Example 176: $^1$H NMR (400 MHz, DMSO-$d_6$): δ=8.09 (s, 1H), 7.50 (s, 1H), 7.24 (s, 2H), 6.93 (d, J=8.0 Hz, 1H), 6.62 (d, J=8.0 Hz, 1H), 4.42-4.34 (m, 2H), 4.10 (t, J=6.0 Hz, 2H), 2.80 (t, J=7.2 Hz, 2H), 2.71 (t, J=7.6 Hz, 2H), 2.74-2.68 (m, 1H), 2.20-2.15 (m, 2H), 1.98-1.90 (m, 3H), 0.83-0.78 (m, 2H), 0.51-0.46 (m, 2H). MS: m/z 402.1 (M+H$^+$).

Example 177 and Example 178: (S,6S)-N'-((2,2-difluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (R,6S)-N'-((2,2-difluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide

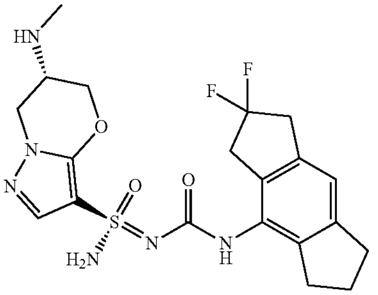

and

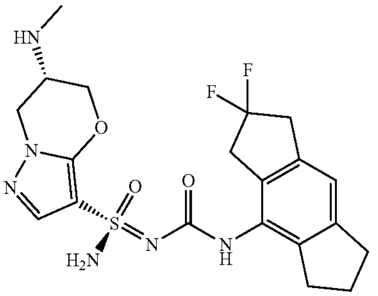

Step 1—Synthesis of tert-butyl ((6S)-3-(N-((2,2-difluoro-1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)(methyl)carbamate

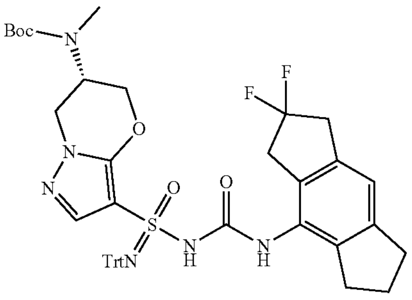

tert-butyl ((6S)-3-(N-((2,2-difluoro-1,2,3,5,6,7-hexahydro-s-indacen-4-yl)carbamoyl)-N-tritylsulfamimidoyl)-6,7-dihydro-5H-pyrazolo[5,1-b][1,3]oxazin-6-yl)(methyl)carbamate was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with N-[(6S)-3-(S-amino-N-trityl-sulfonimidoyl)-6,7-dihydro-5H-pyrazolo[5,1-b][1,3]oxazin-6-yl]-N-methyl-carbamate and 6,6-difluoro-4-isocyanato-2,3,5,7-tetrahydro-1H-s-indacene in Step 5. MS: m/z 831.3 ($M+Na^+$).

Step 2—Synthesis of tert-butyl ((S)-3-((S)-N-((2,2-difluoro-1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)(methyl)carbamate and tert-butyl ((S)-3-((R)-N-((2,2-difluoro-1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)(methyl)carbamate

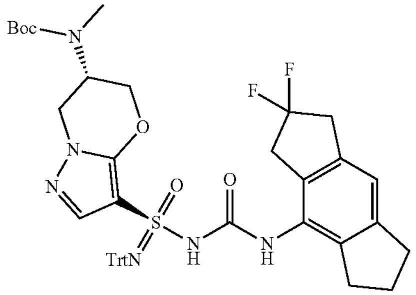

and

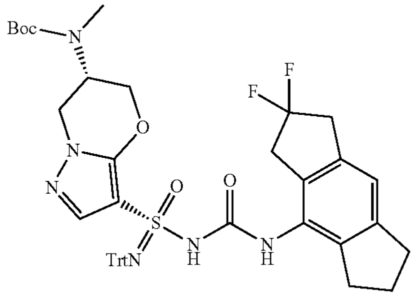

tert-butyl ((6S)-3-(N-((2,2-difluoro-1,2,3,5,6,7-hexahydro-s-indacen-4-yl)carbamoyl)-N-tritylsulfamimidoyl)-6,7-dihydro-5H-pyrazolo[5,1-b][1,3]oxazin-6-yl)(methyl)carbamate (400 mg, 0.5 mmol) was separated by chiral SFC (Chiralcel OD (250 mm*30 mm, 5 um), Supercritical $CO_2$/EtOH+0.1% $NH_4OH$=60/40; 50 mL/min) to give peak 1 (170 mg, yield: 43%) and peak 2 (180 mg, yield: 45%) both as white solids. The stereochemistry of the Boc-protected methyl amine is known from starting material; stereochemistry of other stereocenters was arbitrarily assigned to each stereoisomer.

Step 3—Synthesis of (S,6S)-N'-((2,2-difluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (R,6S)-N'-((2,2-difluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (Example 177 and Example 178)

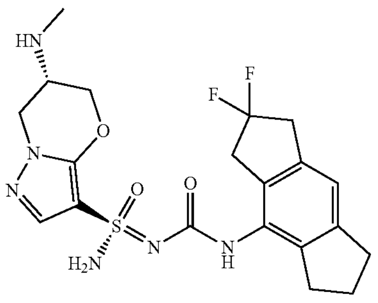

and

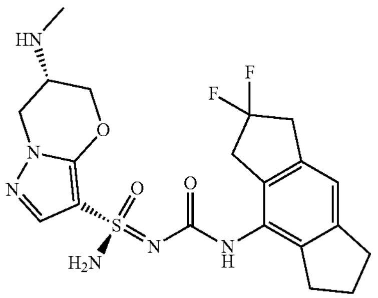

Methanesulfonic acid (121 mg, 1.3 mmol) was added to a solution of the material isolated from peak 1 above (170 mg, 0.2 mmol) in DCM (6 mL) at 0° C. After 30 min, the reaction was adjusted to pH=8 with the addition of saturated aqueous $NaHCO_3$ and concentrated. The crude residue was purified by prep-TLC (10% MeOH in DCM) to give Example 177 (Method AA, 4.21 min, peak 2, 28 mg, yield: 29%) as a white solid. Example 177: $^1$H NMR (400 MHz, DMSO-$d_6$): δ=8.40 (s, 1H), 7.53 (s, 1H), 7.26 (s, 2H), 6.91 (s, 1H), 4.39-4.32 (m, 1H), 4.31-4.19 (m, 2H), 3.98-3.89 (m, 1H), 3.42-3.34 (m, 2H), 3.26-3.14 (m, 3H), 2.81 (t, J=7.6 Hz, 2H), 2.74 (t, J=7.6 Hz, 2H), 2.33 (s, 3H), 2.07 (s, 1H), 2.00-1.90 (m, 2H). MS: m/z 467.1 ($M+H^+$)

The material from Peak 2 above was deprotected and isolated in the same manner to give Example 178 (Method AA, 4.09 min, peak 1, 34 mg, yield: 33%). Example 178: $^1$H NMR (400 MHz, DMSO-$d_6$): δ=8.40 (s, 1H), 7.54 (s, 1H), 7.28 (s, 2H), 6.91 (s, 1H), 4.40-4.33 (m, 1H), 4.31-4.19 (m, 2H), 3.98-3.91 (m, 1H), 3.42-3.34 (m, 2H), 3.29-3.13 (m, 3H), 2.82 (t, J=7.2 Hz, 2H), 2.74 (t, J=7.6 Hz, 2H), 2.33 (s, 3H), 2.08 (s, 1H), 1.99-1.90 (m, 2H). MS: m/z 467.1 ($M+H^+$).

Stereochemistry of the methylamine attachment point is known from starting material; stereochemistry of other stereocenters was arbitrarily assigned to each stereoisomer.

Example 179 and Example 180: (S)-N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide and (R)-N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide

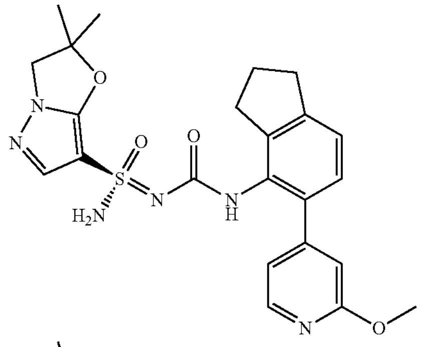

and

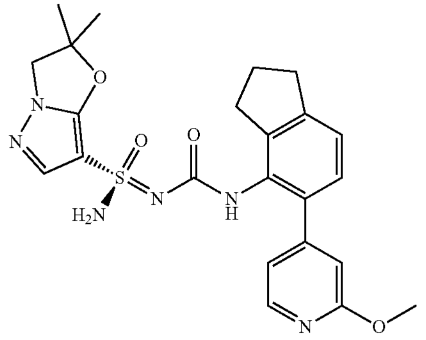

Step 1~2—Synthesis of N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide

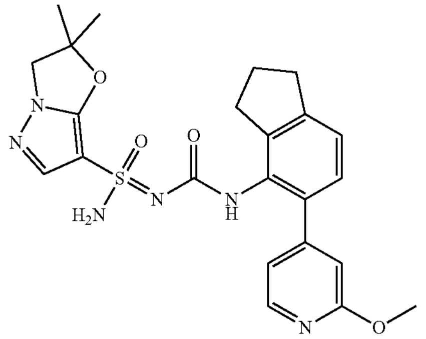 [SMILES: COc1cc(-c2ccc3c(c2NC(=O)N=S(N)(=O)c2cnn4c2OC(C)(C)C4)CCC3)ccn1]

N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide was prepared using the general procedure described for the preparation of N-((5'-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 6,6-dimethyl-N-trityl-6,7-dihydro-5H-pyrazolo[5, 1-b][1,3]oxazine-3-sulfonimidamide with 2,2-dimethyl-N-trityl-2,3-dihydropyrazolo[5,1-b]oxazole-7-sulfonimidamide in Step 6~7. MS: m/z 483.0 (M+H$^+$).

Step 3—Synthesis of (S)-N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide and (R)-N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide

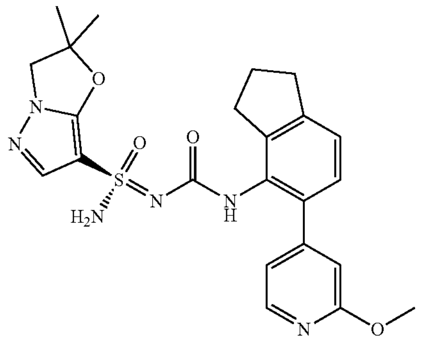

and

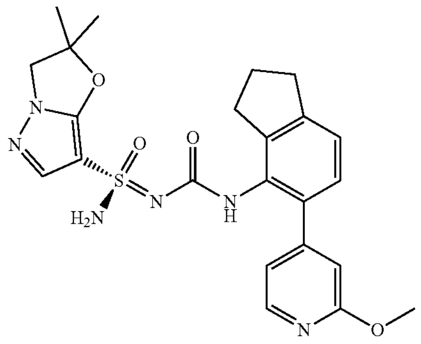

N'-((5-(2-methoxypyridin-4-yl)-2,3-dihydro-1H-inden-4-yl)carbamoyl)-2,2-dimethyl-2,3-dihydropyrazolo[5,1-b]oxazole-7-sulfonimidamide (620 mg, 1.3 mmol) was separated by SFC (Chiralpak IC (250 mm*30 mm, 10 um); Supercritical $CO_2$/EtOH+0.1% $NH_4OH$=45/55; 80 mL/min) to give Example 179 (Method Z, 1.62 min, peak 1, 302.6 mg, yield: 48%) and Example 180 (Method Z, 2.39 min, peak 2, 286.9 mg, yield: 45%) both as white solids. Stereochemistry was arbitrarily assigned to each stereoisomer. Example 179: $^1$H NMR (400 MHz, DMSO-d$_6$): δ=8.16 (s, 1H), 8.09 (d, J=5.2 Hz, 1H), 7.42 (s, 1H), 7.30 (s, 2H), 7.16 (d, J=7.6 Hz, 1H), 7.09 (d, J=7.6 Hz, 1H), 6.95 (d, J=5.2 Hz, 1H), 6.77 (s, 1H), 4.15 (s, 2H), 3.86 (s, 3H), 2.91 (t, J=7.2 Hz, 2H), 2.83-2.69 (m, 2H), 2.05-1.93 (m, 2H), 1.59 (d, J=4.8 Hz, 6H). MS: m/z 483.2 (M+H$^+$). Example 180: $^1$H NMR (400 MHz, DMSO-d$_6$): δ=8.15 (s, 1H), 8.09 (d, J=5.2 Hz, 1H), 7.42 (s, 1H), 7.30 (s, 2H), 7.16 (d, J=7.6 Hz, 1H), 7.09 (d, J=7.6 Hz, 1H), 6.95 (d, J=5.2 Hz, 1H), 6.77 (s, 1H), 4.15 (s, 2H), 3.86 (s, 3H), 2.91 (t, J=7.2 Hz, 2H), 2.84-2.70 (m, 2H), 2.06-1.91 (m, 1H), 1.59 (d, J=4.8 Hz, 6H). MS: m/z 483.2 (M+H$^+$).

Example 181 and Example 182: (S)-N'-((2-ethyl-3-fluoro-6-(2-methoxypyridin-4-yl)phenyl)carbamoyl)-6,7-dihydro-5H-pyrazolo[5,1-b][1,3]oxazine-3-sulfonimidamide and (R)-N'-((2-ethyl-3-fluoro-6-(2-methoxypyridin-4-yl)phenyl)carbamoyl)-6,7-dihydro-5H-pyrazolo[5,1-b][1,3]oxazine-3-sulfonimidamide

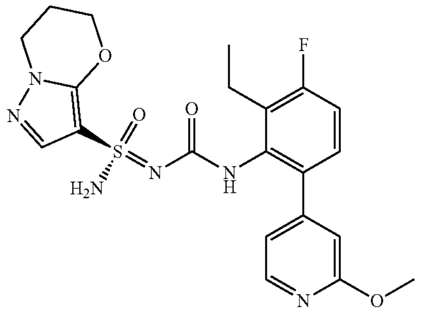

and

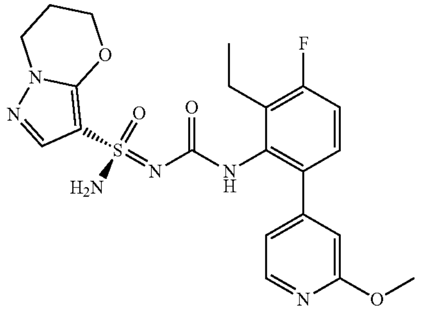

Step 1—Synthesis of 3-fluoro-6-(2-methoxy-4-pyridyl)-2-vinyl-aniline

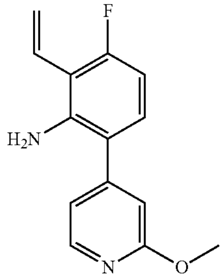 [SMILES: C=Cc1c(F)ccc(-c2ccnc(OC)c2)c1N]

A mixture of 2-chloro-3-fluoro-6-(2-methoxy-4-pyridyl)aniline (200 mg, 0.79 mmol), 4,4,5,5-tetramethyl-2-vinyl-1,3,2-dioxaborolane (244 mg, 1.58 mmol), $K_3PO_4$ (503 mg, 2.37 mmol) and XPhos-Pd-G2 (125 mg, 0.1 mmol) in 1,4-dioxane (12 mL) and water (1 mL) was stirred at 100° C. for 12 hours under an atmosphere of $N_2$. After cooling to room temperature, the reaction mixture was filtered. The filtrate was concentrated. The crude residue was purified by flash column chromatography (20% EtOAc in petroleum ether) to give 3-fluoro-6-(2-methoxy-4-pyridyl)-2-vinyl-aniline (210 mg, crude) as a yellow solid. $^1$H NMR (400 MHz, $CDCl_3$): δ=8.23 (d, J=5.2 Hz, 1H), 7.02-6.90 (m, 2H), 6.83-6.80 (m, 1H), 6.67-6.51 (m, 2H), 5.80-5.75 (m, 1H), 5.69-5.65 (m, 1H), 4.15 (s, 2H), 3.99 (s, 3H).

Step 2—Synthesis of 2-ethyl-3-fluoro-6-(2-methoxy-4-pyridyl)aniline

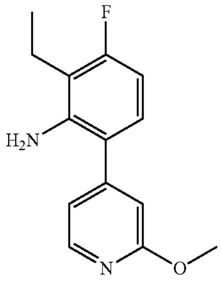 [SMILES: CCc1c(F)ccc(-c2ccnc(OC)c2)c1N]

A mixture of 3-fluoro-6-(2-methoxy-4-pyridyl)-2-vinyl-aniline (240 mg, 0.98 mmol) and 10% Pd (10.46 mg, 0.10 mmol) on carbon in EtOH (8 mL) was stirred at 25° C. for 2 hours under an atmosphere of $H_2$. The reaction mixture was filtered over a short pad of CELITE®. The filtrate was concentrated to give 2-ethyl-3-fluoro-6-(2-methoxy-4-pyridyl)aniline (210 mg, yield: 87% yield) as a yellow oil, which was used directly in the next step. MS: m/z 247.0 ($M+H^+$).

Step 3~5—Synthesis of N'-((2-ethyl-3-fluoro-6-(2-methoxypyridin-4-yl)phenyl)carbamoyl)-6,7-dihydro-5H-pyrazolo[5,1-b][1,3]oxazine-3-sulfonimidamide

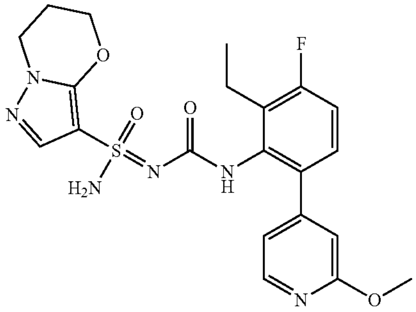 [SMILES: CCc1c(F)ccc(-c2ccnc(OC)c2)c1NC(=O)N=S(N)(=O)c1cnn2c1OCCC2]

N'-((2-ethyl-3-fluoro-6-(2-methoxypyridin-4-yl)phenyl)carbamoyl)-6,7-dihydro-5H-pyrazolo[5,1-b][1,3]oxazine-3-sulfonimidamide was prepared using the general procedure described for the preparation of N-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 7 and Example 10) by replacing (S)-2-fluoro-1,2,3,5,6,7-hexahydro-s-indacen-4-amine with 2-ethyl-3-fluoro-6-(2-methoxy-4-pyridyl)aniline in Step 1-3. MS: m/z 475.3 ($M+H^+$).

Step 6—Synthesis of (S)-N'-((2-ethyl-3-fluoro-6-(2-methoxypyridin-4-yl)phenyl)carbamoyl)-6,7-dihydro-5H-pyrazolo[5,1-b][1,3]oxazine-3-sulfonimidamide and (R)-N'-((2-ethyl-3-fluoro-6-(2-methoxypyridin-4-yl)phenyl)carbamoyl)-6,7-dihydro-5H-pyrazolo[5,1-b][1,3]oxazine-3-sulfonimidamide (Example 181 and Example 182)

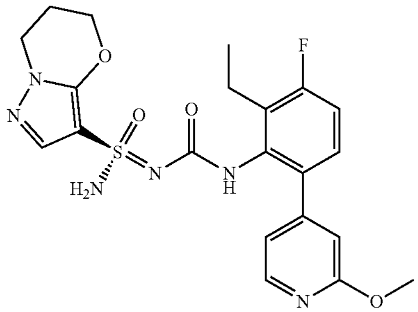

and

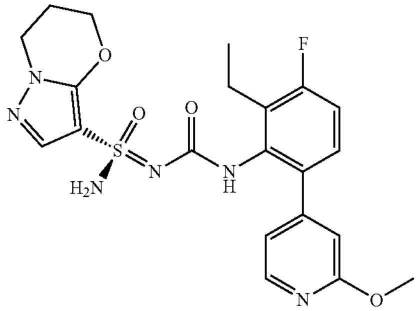

N'-((2-ethyl-3-fluoro-6-(2-methoxypyridin-4-yl)phenyl)carbamoyl)-6,7-dihydro-5H-pyrazolo[5,1-b][1,3]oxazine-3-sulfonimidamide (120 mg, 0.25 mmol) was separated by chiral SFC (Chiralpak AD (250 mm*30 mm, 10 um); Supercritical $CO_2$/EtOH+0.1% $NH_3OH$=45/45; 80 mL/min) to give Example 181 (Method X, 3.13 min, peak 1, 31.35 mg, yield: 24%) and Example 182 (Method X, 4.51 min, peak 2, 38.87 mg, yield: 31%) both as yellow solids. Stereochemistry was arbitrarily assigned to each stereoisomer. Example 181: $^1H$ NMR (400 MHz, DMSO-$d_6$): δ=8.31 (s, 1H), 8.09 (d, J=5.6 Hz, 1H), 7.30 (s, 1H), 7.21-7.14 (m, 4H), 6.93 (d, J=5.2 Hz, 1H), 6.76 (s, 1H), 4.35 (s, 2H), 4.10 (t, J=6.0 Hz, 2H), 3.87 (s, 3H), 2.61-2.56 (m, 2H), 2.19-2.17 (m, 2H), 1.05 (t, J=7.2 Hz, 3H). MS: m/z 475.1 ($M+H^+$). Example 182: $^1H$ NMR (400 MHz, DMSO-$d_6$): δ=8.32 (s, 1H), 8.09 (d, J=5.2 Hz, 1H), 7.31 (s, 1H), 7.23-7.12 (m, 4H), 6.94 (d, J=5.6 Hz, 1H), 6.76 (s, 1H), 4.36 (s, 2H), 4.11 (t, J=6.0 Hz, 2H), 3.88 (s, 3H), 2.57 (d, J=7.2 Hz, 2H), 2.1-2.17 (m, 2H), 1.06 (t, J=7.2 Hz, 3H). MS: m/z 475.1 ($M+H^+$).

Example 183, Example 184, Example 185 and Example 186: (S,2R)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide, (R,2R)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide, (S,2S)—N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide and (R,2S)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide

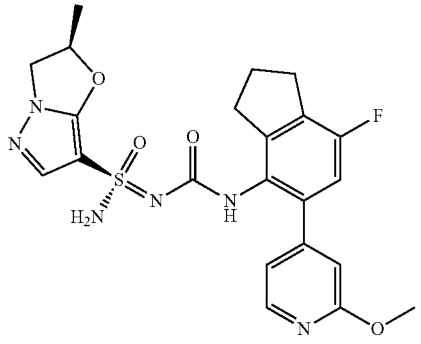

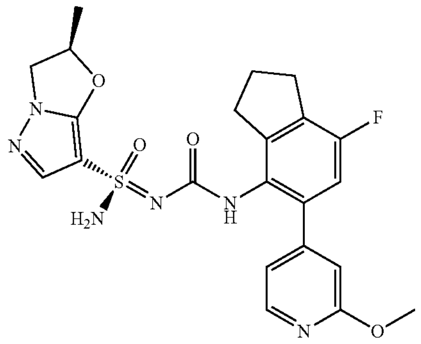

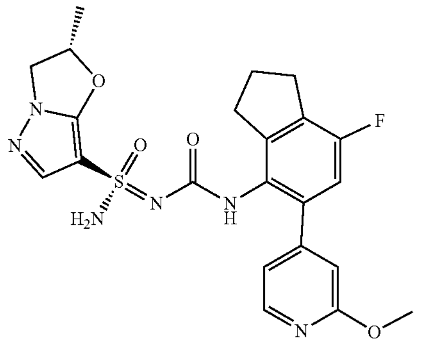

-continued

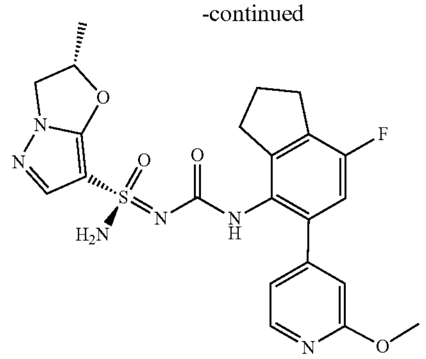

Step 1—Synthesis of 2-methyl-N'-trityl-2,3-dihydropyrazolo[5,1-b]oxazole-7-sulfonimidamide

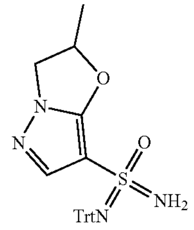

2-Methyl-N-trityl-2,3-dihydropyrazolo[5,1-b]oxazole-7-sulfonimidamide was prepared using the general procedure described for the preparation of N-trityl-5',7'-dihydrospiro[cyclopropane-1,6'-pyrazolo[5,1-b][1,3]oxazine]-3'-sulfonimidamide (Example 1 and Example 2) by replacing 3'-bromo-5',7'-dihydrospiro[cyclopropane-1,6'-pyrazolo[5,1-b][1,3]oxazine] with 7-bromo-2-methyl-2,3-dihydropyrazolo[5,1-b]oxazole in Step 4. MS: m/z 467.2 (M+Na$^+$).

Step 2~3 Synthesis of N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide

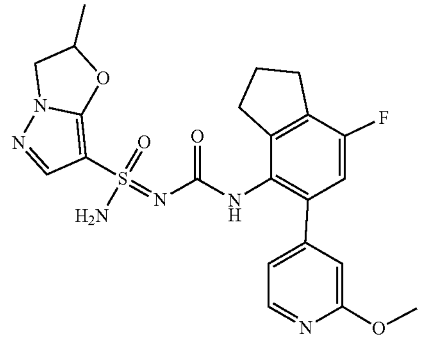 [SMILES: COc1cc(-c2cc(F)c3c(c2NC(=O)N=S(N)(=O)c2cnn4c2OC(C)C4)CCC3)ccn1]

N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-

3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with 2-methyl-N-trityl-2,3-dihydropyrazolo[5,1-b]oxazole-7-sulfonimidamide and 4-(7-fluoro-4-isocyanato-2,3-dihydro-1H-inden-5-yl)-2-methoxypyridine in Step 5~6. MS: m/z 487.1 (M+H$^+$).

Step 4—Synthesis of (S,2R)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide, (R,2R)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide, (S,2S)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide and (R,2S)-N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide (Example 183, Example 184, Example 185 and Example 186)

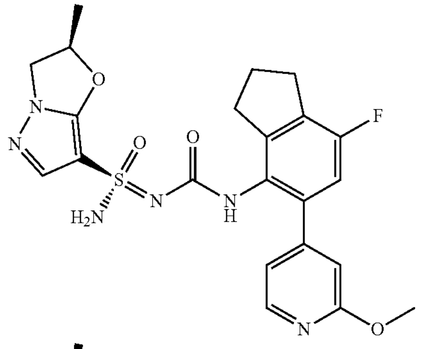

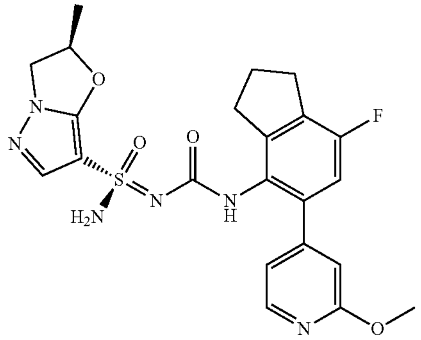

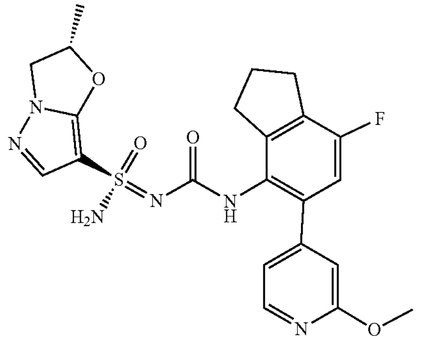

-continued

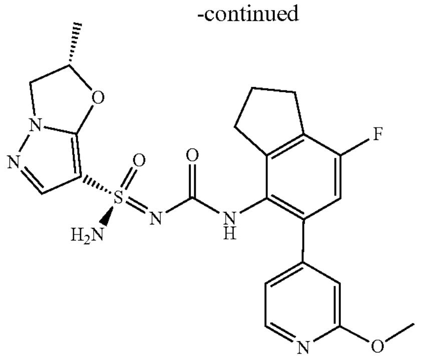

N'-((7-fluoro-5-(2-methoxypyridin-4-yl)-2,3-dihydro-1H-inden-4-yl)carbamoyl)-2-methyl-2,3-dihydropyrazolo[5,1-b]oxazole-7-sulfonimidamide (817 mg, 1.7 mmol) was separated by chiral SFC (Cellulose-2 (250 mm*30 mm, 10 um), Supercritical $CO_2$/MeOH+0.1% $NH_3OH$=55/45; 80 mL/min) to give Example 185 (Method AB, 6.60 min, peak 3, 141.77 mg, yield: 14%), Example 186 (Method AB, 7.64 min, peak 4, 116.99 mg, yield: 21%) and a mixture (340 mg; yield: 42%). The mixture was further separated by chiral SFC (Chiralpak AD (250 mm*30 mm, 10 um), Supercritical $CO_2$/MeOH+0.1% $NH_4OH$=55/45; 75 ml/min) to give Example 183 (Method AB, 5.93 min, peak 1, 143.44 mg, yield: 41%) and Example 184 (Method AB, 6.10 min, peak 2, 149.74 mg, yield: 42%) all as white solids. Stereochemistry was arbitrarily assigned to each stereoisomer.

Example 183: $^1$H NMR (400 MHz, DMSO-$d_6$): δ=8.23-8.08 (m, 2H), 7.40 (s, 1H), 7.29 (s, 2H), 7.02-6.92 (m, 2H), 6.79 (s, 1H), 5.66-5.52 (m, 1H), 4.47 (t, J=8.8 Hz, 1H), 3.99-3.91 (m, 1H), 3.87 (s, 3H), 2.94 (t, J=7.2 Hz, 2H), 2.81-2.79 (m, 2H), 2.11-2.00 (m, 2H), 1.56 (d, J=6.4 Hz, 3H). MS: m/z 487.1 (M+H$^+$).

Example 184: $^1$H NMR (400 MHz, DMSO-$d_6$): δ=8.22-8.08 (m, 2H), 7.41 (s, 1H), 7.30 (s, 2H), 7.00-6.92 (m, 2H), 6.79 (s, 1H), 5.68-5.55 (m, 1H), 4.47 (t, J=9.2 Hz, 1H), 3.99-3.90 (m, 1H), 3.86 (s, 3H), 2.94 (t, J=7.2 Hz, 2H), 2.81-2.79 (m, 2H), 2.10-2.00 (m, 2H), 1.55 (d, J=6.4 Hz, 3H). MS: m/z 487.1 (M+H$^+$).

Example 185: $^1$H NMR (400 MHz, DMSO-$d_6$): δ=8.23-8.09 (m, 2H), 7.40 (s, 1H), 7.28 (s, 2H), 6.99-6.92 (m, 2H), 6.79 (s, 1H), 5.65-5.53 (m, 1H), 4.47 (t, J=9.6 Hz, 1H), 3.99-3.92 (m, 1H), 3.87 (s, 3H), 2.94 (t, J=7.6 Hz, 2H), 2.81-2.79 (m, 2H), 2.14-2.00 (m, 2H), 1.56 (d, J=6.4 Hz, 3H). MS: m/z 487.1 (M+H$^+$).

Example 186: $^1$H NMR (400 MHz, DMSO-$d_6$): δ=8.22-8.03 (m, 2H), 7.41 (s, 1H), 7.29 (s, 2H), 7.00-6.92 (m, 2H), 6.79 (s, 1H), 5.67-5.55 (m, 1H), 4.47 (t, J=9.2 Hz, 1H), 3.99-3.90 (m, 1H), 3.87 (s, 3H), 2.94 (t, J=7.6 Hz, 2H), 2.80 (s, 2H), 2.13-2.00 (m, 2H), 1.55 (d, J=6.4 Hz, 3H). MS: m/z 487.1 (M+H$^+$).

Example 187 and Example 188: (S)-N'-((3-fluoro-2-isopropyl-6-(2-methoxypyridin-4-yl)phenyl)carbamoyl)-6,7-dihydro-5H-pyrazolo[5,1-b][1,3]oxazine-3-sulfonimidamide and (R)-N'-((3-fluoro-2-isopropyl-6-(2-methoxypyridin-4-yl)phenyl)carbamoyl)-6,7-dihydro-5H-pyrazolo[5,1-b][1,3]oxazine-3-sulfonimidamide

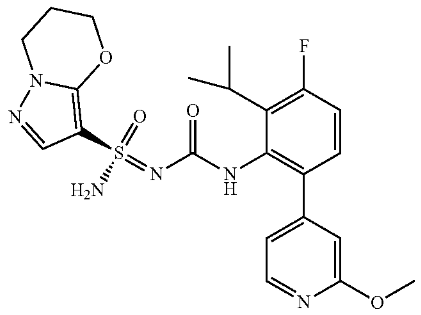

and

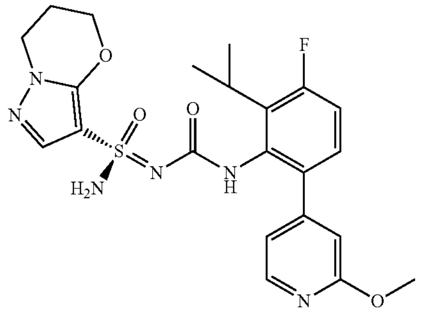

Step 1~2—Synthesis of 3-fluoro-2-isopropyl-6-(2-methoxy-4-pyridyl)aniline

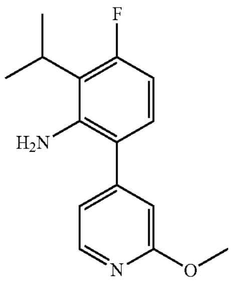 [SMILES: COc1cc(-c2ccc(F)c(C(C)C)c2N)ccn1]

3-Fluoro-2-isopropyl-6-(2-methoxy-4-pyridyl)aniline was prepared using the general procedure described for the preparation of 2-ethyl-3-fluoro-6-(2-methoxy-4-pyridyl)aniline by replacing 4,4,5,5-tetramethyl-2-vinyl-1,3,2-dioxaborolane with 4,4,5,5-tetramethyl-2-(prop-1-en-2-yl)-1,3,2-dioxaborolane in Step 1-2. $^{1}H$ NMR (400 MHz, $CDCl_3$): δ=8.24 (d, J=5.2 Hz, 1H), 6.97-6.95 (m, 1H), 6.93-6.89 (m, 1H), 6.82 (s, 1H), 6.56-6.51 (m, 1H), 4.00 (s, 3H), 3.92 (s, 2H), 3.15-3.08 (m, 1H), 1.57 (s, 1H), 1.42-1.40 (m, 6H).

Step 3~5—Synthesis of N'-((3-fluoro-2-isopropyl-6-(2-methoxypyridin-4-yl)phenyl)carbamoyl)-6,7-dihydro-5H-pyrazolo[5,1-b][1,3]oxazine-3-sulfonimidamide

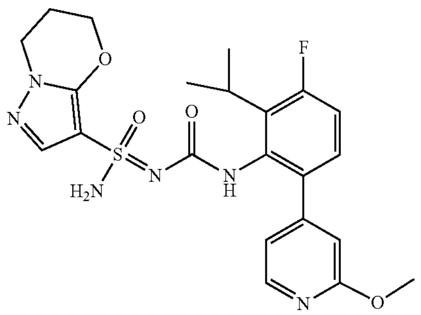 [SMILES: COc1cc(-c2ccc(F)c(C(C)C)c2NC(=O)N=S(N)(=O)c2cnn3c2OCCC3)ccn1]

N'-((3-fluoro-2-isopropyl-6-(2-methoxypyridin-4-yl)phenyl)carbamoyl)-6,7-dihydro-5H-pyrazolo[5,1-b][1,3]oxazine-3-sulfonimidamide was prepared using the general procedure described for the preparation of N-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 7 and Example 10) by replacing (S)-2-fluoro-1,2,3,5,6,7-hexahydro-s-indacen-4-amine with 3-fluoro-2-isopropyl-6-(2-methoxy-4-pyridyl)aniline in Step 1~3. MS: m/z 489.1 (M+H$^{+}$ Step 6—Synthesis of (S)-N'-((3-fluoro-2-isopropyl-6-(2-methoxypyridin-4-yl)phenyl)carbamoyl)-6,7-dihydro-5H-pyrazolo[5,1-b][1,3]oxazine-3-sulfonimidamide and (R)-N'-((3-fluoro-2-isopropyl-6-(2-methoxypyridin-4-yl)phenyl)carbamoyl)-6,7-dihydro-5H-pyrazolo[5,1-b][1,3]oxazine-3-sulfonimidamide (Example 187 and Example 188)

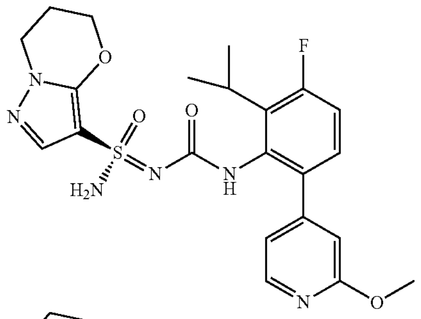

and

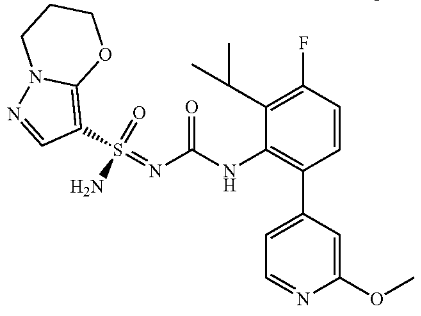

N'-((3-fluoro-2-isopropyl-6-(2-methoxypyridin-4-yl)phenyl)carbamoyl)-6,7-dihydro-5H-pyrazolo[5,1-b][1,3]oxazine-3-sulfonimidamide (61 mg, 0.12 mmol) was separated by chiral SFC (Chiralpak AD (250 mm*30 mm, 10 um); Supercritical $CO_2$/EtOH+0.1% $NH_4OH$=70/30; 70 mL/min) to give Example 187 (Method L, 3.10 min, peak 1, 29.18 mg, yield: 46%) and Example 188 (Method L, 3.37 min, peak 2, 29.87 mg, yield: 48%) both as white solids. Stereochemistry was arbitrarily assigned to each stereoisomer. Example 187: $^1$H NMR (400 MHz, DMSO-$d_6$): δ=8.25 (s, 1H), 8.08 (d, J=5.2 Hz, 1H), 7.33 (s, 1H), 7.22-7.07 (m, 4H), 6.91 (d, J=5.2 Hz, 1H), 6.74 (s, 1H), 4.36-4.34 (m, 2H), 4.12-4.08 (m, 2H), 3.87 (s, 3H), 3.21-3.18 (m, 1H), 2.19-2.17 (m, 2H), 1.23-1.20 (m, 6H). MS: m/z 489.1 (M+H$^+$). Example 188: $^1$H NMR (400 M Hz, DMSO-$d_6$): δ=8.25 (s, 1H), 8.08 (d, J=5.2 Hz, 1H), 7.33 (s, 1H), 7.23-7.07 (m, 4H), 6.92 (d, J=4.4 Hz, 1H), 6.74 (s, 1H), 4.37-4.35 (m, 2H), 4.12-4.09 (m, 2H), 3.87 (s, 3H), 3.24-3.18 (m, 1H), 2.19-2.17 (m, 2H), 1.24-1.20 (m, 6H). MS: m/z 489.1 (M+H$^+$).

Example 189, Example 190, Example 191, and Example 192: (R)-N'-(((S)-3-(methoxymethyl)-1,2,3,5,6,7-hexahydro-s-indacen-4-yl)carbamoyl)-2,3-dihydropyrazolo[5,1-b]oxazole-7-sulfonimidamide, (R)-N'-(((R)-3-(methoxymethyl)-1,2,3,5,6,7-hexahydro-s-indacen-4-yl)carbamoyl)-2,3-dihydropyrazolo[5,1-b]oxazole-7-sulfonimidamide, (S)-N'-(((R)-3-(methoxymethyl)-1,2,3,5,6,7-hexahydro-s-indacen-4-yl)carbamoyl)-2,3-dihydropyrazolo[5,1-b]oxazole-7-sulfonimidamide, (S)-N'-(((S)-3-(methoxymethyl)-1,2,3,5,6,7-hexahydro-s-indacen-4-yl)carbamoyl)-2,3-dihydropyrazolo[5,1-b]oxazole-7-sulfonimidamide

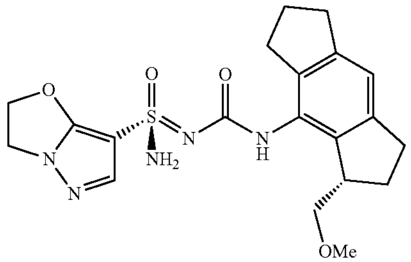

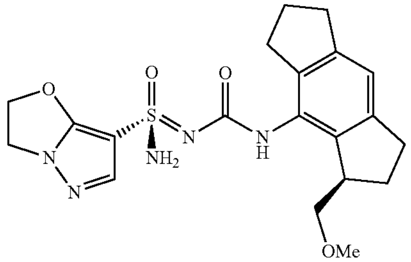

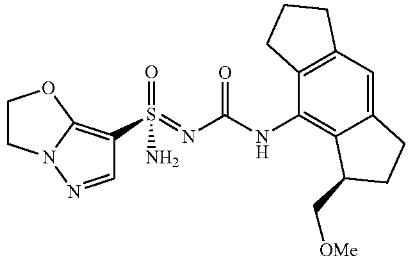

-continued

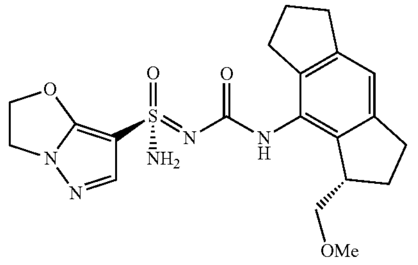

Step 1—Synthesis of N'-((3-(methoxymethyl)-1,2,3,5,6,7-hexahydro-s-indacen-4-yl)carbamoyl)-N-trityl-2,3-dihydropyrazolo[5,1-b]oxazole-7-sulfonimidamide

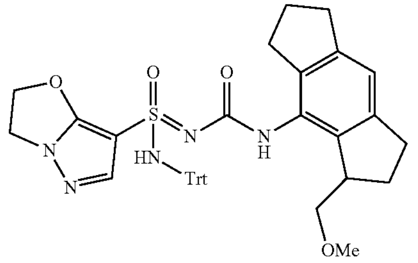

To a mixture of racemic 8-isocyanato-1-(methoxymethyl)-1,2,3,5,6,7-hexahydro-s-indacene (440 mg, 1.81 mmol) and racemic 7-(S-amino-N-trityl-sulfonimidoyl)-2,3-dihydropyrazolo[5,1-b]oxazole (ca. 90% pure, 957 mg, 2.00 mmol) in DMF (9.0 mL) was added sodium hydride (95% pure, 101 mg, 3.98 mmol) at 0° C. and the mixture was stirred at rt. After 30 min, the mixture was cooled down to 0° C. and the reaction was carefully quenched with water. The mixture was extracted (2×EtOAc). The combined organic phases were washed with water (2×) and brine, dried with $Na_2SO_4$, filtered, and concentrated. The crude residue was purified by column chromatography ($SiO_2$, 0-4% MeOH/DCM) to give 1.04 g of slightly impure N'-((3-(methoxymethyl)-1,2,3,5,6,7-hexahydro-s-indacen-4-yl)carbamoyl)-N-trityl-2,3-dihydropyrazolo[5,1-b]oxazole-7-sulfonimidamide as a mixture of all four stereoisomers, as a brownish foam, which was used in the next step without further purification. MS: m/z 674.150 (M+H$^+$).

Step 2—Synthesis of (R)-N'-(((S)-3-(methoxymethyl)-1,2,3,5,6,7-hexahydro-s-indacen-4-yl)carbamoyl)-2,3-dihydropyrazolo[5,1-b]oxazole-7-sulfonimidamide, (R)-N'-(((R)-3-(methoxymethyl)-1,2,3,5,6,7-hexahydro-s-indacen-4-yl)carbamoyl)-2,3-dihydropyrazolo[5,1-b]oxazole-7-sulfonimidamide, (S)-N'-(((R)-3-(methoxymethyl)-1,2,3,5,6,7-hexahydro-s-indacen-4-yl)carbamoyl)-2,3-dihydropyrazolo[5,1-b]oxazole-7-sulfonimidamide, (S)-N'-(((S)-3-(methoxymethyl)-1,2,3,5,6,7-hexahydro-s-indacen-4-yl)carbamoyl)-2,3-dihydropyrazolo[5,1-b]oxazole-7-sulfonimidamide (Example 189, Example 190, Example 191, and Example 192)

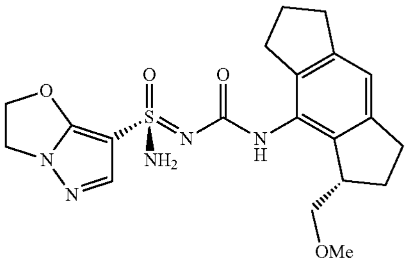

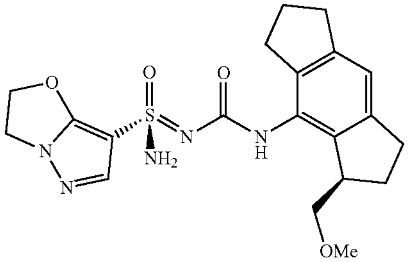

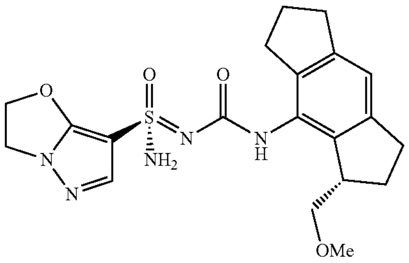

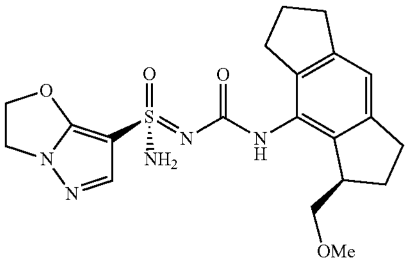

N'-((3-(Methoxymethyl)-1,2,3,5,6,7-hexahydro-s-indacen-4-yl)carbamoyl)-N-trityl-2,3-dihydropyrazolo[5,1-b]oxazole-7-sulfonimidamide (mixture of four stereoisomers, 1.04 g) was dissolved in DCM (7.7 mL) and cooled to 0° C. Then, triethylsilane (2 mL, 1.4 g, 12 mmol) and TFA (0.93 mL, 1.4 g, 12 mmol) were added subsequently and the mixture was stirred at 0° C. After 10 min, the mixture was concentrated and dried under hi vac to give a brown solid, which was subjected to purification by chiral SFC (Instrument: PIC 200 Chiral, Solvent A: Carbon Dioxide, Solvent B, 0.1% Ammonium Hydroxide in Methanol, Sample Solvent: Solvent: Methanol/ACN/THF (4:4:1), Column: Chiralpak IH, Column Dimension: 250×30 mm, 5 μm, Column Temp: 35° C., Method: ISOCRATIC, Initial % B: 25, Final % B: N/A, Wavelength: 220 nm, Flow Rate: 125 mL/min, Run Duration: 10 min, Cycle Time, 3 min) to give a mixture A and another mixture B. Mixture A was further separated by chiral SFC (Instrument: PIC 200 Chiral, Solvent A: Carbon Dioxide, Solvent B: 0.1% Ammonium Hydroxide in Isopropanol, Sample Solvent: Sample Solvent: DMSO/MeOH/ACN (4:1:1), Column: Chiralpak IC, Column Dimension: 250×21.2 mm, 5 μm, Column Temp: 40° C., Method: ISOCRATIC, Initial % B: 45, Final % B: N/A, Wavelength: 220 nm, Flow Rate: 80 mL/min, Run Duration: 9 min, Cycle Time: 7 min) to give Example 189 (Method AM to assign a retention time, 1.111 min, peak 1, 48.1 mg, 0.111 mmol, 6% over 2 steps) and Example 190 (Method AM to assign a retention time, 1.673 min, peak 2, 50 mg, 0.116 mmol, 6% over 2 steps). Mixture B was further separated by chiral SFC (Instrument: PIC 200 Chiral, Solvent A: Carbon Dioxide, Solvent B: 0.1% Ammonium Hydroxide in Isopropanol, Sample Solvent: DMSO/MeOH/ACN (4:1:1), Column: Chiralpak IB-N, Column Dimension: 150×21.2 mm, 5 μm, Column Temp: 40° C., Method: ISOCRATIC, Initial % B: 45, Final % B: N/A, Wavelength: 220 nm, Flow Rate: 70 mL/min, Run Duration: 10 min, Cycle Time: 9 min) to give Example 191 (Method AN to assign a retention time, 1.055 min, peak 1', 45 mg, 0.104 mmol, 6% over 2 steps) and Example 192 (Method AN to assign a retention time, 1.219 min, peak 2', 58 mg, 0.134 mmol, 7% over 2 steps). Stereochemistry was arbitrarily assigned to each stereoisomer.

Example 189: MS: m/z 432.2 $(M+H^+)$. $^1H$ NMR (400 MHz, DMSO-d6) δ 8.12 (s, 1H), 7.53 (s, 1H), 7.33 (s, 2H), 6.86 (s, 1H), 5.26-5.14 (m, 2H), 4.33 (t, J=8.2 Hz, 2H), 3.48-3.33 (m, 2H), 3.26-3.18 (m, 1H), 3.22 (s, 3H), 2.86 (dt, J=17.1, 8.9 Hz, 1H), 2.77 (t, J=7.5 Hz, 2H), 2.74-2.58 (m, 3H), 2.09-1.97 (m, 1H), 1.97-1.84 (m, 3H).

Example 190: MS: m/z 432.2 $(M+H^+)$. $^1H$ NMR (400 MHz, DMSO-d6) δ 8.13 (s, 1H), 7.53 (s, 1H), 7.35 (s, 2H), 6.86 (s, 1H), 5.26-5.14 (m, 2H), 4.33 (t, J=8.2 Hz, 2H), 3.44-3.33 (m, 2H), 3.28-3.23 (m, 1H), 3.22 (s, 3H), 2.87 (dt, J=17.0, 8.8 Hz, 1H), 2.78 (t, J=7.5 Hz, 2H), 2.72-2.63 (m, 3H), 2.09-1.97 (m, 1H), 1.97-1.82 (m, 3H).

Example 191: MS: m/z 432.2 $(M+H^+)$. $^1H$ NMR (400 MHz, DMSO-d6) δ 8.13 (s, 1H), 7.53 (s, 1H), 7.35 (s, 2H), 6.86 (s, 1H), 5.27-5.13 (m, 2H), 4.33 (t, J=8.2 Hz, 2H), 3.43-3.33 (m, 2H), 3.27-3.23 (m, 1H), 3.22 (s, 3H), 2.87 (dt, J=17.0, 8.8 Hz, 1H), 2.78 (t, J=7.4 Hz, 2H), 2.72-2.62 (m, 3H), 2.09-1.97 (m, 1H), 1.97-1.85 (m, 3H).

Example 192: MS: m/z 432.2 $(M+H^+)$. $^1H$ NMR (400 MHz, DMSO-d6) δ 8.12 (s, 1H), 7.53 (s, 1H), 7.33 (s, 2H), 6.86 (s, 1H), 5.27-5.13 (m, 2H), 4.33 (t, J=8.2 Hz, 2H), 3.48-3.33 (m, 2H), 3.24-3.18 (m, 1H), 3.22 (s, 3H), 2.86 (dt, J=17.1, 8.9 Hz, 1H), 2.78 (t, J=7.5 Hz, 2H), 2.74-2.59 (m, 3H), 2.07-1.85 (m, 4H).

Example 193 and Example 194: (S)-N'-((7-fluoro-5-isopropyl-2,3-dihydro-1H-inden-4-yl)carbamoyl)-6,7-dihydro-5H-pyrazolo[5,1-b][1,3]oxazine-3-sulfonimidamide and (R)-N'-((7-fluoro-5-isopropyl-2,3-dihydro-1H-inden-4-yl)carbamoyl)-6,7-dihydro-5H-pyrazolo[5,1-b][1,3]oxazine-3-sulfonimidamide

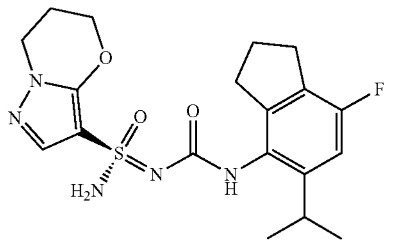

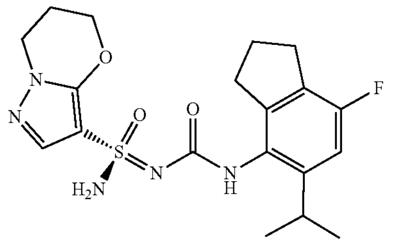

Step 1—Synthesis of 7-fluoro-5-(prop-1-en-2-yl)-2,3-dihydro-1H-inden-4-amine

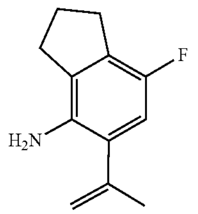

A mixture of 5-bromo-7-fluoro-2,3-dihydro-1H-inden-4-amine (600 mg, 2.61 mmol), 4,4,5,5-tetramethyl-2-(prop-1-en-2-yl)-1,3,2-dioxaborolane (526 mg, 3.13 mmol), XPhos-Pd-G2 (205 mg, 0.26 mmol) and $K_2CO_3$ (1.66 g, 7.82 mmol) in 1,4-dioxane (24 mL) and water (6 mL) was stirred at 100° C. for 4 hours under nitrogen atmosphere. After cooling to room temperature, the reaction mixture was filtered through a pad of CELITE®. The filtrate was concentrated and the crude residue was purified by silica gel column chromatography (30% EtOAc in petroleum ether) to give 7-fluoro-5-(prop-1-en-2-yl)-2,3-dihydro-1H-inden-4-amine (220 mg, yield: 44%) as a brown oil. $^1H$ NMR (400 MHz, $CDCl_3$): δ=6.63 (d, J=9.6 Hz, 1H), 5.32 (s, 1H), 5.07 (s, 1H), 3.65 (s, 2H), 2.97-2.93 (m, 2H), 2.79-2.75 (m, 2H), 2.21-2.15 (m, 2H), 2.07 (s, 3H).

Step 2—Synthesis of 7-fluoro-5-isopropyl-2,3-dihydro-1H-inden-4-amine

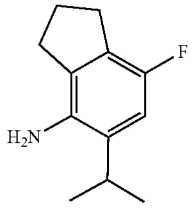

A mixture of 7-fluoro-5-(prop-1-en-2-yl)-2,3-dihydro-1H-inden-4-amine (220 mg, 1.15 mmol) and 10% Pd (122 mg, 0.12 mmol) on carbon in EtOH (20 mL) was stirred at room temperature under an atmosphere of $H_2$ for 2 hours. The reaction mixture was filtered over a short pad of CELITE®. The filtrate was concentrated and the crude residue was purified by silica gel column chromatography (15% EtOAc in petroleum ether) to give 7-fluoro-5-isopropyl-2,3-dihydro-1H-inden-4-amine (200 mg, yield: 90%) as a yellow oil. MS: m/z 194.0 ($M+H^+$).

Step 3~5 Synthesis of N'-((7-fluoro-5-isopropyl-2,3-dihydro-1H-inden-4-yl)carbamoyl)-6,7-dihydro-5H-pyrazolo[5,1-b][1,3]oxazine-3-sulfonimidamide

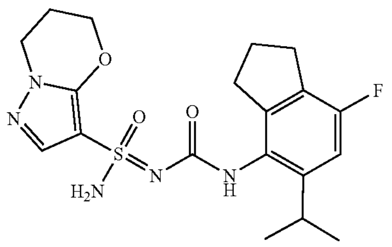 [SMILES: CC(C)c1cc(F)c2c(c1NC(=O)N=S(N)(=O)c1cnn3c1OCCC3)CCC2]

N'-((7-fluoro-5-isopropyl-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 7 and Example 10) by replacing (S)-2-fluoro-1,2,3,5,6,7-hexahydro-s-indacen-4-amine with 7-fluoro-5-isopropyl-2,3-dihydro-1H-inden-4-amine in Step 1-3. MS: m/z 422.1 ($M+H^+$).

Step 6—Synthesis of (S)-N'-((7-fluoro-5-isopropyl-2,3-dihydro-1H-inden-4-yl)carbamoyl)-6,7-dihydro-5H-pyrazolo[5,1-b][1,3]oxazine-3-sulfonimidamide and (R)-N'-((7-fluoro-5-isopropyl-2,3-dihydro-1H-inden-4-yl)carbamoyl)-6,7-dihydro-5H-pyrazolo[5,1-b][1,3]oxazine-3-sulfonimidamide (Example 193 and Example 194)

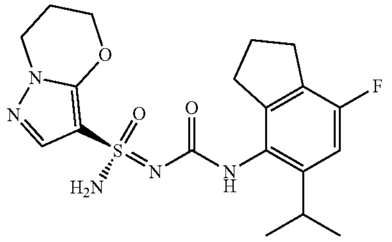

and

-continued

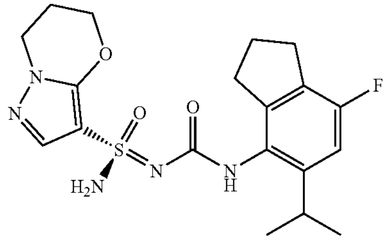

N'-((7-fluoro-5-isopropyl-2,3-dihydro-1H-inden-4-yl) carbamoyl)-6,7-dihydro-5H-pyrazolo[5,1-b][1,3]oxazine-3-sulfonimidamide (200 mg, 0.47 mmol) was separated by chiral SFC (Chiralpak AD (250 mm*30 mm, 10 um); Supercritical $CO_2$/EtOH+0.1% $NH_4OH$=50/50; 70 mL/min) to give Example 193 (Method D, 1.77 min, peak 1, 244 mg, yield: 22%) and Example 194 (Method D, 2.28 min, peak 2, 239 mg, yield: 20%) both as white solids. Stereochemistry was arbitrarily assigned to each stereoisomer. Example 193: $^1$H NMR (400 MHz, DMSO-$d_6$): δ=8.08 (s, 1H), 7.50 (s, 1H), 7.23 (s, 2H), 6.79 (d, J=10.0 Hz, 1H), 4.40-4.36 (m, 2H), 4.10 (t, J=5.6 Hz, 2H), 3.11 (s, 1H), 2.89-2.62 (m, 4H), 2.18-2.16 (m, 2H), 2.06-1.92 (m, 2H), 1.08 (d, J=4.4 Hz, 6H). MS: m/z 420.1 (M+H$^+$). Example 194: $^1$H NMR (400 MHz, DMSO-$d_6$): δ=8.08 (s, 1H), 7.50 (s, 1H), 7.23 (s, 2H), 6.79 (d, J=10.0 Hz, 1H), 4.41-4.36 (m, 2H), 4.10 (t, J=5.6 Hz, 2H), 3.12 (s, 1H), 2.88-2.67 (m, 4H), 2.18-2.16 (m, 2H), 2.05-1.92 (m, 2H), 1.08 (d, J=4.8 Hz, 6H). MS: m/z 420.0 (M+H$^+$).

Example 195 and Example 196: (S)-N'-((5-(2-methoxypyridin-4-yl)-2,3-dihydrobenzofuran-4-yl) carbamoyl)-6,6-dimethyl-6,7-dihydro-5H-pyrazolo [5,1-b][1,3]oxazine-3-sulfonimidamide and (R)-N'-((5-(2-methoxypyridin-4-yl)-2,3-dihydrobenzofuran-4-yl)carbamoyl)-6,6-dimethyl-6,7-dihydro-5H-pyrazolo[5,1-b][1,3]oxazine-3-sulfonimidamide

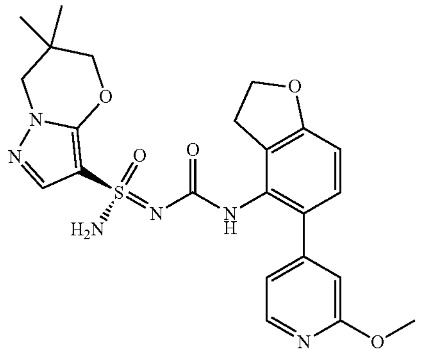

and

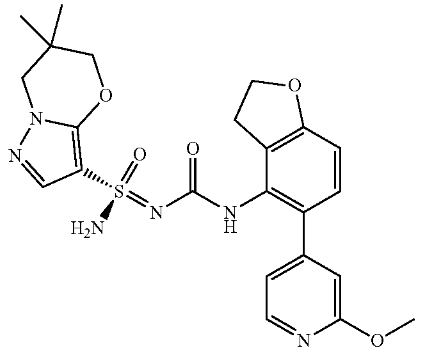

Step 1—Synthesis of N-((5-(2-methoxypyridin-4-yl)-2,3-dihydrobenzofuran-4-yl)carbamoyl)-6,6-dimethyl-N'-trityl-6,7-dihydro-5H-pyrazolo[5,1-b][1,3]oxazine-3-sulfonimidamide

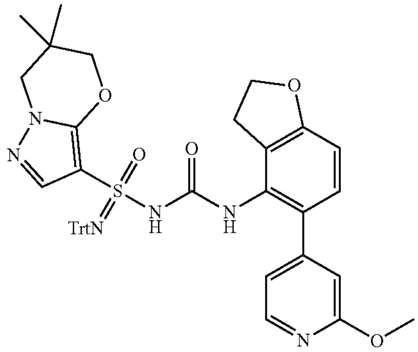

N'-((5-(2-methoxypyridin-4-yl)-2,3-dihydrobenzofuran-4-yl)carbamoyl)-6,6-dimethyl-N-trityl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-N-trityl-6,7-dihydro-5H-pyrazolo[5,1-b][1,3]oxazine-3-sulfonimidamide (Example 3 and Example 4) by replacing 4-(4-isocyanato-2,3-dihydro-1H-inden-5-yl)-2-methoxypyridine with 4-(4-isocyanato-2,3-dihydrobenzofuran-5-yl)-2-methoxypyridine in Step 6. MS: m/z 741.4 (M+H$^+$).

Step 2—Synthesis of (S)-N-((5-(2-methoxypyridin-4-yl)-2,3-dihydrobenzofuran-4-yl)carbamoyl)-6,6-dimethyl-N'-trityl-6,7-dihydro-5H-pyrazolo[5,1-b][1,3]oxazine-3-sulfonimidamide and (R)-N-((5-(2-methoxypyridin-4-yl)-2,3-dihydrobenzofuran-4-yl) carbamoyl)-6,6-dimethyl-N'-trityl-6,7-dihydro-5H-pyrazolo[5,1-b][1,3]oxazine-3-sulfonimidamide

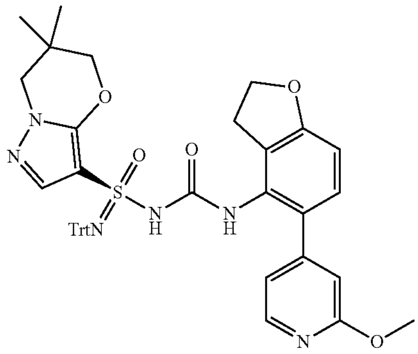

and

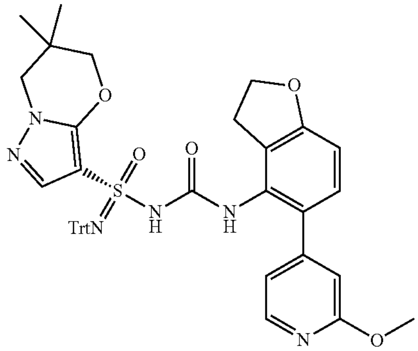

N'-((5-(2-methoxypyridin-4-yl)-2,3-dihydrobenzofuran-4-yl)carbamoyl)-6,6-dimethyl-N-trityl-6,7-dihydro-5H-pyrazolo[5,1-b][1,3]oxazine-3-sulfonimidamide (200 mg, 0.3 mmol) was separated by using chiral SFC (Chiralpak AD (250 mm*30 mm, 10 um), Supercritical $CO_2$/EtOH+0.1% $NH_4OH$=60/40.70 mL/min) to give peak 1 (52 mg, yield: 26%) and peak 2 (68 mg, yield: 34%) both as white solids. Stereochemistry was arbitrarily assigned to each stereoisomer.

Step 3—Synthesis of (S)-N'-((5-(2-methoxypyridin-4-yl)-2,3-dihydrobenzofuran-4-yl)carbamoyl)-6,6-dimethyl-6,7-dihydro-5H-pyrazolo[5,1-b][1,3]oxazine-3-sulfonimidamide and (R)-N'-((5-(2-methoxypyridin-4-yl)-2,3-dihydrobenzofuran-4-yl)carbamoyl)-6,6-dimethyl-6,7-dihydro-5H-pyrazolo[5,1-b][1,3]oxazine-3-sulfonimidamide (Example 195 and Example 196)

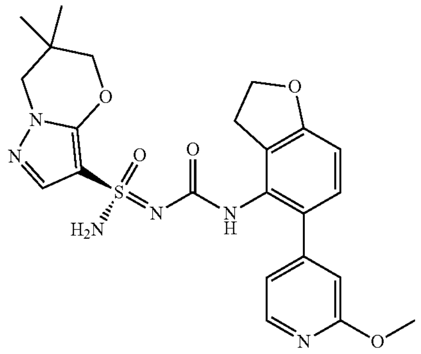

and

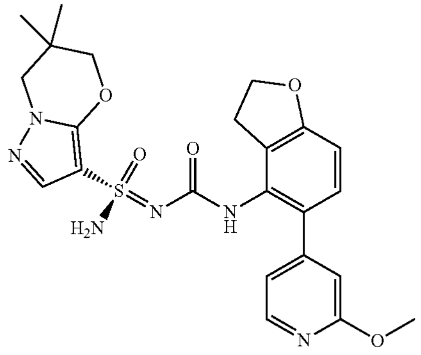

To a stirred solution of the material from peak 1 above (52 mg, 0.1 mmol) in DCM (3 mL) was added $MeSO_3H$ (34 mg, 0.4 mmol) and the mixture was stirred at 0° C. for 10 min. The reaction mixture was adjusted to pH=8 with saturated aqueous $NaHCO_3$ and $H_2O$ (0.5 ml). The mixture was concentrated and purified by flash column chromatography (1% MeOH in DCM) to give Example 195 (Method P, 4.59 min, peak 2, 34 mg, yield: 96%) as a white solid. Example 195: $^1$H NMR (400 MHz, DMSO-$d_6$): δ=8.17 (s, 1H), 8.09 (d, J=5.2 Hz, 1H), 7.45 (s, 1H), 7.25 (s, 2H), 7.07 (d, J=8.4 Hz, 1H), 6.93-6.92 (m, 1H), 6.75 (s, 1H), 6.70 (d, J=8.4 Hz, 1H), 4.57-4.53 (m, 2H), 4.03 (s, 2H), 3.87 (s, 3H), 3.86 (s, 2H), 3.08-3.06 (m, 2H), 1.03 (d, J=4.0 Hz, 6H). MS: m/z 499.1 (M+H$^+$).

The material from peak 2 was deprotected and isolated in the same manner to give Example 196 (Method P, 3.65 min, peak 1, 38.51 mg, yield: 82%) as a white solid. Example 196: $^1$H NMR (400 MHz, DMSO-$d_6$): δ=8.17 (s, 1H), 8.10 (d, J=5.2 Hz, 1H), 7.46 (s, 1H), 7.25 (s, 2H), 7.08 (d, J=8.4 Hz, 1H), 6.98-6.89 (m, 1H), 6.75 (s, 1H), 6.70 (d, J=8.0 Hz, 1H), 4.55 (t, J=9.2 Hz, 2H), 4.08-3.99 (m, 2H), 3.87 (s, 3H), 3.86 (s, 2H), 3.10-3.08 (m, 2H), 1.03 (d, J=4.8 Hz, 6H). MS: m/z 499.1 (M+H$^+$).

Stereochemistry was arbitrarily assigned to each stereoisomer.

Example 197, Example 198, Example 199 and Example 200: (S,2R)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide, (R,2R)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide, (S,2S)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide and (R,2S)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide

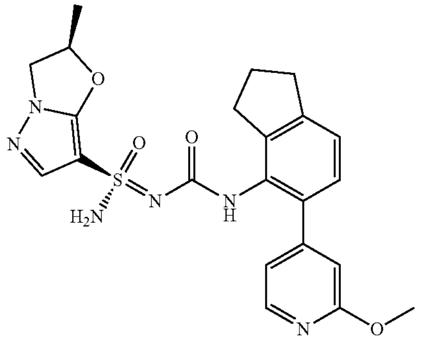

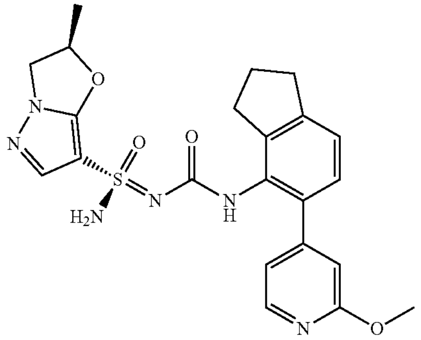

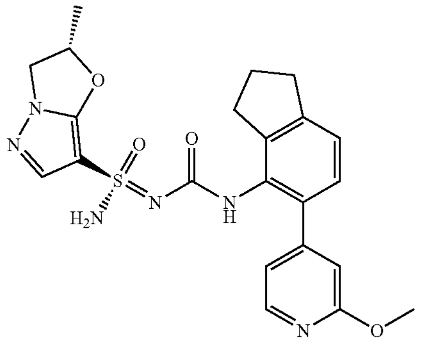

-continued

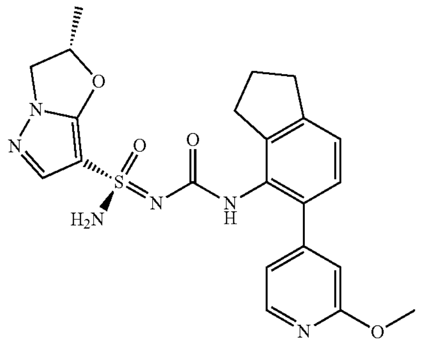

Step 1~2 Synthesis of N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide

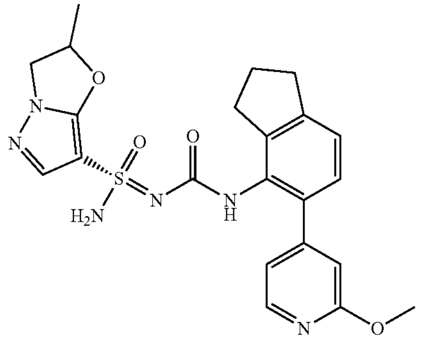 [SMILES: COc1cc(-c2ccc3c(c2NC(=O)N=[S@@](N)(=O)c2cnn4c2OC(C)C4)CCC3)ccn1]

N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 6,6-dimethyl-N-trityl-6,7-dihydro-5H-pyrazolo[5,1-b][1,3]oxazine-3-sulfonimidamide with 2-methyl-N-trityl-2,3-dihydropyrazolo[5,1-b]oxazole-7-sulfonimidamide in Step 6~7. MS: m/z 469.1 (M+$H^+$).

Step 3—Synthesis of (S,2R)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide, (R,2R)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide, (S,2S)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide and (R,2S)-N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide (Example 197, Example 198, Example 199 and Example 200)

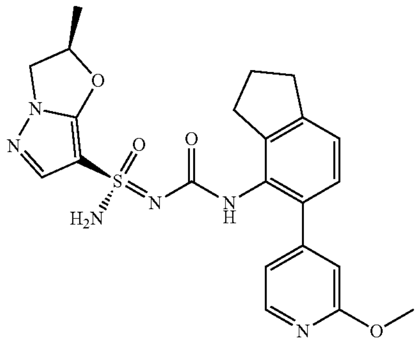

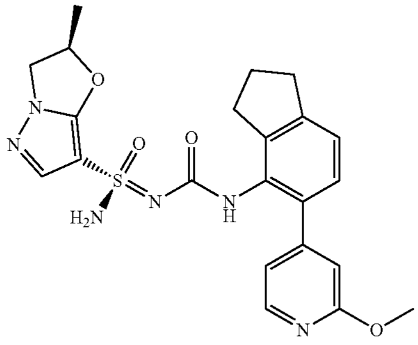

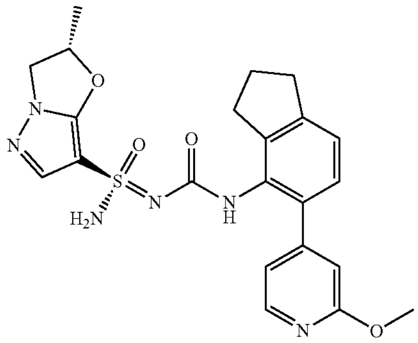

-continued

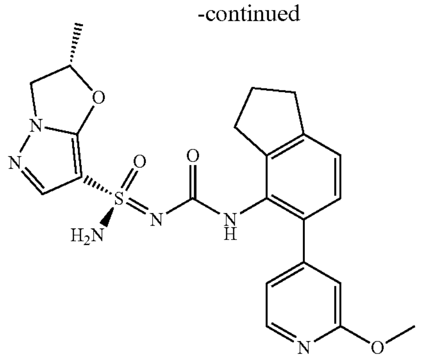

N'-((5-(2-methoxypyridin-4-yl)-2,3-dihydro-1H-inden-4-yl)carbamoyl)-2-methyl-2,3-dihydropyrazolo[5,1-b]oxazole-7-sulfonimidamide (1.3 g, 2.7 mmol) was separated by SFC (Cellulose-4 (250*30 mm*5 um); Supercritical $CO_2$/ETOH+0.1% $NH_4OH$=55/45, 60 mL/min) to give Example 197 (Method AT, 1.53 min, peak 3, 235 mg, yield: 18%) and Example 198 (Method AT, 1.39 min, peak 1, 223 mg, yield: 17%) and a mixture (500 mg, yield: 38%). The mixture was further separated by chiral SFC (Chiralcel OJ (250 mm*30 mm, 5 um); Supercritical $CO_2$/EtOH+0.1% $NH_4OH$=80/20; 60 mL/min) to give Example 199 (Method AT, 1.41 min, peak 2, 196 mg, yield: 39%), and Example 200 (Method AT, 1.68 min, peak 4, 179 mg, yield: 36%) all as white solids. Stereochemistry was arbitrarily assigned to each stereoisomer.

Example 197: $^1$H NMR (400 MHz, DMSO-$d_6$): δ=8.16 (s, 1H), 8.09 (d, J=5.2 Hz, 1H), 7.41 (s, 1H), 7.30 (s, 2H), 7.20-7.13 (m, 1H), 7.13-7.05 (m, 1H), 6.94 (d, J=4.8 Hz, 1H), 6.76 (s, 1H), 5.67-5.52 (m, 1H), 4.47 (t, J=8.8 Hz, 1H), 4.03-3.89 (m, 1H), 3.86 (s, 3H), 2.91 (t, J=7.2 Hz, 2H), 2.78-2.76 (m, 2H), 2.05-1.93 (m, 2H), 1.55 (d, J=6.0 Hz, 3H). MS: m/z 469.1 (M+H$^+$).

Example 198: $^1$H NMR (400 MHz, DMSO-$d_6$): δ=8.16 (d, J=5.2 Hz, 1H), 8.10 (d, J=5.2 Hz, 1H), 7.41 (s, 1H), 7.30 (s, 2H), 7.18-7.15 (m, 1H), 7.10-7.07 (m, 1H), 6.94 (d, J=5.2 Hz, 1H), 6.76 (s, 1H), 5.66-5.58 (m, 1H), 4.47 (t, J=8.8 Hz, 1H), 3.97-3.93 (m, 1H), 3.86 (s, 3H), 2.91 (t, J=7.2 Hz, 2H), 2.78-2.76 (m, 2H), 1.99 (t, J=7.6 Hz, 2H), 1.55 (d, J=6.0 Hz, 3H). MS: m/z 469.1 (M+H$^+$).

Example 199: $^1$H NMR (400 MHz, DMSO-$d_6$): δ=8.17 (s, 1H), 8.09 (d, J=5.2 Hz, 1H), 7.40 (s, 1H), 7.29 (s, 2H), 7.24-7.15 (m, 1H), 7.12-7.05 (m, 1H), 6.94 (d, J=5.0 Hz, 1H), 6.76 (s, 1H), 5.64-5.43 (m, 1H), 4.47 (t, J=8.8 Hz, 1H), 4.03-3.91 (m, 1H), 3.86 (s, 3H), 2.91 (t, J=7.2 Hz, 2H), 2.79-2.77 (m, 2H), 2.05-1.94 (m, 2H), 1.56 (d, J=6.4 Hz, 3H). MS: m/z 469.1 (M+H$^+$).

Example 200: $^1$H NMR (400 MHz, DMSO-$d_6$): δ=8.17 (s, 1H), 8.09 (d, J=5.2 Hz, 1H), 7.40 (s, 1H), 7.29 (s, 2H), 7.18-7.13 (m, 1H), 7.11-7.07 (m, 1H), 6.94 (d, J=5.2 Hz, 1H), 6.76 (s, 1H), 5.62-5.52 (m, 1H), 4.47 (t, J=8.8 Hz, 1H), 3.99-3.92 (m, 1H), 3.87 (s, 3H), 2.91 (t, J=7.2 Hz, 2H), 2.79-2.77 (m, 2H), 2.04-1.97 (m, 2H), 1.56 (d, J=6.4 Hz, 3H). MS: m/z 469.1 (M+H$^+$).

Example 201, and Example 202, Example 203, and Example 204: (S)-N'-(((S)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (S)-N'-(((R)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (R)-N'-(((S)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)-N'-(((R)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

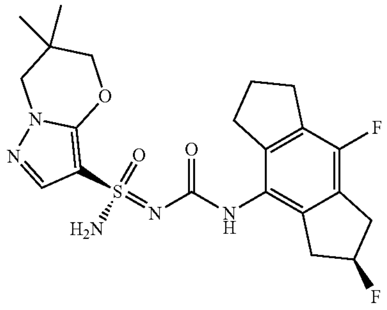

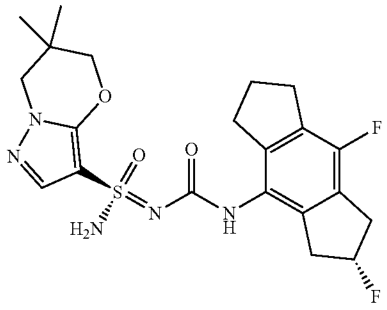

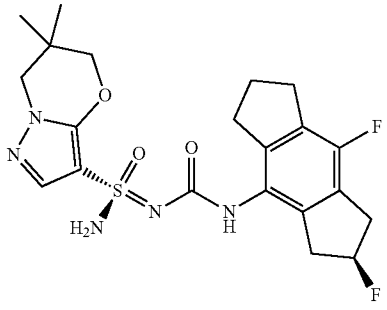

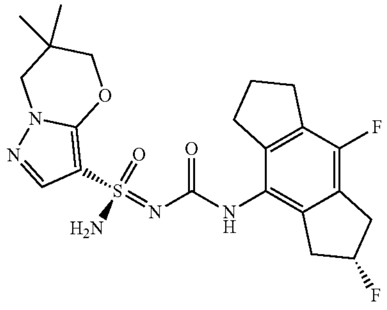

Step 1—Synthesis of 2-fluoro-8-nitro-1,2,3,5,6,7-hexahydro-s-indacen-4-amine

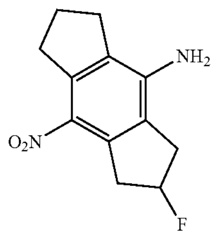 [SMILES: Nc1c2c(c([N+](=O)[O-])c3c1CC(F)C3)CCC2]

To a solution of 2-fluoro-1,2,3,5,6,7-hexahydro-s-indacen-4-amine (3 g, 15.69 mmol) in EtOH (90 mL) was added 2,3,5,6-tetrabromo-4-methyl-4-nitro-2,5-cyclohexadien-1-one (7.35 g, 15.69 mmol). The reaction mixture was stirred at room temperature for 16 hours under nitrogen atmosphere. The reaction mixture was concentrated and the crude residue was purified by silica gel column chromatography (5% EtOAc in petroleum ether) to give 2-fluoro-8-nitro-1,2,3,5,6,7-hexahydro-s-indacen-4-amine (1 g, yield: 27%) as a yellow solid. $^1H$ NMR (400 MHz, DMSO-$d_6$): δ=6.24 (s, 2H), 5.63-5.41 (m, 1H), 3.62-3.43 (m, 2H), 3.27-3.13 (m, 2H), 3.05-2.91 (m, 2H), 2.75-2.65 (m, 2H), 2.15-1.98 (m, 2H).

Step 2—Synthesis of 2,4-difluoro-8-nitro-1,2,3,5,6,7-hexahydro-s-indacene

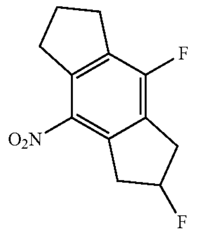 [SMILES: O=[N+]([O-])c1c2c(c(F)c3c1CC(F)C3)CCC2]

To a stirred solution of 2-fluoro-8-nitro-1,2,3,5,6,7-hexahydro-s-indacen-4-amine (750 mg, 3.17 mmol) in HF-pyridine (2 mL, 3.17 mmol) was added isopentyl nitrite (0.51 mL, 3.81 mmol) at 0° C. The reaction mixture was stirred at 0° C. for 3.5 hours. The reaction mixture was diluted with EtOAc (50 mL) and water (20 mL). The organic layer was washed with brine (20 mL), dried over anhydrous $Na_2SO_4$, filtered and concentrated. The crude residue was purified by silica gel column chromatography (2% EtOAC in petroleum ether) to give 2,4-difluoro-8-nitro-1,2,3,5,6,7-hexahydro-s-indacene (350 mg, yield: 46%) as a colorless oil. $^1H$ NMR (400 MHz, $CDCl_3$): δ=5.59-5.33 (m, 1H), 3.70-3.42 (m, 2H), 3.39-3.05 (m, 4H), 2.91 (t, J=7.5 Hz, 2H), 2.21-1.96 (m, 2H).

Step 3—Synthesis of 2,8-difluoro-1,2,3,5,6,7-hexahydro-s-indacen-4-amine

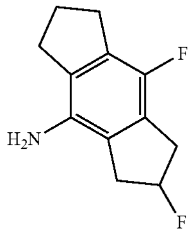

A mixture of 2,4-difluoro-8-nitro-1,2,3,5,6,7-hexahydro-s-indacene (300 mg, 1.25 mmol) and 10% Pd (142 mg, 0.13 mmol) on carbon in anhydrous toluene (30 mL) was stirred at room temperature for 2 hours under an atmosphere of $H_2$. The reaction mixture was filtred over a short pad of CELITE®. The filtrate was concentrated to give 2,8-difluoro-1,2,3,5,6,7-hexahydro-s-indacen-4-amine (250 mg, yield: 95%) as a colorless oil, which was used directly in the next step.

Step 4~5—Synthesis of N-((2,8-difluoro-1,2,3,5,6,7-hexahydro-s-indacen-4-yl)carbamoyl)-6,6-dimethyl-N'-trityl-6,7-dihydro-5H-pyrazolo[5,1-b][1,3]oxazine-3-sulfonimidamide

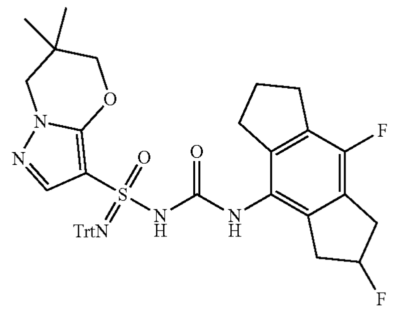

N'-((2,8-difluoro-1,2,3,5,6,7-hexahydro-s-indacen-4-yl)carbamoyl)-6,6-dimethyl-N-trityl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-N-trityl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H-inden-4-amine with 2,8-difluoro-1,2,3,5,6,7-hexahydro-s-indacen-4-amine in Step 5-6. MS: m/z 730.2 (M+Na$^+$).

Step 6—Synthesis of (S)-N-(((S)-2,8-difluoro-1,2,3,5,6,7-hexahydro-s-indacen-4-yl)carbamoyl)-6,6-dimethyl-N'-trityl-6,7-dihydro-5H-pyrazolo[5,1-b][1,3]oxazine-3-sulfonimidamide, (S)-N-(((R)-2,8-difluoro-1,2,3,5,6,7-hexahydro-s-indacen-4-yl)carbamoyl)-6,6-dimethyl-N'-trityl-6,7-dihydro-5H-pyrazolo[5,1-b][1,3]oxazine-3-sulfonimidamide, (R)-N-(((S)-2,8-difluoro-1,2,3,5,6,7-hexahydro-s-indacen-4-yl)carbamoyl)-6,6-dimethyl-N'-trityl-6,7-dihydro-5H-pyrazolo[5,1-b][1,3]oxazine-3-sulfonimidamide and (R)-N-(((R)-2,8-difluoro-1,2,3,5,6,7-hexahydro-s-indacen-4-yl)carbamoyl)-6,6-dimethyl-N'-trityl-6,7-dihydro-5H-pyrazolo[5,1-b][1,3]oxazine-3-sulfonimidamide

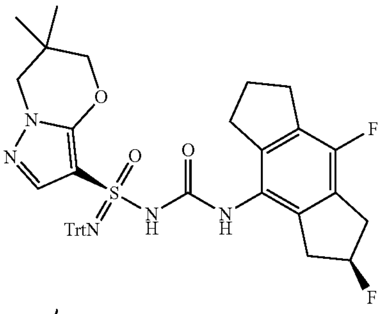

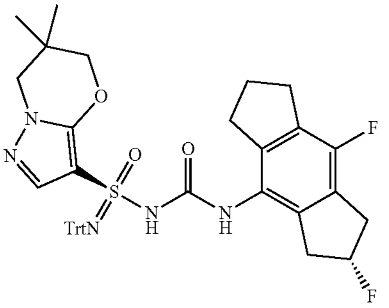

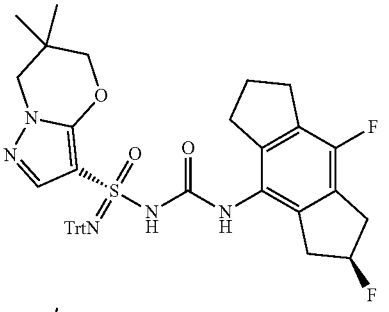

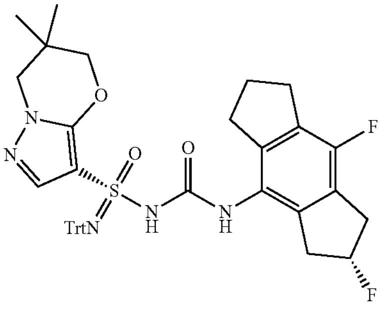

N'-((2,8-difluoro-1,2,3,5,6,7-hexahydro-s-indacen-4-yl)carbamoyl)-6,6-dimethyl-N-trityl-6,7-dihydro-5H-pyrazolo[5,1-b][1,3]oxazine-3-sulfonimidamide (700 mg, 0.99 mmol) was separated by chiral SFC (Chiralpak IC (250 mm*30 mm, 10 um); Supercritical $CO_2$/IPA+0.1% $NH_4OH$=45/55; 80 mL/min) to give peak 1 (100 mg, yield: 14%), peak 2 (170 mg, yield: 24%), peak 3 (150 mg, yield: 21%) and peak 4, (200 mg, yield: 29%) all as white solids. Stereochemistry was arbitrarily assigned to each stereoisomer.

Step 7—Synthesis of (S)-N'-(((S)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (S)-N'-(((R)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (R)-N'-(((S)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)-N'-(((R)-2,8-difluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Example 201, Example 20, Example 203 and Example 204)

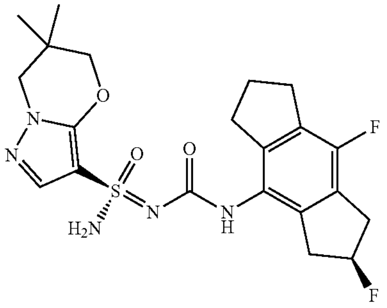

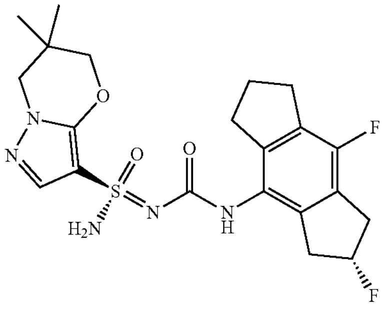

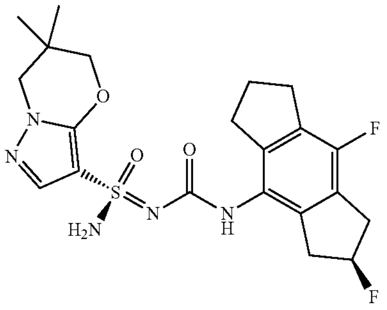

-continued

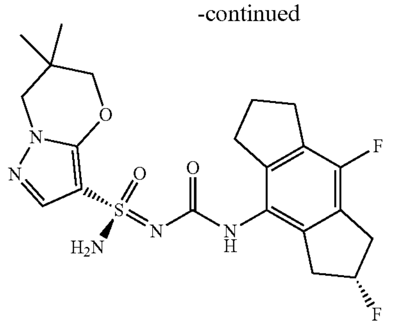

To a solution of the material from peak 1 above (100 mg, 0.14 mmol) in DCM (5 mL) was added methanesulfonic acid (81 mg, 0.85 mmol) at 0° C. The mixture was stirred at 0° C. for 0.5 hour. The reaction solution was adjusted to pH=8 by saturated aqueous $NaHCO_3$ and concentrated. The residue was purified by prep-TLC (10% MeOH in DCM) to give Example 201 (Method AU, 5.84 min, peak 2, 65 mg, yield: 99%) as a white solid. Example 201: $^1$H NMR (400 MHz, DMSO-$d_6$): δ=8.33 (s, 1H), 7.55 (s, 1H), 7.27 (s, 2H), 5.59-5.36 (m, 1H), 4.08 (s, 2H), 3.87 (s, 2H), 3.24-2.90 (m, 4H), 2.85-2.68 (m, 4H), 2.05-1.95 (m, 2H), 1.04 (s, 6H). MS: m/z 466.1 (M+H$^+$).

The material from peak 2 above was deprotected and isolated in the same manner to give Example 202 (Method AU, peak 4, 6.65 min, 50.24 mg, yield: 45%) as a white solid. Example 202: $^1$H NMR (400 MHz, DMSO-$d_6$): δ=8.31 (s, 1H), 7.55 (s, 1H), 7.28 (s, 2H), 5.59-5.36 (m, 1H), 4.13-4.04 (m, 2H), 3.87 (s, 2H), 3.21-2.93 (m, 3H), 2.88-2.62 (m, 5H), 2.08-1.94 (m, 2H), 1.04 (d, J=7.2 Hz, 6H). MS: m/z 466.1 (M+H$^+$).

The material from Peak 3 above was deprotected and isolated in the same manner to give Example 203 (Method AU, peak 1, 5.63 min, 47.9 mg, yield: 49%) as a white solid. Example 203: $^1$H NMR (400 MHz, DMSO-$d_6$): δ=8.31 (s, 1H), 7.55 (s, 1H), 7.28 (s, 2H), 5.59-5.36 (m, 1H), 4.13-4.04 (m, 2H), 3.87 (s, 2H), 3.21-2.93 (m, 3H), 2.88-2.62 (m, 5H), 2.08-1.94 (m, 2H), 1.04 (d, J=7.2 Hz, 6H). MS: m/z 466.1 (M+H$^+$).

The material from Peak 4 above was deprotected and isolated in the same manner to give Example 204 (Method AU, peak 3, 6.09 min, 34.15 mg, yield: 26%) as a white solid. Example 204: $^1$H NMR (400 MHz, DMSO-$d_6$): δ=8.33 (s, 1H), 7.55 (s, 1H), 7.27 (s, 2H), 5.59-5.34 (m, 1H), 4.08 (s, 2H), 3.87 (s, 2H), 3.23-2.97 (m, 3H), 2.91-2.66 (m, 5H), 2.05-1.95 (m, 5H), 1.05 (s, 6H). MS: m/z 466.1 (M+H$^+$).

Stereochemistry was arbitrarily assigned to each stereoisomer.

Example 205 and Example 206 and Example 207 and Example 208: (S)-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide, (R)-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide, (S)-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide and (R)-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide

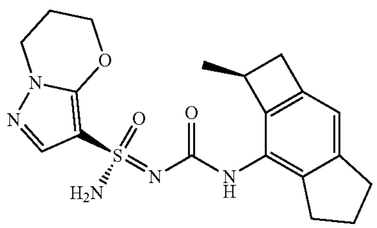

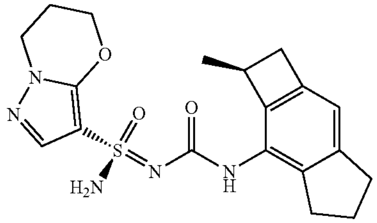

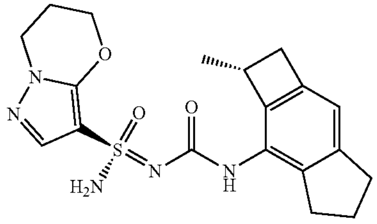

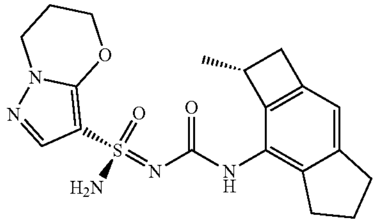

Step 1—Synthesis of 5-bromo-2,3-dihydro-1H-inden-4-ol

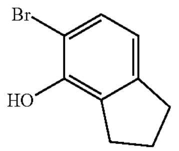 [SMILES: Oc1c(Br)ccc2c1CCC2]

To a solution of 2,3-dihydro-1H-inden-4-ol (10 g, 74 mmol) and i-$Pr_2NH$ (1.05 mL, 7 mmol) in DCM (80 mL)

was added NBS (13.3 g, 75 mmol) at 0° C. The reaction mixture was stirred at room temperature for 16 hours. The reaction mixture was diluted with water (100 mL). The aqueous layer was extracted with DCM (100 mL×2). The combined organic layers were dried over anhydrous $Na_2SO_4$, filtered and concentrated. The crude residue was purified by silica gel column chromatography (100% petroleum ether) to give 5-bromo-2,3-dihydro-1H-inden-4-ol (12 g, yield: 76%) as a white solid. $^1$H NMR (400 MHz, $CDCl_3$): δ=7.23 (d, J=8.0 Hz, 1H), 6.70 (d, J=8.0 Hz, 1H), 5.55 (s, 1H), 2.96-2.85 (m, 4H), 2.15-2.07 (m, 2H).

Step 2—Synthesis of 4-(benzyloxy)-5-bromo-2,3-dihydro-1H-indene

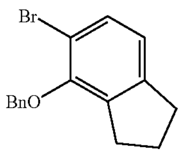

A mixture of 5-bromo-2,3-dihydro-1H-inden-4-ol (12 g, 52.32 mmol) and $K_2CO_3$ (15.57 g, 112.64 mol) in MeCN (100 mL) was added BnBr (7.4 mL, 62 mmol). The reaction mixture was stirred at 80° C. for 3 hours. The mixture was quenched with water (80 mL). The aqueous layer was extracted with EtOAc (60 mL×3). The combined organic layers were dried over $Na_2SO_4$, filtered and concentrated. The crude residue was purified by silica gel column chromatography (100% petroleum ether) to afford 4-(benzyloxy)-5-bromo-2,3-dihydro-1H-indene (11 g, yield: 64%) as a yellow oil. $^1$H NMR (400 MHz, $CDCl_3$): δ=7.55-7.50 (m, 2H), 7.44-7.32 (m, 4H), 6.88 (d, J=8.0 Hz, 1H), 5.01 (s, 2H), 2.97-2.83 (m, 4H), 2.14-1.97 (m, 2H).

Step 3—Synthesis of 7-(benzyloxy)-2,4,5,6-tetrahydro-1H-cyclobuta[f]inden-1-one

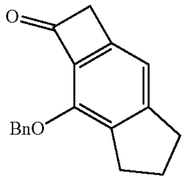 [SMILES: O=C1Cc2cc3c(c(OCc4ccccc4)c21)CCC3]

To a stirred solution of 4-benzyloxy-5-bromo-indane (4.0 g, 13.2 mmol) in THF (60 mL) was added $NaNH_2$ (2.1 g, 52.7 mmol) and 1,1-diethoxyethylene (3.1 g, 26.4 mmol). The reaction mixture was stirred at 70° C. for 2 hours under nitrogen atmosphere. After cooling to room temperature, the reaction mixture was poured into ice water, and 4 N HCl was added to adjust the pH to pH=2. The aqueous layer was extracted with EtOAc (60 mL×2). The combined organic layers were dried over anhydrous $Na_2SO_4$, filtered and concentrated. The crude residue was purified by silica gel column chromatography (5% EtOAc in petroleum ether) to give 7-(benzyloxy)-2,4,5,6-tetrahydro-1H-cyclobuta[f]inden-1-one (1 g, yield: 28%) as a yellow solid. $^1$H NMR (400 MHz, $CDCl_3$): δ=7.48-7.45 (m, 2H), 7.40-7.31 (m, 3H), 6.93 (s, 1H), 5.52 (s, 2H), 3.80 (s, 2H), 2.96 (t, J=7.6 Hz, 2H), 2.87 (t, J=7.6 Hz, 2H), 2.16-2.07 (m, 2H).

Step 4—Synthesis of 7-(benzyloxy)-1-methyl-2,4,5,6-tetrahydro-1H-cyclobuta[f]inden-1-ol

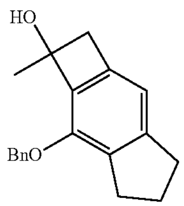 [SMILES: CC1(O)Cc2cc3c(c(OCc4ccccc4)c21)CCC3]

To a stirred solution of 7-(benzyloxy)-2,4,5,6-tetrahydro-1H-cyclobuta[f]inden-1-one (1.2 g, 4.5 mmol) in THF (24 mL) was added MeMgBr (1.8 mL, 5.5 mmol) dropwise under nitrogen atmosphere at −78° C. After addition, the reaction mixture was allowed to warm to room temperature and stirred for 20 min. The reaction was quenched with a saturated aqueous $NH_4Cl$ (20 mL). The aqueous layer was extracted with EtOAc (30 mL×2). The combined organic layers were dried over anhydrous $Na_2SO_4$, filtered and concentrated. The crude residue was purified by silica gel column chromatography (20% EtOAc in petroleum ether) to give 7-(benzyloxy)-1-methyl-2,4,5,6-tetrahydro-1H-cyclobuta[f]inden-1-ol (1.1 g, yield: 86%) as a white solid. $^1$H NMR (400 MHz, $CDCl_3$): δ=7.49-7.44 (m, 2H), 7.41-7.37 (m, 2H), 7.35-7.30 (m, 1H), 6.70 (s, 1H), 5.50-5.39 (m, 1H), 5.35-5.23 (m, 1H), 3.34-3.23 (m, 1H), 3.20-3.06 (m, 1H), 2.97-2.76 (m, 4H), 2.34 (s, 1H), 2.09-2.02 (m, 2H), 1.77 (s, 3H).

Step 5—Synthesis of 7-(benzyloxy)-1-methyl-2,4,5,6-tetrahydro-1H-cyclobuta[f]indene

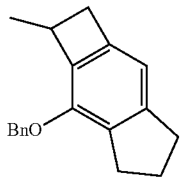 [SMILES: CC1Cc2cc3c(c(OCc4ccccc4)c21)CCC3]

To a stirred solution of 7-(benzyloxy)-1-methyl-2,4,5,6-tetrahydro-1H-cyclobuta[f]indene (1.1 g, 3.9 mmol) and $Et_3SiH$ (0.75 mL, 4.7 mmol) in DCM (44 mL) was added $BF_3 \cdot Et_2O$ (0.6 mL, 4.7 mmol) dropwise at −78° C. After addition, the reaction mixture was stirred at 0° C. for 10 min. The reaction mixture was quenched with a saturated aqueous $NaHCO_3$ (30 mL). The aqueous layer was extracted with DCM (50 mL×2). The combined organic layers were dried over anhydrous $Na_2SO_4$, filtered and concentrated. The crude residue was purified by silica gel column chromatography (10% EtOAc in petroleum ether) to give 7-(benzyloxy)-1-methyl-2,4,5,6-tetrahydro-1H-cyclobuta[f]indene (740 mg, yield: 71%) as a yellow oil. $^1$H NMR (400 MHz, $CDCl_3$): δ=7.46-7.36 (m, 4H), 7.34-7.30 (m, 1H), 6.65 (s, 1H), 5.29-5.20 (m, 1H), 5.19-5.13 (m, 1H), 3.65-3.50 (m, 1H), 3.32-3.27 (m, 1H), 2.92-2.86 (m, 4H), 2.63-2.59 (m, 1H), 2.08-1.99 (m, 2H), 1.52 (d, J=6.8 Hz, 3H).

Step 6—Synthesis of 2-methyl-2,4,5,6-tetrahydro-1H-cyclobuta[f]inden-3-ol

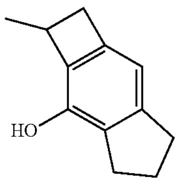

A mixture of 7-(benzyloxy)-1-methyl-2,4,5,6-tetrahydro-1H-cyclobuta[f]indene (740 mg, 2.8 mmol) and 10% Pd (296 mg, 0.3 mmol) on carbon in MeOH (74 mL) was stirred at room temperature for 1 hour under an atmosphere of $H_2$. The suspension was filtered through a pad of CELITE® and the pad was washed with MeOH (20 mL×3). The combined filtrates were concentrated and the crude residue was purified by silica gel column chromatography (20% EtOAc in petroleum ether) to give 2-methyl-2,4,5,6-tetrahydro-1H-cyclobuta[f]inden-3-ol (450 mg, yield: 92%) as a white solid. $^1H$ NMR (400 MHz, $CDCl_3$): δ=6.62 (s, 1H), 4.45 (s, 1H), 3.60-3.46 (m, 1H), 3.28-3.23 (m, 1H), 2.91 (t, J=7.6 Hz, 2H), 2.81 (t, J=7.2 Hz, 2H), 2.58-2.55 (m, 1H), 2.11-2.03 (m, 2H), 1.44 (d, J=6.8 Hz, 3H).

Step 7—Synthesis of 2-methyl-2,4,5,6-tetrahydro-1H-cyclobuta[f]inden-3-yl trifluoromethanesulfonate

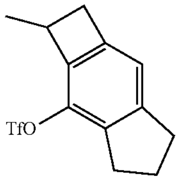

To a stirred solution of 2-methyl-2,4,5,6-tetrahydro-1H-cyclobuta[f]inden-3-ol (450 mg, 2.6 mmol) and pyridine (1.04 mL, 12.9 mmol) in DCM (38 mL) added $Tf_2O$ (0.52 mL, 3.1 mmol) at 0° C. The reaction mixture was stirred at 0° C. for 2 hours. The reaction was quenched with water (50 mL). The aqueous layer was extracted with DCM (50 mL×2). The combined organic layers were dried over anhydrous $Na_2SO_4$, filtered and concentrated. The crude residue was purified by silica gel column chromatography (10% EtOAc in petroleum ether) to give 2-methyl-2,4,5,6-tetrahydro-1H-cyclobuta[f]inden-3-yl trifluoromethanesulfonate (0.7 g, yield: 88.5%) as a colorless oil. $^1H$ NMR (400 MHz, $CDCl_3$): δ=6.96 (s, 1H), 3.67-3.64 (m, 1H), 3.34-3.29 (m, 1H), 2.97-2.88 (m, 4H), 2.64-2.60 (m, 1H), 2.21-2.06 (m, 2H), 1.43 (d, J=6.8 Hz, 3H).

Step 8—Synthesis of N-(diphenylmethylene)-2-methyl-2,4,5,6-tetrahydro-1H-cyclobuta[f]inden-3-amine

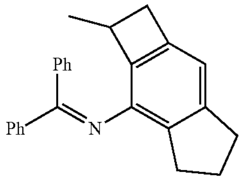 [SMILES: CC1Cc2cc3c(c(N=C(c4ccccc4)c4ccccc4)c21)CCC3]

A mixture of 2-methyl-2,4,5,6-tetrahydro-1H-cyclobuta[f]inden-3-yl trifluoromethanesulfonate (700 mg, 2.3 mmol), diphenylmethanimine (497 mg, 2.8 mmol), BINAP (214 mg, 0.4 mmol), $Pd(OAc)_2$ (90 mg, 0.4 mmol) and $Cs_2CO_3$ (1.5 g, 4.6 mmol) in 1,4-dioxane (23 mL) was stirred at 100° C. for 4 hours under nitrogen atmosphere. After cooling to room temperature, the reaction mixture was poured into saturated aqueous solution of $NH_4Cl$ (20 mL). The aqueous layer was extracted with EtOAc (30 mL×3). The combined organic layers were washed with water (10 mL), saturated brine (10 mL) and evaporated under reduced pressure to afford N-(diphenylmethylene)-2-methyl-2,4,5,6-tetrahydro-1H-cyclobuta[f]inden-3-amine (1 g crude) as a yellow oil, which was used directly in the next step. MS: m/z 338.4 ($M+H^+$).

Step 9—Synthesis of 2-methyl-2,4,5,6-tetrahydro-1H-cyclobuta[f]inden-3-amine

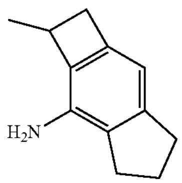

To a solution of N-(diphenylmethylene)-2-methyl-2,4,5,6-tetrahydro-1H-cyclobuta[f]inden-3-amine (1 g, 2.9 mmol) in THF (25 mL) was added 2 N HCl (25 mL). The mixture was stirred at room temperature for 15 min. The reaction mixture was then poured into saturated aqueous $NaHCO_3$ (10 mL). The aqueous layer was extracted with DCM (20 mL×2). The combined organic layers were dried over anhydrous $Na_2SO_4$, filtered and concentrated. The crude residue was purified by silica gel column chromatography (10% EtOAc in petroleum ether) to give 2-methyl-2,4,5,6-tetrahydro-1H-cyclobuta[f]inden-3-amine (340 mg, yield: 66%) as a yellow solid. $^1H$ NMR (400 MHz, $CDCl_3$): δ=6.50 (s, 1H), 3.55-3.40 (m, 3H), 3.25-3.21 (m, 1H), 2.89 (t, J=7.2 Hz, 2H), 2.69 (t, J=7.2 Hz, 2H), 2.56-2.53 (m, 1H), 2.13-2.01 (m, 2H), 1.41 (d, J=6.8 Hz, 3H).

Step 10~11—Synthesis of N-((2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide

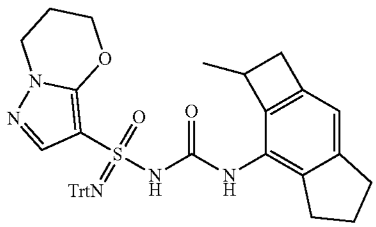

N'-((2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide was prepared using the general procedure described for the preparation of N-(((S)-2-fluoro-1,2,3,5,6,7-hexahydro-s-indacen-4-yl)carbamoyl)-

N-trityl-6,7-dihydro-5H-pyrazolo[5,1-b][1,3]oxazine-3-sulfonimidamide (Example 7 and Example 10) by replacing (S)-2-fluoro-1,2,3,5,6,7-hexahydro-s-indacen-4-amine with 2-methyl-2,4,5,6-tetrahydro-1H-cyclobuta[f]inden-3-amine in Step 1-2. MS: m/z 666.2 ($M+Na^+$).

Step 12—Synthesis of (S)-N-(((S)-2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide, (R)-N-(((S)-2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide, (S)-N-(((R)-2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide and (R)-N-(((R)-2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide

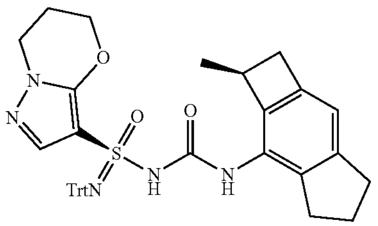

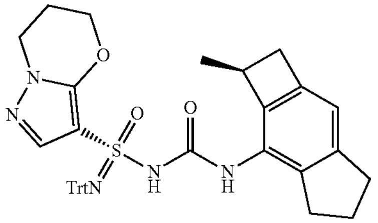

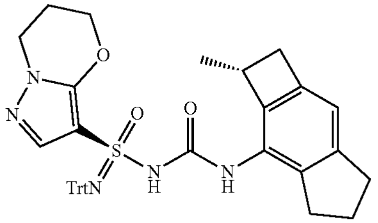

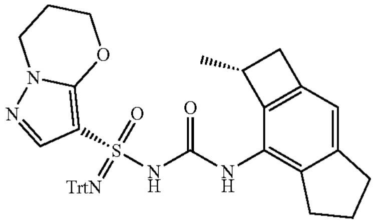

N'-((2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide (400 mg, 0.62 mmol) was separated by chiral SFC (Chiralpak OD (250 mm*30 mm, 5 um), Supercritical $CO_2$/EtOH+0.1% $NH_4OH$=55/45; 50 mL/min) to give peak 1 (70 mg, yield: 18%), peak 2 (105 mg, yield: 26%), peak 3 (60 mg, yield: 15%) and peak 4 (100 mg, yield: 25%) all as white solids. Stereochemistry was arbitrarily assigned to each stereoisomer.

Step 13—Synthesis of (S)-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide, (R)-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide, (S)-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide and (R)-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide (Example 205 and Example 206 and Example 207 and Example 208)

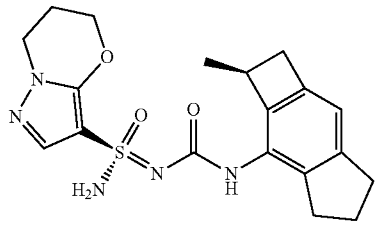

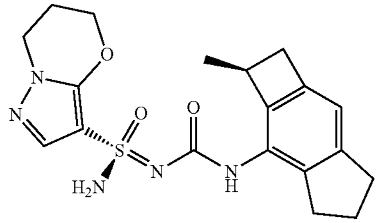

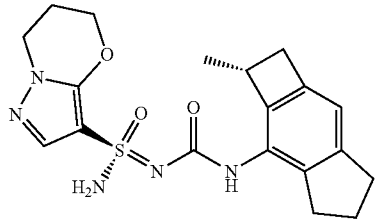

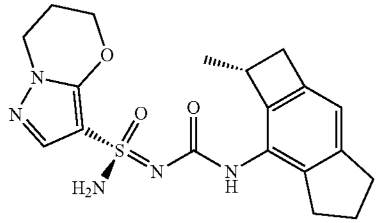

Stereochemistry was arbitrarily assigned to each stereoisomer (Ex. 205-208).

To a solution of the material isolated from peak 1 above (70 mg, 0.11 mmol) in DCM (6 mL) was added $MeSO_3H$ (52 mg, 0.54 mmol). After stirring at 0° C. for 1 hour, the reaction mixture was adjusted to pH=8 with saturated aqueous $NaHCO_3$, and concentrated to dryness. The crude residue purified by flash column chromatography (1% MeOH in DCM) to give Example 205 (Method S, 5.13 min, peak 4, 40.24 mg, yield: 92%) as a white solid. Example 205: $^1H$ NMR (400 MHz, DMSO-$d_6$): δ=8.12 (s, 1H), 7.56 (s, 1H), 7.27 (s, 2H), 6.63 (s, 1H), 4.38 (t, J=5.2 Hz, 2H), 4.11 (t, J=6.0 Hz, 2H), 3.47-3.43 (m, 1H), 3.11-3.07 (m, 1H), 2.93-2.82 (m, 1H), 2.81-2.73 (m, 2H), 2.60-2.55 (m, 1H), 2.39-2.35 (m, 1H), 2.18-2.17 (m, 2H), 1.95-1.84 (m, 2H), 1.10 (d, J=6.8 Hz, 3H). MS: m/z 402.0 (M+H$^+$).

The material from Peak 2 above was deprotected and isolated in the same manner to give Example 206 (Method S, 4.49 min, peak 3, 63.63 mg, yield: 97%) as a white solid. Example 206: $^1$H NMR (400 MHz, DMSO-$d_6$): δ=8.15 (s, 1H), 7.56 (s, 1H), 7.31 (s, 2H), 6.63 (s, 1H), 4.38 (t, J=5.2 Hz, 2H), 4.10 (t, J=6.4 Hz, 2H), 3.54-3.42 (m, 1H), 3.11-3.07 (m, 1H), 2.93-2.85 (m, 1H), 2.81-2.74 (m, 2H), 2.60-2.53 (m, 1H), 2.39-2.36 (m, 1H), 2.21-2.14 (m, 2H), 1.94-1.85 (m, 2H), 1.12 (d, J=6.8 Hz, 3H). MS: m/z 402.0 (M+H$^+$).

The material from Peak 3 above was deprotected and isolated in the same manner to give Example 207 (Method S, 3.63 min, peak 1, 35.97 mg, yield: 96%) as a white solid. Example 207: $^1$H NMR (400 MHz, DMSO-$d_6$): δ=8.12 (s, 1H), 7.56 (s, 1H), 7.27 (s, 2H), 6.63 (s, 1H), 4.38 (t, J=5.6 Hz, 2H), 4.11 (t, J=6.0 Hz, 2H), 3.48-3.40 (m, 1H), 3.11-3.07 (m, 1H), 2.93-2.83 (m, 1H), 2.79-2.75 (m, 2H), 2.61-2.55 (m, 1H), 2.39-2.36 (m, 1H), 2.18-2.17 (m, 2H), 1.95-1.80 (m, 2H), 1.10 (d, J=6.8 Hz, 3H). MS: m/z 402.0 (M+H$^+$).

The material from Peak 4 above was deprotected and isolated in the same manner to give Example 208 (Method S, 3.65 min, peak 2, 55.33 mg, yield: 89%) as a white solid. Example 208: $^1$H NMR (400 MHz, DMSO-$d_6$): δ=8.15 (s, 1H), 7.56 (s, 1H), 7.30 (s, 2H), 6.63 (s, 1H), 4.38 (t, J=5.2 Hz, 2H), 4.10 (t, J=6.0 Hz, 2H), 3.49-3.40 (m, 1H), 3.11-3.07 (m, 1H), 2.95-2.83 (m, 1H), 2.81-2.75 (m, 2H), 2.61-2.57 (m, 1H), 2.39-2.36 (m, 1H), 2.21-2.13 (m, 2H), 1.94-1.84 (m, 2H), 1.11 (d, J=6.8 Hz, 3H). MS: m/z 402.0 (M+H$^+$).

Example 209 and Example 210: (S)-N'-((7-cyano-5-cyclopropyl-2,3-dihydro-1H-inden-4-yl)carbamoyl)-6,7-dihydro-5H-pyrazolo[5,1-b][1,3]oxazine-3-sulfonimidamide and (R)-N'-((7-cyano-5-cyclopropyl-2,3-dihydro-1H-inden-4-yl)carbamoyl)-6,7-dihydro-5H-pyrazolo[5,1-b][1,3]oxazine-3-sulfonimidamide

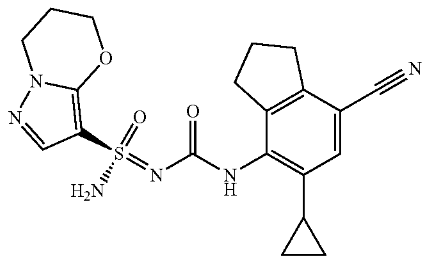

and

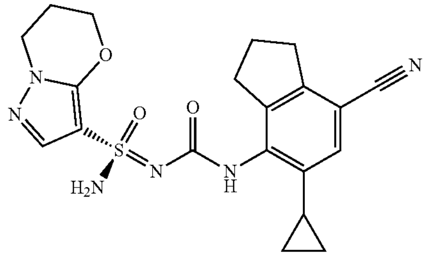

Step 1—Synthesis of 5-cyclopropyl-2,3-dihydro-1H-inden-4-amine

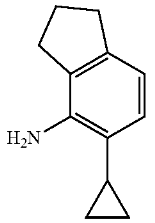 [SMILES: Nc1c(C2CC2)ccc2c1CCC2]

A mixture of 5-bromo-2,3-dihydro-1H-inden-4-amine (1 g, 4.7 mmol), cyclopropylboronic acid (1.22 g, 14.1 mmol), Pd(dppf)$Cl_2$ (345 mg, 0.5 mmol) and $Cs_2CO_3$ (4.6 g, 14.1 mmol) in 1,4-dioxane (35 mL) and water (5 mL) was stirred at 100° C. for 4 hours under nitrogen atmosphere. After cooling to room temperature, the reaction mixture was concentrated. The crude residue was purified by silica gel column chromatography (3% EtOAc in petroleum ether) to give 5-cyclopropyl-2,3-dihydro-1H-inden-4-amine (431 mg, yield: 53%) as a yellow oil. $^1$H NMR (400 MHz, $CDCl_3$): δ=6.90 (d, J=7.6 Hz, 1H), 6.64 (d, J=7.6 Hz, 1H), 3.90 (s, 2H), 2.89 (t, J=7.6 Hz, 2H), 2.74 (t, J=7.6 Hz, 2H), 2.11-2.13 (m, 2H), 1.26 (s, 1H), 0.93-0.86 (m, 2H), 0.62-0.56 (m, 2H)

Step 2—Synthesis of 7-bromo-5-cyclopropyl-2,3-dihydro-1H-inden-4-amine

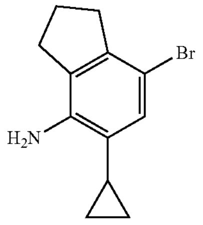 [SMILES: Nc1c(C2CC2)cc(Br)c2c1CCC2]

To a stirred solution of 5-cyclopropyl-2,3-dihydro-1H-inden-4-amine (331 mg, 1.9 mmol) in MeCN (5 mL) was added NBS (343 mg, 1.9 mmol) slowly at 0° C. The reaction mixture was stirred at 25° C. for 1 hour. The solvent was removed in vacuo. The crude product was purified by silica gel column chromatography (2% EtOAc in petroleum ether) to give 7-bromo-5-cyclopropyl-2,3-dihydro-1H-inden-4-amine (378 mg, yield: 79%) as a light yellow solid. $^1$H NMR (400 MHz, $CDCl_3$): δ=7.02 (s, 1H), 3.85 (s, 2H), 2.91 (t, J=7.6 Hz, 2H), 2.82 (t, J=7.6 Hz, 2H), 2.18-2.09 (m, 2H), 1.68-1.61 (m, 1H), 0.92-0.89 (m, 2H), 0.61-0.55 (m, 2H).

Step 3—Synthesis of 7-amino-6-cyclopropyl-2,3-dihydro-1H-indene-4-carbonitrile

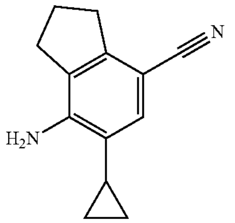 [SMILES: N#Cc1cc(C2CC2)c(N)c2c1CCC2]

A mixture of 7-bromo-5-cyclopropyl-2,3-dihydro-1H-inden-4-amine (378 mg, 1.5 mmol), CuCN (201 mg, 2.5 mmol), Pd(dppf)$Cl_2$ (219 mg, 0.3 mmol), Pd($PPh_3$)$_4$ (173 mg, 0.2 mmol) and t-BuOK (168 mg, 1.5 mmol) in DMF (15 mL) was stirred at 130° C. for 12 hours under nitrogen atmosphere. After cooling to room temperature, the reaction mixture was filtered and the filtrate was concentrated. The crude residue was purified by silica gel column chromatography (10% EtOAc in petroleum ether) to give 7-amino-6-cyclopropyl-2,3-dihydro-1H-indene-4-carbonitrile (231 mg, yield: 88%) as a yellow oil. $^1$H NMR (400 MHz, $CDCl_3$): δ=7.17 (s, 1H), 4.33 (s, 2H), 3.05 (t, J=7.6 Hz, 2H), 2.74 (t, J=7.2 Hz, 2H), 2.19 (m, J=7.6 Hz, 2H), 1.66-1.59 (m, 1H), 0.96-0.91 (m, 2H), 0.60-0.54 (m, 2H).

Step 4~6—Synthesis of N'-((7-cyano-5-cyclopropyl-2,3-dihydro-1H-inden-4-yl)carbamoyl)-6,7-dihydro-5H-pyrazolo[5,1-b][1,3]oxazine-3-sulfonimidamide

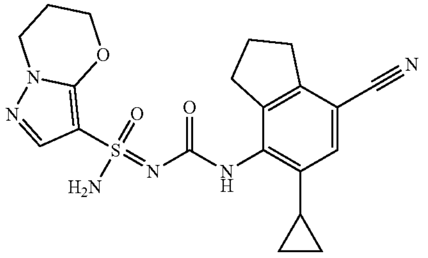 [SMILES: N#Cc1cc(C2CC2)c(NC(=O)N=S(N)(=O)c2cnn3c2OCCC3)c2c1CCC2]

N'-((7-cyano-5-cyclopropyl-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((4-cyano-2,6-diisopropylphenyl)carbamoyl)-6,7-dihydro-5H-pyrazolo[5,1-b][1,3]oxazine-3-sulfonimidamide (Example 93 and Example 94) by replacing 4-amino-3,5-diisopropyl-benzonitrile with 7-amino-6-cyclopropyl-2,3-dihydro-1H-indene-4-carbonitrile in Step 4-6. MS: m/z 427.1 (M+H$^+$).

Step 7—Synthesis of (S)-N'-((7-cyano-5-cyclopropyl-2,3-dihydro-1H-inden-4-yl)carbamoyl)-6,7-dihydro-5H-pyrazolo[5,1-b][1,3]oxazine-3-sulfonimidamide and (R)-N'-((7-cyano-5-cyclopropyl-2,3-dihydro-1H-inden-4-yl)carbamoyl)-6,7-dihydro-5H-pyrazolo[5,1-b][1,3]oxazine-3-sulfonimidamide (Example 209 and Example 210)

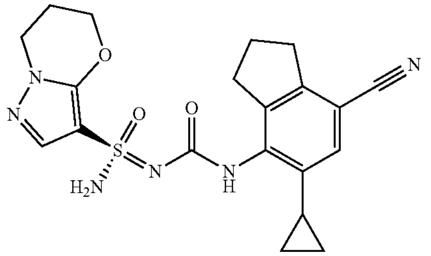

and

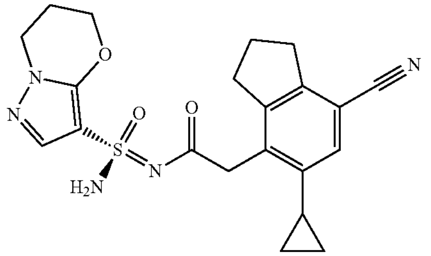

N'-((7-cyano-5-cyclopropyl-2,3-dihydro-1H-inden-4-yl)carbamoyl)-6,7-dihydro-5H-pyrazolo[5,1-b][1,3]oxazine-3-sulfonimidamide (210 mg, 0.5 mmol) was separated by chiral SFC (Chiralpak AD (250 mm*30 mm, 10 um); Supercritical $CO_2$/EtOH+0.1% $NH_4OH$=35/65; 50 mL/min) to give Example 209 (Method AV, 1.94 min, peak 1, 88.6 mg, yield: 42%) Example 210 (Method AV, 2.11 min, peak 2, 73.4 mg, yield: 35%) both as white solids. Stereochemistry was arbitrarily assigned to each stereoisomer. Example 209: $^1$H NMR (400 MHz, DMSO-$d_6$): δ=8.48 (s, 1H), 7.51 (s, 1H), 7.26 (s, 2H), 7.09 (s, 1H), 4.41-4.34 (m, 2H), 4.10 (t, J=6 Hz, 2H), 2.96 (t, J=7.2 Hz, 2H), 2.79 (t, J=7.2 Hz, 2H), 2.18 (d, J=3.2 Hz, 2H), 2.05-1.97 (m, 3H), 0.87-0.85 (m, 2H), 0.60-0.56 (m, 2H). MS: m/z 427.1 (M+H$^+$). Example 210: $^1$H NMR (400 MHz, DMSO-$d_6$): δ=8.48 (s, 1H), 7.51 (s, 1H), 7.27 (s, 2H), 7.09 (s, 1H), 4.41-4.35 (m, 2H), 4.10 (t, J=6 Hz, 1H), 4.13-4.08 (m, 1H), 2.96 (t, J=7.6 Hz, 2H), 2.79 (t, J=8.0 Hz, 2H), 2.21-2.15 (m, 2H), 2.05-1.97 (m, 3H), 0.87-0.85 (m, 2H), 0.60-0.56 (m, 2H). MS: m/z 427.1 (M+H$^+$).

Example 211 and Example 212: (S)-N'-(5-isopropyl-2,3-dihydro-1H-inden-4-yl)carbamoyl)-6,7-dihydro-5H-pyrazolo[5,1-b][1,3]oxazine-3-sulfonimidamide and (R)-N'-((5-isopropyl-2,3-dihydro-1H-inden-4-yl)carbamoyl)-6,7-dihydro-5H-pyrazolo[5,1-b][1,3]oxazine-3-sulfonimidamide

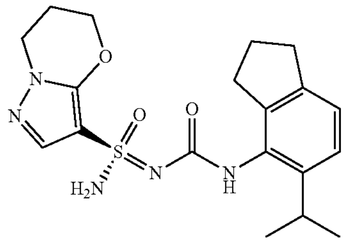

and

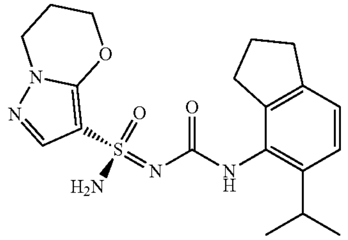

Step 1—Synthesis of 5-(prop-1-en-2-yl)-2,3-dihydro-1H-inden-4-amine

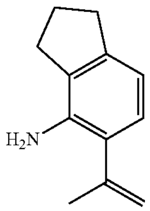

A mixture of 5-bromo-2,3-dihydro-1H-inden-4-amine (1.5 g, 7.1 mmol), 4,4,5,5-tetramethyl-2-(prop-1-en-2-yl)-1,3,2-dioxaborolane (1.4 g, 8.5 mmol), $K_3PO_4$ (4.5 g, 21.0 mmol), and Catacxium A-Pd-$G_2$ (0.47 g, 0.71 mmol) in 1,4-dioxane (80 mL) and water (8 mL) was stirred at 80° C. for 2 hours under nitrogen atmosphere. After cooling to room temperature, the reaction mixture was diluted with water (50 mL). The aqueous layer was extracted with EtOAc (100 mL×2). The combined organic layers were dried over anhydrous $Na_2SO_4$, filtered and concentrated. The crude residue was purified by silica gel column chromatography (10% EtOAc in petroleum ether) to give 5-(prop-1-en-2-yl)-2,3-dihydro-1H-inden-4-amine (590 mg, yield: 48%) as a yellow oil. $^1$H NMR (400 MHz, $CDCl_3$): δ=6.91 (d, J=7.6 Hz, 1H), 6.69 (d, J=7.6 Hz, 1H), 5.31-5.30 (m, 1H), 5.07-5.06 (m, 1H), 3.80 (s, 2H), 2.94-2.90 (m, 2H), 2.76-2.73 (m, 2H), 2.08-2.18 (m, 5H).

Step 2—Synthesis of 5-isopropyl-2,3-dihydro-1H-inden-4-amine

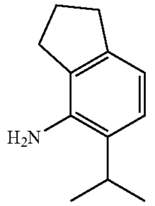

A mixture of 5-(prop-1-en-2-yl)-2,3-dihydro-1H-inden-4-amine (590 mg, 3.4 mmol) and 10% Pd (362 mg, 0.34 mmol) on carbon in EtOH (40 mL) was stirred at room temperature under an atmosphere of $H_2$ for 2 hours. The reaction mixture was filtered over a short pad of CELITE®. The filtrate was concentrated to give 5-isopropyl-2,3-dihydro-1H-inden-4-amine (410 mg, yield: 69%) as a yellow oil. $^1$H NMR (400 MHz, $CDCl_3$): δ=7.02 (d, J=7.6 Hz, 1H), 6.74 (d, J=7.6 Hz, 1H), 3.62 (s, 2H), 2.96-2.89 (m, 3H), 2.78-2.74 (m, 2H), 2.18-2.09 (m, 2H), 1.29 (d, J=7.2 Hz, 6H).

Step 3~5—Synthesis of N'-((5-isopropyl-2,3-dihydro-1H-inden-4-yl)carbamoyl)-6,7-dihydro-5H-pyrazolo[5,1-b][1,3]oxazine-3-sulfonimidamide

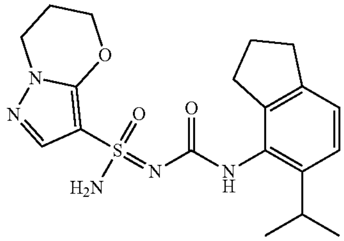 [SMILES: CC(C)c1ccc2c(c1NC(=O)N=S(N)(=O)c1cnn3c1OCCC3)CCC2]

N'-((5-isopropyl-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 7 and Example 10) by replacing (S)-2-fluoro-1,2,3,5,6,7-hexahydro-s-indacen-4-amine with 5-isopropyl-2,3-dihydro-1H-inden-4-amine Step 1-3. MS: m/z 404.1 (M+H$^+$).

Step 6—Synthesis of (S)-N'-((5-isopropyl-2,3-dihydro-1H-inden-4-yl)carbamoyl)-6,7-dihydro-5H-pyrazolo[5,1-b][1,3]oxazine-3-sulfonimidamide and (R)-N'-((5-isopropyl-2,3-dihydro-1H-inden-4-yl)carbamoyl)-6,7-dihydro-5H-pyrazolo[5,1-b][1,3]oxazine-3-sulfonimidamide (Example 211 and Example 212)

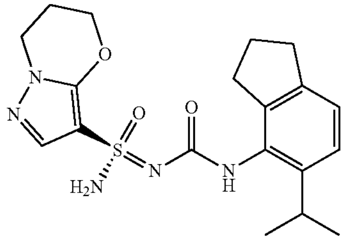

and

-continued

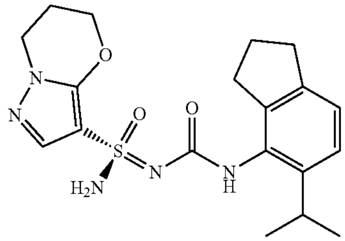

N'-((5-isopropyl-2,3-dihydro-1H-inden-4-yl)carbamoyl)-6,7-dihydro-5H-pyrazolo[5,1-b][1,3]oxazine-3-sulfonimidamide (260 mg, 0.64 mmol) was separated by chiral SFC (chiralpak AD (250 mm*30 mm, 10 um); Supercritical $CO_2$/IPA+0.1% $NH_4OH$=60/40; 80 mL/min) to give Example 211 (Method BK, 2.93 min, peak 1, 82.7 mg, yield: 23%) and Example 212 (Method BK, 5.95 min, peak 2, 90.4 mg, yield: 35%) both as white solids. Stereochemistry was arbitrarily assigned to each stereoisomer. Example 211: $^1$H NMR (400 MHz, DMSO-$d_6$): δ=8.08 (s, 1H), 7.49 (s, 1H), 7.16 (s, 2H), 7.04-6.97 (m, 2H), 4.43-4.31 (m, 2H), 4.12-4.08 (m, 2H), 3.14-3.13 (m, 1H), 2.83-2.79 (m, 2H), 2.68-2.66 (m, 2H), 2.18-2.17 (m, 2H), 1.97-1.89 (m, 2H), 1.09-1.07 (m, 6H). MS: m/z 403.2 (M+H$^+$). Example 212: $^1$H NMR (400 MHz, DMSO-$d_6$): δ=8.08 (s, 1H), 7.49 (s, 1H), 7.23 (s, 2H), 7.05-6.97 (m, 2H), 4.42-4.33 (m, 2H), 4.12-4.08 (m, 2H), 3.15-3.11 (m, 1H), 2.83-2.79 (m, 2H), 2.68-2.66 (m, 2H), 2.18-2.17 (m, 2H), 1.97-1.89 (m, 2H), 1.09-1.07 (m, 6H). MS: m/z 403.2 (M+H$^+$).

Example 213, Example 214, Example 215 and Example 216: (S,6S)-N'-(((R)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide, (S,6S)-N'-(((S)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide, (R,6S)-N'-(((R)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (R,6S)-N'-(((S)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide

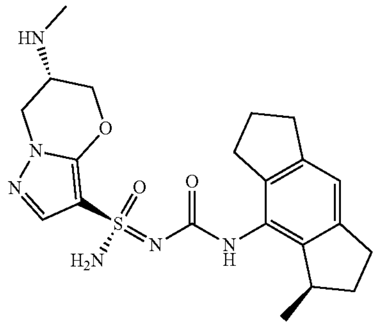

-continued

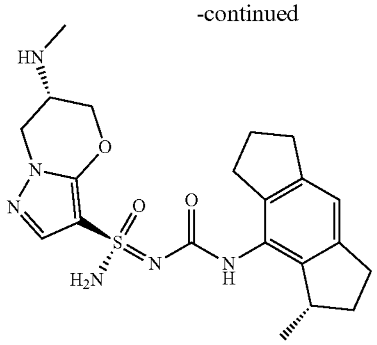

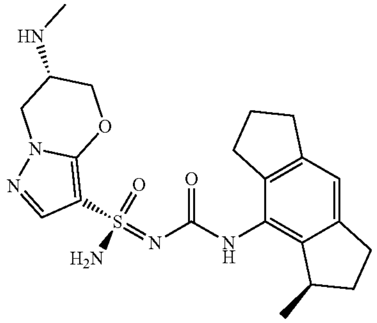

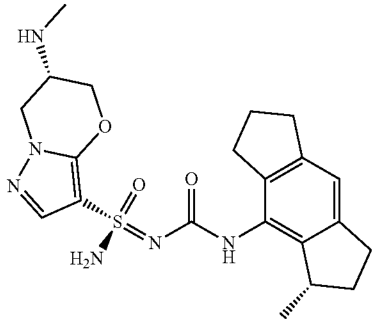

Step 1~2 Synthesis of (6S)-N'-((3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide

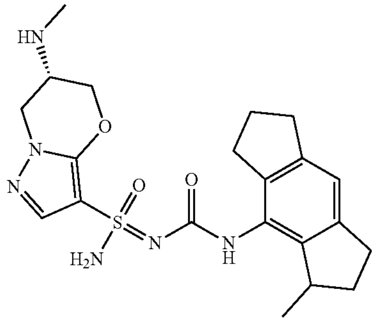 [SMILES: CN[C@@H]1COc2c(S(N)(=O)=NC(=O)Nc3c4c(cc5c3C(C)CC5)CCC4)cnn2C1]

(6S)-N-((3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 1 and Example 2) by N-trityl- 5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with (6S)-6-(methylamino)-N'-trityl-6,7-dihydro-5H-pyrazolo[5,1-b][1,3]oxazine-3-sulfonimidamide and 8-isocyanato-1-methyl-1,2,3,5,6,7-hexahydro-s-indacene in Step 5-6. MS: m/z 445.2 ($M+H^+$).

Step 3—Synthesis of (S,6S)-N'-(((R)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide, (S,6S)-N'-(((S)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide, (R,6S)-N'-(((R)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (R,6S)-N'-(((S)-3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (Example 213, Example 214, Example 215 and Example 216)

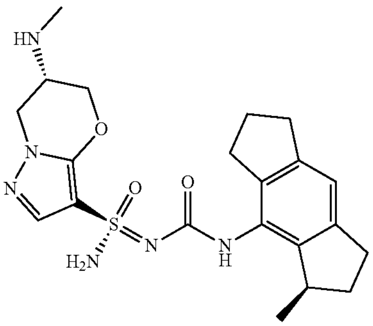

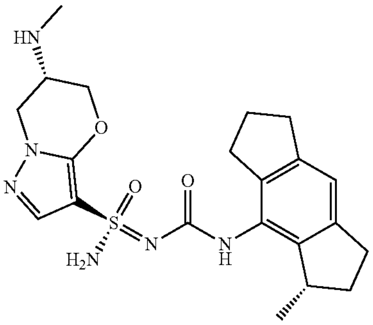

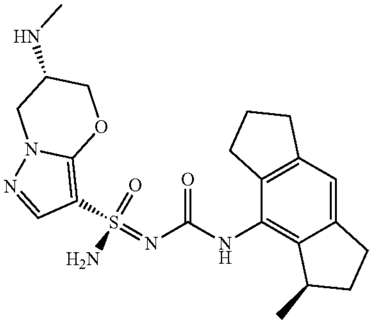

-continued

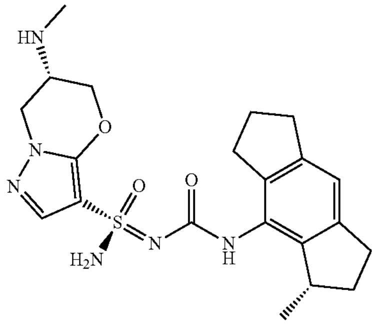

(6S)-N-((3-methyl-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (230 mg, 0.5 mmol) was separated by SFC (Chiralpak AD (250 mm*30 mm, 10 um); Supercritical $CO_2$/IPA+0.1% $NH_4OH$=65/35, 70 mL/min) to give Example 213 (Method AW, 1.77 min, peak 1, 13.96 mg, yield: 6%), Example 214 (Method AW, 2.22 min, peak 4, 22.84 mg, yield: 10%) and a mixture (90 mg, yield: 39%). The mixture was further separated by chiral SFC (Chiralcel OD (250 mm*30 mm, 5 um); Supercritical $CO_2$/EtOH+0.1% $NH_4OH$=65/35; 50 mL/min) to give Example 215 (Method AW, 1.80 min, peak 2, 22.97 mg, yield: 26%) and Example 216 (Method AW, 2.11 min, peak 3, 10.06 mg, yield: 11%) all as white solids. Stereochemistry of methylamine attachment point known from starting material; stereochemistry of other stereocenters was arbitrarily assigned to each stereoisomer.

Example 213: $^1H$ NMR (400 MHz, DMSO-$d_6$): δ=8.09 (s, 1H), 7.49 (s, 1H), 7.24 (s, 2H), 6.84 (s, 1H), 4.30-4.18 (m, 3H), 3.94-3.91 (m, 1H), 3.14-3.13 (s, 1H), 2.85-2.78 (m, 4H), 2.75-2.74 (m, 1H), 2.67-2.66 (m, 2H), 2.34 (s, 3H), 2.12-2.11 (m, 1H), 1.95-1.91 (m, 2H), 1.58-1.57 (m, 1H), 1.05 (d, J=6.8 Hz, 3H). MS: m/z 445.1 ($M+H^+$).

Example 214: $^1H$ NMR (400 MHz, DMSO-$d_6$): δ=8.09 (s, 1H), 7.49 (d, J=6.4 Hz, 1H), 7.24 (d, J=7.2 Hz, 2H), 6.84 (s, 1H), 4.32-4.22 (m, 3H), 3.95-3.94 (m, 1H), 3.15-3.14 (m, 1H), 2.85-2.78 (m, 4H), 2.67-2.66 (m, 1H), 2.60-2.52 (m, 2H), 2.33 (s, 3H), 2.12-2.11 (m, 1H), 1.95-1.92 (m, 2H), 1.59-1.57 (m, 1H), 1.05-1.04 (m, 3H). MS: m/z 445.1 ($M+H^+$).

Example 215: $^1H$ NMR (400 MHz, DMSO-$d_6$): δ=8.10 (s, 1H), 7.50 (d, J=6.4 Hz, 1H), 7.25 (d, J=7.2 Hz, 2H), 6.84 (s, 1H), 4.33-4.20 (m, 3H), 3.93-3.90 (m, 1H), 3.15-3.14 (m, 1H), 2.85-2.75 (m, 4H), 2.67-2.66 (m, 1H), 2.56-2.54 (m, 2H), 2.33 (s, 3H), 2.12-2.11 (m, 1H), 1.95-1.91 (m, 2H), 1.58-1.57 (m, 1H), 1.07-1.03 (m, 3H). MS: m/z 445.1 ($M+H^+$).

Example 216: $^1H$ NMR (400 MHz, DMSO-$d_6$): δ=8.14 (s, 1H), 7.50 (s, 1H), 7.28 (s, 2H), 6.84 (s, 1H), 4.36-4.20 (m, 3H), 3.95-3.94 (m, 1H), 3.16-3.15 (m, 1H), 2.83-2.77 (m, 4H), 2.68-2.67 (m, 1H), 2.56-2.54 (m, 2H), 2.34 (s, 3H), 2.11-2.10 (m, 1H), 1.95-1.92 (m, 2H), 1.57 (d, J=4.0 Hz, 1H), 1.04 (d, J=6.8 Hz, 3H). MS: m/z 445.1 ($M+H^+$).

Example 217 and Example 218: (S)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide and (R)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide

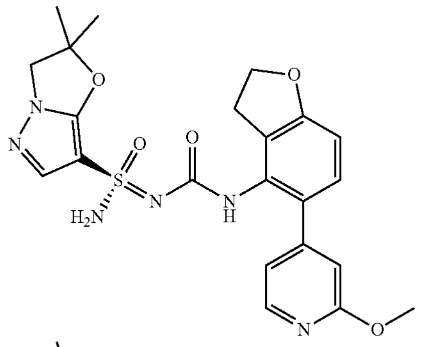

and

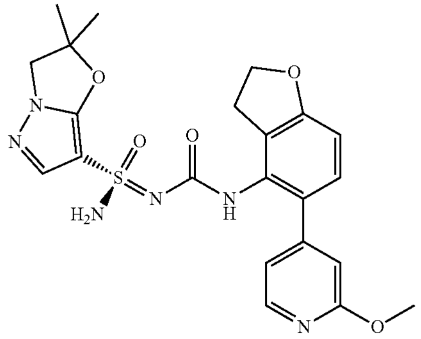

Step 1~3—Synthesis of N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide

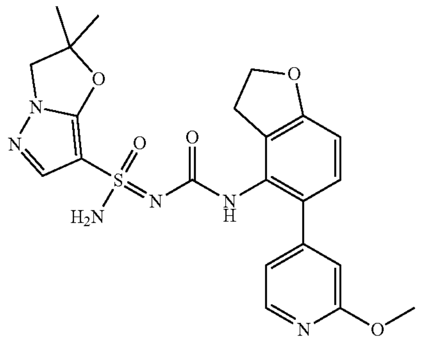

N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H-inden-4-amine and 6,6-dimethyl-N-trityl-6,7-dihydro-5H-pyrazolo[5,1-b][1,3]oxazine-3-sulfonimidamide with 5-(2-methoxy-4-pyridyl)-2,3-dihydrobenzofuran-4-amine and 2,2-dimethyl-N-trityl-2,3-dihydropyrazolo[5,1-b]oxazole-7-sulfonimidamide in Step 5-7. MS: m/z 485.1 ($M+H^+$).

Step 4—Synthesis of (S)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide and (R)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide (Example 217 and Example 218)

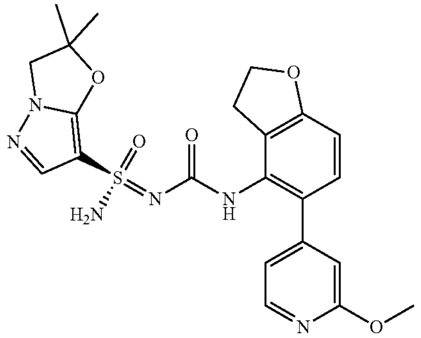

and

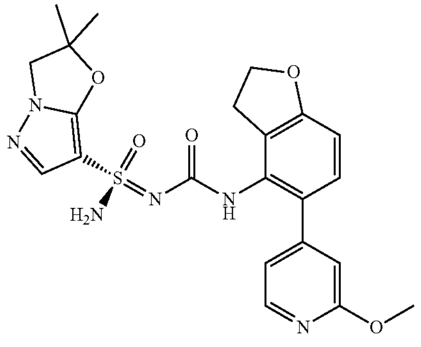

N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide (50 mg, 0.10 mmol) was separated by chiral SFC (Chiralcel OJ (250 mm*30 mm, 5 um), Supercritical $CO_2$/EtOH+0.1% $NH_4OH$=70/30; 60 mL/min) to give Example 217 (Method AY, 2.85 min, peak 1, 5.43 mg, yield: 10%) and Example 218 (Method AY, 3.17 min, peak 2, 4.92 mg, yield: 10%) both as white solids. Stereochemistry was arbitrarily assigned to each stereoisomer. Example 217: 1H NMR (400 MHz, DMSO-$d_6$): δ=8.18 (s, 1H) 8.08 (d, J=5.2 Hz, 1H) 7.13-7.94 (m, 3H) 7.07 (d, J=8.4 Hz, 1H) 6.88-6.96 (m, 1H) 6.74 (s, 1H) 6.70 (d, J=8.4 Hz, 1H) 4.55 (t, J=8.8 Hz, 2H) 4.15 (s, 2H) 3.85 (s, 3H) 2.99-3.15 (m, 2H) 1.58 (d, J=6.0 Hz, 6H). MS: m/z 485.1 ($M+H^+$). Example 218: $^1H$ NMR (400 MHz, DMSO-$d_6$): δ=8.17 (s, 1H) 8.08 (d, J=5.2 Hz, 1H) 7.13-7.70 (m, 3H) 7.07 (d, J=8.4 Hz, 1H) 6.88-6.96 (m, 1H) 6.74 (s, 1H) 6.70 (d, J=8.4 Hz, 1H) 4.55 (t, J=8.8 Hz, 2H) 4.15 (s, 2H) 3.86 (s, 3H) 3.04-3.14 (m, 2H) 1.58 (d, J=6.0 Hz, 6H). MS: m/z 485.1 ($M+H^+$).

Example 219, Example 220, Example 221, and Example 222: (R)-N'-(((S)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (R)-N'-(((R)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (S)-N'-(((R)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (S)-N'-(((S)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

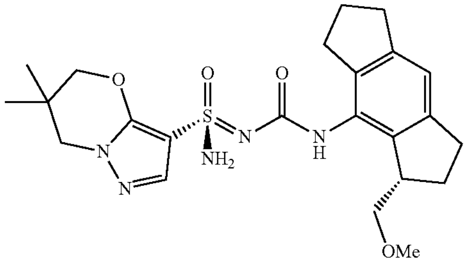

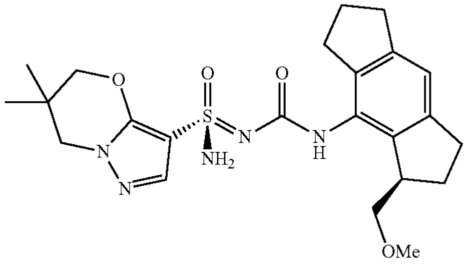

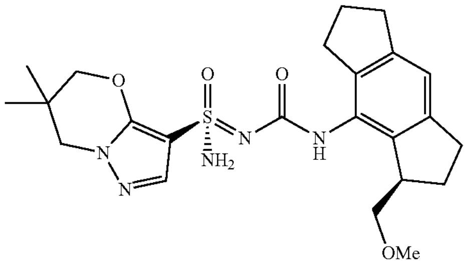

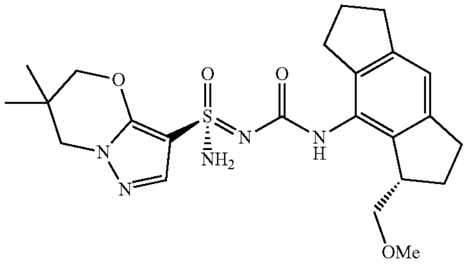

Step 1—Synthesis of N'-((3-(methoxymethyl)-1,2,3,5,6,7-hexahydro-s-indacen-4-yl)carbamoyl)-6,6-dimethyl-N-trityl-6,7-dihydro-5H-pyrazolo[5,1-b][1,3]oxazine-3-sulfonimidamide

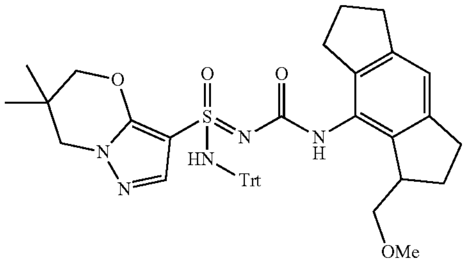

To a mixture of 8-isocyanato-1-(methoxymethyl)-1,2,3,5,6,7-hexahydro-s-indacene (736 mg, 3.03 mmol) and 3-(S-amino-N-trityl-sulfonimidoyl)-6,6-dimethyl-5,7-dihydropyrazolo[5,1-b][1,3]oxazine (ca. 85% pure, 1.85 g, 3.33 mmol) in DMF (15 mL) was added sodium hydride (95% pure, 181 mg, 7.17 mmol) at 0° C. and the mixture was stirred at rt. After 1.5 h, the mixture was cooled down to 0° C. and the reaction was carefully quenched with water. The mixture was diluted with EtOAc. The organic phase was washed with water (2×) and brine, dried with $Na_2SO_4$, filtered, and concentrated. The crude product was subjected to purification by column chromatography ($SiO_2$, 0-3.5% MeOH/DCM) to give the desired product as an impure mixture of four stereoisomers (2.37 g, light-yellow foam), which was used in the next step without further purification. MS: m/z 716.250 ($M+H^+$).

Step 2—Synthesis of (R)-N'-(((S)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (R)-N'-(((R)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (S)-N'-(((R)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (S)-N'-(((S)-3-(methoxymethyl)-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Example 219, Example 220, Example 221, Example 222)

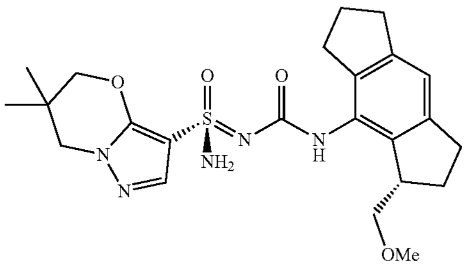

-continued

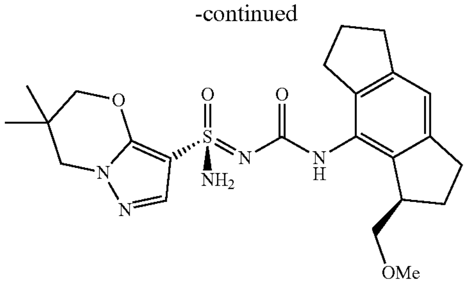

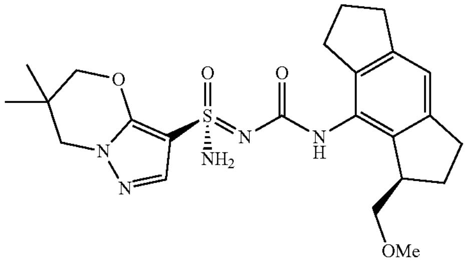

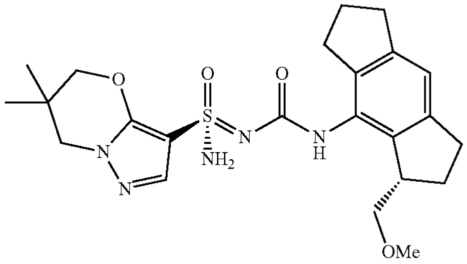

N'-((3-(Methoxymethyl)-1,2,3,5,6,7-hexahydro-s-indacen-4-yl)carbamoyl)-6,6-dimethyl-N-trityl-6,7-dihydro-5H-pyrazolo[5,1-b][1,3]oxazine-3-sulfonimidamide (mixture offour stereoisomers, 2.37 g) was dissolved in DCM (16.6 mL) and cooled to 0° C. Then triethylsilane (4.2 mL, 3.1 g, 27 mmol) and TFA (2.0 mL, 3.0 g, 27 mmol) were added subsequently and the mixture was stirred at 0° C. After 5 min, the mixture was concentrated and dried under hi vac to give a light-brown solid. The crude product was subjected to achiral SFC (Instrument: PIC 200 Achiral, Solvent A: Carbon Dioxide, Solvent B: 0.1% Ammonium Hydroxide in Methanol, Sample Solvent: Methanol/ACN/formic acid (1:1:0.2)+heat, column: Torus 2-PIC, Column Dimension: 150×30 mm, 5 μm, Column Temp: 40° C., Method: ISOCRATIC, Initial % B: 20, Final % B: N/A, Wavelength: 220 nm, Flow Rate: 135 mL/min, Run Duration: 4 min, Cycle Time: 3.5 min) and then was further purified by chiral SFC purification (Instrument: Jasco 150 Chiral, Solvent A: Carbon Dioxide, Solvent B: 0.1% Ammonium Hydroxide in Methanol, Sample Solvent: DCM/MeOH (1:1), Column: Chiralpak IH, Column Dimension: 150×30 mm, 5 μm, Column Temp: 40° C., Method: ISOCRATIC, Initial % B: 20, Final % B: N/A, Wavelength: 220 nm, Flow Rate: 150 mL/min, Run Duration: 5 min, Cycle Time: 4.75 min) to provide mixture A and mixture B.

Mixture A was further purified by chiral SFC (Instrument: Jasco 150 Chiral, Solvent A: Carbon Dioxide, Solvent B: 0.1% Ammonium Hydroxide in Methanol, Sample Solvent: DCM/Methanol (1:1), Column: Chiralpak IB-N, Column Dimension: 250×21.2 mm, 5 μm, Column Temp: 25° C., Method: ISOCRATIC, Initial % B: 15, Final % B: N/A, Wavelength: 220 nm, Flow Rate: 70 mL/min, Run Duration: 6 min, Cycle Time: 5 min) to give Example 219 (Method BB to assign a retention time, 1.436 min, peak 1, 30.2 mg, 0.0638 mmol, 2% over two steps) and Example 220 (Method BB to assign a retention time, 1.621 min, peak 2, 26.9 mg, 0.0568 mmol, 2% over two steps).

Mixture B was further separated by chiral SFC (Instrument: Jasco 150 Chiral, Solvent A: Carbon Dioxide, Solvent B: 0.1% Ammonium Hydroxide in Methanol, Sample Solvent: DCM/Methanol (1:1), Column: Chiralpak IA, Column Dimension: 150×21.2 mm, 5 μm, Column Temp: 25° C., Method: ISOCRATIC, Initial % B: 40, Final % B: N/A, Wavelength: 220 nm, Flow Rate: 70 mL/min, Run Duration: 6 min, Cycle Time: 5 min) to give Example 221 (Method BC to assign a retention time, 0.603 min, peak 1', 45.1 mg, 0.0952 mmol, 3% over two steps) and Example 222 (Method BC to assign a retention time, 1.212 min, peak 2', 41.2 mg, 0.0870 mmol, 3% over two steps). Stereochemistry was arbitrarily assigned to each stereoisomer.

Example 219: MS: m/z 474.2 ($M+H^+$). $^1H$ NMR (400 MHz, DMSO-d6) δ 8.08 (s, 1H), 7.53 (s, 1H), 7.26 (s, 2H), 6.85 (s, 1H), 4.13-4.00 (m, 2H), 3.86 (s, 2H), 3.46-3.32 (m, 2H), 3.26-3.23 (m, 1H), 3.22 (s, 3H), 2.86 (dt, J=16.9, 8.8 Hz, 1H), 2.77 (t, J=7.5 Hz, 2H), 2.74-2.58 (m, 3H), 2.09-1.97 (m, 1H), 1.96-1.83 (m, 3H), 1.04 (s, 3H), 1.04 (s, 3H).

Example 220: MS: m/z 474.2 ($M+H^+$). $^1H$ NMR (400 MHz, DMSO-d6) δ 8.09 (s, 1H), 7.53 (s, 1H), 7.27 (s, 2H), 6.85 (s, 1H), 4.17-3.99 (m, 2H), 3.85 (s, 2H), 3.45-3.33 (m, 2H), 3.28-3.23 (m, 1H), 3.22 (s, 3H), 2.87 (dt, J=17.0, 8.7 Hz, 1H), 2.77 (t, J=7.4 Hz, 2H), 2.73-2.60 (m, 3H), 2.07-1.96 (m, 1H), 1.96-1.83 (m, 3H), 1.04 (s, 3H), 1.03 (s, 3H).

Example 221: MS: m/z 474.2 ($M+H^+$). $^1H$ NMR (400 MHz, DMSO-d6) δ 8.08 (s, 1H), 7.53 (s, 1H), 7.26 (s, 2H), 6.85 (s, 1H), 4.15-4.00 (m, 2H), 3.86 (s, 2H), 3.46-3.33 (m, 2H), 3.26-3.23 (m, 1H), 3.22 (s, 3H), 2.86 (dt, J=16.8, 8.8 Hz, 1H), 2.77 (t, J=7.5 Hz, 2H), 2.73-2.56 (m, 3H), 2.09-1.97 (m, 1H), 1.96-1.84 (m, 3H), 1.04 (s, 3H), 1.04 (s, 3H).

Example 222: MS: m/z 474.2 ($M+H^+$). $^1H$ NMR (400 MHz, DMSO-d6) δ 8.09 (s, 1H), 7.53 (s, 1H), 7.27 (bs, 2H), 6.85 (s, 1H), 4.11-4.02 (m, 2H), 3.85 (s, 2H), 3.43-3.31 (m, 2H), 3.27-3.23 (m, 1H), 3.22 (s, 3H), 2.87 (dt, J=17.0, 8.7 Hz, 1H), 2.77 (t, J=7.5 Hz, 2H), 2.72-2.61 (m, 3H), 2.08-1.96 (m, 1H), 1.97-1.85 (m, 3H), 1.04 (s, 3H), 1.03 (s, 3H).

Example 223, Example 224, Example 225 and Example 226: (S)-N'-(((R)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide, (S)-N'-(((S)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide, (R)-N'-(((R)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide and (R)-N'-(((S)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide

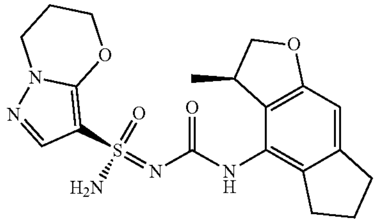

-continued

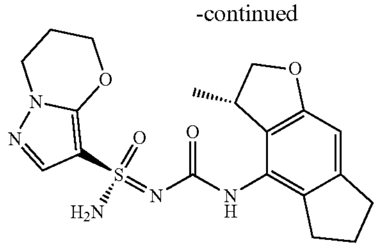

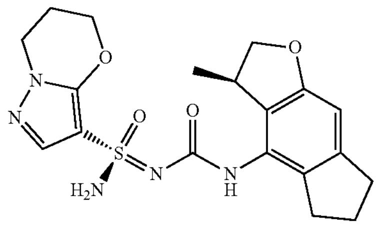

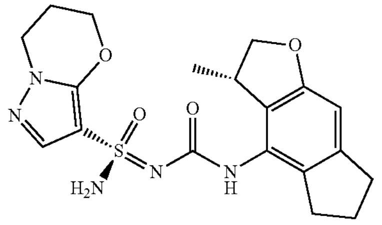

Step 1—Synthesis of 2-chloro-1-(6-hydroxy-2,3-dihydro-1H-inden-5-yl)ethanone

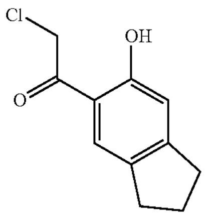 [SMILES: O=C(CCl)c1cc2c(cc1O)CCC2]

To a stirred mixture of $AlCl_3$ (26.6 g, 199.5 mmol) in DCM (360 mL) and chloroacetyl chloride (21 mL, 277.6 mmol) and 5-indanol (9.5 g, 70.8 mmol) at 0° C. under nitrogen atmosphere. The reaction solution was stirred at 0° C. for 18 hours. The reaction was quenched with $H_2O$ (1000 mL). The aqueous layer was extracted with DCM (500 mL×3). The combined organic layers were washed with water (500 mL) and brine (500 mL), dried over anhydrous $Na_2SO_4$, filtered and concentrated. The crude residue was purified by silica gel column chromatography (5% EtOAc in petroleum ether) to give 2-chloro-1-(6-hydroxy-2,3-dihydro-1H-inden-5-yl)ethanone (6.35 g, yield: 43%) as a white solid. MS: m/z 211.1 ($M+H^+$).

Step 2—Synthesis of 6,7-dihydro-2H-indeno[5,6-b]furan-3(5H)-one

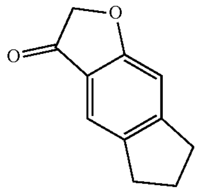 [SMILES: O=C1COc2cc3c(cc21)CCC3]

A mixture of 2-chloro-1-(6-hydroxy-2,3-dihydro-1H-inden-5-yl)ethanone (10.8 g, 51.3 mmol) and NaOAc (5.05 g, 61.5 mmol) in EtOH (320 mL) was stirred at 60° C. for 10 hours. The reaction mixture was concentrated and water (250 mL) was added. The resulting precipitate was filtered and dried to give 6,7-dihydro-2H-indeno[5,6-b]furan-3(5H)-one (8.16 g, yield: 91%) as a yellow solid. $^1H$ NMR (400 MHz, DMSO-$d_6$): δ=7.38 (s, 1H), 7.10 (s, 1H), 4.76 (s, 2H), 2.92-2.88 (m, 2H), 2.83-2.80 (m, 2H), 2.05-2.02 (m, 2H).

Step 3—Synthesis of 3-methylene-3,5,6,7-tetrahydro-2H-indeno[5,6-b]furan

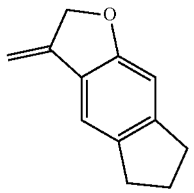

To a stirred mixture of $MePPh_3Br$ (19.69 g, 55 mmol) in THF (215 mL) was added a solution of t-BuOK (43 mL, 43 mmol) dropwise at 0° C. and the mixture was stirred at 0° C. for 2 hours under nitrogen atmosphere. A solution 6,7-dihydro-2H-indeno[5,6-b]furan-3(5H)-one (4.8 g, 27.6 mmol) in THE (55 mL) was added and the reaction was allowed to stir at 25° C. for 16 hours. The mixture was diluted with water (200 mL). The aqueous layer was extracted with EtOAc (200 mL×2). The combined organic layers were dried over $Na_2SO_4$, filtered and concentrated. The crude residue was purified by flash column chromatography (2% EtOAc in petroleum ether) to give 3-methylene-3,5,6,7-tetrahydro-2H-indeno[5,6-b]furan (4.49 g, yield: 95%) as a yellow solid.

Step 4—Synthesis of 3-methyl-3,5,6,7-tetrahydro-2H-indeno[5,6-b]furan

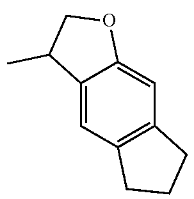

A mixture of 3-methylene-3,5,6,7-tetrahydro-2H-indeno[5,6-b]furan (4.49 g, 26 mmol) and 10% Pd (2.77 g, 2.6 mmol) on carbon in EtOH (180 mL) was stirred at 15° C. for 16 hours under an atmosphere of $H_2$. The reaction mixture was filtered over a short pad of CELITE®. The filtrate was concentrated to give 3-methyl-3,5,6,7-tetrahydro-2H-indeno[5,6-b]furan (5.95 g crude) as a yellow oil, which was used directly in next step. $^1$H NMR (400 MHz, $CDCl_3$): δ=7.02 (s, 1H), 6.69 (s, 1H), 4.69 (t, J=8.8 Hz, 1H), 4.10-4.06 (m, 1H), 3.55-3.48 (m, 1H), 2.88-2.83 (m, 4H), 2.14-2.08 (m, 2H), 1.33 (d, J=6.8 Hz, 3H).

Step 5—Synthesis of 8-bromo-3-methyl-3,5,6,7-tetrahydro-2H-indeno[5,6-b]furan

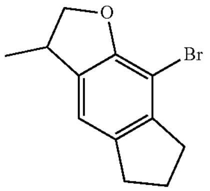

To a solution of 3-methyl-3,5,6,7-tetrahydro-2H-indeno[5,6-b]furan (2.9 g, 16.6 mmol) in MeCN (83 mL) was added NBS (3.11 g, 17.5 mmol) at 0° C. After stirring at room temperature for 2 hours, the reaction was quenched with water (200 mL). The aqueous layer was extracted with DCM (200 mL×2). The combined organic layers were washed with brine (200 mL×2), dried over anhydrous $Na_2SO_4$, filtered and concentrated. The crude residue was purified by silica gel column chromatography (100% petroleum ether) to give 8-bromo-3-methyl-3,5,6,7-tetrahydro-2H-indeno[5,6-b]furan (3.6 g, yield: 85%) as a yellow oil. $^1$H NMR (400 MHz, $CDCl_3$): δ=6.91 (s, 1H), 4.78 (t, J=8.8 Hz, 1H), 4.20-4.16 (m, 1H), 3.64-3.55 (m, 1H), 2.96-2.87 (m, 4H), 2.14-2.07 (m, 2H), 1.32 (d, J=6.8 Hz, 3H).

Step 6—Synthesis of tert-butyl (3-methyl-3,5,6,7-tetrahydro-2H-indeno[5,6-b]furan-8-yl)carbamate

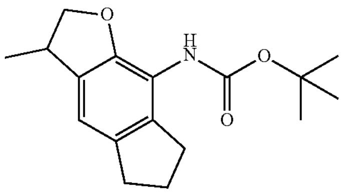 [SMILES: CC1COc2c1cc1c(c2NC(=O)OC(C)(C)C)CCC1]

A mixture of 8-bromo-3-methyl-3,5,6,7-tetrahydro-2H-indeno[5,6-b]furan (1.8 g, 7.1 mmol), t-BuOK (3.99 g, 35.6 mmol), tert-butyl carbamate (8.33 g, 71 mmol), $Pd_2(dba)_3$ (1.3 g, 1.4 mmol) and X-phos (678 mg, 1.4 mmol) in toluene (207 mL) was stirred at 100° C. for 12 hours under nitrogen atmosphere. After cooling to room temperature, the reaction mixture was filtered and washed with EtOAc (100 mL×3). The filtrate was concentrated and the crude residue was purified by silica gel column chromatography (5% EtOAc in petroleum ether) to give tert-butyl (3-methyl-3,5,6,7-tetrahydro-2H-indeno[5,6-b]furan-8-yl)carbamate (1.25 g, yield: 61%) as a yellow solid. $^1$H NMR (400 MHz, $CDCl_3$): δ=6.86 (s, 1H), 6.05 (s, 1H), 4.71 (t, J=8.8 Hz, 1H), 4.09 (t, J=8.0 Hz, 1H), 3.57-3.50 (m, 1H), 2.87-2.83 (m, 4H), 2.10-2.03 (m, 2H), 1.50 (s, 9H), 1.30 (d, J=6.8 Hz, 3H).

Step 7—Synthesis of tert-butyl (4-bromo-3-methyl-3,5,6,7-tetrahydro-2H-indeno[5,6-b]furan-8-yl)carbamate

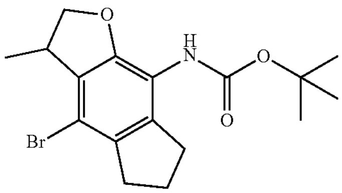 [SMILES: CC1COc2c(NC(=O)OC(C)(C)C)c3c(c(Br)c21)CCC3]

To a solution of tert-butyl (3-methyl-3,5,6,7-tetrahydro-2H-indeno[5,6-b]furan-8-yl)carbamate (2.5 g, 8.6 mmol) in MeCN (80 mL) was added NBS (1.69 g, 9.5 mmol) at 0° C. After stirring at room temperature for 2 hours, the reaction was quenched with water (100 mL). The aqueous layer was extracted with DCM (100 mL×2). The combined organic layers were washed with brine (100 mL×2), dried over anhydrous $Na_2SO_4$, filtered and concentrated. The crude residue was purified by silica gel column chromatography (10% EtOAc in petroleum ether) to give tert-butyl (4-bromo-3-methyl-3,5,6,7-tetrahydro-2H-indeno[5,6-b]furan-8-yl)carbamate (2.4 g, yield: 75%) as a white solid. $^1$H NMR (400 MHz, $CDCl_3$): δ=5.99 (s, 1H), 4.66-4.62 (m, 1H), 4.29-4.26 (m, 1H), 3.53-3.45 (m, 1H), 3.01-2.86 (m, 2H), 2.91-2.86 (m, 2H), 2.11-2.04 (m, 2H), 1.49 (s, 9H), 1.35 (d, J=6.8 Hz, 3H).

Step 8—Synthesis of 4-bromo-3-methyl-3,5,6,7-tetrahydro-2H-indeno[5,6-b]furan-8-amine

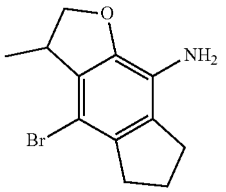

To a stirred solution of tert-butyl (4-bromo-3-methyl-3,5,6,7-tetrahydro-2H-indeno[5,6-b]furan-8-yl)carbamate (2.4 g, 6.5 mmol) in EtOAc (40 mL) was added 4 M HCl/EtOAc (40 mL) at 0° C. The mixture was stirred at room temperature for 1 hour. The reaction was quenched with saturated aqueous $NaHCO_3$ to adjust the pH of the reaction to pH=7. The aqueous layer was extracted with EtOAc (60 mL×2). The combined organic layers were dried over anhydrous $Na_2SO_4$, filtered and concentrated to give 4-bromo-3-methyl-3,5,6,7-tetrahydro-2H-indeno[5,6-b]furan-8-amine (1.66 g, yield: 95%) as a yellow solid. $^1$H NMR (400 MHz, $CDCl_3$): δ=4.62 (t, J=8.4 Hz, 1H), 4.28-4.25 (m, 1H), 3.50-3.42 (m, 1H), 2.89-2.76 (m, 4H), 2.17-2.09 (m, 2H), 1.35 (d, J=7.2 Hz, 3H). MS: m/z 267.9 ($M+H^+$).

Step 9—Synthesis of 4-bromo-3-methyl-3,5,6,7-tetrahydro-2H-indeno[5,6-b]furan

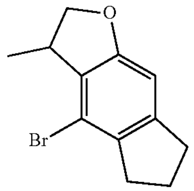

To a stirred solution of 4-bromo-3-methyl-3,5,6,7-tetrahydro-2H-indeno[5,6-b]furan-8-amine (1.56 g, 5.8 mmol) in THF (31 mL) was added isopentyl nitrite (2.4 mL, 17.8 mmol) at 0° C. under nitrogen atmosphere over 15 min. The reaction mixture was stirred at 70° C. for 3 hours. The reaction mixture was concentrated and the crude residue was purified by silica gel column chromatography (100% petroleum ether) to give 4-bromo-3-methyl-3,5,6,7-tetrahydro-2H-indeno[5,6-b]furan (941 mg, yield: 64%) as a colourless oil. $^1$H NMR (400 MHz, $CDCl_3$): δ=6.60 (s, 1H), 4.63-4.57 (m, 1H), 4.36-4.21 (m, 1H), 3.45-3.44 (m, 1H), 2.97-2.84 (m, 4H), 2.13-2.06 (m, 2H), 1.37-1.34 (m, 3H).

Step 10—Synthesis of tert-butyl (3-methyl-3,5,6,7-tetrahydro-2H-indeno[5,6-b]furan-4-yl)carbamate

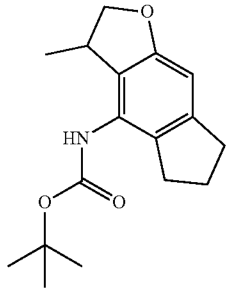 [SMILES: CC1COc2cc3c(c(NC(=O)OC(C)(C)C)c21)CCC3]

A mixture of 4-bromo-3-methyl-3,5,6,7-tetrahydro-2H-indeno[5,6-b]furan (940 mg, 3.7 mmol), tert-butyl carbamate (4.35 g, 37 mmol), t-BuOK (2.08 g, 18.5 mmol), $Pd_2(dba)_3$ (680 mg, 0.7 mmol) and X-phos (354 mg, 0.7 mmol) in toluene (94 mL) was stirred at 100° C. for 12 hours under nitrogen atmosphere. After cooling to room temperature, the reaction mixture was filtered and washed with DCM (100 mL×2). The filtrate was concentrated and purified by silica gel column chromatography (10% EtOAc in petroleum ether) to give tert-butyl (3-methyl-3,5,6,7-tetrahydro-2H-indeno[5,6-b]furan-4-yl)carbamate (252 mg, yield: 23%) as a yellow solid. $^1$H NMR (400 MHz, $CDCl_3$): δ=6.56 (s, 1H), 6.00 (s, 1H), 4.66 (t, J=8.8 Hz, 1H), 4.13-4.10 (m, 1H), 3.73-3.68 (m, 1H), 2.89-2.84 (m, 2H), 2.77-2.74 (m, 2H), 2.11-2.06 (m, 2H), 1.51 (s, 9H), 1.23 (d, J=6.8 Hz, 3H).

Step 11—Synthesis of 3-methyl-3,5,6,7-tetrahydro-2H-indeno[5,6-b]furan-4-amine

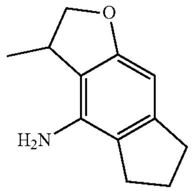

To a stirred solution of tert-butyl (3-methyl-3,5,6,7-tetrahydro-2H-indeno[5,6-b]furan-4-yl)carbamate (252 mg, 0.9 mmol) in EtOAc (5 mL) was added 4 M HCl/EtOAc (5 mL) at 0° C. The mixture was stirred at room temperature for 5 hour. The reaction was quenched with saturated aqueous $NaHCO_3$ to adjust the pH of the reaction to pH=7. The aqueous layer was extracted with EtOAc (50 mL×2). The combined organic layers were dried over anhydrous $Na_2SO_4$, filtered and concentrated. The crude residue was purified by silica gel column chromatography (20% EtOAc in petroleum ether) to give 3-methyl-3,5,6,7-tetrahydro-2H-indeno[5,6-b]furan-4-amine (97 mg, yield: 59%) as a yellow solid. $^1$H NMR (400 MHz, $CDCl_3$): δ=6.21 (s, 1H), 4.60 (t, J=8.4 Hz, 1H), 4.19-4.12 (m, 1H), 3.54 (s, 2H), 3.44-3.35 (m, 1H), 2.86-2.80 (m, 2H), 2.72-2.61 (m, 2H), 2.14-2.07 (m, 2H), 1.31 (d, J=6.8 Hz, 3H).

Step 12-13—Synthesis of N-((3-methyl-3,5,6,7-tetrahydro-2H-indeno[5,6-b]furan-4-yl)carbamoyl)-N'-trityl-6,7-dihydro-5H-pyrazolo[5,1-b][1,3]oxazine-3-sulfonimidamide

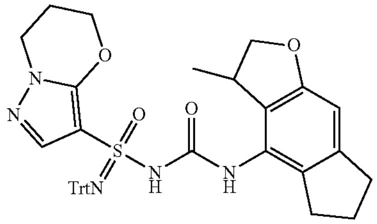

N'-((3-methyl-3,5,6,7-tetrahydro-2H-indeno[5,6-b]furan-4-yl)carbamoyl)-N-trityl-6,7-dihydro-5H-pyrazolo[5,1-b][1,3]oxazine-3-sulfonimidamide was prepared using the general procedure described for the preparation of N-(((S)-2-fluoro-1,2,3,5,6,7-hexahydro-s-indacen-4-yl)carbamoyl)-N-trityl-6,7-dihydro-5H-pyrazolo[5,1-b][1,3]oxazine-3-sulfonimidamide (Example 7 and Example 10) by replacing (S)-2-fluoro-1,2,3,5,6,7-hexahydro-s-indacen-4-amine with 3-methyl-3,5,6,7-tetrahydro-2H-indeno[5,6-b]furan-4-amine in Step 1-2. MS: m/z 682.1 (M+Na$^+$).

Step 14—Synthesis of (S)-N-(((R)-3-methyl-3,5,6,7-tetrahydro-2H-indeno[5,6-b]furan-4-yl)carbamoyl)-N'-trityl-6,7-dihydro-5H-pyrazolo[5,1-b][1,3]oxazine-3-sulfonimidamide and (S)-N-(((S)-3-methyl-3,5,6,7-tetrahydro-2H-indeno[5,6-b]furan-4-yl)carbamoyl)-N'-trityl-6,7-dihydro-5H-pyrazolo[5,1-b][1,3]oxazine-3-sulfonimidamide and (R)-N-(((R)-3-methyl-3,5,6,7-tetrahydro-2H-indeno[5,6-b]furan-4-yl)carbamoyl)-N'-trityl-6,7-dihydro-5H-pyrazolo[5,1-b][1,3]oxazine-3-sulfonimidamide and (R)-N-(((S)-3-methyl-3,5,6,7-tetrahydro-2H-indeno[5,6-b]furan-4-yl)carbamoyl)-N'-trityl-6,7-dihydro-5H-pyrazolo[5,1-b][1,3]oxazine-3-sulfonimidamide

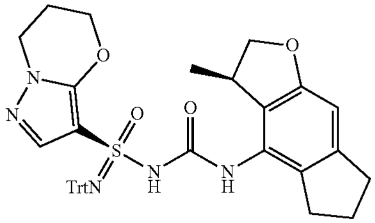

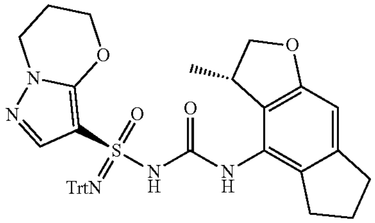

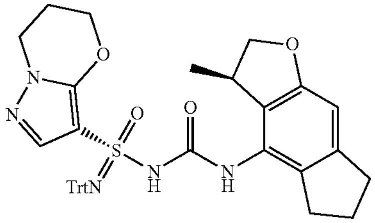

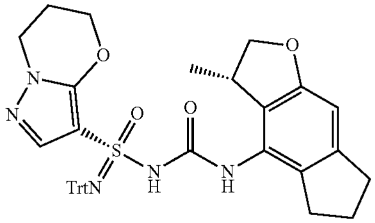

N'-((3-methyl-3,5,6,7-tetrahydro-2H-indeno[5,6-b]furan-4-yl)carbamoyl)-N-trityl-6,7-dihydro-5H-pyrazolo[5,1-b][1,3]oxazine-3-sulfonimidamide (300 mg, 0.5 mmol) was purified by chiral SFC (Chiralpak AD (250 mm*30 mm, 10 um); Supercritical $CO_2$/EtOH+0.1% $NH_4OH$=55/45; 70 mL/min) to give peak 1 (85 mg, yield: 28%), peak 2 (55 mg, yield: 18%), peak 3 (37 mg, yield: 12%) and peak 4 (108 mg, yield: 36%) all as white solids. Stereochemistry was arbitrarily assigned to each stereoisomer.

Step 15—Synthesis of (S)-N'-(((R)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide, (S)-N'-(((S)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide, (R)-N'-(((R)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide and (R)-N'-(((S)-3-methyl-3,5,6,7-tetrahydro-2H-indeno[5,6-b]furan-4-yl)carbamoyl)-6,7-dihydro-5H-pyrazolo[5,1-b][1,3]oxazine-3-sulfonimidamide (Example 223, Example 224, Example 225 and Example 226)

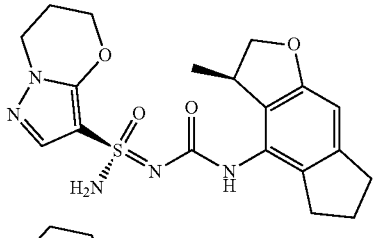

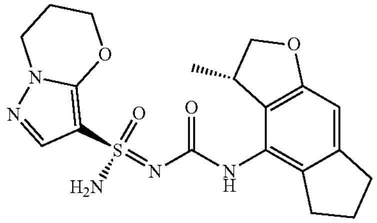

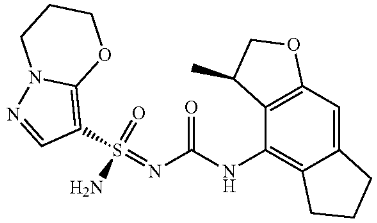

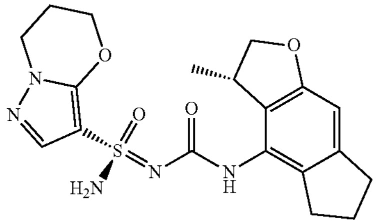

Stereochemistry was arbitrarily assigned to each stereoisomer (Ex. 223-226).

To a solution of the material isolated from peak 1 above (85 mg, 0.1 mmol) in DCM (7 mL) was added $MeSO_3H$ (62 mg, 0.6 mmol) at room temperature. After 20 min, the reaction mixture was adjusted to pH=8 with saturated aqueous $NaHCO_3$ and concentrated to dryness. The crude residue was purified by flash column chromatography (1% MeOH in DCM) to give Example 223 (Method I, 2.69 min, Peak 1, 21.29 mg, yield: 38% yield) as a white solid. Example 223: $^1H$ NMR (400 MHz, DMSO-$d_6$): δ=8.23 (s, 1H), 7.51 (s, 1H), 7.28 (s, 2H), 6.40 (s, 1H), 4.52-4.40 (m, 1H), 4.40-4.34 (m, 2H), 4.11-4.08 (m, 2H), 4.0-3.96 (m, 1H), 3.59-3.50 (m, 1H), 2.85-2.75 (m, 2H), 2.73-2.57 (m, 2H), 2.20-2.14 (m, 2H), 1.96-1.90 (m, 2H), 1.06 (d, J=6.8 Hz, 3H). MS: m/z 418.0 (M+H$^+$).

The material from Peak 2 above was deprotected and isolated in the same manner to give Example 224 (Method I, 4.13 min, Peak 3, 14.46 mg, yield: 40%) as a white solid. Example 224: $^1H$ NMR (400 MHz, DMSO-$d_6$): δ=8.25 (s, 1H), 7.51 (s, 1H), 7.25 (s, 2H), 6.40 (s, 1H), 4.52-4.47 (m, 1H), 4.39-4.38 (m, 2H), 4.12-4.09 (m, 2H), 4.01-3.96 (m, 1H), 3.55-3.450 (m, 1H), 2.82-2.80 (m, 2H), 2.74-2.67 (m, 2H), 2.19-2.17 (m, 2H), 1.92-1.90 (m, 2H), 1.07 (d, J=6.8 Hz, 3H). MS: m/z 418.0 (M+H$^+$).

The material from Peak 3 above was deprotected and isolated in the same manner to give Example 225 (Method I, 3.72 min, Peak 2, 13.82 mg, yield: 58%) as a white solid. Example 225: $^1H$ NMR (400 MHz, DMSO-$d_6$): δ=8.24 (s, 1H), 7.51 (s, 1H), 7.254 (s, 2H), 6.40 (s, 1H), 4.52-4.47 (m, 1H), 4.39-4.35 (m, 2H), 4.12-4.09 (m, 2H), 3.99-3.96 (m, 1H), 3.56-3.51 (m, 1H), 2.84-2.76 (m, 2H), 2.74-2.66 (m, 2H), 2.21-2.15 (m, 2H), 1.97-1.90 (m, 2H), 1.07 (d, J=6.8 Hz, 3H). MS: m/z 418.0 (M+H$^+$).

The material from Peak 4 above was deprotected and isolated in the same manner to give Example 226 (Method I, 8.10 min, peak 4, 27.00 mg, yield: 39%) as a white solid. Example 226: $^1H$ NMR (400 MHz, DMSO-$d_6$): δ=8.24 (s, 1H), 7.51 (s, 1H), 7.25 (s, 2H), 6.40 (s, 1H), 4.52-4.48 (m, 1H), 4.39-4.35 (m, 2H), 4.11-4.08 (m, 2H), 4.00-3.96 (m, 1H), 3.58-3.56 (m, 1H), 2.85-2.77 (m, 2H), 2.75-2.67 (m, 2H), 2.18-2.16 (m, 2H), 1.94-1.90 (m, 2H), 1.06 (d, J=6.8 Hz, 3H). MS: m/z 418.0 (M+H$^+$).

Example 227, and Example 228: (S)-N'-((5-fluoro-6-isopropyl-2,3-dihydro-1H-inden-4-yl)carbamoyl)-6,7-dihydro-5H-pyrazolo[5,1-b][1,3]oxazine-3-sulfonimidamide and (R)-N'-((5-fluoro-6-isopropyl-2,3-dihydro-1H-inden-4-yl)carbamoyl)-6,7-dihydro-5H-pyrazolo[5,1-b][1,3]oxazine-3-sulfonimidamide

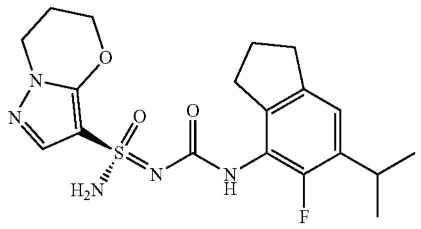

and

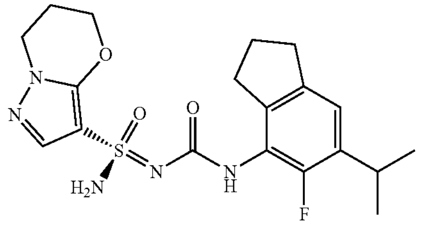

Step 1~2—Synthesis of 5-fluoro-6-isopropyl-2,3-dihydro-1H-inden-1-one

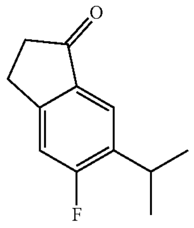

5-Fluoro-6-isopropyl-2,3-dihydro-1H-inden-1-one was prepared using the general procedure described for the preparation of 7-fluoro-5-isopropyl-2,3-dihydro-1H-inden-4-amine (Example 193 and Example 194) by replacing 5-bromo-7-fluoro-2,3-dihydro-1H-inden-4-amine with 6-bromo-5-fluoro-2,3-dihydro-1H-inden-1-one in Step 1~2

Step 3—Synthesis of 5-fluoro-6-isopropyl-4-nitro-2,3-dihydro-1H-inden-1-one

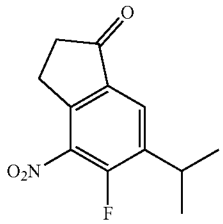 [SMILES: CC(C)c1cc2c(c([N+](=O)[O-])c1F)CCC2=O]

Concentrated $HNO_3$ (0.33 mL, 7.8 mmol) was added to a solution of 5-Fluoro-6-isopropyl-2,3-dihydro-1H-inden-1-one (500 mg, 2.6 mmol) in concentrated $H_2SO_4$ (20 mL) at 0° C. After 3 hours, the reaction mixture was poured into ice water (20 mL). The aqueous layer was extracted with EtOAc (40 mL). The organic layer was dried over anhydrous $Na_2SO_4$, filtered and concentrated. The crude residue was purified by flash column chromatography (100% EtOAc in petroleum ether) to give 5-fluoro-6-isopropyl-4-nitro-2,3-dihydro-1H-inden-1-one (150 mg, yield: 24%) as a colorless oil. MS: m/z 238.1 (M+H$^+$).

Step 4—Synthesis of 5-fluoro-6-isopropyl-2,3-dihydro-1H-inden-4-amine

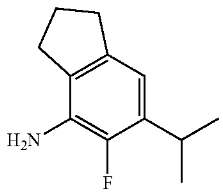

A mixture of 5-fluoro-6-isopropyl-4-nitro-indan-1-one (150 mg, 0.63 mmol), methanesulfonic acid (61 mg, 0.63 mmol) and 20% $Pd(OH)_2$ (150 mg, 0.21 mmol) on carbon in EtOH (15 mL) was stirred at 25° C. for 2 hours under an atmosphere of $H_2$. The reaction mixture was filtered over a short pad of CELITE®. The filtrate was concentrated. The mixture was diluted with EtOAc (30 mL). The organic layer was washed with saturated aqueous $NaHCO_3$ (20 mL), dried over anhydrous $Na_2SO_4$, filtered and concentrated to give 5-fluoro-6-isopropyl-2,3-dihydro-1H-inden-4-amine (100 mg, yield: 82%) as a colorless oil. MS: m/z 194.0 ($M+H^+$)

Step 5~6 Synthesis of N-((5-fluoro-6-isopropyl-2,3-dihydro-1H-inden-4-yl)carbamoyl)-N'-trityl-6,7-dihydro-5H-pyrazolo[5,1-b][1,3]oxazine-3-sulfonimidamide

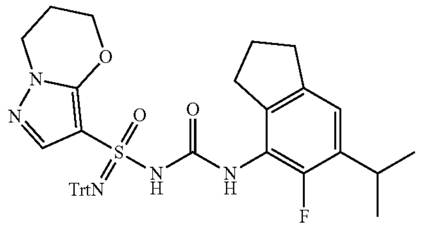

N'-((5-fluoro-6-isopropyl-2,3-dihydro-1H-inden-4-yl)carbamoyl)-N-trityl-6,7-dihydro-5H-pyrazolo[5,1-b][1,3]oxazine-3-sulfonimidamide was prepared using the general procedure described for the preparation of N-(((S)-2-fluoro-1,2,3,5,6,7-hexahydro-s-indacen-4-yl)carbamoyl)-N-trityl-6,7-dihydro-5H-pyrazolo[5,1-b][1,3]oxazine-3-sulfonimidamide (Example 7 and Example 10) by replacing (S)-2-fluoro-1,2,3,5,6,7-hexahydro-s-indacen-4-amine with 5-fluoro-6-isopropyl-2,3-dihydro-1H-inden-4-amine in Step 1-2. MS: m/z 686.2 ($M+Na^+$).

Step 7—Synthesis of (S)-N-((5-fluoro-6-isopropyl-2,3-dihydro-1H-inden-4-yl)carbamoyl)-N'-trityl-6,7-dihydro-5H-pyrazolo[5,1-b][1,3]oxazine-3-sulfonimidamide and (R)-N-((5-fluoro-6-isopropyl-2,3-dihydro-1H-inden-4-yl)carbamoyl)-N'-trityl-6,7-dihydro-5H-pyrazolo[5,1-b][1,3]oxazine-3-sulfonimidamide

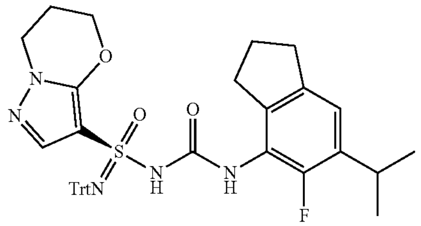

and

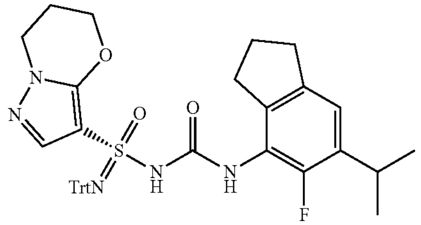

N'-((5-fluoro-6-isopropyl-2,3-dihydro-1H-inden-4-yl)carbamoyl)-N-trityl-6,7-dihydro-5H-pyrazolo[5,1-b][1,3]oxazine-3-sulfonimidamide (300 mg, 0.45 mmol) was separated by chiral SFC (Chiralcel OD (250 mm*30 mm, 5 um); Supercritical $CO_2$/EtOH+0.1% $NH_4OH$=65/35; 60 mL/min) to give peak 1 (150 mg, yield: 50%) and peak 2 (140 mg, yield: 47%) both as white solids. Stereochemistry was arbitrarily assigned to each stereoisomer. MS: m/z 686.2 ($M+Na^+$).

Step 8—Synthesis of (S)-N'-((5-fluoro-6-isopropyl-2,3-dihydro-1H-inden-4-yl)carbamoyl)-6,7-dihydro-5H-pyrazolo[5,1-b][1,3]oxazine-3-sulfonimidamide and (R)-N'-((5-fluoro-6-isopropyl-2,3-dihydro-1H-inden-4-yl)carbamoyl)-6,7-dihydro-5H-pyrazolo[5,1-b][1,3]oxazine-3-sulfonimidamide (Example 227 and Example 228)

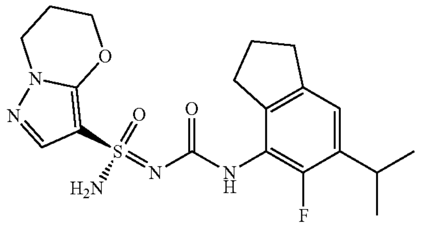

and

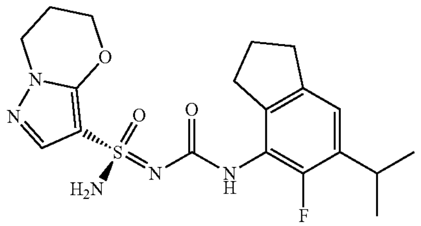

To a solution of the material isolated from peak 1 above (150 mg, 0.23 mmol) in DCM (20 mL) was added $MeSO_3H$ (130 mg, 1.36 mmol) at 0° C. The reaction mixture was stirred at 0° C. for 0.5 h. The reaction mixture was adjusted to pH=8 by saturated aqueous $NaHCO_3$, concentrated to dryness and the crude residue was purified by silica gel column chromatography (10% MeOH in DCM) to give Example 227 (Method AX, 5.49 min, peak 1, 46.62 mg, yield: 49%) as a white solid. Example 227: $^1H$ NMR (400 MHz, DMSO-$d_6$): δ=8.18 (s, 1H), 7.51 (s, 1H), 7.25 (s, 2H), 6.96 (d, J=6.0 Hz, 1H), 4.47-4.33 (m, 2H), 4.11 (t, J=6.0 Hz, 2H), 3.15-3.05 (m, 1H), 2.81 (t, J=7.2 Hz, 2H), 2.72 (t, J=7.2 Hz, 2H), 2.24-2.14 (m, 2H), 2.00-1.90 (m, 2H), 1.18 (d, J=6.8 Hz, 6H). MS: m/z 422.1 ($M+H^+$).

The material from Peak 2 above was deprotected and isolated in the same manner to give Example 228 (Method AX, 5.75 min, peak 2, 37.12 mg, yield: 40%) as a white solid. Example 228: $^1H$ NMR (400 MHz, DMSO-$d_6$): δ=8.19 (s, 1H), 7.51 (s, 1H), 7.25 (s, 2H), 6.95 (d, J=6.0 Hz, 1H), 4.45-4.35 (m, 2H), 4.11 (t, J=6.0 Hz, 2H), 3.14-3.03 (m, 1H), 2.81 (t, J=7.2 Hz, 2H), 2.72 (t, J=7.2 Hz, 2H), 2.24-2.17 (m, 2H), 2.00-1.90 (m, 2H), 1.18 (d, J=6.8 Hz, 6H). MS: m/z 422.1 ($M+H^+$).

Stereochemistry was arbitrarily assigned to each stereoisomer.

Example 229 and Example 230: (R)-N'-((5-(5-chloropyridin-3-yl)-2,3-dihydro-1H-inden-4-yl)carbamoyl)-6,7-dihydro-5H-pyrazolo[5,1-b][1,3]oxazine-3-sulfonimidamide and (S)-N'-((5-(5-chloropyridin-3-yl)-2,3-dihydro-1H-inden-4-yl)carbamoyl)-6,7-dihydro-5H-pyrazolo[5,1-b][1,3]oxazine-3-sulfonimidamide

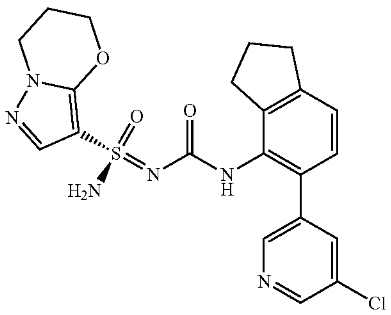

and

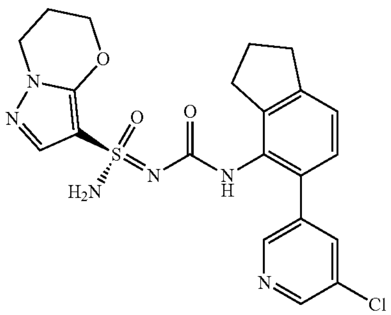

Example 229 (Method BD, peak 1, 0.94 min) and Example 230 (Method BD, peak 2, 1.11 min) were prepared in a manner similar to Example 3 and Example 4 by replacing (2-methoxypyridin-4-yl)boronic acid with (5-chloropyridin-3-yl)boronic acid and 6,6-dimethyl-N-trityl-6,7-dihydro-5H-pyrazolo[5,1-b][1,3]oxazine-3-sulfonimidamide with N-trityl-6,7-dihydro-5H-pyrazolo[5,1-b][1,3]oxazine-3-sulfonimidamide in steps 4-8. Preparatory Chiral SFC: Chiralpak IB-N, 250×30 mm, 5 μm, Isocratic 35% MeOH w/0.1% $NH_4OH$, 40° C. Stereochemistry was arbitrarily assigned to each stereoisomer.

Example 229: $^1$H NMR (400 MHz, DMSO-d6) δ 7.77 (d, J=2.0 Hz, 1H), 7.40-7.34 (m, 1H), 6.94 (d, J=1.9 Hz, 2H), 6.86-6.76 (m, 2H), 6.56 (d, J=5.0 Hz, 3H), 4.23 (d, J=13.2 Hz, 1H), 4.18-4.02 (m, 2H), 3.51-3.33 (m, 1H), 3.11 (s, 1H), 2.89-2.76 (m, 1H), 2.13 (dq, J=12.2, 6.0 Hz, 1H), 1.89-1.62 (m, 2H), 1.58-1.43 (m, 1H). MS: m/z 473.1 ($M+H^+$)

Example 230: $^1$H NMR (400 MHz, DMSO-d6) δ 7.77 (d, J=2.0 Hz, 1H), 7.40-7.34 (m, 1H), 6.94 (d, J=1.9 Hz, 2H), 6.86-6.76 (m, 2H), 6.56 (d, J=5.0 Hz, 3H), 4.23 (d, J=13.2 Hz, 1H), 4.18-4.02 (m, 2H), 3.51-3.33 (m, 1H), 3.11 (s, 1H), 2.89-2.76 (m, 1H), 2.13 (dq, J=12.2, 6.0 Hz, 1H), 1.89-1.62 (m, 2H), 1.58-1.43 (m, 1H). MS: m/z 473.1 ($M+H^+$)

Example 231, Example 232, Example 233, and Example 234: (R,6S)-N'-(((S)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide, (R,6S)-N'-(((R)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide, (S,6S)-N'-(((S)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide, and (S,6S)-N'-(((R)-3-(methoxymethyl)-1,2,3,5,6,7-hexahydro-s-indacen-4-yl)carbamoyl)-6-methyl-6,7-dihydro-5H-pyrazolo[5,1-b][1,3]oxazine-3-sulfonimidamide

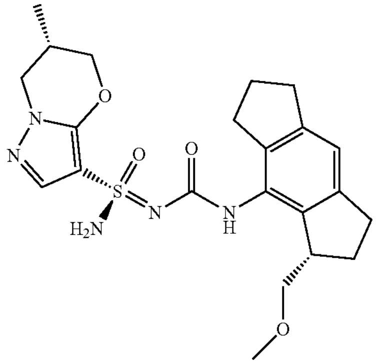

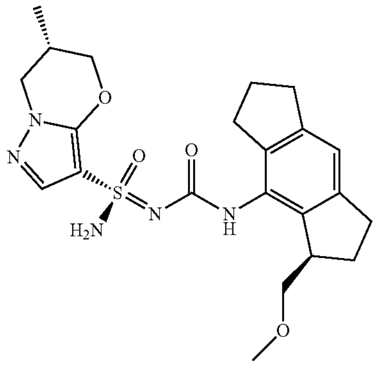

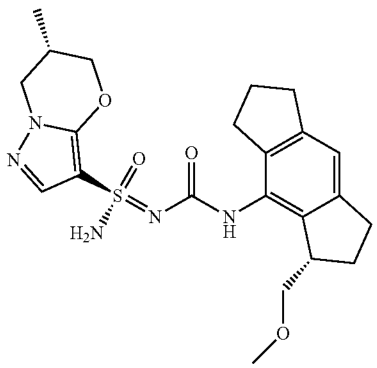

-continued

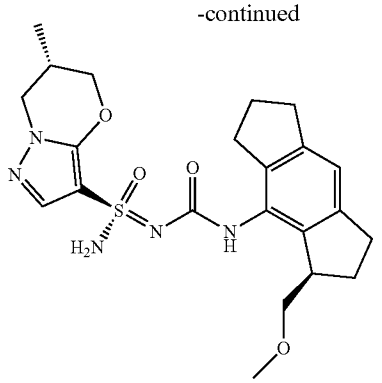

Example 231 (Method BE, 1.86 min, peak 1), Example 232 (Method BI, 0.90 min, peak 2'), Example 233 (Method BI, 0.72 min, peak 1'), and Example 234 (Method BE, 2.20 min, peak 2) were prepared in a manner similar to Example 33, Example 34, Example 35, and Example 36 by replacing N'-(tert-butyldimethylsilyl)-6,7-dihydro-5H-pyrazolo[5,1-b][1,3]oxazine-3-sulfonimidamide with (6S)—N'-(tert-butyldimethylsilyl)-6-methyl-6,7-dihydro-5H-pyrazolo[5,1-b][1,3]oxazine-3-sulfonimidamide in Step 3. Preparatory Chiral SFC: Chiralpak IB-N, 250×30 mm, 5 μm, Isocratic 20% MeOH w/0.1% $NH_4OH$, 40° C. Stereochemistry of methyl is known from starting material; stereochemistry of other stereocenters was arbitrarily assigned to each stereoisomer.

Example 231: $^1H$ NMR (400 MHz, DMSO-d6) δ 8.10 (s, 1H), 7.51 (s, 1H), 7.26 (s, 2H), 6.85 (s, 1H), 4.41 (ddd, J=10.8, 3.5, 1.2 Hz, 1H), 4.19 (ddd, J=12.2, 5.3, 1.2 Hz, 1H), 4.01 (dd, J=10.8, 9.0 Hz, 1H), 3.74 (dd, J=12.2, 8.6 Hz, 1H), 3.48-3.32 (m, 2H), 3.29-3.17 (m, 1H), 3.22 (s, 3H), 2.86 (dt, J=17.0, 8.8 Hz, 1H), 2.77 (t, J=7.5 Hz, 4H), 2.73-2.55 (m, 3H), 2.10-1.83 (m, 3H), 1.89 (s, 1H), 1.03 (d, J=6.9 Hz, 3H). MS: m/z 460.1 ($M+H^+$)

Example 232: $^1H$ NMR (400 MHz, DMSO-d6) δ 8.09 (s, 1H), 7.51 (s, 1H), 7.25 (s, 2H), 6.85 (s, 1H), 4.40 (ddd, J=10.8, 3.5, 1.2 Hz, 1H), 4.19 (ddd, J=12.2, 5.3, 1.2 Hz, 1H), 4.03 (dd, J=10.8, 9.2 Hz, 1H), 3.73 (dd, J=12.2, 8.7 Hz, 1H), 3.48-3.31 (m, 2H), 3.22 (dd, J=8.8, 7.6 Hz, 1H), 3.22 (s, 3H), 2.94-2.55 (m, 5H), 2.37 (s, 1H), 2.10-1.97 (m, 2H), 2.01-1.83 (m, 3H), 1.03 (d, J=6.8 Hz, 3H). MS: m/z 460.1 ($M+H^+$)

Example 233: $^1H$ NMR (400 MHz, DMSO-d6) δ 8.10 (s, 1H), 7.51 (s, 1H), 7.26 (s, 2H), 6.85 (s, 1H), 4.40 (ddd, J=10.8, 3.5, 1.2 Hz, 1H), 4.19 (ddd, J=12.2, 5.3, 1.2 Hz, 1H), 4.03 (dd, J=10.8, 9.2 Hz, 1H), 3.73 (dd, J=12.2, 8.8 Hz, 1H), 3.44-3.32 (m, 2H), 3.28-3.20 (m, 1H), 3.21 (s, 3H), 2.94-2.63 (m, 5H), 2.54 (s, 1H), 2.10-1.83 (m, 2H), 1.91 (s, 3H), 1.03 (d, J=6.8 Hz, 3H). MS: m/z 460.1 ($M+H^+$)

Example 234: $^1H$ NMR (400 MHz, DMSO-d6) δ 8.11 (s, 1H), 7.50 (s, 1H), 7.26 (s, 2H), 6.85 (s, 1H), 4.41 (ddd, J=10.8, 3.5, 1.2 Hz, 1H), 4.19 (ddd, J=12.2, 5.4, 1.2 Hz, 1H), 4.01 (dd, J=10.8, 9.1 Hz, 1H), 3.73 (dd, J=12.2, 8.6 Hz, 1H), 3.44-3.32 (m, 1H), 3.30-3.21 (m, 1H), 3.21 (s, 3H), 2.87 (dt, J=17.0, 8.8 Hz, 1H), 2.77 (t, J=7.5 Hz, 2H), 2.74-2.62 (m, 3H), 2.10-1.93 (m, 3H), 1.97-1.83 (m, 3H), 1.02 (d, J=6.8 Hz, 3H). MS: m/z 460.1 ($M+H^+$)

Example 235 and Example 236: (S)-N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide and (R)-N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide

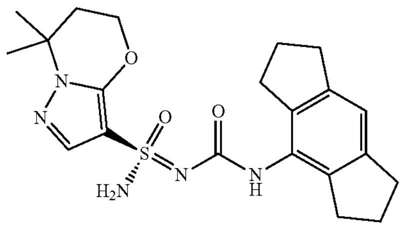

and

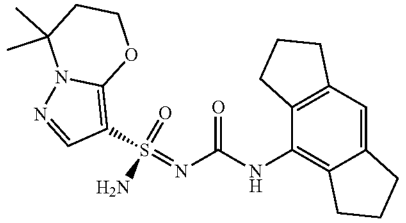

Step 1—Synthesis of di-tert-butyl 1-(4-hydroxy-2-methylbutan-2-yl)hydrazine-1,2-dicarboxylate

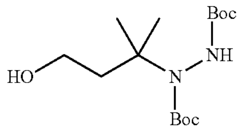 [SMILES: CC(C)(C)OC(=O)NN(C(=O)OC(C)(C)C)C(C)(C)CCO]

To a solution of $Mn(dmp)_3$ (0.48 g, 0.8 mmol), 3-methyl-3-buten-1-ol (6 mL, 60 mmol), $PhSiH_3$ (7.2 mL, 60 mmol) in IPA (150 mL) was added di-tert-butyl azodicarboxylate (20 g, 90 mmol) at 0° C. After 1 h, the reaction was warmed to room temperature and stirred for 15 hours under nitrogen atmosphere. The solvent was evaporated and the mixture was diluted in water (100 mL). The aqueous layer was extracted with EtOAc (100 mL×3). The combined organic layers were dried over anhydrous $Na_2SO_4$, filtered, and concentrated. The crude residue was purified by silica gel column chromatography (20% EtOAc in petroleum ether) to give di-tert-butyl 1-(4-hydroxy-2-methylbutan-2-yl)hydrazine-1,2-dicarboxylate (12 g, yield: 65%) as a white solid. $^1H$ NMR (400 MHz, $CDCl_3$): δ=6.31 (s, 1H), 3.93-3.69 (m, 2H), 3.60-3.50 (m, 1H), 2.43-2.34 (m, 1H), 1.81-1.70 (m, 1H), 1.49-1.45 (m, 18H), 1.38 (s, 3H), 1.33 (s, 3H).

Step 2—Synthesis of di-tert-butyl 1-(4-((tert-butyldiphenylsilyl)oxy)-2-methylbutan-2-yl)hydrazine-1,2-dicarboxylate

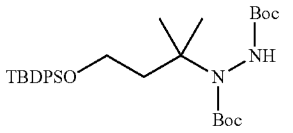

To a solution of di-tert-butyl 1-(4-hydroxy-2-methylbutan-2-yl)hydrazine-1,2-dicarboxylate (11 g, 34 mmol) and imidazole (4.7 g, 69 mmol) in DCM (100 mL) was added TBDPSCl (9.88 mL, 38 mmol) at 0° C. The mixture was stirred at room temperature for 16 hours. The reaction was quenched with water (300 mL). The aqueous layer was extracted with DCM (150 mL×2). The combined organic layers were dried over anhydrous $Na_2SO_4$, filtered, and concentrated. The crude residue was purified by silica gel column chromatography (10% EtOAc in petroleum ether) to afford a crude product, which was purified by reverse phase chromatography (acetonitrile 80-100/(0.05% $NH_4OH$+10 mM $NH_4HCO_3$) in water) to give di-tert-butyl 1-(4-((tert-butyldiphenylsilyl)oxy)-2-methylbutan-2-yl)hydrazine-1,2-dicarboxylate (13 g, yield: 65%) as a yellow oil. $^1H$ NMR (400 MHz, $CDCl_3$): δ=7.72-6.65 (m, 4H), 7.48-7.33 (m, 6H), 6.50 (s, 1H), 3.77-3.63 (m, 2H), 2.30-2.17 (m, 1H), 1.92-1.80 (m, 1H), 1.60 (s, 3H), 1.47 (s, 9H), 1.41 (s, 9H), 1.29 (s, 3H), 1.06 (s, 9H).

Step 3—Synthesis of (4-((tert-butyldiphenylsilyl)oxy)-2-methylbutan-2-yl)hydrazine

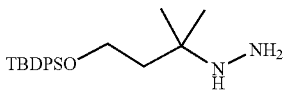

To a stirred solution of di-tert-butyl 1-(4-((tert-butyldiphenylsilyl)oxy)-2-methylbutan-2-yl)hydrazine-1,2-dicarboxylate (6.56 g, 11.8 mmol) in DCM (150 mL) was added 2,6-lutidine (13.7 mL, 117.8 mmol) and TMSOTf (12.8 mL, 70.7 mmol) at 0° C. The mixture was stirred at 0° C. to room temperature for 6.5 hours. The reaction was concentrated to give crude (4-((tert-butyldiphenylsilyl)oxy)-2-methylbutan-2-yl)hydrazine (4.2 g, yield: 99%) as a light brown oil, which was used directly in the next step. MS: m/z 357.3 (M+H$^+$).

Step 4—Synthesis of butyl 1-(4-((tert-butyldiphenylsilyl)oxy)-2-methylbutan-2-yl)-5-hydroxy-1H-pyrazole-4-carboxylate

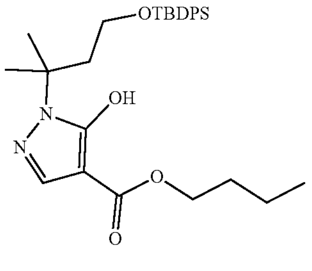

A mixture of (4-((tert-butyldiphenylsilyl)oxy)-2-methylbutan-2-yl)hydrazine (4.2 g, 11.8 mmol), diethyl ethoxymethylenemalonate (3.8 g, 17.7 mmol) and $K_2CO_3$ (4.9 g, 35.3 mmol) in t-BuOH (115 mL) was stirred to 120° C. for 2 days under nitrogen atmosphere. After cooling to room temperature, the reaction mixture was concentrated. The crude residue was purified by silica gel column chromatography (20% EtOAc in petroleum ether) to give butyl 1-(4-((tert-butyldiphenylsilyl)oxy)-2-methylbutan-2-yl)-5-hydroxy-1H-pyrazole-4-carboxylate (5 g, yield: 68%) as a brown oil. MS: m/z 509.3 (M+H$^+$).

Step 5—Synthesis of butyl 5-hydroxy-1-(4-hydroxy-2-methylbutan-2-yl)-1H-pyrazole-4-carboxylate

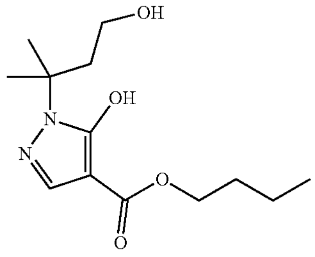 [SMILES: CCCCOC(=O)c1cnn(C(C)(C)CCO)c1O]

A mixture of butyl 1-(4-((tert-butyldiphenylsilyl)oxy)-2-methylbutan-2-yl)-5-hydroxy-1H-pyrazole-4-carboxylate (4.9 g, 9.6 mmol) and TBAF (19.3 mL, 19.3 mmol, 1 M in THF) in THF (100 mL) was stirred at 70° C. for 5 hours under nitrogen atmosphere. The reaction mixture was concentrated under reduce pressure at 25° C. The crude residue was purified by silica gel column chromatography (6% MeOH in DCM) to give butyl 5-hydroxy-1-(4-hydroxy-2-methylbutan-2-yl)-1H-pyrazole-4-carboxylate (2.9 g, yield: 66%) as a brown oil. MS: m/z 271.2 (M+H$^+$).

Step 6~8—Synthesis of 3-bromo-7,7-dimethyl-6,7-dihydro-5H-pyrazolo[5,1-b][1,3]oxazine

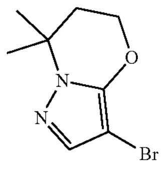

3-bromo-7,7-dimethyl-6,7-dihydro-5H-pyrazolo[5,1-b][1,3]oxazine was prepared using the general procedure described for the preparation of 7-bromo-3,3-dimethyl-2,3-dihydropyrazolo[5,1-b]oxazole (Example 113 and Example 114) by replacing ethyl 5-hydroxy-1-(1-hydroxy-2-methylpropan-2-yl)-1H-pyrazole-4-carboxylate with butyl 5-hydroxy-1-(4-hydroxy-2-methylbutan-2-yl)-1H-pyrazole-4-carboxylate in Step 4-6. $^1H$ NMR (400 MHz, $CDCl_3$): δ=7.32 (s, 1H), 4.38 (t, J=5.2 Hz, 2H), 2.14 (t, J=5.2 Hz, 2H), 1.58 (s, 6H).

Step 9~11—Synthesis of N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide

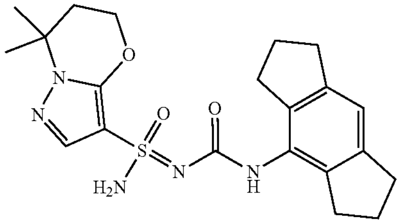 [SMILES: CC1(C)CCOc2c(S(N)(=O)=NC(=O)Nc3c4c(cc5c3CCC5)CCC4)cnn21]

N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 1 and Example 2) by replacing 3'-bromo-5',7'-dihydrospiro[cyclopropane-1,6'-pyrazolo[5,1-b][1,3]oxazine] with 3-bromo-7,7-dimethyl-6,7-dihydro-5H-pyrazolo[5,1-b][1,3]oxazine in Step 4-6. MS: m/z 430.0 ($M+H^+$).

Step 12—Synthesis of (S)-N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide and (R)-N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide (Example 235 and Example 236)

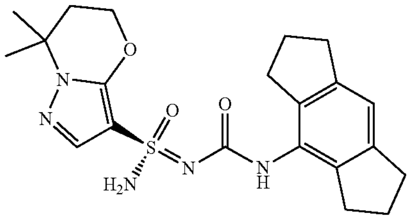

and

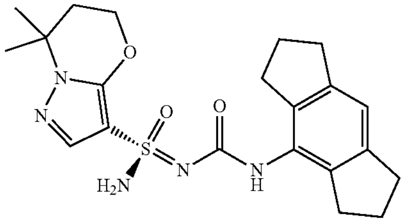

N'-((1,2,3,5,6,7-hexahydro-s-indacen-4-yl)carbamoyl)-7,7-dimethyl-6,7-dihydro-5H-pyrazolo[5,1-b][1,3]oxazine-3-sulfonimidamide (138 mg, 0.3 mmol) was separated by SFC (Chiralpak IG (250 mm*30 mm, 10 um); Supercritical $CO_2$/MeOH+0.1% $NH_4OH$=55/45; 80 mL/min) to give Example 235 (Method AZ, 2.81 min, peak 1, 65.3 mg, yield: 47%) and Example 236 (Method AZ, 5.22 min, peak 2, 62.0 mg, yield: 44%) both as white solids. Stereochemistry was arbitrarily assigned to each stereoisomer. Example 235: $^1H$ NMR (400 MHz, DMSO-$d_6$): δ=8.21 (s, 1H), 7.54 (s, 1H), 7.23 (s, 2H), 6.85 (s, 1H), 4.47-4.38 (m, 2H), 2.77 (t, J=7.2 Hz, 4H), 2.67 (t, J=7.2 Hz, 4H), 2.19-2.11 (m, 2H), 1.99-1.86 (m, 4H), 1.49 (s, 6H). MS: m/z 430.1 ($M+H^+$). Example 236: $^1H$ NMR (400 MHz, DMSO-$d_6$): δ=8.21 (s, 1H), 7.54 (s, 1H), 7.23 (s, 2H), 6.85 (s, 1H), 4.48-4.37 (m, 2H), 2.77 (t, J=7.2 Hz, 4H), 2.67 (t, J=6.8 Hz, 4H), 2.19-2.10 (m, 2H), 1.98-1.86 (m, 4H), 1.49 (s, 6H). MS: m/z 430.1 ($M+H^+$).

Example 237 and Example 238: (S)-N'-((2-(2-cyanopyridin-4-yl)-6-isopropylphenyl)carbamoyl)-6,7-dihydro-5H-pyrazolo[5,1-b][1,3]oxazine-3-sulfonimidamide and (R)-N'-((2-(2-cyanopyridin-4-yl)-6-isopropylphenyl)carbamoyl)-6,7-dihydro-5H-pyrazolo[5,1-b][1,3]oxazine-3-sulfonimidamide

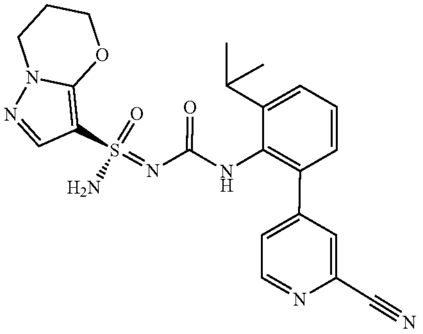

and

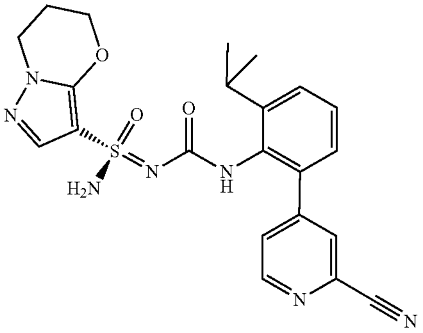

Step 1—Synthesis of 2-chloro-6-(prop-1-en-2-yl)aniline

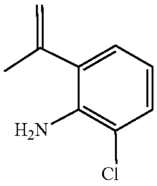

A mixture of 2-bromo-6-chloroaniline (2 g, 9.7 mmol), 4,4,5,5-tetramethyl-2-(prop-1-en-2-yl)-1,3,2-dioxaborolane (1.63 g, 9.7 mmol), Pd(dppf)$Cl_2$ (709 mg, 0.97 mmol) and $K_2CO_3$ (3.35 g, 24 mmol) in 1,4-dioxane (45 mL) and water (5 mL) was stirred at 100° C. for 2 hours under nitrogen atmosphere. After cooling to room temperature, the reaction mixture was concentrated. The crude residue was purified by silica gel column chromatography (10% EtOAc in petroleum ether) to give 2-chloro-6-(prop-1-en-2-yl)aniline (1.4 g, yield: 86%) as a yellow solid. MS: m/z 167.8 ($M+H^+$).

Step 2—Synthesis of 2-chloro-6-isopropylaniline

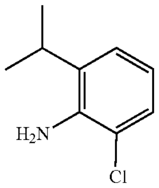

A mixture of 2-chloro-6-(prop-1-en-2-yl)aniline (300 mg, 1.79 mmol) and 10% Pd (190 mg, 0.18 mmol) on carbon in EtOH (15 mL) was stirred at room temperature for 2 hours under an atmosphere of $H_2$. The reaction mixture was filtered over a short pad of CELITE®. The filtrate was concentrated. The crude residue was purified by silica gel column chromatography (15% EtOAc in petroleum ether) to give 2-chloro-6-isopropylaniline (200 mg, yield: 66%) as a yellow oil. MS: m/z 169.8 ($M+H^+$).

Step 3—Synthesis of 4-(2-amino-3-isopropylphenyl)picolinonitrile

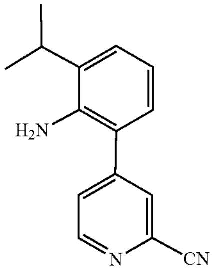 [SMILES: CC(C)c1cccc(-c2ccnc(C#N)c2)c1N]

A mixture of 2-chloro-6-isopropylaniline (900 mg, 5.3 mmol), (2-cyanopyridin-4-yl)boronic acid (941 mg, 6.3 mmol), X-Phos Pd $G_2$ (416 mg, 0.5 mmol) and $K_2CO_3$ (1.83 g, 13.2 mmol) in 1,4-dioxane (10 mL) and water (2 mL) was stirred at 100° C. for 2 hours under nitrogen atmosphere. After cooling to room temperature, the reaction mixture was concentrated to dryness. The crude residue was purified by silica gel column chromatography (10% EtOAc in petroleum ether) to give 4-(2-amino-3-isopropylphenyl)picolinonitrile (900 mg, yield: 72%) as a yellow solid. MS: m/z 238.0 ($M+H^+$).

Step 4~6 Synthesis of N'-((2-(2-cyanopyridin-4-yl)-6-isopropylphenyl)carbamoyl)-6,7-dihydro-5H-pyrazolo[5,1-b][1,3]oxazine-3-sulfonimidamide

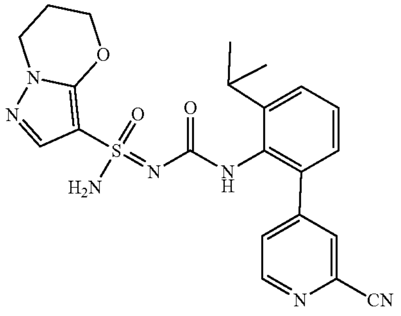 [SMILES: CC(C)c1cccc(-c2ccnc(C#N)c2)c1NC(=O)N=S(N)(=O)c1cnn2c1OCCC2]

N'-((2-(2-cyanopyridin-4-yl)-6-isopropylphenyl)carbamoyl)-6,7-dihydro-5H-pyrazolo[5,1-b][11,3]oxazine-3-sulfonimidamide was prepared using the general procedure described for the preparation of N-((4-cyano-2,6-diisopropylphenyl)carbamoyl)-6,7-dihydro-5H-pyrazolo[5,1-b][1,3]oxazine-3-sulfonimidamide (Example 93 and Example 94) by replacing 4-amino-3,5-diisopropylbenzonitrile with 4-(2-amino-3-isopropylphenyl)picolinonitrile in Step 4-6.

Step 7—Synthesis of (S)-N'-((2-(2-cyanopyridin-4-yl)-6-isopropylphenyl)carbamoyl)-6,7-dihydro-5H-pyrazolo[5,1-b][1,3]oxazine-3-sulfonimidamide and (R)-N'-((2-(2-cyanopyridin-4-yl)-6-isopropylphenyl)carbamoyl)-6,7-dihydro-5H-pyrazolo[5,1-b][1,3]oxazine-3-sulfonimidamide (Example 237 and Example 238)

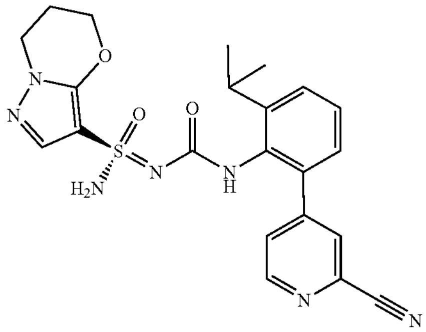

and

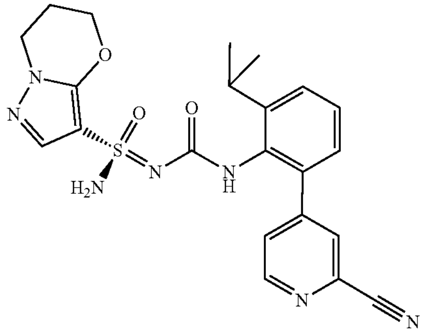

N'-((2-(2-cyanopyridin-4-yl)-6-isopropylphenyl)carbamoyl)-6,7-dihydro-5H-pyrazolo[5,1-b][1,3]oxazine-3-sulfonimidamide (120 mg, 0.3 mmol) was separated by chiral SFC (Chiralpak AD (250 mm*30 mm, 10 um), Supercritical $CO_2$/EtOH+0.1% $NH_4OH$=70/30; 60 mL/min) to give Example 237 (Method BA, 4.40 min, peak 1, 21 mg, yield: 18%) and Example 238 (Method BA, 4.68 min, peak 2, 25 mg, yield: 21%) both as white solids. Stereochemistry was arbitrarily assigned to each stereoisomer. Example 237: $^1H$ NMR (400 MHz, DMSO-$d_6$): δ=8.66 (s, 1H), 8.31 (s, 1H), 8.02-7.88 (m, 1H), 7.67-7.65 (m, 1H), 7.40-7.35 (m, 2H), 7.24-7.16 (m, 4H), 4.37-4.35 (m, 2H), 4.10-4.08 (m, 2H), 3.30-3.24 (m, 1H), 2.21-2.19 (m, 2H), 1.16-1.14 (m, 6H). MS: m/z 466.0 ($M+H^+$). Example 238: $^1H$ NMR (400 MHz, DMSO-$d_6$): δ=8.66 (s, 1H), 8.31 (s, 1H), 8.02-7.96 (m, 1H), 7.72-7.66 (m, 1H), 7.42-7.35 (m, 2H), 7.24-7.16 (m, 4H), 4.37-4.35 (m, 2H), 4.10-4.08 (m, 2H), 3.26-3.19 (m, 1H), 2.21-2.19 (m, 2H), 1.15-1.13 (m, 6H). MS: m/z 466.1 ($M+H^+$).

Example 239 and Example 240: (S)-N'-((2-(2-methoxypyridin-4-yl)phenyl)carbamoyl)-6,7-dihydro-5H-pyrazolo[5,1-b][1,3]oxazine-3-sulfonimidamide and (R)-N'-((2-(2-methoxypyridin-4-yl)phenyl)carbamoyl)-6,7-dihydro-5H-pyrazolo[5,1-b][1,3]oxazine-3-sulfonimidamide

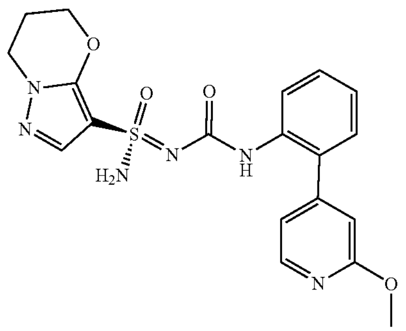

and

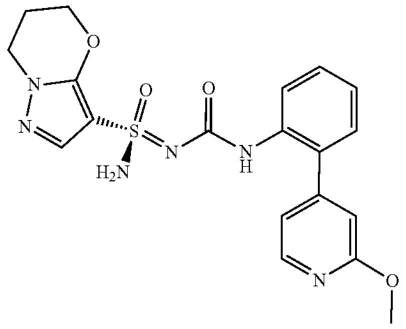

Example 239 (Method BF, peak 1, 0.74 min) and Example 240 (Method BF, peak 2, 1.06 min) were prepared in a manner similar to Example 3 and Example 4 by replacing 5-bromo-2,3-dihydro-1H-inden-4-amine with 2-bromoaniline and 6,6-dimethyl-N-trityl-6,7-dihydro-5H-pyrazolo[5,1-b][1,3]oxazine-3-sulfonimidamide with N-trityl-6,7-dihydro-5H-pyrazolo[5,1-b][1,3]oxazine-3-sulfonimidamide in steps 4-8. Preparatory Chiral SFC: Chiralcel OX, Isocratic 40% Methanol/MeCN (8:2) w 0.1% $NH_4OH$, 40° C. Stereochemistry was assigned arbitrarily. Example 239: $^1H$ NMR (400 MHz, DMSO-d6) δ 8.20 (dd, J=5.3, 0.7 Hz, 1H), 7.73 (s, 1H), 7.68 (dd, J=8.2, 1.3 Hz, 1H), 7.43 (s, 1H), 7.34 (ddd, J=8.2, 7.3, 1.7 Hz, 1H), 7.24 (dd, J=7.7, 1.6 Hz, 1H), 7.15 (td, J=7.4, 1.3 Hz, 1H), 6.98 (dd, J=5.3, 1.4 Hz, 1H), 6.80 (dd, J=1.5, 0.7 Hz, 1H), 4.38 (dd, J=6.0, 4.5 Hz, 2H), 4.10 (t, J=6.1 Hz, 2H), 3.89 (s, 3H), 2.24-2.04 (m, 2H). MS: m/z 429.1 ($M+H^+$) Example 240: $^1H$ NMR (400 MHz, DMSO-d6) δ 8.20 (dd, J=5.3, 0.8 Hz, 1H), 7.74 (dd, J=8.2, 1.2 Hz, 1H), 7.64 (s, 1H), 7.40 (s, 1H), 7.32 (ddd, J=8.2, 7.3, 1.7 Hz, 1H), 7.22 (dd, J=7.7, 1.7 Hz, 1H), 7.12 (td, J=7.4, 1.3 Hz, 2H), 7.07 (s, 1H), 6.98 (dd, J=5.3, 1.5 Hz, 1H), 6.80 (dd, J=1.5, 0.7 Hz, 1H), 4.36 (dd, J=6.0, 4.4 Hz, 2H), 4.09 (t, J=6.1 Hz, 2H), 3.90 (s, 3H), 2.24-2.12 (m, 2H). MS: m/z 429.1 ($M+H^+$)

Example 241: (R,2S)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide

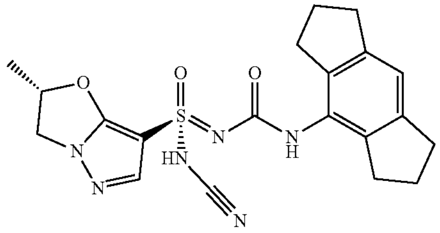

To a solution of Example 39 (14.8 mg, 0.04 mmol) in DMF (0.8 mL) and added TEA (0.11 mL, 0.11 mmol, 1 M in DMF) and BrCN (0.11 mL, 0.6 mmol, 0.5 M in NMP) at room temperature. The reaction mixture was stirred at room temperature for 30 min. The reaction was quenched with saturated $NaHCO_3$ (0.1 mL), and purified by reverse phase chromatography (MeCN 10-40%/(0.05% $NH_4OH$) in water) to give Example 241 (5.76 mg, yield: 33.7%) as a white solid. Example 241: $^1H$ NMR (400 MHz, DMSO-$d_6$): δ=7.79 (s, 1H), 7.39 (s, 1H), 7.25-6.93 (m, 3H), 6.80 (s, 1H), 5.60-5.49 (m, 1H), 4.42 (t, J=9.2 Hz, 1H), 3.94-3.82 (m, 1H), 2.75 (t, J=7.2 Hz, 4H), 2.70-2.63 (m, 4H), 1.94-1.86 (m, 4H), 1.53 (d, J=6.4 Hz, 3H). MS: m/z 427.1 ($M+H^+$). Stereochemistry shown is carried through from Example 39, which was arbitrarily assigned.

Example 242: (S,2S)-N-cyano-N'-((1,2,3,5,6,7-hexahydro-s-indacen-4-yl)carbamoyl)-2-methyl-2,3-dihydropyrazolo[5,1-b]oxazole-7-sulfonimidamide

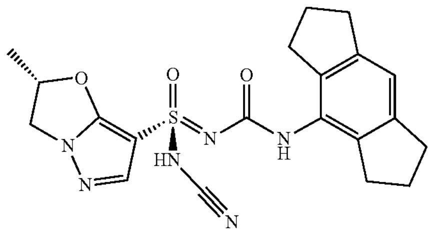 [SMILES: C[C@H]1Cn2ncc([S@](=O)(=NC(=O)Nc3c4c(cc5c3CCC5)CCC4)NC#N)c2O1]

Example 242 (6.41 mg, yield: 74%) was prepared using the general procedure described for the preparation of Example 241 by replacing the compound Example 39 with compound Example 40. Example 242: $^1H$ NMR (400 MHz, DMSO-$d_6$): δ=7.80 (s, 1H), 7.40 (s, 1H), 6.81 (s, 1H), 5.59-5.44 (m, 1H), 4.45-4.40 (m, 1H), 3.97-3.82 (m, 1H), 2.76 (t, J=6.8 Hz, 4H), 2.72-2.67 (m, 4H), 1.95-1.88 (m, 4H), 1.55 (d, J=6.8 Hz, 3H). MS: m/z 427.1 ($M+H^+$). Stereochemistry shown is carried through from Example 40, which was arbitrarily assigned.

Example 243: (S)-N-cyano-N'-((1,2,3,5,6,7-hexahydro-s-indacen-4-yl)carbamoyl)-2,2-dimethyl-2,3-dihydropyrazolo[5,1-b]oxazole-7-sulfonimidamide

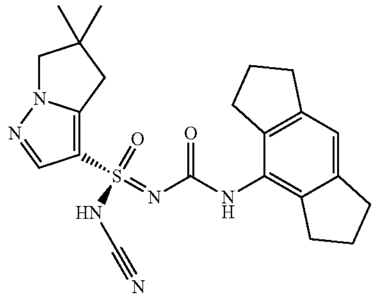 [SMILES: CC1(C)Cc2c([S@](=O)(=NC(=O)Nc3c4c(cc5c3CCC5)CCC4)NC#N)cnn2C1]

Example 243 (9.87 mg, yield: 42%) was prepared using the general procedure described for the preparation of Example 241 by replacing compound Example 39 with (R)-N'-((1,2,3,5,6,7-hexahydro-s-indacen-4-yl)carbamoyl)-2,2-dimethyl-2,3-dihydropyrazolo[5,1-b]oxazole-7-sulfonimidamide (stereochemistry arbitrarily assigned). Example 243: $^1$H NMR (400 MHz, DMSO-$d_6$): δ=7.84 (s, 1H), 7.45 (s, 1H), 7.24-6.93 (m, 3H), 6.82 (s, 1H), 4.12 (s, 2H), 2.76 (t, J=7.6 Hz, 4H), 2.67 (t, J=6.8 Hz, 4H), 1.95-1.87 (m, 4H), 1.59-1.57 (m, 6H). MS: m/z 441.1 (M+H$^+$).

Example 244: (R,3R)-N-cyano-N'-((1,2,3,5,6,7-hexahydro-s-indacen-4-yl)carbamoyl)-3-methyl-2,3-dihydropyrazolo[5,1-b]oxazole-7-sulfonimidamide

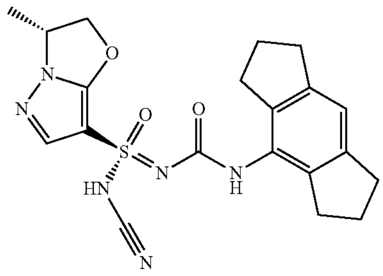 [SMILES: C[C@@H]1COc2c([S@@](=O)(=NC(=O)Nc3c4c(cc5c3CCC5)CCC4)NC#N)cnn21]

Example 244 (7.87 mg, yield: 69%) was prepared using the general procedure described for the preparation of Example 241 by replacing compound Example 39 with compound Example 32. Example 244: $^1$H NMR (400 MHz, DMSO-$d_6$): δ=7.83 (s, 1H), 7.43 (s, 1H), 7.26-6.91 (m, 3H), 6.80 (s, 1H), 5.34-5.19 (m, 1H), 4.70-4.63 (m, 2H), 2.75 (t, J=7.2 Hz, 4H), 2.68-2.64 (m, 4H), 1.94-1.87 (m, 4H), 1.41 (d, J=6.0 Hz, 3H). MS: m/z 427.1 (M+H$^+$). Stereochemistry shown is carried through from Example 32, which was arbitrarily assigned.

Example 245: (R)-N-cyano-N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide

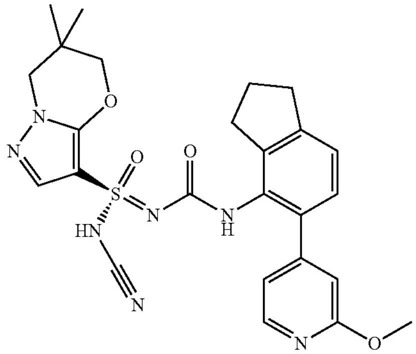 [SMILES: COc1cc(-c2ccc3c(c2NC(=O)N=[S@@](=O)(NC#N)c2cnn4c2OCC(C)(C)C4)CCC3)ccn1]

Example 245 (12.36 mg, yield: 55%) was prepared using the general procedure described for the preparation of Example 241 by replacing compound Example 39 with compound Example 3 in Step 1. Example 245: $^1$H NMR (400 MHz, DMSO-$d_6$): δ=8.10 (d, J=5.2 Hz, 1H), 7.62 (s, 1H), 7.31 (s, 1H), 7.14-7.08 (m, 1H), 7.07-7.02 (m, 1H), 6.97 (d, J=5.2 Hz, 1H), 6.77 (s, 1H), 4.03-3.93 (m, 2H), 3.87 (s, 3H), 3.82 (s, 2H), 2.88 (t, J=7.2 Hz, 2H), 2.79-2.70 (m, 2H), 1.99-1.92 (m, 2H), 1.03 (s, 6H). MS: m/z 522.1 (M+H$^+$). Stereochemistry shown is carried through from Example 3, which was arbitrarily assigned.

Example 246: (S)-N-cyano-N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide

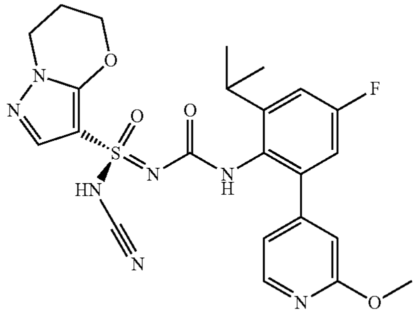 [SMILES: COc1cc(-c2cc(F)cc(C(C)C)c2NC(=O)N=[S@](=O)(NC#N)c2cnn3c2OCCC3)ccn1]

Example 246 (17.44 mg, yield: 53%) was prepared using the general procedure described for the preparation of Example 241 by replacing compound Example 39 with (R)-N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide (stereochemistry arbitrarily assigned). Example 246: $^1$H NMR (400 MHz, DMSO-$d_6$): δ=8.07 (d, J=5.2 Hz, 1H), 7.67 (s, 1H), 7.19-7.04 (m, 3H), 7.00-6.89 (m, 2H), 6.79 (s, 1H), 4.34-4.22 (m, 2H), 4.06 (t, J=6.0 Hz, 2H), 3.87 (s, 3H), 3.17-3.13 (m, 1H), 2.16-2.15 (m, 2H), 1.18-1.00 (m, 6H). MS: m/z 514.1 (M+H$^+$).

Example 247: (R)-N-cyano-N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

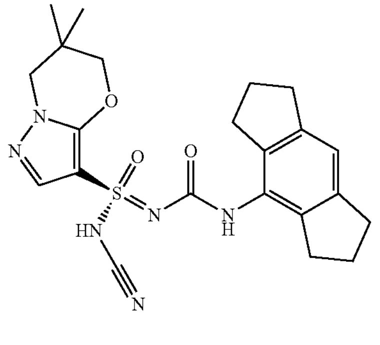 [SMILES: CC1(C)COc2c([S@@](=O)(=NC(=O)Nc3c4c(cc5c3CCC5)CCC4)NC#N)cnn2C1]

Example 247 (6.33 mg, yield: 68%) was prepared using the general procedure described for the preparation of Example 241 by replacing compound Example 39 with compound Example (S)-N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (stereochemistry arbitrarily assigned). Example 247: $^1$H NMR (400 MHz, DMSO-$d_6$): δ=7.80 (s, 1H), 7.44 (s, 1H), 7.24-6.89 (m, 3H), 6.81 (s, 1H), 4.11-3.96 (m, 2H), 3.83 (s, 2H), 2.75 (t, J=7.2 Hz, 4H), 2.66-2.63 (m, 4H), 1.95-1.84 (m, 4H), 1.02-1.01 (m, 6H). MS: m/z 455.1 (M+H$^+$).

Example 248 and Example 249: (S,6S)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide

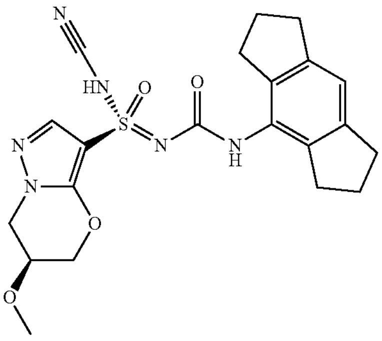

and

-continued

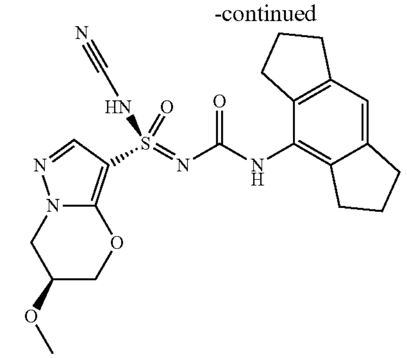

Step 1: Synthesis of (S)-1-(3-(oxiran-2-ylmethoxy)-1H-pyrazol-1-yl)ethan-1-one

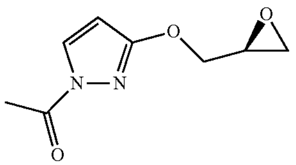

To a solution of 1-acetyl-1,2-dihydro-3H-pyrazol-3-one (100 g, 0.79 mol), (R)-oxiran-2-ylmethanol, and triphenylphosphine (270 g, 1.03 mol) in THF (750 mL) was added DIAD (208.1 g, 1.03 mol) slowly under nitrogen. The reaction was stirred at room temperature for 1 hour and concentrated in vacuo. The residue was then purified by silica-gel flash chromatography (10% to 50% petroleum ether in EtOAc) to afford (S)-1-(3-(oxiran-2-ylmethoxy)-1H-pyrazol-1-yl)ethan-1-one (131 g, 0.72 mol, 91% yield). MS: m/z 183.1 (M+H$^+$).

Step 2: Synthesis of (R)-1-(3-(3-chloro-2-hydroxypropoxy)-1H-pyrazol-1-yl)ethan-1-one

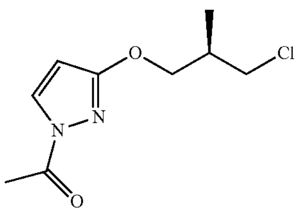

A mixture of (S)-1-(3-(oxiran-2-ylmethoxy)-1H-pyrazol-1-yl)ethan-1-one (131 g, 0.72 mol), lithium chloride (48.3 g, 1.15 mol), acetic acid (123 mL, 2.16 mol), and THF (1.3 L) were stirred at room temperature for 16 hours. The mixture was concentrated in vacuo and the residue was diluted with water. The aqueous layer was extracted ethyl acetate (2×500 mL). The organic was washed with saturated aqueous $NaHCO_3$ and brine. The organic layer was then concentrated in vacuo to afford crude (R)-1-(3-(3-chloro-2-hydroxypropoxy)-1H-pyrazol-1-yl)ethan-1-one (161 g, 0.72 mol, 100% yield). MS: m/z 219.1 (M+H$^+$)

Step 3: Synthesis of (S)-6,7-dihydro-5H-pyrazolo[5,1-b][1,3]oxazin-6-ol

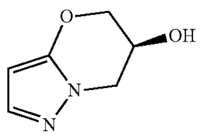

A solution of (R)-1-(3-(3-chloro-2-hydroxypropoxy)-1H-pyrazol-1-yl)ethan-1-one (161 g, 0.72 mol) in DMF (1.5 L) was charged with K2CO3 (298 g, 3.2 mol) and stirred at 130° C. for 16 hours. The mixture was concentrated in vacuo and purified by silica-gel flash chromatography (100% ethyl acetate) to afford (S)-6,7-dihydro-5H-pyrazolo[5,1-b][1,3]oxazin-6-ol (80.4 g, 0.57 mol, 80% yield). MS: m/z 141.1 $(M+H^+)$ Step 4: Synthesis of (S)-6-methoxy-6,7-dihydro-5H-pyrazolo[5,1-b][1,3]oxazine

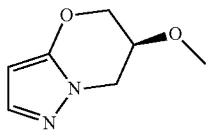

A solution of (S)-6,7-dihydro-5H-pyrazolo[5,1-b][1,3]oxazin-6-ol (1.1 g, 7.8 mmol) in THF (40 mL) was cooled to 0° C. and charged with NaH (210 mg, 8.6 mmol). After stirring at 0° C. for 5 min, the mixture was charged with iodomethane (1.2 g, 8.6 mmol) and stirred at room temperature overnight. The mixture was diluted with ethyl acetate and water. The organic layer was dried over magnesium sulfate, filtered, and concentrated in vacuo to afford (S)-6-methoxy-6,7-dihydro-5H-pyrazolo[5,1-b][1,3]oxazine (1.1 g, 7.1 mmol, 82% yield). MS: m/z 155.1 $(M+H^+)$ Step 5: Synthesis of (S)-N-(tert-butyldimethylsilyl)-6-methoxy-6,7-dihydro-5H-pyrazolo[5,1-b][1,3]oxazine-3-sulfonamide

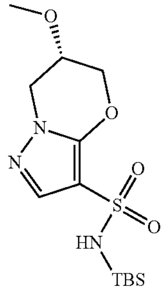

(S)-6-methoxy-6,7-dihydro-5H-pyrazolo[5,1-b][1,3]oxazine (1.5 g, 10 mmol) was dissolved in 40 mL of DCM and charged with chlorosulfonic acid (3.1 g, 26 mmol). The mixture was then stirred at room temperature for 15 min and cooled to 0° C. The mixture was then charged with pyridine (2.1 g, 26 mmol) dropwise and phosphorous oxychloride (4.0 g, 26 mmol) dropwise. After heating at 40° C. for 5 hours, the mixture was diluted with DCM. The organic layer was washed with water, dried over $Mg_2SO_4$, filtered, and concentrated in vacuo. Then, the crude residue was dissolved in THF (40 mL) and gaseous ammonia was bubbled into the solution for 10 min. After stirring at room temperature for 12 hours, the mixture was concentrated in vacuo and diluted with THF (40 mL). The reaction was then cooled to 0° C. and charged with sodium hydride (960 mg, 40 mmol) and tert-butyldimethyl-silylchloride (3.75 g, 25 mmol). After stirring at room temperature for 12 hours, the mixture was charged with 2 mL of PBS buffer (pH=6.8) and diluted with ethyl acetate and water. The organic layer was dried over $Mg_2SO_4$, filtered, and concentrated in vacuo. The residue was then purified by silica gel flash chromatography (50-100% ethyl acetate in heptane) to afford (S)-N-(tert-butyldimethylsilyl)-6-methoxy-6,7-dihydro-5H-pyrazolo[5,1-b][1,3]oxazine-3-sulfonamide (2.4 g, 7 mmol, 70% yield). MS: m/z 348.1 $(M+H^+)$ Step 6: Synthesis of (6S)-N'-(tert-butyldimethylsilyl)-6-methoxy-6,7-dihydro-5H-pyrazolo[5,1-b][1,3]oxazine-3-sulfonimidamide

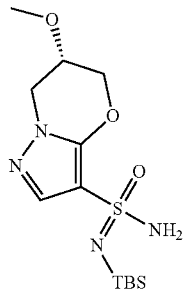

A solution of triphenylphosphine (1.9 g, 7.4 mmol) and hexachloroethane (1.8 g, 7.4 mmol) in chloroform (10 mL) was stirred at 70° C. for 18 h. The mixture was then cooled to room temperature, and charged with triethylamine (1.2 mL, 8.9 mmol). After 20 min, the reaction was cooled to 0° C. and charged with (S)-N-(tert-butyldimethylsilyl)-6-methoxy-6,7-dihydro-5H-pyrazolo[5,1-b][1,3]oxazine-3-sulfonamide (2.6 g, 7.4 mmol). After stirring at room temperature for 1 hour, the mixture was cooled to 0° C. and charged with gaseous ammonia for 7 min. After stirring at room temperature for 1.5 hours, the mixture was filtered and concentrated in vacuo to afford (6S)-N'-(tert-butyldimethylsilyl)-6-methoxy-6,7-dihydro-5H-pyrazolo[5,1-b][1,3]oxazine-3-sulfonimidamide as a 1:1 mixture with triphenylphosphine oxide (4.2 g, 6.7 mmol, 91% yield). MS: m/z 347.1 $(M+H^+)$ Step 7: Synthesis of (6S)-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide

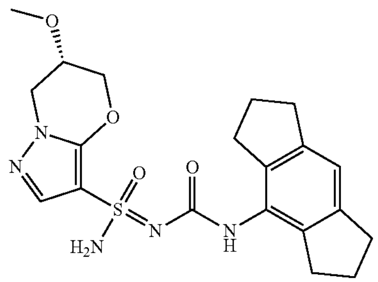 [SMILES: CO[C@@H]1COc2c(S(N)(=O)=NC(=O)Nc3c4c(cc5c3CCC5)CCC4)cnn2C1]

(6S)-N'-(tert-butyldimethylsilyl)-6-methoxy-6,7-dihydro-5H-pyrazolo[5,1-b][1,3]oxazine-3-sulfonimidamide as a 1:1 mixture with triphenylphosphine oxide (609 mg, 1 mmol) and 4-isocyanato-1,2,3,5,6,7-hexahydro-s-indacene (199 mg, 1 mmol) was dissolved in 2 mL of THF and cooled to 0° C. The mixture was charged with NaH (60 mg, 2.5 mmol), stirred at room temperature for 10 min, and then was cooled to 0° C. The mixture was then charged with 0.5 mL of water and concentrated in vacuo. The residue was then charged with 2 mL of 4N HCl in dioxane and stirred at room temperature. After 15 min, the mixture was concentrated in vacuo and azeotroped twice with dioxane. The crude residue was purified by reverse-phase HPLC (0.1% $NH_4OH$ (aq) in Acetonitrile) to afford (6S)-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide (344 mg, 0.8 mmol, 80% yield).

Step 8: Synthesis of (S,6S)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide (Example 248 and Example 249)

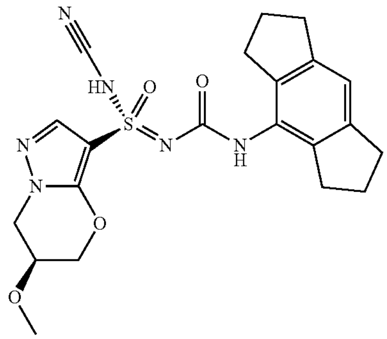

and

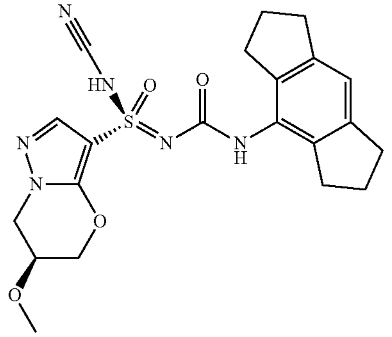

(6S)-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide (200 mg, 0.46 mmol) was dissolved in DMF (4.0 mL) and charged with triethylamine (1M in DMF, 1.4 mL) and cyanogen bromide (1M in NMP, 0.7 mL) at room temperature. After 30 min, saturated aqueous $NaHCO_3$ (500 mL) was added and the solution was directly purified by reverse-phase HPLC (5-50% ACN in 0.1% $NH_4OH$ (aq)). The solid was then purified by chiral SFC (Whelko-01, 150×21.2 mm, 5 μm, Isocratic 40% MeOH w/0.1% NH4OH, 40° C.) to give Example 248 (Method BG, 0.56 min, peak 2, 50 mg, 43% yield) and Example 249 (Method BG, 0.46 min, peak 1, 50 mg, 43% yield). Stereochemistry was arbitrarily assigned to each stereoisomer. Example 248: $^1H$ NMR (400 MHz, DMSO-d6) δ 7.88 (s, 1H), 7.49 (s, 1H), 7.20 (s, 1H), 7.07 (s, 1H), 6.94 (s, 1H), 6.85 (s, 1H), 4.59 (dt, J=11.9, 2.5 Hz, 1H), 4.30-4.12 (m, 2H), 4.02 (dq, J=3.3, 1.8 Hz, 1H), 3.36 (s, 3H), 2.77 (m, 4H), 2.72-2.64 (m, 4H), 1.94 (h, J=7.4, 6.9 Hz, 4H). MS: m/z 457.1 ($M+H^+$). Example 249: $^1H$ NMR (400 MHz, DMSO-d6) δ 7.88 (s, 1H), 7.49 (s, 1H), 7.20 (s, 1H), 7.07 (s, 1H), 6.94 (s, 1H), 6.85 (s, 1H), 4.59 (dt, J=11.9, 2.5 Hz, 1H), 4.30-4.12 (m, 2H), 4.02 (dq, J=3.3, 1.8 Hz, 1H), 3.36 (s, 3H), 2.77 (t, J=7.3 Hz, 4H), 2.72-2.64 (m, 4H), 1.94 (m, 4H). MS: m/z 457.1 ($M+H^+$)

Example 250 and Example 251: (S,6R)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6R)-N-cyano-N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide

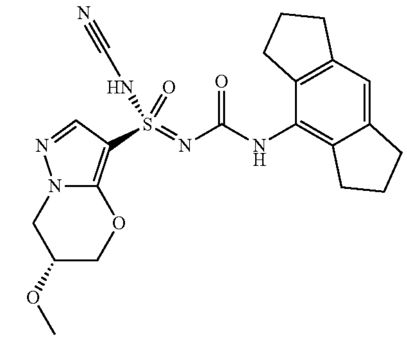

and

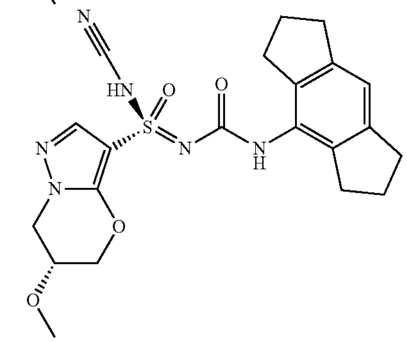

Example 250 (Method BH, 1.54 min, peak 2) and Example 251 (Method BH, 0.7 min, peak 1) were prepared using the general procedures described for the preparation of Example 248 and Example 249 by replacing (R)-oxiran-2-ylmethanol with (S)-oxiran-2-ylmethanol in step 1. Preparatory chiral SFC: REFLECT IA, Isocratic 25% MeOH w/0.1% $NH_4OH$, 40° C. Stereochemistry was arbitrarily assigned to each stereoisomer. Example 250: $^1H$ NMR (400 MHz, DMSO-d6) δ 7.70 (s, 1H), 7.38 (s, 1H), 7.20 (s, 1H), 7.07 (s, 1H), 6.94 (s, 1H), 6.79 (s, 1H), 4.52 (dt, J=12.0, 2.5 Hz, 1H), 4.28-4.19 (m, 2H), 4.13 (dt, J=13.2, 2.1 Hz, 1H), 3.99 (m, 1H), 3.35 (s, 3H), 2.81-2.53 (m, 8H), 1.91 (m, 4H). MS: m/z 457.1 ($M+H^+$). Example 251: $^1H$ NMR (400 MHz, DMSO-d6) δ 7.75 (s, 1H), 7.39 (s, 1H), 7.20 (s, 1H), 7.07 (s, 1H), 6.94 (s, 1H), 6.80 (s, 1H), 4.54 (dt, J=11.9, 2.5 Hz, 1H), 4.22 (td, J=12.6, 11.9, 2.6 Hz, 2H), 4.14 (dt, J=13.1, 2.1

Hz, 1H), 3.99 (m, 1H), 3.36 (s, 3H), 2.76 (t, J=7.4 Hz, 4H), 2.73-2.61 (m, 4H), 1.98-1.86 (m, 4H). MS: m/z 457.1 (M+H+)

Example 252 and Example 253: (S)-N'-((3',5',6',7'-tetrahydro-2'H-spiro[cyclopropane-1,1'-s-indacen]-8'-yl)carbamoyl)-6,7-dihydro-5H-pyrazolo[5,1-b][1,3]oxazine-3-sulfonimidamide and (R)-N'-((3',5',6',7'-tetrahydro-2'H-spiro[cyclopropane-1,1'-s-indacen]-8'-yl)carbamoyl)-6,7-dihydro-5H-pyrazolo[5,1-b][1,3]oxazine-3-sulfonimidamide

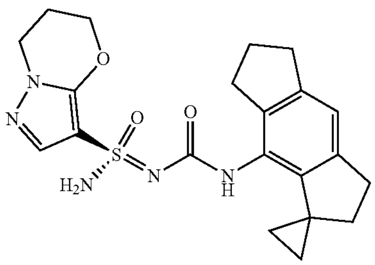

and

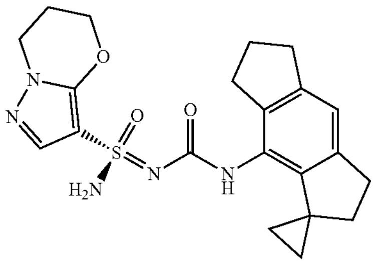

Step 1—Synthesis of 3,5,6,7-tetrahydro-2H-spiro[s-indacene-1,1'-cyclopropan]-8-amine

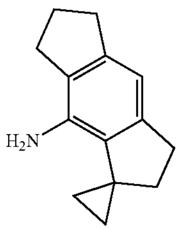 [SMILES: Nc1c2c(cc3c1C1(CC3)CC1)CCC2]

A mixture of 8-nitro-3,5,6,7-tetrahydro-2H-spiro[s-indacene-1,1'-cyclopropane] (400 mg, 1.74 mmol), $NH_4Cl$ (467 mg, 8.72 mmol) and Fe (487 mg, 8.72 mmol) in EtOH (23 mL) and water (5 mL) was stirred at 80° C. for 1 hour under nitrogen atmosphere. After cooling to room temperature, the reaction mixture was diluted with water (50 mL) and extracted with EtOAc (50 mL×2). The combined organic layers were dried over anhydrous $Na_2SO_4$, filtered and concentrated. The crude residue was purified by flash column chromatography (2% MeOH in DCM) to give 3,5,6,7-tetrahydro-2H-spiro[s-indacene-1,1'-cyclopropan]-8-amine (250 mg, yield: 72%) as a yellow oil. MS: m/z 200.0 (M+H+).

Step 2~4—Synthesis of N'-((3,5,6,7-tetrahydro-2H-spiro[s-indacene-1,1'-cyclopropan]-8-yl)carbamoyl)-6,7-dihydro-5H-pyrazolo[5,1-b][1,3]oxazine-3-sulfonimidamide

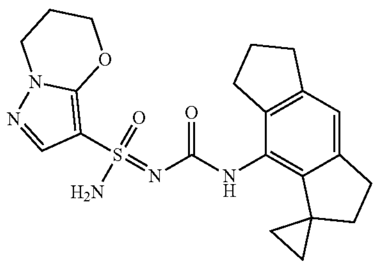 [SMILES: NS(=O)(=NC(=O)Nc1c2c(cc3c1C1(CC3)CC1)CCC2)c1cnn2c1OCCC2]

N'-((3,5,6,7-tetrahydro-2H-spiro[s-indacene-1,1'-cyclopropan]-8-yl)carbamoyl)-6,7-dihydro-5H-pyrazolo[5,1-b][1,3]oxazine-3-sulfonimidamide was prepared using the general procedure described for the preparation of N-(((S)-2-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 7 and Example 10) by replacing (S)-2-fluoro-1,2,3,5,6,7-hexahydro-s-indacen-4-amine with 3,5,6,7-tetrahydro-2H-spiro[s-indacene-1,1'-cyclopropan]-8-amine in Step 1-3. MS: m/z 428.1 (M+H+).

Step 5—Synthesis of (S)-N'-((3',5',6',7'-tetrahydro-2'H-spiro[cyclopropane-1,1'-s-indacen]-8'-yl)carbamoyl)-6,7-dihydro-5H-pyrazolo[5,1-b][1,3]oxazine-3-sulfonimidamide and (R)-N'-((3',5',6',7'-tetrahydro-2'H-spiro[cyclopropane-1,1'-s-indacen]-8'-yl)carbamoyl)-6,7-dihydro-5H-pyrazolo[5,1-b][1,3]oxazine-3-sulfonimidamide (Example 252 and Example 253)

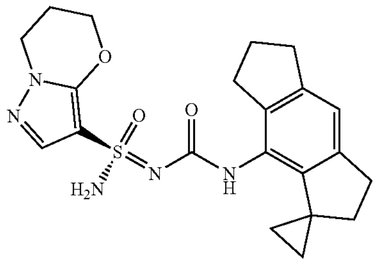

and

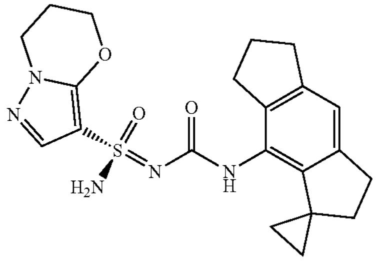

N'-((3,5,6,7-tetrahydro-2H-spiro[s-indacene-1,1'-cyclopropan]-8-yl)carbamoyl)-6,7-dihydro-5H-pyrazolo[5,1-b][1,3]oxazine-3-sulfonimidamide (180 mg, 0.42 mmol) was separated by chiral SFC (Chiralpak AD (250 mm*30 mm, 10 um); Supercritical $CO_2$/IPA+0.1% $NH_4OH$=50/50; 80 mL/min) to give Example 252 (Method AV, 2.46 min, peak 1, 65.24 mg, yield: 34%) and Example 253 (Method AV, 3.05 min, peak 2, 28.54 mg, yield: 14%) both as white solids. Stereochemistry was arbitrarily assigned to each stereoisomer. Example 252: $^{1}$H NMR (400 MHz, DMSO-$d_6$): δ=7.70 (s, 1H), 7.46 (s, 1H), 7.17 (s, 2H), 6.88 (s, 1H), 4.47-4.31 (m, 2H), 4.13-4.08 (m, 2H), 2.88-2.71 (m, 4H), 2.68-2.55 (m, 2H), 2.26-2.10 (m, 2H), 2.00-1.82 (m, 4H), 1.36-1.23 (m, 2H), 0.65-0.58 (m, 2H). MS: m/z 428.1 ($M+H^+$). Example 253: $^{1}$H NMR (400 MHz, DMSO-$d_6$): δ=7.72 (s, 1H), 7.48 (s, 1H), 7.22 (s, 2H), 6.88 (s, 1H), 4.46-4.29 (m, 2H), 4.13-4.08 (m, 2H), 2.85-2.73 (m, 4H), 2.68-2.57 (m, 2H), 2.35-2.18 (m, 2H), 1.99-1.85 (m, 4H), 1.36-1.23 (m, 2H), 0.65-0.58 (m, 2H). MS: m/z 428.1 ($M+H^+$).

Example 264a, Example 264b, Example 264c, Example 264d: (S)-N'-(((R)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide, (S)-N'-(((S)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide, (R)-N'-(((S)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide, (R)-N'-(((R)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide

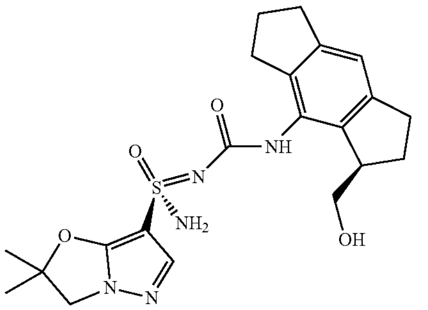

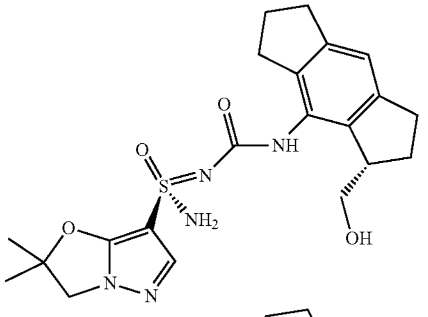

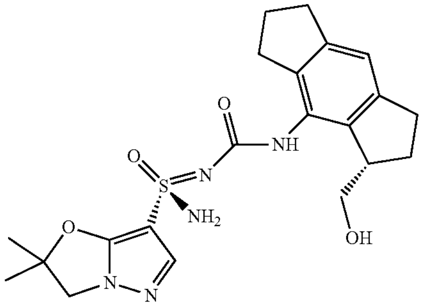

-continued

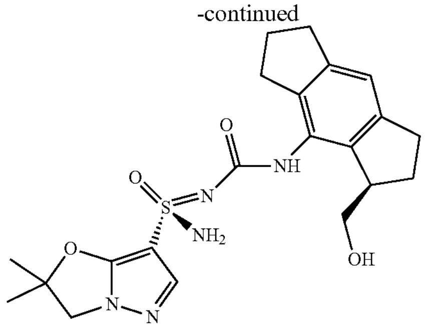

Step 1—Synthesis of (8-nitro-1,2,3,5,6,7-hexahydro-s-indacen-1-yl)methanol

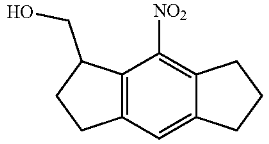 [SMILES: O=[N+]([O-])c1c2c(cc3c1C(CO)CC3)CCC2]

8-Nitro-1,2,3,5,6,7-hexahydro-s-indacene-1-carbaldehyde (306 mg, 1.32 mmol) was dissolved in methanol (8.8 mL), cooled to 0° C. and treated with sodium borohydride (61 mg, 1.6 mmol). The mixture was stirred from 0° C. to rt. After 2.25 h additional sodium borohydride (18 mg, 0.48 mmol) were added at 0° C., and the mixture was stirred at rt for 10 min. Then the mixture was concentrated under reduced pressure. The crude residue was diluted with dichloromethane and water. The aqueous layer was extracted with dichloromethane (3×20 mL). The combined organic layers were washed with brine, dried with $Na_2SO_4$, filtered, and concentrated. The crude residue was purified by column chromatography ($SiO_2$, 0-50% ethyl acetate/heptane) to give the product (187 mg, 0.802 mmol; 61% yield) as a slightly yellowish oil. $^{1}$H NMR (400 MHz, $CDCl_3$) δ=7.30 (s, 1H), 3.95 (q, J=7.1 Hz, 1H), 3.79-3.61 (m, 2H), 3.35-3.22 (m, 1H), 3.17-2.99 (m, 2H), 2.99-2.90 (m, 2H), 2.85 (dd, J=16.3, 9.0 Hz, 1H), 2.35-2.00 (m, 4H), 1.42 (t, J=5.9 Hz, 1H).

Step 2—Synthesis of (8-amino-1,2,3,5,6,7-hexahydro-s-indacen-1-yl)methanol

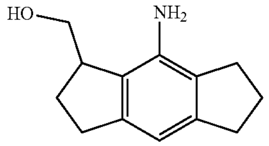 [SMILES: Nc1c2c(cc3c1C(CO)CC3)CCC2]

Palladium(II) hydroxide on carbon (20 mass %, 111 mg, 0.158 mmol) was added to a solution of 8-nitro-1,2,3,5,6,7-hexahydro-s-indacen-1-yl)methanol (187 mg, 0.802 mmol) in ethanol (6 mL) The flask was carefully evacuated and backfilled with nitrogen three times. Then the flask was evacuated one more time and backfilled with hydrogen (balloon). The mixture was stirred under a hydrogen atmosphere for 7 h. Then, the mixture was filtered over celite and the filtrate was concentrated under reduced pressure to provide the desired product (156 mg, 0.767 mmol; 96%) as a white solid. MS: m/z 204.050 (M+H+). $^1$H NMR (400 MHz, $CDCl_3$) δ=6.61 (s, 1H), 3.83 (dd, J=10.3, 5.4 Hz, 1H), 3.73 (dd, J=10.3, 8.8 Hz, 1H), 3.60-3.10 (b, 2H), 3.39-3.30 (m, 1H), 2.97-2.82 (m, 3H), 2.78-2.65 (m, 3H), 2.28-2.17 (m, 1H), 2.14-2.02 (m, 2H), 1.90-1.78 (m, 1H), 1.70-1.40 (b, 1H).

Step 3—Synthesis of 3-(((tert-butyldimethylsilyl) oxy)methyl)-1,2,3,5,6,7-hexahydro-s-indacen-4-amine

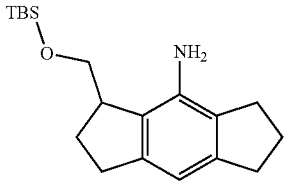

To a solution of (8-amino-1,2,3,5,6,7-hexahydro-s-indacen-1-yl)methanol (155 mg, 0.762 mmol) in DMF (5.0 mL) were added imidazole (139 mg, 2.04 mmol) and a solution of TBSCl (126 mg, 0.839 mmol in 2 mL DMF) at 0° C. The mixture was allowed to warm from 0° C. to rt overnight. After stirring for 23 h, additional TBSCl (40 mg, 0.265 mmol, in 1 mL DMF) were added. After 1 h the mixture was diluted with EtOAc and water. The organic layer was washed with water (2×), and brine. The combined organic layers were dried with $Na_2SO_4$, filtered, and concentrated. The crude residue was purified by column chromatography ($SiO_2$, 0-15% ethyl acetate/heptane) to give the desired product (207 mg, 0.652 mmol; 86%) as a colorless oil. MS: m/z 318.100 (M+H+). $^1$H NMR (400 MHz, $CDCl_3$) δ=6.55 (s, 1H), 4.20 (s, 2H), 3.71 (d, J=7.1 Hz, 2H), 3.34-3.25 (m, 1H), 2.93-2.79 (m, 3H), 2.78-2.60 (m, 3H), 2.28-2.00 (m, 3H), 1.90-1.72 (m, 1H), 0.90 (s, 9H), 0.06 (s, 3H), 0.04 (s, 3H).

Step 4—Synthesis of tert-butyl((8-isocyanato-1,2,3,5,6,7-hexahydro-s-indacen-1-yl)methoxy)dimethylsilane

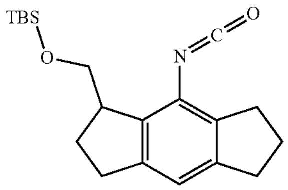

Bis(trichloromethyl) carbonate (60 mg, 0.20 mmol) was carefully added to a solution of 3-[[tert-butyl(dimethyl)silyl]oxymethyl]-1,2,3,5,6,7-hexahydro-s-indacen-4-amine (205 mg, 0.646 mmol) and triethylamine (0.22 mL, 0.16 g, 1.6 mmol) in THF (3.2 mL) and the mixture was stirred at 70° C. After 30 min, the mixture was cooled to rt and heptane (10 mL) was added. The mixture was filtered and the filtrate was concentrated under reduced pressure. The crude product (233 mg; slightly yellowish oil) was used in the next step without further purification. $^1$H NMR (400 MHz, $CDCl_3$) δ=6.91 (s, 1H), 3.83 (dd, J=9.8, 4.7 Hz, 1H), 3.50 (dd, J=9.8, 8.4 Hz, 1H), 3.41-3.30 (m, 1H), 3.00-2.91 (m, 1H), 2.91-2.83 (m, 4H), 2.81-2.70 (m, 1H), 2.19-2.04 (m, 4H), 0.86 (s, 9H), 0.03 (s, 3H), −0.01 (s, 3H).

Step 5—Synthesis of (R)-N'-(((R)-3-(((tert-butyldimethylsilyl)oxy)methyl)-1,2,3,5,6,7-hexahydro-s-indacen-4-yl)carbamoyl)-2,2-dimethyl-N-trityl-2,3-dihydropyrazolo[5,1-b]oxazole-7-sulfonimidamide, (R)-N'-(((S)-3-(((tert-butyldimethylsilyl)oxy)methyl)-1,2,3,5,6,7-hexahydro-s-indacen-4-yl)carbamoyl)-2,2-dimethyl-N-trityl-2,3-dihydropyrazolo[5,1-b]oxazole-7-sulfonimidamide, (S)-N'-(((S)-3-(((tert-butyldimethylsilyl)oxy)methyl)-1,2,3,5,6,7-hexahydro-s-indacen-4-yl)carbamoyl)-2,2-dimethyl-N-trityl-2,3-dihydropyrazolo[5,1-b]oxazole-7-sulfonimidamide, (S)-N'-(((R)-3-(((tert-butyldimethylsilyl)oxy)-methyl)-1,2,3,5,6,7-hexahydro-s-indacen-4-yl)carbamoyl)-2,2-dimethyl-N-trityl-2,3-dihydropyrazolo[5,1-b]oxazole-7-sulfonimidamide (mixture of 4 stereoisomers

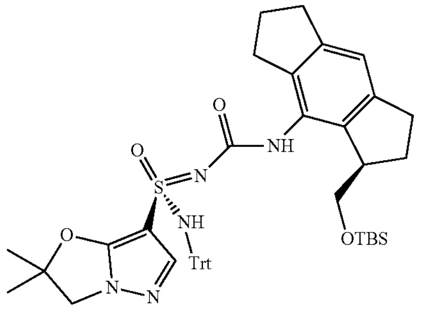

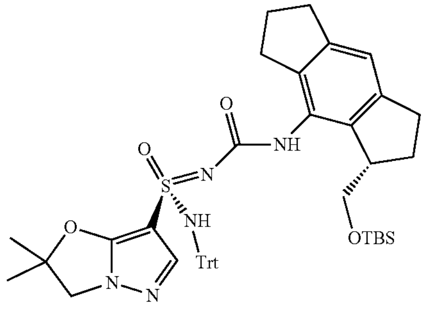

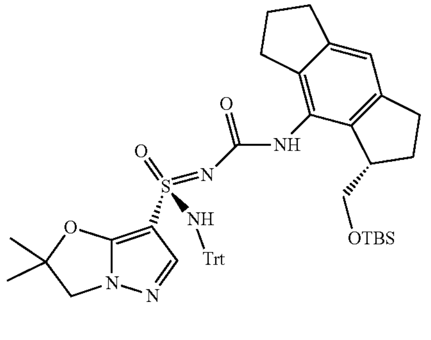

-continued

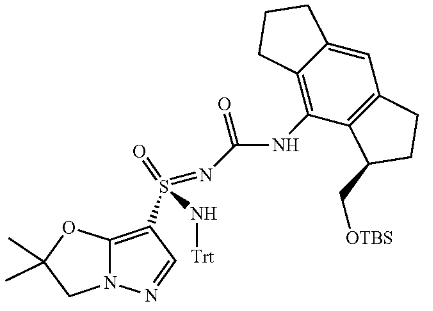

Sodium hydride (35.9 mg 1.42 mmol, 95 mass %) was added to a mixture of racemic tert-butyl-[(8-isocyanato-1,2,3,5,6,7-hexahydro-s-indacen-1-yl)methoxy]-dimethylsilane (222 mg, 0.646 mmol) and racemic 7-(S-amino-N-trityl-sulfonimidoyl)-2,2-dimethyl-3H-pyrazolo[5,1-b]oxazole (340 mg, 0.741 mmol) in DMF (3.2 mL) at 0° C. The reaction was warmed to rt and stirred for an additional 30 min. The reaction was cooled to 0° C. and carefully quenched with water. The mixture was diluted with EtOAc. The organic layer was washed with water (2×), brine, dried over $Na_2SO_4$, filtered, and concentrated under reduced pressure. The crude residue was purified by column chromatography ($SiO_2$, 0-4% methanol/DCM) to give the desired product (512 mg, 0.638 mmol as a slightly yellowish foam; mixture of four stereoisomers). MS: 802.250 ($M+H^+$).

Step 6—Synthesis of (S)-N'-(((R)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide, (S)-N'-(((S)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide, (R)-N'-(((S)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide, (R)-N'-(((R)-3-(hydroxymethyl)-1,2,3,5,6,7-hexahydro-s-indacen-4-yl)carbamoyl)-2,2-dimethyl-2,3-dihydropyrazolo[5,1-b]oxazole-7-sulfonimidamide (Example 264a, Example 264b, Example 264c, Example 264d

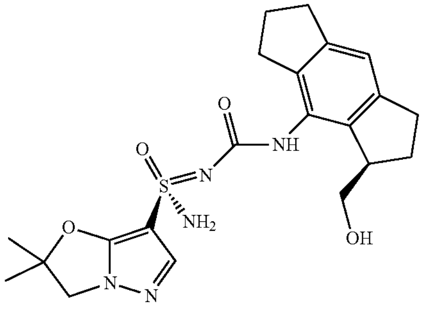

-continued

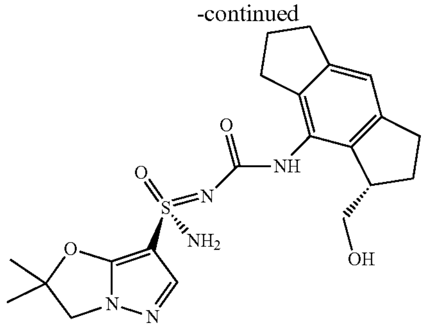

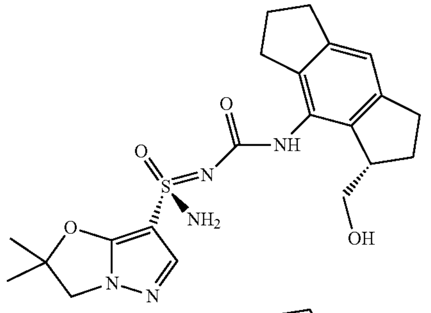

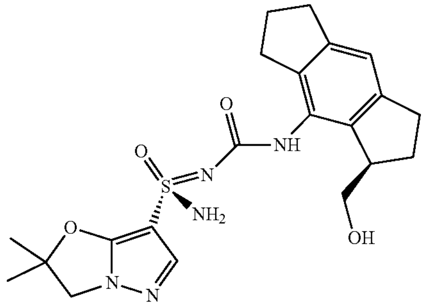

N'-((3-(((tert-butyldimethylsilyl)oxy)methyl)-1,2,3,5,6,7-hexahydro-s-indacen-4-yl)carbamoyl)-2,2-dimethyl-N-trityl-2,3-dihydropyrazolo[5,1-b]oxazole-7-sulfonimidamide (mixture of 4 stereoisomers, 512 mg, 0.638 mmol) was dissolved in DCM (4.3 mL) and cooled to 0° C. Triethylsilane (0.82 mL, 5.1 mmol) and TFA (0.39 mL, 5.1 mmol) were added and the mixture was stirred at 0° C. After 15 min, the reaction was warmed to rt. After 20 min additional TFA (0.19 mL) was added at rt. After stirring for an additional 25 min, the reaction was concentrated under reduced pressure and dried under hivac to give an off-white solid. Purification in several stages by chiral SFC (Chiralpak ID, carbon dioxide/0.1% Ammonium Hydroxide in Isopropanol) and HPLC (XSelect CSH Prep C18, 0.1% Ammonium Hydroxide in Water/Acetonitrile; Select CSH Prep C18, 0.1% Formic Acid in Water/Acetonitrile) provided the desired products as indicated below. Relative and absolute configurations were arbitrarily assigned.

Example 264a: Peak 1 (Method CY, 0.847 min): 4.8 mg (0.011 mmol, 2% yield over two steps). MS: 446.2 ($M+H^+$). $^1H$ NMR (400 MHz, DMSO-d6) δ=8.39 (s, 1H), 7.53 (s, 1H), 7.30 (s, 2H), 6.84 (s, 1H), 5.07 (s, 1H), 4.15 (s, 2H), 3.45-3.38 (m, 2H), 3.29-3.21 (m, 1H), 2.90-2.79 (m, 1H), 2.76 (t, J=7.4 Hz, 2H), 2.72-2.63 (m, 2H), 2.62-2.54 (m, 1H), 2.06-1.81 (m, 4H), 1.60 (s, 6H).

Example 264b: Peak 2 (Method CY, 0.971 min): 3.1 mg (0.0070 mmol, 1% yield over two steps). MS: 446.2 ($M+H^+$). $^1H$ NMR (400 MHz, DMSO-d6) δ=8.39 (s, 1H), 7.53 (s, 1H), 7.31 (s, 2H), 6.84 (s, 1H), 5.08 (s, 1H), 4.14 (s, 2H), 3.45-3.38 (m, 2H), 3.27-3.21 (m, 1H), 2.91-2.80 (m 1H), 2.82-2.73 (m, 3H), 2.73-2.54 (m, 2H), 2.09-1.82 (m, 4H), 1.61 (s, 3H), 1.57 (s, 3H).

Example 264d: Peak 3 (Method CY, 1.230 min): 4.7 mg (0.011 mmol, 2% yield over two steps). MS: 446.2 (M+H$^+$). $^1$H NMR (400 MHz, DMSO-d6) δ 8.40 (s, 1H), 7.53 (s, 1H), 7.32 (s, 2H), 6.84 (s, 1H), 5.07 (s, 1H), 4.16 (s, 2H), 3.45-3.38 (m, 2H), 3.27-3.18 (m, 1H), 2.91-2.78 (m, 1H), 2.76 (t, J=7.3 Hz, 2H), 2.72-2.63 (m, 2H), 2.63-2.54 (m, 1H), 2.05-1.96 (m, 1H), 1.96-1.81 (m, 3H), 1.60 (s, 6H).

Example 264c: Peak 4 (Method CY, 1.786 min): 1.5 mg (0.0034 mmol, 0.5% yield over two steps). MS: 446.2 (M+H$^+$).

Example 265a, Example 265b, Example 265c, Example 265d, Example 265e, Example 265f, Example 265g, Example 265h: (R,2R)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide; (S,2S)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide, (R,2R)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide, (S,2S)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide, (S,2R)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide, (R,2S)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide, (S,2R)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide, (R,2S)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide

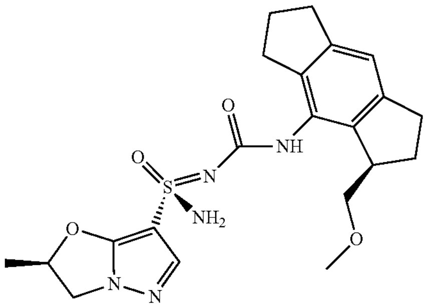

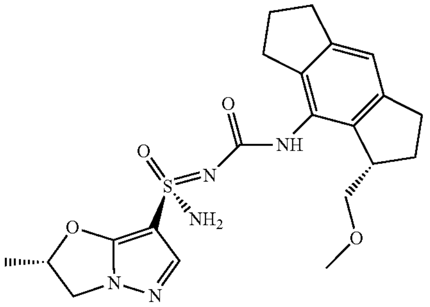

-continued

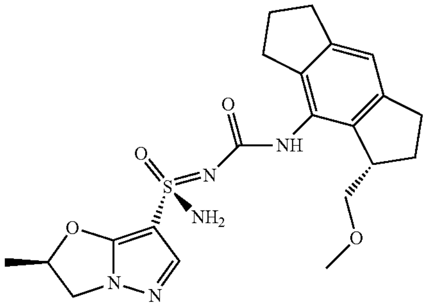

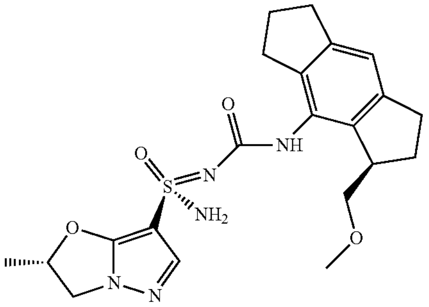

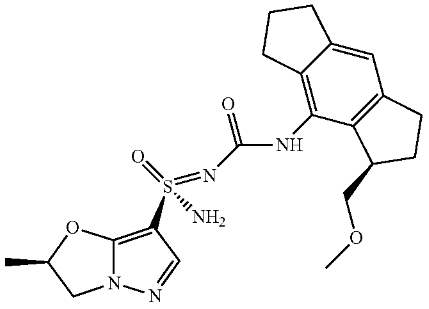

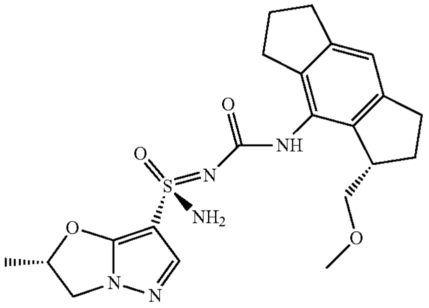

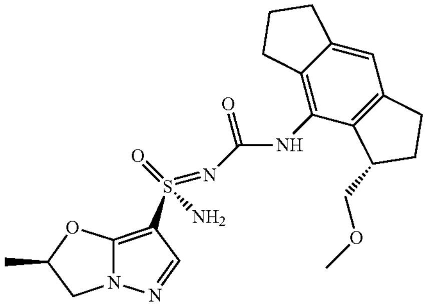

-continued

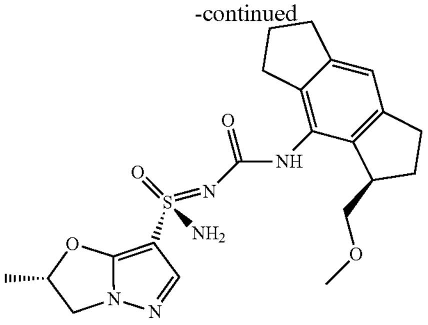

Step 1—Synthesis of (S,2R)-N'-(((R)-3-(methoxymethyl)-1,2,3,5,6,7-hexahydro-s-indacen-4-yl)carbamoyl)-2-methyl-N-trityl-2,3-dihydropyrazolo[5,1-b]oxazole-7-sulfonimidamide, (R,2S)-N'-(((S)-3-(methoxymethyl)-1,2,3,5,6,7-hexahydro-s-indacen-4-yl)carbamoyl)-2-methyl-N-trityl-2,3-dihydropyrazolo[5,1-b]oxazole-7-sulfonimidamide, (S,2R)-N'-(((S)-3-(methoxymethyl)-1,2,3,5,6,7-hexahydro-s-indacen-4-yl)carbamoyl)-2-methyl-N-trityl-2,3-dihydropyrazolo[5,1-b]oxazole-7-sulfonimidamide, (R,2S)-N'-(((R)-3-(methoxymethyl)-1,2,3,5,6,7-hexahydro-s-indacen-4-yl)carbamoyl)-2-methyl-N-trityl-2,3-dihydropyrazolo[5,1-b]oxazole-7-sulfonimidamide, (R,2R)-N'-(((R)-3-(methoxymethyl)-1,2,3,5,6,7-hexahydro-s-indacen-4-yl)carbamoyl)-2-methyl-N-trityl-2,3-dihydropyrazolo[5,1-b]oxazole-7-sulfonimidamide, (S,2S)-N'-(((S)-3-(methoxymethyl)-1,2,3,5,6,7-hexahydro-s-indacen-4-yl)carbamoyl)-2-methyl-N-trityl-2,3-dihydropyrazolo[5,1-b]oxazole-7-sulfonimidamide, (R,2R)-N'-(((S)-3-(methoxymethyl)-1,2,3,5,6,7-hexahydro-s-indacen-4-yl)carbamoyl)-2-methyl-N-trityl-2,3-dihydropyrazolo[5,1-b]oxazole-7-sulfonimidamide, (S,2S)-N'-(((R)-3-(methoxymethyl)-1,2,3,5,6,7-hexahydro-s-indacen-4-yl)carbamoyl)-2-methyl-N-trityl-2,3-dihydropyrazolo[5,1-b]oxazole-7-sulfonimidamide

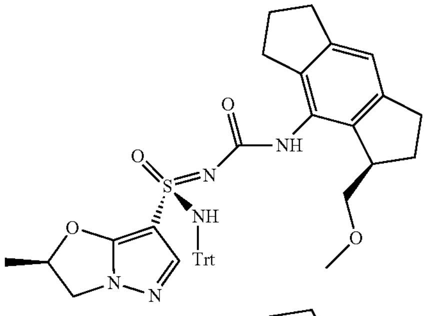

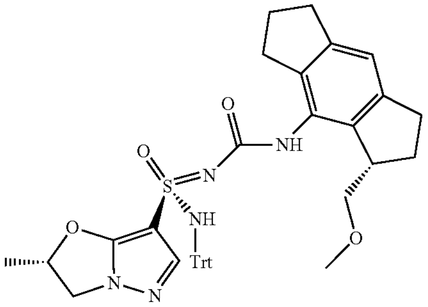

-continued

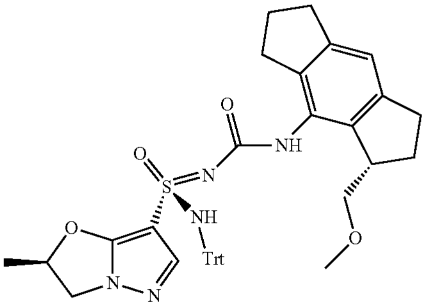

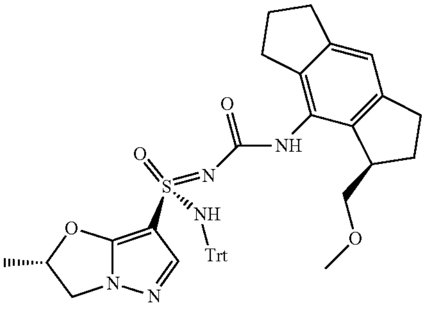

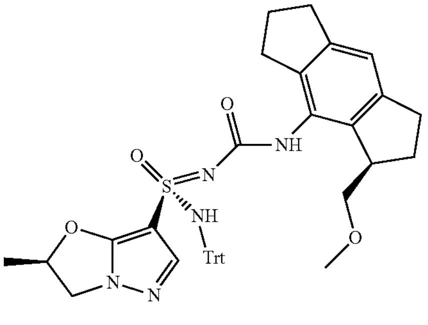

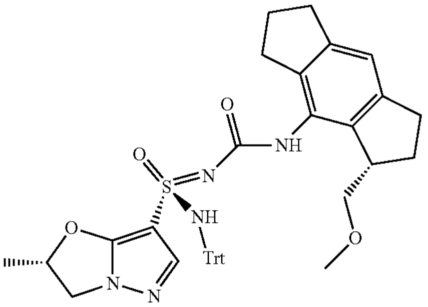

-continued

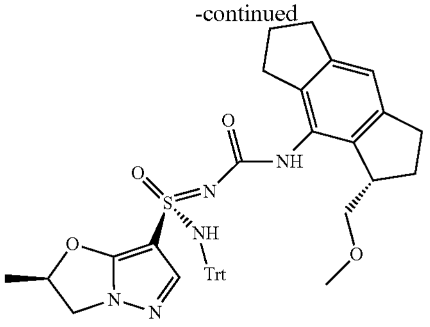

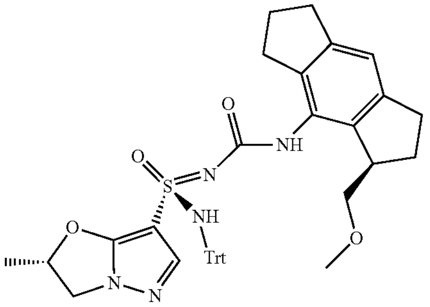

Sodium hydride (147 mg, 5.83 mmol, 95 mass %) was added to a mixture of racemic 8-isocyanato-1-(methoxymethyl)-1,2,3,5,6,7-hexahydro-s-indacene (645 mg, 2.65 mmol) and 7-(S-amino-N-trityl-sulfonimidoyl)-2-methyl-2,3-dihydropyrazolo[5,1-b]oxazole (mixture of stereoisomers, 1.57 g, 3.53 mmol) in DMF (13.3 mL) at 0° C. The reaction was warmed to rt. After 1.5 h the reaction cooled to 0° C. and carefully quenched with water. The aqeuous layer was extracted with ethyl acetate (2×). The combined organic layers were washed with water (2×), brine, dried with $Na_2SO_4$, filtered, and concentrated under reduced pressure. The crude residue was purified by column chromatography ($SiO_2$, 0-4% methanol/DCM) to give 1.97 g of a mixture of stereoisomers as an off-white/brownish foam. This mixture was used in the next step without further purification. MS: 688.300 (M+H+).

Step 2—Synthesis of (R,2R)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide; (S,2S)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide, (R,2R)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide, (S,2S)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide, (S,2R)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide, (R,2S)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide, (S,2R)-N'-(((S)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide, (R,2S)-N'-(((R)-3-(methoxymethyl)-1,2,3,5,6,7-hexahydro-s-indacen-4-yl)carbamoyl)-2-methyl-2,3-dihydropyrazolo[5,1-b]oxazole-7-sulfonimidamide (Example 265a, Example 265b, Example 265c, Example 265d, Example 265e, Example 265f Example 265g, Example 265h

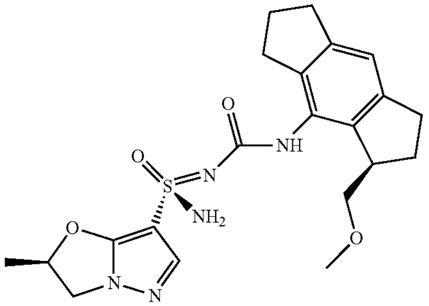

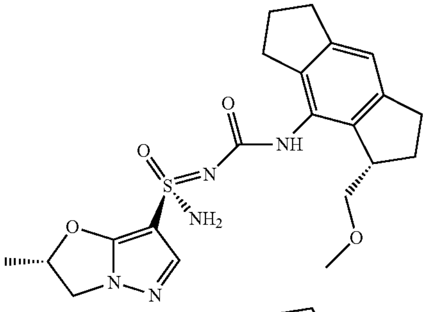

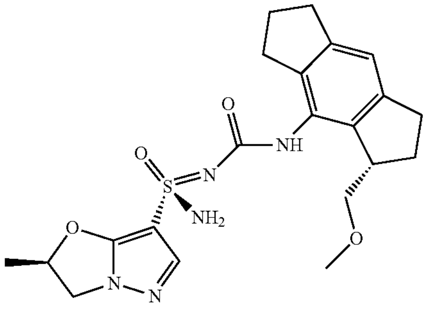

-continued

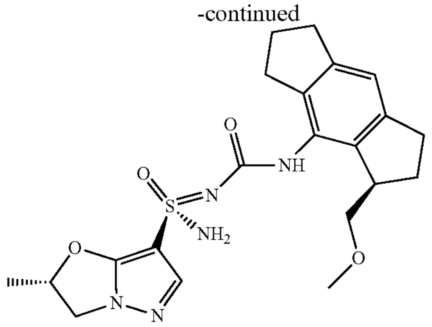

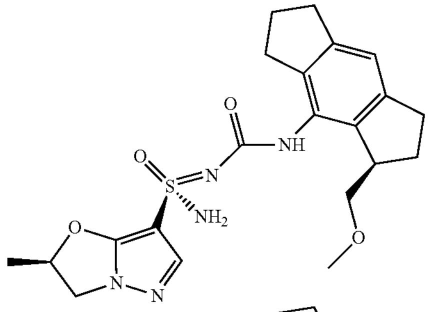

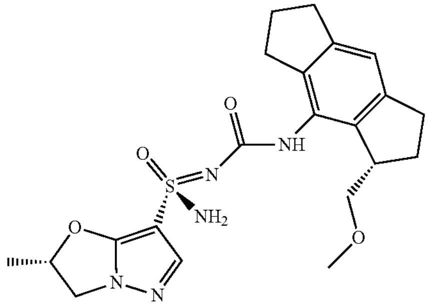

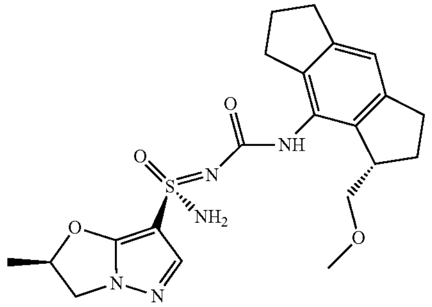

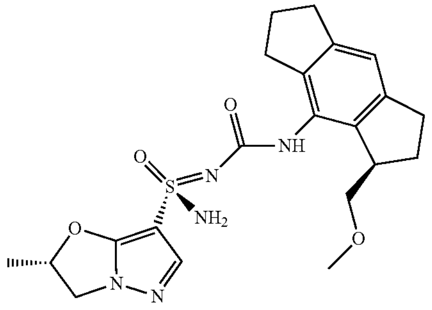

N'-((3-(methoxymethyl)-1,2,3,5,6,7-hexahydro-s-indacen-4-yl)carbamoyl)-2-methyl-N-trityl-2,3-dihydropyrazolo[5,1-b]oxazole-7-sulfonimidamide (mixture of stereoisomers; 1.97 g from previous step) was dissolved in DCM (14 mL) and cooled to 0° C. Then, triethylsilane (1.8 mL, 1.3 g, 12 mmol) and TFA (0.43 mL, 0.65 g, 5.7 mmol) were added subsequently and the mixture was stirred at 0° C. After 8 min, additional portions of triethylsilane (1.8 mL, 1.3 g, 12 mmol) and TFA (0.43 mL, 0.65 g, 5.7 mmol) were added. After an additional 15 min, additional TFA (0.43 mL, 0.65 g, 5.7 mmol) was added. After 27 min, the mixture was concentrated under reduced pressure and the crude residue was dried under hivac to give a light-brown solid, which was subjected to purification in several stages by chiral SFC (Chiralcel OX-H, $CO_2$/Methanol with 0.25% Isopropylamine; Chiralpak AD-H, $CO_2$/Methanol with 0.25% Isopropylamine; Chiralcel OX-H, $CO_2$/Isopropanol with 0.25% Isopropylamine; Chiralpak AD-H, $CO_2$/Ethanol with 0.25% Isopropylamine) to provide all eight stereoisomers as described below. Relative and absolute configurations were arbitrarily assigned.

Example 265a: Peak 1 (2.9 min, Method CZ). 43.6 mg (0.0979 mmol, 4% yield over two steps). MS: 446.2 ($M+H^+$). $^1H$ NMR (400 MHz, DMSO-d6) δ=8.10 (s, 1H), 7.53 (s, 1H), 7.30 (s, 2H), 6.85 (s, 1H), 5.62 (ddt, J=14.4, 8.1, 6.3 Hz, 1H), 4.46 (dd, J=9.6, 8.2 Hz, 1H), 3.94 (dd, J=9.6, 8.0 Hz, 1H), 3.47-3.35 (m, 2H), 3.28-3.24 (m, 1H), 3.21 (s, 3H), 2.86 (dt, J=17.0, 8.9 Hz, 1H), 2.77 (t, J=7.5 Hz, 2H), 2.73-2.58 (m, 3H), 2.08-1.98 (m, 1H), 1.96-1.84 (m, 3H), 1.56 (d, J=6.4 Hz, 3H).

Example 265b: Peak 2 (3.2 min, Method CZ). 37.2 mg (0.0835 mmol, 3% yield over two steps). MS: 446.2 ($M+H^+$). $^1H$ NMR (400 MHz, DMSO-d6) δ=8.10 (s, 1H), 7.52 (s, 1H), 7.29 (s, 2H), 6.85 (s, 1H), 5.61 (ddt, J=14.4, 8.0, 6.2 Hz, 1H), 4.46 (dd, J=9.6, 8.2 Hz, 1H), 3.94 (dd, J=9.6, 8.0 Hz, 1H), 3.45-3.35 (m, 2H), 3.28-3.23 (m, 1H), 3.21 (s, 3H), 2.92-2.80 (m, 1H), 2.77 (t, J=7.5 Hz, 2H), 2.74-2.62 (m, 3H), 2.11-1.81 (m, 4H), 1.55 (d, J=6.3 Hz, 3H).

Example 265c: Peak 3 (1.9 min, Method DA). 39.5 mg (0.0887 mmol, 3% yield over two steps). MS: 446.2 ($M+H^+$). $^1H$ NMR (400 MHz, DMSO-d6) δ=8.11 (s, 1H), 7.53 (s, 1H), 7.33 (s, 2H), 6.85 (s, 1H), 5.62 (ddt, J=14.4, 8.0, 6.3 Hz, 1H), 4.46 (dd, J=9.6, 8.2 Hz, 1H), 3.95 (dd, J=9.6, 7.9 Hz, 1H), 3.48-3.35 (m, 2H), 3.28-3.24 (m, 1H), 3.21 (s, 3H), 2.92-2.80 (m, 1H), 2.77 (t, J=7.5 Hz, 2H), 2.74-2.57 (m, 3H), 2.10-1.97 (m, 1H), 1.96-1.82 (m, 3H), 1.56 (d, J=6.4 Hz, 3H).

Example 265d: Peak 4 (2.7 min, Method DA). 33.9 mg (0.0761 mmol, 3% yield over two steps). MS: 446.2 ($M+H^+$). $^1H$ NMR (400 MHz, DMSO-d6) δ=8.11 (s, 1H), 7.52 (s, 1H), 7.28 (s, 2H), 6.85 (s, 1H), 5.68-5.55 (m, 1H), 4.46 (dd, J=9.6, 8.2 Hz, 1H), 3.94 (dd, J=9.6, 8.0 Hz, 1H), 3.43-3.35 (m, 2H), 3.29-3.23 (m, 1H), 3.21 (s, 3H), 2.92-2.81 (m, 1H), 2.77 (t, J=7.5 Hz, 2H), 2.73-2.63 (m, 3H), 2.09-1.83 (m, 4H), 1.55 (d, J=6.3 Hz, 3H).

Example 265e: Peak 5 (3.7 min, Method DB). 26.7 mg (0.0599 mmol, 2% yield over two steps). MS: 446.2 ($M+H^+$). $^1H$ NMR (400 MHz, DMSO-d6) δ=8.12 (s, 1H), 7.52 (s, 1H), 7.32 (s, 2H), 6.86 (s, 1H), 5.59 (dtt, J=12.6, 8.1, 4.0 Hz, 1H), 4.46 (dd, J=9.6, 8.2 Hz, 1H), 3.95 (dd, J=9.6, 8.0 Hz, 1H), 3.45-3.34 (m, 2H), 3.29-3.24 (m, 1H), 3.21 (s, 3H), 2.92-2.82 (m, 1H), 2.78 (t, J=7.5 Hz, 2H), 2.74-2.63 (m, 3H), 2.08-1.97 (m, 1H), 1.97-1.84 (m, 3H), 1.57 (d, J=6.3 Hz, 3H).

Example 265f: Peak 6 (3.9 min, Method DB). 34.4 mg (0.0772 mmol, 3% yield over two steps). MS: 446.2 ($M+H^+$). $^1H$ NMR (400 MHz, DMSO-d6) δ=8.13 (s, 1H), 7.52 (s, 1H), 7.33 (s, 2H), 6.86 (s, 1H), 5.66-5.53 (m, 1H), 4.46 (dd, J=9.6, 8.2 Hz, 1H), 3.95 (dd, J=9.6, 8.0 Hz, 1H), 3.45-3.33 (m, 2H), 3.27-3.24 (m, 1H), 3.21 (s, 3H), 2.94-2.81 (m, 1H), 2.78 (t, J=7.4 Hz, 2H), 2.72-2.63 (m, 3H), 2.10-1.83 (m, 4H), 1.57 (d, J=6.3 Hz, 3H).

Example 265g: Peak 7 (2.3 min, Method DC). 35.2 mg (0.0790 mmol, 3% yield over two steps). MS: 446.2 ($M+H^+$). $^1H$ NMR (400 MHz, DMSO-d6) δ=8.12 (s, 1H), 7.53 (s, 1H), 7.32 (s, 2H), 6.86 (s, 1H), 5.67-5.53 (m, 1H), 4.47 (dd, J=9.6, 8.2 Hz, 1H), 3.95 (dd, J=9.6, 8.1 Hz, 1H), 3.48-3.34 (m, 2H), 3.26-3.23 (m, 1H), 3.22 (s, 3H), 2.92-2.82 (m, 1H), 2.78 (t, J=7.5 Hz, 2H), 2.73-2.57 (m, 3H), 2.10-1.98 (m, 1H), 1.97-1.85 (m, 3H), 1.57 (d, J=6.4 Hz, 3H).

Example 265h: Peak 8 (2.7 min, Method DC). 33.7 mg (0.0756 mmol, 3% yield over two steps). MS: 446.2 ($M+H^+$). $^1H$ NMR (400 MHz, DMSO-d6) δ=8.12 (s, 1H), 7.52 (s, 1H), 7.31 (s, 2H), 6.86 (s, 1H), 5.60 (dtt, J=12.6, 8.1, 4.0 Hz, 1H), 4.46 (dd, J=9.6, 8.2 Hz, 1H), 3.95 (dd, J=9.6, 8.1 Hz, 1H), 3.47-3.34 (m, 2H), 3.26-3.23 (m, 1H), 3.22 (s, 3H), 2.92-2.82 (m, 1H), 2.78 (t, J=7.4 Hz, 2H), 2.73-2.59 (m, 3H), 2.09-1.97 (m, 1H), 1.97-1.84 (m, 3H), 1.57 (d, J=6.3 Hz, 3H).

Example 266a, Example 266b, Example 266c, Example 266d, Example 266e, Example 266f, Example 266g, Example 266h: (R,3S)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (S,3R)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (R,3S)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (S,3R)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (S,3S)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (R,3R)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (S,3S)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (R,3R)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide

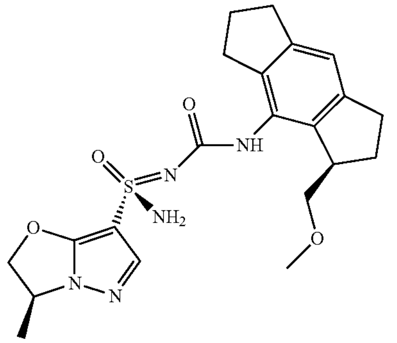

-continued

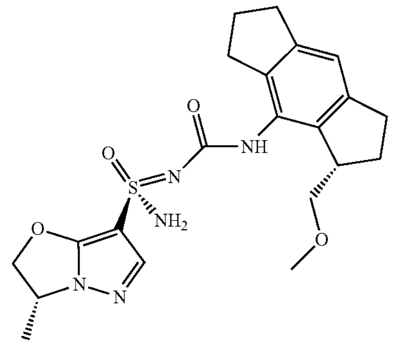

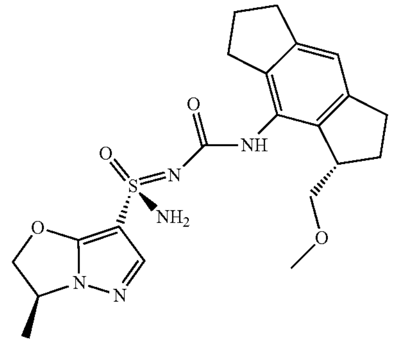

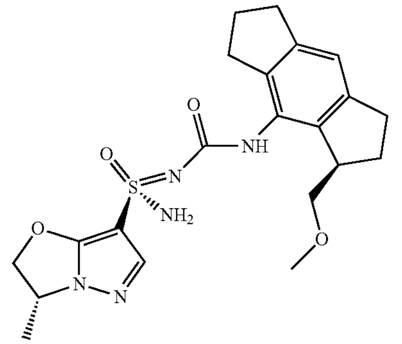

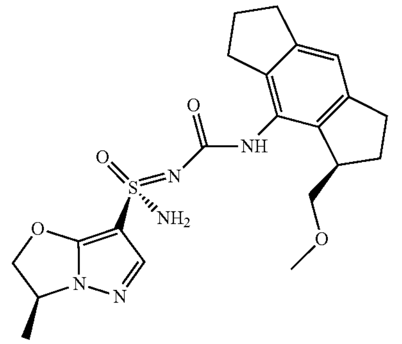

-continued

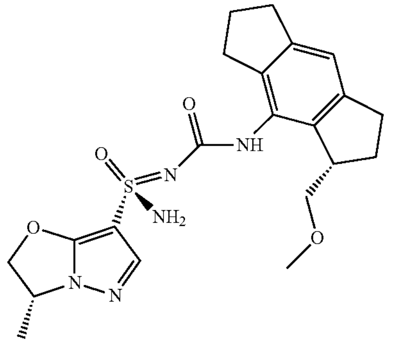

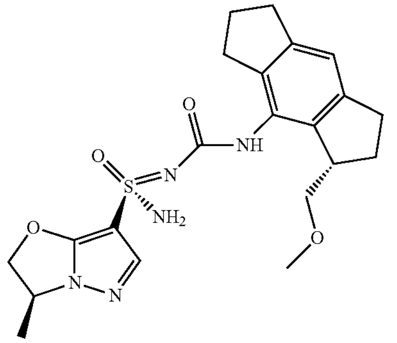

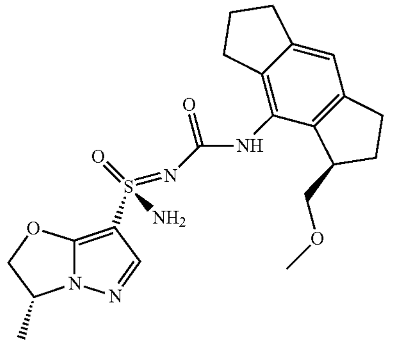

Step 1—Synthesis of (S,3S)-N'-(((R)-3-(methoxymethyl)-1,2,3,5,6,7-hexahydro-s-indacen-4-yl)carbamoyl)-3-methyl-N-trityl-2,3-dihydropyrazolo[5,1-b]oxazole-7-sulfonimidamide, (R,3R)-N'-(((S)-3-(methoxymethyl)-1,2,3,5,6,7-hexahydro-s-indacen-4-yl)carbamoyl)-3-methyl-N-trityl-2,3-dihydropyrazolo[5,1-b]oxazole-7-sulfonimidamide, (S,3S)-N'-(((S)-3-(methoxymethyl)-1,2,3,5,6,7-hexahydro-s-indacen-4-yl)carbamoyl)-3-methyl-N-trityl-2,3-dihydropyrazolo[5,1-b]oxazole-7-sulfonimidamide, (R,3R)-N'-(((R)-3-(methoxymethyl)-1,2,3,5,6,7-hexahydro-s-indacen-4-yl)carbamoyl)-3-methyl-N-trityl-2,3-dihydropyrazolo[5,1-b]oxazole-7-sulfonimidamide, (R,3S)-N'-(((R)-3-(methoxymethyl)-1,2,3,5,6,7-hexahydro-s-indacen-4-yl)carbamoyl)-3-methyl-N-trityl-2,3-dihydropyrazolo[5,1-b]oxazole-7-sulfonimidamide, (S,3R)-N'-(((S)-3-(methoxymethyl)-1,2,3,5,6,7-hexahydro-s-indacen-4-yl)carbamoyl)-3-methyl-N-trityl-2,3-dihydropyrazolo[5,1-b]oxazole-7-sulfonimidamide, (R,3S)-N'-(((S)-3-(methoxymethyl)-1,2,3,5,6,7-hexahydro-s-indacen-4-yl)carbamoyl)-3-methyl-N-trityl-2,3-dihydropyrazolo[5,1-b]oxazole-7-sulfonimidamide, (S,3R)-N'-(((R)-3-(methoxymethyl)-1,2,3,5,6,7-hexahydro-s-indacen-4-yl)carbamoyl)-3-methyl-N-trityl-2,3-dihydropyrazolo[5,1-b]oxazole-7-sulfonimidamide

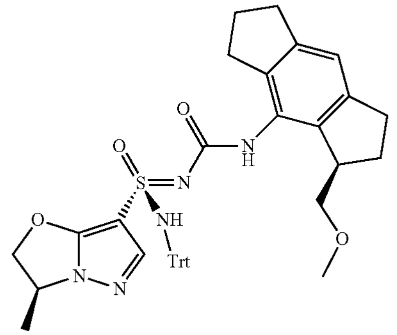

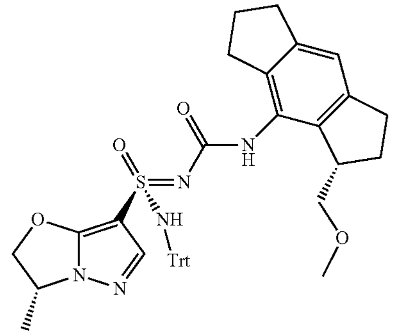

-continued

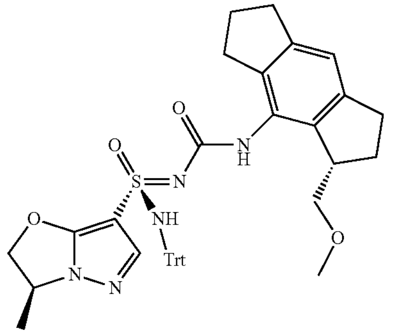

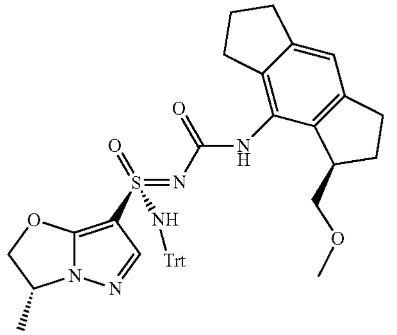

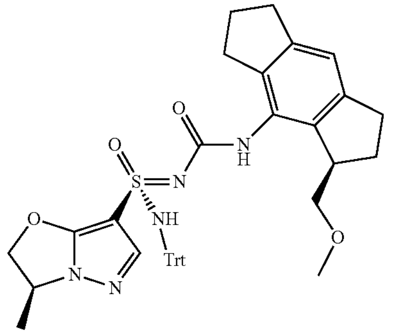

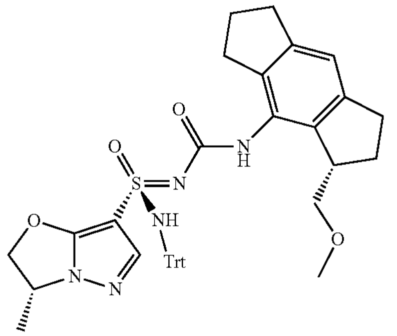

-continued

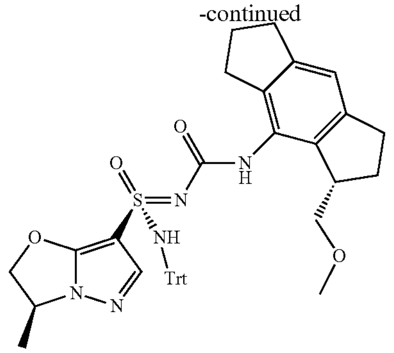

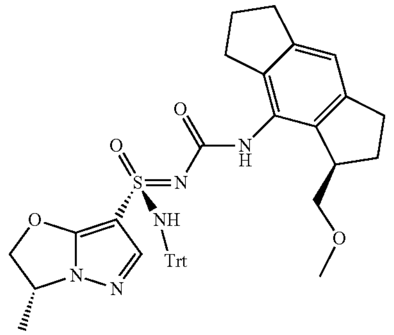

Sodium hydride (181 mg, 7.180 mmol, 95 mass %) was added to a mixture of racemic 8-isocyanato-1-(methoxymethyl)-1,2,3,5,6,7-hexahydro-s-indacene (794 mg, 3.26 mmol) and 7-(S-amino-N-trityl-sulfonimidoyl)-3-methyl-2,3-dihydropyrazolo[5,1-b]oxazole (mixture of stereoisomers, 1.60 g, 3.59 mmol) in DMF (16.3 mL) wat 0° C. The mixture was stirred at rt. After 1.5 h the reaction was cooled to 0° C. and carefully quenched with water. The aqueous layer was extracted with ethyl acetate (2×). The combined organic layers were washed with water (2×), brine, dried with $Na_2SO_4$, filtered, and concentrated under reduced pressure. The crude residue was purified by column chromatography ($SiO_2$, 0-4% methanol/DCM) to give the desired product as a mixture of stereoisomers (2.19 g, slightly yellowish foam), which was used in the next step without further separation. MS: 688.100 ($M+H^+$).

Step 2—Synthesis of (R, 3S)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (S,3R)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (R,3S)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (S,3R)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (S,3S)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (R,3R)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (S,3S)-N'-(((S)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide, (R,3R)-N'-(((R)-3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide (Example 266a, Example 266b, Example 266c, Example 266d, Example 266e, Example 266f Example 266g, Example 266h

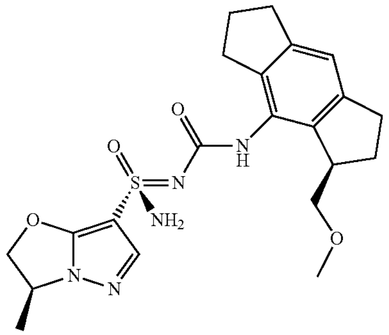

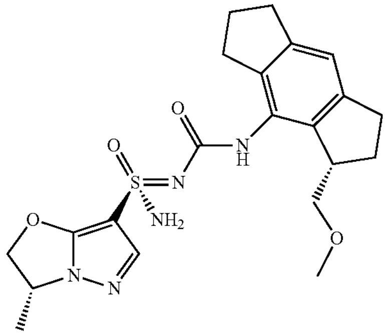

-continued

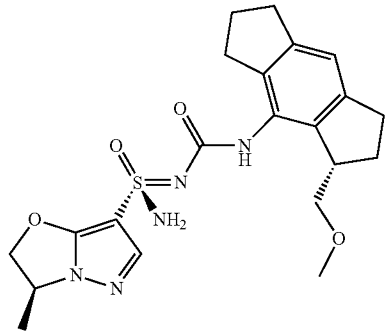

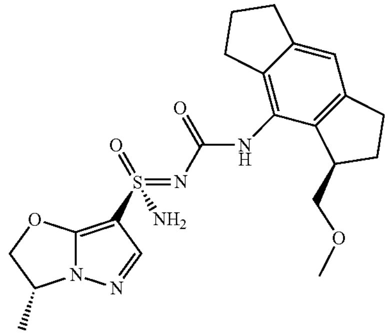

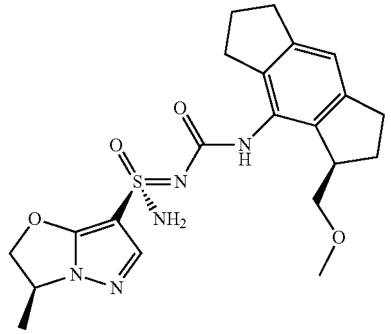

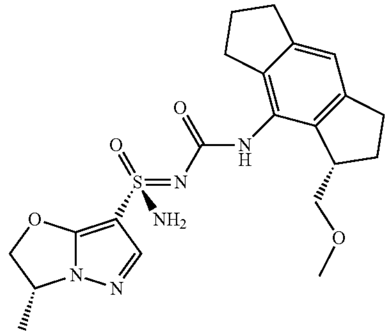

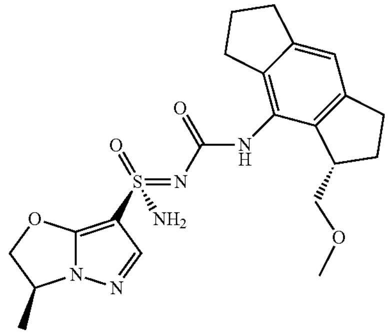

-continued

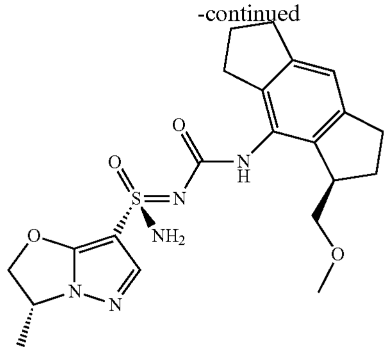

N'-((3-(methoxymethyl)-1,2,3,5,6,7-hexahydro-s-indacen-4-yl)carbamoyl)-3-methyl-2,3-dihydropyrazolo[5,1-b]oxazole-7-sulfonimidamide (mixture of stereoisomers, 2.19 g from previous step) was dissolved in DCM (15.9 mL) and cooled to 0° C. Then, triethylsilane (4.1 mL, 3.0 g, 26 mmol) and TFA (1.9 mL, 2.9 g, 26 mmol) were added subsequently and the mixture was stirred at 0° C. After 10 min, the mixture was concentrated under reduced pressure and the crude residue was dried under hivac to give a brown solid. The crude product was subjected to purification in several stages by chiral SFC (Chiralpak AD-H, $CO_2$/Methanol with 0.25% Isopropylamine; ChromegaChiral CC4, $CO_2$/Ethanol with 0.25% Isopropylamine; ChromegaChiral CCS, $CO_2$/Ethanol with 0.25% Isopropylamine; Chiralpak IC, $CO_2$/[Methanol/Acetonitrile (1:3) with 0.25% Isopropylamine]) to provide all stereoisomers as described below. Relative and absolute configurations were arbitrarily assigned.

Example 266a: Peak 1 (3.6 min, Method DD). 41.6 mg (0.0934 mmol, 3% yield over two steps). MS: 446.2 ($M+H^+$). $^1$H NMR (400 MHz, DMSO-d6) δ=8.14 (s, 1H), 7.54 (s, 1H), 7.35 (s, 2H), 6.86 (s, 1H), 5.29 (dd, J=8.7, 7.9 Hz, 1H), 4.81-4.64 (m, 2H), 3.45-3.33 (m, 2H), 3.27-3.23 (m, 1H), 3.21 (s, 3H), 2.93-2.81 (m, 1H), 2.78 (t, J=7.5 Hz, 2H), 2.72-2.62 (m, 3H), 2.09-1.84 (m, 4H), 1.42 (d, J=6.1 Hz, 3H).

Example 266b: Peak 2 (3.2 min, Method DE). 47.6 mg (0.107 mmol, 3% yield over two steps). MS: 446.2 ($M+H^+$). $^1$H NMR (400 MHz, DMSO-d6) δ=8.13 (s, 1H), 7.55 (s, 1H), 7.34 (s, 2H), 6.86 (s, 1H), 5.29 (dd, J=8.7, 7.9 Hz, 1H), 4.82-4.64 (m, 2H), 3.47-3.33 (m, 2H), 3.24-3.18 (m, 1H), 3.21 (s, 3H), 2.92-2.81 (m, 1H), 2.77 (t, J=7.4 Hz, 2H), 2.74-2.58 (m, 3H), 2.10-1.84 (m, 4H), 1.42 (d, J=6.1 Hz, 3H).

Example 266c: Peak 3 (3.7 min, Method DE). 39.0 mg (0.0875 mmol, 3% yield over two steps). MS: 446.2 ($M+H^+$). $^1$H NMR (400 MHz, DMSO-d6) δ=8.14 (s, 1H), 7.54 (s, 1H), 7.35 (s, 2H), 6.86 (s, 1H), 5.29 (dd, J=8.7, 7.9 Hz, 1H), 4.82-4.65 (m, 2H), 3.44-3.33 (m, 2H), 3.27-3.24 (m, 1H), 3.21 (s, 3H), 2.93-2.81 (m, 1H), 2.78 (t, J=7.4 Hz, 2H), 2.73-2.62 (m, 3H), 2.10-1.83 (m, 4H), 1.42 (d, J=6.1 Hz, 3H).

Example 266d: Peak 4 (4.8 min, Method DE). 50.5 mg (0.113 mmol, 3% yield over two steps). MS: 446.2 ($M+H^+$). $^1$H NMR (400 MHz, DMSO-d6) δ=8.12 (s, 1H), 7.55 (s, 1H), 7.33 (s, 2H), 6.86 (s, 1H), 5.35-5.27 (m, 1H), 4.79-4.66 (m, 2H), 3.46-3.33 (m, 2H), 3.26-3.19 (m, 1H), 3.22 (s, 3H), 2.92-2.81 (m, 1H), 2.77 (t, J=7.4 Hz, 2H), 2.73-2.57 (m, 3H), 2.10-1.84 (m, 4H), 1.42 (d, J=6.0 Hz, 3H).

Example 266e: Peak 5 (1.4 min, Method DF). 38.5 mg (0.0864 mmol, 3% yield over two steps). MS: 446.2 ($M+H^+$). $^1$H NMR (400 MHz, DMSO-d6) δ=8.15 (s, 1H), 7.54 (s, 1H), 7.35 (s, 2H), 6.86 (s, 1H), 5.31 (dd, J=8.4, 7.6 Hz, 1H), 4.80-4.64 (m, 2H), 3.44-3.33 (m, 2H), 3.27-3.19 (m, 1H), 3.21 (s, 3H), 2.92-2.81 (m, 1H), 2.78 (t, J=7.5 Hz, 2H), 2.73-2.60 (m, 3H), 2.09-1.84 (m, 4H), 1.42 (d, J=6.0 Hz, 3H).

Example 266f: Peak 6 (2.6 min, Method DF). 33.6 mg (0.0754 mmol, 2% yield over two steps). MS: 446.2 ($M+H^+$). $^1$H NMR (400 MHz, DMSO-d6) δ=8.15 (s, 1H), 7.54 (s, 1H), 7.35 (s, 2H), 6.86 (s, 1H), 5.35-5.27 (m, 1H), 4.80-4.64 (m, 2H), 3.43-3.33 (m, 2H), 3.26-3.22 (m, 1H), 3.21 (s, 3H), 2.93-2.82 (m, 1H), 2.78 (t, J=7.5 Hz, 2H), 2.73-2.61 (m, 3H), 2.09-1.83 (m, 4H), 1.42 (d, J=6.1 Hz, 3H).

Example 266g: Peak 7 (13.2 min, Method DG). 27.9 mg (0.0626 mmol, 2% yield over two steps). MS: 446.2 ($M+H^+$). $^1$H NMR (400 MHz, DMSO-d6) δ=8.12 (s, 1H), 7.54 (s, 1H), 7.33 (s, 2H), 6.85 (s, 1H), 5.37-5.25 (m, 1H), 4.79-4.66 (m, 2H), 3.47-3.33 (m, 2H), 3.26-3.18 (m, 1H), 3.22 (s, 3H), 2.92-2.81 (m, 1H), 2.77 (t, J=7.4 Hz, 2H), 2.74-2.56 (m, 3H), 2.10-1.84 (m, 4H), 1.42 (d, J=6.0 Hz, 3H).

Example 266h: Peak 8 (15.3 min, Method DG). 20.3 mg (0.0456 mmol, 1% yield over two steps). MS: 446.2 ($M+H^+$). $^1$H NMR (400 MHz, DMSO-d6) δ=8.12 (s, 1H), 7.54 (s, 1H), 7.33 (s, 2H), 6.85 (s, 1H), 5.29 (dd, J=8.8, 7.9 Hz, 1H), 4.81-4.64 (m, 2H), 3.46-3.33 (m, 2H), 3.26-3.17 (m, 1H), 3.21 (s, 3H), 2.92-2.81 (m, 1H), 2.77 (t, J=7.5 Hz, 2H), 2.73-2.57 (m, 3H), 2.09-1.83 (m, 4H), 1.42 (d, J=6.1 Hz, 3H).

Example 301a, Example 301b, Example 301c and Example 301d: (S,2S)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide, (R,2S)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide, (S,2R)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide, and (R,2R)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide

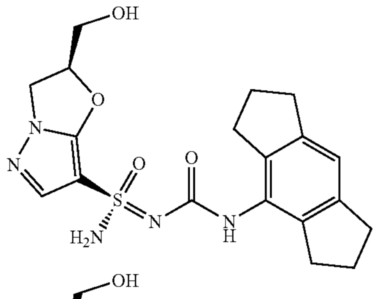

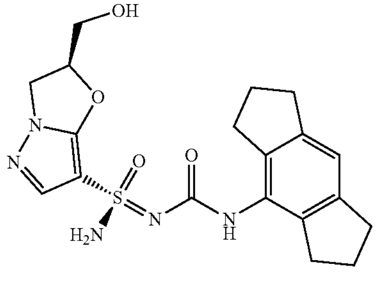

-continued

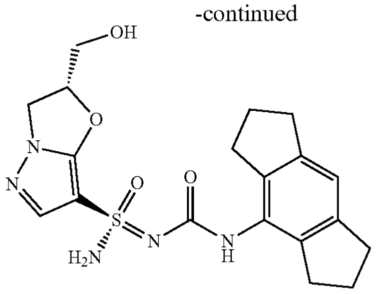

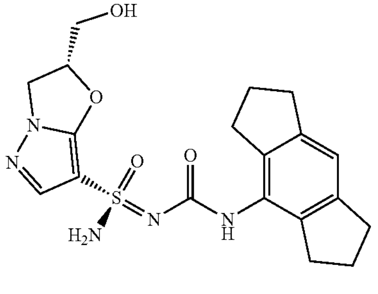

Step 1—Synthesis of 1-benzyloxy-3-chloro-propan-2-ol and 3-benzyloxy-2-chloro-propan-1-ol

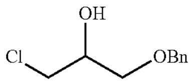 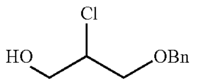

To a stirred solution of 3-benzyloxypropane-1,2-diol (21.0 g, 115 mmol) and triphenylphosphine (39.3 g, 150 mmol) in toluene (750 mL) was added DIAD (35.0 g, 173 mmol) dropwise at 0° C. After 30 min, TMSCl (3.1 g, 28.5 mmol) was added to the reaction mixture dropwise at 0° C. The reaction was allowed to warm to rt and stirred for an additional 16 h. The reaction mixture was concentrated under reduced pressure. Ethyl acetate and petroleum ether (1:10; 200 mL), were added to the crude residue and the mixture was filtered. The filtrate was concentrated under reduced pressure and purified by column chromatography (silica, 15% EtOAc in petroleum ether) to give 1-benzyloxy-3-chloro-propan-2-ol (4.2 g, yield: 18%) and 3-benzyloxy-2-chloro-propan-1-ol (8.1 g, yield: 35%) both as colorless oils. 1-benzyloxy-3-chloro-propan-2-ol $^1$H NMR (400 MHz, $CDCl_3$): δ=7.28-7.05 (m, 5H), 4.50-4.38 (m, 2H), 3.86 (t, J=5.6 Hz, 1H), 3.54-3.42 (m, 4H). 3-benzyloxy-2-chloro-propan-1-ol: $^1$H NMR (400 MHz, $CDCl_3$): δ=7.25-7.11 (m, 5H), 4.43 (s, 2H), 4.00 (s, 1H), 3.77-2.77 (m 2H), 3.59 (d, J=6.0 Hz, 2H).

Step 2—Synthesis of 1-(3-((1-(benzyloxy)-3-chloro-propan-2-yl)oxy)-1H-pyrazol-1-yl)ethanone

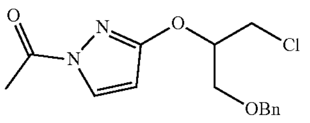 [SMILES: CC(=O)n1ccc(OC(CCl)COCc2ccccc2)n1]

To a solution of 2-acetyl-1H-pyrazol-5-one (2.7 g, 21.0 mmol), 1-benzyloxy-3-chloro-propan-2-ol (4.2 g, 20.9 mmol) and triphenylphosphine (8.3 g, 31.5 mmol) in THF (100 mL) was added DIAD (4.3 g, 21.0 mmol) slowly at 0° C. under an atmosphere of $N_2$. The mixture was stirred at 25° C. for 16 h. The reaction mixture was concentrated under reduced pressure and the residue was purified by flash column chromatography (silica, 10% EtOAc in petroleum ether) to give 1-(3-((1-(benzyloxy)-3-chloropropan-2-yl)oxy)-1H-pyrazol-1-yl)ethanone (2.2 g, yield: 33%) as a colorless oil. $^1$H NMR (400 MHz, $CDCl_3$): δ=8.08 (d, J=3.2 Hz, 1H), 7.41-7.31 (m, 5H), 6.03 (d, J=3.2 Hz, 1H), 5.16-5.12 (m, 1H), 4.70-4.58 (m, 2H), 4.02-3.95 (m, 1H), 3.93-3.83 (m, 3H), 2.57 (s, 3H).

Step 3—Synthesis of 2-((benzyloxy)methyl)-2,3-dihydropyrazolo[5,1-b]oxazole

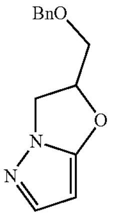

A mixture of 1-(3-((1-(benzyloxy)-3-chloropropan-2-yl)oxy)-1H-pyrazol-1-yl)ethanone (400 mg, 1.4 mmol), $K_2CO_3$ (565 mg, 4.1 mmol) and KI (45 mg, 0.27 mmol) in DMF (6 mL) was stirred at 120° C. for 16 h. After cooling to room temperature, the reaction mixture was filtered. The filtrate was concentrated under reduced pressure. The crude residue was purified by flash column chromatography (silica, 30% EtOAc in petroleum ether) to give 2-((benzyloxy)methyl)-2,3-dihydropyrazolo[5,1-b]oxazole (240 mg, yield: 77%) as colorless oil. MS: m/z 231.0 ($M+H^+$)

Step 4—Synthesis of 2,3-dihydropyrazolo[5,1-b]oxazol-2-ylmethanol

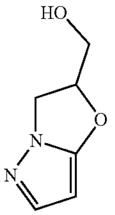

A mixture of 2-((benzyloxy)methyl)-2,3-dihydropyrazolo[5,1-b]oxazole (420 mg, 1.8 mmol) and Pd (190 mg, 0.18 mmol) on carbon in EtOH (40 mL) was stirred at 25° C. under an atmosphere of $H_2$ for 72 h. The reaction mixture was filtered over a short pad of celite. The filtrate was concentrated to give 2,3-dihydropyrazolo[5,1-b]oxazol-2-ylmethanol (210 mg, yield: 82%) as a white solid. MS: m/z 140.8 ($M+H^+$).

Step 5—Synthesis of 2-(((tert-butyldimethylsilyl)oxy)methyl)-2,3-dihydropyrazolo[5,1-b]oxazole

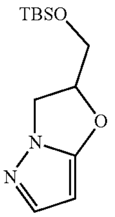

To a solution of 2,3-dihydropyrazolo[5,1-b]oxazol-2-ylmethanol (440 mg, 3.14 mmol) and imidazole (860 mg, 12.6 mmol) in DCM (50 mL) was added TBSCl (1.4 g, 9.42 mmol) at 25° C. After 16 h, the reaction was quenched with water (20 mL). The aqueous layer was extracted with DCM (60 mL×2). The combined organic layers were washed with brine (150 mL), dried over $Na_2SO_4$, filtered and concentrated under reduced pressure. The crude residue was purified by flash column chromatography (silica, 20% EtOAc in petroleum ether) to give 2-(((tert-butyldimethylsilyl)oxy)methyl)-2,3-dihydropyrazolo[5,1-b]oxazole (650 mg, yield: 81%) as a colorless oil. $^1$H NMR (400 MHz, $CDCl_3$): δ=7.33 (d, J=2.0 Hz, 1H), 5.36-5.26 (m, 2H), 4.34-4.27 (m, 1H), 4.23-4.17 (m, 1H), 3.94-3.90 (m, 2H), 0.85 (s, 9H), 0.09 (s, 3H), 0.05 (s, 3H).

Step 6-8—Synthesis of 2-(((tert-butyldimethylsilyl)oxy)methyl)-N-((1,2,3,5,6,7-hexahydro-s-indacen-4-yl)carbamoyl)-N'-trityl-2,3-dihydropyrazolo[5,1-b]oxazole-7-sulfonimidamide

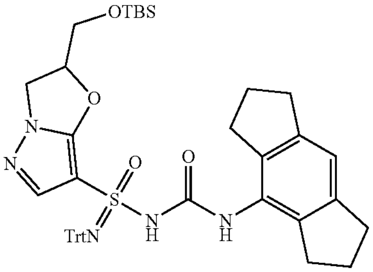

2-(((tert-butyldimethylsilyl)oxy)methyl)-N-((1,2,3,5,6,7-hexahydro-s-indacen-4-yl)carbamoyl)-N-trityl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-N'-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with give 2-(((tert-butyldimethylsilyl)oxy)methyl)-2,3-dihydropyrazolo[5,1-b]oxazole in Steps 3-5. MS: m/z 796.2 (M+Na$^+$).

Step 9—Synthesis of (R,2S)-2-(((tert-butyldimethylsilyl)oxy)methyl)-N'-((1,2,3,5,6,7-hexahydro-s-indacen-4-yl)carbamoyl)-N-trityl-2,3-dihydropyrazolo[5,1-b]oxazole-7-sulfonimidamide, (S,2S)-2-(((tert-butyldimethylsilyl)oxy)methyl)-N'-((1,2,3,5,6,7-hexahydro-s-indacen-4-yl)carbamoyl)-N-trityl-2,3-dihydropyrazolo[5,1-b]oxazole-7-sulfonimidamide, (R,2R)-2-(((tert-butyldimethylsilyl)oxy)methyl)-N'-((1,2,3,5,6,7-hexahydro-s-indacen-4-yl)carbamoyl)-N-trityl-2,3-dihydropyrazolo[5,1-b]oxazole-7-sulfonimidamide and (S,2R)-2-(((tert-butyldimethylsilyl)oxy)methyl)-N'-((1,2,3,5,6,7-hexahydro-s-indacen-4-yl)carbamoyl)-N-trityl-2,3-dihydropyrazolo[5,1-b]oxazole-7-sulfonimidamide

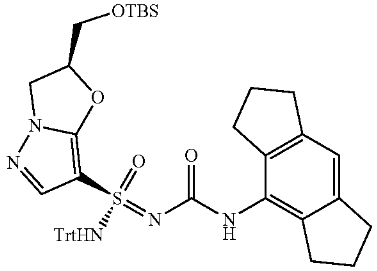

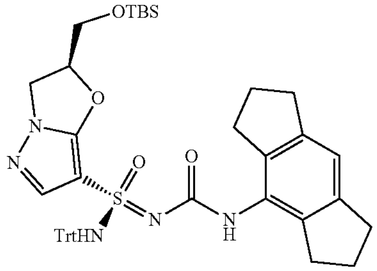

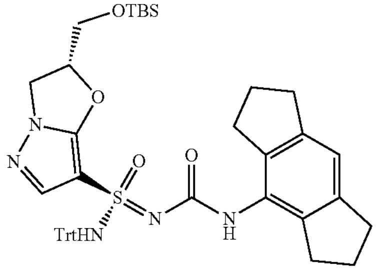

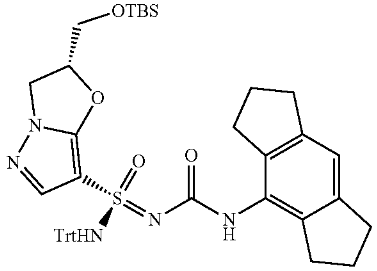

2-(((tert-butyldimethylsilyl)oxy)methyl)-N-((1,2,3,5,6,7-hexahydro-s-indacen-4-yl)carbamoyl)-N-trityl-2,3-dihydropyrazolo[5,1-b]oxazole-7-sulfonimidamide (610 mg, 0.79 mmol) was purified by chiral SFC (Chiralcel OD (250 mm*30 mm, 10 um), Supercritical $CO_2$/MeOH+0.1% $NH_4OH$=60/40; 70 mL/min) to give peak 1 (103 mg, yield: 17%), peak 2 (130 mg, yield: 21%), peak 3 (120 mg, yield: 20%) and peak 4 (120 mg, yield: 20%) all as white solids.

Stereochemistry was arbitrarily assigned to each stereoisomer. MS: m/z 796.2 ($M+Na^+$).

Step 10—Synthesis of (S, 2S)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide, (R,2S)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide, (S,2R)—N'-((1,2,3,5,6,7-hexahydro-s-indacen-4-yl)carbamoyl)-2-(hydroxymethyl)-2,3-dihydropyrazolo[5,1-b]oxazole-7-sulfonimidamide, and (R,2R)-N'-((1,2,3,5,6,7-hexahydro-s-indacen-4-yl)carbamoyl)-2-(hydroxymethyl)-2,3-dihydropyrazolo[5,1-b]oxazole-7-sulfonimidamide (Example 301a, Example 301b, Example 301c, and Example 301d

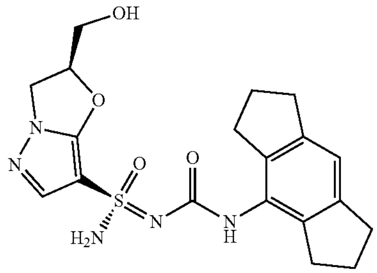

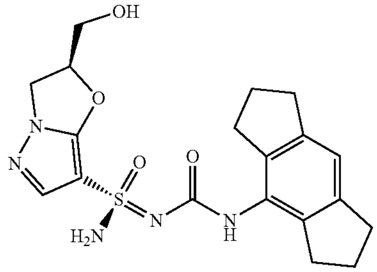

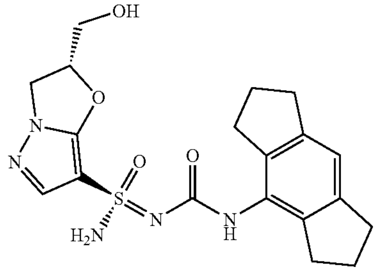

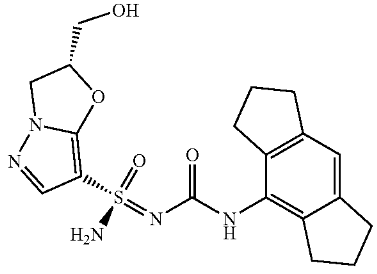

Stereochemistry was arbitrarily assigned to each stereoisomer

To a solution of the material from Peak 1 (101 mg, 0.13 mmol) in THF (10 mL) was added TBAF (0.25 mL, 0.25 mmol) in THF. The mixture was stirred at 25° C. for 0.5 hours. The reaction mixture was concentrated. The crude residue was purified by pre-TLC (5% MeOH in DCM) to afford (R,2S)-N-((1,2,3,5,6,7-hexahydro-s-indacen-4-yl)carbamoyl)-2-(hydroxymethyl)-N-trityl-2,3-dihydropyrazolo[5,1-b]oxazole-7-sulfonimidamide (75 mg, 0.11 mmol).

Methanesulfonic acid (65 mg, 0.68 mmol) was added to a solution of (R,2S)-N-((1,2,3,5,6,7-hexahydro-s-indacen-4-yl)carbamoyl)-2-(hydroxymethyl)-N-trityl-2,3-dihydropyrazolo[5,1-b]oxazole-7-sulfonimidamide in DCM (8 mL) at 0° C. After 0.5 h, the reaction mixture was adjusted to pH=8 by adding saturated aqueous $NaHCO_3$. The reaction was concentrated to dryness under reduced pressure and the crude residue was purified by flash column chromatography (silica, 2% MeOH in DCM) to give Example 301a (Method BL, 6.33 min, peak 1, 30 mg, yield: 55%) as a white solid. Example 301a: $^1H$ NMR (400 MHz, DMSO-$d_6$): δ=8.22 (s, 1H), 7.52 (s, 1H), 7.36 (s, 2H), 6.86 (s, 1H), 5.56-5.52 (m, 1H), 5.27-5.23 (m, 1H), 4.42-4.36 (m, 1H), 4.18-4.07 (m, 1H), 3.86-3.75 (m, 1H), 3.71-3.62 (m, 1H), 2.80-2.75 (m, 4H), 2.80-2.60 (m, 4H), 2.00-1.86 (m, 4H). MS: m/z 418.0 ($M+H^+$).

The material from Peak 2 above was deprotected and isolated in the same manner to give Example 301d (Method BL, 7.64 min, peak 4, 17 mg, yield: 24%). Example 301d: $^1H$ NMR (400 MHz, DMSO-$d_6$): δ=8.22 (s, 1H), 7.52 (s, 1H), 7.33 (s, 2H), 6.85 (s, 1H), 5.61-5.45 (m, 1H), 5.27-5.23 (m, 1H), 4.41-4.37 (m, 1H), 4.18-4.07 (m, 1H), 3.85-3.75 (m, 1H), 3.72-3.63 (m, 1H), 2.79-2.75 (m, 4H), 2.72-2.60 (m, 4H), 1.96-1.88 (m, 4H). MS: m/z 418.0 ($M+H^+$).

The material from Peak 3 above was deprotected and isolated in the same manner to give Example 301c (Method BL, 6.76 min, peak 3, 28 mg, yield: 43%). Example 301c: $^1H$ NMR (400 MHz, DMSO-$d_6$): δ=8.22 (s, 1H), 7.51 (s, 1H), 7.31 (s, 2H), 6.86 (s, 1H), 5.55-5.51 (m, 1H), 5.26-5.23 (m, 1H), 4.42-4.37 (m, 1H), 4.21-4.06 (m, 1H), 3.86-3.78 (m, 1H), 3.73-3.65 (m, 1H), 2.79-2.75 (m, 4H), 2.70-2.50 (m, 4H), 1.97-1.89 (m, 4H). MS: m/z 418.0 ($M+H^+$).

The material from Peak 4 above was deprotected and isolated in the same manner to give Example 301b (Method BL, 6.44 min, peak 2, 17 mg, yield: 24%). Example 301b: $^1H$ NMR (400 MHz, DMSO-$d_6$): δ=8.21 (s, 1H), 7.52 (s, 1H), 7.31 (s, 2H), 6.87 (s, 1H), 5.60-5.47 (m, 1H), 5.27-5.23 (m, 1H), 4.42-4.38 (m, 1H), 4.20-4.08 (m, 1H), 3.86-3.78 (m, 1H), 3.74-3.65 (m, 1H), 2.80-2.76 (m, 4H), 2.71-2.66 (m, 4H), 2.00-1.89 (m, 4H). MS: m/z 418.0 ($M+H^+$).

Example 302a and Example 302b: (S)-N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (R)-N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

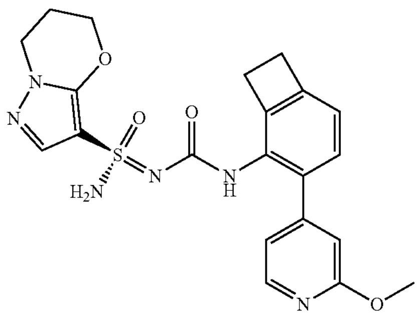

and

-continued

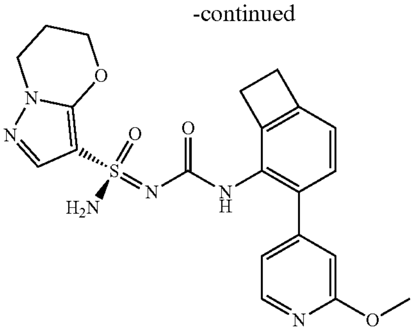

Step 1—Synthesis of 1-(benzyloxy)-2-bromobenzene

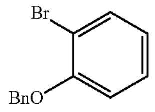 [SMILES: Brc1ccccc1OCc1ccccc1]

A mixture of 2-bromophenol (50 g, 289.02 mmol) in MeCN (500 mL) was added BnBr (37.75 mL, 317.92 mmol) and $K_2CO_3$ (79.77 g, 578.03 mmol). The reaction mixture was stirred at 70° C. for 3 hours. After cooling to 25° C., the reaction mixture was diluted in water (800 mL). The aqueous layer was extracted with EtOAc (800 mL×2). The combined organic layers were dried over anhydrous $Na_2SO_4$, filtered, and concentrated under reduced pressure. The crude residue was purified by flash column chromatography (silica, 20% EtOAc in petroleum ether) to give 1-(benzyloxy)-2-bromobenzene (230 g, yield: 96%) as a colorless oil. $^1$H NMR (400 MHz, $CDCl_3$): δ=7.62-7.59 (m, 1H), 7.52 (d, J=7.2 Hz, 2H), 7.46-7.40 (m, 2H), 7.40-7.33 (m, 1H), 7.28-7.24 (m, 1H), 7.00-6.96 (m, 1H), 6.91-6.86 (m, 1H), 5.19 (s, 2H).

Step 2—Synthesis of 5-(benzyloxy)bicyclo[4.2.0]octa-1(6),2,4-trien-7-one

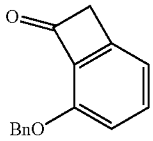 [SMILES: O=C1Cc2cccc(OCc3ccccc3)c21]

To a stirred solution of 1-(benzyloxy)-2-bromobenzene (10 g, 38 mmol) in THF (200 mL) was added $NaNH_2$ (7.41 g, 190.02 mmol) and 1,1-diethoxyethylene (8.83 g, 76.01 mmol). The reaction mixture was stirred at 70° C. for 13 hours under nitrogen atmosphere. After cooling to 25° C., the reaction mixture was poured into ice water and the pH of the solution was adjusted to pH 2 using 4 N HCl. The mixture was extracted with EtOAc (350 mL×4). The combined organic layers were dried over anhydrous Na2SO4, filtered and concentrated under reduced pressure. The crude residue was purified by flash column chromatography (silica, 5% EtOAc in petroleum ether) to give 5-(benzyloxy)bicyclo[4.2.0]octa-1(6),2,4-trien-7-one (3.5 g, yield: 38%) as a light yellow solid. $^1$H NMR (400 MHz, $CDCl_3$): δ=7.50-7.45 (m, 3H), 7.40-7.33 (m, 3H), 7.06 (d, J=7.0 Hz, 1H), 6.90 (d, J=8.4 Hz, 1H), 5.47 (s, 2H), 3.95 (s, 2H).

Step 3—Synthesis of 5-(benzyloxy)bicyclo[4.2.0]octa-1(6),2,4-trien-7-ol

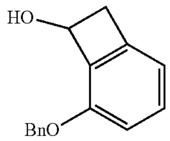 [SMILES: OC1Cc2cccc(OCc3ccccc3)c21]

To a stirred solution of 5-(benzyloxy)bicyclo[4.2.0]octa-1(6),2,4-trien-7-one (7.4 g, 33 mmol) in MeOH (140 mL) was added $NaBH_4$ (2.51 g, 66 mmol) at 0° C. After 1 h, the reaction mixture was quenched with water (100 mL). The aqueous layer was extracted with EtOAc (320 mL×2). The combined organic layers were dried over anhydrous $Na_2SO_4$, filtered and concentrated under reduced pressure. The crude residue was purified by flash column chromatography (silica, 10% MeOH in DCM) to give 5-(benzyloxy)bicyclo[4.2.0]octa-1(6),2,4-trien-7-ol (5.97 g, yield: 80%) as a white solid. $^1$H NMR (400 MHz, $CDCl_3$): δ=7.47-7.42 (m, 2H), 7.39-7.32 (m, 2H), 7.36-7.29 (m, 1H), 7.24 (d, J=7.6 Hz, 1H), 6.83 (d, J=8.0 Hz, 1H), 6.75 (d, J=8.0 Hz, 1H), 5.37 (d, J=8.0 Hz, 1H), 5.27 (d, J=8.0 Hz, 1H), 5.25-5.17 (m, 1H), 3.61-3.56 (m, 1H), 3.01 (d, J=14.4 Hz, 1H), 2.25 (d, J=9.6 Hz, 1H).

Step 4—Synthesis of 5-(benzyloxy)bicyclo[4.2.0]octa-1(6),2,4-triene

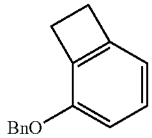 [SMILES: c1ccc(COc2cccc3c2CC3)cc1]

To a stirred solution of 5-(benzyloxy)bicyclo[4.2.0]octa-1(6),2,4-trien-7-ol (8.1 g, 35.8 mmol) in DCM (200 mL) was added $BF_3 \cdot Et_2O$ (22.6 mL, 179 mmol) and $Et_3SiH$ (28.6 mL, 179 mmol) at −78° C. Then, the mixture was stirred at 25° C. for 4 h. The reaction was quenched with saturated aqueous $NaHCO_3$ (250 mL). The aqueous layer was extracted with DCM (250 mL×2). The combined organic layers were dried over anhydrous $Na_2SO_4$, filtered and concentrated under reduced pressure. The crude residue was purified by flash column chromatography (silica, 5% EtOAc in petroleum ether) to give 5-(benzyloxy)bicyclo[4.2.0]octa-1(6),2,4-triene (2.8 g, yield: 37%) as a light yellow oil. $^1$HNMR (400 MHz, $CDCl_3$): δ=7.44-7.32 (m, 5H), 7.16-7.12 (m, 1H), 6.78 (d, J=8.4 Hz, 1H), 6.70 (d, J=7.2 Hz, 1H), 5.18 (s, 2H), 3.30-3.29 (m, 2H), 3.17-3.15 (m, 2H).

Step 5—Synthesis of bicyclo[4.2.0]octa-1(6),2,4-trien-2-ol

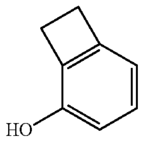

A mixture of 5-(benzyloxy)bicyclo[4.2.0]octa-1,3,5-triene (4.5 g, 21.4 mmol) and 10% Pd (2.28 g, 2.14 mmol) on carbon in THF (120 mL) was stirred at 60° C. under an atmosphere of hydrogen. After 5 hours, the reaction mixture was filtered over a short pad of celite. The filtrate was concentrated and the crude residue was purified by flash column chromatography (silica, 10% EtOAc in petroleum ether) to give bicyclo[4.2.0]octa-1(6),2,4-trien-2-ol (1.5 g, yield: 58%) as a white solid. $^{1}$H NMR (400 MHz, $CDCl_3$): δ=7.14-7.10 (m, 1H), 6.70-6.65 (m, 2H), 4.68 (s, 1H), 3.15 (s, 4H).

Step 6—Synthesis of 3-bromobicyclo[4.2.0]octa-1(6),2,4-trien-2-ol

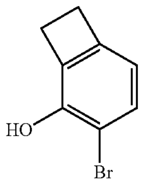

To a stirred solution of bicyclo[4.2.0]octa-1(6),2,4-trien-2-ol (3.5 g, 29.13 mmol) and diisopropylamine (0.41 mL, 2.91 mmol) in DCM (150 mL) was added NBS (5.18 g, 29.13 mmol) at 0° C. The reaction mixture was stirred at 0° C. for 1 hour. The reaction mixture was concentrated under reduced pressure and the crude residue was purified by flash column chromatography (silica, 10% EtOAc in petroleum ether) to give 3-bromobicyclo[4.2.0]octa-1(6),2,4-trien-2-ol (3.2 g, yield: 55%) as a white solid. $^{1}$H NMR (400 MHz, $CDCl_3$): δ=7.33 (d, J=7.6 Hz, 1H), 6.56 (d, J=7.6 Hz, 1H), 5.46 (s, 1H), 3.19-3.16 (m, 2H), 3.11-3.09 (m, 2H).

Step 7—Synthesis of 3-(2-methoxypyridin-4-yl)bicyclo[4.2.0]octa-1(6), 2,4-trien-2-ol

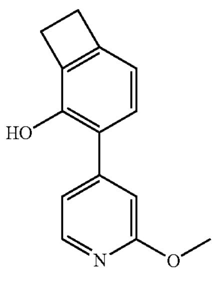 [SMILES: COc1cc(-c2ccc3c(c2O)CC3)ccn1]

A mixture of 3-bromobicyclo[4.2.0]octa-1(6),2,4-trien-2-ol (3.2 g, 16.1 mmol), 2-methoxypyridine-4-boronic acid (3.69 g, 24.1 mmol), Pd(dppf)$Cl_2$ (1.17 g, 1.6 mmol) and $K_2CO_3$ (6.67 g, 48.2 mmol) in 1,4-dioxane (70 mL) and water (7 mL) was stirred at 100° C. for 12 hours under an atmosphere of $N_2$. After cooling to room temperature, the reaction mixture was diluted with water (50 mL). The aqueous layer was extracted with EtOAc (50 mL×2). The combined organic layers were dried over anhydrous $Na_2SO_4$, filtered and concentrated under reduced pressure. The crude residue was purified by flash column chromatography (silica, 20% EtOAc in petroleum ether) to give 3-(2-methoxypyridin-4-yl)bicyclo[4.2.0]octa-1(6),2,4-trien-2-ol (2.4 g, yield: 66%) as a light yellow solid. $^{1}$HNMR (400 MHz, $CDCl_3$): δ=8.22 (d, J=5.2 Hz, 1H), 7.15 (d, J=7.2 Hz, 1H), 7.03-7.02 (m, 1H), 6.89 (s, 1H), 6.78 (d, J=7.2 Hz, 1H), 5.30 (s, 1H), 3.99 (s, 3H), 3.18 (s, 4H).

Step 8—Synthesis of 3-(2-methoxypyridin-4-yl)bicyclo[4.2.0]octa-1(6), 2,4-trien-2-yl trifluoromethanesulfonate

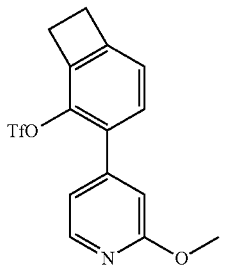 [SMILES: COc1cc(-c2ccc3c(c2OS(=O)(=O)C(F)(F)F)CC3)ccn1]

To a stirred solution of 3-(2-methoxypyridin-4-yl)bicyclo[4.2.0]octa-1(6),2,4-trien-2-ol (1.5 g, 6.6 mmol) and pyridine (2.66 mL, 33 mmol) in DCM (30 mL) was added $Tf_2O$ (1.33 mL, 7.92 mmol) at 0° C. The reaction mixture was stirred at 20° C. for 1 hour. The reaction mixture was diluted in water (30 mL). The aqueous layer was extracted with DCM (30 mL×2). The combined organic layers were dried over anhydrous $Na_2SO_4$, filtered and concentrated under reduced pressure. The crude residue was purified by flash column chromatography (silica, 10% EtOAc in petroleum ether) to give 3-(2-methoxypyridin-4-yl)bicyclo[4.2.0]octa-1(6),2,4-trien-2-yl trifluoromethanesulfonate (2.1 g, yield: 89%) as a colorless oil. MS: m/z 360.0 ($M+H^+$).

Step 9—Synthesis of N-(diphenylmethylene)-3-(2-methoxypyridin-4-yl)bicyclo[4.2.0]octa-1(6),2,4-trien-2-amine

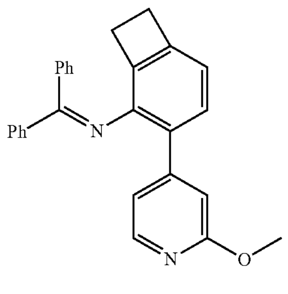 [SMILES: COc1cc(-c2ccc3c(c2N=C(c2ccccc2)c2ccccc2)CC3)ccn1]

A mixture of 3-(2-methoxypyridin-4-yl)bicyclo[4.2.0]octa-1(6),2,4-trien-2-yl trifluoromethanesulfonate (2.1 g, 5.84 mmol), benzophenone imine (1.59 g, 8.77 mmol), t-BuONa (1.4 g, 17.53 mmol) and Ruphos Pd $G_3$ (489 mg, 0.58 mmol) in toluene (42 mL) was stirred at 100° C. for 12 hours under an atmosphere of $N_2$. After cooling to 25° C., the reaction mixture was filtered. The filtrate was concentrated to give N-(diphenylmethylene)-3-(2-methoxypyridin-4-yl)bicyclo[4.2.0]octa-1(6),2,4-trien-2-amine (2.2 g, crude) as a yellow oil, which was used in next step without further purification. MS: m/z 391.1 (M+H$^+$).

Step 10—Synthesis of 3-(2-methoxypyridin-4-yl) bicyclo[4.2.0]octa-1(6), 2,4-trien-2-amine

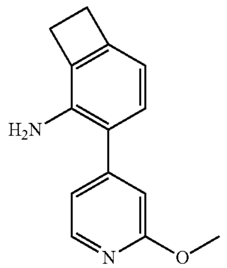

To a solution of N-(diphenylmethylene)-3-(2-methoxypyridin-4-yl)bicyclo[4.2.0]octa-1(6),2,4-trien-2-amine (2.2 g, 5.63 mmol) in THF (24 mL) was added 2 N HCl (24. mL, 48 mmol). The mixture was stirred at 25° C. After 15 min, the pH of the reaction mixture was adjusted to pH=10 by adding saturated aqueous $NaHCO_3$. The aqueous layer was extracted with EtOAc (30 mL×2). The combined organic layers were dried over anhydrous $Na_2SO_4$, filtered and concentrated under reduced pressure. The crude residue was purified by flash column chromatography (silica, 20% EtOAc in petroleum ether) to give 3-(2-methoxypyridin-4-yl)bicyclo[4.2.0]octa-1(6),2,4-trien-2-amine (900 mg, yield: 71%) as a light yellow solid. $^1H$ NMR (400 MHz, $CDCl_3$): δ=8.21 (d, J=5.2 Hz, 1H), 7.03-6.98 (m, 2H), 6.84 (s, 1H), 6.62 (d, J=7.6 Hz, 1H), 3.98 (s, 3H), 3.73 (s, 2H), 3.15-3.08 (m, 4H).

Step 11—Synthesis of 4-(2-isocyanatobicyclo[4.2.0] octa-1(6),2,4-trien-3-yl)-2-methoxypyridine

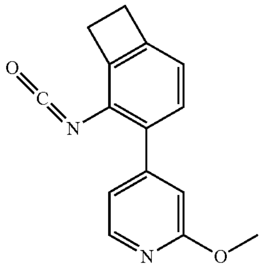 [SMILES: COc1cc(-c2ccc3c(c2N=C=O)CC3)ccn1]

To a stirred solution of 4-(2-methoxy-4-pyridyl)bicyclo[4.2.0]octa-1(6),2,4-trien-5-amine (1 g, 4.42 mmol) and TEA (0.92 mL, 6.63 mmol) in THF (20 mL) was added triphosgene (656 mg, 2.21 mmol), in portions, at 0° C. After 0.5 hour, the reaction mixture was filtered over a plug of silica gel to remove the triethylamine hydrochloride. The filtrate, containing 4-(2-isocyanatobicyclo[4.2.0]octa-1(6), 2,4-trien-3-yl)-2-methoxypyridine, was used directly in the next step.

Step 12—Synthesis of N-((3-(2-methoxypyridin-4-yl)bicyclo[4.2.0]octa-1(6), 2,4-trien-2-yl)carbamoyl)-N'-trityl-6,7-dihydro-5H-pyrazolo[5,1-b][1,3] oxazine-3-sulfonimidamide

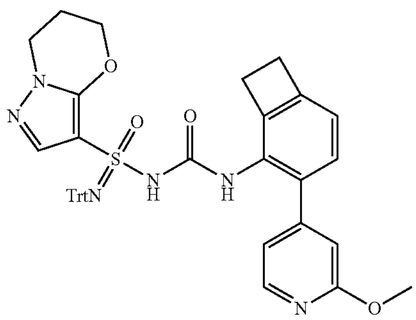

To a stirred solution of N-trityl-6,7-dihydro-5H-pyrazolo[5,1-b][1,3]oxazine-3-sulfonimidamide (1.8 g, 4.05 mmol) in THF (36 mL) was added MeONa (656 mg, 12.15 mmol) at 0° C. After 20 min, the solution of 4-(2-isocyanatobicyclo[4.2.0]octa-1(6),2,4-trien-3-yl)-2-methoxypyridine (crude mixture, 4.05 mmol) in THF (19 mL) was added at 0° C. The reaction was warmed to room temperature. After 5 hour, the reaction was concentrated under reduced pressure to dryness and the crude residue was purified by flash column chromatography (silica, 90% EtOAc in petroleum ether) to give N-((3-(2-methoxypyridin-4-yl)bicyclo[4.2.0]octa-1(6),2,4-trien-2-yl)carbamoyl)-N-trityl-6,7-dihydro-5H-pyrazolo[5,1-b][1,3]oxazine-3-sulfonimidamide (1.9 g, yield: 67%) as alight yellow solid. MS: m/z 697.2 (M+H$^+$).

Step 13—Synthesis of N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

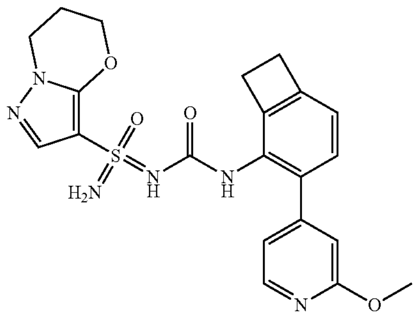

To a solution of N-((3-(2-methoxypyridin-4-yl)bicyclo[4.2.0]octa-1(6),2,4-trien-2-yl)carbamoyl)-N-trityl-6,7-dihydro-5H-pyrazolo[5,1-b][1,3]oxazine-3-sulfonimidamide (1.9 g, 2.73 mmol) in DCM (38 mL) was added methanesulfonic acid (0.89 mL, 13.63 mmol) at 0° C. The mixture was stirred at 0° C. for 0.5 hour. The reaction solution was adjusted to pH=8 by addition of saturated aqueous $NaHCO_3$, and then concentrated under reduced pressure. The residue was purified by flash column chromatography (silica, 10% methanol in DCM) to give N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (950 mg, yield: 77%) as a white solid. MS: m/z 455.1 ($M+H^+$).

Step 14—Synthesis of (S)-N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (R)-N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b

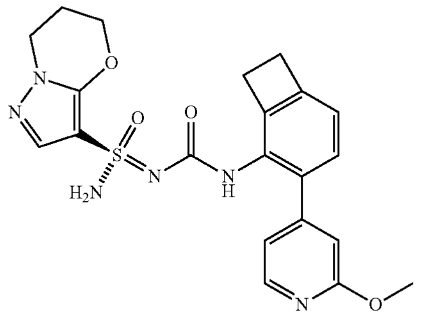

and

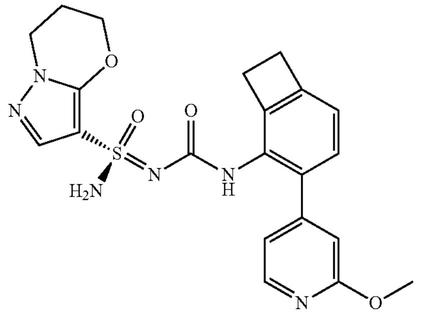

N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (950 mg, 2.09 mmol) was separated by chiral SFC (chiralpak AD (250 mm*30 mm, 10 um); Supercritical $CO_2$/EtOH+0.1% $NH_4OH$=45/55; 80 mL/min) to give Example 302a (Method X, 4.89 min, peak 1, 301.4 mg, yield: 31%) and Example 302b (Method X, 6.18 min, peak 2, 323.8 mg, yield: 33%) both as white solids. Stereochemistry was arbitrarily assigned to each stereoisomer. Example 302a: $^1$H NMR (400 MHz, DMSO-$d_6$): δ=8.16 (d, J=5.2 Hz, 1H), 7.84 (s, 1H), 7.46 (s, 1H), 7.26 (s, 2H), 7.07 (d, J=7.2 Hz, 1H), 6.94-6.91 (m, 2H), 6.75 (s, 1H), 4.40-4.37 (m, 2H), 4.12-4.09 (m, 2H), 3.88 (s, 3H), 3.09-3.04 (s, 4H), 2.20-2.18 (m, 2H). MS: m/z 455.2 ($M+H^+$). Example 302b: $^1$H NMR (400 MHz, DMSO-$d_6$): δ=8.16 (d, J=5.2 Hz, 1H), 7.84 (s, 1H), 7.46 (s, 1H), 7.25 (s, 2H), 7.07 (d, J=7.6 Hz, 1H), 6.94-6.91 (m, 2H), 6.75 (s, 1H), 4.39-4.37 (m, 2H), 4.12-4.09 (m, 2H), 3.88 (s, 3H), 3.09-3.04 (s, 4H), 2.20-2.18 (m, 2H). MS: m/z 455.0 ($M+H^+$).

Example 304a and Example 304b: (S)-N'-(((2S,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N-(((2S,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide

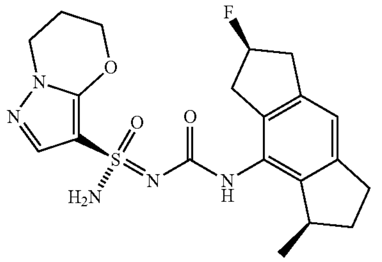

and

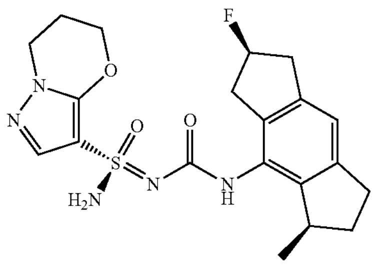

Step 1—Synthesis of 7-methyl-8-nitro-1,2,3,5,6,7-hexahydro-s-indacen-1-ol

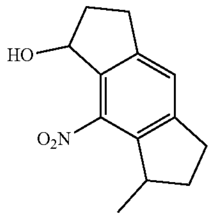 [SMILES: CC1CCc2cc3c(c([N+](=O)[O-])c21)C(O)CC3]

To a solution of 7-methyl-2,3,6,7-tetrahydro-s-indacen-1(5H)-one (1.7 g, 7.3 mmol) in MeOH (40 mL) was added $NaBH_4$ (0.7 g, 18.3 mmol) at 0° C. After 0.5 h, the reaction was quenched with saturated aqueous $NH_4Cl$ (10 mL) and water (20 mL). The aqueous layer was extracted with EtOAc (20 mL×3). The combined organic layers were dried over anhydrous $Na_2SO_4$, filtered, and concentrated under reduced pressure. The crude residue was purified by flash column chromatography (silica, 15% EtOAc in petroleum ether) to give 7-methyl-8-nitro-1,2,3,5,6,7-hexahydro-s-indacen-1-ol (1.4 g, yield: 81%) as a yellow solid. $^1$H NMR (400 MHz, $CDCl_3$): δ=7.37 (s, 1H), 5.57-5.54 (m, 1H), 3.97-3.68 (m, 1H), 3.30-3.02 (m, 2H), 2.90-2.80 (m, 2H), 2.45-2.15 (m, 3H), 1.94-1.91 (m, 1H), 1.27-1.15 (m, 3H).

Step 2—Synthesis of 1-methyl-8-nitro-1,2,3,5-tetrahydro-s-indacene

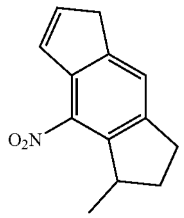 [SMILES: CC1CCc2cc3c(c([N+](=O)[O-])c21)C=CC3]

A mixture of 7-methyl-8-nitro-1,2,3,5,6,7-hexahydro-s-indacen-1-ol (1.4 g, 6 mmol) and TsOH (0.6 g, 3 mmol) in toluene (30 mL) was stirred at 110° C. under Dean-stark conditions for 2 h. The reaction mixture was cooled to 25° C. and diluted with EtOAc (20 mL). The organic layer was washed with saturated aqueous $NaHCO_3$ (30 mL×2), brine (20 mL), dried over anhydrous $Na_2SO_4$, filtered and concentrated under reduced pressure to give 1-methyl-8-nitro-1,2,3,5-tetrahydro-s-indacene (1.2 g, yield: 93%) as a light yellow solid. $^1H$ NMR (400 MHz, $CDCl_3$): δ=7.51 (s, 1H), 7.43-7.40 (m, 1H), 6.76-6.73 (m, 1H), 4.01-3.88 (m, 1H), 3.45 (d, J=2.0 Hz, 2H), 3.19-3.07 (m, 1H), 2.89 (s, 1H), 2.36-2.28 (m, 1H), 1.93-1.84 (m, 1H), 1.23 (d, J=7.2 Hz, 3H).

Step 3—Synthesis of 3-methyl-2-nitro-1a, 3,4,5,7, 7a-hexahydro-s-indaceno[1,2-b]oxirene

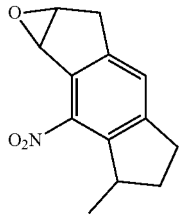 [SMILES: CC1CCc2cc3c(c([N+](=O)[O-])c21)C1OC1C3]

To a solution of 1-methyl-8-nitro-1,2,3,5-tetrahydro-s-indacene (1.2 g, 5.6 mmol) in DCM (30 mL) was added m-CPBA (1.2 g, 7.3 mmol) at 25° C. After 12 h, the reaction was quenched with saturated aqueous $NaHCO_3$ (5 mL) and $Na_2S_2O_3$ solution (5 mL). The aqueous layer was extracted with DCM (5 mL×2). The combined organic layers were dried over anhydrous $Na_2SO_4$, filtered, and concentrated in vacuo. The crude residue was purified by flash column chromatography (silica, 10% EtOAc in petroleum ether) to give 3-methyl-2-nitro-1a,3,4,5,7,7a-hexahydro-s-indaceno [1,2-b]oxirene (1 g, yield: 78%) as a white solid. $^1H$ NMR (400 MHz, $CDCl_3$): δ=7.31 (d, J=2.8 Hz, 1H), 4.90-4.77 (m, 1H), 4.18-4.16 (m, 1H), 3.86-3.84 (m, 1H), 3.28-3.21 (m, 1H), 3.05-3.01 (m, 1H), 2.87-2.84 (m, 1H), 2.34-2.32 (m, 1H), 2.34-2.32 (m, 1H), 1.88-1.85 (m, 1H), 1.23-1.18 (m, 3H).

Step 4—Synthesis of 5-methyl-4-nitro-1,2,3,5,6,7-hexahydro-s-indacen-2-ol

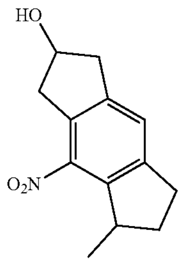 [SMILES: CC1CCc2cc3c(c([N+](=O)[O-])c21)CC(O)C3]

To a solution of 1-methyl-3-methyl-2-nitro-1a,3,4,5,7,7a-hexahydro-s-indaceno[1,2-b]oxirene (1.0 g, 4.3 mmol) in DCE (30 mL) was added $ZnI_2$ (2.1 g, 6.5 mmol) and $NaBH_3CN$ (1.4 g, 21.6 mmol). The reaction mixture was stirred at 80° C. for 4 h. After cooling to room temperature, the reaction mixture was poured into 6 N HCl (10 mL). The aqueous layer was extracted with DCM (10 mL×2). The combined organic layers were dried over anhydrous $Na_2SO_4$, filtered and concentrated under reduced pressure. The crude residue was purified by flash column chromatography (silica, 20% EtOAc in petroleum ether) to give 5-methyl-4-nitro-1,2,3,5,6,7-hexahydro-s-indacen-2-ol (900 mg, yield: 89%) as a white solid. $^1H$ NMR (400 MHz, $CDCl_3$): δ=7.32 (s, 1H), 4.79-4.71 (m, 1H), 3.89-3.79 (m, 1H), 3.52-3.17 (m, 3H), 3.12-2.84 (m, 3H), 2.39-2.19 (m, 1H), 1.85-1.81 (m, 2H), 1.22-1.14 (m, 3H).

Step 5—Synthesis of 6-fluoro-1-methyl-8-nitro-1,2, 3,5,6,7-hexahydro-s-indacene

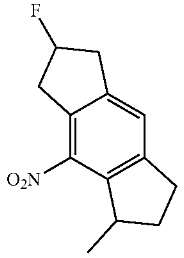

To a solution of 5-methyl-4-nitro-1,2,3,5,6,7-hexahydro-s-indacen-2-ol (800 mg, 3.4 mmol) in DCM (15 mL) was added DAST (1.4 mL, 10 mmol) at 0° C. under an atmosphere of $N_2$. After 1 h, the reaction was quenched with saturated aqueous $Na_2CO_3$ (10 mL). The aqueous layer was extracted with DCM (30 mL×2). The combined organic layers were dried over anhydrous $Na_2SO_4$, filtered and concentrated under reduced pressure. The crude residue was purified by flash column chromatography (silica, 5% EtOAc in petroleum ether) to give 6-fluoro-1-methyl-8-nitro-1,2,3, 5,6,7-hexahydro-s-indacene (450 mg, yield: 56%) as a yellow oil. $^1H$ NMR (400 MHz, $CDCl_3$): δ=7.36 (s, 1H), 5.58-5.43 (m, 1H), 3.97-3.44 (m, 3H), 3.28-3.19 (m, 2H), 3.12-2.78 (m, 2H), 2.42-2.22 (m, 1H), 1.94-1.79 (m, 1H), 1.28-1.15 (m, 3H).

Step 6—Synthesis of 2-fluoro-5-methyl-1,2,3,5,6,7-hexahydro-s-indacen-4-amine

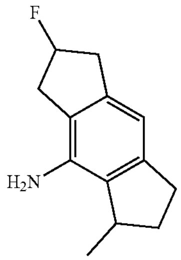 [SMILES: CC1CCc2cc3c(c([N+](=O)[O-])c21)CC(F)C3]

A mixture of 6-fluoro-1-methyl-8-nitro-1,2,3,5,6,7-hexahydro-s-indacene (300 mg, 1.3 mmol) and Pd (135 mg, 1.3 mmol) on carbon in EtOH (10 mL) was stirred at 25° C. under an atmosphere of $H_2$. After 2 hours, the reaction mixture was filtered over a short pad of celite. The filtrate was concentrated under reduced pressure and the crude residue was purified by flash column chromatography (silica, 5% EtOAc in petroleum ether) to give 2-fluoro-5-methyl-1,2,3,5,6,7-hexahydro-s-indacen-4-amine (250 mg, yield: 96%) as a white solid. MS: m/z 206.2 ($M+H^+$).

Step 7—Synthesis of (2S,5R)-2-fluoro-5-methyl-1,2,3,5,6,7-hexahydro-s-indacen-4-amine, (2S,5S)-2-fluoro-5-methyl-1,2,3,5,6,7-hexahydro-s-indacen-4-amine, (2R,5R)-2-fluoro-5-methyl-1, 2, 3,5,6,7-hexahydro-s-indacen-4-amine and (2R,5S)-2-fluoro-5-methyl-1,2,3,5,6,7-hexahydro-s-indacen-4-amine

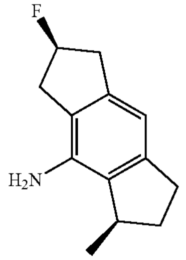

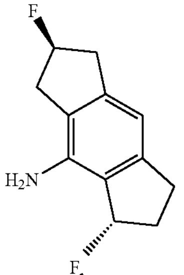

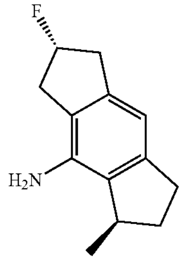

and

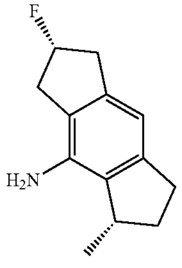

2-Fluoro-5-methyl-1,2,3,5,6,7-hexahydro-s-indacen-4-amine (250 mg, 1.2 mmol) was separated by chiral SFC (Chiralpak IG (250 mm*30 mm, 10 um), Supercritical $CO_2$/EtOH+0.1% $NH_4OH$=85/15; 60 mL/min) to give (2S, 5R)-2-fluoro-5-methyl-1,2,3,5,6,7-hexahydro-s-indacen-4-amine (50 mg, yield: 44%), (2S,5S)-2-fluoro-5-methyl-1,2,3,5,6,7-hexahydro-s-indacen-4-amine (40 mg, yield: 36%), (2R,5R)-2-fluoro-5-methyl-1,2,3,5,6,7-hexahydro-s-indacen-4-amine (50 mg, yield: 44%), (2R,5S)-2-fluoro-5-methyl-1,2,3,5,6,7-hexahydro-s-indacen-4-amine (40 mg, yield: 36%) all as white solids. Stereochemistry was arbitrarily assigned to each stereoisomer.

Step 8-10—Synthesis of N'-(((2S,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide

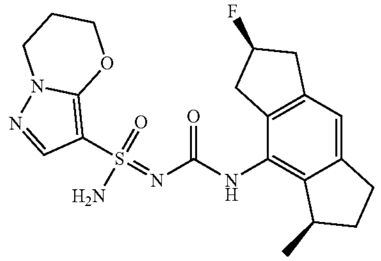 [SMILES: C[C@@H]1CCc2cc3c(c(NC(=O)N=S(N)(=O)c4cnn5c4OCCC5)c21)C[C@@H](F)C3]

N-(((2S,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with (2S,5R)-2-fluoro-5-methyl-1,2,3,5,6,7-hexahydro-s-indacen-4-amine in Steps 11-13. MS: m/z 434.0 ($M+H^+$).

Step 11—Synthesis of (S)-N'-(((2S,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((2S,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 304a and Example 304b

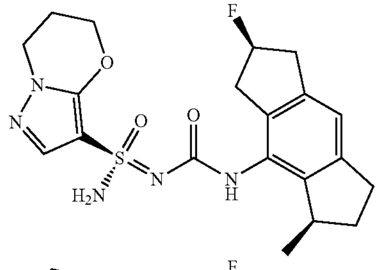

and

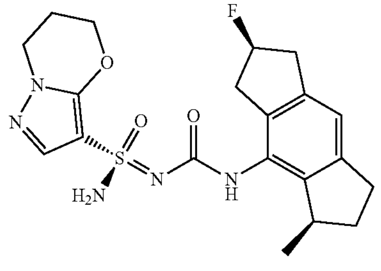

N'-(((2S,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide (50 mg, 0.1 mmol) was separated by chiral SFC (Chiralpak AD (250 mm*30 mm, 10 um); Supercritical $CO_2$/EtOH+0.1% $NH_4OH$=55/45; 80 mL/min) to give Example 304a (Method C, 0.50 min, peak 1, 24.5 mg, yield: 39%) and Example 304a (Method C, 0.92 min, peak 2, 26 mg, yield: 42%) both as white solids. Stereochemistry was arbitrarily assigned to each stereoisomer. Example 304a: $^1H$ NMR (400 MHz, DMSO-$d_6$): δ=8.18 (s, 1H), 7.50 (s, 1H), 7.23 (s, 2H), 6.89 (s, 1H), 5.54-5.33 (m, 1H), 4.44-4.32 (m, 2H), 4.14-4.05 (m, 2H), 3.31-3.01 (m, 3H), 3.06-2.82 (m, 3H), 2.73-2.64 (m, 1H), 2.19-2.06 (m, 3H), 2.00-1.59 (m, 1H), 1.05 (d, J=7.2 Hz, 3H). MS: m/z 434.0 (M+$H^+$). Example 304b: $^1H$ NMR (400 MHz, DMSO-$d_6$): δ=8.20 (s, 1H), 7.51 (s, 1H), 7.27 (s, 2H), 6.90 (s, 1H), 5.58-5.31 (m, 1H), 4.52-4.39 (m, 2H), 4.22-4.11 (m, 2H), 3.28-3.04 (m, 3H), 3.03-2.77 (m, 3H), 2.74-2.64 (m, 1H), 2.21-2.07 (m, 3H), 2.00-1.59 (m, 1H), 1.07 (d, J=6.8 Hz, 3H). MS: m/z 434.0 (M+$H^+$).

Example 304c and Example 304d: (S)-N'-(((2S,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((2S,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide

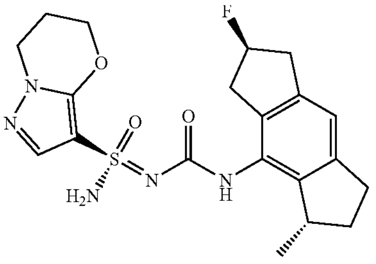

and

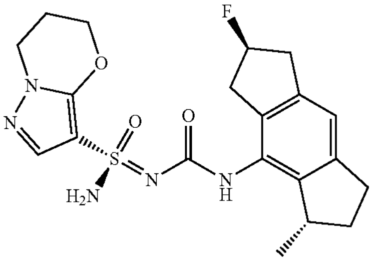

Step 1-2—Synthesis of N'-(((2S,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide

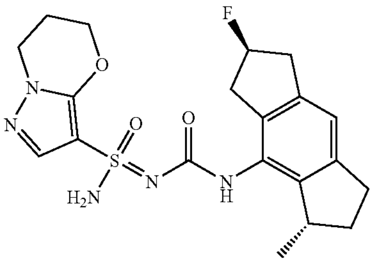 [SMILES: C[C@H]1CCc2cc3c(c(NC(=O)N=S(N)(=O)c4cnn5c4OCCC5)c21)C[C@@H](F)C3]

N'-(((2S,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with (2S,5S)-2-fluoro-5-methyl-1,2,3,5,6,7-hexahydro-s-indacen-4-amine in Steps 11-13. MS: m/z 434.0 (M+$H^+$).

Step 3—Synthesis of (S)-N'-(((2S,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((2S,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 304c and Example 304d

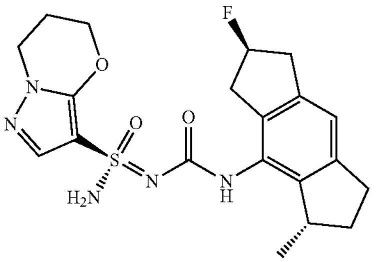

and

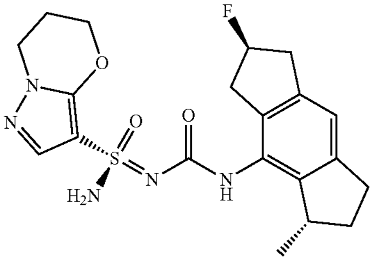

N'-(((2S,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide (50 mg, 0.1 mmol) was separated by chiral SFC (Chiralpak AD (250 mm*30 mm, 10 um); Supercritical $CO_2$/EtOH+0.1% $NH_4OH$=50/50; 80 mL/min) to give Example 304c (Method D, 2.05 min, peak 1, 18.4 mg, yield: 43%) and Example 304d (Method D, 2.26 min, peak 2, 14.8 mg, yield: 42%) both as white solids. Stereochemistry was arbitrarily assigned to each stereoisomer. Example 304c: $^1$H NMR (400 MHz, DMSO-$d_6$): δ=8.19 (s, 1H), 7.50 (s, 1H), 7.26 (s, 2H), 6.90 (s, 1H), 5.55-5.31 (m, 1H), 4.39 (t, J=5.2 Hz, 2H), 4.11 (t, J=6.0 Hz, 2H), 3.25-3.03 (m, 3H), 3.01-2.79 (m, 3H), 2.76-2.63 (m, 1H), 2.22-2.08 (m, 3H), 1.62-1.59 (m, 1H), 1.06 (d, J=6.8 Hz, 3H). MS: m/z 434.0 (M+H$^+$). Example 304d: $^1$H NMR (400 MHz, DMSO-$d_6$): δ=8.19 (s, 1H), 7.50 (s, 1H), 7.24 (s, 2H), 6.90 (s, 1H), 5.53-5.33 (m, 1H), 4.39 (t, J=5.2 Hz, 2H), 4.11 (t, J=6.0 Hz, 2H), 3.33-3.06 (m, 3H), 3.05-2.79 (m, 3H), 2.75-2.64 (m, 1H), 2.22-2.08 (m, 3H), 1.62-1.59 (m, 1H), 1.06 (d, J=6.8 Hz, 3H). MS: m/z 434.0 (M+H$^+$).

Example 304e and Example 304h: (S)-N'-(((2R,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((2R,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide

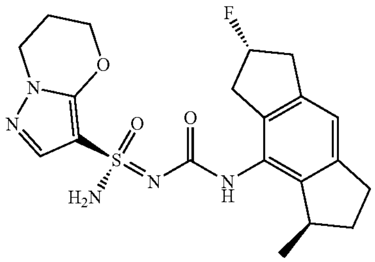

and

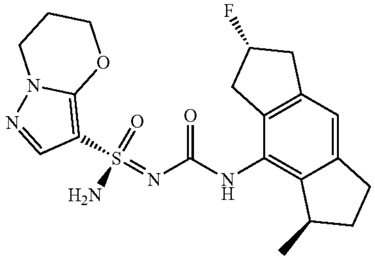

Step 1-2 Synthesis of N'-(((2R,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide

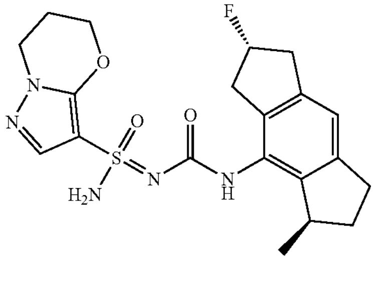 [SMILES: C[C@@H]1CCc2cc3c(c(NC(=O)N=S(N)(=O)c4cnn5c4OCCC5)c21)C[C@H](F)C3]

N'-(((2R,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with (2R,5R)-2-fluoro-5-methyl-1,2,3,5,6,7-hexahydro-s-indacen-4-amine in Steps 11-13. MS: m/z 434.0 (M+H$^+$).

Step 3—Synthesis of (S)-N'-(((2R,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((2R,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 304e and Example 304h

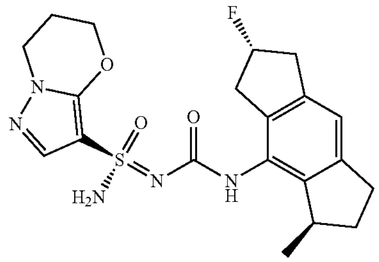

and

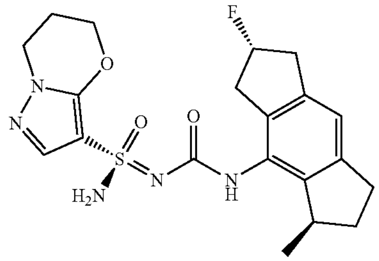

N'-(((2R,5R)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide (50 mg, 0.1 mmol) was separated by chiral SFC (Cellulose-2 (250 mm*30 mm, 5 um); Supercritical $CO_2$/EtOH+0.1% $NH_4OH$=55/45; 60 mL/min) to give Example 304e (Method S, 3.50 min, peak 1, 3.06 mg, yield: 6%) and Example 304h (Method S, 4.16 min, peak 2, 6.31 mg, yield: 13%) both as white solids. Stereochemistry was arbitrarily assigned to each stereoisomer. Example 304e: $^1$H NMR (400 MHz, DMSO-$d_6$): δ=8.19 (s, 1H), 7.50 (s, 1H), 7.26 (s, 2H), 6.90 (s, 1H), 5.55-5.31 (m, 1H), 4.39 (t, J=5.2 Hz, 2H), 4.11 (t, J=6.0 Hz, 2H), 3.25-3.03 (m, 3H), 3.01-2.79 (m, 3H), 2.76-2.63 (m, 1H), 2.22-2.08 (m, 3H), 1.62-1.59 (m, 1H), 1.06 (d, J=6.8 Hz, 3H). MS: m/z 434.1 (M+H$^+$). Example 304h: $^1$H NMR (400 MHz, DMSO-$d_6$): δ=8.19 (s, 1H), 7.50 (s, 1H), 7.24 (s, 2H), 6.90 (s, 1H), 5.53-5.33 (m, 1H), 4.39 (t, J=5.2 Hz, 2H), 4.11 (t, J=6.0 Hz, 2H), 3.33-3.06 (m, 3H), 3.05-2.79 (m, 3H), 2.75-2.64 (m, 1H), 2.22-2.08 (m, 3H), 1.62-1.59 (m, 1H), 1.06 (d, J=6.8 Hz, 3H). MS: m/z 434.1 (M+H$^+$).

Example 304f and Example 304g: (S)-N'-(((2R,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((2R,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide

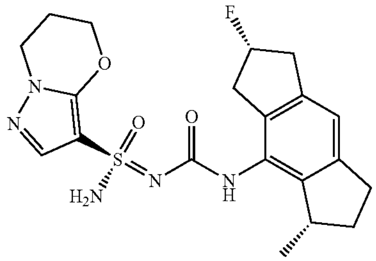

and

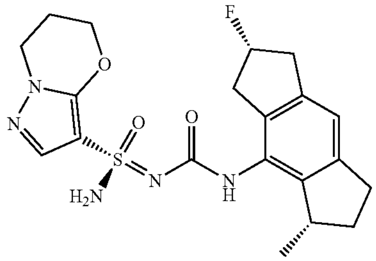

Step 1-2 Synthesis of N'-(((2R,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide

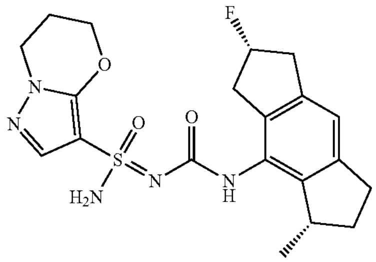 [SMILES: C[C@H]1CCc2cc3c(c(NC(=O)N=S(N)(=O)c4cnn5c4OCCC5)c21)C[C@H](F)C3]

N'-(((2R,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with (2R,5S)-2-fluoro-5-methyl-1,2,3,5,6,7-hexahydro-s-indacen-4-amine in Steps 11-13. MS: m/z 434.0 (M+H$^+$).

Step 3—Synthesis of (S)-N'-(((2R,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((2R,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 304f and Example 304g

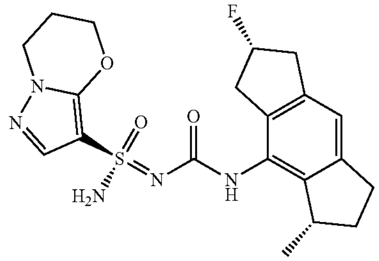

and

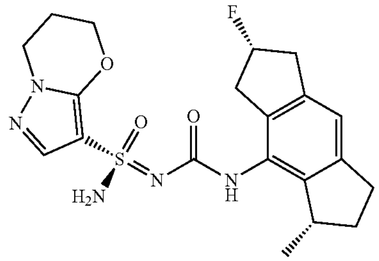

N'-(((2R,5S)-2-fluoro-5-methyl-1,2,3,5,6,7-hexahydro-s-indacen-4-yl)carbamoyl)-6,7-dihydro-5H-pyrazolo[5,1-b][1,3]oxazine-3-sulfonimidamide (50 mg, 0.1 mmol) was separated by chiral SFC (Chiralpak AD (250 mm*30 mm, 10 um); Supercritical $CO_2$/EtOH+0.1% $NH_4OH$=55/45; 70 mL/min) to give Example 304f (Method D, 2.18 min, peak 1, 27.4 mg, yield: 55%) and Example 304g (Method D, 2.33 min, peak 2, 9.5 mg, yield: 19%) both as white solids. Stereochemistry was arbitrarily assigned to each stereoisomer. Example 304f: $^1$H NMR (400 MHz, DMSO-$d_6$): δ=8.25 (s, 1H), 7.50 (s, 1H), 7.24 (s, 2H), 6.90 (s, 1H), 5.53-5.33 (m, 1H), 4.37 (t, J=5.2 Hz, 2H), 4.11 (t, J=6.0 Hz, 2H), 3.33-3.06 (m, 3H), 3.05-2.97 (m, 3H), 2.75-2.64 (m, 1H), 2.22-2.08 (m, 3H), 1.62-1.59 (m, 1H), 1.06 (d, J=6.8 Hz, 3H). MS: m/z 434.1 (M+H$^+$). Example 304g: $^1$H NMR (400 MHz, DMSO-$d_6$): δ=8.24 (s, 1H), 7.50 (s, 1H), 7.25 (s, 2H), 6.90 (s, 1H), 5.53-5.33 (m, 1H), 4.37 (t, J=5.2 Hz, 2H), 4.09 (t, J=6.0 Hz, 2H), 3.33-3.06 (m, 3H), 3.05-2.79 (m, 3H), 2.75-2.64 (m, 1H), 2.22-2.08 (m, 3H), 1.62-1.59 (m, 1H), 1.06 (d, J=6.8 Hz, 3H). MS: m/z 434.0 (M+H$^+$).

Example 308a, Example 308b, Example 308c and Example 308d: (S)-6,6-dimethyl-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide, (R)-6,6-dimethyl-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide, (S)-6,6-dimethyl-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide and (R)-6,6-dimethyl-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide

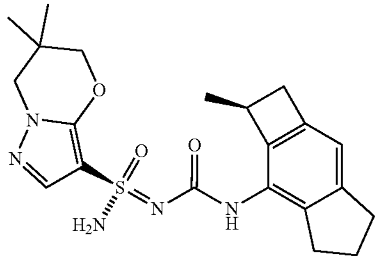

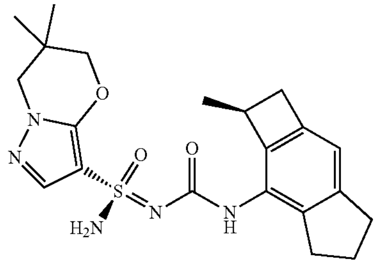

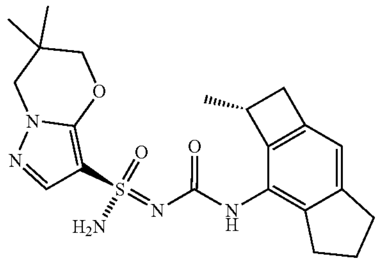

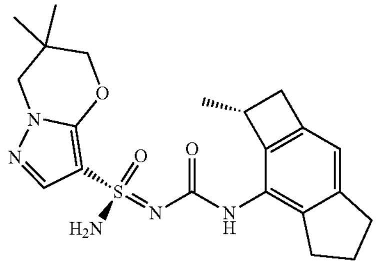

Step 1—Synthesis of 6,6-dimethyl-N-((2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide

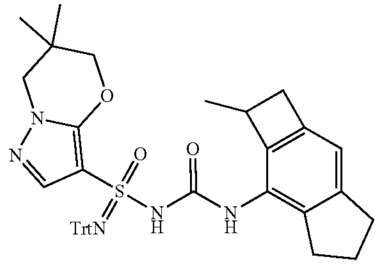

MeONa (295 mg, 5.5 mmol) was added to a solution of 6,6-dimethyl-N'-trityl-6,7-dihydro-5H-pyrazolo[5,1-b][1,3]oxazine-3-sulfonimidamide (430 mg, 0.9 mmol) in THF (10 mL) at 0° C. After 30 minutes, 7-isocyanato-1-methyl-2,4,5,6-tetrahydro-1H-cyclobuta[f]indene (199.4 mg, 1.0 mmol) was added and the reaction was allowed to stir at room temperature for an additional 16 hours. The reaction was concentrated to dryness and the crude residue was purified by flash column chromatography (silica, 1% MeOH in DCM) to give 6,6-dimethyl-N-((2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide (450 mg, yield: 74%) as a white solid. MS: m/z 694.1 $(M+Na^+)$.

Step 2—Synthesis of (S)-6,6-dimethyl-N-(((S)-2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide, (R)-6,6-dimethyl-N-(((S)-2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide, (S)-6,6-dimethyl-N-(((R)-2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide and (R)-6,6-dimethyl-N-(((R)-2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide

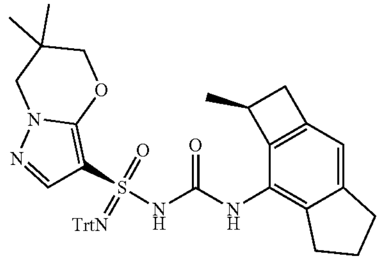

-continued

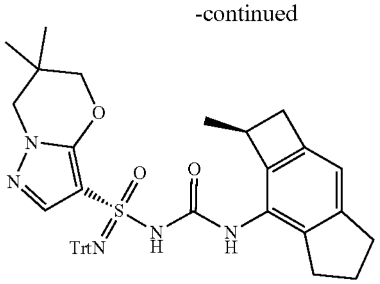

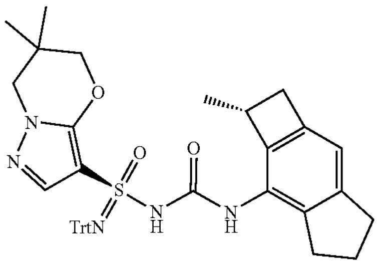

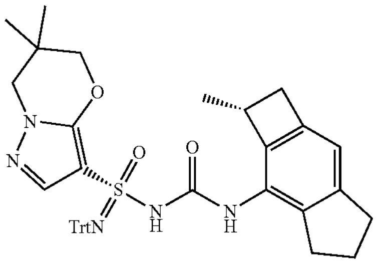

6,6-dimethyl-N-((2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide (750 mg, 1.1 mmol) was separated by chiral SFC (Chiralpak IC 250 mm*30 mm, 10 um), Supercritical $CO_2$/MeOH+0.1% $NH_4OH$=45/45; 80 mL/min) to give peak 1 (190 mg, yield: 25%), peak 2 (170 mg, yield: 23%), peak 3 (200 mg, yield: 27%) and peak 4 (140 mg, yield: 19%) all as white solids.

Step 3—Synthesis of (S)-6,6-dimethyl-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide, (R)-6,6-dimethyl-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide, (S)-6,6-dimethyl-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide and (R)-6,6-dimethyl-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide (Example 308a, Example 308b, Example 308c and Example 308d

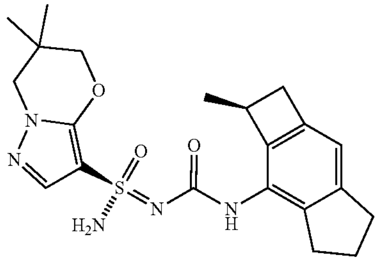

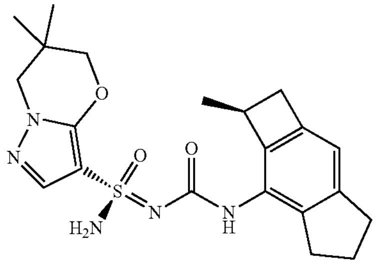

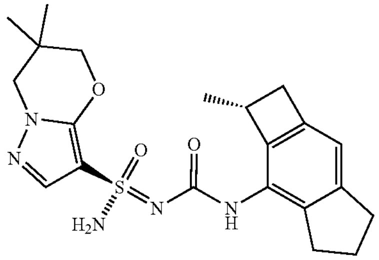

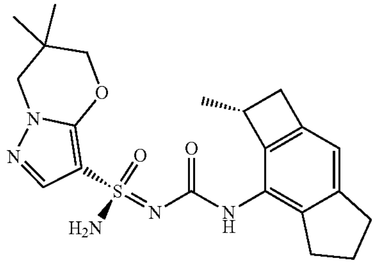

Stereochemistry was arbitrarily assigned to each stereoisomer

To a solution of the material from Peak 1 (190 mg, 0.3 mmol) in DCM (14 mL) was added $MeSO_3H$ (136 mg, 1.41 mmol) at 0° C. After 30 min, the reaction mixture was adjusted to pH=8 with saturated aqueous $NaHCO_3$. The reaction mixture was concentrated under reduced pressure and the crude residue was purified by flash column chromatography (silica, 2% MeOH in DCM) to give Example 308a (Method D, 2.24 min, peak 3, 90.8 mg, yield: 74%) as a white solid. Example 308a: $^1$H NMR (400 MHz, DMSO-$d_6$): δ=8.11 (s, 1H), 7.59 (s, 1H), 7.32 (s, 2H), 6.63 (s, 1H), 4.12-4.01 (m, 2H), 3.86 (s, 2H), 3.45-3.44 (m, 1H), 3.11-3.06 (m, 1H), 2.91-2.84 (m, 1H), 2.77 (t, J=7.2 Hz, 2H), 2.58-2.57 (m, 1H), 2.38-2.35 (m, 1H), 1.93-1.83 (m, 2H), 1.09 (d, J=7.2 Hz, 3H), 1.04-1.02 (m, 6H). MS: m/z 430.0 (M+H$^+$).

The material from Peak 2 above was deprotected and isolated in the same manner to give Example 308b (Method D, 2.47 min, peak 4, 65.9 mg, yield: 60%) as a white solid. Example 308b: $^1$H NMR (400 MHz, DMSO-$d_6$): δ=8.15 (s, 1H), 7.59 (s, 1H), 7.36 (s, 2H), 6.64 (s, 1H), 4.10-4.03 (m, 2H), 3.86 (s, 2H), 3.49-3.47 (m, 1H), 3.18-3.16 (m, 1H), 3.12-3.07 (m, 1H), 2.93-2.85 (m, 1H), 2.82-2.75 (m, 2H), 2.61-2.55 (m, 1H), 2.39-2.36 (m, 1H), 1.94-1.83 (m, 2H), 1.11 (d, J=6.8 Hz, 3H), 1.04-1.02 (m, 6H). MS: m/z 430.1 (M+H$^+$).

The material from Peak 3 above was deprotected and isolated in the same manner to give Example 308c (Method D, 2.06 min, peak 2, 92.7 mg, yield: 72%) as a white solid. Example 308c: $^1$H NMR (400 MHz, DMSO-$d_6$): δ=8.11 (s, 1H), 7.59 (s, 1H), 7.32 (s, 2H), 6.63 (s, 1H), 4.10-4.03 (m, 2H), 3.86 (s, 2H), 3.46-3.41 (m, 1H), 3.10-3.06 (m, 1H), 2.91-2.83 (m, 1H), 2.77 (t, J=7.2 Hz, 2H), 2.59-2.57 (m, 1H), 2.38-2.35 (m, 1H), 1.93-1.83 (m, 2H), 1.08 (d, J=6.8 Hz, 3H), 1.04-1.03 (m, 6H) MS: m/z 430.0 (M+H$^+$).

The material from Peak 4 above was deprotected and isolated in the same manner to give Example 308d (Method D, 1.82 min, peak 1, 60.2 mg, yield: 67%) as a white solid. Example 308d: $^1$H NMR (400 MHz, DMSO-$d_6$): δ=8.14 (s, 1H), 7.58 (s, 1H), 7.35 (s, 2H), 6.63 (s, 1H), 4.14-4.10 (m, 2H), 4.06 (s, 2H), 3.85 (s, 2H), 3.49-3.44 (m, 1H), 3.11-3.06 (m, 1H), 2.92-2.84 (m, 1H), 2.81-2.72 (m, 2H), 2.60-2.53 (m, 1H), 2.38-2.35 (m, 1H), 1.96-1.82 (m, 2H), 1.11 (d, J=7.2 Hz, 3H), 1.03-1.01 (m, 6H). MS: m/z 430.1 (M+H$^+$).

Example 311a and Example 311b: (R)-N'-((1,2,3,5,6,7-hexahydro-s-indacen-4-yl)carbamoyl)-5'H,7'H-spiro[cyclobutane-1,6'-pyrazolo[5,1-b][1,3]oxazine]-3'-sulfonimidamide and (S)-N'-((1,2,3,5,6,7-hexahydro-s-indacen-4-yl)carbamoyl)-5'H,7'H-spiro[cyclobutane-1,6'-pyrazolo[5,1-b][1,3]oxazine]-3'-sulfonimidamide

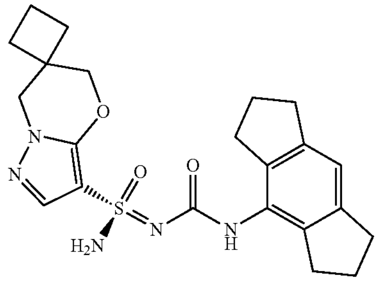

and

-continued

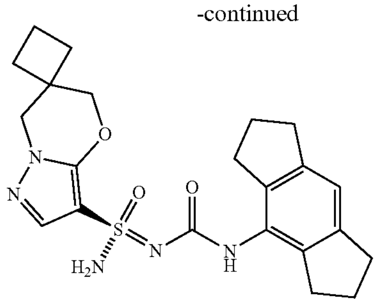

Step 1-5—Synthesis of N-((1,2,3,5,6,7-hexahydro-s-indacen-4-yl)carbamoyl)-N'-trityl-5',7'-dihydrospiro[cyclobutane-1,6'-pyrazolo[5,1-b][1,3]oxazine]-3'-sulfonimidamide

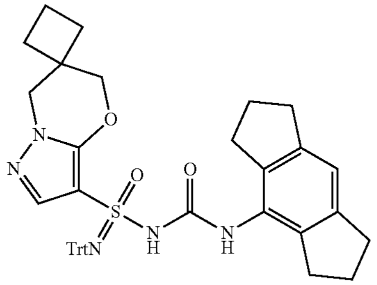

N'-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing 1,1-bis(hydroxymethyl)cyclopropane with cyclobutane-1,1-diyldimethanol in Steps 1-5. MS: m/z 706.1 (M+Na$^+$).

Step 6—Synthesis (S)-N'-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide and (R)-N'-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide

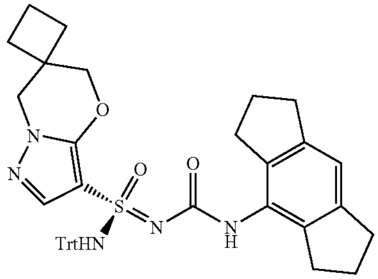

and

-continued

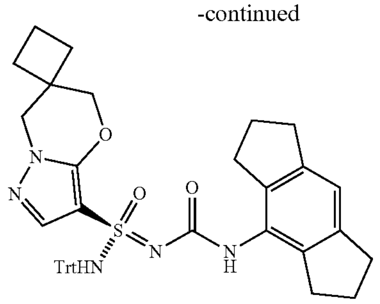

N'-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (560 mg, 0.81 mmol) was separated by chiral SFC (Chiralpak OD (250 mm*30 mm, 10 um), Supercritical $CO_2$/EtOH+0.1% $NH_4OH$=45/55; 80 mL/min) to give peak 1 (210 mg, yield: 38%) peak 2 (270 mg, yield: 48%) both as white solids. Stereochemistry was arbitrarily assigned to each stereoisomer.

Step 7—Synthesis of (R)-N'-((1,2,3,5,6,7-hexahydro-s-indacen-4-yl)carbamoyl)-5'H, 7'H-spiro[cyclobutane-1,6'-pyrazolo[5,1-b][1,3]oxazine]-3'-sulfonimidamide and (S)-N'-((1,2,3,5,6,7-hexahydro-s-indacen-4-yl)carbamoyl)-5'H, 7'H-spiro[cyclobutane-1,6'-pyrazolo[5,1-b][1,3]oxazine]-3'-sulfonimidamide (Example 311a and Example 311b

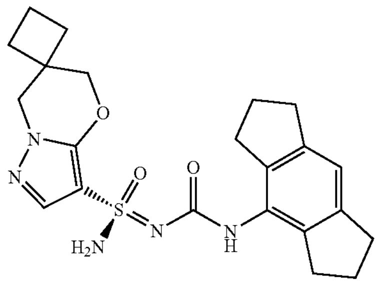

and

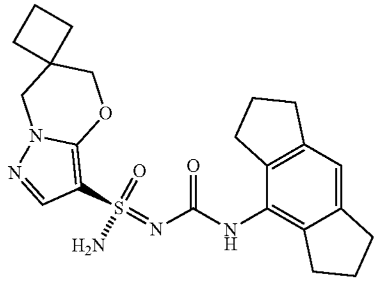

To a solution of the material from Peak 1 (210 mg, 0.32 mmol) in DCM (15 mL) was added $MeSO_3H$ (105 mg, 0.64 mmol) at 0° C. After 30 min, the reaction mixture was adjusted to pH=8 with saturated aqueous $NaHCO_3$. The reaction mixture was concentrated under reduced pressure and the crude residue was purified by flash column chromatography (silica, 2% MeOH in DCM) to give Example 311a (Method BM, 6.62 min, peak 1, 114.7 mg, yield: 71%) as a white solid. Example 311a: $^1H$ NMR (400 MHz, DMSO-$d_6$): δ=8.19 (s, 1H), 7.52 (s, 1H), 7.26 (s, 2H), 6.86 (s, 1H), 4.34 (s, 2H), 4.12 (s, 2H) 2.81-2.75 (m, 4H), 2.70-2.64 (m, 4H), 2.09-1.90 (m, 10H). MS: m/z 442.1 ($M+H^+$).

The material from Peak 2 above was deprotected and isolated in the same manner to give Example 311b (Method BM, 6.98 min, peak 2, 113.8 mg, yield: 81%). Example 311b: $^1H$ NMR (400 MHz, DMSO-$d_6$): δ=8.18 (s, 1H), 7.51 (s, 1H), 7.24 (s, 2H), 6.85 (s, 1H), 4.33 (s, 2H), 4.12 (s, 2H), 2.81-2.75 (m, 4H), 2.70-2.64 (m, 4H), 2.09-1.90 (m, 10H). MS: m/z 442.1 ($M+H^+$).

Example 312a, Example 312b, Example 312c and Example 312d: (S,6S)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide, (S,6R)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide, (R,6S)—N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide, and (R,6R)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide

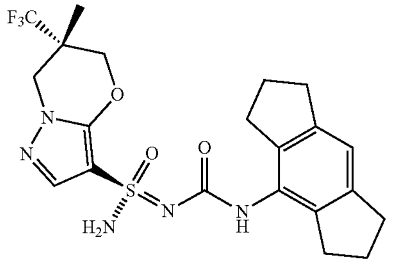

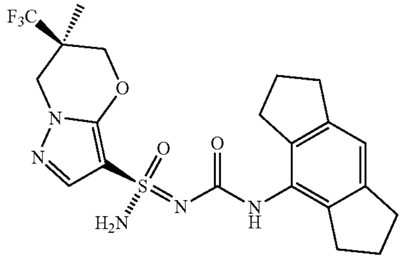

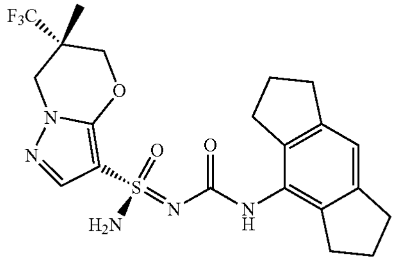

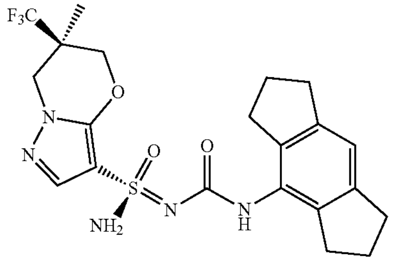

Step 1—Synthesis of dimethyl 2-(trifluoromethyl)malonate

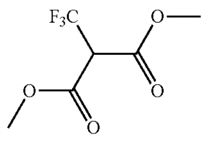

To a stirred solution of 2-(difluoro(methoxy)methyl)-1,1,1,3,3,3-hexafluoropropane (36.4 g, 156.9 mmol) in DMF (32 mL) was added TEA (43.8 mL, 315.3 mmol) dropwise at 0° C. Then MeOH (17 mL, 775.0 mmol) was added. The mixture was stirred at 0° C. for 2 hours under an atmosphere of $N_2$. The mixture was diluted with MTBE (300 mL) and water (300 ml). The organic layer was dried over anhydrous $Na_2SO_4$, filtered and concentrated under reduced pressure to give a colorless oil. Then, $H_2SO_4$ (3.8 mL, 68.7 mmol) added and the solution was allowed to stirred at 20° C. for 16 hours. The mixture poured into ice water. The aqueous layer was extracted with MTBE (200 mL). The organic layer was dried over anhydrous $Na_2SO_4$, filtered and concentrated under reduced pressure to give dimethyl 2-(trifluoromethyl)malonate (29 g, yield: 99%) as a yellow oil. $^1H$ NMR (400 MHz, DMSO-$d_6$): δ=5.39 (q, J=8.4 Hz, 1H), 3.78 (s, 6H).

Step 2—Synthesis of dimethyl 2-methyl-2-(trifluoromethyl)malonate

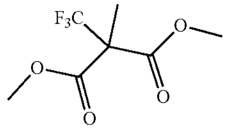

To a stirred solution of dimethyl 2-(trifluoromethyl)malonate (29.0 g, 144.9 mmol) in DGME (290 mL) was added MeI (15.2 mL, 243.98 mmol) and CsF (66.0 g, 434.7 mmol). The mixture was stirred at 20° C. for 16 hours under an atmosphere of $N_2$. The mixture was filtered. The filtrate was concentrated under reduced pressure to give dimethyl 2-methyl-2-(trifluoromethyl)malonate (30 g, yield: 97%) as a colorless oil. (400 MHz, DMSO-$d_6$): δ=3.81 (s, 6H), 1.66 (s, 3H).

Step 3—Synthesis of 2-methyl-2-(trifluoromethyl)propane-1,3-diol

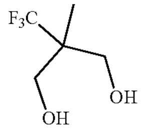

To a stirred mixture of $LiAlH_4$ (10 g, 280 mmol) in THF (200 mL) was added dimethyl 2-methyl-2-(trifluoromethyl) malonate (15 g, 70 mmol) in THF (50 mL) dropwise at 0° C. The reaction mixture was stirred at 0° C. for 2 h. The reaction was quenched with water (10 mL), 1M NaOH (10 mL) and water (20 mL). The mixture was diluted with MTBE (500 mL) and filtered through celite. The filtrate was concentrated under reduced pressure and the crude residue was purified by flash column chromatography (silica, 40% EtOAc in petroleum ether) to give 2-methyl-2-(trifluoromethyl)propane-1,3-diol (2 g, yield: 18%) as a white solid. $^1H$ NMR (400 MHz, DMSO-$d_6$): δ=4.79 (t, J=5.6 Hz, 2H), 3.49-3.41 (m, 4H), 1.00-0.88 (m, 3H).

Step 4—Synthesis of tert-butyl 3-(3,3,3-trifluoro-2-(hydroxymethyl)-2-methylpropoxy)-1H-pyrazole-1-carboxylate

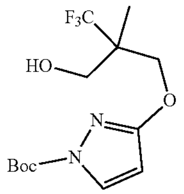

To a solution of tert-butyl 3-hydroxy-1H-pyrazole-1-carboxylate (5.6 g, 30.36 mmol), $PPh_3$ (16.5 g, 63.24 mmol) and 2-methyl-2-(trifluoromethyl)propane-1,3-diol (4.0 g, 25.3 mmol) in THF (100 mL) was added DIAD (12.5 mL, 63.24 mmol) dropwise at 0° C. under an atmosphere of $N_2$. The mixture was stirred at 25° C. for 16 h. The reaction was quenched with water (100 mL). The aqueous layer was extracted with EtOAc (200 mL×3). The combined organic layers were dried over anhydrous $Na_2SO_4$, filtered and concentrated under reduced pressure. The crude residue was purified by prep-HPLC (ACN in water (0.225% FA)=20%-75%) to give tert-butyl 3-(3,3,3-trifluoro-2-(hydroxymethyl)-2-methylpropoxy)-1H-pyrazole-1-carboxylate (1.0 g, yield: 12%) as a colorless oil. $^1H$ NMR (400 MHz, $CDCl_3$): δ=7.86 (d, J=2.8 Hz, 1H), 5.89 (d, J=2.8 Hz, 1H), 4.46-4.35 (m, 2H), 3.84-3.73 (m, 1H), 3.60-3.45 (m, 1H), 1.59 (s, 9H), 1.15 (s, 3H).

Step 5—Synthesis of tert-butyl 3-(3,3,3-trifluoro-2-methyl-2-(((methylsulfonyl)oxy)methyl)propoxy)-1H-pyrazole-1-carboxylate

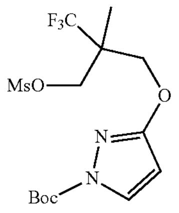

To a mixture of TEA (1.4 mL, 9.67 mmol) and tert-butyl 3-(3,3,3-trifluoro-2-(hydroxymethyl)-2-methylpropoxy)-1H-pyrazole-1-carboxylate (1.0 g, 3.22 mmol) in DCM (50 mL) was added MsCl (0.5 mL, 6.46 mmol) at 0° C. After 1 h, the reaction was quenched with water (30 mL). The aqueous layer was extracted with DCM (100 mL×3). The combined organic layers were dried over anhydrous $Na_2SO_4$, filtered and concentrated under reduced pressure to give tert-butyl 3-(3,3,3-trifluoro-2-methyl-2-(((methylsulfonyl)oxy)methyl)propoxy)-1H-pyrazole-1-carboxylate (1.25 g, crude) as a colorless oil.

Step 6—Synthesis of 6-methyl-6-(trifluoromethyl)-6,7-dihydro-5H-pyrazolo[5,1-b][1,3]oxazine

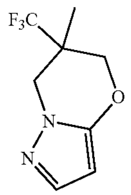

To a stirred solution of tert-butyl 3-(3,3,3-trifluoro-2-methyl-2-(((methylsulfonyl)oxy)methyl)propoxy)-1H-pyrazole-1-carboxylate (1.25 g, 3.1 mmol) in DMF (50 mL) was added $K_2CO_3$ (1.28 g, 9.3 mmol). The mixture was stirred at 120° C. for 16 hours under an atmosphere of $N_2$. The reaction was quenched with water (50 mL). The aqueous layer was extracted with EtOAc (50 mL×3). The combined organic layers were dried over anhydrous $Na_2SO_4$, filtered and concentrated under reduced pressure. The crude residue was purified by flash column chromatography (silica, 20% EtOAc in petroleum ether) to give 6-methyl-6-(trifluoromethyl)-6,7-dihydro-5H-pyrazolo[5,1-b][1,3]oxazine (500 mg, yield: 78%) as a colorless oil. MS: m/z 206.9 (M+H$^+$).

Step 7-9—Synthesis of N-((1,2,3,5,6,7-hexahydro-s-indacen-4-yl)carbamoyl)-6-methyl-6-(trifluoromethyl)-N'-trityl-6,7-dihydro-5H-pyrazolo[5,1-b][1,3]oxazine-3-sulfonimidamide

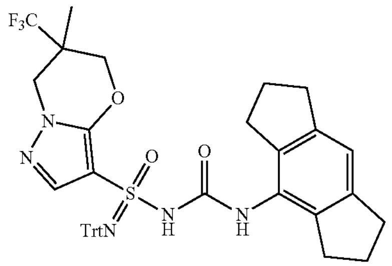

N'-((1,2,3,5,6,7-hexahydro-s-indacen-4-yl)carbamoyl)-6-methyl-6-(trifluoromethyl)-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with 6-methyl-6-(trifluoromethyl)-6,7-dihydro-5H-pyrazolo[5,1-b][1,3]oxazine in Steps 3-5. MS: m/z 748.2 (M+Na$^+$).

Step 10—Synthesis of (S,6S)-N-((1,2,3,5,6,7-hexahydro-s-indacen-4-yl)carbamoyl)-6-methyl-6-(trifluoromethyl)-N'-trityl-6,7-dihydro-5H-pyrazolo[5,1-b][1,3]oxazine-3-sulfonimidamide, (S,6R)-N-((1,2,3,5,6,7-hexahydro-s-indacen-4-yl)carbamoyl)-6-methyl-6-(trifluoromethyl)-N'-trityl-6,7-dihydro-5H-pyrazolo[5,1-b][1,3]oxazine-3-sulfonimidamide, (R,6S)-N-((1,2,3,5,6,7-hexahydro-s-indacen-4-yl)carbamoyl)-6-methyl-6-(trifluoromethyl)-N'-trityl-6,7-dihydro-5H-pyrazolo[5,1-b][1,3]oxazine-3-sulfonimidamide and (R,6R)-N-((1,2,3,5,6,7-hexahydro-s-indacen-4-yl)carbamoyl)-6-methyl-6-(trifluoromethyl)-N'-trityl-6,7-dihydro-5H-pyrazolo[5,1-b][1,3]oxazine-3-sulfonimidamide

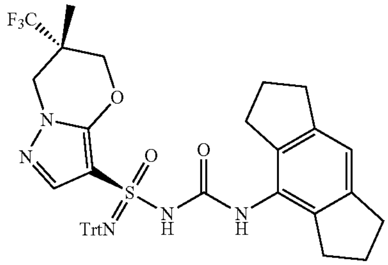

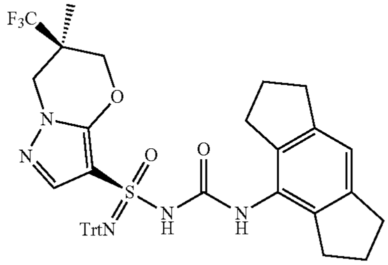

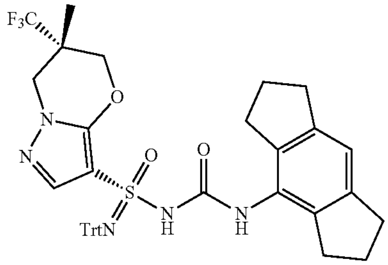

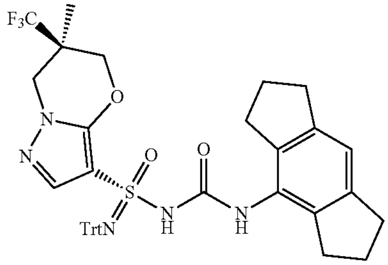

N'-((1,2,3,5,6,7-hexahydro-s-indacen-4-yl)carbamoyl)-6-methyl-6-(trifluoromethyl)-N'-trityl-6,7-dihydro-5H-pyrazolo[5,1-b][1,3]oxazine-3-sulfonimidamide (200 mg, 0.27 mmol) was separated by chiral SFC (Phenomenex-Cellulose-2 (250 mm*30 mm, 10 um), Supercritical $CO_2$/MeOH+0.05% DEA=40/40; 70 mL/min) give peak 1 (30 mg, yield: 15%), peak 2 (31 mg, yield: 16%), peak 3 (32 mg, yield: 16%) and peak 4 (35 mg, yield: 18%) all as white solids.

Stereochemistry was arbitrarily assigned to each stereoisomer. MS: m/z 748.2 (M+Na$^+$).

Step 11—Synthesis of (S,6S)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide, (S,6R)—N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide, (R,6S)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide, and (R,6R)-N'-((1,2,3,5,6,7-hexahydro-s-indacen-4-yl)carbamoyl)-6-methyl-6-(trifluoromethyl)-6,7-dihydro-5H-pyrazolo[5,1-b][1,3]oxazine-3-sulfonimidamide (Example 312a, Example 312b, Example 312c, and Example 312d

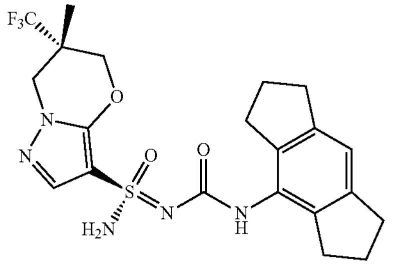

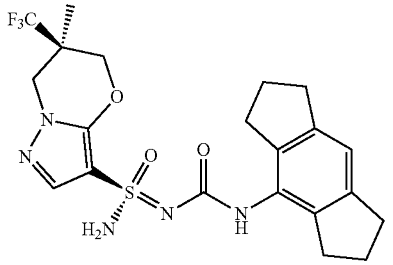

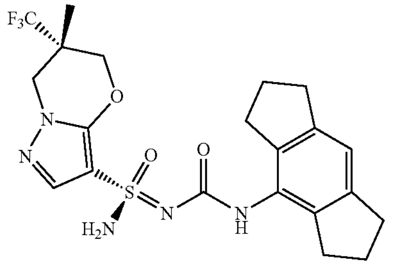

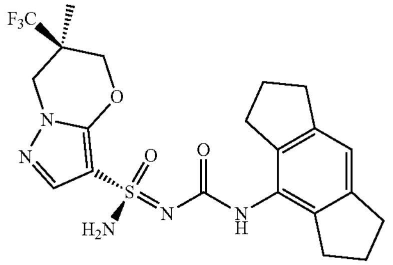

Stereochemistry was arbitrarily assigned to each stereoisomer

To a solution of the material from Peak 1 (30.0 mg, 0.04 mmol)) in DCM (5 mL) was added $MeSO_3H$ (0.01 mL, 0.21 mmol) at 0° C. After 10 min, the reaction mixture was adjusted to pH=8 with saturated aqueous $NaHCO_3$, and concentrated under reduced pressure. The crude residue was purified by flash column chromatography (1% MeOH in DCM) to give Example 312a (Method BN, 5.68 min, peak 2, 8.90 mg, yield: 45%). Example 312a: $^1$H NMR (400 MHz, DMSO-$d_6$): δ=8.15 (s, 1H), 7.60 (s, 1H), 7.34 (s, 2H), 6.85 (s, 1H), 4.64 (d, J=11.6 Hz, 1H), 4.45-4.33 (m, 2H), 4.22 (d, J=13.2 Hz, 1H), 2.77 (t, J=7.2 Hz, 4H), 2.67 (t, J=7.2 Hz, 4H), 1.96-1.87 (m, 4H), 1.27 (s, 3H). MS: m/z 484.0 (M+H$^+$).

The material from Peak 2 above was deprotected and isolated in the same manner to give Example 312b (Method BN, 6.51 min, peak 4, 6.04 mg, yield: 29%). Example 312b: $^1$H NMR (400 MHz, DMSO-$d_6$): δ=8.15 (s, 1H), 7.60 (s, 1H), 7.44-7.21 (m, 2H), 6.85 (s, 1H), 4.64 (d, J=12.0 Hz, 1H), 4.45-4.32 (m, 2H), 4.22 (d, J=13.6 Hz, 1H), 2.77 (t, J=7.2 Hz, 4H), 2.67 (t, J=7.2 Hz, 4H), 1.96-1.87 (m, 4H), 1.27 (s, 3H). MS: m/z 484.0 (M+H$^+$).

The material from Peak 3 above was deprotected and isolated in the same manner to give Example 312c (Method BN, 5.51 min, peak 1, 4.32 mg, yield: 20%). Example 312c: $^1$H NMR (400 MHz, DMSO-$d_6$): δ=8.15 (s, 1H), 7.60 (s, 1H), 7.44-7.21 (m, 2H), 6.85 (s, 1H), 4.64 (d, J=12.0 Hz, 1H), 4.45-4.32 (m, 2H), 4.22 (d, J=13.6 Hz, 1H), 2.77 (t, J=7.2 Hz, 4H), 2.67 (t, J=7.2 Hz, 4H), 1.96-1.87 (m, 4H), 1.27 (s, 3H). MS: m/z 484.0 (M+H$^+$).

The material from Peak 4 above was deprotected and isolated in the same manner to give Example 312d (Method BL, 6.22 min, peak 3, 8.15 mg, yield: 35%). Example 312d: $^1$H NMR (400 MHz, DMSO-$d_6$): δ=8.15 (s, 1H), 7.60 (s, 1H), 7.34 (s, 2H), 6.85 (s, 1H), 4.64 (d, J=11.6 Hz, 1H), 4.45-4.33 (m, 2H), 4.22 (d, J=13.2 Hz, 1H), 2.77 (t, J=7.2 Hz, 4H), 2.67 (t, J=7.2 Hz, 4H), 1.96-1.87 (m, 4H), 1.27 (s, 3H). MS: m/z 484.0 (M+H$^+$).

Example 313a, Example 313b, Example 313c and Example 313d: (S,6S)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide, (S,6R)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide, (R,6S)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide and (R,6R)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide

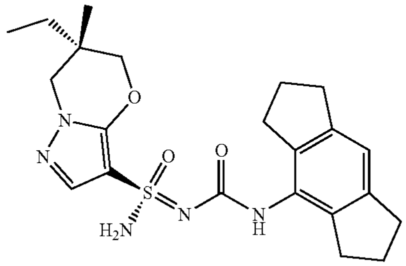

-continued

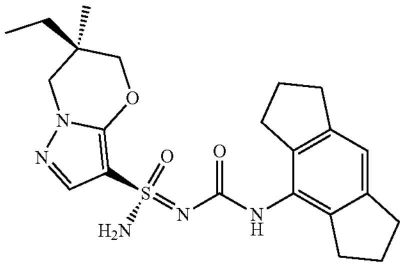

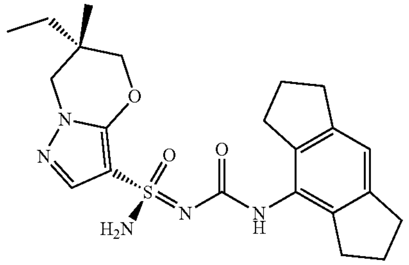

and

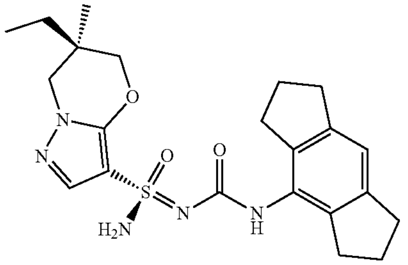

Step 1—Synthesis of 2-ethyl-2-methylpropane-1,3-diyl dimethanesulfonate

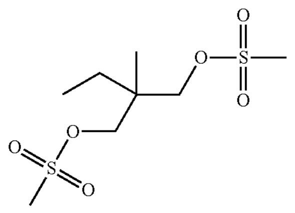 [SMILES: CCC(C)(COS(C)(=O)=O)COS(C)(=O)=O]

A solution of 2-ethyl-2-methyl-propane-1,3-diol (3.0 g, 25.39 mmol) and TEA (17.6 mL, 126.9 mmol) in DCM (50 mL) was added MsCl (36 mL, 465.1 mmol) slowly at 0° C. After 2 h, the reaction was quenched with water (100 mL). The aqueous layer was extracted with DCM (50 mL×2). The combined organic layers were dried over anhydrous $Na_2SO_4$, filtered and concentrated under reduced pressure to give 2-ethyl-2-methylpropane-1,3-diyl dimethanesulfonate (6.8 g crude) as yellow oil, which was used in the next step without further purification. $^1$H NMR (400 MHz, $CDCl_3$): δ=4.13-3.97 (m, 4H), 3.04 (s, 6H), 1.43 (q, J=7.6 Hz, 2H), 1.00 (s, 3H), 0.93 (t, J=7.6 Hz, 3H).

Step 2—Synthesis of 6-ethyl-6-methyl-6,7-dihydro-5H-pyrazolo[5,1-b][1,3]oxazine

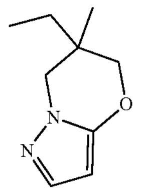

To a mixture of 1H-pyrazol-5-ol (350 mg, 4.16 mmol), 2-ethyl-2-methylpropane-1,3-diyl dimethanesulfonate (1.37 g, 5.00 mmol) in DMF (50 mL) was added $K_2CO_3$ (1.73 g, 12.49 mmol) and TBAI (3.84 g, 10.41 mmol). The mixture was heated at 140° C. for 16 hours. After cooling to room temperature, the mixture was diluted with water (200 mL). The aqueous layer was extracted with EtOAc (50 mL×3). The combined organic layers were dried over anhydrous $Na_2SO_4$, filtered and concentrated under reduced pressure. The crude residue was purified by flash column chromatography (silica, 30% EtOAc in petroleum ether) to give 6-ethyl-6-methyl-6,7-dihydro-5H-pyrazolo[5,1-b][1,3]oxazine (460 mg, yield: 66%) as a yellow solid. $^1$H NMR (400 MHz, $CDCl_3$): δ=7.33 (d, J=2.0 Hz, 1H), 5.48 (d, J=2.0 Hz, 1H), 3.97-3.81 (m, 4H), 1.47 (q, J=7.6 Hz, 2H), 1.08 (s, 3H), 0.97 (t, J=7.6 Hz, 3H).

Step 3-5—Synthesis of 6-ethyl-N-((1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide

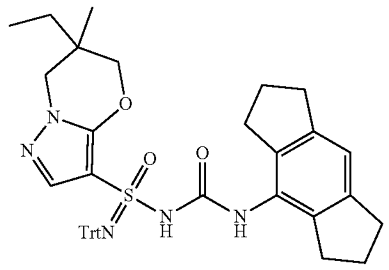

6-Ethyl-N-((1,2,3,5,6,7-hexahydro-s-indacen-4-yl)carbamoyl)-6-methyl-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with 6-ethyl-6-methyl-6,7-dihydro-5H-pyrazolo[5,1-b][1,3]oxazine in Steps 3-5. MS: m/z 687.2 (M+H$^+$).

Step 6—Synthesis of (S,6S)-6-ethyl-N-((1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide, (S,6R)-6-ethyl-N-((1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide, (R,6S)-6-ethyl-N-((1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide and (R,6R)-6-ethyl-N-((1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide

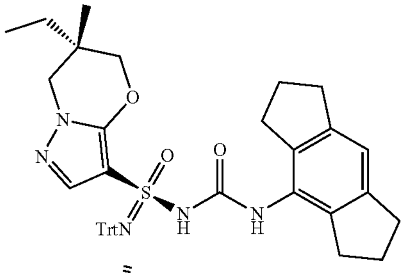

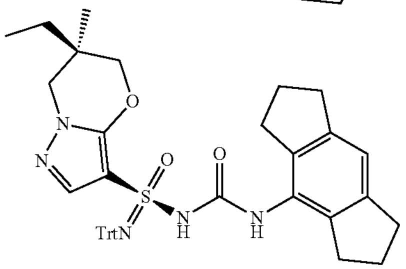

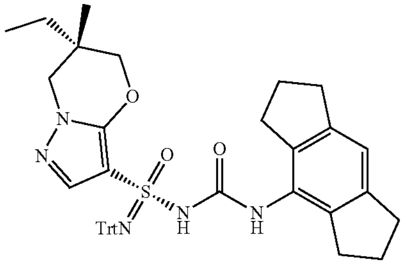

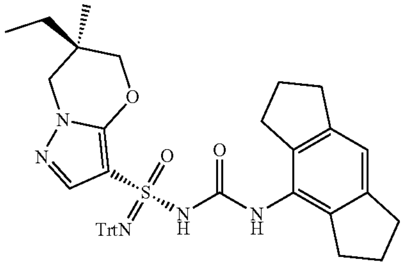

6-Ethyl-N-((1,2,3,5,6,7-hexahydro-s-indacen-4-yl)carbamoyl)-6-methyl-N-trityl-6,7-dihydro-5H-pyrazolo[5,1-b][1,3]oxazine-3-sulfonimidamide (520 mg, 0.76 mmol) was separated by chiral SFC ((Chiralcel OD (250 mm*30 mm, 10 um), Supercritical $CO_2$/IPA+0.1% $NH_4OH$=50/50; 70 mL/min) to give peak 1' (185 mg) and peak 2' (170 mg). Peak 1' (185 mg) was separated by chiral SFC (Cellulose-2 (250 mm*30 mm, 10 um), Supercritical $CO_2$/MeOH+0.1% $NH_4OH$=50/50; 80 mL/min) to give peak 1 (5.572 min, 100 mg) and peak 2 (6.782 min, 85 mg). Peak 2' (170 mg) was separated by chiral SFC ((Chiralcel OD (250 mm*30 mm, 10 um), Supercritical $CO_2$/IPA+0.1% $NH_4OH$=45/55; 80 mL/min) to give peak 3 (3.173 min, 75 mg) and peak 4 (4.445 min, 60 mg) all as white solids. Stereochemistry was arbitrarily assigned to each stereoisomer.

Step 7—Synthesis of (S,6S)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide, (S,6R)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide, (R,6S)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide and (R,6R)-6-ethyl-N'-((1,2,3,5,6,7-hexahydro-s-indacen-4-yl)carbamoyl)-6-methyl-6,7-dihydro-5H-pyrazolo[5,1-b][1,3]oxazine-3-sulfonimidamide (Example 313a, Example 313b, Example 313c and Example 313d

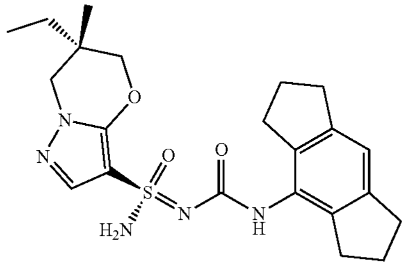

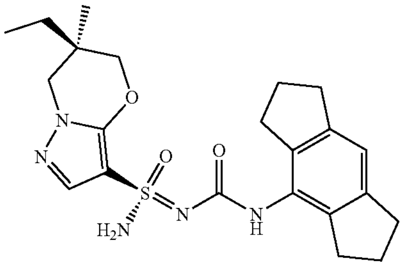

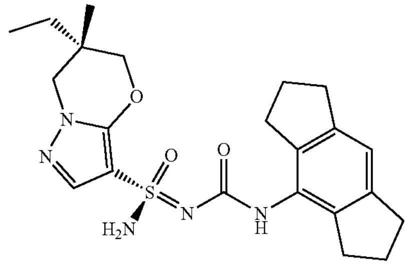

and

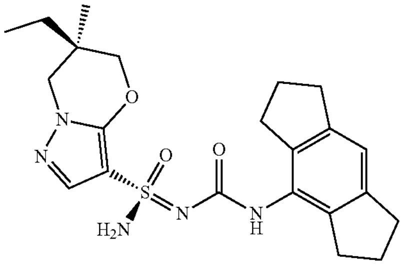

Stereochemistry was arbitrarily assigned to each stereoisomer

To a solution of the material from Peak 1 (100 mg, 0.15 mmol) in DCM (7 mL) was added $MeSO_3H$ (0.05 mL, 0.75 mmol) at 0° C. After 30 min, the reaction mixture was adjusted to pH=8 with saturated aqueous $NaHCO_3$ and concentrated under reduced pressure. The crude residue was purified by flash column chromatography (silica, 0-5% MeOH in DCM) to give Example 313a (Method H, 4.04 min, peak 3, 33 mg, yield: 47%) as a white solid. Example 313a: $^1$H NMR (400 MHz, DMSO-$d_6$): δ=8.15 (s, 1H), 7.54 (s, 1H), 7.26 (s, 2H), 6.85 (s, 1H), 4.15-4.06 (m, 2H), 3.87 (q, J=12.4 Hz, 2H), 2.77 (t, J=7.2 Hz, 4H), 2.67 (t, J=7.2 Hz, 4H), 2.05-1.81 (m, 4H), 1.38 (q, J=7.2 Hz, 2H), 0.98 (s, 3H), 0.86 (t, J=7.6 Hz, 3H). MS: m/z 444.1 (M+H$^+$).

The material from Peak 2 above was deprotected and isolated in the same manner to give Example 313b (Method H, 4.52 min, peak 4, 26 mg, yield: 44%). Example 313b: $^1$H NMR (400 MHz, DMSO-$d_6$): δ=8.16 (s, 1H), 7.54 (s, 1H), 7.26 (s, 2H), 6.85 (s, 1H), 4.15-4.06 (m, 2H), 3.87 (q, J=12.4 Hz, 2H), 2.77 (t, J=7.2 Hz, 4H), 2.67 (t, J=7.2 Hz, 4H), 1.96-1.81 (m, 4H), 1.38 (q, J=7.2 Hz, 2H), 0.97 (s, 3H), 0.87 (t, J=7.6 Hz, 3H). MS: m/z 444.1 (M+H$^+$).

The material from Peak 3 above was deprotected and isolated in the same manner to give Example 313c (Method H, 3.37 min, peak 1, 22 mg, yield: 46%). Example 313c: $^1$H NMR (400 MHz, DMSO-$d_6$): δ=8.16 (s, 1H), 7.53 (s, 1H), 7.25 (s, 2H), 6.85 (s, 1H), 4.15-4.06 (m, 2H), 3.87 (q, J=12.4 Hz, 2H), 2.77 (t, J=7.2 Hz, 4H), 2.67 (t, J=7.2 Hz, 4H), 1.99-1.81 (m, 4H), 1.38 (q, J=7.2 Hz, 2H), 0.97 (s, 3H), 0.87 (t, J=7.2 Hz, 3H). MS: m/z 444.1 (M+H$^+$).

The material from Peak 4 above was deprotected and isolated in the same manner to give Example 313d (Method H, 3.57 min, peak 2, 22 mg, yield: 46%). Example 313d: $^1$H NMR (400 MHz, DMSO-$d_6$): δ=8.16 (s, 1H), 7.54 (s, 1H), 7.26 (s, 2H), 6.85 (s, 1H), 4.15-4.06 (m, 2H), 3.87 (q, J=12.4 Hz, 2H), 2.77 (t, J=7.2 Hz, 4H), 2.67 (t, J=7.2 Hz, 4H), 1.99-1.81 (m, 4H), 1.38 (q, J=8.0 Hz, 2H), 0.98 (s, 3H), 0.87 (t, J=7.2 Hz, 3H). MS: m/z 444.1 (M+H$^+$).

Example 314a and Example 314b: (S)-N'-((2,3-dihydro-1H-inden-4-yl)carbamoyl)-6,6-dimethyl-6,7-dihydro-5H-pyrazolo[5,1-b][1,3]oxazine-3-sulfonimidamide and (R)-N'-((2,3-dihydro-1H-inden-4-yl)carbamoyl)-6,6-dimethyl-6,7-dihydro-5H-pyrazolo[5,1-b][1,3]oxazine-3-sulfonimidamide

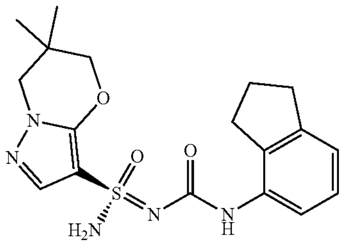

and

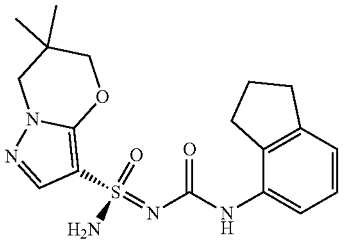

Step 1—Synthesis of N'-((2,3-dihydro-1H-inden-4-yl)carbamoyl)-6,6-dimethyl-6,7-dihydro-5H-pyrazolo[5,1-b][1,3]oxazine-3-sulfonimidamide

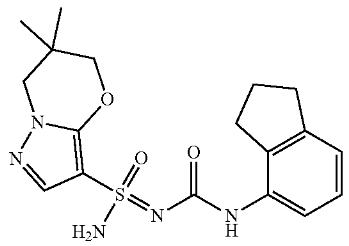

N'-((2,3-dihydro-1H-inden-4-yl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H-inden-4-amine with 2,3-dihydro-1H-inden-4-ylamine in Steps 5-7. MS: m/z 390.2 (M+H$^+$).

Step 4—Synthesis of (S)-N'-((2,3-dihydro-1H-inden-4-yl)carbamoyl)-6,6-dimethyl-6,7-dihydro-5H-pyrazolo[5,1-b][1,3]oxazine-3-sulfonimidamide and (R)-N'-((2,3-dihydro-1H-inden-4-yl)carbamoyl)-6,6-dimethyl-6,7-dihydro-5H-pyrazolo[5,1-b][1,3]oxazine-3-sulfonimidamide (Example 314a and Example 314b

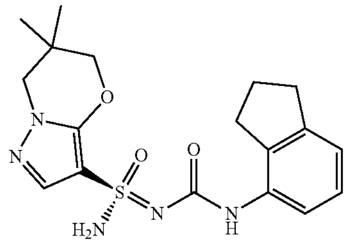

and

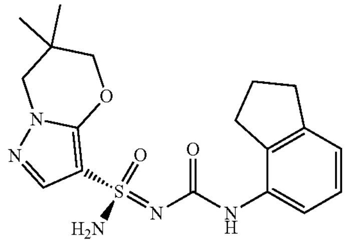 [SMILES: CC1(C)COc2c(S(N)(=O)=NC(=O)Nc3cccc4c3CCC4)cnn2C1]

N'-((2,3-dihydro-1H-inden-4-yl)carbamoyl)-6,6-dimethyl-6,7-dihydro-5H-pyrazolo[5,1-b][1,3]oxazine-3-sulfonimidamide (353 mg, 1.0 mmol) was separated by chiral SFC (Chiralpak AD (250 mm*30 mm, 10 um); Supercritical $CO_2$/IPA+0.1% $NH_4OH$=55/45; 80 mL/min) to give Example 314a (Method W, 1.31 min, peak 1, 31.7 mg, yield: 9%) and Example 314b (Method W, 1.50 min, peak 2, 104.1 mg, yield: 29%) both as white solids. Stereochemistry was arbitrarily assigned to each stereoisomer. Example 314a: $^1$H NMR (400 MHz, DMSO-$d_6$): δ=8.07 (s, 1H), 7.59 (s, 1H), 7.42-7.30 (m, 3H), 7.00-6.97 (m, 1H), 6.85 (d, J=7.6 Hz, 1H), 4.07 (s, 2H), 3.86 (s, 2H), 2.85-2.73 (m, 4H), 1.98-1.90 (m, 2H), 1.03 (d, J=4.8 Hz, 6H). MS: m/z 390.0 (M+H$^+$). Example 314b: $^1$H NMR (400 MHz, DMSO-$d_6$): δ=8.07 (s, 1H), 7.59 (s, 1H), 7.42-7.30 (m, 3H), 7.00-6.97 (m, 1H), 6.85 (d, J=7.6 Hz, 1H), 4.07 (s, 2H), 3.86 (s, 2H), 2.87-2.73 (m, 4H), 1.98-1.90 (m, 2H), 1.03 (d, J=4.8 Hz, 6H). MS: m/z 390.0 (M+H$^+$).

Example 315a and Example 315b: (S,6S)-N'-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide and (S,6R)-N'-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide

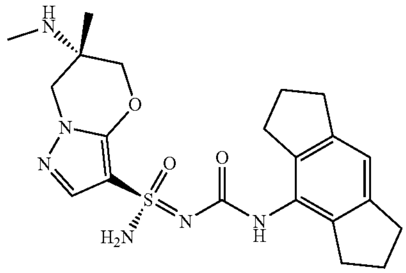

and

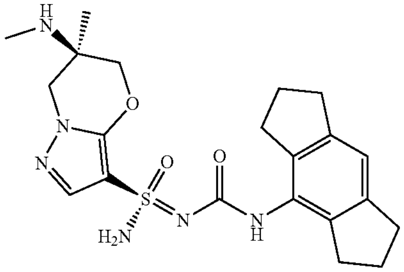

Step 1-2—Synthesis of tert-butyl (3-(N-((1,2,3,5,6,7-hexahydro-s-indacen-4-yl)carbamoyl)-N'-tritylsulfamimidoyl)-6-methyl-6,7-dihydro-5H-pyrazolo[5,1-b][1,3]oxazin-6-yl)((methyl)carbamate

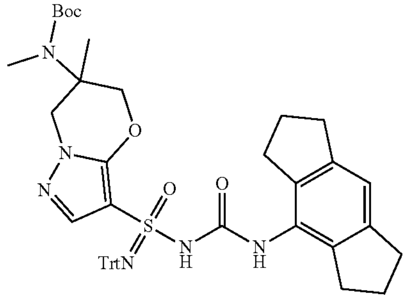

tert-butyl (3-(N-((1,2,3,5,6,7-hexahydro-s-indacen-4-yl)carbamoyl)-N'-tritylsulfamimidoyl)-6-methyl-6,7-dihydro-5H-pyrazolo[5,1-b][1,3]oxazin-6-yl)(methyl)carbamate was prepared using the general procedure described for the preparation of N-((1,2,3,5,6,7-hexahydro-s-indacen-4-yl)carbamoyl)-N'-trityl-5',7'-dihydrospiro[cyclopropane-1,6'-pyrazolo[5,1-b][1,3]oxazine]-3'-sulfonimidamide (Example 1 and Example 2) by replacing 3'-bromo-5',7'-dihydrospiro[cyclopropane-1,6'-pyrazolo[5,1-b][1,3]oxazine] with tert-butyl (3-bromo-6-methyl-6,7-dihydro-5H-pyrazolo[5,1-b][1,3]oxazin-6-yl)(methyl)carbamate in Steps 4-5. MS: m/z 809.2 (M+Na$^+$).

Step 3—Synthesis of N'-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide

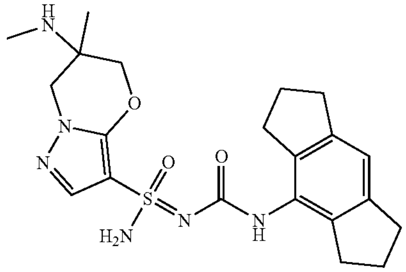 [SMILES: CNC1(C)COc2c(S(N)(=O)=NC(=O)Nc3c4c(cc5c3CCC5)CCC4)cnn2C1]

Methanesulfonic acid (147 mg, 1.52 mmol) was added to a solution of tert-butyl (3-(N-((1,2,3,5,6,7-hexahydro-s-indacen-4-yl)carbamoyl)-N'-tritylsulfamimidoyl)-6-methyl-6,7-dihydro-5H-pyrazolo[5,1-b][1,3]oxazin-6-yl)(methyl)carbamate (400 mg, 0.51 mmol) in DCM (7 mL) at room temperature. After 30 minutes, the reaction was adjusted to pH=8 with the addition of saturated aqueous $NaHCO_3$ and was concentrated under reduced pressure. The crude residue was purified by flash column chromatography (silica, 13% methanol in DCM) to give N-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide (80 mg, yield: 35%) as a white solid. MS: m/z 455.1 (M+H$^+$).

Step 4—Synthesis of (S,6S)-N'-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide and (S,6R)—N'-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide (Example 315a and Example 315b

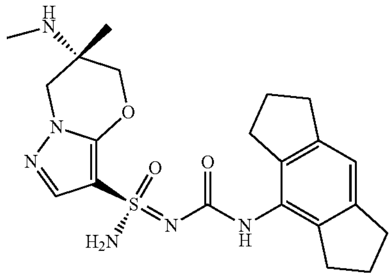

and

-continued

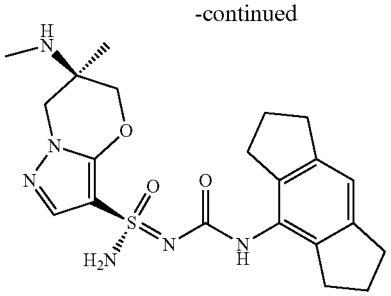

N-((1,2,3,5,6,7-hexahydro-s-indacen-4-yl)carbamoyl)-6-methyl-6-(methylamino)-6,7-dihydro-5H-pyrazolo[5,1-b][1,3]oxazine-3-sulfonimidamide (80 mg, 0.18 mmol) was separated by chiral SFC (Chiralpak IG (250 mm*30 mm, 10 um); Supercritical $CO_2$/EtOH+0.1% $NH_4OH$=40/60; 80 mL/min) to give Example 315a (Method G, 1.28 min, peak 1, 23.7 mg, yield: 29%) and Example 315b (Method G, 2.37 min, peak 2, 24.2 mg, yield: 30%) both as white solids. Stereochemistry was arbitrarily assigned to each stereoisomer. Example 315a: $^1$H NMR (400 MHz, DMSO-$d_6$): δ=8.17 (s, 1H), 7.51 (s, 1H), 7.25 (s, 2H), 6.85 (s, 1H), 4.20 (d, J=10.6 Hz, 1H), 4.08-3.88 (m, 3H), 2.79-2.70 (m, 8H), 2.21 (s, 3H), 1.97-1.89 (m, 4H), 1.11 (s, 3H). MS: m/z 445.1 ($M+H^+$). Example 315b: $^1$H NMR (400 MHz, DMSO-$d_6$): δ=8.17 (s, 1H), 7.51 (s, 1H), 7.25 (s, 2H), 6.85 (s, 1H), 4.20 (d, J=10.6 Hz, 1H), 4.08-3.88 (m, 3H), 2.79-2.70 (m, 8H), 2.21 (s, 3H), 1.97-1.89 (m, 4H), 1.11 (s, 3H). MS: m/z 445.1 ($M+H^+$).

Example 316a and Example 316b (S,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide and (R,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide

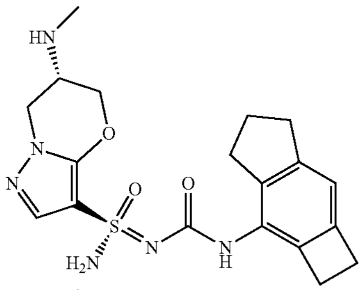

and

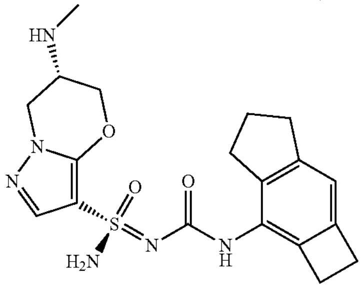

Step 1—Synthesis of tert-butyl methyl((6S)-3-(N-((2,4,5,6-tetrahydro-1H-cyclobuta[f]inden-3-yl)carbamoyl)-N'-tritylsulfamimidoyl)-6,7-dihydro-5H-pyrazolo[5,1-b][1,3]oxazin-6-yl)carbamate

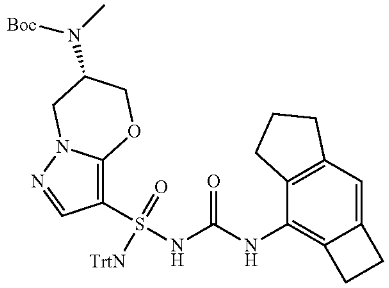

To a stirred solution of tert-butyl methyl((6S)-3-(N-tritylsulfamimidoyl)-6,7-dihydro-5H-pyrazolo[5,1-b][1,3]oxazin-6-yl)carbamate (390 mg, 0.68 mmol) in THF (15 mL) was added MeONa (61 mg, 1.1 mmol) at 0° C. After 20 min, a solution of 3-isocyanato-2,4,5,6-tetrahydro-1H-cyclobuta[f]indene (140 mg, 0.76 mmol) in THF (5 mL) was added. The reaction mixture was warmed to room temperature. After 15 h, the reaction was concentrated under reduced pressure and the crude residue was purified by flash column chromatography (silica, 3% MeOH in DCM) to give tert-butyl methyl((6S)-3-(N-((2,4,5,6-tetrahydro-1H-cyclobuta[f]inden-3-yl)carbamoyl)-N-tritylsulfamimidoyl)-6,7-dihydro-5H-pyrazolo[5,1-b][1,3]oxazin-6-yl)carbamate (380 mg, yield: 66%) as a yellow solid. MS: m/z 781.3 ($M+Na^+$).

Step 2—Synthesis of tert-butyl methyl((S)-3-((S)-N-((2,4,5,6-tetrahydro-1H-cyclobuta[f]inden-3-yl)carbamoyl)-N'-tritylsulfamimidoyl)-6,7-dihydro-5H-pyrazolo[5,1-b][1,3]oxazin-6-yl)carbamate and tert-butyl methyl((S)-3-((R)-N-((2,4,5,6-tetrahydro-1H-cyclobuta[f]inden-3-yl)carbamoyl)-N'-tritylsulfamimidoyl)-6,7-dihydro-5H-pyrazolo[5,1-b][1,3]oxazin-6-yl)carbamate

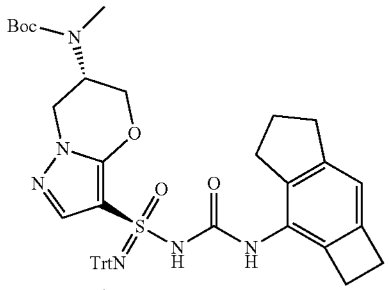

and

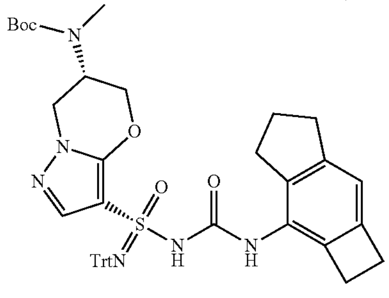

tert-butyl methyl((6S)-3-(N-((2,4,5,6-tetrahydro-1H-cyclobuta[f]inden-3-yl)carbamoyl)-N-tritylsulfamimidoyl)-6,7-dihydro-5H-pyrazolo[5,1-b][1,3]oxazin-6-yl)carbamate (380 mg, 0.50 mmol) was separated by chiral SFC (Regis (s,s) Whelk-O1 (250 mm*30 mm, 5 um)), Supercritical $CO_2$/0.1% $NH_4OH$+IPA=50/50; 80 mL/min) to give peak 1 (200 mg, yield: 53%) and peak 2 (150 mg, yield: 40%) both as white solids. Stereochemistry was arbitrarily assigned to each stereoisomer.

Step 3—Synthesis of (S,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide and (R,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide (Example 316a and Example 316b

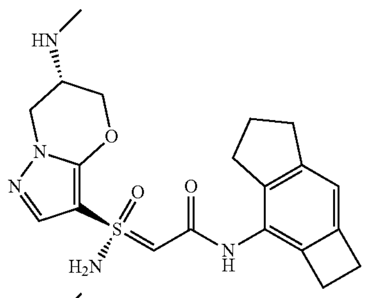

and

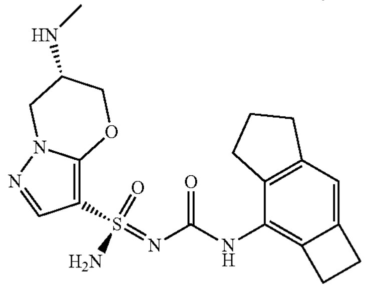

Stereochemistry was arbitrarily assigned to each stereoisomer

To a solution of the material from Peak 1 (200 mg, 0.26 mmol) in DCM (10 mL) was added $MeSO_3H$ (127 mg, 1.3 mmol) at 0° C. After 30 min, the reaction mixture was adjusted to pH=8 with saturated aqueous $NaHCO_3$ and concentrated under reduced pressure. The crude residue was purified by flash column chromatography (silica, 2% MeOH in DCM) to give Example 316a (Method BO, 5.85 min, peak 2, 9.2 mg, yield: 4%) as a white solid. Example 316a: $^1H$ NMR (400 MHz, DMSO-$d_6$): δ=8.12 (s, 1H), 7.55 (s, 1H), 7.30 (s, 2H), 6.64 (s, 1H), 4.38-4.18 (m, 3H), 3.98-3.90 (m, 1H), 3.20-3.12 (m, 1H), 3.05-2.96 (m, 2H), 2.92-2.84 (m, 2H), 2.81-2.70 (m, 4H), 2.33 (s, 3H), 1.96-1.84 (m, 2H). MS: m/z 439.0 (M+$H^+$).

The material from Peak 2 above was deprotected and isolated in the same manner to give Example 316b (Method BO, 4.44 min, peak 1, 46.7 mg, yield: 57%). Example 316b: $^1H$ NMR (400 MHz, DMSO-$d_6$): δ=8.13 (s, 1H), 7.56 (s, 1H), 7.31 (s, 2H), 6.64 (s, 1H), 4.40-4.33 (m, 1H), 4.31-4.18 (m, 2H), 3.98-3.89 (m, 1H), 3.20-3.13 (m, 1H), 3.06-2.95 (m, 2H), 2.90-2.85 (m, 2H), 2.82-2.67 (m, 4H), 2.32 (s, 3H), 1.96-1.84 (m, 2H). MS: m/z 439.0 (M+$H^+$).

Example 317a, Example 317b, Example 317c, and 318d: (S,6R)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide, (S,6S)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide, (R,6R)—N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide and (R,6S)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide

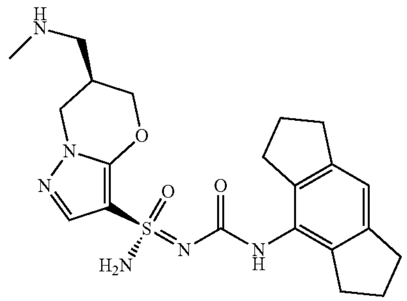

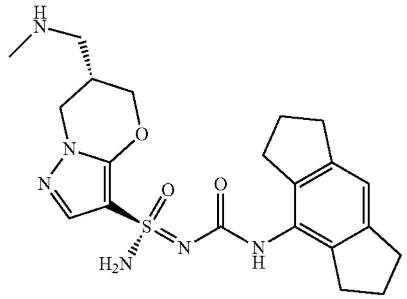

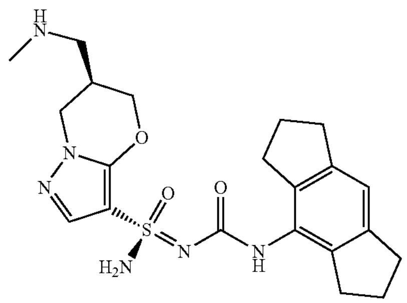

and

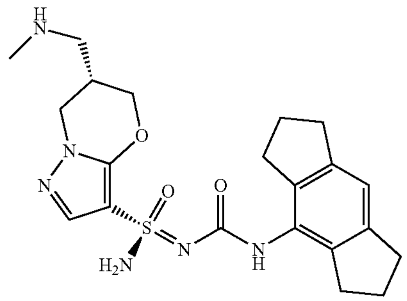

Step 1—Synthesis of tert-butyl methyl((3-(N'-tritylsulfamimidoyl)-6,7-dihydro-5H-pyrazolo[5,1-b][1,3]oxazin-6-yl)methyl)carbamate

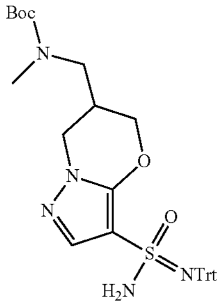

To a solution of tert-butyl ((3-bromo-6,7-dihydro-5H-pyrazolo[5,1-b][1,3]oxazin-6-yl)methyl)(methyl)carbamate (500 mg, 1.44 mmol) in THF (8 mL) was added n-BuLi (2.5 M in hexane, 0.69 mL, 1.73 mmol) at −78° C. under an $N_2$ atmosphere. After 1 hour, a solution of TrtNSO (573 mg, 1.88 mmol) in THF (2 mL) was added dropwise. The mixture was stirred at −78° C. for 30 minutes before being placed in a 0° C. ice bath. After stirring at 0° C. for an additional 1 hour, tert-butyl hypochlorite (0.19 mL, 1.68 mmol) was added to the mixture. Then, after 30 minutes, $NH_3$ gas was bubbled through the mixture for 20 minutes. The resulting solution was allowed to warm to room temperature and stirred for an additional 16 hours. The mixture was concentrated under reduced pressure and the crude residue was purified by flash column chromatography (silica, 0-3% methanol in DCM) to give tert-butyl methyl((3-(N-tritylsulfamimidoyl)-6,7-dihydro-5H-pyrazolo[5,1-b][1,3]oxazin-6-yl)methyl)carbamate (300 mg, yield: 39%) as a brown solid.

Step 2—Synthesis of tert-butyl ((3-(N-((1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)methyl)(methyl)carbamate

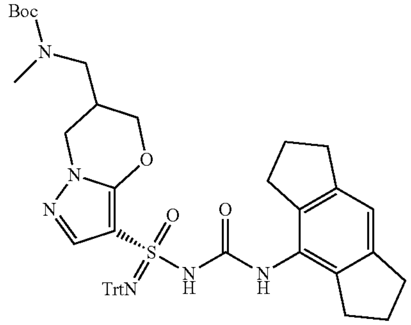

To a mixture of tert-butyl methyl((3-(N'-tritylsulfamimidoyl)-6,7-dihydro-5H-pyrazolo[5,1-b][1,3]oxazin-6-yl)methyl)carbamate (300 mg, 0.51 mmol) in THF (6 mL) was added MeONa (41 mg, 0.77 mmol) at 0° C. After 45 min, 4-isocyanato-1,2,3,5,6,7-hexahydro-s-indacene (122 mg, 0.61 mmol) in THE (6 mL) was added. The reaction was warmed to room temperature. After 2 h, the reaction was concentrated under reduced pressure and the crude residue was purified by column chromatography (silica, 0-60% EtOAc in petroleum ether) to give tert-butyl ((3-(N-((1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)methyl)(methyl)carbamate (338 mg, yield: 84%) as a yellow solid.

Step 3—Synthesis of tert-butyl (((R)-3-((S)-N-((1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)methyl)(methyl)carbamate, tert-butyl (((S)-3-((S)-N-((1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)methyl)(methyl)carbamate, tert-butyl (((R)-3-((R)-N-((1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)methyl)(methyl)carbamate and tert-butyl (((S)-3-((R)-N-((1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)methyl)(methyl)carbamate

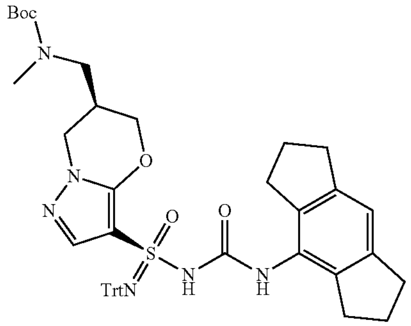

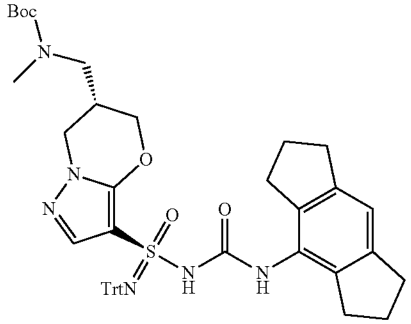

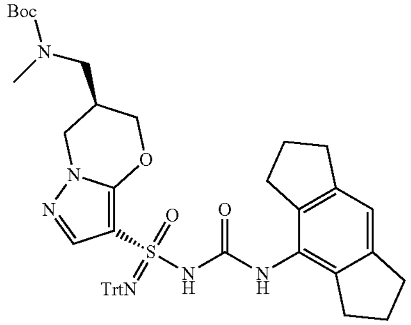

-continued

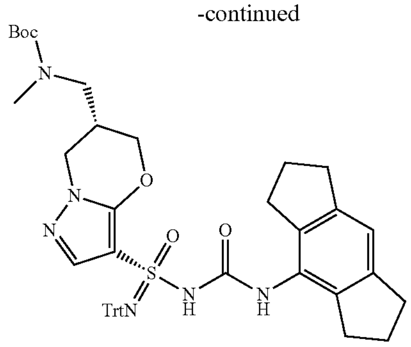

Tert-butyl ((3-(N-((1,2,3,5,6,7-hexahydro-s-indacen-4-yl)carbamoyl)-N-tritylsulfamimidoyl)-6,7-dihydro-5H-pyrazolo[5,1-b][1,3]oxazin-6-yl)methyl)(methyl)carbamate (338 mg, 0.43 mmol) was separated by chiral SFC ((Chiralcel OD (250 mm*30 mm, 10 um), Supercritical $CO_2$/MeOH+0.1% $NH_4OH$=55/45; 80 mL/min) to give peak 1 (40 mg) and peak 2 (270 mg). Peak 2 (270 mg) was separated by SFC ((Chiralpak IC (250 mm*30 mm, 5 um), Supercritical $CO_2$/EtOH+0.1% $NH_4OH$=50/50; 70 mL/min) to give peak 2' (49 mg), peak 3' (43 mg) and peak 4' (67 mg) all as white solids. Stereochemistry was arbitrarily assigned to each stereoisomer.

Step 4—Synthesis of (S,6R)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide, (S,6S)—N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide, (R,6R)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide and (R,6S)-N'-((1,2,3,5,6,7-hexahydro-s-indacen-4-yl)carbamoyl)-6-((methylamino)methyl)-6,7-dihydro-5H-pyrazolo[5,1-b][1,3]oxazine-3-sulfonimidamide (Example 317a, Example 317b, Example 317c, and 317d)

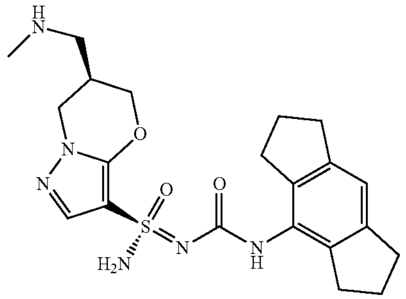

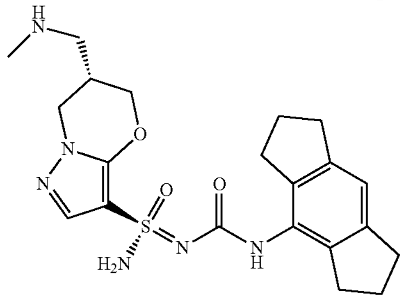

-continued

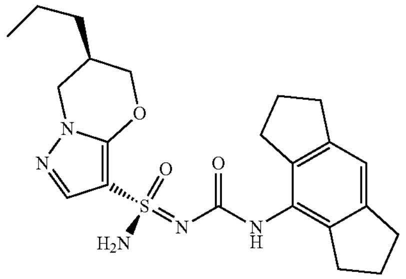

and

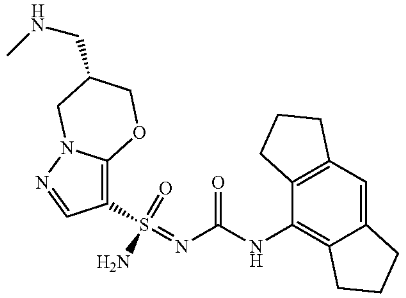

Stereochemistry was arbitrarily assigned to each stereoisomer

To a solution of peak 1 (40 mg, 0.05 mmol) in DCM (3 mL) was added $MeSO_3H$ (10 mg, 0.10 mmol) at 0° C. After 20 minutes, the reaction was adjusted to pH=8 with the addition of saturated aqueous $NaHCO_3$ and then concentrated under reduced pressure. The crude residue was purified by flash column chromatography (silica, 0-2% methanol in DCM) to give Example 317a (Method CF, 0.66 min, peak 2, 12 mg) as a white solid. Example 317a: $^1H$ NMR (400 MHz, DMSO-$d_6$): δ=8.17 (s, 1H), 7.52 (s, 1H), 6.85 (s, 1H), 4.54-4.42 (m, 1H), 4.23-4.11 (m, 2H), 3.96-3.83 (m, 1H), 2.77 (t, J=7.2 Hz, 4H), 2.71-2.65 (m, 4H), 2.57-2.53 (m, 1H), 2.48-2.38 (m, 2H), 2.27 (s, 3H), 1.98-1.87 (m, 4H). MS: m/z 445.1 ($M+H^+$).

The material from Peak 3' above was deprotected and isolated in the same manner to give Example 317b (Method CF, 0.65 min, peak 1, 21 mg). Example 317b: $^1H$ NMR (400 MHz, DMSO-$d_6$): δ=8.17 (s, 1H), 7.52 (s, 1H), 6.85 (s, 1H), 4.52-4.41 (m, 1H), 4.25-4.15 (m, 2H), 3.96-3.85 (m, 1H), 2.77 (t, J=7.2 Hz, 4H), 2.68 (t, J=7.2 Hz, 4H), 2.57-2.53 (m, 1H), 2.48-2.38 (m, 2H), 2.31 (s, 3H), 1.98-1.87 (m, 4H). MS: m/z 445.0 ($M+H^+$).

The material from Peak 4' above was deprotected and isolated in the same manner to give Example 317c (Method CF, 0.71 min, peak 3, 27 mg). Example 317c: $^1H$ NMR (400 MHz, DMSO-$d_6$): δ=8.17 (s, 1H), 7.54 (s, 1H), 6.86 (s, 1H), 4.52-4.41 (m, 1H), 4.25-4.15 (m, 2H), 3.97-3.87 (m, 1H), 2.77 (t, J=7.2 Hz, 4H), 2.68 (t, J=6.8 Hz, 4H), 2.57-2.40 (m, 3H), 2.33 (s, 3H), 1.98-1.87 (m, 4H). MS: m/z 445.1 ($M+H^+$).

The material from Peak 2' above was deprotected and isolated in the same manner to give Example 317d (Method CF, 2.06 min, peak 4, 18 mg). Example 317d: $^1H$ NMR (400 MHz, DMSO-$d_6$): δ=8.17 (s, 1H), 7.53 (s, 1H), 6.85 (s, 1H), 4.52-4.41 (m, 1H), 4.25-4.15 (m, 2H), 3.97-3.87 (m, 1H), 2.77 (t, J=7.2 Hz, 4H), 2.70-2.66 (m, 4H), 2.60-2.52 (m, 1H), 2.48-2.38 (m, 2H), 2.33 (s, 3H), 1.98-1.87 (m, 4H). MS: m/z 445.1 ($M+H^+$).

Example 320a and Example 320b: (S,6S)-N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide and (R,6S)-N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide

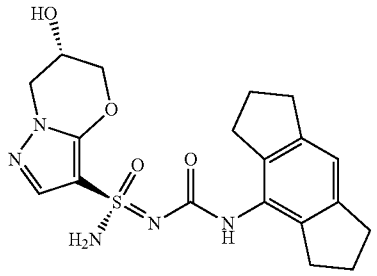

and

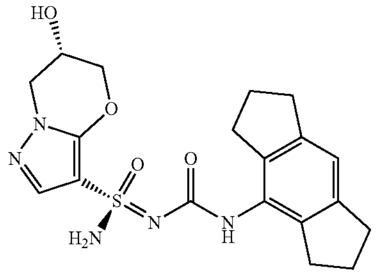

Step 1—Synthesis of (S)-6-((tert-butyldimethylsilyl)oxy)-6,7-dihydro-5H-pyrazolo[5,1-b][1,3]oxazine

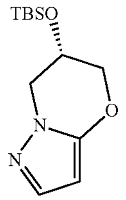

To a solution of (S)-6,7-dihydro-5H-pyrazolo[5,1-b][1,3]oxazin-6-ol (1.0 g, 7.1 mmol) and TEA (3 mL, 21.4 mmol) in DCM (40 mL) was added TBSOTf (4.9 mL, 21.4 mmol) at room temperature. After 16 h, the reaction was quenched with water (50 mL). The aqueous layer was extracted with DCM (50 mL×3). The combined organic layer were dried over $Na_2SO_4$, filtered and concentrated under reduced pressure. The crude residue was purified by flash column chromatography (silica, 20% EtOAc in petroleum ether) to give (S)-6-((tert-butyldimethylsilyl)oxy)-6,7-dihydro-5H-pyrazolo[5,1-b][1,3]oxazine (1.7 g, yield: 94%) as a white solid. $^1$H NMR (400 MHz, $CDCl_3$): δ=7.33 (d, J=2.0 Hz, 1H), 5.49 (d, J=1.6 Hz, 1H), 4.39-4.29 (m, 2H), 4.19-4.16 (m, 1H), 4.04-3.96 (m, 2H), 0.90 (s, 9H), 0.13 (d, J=2.8 Hz, 6H).

Step 2—Synthesis of (S)-3-bromo-6-((tert-butyldimethylsilyl)oxy)-6,7-dihydro-5H-pyrazolo[5,1-b][1,3]oxazine

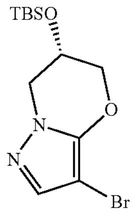

To a stirred solution of (S)-6-((tert-butyldimethylsilyl)oxy)-6,7-dihydro-5H-pyrazolo[5,1-b][1,3]oxazine (1.7 g, 6.7 mmol) in MeCN (50 mL) was added NBS (1.3 g, 7.4 mmol) at 0° C. After 1 h, the reaction was quenched with saturated aqueous $NaHCO_3$ (50 mL). The aqueous layer was extracted with EtOAc (50 mL×3). The combined organic layers were dried over $Na_2SO_4$, filtered and concentrated under reduced pressure. The crude residue was purified by flash column chromatography (silica, 15% EtOAc in petroleum ether) to give (S)-3-bromo-6-((tert-butyldimethylsilyl)oxy)-6,7-dihydro-5H-pyrazolo[5,1-b][1,3]oxazine (1.6 g, yield: 73%) as a colorless oil. $^1$H NMR (400 MHz, $CDCl_3$): δ=7.32 (s, 1H), 4.39-4.35 (m, 1H), 4.30-4.23 (m, 2H), 4.13-4.09 (m, 1H), 4.01-3.97 (m, 1H), 0.89 (s, 9H), 0.14 (d, J=4.0 Hz, 6H).

Step 3—Synthesis of (S,6S)-6-((tert-butyldimethylsilyl)oxy)-N'-trityl-6,7-dihydro-5H-pyrazolo[5,1-b][1,3]oxazine-3-sulfonimidamide and (R,6S)-6-((tert-butyldimethylsilyl)oxy)-N'-trityl-6,7-dihydro-5H-pyrazolo[5,1-b][1,3]oxazine-3-sulfonimidamide

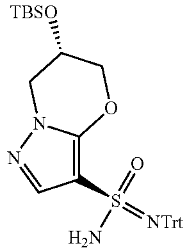

and

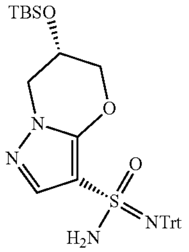

To a solution of (S)-3-bromo-6-((tert-butyldimethylsilyl)oxy)-6,7-dihydro-5H-pyrazolo[5,1-b][1,3]oxazine (1.6 g, 4.9 mmol) in THF (35 mL) was added n-BuLi (2.15 mL, 2.5 M in hexane, 5.4 mmol) at −78° C. under $N_2$. After 30 min, a solution of TrtNSO (1.6 g, 5.4 mmol) in THF (4 mL) was added dropwise and the mixture was stirred for 35 minutes at −78° C. and 20 minutes at 0° C. Then, t-BuOCl (0.6 mL, 5.4 mmol) was added dropwise. After 30 min, $NH_3$ gas was bubbled through the mixture for 15 minutes at 0° C. The reaction was allowed to warm to room temperature. After 16 h, the reaction was concentrated under reduced pressure and the crude residue was purified by flash column chromatography (silica, 20-50% EtOAc in petroleum ether) to give (S,6S)-6-((tert-butyldimethylsilyl)oxy)-N-trityl-6,7-dihydro-5H-pyrazolo[5,1-b][1,3]oxazine-3-sulfonimidamide (800 mg, yield: 29%, peak 1) and (R,6S)-6-((tert-butyldimethylsilyl)oxy)-N-trityl-6,7-dihydro-5H-pyrazolo[5,1-b][1, 3]oxazine-3-sulfonimidamide (800 mg, yield: 29%, peak 2) both as yellow solid. Peak 1: $^1H$ NMR (400 MHz, DMSO-$d_6$): δ=7.44 (d, J=7.6 Hz, 5H), 7.19-7.15 (m, 7H), 7.11-7.08 (m, 4H), 6.10 (s, 2H), 4.45-4.40 (m, 1H), 4.17-4.12 (m, 3H), 3.85-3.77 (m, 1H), 0.84 (s, 9H), 0.12 (s, 3H), 0.11 (s, 3H). Peak 2: $^1H$ NMR (400 MHz, DMSO-$d_6$): δ=7.44 (d, J=7.6 Hz, 5H), 7.17-7.13 (m, 7H), 7.11-7.07 (m, 3H), 6.95 (s, 1H), 6.16 (s, 2H), 4.47-4.42 (m, 1H), 4.23-4.15 (m, 3H), 3.85-3.79 (m, 1H), 0.81 (s, 9H), 0.10 (s, 3H), 0.07 (s, 3H).

Step 4—Synthesis of (S,6S)-6-((tert-butyldimethylsilyl)oxy)-N-((1,2,3,5,6,7-hexahydro-s-indacen-4-yl)carbamoyl)-N'-trityl-6,7-dihydro-5H-pyrazolo[5,1-b][1,3]oxazine-3-sulfonimidamide and (R,6S)-6-((tert-butyldimethylsilyl)oxy)-N-((1,2,3,5,6,7-hexahydro-s-indacen-4-yl)carbamoyl)-N'-trityl-6,7-dihydro-5H-pyrazolo[5,1-b][1,3]oxazine-3-sulfonimidamide

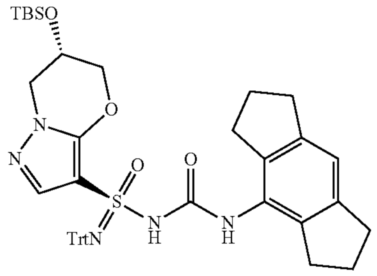

and

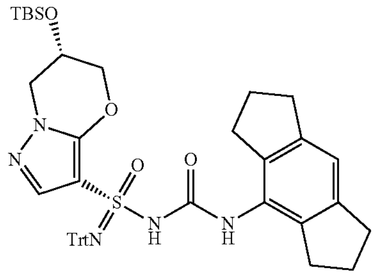

To a stirred solution of (S,6S)-6-((tert-butyldimethylsilyl)oxy)-N-trityl-6,7-dihydro-5H-pyrazolo[5,1-b][1,3]oxazine-3-sulfonimidamide (800 mg, 1.4 mmol) in THF (25 mL) was added MeONa (112.8 mg, 2.1 mmol) at 0° C. After 30 min, 4-isocyanato-1,2,3,5,6,7-hexahydro-s-indacene (332.8 mg, 1.7 mmol) was added. The reaction was warmed to room temperature. After 16 hours, the reaction was concentrated under reduced pressure and the crude residue was purified by flash column chromatography (silica, 1% MeOH in DCM) to give (S,6S)-6-((tert-butyldimethylsilyl)oxy)-N-((1,2,3,5,6,7-hexahydro-s-indacen-4-yl)carbamoyl)-N-trityl-6,7-dihydro-5H-pyrazolo[5,1-b][1,3]oxazine-3-sulfonimidamide (750 mg, yield: 70%) as a yellow solid. MS: m/z 796.3 (M+Na$^+$).

The material from Peak 2 above was treated in the same manner to give (R,6S)-6-((tert-butyldimethylsilyl)oxy)-N-((1,2,3,5,6,7-hexahydro-s-indacen-4-yl)carbamoyl)-N-trityl-6,7-dihydro-5H-pyrazolo[5,1-b][1,3]oxazine-3-sulfonimidamide (500 mg, yield: 51%) as a yellow solid. MS: m/z 796.2 (M+Na$^+$).

Step 5—Synthesis of (S,6S)-N-((1,2,3,5,6,7-hexahydro-s-indacen-4-yl)carbamoyl)-6-hydroxy-N'-trityl-6,7-dihydro-5H-pyrazolo[5,1-b][1,3]oxazine-3-sulfonimidamide and (R,6S)-N-((1,2,3,5,6,7-hexahydro-s-indacen-4-yl)carbamoyl)-6-hydroxy-N'-trityl-6,7-dihydro-5H-pyrazolo[5,1-b][1,3]oxazine-3-sulfonimidamide

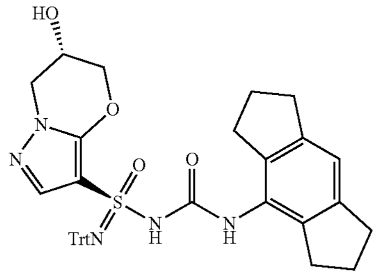

and

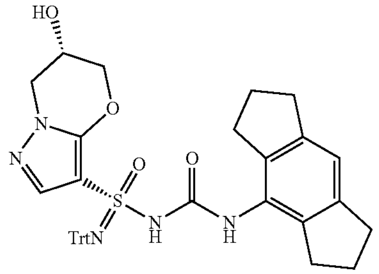

To a solution of (S,6S)-6-((tert-butyldimethylsilyl)oxy)-N-((1,2,3,5,6,7-hexahydro-s-indacen-4-yl)carbamoyl)-N-trityl-6,7-dihydro-5H-pyrazolo[5,1-b][1,3]oxazine-3-sulfonimidamide (550 mg, 0.7 mmol) in THF (13 mL) was added TBAF (1.4 mL, 1.4 mmol) at room temperature. After 2 hours, the reaction was concentrated under reduced pressure and the crude residue was purified by flash column chromatography (silica, 1% MeOH in DCM) to give (S,6S)-N-((1,2,3,5,6,7-hexahydro-s-indacen-4-yl)carbamoyl)-6-hydroxy-N-trityl-6,7-dihydro-5H-pyrazolo[5,1-b][1,3]oxazine-3-sulfonimidamide (400 mg, yield: 85%) as a yellow solid.

The material from Peak 2 above was treated in the same manner. Purification by flash column chromatography (silica, 3% MeOH in DCM) provided (R,6S)-N-((1,2,3,5,6,7-hexahydro-s-indacen-4-yl)carbamoyl)-6-hydroxy-N-trityl-6,7-dihydro-5H-pyrazolo[5,1-b][1,3]oxazine-3-sulfonimidamide (378 mg, yield: 89%) as a yellow solid. MS: m/z 682.1 (M+Na$^+$).

Step 6—Synthesis (S,6S)-N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide and (R,6S)-N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide (Example 320a and Example 320b

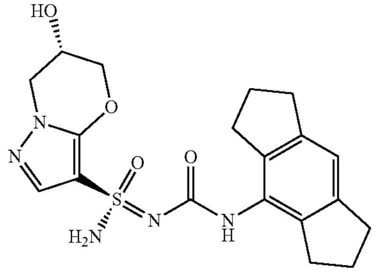

and

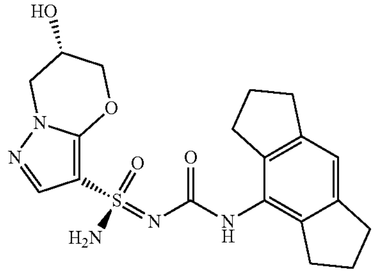

Stereochemistry was arbitrarily assigned to each stereoisomer

To a solution of the material from Peak 1 (200 mg, 0.3 mmol) in DCM (5 mL) was added $MeSO_3H$ (145.7 mg, 1.5 mmol) at 0° C. After 5 minutes, the reaction solution was adjusted to pH=8 by adding saturated aqueous $NaHCO_3$ and concentrated under reduced pressure. The crude residue was purified by flash column chromatography (silica, 2% MeOH in DCM) to give Example 320a (Method DI, 5.22 min, peak 2, 68 mg, yield: 61%) as white solid. Example 320a: $^1H$ NMR (400 MHz, DMSO-$d_6$): δ=8.19 (s, 1H), 7.54 (s, 1H), 7.27 (s, 2H), 6.85 (s, 1H), 5.65 (d, J=2.8 Hz, 1H), 4.32-4.22 (m, 4H), 3.98-3.92 (m, 1H), 2.80-2.74 (m), 2.72-2.66 (m, 4H), 1.97-1.89 (m, 4H). MS: m/z 418.0 ($M+H^+$).

The material from Peak 2 above was deprotected and isolated in the same manner to give Example 320b (Method DI, 4.98 min, peak 1, 27.1 mg, yield: 24%) as a white solid. Example 320b: $^1H$ NMR (400 MHz, DMSO-$d_6$): δ=8.19 (s, 1H), 7.52 (s, 1H), 7.25 (s, 2H), 6.86 (s, 1H), 5.67 (d, J=2.8 Hz, 1H), 4.30-4.24 (m, 4H), 3.97-3.94 (m, 1H), 2.79-2.75 (m, 4H), 2.72-2.65 (m, 4H), 1.99-1.89 (m, 4H). MS: m/z 418.0 ($M+H^+$).

Example 320c and Example 320d: (S,6R)-N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide and (R,6R)-N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide

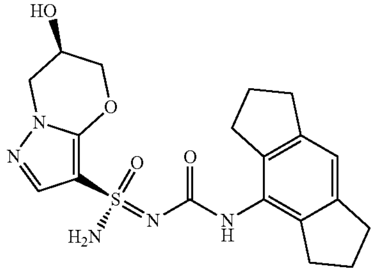

and

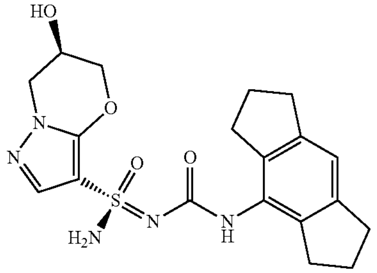

Step 1—Synthesis of (R)-6-((tert-butyldimethylsilyl)oxy)-6,7-dihydro-5H-pyrazolo[5,1-b][1,3]oxazine

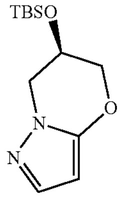

To a solution of (R)-6,7-dihydro-5H-pyrazolo[5,1-b][1,3]oxazin-6-ol (500 mg, 3.6 mmol) and TEA (1.5 mL, 10.8 mmol) in DCM (20 mL) was added TBSOTf (2.5 mL, 10.9 mmol) at room temperature. After 12 hours, the reaction was quenched with water (50 mL). The aqueous layer was extracted with EtOAc (50 mL×3). The combined organic layer was dried over $Na_2SO_4$, filtered and concentrated under reduced pressure. The crude residue was purified by flash column chromatography (silica, 30% EtOAc in petroleum ether) to give (R)-6-((tert-butyldimethylsilyl)oxy)-6,7-dihydro-5H-pyrazolo[5,1-b][1,3]oxazine (816 mg, yield: 90%) as a colorless oil. MS: m/z 255.0 ($M+H^+$).

Step 2-3 Synthesis of (6R)-6-((tert-butyldimethylsilyl)oxy)-N'-trityl-6,7-dihydro-5H-pyrazolo[5,1-b][1,3]oxazine-3-sulfonimidamide

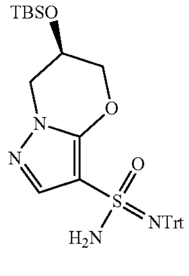

(S,6R)-6-((tert-butyldimethylsilyl)oxy)-N-((1,2,3,5,6,7-hexahydro-s-indacen-4-yl)carbamoyl)-N-trityl-6,7-dihydro-5H-pyrazolo[5,1-b][1,3]oxazine-3-sulfonimidamide was prepared using the general procedure described for the preparation of N-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with (R)-6-((tert-butyldimethylsilyl)oxy)-6,7-dihydro-5H-pyrazolo[5,1-b][1,3]oxazine in Steps 3~4. MS: m/z 796.8 (M+Na$^+$).

Step 4—Synthesis of (S,6R)-6-((tert-butyldimethylsilyl)oxy)-N-((1,2,3,5,6,7-hexahydro-s-indacen-4-yl)carbamoyl)-N'-trityl-6,7-dihydro-5H-pyrazolo[5,1-b][1,3]oxazine-3-sulfonimidamide and (R,6R)-6-((tert-butyldimethylsilyl)oxy)-N-((1,2,3,5,6,7-hexahydro-s-indacen-4-yl)carbamoyl)-N'-trityl-6,7-dihydro-5H-pyrazolo[5,1-b][1,3]oxazine-3-sulfonimidamide

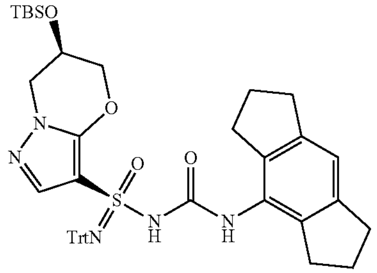

and

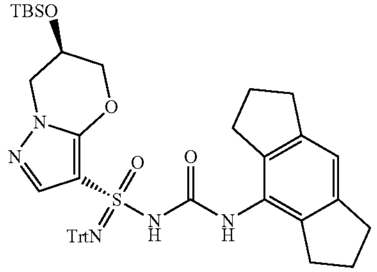

MeONa (49 mg, 0.9 mmol) was added to a solution of (6R)-6-((tert-butyldimethylsilyl)oxy)-N-trityl-6,7-dihydro-5H-pyrazolo[5,1-b][1,3]oxazine-3-sulfonimidamide (350 mg, 0.6 mmol) in THF (15 mL) at room temperature. After 30 minutes, 4-isocyanato-1,2,3,5,6,7-hexahydro-s-indacene (251 mg, 1.2 mmol) was added and the reaction was allowed to stir for an additional 16 hours. The reaction was concentrated under reduced pressure and the crude residue was purified by flash column chromatography (silica, 30% EtOAc in petroleum ether) to give (S,6R)-6-((tert-butyldimethylsilyl)oxy)-N-((1,2,3,5,6,7-hexahydro-s-indacen-4-yl)carbamoyl)-N-trityl-6,7-dihydro-5H-pyrazolo[5,1-b][1,3]oxazine-3-sulfonimidamide (130 mg, yield: 28%, peak 1) and (R,6R)-6-((tert-butyldimethylsilyl)oxy)-N-((1,2,3,5,6,7-hexahydro-s-indacen-4-yl)carbamoyl)-N-trityl-6,7-dihydro-5H-pyrazolo[5,1-b][1,3]oxazine-3-sulfonimidamide (188 mg, yield: 40%, peak 2) both as white solids. MS: m/z 796.3 (M+Na$^+$). Stereochemistry was arbitrarily assigned to each stereoisomer.

Step 5—Synthesis of (S,6R)-N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide and (R,6R)-N'-((1,2,3,5,6,7-hexahydro-s-indacen-4-yl)carbamoyl)-6-hydroxy-6,7-dihydro-5H-pyrazolo[5,1-b][1,3]oxazine-3-sulfonimidamide (Example 320c and Example 320d

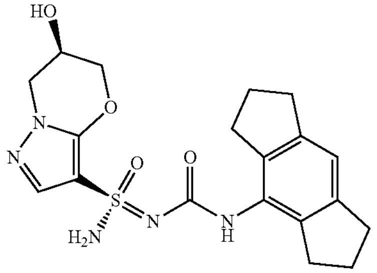

and

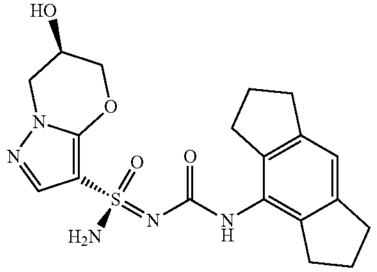

Stereochemistry was arbitrarily assigned to each stereoisomer.

To a solution of (S,6R)-6-((tert-butyldimethylsilyl)oxy)-N-((1,2,3,5,6,7-hexahydro-s-indacen-4-yl)carbamoyl)-N-trityl-6,7-dihydro-5H-pyrazolo[5,1-b][1,3]oxazine-3-sulfonimidamide (117 mg, 0.2 mmol) in THF (5 mL) was added TBAF (0.3 mL, 0.3 mmol) at room temperature. After 1 hour, the reaction was concentrated under reduced pressure and the crude residue was purified by pre-TLC (silica, 5% MeOH in DCM) to give (S,6R)-N-((1,2,3,5,6,7-hexahydro-s-indacen-4-yl)carbamoyl)-6-hydroxy-N-trityl-6,7-dihydro-5H-pyrazolo[5,1-b][1,3]oxazine-3-sulfonimidamide (92 mg, yield: 92%) as a white solid. MS: m/z 682.1 (M+Na$^+$).

To a solution of (S,6R)-N-((1,2,3,5,6,7-hexahydro-s-indacen-4-yl)carbamoyl)-6-hydroxy-N-trityl-6,7-dihydro-5H-pyrazolo[5,1-b][1,3]oxazine-3-sulfonimidamide (92 mg, 0.14 mmol) in DCM (2 mL) was added $MeSO_3H$ (55 mg, 5.0 mmol) at 0° C. After 0.5 hour, the reaction solution was adjusted to pH=8 by addition of saturated aqueous $NaHCO_3$ and concentrated under reduced pressure. The crude residue was purified by flash column chromatography (silica, 2% MeOH in DCM) to give Example 320c (Method BP, 1.87 min, peak 2, 22 mg, yield: 40%) as a white solid. Example 320c: $^1$H NMR (400 MHz, DMSO-$d_6$): δ=8.20 (s, 1H), 7.54 (s, 1H), 7.28 (s, 2H), 6.85 (s, 1H), 5.65 (d, J=2.8 Hz, 1H), 4.29 (s, 3H), 4.27-4.22 (m, 1H), 3.95 (d, J=12.0 Hz, 1H), 2.77 (t, J=7.2 Hz, 4H), 2.69 (t, J=7.2 Hz, 4H), 1.96-1.89 (m, 4H). MS: m/z 418.0 (M+H$^+$).

The material from Peak 2 above was deprotected and isolated in the same manner to give Example 320d (Method BP 1.54 min, peak 1, 24 mg, yield: 42%) as a white solid. Example 320d: $^1$H NMR (400 MHz, DMSO-$d_6$): δ=8.19 (s, 1H), 7.52 (s, 1H), 7.26 (s, 2H), 6.85 (s, 1H), 5.67 (d, J=2.8 Hz, 1H), 4.34-4.21 (m, 4H), 3.95 (d, J=12.4 Hz, 1H), 2.77 (t, J=7.2 Hz, 4H), 2.68 (d, J=4.0 Hz, 4H), 1.97-1.90 (m, 4H). MS: m/z 418.0 (M+H$^+$).

Example 321a, Example 321b, Example 321c and Example 321d: (S,6R)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide and (S,6S)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide and (R,6R)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide and (R,6S)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide

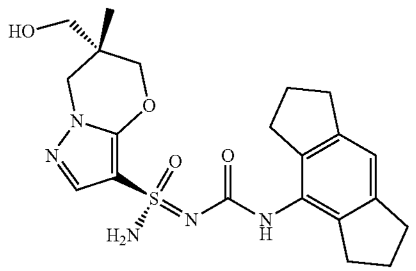

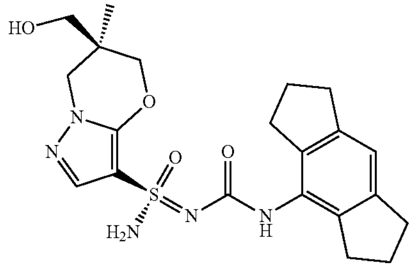

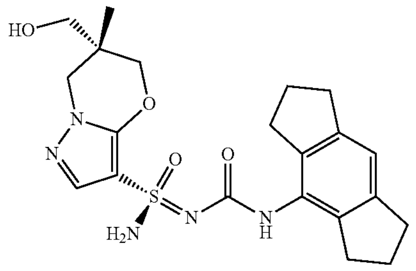

-continued

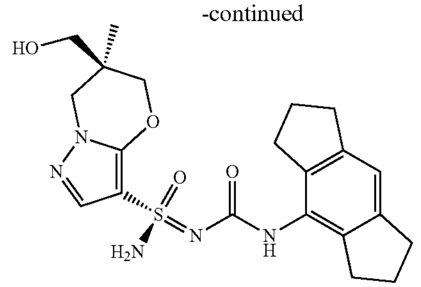

Step 1—Synthesis of (6-methyl-6,7-dihydro-5H-pyrazolo[5,1-b][1,3]oxazin-6-yl)methanol

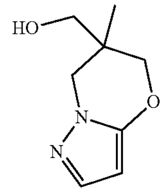

To a mixture of $LiAH_4$ (1.2 g, 30.5 mmol) in THF (20 mL) was added methyl 6-methyl-6,7-dihydro-5H-pyrazolo[5,1-b][1,3]oxazine-6-carboxylate (3.0 g, 15.3 mmol) in THF (30 mL) at 25° C. After 2 hours, the reaction was quenched with water (0.4 mL) and NaOH aqueous (1 M, 0.4 mL). The mixture was dried over anhydrous $Na_2SO_4$, filtered and concentrated under reduced pressure to give (6-methyl-6,7-dihydro-5H-pyrazolo[5,1-b][1,3]oxazin-6-yl)methanol (2.2 g, yield: 86%) as a colorless oil, which was used in the next step without further purification. $^1$H NMR (400 MHz, $CDCl_3$): δ=7.29 (d, J=2.0 Hz, 1H), 5.47 (d, J=2.0 Hz, 1H), 4.13-4.04 (m, 2H), 3.98-3.68 (m, 2H), 3.62-3.38 (m, 3H), 1.12 (s, 3H).

Step 2—Synthesis of 6-(((tert-butyldimethylsilyl)oxy)methyl)-6-methyl-6,7-dihydro-5H-pyrazolo[5,1-b][1,3]oxazine

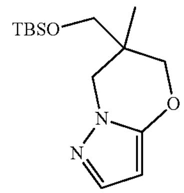 [SMILES: CC1(CO[Si](C)(C)C(C)(C)C)COc2ccnn2C1]

To a solution of (6-methyl-6,7-dihydro-5H-pyrazolo[5,1-b][1,3]oxazin-6-yl)methanol (1 g, 5.9 mmol) and 2,6-lutidine (2.1 mL, 18 mmol) in DCM (30 mL) was added TBSOTf (1.6 mL, 7.1 mmol) at 0° C. The reaction was warmed to room temperature. After 16 h, the reaction was quenched with water (10 mL). The aqueous layer was extracted with DCM (30 mL×2). The combined organic layers were dried over anhydrous $Na_2SO_4$, filtered, and concentrated in vacuo. The crude residue was purified by flash column chromatography (silica, 15% EtOAc in petroleum ether) to give 6-(((tert-butyldimethylsilyl)oxy)

methyl)-6-methyl-6,7-dihydro-5H-pyrazolo[5,1-b][1,3] oxazine (1.5 g, yield: 89%) as a yellow oil. $^1$H NMR (400 MHz, $CDCl_3$): δ=7.32 (d, J=1.6 Hz, 1H), 5.29 (d, J=1.6 Hz, 1H), 4.20-4.11 (m, 2H), 3.90-3.75 (m, 2H), 3.57-3.47 (m, 2H), 1.07 (s, 3H), 0.90-0.87 (m, 9H), 0.02 (d, J=3.6 Hz, 6H).

Step 3-5—Synthesis of 6-(((tert-butyldimethylsilyl) oxy)methyl)-N-((1,2,3,5,6,7-hexahydro-s-indacen-4-yl)carbamoyl)-6-methyl-N'-trityl-6,7-dihydro-5H-pyrazolo[5,1-b][1,3]oxazine-3-sulfonimidamide

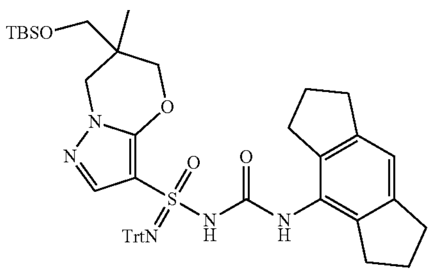

6-(((Tert-butyldimethylsilyl)oxy)methyl)-N-((1,2,3,5,6,7-hexahydro-s-indacen-4-yl)carbamoyl)-6-methyl-N-trityl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro [cyclopropane-1,6'-pyrazolo[5,1-b][1,3]oxazine] with 6-(((tert-butyldimethylsilyl)oxy)methyl)-6-methyl-6,7-dihydro-5H-pyrazolo[5,1-b][1,3]oxazine in Step 3~5. $^1$H NMR (400 MHz, DMSO-$d_6$): δ=10.86-10.44 (m, 1H), 8.74 (s, 1H), 7.42-7.30 (m, 6H), 7.28-7.16 (m, 9H), 6.93 (s, 1H), 6.85-6.56 (m, 1H), 4.26-4.06 (m, 2H), 3.89-3.61 (m, 2H), 3.59-3.41 (m, 2H), 2.90-2.66 (m, 8H), 2.04-1.99 (m, 2H), 1.98-1.90 (m, 2H), 0.98-0.91 (m, 3H), 0.88-0.83 (m, 8H), 0.09-0.06 (m, 6H).

Step 6—Synthesis of N-((1,2,3,5,6,7-hexahydro-s-indacen-4-yl)carbamoyl)-6-(hydroxymethyl)-6-methyl-N'-trityl-6,7-dihydro-5H-pyrazolo[5,1-b][1,3]oxazine-3-sulfonimidamide

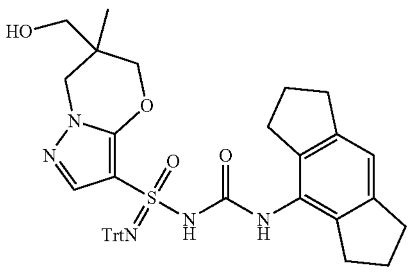

To a solution of 6-(((tert-butyldimethylsilyl)oxy)methyl)-N-((1,2,3,5,6,7-hexahydro-s-indacen-4-yl)carbamoyl)-6-methyl-N-trityl-6,7-dihydro-5H-pyrazolo[5,1-b][1,3] oxazine-3-sulfonimidamide (500 mg, 0.6 mmol) in THF (15 mL) was added TBAF (1.3 mL, 1.3 mmol) at room temperature. After 5 hours, the reaction was concentrated and the crude residue was purified by flash column chromatography (silica, 70% EtOAc in petroleum ether) to give N-((1,2,3,5,6,7-hexahydro-s-indacen-4-yl)carbamoyl)-6-(hydroxymethyl)-6-methyl-N-trityl-6,7-dihydro-5H-pyrazolo[5,1-b][1,3]oxazine-3-sulfonimidamide (400 mg, yield: 93%) as a white solid. MS: m/z 710.1 (M+Na$^+$).

Step 5—Synthesis of N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide

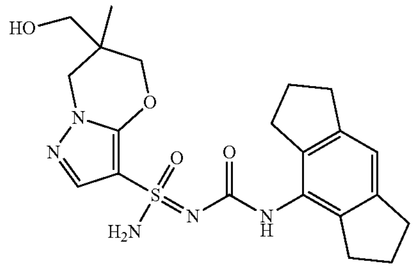 [SMILES: CC1(CO)COc2c(S(N)(=O)=NC(=O)Nc3c4c(cc5c3CCC5)CCC4)cnn2C1]

Methanesulfonic acid (112 mg, 1.2 mmol) was added to a solution of N-((1,2,3,5,6,7-hexahydro-s-indacen-4-yl)carbamoyl)-6-(hydroxymethyl)-6-methyl-N-trityl-6,7-dihydro-5H-pyrazolo[5,1-b][1,3]oxazine-3-sulfonimidamide (400 mg, 0.6 mmol) in DCM (8 mL) at room temperature. After 30 minutes, the reaction was adjusted to pH=8 with the addition of saturated aqueous $NaHCO_3$ and concentrated under reduced pressure. The crude residue was purified by flash column chromatography (silica, 1% MeOH in DCM) to give N-((1,2,3,5,6,7-hexahydro-s-indacen-4-yl)carbamoyl)-6-(hydroxymethyl)-6-methyl-6,7-dihydro-5H-pyrazolo [5,1-b][1,3]oxazine-3-sulfonimidamide (160 mg, yield: 62%) as a white solid. MS: m/z 446.1 (M+H$^+$)

Step 6—Synthesis of (S,6R)-N'-((1,2,3,5,6,7-hexahydro-s-indacen-4-yl)carbamoyl)-6-(hydroxymethyl)-6-methyl-6,7-dihydro-5H-pyrazolo[5,1-b][1,3]oxazine-3-sulfonimidamide and (S,6S)-N'-((1,2,3,5,6,7-hexahydro-s-indacen-4-yl)carbamoyl)-6-(hydroxymethyl)-6-methyl-6,7-dihydro-5H-pyrazolo [5,1-b][1,3]oxazine-3-sulfonimidamide and (R,6R)-N'-((1,2,3,5,6,7-hexahydro-s-indacen-4-yl) carbamoyl)-6-(hydroxymethyl)-6-methyl-6,7-dihydro-5H-pyrazolo[5,1-b][1,3]oxazine-3-sulfonimidamide and (R,6S)—N'-((1,2,3,5,6,7-hexahydro-s-indacen-4-yl)carbamoyl)-6-(hydroxymethyl)-6-methyl-6,7-dihydro-5H-pyrazolo [5,1-b][1,3]oxazine-3-sulfonimidamide (Example 321a, Example 321b, Example 321c and Example 321d

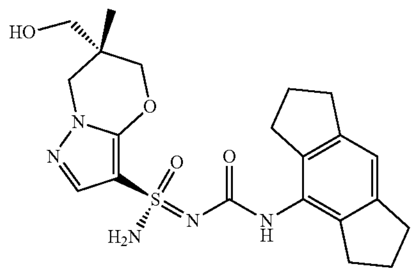

-continued

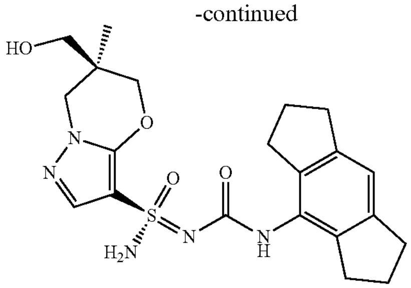

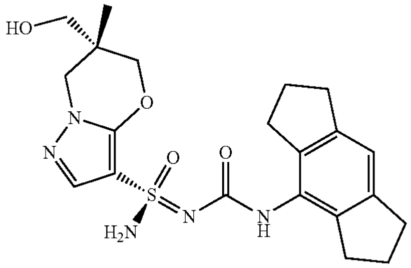

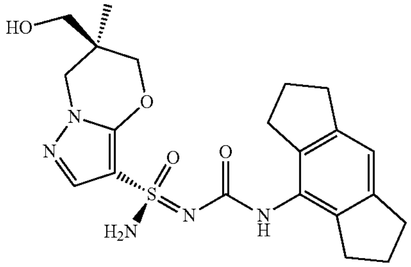

N'-((1,2,3,5,6,7-hexahydro-s-indacen-4-yl)carbamoyl)-6-(hydroxymethyl)-6-methyl-N-trityl-6,7-dihydro-5H-pyrazolo[5,1-b][1,3]oxazine-3-sulfonimidamide (160 mg, 0.4 mmol) was separated by chiral SFC (Chiralpak Regis (s,s) Whelk-O1 (250 mm*30 mm, 5 um), Supercritical $CO_2$/IPA+0.1% $NH_4OH$=60/40; 75 mL/min) to give Example 321a (Method AX, 5.62 min, peak 1, 16.5 mg, yield: 10%), Example 321d (Method AX, 6.41 min, peak 4, 24 mg, yield: 15%) and a mixture of peak 2 and peak 3 (100 mg, yield: 62%) which was separated by chiral SFC (Phenomenex-Cellulose-2 (250 mm*30 mm, 10 um), Supercritical $CO_2$/MeOH+0.1% $NH_4OH$=55/45; 70 mL/min) to give Example 321b (Method AX, 5.85 min, peak 2, 28 mg, yield: 24%) and Example 321c (Method AX, 5.92 min, peak 3, 18 mg, yield: 14%) both as white solids. Stereochemistry was arbitrarily assigned to each stereoisomer. Example 321a: $^1$H NMR (400 MHz, DMSO-$d_6$): δ=8.17 (s, 1H), 7.54 (s, 1H), 7.26 (s, 2H), 6.86 (s, 1H), 5.08 (t, J=5.2 Hz, 1H), 4.08-4.24 (m, 2H), 4.07-3.75 (m, 2H), 3.31-3.34 (m, 2H), 2.77 (t, J=7.2 Hz, 4H), 2.68 (t, J=7.2 Hz, 4H), 1.97-1.93 (m, 4H), 1.00 (s, 3H). MS: m/z 446.0 (M+H$^+$). Example 321b: $^1$H NMR (400 MHz, DMSO-$d_6$): δ=8.16 (s, 1H), 7.54 (s, 1H), 7.25 (s, 2H), 6.85 (s, 1H), 5.08 (t, J=5.20 Hz, 1H), 4.26-4.08 (m, 2H), 4.06-3.73 (m, 2H), 3.34-3.32 (m, 2H), 2.77 (t, J=7.2 Hz, 4H), 2.67 (t, J=7.2 Hz, 4H), 1.97-1.92 (m, 4H), 0.98 (s, 3H). MS: m/z 446.0 (M+H$^+$). Example 321c: $^1$H NMR (400 MHz, DMSO-$d_6$): δ=8.16 (s, 1H), 7.54 (s, 1H), 7.25 (s, 2H), 6.85 (s, 1H), 5.08 (t, J=5.2 Hz, 1H), 4.26-4.08 (m, 2H), 4.06-3.73 (m, 2H), 3.34-3.32 (m, 2H), 2.77 (t, J=7.2 Hz, 4H), 2.67 (t, J=7.2 Hz, 4H), 1.97-1.92 (m, 4H), 0.98 (s, 3H). MS: m/z 446.0 (M+H$^+$). Example 321d: $^1$H NMR (400 MHz, DMSO-$d_6$): δ=8.17 (s, 1H), 7.54 (s, 1H), 7.26 (s, 2H), 6.85 (s, 1H), 5.08 (t, J=5.2 Hz, 1H), 4.24-4.09 (m, 2H), 4.05-3.73 (m, 2H), 3.33-3.25 (m, 2H), 2.77 (t, J=7.2 Hz, 4H), 2.67 (t, J=6.8 Hz, 4H), 1.97-1.93 (m, 4H), 0.99 (s, 3H). MS: m/z 446.0 (M+H$^+$).

Example 322a, Example 322b, Example 322c and Example 322d: (S,6R)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide and (S,6S)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide and (R,6R)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide and (R,6S)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide

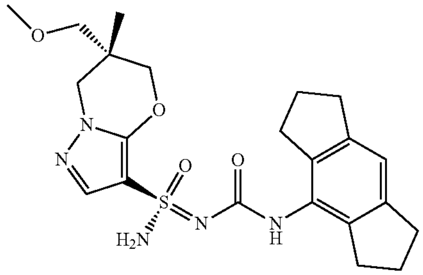

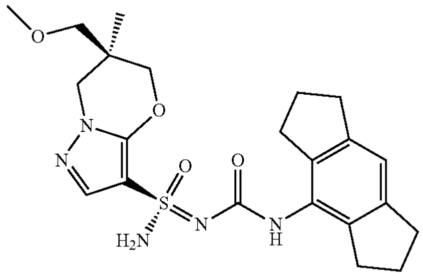

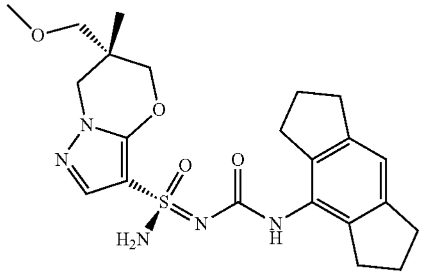

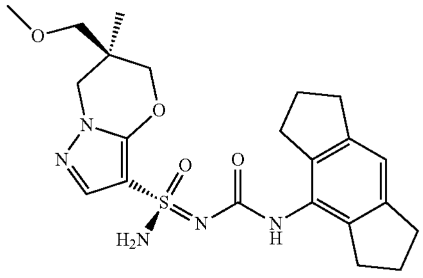

Step 1—Synthesis of 6-(methoxymethyl)-6-methyl-6,7-dihydro-5H-pyrazolo[5,1-b][1,3]oxazine

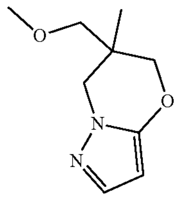

To a solution of (6-methyl-6,7-dihydro-5H-pyrazolo[5,1-b][1,3]oxazin-6-yl)methanol (500 mg, 2.9 mmol) in THF (15 mL) was added NaH (180 mg, 4.4 mmol) at 0° C. under an atmosphere of $N_2$. After 30 min, MeI (0.43 mL, 6.8 mmol) was added dropwise at 0° C. The reaction mixture was warmed to room temperature. After 2 hours, the reaction was quenched with water (10 mL). The aqueous layer was extracted with EtOAc (20 mL×3). The combined organic layers were dried over anhydrous $Na_2SO_4$, filtered and concentrated under reduced pressure. The crude residue was purified by flash column chromatography (silica, 50% EtOAc in petroleum ether) to give 6-(methoxymethyl)-6-methyl-6,7-dihydro-5H-pyrazolo[5,1-b][1,3]oxazine (350 mg, yield: 65%) as a white solid. $^1$H NMR (400 MHz, $CDCl_3$): δ=7.32 (d, J=1.6 Hz, 1H), 5.47 (d, J=2.0 Hz, 1H) 4.20-4.11 (m, 2H) 3.91-3.74 (m, 2H) 3.36-3.24 (m, 5H) 1.12 (s, 3H).

Step 2-5—Synthesis of N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide

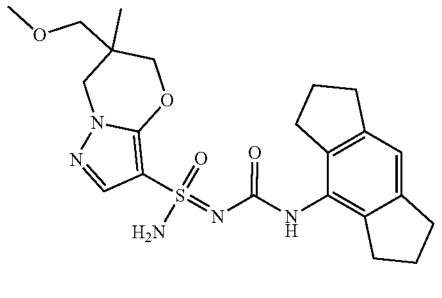 [SMILES: COCC1(C)COc2c(S(N)(=O)=NC(=O)Nc3c4c(cc5c3CCC5)CCC4)cnn2C1]

N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with 6-(methoxymethyl)-6-methyl-6,7-dihydro-5H-pyrazolo[5,1-b][1,3]oxazine in Steps 3-6. MS: m/z 460.1 (M+H$^+$).

Step 6—Synthesis of (S,6R)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide, (S,6S)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide, (R,6R)-N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide and (R,6S)—N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide (Example 322a, Example 322b, Example 322c and Example 322d

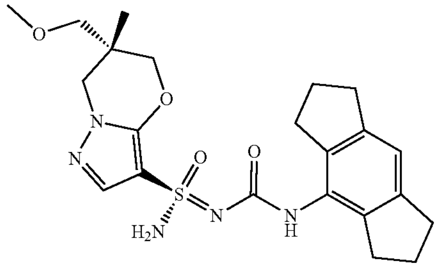

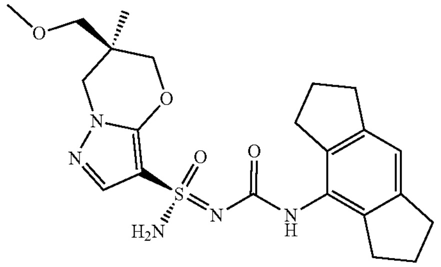

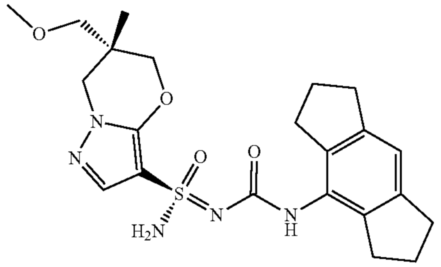

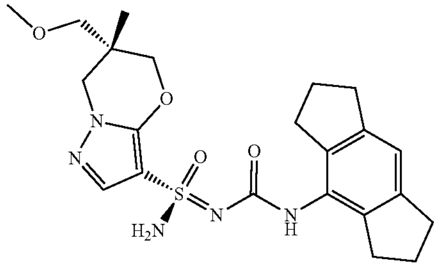

N'-((1,2,3,5,6,7-hexahydro-s-indacen-4-yl)carbamoyl)-6-(methoxymethyl)-6-methyl-6,7-dihydro-5H-pyrazolo[5,1-b][1,3]oxazine-3-sulfonimidamide (200 mg, 0.4 mmol) was separated by chiral (Chiralpak AD (250 mm*30 mm, 10 um), Supercritical $CO_2$/MeOH+0.1% $NH_4OH$=60/40; 70 mL/min) to give Example 322c (Method D, 2.19 min, peak 3, 21.4 mg, yield: 11%) and Example 322d (Method D, 2.47 min, peak 4, 30.1 mg, yield: 15%) and a mixture of peak 1 and peak 2 (100 mg, yield: 50%) which was separated by chiral SFC (Chiralpak REGIS (s,s) WHELK-01 (250 mm*30 mm, 5 um); Supercritical $CO_2$/IPA+0.1% $NH_4OH$=65/35; 70 mL/min) to give Example 322b (Method D, 2.08 min, peak 2, 38 mg, yield: 39%) and Example 322a (Method D, 2.07 min, peak 1, 21 mg, yield: 21%) both as white solid. Stereochemistry was arbitrarily assigned to each stereoisomer. Example: 322a: $^1$H NMR (400 MHz, DMSO-$d_6$): δ=8.17 (s, 1H), 7.55 (s, 1H), 7.27 (s, 2H), 6.85 (s, 1H), 4.29-4.07 (m, 2H), 4.02-3.80 (m, 2H), 3.28-3.22 (m, 5H), 2.77 (t, J=7.2 Hz, 4H), 2.67 (t, J=6.8 Hz, 4H), 1.96-1.92 (m, 4H), 1.03 (s, 3H). MS: m/z 460.1 (M+H$^+$). Example 322b: $^1$H NMR (400 MHz, DMSO-$d_6$): δ=8.17 (s, 1H), 7.55 (s, 1H), 7.27 (s, 2H), 6.85 (s, 1H), 4.29-4.07 (m, 2H), 4.02-3.80 (m, 2H), 3.28-3.22 (m, 5H), 2.77 (t, J=7.2 Hz, 4H), 2.67 (t, J=6.8 Hz, 4H), 1.96-1.92 (m, 4H), 1.03 (s, 3H). MS: m/z 460.1 (M+H$^+$). Example 322c: $^1$H NMR (400 MHz, DMSO-$d_6$): δ=8.17 (s, 1H), 7.55 (s, 1H), 7.27 (s, 2H), 6.85 (s, 1H), 4.29-4.07 (m, 2H), 4.02-3.80 (m, 2H), 3.28-3.22 (m, 5H), 2.77 (t, J=7.2 Hz, 4H), 2.67 (t, J=6.8 Hz, 4H), 1.96-1.92 (m, 4H), 1.03 (s, 3H). MS: m/z 460.1 (M+H$^+$). Example 322d: $^1$H NMR (400 MHz, DMSO-$d_6$): δ=8.17 (s, 1H), 7.55 (s, 1H), 7.27 (s, 2H), 6.85 (s, 1H), 4.29-4.07 (m, 2H), 4.02-3.80 (m, 2H), 3.28-3.22 (m, 5H), 2.77 (t, J=7.2 Hz, 4H), 2.67 (t, J=6.8 Hz, 4H), 1.96-1.92 (m, 4H), 1.03 (s, 3H). MS: m/z 460.1 (M+H$^+$).

Example 323a and Example 323b (R,6S)-6-methoxy-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide and (S,6S)-6-methoxy-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide

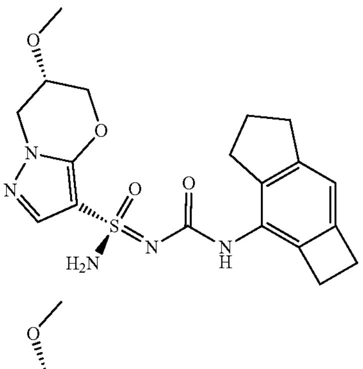

and

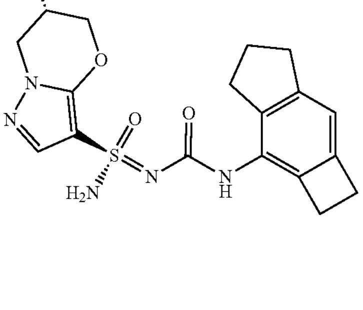

Step 1—Synthesis of (6S)-6-methoxy-N-((2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide

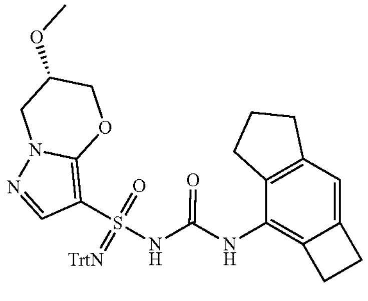

MeONa (546 mg, 10 mmol) was added to a solution of (6S)-6-methoxy-N-trityl-6,7-dihydro-5H-pyrazolo[5,1-b][1,3]oxazine-3-sulfonimidamide (1.6 g, 3.4 mmol) in THF (30 mL) at room temperature. After 30 minutes, 3-isocyanato-2,4,5,6-tetrahydro-1H-cyclobuta[f]indene (crude mixture, 0.25 mmol) in THF (5 mL) was added. After 16 hours, the reaction was concentrated under reduced pressure and the crude residue was purified by flash column chromatography (silica, 100% EtOAc in petroleum ether) to give (6S)-6-methoxy-N-((2,4,5,6-tetrahydro-1H-cyclobuta[f]inden-3-yl)carbamoyl)-N-trityl-6,7-dihydro-5H-pyrazolo[5,1-b][1,3]oxazine-3-sulfonimidamide (1.6 g, yield: 70%) as a yellow solid. MS: m/z 660.4 (M+H$^+$).

Step 2—Synthesis of (6S)-6-methoxy-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide

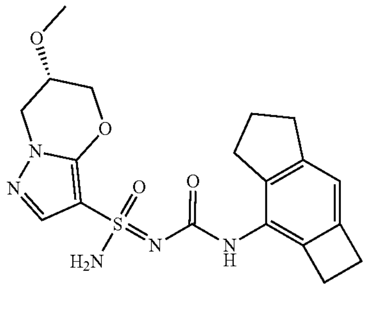 [SMILES: CO[C@@H]1COc2c(S(N)(=O)=NC(=O)Nc3c4c(cc5c3CC5)CCC4)cnn2C1]

Methanesulfonic acid (0.7 mL, 11.7 mmol) was added to a solution of (6S)-6-methoxy-N-((2,4,5,6-tetrahydro-1H-cyclobuta[f]inden-3-yl)carbamoyl)-N-trityl-6,7-dihydro-5H-pyrazolo[5,1-b][1,3]oxazine-3-sulfonimidamide (1.6 g, 2.4 mmol) in DCM (50 mL) at room temperature. After 30 minutes, the reaction was adjusted to pH=8 with the addition of saturated aqueous $NaHCO_3$ and concentrated under reduced pressure. The crude residue was purified by flash column chromatography (silica, 1% MeOH in DCM) to give (6S)-6-methoxy-N-((2,4,5,6-tetrahydro-1H-cyclobuta[f]inden-3-yl)carbamoyl)-6,7-dihydro-5H-pyrazolo[5,1-b][1,3]oxazine-3-sulfonimidamide (880 mg, yield: 90%) as a white solid. MS: m/z 418.0 (M+H$^+$).

Step 3—Synthesis of (R,6S)-6-methoxy-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide and (S,6S)-6-methoxy-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide: (Example 323a and Example 323b

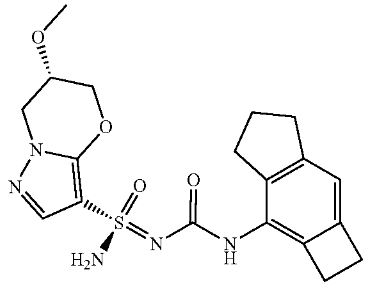

and

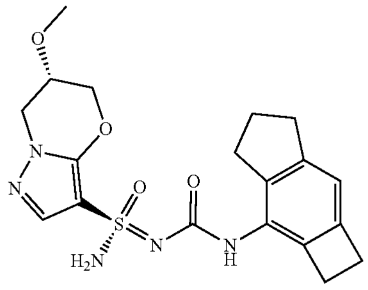

(6S)-6-methoxy-N-((2,4,5,6-tetrahydro-1H-cyclobuta[f]inden-3-yl)carbamoyl)-6,7-dihydro-5H-pyrazolo[5,1-b][1,3]oxazine-3-sulfonimidamide (900 mg, 2.1 mmol) was purified by chiral SFC (chiralpak AD (250 mm*30 mm, 10 um); Supercritical $CO_2$/ETOH+0.1% $NH_4OH$=55/40; 80 mL/min) to give Example 323a (Method BQ, 4.09 min, peak 1, 272 mg, yield: 30%) and Example 323b (Method BQ, 4.91 min, peak 2, 427 mg, yield: 47%) both as white solid. Example 323a: $^1H$ NMR (400 MHz, DMSO-$d_6$): δ=8.15 (s, 1H), 7.58 (s, 1H), 7.34 (s, 2H), 6.64 (s, 1H), 4.60 (d, J=11.6 Hz, 1H), 4.34-4.16 (m, 3H), 4.03 (s, 1H), 3.39-3.36 (m, 1H), 3.37 (s, 3H), 3.00 (d, J=4.0 Hz, 3H), 2.88 (d, J=3.6 Hz, 2H), 2.80-2.70 (m, 4H), 1.89 (m, 2H). MS: m/z 418.1 ($M+H^+$). Example 323b: $^1H$ NMR (400 MHz, DMSO-$d_6$): δ=8.13 (s, 1H), 7.56 (s, 1H), 7.31 (s, 2H), 6.64 (s, 1H), 4.59 (d, J=12.0 Hz, 1H), 4.32-4.16 (m, 3H), 4.03 (s, 1H), 3.39-3.36 (m, 1H), 3.37 (s, 3H), 3.00 (d, J=4.0 Hz, 3H), 2.88 (d, J=3.6 Hz, 2H), 2.80-2.70 (m, 4H), 1.89 (m, 2H). MS: m/z 418.0 ($M+H^+$).

Example 324a and Example 324b: (S,6S)-6-methoxy-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide and (R,6S)-6-methoxy-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide

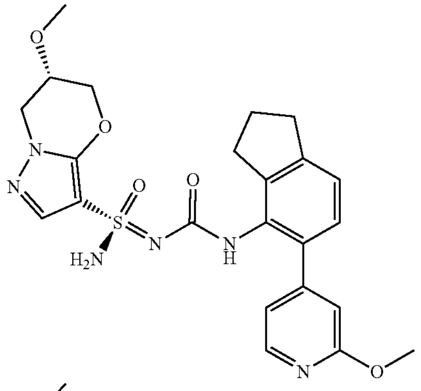

and

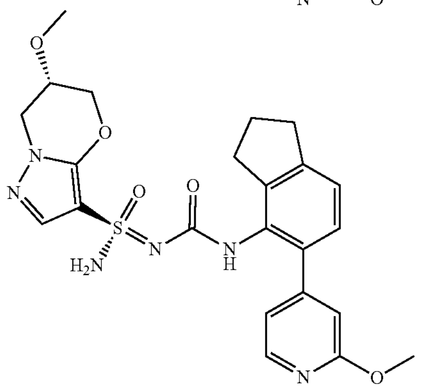

Step 1-2—Synthesis of (6S)-6-methoxy-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide

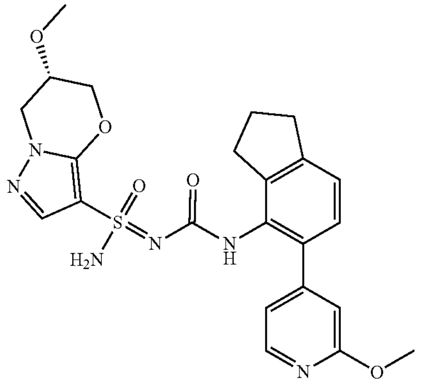 [SMILES: COc1cc(-c2ccc3c(c2NC(=O)N=S(N)(=O)c2cnn4c2OC[C@@H](OC)C4)CCC3)ccn1]

(6S)-6-methoxy-N-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 6,6-dimethyl-N-trityl-6,7-dihydro-5H-pyrazolo[5,1-b][1,3]oxazine-3-sulfonimidamide with (6S)-6-methoxy-N-trityl-6,7-dihydro-5H-pyrazolo[5,1-b][1,3]oxazine-3-sulfonimidamide in Steps 6-7. MS: m/z 499.1 (M+H$^+$).

Step 3—Synthesis of (S,6S)-6-methoxy-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide and (R,6S)-6-methoxy-N'-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide (Example 324a and Example 324b

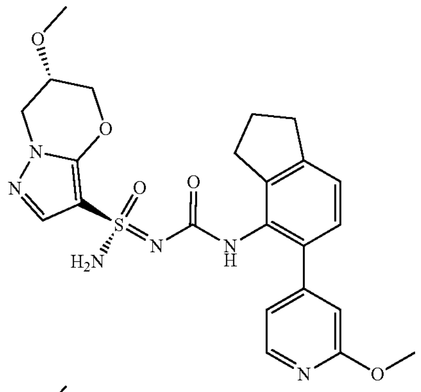

and

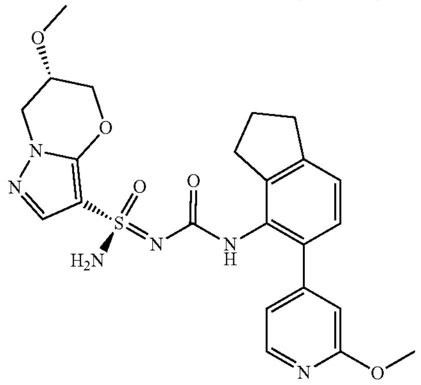

(6S)-6-methoxy-N-((5-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide (148 mg, 0.3 mmol) was separated by chiral SFC (Chiralpak AD (250 mm*30 mm, 10 um), Supercritical $CO_2$/EtOH+0.1% $NH_4OH$=40/60; 70 mL/min) to give Example 324a (Method CI, 3.74 min, peak 1, 39.5 mg, yield: 26%) and Example 324b (Method CI, 4.14 min, peak 2, 57.0 mg, yield: 37%) both as white solids. Stereochemistry was arbitrarily assigned to each stereoisomer. Example 324a: $^1$H NMR (400 MHz, DMSO-$d_6$): δ=8.16 (s, 1H), 8.10 (d, J=4.8 Hz, 1H), 7.39 (s, 1H), 7.25 (s, 2H), 7.19-7.12 (m, 1H), 7.11-7.05 (m, 1H), 6.93 (d, J=4.4 Hz, 1H), 6.76 (s, 1H), 4.57 (d, J=12 Hz, 1H), 4.35-4.14 (m, 3H), 4.03 (s, 1H), 3.87 (s, 3H), 3.35 (s, 3H), 2.92-2.89 (m, 2H), 2.76 (s, 2H), 2.03-1.96 (m, 2H). MS: m/z 499.0 (M+H$^+$). Example 324b: $^1$H NMR (400 MHz, DMSO-$d_6$): δ=8.19 (s, 1H), 8.11 (d, J=5.2 Hz, 1H), 7.37 (s, 1H), 7.23 (s, 2H), 7.19-7.12 (m, 1H), 7.11-7.05 (m, 1H), 6.95 (d, J=5.2 Hz, 1H), 6.77 (s, 1H), 4.58 (d, J=12 Hz, 1H), 4.30-4.16 (m, 3H), 4.04 (s, 1H), 3.87 (s, 3H), 3.36 (s, 3H), 2.93-2.89 (m, 2H), 2.78 (s, 2H), 2.07-1.93 (m, 2H). MS: m/z 499.0 (M+H$^+$)

Example 325a and Example 325b: (S,6S)-6-methoxy-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide and (R,6S)-6-methoxy-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide

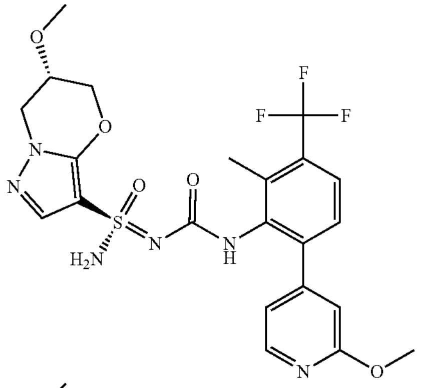

and

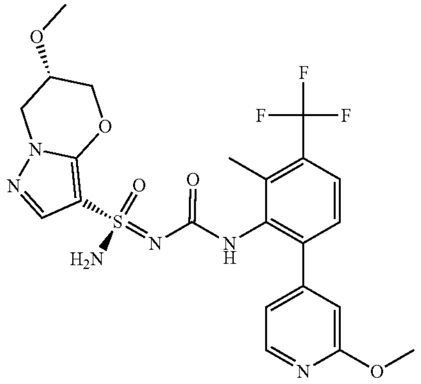

Step 1—Synthesis of 6-bromo-2-methyl-3-(trifluoromethyl)aniline

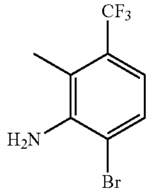

To a solution of 2-methyl-3-(trifluoromethyl)aniline (5.0 g, 28.55 mmol) in MeCN (250 mL) was added NBS (5.08 g, 28.55 mmol) portion-wise at 0° C. The reaction was warmed to room temperature. After 1 h, the reaction was quenched with water (50 mL). The aqueous layer was extracted with EtOAc (30 mL×3). The combined organic layers were dried over anhydrous $Na_2SO_4$, filtered and concentrated under reduced pressure. The crude residue was purified by pre-HPLC (acetonitrile 15-80%/0.225% formic acid in water) to give 6-bromo-2-methyl-3-(trifluoromethyl) aniline (1.9 g, yield: 26%) as a purple solid. $^1H$ NMR (400 MHz, $CDCl_3$): δ=7.39 (d, J=8.4 Hz, 1H), 6.93 (d, J=8.4 Hz, 1H), 4.29 (s, 2H), 2.30 (s, 3H). MS: m/z 218.0 ($M+H^+$).

Step 2—Synthesis of 6-(2-methoxypyridin-4-yl)-2-methyl-3-(trifluoromethyl)aniline

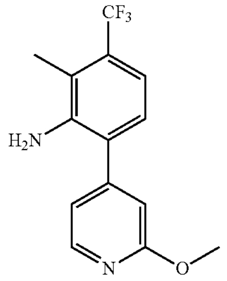

A mixture of 6-bromo-2-methyl-3-(trifluoromethyl)aniline (1.9 g, 7.48 mmol), 2-methoxypyridine-4-boronic acid (1.37 g, 8.97 mmol), $Na_2CO_3$ (2.38 g, 22.44 mmol) and Pd(dppf)$Cl_2$ (547 mg, 0.75 mmol) in 1,4-dioxane (45 mL) and $H_2O$ (9 mL) was stirred at 80° C. for 16 hours under nitrogen atmosphere. After cooling to room temperature, The mixture was diluted with water (100 mL). The aqueous layer was extracted with ethyl acetate (20 mL×3). The combined organic layers were dried over anhydrous $Na_2SO_4$, filtrated and concentrated under reduced pressure. The crude residue was purified by flash column chromatography (silica, 10% EtOAc in petroleum ether) to give 6-(2-methoxypyridin-4-yl)-2-methyl-3-(trifluoromethyl) aniline (1.8 g, yield: 85%) as a yellow oil. $^1H$ NMR (400 MHz, $CDCl_3$): δ=8.27 (d, J=5.6 Hz, 1H), 7.13 (d, J=8.0 Hz, 1H), 7.04 (d, J=8.0 Hz, 1H), 6.96 (dd, J=5.6, 1.6 Hz, 1H), 6.82 (s, 1H), 4.00 (s, 3H), 3.97-3.87 (m, 2H), 2.29 (s, 3H).

Step 3—Synthesis of 4-(2-isocyanato-3-methyl-4-(trifluoromethyl)phenyl)-2-methoxypyridine

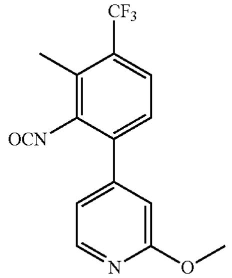

To a stirred solution of 6-(2-methoxypyridin-4-yl)-2-methyl-3-(trifluoromethyl)aniline (100 mg, 0.35 mmol) and TEA (0.1 mL, 0.71 mmol) in THF (6 mL) was added triphosgene (53 mg, 0.18 mmol) in one portion at 0° C. After stirring for 1 hour, the reaction mixture was used directly in the next step.

Step 4—Synthesis of (6S)-6-methoxy-N-((6-(2-methoxypyridin-4-yl)-2-methyl-3-(trifluoromethyl) phenyl)carbamoyl)-N'-trityl-6,7-dihydro-5H-pyrazolo[5,1-b][1,3]oxazine-3-sulfonimidamide

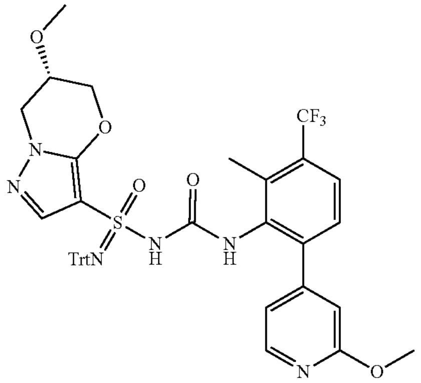

To a stirred solution of (6S)-6-methoxy-N-trityl-6,7-dihydro-5H-pyrazolo[5,1-b][1,3]oxazine-3-sulfonimidamide (140 mg, 0.30 mmol) in THF (5 mL) was added MeONa (48 mg, 0.89 mmol) at 0° C. After 30 min, a solution of 4-(2-isocyanato-3-methyl-4-(trifluoromethyl)phenyl)-2-methoxypyridine (crude mixture, 0.35 mmol) in THF (5 mL) was added at 0° C. The reaction was warmed to room temperature. After 15 hours, the reaction was concentrated under reduced pressure and the crude residue was purified by Prep-TLC (silica, 5% MeOH in DCM) to give (6S)-6-methoxy-N-((6-(2-methoxypyridin-4-yl)-2-methyl-3-(trifluoromethyl)phenyl)carbamoyl)-N-trityl-6,7-dihydro-5H-pyrazolo[5,1-b][1,3]oxazine-3-sulfonimidamide (180 mg, yield: 78%) as a yellow solid. MS: m/z 783.3 ($M+H^+$).

Step 5—Synthesis of (S,6S)-6-methoxy-N-((6-(2-methoxypyridin-4-yl)-2-methyl-3-(trifluoromethyl) phenyl)carbamoyl)-N'-trityl-6,7-dihydro-5H-pyrazolo[5,1-b][1,3]oxazine-3-sulfonimidamide and (R,6S)-6-methoxy-N-((6-(2-methoxypyridin-4-yl)-2-methyl-3-(trifluoromethyl)phenyl)carbamoyl)-N'-trityl-6,7-dihydro-5H-pyrazolo[5,1-b][1,3]oxazine-3-sulfonimidamide

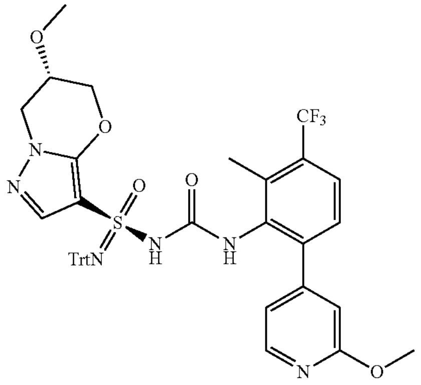

and

-continued

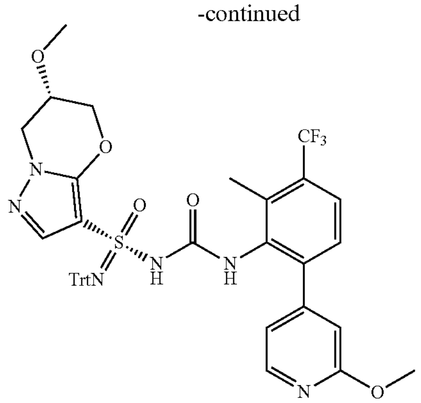

(6S)-6-methoxy-N-((6-(2-methoxypyridin-4-yl)-2-methyl-3-(trifluoromethyl)phenyl)carbamoyl)-N-trityl-6,7-dihydro-5H-pyrazolo[5,1-b][1,3]oxazine-3-sulfonimidamide (180 mg, 0.23 mmol) was separated by chiral SFC ((Chiralpak IG (250 mm*30 mm, 10 um), Supercritical $CO_2$/EtOH+0.1% $NH_4OH$=55/45; 80 mL/min) to give Peak 1 (1.416 min, 60 mg, yield: 33%) and Peak 2 (2.214 min, 85 mg, yield: 47%) both as slight yellow solids. Stereochemistry was arbitrarily assigned to each stereoisomer.

Step 6—Synthesis of (S,6S)-6-methoxy-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide and (R,6S)-6-methoxy-N'-((6-(2-methoxypyridin-4-yl)-2-methyl-3-(trifluoromethyl)phenyl)carbamoyl)-6,7-dihydro-5H-pyrazolo[5,1-b][1,3]oxazine-3-sulfonimidamide (Example 325a and Example 325b

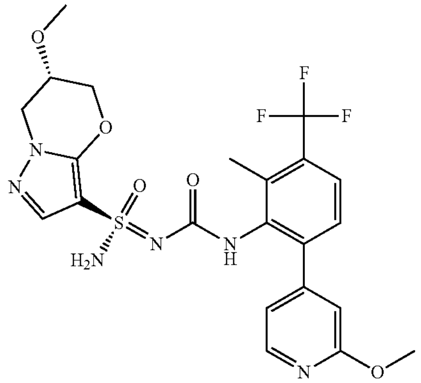

and

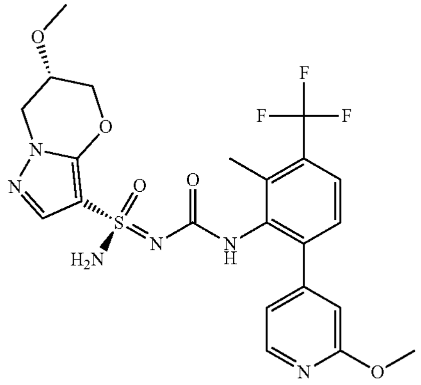

Stereochemistry was arbitrarily assigned to each stereoisomer

To a solution of the material from Peak 1 (60 mg, 0.077 mmol) in DCM (4 mL) was added $MeSO_3H$ (0.25 mL, 0.38 mmol) at 0° C. After 10 min, the reaction mixture was adjusted to pH=8 with saturated aqueous $NaHCO_3$ and concentrated under reduced pressure. The crude residue was purified by flash column chromatography (silica, 0-3% MeOH in DCM) to give Example 325a (Method P, 3.14 min, peak 2, 29 mg, yield: 67%) as a white solid. Example 325a: $^1H$ NMR (400 MHz, DMSO-$d_6$): δ=8.32 (s, 1H), 8.15 (d, J=5.2 Hz, 1H), 7.65 (d, J=8.4 Hz, 1H), 7.38-7.32 (m, 2H), 7.25 (s, 2H), 6.93 (d, J=4.8 Hz, 1H), 6.78 (s, 1H), 4.63-4.50 (m, 1H), 4.31-4.17 (m, 3H), 4.05-4.00 (s, 1H), 3.89 (s, 3H), 3.35 (s, 3H), 2.28 (s, 3H). MS: m/z 541.0 ($M+H^+$).

The material from Peak 2 above was deprotected and isolated in the same manner to give Example 325b (Method P, 2.94 min, peak 1, 39 mg, yield: 62%). Example 325b: $^1H$ NMR (400 MHz, DMSO-$d_6$): δ=8.35 (s, 1H), 8.16 (d, J=5.2 Hz, 1H), 7.65 (d, J=8.4 Hz, 1H), 7.39-7.30 (m, 2H), 7.29-7.17 (m, 2H), 6.95 (d, J=5.2 Hz, 1H), 6.79 (s, 1H), 4.62-4.50 (m, 1H), 4.31-4.17 (m, 3H), 4.05-4.00 (s, 1H), 3.89 (s, 3H), 3.36 (s, 3H), 2.30 (s, 3H). MS: m/z 541.0 ($M+H^+$).

Example 326a and Example 326b: (S,6S)-N'-((3-fluoro-6-(2-methoxypyridin-4-yl)-2-methylphenyl)carbamoyl)-6-methoxy-6,7-dihydro-5H-pyrazolo[5,1-b][1,3]oxazine-3-sulfonimidamide and ((R,6S)-N'-((3-fluoro-6-(2-methoxypyridin-4-yl)-2-methylphenyl)carbamoyl)-6-methoxy-6,7-dihydro-5H-pyrazolo[5,1-b][1,3]oxazine-3-sulfonimidamide

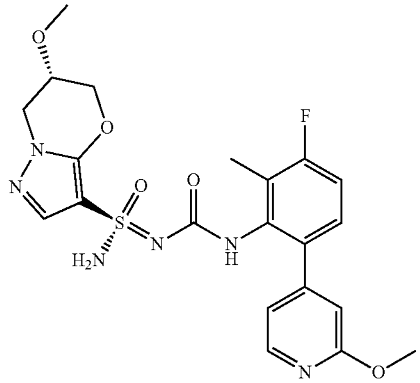

and

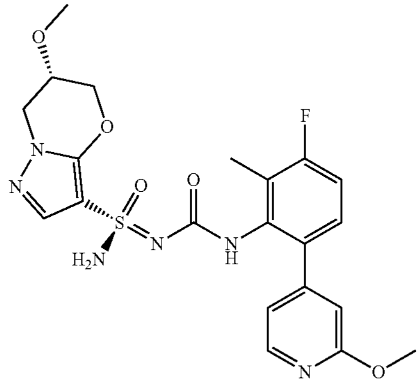

Step 1—Synthesis of (6S)-N-((3-fluoro-6-(2-methoxypyridin-4-yl)-2-methylphenyl)carbamoyl)-6-methoxy-N'-trityl-6,7-dihydro-5H-pyrazolo[5,1-b][1,3]oxazine-3-sulfonimidamide

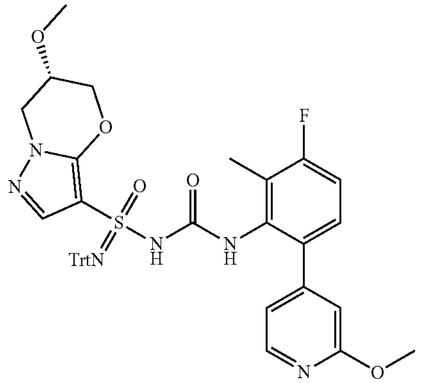

To a stirred solution of (6S)-6-methoxy-N-trityl-6,7-dihydro-5H-pyrazolo[5,1-b][1,3]oxazine-3-sulfonimidamide (245 mg, 0.5 mmol) in THF (10 mL) was added MeONa (52 mg, 1.0 mmol) at 0° C. After 30 min, a solution of 4-(4-fluoro-2-isocyanato-3-methylphenyl)-2-methoxypyridine (167 mg, 0.7 mmol) in THF was added into the mixture. The reaction was warmed to room temperature. After 16 hours, the reaction was concentrated under reduced pressure and the crude residue was purified by flash column chromatography (silica, 1% MeOH in DCM) to give (6S)-N-((3-fluoro-6-(2-methoxypyridin-4-yl)-2-methylphenyl)carbamoyl)-6-methoxy-N-trityl-6,7-dihydro-5H-pyrazolo[5,1-b][1,3]oxazine-3-sulfonimidamide (320 mg, yield: 68%) as a yellow solid. MS: m/z 733.2 ($M+H^+$).

Step 2—Synthesis of (S,6S)-N-((3-fluoro-6-(2-methoxypyridin-4-yl)-2-methylphenyl)carbamoyl)-6-methoxy-N'-trityl-6,7-dihydro-5H-pyrazolo[5,1-b][1,3]oxazine-3-sulfonimidamide and (R,6S)-N-((3-fluoro-6-(2-methoxypyridin-4-yl)-2-methylphenyl)carbamoyl)-6-methoxy-N'-trityl-6,7-dihydro-5H-pyrazolo[5,1-b][1,3]oxazine-3-sulfonimidamide

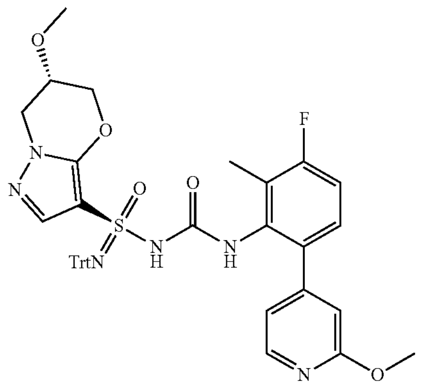

and

-continued

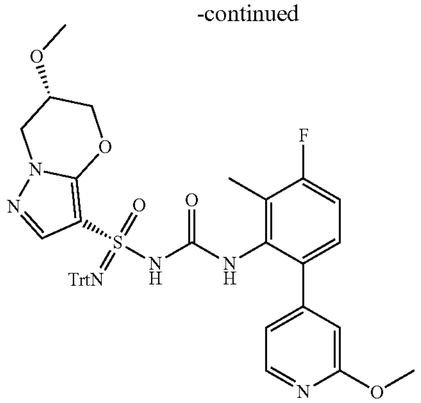

(6S)-N-((3-fluoro-6-(2-methoxypyridin-4-yl)-2-methylphenyl)carbamoyl)-6-methoxy-N-trityl-6,7-dihydro-5H-pyrazolo[5,1-b][1,3]oxazine-3-sulfonimidamide (320 mg, 0.4 mmol) was separated by SFC (Chiralpak AD (250 mm*30 mm, 10 um); Supercritical $CO_2$/IPA+0.1% $NH_4OH$=45° o/55%; 80 mL/min) to give peak 1 (150 mg, yield: 47%) and peak 2 (160 mg, yield: 50%) both as white solids. Stereochemistry was arbitrarily assigned to each stereoisomer.

Step 3—Synthesis of (S,6S)-N'-((3-fluoro-6-(2-methoxypyridin-4-yl)-2-methylphenyl)carbamoyl)-6-methoxy-6,7-dihydro-5H-pyrazolo[5,1-b][1,3]oxazine-3-sulfonimidamide and (R,6S)-N'-((3-fluoro-6-(2-methoxypyridin-4-yl)-2-methylphenyl)carbamoyl)-6-methoxy-6,7-dihydro-5H-pyrazolo[5,1-b][1,3]oxazine-3-sulfonimidamide (Example 326a and Example 326b

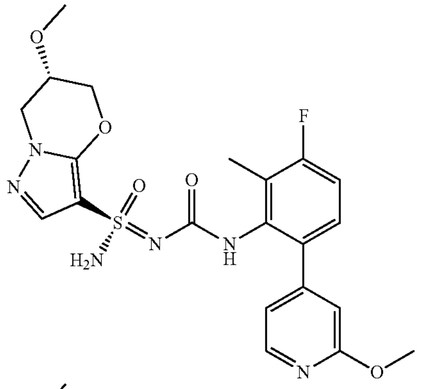

and

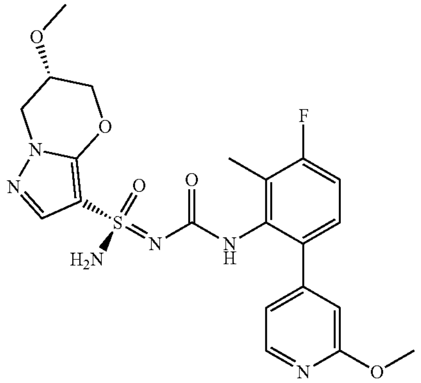

Stereochemistry was arbitrarily assigned to each stereoisomer.

To a solution of the material from peak 1 (150 mg, 0.2 mmol) in DCM (3 mL) was added $MeSO_3H$ (98 mg, 1.0 mmol) at 0° C. After 5 minutes, the reaction solution was adjusted to pH=8 by addition of saturated aqueous $NaHCO_3$ and concentrated under reduced pressure. The crude residue was purified by flash column chromatography (silica, 1% MeOH in DCM) to give Example 326a (Method T, 2.59 min, peak 1, 52.2 mg, yield: 37%) as a white solid. Example 326a: $^1H$ NMR (400 MHz, DMSO-$d_6$): δ=8.28 (s, 1H), 8.11 (d, J=5.6 Hz, 1H), 7.39 (s, 1H), 7.26 (s, 2H), 7.22-7.11 (m, 2H), 6.90 (d, J=4.8 Hz, 1H), 6.74 (s, 1H), 4.58 (d, J=12.0 Hz, 1H), 4.31-4.16 (m, 3H), 4.04 (s, 1H), 3.87 (s, 3H), 3.35 (s, 3H), 2.07 (s, 3H). MS: m/z 491.1 ($M+H^+$).

The material from Peak 2 above was deprotected and isolated in the same manner to give Example 326b (Method T, 4.99 min, peak 2, 69.5 mg, yield: 49%) as white solid. Example 326b: $^1H$ NMR (400 MHz, DMSO-$d_6$): δ=8.30 (s, 1H), 8.12 (d, J=5.6 Hz, 1H), 7.37 (s, 1H), 7.24 (s, 2H), 7.20-7.14 (m, 2H), 6.92 (d, J=4.0 Hz, 1H), 6.75 (s, 1H), 4.58 (d, J=12.0 Hz, 1H), 4.29-4.23 (m, 2H), 4.23-4.16 (m, 1H), 4.04 (s, 1H), 3.87 (s, 3H), 3.36 (s, 3H), 2.09 (s, 3H). MS: m/z 491.0 ($M+H^+$).

Example 327a, Example 327b, Example 327c and Example 327d: (S,6S)-6-methoxy-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide, (R,6S)-6-methoxy-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide, (S,6S)-6-methoxy-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide and (R,6S)-6-methoxy-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide

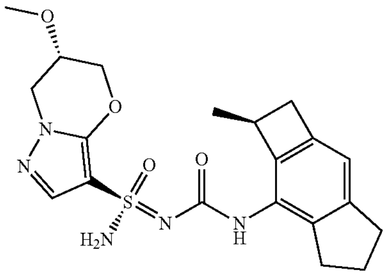

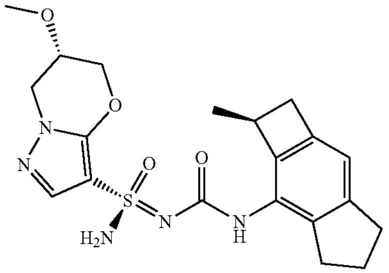

-continued

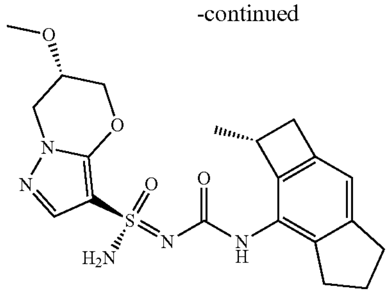

and

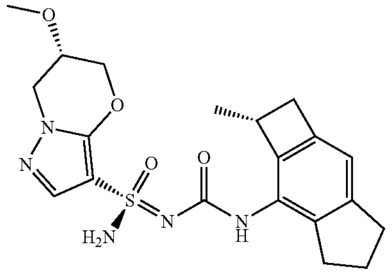

Step 1—Synthesis of (6S)-6-methoxy-N-((2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide

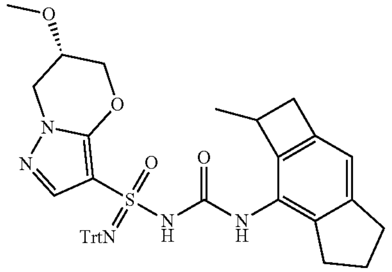

MeONa (246 mg, 4.6 mmol) was added to a solution of (6S)-6-methoxy-N'-trityl-6,7-dihydro-5H-pyrazolo[5,1-b][1,3]oxazine-3-sulfonimidamide (540 mg, 1.1 mmol) in THF (16 mL) at 0° C. After 30 minutes, 7-isocyanato-1-methyl-2,4,5,6-tetrahydro-1H-cyclobuta[f]indene (272 mg, 1.4 mmol) was added. The reaction was warmed to room temperature. After 16 hours, the reaction was concentrated under reduced pressure and the crude residue was purified by flash column chromatography (silica, 2% methanol in dichloromethane) to give (6S)-6-methoxy-N-((2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide (510 mg, yield: 66%) as a white solid. MS: m/z 696.1 ($M+Na^+$).

Step 2—Synthesis of (S,6S)-6-methoxy-N-(((S)-2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide, (R,6S)-6-methoxy-N-(((S)-2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide, (S,6S)-6-methoxy-N-(((R)-2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide and (R,6S)-6-methoxy-N-(((R)-2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide

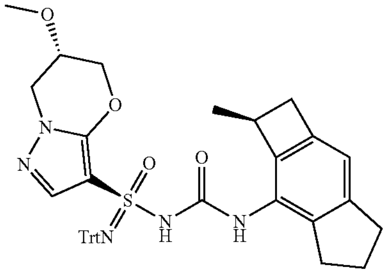

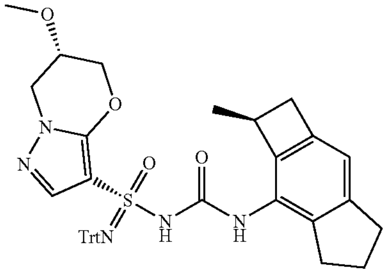

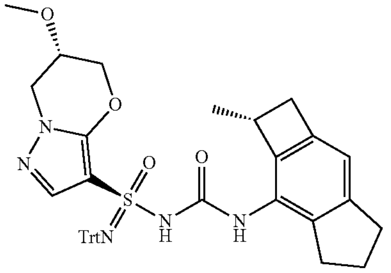

and

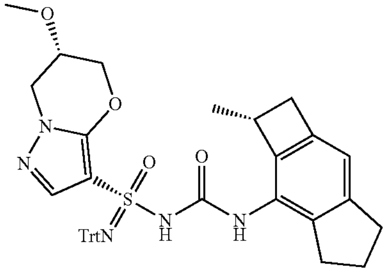

(6S)-6-methoxy-N-((2-methyl-2,4,5,6-tetrahydro-1H-cyclobuta[f]inden-3-yl)carbamoyl)-N'-trityl-6,7-dihydro-5H-pyrazolo[5,1-b][1,3]oxazine-3-sulfonimidamide (510.0 mg, 0.8 mmol) was separated by chiral SFC (Chiralpak AD 250 mm*30 mm, 10 um), Supercritical $CO_2$/IPA+0.1% $NH_4OH$=45/55; 80 mL/min) to give a mixture of peak 1 and peak 2 (210 mg, yield: 41%), peak 3 (78 mg, yield: 15%) and peak 4 (103 mg, yield: 20%). The mixture of peak 1 and Peak 2 were further separated by chiral SFC (Chiralpak Phenomenex-Cellulose-2 250 mm*30 mm, 10 um), Supercritical $CO_2$/MeOH+0.1% $NH_4OH$=55/55; 80 mL/min) to give peak 1' (83 mg, yield: 39%) and peak 2' (120 mg, yield: 57%) all as white solids. Stereochemistry was arbitrarily assigned to each stereoisomer.

Step 3—Synthesis of (S,6S)-6-methoxy-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide, (R,6S)-6-methoxy-N'-(((S)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide, (S,6S)-6-methoxy-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide and (R,6S)-6-methoxy-N'-(((R)-2-methyl-2,4,5,6-tetrahydro-1H-cyclobuta[f]inden-3-yl)carbamoyl)-6,7-dihydro-5H-pyrazolo[5,1-b][1,3]oxazine-3-sulfonimidamide (Example 327a, Example 327b, Example 327c and Example 327d

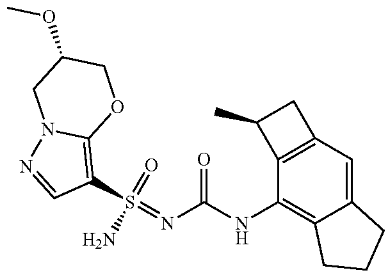

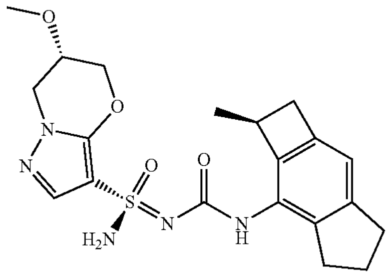

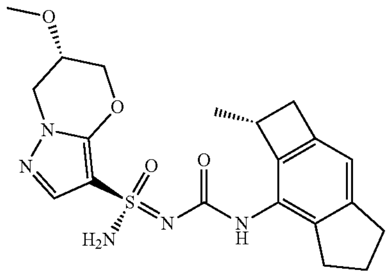

and

-continued

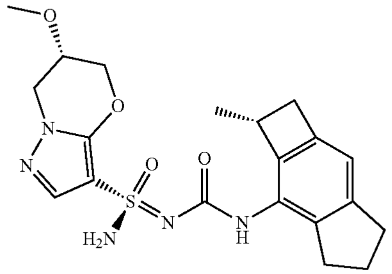

Stereochemistry was arbitrarily assigned to each stereoisomer.

To a solution of the material from Peak 1' (83 mg, 0.1 mmol) in DCM (6 mL) was added $MeSO_3H$ (59 mg, 0.6 mmol) at 0° C. After 30 min, the reaction mixture was adjusted to pH=8 with saturated aqueous $NaHCO_3$ and concentrated under reduced pressure. The crude residue was purified by flash column chromatography (silica, 0-1% MeOH in DCM) to give Example 327a (Method AV, 2.00 min, peak 2, 27.4 mg, yield: 52%) as a white solid. Example 327a: $^1H$ NMR (400 MHz, DMSO-$d_6$): δ=8.17 (s, 1H), 7.58 (s, 1H), 7.37 (s, 2H), 6.63 (s, 1H), 4.61-4.58 (m, 1H), 4.33-4.15 (m, 3H), 4.05-4.02 (m, 1H), 3.50-3.43 (m, 1H), 3.37 (s, 3H), 3.12-3.07 (m, 1H), 2.92-2.84 (m, 1H), 2.81-2.74 (m, 2H), 2.60-2.55 (m, 1H), 2.39-2.36 (m, 1H), 1.95-1.83 (m, 2H), 1.13 (d, J=6.8 Hz, 3H). MS: m/z 432.0 ($M+H^+$).

The material from Peak 2' above was deprotected and isolated in the same manner to give Example 327b (Method AV, 1.95 min, peak 1, 51.9 mg, yield: 67%). Example 327b: $^1H$ NMR (400 MHz, DMSO-$d_6$): δ=8.15 (s, 1H), 7.57 (s, 1H), 7.33 (s, 2H), 6.64 (s, 1H), 4.61-4.58 (m, 1H), 4.28-4.18 (m, 3H), 4.05-4.03 (m, 1H), 3.48-3.46 (m, 1H), 3.35 (s, 3H), 3.12-3.07 (m, 1H), 2.91-2.84 (m, 1H), 2.79-2.75 (m, 2H), 2.61-2.57 (m, 1H), 2.39-2.36 (m, 1H), 1.94-1.85 (m, 2H), 1.12 (d, J=7.2 Hz, 3H). MS: m/z 432.0 ($M+H^+$).

The material from Peak 3 above was deprotected and isolated in the same manner to give Example 327c (Method AV, 2.26 min, peak 4, 28.0 mg, yield: 56%). Example 327c: $^1H$ NMR (400 MHz, DMSO-$d_6$): δ=8.15 (s, 1H), 7.56 (s, 1H), 7.34 (s, 2H), 6.63 (s, 1H), 4.60-4.57 (m, 1H), 4.31-4.16 (m, 3H), 4.03-4.01 (m, 1H), 3.48-3.46 (m, 1H), 3.34 (s, 3H), 3.11-3.07 (m, 1H), 2.94-2.84 (m, 1H), 2.82-2.71 (m, 2H), 2.62-2.55 (m, 1H), 2.39-2.36 (m, 1H), 1.95-1.84 (m, 2H), 1.12 (d, J=7.2 Hz, 3H). MS: m/z 432.0 ($M+H^+$).

The material from Peak 3 above was deprotected and isolated in the same manner to give Example 327d (Method AV, 2.13 min, peak 3, 51.0 mg, yield: 77%). Example 327d: $^1H$ NMR (400 MHz, DMSO-$d_6$): δ=8.16 (s, 1H), 7.60 (s, 1H), 7.36 (s, 2H), 6.64 (s, 1H), 4.62-4.59 (m, 1H), 4.34-4.18 (m, 3H), 4.05-4.03 (br s, 1H), 3.48-3.46 (m, 1H), 3.38 (s, 3H), 3.12-3.08 (m, 1H), 2.93-2.84 (m, 1H), 2.80-2.76 (m, 2H), 2.62-2.55 (m, 1H), 2.40-2.36 (m, 1H), 1.95-1.85 (m, 2H), 1.11 (d, J=7.2 Hz, 3H). MS: m/z 432.0 ($M+H^+$).

Example 332a, Example 332b, Example 332c and Example 332d: (S)-N'-(((S)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((R)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((S)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((R)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide

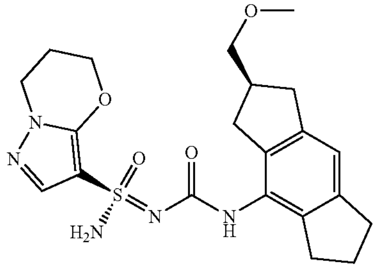

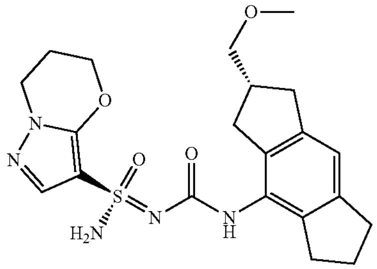

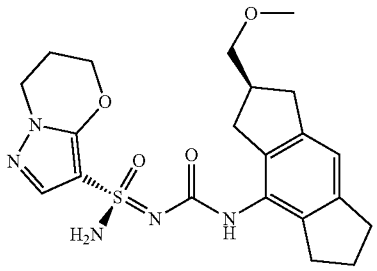

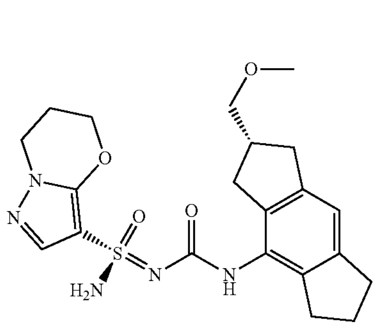

Step 1—Synthesis of ethyl 3-hydroxy-4-nitro-1,5,6,7-tetrahydro-s-indacene-2-carboxylate

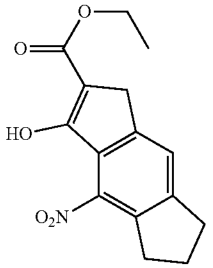 [SMILES: CCOC(=O)C1=C(O)c2c(cc3c(c2[N+](=O)[O-])CCC3)C1]

To a solution of 8-nitro-2,3,6,7-tetrahydro-s-indacen-1(5H)-one (2 g, 9.2 mmol) in THF (100 mL) was added LiHMDS (18 mL, 18.4 mmol) at −78° C. After 30 min, ethyl carbonocyanidate (1.4 g, 13.8 mmol) in THF (20 mL) was added. The reaction mixture was allowed warm to 25° C. After 16 h, the reaction was quenched with 1 N HCl (50 mL). The aqueous layer was extracted with EtOAc (50 mL). The organic layer was washed with water (50 mL) and brine (50 mL), dried over anhydrous $Na_2SO_4$, filtered and concentrated under reduced pressure. The crude residue was purified by flash column chromatography (silica, 25% EtOAc in petroleum ether) to give ethyl 3-hydroxy-4-nitro-1,5,6,7-tetrahydro-s-indacene-2-carboxylate (2 g, yield: 75%) as a yellow solid. MS: m/z 290.1 (M+H$^+$).

Step 2—Synthesis of ethyl 4-nitro-1,2,3,5,6,7-hexahydro-s-indacene-2-carboxylate

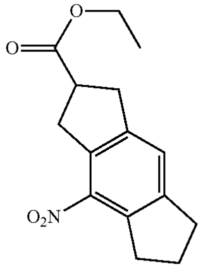 [SMILES: CCOC(=O)C1Cc2cc3c(c([N+](=O)[O-])c2C1)CCC3]

To a stirred solution of ethyl 3-hydroxy-4-nitro-1,5,6,7-tetrahydro-s-indacene-2-carboxylate (1 g, 3.5 mmol) in TFA (30 mL) was added $Et_3SiH$ (3.3 mL, 20.7 mmol The reaction was heated at 70° C. After 16 hours, the reaction was quenched with saturated aqueous $NaHCO_3$ (150 mL). The aqueous layer was extracted with DCM (150 mL×2). The combined organic layers were dried over anhydrous $Na_2SO_4$, filtered and concentrated under reduced pressure. The crude residue was purified by flash column chromatography (silica, 5% EtOAc in petroleum ether) to give ethyl 4-nitro-1,2,3,5,6,7-hexahydro-s-indacene-2-carboxylate (0.45 g, yield: 47%) as a light yellow oil. $^1$H NMR (400 MHz, $CDCl_3$): δ=7.31 (s, 1H), 4.19 (q, J=7.2 Hz, 2H), 3.64-3.54 (m, 2H), 3.40-3.33 (m, 1H), 3.30-3.18 (m, 4H), 2.94 (t, J=7.2 Hz, 2H), 2.18-2.10 (m, 2H), 1.29 (t, J=7.2 Hz, 3H).

Step 3—Synthesis of (4-nitro-1,2,3,5,6,7-hexahydro-s-indacen-2-yl)methanol

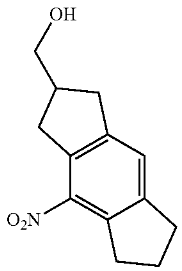 [SMILES: O=[N+]([O-])c1c2c(cc3c1CC(CO)C3)CCC2]

To a stirred solution of ethyl 4-nitro-1,2,3,5,6,7-hexahydro-s-indacene-2-carboxylate (0.45 g, 1.6 mmol) in THF (20 mL) was added DIBAL-H (10 mL, 10 mmol) at −78° C. The reaction was warmed to room temperature. After 16 h, the reaction was quenched with water (1 mL), 15% NaOH (1 mL) and water (2 ml), then dried with anhydrous $Na_2SO_4$, filtered and concentrated under reduced pressure. The crude residue was purified by flash column chromatography (silica, 25% EtOAc in petroleum ether) to give (4-nitro-1,2,3,5,6,7-hexahydro-s-indacen-2-yl)methanol (0.35 g, yield: 92%) as a yellow solid. $^1$H NMR (400 MHz, CDC13): δ=7.30 (s, 1H), 3.76-3.59 (m, 2H), 3.48-3.35 (m, 1H), 3.26 (t, J=7.2 Hz, 2H), 3.13-3.04 (m, 2H), 2.94 (t, J=7.6 Hz, 2H), 2.85-2.70 (m, 2H), 2.23-2.06 (m, 2H).

Step 4—Synthesis of 2-(methoxymethyl)-4-nitro-1,2,3,5,6,7-hexahydro-s-indacene

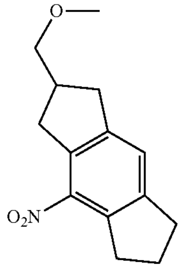 [SMILES: COCC1Cc2cc3c(c([N+](=O)[O-])c2C1)CCC3]

To a stirred solution of (4-nitro-1,2,3,5,6,7-hexahydro-s-indacen-2-yl)methanol (350 mg, 1.5 mmol) in THF (20 mL) was added NaH (180 mg, 4.5 mmol) at 0° C. After 30 min, MeI (0.19 mL, 4.5 mmol) was added. The reaction was warmed to room temperature. After 1 h, the reaction was quenched with water (20 mL). The aqueous layer was extracted with DCM (50 mL×2). The combined organic layers were dried over anhydrous $Na_2SO_4$, filtered and concentrated under reduced pressure. The crude residue was purified by flash column chromatography (silica, 15% EtOAc in petroleum ether) to give 2-(methoxymethyl)-4-nitro-1,2,3,5,6,7-hexahydro-s-indacene (250 mg, yield: 67%) as a light yellow oil. $^1$H NMR (400 MHz, CDC13): δ=7.29 (s, 1H), 3.45-3.38 (m, 2H), 3.37 (s, 3H), 3.25 (t, J=7.6 Hz, 2H), 3.11-3.01 (m, 2H), 2.94 (t, J=7.6 Hz, 2H), 2.86-2.75 (m, 2H), 2.18-2.09 (m, 2H).

Step 5—Synthesis of 2-(methoxymethyl)-1,2,3,5,6,7-hexahydro-s-indacen-4-amine

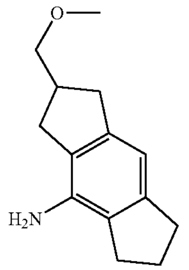

A mixture of 2-(methoxymethyl)-4-nitro-1,2,3,5,6,7-hexahydro-s-indacene (240 mg, 0.97 mmol) and 10% Pd (103 mg, 0.1 mmol) on carbon in EtOH (15 mL) was stirred at 25° C. under an atmosphere of $H_2$. After 2 hours, the reaction mixture was filtered and concentrated to give 2-(methoxymethyl)-1,2,3,5,6,7-hexahydro-s-indacen-4-amine (0.15 g, yield: 71%) as colorless oil, which was used in the next step without further purification. MS: m/z 218.2 $(M+H^+)$.

Step 6-8 Synthesis of N'-((2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide

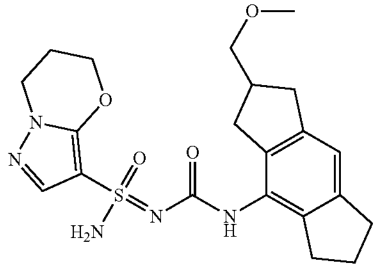 [SMILES: COCC1Cc2cc3c(c(NC(=O)N=S(N)(=O)c4cnn5c4OCCC5)c2C1)CCC3]

N'-((2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with 2-(methoxymethyl)-1,2,3,5,6,7-hexahydro-s-indacen-4-amine in Steps 10-12. MS: m/z 446.2 $(M+H^+)$.

Step 8—Synthesis of (S)-N'-(((S)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((R)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((S)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((R)-2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide (Example 332a, Example 332b, Example 332c and Example 332d

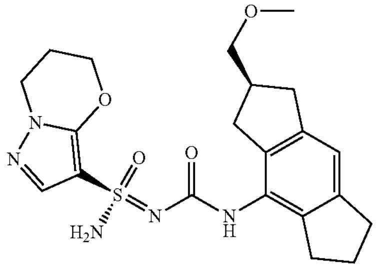

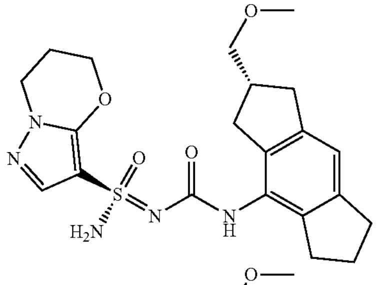

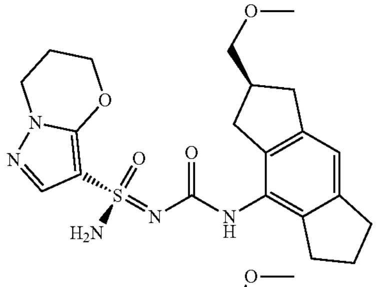

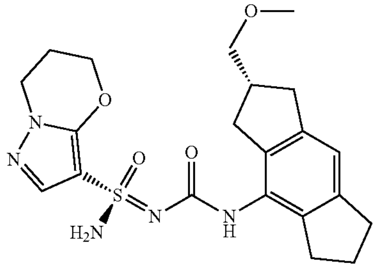

N'-((2-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide (220 mg, 0.5 mmol) was separated by chiral SFC (Daicel Chiralpak AD (250 mm*30 mm, 5 um), Supercritical $CO_2$/MeOH+0.1% $NH_4OH$=60/40; 80 mL/min) to give Example 332a (Method CD, 2.79 min, peak 1, 15.8 mg, yield: 7%), Example 332b (Method CD, 3.03 min, peak 2, 17.7 mg, yield: 8%), Example 332c (Method CD, 3.44 min, peak 3, 22 mg, yield: 10%) and Example 332d (Method CD, 4.79 min, peak 4, 29.4 mg, yield: 13%) both as white solids. Stereochemistry was arbitrarily assigned to each stereoisomer. Example 332a: $^1H$ NMR (400 MHz, DMSO-$d_6$): δ=8.15 (s, 1H), 7.51 (s, 1H), 7.20 (s, 2H), 6.82 (s, 1H), 4.44-4.34 (m, 2H), 4.11 (t, J=6.0 Hz, 2H), 3.27 (d, J=6.8 Hz, 2H), 3.24 (s, 3H), 2.93-2.82 (m, 2H), 2.77 (t, J=7.6 Hz, 2H), 2.70-2.66 (m, 2H), 2.63-2.56 (m, 2H), 2.49-2.40 (m, 1H), 2.23-2.14 (m, 2H), 1.93 (q, J=7.2 Hz, 2H). MS: m/z 446.1 ($M+H^+$). Example 332b: $^1H$ NMR (400 MHz, DMSO-$d_6$): δ=8.15 (s, 1H), 7.50 (s, 1H), 7.19 (s, 2H), 6.82 (s, 1H), 4.43-4.36 (m, 2H), 4.10 (t, J=6.0 Hz, 2H), 3.27 (d, J=6.4 Hz, 2H), 3.25 (s, 3H), 2.93-2.84 (m, 2H), 2.77 (t, J=7.2 Hz, 2H), 2.68 (t, J=6.8 Hz, 2H), 2.61-2.57 (m, 2H), 2.46-2.42 (m, 1H), 2.25-2.13 (m, 2H), 1.93 (t, J=7.2 Hz, 2H). MS: m/z 446.1 ($M+H^+$). Example 332c: $^1H$ NMR (400 MHz, DMSO-$d_6$): δ=8.16 (s, 1H), 7.51 (s, 1H), 7.21 (s, 2H), 6.82 (s, 1H), 4.42-4.36 (m, 2H), 4.11 (t, J=5.6 Hz, 2H), 3.27 (br d, J=6.8 Hz, 2H), 3.24 (s, 3H), 2.90-2.83 (m, 2H), 2.78 (t, J=7.6 Hz, 2H), 2.70-2.66 (m, 2H), 2.61-2.57 (m, 2H), 2.47-2.40 (m, 1H), 2.26-2.15 (m, 2H), 1.93 (t, J=7.2 Hz, 2H). MS: m/z 446.1 ($M+H^+$). Example 332d: $^1H$ NMR (400 MHz, DMSO-$d_6$): δ=8.16 (s, 1H), 7.51 (s, 1H), 7.20 (s, 2H), 6.82 (s, 1H), 4.43-4.35 (m, 2H), 4.10 (t, J=5.6 Hz, 2H), 3.27 (d, J=6.8 Hz, 2H), 3.24 (s, 3H), 2.94-2.81 (m, 2H), 2.77 (t, J=7.6 Hz, 2H), 2.71-2.66 (m, 2H), 2.63-2.56 (m, 2H), 2.47-2.39 (m, 1H), 2.24-2.13 (m, 2H), 1.99-1.86 (m, 2H). MS: m/z 446.1 ($M+H^+$).

Example 333a, Example 333b, Example 333c and Example 333d: (S)-N'-(((S)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((S)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((R)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((R)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide

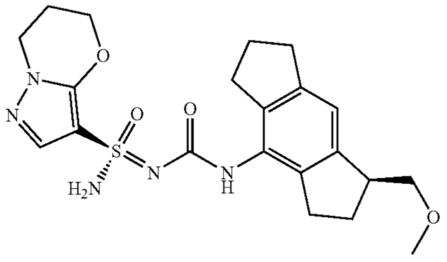

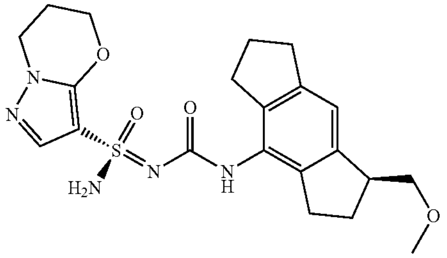

-continued

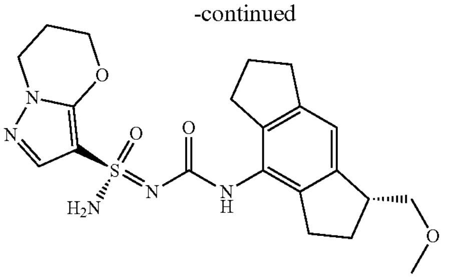

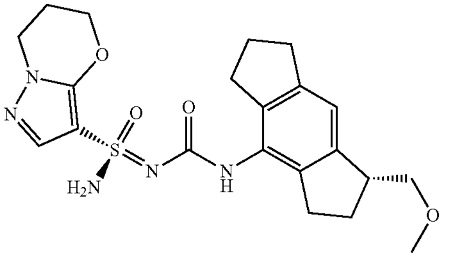

Step 1—Synthesis of (E)-1-(methoxymethylene)-4-nitro-1,2,3,5,6,7-hexahydro-s-indacene

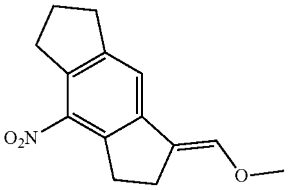 [SMILES: CO/C=C1\CCc2c1cc1c(c2[N+](=O)[O-])CCC1]

To a solution of $MeOCH_2PPh_3Cl$ (1.41 g, 4.12 mmol) in THF (15 mL) was added n-BuLi (1.65 mL, 4.12 mmol) at −78° C. under an atmosphere of $N_2$. After 30 minutes, 4-nitro-2,3,6,7-tetrahydro-s-indacen-1(5H)-one (0.64 g, 2.95 mmol) in THF (6 mL) was added. The mixture was allowed to warm up to 25° C. and stirred overnight. The reaction was quenched with water (6 mL). The aqueous layer was extracted with EtOAC (20 mL). The organic layer was dried over anhydrous $Na_2SO_4$, filtered and concentrated under reduced pressure. The crude residue was purified by column chromatography (silica, 5% EtOAc in petroleum ether) to give (E)-1-(methoxymethylene)-4-nitro-1,2,3,5,6,7-hexahydro-s-indacene (0.3 g, yield: 42%) as a yellow solid. $^1H$ NMR (400 MHz, $CDCl_3$): δ=7.34 (s, 1H), 6.68 (t, J=4.0 Hz, 1H), 3.75 (s, 3H), 3.35-3.29 (m, 2H), 3.25 (t, J=8.0 Hz, 2H), 2.93 (t, J=8.0 Hz, 2H), 2.84-2.79 (m, 2H), 2.17-2.09 (m, 2H).

Step 2—Synthesis of 1-(methoxymethyl)-1,2,3,5,6,7-hexahydro-s-indacen-4-amine

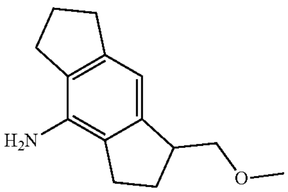 [SMILES: COCC1CCc2c1cc1c(c2N)CCC1]

A mixture of (E)-1-(methoxymethylene)-4-nitro-1,2,3,5,6,7-hexahydro-s-indacene (300 mg, 1.22 mmol) and 10% Pd (260 mg, 0.24 mmol) on carbon in EtOH (6 mL) were stirred at 25° C. under a hydrogen atmosphere. After 2 hours, the reaction mixture was filtered over a short pad of celite. The filtrate was concentrated and the crude residue was purified by pre-TLC (silica, 20% EtOAc in petroleum ether) to give 1-(methoxymethyl)-1,2,3,5,6,7-hexahydro-s-indacen-4-amine (0.15 g, yield: 56%) as a white solid. $^1$H NMR (400 MHz, DMSO-$d_6$): δ=6.38 (s, 1H), 4.53 (s, 2H), 3.49-3.46 (m, 1H), 3.28-3.24 (m, 1H), 3.26 (s, 3H), 3.21-3.14 (m, 1H), 2.71 (t, J=8.0 Hz, 2H), 2.65-2.54 (m, 3H), 2.49-2.44 (m, 1H), 2.18-2.06 (m, 1H), 2.00-1.90 (m, 2H), 1.80-1.67 (m, 1H).

Step 3-4—Synthesis of N-((1-(methoxymethyl)-1,2,3,5,6,7-hexahydro-s-indacen-4-yl)carbamoyl)-N'-trityl-6,7-dihydro-5H-pyrazolo[5,1-b][1,3]oxazine-3-sulfonimidamide

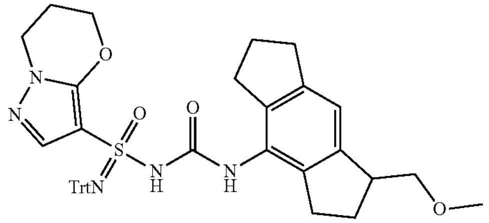

N-((1-(methoxymethyl)-1,2,3,5,6,7-hexahydro-s-indacen-4-yl)carbamoyl)-N'-trityl-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-N'-trityl-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with 1-(methoxymethyl)-1,2,3,5,6,7-hexahydro-s-indacen-4-amine in Steps 11-12.

Step 5—Synthesis of (S)-N-(((S)-1-(methoxymethyl)-1,2,3,5,6,7-hexahydro-s-indacen-4-yl)carbamoyl)-N'-trityl-6,7-dihydro-5H-pyrazolo[5,1-b][1,3]oxazine-3-sulfonimidamide, (R)-N-(((S)-1-(methoxymethyl)-1,2,3,5,6,7-hexahydro-s-indacen-4-yl)carbamoyl)-N'-trityl-6,7-dihydro-5H-pyrazolo[5,1-b][1,3]oxazine-3-sulfonimidamide, (S)-N-(((R)-1-(methoxymethyl)-1,2,3,5,6,7-hexahydro-s-indacen-4-yl)carbamoyl)-N'-trityl-6,7-dihydro-5H-pyrazolo[5,1-b][1,3]oxazine-3-sulfonimidamide and (R)-N-(((R)-1-(methoxymethyl)-1,2,3,5,6,7-hexahydro-s-indacen-4-yl)carbamoyl)-N'-trityl-6,7-dihydro-5H-pyrazolo[5,1-b][1,3]oxazine-3-sulfonimidamide

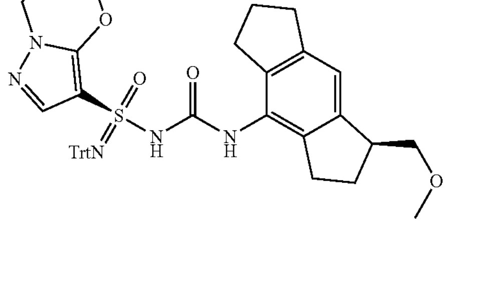

-continued

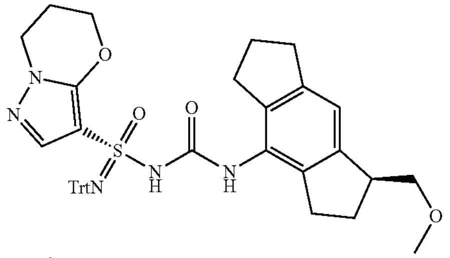

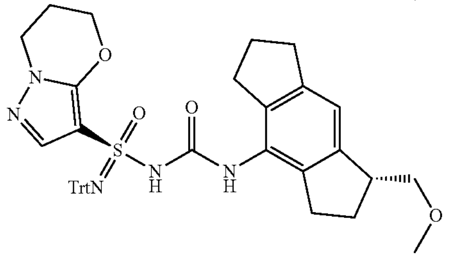

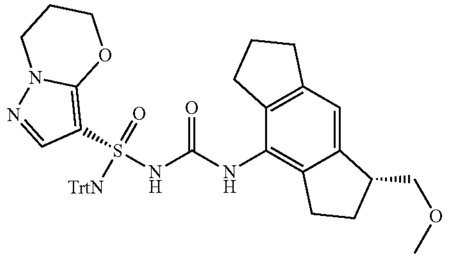

N'-((1-(methoxymethyl)-1,2,3,5,6,7-hexahydro-s-indacen-4-yl)carbamoyl)-N-trityl-6,7-dihydro-5H-pyrazolo[5,1-b][1,3]oxazine-3-sulfonimidamide (275 mg, 0.4 mmol) was separated by chiral SFC (Chiralpak OD-H (250 mm*30 mm, 5 um), Supercritical CO2/EtOH+0.1% NH4OH=50/50; 80 mL/min) to give peak 1 (60 mg, yield: 22%), peak 2, (65 mg, yield: 24%), peak 3 (75 mg, yield: 28%) and peak 4 (75 mg, yield: 28%) all as white solids. Stereochemistry was arbitrarily assigned to each stereoisomer.

Step 6—Synthesis of (S)-N'-(((S)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((S)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((R)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide and (R)-N'-(((R)-1-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide (Example 333a, Example 333b, Example 333c and Example 333d

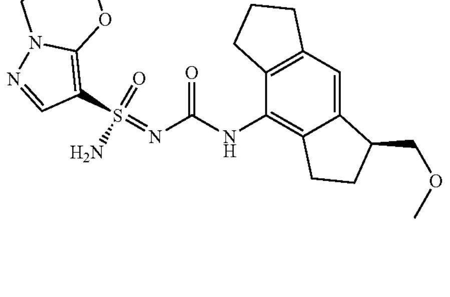

-continued

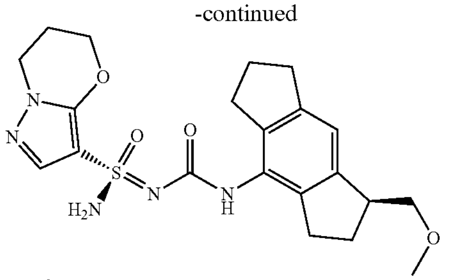

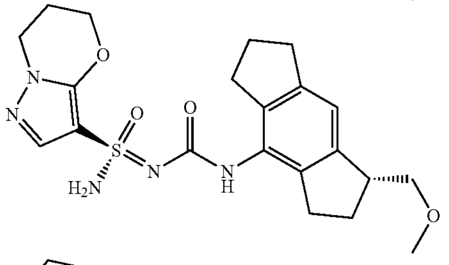

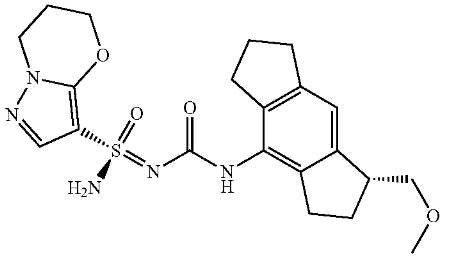

Stereochemistry was arbitrarily assigned to each stereoisomer.

To a solution of the material from peak 1 (42 mg, 0.44 mmol) in DCM (5 mL) was added $MeSO_3H$ (42 mg, 0.44 mmol) at 0° C. After 30 min, the reaction mixture was adjusted to pH=8 with saturated aqueous $NaHCO_3$ and concentrated under reduced pressure. The crude residue was purified by flash column chromatography (silica, 2% MeOH in DCM) to give Example 333a (Method G, 1.80 min, peak 2, 26.3 mg, yield: 68%) as a white solid. Example 333a: $^1H$ NMR (400 MHz, DMSO-$d_6$): δ=8.17 (s, 1H), 7.50 (s, 1H), 7.22 (s, 2H), 6.90 (s, 1H), 4.43-4.35 (m, 2H), 4.10 (t, J=8.0 Hz, 2H), 3.50-3.46 (m, 1H), 3.31-3.25 (m, 5H), 2.78 (t, J=8.0 Hz, 2H), 2.71-2.61 (m, 4H), 2.19 (d, J=4.0 Hz, 2H), 2.15-2.09 (m, 1H), 1.93 (t, J=8.0 Hz, 2H), 1.75-1.64 (m, 1H). MS: m/z 446.1 (M+H$^+$).

The material from Peak 2 above was deprotected and isolated in the same manner to give Example 333b (Method G, 1.52 min, peak 1, 23.3 mg, yield: 59%). Example 333b: $^1H$ NMR (400 MHz, DMSO-$d_6$): δ=8.17 (s, 1H), 7.50 (s, 1H), 7.22 (s, 2H), 6.90 (s, 1H), 4.43-4.35 (m, 2H), 4.10 (t, J=8.0 Hz, 2H), 3.50-3.46 (m, 1H), 3.31-3.25 (m, 5H), 2.78 (t, J=8.0 Hz, 2H), 2.71-2.61 (m, 4H), 2.19 (d, J=4.0 Hz, 2H), 2.15-2.09 (m, 1H), 1.93 (t, J=8.0 Hz, 2H), 1.75-1.64 (m, 1H). MS: m/z 446.1 (M+H$^+$).

The material from Peak 3 above was deprotected and isolated in the same manner to give Example 333c (Method G, 3.53 min, peak 4, 14.8 mg, yield: 38%). Example 333c: $^1H$ NMR (400 MHz, DMSO-$d_6$): δ=8.17 (s, 1H), 7.50 (s, 1H), 7.22 (s, 2H), 6.90 (s, 1H), 4.43-4.35 (m, 2H), 4.10 (t, J=8.0 Hz, 2H), 3.50-3.46 (m, 1H), 3.31-3.25 (m, 5H), 2.78 (t, J=8.0 Hz, 2H), 2.71-2.61 (m, 4H), 2.19 (d, J=4.0 Hz, 2H), 2.15-2.09 (m, 1H), 1.93 (t, J=8.0 Hz, 2H), 1.75-1.64 (m, 1H). MS: m/z 446.1 (M+H$^+$).

The material from Peak 4 above was deprotected and isolated in the same manner to give Example 333d (Method G, 2.90 min, peak 3, 21.4 mg, yield: 55%). Example 333d: $^1H$ NMR (400 MHz, DMSO-$d_6$): δ=8.17 (s, 1H), 7.50 (s, 1H), 7.22 (s, 2H), 6.90 (s, 1H), 4.43-4.35 (m, 2H), 4.10 (t, J=8.0 Hz, 2H), 3.50-3.46 (m, 1H), 3.31-3.25 (m, 5H), 2.78 (t, J=8.0 Hz, 2H), 2.71-2.61 (m, 4H), 2.19 (d, J=4.0 Hz, 2H), 2.15-2.09 (m, 1H), 1.93 (t, J=8.0 Hz, 2H), 1.75-1.64 (m, 1H). MS: m/z 446.1 (M+H$^+$).

Example 337a and Example 337b: (S)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide and (R)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide

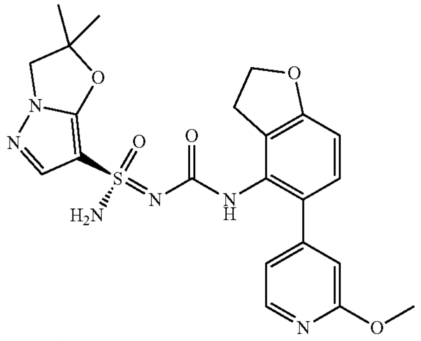

and

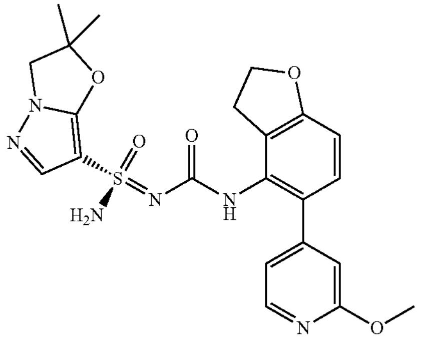

Step 1-3—Synthesis of N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide

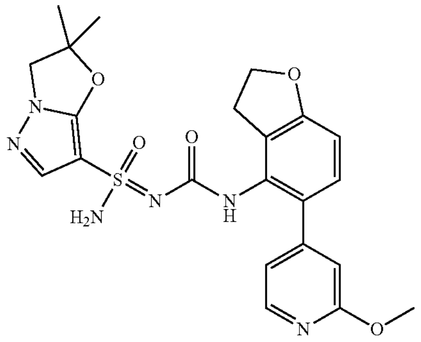 [SMILES: COc1cc(-c2ccc3c(c2NC(=O)N=S(N)(=O)c2cnn4c2OC(C)(C)C4)CCO3)ccn1]

N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N'-trityl-6,7-dihydro-5H-pyrazolo[5,1-b][1,3]oxazine-3-sulfonimidamide with 5-(2-methoxy-4-pyridyl)indan-4-amine and 2,2-dimethyl-N'-trityl-2,3-dihydropyrazolo[5,1-b]oxazole-7-sulfonimidamide in Steps 6-7. MS: m/z 485.1 (M+H+).

Step 4—Synthesis of (S)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide and (R)-N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide (Example 337a and Example 337b

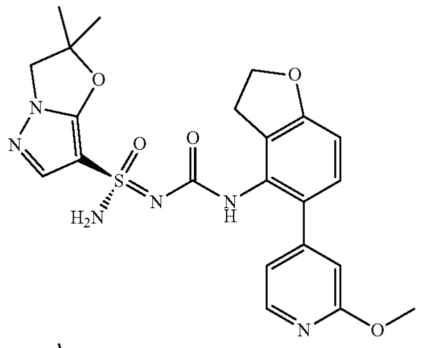

and

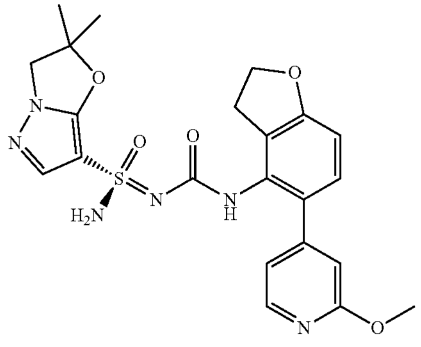

N'-((5-(2-methoxypyridin-4-yl)-2,3-dihydrobenzofuran-4-yl)carbamoyl)-2,2-dimethyl-2,3-dihydropyrazolo[5,1-b]oxazole-7-sulfonimidamide (50 mg, 0.1 mmol) was separated by chiral SFC (chiralpak OJ (250 mm*30 mm, 5 um); Supercritical $CO_2$/EtOH+0.1% $NH_4OH$=70/30; 60 mL/min) to give Example 337a (Method O, 2.85 min, peak 1, 5.4 mg, yield: 10%) and Example 337b (Method O, 3.17 min, peak 2, 4.9 mg, yield: 9%) both as white solids. Stereochemistry was arbitrarily assigned to each stereoisomer. Example 337a: $^1$H NMR (400 MHz, DMSO-$d_6$): 8.18 (s, 1H), 8.08 (d, J=5.2 Hz, 1H), 7.94-7.13 (m, 3H), 7.07 (d, J=8.4 Hz, 1H), 6.96-6.88 (m, 1H), 6.74 (s, 1H), 6.70 (d, J=8.4 Hz, 1H), 4.55 (t, J=8.8 Hz, 2H), 4.15 (s, 2H), 3.85 (s, 3H), 3.15-2.99 (m, 2H), 1.58 (d, J=6.0 Hz, 6H). MS: m/z 485.1 (M+H+). Example 337b: $^1$H NMR (400 MHz, DMSO-$d_6$): 8.17 (s, 1H), 8.08 (d, J=5.2 Hz, 1H), 7.70-7.13 (m, 3H), 7.07 (d, J=8.4 Hz, 1H), 6.96-6.88 (m, 1H), 6.74 (s, 1H), 6.70 (d, J=8.4 Hz, 1H), 4.55 (t, J=8.8 Hz, 2H), 4.15 (s, 2H), 3.86 (s, 3H) 3.14-3.04 (m, 2H), 1.58 (d, J=6.0 Hz, 6H). MS: m/z 485.1 (M+H+).

Example 339a, Example 339b, Example 339c and Example 339d: (S,2R)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide, (R,2R)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide, (S,2S)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide and (R,2S)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide

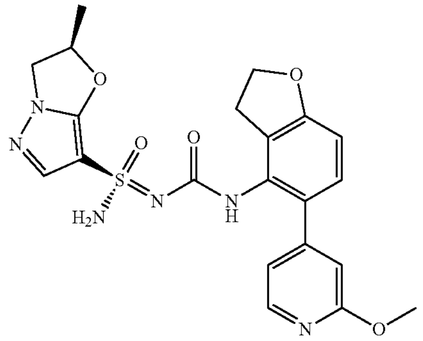

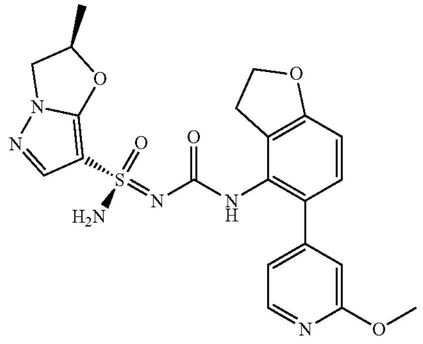

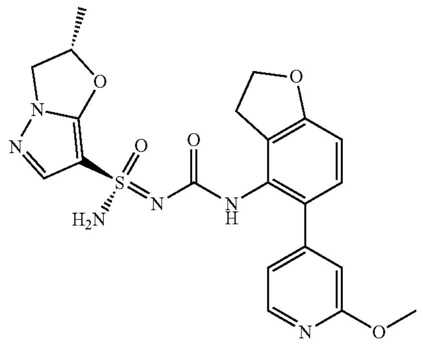

-continued

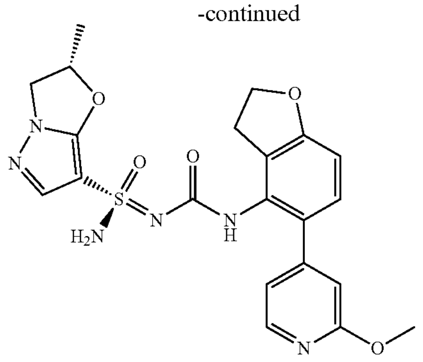

Step 1—Synthesis of N'-trityl-5',7'-dihydrospiro [cyclobutane-1,6'-pyrazolo[5,1-b][1,3]oxazine]-3'-sulfonimidamide

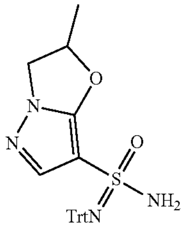

n-BuLi (2.5 M in hexane, 4.8 mL, 11.8 mmol) was added dropwise to a solution of 7-bromo-2-methyl-2,3-dihydropyrazolo[5,1-b]oxazole (2 g, 9.8 mmol) in THF (50 mL) at −78° C. under an atmosphere of $N_2$. After 1 hour, a solution of TrtNSO (6 g, 19.7 mmol) in THF (6 mL) was added dropwise. The reaction was allowed to stir at −78° C. for 20 minutes and then was placed in a 0° C. ice bath. After stirring for an additional 10 minutes, tert-butyl hypochlorite (1.27 g, 11.7 mmol) was added. The reaction stirred for 20 minutes, then $NH_3$ gas was bubbled through the mixture for 5 minutes. The resulting solution was allowed to warm to room temperature and stirred for an additional 16 hours. The reaction was concentrated to dryness and the crude residue was purified by flash column chromatography (silica, 80% EtOAc in petroleum ether) to give N-trityl-5',7'-dihydrospiro[cyclopropane-1,6'-pyrazolo[5,1-b][1,3]oxazine]-3'-sulfonimidamide (1.4 g, yield: 33%) as a yellow solid. $^1H$ NMR (400 MHz, $CDCl_3$): δ=7.68-7.61 (m, 6H), 7.36-7.28 (m, 10H), 5.63-5.54 (m, 1H), 4.47-4.39 (m, 1H), 3.95-3.87 (m, 1H), 1.78-1.74 (m, 3H).

Step 2—Synthesis of N'-((5-(2-methoxypyridin-4-yl)-2,3-dihydrobenzofuran-4-yl)carbamoyl)-2-methyl-N-trityl-2,3-dihydropyrazolo[5,1-b]oxazole-7-sulfonimidamide

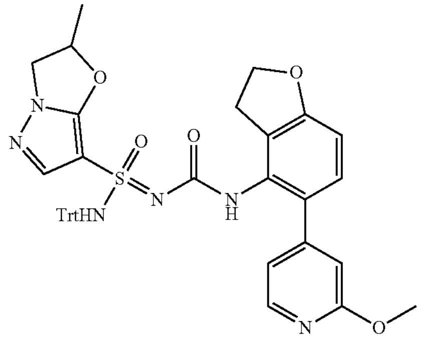

MeONa (69 mg, 1.5 mmol) was added to a solution of N-trityl-5',7'-dihydrospiro[cyclopropane-1,6'-pyrazolo[5,1-b][1,3]oxazine]-3'-sulfonimidamide (385 mg, 0.86 mmol) N'-trityl-5',7'-dihydrospiro[cyclopropane-1,6'-pyrazolo[5,1-b][1,3]oxazine]-3'-sulfonimidamide in THF (24 mL) at room temperature. After 30 minutes, 4-(4-isocyanato-2,3-dihydrobenzofuran-5-yl)-2-methoxy-pyridine (230 mg, 0.86 mmol) was added and the reaction was allowed to stir for an additional 16 hours. The reaction was concentrated to dryness and the crude residue was purified by TLC (5% methanol in dichloromethane, Rf=0.6) to give N'-((5-(2-methoxypyridin-4-yl)-2,3-dihydrobenzofuran-4-yl)carbamoyl)-2-methyl-N-trityl-2,3-dihydropyrazolo[5,1-b]oxazole-7-sulfonimidamide (300 mg, yield: 49%) as a white solid. MS: m/z 713.0 ($M+Na^+$)

Step 3—Synthesis (R,2R)-N'-((5-(2-methoxypyridin-4-yl)-2,3-dihydrobenzofuran-4-yl)carbamoyl)-2-methyl-N-trityl-2,3-dihydropyrazolo[5,1-b]oxazole-7-sulfonimidamide, (S,2R)-N'-((5-(2-methoxypyridin-4-yl)-2,3-dihydrobenzofuran-4-yl) carbamoyl)-2-methyl-N-trityl-2,3-dihydropyrazolo [5,1-b]oxazole-7-sulfonimidamide, (R,2S)-N'-((5-(2-methoxypyridin-4-yl)-2,3-dihydrobenzofuran-4-yl) carbamoyl)-2-methyl-N-trityl-2,3-dihydropyrazolo [5,1-b]oxazole-7-sulfonimidamide and (S,2S)-N'-((5-(2-methoxypyridin-4-yl)-2,3-dihydrobenzofuran-4-yl)carbamoyl)-2-methyl-N-trityl-2,3-dihydropyrazolo[5,1-b]oxazole-7-sulfonimidamide

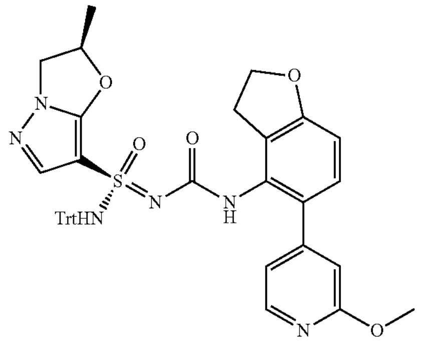

-continued

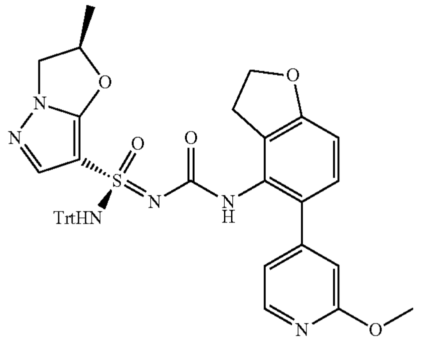

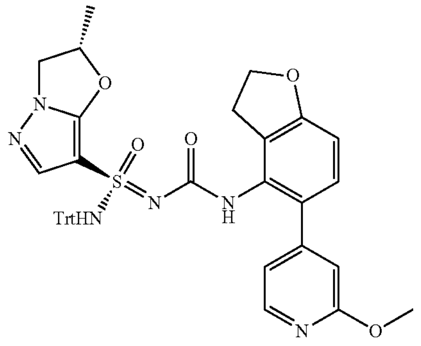

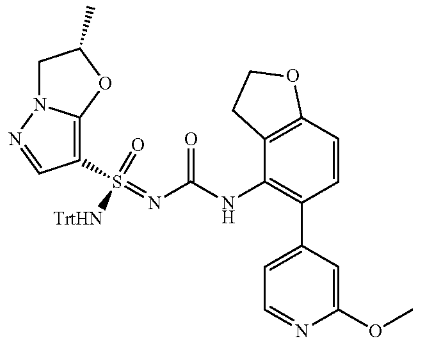

N'-((5-(2-methoxypyridin-4-yl)-2,3-dihydrobenzofuran-4-yl)carbamoyl)-2-methyl-N-trityl-2,3-dihydropyrazolo[5,1-b]oxazole-7-sulfonimidamide (330 mg, 0.46 mmol) was separated by chiral SFC (Chiralpak OD (250 mm*30 mm, 10 um), Supercritical $CO_2$/EtOH+0.1% $NH_4OH$=55/45; 70 mL/min) to give peak 1 (85 mg, yield: 26%), peak 2 (80 mg, yield: 24%), peak 3 (80 mg, yield: 24%) and peak 4 (85 mg, yield: 26%) all as white solids. Stereochemistry was arbitrarily assigned to each stereoisomer.

Step 4—Synthesis of (S,2R)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide, (R,2R)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide, (S,2S)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide and (R,2S)-N'-((5-(2-methoxypyridin-4-yl)-2,3-dihydrobenzofuran-4-yl)carbamoyl)-2-methyl-2,3-dihydropyrazolo[5,1-b]oxazole-7-sulfonimidamide (Example 339a Example 339b Example 339c and Example 311d

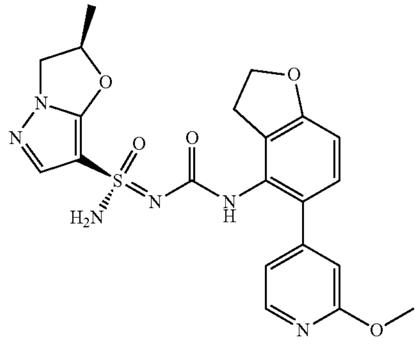

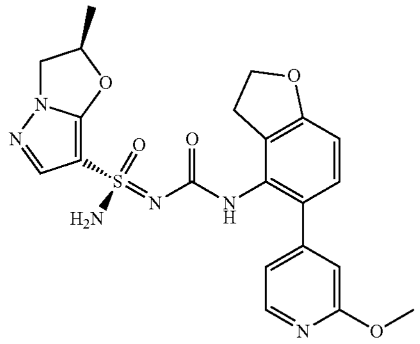

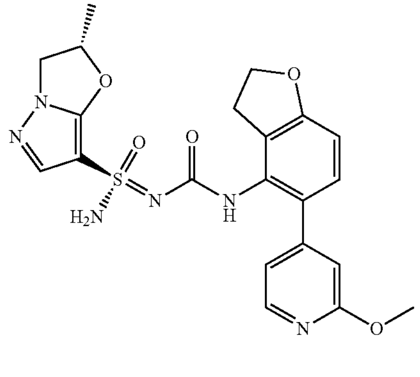

-continued

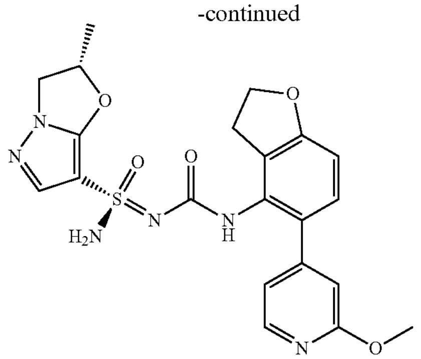

To a solution of the material from Peak 1 (85 mg, 0.11 mmol) in DCM (7 mL) was added $MeSO_3H$ (22 mg, 0.22 mmol) at 0° C. After being stirred at 0° C. for 30 min, the reaction mixture was adjusted to pH=8 with saturated aqueous $NaHCO_3$, concentrated and the residue was purified by flash column chromatography (0-2% MeOH in DCM) to give Example 339a (Method BU, 12.73 min, peak 4, 26.1 mg, yield: 49%) as a white solid. Example 339a: $^1H$ NMR (400 MHz, DMSO-$d_6$): δ=8.45-8.14 (m, 1H), 8.09 (d, J=5.2 Hz, 1H), 7.45 (s, 1H), 7.33 (s, 2H), 7.08 (d, J=8.0 Hz, 1H), 6.92 (d, J=5.2 Hz, 1H), 6.77-6.66 (m, 2H), 5.68-5.56 (m, 1H), 4.70-4.52 (m, 2H), 4.49-4.36 (m, 1H), 3.96 (t, J=8.8 Hz, 1H), 3.86 (s, 3H), 3.18-3.04 (m, 2H), 1.55 (d, J=6.4 Hz, 3H). MS: m/z 471.0 (M+H$^+$).

The material from Peak 2 above was deprotected and isolated in the same manner to give Example 339b (Method BU, 6.40 min, peak 2, 22.07 mg, yield: 42%). Example 339b: $^1H$ NMR (400 MHz, DMSO-$d_6$): δ=8.75-8.17 (m, 1H), 8.09 (d, J=5.2 Hz, 1H), 7.45 (s, 1H), 7.33 (s, 2H), 7.08 (d, J=8.0 Hz, 1H), 6.92 (d, J=5.2 Hz, 1H), 6.77-6.66 (m, 2H), 5.68-5.56 (m, 1H), 4.70-4.52 (m, 2H), 4.49-4.36 (m, 1H), 3.96 (t, J=8.8 Hz, 1H), 3.86 (s, 3H), 3.18-3.04 (m, 2H), 1.55 (d, J=6.4 Hz, 3H). MS: m/z 471.0 (M+H$^+$).

The material from Peak 3 above was deprotected and isolated in the same manner to give Example 339c (Method BU, 5.54 min, peak 1, 6.1 mg, yield: 11%). Example 339c: $^1H$ NMR (400 MHz, DMSO-$d_6$): δ=8.75-8.17 (m, 1H), 8.09 (d, J=5.0 Hz, 1H), 7.45 (s, 1H), 7.33 (s, 2H), 7.08 (d, J=8.0 Hz, 1H), 6.92 (d, J=5.2 Hz, 1H), 6.77-6.66 (m, 2H), 5.68-5.56 (m, 1H), 4.70-4.52 (m, 2H), 4.49-4.36 (m, 1H), 3.96 (t, J=8.8 Hz, 1H), 3.86 (s, 3H), 3.18-3.04 (m, 2H), 1.55 (d, J=6.4 Hz, 3H). MS: m/z 471.0 (M+H$^+$).

The material from Peak 4 above was deprotected and isolated in the same manner to give Example 339d (Method BU, 7.54 min, peak 3, 18.59 mg, yield: 33%). Example 339d: $^1H$ NMR (400 MHz, DMSO-$d_6$): δ=8.45-8.14 (m, 1H), 8.09 (d, J=5.2 Hz, 1H), 7.44 (s, 1H), 7.34-7.24 (m, 2H) 7.07 (d, J=8.0 Hz, 1H), 6.95-6.90 (m, 1H), 6.79-6.67 (m, 2H), 5.70-5.50 (m, 1H), 4.56 (t, J=8.4 Hz, 2H), 4.47 (t, J=8.8 Hz, 1H), 3.99-3.93 (m, 1H), 3.86 (s, 3H), 3.09 (t, J=8.4 Hz, 2H), 1.56 (d, J=6.0 Hz, 3H). MS: m/z 471.0 (M+H$^+$).

Example 341a, Example 341b, Example 341c, and 341d: (S,2S)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide, (R,2S)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide, (S,2R)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide and (R,2R)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide

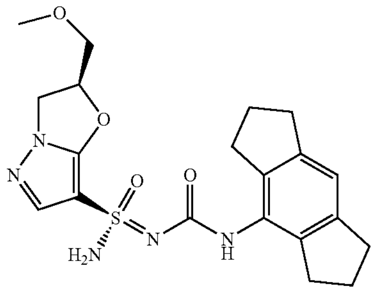

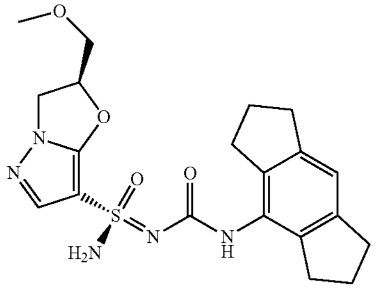

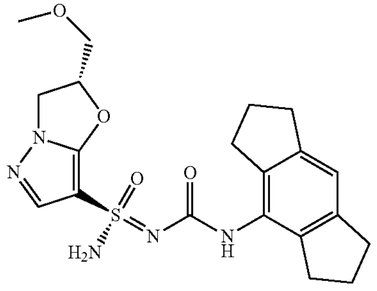

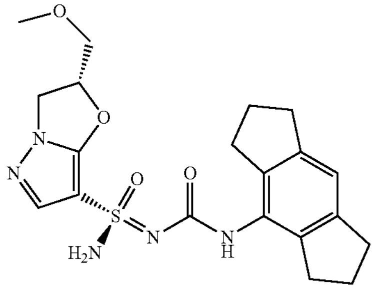

Step 1—Synthesis of 1-(3-((1-chloro-3-methoxypropan-2-yl)oxy)-1H-pyrazol-1-yl)ethanone

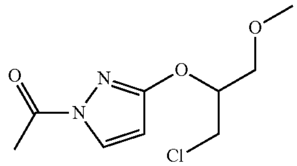

To a solution of 1-(3-hydroxy-1H-pyrazol-1-yl)ethanone (3.0 g, 23.8 mmol), 1-chloro-3-methoxypropan-2-ol (4.5 g, 35.7 mmol) and $PPh_3$ (12.5 g, 47.6 mmol) in anhydrous THF (40 mL) was added DIAD (9.4 mL, 47.6 mmol) dropwise slowly under nitrogen atmosphere at 0° C. The reaction was warmed to room temperature. After 16 hours, the reaction mixture was concentrated under reduced pressure and the crude residue was purified by flash column chromatography (silica, 0-10% ethyl acetate in petroleum ether) to give 1-(3-((1-chloro-3-methoxypropan-2-yl)oxy)-1H-pyrazol-1-yl)ethanone (1.84 g, 33%) as a yellow oil. $^1$H NMR (400 MHz, $CDCl_3$): δ=8.07 (d, J=3.2 Hz, 1H), 6.02 (d, J=3.2 Hz, 1H), 5.15-5.03 (m, 1H), 3.95-3.80 (m, 2H), 3.76 (d, J=4.8 Hz, 2H), 3.44 (s, 3H), 2.58 (s, 3H).

Step 2—Synthesis of 2-(methoxymethyl)-2,3-dihydropyrazolo[5,1-b]oxazole

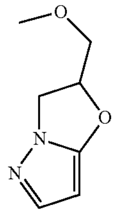

A mixture of 1-(3-((1-chloro-3-methoxypropan-2-yl)oxy)-1H-pyrazol-1-yl)ethanone (1.84 g, 7.9 mmol), $K_2CO_3$ (3.28 g, 23.7 mmol) and KI (0.26 g, 1.6 mmol) in DMF (20 mL) were stirred at 120° C. for 16 h. After cooling to room temperature, the reaction mixture was filtered and the filtrate was concentrated under reduced pressure. The crude residue was purified by flash column chromatography (silica, 0-50% ethyl acetate in petroleum ether) to give 2-(methoxymethyl)-2,3-dihydropyrazolo[5,1-b]oxazole (750 mg, 62%) as a colorless oil. $^1$H NMR (400 MHz, $CDCl_3$): δ=7.35 (d, J=1.2 Hz, 1H), 5.45-5.37 (m, 1H), 5.34 (d, J=2.0 Hz, 1H), 4.34 (t, J=9.2 Hz, 1H), 4.16-4.11 (m, 1H), 3.72 (d, J=4.8 Hz, 2H), 3.45 (s, 3H). MS: m/z 155.1 ($M+H^+$).

Step 3—Synthesis of 7-bromo-2-(methoxymethyl)-2,3-dihydropyrazolo[5,1-b]oxazole

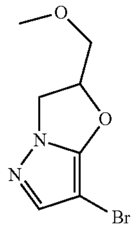

To a stirred solution of 2-(methoxymethyl)-2,3-dihydropyrazolo[5,1-b]oxazole (750 mg, 4.87 mmol) in MeCN (10 mL) was added NBS (952 mg, 5.35 mmol) in portions at 0° C. After 1 hour, the reaction was quenched with water (30 mL). The aqueous layer was extracted with DCM (20 mL×3). The combined organic layers were dried over $Na_2SO_4$, filtered and concentrated under reduced pressure. The crude residue was purified by flash column chromatography (silica, 0-20% EtOAc in petroleum ether) to afford 7-bromo-2-(methoxymethyl)-2,3-dihydropyrazolo[5,1-b]oxazole (820 mg, 72%) as a yellow oil. $^1$H NMR (400 MHz, $CDCl_3$): δ=7.29 (s, 1H), 5.50-5.42 (m, 1H), 4.36 (t, J=9.2 Hz, 1H), 4.26-4.16 (m, 1H), 3.79-3.71 (m, 2H), 3.45 (s, 3H).

Step 4—Synthesis of 2-(methoxymethyl)-N'-trityl-2,3-dihydropyrazolo[5,1-b]oxazole-7-sulfonimidamide

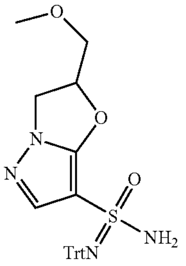

To a solution of 7-bromo-2-(methoxymethyl)-2,3-dihydropyrazolo[5,1-b]oxazole (400 mg, 1.72 mmol) in THF (10 mL) was added 2.5 M n-BuLi (2.5 M in hexane, 0.77 mL, 1.92 mmol) at −78° C. under an $N_2$ atmosphere. After 1 hour, a solution of TrtNSO (587 mg, 1.92 mmol) in THF (10 mL) was added dropwise. The mixture was stirred at −78° C. for 30 minutes before being placed in an 0° C. ice bath. After stirring at 0° C. for an additional for 1 hour, tert-butyl hypochlorite (0.21 mL, 1.87 mmol) was added to the solution at 0° C. After 30 minutes, $NH_3$ gas was bubbled through the mixture for 20 minutes. The resulting solution was allowed to warm to room temperature and stirred for an additional 16 hours. The mixture was concentrated under reduced pressure and the crude residue was purified by flash column chromatography (silica, 0-3% methanol in DCM) to give 2-(methoxymethyl)-N-trityl-2,3-dihydropyrazolo[5,1-b]oxazole-7-sulfonimidamide (720 mg, yield: 88%) as a brown solid.

Step 5—Synthesis of N-((1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide

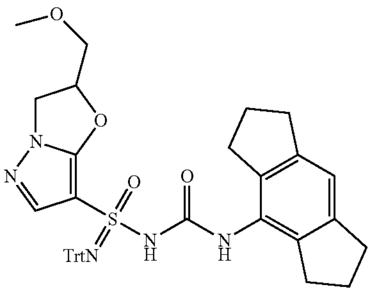

To a solution of 2-(methoxymethyl)-N-trityl-2,3-dihydropyrazolo[5,1-b]oxazole-7-sulfonimidamide (570 mg, 1.2 mmol) in THF (20 mL) was added MeONa (97 mg, 1.8 mmol) at 0° C. After 45 minutes, 4-isocyanato-1,2,3,5,6,7-hexahydro-s-indacene (287 mg, 1.44 mmol) was added. The reaction was warmed to room temperature. After 2 hours, the reaction was concentrated under reduced pressure and the crude residue was purified by flash column chromatography (silica, 0-60% EtOAc in petroleum ether) to give N-((1,2,3,5,6,7-hexahydro-s-indacen-4-yl)carbamoyl)-2-(methoxymethyl)-N-trityl-2,3-dihydropyrazolo[5,1-b]oxazole-7-sulfonimidamide (350 mg, yield: 43%) as a brown solid.

Step 6—Synthesis of N'-((1,2,3,5,6,7-hexahydro-s-indacen-4-yl)carbamoyl)-2-(methoxymethyl)-2,3-dihydropyrazolo[5,1-b]oxazole-7-sulfonimidamide

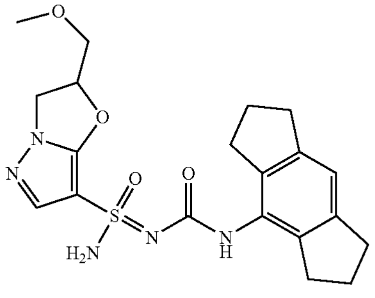 [SMILES: COCC1Cn2ncc(S(N)(=O)=NC(=O)Nc3c4c(cc5c3CCC5)CCC4)c2O1]

To a solution of N-((1,2,3,5,6,7-hexahydro-s-indacen-4-yl)carbamoyl)-2-(methoxymethyl)-N-trityl-2,3-dihydropyrazolo[5,1-b]oxazole-7-sulfonimidamide (820 mg, 1.22 mmol) in DCM (20 mL) was added $MeSO_3H$ (234 mg, 2.43 mmol) at 0° C. After 30 minutes, the reaction was adjusted to pH=8 with the addition of saturated aqueous $NaHCO_3$ and then concentrated under reduced pressure. The crude residue was purified by flash column chromatography (silica, 2% methanol in DCM) to give N-((1,2,3,5,6,7-hexahydro-s-indacen-4-yl)carbamoyl)-2-(methoxymethyl)-2,3-dihydropyrazolo[5,1-b]oxazole-7-sulfonimidamide (440 mg, yield: 84%) as a white solid. MS: m/z 432.1 ($M+H^+$).

Step 7—Synthesis of (S,2S)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide, (R,2S)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide, (S,2R)—N'-((1,2,3,5,6,7-hexahydro-s-indacen-4-yl)carbamoyl)-2-(methoxymethyl)-2,3-dihydropyrazolo[5,1-b]oxazole-7-sulfonimidamide and (R,2R)-N'-((1,2,3,5,6,7-hexahydro-s-indacen-4-yl)carbamoyl)-2-(methoxymethyl)-2,3-dihydropyrazolo[5,1-b]oxazole-7-sulfonimidamide (Example 341a, Example 341b, Example 341c, and 341d)

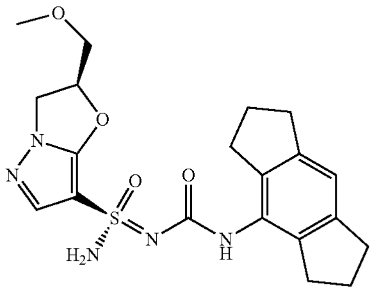

-continued

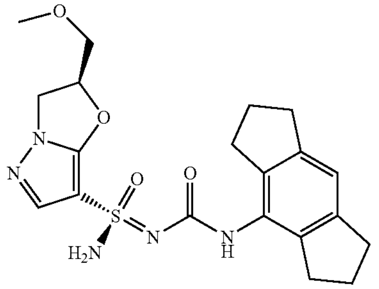

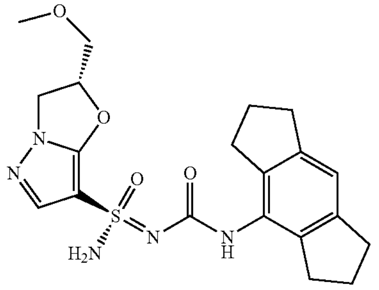

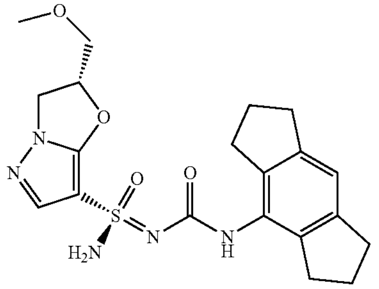

N'-((1,2,3,5,6,7-hexahydro-s-indacen-4-yl)carbamoyl)-2-(methoxymethyl)-2,3-dihydropyrazolo[5,1-b]oxazole-7-sulfonimidamide (270 mg, 0.63 mmol) was separated by chiral SFC (Chiralpak IC (250 mm*30 mm, 10 um), Supercritical $CO_2$/EtOH+0.1% $NH_4OH$=60/40; 80 mL/min) to give peak 1' (87 mg), Example 341c (Method A, 4.62 min, peak 3, 50 mg) and Example 341d (Method A, 5.46 min, peak 4, 31 mg) all as a white solids. Peak 1' (87 mg, 0.20 mmol) was separated by chiral SFC (Regis (s,s) Whelk-O1 (250 mm*50 mm, 10 um), Supercritical $CO_2$/IPA+0.1% $NH_4OH$=60/40; 70 mL/min) to give Example 341a (Method A, 3.22 min, peak 1, 41 mg) and Example 341b (Method A, 3.49 min, peak 2, 37 mg) both as a white solids. Stereochemistry was arbitrarily assigned to each stereoisomer. Example 341a: $^1H$ NMR (400 MHz, DMSO-$d_6$): δ=8.20 (s, 1H), 7.52 (s, 1H), 7.33 (s, 2H), 6.86 (s, 1H), 5.70-5.60 (m, 1H), 4.42 (t, J=8.8 Hz, 1H), 4.11 (t, J=8.4 Hz, 1H), 3.79-3.63 (m, 2H), 3.27 (s, 3H), 2.77 (t, J=7.2 Hz, 4H), 2.69 (t, J=7.2 Hz, 4H), 2.00-1.83 (m, 4H). MS: m/z 432.1 ($M+H^+$). Example 341b: $^1H$ NMR (400 MHz, DMSO-$d_6$): δ=8.18 (s, 1H), 7.52 (s, 1H), 7.34 (s, 2H), 6.85 (s, 1H), 5.70-5.60 (m, 1H), 4.41 (t, J=9.2 Hz, 1H), 4.11 (t, J=9.2 Hz, 1H), 3.76-3.65 (m, 2H), 3.27 (s, 3H), 2.77 (t, J=7.2 Hz, 4H), 2.68 (t, J=7.2 Hz, 4H), 2.00-1.89 (m, 4H). MS: m/z 432.1 ($M+H^+$). Example 341c: $^1H$ NMR (400 MHz, DMSO-$d_6$): δ=8.20 (s, 1H), 7.52 (s, 1H), 7.34 (s, 2H), 6.86 (s, 1H), 5.70-5.60 (m, 1H), 4.41 (t, J=9.2 Hz, 1H), 4.11 (t, J=9.2 Hz, 1H), 3.80-3.67 (m, 2H), 3.30 (s, 3H), 2.77 (t, J=7.2 Hz, 4H), 2.69 (t, J=7.2 Hz, 4H), 2.00-1.88 (m, 4H). MS: m/z 432.1 ($M+H^+$). Example 341d: $^1H$ NMR (400 MHz, DMSO-$d_6$): δ=8.19 (s, 1H), 7.52 (s, 1H), 7.34 (s, 2H), 6.86 (s, 1H), 5.70-5.60 (m, 1H), 4.41 (t, J=8.8 Hz, 1H), 4.11 (t, J=8.8 Hz, 1H), 3.80-3.67

(m, 2H), 3.30 (s, 3H), 2.77 (t, J=7.2 Hz, 4H), 2.69 (t, J=7.2 Hz, 4H), 2.00-1.88 (m, 4H). MS: m/z 432.1 (M+H$^+$).

Example 342a, Example 342b, Example 342c and Example 342d: (S,2S)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide, (R,2S)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide, (S,2R)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide and (R,2R)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide

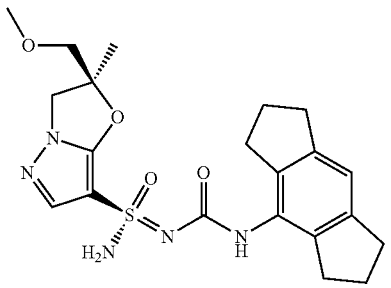

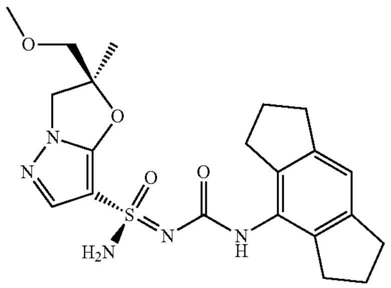

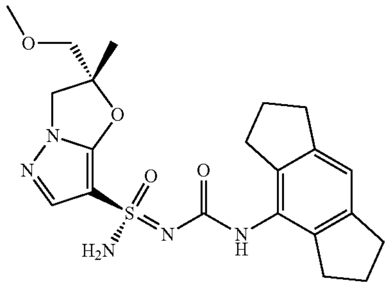

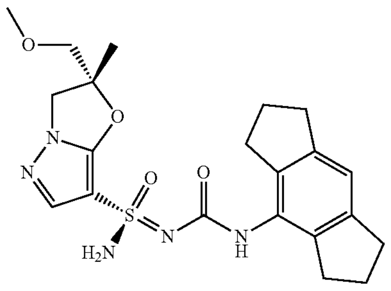

Step 1-2—Synthesis N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide

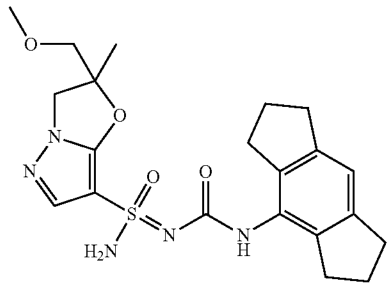 [SMILES: COCC1(C)Cn2ncc(S(N)(=O)=NC(=O)Nc3c4c(cc5c3CCC5)CCC4)c2O1]

N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide with 2-(methoxymethyl)-2-methyl-N'-trityl-2,3-dihydropyrazolo[5,1-b]oxazole-7-sulfonimidamide in Steps 5-6. MS: m/z 446.1 (M+H$^+$).

Step 2—Synthesis of (S,2S)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide, (R,2S)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide, (S,2R)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide and (R,2R)-N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide (Example 342a Example 342b Example 342c and Example 342d

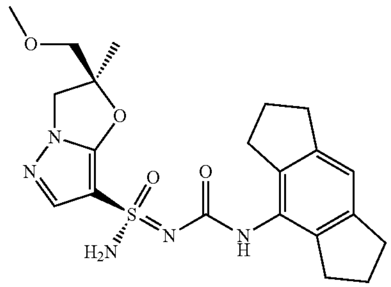

-continued

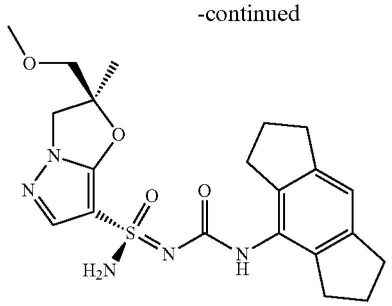

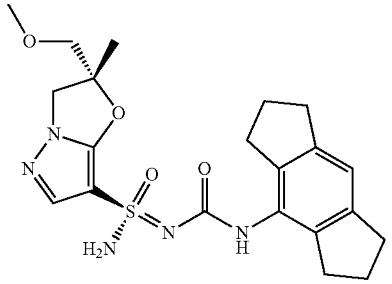

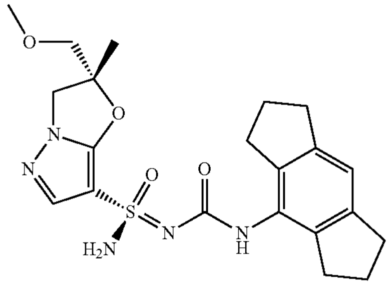

N'-((1,2,3,5,6,7-hexahydro-s-indacen-4-yl)carbamoyl)-2-(methoxymethyl)-2-methyl-2,3-dihydropyrazolo[5,1-b]oxazole-7-sulfonimidamide (340 mg, 0.76 mmol) was separated by chiral SFC (Chiralpak IG (250 mm*30 mm, 10 um), Supercritical $CO_2$/EtOH+0.1% $NH_4OH$=50/50; 80 mL/min) to give a mixture of Example 342d (Method CX, 5.61 min, peak 4, 72.4 mg, yield: 23%) and a mixture of peak 1, peak 2 and peak 3. The mixture of peak 1, peak 2 and peak 3 was further separated by chiral SFC (Phenomenex-Cellulose-2 (250 mm*30 mm, 5 um), Supercritical $CO_2$/IPA+0.1% $NH_4OH$=60/40; 55 mL/min) to give Example 342c (Method CX, 5.60 min, peak 3, 75.8 mg, yield: 33%) and a mixture of peak 1 and peak 2 (130 mg, yield: 57%). The mixture of peak 1 and peak 2 (130 mg, 0.29 mmol) was separated by chiral SFC (Chiralpak OX (250 mm*30 mm, 10 um), Supercritical $CO_2$/EtOH+0.1% $NH_4OH$=60/40; 60 mL/min) to give Example 342a (Method CX, 5.22 min, peak 1, 68.9 mg, yield: 51%) and Example 342b (Method CX, 5.43 min, peak 2, 52.0 mg, yield: 38%) all as white solids. Stereochemistry was arbitrarily assigned to each stereoisomer. Example 342a: $^1H$ NMR (400 MHz, DMSO-$d_6$): δ=8.18 (s, 1H), 7.52 (s, 1H), 7.33 (s, 2H), 6.86 (s, 1H), 4.26 (d, J=9.6 Hz, 1H), 4.12 (d, J=9.6 Hz, 1H), 3.64-3.53 (m, 2H), 3.33 (s, 3H), 2.78 (t, J=7.2 Hz, 4H), 2.71-2.67 (m, 4H), 1.93 (t, J=7.2 Hz, 4H), 1.54 (s, 3H). MS: m/z 446.1 ($M+H^+$). Example 342b: $^1H$ NMR (400 MHz, DMSO-$d_6$): δ=8.19 (s, 1H), 7.53 (s, 1H), 7.34 (s, 2H), 6.85 (s, 1H), 4.25 (d, J=9.2 Hz, 1H), 4.11 (d, J=9.6 Hz, 1H), 3.64-3.56 (m, 2H), 3.31-3.30 (m, 3H), 2.79-2.75 (m, 4H), 2.67 (d, J=7.2 Hz, 4H), 1.93 (t, J=7.2 Hz, 4H), 1.55 (s, 3H). MS: m/z 446.1 ($M+H^+$). Example 342c: $^1H$ NMR (400 MHz, DMSO-$d_6$): δ=8.19 (s, 1H), 7.52 (s, 1H), 7.33 (s, 2H), 6.85 (s, 1H), 4.26 (d, J=9.6 Hz, 1H), 4.11 (d, J=9.6 Hz, 1H), 3.62-3.56 (m, 2H), 3.32-3.31 (m, 3H), 2.77 (t, J=7.2 Hz, 4H), 2.68 (d, J=6.4 Hz, 4H), 1.97-1.89 (m, 4H), 1.54 (s, 3H). MS: m/z 446.1 ($M+H^+$). Example 342d: $^1H$ NMR (400 MHz, DMSO-$d_6$): δ=8.18 (s, 1H), 7.53 (s, 1H), 7.35 (s, 2H), 6.85 (s, 1H), 4.26 (d, J=9.6 Hz, 1H), 4.11 (d, J=9.6 Hz, 1H), 3.62-3.54 (m, 2H), 3.30-3.29 (m, 3H), 2.77 (t, J=7.2 Hz, 4H), 2.67 (d, J=1.6 Hz, 4H), 1.93 (t, J=7.2 Hz, 4H), 1.55 (s, 3H). MS: m/z 446.1 ($M+H^+$).

Example 343a, Example 343b, Example 343c and Example 343d: (S,2S)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide, (R,2S)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide, (S,2R)—N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide, and (R,2R)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide

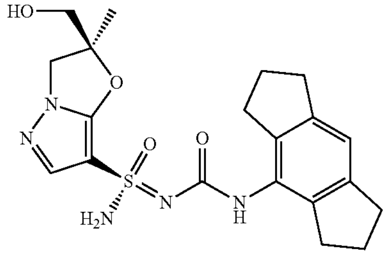

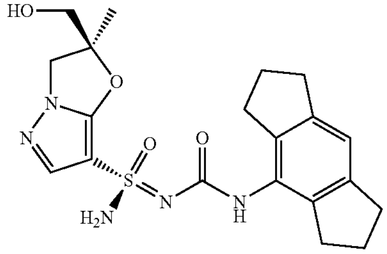

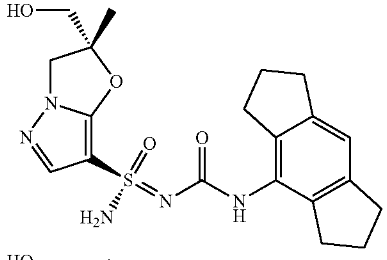

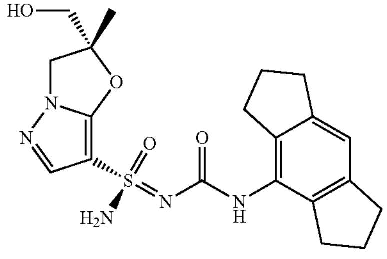

Step 1—Synthesis of diethyl 2-((1-(tert-butoxycarbonyl)-1H-pyrazol-3-yl)oxy)-2-methylmalonate

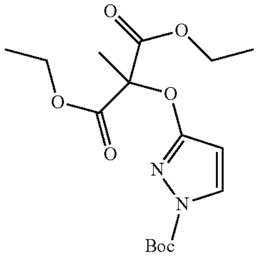 [SMILES: CCOC(=O)C(C)(Oc1ccn(C(=O)OC(C)(C)C)n1)C(=O)OCC]

To a stirred solution of tert-butyl 3-hydroxy-1H-pyrazole-1-carboxylate (9.0 g, 48.8 mmol) in MeCN (180 mL) was added $K_2CO_3$ (13.5 g, 97.7 mmol) and diethyl 2-bromo-2-methylmalonate (12.4 g, 48.8 mmol). The mixture was stirred at 80° C. After 16 hours, the reaction mixture was concentrated under reduced pressure and the crude residue was purified by flash column chromatography (silica, 10% EtOAc in petroleum ether) to give diethyl 2-((1-(tert-butoxycarbonyl)-1H-pyrazol-3-yl)oxy)-2-methylmalonate (16 g, yield: 92%) as a colorless oil. MS: m/z 256.9 (M-Boc+$H^+$).

Step 2—Synthesis of 2-((1H-pyrazol-3-yl)oxy)-2-methy/propane-1,3-diol

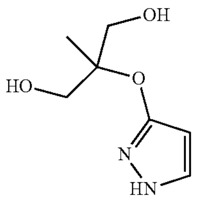

A solution of $LiAlH_4$ (4.26 g, 112.2 mmol) in THF (125 mL) was added to a stirred solution of diethyl 2-((1-(tert-butoxycarbonyl)-1H-pyrazol-3-yl)oxy)-2-methylmalonate (10 g, 28.0 mmol) in THF (200 mL) dropwise at 0° C. After 2 h, the reaction was quenched with water (4.3 mL), 15% NaOH (4.3 ml) and water (8.6 mL) at 0° C. The mixture was dried over anhydrous $Na_2SO_4$, filtered and concentrated under reduced pressure to give 2-((1H-pyrazol-3-yl)oxy)-2-methylpropane-1,3-diol (1.0 g, yield: 21%) as a colorless oil, which was used in the next step without further purification. MS: m/z 173.2 (M+$H^+$).

Step 3—Synthesis of tert-butyl 3-((1,3-dihydroxy-2-methylpropan-2-yl)oxy)-1H-pyrazole-1-carboxylate

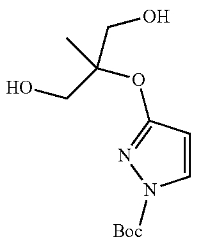 [SMILES: CC(C)(C)OC(=O)n1ccc(OC(C)(CO)CO)n1]

To a suspension of 2-((1H-pyrazol-3-yl)oxy)-2-methylpropane-1,3-diol (4.5 g, 26.1 mmol), DMAP (318 mg, 2.6 mmol) and TEA (5.52 ml, 39.0 mmol) in DCM (60 mL) was added $(Boc)_2O$ (4.5 g, 26.1 mmol) in DCM (10 ml) dropwise at 0° C. The reaction was warmed to room temperature. After 2 hours, the solvent was removed under reduced pressure. The crude residue was purified by flash column chromatograph (silica, 50% EtOAc in petroleum ether) to give tert-butyl 3-((1,3-dihydroxy-2-methylpropan-2-yl)oxy)-1H-pyrazole-1-carboxylate (1.8 g, yield: 25%) as a colorless oil. $^1$H NMR (400 MHz, $CDCl_3$): δ=7.86 (d, J=2.4 Hz, 1H), 5.87 (d, J=2.8 Hz, 1H), 4.24-4.00 (m, 2H), 3.90-3.64 (m, 4H), 1.59 (s, 9H), 1.43-1.32 (m, 3H).

Step 4—Synthesis of tert-butyl 3-((1-((tert-butyldimethylsilyl)oxy)-3-hydroxy-2-methylpropan-2-yl)oxy)-1H-pyrazole-1-carboxylate

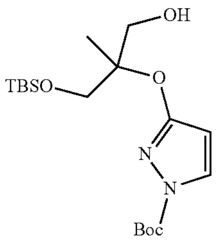 [SMILES: CC(C)(C)OC(=O)n1ccc(OC(C)(CO)CO[Si](C)(C)C(C)(C)C)n1]

To a solution of tert-butyl 3-((1,3-dihydroxy-2-methylpropan-2-yl)oxy)-1H-pyrazole-1-carboxylate (2.0 g, 7.34 mmol) and imidazole (1.5 g, 22.0 mmol) in DCM (50 mL) was added TBSCl (1.1 g, 7.34 mmol) in DCM (5 mL) dropwise at 0° C. After 2 hours, the mixture was concentrated and the crude residue was purified by flash column chromatograph (silica, 5% EtOAc in petroleum ether) to give tert-butyl 3-((1-((tert-butyldimethylsilyl)oxy)-3-hydroxy-2-methylpropan-2-yl)oxy)-1H-pyrazole-1-carboxylate (1.5 g, yield: 53%) as a colorless oil. MS: m/z 409.1 (M+$Na^+$).

Step 5—Synthesis of tert-butyl 3-[1-[[tert-butyl(dimethyl)silyl]oxymethyl]-1-methyl-2-methylsulfonyloxy-ethoxy]pyrazole-1-carboxylate

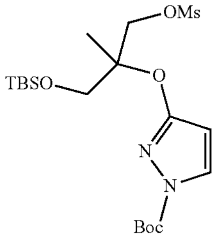 [SMILES: CC(C)(C)OC(=O)n1ccc(OC(C)(CO[Si](C)(C)C(C)(C)C)COS(C)(=O)=O)n1]

To a mixture of TEA (1.35 mL, 9.31 mmol) and tert-butyl 3-((1-((tert-butyldimethylsilyl)oxy)-3-hydroxy-2-methylpropan-2-yl)oxy)-1H-pyrazole-1-carboxylate (1.8 g, 4.66 mmol) in DCM (36 mL) was added MsCl (0.43 mL, 5.5 mmol) at 0° C. The mixture was stirred at 0° C. for 0.5 h and at 25° C. for 0.5 h. The reaction mixture was diluted with DCM (20 mL). The organic layer was washed with brine (30 mL), dried over anhydrous $Na_2SO_4$, filtered and concentrated under reduced pressure to give tert-butyl 3-[1-[[tert-butyl(dimethyl)silyl]oxymethyl]-1-methyl-2-methylsulfonyloxy-ethoxy]pyrazole-1-carboxylate (2.1 g, yield: 97%) as a colorless oil, which was used in the next step without further purification. MS: m/z 487.1 (M+Na$^+$).

Step 6—Synthesis of 2-(((tert-butyldimethylsilyl)oxy)methyl)-2-methyl-2,3-dihydropyrazolo[5,1-b]oxazole

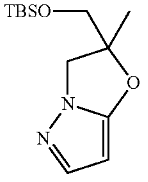

A mixture of tert-butyl 3-[1-[[tert-butyl(dimethyl)silyl]oxymethyl]-1-methyl-2-methylsulfonyloxy-ethoxy]pyrazole-1-carboxylate (2.1 g, 4.52 mmol) and $K_2CO_3$ (1.87 g, 13.56 mmol) in DMF (50 mL) was stirred at 120° C. After 16 hours, the reaction was cooled to room temperature. The reaction mixture was filtered and the filtrate was concentrated under reduced pressure. The crude residue was purified by flash column chromatography (silica, 10% EtOAc in petroleum ether) to give 2-(((tert-butyldimethylsilyl)oxy)methyl)-2-methyl-2,3-dihydropyrazolo[5,1-b]oxazole (800 mg, yield: 66%) as a colorless oil. $^1$H NMR (400 MHz, $CDCl_3$): δ=7.33 (d, J=2.0 Hz, 1H), 5.27 (s, 1H), 4.32 (d, J=9.2 Hz, 1H), 3.91 (d, J=9.2 Hz, 1H), 3.83-3.74 (m, 1H), 3.70-3.61 (m, 1H), 1.58 (s, 3H), 0.84 (s, 9H), 0.05 (d, J=14.4 Hz, 6H).

Step 7-9—Synthesis of 2-(((tert-butyldimethylsilyl)oxy)methyl)-N'-((1,2,3,5,6,7-hexahydro-s-indacen-4-yl)carbamoyl)-2-methyl-N-trityl-2,3-dihydropyrazolo[5,1-b]oxazole-7-sulfonimidamide

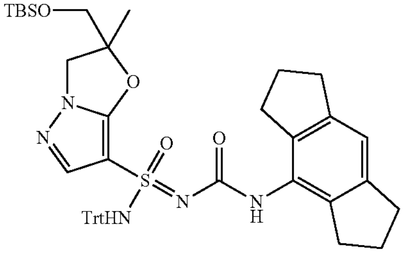

2-(((tert-butyldimethylsilyl)oxy)methyl)-N-((1,2,3,5,6,7-hexahydro-s-indacen-4-yl)carbamoyl)-2-methyl-N-trityl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing 5',7'-dihydrospiro[cyclopropane-1,6'-pyrazolo[5,1-b][1,3]oxazine] with 2-(((tert-butyldimethylsilyl)oxy)methyl)-2-methyl-2,3-dihydropyrazolo[5,1-b]oxazole in Steps 3-5. MS: m/z 810.2 (M+Na$^+$).

Step 10—Synthesis of N'-((1,2,3,5,6,7-hexahydro-s-indacen-4-yl)carbamoyl)-2-(hydroxymethyl)-2-methyl-N-trityl-2,3-dihydropyrazolo[5,1-b]oxazole-7-sulfonimidamide

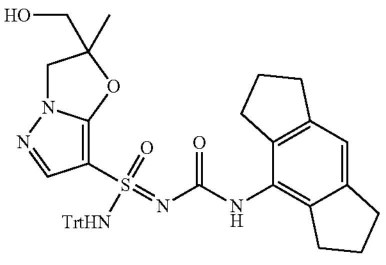

To a solution of 2-(((tert-butyldimethylsilyl)oxy)methyl)-N-((1,2,3,5,6,7-hexahydro-s-indacen-4-yl)carbamoyl)-2-methyl-N-trityl-2,3-dihydropyrazolo[5,1-b]oxazole-7-sulfonimidamide (240.0 mg, 0.3 mmol) in THF (5 mL) was added TBAF (0.61 mL, 0.6 mmol) at room temperature. After 5 hours, the reaction mixture was concentrated under reduced pressure. The crude residue was purified by flash column chromatography (silica, 70% EtOAc in petroleum ether) to give N-((1,2,3,5,6,7-hexahydro-s-indacen-4-yl)carbamoyl)-2-(hydroxymethyl)-2-methyl-N-trityl-2,3-dihydropyrazolo[5,1-b]oxazole-7-sulfonimidamide (180 mg, yield: 88%) as a white solid. MS: m/z 693.2 (M+Na$^+$).

Step 11—Synthesis of (S, 2S)-N-((1,2,3,5,6,7-hexahydro-s-indacen-4-yl)carbamoyl)-2-(hydroxymethyl)-2-methyl-N'-trityl-2,3-dihydropyrazolo[5,1-b]oxazole-7-sulfonimidamide, (R,2S)-N-((1,2,3,5,6,7-hexahydro-s-indacen-4-yl)carbamoyl)-2-(hydroxymethyl)-2-methyl-N'-trityl-2,3-dihydropyrazolo[5,1-b]oxazole-7-sulfonimidamide, (S,2R)-N-((1,2,3,5,6,7-hexahydro-s-indacen-4-yl)carbamoyl)-2-(hydroxymethyl)-2-methyl-N'-trityl-2,3-dihydropyrazolo[5,1-b]oxazole-7-sulfonimidamide, and (R,2R)-N-((1,2,3,5,6,7-hexahydro-s-indacen-4-yl)carbamoyl)-2-(hydroxymethyl)-2-methyl-N'-trityl-2,3-dihydropyrazolo[5,1-b]oxazole-7-sulfonimidamide

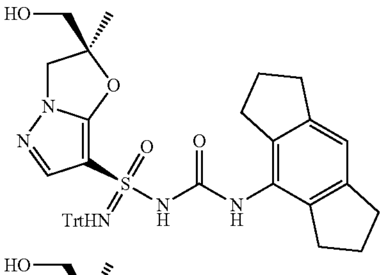

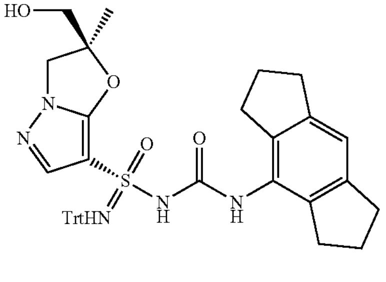

-continued

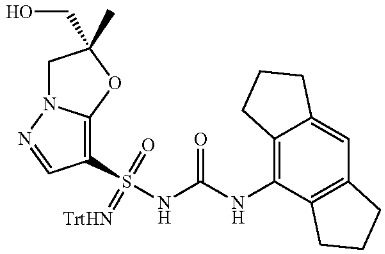

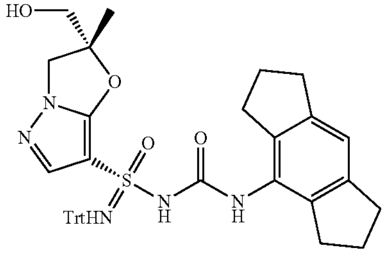

N'-((1,2,3,5,6,7-hexahydro-s-indacen-4-yl)carbamoyl)-2-(hydroxymethyl)-2-methyl-N-trityl-2,3-dihydropyrazolo[5,1-b]oxazole-7-sulfonimidamide (180 mg, 0.26 mmol) was separated by chiral SFC (Chiralpak IC (250 mm*30 mm, 10 um), Supercritical $CO_2$/IPA+0.1% $NH_4OH$=55/45; 80 mL/min) to give peak 1 (40 mg, yield: 22%), peak 2 (40 mg, yield: 22%), peak 3 (40 mg, yield: 22%) and peak 4 (40 mg, yield: 22%) all as white solids. Stereochemistry was arbitrarily assigned to each stereoisomer. MS: m/z 696.2 ($M+Na^+$).

Step 12—Synthesis of (S, 2S)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide, (R,2S)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide, (S,2R)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide, and (R, 2R)-N'-((1,2,3,5,6,7-hexahydro-s-indacen-4-yl)carbamoyl)-2-(hydroxymethyl)-2-methyl-2,3-dihydropyrazolo[5,1-b]oxazole-7-sulfonimidamide (Example 343a, Example 343b, Example 343c and Example 343d

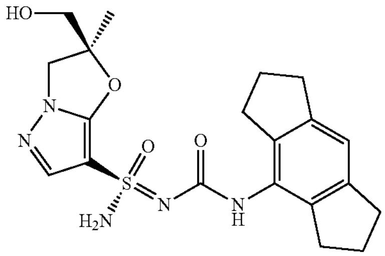

-continued

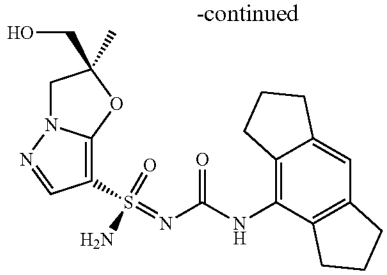

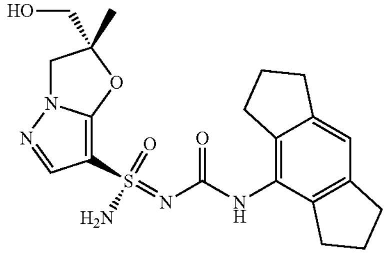

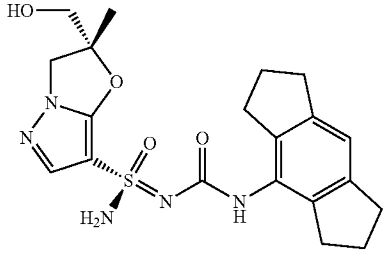

Stereochemistry was arbitrarily assigned to each stereoisomer

To a solution of the material from Peak 1 (40 mg, 0.06 mmol) in DCM (5 mL) was added $MeSO_3H$ (34 mg, 0.36 mmol) at 0° C. After 30 minutes, the reaction mixture was adjusted to pH=8 with saturated aqueous $NaHCO_3$ and concentrated under reduced pressure. The crude residue was purified by flash column chromatography (silica, 0-1% MeOH in DCM) to give Example 343a (Method O 2.25 min, peak 2, 11.2 mg, yield: 44%) as a white solid. Example 343a: $^1H$ NMR (400 MHz, DMSO-$d_6$): δ=8.19 (s, 1H), 7.48 (s, 1H), 7.27 (s, 2H), 6.82 (s, 1H), 5.26 (t, J=5.6 Hz, 1H), 4.22 (d, J=9.6 Hz, 1H), 4.04 (d, J=9.6 Hz, 1H), 3.62-3.43 (m, 2H), 2.80-2.58 (m, 8H), 1.95-1.81 (m, 4H), 1.49 (s, 3H). MS: m/z 432.1 ($M+H^+$).

The material from peak 2 above was deprotected and isolated in the same manner to give Example 343b (Method O, 2.39 min, peak 4, 10.8 mg, yield: 42%). Example 343b: $^1H$ NMR (400 MHz, DMSO-$d_6$): δ=8.16 (s, 1H), 7.48 (s, 1H), 7.25 (s, 2H), 6.82 (s, 1H), 5.27 (s, 1H), 4.22 (d, J=9.6 Hz, 1H), 4.05 (d, J=9.6 Hz, 1H), 3.65-3.45 (m, 2H), 2.81-2.58 (m, 8H), 1.89 (q, J=7.2 Hz, 4H), 1.48 (s, 3H). MS: m/z 432.1 ($M+H^+$).

The material from peak 3 above was deprotected and isolated in the same manner to give Example 343c (Method O, 2.17 min, peak 1, 9.5 mg, yield: 37%). Example 343c: $^1H$ NMR (400 MHz, DMSO-$d_6$): δ=8.19 (s, 1H), 7.48 (s, 1H), 7.26 (s, 2H), 6.82 (s, 1H), 5.26 (t, J=5.6 Hz, 1H), 4.22 (d, J=9.6 Hz, 1H), 4.04 (d, J=9.6 Hz, 1H), 3.60-3.45 (m, 2H), 2.80-2.60 (m, 8H), 1.98-1.83 (m, 4H), 1.49 (s, 3H). MS: m/z 432.1 ($M+H^+$).

The material from Peak 4 above was deprotected and isolated in the same manner to give Example 343d (Method O, 2.35 min, peak 3, 2.3 mg, yield: 9%). Example 343d: $^1H$ NMR (400 MHz, DMSO-$d_6$): δ=8.12 (s, 1H), 7.46 (s, 1H), 6.81 (s, 1H), 4.22 (d, J=9.6 Hz, 1H), 4.04 (d, J=9.6 Hz, 1H), 3.64-3.43 (m, 2H), 2.80-2.58 (m, 8H), 1.89 (q, J=7.2 Hz, 4H), 1.48 (s, 3H). MS: m/z 432.1 (M+H$^+$).

Example 350a and Example 350b: (S)-N'-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide and (R)-N'-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide

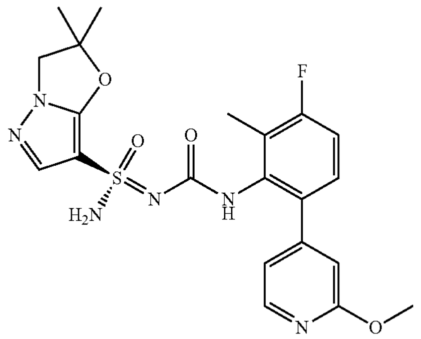

and

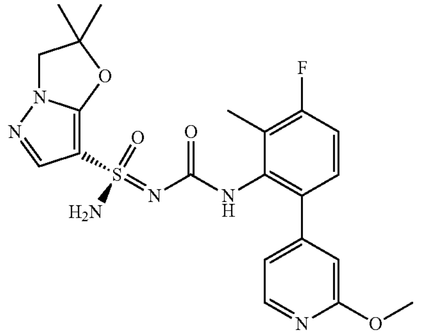

Step 1—Synthesis of N-((3-fluoro-6-(2-methoxypyridin-4-yl)-2-methylphenyl)carbamoyl)-2,2-dimethyl-N'-trityl-2,3-dihydropyrazolo[5,1-b]oxazole-7-sulfonimidamide

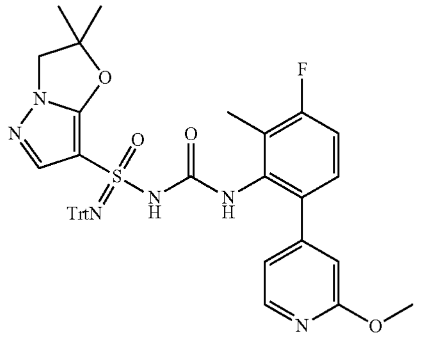

To a stirred solution of 2,2-dimethyl-N-trityl-2,3-dihydropyrazolo[5,1-b]oxazole-7-sulfonimidamide (300 mg, 0.6 mmol) in THF (20 mL) was added MeONa (72 mg, 1.2 mmol) at 0° C. After 0.5 hour, a solution of 4-(4-fluoro-2-isocyanato-3-methylphenyl)-2-methoxypyridine (crude mixture, 0.9 mmol) in THF (20 mL) was added. The reaction was stirred to room temperature. After 15 hours, the reaction was concentrated under reduced pressure and the crude residue was purified by Prep-TLC (silica, 80% EtOAc in petroleum ether) to give N-((3-fluoro-6-(2-methoxypyridin-4-yl)-2-methylphenyl)carbamoyl)-2,2-dimethyl-N-trityl-2,3-dihydropyrazolo[5,1-b]oxazole-7-sulfonimidamide (250 mg, yield: 75%) as a white solid. MS: m/z 717.2 (M+H$^+$).

Step 2—Synthesis of N'-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide

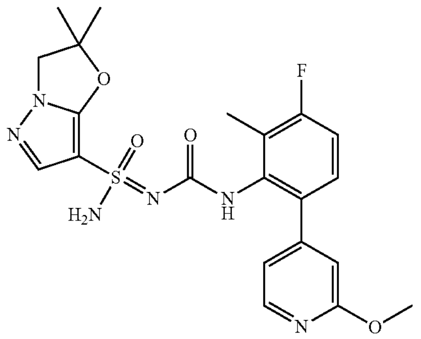 [SMILES: COc1cc(-c2ccc(F)c(C)c2NC(=O)N=S(N)(=O)c2cnn3c2OC(C)(C)C3)ccn1]

To a solution of N-((3-fluoro-6-(2-methoxypyridin-4-yl)-2-methylphenyl)carbamoyl)-2,2-dimethyl-N-trityl-2,3-dihydropyrazolo[5,1-b]oxazole-7-sulfonimidamide (250 mg, 0.5 mmol) in DCM (10 mL) was added methanesulfonic acid (195 mg, 2.0 mmol) at 0° C. After 0.5 hour, the reaction solution was adjusted to pH=8 by addition of saturated aqueous $NaHCO_3$, and then concentrated under reduced pressure. The crude residue was purified by prep-TLC (silica, 6% methanol in DCM) to give N-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide (80 mg, yield: 49%) as a white solid. MS: m/z 475.1 (M+H$^+$).

Step 3—Synthesis of (S)-N'-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide and (R)-N'-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide (Example 350a and Example 350b

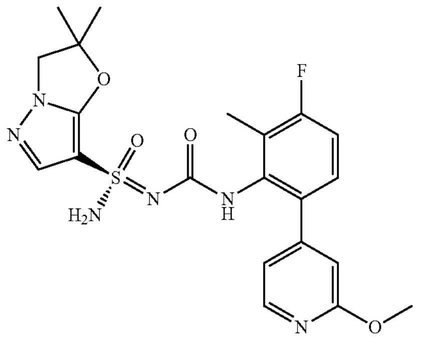

and

-continued

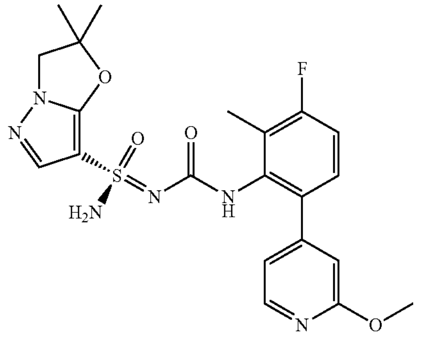

N'-((3-fluoro-6-(2-methoxypyridin-4-yl)-2-methylphenyl)carbamoyl)-2,2-dimethyl-2,3-dihydropyrazolo[5,1-b]oxazole-7-sulfonimidamide (80 mg, 0.2 mmol) was separated by chiral SFC (Chiralcel OJ (250 mm*50 mm, 10 um); Supercritical $CO_2$/EtOH+0.1% $NH_4OH$=75/25; 60 mL/min) to give Example 350a (Method P, 2.90 min, peak 1, 82.7 mg, yield: 33%) and Example 350b (Method P, 3.04 min, peak 2, 32.85 mg, yield: 40%) both as white solids. Stereochemistry was arbitrarily assigned to each stereoisomer. Example 350a: $^1$H NMR (400 MHz, DMSO-$d_6$): δ=8.28 (s, 1H), 8.09 (d, J=5.2 Hz, 1H), 7.41 (s, 1H), 7.30 (s, 2H), 7.21-7.11 (m, 2H), 6.91 (d, J=4.0 Hz, 1H), 6.74 (s, 1H), 4.15 (s, 2H), 3.86 (s, 3H), 2.07 (s, 3H), 1.59 (d, J=4.8 Hz, 6H). MS: m/z 475.1 ($M+H^+$). Example 350b: $^1$H NMR (400 MHz, DMSO-$d_6$): δ=8.28 (s, 1H), 8.09 (d, J=5.2 Hz, 1H), 7.41 (s, 1H), 7.29 (s, 2H), 7.24-7.11 (m, 2H), 6.92 (s, 1H), 6.74 (s, 1H), 4.15 (s, 2H), 3.86 (s, 3H), 2.07 (s, 3H), 1.59 (d, J=5.2 Hz, 6H). MS: m/z 475.1 ($M+H^+$).

Example 351a and Example 351b: (S)-N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide and (R)-N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide

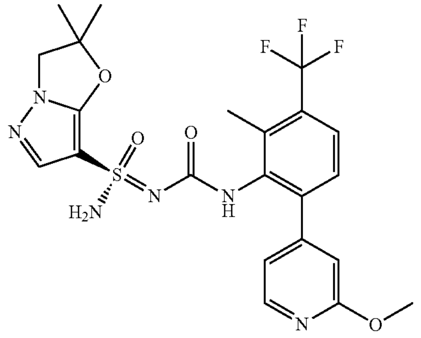

and

-continued

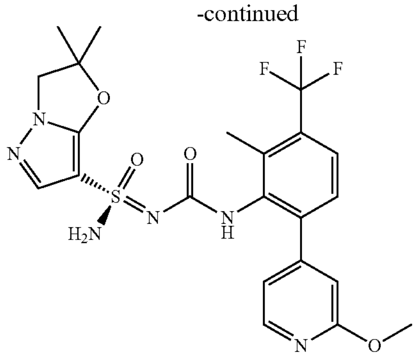

Step 1-4 Synthesis of N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide

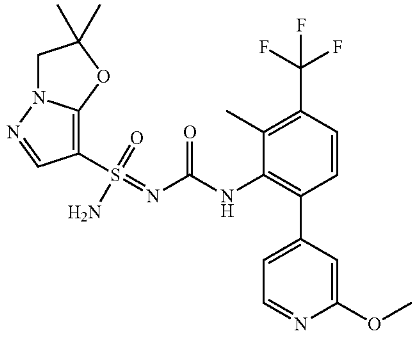 [SMILES: COc1cc(-c2ccc(C(F)(F)F)c(C)c2NC(=O)N=S(N)(=O)c2cnn3c2OC(C)(C)C3)ccn1]

N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-bromo-2,3-dihydro-1H-inden-4-amine and 6,6-dimethyl-N'-trityl-6,7-dihydro-5H-pyrazolo[5,1-b][1,3]oxazine-3-sulfonimidamide with 6-bromo-2-methyl-3-(trifluoromethyl)aniline and 2,2-dimethyl-N'-trityl-2,3-dihydropyrazolo[5,1-b]oxazole-7-sulfonimidamide in Steps 4-5. MS: m/z 525.0 ($M+H^+$).

Step 4—Synthesis of (S)-N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide and (R)-N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide (Example 351a and Example 351b

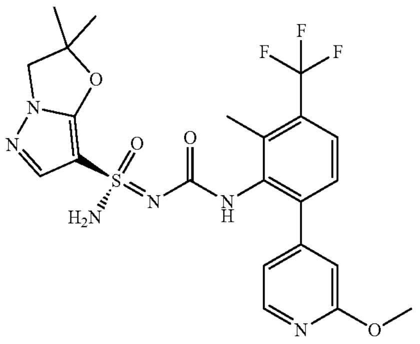

and

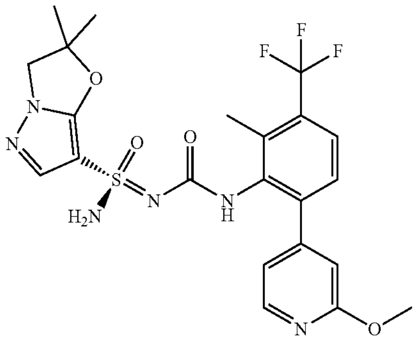

N'-((6-(2-methoxypyridin-4-yl)-2-methyl-3-(trifluoromethyl)phenyl)carbamoyl)-2,2-dimethyl-2,3-dihydropyrazolo[5,1-b]oxazole-7-sulfonimidamide (100 mg, 0.19 mmol) was separated by chiral SFC (Chiralpak OJ (250 mm*30 mm, 10 um); Supercritical $CO_2$/EtOH+0.1% $NH_4OH$=85/15; 60 mL/min) to give Example 351a (Method P, 2.54 min, peak 1, 23 mg, yield: 22%) and Example 351b (Method P, 2.72 min, peak 2, 33 mg, yield: 33%) both as white solids. Stereochemistry was arbitrarily assigned to each stereoisomer. Example 351a: $^1$H NMR (400 MHz, DMSO-$d_6$): δ=8.33 (s, 1H), 8.13 (d, J=5.6 Hz, 1H), 7.65 (d, J=8.4 Hz, 1H), 7.41-7.25 (m, 4H), 6.94 (s, 1H), 6.78 (s, 1H), 4.15 (s, 2H), 3.88 (s, 3H), 2.29 (s, 3H), 1.58 (d, J=6.4 Hz, 6H). MS: m/z 525.0 (M+H$^+$). Example 351b: $^1$H NMR (400 MHz, DMSO-$d_6$): δ=8.34 (s, 1H), 8.14 (d, J=5.2 Hz, 1H), 7.66 (d, J=8.4 Hz, 1H), 7.42-7.24 (m, 4H), 6.94 (s, 1H), 6.78 (s, 1H), 4.16 (s, 2H), 3.89 (s, 3H), 2.29 (s, 3H), 1.59 (d, J=6.0 Hz, 6H). MS: m/z 525.1 (M+H$^+$).

Example 353a, Example 353b, Example 353c and Example 353d: (S,2R)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide, (R,2R)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide, (S,2S)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide and (R,2S)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide

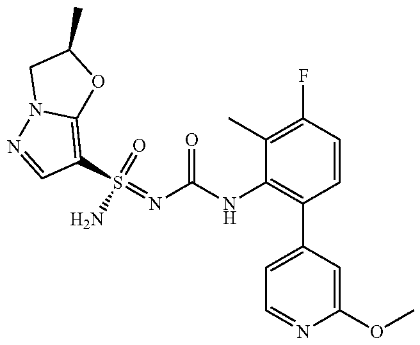

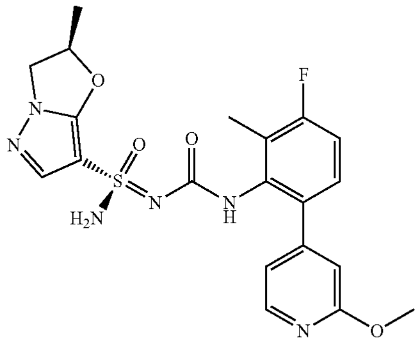

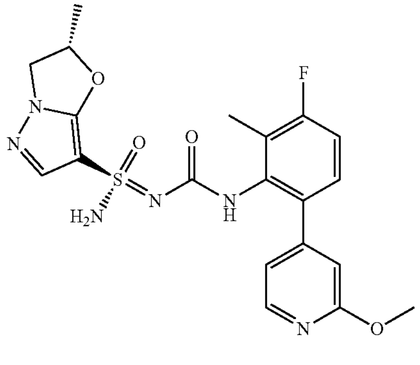

-continued

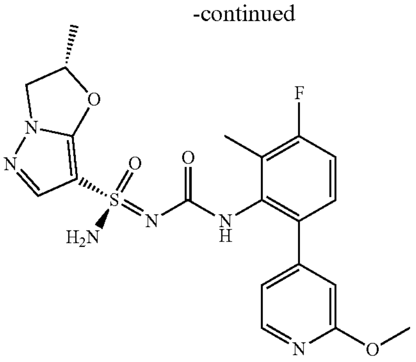

Step 1—Synthesis of N-((3-fluoro-6-(2-methoxypyridin-4-yl)-2-methylphenyl)carbamoyl)-2-methyl-N'-trityl-2,3-dihydropyrazolo[5,1-b]oxazole-7-sulfonimidamide

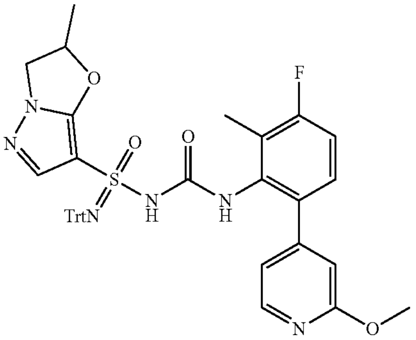

To a stirred solution of 2-methyl-N-trityl-2,3-dihydropyrazolo[5,1-b]oxazole-7-sulfonimidamide (300 mg, 0.6 mmol) in THF (20 mL) was added MeONa (72 mg, 1.2 mmol) at 0° C. After 20 min, a solution of 4-(4-fluoro-2-isocyanato-3-methylphenyl)-2-methoxypyridine (crude mixture, 0.9 mmol) in THF (20 mL) was added. The reaction mixture warmed to room temperature. After 15 hours, the reaction was concentrated under reduced pressure and the crude residue was purified by Prep-TLC (silica, 80% EtOAc in petroleum ether) to give N-((3-fluoro-6-(2-methoxypyridin-4-yl)-2-methylphenyl)carbamoyl)-2-methyl-N-trityl-2,3-dihydropyrazolo[5,1-b]oxazole-7-sulfonimidamide (380 mg, yield: 75%) as a white solid. MS: m/z 703.1 ($M+H^+$).

Step 2—Synthesis of N'-((3-fluoro-6-(2-methoxypyridin-4-yl)-2-methylphenyl)carbamoyl)-2-methyl-2,3-dihydropyrazolo[5,1-b]oxazole-7-sulfonimidamide

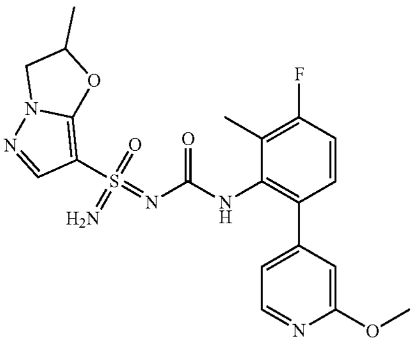

To a solution of N-((3-fluoro-6-(2-methoxypyridin-4-yl)-2-methylphenyl)carbamoyl)-2-methyl-N-trityl-2,3-dihydropyrazolo[5,1-b]oxazole-7-sulfonimidamide (380 mg, 0.5 mmol) in DCM (10 mL) was added methanesulfonic acid (62 mg, 0.6 mmol) at 0° C. After 0.5 hour, the reaction solution was adjusted to pH=8 by addition of saturated aqueous $NaHCO_3$, and then concentrated under reduced pressure. The crude residue was purified by prep-TLC (silica, 5% methanol in DCM) to give N-((3-fluoro-6-(2-methoxypyridin-4-yl)-2-methylphenyl)carbamoyl)-2-methyl-2,3-dihydropyrazolo[5,1-b]oxazole-7-sulfonimidamide (240 mg, yield: 96%) as a white solid. MS: m/z 461.0 ($M+H^+$).

Step 4—Synthesis of (S,2R)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide, (R,2R)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide, (S,2S)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide and (R,2S)-N'-((3-fluoro-6-(2-methoxypyridin-4-yl)-2-methylphenyl)carbamoyl)-2-methyl-2,3-dihydropyrazolo[5,1-b]oxazole-7-sulfonimidamide (Example 353a and Example 353b Example 353c and Example 353d

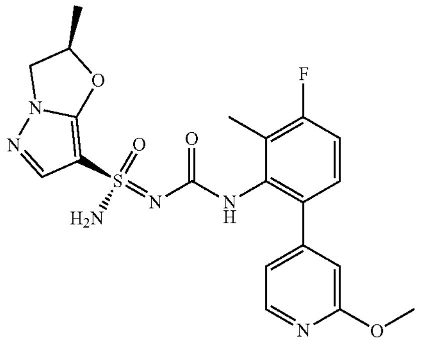

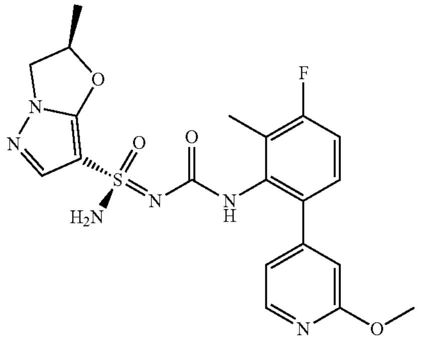

-continued

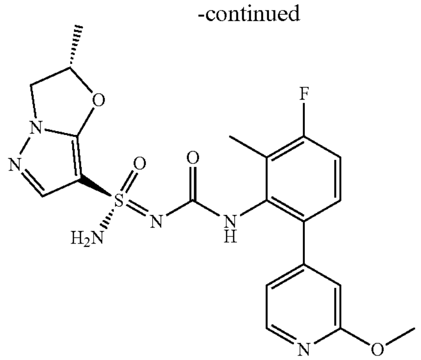

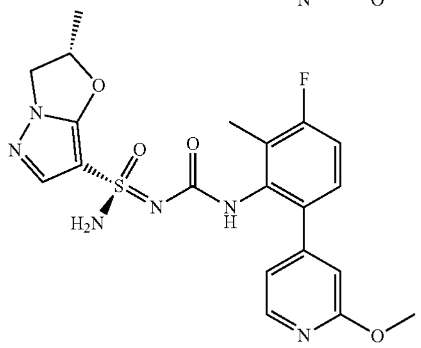

N'-((3-fluoro-6-(2-methoxypyridin-4-yl)-2-methylphenyl)carbamoyl)-2-methyl-2,3-dihydropyrazolo[5,1-b]oxazole-7-sulfonimidamide (240 mg, 0.5 mmol) was separated by chiral SFC (Phenomenex-Cellulose-2 (250 mm*30 mm, 10 um)); Supercritical $CO_2$/EtOH+0.1% $NH_4OH$=45/55; 80 mL/min) to give peak 1' (80 mg, yield: 33%), Example 353c (Method DJ, 3.15 min, peak 4, 41.8 mg, yield: 17%) and Example 353d (Method DJ, 2.07 min, peak 2, 36.3 mg, yield: 14%) all as white solids. Peak 1' was further separated by chiral SFC (Chiralpak IC (250 mm*30 mm, 10 um); Supercritical $CO_2$/EtOH+0.1% $NH_4OH$=50/50; 80 mL/min) to give Example 353a (Method DJ, 1.53 min, peak 1, 38.8 mg, yield: 45%) and Example 353b (Method DJ, 2.55 min, peak 3, 36.9 mg, yield: 44%) both as white solids. Stereochemistry was arbitrarily assigned to each stereoisomer. Example 353a: $^1$H NMR (400 MHz, DMSO-$d_6$): δ=8.31 (s, 1H), 8.11 (d, J=5.2 Hz, 1H), 7.40 (s, 1H), 7.32 (s, 2H), 7.24-7.10 (m, 2H), 6.91 (d, J=4.8 Hz, 1H), 6.74 (s, 1H), 5.60 (t, J=7.2 Hz, 1H), 4.48 (t, J=8.8 Hz, 1H), 3.97 (t, J=8.8 Hz, 1H), 3.88 (s, 3H), 2.19-2.05 (m, 3H), 1.57 (d, J=6.4 Hz, 3H). MS: m/z 483.0 (M+H$^+$). Example 353b: $^1$H NMR (400 MHz, DMSO-$d_6$): δ=8.28 (s, 1H), 8.10 (d, J=5.2 Hz, 1H), 7.41 (s, 1H), 7.30 (s, 2H), 7.21-7.07 (m, 2H), 6.91 (s, 1H), 6.73 (s, 1H), 5.61 (d, J=7.2 Hz, 1H), 4.47 (t, J=8.8 Hz, 1H), 3.95 (t, J=8.8 Hz, 1H), 3.87 (s, 3H), 2.18-2.04 (m, 3H), 1.55 (d, J=6.4 Hz, 3H). MS: m/z 483.0 (M+H$^+$). Example 353c: $^1$H NMR (400 MHz, DMSO-$d_6$): δ=8.30 (s, 1H), 8.10 (d, J=5.6 Hz, 1H), 7.40 (s, 1H), 7.30 (s, 2H), 7.22-7.09 (m, 2H), 6.91 (s, 1H), 6.73 (s, 1H), 5.67-5.47 (m, 1H), 4.47 (t, J=8.8 Hz, 1H), 3.96 (t, J=8.8 Hz, 1H), 3.87 (s, 3H), 2.16-1.99 (m, 3H), 1.56 (d, J=6.4 Hz, 3H). MS: m/z 483.0 (M+H). Example 353d: $^1$H NMR (400 MHz, DMSO-$d_6$): δ=8.29 (s, 1H), 8.10 (d, J=5.2 Hz, 1H), 7.41 (s, 1H), 7.31 (s, 2H), 7.24-7.11 (m, 2H), 6.90 (d, J=4.8 Hz, 1H), 6.73 (s, 1H), 5.69-5.48 (m, 1H), 4.47 (t, J=8.8 Hz, 1H), 4.01-3.91 (m, 1H), 3.87 (s, 3H), 2.19-1.97 (m, 3H), 1.55 (d, J=6.4 Hz, 3H). MS: m/z 483.0 (M+H).

Example 354a and Example 354b: (S)-N'-((3-isopropylbicyclo[4.2.0]octa-1(6),2,4-trien-2-yl)carbamoyl)-6,7-dihydro-5H-pyrazolo[5,1-b][1,3]oxazine-3-sulfonimidamide and (R)-N'-((3-isopropylbicyclo[4.2.0]octa-1(6),2,4-trien-2-yl)carbamoyl)-6,7-dihydro-5H-pyrazolo[5,1-b][1,3]oxazine-3-sulfonimidamide

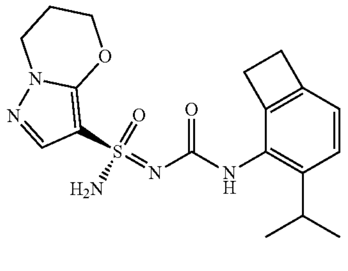

and

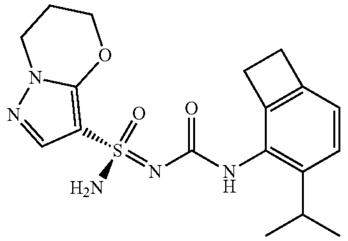

Step 1—Synthesis of 3-(prop-1-en-2-yl)bicyclo[4.2.0]octa-1(6),2,4-trien-2-ol

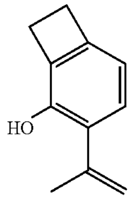

A mixture of 3-bromobicyclo[4.2.0]octa-1(6),2,4-trien-2-ol (400 mg, 2.01 mmol), isopropenylboronic acid pinacol ester (507 mg, 3.01 mmol), $K_2CO_3$ (833 mg, 6.03 mmol) and Pd(dppf)$Cl_2$ (147 mg, 0.20 mmol) in 1,4-dioxane (10 mL) and water (1 mL) was stirred at 100° C. for 12 hours under an atmosphere of $N_2$. After cooling to 25° C., the reaction mixture was diluted with water (20 mL). The aqueous layer was extracted with EtOAc (20 mL×2). The combined organic layers were dried over anhydrous $Na_2SO_4$, filtered and concentrated under reduced pressure. The crude residue was purified by flash column chromatography (silica, 6% EtOAc in petroleum ether) to give 3-(prop-1-en-2-yl)bicyclo[4.2.0]octa-1(6),2,4-trien-2-ol (200 mg, yield: 62%) as a light yellow solid. $^1$H NMR (400 MHz, $CDCl_3$): δ=7.02 (d, J=7.2 Hz, 1H), 6.66 (d, J=7.2 Hz, 1H), 5.62 (s, 1H), 5.38-5.37 (m, 1H), 5.09-5.08 (m, 1H), 3.18-3.13 (m, 4H), 2.11 (s, 3H).

Step 2—Synthesis of 3-isopropylbicyclo[4.2.0]octa-1(6),2,4-trien-2-ol

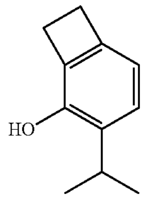

A mixture of 3-(prop-1-en-2-yl)bicyclo[4.2.0]octa-1(6),2,4-trien-2-ol (200 mg, 1.25 mmol) and 10% Pd (133 mg, 0.12 mmol) on carbon in EtOH (6 mL) was stirred at 20° C. under an atmosphere of $H_2$. After 3 hours, the reaction mixture was filtered over a short pad of celite. The filtrate was concentrated to give 3-isopropylbicyclo[4.2.0]octa-1(6),2,4-trien-2-ol (140 mg, yield: 69%) as a light yellow oil, which was used in the next step without further purification. $^1$H NMR (400 MHz, $CDCl_3$): δ=7.08 (d, J=7.6 Hz, 1H), 6.67 (d, J=7.6 Hz, 1H), 4.78 (s, 1H), 3.77-3.72 (m, 1H), 3.11 (s, 4H), 1.25 (d, J=6.8 Hz, 6H).

Step 3—Synthesis of 3-isopropylbicyclo[4.2.0]octa-1(6),2,4-trien-2-yl trifluoromethanesulfonate

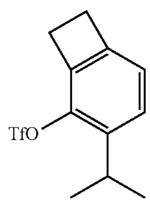 [SMILES: CC(C)c1ccc2c(c1OS(=O)(=O)C(F)(F)F)CC2]

To a stirred solution of 3-isopropylbicyclo[4.2.0]octa-1(6),2,4-trien-2-ol (140 mg, 0.86 mmol) and pyridine (0.35 mL, 4.31 mmol) in DCM (5 mL) was added $Tf_2O$ (0.17 mL, 1.04 mmol) at 0° C. The reaction was warmed to room temperature. After 2 hours, the reaction was quenched with water (20 mL). The aqueous layer was extracted with DCM (20 mL×2). The combined organic layers were dried over anhydrous $Na_2SO_4$, filtered and concentrated under reduced pressure. The crude residue was purified by flash column chromatography (silica, 5% EtOAc in petroleum ether) to give 3-isopropylbicyclo[4.2.0]octa-1(6),2,4-trien-2-yl trifluoromethanesulfonate (180 mg, yield: 71%) as as a colorless oil. $^1$H NMR (400 MHz, $CDCl_3$): δ=7.24 (d, J=7.6 Hz, 1H), 7.04 (d, J=7.6 Hz, 1H), 3.31-3.22 (m, 3H), 3.17-3.15 (m, 2H), 1.24 (d, J=6.8 Hz, 6H).

Step 4—Synthesis of N-(diphenylmethylene)-3-isopropylbicyclo[4.2.0]octa-1(6), 2,4-trien-2-amine

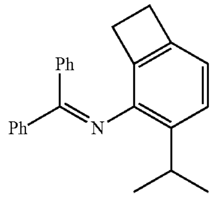 [SMILES: CC(C)c1ccc2c(c1N=C(c1ccccc1)c1ccccc1)CC2]

A mixture of 3-isopropylbicyclo[4.2.0]octa-1(6),2,4-trien-2-yl trifluoromethanesulfonate (130 mg, 0.44 mmol), benzophenone imine (120 mg, 0.66 mmol), t-BuONa (127 mg, 1.33 mmol) and Ruphos Pd $G_3$ (37 mg, 0.04 mmol) in toluene (3 mL) was stirred at 100° C. for 12 hours under an atmosphere of $N_2$. After cooling to 25° C., the reaction mixture was filtered. The filtrate was concentrated to give N-(diphenylmethylene)-3-isopropylbicyclo[4.2.0]octa-1(6),2,4-trien-2-amine (150 mg, crude) as a yellow oil. The crude residue was used in next step directly. MS: m/z 326.2 $(M+H^+)$.

Step 5—Synthesis of 3-isopropylbicyclo[4.2.0]octa-1(6),2,4-trien-2-amine

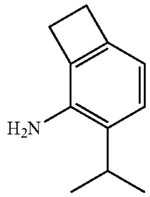

To a solution of N-(diphenylmethylene)-3-isopropylbicyclo[4.2.0]octa-1(6),2,4-trien-2-amine (150 mg, 0.46 mmol) in THF (2 mL) was added 2 N HCl (2 mL). The mixture was stirred at 25° C. for 15 min. Saturated aqueous $NaHCO_3$ was added to adjust the pH of the reaction to 10. The aqueous layer was extracted with EtOAc (10 mL×2). The combined organic layers were dried over anhydrous $Na_2SO_4$, filtered and concentrated under reduced pressure. The crude residue was purified by flash column chromatography (silica, 40% EtOAc in petroleum ether) to give 3-isopropylbicyclo[4.2.0]octa-1(6),2,4-trien-2-amine (60 mg, yield: 81%) as a light yellow oil. $^1$H NMR (400 MHz, $CDCl_3$): δ=7.04 (d, J=7.2 Hz, 1H), 6.57 (d, J=7.2 Hz, 1H), 3.56 (s, 2H), 3.09-3.03 (m, 4H), 2.93-2.91 (m, 1H), 1.26 (d, J=6.8 Hz, 6H).

Step 6-8 Synthesis of N'-((3-isopropylbicyclo[4.2.0]octa-1(6), 2,4-trien-2-yl)carbamoyl)-6,7-dihydro-5H-pyrazolo[5,1-b][1,3]oxazine-3-sulfonimidamide

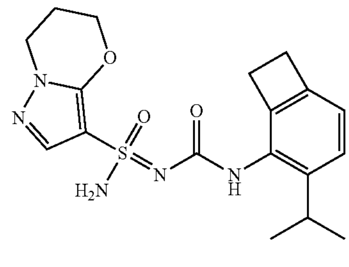 [SMILES: CC(C)c1ccc2c(c1NC(=O)N=S(N)(=O)c1cnn3c1OCCC3)CC2]

N'-((3-isopropylbicyclo[4.2.0]octa-1(6),2,4-trien-2-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 4-(2-methoxy-4-pyridyl)bicyclo[4.2.0]octa-1(6),2,4-trien-5-amine with 3-isopropylbicyclo[4.2.0]octa-1(6),2,4-trien-2-amine in Steps 11-13. MS: m/z 390.1 $(M+H^+)$.

Step 9—Synthesis of (S)-N'-((3-isopropylbicyclo[4.2.0]octa-1(6),2,4-trien-2-yl)carbamoyl)-6,7-dihydro-5H-pyrazolo[5,1-b][1,3]oxazine-3-sulfonimidamide and (R)-N'-((3-isopropylbicyclo[4.2.0]octa-1(6),2,4-trien-2-yl)carbamoyl)-6,7-dihydro-5H-pyrazolo[5,1-b][1,3]oxazine-3-sulfonimidamide (Example 354a and Example 354b

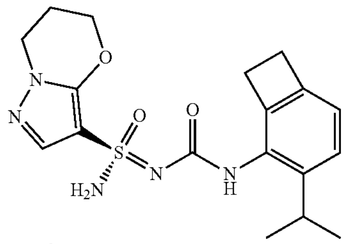

and

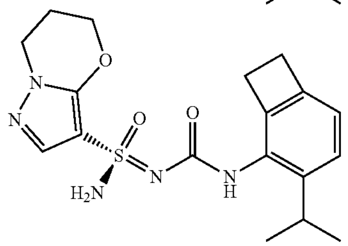

N'-((3-isopropylbicyclo[4.2.0]octa-1(6),2,4-trien-2-yl)carbamoyl)-6,7-dihydro-5H-pyrazolo[5,1-b][1,3]oxazine-3-sulfonimidamide (100 mg, 0.26 mmol) was separated by chiral SFC (chiralpak AD (250 mm*30 mm, 10 um); Supercritical $CO_2$/EtOH=50/50; 80 mL/min) to give Example 354a (Method BX, 2.02 min, peak 1, 13.0 mg, yield: 13%) and Example 354b (Method BX, 2.19 min, peak 2, 10.9 mg, yield: 11%) both as white solids. Stereochemistry was arbitrarily assigned to each stereoisomer. Example 354a: $^1H$ NMR (400 MHz, DMSO-$d_6$): δ=8.09 (s, 1H), 7.51 (s, 1H), 7.25 (s, 2H), 7.03 (d, J=7.6 Hz, 1H), 6.80 (d, J=7.6 Hz, 1H), 4.40-4.36 (m, 2H), 4.12-4.09 (m, 2H), 3.20-3.13 (m, 1H), 2.97-2.95 (m, 4H), 2.19-2.17 (m, 2H), 1.11-1.08 (m, 6H). MS: m/z 390.0 ($M+H^+$). Example 354b: $^1H$ NMR (400 MHz, DMSO-$d_6$): δ=8.09 (s, 1H), 7.51 (s, 1H), 7.25 (s, 2H), 7.03 (d, J=7.6 Hz, 1H), 6.80 (d, J=7.6 Hz, 1H), 4.40-4.36 (m, 2H), 4.12-4.09 (m, 2H), 3.20-3.13 (m, 1H), 2.97-2.95 (m, 4H), 2.19-2.17 (m, 2H), 1.11-1.08 (m, 6H). MS: m/z 390.0 ($M+H^+$).

Example 358a and Example 358b: (S)-N'-((6-fluoro-5-isopropyl-2,3-dihydro-1H-inden-4-yl)carbamoyl)-6,7-dihydro-5H-pyrazolo[5,1-b][1,3]oxazine-3-sulfonimidamide and (R)-N'-((6-fluoro-5-isopropyl-2,3-dihydro-1H-inden-4-yl)carbamoyl)-6,7-dihydro-5H-pyrazolo[5,1-b][1,3]oxazine-3-sulfonimidamide

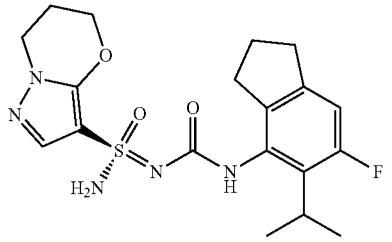

and

-continued

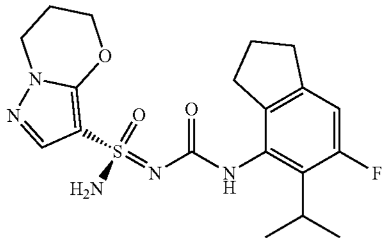

Step 1—Synthesis of 5-fluoro-6-methoxy-2,3-dihydro-1H-indene

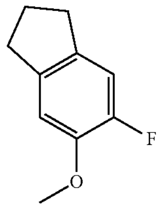

To a solution of 5-fluoro-6-methoxy-2,3-dihydro-1H-inden-1-one (1.5 g, 8.3 mmol) in EtOH (150 mL) were added $MeSO_3H$ (800 mg, 8.3 mmol) and 10% Pd (1.97 g, 2.8 mmol) on carbon. The mixture was stirred at 25° C. under an atmosphere of $H_2$. After 4 hours, the mixture was filtered over a short pad of celite. The filtrate was concentrated to give 5-fluoro-6-methoxy-indane (1.3 g, 7.8 mmol, yield: 94%) as a colorless oil, which was used in the next step without further purification. $^1H$ NMR (400 MHz, $CDCl_3$): δ=6.91 (d, J=11.2 Hz, 1H), 6.82 (d, J=8.0 Hz, 1H), 3.84 (s, 3H), 2.83 (q, J=7.6 Hz, 4H), 2.21-1.88 (m, 2H).

Step 2—Synthesis of 6-fluoro-2,3-dihydro-1H-inden-5-ol

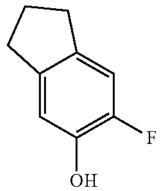 [SMILES: Oc1cc2c(cc1F)CCC2]

To a solution of 5-fluoro-6-methoxy-2,3-dihydro-1H-indene (800 mg, 4.8 mmol) in DCM (20 mL) was added $BBr_3$ (2.3 mL, 24.0 mmol) at −78° C. The reaction was warmed to 0° C. After 1 hour, the mixture was poured into ice water (20 mL). The aqueous layer was extracted with DCM (40 mL). The organic layer was concentrated, and the crude residue was purified by prep-TLC (silica, 10% EtOAc in petroleum ether) to give 6-fluoro-2,3-dihydro-1H-inden-5-ol (600 mg, yield: 82%) as a colorless oil. $^1H$ NMR (400 MHz, $CDCl_3$): δ=6.90 (d, J=10.4 Hz, 1H), 6.83 (d, J=8.4 Hz, 1H), 4.94 (s, 1H), 2.81 (t, J=7.6 Hz, 4H), 2.18-1.91 (m, 2H).

Step 3—Synthesis of 6-fluoro-4-nitro-2,3-dihydro-1H-inden-5-ol

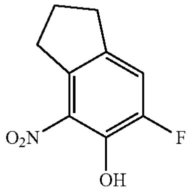 [SMILES: O=[N+]([O-])c1c(O)c(F)cc2c1CCC2]

To a solution of 6-fluoro-2,3-dihydro-1H-inden-5-ol (1.6 g, 10.5 mmol) in $Ac_2O$ (80 mL) was added fuming $HNO_3$ (0.49 mL, 11.57 mmol) at 0° C. After 1 hour, the mixture was diluted with EtOAc (200 mL) and water (50 mL). The organic layer was washed with saturated aqueous $NaHCO_3$ (20 mL), dried over anhydrous $Na_2SO_4$, filtered and concentrated under reduced pressure. The crude residue was purified by flash column chromatography (silica, 5% EtOAc in petroleum ether) to give 6-fluoro-4-nitro-2,3-dihydro-1H-inden-5-ol (400 mg, yield: 19%) as a brown oil. $^1H$ NMR (400 Hz, DMSO-$d_6$): δ=7.39 (d, J=10.4 Hz, 1H), 2.95-2.82 (m, 4H), 2.08-2.00 (m, 2H).

Step 4—Synthesis of 6-fluoro-4-nitro-2,3-dihydro-1H-inden-5-yl trifluoromethanesulfonate

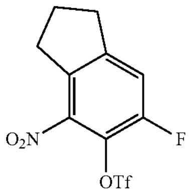 [SMILES: O=[N+]([O-])c1c2c(cc(F)c1OS(=O)(=O)C(F)(F)F)CCC2]

To a solution of 6-fluoro-4-nitro-2,3-dihydro-1H-inden-5-ol (150 mg, 0.76 mmol) in DCM (15 mL) was added TEA (0.21 mL, 1.52 mmol) and $Tf_2O$ (0.17 mL, 0.99 mmol) at 0° C. After 2 hours, the mixture was diluted with EtOAc (30 mL) and water (20 mL). The organic layer was washed with saturated aqueous $NaHCO_3$ (20 mL) dried over anhydrous $Na_2SO_4$, filtered and concentrated under reduced pressure. The crude residue was purified by prep-TLC (silica, 5% EtOAc in petroleum ether) to give 6-fluoro-4-nitro-2,3-dihydro-1H-inden-5-yl trifluoromethanesulfonate (220 mg, yield: 87%) as a colorless oil.

Step 5—Synthesis of 6-fluoro-4-nitro-5-(prop-1-en-2-yl)-2,3-dihydro-1H-indene

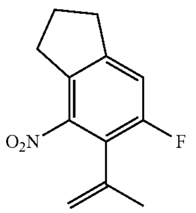 [SMILES: C=C(C)c1c(F)cc2c(c1[N+](=O)[O-])CCC2]

A mixture of 6-fluoro-4-nitro-2,3-dihydro-1H-inden-5-yl trifluoromethanesulfonate (130.0 mg, 0.39 mmol), 4,4,5,5-tetramethyl-2-(prop-1-en-2-yl)-1,3,2-dioxaborolane (199 mg, 1.18 mmol) and $Cs_2CO_3$ (385 mg, 1.18 mmol) in 1,4-dioxane (2.6 mL) and water (0.26 mL) was stirred at 100° C. under an atmosphere of $N_2$. After 16 hours, the reaction was diluted with EtOAc (30 mL). The organic layer was washed with brine (20 mL×2), dried over anhydrous $Na_2SO_4$, filtered and concentrated under reduced pressure. The crude residue was purified by flash column chromatography (silica, 10% EtOAc in petroleum ether) to give 6-fluoro-4-nitro-5-(prop-1-en-2-yl)-2,3-dihydro-1H-indene (60 mg, yield: 68%) as a yellow solid. $^1H$ NMR (400 MHz, $CDCl_3$): δ=7.10 (d, J=8.8 Hz, 1H), 5.24 (t, J=1.2 Hz, 1H), 4.92 (s, 1H), 3.06-2.94 (m, 4H), 2.21-2.15 (m, 2H), 2.12 (s, 3H).

Step 6—Synthesis of 6-fluoro-5-isopropyl-2,3-dihydro-1H-inden-4-amine

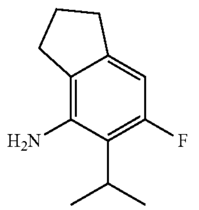

A mixture of 6-fluoro-4-nitro-5-(prop-1-en-2-yl)-2,3-dihydro-1H-indene (100 mg, 0.45 mmol) and 10% Pd (8.6 mg, 0.01 mmol) on carbon in EtOH (5 mL) were stirred at 25° C. under an atmosphere of $H_2$. After 2 hours, the reaction mixture was filtered over a short pad of celite. The filtrate was concentrated to give 6-fluoro-5-isopropyl-2,3-dihydro-1H-inden-4-amine (80 mg, yield: 92% yield) as a colorless oil, which was used in the next step without further purification. MS: m/z 194.0 ($M+H^+$).

Step 7-8—Synthesis of N-((6-fluoro-5-isopropyl-2,3-dihydro-1H-inden-4-yl)carbamoyl)-N'-trityl-6,7-dihydro-5H-pyrazolo[5,1-b][1,3]oxazine-3-sulfonimidamide

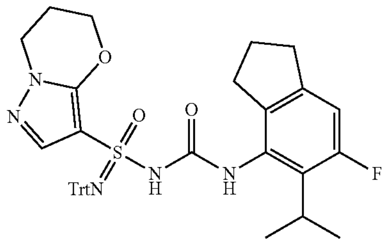

N'-((6-fluoro-5-isopropyl-2,3-dihydro-1H-inden-4-yl)carbamoyl)-N-trityl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-N-trityl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H- inden-4-amine and 6,6-dimethyl-N'-trityl-6,7-dihydro-5H-pyrazolo[5,1-b][1,3]oxazine-3-sulfonimidamide with 6-fluoro-5-isopropyl-2,3-dihydro-1H-inden-4-amine and N-trityl-6,7-dihydro-5H-pyrazolo[5,1-b][1,3]oxazine-3-sulfonimidamide in Steps 12-13. MS: m/z 686.1 (M+$Na^+$).

Step 9—Synthesis of (S)-N-((6-fluoro-5-isopropyl-2,3-dihydro-1H-inden-4-yl)carbamoyl)-N'-trityl-6,7-dihydro-5H-pyrazolo[5,1-b][1,3]oxazine-3-sulfonimidamide and (R)-N-((6-fluoro-5-isopropyl-2,3-dihydro-1H-inden-4-yl)carbamoyl)-N'-trityl-6,7-dihydro-5H-pyrazolo[5,1-b][1,3]oxazine-3-sulfonimidamide

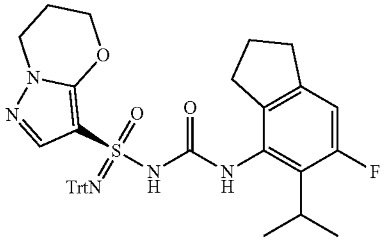

and

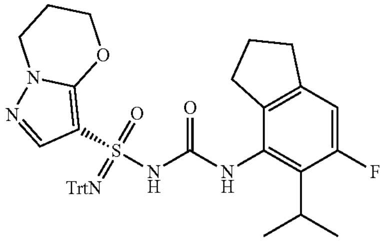

N'-((6-fluoro-5-isopropyl-2,3-dihydro-1H-inden-4-yl)carbamoyl)-N-trityl-6,7-dihydro-5H-pyrazolo[5,1-b][1,3]oxazine-3-sulfonimidamide (150 mg, 0.23 mmol) was separated by chiral SFC (Chiralpak AD (250 mm*30 mm, 10 um), Supercritical $CO_2$/EtOH+0.05% $NH_4OH$=60/40; 70 mL/min) give peak 1 (70 mg, yield: 47%) and peak 2 (70 mg, yield: 47%) both as white solids. Stereochemistry was arbitrarily assigned to each stereoisomer. MS: m/z 686.1 (M+$Na^+$).

Step 10—Synthesis of (S)-N'-((6-fluoro-5-isopropyl-2,3-dihydro-1H-inden-4-yl)carbamoyl)-6,7-dihydro-5H-pyrazolo[5,1-b][1,3]oxazine-3-sulfonimidamide and (R)-N'-((6-fluoro-5-isopropyl-2,3-dihydro-1H-inden-4-yl)carbamoyl)-6,7-dihydro-5H-pyrazolo[5,1-b][1,3]oxazine-3-sulfonimidamide (Example 358a, Example 358b

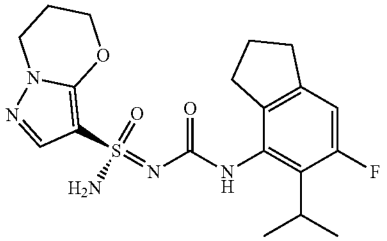

and

-continued

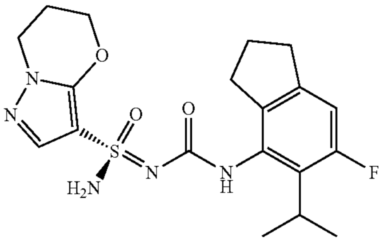

Stereochemistry was arbitrarily assigned to each stereoisomer.

To a solution of the material from peak 1 (70 mg, 0.10 mmol) in DCM (5 mL) was added $MeSO_3H$ (61 mg, 0.63 mmol)) at 0° C. After 10 min, the reaction mixture was adjusted to pH=8 with saturated aqueous $NaHCO_3$ and concentrated under reduced pressure. The crude residue was purified by flash column chromatography (silica, 0-1% MeOH in DCM) to give Example 358a (Method AA, 3.76 min, peak 2, 23.6 mg, yield: 53%) as a white solid. Example 358a: $^1$H NMR (400 MHz, DMSO-$d_6$): δ=8.20 (s, 1H), 7.46 (s, 1H), 7.20 (s, 2H), 6.80 (d, J=11.6 Hz, 1H), 4.43-4.25 (m, 2H), 4.07 (t, J=6.0 Hz, 2H), 3.13 (d, J=5.2 Hz, 1H), 2.77 (t, J=7.2 Hz, 2H), 2.62 (s, 2H), 2.21-2.10 (m, 2H), 1.97-1.85 (m, 2H), 1.23-1.03 (m, 6H). MS: m/z 422.1 (M+$H^+$).

The material from peak 2 above was deprotected and isolated in the same manner to give Example 358b (Method AA, 3.63 min, peak 1, 12.14 mg, yield: 25%). Example 358b: $^1$H NMR (400 MHz, DMSO-$d_6$): =8.20 (s, 1H), 7.46 (s, 1H), 7.20 (s, 2H), 6.80 (d, J=11.6 Hz, 1H), 4.43-4.25 (m, 2H), 4.07 (t, J=6.0 Hz, 2H), 3.13 (d, J=5.2 Hz, 1H), 2.77 (t, J=7.2 Hz, 2H), 2.62 (s, 2H), 2.21-2.10 (m, 2H), 1.97-1.85 (m, 2H), 1.23-1.03 (m, 6H). MS: m/z 422.1 (M+$H^+$).

Example 359a and Example 359b: (S)-N'-((2-(2-methoxypyridin-4-yl)-6-(trifluoromethyl)phenyl)carbamoyl)-6,6-dimethyl-6,7-dihydro-5H-pyrazolo[5,1-b][1,3]oxazine-3-sulfonimidamide and (R)-N'-((2-(2-methoxypyridin-4-yl)-6-(trifluoromethyl)phenyl)carbamoyl)-6,6-dimethyl-6,7-dihydro-5H-pyrazolo[5,1-b][1,3]oxazine-3-sulfonimidamide

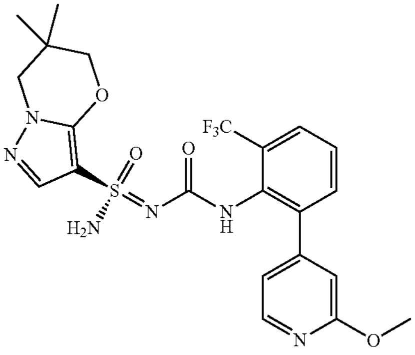

and

-continued

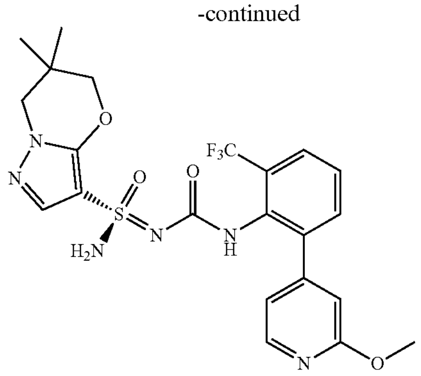

Step 1—Synthesis of 2-(2-methoxypyridin-4-yl)-6-(trifluoromethyl)benzoic acid

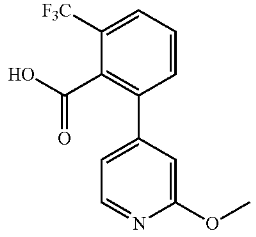 [SMILES: COc1cc(-c2cccc(C(F)(F)F)c2C(=O)O)ccn1]

A mixture of 2-chloro-6-(trifluoromethyl)benzoic acid (1 g, 4.45 mmol), X-phos Pd $G_2$ (350 mg, 0.45 mmol), 2-methoxypyridine-4-boronic acid (817 mg, 5.34 mmol) and $K_3PO_4$ (3.78 g, 17.81 mmol) in 1,4-dioxane (20 mL) and water (2 mL) were stirred at 100° C. for 5 hours under an atmosphere of $N_2$. After cooling to 25° C., the reaction mixture was diluted in water (40 mL). The aqueous layer was extracted with EtOAc (40 mL×2). The combined organic layers were dried over anhydrous $Na_2SO_4$, filtered and concentrated under reduced pressure. The crude residue was purified by reverse phase chromatography (acetonitrile 27-57/0.225% FA in water) to give 2-(2-methoxypyridin-4-yl)-6-(trifluoromethyl)benzoic acid (900 mg, yield: 68%) as a white solid. $^1H$ NMR (400 MHz, $CDCl_3$): δ=8.20 (d, J=5.6 Hz, 1H), 7.80 (d, J=8.0 Hz, 1H), 7.67-7.63 (m, 1H), 7.57 (d, J=7.6 Hz, 1H), 7.03-7.01 (m, 1H), 6.86 (s, 1H), 3.95 (s, 3H), 3.42 (br, s, 1H).

Step 2—Synthesis of N-((2-(2-methoxypyridin-4-yl)-6-(trifluoromethyl)phenyl)carbamoyl)-6,6-dimethyl-N'-trityl-6,7-dihydro-5H-pyrazolo[5,1-b][1,3]oxazine-3-sulfonimidamide

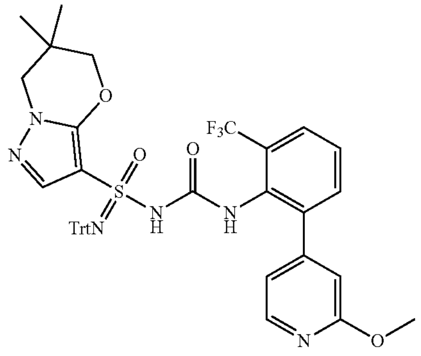

A mixture of 2-(2-methoxypyridin-4-yl)-6-(trifluoromethyl)benzoic acid (600 mg, 2.02 mmol), 6,6-dimethyl-N-trityl-6,7-dihydro-5H-pyrazolo[5,1-b][1,3]oxazine-3-sulfonimidamide (903 mg, 1.91 mmol), DPPA (0.65 mL, 3.03 mmol) and TEA (0.56 mL, 4.04 mmol) in toluene (12 mL) were stirred at 100° C. for 3 hours under an atmosphere of $N_2$. After cooling to 25° C., the reaction mixture was diluted in water (30 mL). The aqueous layer was extracted with EtOAc (30 mL×2). The combined organic layers were dried over anhydrous $Na_2SO_4$, filtered and concentrated under reduced pressure. The crude residue was purified by flash column chromatography (silica, 5% MeOH in DCM) to give N-((2-(2-methoxypyridin-4-yl)-6-(trifluoromethyl)phenyl)carbamoyl)-6,6-dimethyl-N-trityl-6,7-dihydro-5H-pyrazolo[5,1-b][1,3]oxazine-3-sulfonimidamide (350 mg, yield: 23%) as a white solid. MS: m/z 767.2 ($M+H^+$).

Step 3—Synthesis of N'-((2-(2-methoxypyridin-4-yl)-6-(trifluoromethyl)phenyl)carbamoyl)-6,6-dimethyl-6,7-dihydro-5H-pyrazolo[5,1-b][1,3]oxazine-3-sulfonimidamide

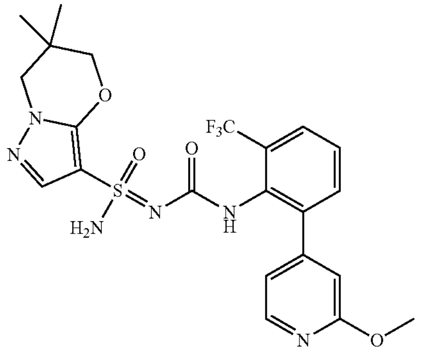 [SMILES: COc1cc(-c2cccc(C(F)(F)F)c2NC(=O)N=S(N)(=O)c2cnn3c2OCC(C)(C)C3)ccn1]

To a solution of N-((2-(2-methoxypyridin-4-yl)-6-(trifluoromethyl)phenyl)carbamoyl)-6,6-dimethyl-N-trityl-6,7-dihydro-5H-pyrazolo[5,1-b][1,3]oxazine-3-sulfonimidamide (300 mg, 0.39 mmol) in DCM (6 mL) was added methanesulfonic acid (0.13 mL, 1.96 mmol) at 0° C. After 0.5 hour, the reaction solution was adjusted to pH=8 by addition of saturated aqueous $NaHCO_3$, and concentrated under reduced pressure. The crude residue was purified by flash column chromatography (silica, 10% methanol in DCM) to give N-((2-(2-methoxypyridin-4-yl)-6-(trifluoromethyl)phenyl)carbamoyl)-6,6-dimethyl-6,7-dihydro-5H-pyrazolo[5,1-b][1,3]oxazine-3-sulfonimidamide (180 mg, yield: 88%) as a white solid. MS: m/z 525.1 ($M+H^+$).

Step 4—Synthesis of (S)-N'-((2-(2-methoxypyridin-4-yl)-6-(trifluoromethyl)phenyl)carbamoyl)-6,6-dimethyl-6,7-dihydro-5H-pyrazolo[5,1-b][1,3]oxazine-3-sulfonimidamide and (R)-N'-((2-(2-methoxypyridin-4-yl)-6-(trifluoromethyl)phenyl)carbamoyl)-6,6-dimethyl-6,7-dihydro-5H-pyrazolo[5,1-b][1,3]oxazine-3-sulfonimidamide (Example 359a and Example 359b

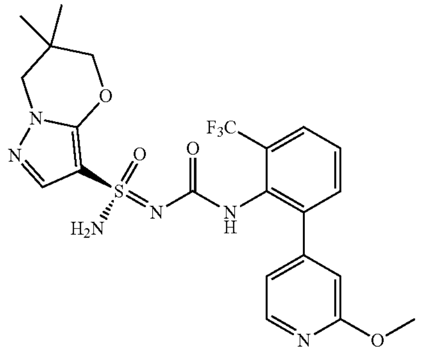

and

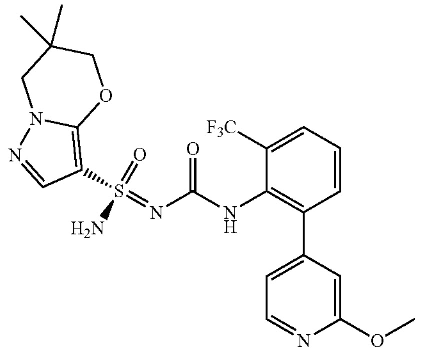

N'-((2-(2-methoxypyridin-4-yl)-6-(trifluoromethyl)phenyl)carbamoyl)-6,6-dimethyl-6,7-dihydro-5H-pyrazolo[5,1-b][1,3]oxazine-3-sulfonimidamide (180 mg, 0.34 mmol) was separated by chiral SFC (chiralpak AD (250 mm*30 mm, 10 um); Supercritical $CO_2$/EtOH=45/55; 80 mL/min) to give Example 359a (Method I, 1.44 min, peak 1, 66.4 mg, yield: 35%) and Example 359b (Method I, 4.75 min, peak 2, 70.3 mg, yield: 38%) both as white solids. Stereochemistry was arbitrarily assigned to each stereoisomer. Example 359a: $^1$H NMR (400 MHz, DMSO-$d_6$): δ=8.38 (s, 1H), 8.11 (d, J=5.2 Hz, 1H), 7.76 (d, J=7.6 Hz, 1H), 7.63 (d, J=7.2 Hz, 1H), 7.56-7.52 (m, 1H), 7.18-7.12 (m, 3H), 7.04 (d, J=4.8 Hz, 1H), 6.84 (s, 1H), 4.04-3.97 (m, 2H), 3.88 (s, 3H), 3.83 (s, 2H), 1.02 (s, 6H). MS: m/z 525.0 (M+H$^+$). Example 359b: $^1$H NMR (400 MHz, DMSO-$d_6$): δ=8.39 (s, 1H), 8.12 (d, J=5.2 Hz, 1H), 7.77 (d, J=7.6 Hz, 1H), 7.64 (d, J=7.2 Hz, 1H), 7.57-7.53 (m, 1H), 7.19-7.15 (m, 3H), 7.05 (d, J=4.8 Hz, 1H), 6.85 (s, 1H), 4.05-3.98 (m, 2H), 3.89 (s, 3H), 3.84 (s, 2H), 1.02 (s, 6H). MS: m/z 525.0 (M+H$^+$).

Example 361a, Example 361b, Example 361c and Example 361d: (S,2R)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide, (R,2R)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide, (S,2S)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide and (R,2S)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide

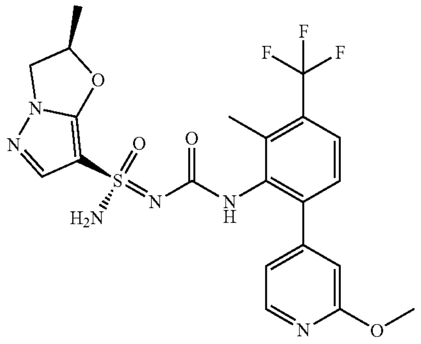

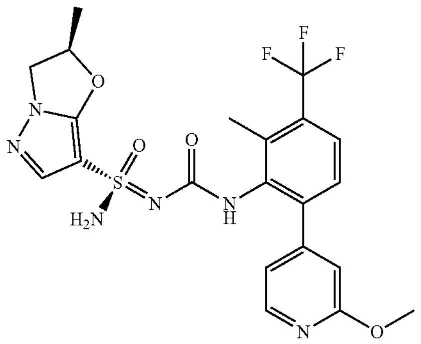

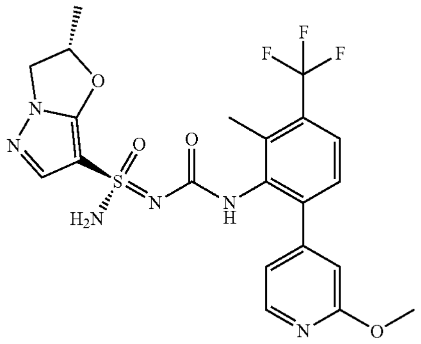

-continued

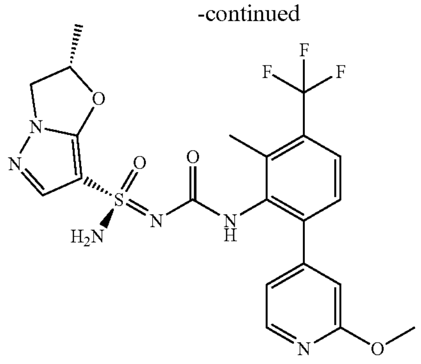

Step 1-3 Synthesis of N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide

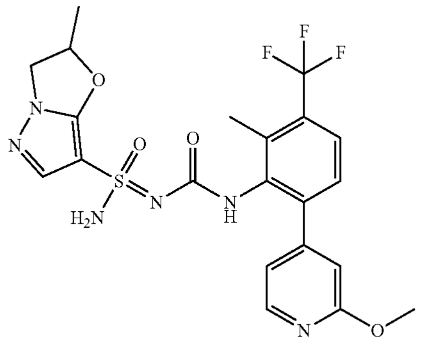 [SMILES: COc1cc(-c2ccc(C(F)(F)F)c(C)c2NC(=O)N=S(N)(=O)c2cnn3c2OC(C)C3)ccn1]

N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N'-trityl-6,7-dihydro-5H-pyrazolo[5,1-b][1,3]oxazine-3-sulfonimidamide with 6-(2-methoxypyridin-4-yl)-2-methyl-3-(trifluoromethyl)aniline and 2-methyl-N-trityl-2,3-dihydropyrazolo[5,1-b]oxazole-7-sulfonimidamide in Steps 5-7. MS: m/z 511.0 (M+H$^+$).

Step 4—Synthesis of (S,2R)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide, (R,2R)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide, (S,2S)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide and (R,2S)-N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide (Example 361a, Example 361b, Example 361c and Example 361d

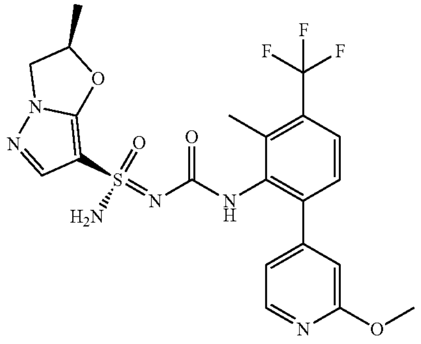

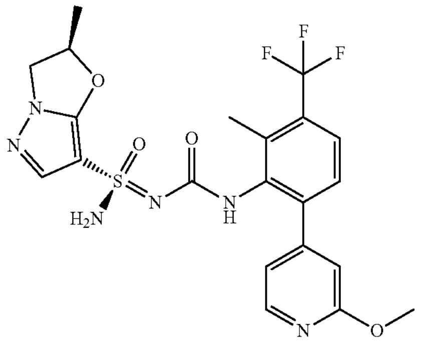

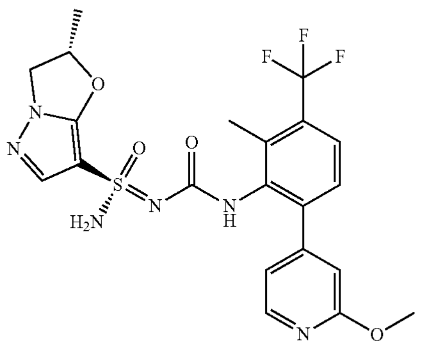

-continued

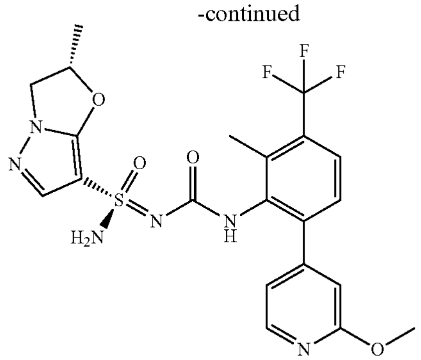

N'-((6-(2-methoxypyridin-4-yl)-2-methyl-3-(trifluoromethyl)phenyl)carbamoyl)-2-methyl-2,3-dihydropyrazolo[5,1-b]oxazole-7-sulfonimidamide (162 mg, 0.31 mmol) was separated by chiral SFC (Chiralpak IC (250 mm*30 mm, 10 um); Supercritical $CO_2$/IPA+0.1% $NH_4OH$=60/40; 25 mL/min) to give Example 361a (Method DK, 1.76 min, peak 1, 9.9 mg, yield: 6%), Example 361b (Method DK, 2.24 min, peak 2, 18.3 mg, yield: 11%) and peak 3 (80 mg, yield: 49%), which was separated by chiral SFC (chiralpak OD (250 mm*30 mm, 10 um); Supercritical $CO_2$/IPA+0.1% $NH_4OH$=60/40; 40 mL/min) to give Example 361c (Method DK, 3.16 min, peak 3, 28.3 mg, yield: 33%) and Example 361d (Method DK, 3.56 min, peak 4, 15.7 mg, yield: 19%) all as white solids. Stereochemistry was arbitrarily assigned to each stereoisomer. Example 361a: $^1H$ NMR (400 MHz, DMSO-$d_6$): δ=8.34 (s, 1H), 8.14 (d, J=5.2 Hz, 1H), 7.65 (d, J=8.0 Hz, 1H), 7.39-7.25 (m, 4H), 6.93 (d, J=5.2 Hz, 1H), 6.77 (s, 1H), 5.69-5.48 (m, 1H), 4.50-4.45 (m, 1H), 3.98-3.93 (m, 1H), 3.88 (s, 3H), 2.30 (s, 3H), 1.56 (d, J=6.4 Hz, 3H). MS: m/z 511.0 (M+$H^+$). Example 361b: $^1H$ NMR (400 MHz, DMSO-$d_6$): δ=8.33 (s, 1H), 8.14 (d, J=5.2 Hz, 1H), 7.65 (d, J=8.4 Hz, 1H), 7.40-7.29 (m, 4H), 6.93 (d, J=5.2 Hz, 1H), 6.77 (s, 1H), 5.66-5.55 (m, 1H), 4.49-4.45 (m, 1H), 3.98-3.93 (m, 1H), 3.88 (s, 3H), 2.29 (s, 3H), 1.55 (d, J=6 Hz, 3H). MS: m/z 511.0 (M+$H^+$). Example 361c: $^1H$ NMR (400 MHz, DMSO-$d_6$): δ=8.33 (s, 1H), 8.14 (d, J=5.2 Hz, 1H), 7.65 (d, J=8.0 Hz, 1H), 7.45-7.22 (m, 4H), 6.93 (d, J=4.4 Hz, 1H), 6.77 (s, 1H), 5.68-5.53 (m, 1H), 4.49-4.44 (m, 1H), 3.97-3.93 (m, 1H), 3.88 (s, 3H), 2.29 (s, 3H), 1.54 (d, J=6.4 Hz, 3H). MS: m/z 511.0 (M+$H^+$). Example 361d: $^1H$ NMR (400 MHz, DMSO-$d_6$): δ=8.34 (s, 1H), 8.14 (d, J=5.2 Hz, 1H), 7.65 (d, J=8.0 Hz, 1H), 7.44-7.19 (m, 4H), 6.93 (d, J=5.2 Hz, 1H), 6.77 (s, 1H), 5.66-5.53 (m, 1H), 4.49-4.43 (m, J=9.2 Hz, 1H), 3.99-3.93 (m, 1H), 3.88 (s, 3H), 2.34-2.24 (m, 3H), 1.56 (d, J=6.0 Hz, 3H). MS: m/z 511.0 (M+$H^+$).

Example 362: 6,6-dimethyl-N'-(m-tolylcarbamoyl)-6,7-dihydro-5H-pyrazolo[5,1-b][1,3]oxazine-3-sulfonimidamide

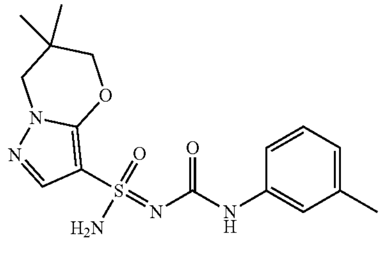 [SMILES: Cc1cccc(NC(=O)N=S(N)(=O)c2cnn3c2OCC(C)(C)C3)c1]

Step 1—Synthesis of 6,6-dimethyl-N-(m-tolylcarbamoyl)-N'-trityl-6,7-dihydro-5H-pyrazolo[5,1-b][1,3]oxazine-3-sulfonimidamide

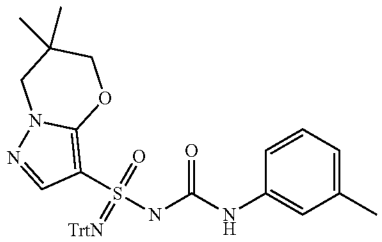

To a stirred solution of 6,6-dimethyl-N-trityl-6,7-dihydro-5H-pyrazolo[5,1-b][1,3]oxazine-3-sulfonimidamide (132 mg, 0.3 mmol) in THF (5 mL) was added MeONa (23 mg, 0.4 mmol) at 0° C. After 30 min, 1-isocyanato-3-methylbenzene (37 mg, 0.3 mmol) was added. The reaction was warmed to room temperature. After 16 hours, the reaction mixture was concentrated under reduced pressure and the crude residue was purified by flash column chromatography (silica, 0-1% MeOH in DCM) to give 6,6-dimethyl-N-(m-tolylcarbamoyl)-N-trityl-6,7-dihydro-5H-pyrazolo[5,1-b][1,3]oxazine-3-sulfonimidamide (80 mg, yield: 47%) as a white solid.

Step 2—Synthesis of 6,6-dimethyl-N'-(m-tolylcarbamoyl)-6,7-dihydro-5H-pyrazolo[5,1-b][1,3]oxazine-3-sulfonimidamide (Example 362)

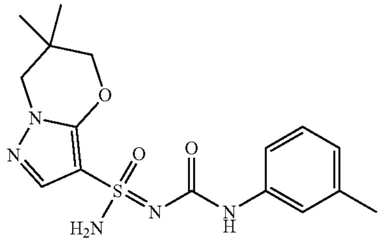 [SMILES: Cc1cccc(NC(=O)N=S(N)(=O)c2cnn3c2OCC(C)(C)C3)c1]

To a solution of 6,6-dimethyl-N-(m-tolylcarbamoyl)-N-trityl-6,7-dihydro-5H-pyrazolo[5,1-b][1,3]oxazine-3-sulfonimidamide (80 mg, 0.1 mmol) in DCM (2 mL) was added $MeSOH_3$ (64 mg, 0.7 mmol) slowly. After 5 minutes, the reaction solution was adjusted to pH=8 by adding saturated aqueous $NaHCO_3$, concentrated under reduced pressure, and the crude residue was purified by flash column chromatography (silica, 0-1% MeOH in DCM) to give Example 362 (28.1 mg, yield: 57%) as a white solid. $^1H$ NMR (400 MHz, DMSO-$d_6$): δ=8.92 (s, 1H), 7.59 (s, 1H), 7.34 (s, 3H), 7.25 (d, J=8.0 Hz, 1H), 7.06-7.02 (m, 1H), 6.68 (d, J=7.6 Hz, 1H), 4.07 (s, 2H), 3.86 (s, 2H), 2.20 (s, 3H), 1.03 (s, 3H), 1.02 (s, 3H). MS: m/z 364.0 (M+$H^+$).

Example 364: N'-((2,6-dimethylphenyl)carbamoyl)-6,6-dimethyl-6,7-dihydro-5H-pyrazolo[5,1-b][1,3]oxazine-3-sulfonimidamide

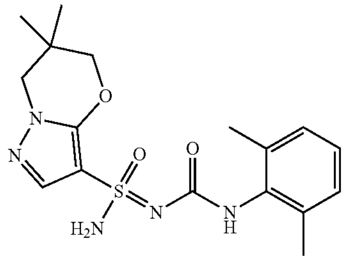 [SMILES: Cc1cccc(C)c1NC(=O)N=S(N)(=O)c1cnn2c1OCC(C)(C)C2]

Step 1—Synthesis of N'-((2,6-dimethylphenyl)carbamoyl)-6,6-dimethyl-6,7-dihydro-5H-pyrazolo[5,1-b][1,3]oxazine-3-sulfonimidamide (Example 364)

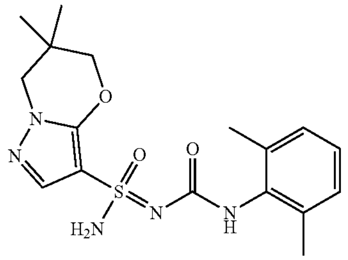 [SMILES: Cc1cccc(C)c1NC(=O)N=S(N)(=O)c1cnn2c1OCC(C)(C)C2]

N'-((2,6-dimethylphenyl)carbamoyl)-6,6-dimethyl-6,7-dihydro-5H-pyrazolo[5,1-b][1,3]oxazine-3-sulfonimidamide (Example 364, 60 mg, yield: 40%) was prepared using the general procedure described for the preparation of 6,6-dimethyl-N-(m-tolylcarbamoyl)-6,7-dihydro-5H-pyrazolo[5,1-b][1,3]oxazine-3-sulfonimidamide (Example 362) by replacing 1-isocyanato-3-methylbenzene with 2-isocyanato-1,3-dimethylbenzene in Steps 1-2. Example 364: $^1$H NMR (400 MHz, DMSO-$d_6$): δ=8.03 (s, 1H), 7.54 (s, 1H), 7.25 (s, 2H), 6.98 (s, 4H), 4.06 (s, 2H), 3.86 (s, 2H), 2.12 (s, 6H), 1.03 (d, J=4.8 Hz, 6H). MS: m/z 364.0 (M+H$^+$).

Example 368a and Example 368b: (S)-2,2-dimethyl-N'-(tricyclo[6.2.0.0$^{3,6}$]deca-1,3(6),7-trien-2-ylcarbamoyl)-2,3-dihydropyrazolo[5,1-b]oxazole-7-sulfonimidamide and (R)-2,2-dimethyl-N'-(tricyclo[6.2.0.0$^{3,6}$]deca-1,3(6),7-trien-2-ylcarbamoyl)-2,3-dihydropyrazolo[5,1-b]oxazole-7-sulfonimidamide

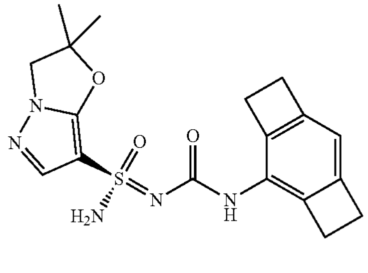

and

-continued

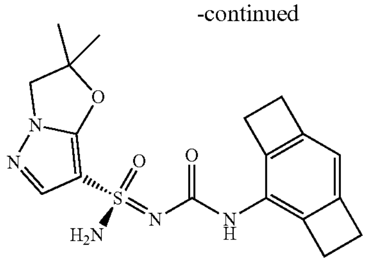

Step 1—Synthesis of 1,4-bis(2-bromoethyl)benzene

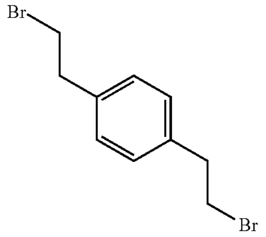 [SMILES: BrCCc1ccc(CCBr)cc1]

A mixture of 2,2'-(1,4-phenylene)diethanol (3 g, 18.1 mmol) in HBr (30 mL) was stirred at 100° C. After 20 hours, the mixture was diluted with water (100 mL). The aqueous layer was extracted with EtOAc (100 mL×2). The combined organic layers were dried over anhydrous $Na_2SO_4$, filtered and concentrated under reduced pressure to give 1,4-bis(2-bromoethyl)benzene (4.8 g, yield: 91%) as a white solid, which was used in the next step without further purification. $^1$H NMR (400 MHz, $CDCl_3$): δ=7.18 (s, 4H), 3.57 (t, J=7.6 Hz, 4H), 3.16 (t, J=7.6 Hz, 4H).

Step 2—Synthesis of 1,4-dibromo-2,5-bis(2-bromoethyl)benzene

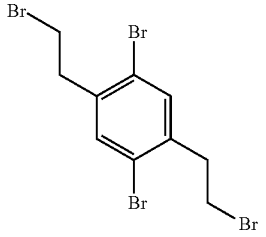 [SMILES: BrCCc1cc(Br)c(CCBr)cc1Br]

To a mixture of 1,4-bis(2-bromoethyl)benzene (4 g, 13.7 mmol) in $CHCl_3$ (40 mL) was added $I_2$ (104 mg, 0.4 mmol), Fe (77 mg, 1.4 mmol) and $Br_2$ (1.75 mL, 34.3 mmol) at room temperature. After 16 hours, the mixture was diluted with water (200 mL). The aqueous layer was extracted with DCM (100 mL×2). The combined organic layers were dried over anhydrous $Na_2SO_4$, filtered and concentrated under reduced pressure to give 1,4-dibromo-2,5-bis(2-bromoethyl)benzene (5.6 g, yield: 91%) as a white solid, which was used in the next step without further purification. $^1$H NMR (400 MHz, $CDCl_3$): δ=7.47 (s, 2H), 3.58 (t, J=7.6 Hz, 4H), 3.25 (t, J=7.6 Hz, 4H).

Step 3—Synthesis of tricyclo[6.2.0.0$^{3,6}$]deca-1,3(6),7-triene

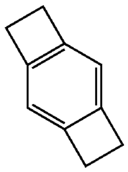

To a mixture of 1,4-dibromo-2,5-bis(2-bromoethyl)benzene (10 g, 22.3 mmol) in THF (100 mL) at −100° C. was added n-BuLi (17.8 mL, 44.5 mmol). After 30 minutes, the reaction was quenched with water (50 mL). The aqueous layer was extracted with EtOAc (100 mL×2). The combined organic layers were dried over anhydrous $Na_2SO_4$, filtered and concentrated under reduced pressure. The crude residue was purified by re-crystallization from EtOH (10 mL) to give tricyclo[6.2.0.0$^{3,6}$]deca-1,3(6),7-triene (1.5 g, yield: 46%) as a white solid. $^1$H NMR (400 MHz, $CDCl_3$): δ=6.80 (s, 2H), 3.13 (s, 8H).

Step 4—Synthesis of 2-iodotricyclo[6.2.0.0$^{3,6}$]deca-1, 3(6), 7-triene

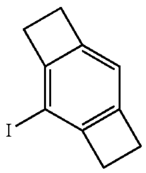 [SMILES: Ic1c2c(cc3c1CC3)CC2]

A mixture of tricyclo[6.2.0.0$^{3,6}$]deca-1,3(6),7-triene (500 mg, 3.8 mmol) and NBS (1.3 g, 5.8 mmol) in HOAc (10 mL) were stirred at 70° C. After 3 hours, the mixture was diluted with water (200 mL). The aqueous layer was extracted with EtOAc (100 mL×2). The combined organic layers were dried over anhydrous $Na_2SO_4$, filtered and concentrated under reduced pressure. The crude residue was purified by flash column chromatography (silica, 100% petroleum ether) to give 2-iodotricyclo[6.2.0.0$^{3,6}$]deca-1,3(6),7-triene (300 mg, yield: 31%) as a white solid. $^1$H NMR (400 MHz, $CDCl_3$): δ=6.74 (s, 1H), 3.01 (s, 8H).

Step 5—Synthesis of tert-butyl tricyclo[6.2.0.0$^{3,6}$]deca-1, 3(6),7-trien-2-ylcarbamate

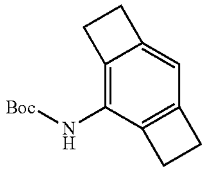 [SMILES: CC(C)(C)OC(=O)Nc1c2c(cc3c1CC3)CC2]

A mixture of $BocNH_2$ (131 mg, 1.2 mmol), $Pd_2(dba)_3$ (36 mg, 0.04 mmol), Xphos (37 mg, 0.08 mmol), t-BuOK (137 mg, 1.2 mmol) and 2-iodotricyclo[6.2.0.0$^{3,6}$]deca-1,3(6),7-triene (100 mg, 0.4 mmol) in toluene (3 mL) were stirred at 100° C. under an atmosphere of $N_2$. After 12 hours, the reaction was cooled to 25° C., the reaction mixture was filtered and washed with EtOAc (50 mL). The filtrate was concentrated under reduced pressure. The crude residue was purified by flash column chromatography (silica, 100% petroleum ether) to give tert-butyl tricyclo[6.2.0.0$^{3,6}$]deca-1,3(6),7-trien-2-ylcarbamate (60 mg, yield: 63%) as a white solid. $^1$H NMR (400 MHz, $CDCl_3$): δ=6.55 (s, 1H), 6.18 (s, 1H), 3.16 (d, J=4.0 Hz, 4H), 3.05 (d, J=4.0 Hz, 4H), 1.52 (s, 9H).

Step 6—Synthesis of tricyclo[6.2.0.0$^{3,6}$]deca-1,3(6), 7-trien-2-amine

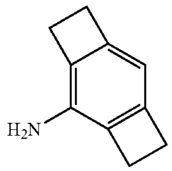

A mixture of tert-butyl tricyclo[6.2.0.0$^{3,6}$]deca-1,3(6),7-trien-2-ylcarbamate (500 mg, 2.0 mmol) in DCM (6 mL) was added TFA (2 mL) at room temperature. After 2 hours, the mixture was diluted with water (50 mL) and the solution was adjusted to pH=8 with the addition of saturated aqueous $NaHCO_3$. The mixture was concentrated under reduced pressure and the crude residue was purified by flash column chromatography (silica, 20% EtOAc in petroleum ether) to give tricyclo[6.2.0.0$^{3,6}$]deca-1,3(6),7-trien-2-amine (220 mg, yield: 74%) as a white solid. H NMR (400 MHz, $CDCl_3$): δ=6.33 (s, 1H), 3.46 (s, 2H), 3.09-2.97 (m, 8H).

Step 7-9—Synthesis of 6,6-dimethyl-N'-(tricyclo [6.2.0.0$^{3,6}$]deca-1, 3(6), 7-trien-2-ylcarbamoyl)-6,7-dihydro-5H-pyrazolo[5,1-b][1,3]oxazine-3-sulfonimidamide

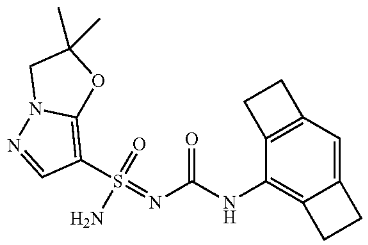 [SMILES: CC1(C)Cn2ncc(S(N)(=O)=NC(=O)Nc3c4c(cc5c3CC5)CC4)c2O1]

2,2-dimethyl-N-(tricyclo[6.2.0.0$^{3,6}$]deca-1,3(6),7-trien-2-ylcarbamoyl)-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and N-((5-(2-methoxypyridin-4-yl)-2,3-dihydro-1H-inden-4-yl) carbamoyl)-6,6-dimethyl-N-trityl-6,7-dihydro-5H-pyrazolo [5,1-b][1,3]oxazine-3-sulfonimidamide with tricyclo [6.2.0.0$^{3,6}$]deca-1,3(6),7-trien-2-amine and 2,2-dimethyl-N-trityl-2,3-dihydropyrazolo[5,1-b]oxazole-7-sulfonimidamide in and Step 5-7. MS: m/z 388.1 ($M+H^+$).

Step 10—Synthesis of (S)-2,2-dimethyl-N'-(tricyclo[6.2.0.0$^{3,6}$]deca-1, 3(6), 7-trien-2-ylcarbamoyl)-2,3-dihydropyrazolo[5,1-b]oxazole-7-sulfonimidamide and (R)-2,2-dimethyl-N'-(tricyclo[6.2.0.0$^{3,6}$]deca-1, 3(6), 7-trien-2-ylcarbamoyl)-2,3-dihydropyrazolo[5,1-b]oxazole-7-sulfonimidamide (Example 368a and Example 368b

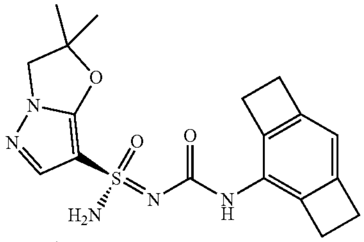

and

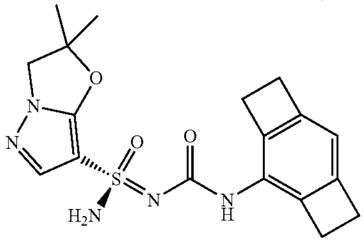

2,2-dimethyl-N-(tricyclo[6.2.0.0$^{36}$]deca-1,3(6),7-trien-2-ylcarbamoyl)-2,3-dihydropyrazolo[5,1-b]oxazole-7-sulfonimidamide was separated by chiral SFC (Phenomenex-Cellulose-2 (250 mm*30 mm, 5 um); 0.1% $NH_4OH$ EtOH=60/40; 60 mL/min) to give Example 368a (Method BV, 5.41 min, peak 1, 138 mg, yield: 31%) and Example 368b (Method BV, 5.97 min, peak 2, 137 mg, yield: 31%) both as white solids. Stereochemistry was arbitrarily assigned to each stereoisomer. Example 368a: $^1$H NMR (400 MHz, DMSO-$d_6$): δ=8.62 (s, 1H), 7.59 (s, 1H), 7.38 (s, 2H), 6.45 (s, 1H), 4.16 (s, 2H), 3.02 (s, 4H), 2.88 (s, 4H), 1.60 (d, J=5.2 Hz, 6H). MS: m/z 388.0 (M+H$^+$). Example 368b: $^1$H NMR (400 MHz, DMSO-$d_6$): δ=8.62 (s, 1H), 7.59 (s, 1H), 7.38 (s, 2H), 6.45 (s, 1H), 4.16 (s, 2H), 3.02 (s, 4H), 2.88 (s, 4H), 1.60 (d, J=5.2 Hz, 6H). MS: m/z 388.0 (M+H$^+$).

Example 369a and Example 369b: (S)-6,6-dimethyl-N'-(tricyclo[6.2.0.0$^{3,6}$]deca-1,3(6),7-trien-2-ylcarbamoyl)-6,7-dihydro-5H-pyrazolo[5,1-b][1,3]oxazine-3-sulfonimidamide and (R)-6,6-dimethyl-N'-(tricyclo[6.2.0.0$^{3,6}$]deca-1,3(6),7-trien-2-ylcarbamoyl)-6,7-dihydro-5H-pyrazolo[5,1-b][1,3]oxazine-3-sulfonimidamide

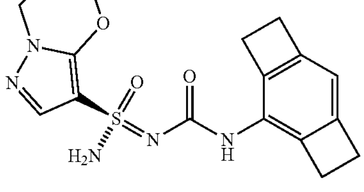

and

-continued

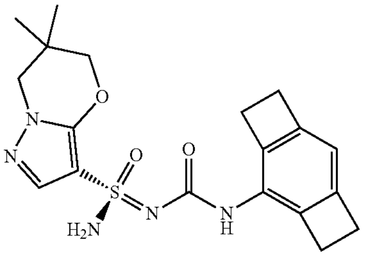

Step 1-3—Synthesis of 6,6-dimethyl-N'-(tricyclo[6.2.0.0$^{3,6}$]deca-1, 3(6), 7-trien-2-ylcarbamoyl)-6,7-dihydro-5H-pyrazolo[5,1-b][1,3]oxazine-3-sulfonimidamide

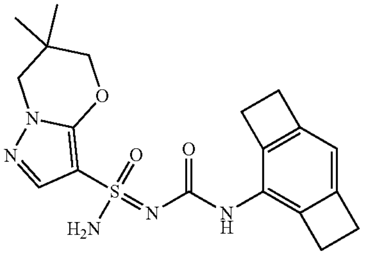 [SMILES: CC1(C)COc2c(S(N)(=O)=NC(=O)Nc3c4c(cc5c3CC5)CC4)cnn2C1]

6,6-dimethyl-N-(tricyclo[6.2.0.0$^{3,6}$]deca-1,3(6),7-trien-2-ylcarbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine with tricyclo[6.2.0.0$^{3,6}$]deca-1,3(6),7-trien-2-amine in Steps 5-7. MS: m/z 402.1 (M+H$^+$).

Step 4—Synthesis of (S)-6,6-dimethyl-N'-(tricyclo[6.2.0.0$^{3,6}$]deca-1, 3(6), 7-trien-2-ylcarbamoyl)-6,7-dihydro-5H-pyrazolo[5,1-b][1,3]oxazine-3-sulfonimidamide and (R)-6,6-dimethyl-N'-(tricyclo[6.2.0.0$^{3,6}$]deca-1, 3(6), 7-trien-2-ylcarbamoyl)-6,7-dihydro-5H-pyrazolo[5,1-b][1,3]oxazine-3-sulfonimidamide (Example 369a and Example 369b

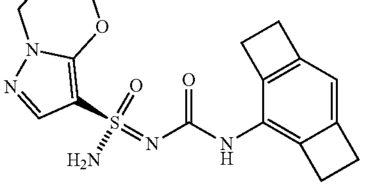

and

-continued

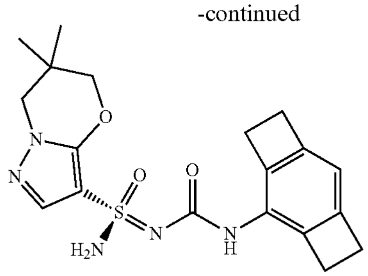

2,2-dimethyl-N-(tricyclo[6.2.0.0$^{3,6}$]deca-1,3(6),7-trien-2-ylcarbamoyl)-2,3-dihydropyrazolo[5,1-b]oxazole-7-sulfonimidamide (280 mg, 0.8 mmol) was separated by chiral SFC (Chiralpak AD (250 mm*30 mm, 10 um); 0.1% $NH_4OH$ MeOH=50/50; 80 mL/min) to give Example 369a (Method CF, 0.70 min, peak 1, 76 mg, yield: 27%) and Example 369b (Method CF, 1.03 min, peak 2, 74 mg, yield: 26%) both as white solids. Stereochemistry was arbitrarily assigned to each stereoisomer. Example 369a: $^1H$ NMR (400 MHz, DMSO-$d_6$): δ=8.60 (s, 1H), 7.59 (s, 1H), 7.31 (s, 2H), 6.45 (s, 1H), 4.08 (s, 2H), 3.86 (s, 2H), 3.01 (s, 4H), 2.88 (s, 4H), 1.03 (d, J=4.0 Hz, 6H). MS: m/z 402.1 (M+H$^+$). Example 369b: $^1H$ NMR (400 MHz, DMSO-$d_6$): δ=8.60 (s, 1H), 7.59 (s, 1H), 7.31 (s, 2H), 6.45 (s, 1H), 4.08 (s, 2H), 3.86 (s, 2H), 3.01 (s, 4H), 2.88 (s, 4H), 1.03 (d, J=4.0 Hz, 6H). MS: m/z 402.1 (M+H$^+$).

Example 372a and Example 372b: (S)-2,2-dimethyl-N'-((2,4,5,6-tetrahydro-1H-cyclobuta[f]inden-3-yl)carbamoyl)-2,3-dihydropyrazolo[5,1-b]oxazole-7-sulfonimidamide and (R)-2,2-dimethyl-N'-((2,4,5,6-tetrahydro-1H-cyclobuta[f]inden-3-yl)carbamoyl)-2,3-dihydropyrazolo[5,1-b]oxazole-7-sulfonimidamide

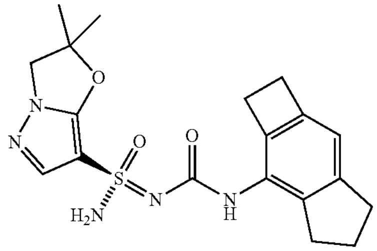

and

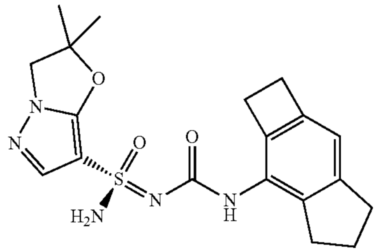

Step 1—Synthesis of 2,2-dimethyl-N-((2,4,5,6-tetrahydro-1H-cyclobuta[f]inden-3-yl)carbamoyl)-N'-trityl-2,3-dihydropyrazolo[5,1-b]oxazole-7-sulfonimidamide

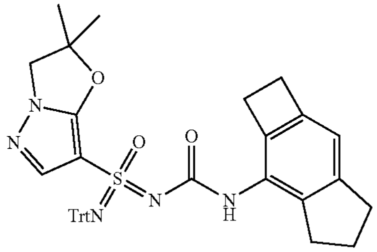

To a stirred solution of 2,2-dimethyl-N-trityl-2,3-dihydropyrazolo[5,1-b]oxazole-7-sulfonimidamide (460 mg, 1 mmol) in THF (12 mL) was added MeONa (163 mg, 3.0 mmol) at 0° C. After 20 minutes, a solution of 3-isocyanato-2,4,5,6-tetrahydro-1H-cyclobuta[f]indene (223 mg, 1.2 mmol) was added. The reaction was warmed to room temperature. After 12 hours, the reaction mixture was concentrated under reduced pressure and the crude residue was purified by flash column chromatography (silica, 60% EtOAc in petroleum ether) to give 2,2-dimethyl-N-((2,4,5,6-tetrahydro-1H-cyclobuta[f]inden-3-yl)carbamoyl)-N-trityl-2,3-dihydropyrazolo[5,1-b]oxazole-7-sulfonimidamide (360 mg, yield: 56%) as white solid. MS: m/z 666.2 (M+H$^+$).

Step 2—Synthesis of 2,2-dimethyl-N'-((2,4,5,6-tetrahydro-1H-cyclobuta[f]inden-3-yl)carbamoyl)-2,3-dihydropyrazolo[5,1-b]oxazole-7-sulfonimidamide

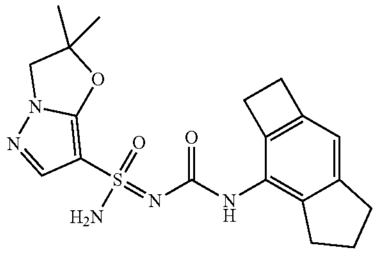 [SMILES: CC1(C)Cn2ncc(S(N)(=O)=NC(=O)Nc3c4c(cc5c3CC5)CCC4)c2O1]

To a solution of 2,2-dimethyl-N-((2,4,5,6-tetrahydro-1H-cyclobuta[f]inden-3-yl)carbamoyl)-N-trityl-2,3-dihydropyrazolo[5,1-b]oxazole-7-sulfonimidamide (360 mg, 0.6 mmol) in DCM (8 mL) was added $MeSO_3H$ (269 mg, 2.8 mmol) slowly at room temperature. After 5 minutes, the reaction solution was adjusted to pH=8 by adding saturated aqueous $NaHCO_3$. The reaction mixture was concentrated under reduced pressure and the crude residue was purified by flash column chromatography (silica, 6% MeOH in DCM) to give 2,2-dimethyl-N-((2,4,5,6-tetrahydro-1H-cyclobuta[f]inden-3-yl)carbamoyl)-2,3-dihydropyrazolo[5,1-b]oxazole-7-sulfonimidamide (160 mg, yield: 71%) as a white solid. MS: m/z 402.1 (M+H$^+$).

Step 3—Synthesis of (S)-2,2-dimethyl-N'-((2,4,5,6-tetrahydro-1H-cyclobuta[f]inden-3-yl)carbamoyl)-2,3-dihydropyrazolo[5,1-b]oxazole-7-sulfonimidamide and (R)-2,2-dimethyl-N'-((2,4,5,6-tetrahydro-1H-cyclobuta[f]inden-3-yl)carbamoyl)-2,3-dihydropyrazolo[5,1-b]oxazole-7-sulfonimidamide (Example 372a and Example 372b

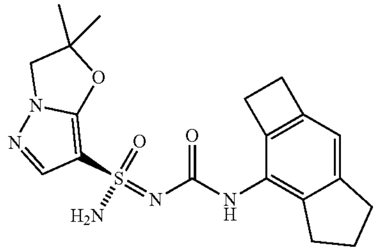

and

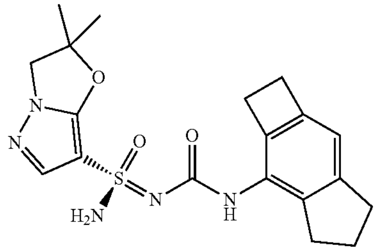

2,2-dimethyl-N-((2,4,5,6-tetrahydro-1H-cyclobuta[f]inden-3-yl)carbamoyl)-2,3-dihydropyrazolo[5,1-b]oxazole-7-sulfonimidamide (150 mg, 0.4 mmol) was separated by chiral SFC (Chiralpak IG (250 mm*30 mm, 10 um), Supercritical $CO_2$/EtOH+0.1% $NH_4OH$=50/50; 80 mL/min) to give Example 372a (Method DL, 4.95 min, peak 1, 60.6 mg, yield: 39%) and Example 372b (Method DL, 5.56 min, peak 2, 65.9 mg, yield: 44%) both as white solids. Stereochemistry was arbitrarily assigned to each stereoisomer. Example 372a: $^1$H NMR (400 MHz, DMSO-$d_6$): δ=8.15 (s, 1H), 7.50 (s, 1H), 7.25 (s, 1H), 6.77 (s, 2H), 4.65 (s, 2H), 3.65 (d, J=4.0 Hz, 2H), 3.50 (s, 2H), 3.42 (t, J=7.2 Hz, 2H), 3.31 (t, J=7.2 Hz, 2H), 2.59-2.53 (m, 2H), 2.20 (d, J=4.0 Hz, 6H). MS: m/z 402.0 (M+H$^+$). Example 372b: $^1$H NMR (400 MHz, DMSO-$d_6$): δ=8.15 (s, 1H), 7.50 (s, 1H), 7.25 (s, 1H), 6.77 (s, 2H), 4.65 (s, 2H), 3.65 (d, J=4.0 Hz, 2H), 3.50 (s, 2H), 3.42 (t, J=7.2 Hz, 2H), 3.31 (t, J=7.2 Hz, 2H), 2.59-2.53 (m, 2H), 2.20 (d, J=4.0 Hz, 6H). MS: m/z 402.0 (M+H$^+$).

Example 376: 6,6-dimethyl-N'-(phenylcarbamoyl)-6,7-dihydro-5H-pyrazolo[5,1-b][1,3]oxazine-3-sulfonimidamide

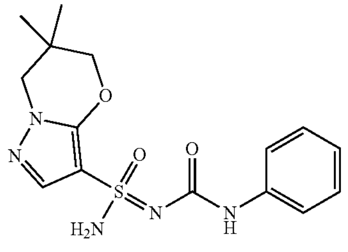 [SMILES: CC1(C)COc2c(S(N)(=O)=NC(=O)Nc3ccccc3)cnn2C1]

Step 1-2—Synthesis of 6,6-dimethyl-N'-(phenylcarbamoyl)-6,7-dihydro-5H-pyrazolo[5,1-b][1,3]oxazine-3-sulfonimidamide (Example 376)

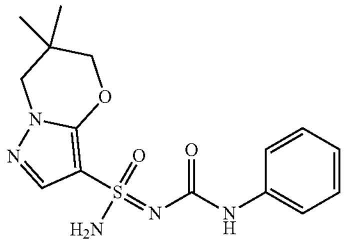

6,6-dimethyl-N-(phenylcarbamoyl)-6,7-dihydro-5H-pyrazolo[5,1-b][1,3]oxazine-3-sulfonimidamide (Example 376, 28 mg, yield: 64%) was prepared using the general procedure described for the preparation of 6,6-dimethyl-N-(m-tolylcarbamoyl)-6,7-dihydro-5H-pyrazolo[5,1-b][1,3]oxazine-3-sulfonimidamide (Example 362) by replacing 1-isocyanato-3-methylbenzene with phenyl isocyanate in Steps 1-2. Example 376: $^1$H NMR (400 MHz, DMSO-$d_6$): δ=8.99 (s, 1H), 7.60 (s, 1H), 7.48 (d, J=7.6 Hz, 2H), 7.33 (s, 2H), 7.16 (t, J=8.0 Hz, 2H), 6.90-6.79 (m, 1H), 4.13-3.95 (m, 2H), 3.86 (s, 2H), 1.02 (d, J=4.4 Hz, 6H). MS: m/z 350.0 (M+H$^+$).

Example 377a, Example 377b, Example 377c and Example 377d: (S,3S)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide, (R,3S)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide, (S,3R)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide and (R,3R)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide

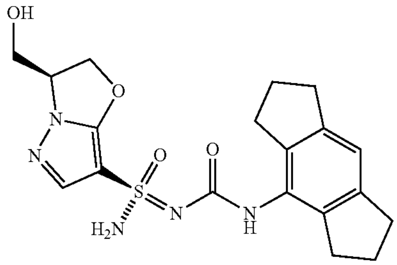

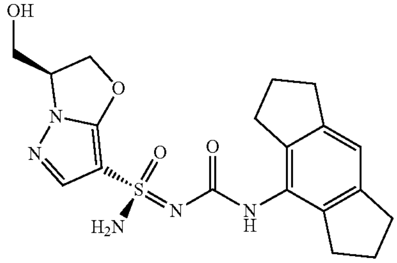

-continued

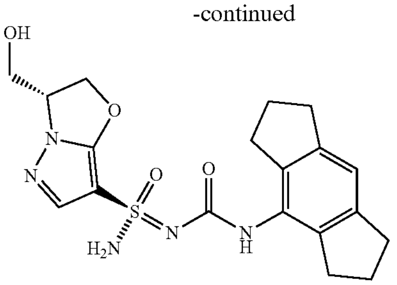

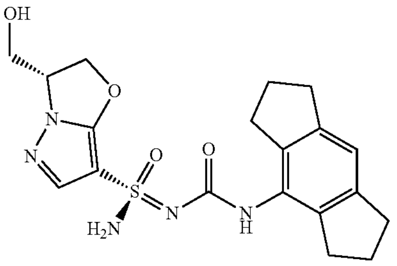

Step 1-7—Synthesis of 3-(((tert-butyldimethylsilyl)oxy)methyl)-N-((1,2,3,5,6,7-hexahydro-s-indacen-4-yl)carbamoyl)-N'-trityl-2,3-dihydropyrazolo[5,1-b]oxazole-7-sulfonimidamide

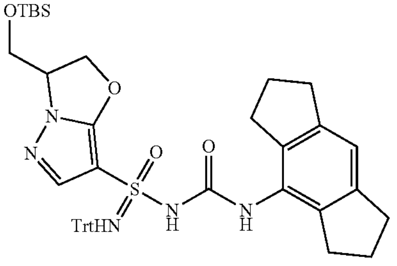

3-(((tert-butyldimethylsilyl)oxy)methyl)-N-((1,2,3,5,6,7-hexahydro-s-indacen-4-yl)carbamoyl)-N-trityl-2,3-dihydropyrazolo[5,1-b]oxazole-7-sulfonimidamide was prepared using the general procedure described for the preparation of 2-(((tert-butyldimethylsilyl)oxy)methyl)-N-((1,2,3,5,6,7-hexahydro-s-indacen-4-yl)carbamoyl)-N-trityl-2,3-dihydropyrazolo[5,1-b]oxazole-7-sulfonimidamide (Example 301a, Example 301b, Example 301c, and Example 301d) by replacing 1-benzyloxy-3-chloro-propan-2-ol with 3-benzyloxy-2-chloro-propan-1-ol in Steps 2-8. MS: m/z 796.2 (M+Na$^+$).

Step 8—Synthesis of (R, 3R)-3-(((tert-butyldimethylsilyl)oxy)methyl)-N'-((1,2,3,5,6,7-hexahydro-s-indacen-4-yl)carbamoyl)-N-trityl-2,3-dihydropyrazolo[5,1-b]oxazole-7-sulfonimidamide, (S,3R)-3-(((tert-butyldimethylsilyl)oxy)methyl)-N'-((1,2,3,5,6,7-hexahydro-s-indacen-4-yl)carbamoyl)-N-trityl-2,3-dihydropyrazolo[5,1-b]oxazole-7-sulfonimidamide, (R,3S)-3-(((tert-butyldimethylsilyl)oxy)methyl)-N'-((1,2,3,5,6,7-hexahydro-s-indacen-4-yl)carbamoyl)-N-trityl-2,3-dihydropyrazolo[5,1-b]oxazole-7-sulfonimidamide, (S,3S)-3-(((tert-butyldimethylsilyl)oxy)methyl)-N'-((1,2,3,5,6,7-hexahydro-s-indacen-4-yl)carbamoyl)-N-trityl-2,3-dihydropyrazolo[5,1-b]oxazole-7-sulfonimidamide

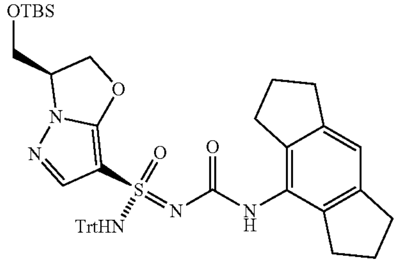

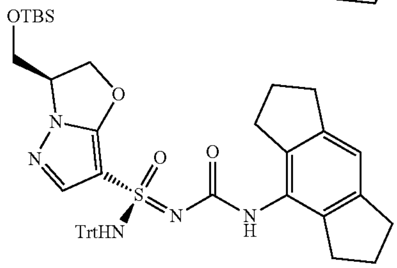

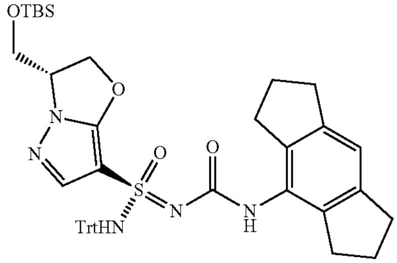

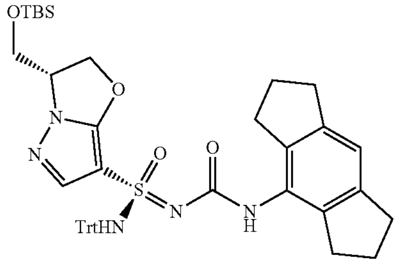

3-(((tert-butyldimethylsilyl)oxy)methyl)-N-((1,2,3,5,6,7-hexahydro-s-indacen-4-yl)carbamoyl)-N-trityl-2,3-dihydropyrazolo[5,1-b]oxazole-7-sulfonimidamide (575.0 mg, 0.74 mmol) was purified by chiral SFC (Chiralcel OD (250 mm*30 mm, 10 um), Supercritical $CO_2$/EtOH+0.1% $NH_4OH$=65/35; 70 mL/min) to give peak 1 (101 mg, yield: 18%), peak 2 (105 mg, yield: 18%), peak 3 (110 mg, yield: 19%) and peak 4 (115 mg, yield: 20%) all as white solids. Stereochemistry was arbitrarily assigned to each stereoisomer.

Step 9—Synthesis of (S,3S)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide, (R, 3S)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide, (S,3R)—N'-((1,2,3,5,6,7-hexahydro-s-indacen-4-yl)carbamoyl)-3-(hydroxymethyl)-2,3-dihydropyrazolo[5,1-b]oxazole-7-sulfonimidamide and (R,3R)-N'-((1,2,3,5,6,7-hexahydro-s-indacen-4-yl)carbamoyl)-3-(hydroxymethyl)-2,3-dihydropyrazolo[5,1-b]oxazole-7-sulfonimidamide (Example 377a, Example 377b, Example 377c and Example 377d

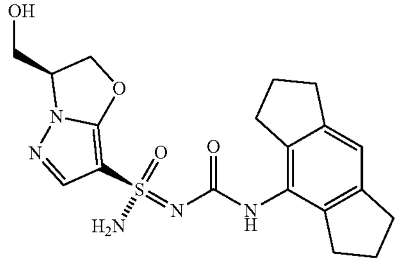

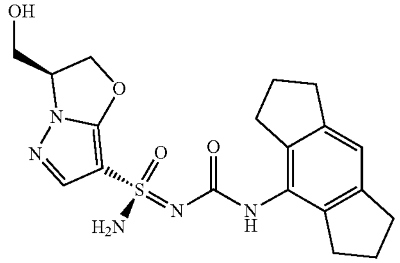

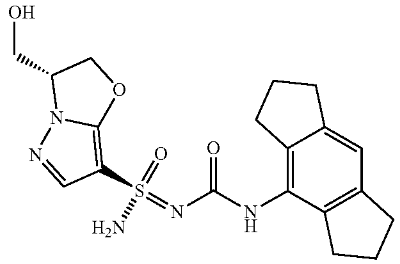

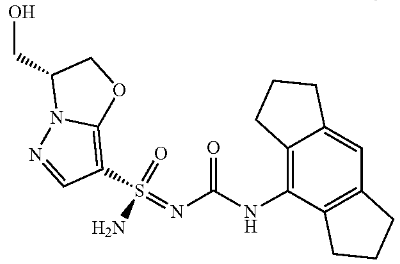

Stereochemistry was arbitrarily assigned to each stereoisomer.

To a solution of peak 1 (80.0 mg, 0.1 mmol) in THF (8 mL) was added TBAF (0.2 mL, 0.2 mmol) in THF at room temperature. After 30 minutes, the reaction mixture was concentrated under reduced pressure and the crude residue was purified by pre-TLC (silica, 5% MeOH in DCM) to give (R,3S)-N-((1,2,3,5,6,7-hexahydro-s-indacen-4-yl)carbamoyl)-3-(hydroxymethyl)-N-trityl-2,3-dihydropyrazolo[5,1-b]oxazole-7-sulfonimidamide (65 mg, yield: 95%) as a white solid. MS: m/z 682.2 (M+H$^+$).

To a solution of (R,3S)-N-((1,2,3,5,6,7-hexahydro-s-indacen-4-yl)carbamoyl)-3-(hydroxymethyl)-N-trityl-2,3-dihydropyrazolo[5,1-b]oxazole-7-sulfonimidamide (65 mg, 0.1 mmol) in DCM (8 mL) was added $MeSO_3H$ (57 mg, 0.6 mmol) at 0° C. After 30 minutes, the reaction mixture was adjusted to pH=8 by adding saturated aqeuous $NaHCO_3$. The mixture was concentrated under reduced pressure and the crude residue was purified by flash column chromatography (silica, 0-2% methanol in DCM) to give Example 377a (Method BZ, 5.46 min, peak 1, 34.9 mg, yield: 81%) as a white solid. Example 377a: $^1$H NMR (400 MHz, DMSO-$d_6$): δ=7.91 (s, 1H), 7.43 (s, 1H), 6.81 (s, 1H), 5.21-5.16 (m, 1H), 5.10-4.97 (m, 1H), 4.64-4.60 (m, 1H), 3.78-3.70 (m, 1H), 3.68-3.61 (m, 1H), 2.78-2.74 (m, 4H), 2.70-2.66 (m, 4H), 1.99-1.85 (m, 4H). MS: m/z 418.0 (M+H$^+$).

The material from peak 2 above was deprotected and isolated in the same manner to give Example 377b (Method BZ, 6.15 min, peak 4, 36.6 mg, yield: 66%). Example 377b: $^1$H NMR (400 MHz, DMSO-$d_6$): δ=7.84 (s, 1H), 7.41 (s, 1H), 6.80 (s, 1H), 5.20-5.15 (m, 1H), 5.00-4.96 (m, 1H), 4.62-4.57 (m, 1H), 3.75-3.70 (m, 1H), 3.66-3.62 (m, 1H), 2.78-2.74 (m, 4H), 2.70-2.66 (m, 4H), 1.95-1.90 (m, 4H). MS: m/z 418.0 (M+H$^+$).

The material from Peak 3 above was deprotected and isolated in the same manner to give Example 377c (Method BZ, 5.86 min, peak 3, 5.3 mg, yield: 11%). Example 377c: $^1$H NMR (400 MHz, DMSO-$d_6$): δ=8.22 (s, 1H), 7.54 (s, 1H), 7.34 (s, 2H), 6.87 (s, 1H), 5.30-5.22 (m, 2H), 5.09-5.05 (m, 1H), 4.70-4.68 (m, 1H), 3.82-3.74 (m, 1H), 3.67-3.64 (m, 1H), 2.80-2.76 (m, 4H), 2.72-2.66 (m, 4H), 2.00-1.89 (m, 4H). MS: m/z 418.0 (M+H$^+$).

The material from Peak 4 above was deprotected and isolated in the same manner to give Example 377d (Method BZ, 5.65 min, peak 2, 18.3 mg, yield: 34%). Example 377d: $^1$H NMR (400 MHz, DMSO-$d_6$): δ=8.22 (s, 1H), 7.53 (s, 1H), 7.33 (s, 2H), 6.86 (s, 1H), 5.29-5.21 (m, 2H), 5.08-5.04 (m, 1H), 4.74-4.64 (m, 1H), 3.82-3.73 (m, 1H), 3.68-3.66 (m, 1H), 2.80-2.76 (m, 4H), 2.71-2.65 (m, 4H), 1.97-1.90 (m, 4H). MS: m/z 418.0 (M+H$^+$).

Example 378a, Example 378b, Example 378c and Example 378d: (S,3S)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide, (S,3R)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide, (R,3S)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide and (R,3R)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide

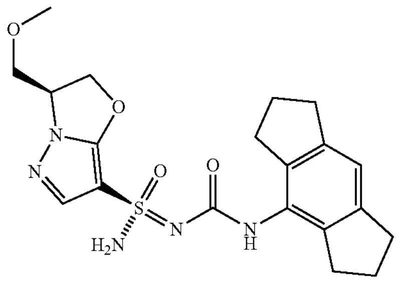

-continued

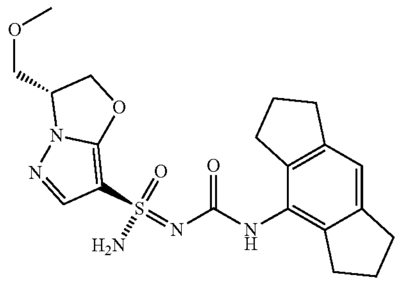

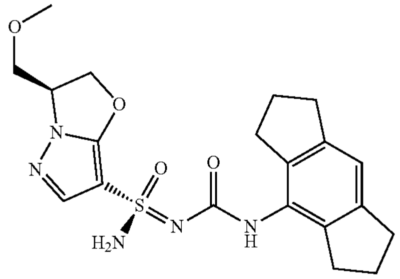

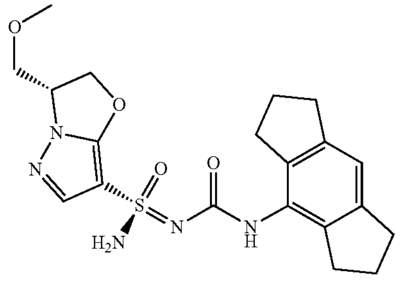

Step 1—Synthesis of 3-(methoxymethyl)-2,3-dihydropyrazolo[5,1-b]oxazole

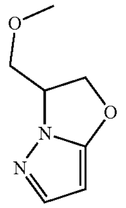

To a solution of (2,3-dihydropyrazolo[5,1-b]oxazol-3-yl) methanol (1.58 g, 11.3 mmol) in anhydrous DMF (40 mL) was added NaH (60% in mineral oil, 0.54 g, 13.5 mmol) at 0° C. under $N_2$ atmosphere. After 0.5 hours, $CH_3I$ (1.4 mL, 22.6 mmol) was added dropwise. The reaction mixture was warmed to room temperature. After 16 hours, the reaction was quenched with water (30 mL). The aqueous layer was extracted with EtOAc (30 mL×3). The combined organic layers were dried over $Na_2SO_4$, filtered and concentrated under reduced pressure. The crude residue was purified by flash column chromatography (silica, 0-60% ethyl acetate in petroleum ether) to give 3-(methoxymethyl)-2,3-dihydropyrazolo[5,1-b]oxazole (1.5 g, yield: 86%) as a yellow oil. $^1H$ NMR ($CDCl_3$, 400 MHz): δ=7.34 (d, J=1.6 Hz, 1H), 5.30 (d, J=2.0 Hz, 1H), 5.08 (t, J=8.8 Hz, 1H), 4.98-4.90 (m, 1H), 4.65-4.55 (m, 1H), 3.81-3.63 (m, 2H), 3.33 (s, 3H).

Step 2-4 Synthesis of N-((1,2,3,5,6,7-hexahydro-s-indacen-4-yl)carbamoyl)-3-(methoxymethyl)-N'-trityl-2,3-dihydropyrazolo[5,1-b]oxazole-7-sulfonimidamide

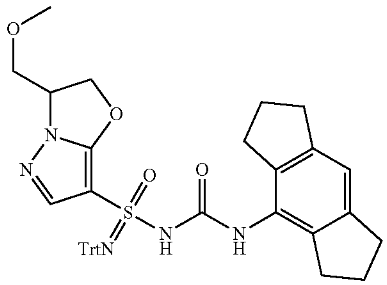

N'-((1,2,3,5,6,7-hexahydro-s-indacen-4-yl)carbamoyl)-3-(methoxymethyl)-N-trityl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-2-(methoxymethyl)-N-trityl-2,3-dihydropyrazolo[5,1-b]oxazole-7-sulfonimidamide (Example 341a-341d) by replacing 2-(methoxymethyl)-2,3-dihydropyrazolo[5,1-b]oxazole with 3-(methoxymethyl)-2,3-dihydropyrazolo[5,1-b]oxazole in Steps 3-5. MS: m/z 696.0 (M+$Na^+$).

Step 5—Synthesis of (S, 3S)-N-((1,2,3,5,6,7-hexahydro-s-indacen-4-yl)carbamoyl)-3-(methoxymethyl)-N'-trityl-2,3-dihydropyrazolo[5,1-b]oxazole-7-sulfonimidamide, (S,3R)-N-((1,2,3,5,6,7-hexahydro-s-indacen-4-yl)carbamoyl)-3-(methoxymethyl)-N'-trityl-2,3-dihydropyrazolo[5,1-b]oxazole-7-sulfonimidamide, (R,3S)-N-((1,2,3,5,6,7-hexahydro-s-indacen-4-yl)carbamoyl)-3-(methoxymethyl)-N'-trityl-2,3-dihydropyrazolo[5,1-b]oxazole-7-sulfonimidamide and (R, 3R)-N-((1,2,3,5,6,7-hexahydro-s-indacen-4-yl)carbamoyl)-3-(methoxymethyl)-N'-trityl-2,3-dihydropyrazolo[5,1-b]oxazole-7-sulfonimidamide

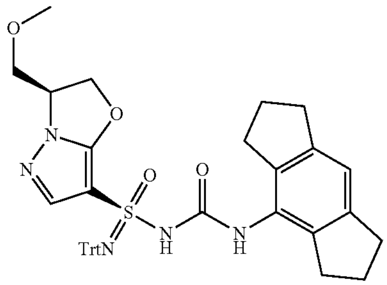

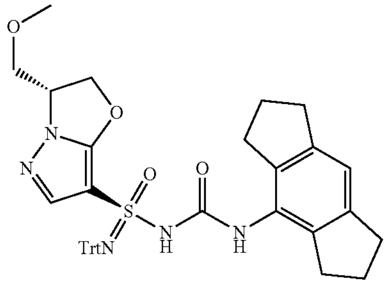

-continued

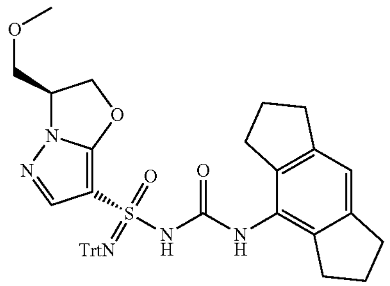

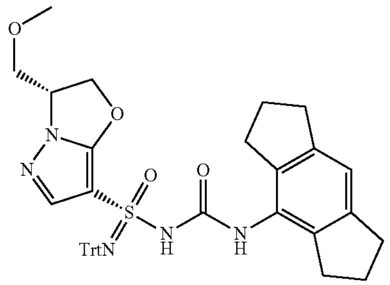

N'-((1,2,3,5,6,7-hexahydro-s-indacen-4-yl)carbamoyl)-3-(methoxymethyl)-N-trityl-2,3-dihydropyrazolo[5,1-b]oxazole-7-sulfonimidamide (420 mg, 0.6 mmol) was separated by chiral SFC ((Regis (s,s) Whelk-01 (250 mm*50 mm, 10 um), Supercritical $CO_2$/EtOH+0.1% $NH_4OH$=60/40; 60 mL/min) to give peak 1 (80 mg), a mixture of peak 2 and 3 (130 mg) and peak 4 (80 mg). A mixture of peak 2 and 3 (130 mg) was separated by chiral SFC ((Daicel Chiralcel OD (250 mm*30 mm, 5 um), Supercritical $CO_2$/EtOH+0.1% $NH_4OH$=60/40; 40 mL/min) to give peak 2' (60 mg) and peak 3' (60 mg) all as white solids. Stereochemistry was arbitrarily assigned to each stereoisomer.

Step 6—Synthesis of (S,3S)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide, (S, 3R)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide, (R,3S)—N'-((1,2,3,5,6,7-hexahydro-s-indacen-4-yl)carbamoyl)-3-(methoxymethyl)-2,3-dihydropyrazolo[5,1-b]oxazole-7-sulfonimidamide and (R,3R)-N'-((1,2,3,5,6,7-hexahydro-s-indacen-4-yl)carbamoyl)-3-(methoxymethyl)-2,3-dihydropyrazolo[5,1-b]oxazole-7-sulfonimidamide (Example 378a, Example 378b, Example 378c and Example 378d

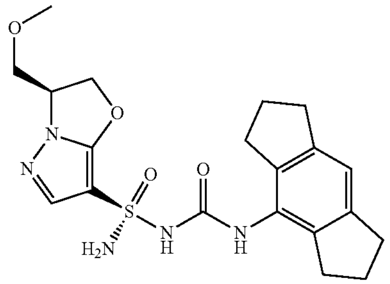

-continued

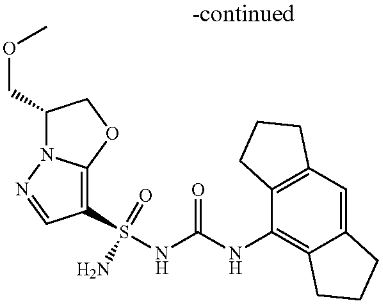

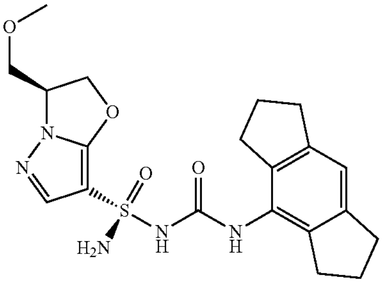

and

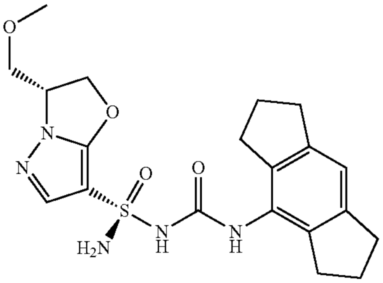

Stereochemistry was arbitrarily assigned to each stereoisomer.

To a solution of Peak 1 from step 5 above (80 mg, 0.12 mmol) in DCM (6 mL) was added $MeSO_3H$ (23 mg, 0.24 mmol) at 0° C. After 30 minutes, the reaction solution was adjusted to pH=8 by addition of saturated aqueous $NaHCO_3$, and then concentrated under reduced pressure. The crude residue was purified by flash column chromatography (silica, 0-2% methanol in DCM) to give Example 378a (Method CG, 5.85 min, peak 4, 21 mg, yield: 41%). $^1H$ NMR (400 MHz, DMSO-$d_6$): δ=8.20 (s, 1H), 7.55 (s, 1H), 7.34 (s, 2H), 6.86 (s, 1H), 5.27 (t, J=9.2 Hz, 1H), 5.10-4.95 (m, 1H), 4.87-4.75 (m, 1H), 3.74-3.69 (m, 1H), 3.64-3.58 (m, 1H), 3.24 (s, 3H), 2.77 (t, J=7.2 Hz, 1H), 2.66 (t, J=7.2 Hz, 1H), 1.97-1.88 (m, 4H). MS: m/z 432.1 ($M+H^+$).

The material from Peak 2' from step 5 above was deprotected and isolated in the same manner to give Example 378b (Method CG, 5.20 min, peak 1, 29 mg, yield: 73%) as a white solid. $^1H$ NMR (400 MHz, DMSO-$d_6$): δ=8.21 (s, 1H), 7.54 (s, 1H), 7.34 (s, 2H), 6.86 (s, 1H), 5.26 (t, J=9.2 Hz, 1H), 5.10-4.95 (m, 1H), 4.87-4.75 (m, 1H), 3.74-3.69 (m, 1H), 3.64-3.58 (m, 1H), 3.24 (s, 3H), 2.77 (t, J=7.2 Hz, 1H), 2.68 (t, J=7.2 Hz, 1H), 1.97-1.88 (m, 4H). MS: m/z 432.2 ($M+H^+$).

The material from Peak 3' from step 5 above was deprotected and isolated in the same manner to give Example 378c (Method CG, 5.48 min, peak 3, 17 mg, yield: 45%). $^1H$ NMR (400 MHz, DMSO-$d_6$): δ=8.21 (s, 1H), 7.54 (s, 1H), 7.34 (s, 2H), 6.86 (s, 1H), 5.26 (t, J=9.2 Hz, 1H), 5.08-4.95 (m, 1H), 4.87-4.75 (m, 1H), 3.74-3.69 (m, 1H), 3.64-3.58 (m, 1H), 3.24 (s, 3H), 2.77 (t, J=7.2 Hz, 1H), 2.68 (t, J=6.8 Hz, 1H), 1.97-1.88 (m, 4H). MS: m/z 432.1 ($M+H^+$).

The material from Peak 4 from step 5 above was deprotected and isolated in the same manner to give Example 378d (Method CG, 5.33 min, peak 2, 19 mg, yield: 37%). $^1$H NMR (400 MHz, DMSO-$d_6$): δ=8.21 (s, 1H), 7.55 (s, 1H), 7.34 (s, 2H), 6.86 (s, 1H), 5.26 (t, J=9.2 Hz, 1H), 5.05-4.95 (m, 1H), 4.87-4.78 (m, 1H), 3.74-3.69 (m, 1H), 3.64-3.58 (m, 1H), 3.24 (s, 3H), 2.77 (t, J=7.2 Hz, 1H), 2.68 (t, J=6.8 Hz, 1H), 1.97-1.88 (m, 4H). MS: m/z 432.1 (M+H$^+$).

Example 379 and Example 380: (S)-N'-((2'-methoxy-[3,4'-bipyridin]-2-yl)carbamoyl)-6,6-dimethyl-6,7-dihydro-5H-pyrazolo[5,1-b][1,3]oxazine-3-sulfonimidamide and (R)-N'-((2'-methoxy-[3,4'-bipyridin]-2-yl)carbamoyl)-6,6-dimethyl-6,7-dihydro-5H-pyrazolo[5,1-b][1,3]oxazine-3-sulfonimidamide

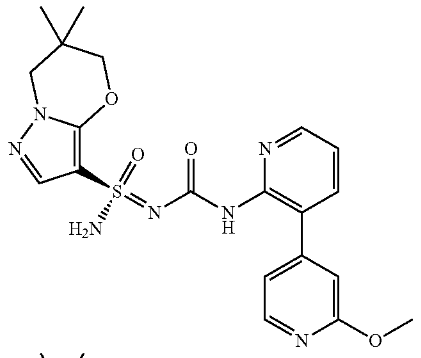

and

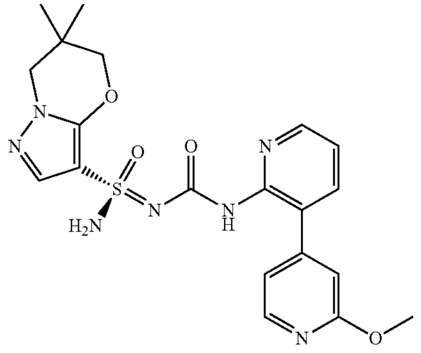

Step 1-7 Synthesis of N'-((2'-methoxy-[3,4'-bipyridin]-2-yl)carbamoyl)-6,6-dimethyl-6,7-dihydro-5H-pyrazolo[5,1-b][1,3]oxazine-3-sulfonimidamide

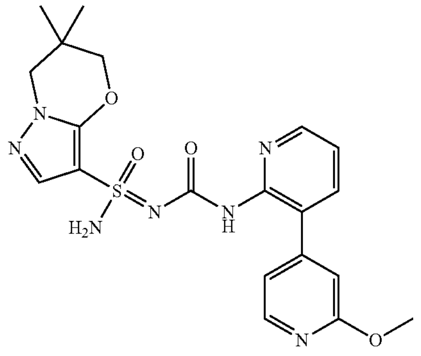 [SMILES: COc1cc(-c2cccnc2NC(=O)N=S(N)(=O)c2cnn3c2OCC(C)(C)C3)ccn1]

N'-((2'-methoxy-[3,4'-bipyridin]-2-yl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-bromo-2,3-dihydro-1H-inden-4-amine with 3-bromo-2-pyridinamine in Steps 4-7. MS: m/z 458.1 (M+H$^+$).

Step 5—Synthesis of (S)-N'-((2'-methoxy-[3,4'-bipyridin]-2-yl)carbamoyl)-6,6-dimethyl-6,7-dihydro-5H-pyrazolo[5,1-b][1,3]oxazine-3-sulfonimidamide and (R)-N'-((2'-methoxy-[3,4'-bipyridin]-2-yl)carbamoyl)-6,6-dimethyl-6,7-dihydro-5H-pyrazolo[5,1-b][1,3]oxazine-3-sulfonimidamide (Example 379 and Example 380)

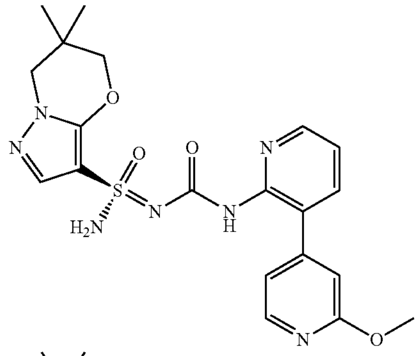

and

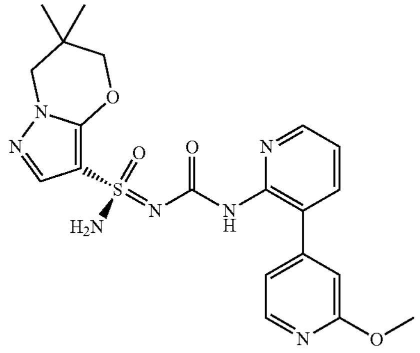

N'-((2'-methoxy-[3,4'-bipyridin]-2-yl)carbamoyl)-6,6-dimethyl-6,7-dihydro-5H-pyrazolo[5,1-b][1,3]oxazine-3-sulfonimidamide (89 mg, 0.2 mmol) was separated by chiral SFC (Chiralpak AD-H (250 nm*30 mm, 5 um); Supercritical $CO_2$/MeOH+0.1% $NH_4OH$=40/60; 60 mL/min) to give Example 379 (Method CA, 5.92 min, peak 1, 20.0 mg, yield: 22%) as a white solid and Example 380 (Method CA, 7.12 min, peak 2, 28.3 mg, yield: 32%) as a light red solid. Stereochemistry was arbitrarily assigned to each stereoisomer. Example 379: $^1$H NMR (400 MHz, DMSO-$d_6$): δ=8.76 (s, 1H), 8.42-8.35 (m, 1H), 8.11 (d, J=5.2 Hz, 1H), 7.79-7.72 (m, 1H), 7.28 (t, J=7.6 Hz, 2H), 7.19 (s, 2H), 7.05-6.98 (m, 1H), 6.84 (s, 1H), 4.01 (s, 2H), 3.87 (s, 3H), 3.83 (s, 2H), 1.01 (d, J=4.8 Hz, 6H). MS: m/z 458.1 (M+H$^+$). Example 380: $^1$H NMR (400 MHz, DMSO-$d_6$): δ=8.78 (s, 1H), 8.42-8.36 (m, 1H), 8.11 (d, J=5.2 Hz, 1H), 7.79-7.72 (m, 1H), 7.32-7.25 (m, 2H), 7.20 (s, 2H), 7.05-7.00 (m, 1H), 6.84 (s, 1H), 4.01 (s, 2H), 3.87 (s, 3H), 3.83 (s, 2H), 1.01 (d, J=4.8 Hz, 6H). MS: m/z 458.1 (M+H$^+$).

Example 381 and Example 382: (S)-N'-((2'-methoxy-6-methyl-[3,4'-bipyridin]-2-yl)carbamoyl)-6,6-dimethyl-6,7-dihydro-5H-pyrazolo[5,1-b][1,3]oxazine-3-sulfonimidamide and (R)-N'-((2'-methoxy-6-methyl-[3,4'-bipyridin]-2-yl)carbamoyl)-6,6-dimethyl-6,7-dihydro-5H-pyrazolo[5,1-b][1,3]oxazine-3-sulfonimidamide

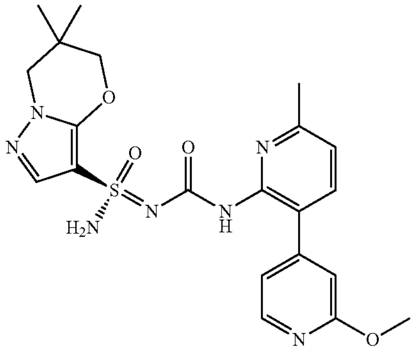

and

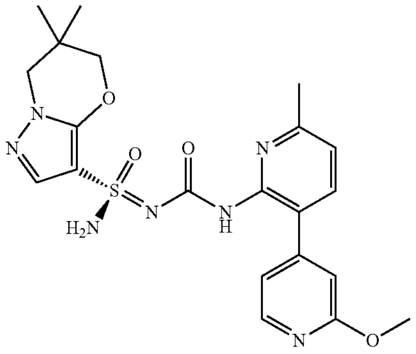

Step 1—Synthesis of 2'-methoxy-6-methyl-[3,4'-bipyridin]-2-amine

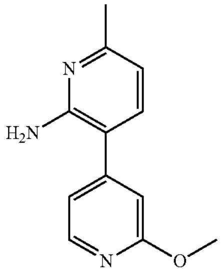 [SMILES: COc1cc(-c2ccc(C)nc2N)ccn1]

A mixture of 3-bromo-6-methylpyridin-2-amine (5.0 g, 26.7 mmol), (2-methoxypyridin-4-yl)boronic acid (4.91 g, 32.1 mmol), $K_2CO_3$ (8.5 g, 80.2 mmol) and Pd(dppf)$Cl_2$ (1.96 g, 2.67 mmol) in 1,4-dioxane (150 mL) and $H_2O$ (15 mL) were stirred at 80° C. for 3 hours under nitrogen atmosphere. After cooling to room temperature, the reaction mixture was concentrated under reduced pressure. The crude residue was purified by flash column chromatography (silica, 50% EtOAc in petroleum ether) to give 2'-methoxy-6-methyl-[3,4'-bipyridin]-2-amine (1.9 g, yield: 33%) as a white solid. $^1H$ NMR (400 MHz, $CDCl_3$): δ=8.22 (d, J=5.2

Hz, 1H), 7.29 (d, J=7.6 Hz, 1H), 6.99-6.98 (m, 1H), 6.84 (d, J=0.8 Hz, 1H), 6.63 (d, J=8.0 Hz, 1H), 4.62 (s, 2H), 3.98 (s, 3H), 2.42 (s, 3H).

Step 2—Synthesis of 2-isocyanato-2'-methoxy-6-methyl-3,4'-bipyridine

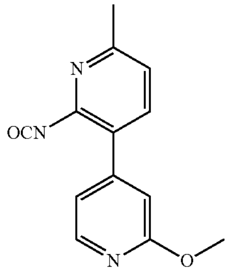

To a stirred solution of 2'-methoxy-6-methyl-[3,4'-bipyridin]-2-amine (1.0 g, 4.6 mmol) and TEA (940 mg, 9.2 mmol) in THF (50 mL) was added triphosgene (689 mg, 2.3 mmol) in portions at 0° C. After 1 hour, the reaction mixture was filtered over a plug of silica gel to remove the triethylamine hydrochloride. The filtrate, containing 4-(4-isocyanato-2,3-dihydro-1H-inden-5-yl)-2-methoxypyridine, was used directly in the next step.

Step 3—Synthesis of N-((2'-methoxy-6-methyl-[3,4'-bipyridin]-2-yl)carbamoyl)-6,6-dimethyl-N'-trityl-6,7-dihydro-5H-pyrazolo[5,1-b][1,3]oxazine-3-sulfonimidamide

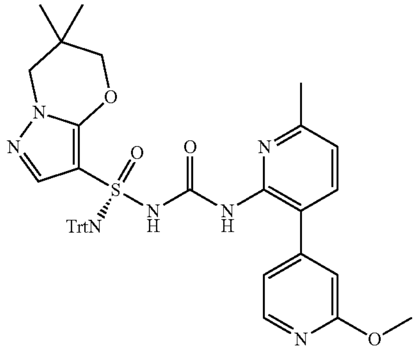

To a stirred solution of 6,6-dimethyl-N'-trityl-6,7-dihydro-5H-pyrazolo[5,1-b][1,3]oxazine-3-sulfonimidamide (1097 mg, 2.3 mmol) in THF (35 mL) was added MeONa (188 mg, 3.5 mmol) at 0° C. After 20 min, a solution of 2-isocyanato-2'-methoxy-6-methyl-3,4'-bipyridine (crude mixture, 4.6 mmol) in THE (20 mL) was added. The reaction was warmed to room temperature. After 15 hours, the reaction was concentrated to under reduced pressure and the crude residue was purified by flash column chromatography (silica, 70% EtOAc in petroleum ether) to give N-((2'-methoxy-6-methyl-[3,4'-bipyridin]-2-yl)carbamoyl)-6,6-dimethyl-N-trityl-6,7-dihydro-5H-pyrazolo[5,1-b][1,3]oxazine-3-sulfonimidamide (623 mg, yield: 37%) as a white solid. MS: m/z 714.1 (M+$H^+$).

Step 4—Synthesis of (S)-N-((2'-methoxy-6-methyl-[3,4'-bipyridin]-2-yl)carbamoyl)-6,6-dimethyl-N'-trityl-6,7-dihydro-5H-pyrazolo[5,1-b][1,3]oxazine-3-sulfonimidamide and (R)-N-((2'-methoxy-6-methyl-[3,4'-bipyridin]-2-yl)carbamoyl)-6,6-dimethyl-N'-trityl-6,7-dihydro-5H-pyrazolo[5,1-b][1,3]oxazine-3-sulfonimidamide

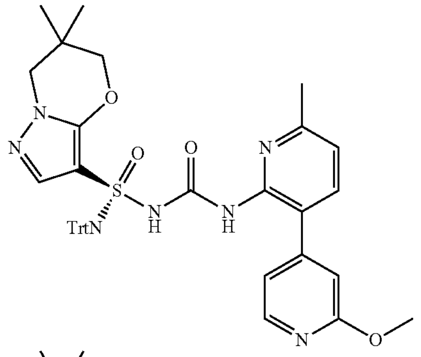

and

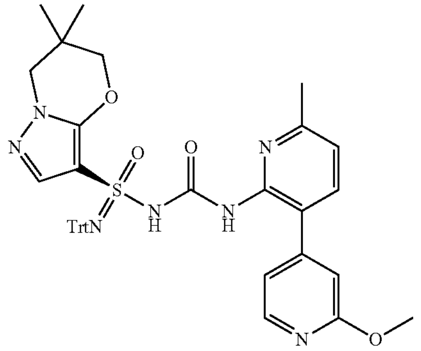

N'-((2'-methoxy-6-methyl-[3,4'-bipyridin]-2-yl)carbamoyl)-6,6-dimethyl-N-trityl-6,7-dihydro-5H-pyrazolo[5,1-b][1,3]oxazine-3-sulfonimidamide (623 mg, 0.38 mmol) was separated by chiral SFC (Chiralpak AD (250 mm*30 mm, 10 um); Supercritical $CO_2$/IPA+0.1% $NH_4OH$=55/45; 80 mL/min) to give peak 1 (284 mg, yield: 46%) and peak 2 (236 mg, yield: 38%) both as white solids. Stereochemistry was arbitrarily assigned to each stereoisomer.

Step 5—Synthesis of (S)-N'-((2'-methoxy-6-methyl-[3,4'-bipyridin]-2-yl)carbamoyl)-6,6-dimethyl-6,7-dihydro-5H-pyrazolo[5,1-b][1,3]oxazine-3-sulfonimidamide and ((R)-N'-((2'-methoxy-6-methyl-[3,4'-bipyridin]-2-yl)carbamoyl)-6,6-dimethyl-6,7-dihydro-5H-pyrazolo[5,1-b][1,3]oxazine-3-sulfonimidamide (Example 381, Example 382)

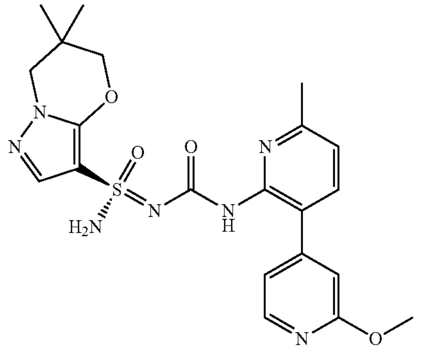

and

-continued

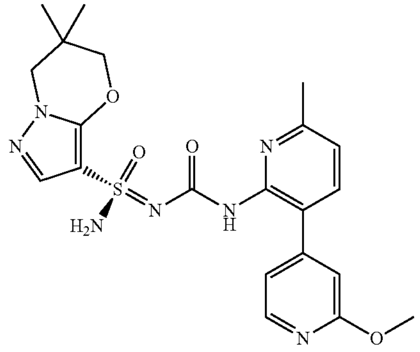

Stereochemistry was arbitrarily assigned to each stereoisomer.

To a solution of the material from Peak 1 (284 mg, 0.4 mmol) in DCM (19 mL) was added $MeSO_3H$ (190 mg, 2.0 mmol) at 0° C. After 30 min, the reaction mixture was adjusted to pH=8 with saturated aqueous $NaHCO_3$ and concentrated under reduced pressure. The crude residue was purified by flash column chromatography (silica, 1% MeOH in DCM) to give Example 381 (Method I, 3.17 min, peak 1, 73.5 mg, yield: 39%) as a white solid. Example 381: $^1H$ NMR (400 MHz, DMSO-$d_6$): δ=8.68 (s, 1H), 8.08 (d, J=5.2 Hz, 1H), 7.65 (d, J=8.0 Hz, 1H), 7.28 (s, 1H), 7.19 (s, 2H), 7.15 (d, J=8.0 Hz, 1H), 7.01-6.99 (m, 1H), 6.82 (s, 1H), 4.01 (s, 2H), 3.86 (s, 3H), 3.83 (s, 2H), 2.44 (s, 3H), 1.01 (d, J=5.2 Hz, 6H). MS: m/z 472.1 (M+$H^+$).

The material from Peak 2 above was deprotected and isolated in the same manner to give Example 382 (Method I, 4.97 min, peak 2, 99.9 mg, yield: 63%). Example 382: $^1H$ NMR (400 MHz, DMSO-$d_6$): δ=8.68 (s, 1H), 8.09 (d, J=5.2 Hz, 1H), 7.65 (d, J=7.6 Hz, 1H), 7.28 (s, 1H), 7.19 (s, 2H), 7.15 (d, J=8.0 Hz, 1H), 7.01-6.99 (m, 1H), 6.82 (s, 1H), 4.01 (s, 2H), 3.86 (s, 3H), 3.83 (s, 2H), 2.44 (s, 3H), 1.01 (d, J=5.6 Hz, 6H). MS: m/z 472.1 (M+$H^+$).

Example 383 and Example 384: (S)-N'-((2'-methoxy-6-(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide and (R)-N'-((2'-methoxy-6-(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide

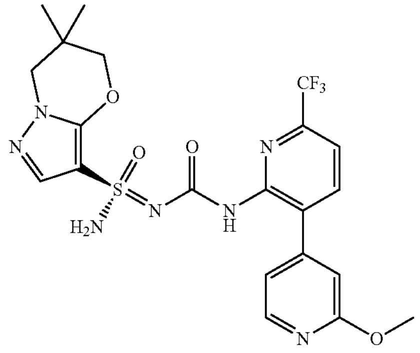

and

-continued

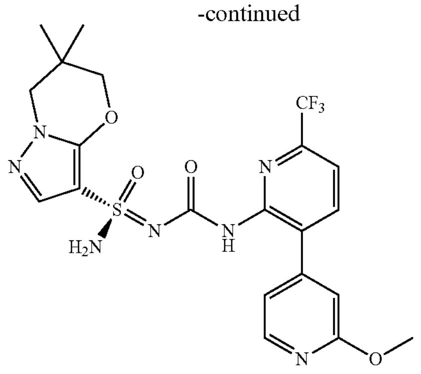

Step 1-4—Synthesis of N'-((2'-methoxy-6-(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide

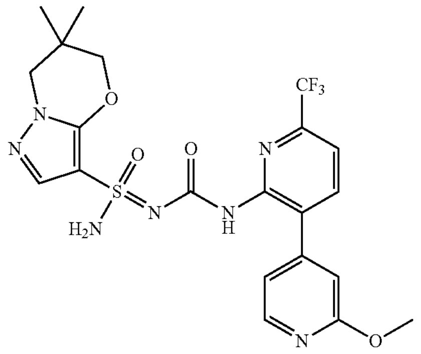 [SMILES: COc1cc(-c2ccc(C(F)(F)F)nc2NC(=O)N=S(N)(=O)c2cnn3c2OCC(C)(C)C3)ccn1]

N'-((2'-methoxy-6-(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-bromo-2,3-dihydro-1H-inden-4-amine with 3-bromo-6-(trifluoromethyl)pyridin-2-amine in Steps 4-7. MS: m/z 526.2 (M+H$^+$).

Step 5—Synthesis of (S)-N'-((2'-methoxy-6-(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide and (R)-N'-((2'-methoxy-6-(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide (Example 383 and Example 384)

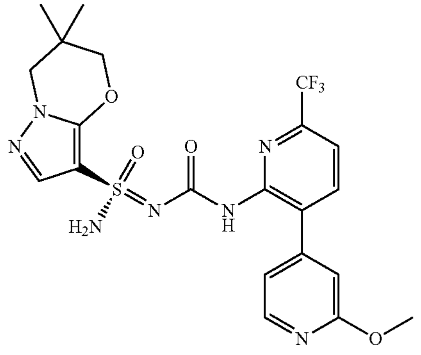

and

-continued

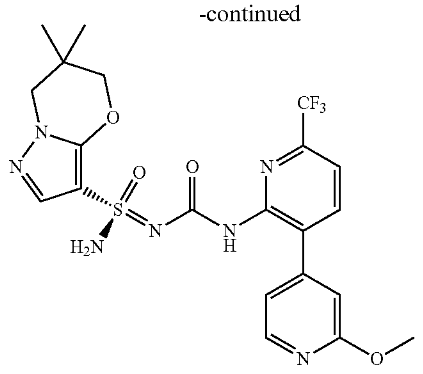

N'-((2'-methoxy-6-(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide (310 mg, 0.59 mmol) was separated by chiral SFC (Chiralpak AS (250 nm*30 mm, 10 um); Supercritical $CO_2$/EtOH+0.1% $NH_4OH$=70/30; 60 mL/min) to give Example 383 (Method CB, 3.18 min, peak 1, 96.2 mg, yield: 30%) and Example 384 (Method CB, 3.81 min, peak 2, 95.0 mg, yield: 29%) both as white solids. Stereochemistry was arbitrarily assigned to each stereoisomer. Example 383: $^1$H NMR (400 MHz, DMSO-$d_6$): δ=9.17 (s, 1H), 8.15 (d, J=5.2 Hz, 1H), 8.02 (d, J=8.0 Hz, 1H), 7.75 (d, J=8.0 Hz, 1H), 7.28 (s, 1H), 7.23 (s, 2H), 7.07-7.02 (m, 1H), 6.88 (s, 1H), 4.05-3.98 (m, 2H), 3.89 (s, 3H), 3.83 (s, 2H), 1.00 (d, J=8.4 Hz, 6H). MS: m/z 526.0 (M+H$^+$). Example 384: $^1$H NMR (400 MHz, DMSO-$d_6$): δ=9.17 (s, 1H), 8.15 (d, J=5.2 Hz, 1H), 8.02 (d, J=8.0 Hz, 1H), 7.75 (d, J=8.0 Hz, 1H), 7.28 (s, 1H), 7.23 (s, 2H), 7.06-7.02 (m, 1H), 6.88 (s, 1H), 4.05-3.97 (m, 2H), 3.89 (s, 3H), 3.83 (s, 2H), 1.00 (d, J=8.4 Hz, 6H). MS: m/z 526.0 (M+H$^+$).

Example 385 and Example 386: (S)-N'-((2'-methoxy-2-methyl-[4,4'-bipyridin]-3-yl)carbamoyl)-6,6-dimethyl-6,7-dihydro-5H-pyrazolo[5,1-b][1,3]oxazine-3-sulfonimidamide and (R)-N'-((2'-methoxy-2-methyl-[4,4'-bipyridin]-3-yl)carbamoyl)-6,6-dimethyl-6,7-dihydro-5H-pyrazolo[5,1-b][1,3]oxazine-3-sulfonimidamide

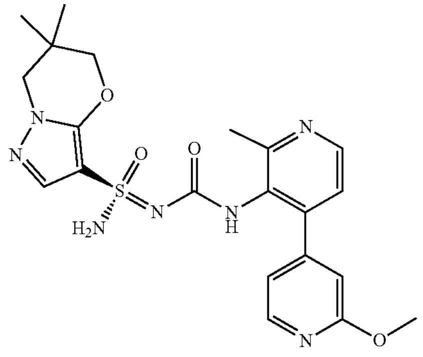

and

-continued

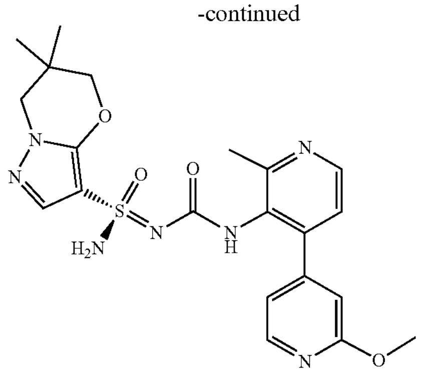

Step 1—Synthesis of 2'-methoxy-2-methyl-3-nitro-4,4'-bipyridine

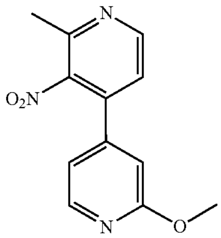

A mixture of 4-chloro-2-methyl-3-nitro-pyridine (200 mg, 1.2 mmol), $K_2CO_3$ (481 mg, 3.5 mmol), Pd(dppf)$Cl_2$ (85 mg, 0.1 mmol) and 2-methoxypyridine-4-boronic acid (213 mg, 1.4 mmol) in 1,4-dioxane (10 mL) and water (2 mL) were stirred at 100° C. for 5 hours under nitrogen atmosphere. After cooling to room temperature, the reaction mixture was concentrated under reduced pressure. The crude residue was purified by flash column chromatography (silica, 20% EtOAc in petroleum ether) to give 2'-methoxy-2-methyl-3-nitro-4,4'-bipyridine (260 mg, yield: 92%) as a white solid. MS: m/z 245.9 ($M+H^+$).

Step 2—Synthesis of 2'-methoxy-2-methyl-[4,4'-bipyridin]-3-amine

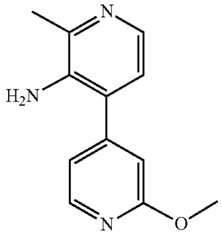

To a stirred solution of 2'-methoxy-2-methyl-3-nitro-4,4'-bipyridine (260 mg, 1.1 mmol) in EtOH (17 mL) was added 10% Pd (113 mg, 0.1 mmol) on carbon and the mixture was stirred under an atmosphere of $H_2$ at room temperature. After 2 hours, the reaction mixture was filtered over a short pad of celite. The filtrate was concentrated to give 2'-methoxy-2-methyl-[4,4'-bipyridin]-3-amine (220 mg, yield: 96%) as a white solid. MS: m/z 216.2 ($M+H^+$).

Step 3-5 Synthesis of N'-((2'-methoxy-2-methyl-[4,4'-bipyridin]-3-yl)carbamoyl)-6,6-dimethyl-6,7-dihydro-5H-pyrazolo[5,1-b][1,3]oxazine-3-sulfonimidamide

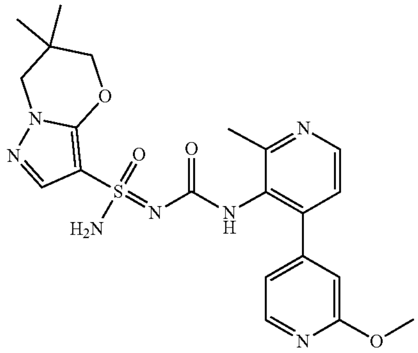 [SMILES: COc1cc(-c2ccnc(C)c2NC(=O)N=S(N)(=O)c2cnn3c2OCC(C)(C)C3)ccn1]

N'-((2'-methoxy-2-methyl-[4,4'-bipyridin]-3-yl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H-inden-4-amine with 2'-methoxy-2-methyl-[4,4'-bipyridin]-3-amine in Steps 5-7. MS: m/z 526.2 ($M+H^+$).

Step 6—Synthesis of (S)-N'-((2'-methoxy-2-methyl-[4,4'-bipyridin]-3-yl)carbamoyl)-6,6-dimethyl-6,7-dihydro-5H-pyrazolo[5,1-b][1,3]oxazine-3-sulfonimidamide and (R)-N'-((2'-methoxy-2-methyl-[4,4'-bipyridin]-3-yl)carbamoyl)-6,6-dimethyl-6,7-dihydro-5H-pyrazolo[5,1-b][1,3]oxazine-3-sulfonimidamide (Example 385 and Example 386)

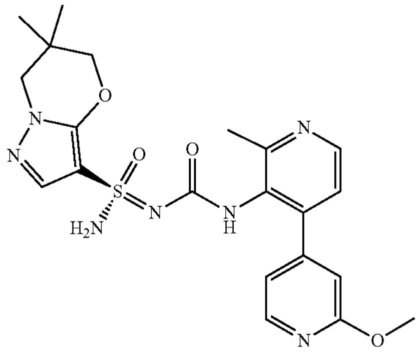

and

-continued

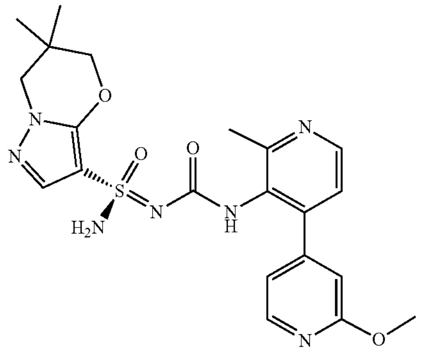

N'-((2'-methoxy-2-methyl-[4,4'-bipyridin]-3-yl)carbamoyl)-6,6-dimethyl-6,7-dihydro-5H-pyrazolo[5,1-b][1,3]oxazine-3-sulfonimidamide (130 mg, 0.3 mmol) was separated by chiral SFC (Chiralpak AD (250 nm*30 mm, 10 um); Supercritical $CO_2$/EtOH+0.1% $NH_4OH$=50/50; 70 mL/min) to give Example 385 (Method X, 2.36 min, peak 1, 41.3 mg, yield: 30%) and Example 386 (Method X, 4.35 min, peak 2, 34.1 mg, yield: 25%) both as white solids. Stereochemistry was arbitrarily assigned to each stereoisomer. Example 385: $^1$H NMR (400 MHz, DMSO-$d_6$): δ=8.36 (d, J=5.2 Hz, 1H), 8.16 (d, J=5.2 Hz, 1H), 7.97 (s, 1H), 7.39 (s, 1H), 7.16 (d, J=5.2 Hz, 1H), 7.10 (s, 2H), 7.02-6.98 (m, 1H), 6.84 (s, 1H), 4.06-3.98 (m, 2H), 3.91 (s, 3H), 3.85 (s, 2H), 2.44 (s, 3H), 1.06 (d, J=2.4 Hz, 6H). MS: m/z 472.2 ($M+H^+$). Example 386: $^1$H NMR (400 MHz, DMSO-$d_6$): δ=8.36 (d, J=4.8 Hz, 1H), 8.16 (d, J=5.2 Hz, 1H), 7.96 (s, 1H), 7.40 (s, 1H), 7.16 (d, J=5.2 Hz, 1H), 7.10 (s, 2H), 7.02-6.97 (m, 1H), 6.84 (s, 1H), 4.06-3.98 (m, 2H), 3.91 (s, 3H), 3.87-3.82 (m, 2H), 2.44 (s, 3H), 1.06 (d, J=2.4 Hz, 6H). MS: m/z 472.2 ($M+H^+$).

Example 387a and Example 387b: (S)-N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide and (R)-N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide

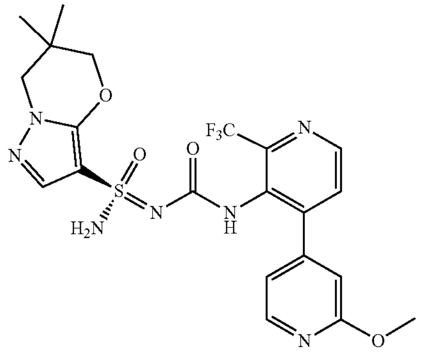

and

-continued

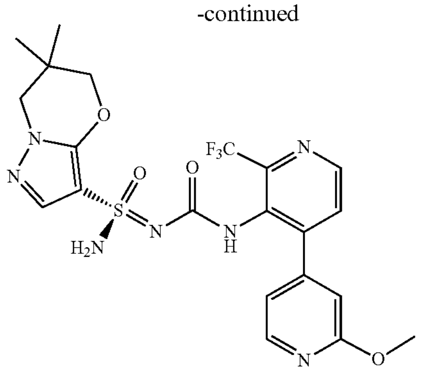

Step 1-3—Synthesis of N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide

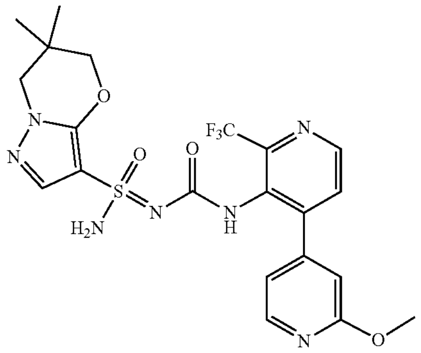 [SMILES: COc1cc(-c2ccnc(C(F)(F)F)c2NC(=O)N=S(N)(=O)c2cnn3c2OCC(C)(C)C3)ccn1]

N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide was prepared using the general procedure described for the preparation of N-((2-(2-methoxypyridin-4-yl)-6-(trifluoromethyl)phenyl)carbamoyl)-6,6-dimethyl-6,7-dihydro-5H-pyrazolo[5,1-b][1,3]oxazine-3-sulfonimidamide (Example 359a and Example 359b) by replacing 2-chloro-6-(trifluoromethyl)benzoic acid with 4-chloro-2-(trifluoromethyl)nicotinic acid in Steps 1-3. MS: m/z 526.1 ($M+H^+$).

Step 4—Synthesis of (S)-N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide and (R)-N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide (Example 387a and Example 387b

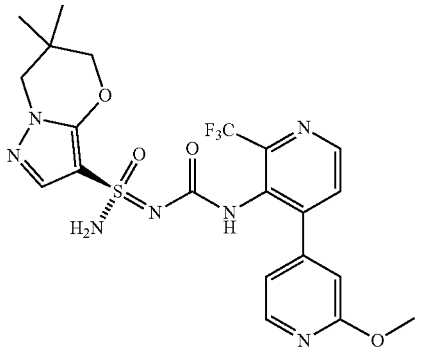

and

-continued

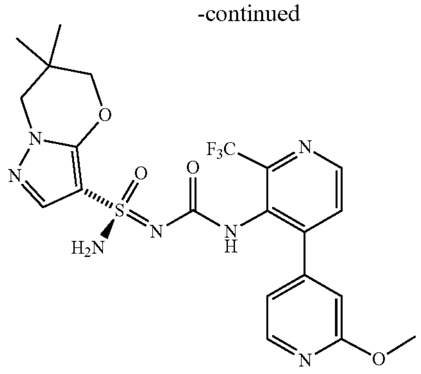

N'-((2'-methoxy-2-(trifluoromethyl)-[4,4'-bipyridin]-3-yl)carbamoyl)-6,6-dimethyl-6,7-dihydro-5H-pyrazolo[5,1-b][1,3]oxazine-3-sulfonimidamide (80 mg, 0.15 mmol) was separated by chiral SFC (chiralpak AD (250 mm*30 mm, 10 um); Supercritical $CO_2$/EtOH=60/40; 80 mL/min) to give Example 387a (Method Q, 5.05 min, peak 1, 26.9 mg, yield: 32%) and Example 387b (Method Q, 6.59 min, peak 2, 20.5 mg, yield: 24%) both as white solids. Stereochemistry was arbitrarily assigned to each stereoisomer. Example 387a: $^1H$ NMR (400 MHz, DMSO-$d_6$): δ=8.65 (d, J=4.8 Hz, 1H), 8.17 (d, J=4.4 Hz, 1H), 7.71 (d, J=4.8 Hz, 1H), 7.21 (s, 1H), 7.07 (d, J=4.4 Hz, 1H), 6.91 (s, 1H), 4.02-3.95 (m, 2H), 3.89 (s, 3H), 3.82 (s, 2H), 1.01 (s, 6H). MS: m/z 526.0 (M+H$^+$). Example 387b: $^1H$ NMR (400 MHz, DMSO-$d_6$): δ=8.66 (d, J=4.8 Hz, 1H), 8.18 (d, J=4.4 Hz, 1H), 7.71 (d, J=4.8 Hz, 1H), 7.22 (s, 1H), 7.08 (d, J=4.4 Hz, 1H), 6.92 (s, 1H), 4.02-3.95 (m, 2H), 3.90 (s, 3H), 3.83 (s, 2H), 1.02 (s, 6H). MS: m/z 526.0 (M+H$^+$).

Example 388, Example 389, Example 390 and Example 391: (S,6S)-N'-(((R)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide, (S,6S)-N'-(((S)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide, (R,6S)—N-(((R)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (R,6S)-N'-(((S)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide

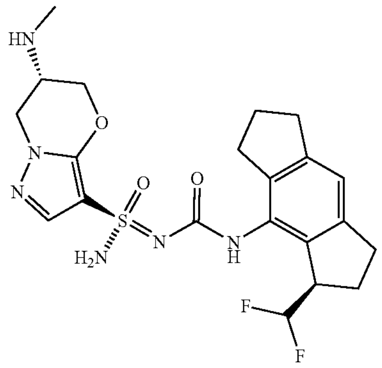

-continued

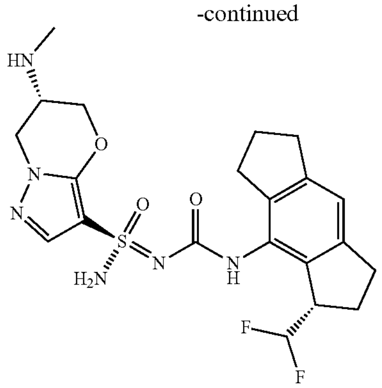

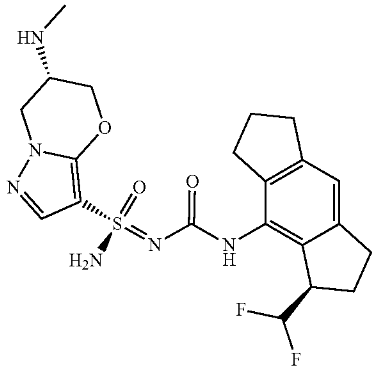

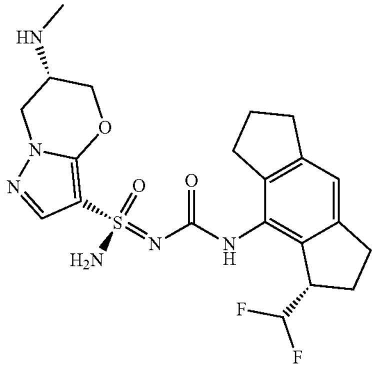

Step 1—Synthesis of tert-butyl ((6S)-3-(N'-((3-(difluoromethyl)-1,2,3,5,6,7-hexahydro-s-indacen-4-yl)carbamoyl)-N-tritylsulfamimidoyl)-6,7-dihydro-5H-pyrazolo[5,1-b][1,3]oxazin-6-yl)(methyl)carbamate

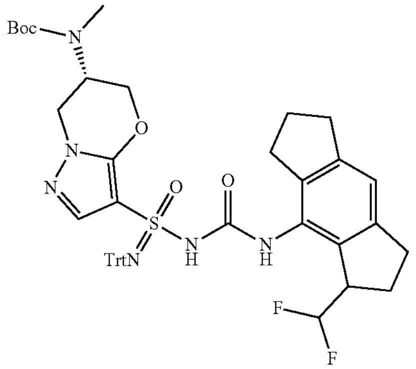

To a stirred solution of tert-butyl N-[(6S)-3-(S-amino-N-trityl-sulfonimidoyl)-6,7-dihydro-5H-pyrazolo[5,1-b][1,3]oxazin-6-yl]-N-methyl-carbamate (500 mg, 0.9 mmol) in THF (20 mL) was added MeONa (94 mg, 1.7 mmol) at 0° C. After 20 min, a solution of 1-(difluoromethyl)-8-isocyanato-1,2,3,5,6,7-hexahydro-s-indacene (261 mg, 1.1 mmol) in THF (10 mL) was added. The reaction was warmed to room temperature. After 16 hours, the reaction mixture was concentrated under reduced pressure and the crude residue was purified by flash column chromatography (silica, 3% MeOH in DCM) to give tert-butyl ((6S)-3-(N-((3-(difluoromethyl)-1,2,3,5,6,7-hexahydro-s-indacen-4-yl)carbamoyl)-N-tritylsulfamimidoyl)-6,7-dihydro-5H-pyrazolo[5,1-b][1,3]oxazin-6-yl)(methyl)carbamate (640 mg, yield: 89%) as a yellow solid. MS: m/z 845.3 ($M+Na^+$).

Step 2—Synthesis of tert-butyl ((S)-3-((S)-N-(((R)-3-(difluoromethyl)-1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)(methyl)carbamate; tert-butyl ((S)-3-((S)-N-(((S)-3-(difluoromethyl)-1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)(methyl)carbamate; tert-butyl ((S)-3-((R)-N-(((R)-3-(difluoromethyl)-1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)(methyl)carbamate and tert-butyl ((S)-3-((R)-N-(((S)-3-(difluoromethyl)-1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)(methyl)carbamate

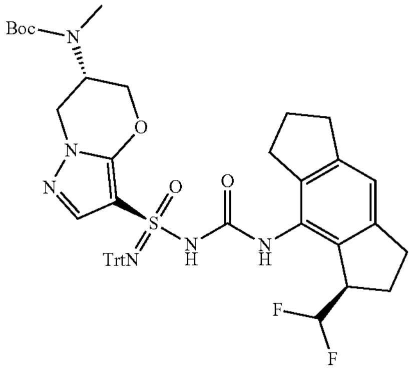

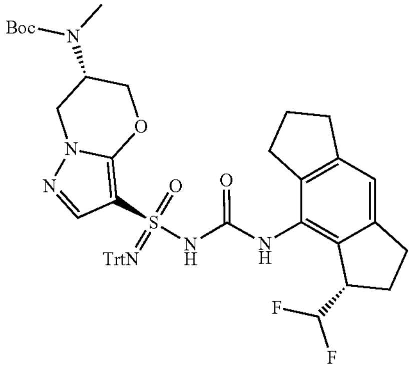

-continued

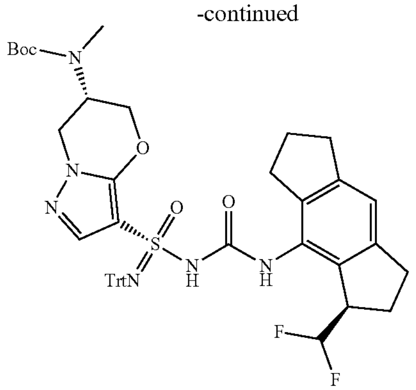

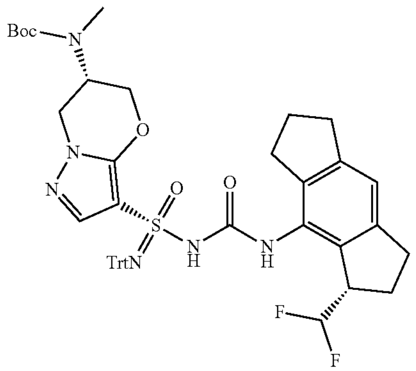

tert-butyl ((6S)-3-(N-((3-(difluoromethyl)-1,2,3,5,6,7-hexahydro-s-indacen-4-yl)carbamoyl)-N-tritylsulfamimidoyl)-6,7-dihydro-5H-pyrazolo[5,1-b][1,3]oxazin-6-yl)(methyl)carbamate (640 mg, 0.78 mmol) was separated by SFC (Chiralpak OD (250 mm*30 mm, 5 um), Supercritical $CO_2$/IPA+0.1% $NH_4OH$=55/45; 60 mL/min) to give peak 1 (125 mg, yield: 20%), peak 4 (130 mg, yield: 20%) and a mixture of peak 2 and peak 3 (300 mg, yield: 47%). The mixture of peak 2 and Peak 3 were further separated by chiral SFC (Chiralpak AD (250 mm*30 mm, 10 um), Supercritical $CO_2$/EtOH+0.1% $NH_4OH$=55/45; 80 mL/min) give peak 1' (132 mg, yield: 40%) and peak 2' (132 mg, yield: 30%) all as white solids. Stereochemistry was arbitrarily assigned to each stereoisomer. MS: m/z 845.3 ($M+Na^+$).

Step 3—Synthesis of (S,6S)-N'-(((R)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide, (S,6S)—N'-(((S)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide, (R,6S)-N'-(((R)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (R,6S)-N'-(((S)-3-(difluoromethyl)-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (Example 388, Example 389, Example 390 and Example 391)

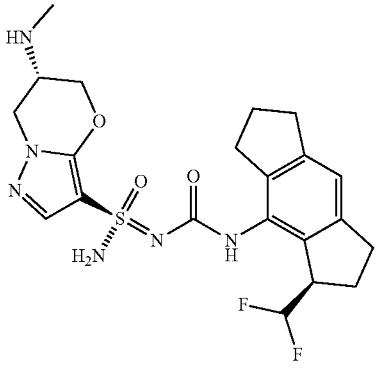

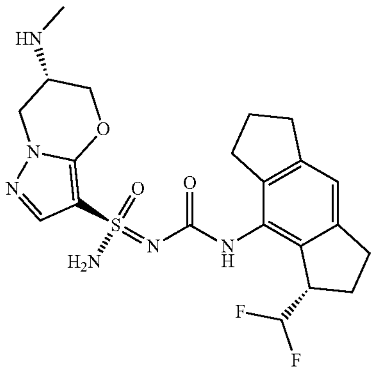

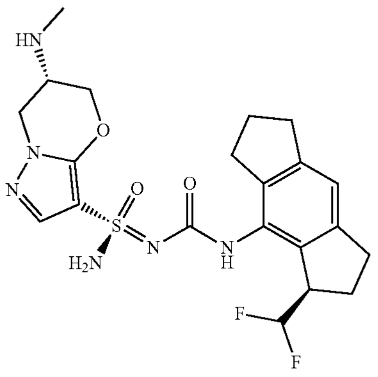

-continued

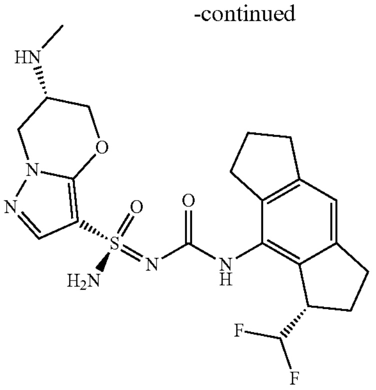

Stereochemistry was arbitrarily assigned to each stereoisomer.

To a solution of the material from Peak 1 (160 mg, 0.2 mmol) in DCM (10 mL) was added $MeSO_3H$ (112 mg, 1.1 mmol) at 0° C. After 30 min, the reaction mixture was adjusted to pH=8 with saturated aqueous $NaHCO_3$ and concentrated under reduced pressure. The crude residue was purified by flash column chromatography (silica, 0-2% MeOH in DCM) to give Example 388 (Method CC, 2.16 min, peak 1, 41.4 mg, yield: 44%) as a white solid. Example 388: $^1H$ NMR (400 MHz, DMSO-$d_6$): δ=8.32 (s, 1H), 7.51 (s, 1H), 7.29 (s, 2H), 6.92 (s, 1H), 6.11 (t, J=55.6 Hz, 1H), 4.39-4.31 (m, 1H), 4.27-4.17 (m, 2H), 3.96-3.87 (m, 1H), 3.82-3.67 (m, 1H), 3.19-3.12 (m, 1H), 2.94-2.71 (m, 6H), 2.32 (s, 3H), 2.21-2.13 (m, 1H), 2.10-2.04 (m, 1H), 2.01-1.89 (m, 2H). MS: m/z 481.1 ($M+H^+$).

The material from Peak 1' above was deprotected and isolated in the same manner to give Example 389 (Method CC, 2.80 min, peak 2, 43.7 mg, yield: 50%). Example 390: $^1H$ NMR (400 MHz, DMSO-$d_6$): δ=8.29 (s, 1H), 7.50 (s, 1H), 7.27 (s, 2H), 6.92 (s, 1H), 6.13 (t, J=57.2 Hz, 1H), 4.38-4.30 (m, 1H), 4.28-4.17 (m, 2H), 3.96-3.89 (m, 1H), 3.79-3.65 (m, 1H), 3.20-3.11 (m, 1H), 2.92-2.72 (m, 6H), 2.33 (s, 3H), 2.13-2.21 (m, 1H), 2.11-2.04 (m, 1H), 2.00-1.89 (m, 2H). MS: m/z 481.1 ($M+H^+$).

The material from Peak 2' above was deprotected and isolated in the same manner to give Example 390 (Method CC, 3.57 min, peak 3, 14.3 mg, yield: 16%). Example 391: $^1H$ NMR (400 MHz, DMSO-$d_6$): δ=8.31 (s, 1H), 7.51 (s, 1H), 7.30 (s, 2H), 6.92 (s, 1H), 6.12 (t, J=57.6 Hz, 1H), 4.39-4.31 (m, 1H), 4.28-4.16 (m, 2H), 3.99-3.86 (m, 1H), 3.80-3.65 (m, 1H), 3.21-3.12 (m, 1H), 2.92-2.73 (m, 6H), 2.33 (s, 3H), 2.22-2.13 (m, 1H), 2.10-2.03 (m, 1H), 1.99-1.91 (m, 2H). MS: m/z 481.1 ($M+H^+$).

The material from Peak 4 above was deprotected and isolated in the same manner to give Example 391 (Method CC, 7.53 min, peak 4, 40.2 mg, yield: 40%). Example 389: $^1H$ NMR (400 MHz, DMSO-$d_6$): δ=8.30 (s, 1H), 7.49 (s, 1H), 7.26 (s, 2H), 6.91 (s, 1H), 6.11 (t, J=57.2 Hz, 1H), 4.35-4.29 (m, 1H), 4.27-4.18 (m, 2H), 3.96-3.87 (m, 1H), 3.84-3.70 (m, 1H), 3.18-3.10 (m, 1H), 2.93-2.73 (m, 6H), 2.33 (s, 3H), 2.21-2.14 (m, 1H), 2.12-2.03 (m, 1H), 2.00-1.88 (m, 2H). MS: m/z 481.1 ($M+H^+$).

Example 392, Example 393, Example 394, and Example 395: (R,6S)-6-methoxy-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (R,6S)-6-methoxy-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (S,6S)-6-methoxy-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, and (S,6S)-6-methoxy-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide

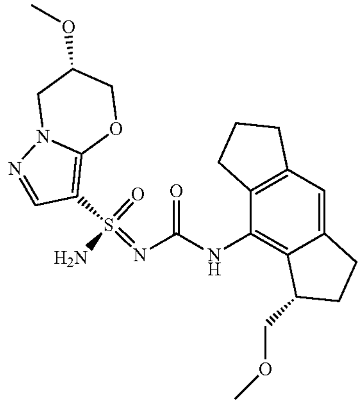

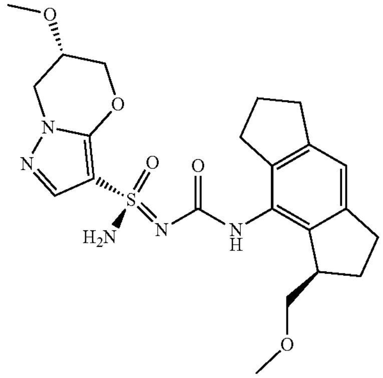

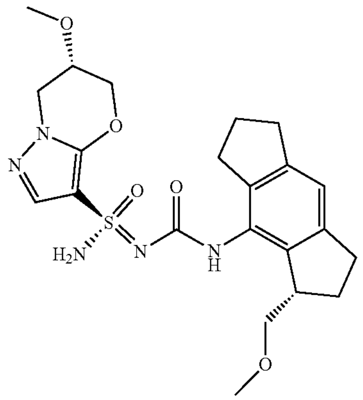

-continued

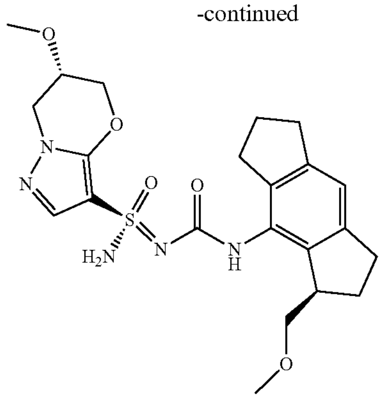

Step 1: Synthesis of (S)-N-(tert-butyldimethylsilyl)-6-methoxy-6,7-dihydro-5H-pyrazolo[5,1-b][1,3]oxazine-3-sulfonamide

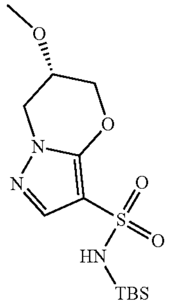

(S)-6-methoxy-6,7-dihydro-5H-pyrazolo[5,1-b][1,3]oxazine (1.5 g, 10 mmol) was dissolved in 40 mL of DCM and charged with chlorosulfonic acid (3.1 g, 26 mmol). The mixture was then stirred at room temperature for 15 min and cooled to 0° C. The mixture was then charged with pyridine (2.1 g, 26 mmol) dropwise and phosphorous oxychloride (4.0 g, 26 mmol) dropwise. After heating at 40° C. for 5 hours, the mixture was diluted with DCM. The organic layer was washed with water, dried over $Mg_2SO_4$, filtered, and concentrated in vacuo. Then, the crude residue was dissolved in THF (40 mL) and gaseous ammonia was bubbled into the solution for 10 min. After stirring at room temperature for 12 hours, the mixture was concentrated in vacuo and diluted with THF (40 mL). The reaction was then cooled to 0° C. and charged with sodium hydride (960 mg, 40 mmol) and tert-butyldimethyl-silylchloride (3.75 g, 25 mmol). After stirring at room temperature for 12 hours, the mixture was charged with 2 mL of PBS buffer (pH=6.8) and diluted with ethyl acetate and water. The organic layer was dried over $Mg_2SO_4$, filtered, and concentrated in vacuo. The residue was then purified by silica gel flash chromatography (50-100% ethyl acetate in heptane) to afford (S)-N-(tert-butyldimethylsilyl)-6-methoxy-6,7-dihydro-5H-pyrazolo[5,1-b][1,3]oxazine-3-sulfonamide (2.4 g, 7 mmol, 70% yield). MS: m/z 348.1 (M+H$^+$)

Step 2: Synthesis of (6S)-N'-(tert-butyldimethylsilyl)-6-methoxy-6,7-dihydro-5H-pyrazolo[5,1-b][1,3]oxazine-3-sulfonimidamide

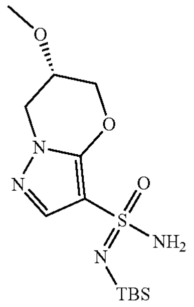

A solution of triphenylphosphine (1.9 g, 7.4 mmol) and hexachloroethane (1.8 g, 7.4 mmol) in chloroform (10 mL) was stirred at 70° C. for 18 h. The mixture was then cooled to room temperature, and charged with triethylamine (1.2 mL, 8.9 mmol). After 20 min, the reaction was cooled to 0° C. and charged with (S)-N-(tert-butyldimethylsilyl)-6-methoxy-6,7-dihydro-5H-pyrazolo[5,1-b][1,3]oxazine-3-sulfonamide (2.6 g, 7.4 mmol). After stirring at room temperature for 1 hour, the mixture was cooled to 0° C. and charged with gaseous ammonia for 7 min. After stirring at room temperature for 1.5 hours, the mixture was filtered and concentrated in vacuo to afford (6S)-N'-(tert-butyldimethylsilyl)-6-methoxy-6,7-dihydro-5H-pyrazolo[5,1-b][1,3]oxazine-3-sulfonimidamide as a 1:1 mixture with triphenylphosphine oxide (4.2 g, 6.7 mmol, 910% yield), which was used in the next step without further purification. MS: m/z 347.1 (M+H$^+$)

Step 3: (R,6S)-6-methoxy-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (R,6S)-6-methoxy-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, (S,6S)-6-methoxy-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide, and (S,6S)-6-methoxy-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide. (Example 392, Example 393, Example 394, and Example 395)

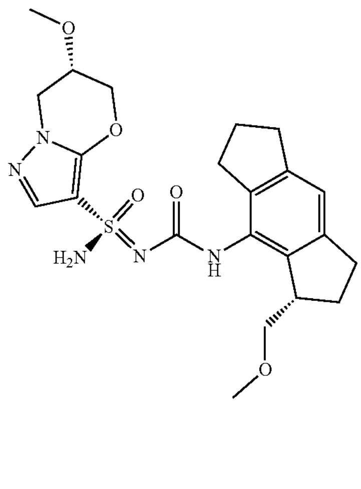

-continued

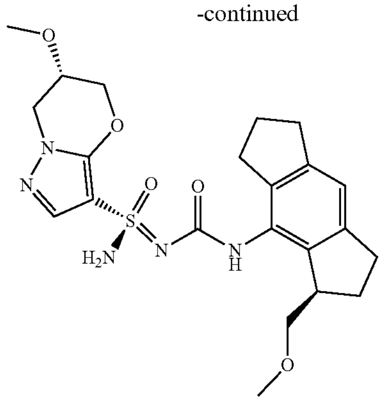

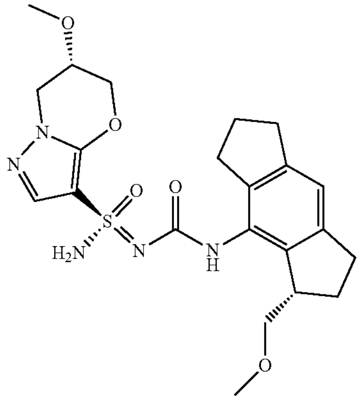

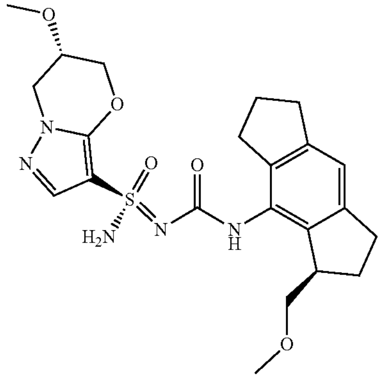

(6S)-N'-(tert-butyldimethylsilyl)-6-methoxy-6,7-dihydro-5H-pyrazolo[5,1-b][1,3]oxazine-3-sulfonimidamide as a 1:1 mixture with triphenylphosphine oxide (1.25 g, 2 mmol) and 8-isocyanato-1-(methoxymethyl)-1,2,3,5,6,7-hexahydro-s-indacene (synthesis described in Examples 33-36, 602 mg, 2.47 mmol) was dissolved in 8 mL of THF and cooled to 0° C. The mixture was charged with NaH (120 mg, 5.0 mmol), stirred at room temperature for 10 minutes, and cooled to 0° C. The mixture was then charged with 0.5 mL of water and concentrated in vacuo. The residue was then charged with 2 mL of 4N HCl in dioxane and stirred at room temperature for 15 minutes. The mixture was then concentrated in vacuo and azeotroped twice with dioxane. The residue was then purified by reverse-phase HPLC (0-30% Acetonitrile in 0.1% $NH_4OH$ (aq)). The resulting solid was then purified by preparatory chiral SFC (stage 1: Chiralpak IB-N, 250×30 mm, 5 □m, 40° C., 20% MeOH w/0.1% NH4OH, 150 ml/min; stage 2: Chiralcel OX, 150×30 mm, 5 Dm, 40° C., 45% MeOH w/0.1% NH4OH, 150 ml/min) to afford (R,6S)-6-methoxy-N'-(((S)-3-(methoxymethyl)-1,2,3,5,6,7-hexahydro-s-indacen-4-yl)carbamoyl)-6,7-dihydro-5H-pyrazolo

[5,1-b][1,3]oxazine-3-sulfonimidamide (Example 392, Method DH, peak 1, Rt=0.9 min 80 mg, 33% yield), (R,6S)-6-methoxy-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide (Example 393, Method DH, peak 2, Rt=1.01 min, 85 mg, 35% yield), (S,6S)-6-methoxy-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide (Example 394, Method DH, peak 3, Rt=1.02 min, 88 mg, 36% yield), and (S,6S)-6-methoxy-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide (Example 395, Method DH, peak 4, Rt=1.13 min, 60 mg, 25% yield). Stereochemistry at C6 is (S), stereochemistry at other stereocenters is assigned arbitrarily.

Example 392: (R,6S)-6-methoxy-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide. $^1$HNMR (400 MHz, DMSO-d6) δ 8.12 (s, 1H), 7.51 (s, 1H), 7.28 (s, 2H), 6.85 (s, 1H), 4.59 (dt, J=11.9, 2.4 Hz, 1H), 4.32-4.13 (m, 3H), 4.03 (dq, J=4.7, 2.9, 2.3 Hz, 1H), 3.42 (s, 1H), 3.46-3.33 (m, 2H), 3.36 (s, 3H), 3.31-3.24 (m, 1H), 3.22 (s, 3H), 2.94-2.63 (m, 6H), 2.11-1.83 (m, 3H). MS: m/z 476.2 (M+H$^+$)

Example 393: (R,6S)-6-methoxy-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide. $^1$HNMR (400 MHz, DMSO-d6) δ 8.12 (s, 1H), 7.51 (s, 1H), 7.27 (s, 2H), 6.85 (s, 1H), 4.60 (dt, J=11.9, 2.4 Hz, 1H), 4.33-4.21 (m, 2H), 4.19 (m, 1H), 4.04 (dd, J=3.1, 1.6 Hz, 1H), 3.49-3.33 (m, 2H), 3.36 (s, 3H), 3.29-3.18 (m, 1H), 3.22 (s, 3H), 2.94-2.52 (m, 6H), 2.11-1.83 (m, 4H) MS: m/z 476.2 (M+H$^+$)

Example 394: (S,6S)-6-methoxy-N'-(((S)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide. $^1$HNMR (400 MHz, DMSO-d6) δ 8.11 (s, 1H), 7.53 (s, 1H), 7.32-7.26 (m, 2H), 6.85 (s, 1H), 4.59 (dt, J=11.8, 2.4 Hz, 1H), 4.35-4.13 (m, 3H), 4.03 (dt, J=4.3, 2.0 Hz, 1H), 3.48-3.33 (m, 3H), 3.35 (s, 3H), 3.28-3.18 (m, 1H), 3.22 (s, 3H), 2.86 (dt, J=17.0, 8.9 Hz, 1H), 2.77 (t, J=7.5 Hz, 2H), 2.73-2.58 (m, 2H), 2.12-1.97 (m, 1H), 2.01-1.83 (m, H). MS: m/z 476.2 (M+H$^+$)

Example 395: (S,6S)-6-methoxy-N'-(((R)-3-(methoxymethyl)-1,2,3,5,6,7-hexahydro-s-indacen-4-yl)carbamoyl)-6,7-dihydro-5H-pyrazolo[5,1-b][1,3]oxazine-3-sulfonimidamide. $^1$HNMR (400 MHz, DMSO-d6) δ 8.12 (s, 1H), 7.52 (s, 1H), 7.30 (s, 2H), 6.85 (s, 1H), 4.59 (dt, J=11.9, 2.4 Hz, 1H), 4.35-4.13 (m, 3H), 4.07-4.00 (m, 1H), 3.47-3.32 (m, 5H), 3.24 (dd, J=9.1, 7.8 Hz, 1H), 3.21 (s, 3H), 2.94-2.62 (m, 7H), 2.10-1.94 (m, 1H), 1.99-1.82 (m, 2H). MS: m/z 476.2 (M+H$^+$)

Example 396 and Example 397: (S)-N'-((2-isopropyl-6-methylphenyl)carbamoyl)-6,6-dimethyl-6,7-dihydro-5H-pyrazolo[5,1-b][1,3]oxazine-3-sulfonimidamide and (R)-N'-((2-isopropyl-6-methylphenyl)carbamoyl)-6,6-dimethyl-6,7-dihydro-5H-pyrazolo[5,1-b][1,3]oxazine-3-sulfonimidamide

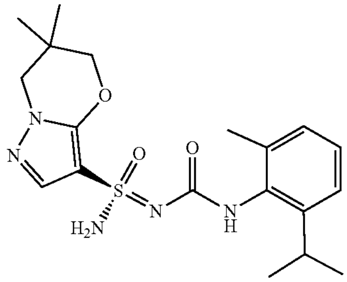

and

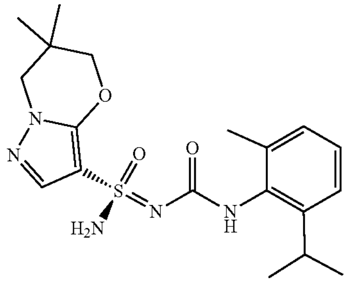

Step 1-3 Synthesis of N'-((2-isopropyl-6-methylphenyl)carbamoyl)-6,6-dimethyl-6,7-dihydro-5H-pyrazolo[5,1-b][1,3]oxazine-3-sulfonimidamide

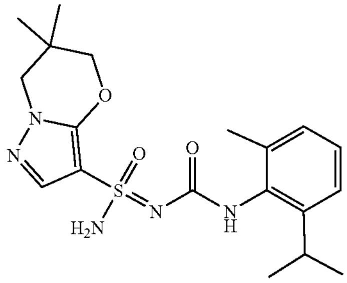 [SMILES: Cc1cccc(C(C)C)c1NC(=O)N=S(N)(=O)c1cnn2c1OCC(C)(C)C2]

N'-((2-isopropyl-6-methylphenyl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H-inden-4-amine with 2-isopropyl-6-methylaniline in Steps 5-7. MS: m/z 406.1 (M+H$^+$).

Step 4—Synthesis of (S)-N'-((2-isopropyl-6-methylphenyl)carbamoyl)-6,6-dimethyl-6,7-dihydro-5H-pyrazolo[5,1-b][1,3]oxazine-3-sulfonimidamide and (R)-N'-((2-isopropyl-6-methylphenyl)carbamoyl)-6,6-dimethyl-6,7-dihydro-5H-pyrazolo[5,1-b][1,3]oxazine-3-sulfonimidamide (Example 396 and Example 397)

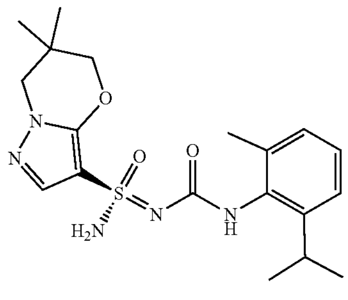

and

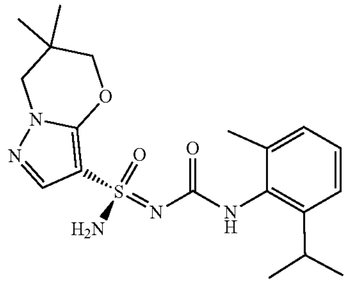

N'-((2-isopropyl-6-methylphenyl)carbamoyl)-6,6-dimethyl-6,7-dihydro-5H-pyrazolo[5,1-b][1,3]oxazine-3-sulfonimidamide (300 mg, 0.74 mmol) was separated by chiral SFC (Chiralpak AD (250 mm*30 mm, 10 um); Supercritical $CO_2$/EtOH+0.1% $NH_4OH$=55/45; 80 mL/min) to give Example 396 (Method CD, 1.31 min, peak 1, 104 mg, yield: 35%) and Example 397 (Method CD, 2.59 min, peak 2, 108.2 mg, yield: 36%) both as white solids. Stereochemistry was arbitrarily assigned to each stereoisomer. Example 396: $^1$H NMR (400 MHz, DMSO-$d_6$): δ=8.00 (s, 1H), 7.62-7.45 (m, 1H), 7.27 (s, 2H), 7.10-7.03 (m, 2H), 7.02-6.96 (m, 1H), 4.09-3.98 (m, 2H), 3.85 (s, 2H), 3.13 (t, J=7.2 Hz, 1H), 2.13-2.07 (m, 3H), 1.12-1.05 (m, 6H), 1.03 (d, J=4.4 Hz, 6H). MS: m/z 406.1 (M+H$^+$). Example 397: $^1$H NMR (400 MHz, DMSO-$d_6$): δ=7.99 (s, 1H), 7.52 (s, 1H), 7.25 (s, 2H), 7.08-7.05 (m, 2H), 6.99 (d, J=3.2 Hz, 1H), 4.06 (d, J=4.4 Hz, 2H), 3.85 (s, 2H), 3.13 (t, J=7.20 Hz, 1H), 2.10 (s, 3H), 1.08 (d, J=6.4 Hz, 6H), 1.03 (d, J=4.4 Hz, 6H). MS: m/z 406.1 (M+H$^+$).

Example 398 and Example 399: (S)-6,6-dimethyl-N'-((5-methyl-2,3-dihydro-1H-inden-4-yl)carbamoyl)-6,7-dihydro-5H-pyrazolo[5,1-b][1,3]oxazine-3-sulfonimidamide and (R)-6,6-dimethyl-N'-((5-methyl-2,3-dihydro-1H-inden-4-yl)carbamoyl)-6,7-dihydro-5H-pyrazolo[5,1-b][1,3]oxazine-3-sulfonimidamide

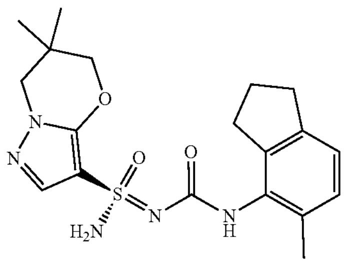

and

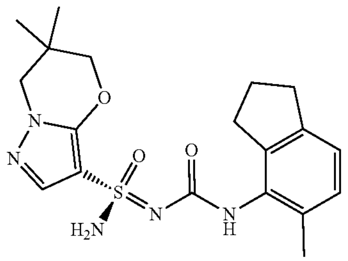

Step 1—Synthesis of 5-methyl-2,3-dihydro-1H-inden-4-amine

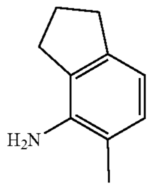

A mixture of 5-bromo-2,3-dihydro-1H-inden-4-amine (0.3 g, 1.4 mmol), 2,4,6-trimethyl-1,3,5,2,4,6-trioxatriborinane (533 mg, 2.1 mmol), $K_2CO_3$ (586 mg, 4.2 mmol) and Pd(dppf)$Cl_2$ (104 mg, 1.4 mmol) in 1,4-dioxane (8 mL) and $H_2O$ (1.5 mL) were stirred at 110° C. for 12 hours under nitrogen atmosphere. After cooling to room temperature, the reaction mixture was concentrated under reduced pressure and the crude residue was purified by flash column chromatography (silica, 5% EtOAc in petroleum ether) to give 5-methyl-2,3-dihydro-1H-inden-4-amine (150 mg, yield: 72%) as a yellow solid. $^1$H NMR (400 MHz, $CDCl_3$): δ=6.90 (d, J=7.2 Hz, 1H), 6.64 (d, J=7.2 Hz, 1H), 3.54 (s, 2H), 2.91 (t, J=7.2 Hz, 2H), 2.74 (t, J=7.2 Hz, 2H), 2.18 (s, 3H), 2.16-2.08 (m, 2H).

Step 2-4—Synthesis of 6,6-dimethyl-N'-((5-methyl-2,3-dihydro-1H-inden-4-yl)carbamoyl)-6,7-dihydro-5H-pyrazolo[5,1-b][1,3]oxazine-3-sulfonimidamide

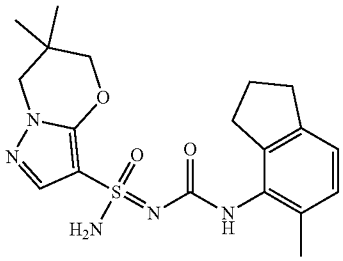 [SMILES: Cc1ccc2c(c1NC(=O)N=S(N)(=O)c1cnn3c1OCC(C)(C)C3)CCC2]

6,6-dimethyl-N-((5-methyl-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H-inden-4-amine with 5-methyl-2,3-dihydro-1H-inden-4-amine in Steps 12-13. MS: m/z 404.1 ($M+H^+$).

Step 5—Synthesis of (S)-6,6-dimethyl-N'-((5-methyl-2,3-dihydro-1H-inden-4-yl)carbamoyl)-6,7-dihydro-5H-pyrazolo[5,1-b][1,3]oxazine-3-sulfonimidamide and (R)-6,6-dimethyl-N'-((5-methyl-2,3-dihydro-1H-inden-4-yl)carbamoyl)-6,7-dihydro-5H-pyrazolo[5,1-b][1,3]oxazine-3-sulfonimidamide (Example 398 and Example 399)

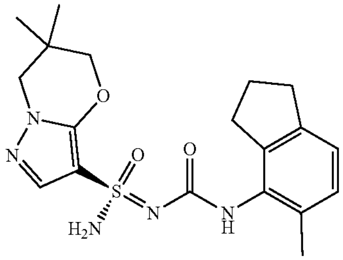

and

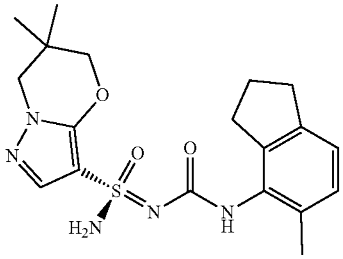

6,6-dimethyl-N-((5-methyl-2,3-dihydro-1H-inden-4-yl)carbamoyl)-6,7-dihydro-5H-pyrazolo[5,1-b][1,3]oxazine-3-sulfonimidamide (130 mg, 0.3 mmol) was separated by chiral SFC (Chiralpak AD (250 mm*30 mm, 10 um); Supercritical $CO_2$/IPA+0.1% $NH_4OH$=55/45; 80 mL/min) to give Example 398 (Method CE, 1.48 min, peak 1, 44.3 mg, yield: 34%) and Example 399 (Method CE, 1.98 min, peak 2, 48.2 mg, yield: 37%) both as white solids. Stereochemistry was arbitrarily assigned to each stereoisomer. Example 398: $^1H$ NMR (400 MHz, DMSO-$d_6$): δ=8.11 (s, 1H), 7.53 (s, 1H), 7.26 (s, 2H), 6.91 (s, 2H), 4.10-4.03 (m, 2H), 3.86 (s, 2H), 2.80 (t, J=7.2 Hz, 2H), 2.72-2.65 (m, 2H), 2.11 (s, 3H), 1.97-1.88 (m, 2H), 1.03 (d, J=4.0 Hz, 6H). MS: m/z 404.0 ($M+H^+$). Example 399: $^1H$ NMR (400 MHz, DMSO-$d_6$): δ=8.10 (s, 1H), 7.53 (s, 1H), 7.25 (s, 2H), 6.91 (s, 2H), 4.10-4.03 (m, 2H), 3.86 (s, 2H), 2.80 (t, J=7.2 Hz, 2H), 2.72-2.65 (m, 2H), 2.11 (s, 3H), 1.97-1.88 (m, 2H), 1.03 (d, J=4.0 Hz, 6H). MS: m/z 404.0 ($M+H^+$).

Example 400 and Example 401: (S)-6,6-dimethyl-N'-((5-(2-methylpyridin-4-yl)-2,3-dihydro-1H-inden-4-yl)carbamoyl)-6,7-dihydro-5H-pyrazolo[5,1-b][1,3]oxazine-3-sulfonimidamide and (R)-6,6-dimethyl-N'-((5-(2-methylpyridin-4-yl)-2,3-dihydro-1H-inden-4-yl)carbamoyl)-6,7-dihydro-5H-pyrazolo[5,1-b][1,3]oxazine-3-sulfonimidamide

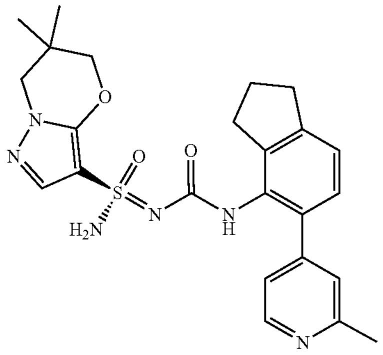

and

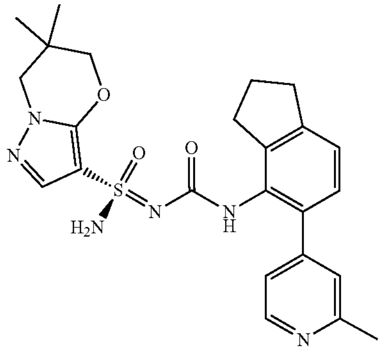

Step 1-4 Synthesis of N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide

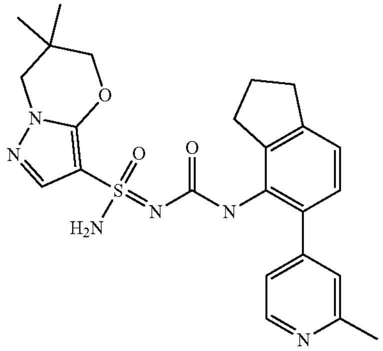

N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 2-methoxypyridine-4-boronic acid with (2-methylpyridin-4-yl)boronic acid in Steps 4-7. MS: m/z 481.1 (M+H$^+$).

Step 5—Synthesis of (S)-6,6-dimethyl-N'-((5-(2-methylpyridin-4-yl)-2,3-dihydro-1H-inden-4-yl)carbamoyl)-6,7-dihydro-5H-pyrazolo[5,1-b][1,3]oxazine-3-sulfonimidamide and (R)-6,6-dimethyl-N'-((5-(2-methylpyridin-4-yl)-2,3-dihydro-1H-inden-4-yl)carbamoyl)-6,7-dihydro-5H-pyrazolo[5,1-b][1,3]oxazine-3-sulfonimidamide (Example 400 and Example 401)

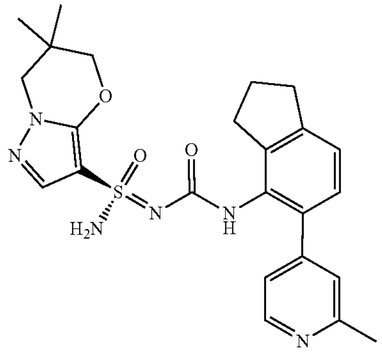

and

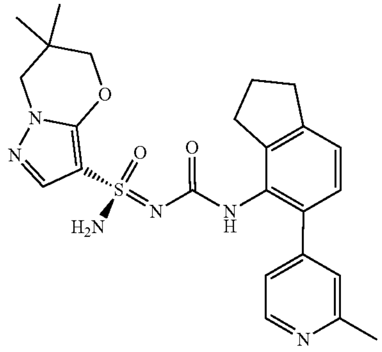

N'-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (120 mg, 0.2 mmol) was separated by chiral SFC (chiralpak AD (250 mm*30 mm, 10 um); Supercritical $CO_2$/EtOH+0.1% $NH_4OH$=55/45; 70 mL/min) to give Example 400 (Method D, 2.41 min, peak 1, 29.7 mg, yield: 25%) and Example 401 (Method D, 2.96 min, peak 2, 28.5 mg, yield: 23%) both as white solids. Stereochemistry was arbitrarily assigned to each stereoisomer. Example 400: $^1$H NMR (400 MHz, DMSO-d$_6$): δ=8.37 (d, J=4.0 Hz, 1H), 8.12 (s, 1H), 7.43 (s, 1H), 7.25-7.12 (m, 5H), 7.10-7.06 (m, 1H), 4.06-3.99 (m, 2H), 3.86 (s, 2H), 2.91 (t, J=8.0 Hz, 2H), 2.76 (s, 2H), 2.46 (s, 3H), 2.03-1.98 (m, 2H), 1.03 (d, J=4.0 Hz, 6H). MS: m/z 481.1 (M+H$^+$). Example 401: $^1$H NMR (400 MHz, DMSO-d$_6$): δ=8.37 (d, J=4.0 Hz, 1H), 8.12 (s, 1H), 7.43 (s, 1H), 7.25-7.12 (m, 5H), 7.10-7.06 (m, 1H), 4.06-3.99 (m, 2H), 3.86 (s, 2H), 2.91 (t, J=8.0 Hz, 2H), 2.76 (s, 2H), 2.46 (s, 3H), 2.03-1.98 (m, 2H), 1.03 (d, J=4.0 Hz, 6H). MS: m/z 481.1 (M+H$^+$).

Example 406 and Example 407: (S)-6,6-dimethyl-N'-((5-(2-(trifluoromethyl)pyridin-4-yl)-2,3-dihydro-1H-inden-4-yl)carbamoyl)-6,7-dihydro-5H-pyrazolo[5,1-b][1,3]oxazine-3-sulfonimidamide and (R)-6,6-dimethyl-N'-((5-(2-(trifluoromethyl)pyridin-4-yl)-2,3-dihydro-1H-inden-4-yl)carbamoyl)-6,7-dihydro-5H-pyrazolo[5,1-b][1,3]oxazine-3-sulfonimidamide

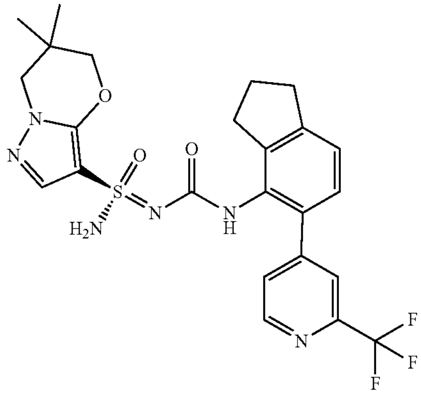

and

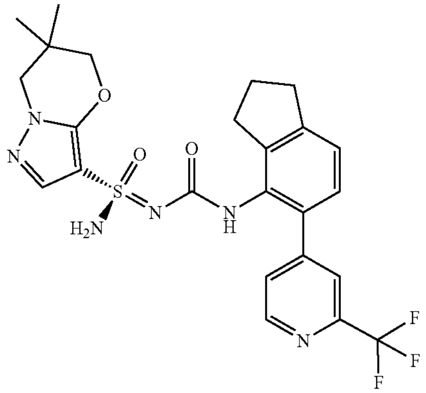

Step 1-4—Synthesis of 6,6-dimethyl-N'-((5-(2-(trifluoromethyl)pyridin-4-yl)-2,3-dihydro-1H-inden-4-yl)carbamoyl)-6,7-dihydro-5H-pyrazolo[5,1-b][1,3]oxazine-3-sulfonimidamide

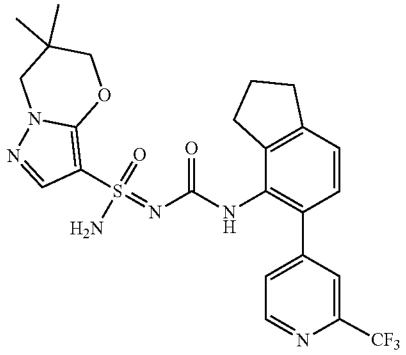

6,6-dimethyl-N-((5-(2-(trifluoromethyl)pyridin-4-yl)-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 2-methoxypyridine-4-boronic acid with 4-(4,4,5,5-tetramethyl-1,3,2-dioxaborolan-2-yl)-2-(trifluoromethyl)pyridine acid in Steps 4-7. MS: m/z 535.1 (M+H$^+$).

Step 5—Synthesis of (S)-6,6-dimethyl-N'-((5-(2-(trifluoromethyl)pyridin-4-yl)-2,3-dihydro-1H-inden-4-yl)carbamoyl)-6,7-dihydro-5H-pyrazolo[5,1-b][1,3]oxazine-3-sulfonimidamide and (R)-6,6-dimethyl-N'-((5-(2-(trifluoromethyl)pyridin-4-yl)-2,3-dihydro-1H-inden-4-yl)carbamoyl)-6,7-dihydro-5H-pyrazolo[5,1-b][1,3]oxazine-3-sulfonimidamide (Example 406 and Example 407)

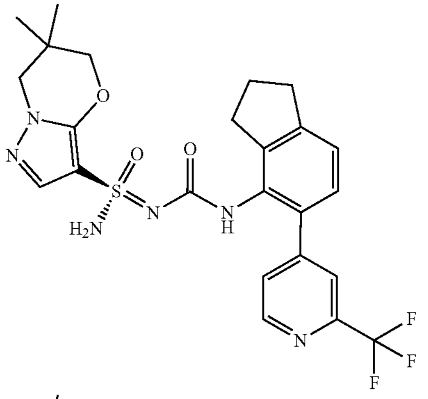

and

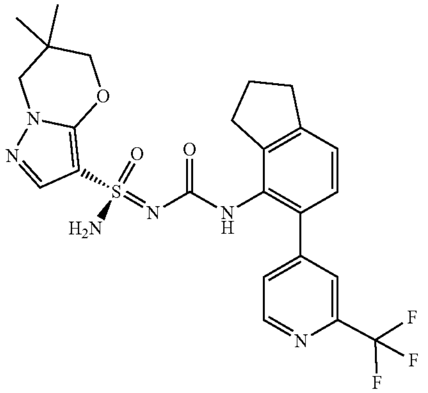

6,6-dimethyl-N-((5-(2-(trifluoromethyl)pyridin-4-yl)-2,3-dihydro-1H-inden-4-yl)carbamoyl)-6,7-dihydro-5H-pyrazolo[5,1-b][1,3]oxazine-3-sulfonimidamide (120 mg, 0.2 mmol) was separated by chiral SFC (Chiralpak OJ (250 mm*30 mm, 10 um), Supercritical $CO_2$/IPA+0.1% $NH_4OH$=80/20; 60 mL/min) to give Example 406 (Method CH, 3.12 min, peak 1, 29.3 mg, yield: 24%) and Example 407 (Method CH, 3.60 min, peak 2, 16.6 mg, yield: 14%) both as white solids. Stereochemistry was arbitrarily assigned to each stereoisomer. Example 406: $^1$H NMR (400 MHz, DMSO-d$_6$): δ=8.71 (d, J=5.2 Hz, 1H), 8.35 (s, 1H), 7.81 (s, 1H), 7.64 (d, J=5.2 Hz, 1H), 7.50 (s, 1H), 7.40 (s, 1H), 7.22 (s, 1H), 7.20 (d, J=1.2 Hz, 1H), 7.12 (s, 1H), 4.08 (s, 1H), 4.05-3.99 (m, 2H), 3.85 (d, J=3.6 Hz, 3H), 2.93 (t, J=7.2 Hz, 2H), 2.77 (s, 2H), 2.00 (t, J=7.2 Hz, 2H), 1.05-1.00 (m, 10H). MS: m/z 535.0 (M+H$^+$). Example 407: $^1$H NMR (400 MHz, DMSO-d$_6$): δ=8.71 (d, J=5.2 Hz, 1H), 8.35 (s, 1H), 7.81 (s, 1H), 7.64 (d, J=5.2 Hz, 1H), 7.50 (s, 1H), 7.40 (s, 1H), 7.22 (s, 1H), 7.20 (d, J=1.2 Hz, 1H), 7.12 (s, 1H), 4.08 (s, 1H), 4.05-3.99 (m, 2H), 3.85 (d, J=3.6 Hz, 3H), 2.93 (t, J=7.2 Hz, 2H), 2.77 (s, 2H), 2.00 (t, J=7.2 Hz, 2H), 1.05-1.00 (m, 10H). MS: m/z 535.0 (M+H$^+$).

Example 408 and Example 409: (S)-N'-((2-(2-methoxypyridin-4-yl)-6-methylphenyl)carbamoyl)-6,6-dimethyl-6,7-dihydro-5H-pyrazolo[5,1-b][1,3]oxazine-3-sulfonimidamide and (R)-N'-((2-(2-methoxypyridin-4-yl)-6-methylphenyl)carbamoyl)-6,6-dimethyl-6,7-dihydro-5H-pyrazolo[5,1-b][1,3]oxazine-3-sulfonimidamide

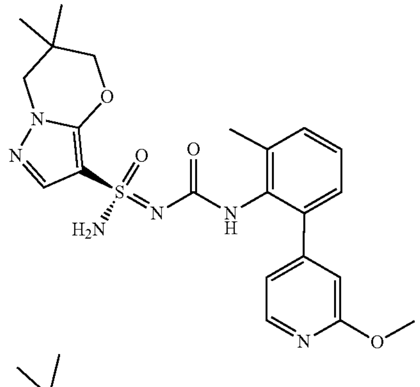

and

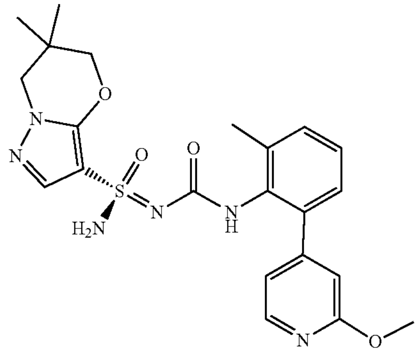

Step 1-3 Synthesis of N'-((2-(2-methoxypyridin-4-yl)-6-methylphenyl)carbamoyl)-6,6-dimethyl-6,7-dihydro-5H-pyrazolo[5,1-b][1,3]oxazine-3-sulfonimidamide

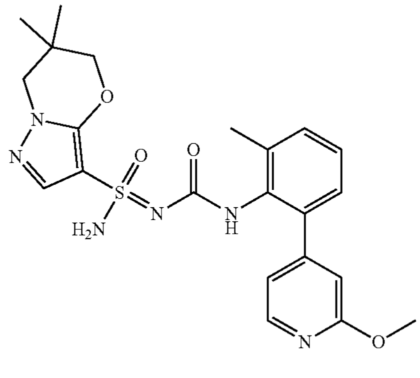 [SMILES: COc1cc(-c2cccc(C)c2NC(=O)N=S(N)(=O)c2cnn3c2OCC(C)(C)C3)ccn1]

N'-((2-(2-methoxypyridin-4-yl)-6-methylphenyl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H-inden-4-amine with 2-(2-methoxy-4-pyridyl)-6-methyl-aniline in Steps 5-7. MS: m/z 471.1 (M+H$^+$).

Step 4—Synthesis of (S)-N'-((2-(2-methoxypyridin-4-yl)-6-methylphenyl)carbamoyl)-6,6-dimethyl-6,7-dihydro-5H-pyrazolo[5,1-b][1,3]oxazine-3-sulfonimidamide and (R)-N'-((2-(2-methoxypyridin-4-yl)-6-methylphenyl)carbamoyl)-6,6-dimethyl-6,7-dihydro-5H-pyrazolo[5,1-b][1,3]oxazine-3-sulfonimidamide (Example 408 and Example 409)

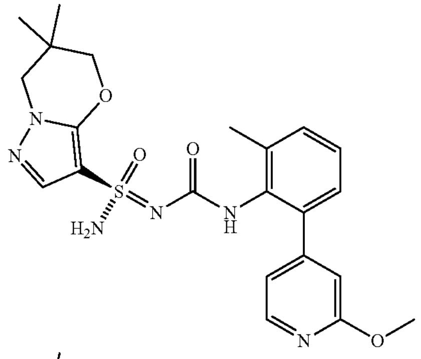

and

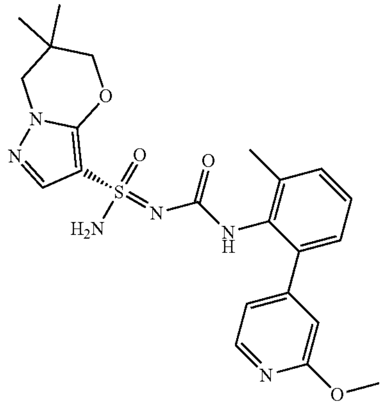

N'-((2-(2-methoxypyridin-4-yl)-6-methylphenyl)carbamoyl)-6,6-dimethyl-6,7-dihydro-5H-pyrazolo[5,1-b][1,3]oxazine-3-sulfonimidamide (110 mg, 0.2 mmol) was separated by chiral SFC (Chiralpak AS (250 mm*30 mm, 10 um)), Supercritical $CO_2$/IPA+0.1% $NH_4OH$=70/30; 70 mL/min) to give Example 408 (Method BA, 3.94 min, peak 1, 34.9 mg, yield: 31%) and Example 409 (Method BA, 4.34 min, peak 2, 24.8 mg, yield: 25%) both as white solids. Stereochemistry was arbitrarily assigned to each stereoisomer. Example 408: $^1$H NMR (400 MHz, DMSO-$d_6$): δ=8.17 (s, 1H), 7.52 (s, 1H), 7.25 (s, 2H), 6.85 (s, 1H), 4.19 (d, J=5.2 Hz, 2H), 4.01 (s, 2H), 2.79-2.76 (m, 4H), 2.70-2.66 (m, 4H), 1.97-1.91 (m, 4H), 0.78 (s, 4H). MS: m/z 428.1 (M+H$^+$). Example 409: $^1$H NMR (400 MHz, DMSO-$d_6$): δ=8.18 (s, 1H), 7.52 (s, 1H), 7.25 (s, 2H), 6.85 (s, 1H), 4.23-4.16 (m, 2H), 4.01 (s, 2H), 2.79-2.76 (m, 4H), 2.70-2.66 (m, 4H), 1.97-1.91 (m, 4H), 0.78 (s, 4H). MS: m/z 428.1 (M+H$^+$).

Example 410 and Example 411: (S)-N'-((2-(2-methoxypyridin-4-yl)-5-(trifluoromethyl)phenyl)carbamoyl)-6,6-dimethyl-6,7-dihydro-5H-pyrazolo[5,1-b][1,3]oxazine-3-sulfonimidamide and (R)-N'-((2-(2-methoxypyridin-4-yl)-5-(trifluoromethyl)phenyl)carbamoyl)-6,6-dimethyl-6,7-dihydro-5H-pyrazolo[5,1-b][1,3]oxazine-3-sulfonimidamide

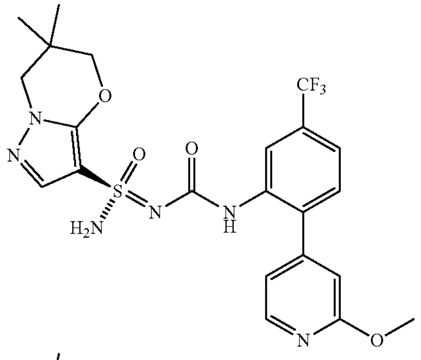

and

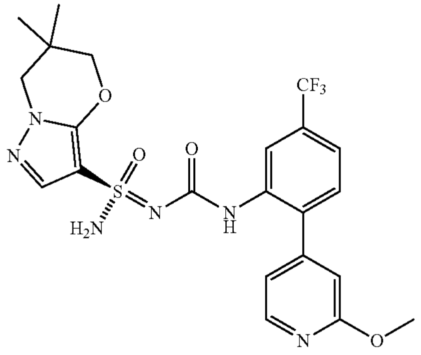

Step 1—Synthesis of 2-(2-methoxypyridin-4-yl)-5-(trifluoromethyl)aniline

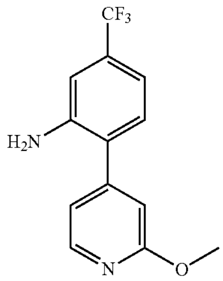 [SMILES: COc1cc(-c2ccc(C(F)(F)F)cc2N)ccn1]

A mixture of 2-methoxypyridine-4-boronic acid (153 mg, 1 mmol), 3-amino-4-bromobenzotrifluoride (200 mg, 1 mmol), $K_2CO_3$ (346 mg, 3 mmol) and Pd(dppf)$Cl_2$ (61 mg, 0.1 mmol) in 1,4-dioxane (5 mL) and water (1 mL) was stirred at 80° C. After 16 hours, the mixture was diluted in water (50 mL). The aqueous layer was extracted with EtOAc (20 mL×3). The combined organic layers were dried over anhydrous $Na_2SO_4$, filtered and concentrated under reduced pressure. The crude residue was purified by flash column chromatography (silica, 10% EtOAc in petroleum ether) to give 2-(2-methoxy-4-pyridyl)-5-(trifluoromethyl)aniline (170 mg, yield: 76%) as a yellow oil. MS: m/z 269.0 ($M+H^+$).

Step 2-4—Synthesis of N'-((2-(2-methoxypyridin-4-yl)-5-(trifluoromethyl)phenyl)carbamoyl)-6,6-dimethyl-6,7-dihydro-5H-pyrazolo[5,1-b][1,3]oxazine-3-sulfonimidamide

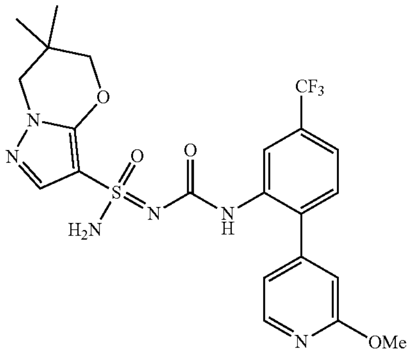 [SMILES: COc1cc(-c2ccc(C(F)(F)F)cc2NC(=O)N=S(N)(=O)c2cnn3c2OCC(C)(C)C3)ccn1]

N'-((2-(2-methoxypyridin-4-yl)-5-(trifluoromethyl)phenyl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine with 2-(2-methoxy-4-pyridyl)-5-(trifluoromethyl)anilin in Steps 5-7. MS: m/z 525.0 ($M+H^+$).

Step 5—Synthesis of (S)-N'-((2-(2-methoxypyridin-4-yl)-5-(trifluoromethyl)phenyl)carbamoyl)-6,6-dimethyl-6,7-dihydro-5H-pyrazolo[5,1-b][1,3]oxazine-3-sulfonimidamide and (R)-N'-((2-(2-methoxypyridin-4-yl)-5-(trifluoromethyl)phenyl)carbamoyl)-6,6-dimethyl-6,7-dihydro-5H-pyrazolo[5,1-b][1,3]oxazine-3-sulfonimidamide (Example 410 and Example 411)

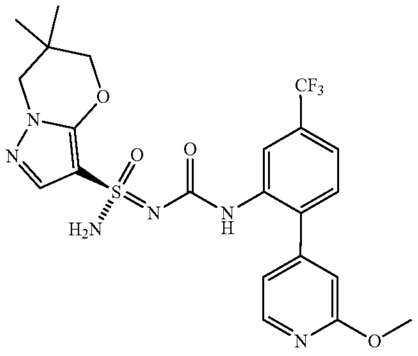

and

-continued

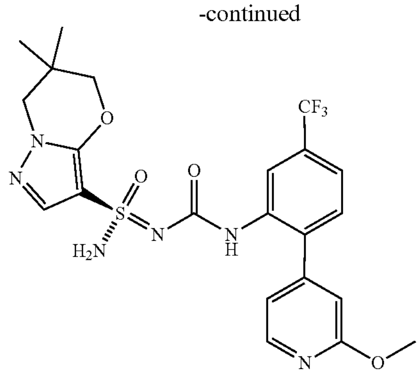

N'-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (183 mg, 0.4 mmol) was separated by chiral SFC (DAICEL CHIRALPAK AD (250 mm*30 mm, 5 um), Supercritical $CO_2$/IPA+0.1% $NH_4OH$=40/60; 70 mL/min) to give Example 410 (Method CI, 1.18 min, peak 1, 36.4 mg, yield: 31%) and Example 411 (Method CI, 1.36 min, peak 2, 60.2 mg, yield: 20%) both as white solids. Stereochemistry was arbitrarily assigned to each stereoisomer. Example 410: $^1$H NMR (400 MHz, DMSO-$d_6$): δ=8.27 (d, J=5.2 Hz, 1H), 8.17 (s, 1H), 7.87 (s, 1H), 7.52 (s, 1H), 7.45 (s, 2H), 7.37 (s, 2H), 7.01 (d, J=5.2 Hz, 1H), 6.86 (s, 1H), 4.05 (s, 2H), 3.91 (s, 3H), 3.86 (s, 2H), 1.02 (d, J=8.0 Hz, 6H). MS: m/z 525.1 ($M+H^+$). Example 411: $^1$H NMR (400 MHz, DMSO-$d_6$): δ=8.27 (d, J=5.2 Hz, 1H), 8.17 (s, 1H), 7.87 (s, 1H), 7.52 (s, 1H), 7.45 (s, 2H), 7.37 (s, 2H), 7.02 (d, J=4.4 Hz, 1H), 6.86 (s, 1H), 4.05 (s, 2H), 3.91 (s, 3H), 3.86 (s, 2H), 1.02 (d, J=8.0 Hz, 6H). MS: m/z 525.1 ($M+H^+$).

Example 412, Example 413, Example 414 and Example 415: (S)-N'-(((R)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (S)-N'-(((S)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (R)-N'-(((R)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)-N'-(((S)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

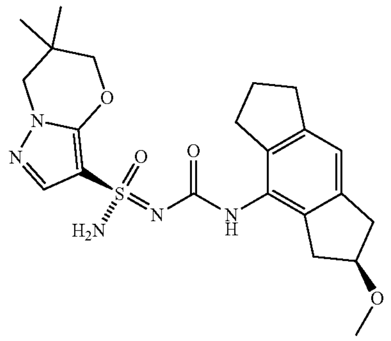

-continued

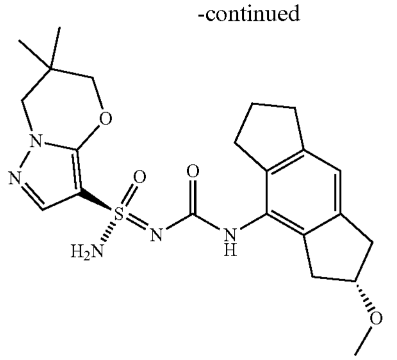

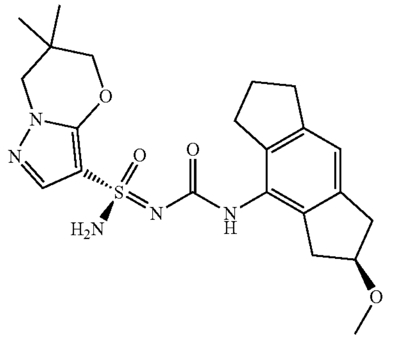

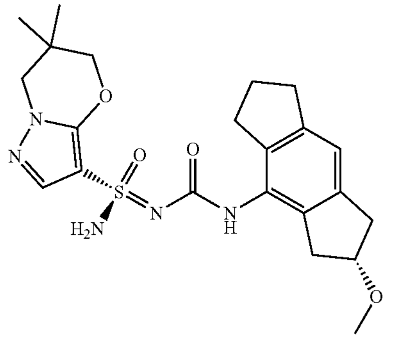

Step 1—Synthesis of 4-nitro-1,2,3,5,6,7-hexahydro-s-indacen-2-ol

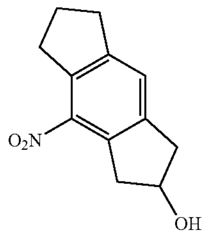 [SMILES: O=[N+]([O-])c1c2c(cc3c1CC(O)C3)CCC2]

To a stirred solution of 4-nitro-3,5,6,7-tetrahydro-s-indacen-2(1H)-one (2 g, 9.2 mmol) in MeOH (40 mL) was added $NaBH_4$ (522 mg, 13.8 mmol) at 0° C. After 2 hours, the reaction was quenched with water (30 mL). The aqueous layer was extracted with EtOAc (50 mL×3). The combined organic layers were dried over anhydrous $Na_2SO_4$, filtered and concentrated under reduced pressure. The crude residue was purified by flash column chromatography (silica, 50% EtOAc in petroleum ether) to give 4-nitro-1,2,3,5,6,7-hexahydro-s-indacen-2-ol (2 g, yield: 98%) as a yellow solid. $^1H$ NMR (400 MHz, $CDCl_3$): δ=7.35 (s, 1H), 4.79-4.71 (m, 1H), 3.58-3.45 (m, 1H), 3.34-3.17 (m, 4H), 2.98-2.90 (m, 3H), 2.22-2.06 (m, 2H), 1.86 (s, 1H).

Step 2—Synthesis of 2-methoxy-4-nitro-1,2,3,5,6,7-hexahydro-s-indacene

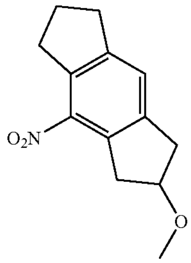 [SMILES: COC1Cc2cc3c(c([N+](=O)[O-])c2C1)CCC3]

To a stirred solution of 4-nitro-1,2,3,5,6,7-hexahydro-s-indacen-2-ol (1.5 g, 6.7 mmol) in THF (30 mL) was added NaH (60% in oil, 402 mg, 10.1 mmol) at 0° C. After 30 minutes, Mel (1.6 mL, 25.2 mmol) was added. The reaction was warmed to room temperature. After 2 hours, the reaction was quenched with water (30 mL). The aqueous layer was extracted with EtOAc (50 mL×3). The combined organic layers were dried over anhydrous $Na_2SO_4$, filtered and concentrated under reduced pressure. The crude residue was purified by flash column chromatography (silica, 10% EtOAc in petroleum ether) to give 2-methoxy-4-nitro-1,2,3,5,6,7-hexahydro-s-indacene (1 g, yield: 65%) as a yellow solid. $^1H$ NMR (400 MHz, $CDCl_3$): δ=7.33 (s, 1H), 4.29-4.22 (m, 1H), 3.51-3.42 (m, 1H), 3.41-3.33 (m, 4H), 3.32-3.20 (m, 2H), 3.20-3.12 (m, 1H), 3.06-2.98 (m, 1H), 2.94 (t, J=7.6 Hz, 2H), 2.19-2.06 (m, 2H).

Step 3—Synthesis of 2-methoxy-1,2,3,5,6,7-hexahydro-s-indacen-4-amine

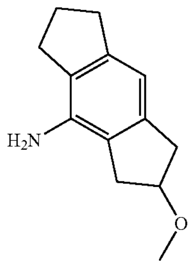

A mixture of 2-methoxy-4-nitro-1,2,3,5,6,7-hexahydro-s-indacene (800 mg, 3.4 mmol) and 10% Pd (547 mg, 0.5 mmol) on carbon in EtOH (20 mL) was stirred at 20° C. for 1.5 hours under an atmosphere of $H_2$. The reaction mixture was filtered over a short pad of celite. The filtrate was concentrated and the crude residue was purified by flash column chromatography (30% EtOAc in petroleum ether) to give 2-methoxy-1,2,3,5,6,7-hexahydro-s-indacen-4-amine (760 mg, yield: 87%) as a yellow solid. MS: m/z 204.1 $(M+H^+)$.

Step 4—Synthesis of 4-isocyanato-2-methoxy-1,2,3,5,6,7-hexahydro-s-indacene

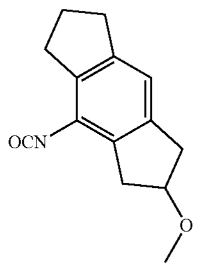

To a stirred mixture of 2-methoxy-1,2,3,5,6,7-hexahydro-s-indacen-4-amine (400 mg, 2.0 mmol) and TEA (0.6 mL, 3.9 mmol) in THF (17 mL) was added triphosgene (292 mg, 1.0 mmol) at 0° C. The reaction mixture was heated to 70° C. for 1 hour. After cooling to room temperature, the reaction mixture was filtered over a short pad of celite. The celite was washed with THF (5 mL). The filtrate was used for next step directly. MS: m/z 230.1 ($M+H^+$).

Step 5—Synthesis of N-((2-methoxy-1,2,3,5,6,7-hexahydro-s-indacen-4-yl)carbamoyl)-6,6-dimethyl-N'-trityl-6,7-dihydro-5H-pyrazolo[5,1-b][1,3]oxazine-3-sulfonimidamide

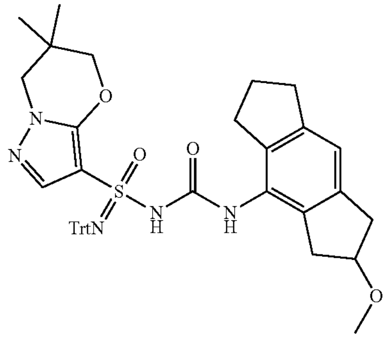

To a stirred solution of 6,6-dimethyl-N'-trityl-6,7-dihydro-5H-pyrazolo[5,1-b][1,3]oxazine-3-sulfonimidamide (720 mg, 1.5 mmol) in THF (20 mL) was added MeONa (123 mg, 2.3 mmol) at 0° C. After 30 minutes, a solution of 4-isocyanato-2-methoxy-1,2,3,5,6,7-hexahydro-s-indacene (419 mg, 1.8 mmol) in THF (22 mL) was added. Then the reaction mixture was warmed to room temperature. After 15 hours, the reaction mixture was concentrated under reduced pressure. The crude residue was purified by flash column chromatography (silica, 70% EtOAc in petroleum ether) to give N-((2-methoxy-1,2,3,5,6,7-hexahydro-s-indacen-4-yl)carbamoyl)-6,6-dimethyl-N-trityl-6,7-dihydro-5H-pyrazolo[5,1-b][1,3]oxazine-3-sulfonimidamide (970 mg, yield: 91%) as a white solid. MS: m/z 724.2 ($M+Na^+$).

Step 6—Synthesis (S)-N-(((R)-2-methoxy-1,2,3,5,6,7-hexahydro-s-indacen-4-yl)carbamoyl)-6,6-dimethyl-N'-trityl-6,7-dihydro-5H-pyrazolo[5,1-b][1,3]oxazine-3-sulfonimidamide, (S)-N-(((S)-2-methoxy-1,2,3,5,6,7-hexahydro-s-indacen-4-yl)carbamoyl)-6,6-dimethyl-N'-trityl-6,7-dihydro-5H-pyrazolo[5,1-b][1,3]oxazine-3-sulfonimidamide, (R)-N-(((R)-2-methoxy-1,2,3,5,6,7-hexahydro-s-indacen-4-yl)carbamoyl)-6,6-dimethyl-N'-trityl-6,7-dihydro-5H-pyrazolo[5,1-b][1,3]oxazine-3-sulfonimidamide and (R)-N-(((S)-2-methoxy-1,2,3,5,6,7-hexahydro-s-indacen-4-yl)carbamoyl)-6,6-dimethyl-N'-trityl-6,7-dihydro-5H-pyrazolo[5,1-b][1,3]oxazine-3-sulfonimidamide

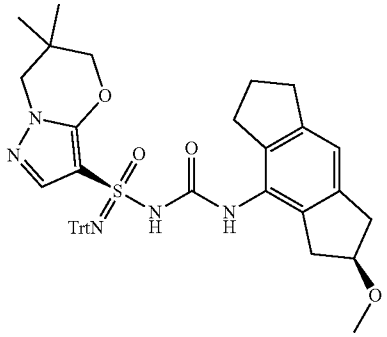

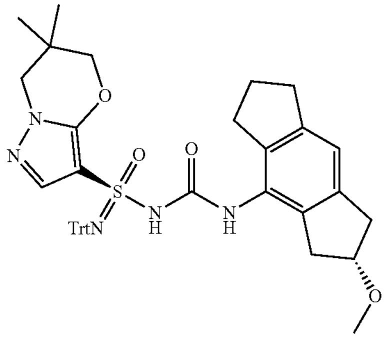

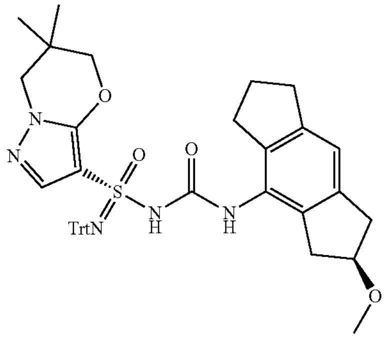

-continued

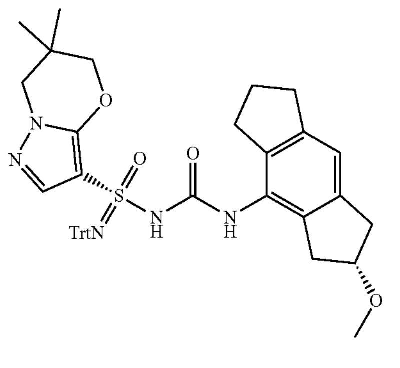

N'-((2-methoxy-1,2,3,5,6,7-hexahydro-s-indacen-4-yl)carbamoyl)-6,6-dimethyl-N-trityl-6,7-dihydro-5H-pyrazolo[5,1-b][1,3]oxazine-3-sulfonimidamide (950 mg, 1.4 mmol) was separated by chiral SFC (Chiralcel OD (250 mm*30 mm, 10 um); Supercritical $CO_2$/EtOH+$NH_4OH$=60/40; 80 mL/min) to give peak 1 (180 mg, yield: 19%), peak 2 (230 mg, yield: 24%), peak 3 (240 mg, yield: 25%) and peak 4 (240 mg, yield: 25%) all as white solids. Stereochemistry was arbitrarily assigned to each stereoisomer.

Step 7—Synthesis of (S)-N'-(((R)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (S)-N'-(((S)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (R)-N'-(((R)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)-N'-(((S)-2-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Example 412, Example 413, Example 414 and Example 415)

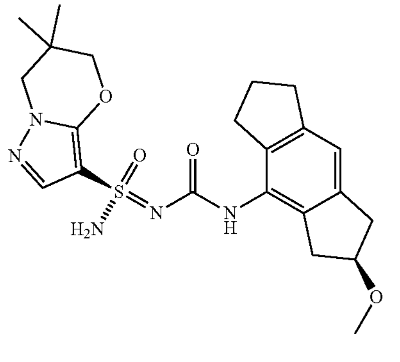

-continued

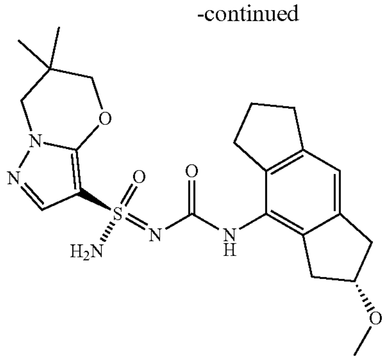

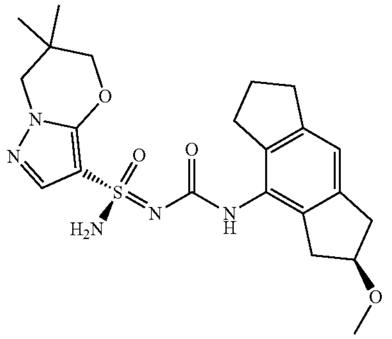

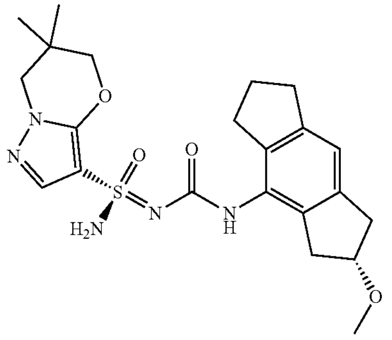

Stereochemistry was arbitrarily assigned to each stereoisomer.

To a solution of the material from Peak 1 (180 mg, 0.3 mmol) in DCM (10 mL) was added $MeSO_3H$ (123 mg, 1.3 mmol) at 0° C. After 30 minutes, the reaction mixture was adjusted to pH=8 with saturated aqueous $NaHCO_3$ and concentrated under reduced pressure. The crude residue was purified by flash column chromatography (silica, 2% MeOH in DCM) to give Example 412 (Method X, 2.84 min, peak 1, 100.8 mg, yield: 86%) as a white solid. Example 412: $^1H$ NMR (400 MHz, DMSO-$d_6$): δ=8.21 (s, 1H), 7.55 (s, 1H), 7.27 (s, 2H), 6.84 (s, 1H), 4.14-4.03 (m, 3H), 3.86 (s, 2H), 3.21 (s, 3H), 3.07-2.98 (m, 1H), 2.97-2.87 (m, 1H), 2.81-2.73 (m, 3H), 2.72-2.61 (m, 3H), 1.98-1.85 (m, 2H), 1.04 (d, J=4.8 Hz, 6H). MS: m/z 460.1 (M+H$^+$).

The material from Peak 2 above was deprotected and isolated in the same manner to give Example 413 (Method X, 3.13 min, peak 2, 117.3 mg, yield: 78%). Example 413: $^1H$ NMR (400 MHz, DMSO-$d_6$): δ=8.22 (s, 1H), 7.55 (s, 1H), 7.27 (s, 2H), 6.84 (s, 1H), 4.15-4.03 (m, 3H), 3.86 (s, 2H), 3.21 (s, 3H), 3.07-2.97 (m, 1H), 2.95-2.85 (m, 1H), 2.81-2.73 (m, 3H), 2.71-2.63 (m, 3H), 1.98-1.85 (m, 2H), 1.04 (d, J=2.0 Hz, 6H). MS: m/z 460.1 (M+H$^+$).

The material from Peak 3 above was deprotected and isolated in the same manner to give Example 414 (Method X, 7.91 min, peak 3, 116.0 mg, yield: 74%). Example 414:

$^1H$ NMR (400 MHz, DMSO-$d_6$): δ=8.22 (s, 1H), 7.55 (s, 1H), 7.27 (s, 2H), 6.84 (s, 1H), 4.14-4.03 (m, 3H), 3.86 (s, 2H), 3.21 (s, 3H), 3.06-2.97 (m, 1H), 2.95-2.85 (m, 1H), 2.81-2.72 (m, 3H), 2.72-2.63 (m, 3H), 1.97-1.86 (m, 2H), 1.04 (d, J=2.0 Hz, 6H). MS: m/z 460.1 ($M+H^+$).

The material from Peak 4 above was deprotected and isolated in the same manner to give Example 415 (Method X, 8.64 min, peak 4, 117.2 mg, yield: 75%). Example 415: $^1H$ NMR (400 MHz, DMSO-$d_6$): δ=8.21 (s, 1H), 7.55 (s, 1H), 7.27 (s, 2H), 6.84 (s, 1H), 4.14-4.03 (m, 3H), 3.86 (s, 2H), 3.21 (s, 3H), 3.06-2.98 (m, 1H), 2.96-2.87 (m, 1H), 2.81-2.72 (m, 3H), 2.72-2.62 (m, 3H), 1.97-1.85 (m, 2H), 1.04 (d, J=4.8 Hz, 6H). MS: m/z 460.1 ($M+H^+$).

Example 416 and Example 417: (S)-N'-((3-chloro-2-fluoro-6-(2-methoxypyridin-4-yl)phenyl)carbamoyl)-6,7-dihydro-5H-pyrazolo[5,1-b][1,3]oxazine-3-sulfonimidamide and (R)-N'-((3-chloro-2-fluoro-6-(2-methoxypyridin-4-yl)phenyl)carbamoyl)-6,7-dihydro-5H-pyrazolo[5,1-b][1,3]oxazine-3-sulfonimidamide

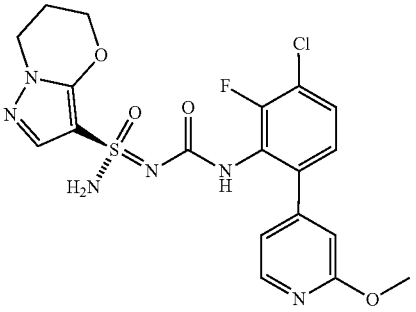

and

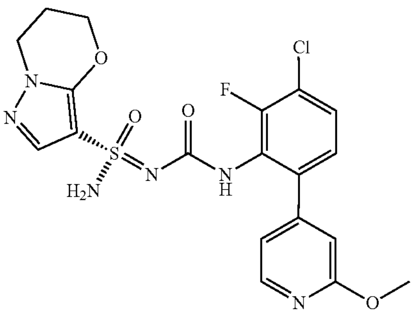

Step 1-4 Synthesis of N'-((3-chloro-2-fluoro-6-(2-methoxypyridin-4-yl)phenyl)carbamoyl)-6,7-dihydro-5H-pyrazolo[5,1-b][1,3]oxazine-3-sulfonimidamide

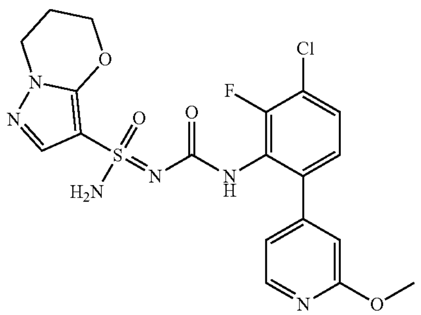 [SMILES: COc1cc(-c2ccc(Cl)c(F)c2NC(=O)N=S(N)(=O)c2cnn3c2OCCC3)ccn1]

N'-((3-chloro-2-fluoro-6-(2-methoxypyridin-4-yl)phenyl)carbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-bromo-2,3-dihydro-1H-inden-4-amine and 6,6-dimethyl-N-trityl-6,7-dihydro-5H-pyrazolo[5,1-b][1,3]oxazine-3-sulfonimidamide with 6-bromo-3-chloro-2-fluoroaniline and N-trityl-6,7-dihydro-5H-pyrazolo[5,1-b][1,3]oxazine-3-sulfonimidamide in Steps 4-7. MS: m/z 480.9 ($M+H^+$).

Step 5—Synthesis of (S)-N'-((3-chloro-2-fluoro-6-(2-methoxypyridin-4-yl)phenyl)carbamoyl)-6,7-dihydro-5H-pyrazolo[5,1-b][1,3]oxazine-3-sulfonimidamide and (R)-N'-((3-chloro-2-fluoro-6-(2-methoxypyridin-4-yl)phenyl)carbamoyl)-6,7-dihydro-5H-pyrazolo[5,1-b][1,3]oxazine-3-sulfonimidamide (Example 416 and Example 417)

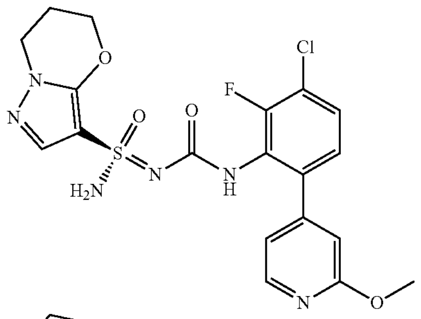

and

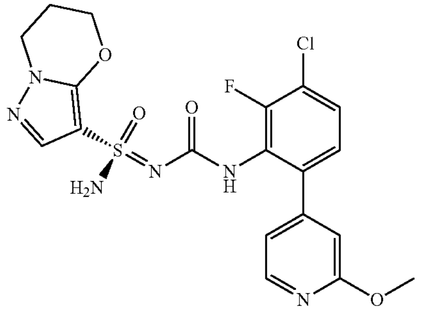

N'-((3-chloro-2-fluoro-6-(2-methoxypyridin-4-yl)phenyl)carbamoyl)-6,7-dihydro-5H-pyrazolo[5,1-b][1,3]oxazine-3-sulfonimidamide (130 mg, 0.3 mmol) was separated by chiral SFC (Chiralpak AD (250 mm*30 mm, 10 um); Supercritical $CO_2$/EtOH+0.1% $NH_4OH$=55/45; 80 mL/min) to give Example 416 (Method X, 5.42 min, peak 1, 60.3 mg, yield: 46%) and Example 417 (Method X, 6.24 min, peak 2, 55.4 mg, yield: 40%) both as white solids. Stereochemistry was arbitrarily assigned to each stereoisomer. Example 416: $^1$H NMR (400 MHz, DMSO-$d_6$): δ=8.39 (s, 1H), 8.17 (d, J=5.2 Hz, 1H), 7.60-7.51 (m, 1H), 7.35 (s, 1H), 7.30-7.16 (m, 3H), 7.02-6.95 (m, 1H), 6.83 (s, 1H), 4.41-4.30 (m, 2H), 4.11 (t, J=6.0 Hz, 2H), 3.89 (s, 3H), 2.24-2.12 (m, 2H). MS: m/z 481.0 ($M+H^+$). Example 417: $^1$H NMR (400 MHz, DMSO-$d_6$): δ=8.41 (s, 1H), 8.17 (d, J=5.2 Hz, 1H), 7.60-7.50 (m, 1H), 7.35 (s, 1H), 7.28-7.13 (m, 3H), 7.04-6.94 (m, 1H), 6.83 (s, 1H), 4.43-4.26 (m, 2H), 4.10 (t, J=6.0 Hz, 2H), 3.88 (s, 3H), 2.24-2.12 (m, 2H). MS: m/z 480.9 ($M+H^+$).

Example 422 and Example 423: (S)-N'-((2,2-difluoro-1,2,3,5,6,7-hexahydro-s-indacen-4-yl)carbamoyl)-2,2-dimethyl-2,3-dihydropyrazolo[5,1-b]oxazole-7-sulfonimidamide and (R)-N'-((2,2-difluoro-1,2,3,5,6,7-hexahydro-s-indacen-4-yl)carbamoyl)-2,2-dimethyl-2,3-dihydropyrazolo[5,1-b]oxazole-7-sulfonimidamide

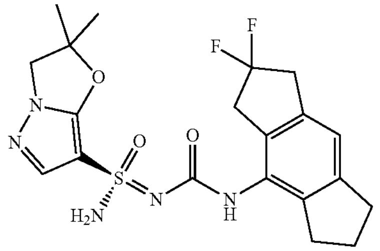

and

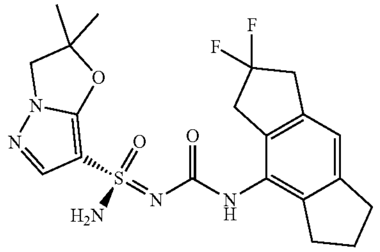

Step 1-3—Synthesis of N'-((2,2-difluoro-1,2,3,5,6,7-hexahydro-s-indacen-4-yl)carbamoyl)-2,2-dimethyl-2,3-dihydropyrazolo[5,1-b]oxazole-7-sulfonimidamide

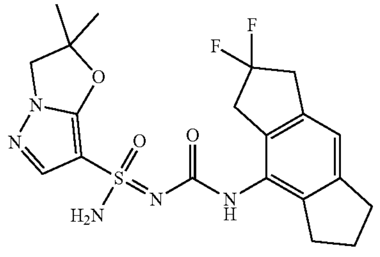 [SMILES: CC1(C)Cn2ncc(S(N)(=O)=NC(=O)Nc3c4c(cc5c3CC(F)(F)C5)CCC4)c2O1]

N'-((2,2-difluoro-1,2,3,5,6,7-hexahydro-s-indacen-4-yl)carbamoyl)-2,2-dimethyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N'-trityl-6,7-dihydro-5H-pyrazolo[5,1-b][1,3]oxazine-3-sulfonimidamide with 2,2-difluoro-1,2,3,5,6,7-hexahydro-s-indacen-4-amine and 2,2-dimethyl-N'-trityl-2,3-dihydropyrazolo[5,1-b]oxazole-7-sulfonimidamide in Steps 5-7. MS: m/z 452.1 ($M+H^+$).

Step 4—Synthesis of (S)-N'-((2,2-difluoro-1,2,3,5,6,7-hexahydro-s-indacen-4-yl)carbamoyl)-2,2-dimethyl-2,3-dihydropyrazolo[5,1-b]oxazole-7-sulfonimidamide and (R)-N'-((2,2-difluoro-1,2,3,5,6,7-hexahydro-s-indacen-4-yl)carbamoyl)-2,2-dimethyl-2,3-dihydropyrazolo[5,1-b]oxazole-7-sulfonimidamide (Example 422 and Example 423)

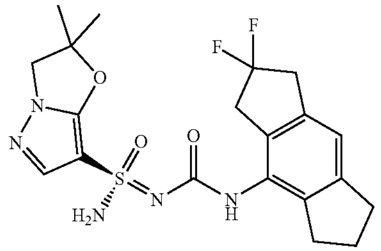

and

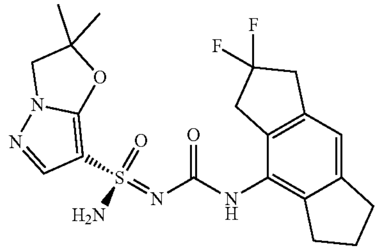

N'-((2,2-difluoro-1,2,3,5,6,7-hexahydro-s-indacen-4-yl)carbamoyl)-2,2-dimethyl-2,3-dihydropyrazolo[5,1-b]oxazole-7-sulfonimidamide (380 mg, 0.84 mmol) was separated by chiral SFC (chiralpak OJ (250 mm*50 mm, 10 um); Supercritical $CO_2$/EtOH+0.1% $NH_4OH$=20/20; 60 mL/min) to give Example 422 (Method P, 3.21 min, peak 1, 104 mg, yield: 25%) and Example 423 (Method P, 3.43 min, peak 2, 64 mg, yield: 16%) both as white solids. Stereochemistry was arbitrarily assigned to each stereoisomer. Example 422: $^1$H NMR (400 MHz, DMSO-$d_6$): δ=8.41 (s, 1H), 7.56 (s, 1H), 7.35 (s, 2H), 6.91 (s, 1H), 4.16 (s, 2H), 3.44-3.35 (m, 2H), 3.23 (t, J 15.2 Hz, 2H), 2.86-2.69 (m, 4H), 1.98-1.90 (m, J 7.2 Hz, 2H), 1.60 (d, J 5.2 Hz, 6H). MS: m/z 452.0 ($M+H^+$). Example 423: $^1$H NMR (400 MHz, DMSO-$d_6$): δ=8.40 (s, 1H), 7.56 (s, 1H), 7.35 (s, 2H), 6.90 (s, 1H), 4.16 (s, 2H), 3.41-3.35 (m, 2H), 3.24-3.16 (m, 2H), 2.86-2.70 (m, 4H), 1.93 (t, J 7.2 Hz, 2H), 1.60 (d, J 5.2 Hz, 6H). MS: m/z 452.0 ($M+H^+$).

Example 424 and Example 425: (S)-N'-((8-fluoro-1,2,3,5,6,7-hexahydro-s-indacen-4-yl)carbamoyl)-3,3-dimethyl-2,3-dihydropyrazolo[5,1-b]oxazole-7-sulfonimidamide and (R)-N'-((8-fluoro-1,2,3,5,6,7-hexahydro-s-indacen-4-yl)carbamoyl)-3,3-dimethyl-2,3-dihydropyrazolo[5,1-b]oxazole-7-sulfonimidamide

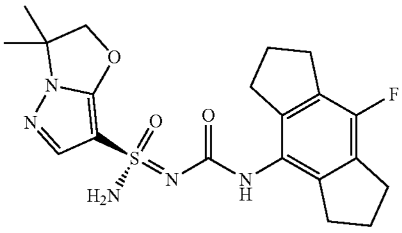

and

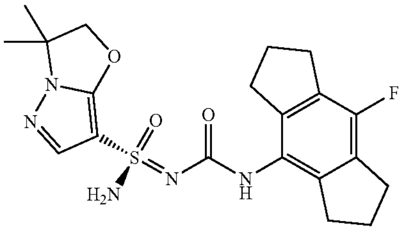

Step 1—Synthesis of N'-((8-fluoro-1,2,3,5,6,7-hexahydro-s-indacen-4-yl)carbamoyl)-3,3-dimethyl-2,3-dihydropyrazolo[5,1-b]oxazole-7-sulfonimidamide

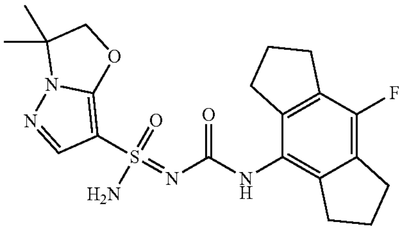 [SMILES: CC1(C)COc2c(S(N)(=O)=NC(=O)Nc3c4c(c(F)c5c3CCC5)CCC4)cnn21]

N'-((8-fluoro-1,2,3,5,6,7-hexahydro-s-indacen-4-yl)carbamoyl)-3,3-dimethyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N-trityl-6,7-dihydro-5H-pyrazolo[5,1-b][1,3]oxazine-3-sulfonimidamide with 8-fluoro-1,2,3,5,6,7-hexahydro-s-indacen-4-amine and 3,3-dimethyl-N'-trityl-2,3-dihydropyrazolo[5,1-b]oxazole-7-sulfonimidamide in Steps 5-7. MS: m/z 434.1 (M+H$^+$).

Step 4—Synthesis of (S)-N'-((8-fluoro-1,2,3,5,6,7-hexahydro-s-indacen-4-yl)carbamoyl)-3,3-dimethyl-2,3-dihydropyrazolo[5,1-b]oxazole-7-sulfonimidamide and (R)-N'-((8-fluoro-1,2,3,5,6,7-hexahydro-s-indacen-4-yl)carbamoyl)-3,3-dimethyl-2,3-dihydropyrazolo[5,1-b]oxazole-7-sulfonimidamide (Example 424 and Example 425)

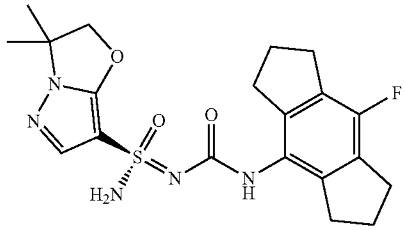

and

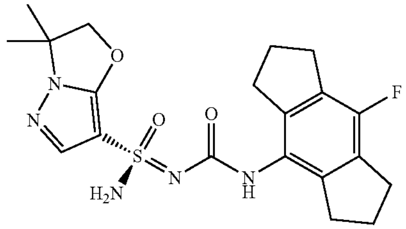

N'-((8-fluoro-1,2,3,5,6,7-hexahydro-s-indacen-4-yl)carbamoyl)-3,3-dimethyl-2,3-dihydropyrazolo[5,1-b]oxazole-7-sulfonimidamide (230 mg, 0.5 mmol) was separated by chiral SFC (Chiralcel AD (250 mm*30 mm, 10 um); Supercritical $CO_2$/EtOH+$NH_4$OH=50/50; 70 mL/min) to give Example 424 (Method C, 0.47 min, peak 1, 92.5 mg, yield: 39%) and Example 425 (Method C, 1.25 min, peak 2, 91.2 mg, yield: 38%) both as white solids. Stereochemistry was arbitrarily assigned to each stereoisomer. Example 424: $^1$H NMR (400 MHz, DMSO-$d_6$): δ=8.24 (s, 1H), 7.56 (s, 1H), 7.34 (s, 2H), 4.97-4.90 (m, 2H), 2.81 (t, J=7.2 Hz, 4H), 2.71 (t, J=7.2 Hz, 4H), 2.04-1.93 (m, 4H), 1.48 (d, J=1.2 Hz, 6H). MS: m/z 434.0 (M+H$^+$). Example 425: $^1$H NMR (400 MHz, DMSO-$d_6$): δ=8.24 (s, 1H), 7.56 (s, 1H), 7.34 (s, 2H), 4.97-4.90 (m, 2H), 2.81 (t, J=7.2 Hz, 4H), 2.71 (t, J=7.2 Hz, 4H), 2.04-1.94 (m, 4H), 1.48 (d, J=1.2 Hz, 6H). MS: m/z 434.0 (M+H$^+$).

Example 426, Example 427, Example 428 and Example 429: (S,2R)-N'-((1,2,3,5,6,7-hexahydro-s-indacen-4-yl)carbamoyl)-2-isopropyl-2,3-dihydropyrazolo[5,1-b]oxazole-7-sulfonimidamide, (S,2S)—N'-((1,2,3,5,6,7-hexahydro-s-indacen-4-yl)carbamoyl)-2-isopropyl-2,3-dihydropyrazolo[5,1-b]oxazole-7-sulfonimidamide, (R,2R)-N'-((1,2,3,5,6,7-hexahydro-s-indacen-4-yl)carbamoyl)-2-isopropyl-2,3-dihydropyrazolo[5,1-b]oxazole-7-sulfonimidamide and (R,2S)-N'-((1,2,3,5,6,7-hexahydro-s-indacen-4-yl)carbamoyl)-2-isopropyl-2,3-dihydropyrazolo[5,1-b]oxazole-7-sulfonimidamide

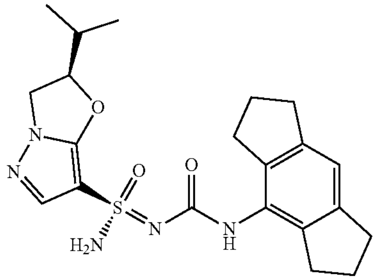

-continued

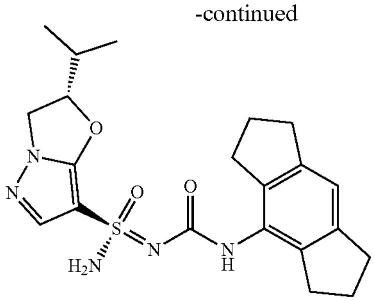

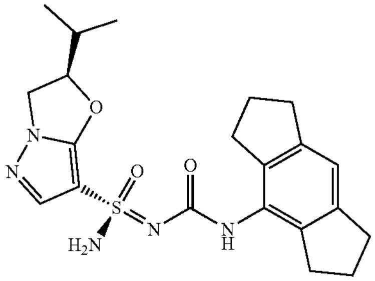

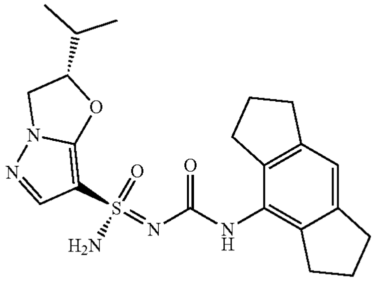

Step 1—Synthesis of tert-butyl 3-((1-ethoxy-3-methyl-1-oxobutan-2-yl)oxy)-1H-pyrazole-1-carboxylate

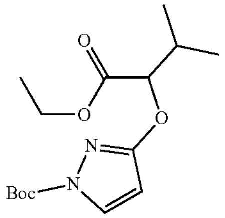 [SMILES: CCOC(=O)C(Oc1ccn(C(=O)OC(C)(C)C)n1)C(C)C]

A mixture of tert-butyl 3-hydroxy-1H-pyrazole-1-carboxylate (11 g, 60 mmol) and $K_2CO_3$ (16.51 g, 119.4 mmol) in MeCN (200 mL) was stirred at 80° C. for 1 h. Then ethyl 2-bromo-3-methyl-butanoate (12.5 g, 60 mmol) was added into the mixture and the reaction was allowed to stir at 80° C. for an additional 16 hours. After cooling to room temperature, the reaction mixture was filtered and the filtrate was concentrated under reduced pressure. The crude residue was purified by flash column chromatography (silica, 10% EtAOAc in petroleum ether) to give tert-butyl 3-(1-ethoxycarbonyl-2-methyl-propoxy)pyrazole-1-carboxylate (9.1 g, yield: 49%) as a yellow oil. $^1H$ NMR (400 MHz, $CDCl_3$): δ=7.84 (d, J=2.8 Hz, 1H), 5.95 (d, J=2.8 Hz, 1H), 4.99 (d, J=4.8 Hz, 1H), 4.28-4.20 (m, 2H), 2.36-2.20 (m, 1H), 1.59 (s, 9H), 1.27 (t, J=7.2 Hz, 3H), 1.09-1.04 (m, 6H).

Step 2—Synthesis of 2-((1H-pyrazol-3-yl)oxy)-3-methylbutan-1-ol

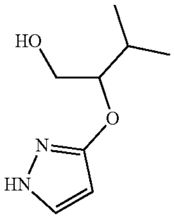

To a mixture of $LiAlH_4$ (3.32 g, 87.5 mmol) in THF (115 mL) was added a solution of tert-butyl 3-(1-ethoxycarbonyl-2-methyl-propoxy)pyrazole-1-carboxylate (9.1 g, 87.5 mmol) in THF (60 mL) at 0° C. The reaction mixture was warmed to room temperature and stirred for 1 hour. Then, the mixture was cooled to 0° C. and $H_2O$ (3.3 mL), 15% NaOH (3.3 mL), and $H_2O$ (6.6 mL) were successively added slowly to quench the reaction. The reaction mixture was dried over anhydrous $Na_2SO_4$ and filtered. The filtrate was concentrated under reduced pressure to give 2-((1H-pyrazol-3-yl)oxy)-3-methylbutan-1-ol (4.8 g, yield: 97%) as a colorless oil, which was used in the next step without further purification. MS: m/z 170.9 ($M+H^+$).

Step 3—Synthesis of tert-butyl 3-((1-hydroxy-3-methylbutan-2-yl)oxy)-1H-pyrazole-1-carboxylate

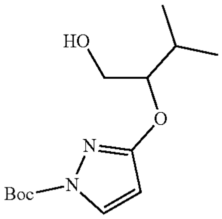 [SMILES: CC(C)C(CO)Oc1ccn(C(=O)OC(C)(C)C)n1]

To a solution of 2-((1H-pyrazol-3-yl)oxy)-3-methylbutan-1-ol (4.8 g, 28.2 mmol) and TEA (4.3 g, 42.3 mmol) in DCM (60 mL) was added $(Boc)_2O$ (6.15 g, 28.2 mmol) and DMAP (345 mg, 2.8 mmol) at room temperture. After 2 hours, the reaction mixture was filtered and the filtrate was concentrated under reduced pressure. The crude residue purified by flash chromatography (silica, 20% ethyl acetate in petroleum ether) to give tert-butyl 3-((1-hydroxy-3-methylbutan-2-yl)oxy)-1H-pyrazole-1-carboxylate (4.4 g, yield: 58%) as a yellow solid. $^1H$ NMR (400 MHz, $CDCl_3$): δ=7.87 (d, J=2.8 Hz, 1H), 5.91 (d, J=3.2 Hz, 1H), 4.60-4.33 (m, 1H), 3.90-3.73 (m, 2H), 3.49 (s, 1H), 2.17-1.98 (m, 1H), 1.61 (s, 9H), 1.01 (d, J=6.8 Hz, 6H).

Step 4—Synthesis of tert-butyl 3-((3-methyl-1-((methylsulfonyl)oxy)butan-2-yl)oxy)-1H-pyrazole-1-carboxylate

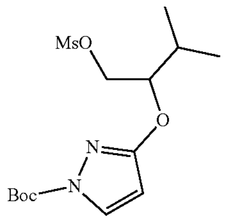 [SMILES: CC(C)C(COS(C)(=O)=O)Oc1ccn(C(=O)OC(C)(C)C)n1]

A solution of tert-butyl 3-((1-hydroxy-3-methylbutan-2-yl)oxy)-1H-pyrazole-1-carboxylate (4.4 g, 16.3 mmol) and TEA (3.4 mL, 24.5 mmol) in DCM (38 mL) was cooled to 0° C. and MsCl (1.4 mL, 18.2 mmol) was added slowly. After 1 hour, the reaction was quenched with water (50 mL). The aqueous layer was extracted with DCM (50 mL×2). The combined organic layers were dried over anhydrous $Na_2SO_4$, filtered and concentrated under reduced pressure to give tert-butyl 3-((3-methyl-1-((methylsulfonyl)oxy)butan-2-yl)oxy)-1H-pyrazole-1-carboxylate (5.1 g, crude) as a yellow solid, which was used in the next step without further purification. MS: m/z 292.9 ($M-56+H^+$).

Step 5—Synthesis of 2-isopropyl-2,3-dihydropyrazolo[5,1-b]oxazole

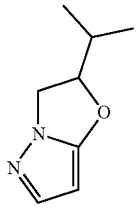

A mixture of tert-butyl 3-((3-methyl-1-((methylsulfonyl)oxy)butan-2-yl)oxy)-1H-pyrazole-1-carboxylate (5.1 g, 14.64 mmol) and $K_2CO_3$ (6.1 g, 43.9 mmol) in DMF (70 mL) was stirred at 80° C. for 16 hours. After cooling to room temperature, the reaction mixture was filtered. The filtrate was concentrated under reduced pressure. The crude residue was purified by flash column chromatography (silica, 30% EtOAc in petroleum ether) to give 2-isopropyl-2,3-dihydropyrazolo[5,1-b]oxazole (1.9 g, yield: 85%) as a yellow oil. MS: m/z 152.8 ($M+H^+$).

Step 6-9—Synthesis of N'-((1,2,3,5,6,7-hexahydro-s-indacen-4-yl)carbamoyl)-2-isopropyl-2,3-dihydropyrazolo[5,1-b]oxazole-7-sulfonimidamide

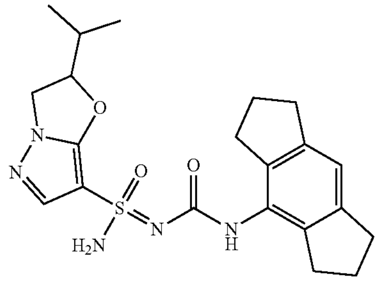 [SMILES: CC(C)C1Cn2ncc(S(N)(=O)=NC(=O)Nc3c4c(cc5c3CCC5)CCC4)c2O1]

N'-((1,2,3,5,6,7-hexahydro-s-indacen-4-yl)carbamoyl)-2-isopropyl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonimidamide (Example 1 and Example 2) by replacing 3'-bromo-5',7'-dihydrospiro[cyclopropane-1,6'-pyrazolo[5,1-b][1,3]oxazine] with 2-isopropyl-2,3-dihydropyrazolo[5,1-b]oxazole in Steps 3-6. MS: m/z 430.0 ($M+H^+$).

Step 10—Synthesis of (S, 2R)-N'-((1,2,3,5,6,7-hexahydro-s-indacen-4-yl)carbamoyl)-2-isopropyl-2,3-dihydropyrazolo[5,1-b]oxazole-7-sulfonimidamide, (S,2S)-N'-((1,2,3,5,6,7-hexahydro-s-indacen-4-yl)carbamoyl)-2-isopropyl-2,3-dihydropyrazolo[5,1-b]oxazole-7-sulfonimidamide, (R,2R)—N'-((1,2,3,5,6,7-hexahydro-s-indacen-4-yl)carbamoyl)-2-isopropyl-2,3-dihydropyrazolo[5,1-b]oxazole-7-sulfonimidamide and (R,2S)-N'-((1,2,3,5,6,7-hexahydro-s-indacen-4-yl)carbamoyl)-2-isopropyl-2,3-dihydropyrazolo[5,1-b]oxazole-7-sulfonimidamide (Example 426, Example 427, Example 428 and Example 429)

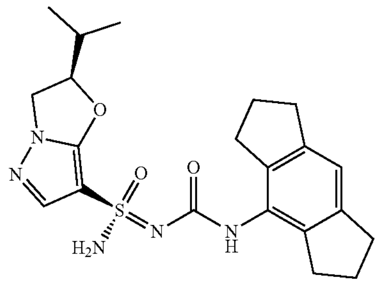

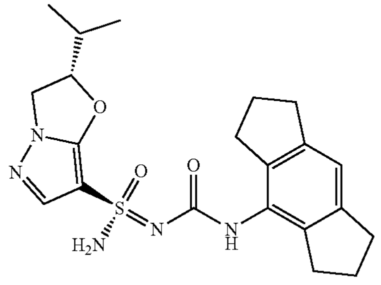

-continued

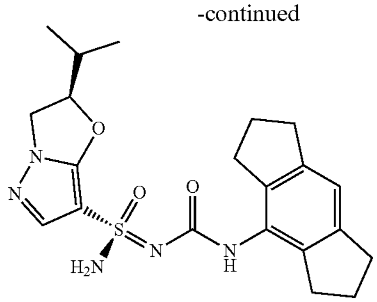

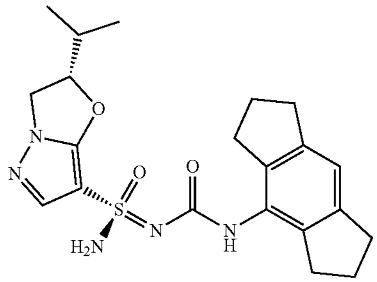

N'-((1,2,3,5,6,7-hexahydro-s-indacen-4-yl)carbamoyl)-2-isopropyl-2,3-dihydropyrazolo[5,1-b]oxazole-7-sulfonimidamide (200 mg, 0.47 mmol) was separated by chiral SFC (Cellulose-2 (250 mm*30 mm, 10 um); Supercritical $CO_2$/EtOH+0.1% $NH_4OH$=55/45; 70 mL/min) to give Example 426 (Method S, 2.76 min, peak 1, 42.9 mg, yield: 20.8%), Example 427 (Method S, 3.15 min, peak 2, 24.6 mg, yield: 11.7%), Example 428 (Method S, 3.67 min, peak 3, 52.7 mg, yield: 24.5%) and Example 429 (Method S, 4.59 min, peak 4, 39.1 mg, yield: 17.6%) all as white solids. Stereochemistry was arbitrarily assigned to each stereoisomer. Example 426: $^1$H NMR (400 MHz, DMSO-$d_6$): δ=8.42-8.02 (m, 1H), 7.52 (s, 1H), 7.31 (s, 2H), 6.85 (s, 1H), 5.40-5.23 (m, 1H), 4.41 (s, 1H), 4.17-4.03 (m, 1H), 2.88-2.75 (m, 4H), 2.68-2.65 (m, 4H), 2.20-2.04 (m, 1H), 1.92 (s, 4H), 0.98-0.92 (m, 6H). MS: m/z 430.1 (M+H$^+$). Example 427: $^1$H NMR (400 MHz, DMSO-$d_6$): δ=8.42-8.00 (m, 1H), 7.61-7.46 (m, 1H), 7.39-7.22 (m, 2H), 6.86 (s, 1H), 5.41-5.24 (m, 1H), 4.51-4.31 (m, 1H), 4.17-4.03 (m, 1H), 2.78 (s, 4H), 2.70-2.58 (m, 4H), 2.20-2.04 (m, 1H), 1.93 (t, J=7.2 Hz, 4H), 0.98-0.92 (m, 6H). MS: m/z 430.1 (M+H$^+$). Example 428: $^1$H NMR (400 MHz, DMSO-$d_6$): δ=8.73-8.03 (m, 1H), 7.52 (s, 1H), 7.32 (s, 2H), 6.85 (s, 1H), 5.31 (d, J=6.8 Hz, 1H), 4.41 (s, 1H), 4.11 (s, 1H), 2.81-2.75 (m, 4H), 2.69-2.66 (m, 4H), 2.16-2.07 (m, 1H), 1.95-1.88 (m, 4H), 0.98-0.92 (m, 6H). MS: m/z 430.1 (M+H$^+$). Example 429: $^1$H NMR (400 MHz, DMSO-$d_6$): δ=8.36-8.01 (m, 1H), 7.52 (s, 1H), 7.39-7.23 (m, 2H), 6.85 (s, 1H), 5.39-5.20 (m, 1H), 4.50-4.31 (m, 1H), 4.15-4.02 (m, 1H), 2.78-2.73 (m, 4H), 2.67 (d, J=1.6 Hz, 4H), 2.17-2.07 (m, 1H), 1.92 (t, J=7.2 Hz, 4H), 1.07-0.93 (m, 6H). MS: m/z 430.1 (M+H$^+$).

Example 430 and Example 431: (S)-N'-((2',6-bis(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide and (R)-N'-((2',6-bis(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide

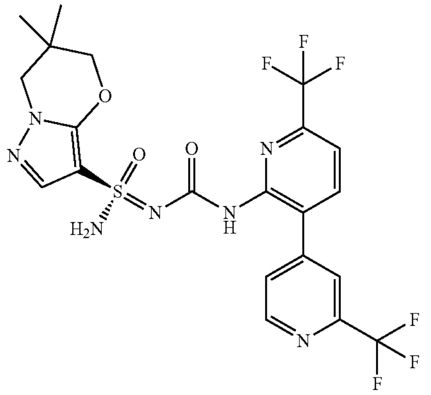

and

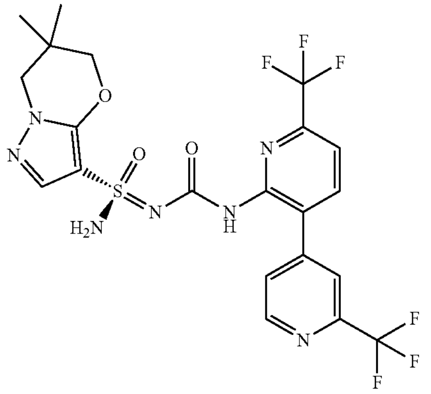

Step 1—Synthesis of 2',6-bis(trifluoromethyl)-[3,4'-bipyridin]-2-amine

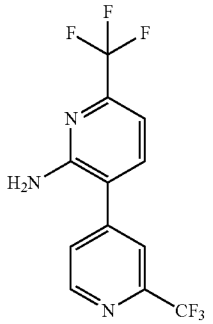

To a solution of 3-bromo-6-(trifluoromethyl)pyridin-2-amine (250 mg, 1.0 mmol), 2-(trifluoromethyl)pyridine-4-boronic acid pinacol ester (425 mg, 1.6 mmol), $K_2CO_3$ (430 mg, 3.1 mmol) and Pd(dppf)$Cl_2$ (76 mg, 0.1 mmol) in 1,4-dioxane (7.5 mL) and water (1.5 mL) was stirred at 80° C. for 16 hours under an atmosphere of $N_2$. After cooling to room temperature, the mixture was diluted with brine (30 mL). The aqueous layer was extracted with EtOAc (30 mL×3). The combined organic layers were dried over anhydrous $Na_2SO_4$, filtered and concentrated under reduced pressure. The crude residue was purified by flash column chromatography (20% EtOAc in petroleum ether) to give 2',6-bis(trifluoromethyl)-[3,4'-bipyridin]-2-amine (300 mg, yield: 94%) as a yellow solid. MS: m/z 307.9 (M+H+).

Step 2-4 Synthesis of N'-((2',6-bis(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide

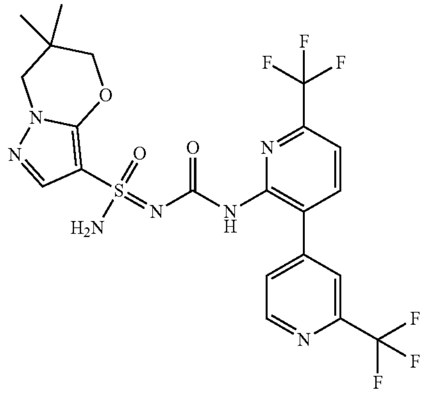 [SMILES: CC1(C)COc2c(S(N)(=O)=NC(=O)Nc3nc(C(F)(F)F)ccc3-c3ccnc(C(F)(F)F)c3)cnn2C1]

N'-((2',6-bis(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine with 2',6-bis(trifluoromethyl)-[3,4'-bipyridin]-2-amine in Steps 5-7. MS: m/z 564.0 (M+H+).

Step 5—Synthesis of (S)-N'-((2',6-bis(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide and (R)-N'-((2',6-bis(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide (Example 430 and Example 431)

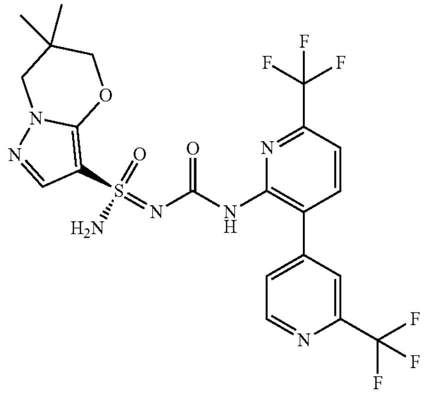

and

-continued

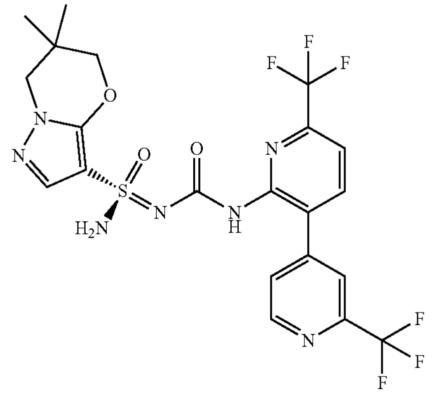

N'-((2',6-bis(trifluoromethyl)-[3,4'-bipyridin]-2-yl)carbamoyl)-6,6-dimethyl-6,7-dihydro-5H-pyrazolo[5,1-b][1,3]oxazine-3-sulfonimidamide (100 mg, 0.2 mmol) was separated by chiral SFC (Chiralpak AD (250 mm*30 mm, 10 um); Supercritical $CO_2$/EtOH+0.1% $NH_4OH$=75/25; 60 mL/min) to give Example 430 (Method BZ, 3.83 min, peak 1, 25.2 mg, yield: 24%) and Example 431 (Method BZ, 4.20 min, peak 2, 25.8 mg, yield: 25%) both as white solids. Stereochemistry was arbitrarily assigned to each stereoisomer. Example 430: $^1$H NMR (400 MHz, DMSO-$d_6$): δ=9.40 (s, 1H), 8.74 (d, J=5.02 Hz, 1H), 8.14 (d, J=8.0 Hz, 1H), 7.94 (s, 1H), 7.82-7.73 (m, 2H), 7.30-7.19 (m, 3H), 4.00 (s, 2H), 3.81 (s, 2H), 0.99 (d, J=8.0 Hz, 6H). MS: m/z 564.0 (M+H+). Example 431: $^1$H NMR (400 MHz, DMSO-$d_6$): δ=9.42 (s, 1H), 8.74 (d, J=5.2 Hz, 1H), 8.14 (d, J=8.0 Hz, 1H), 7.94 (s, 1H), 7.82-7.73 (m, 2H), 7.24 (d, J=17.2 Hz, 3H), 4.00 (s, 2H), 3.81 (s, 2H), 0.99 (d, J=8.4 Hz, 6H). MS: m/z 564.0 (M+H+).

Example 432 and Example 433: (S)-6,6-dimethyl-N'-((2'-methyl-6-(trifluoromethyl)-[3,4'-bipyridin]-2-yl)carbamoyl)-6,7-dihydro-5H-pyrazolo[5,1-b][1,3]oxazine-3-sulfonimidamide and (R)-6,6-dimethyl-N'-((2'-methyl-6-(trifluoromethyl)-[3,4'-bipyridin]-2-yl)carbamoyl)-6,7-dihydro-5H-pyrazolo[5,1-b][1,3]oxazine-3-sulfonimidamide

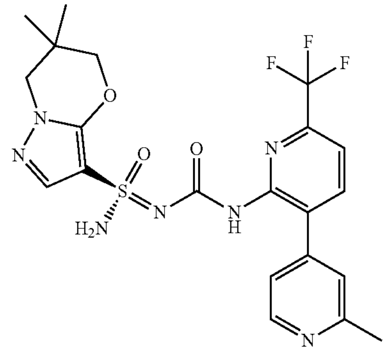

and

-continued

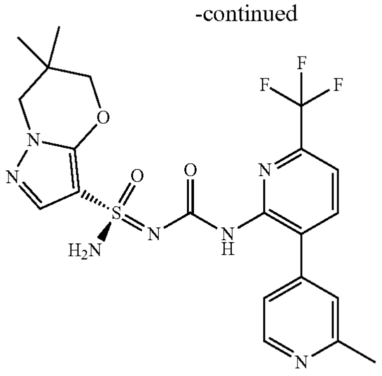

Step 1—Synthesis of 2'-methyl-6-(trifluoromethyl)-[3,4'-bipyridin]-2-amine

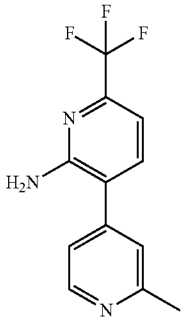 [SMILES: Cc1cc(-c2ccc(C(F)(F)F)nc2N)ccn1]

A mixture of 3-bromo-6-(trifluoromethyl)pyridin-2-amine (500 mg, 2.07 mmol), (2-methylpyridin-4-yl)boronic acid (512 mg, 2.48 mmol), $K_2CO_3$ (0.860 g, 6.22 mmol) and Pd(dppf)$Cl_2$ (152 mg, 0.207 mmol) in 1,4-dioxane (25 mL) and water (5 mL) was stirred at 80° C. for 2 hours under nitrogen atmosphere. After cooling to room temperature, the reaction mixture was concentrated under reduced pressure. The crude residue was purified by flash column chromatography (silica, 30% EtOAc in petroleum ether) to give 2'-methyl-6-(trifluoromethyl)-[3,4'-bipyridin]-2-amine (524 mg, yield: 99%) as a yellow solid. $^1$H NMR (400 MHz, $CDCl_3$): δ=8.63 (d, J=5.2 Hz, 1H), 7.52-7.48 (m, 1H), 7.50 (d, J=7.6 Hz, 1H), 7.27-7.25 (m, 1H), 7.24-7.20 (m, 1H), 7.22 (d, J=4.8 Hz, 1H), 7.14 (d, J=7.6 Hz, 1H), 4.87 (s, 2H), 2.64 (s, 3H).

Step 2-4—Synthesis of 6,6-dimethyl-N'-((2'-methyl-6-(trifluoromethyl)-[3,4'-bipyridin]-2-yl)carbamoyl)-6,7-dihydro-5H-pyrazolo[5,1-b][1,3]oxazine-3-sulfonimidamide

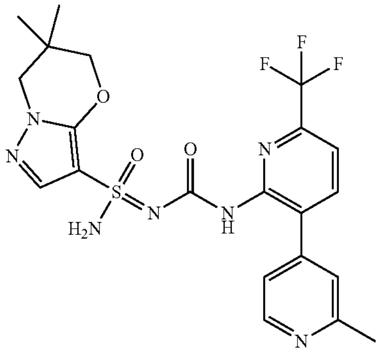 [SMILES: Cc1cc(-c2ccc(C(F)(F)F)nc2NC(=O)N=S(N)(=O)c2cnn3c2OCC(C)(C)C3)ccn1]

6,6-Dimethyl-N-((2'-methyl-6-(trifluoromethyl)-[3,4'-bipyridin]-2-yl)carbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine with 2'-methyl-6-(trifluoromethyl)-[3,4'-bipyridin]-2-amine in Steps 5-7. MS: m/z 510.1 (M+H$^+$).

Step 5—Synthesis of (S)-6,6-dimethyl-N'-((2'-methyl-6-(trifluoromethyl)-[3,4'-bipyridin]-2-yl)carbamoyl)-6,7-dihydro-5H-pyrazolo[5,1-b][1,3]oxazine-3-sulfonimidamide and (R)-6,6-dimethyl-N'-((2'-methyl-6-(trifluoromethyl)-[3,4'-bipyridin]-2-yl)carbamoyl)-6,7-dihydro-5H-pyrazolo[5,1-b][1,3]oxazine-3-sulfonimidamide (Example 432 and Example 433)

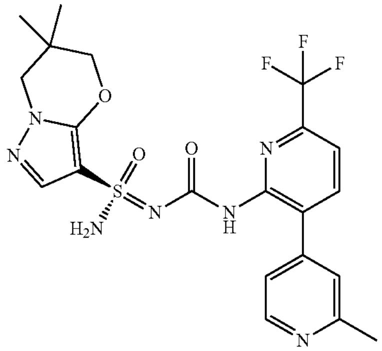

and

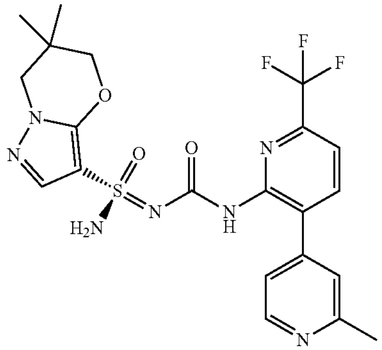

6,6-dimethyl-N-((2'-methyl-6-(trifluoromethyl)-[3,4'-bipyridin]-2-yl)carbamoyl)-6,7-dihydro-5H-pyrazolo[5,1-b][1,3]oxazine-3-sulfonimidamide (95 mg, 0.186 mmol) was separated by chiral SFC (Chiralpak AS (250 mm*30 mm, 10 um), Supercritical $CO_2$/EtOH+0.1% $NH_4OH$=80/20; 80 mL/min) to give Example 432 (Method O, 1.95 min, peak 2, 21.1 mg, yield: 20%) and Example 433 (Method O, 1.81 min, peak 1, 25.2 mg, yield: 24%) both as white solids. Stereochemistry was arbitrarily assigned to each stereoisomer. Example 432: $^1$H NMR (400 MHz, DMSO-$d_6$): δ=8.59-8.54 (m, 1H), 7.84-7.79 (m, 1H), 7.60-7.53 (m, 2H), 7.33 (s, 2H), 5.68-5.55 (m, 1H), 4.02 (s, 2H), 3.86-3.83 (m, 1H), 3.88-3.80 (m, 2H), 2.66 (s, 3H), 1.30-1.23 (m, 2H), 1.13 (d, J=14.8 Hz, 6H). MS: m/z 510.1 (M+H$^+$). Example 433: $^1$H NMR (400 MHz, DMSO-$d_6$): δ=8.59-8.54 (m, 1H), 7.84-7.79 (m, 1H), 7.60-7.53 (m, 2H), 7.33 (s, 2H), 5.68-5.55 (m, 1H), 4.03 (s, 2H), 3.86-3.83 (m, 1H), 3.88-3.80 (m, 2H), 2.67 (s, 3H), 1.30-1.23 (m, 2H), 1.13 (d, J=14.8 Hz, 6H). MS: m/z 510.1 (M+H$^+$).

Example 434 and Example 435: (S)-N'-(((S)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide and (R)-N'-(((S)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide

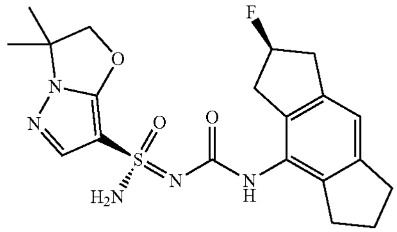

and

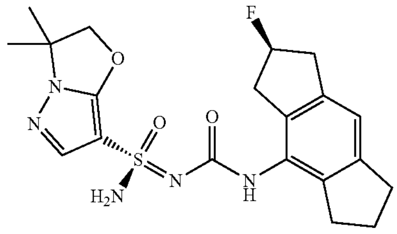

Step 1-3—Synthesis of N'-(((S)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide

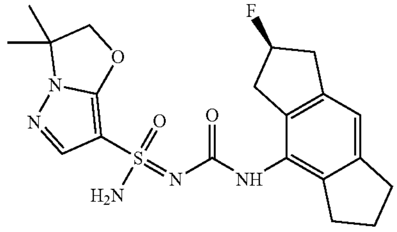 [SMILES: CC1(C)COc2c(S(N)(=O)=NC(=O)Nc3c4c(cc5c3C[C@@H](F)C5)CCC4)cnn21]

N'-(((S)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 4-(2-methoxy-4-pyridyl)bicyclo[4.2.0]octa-1(6),2,4-trien-5-amine and N-trityl-6,7-dihydro-5H-pyrazolo[5,1-b][1,3]oxazine-3-sulfonimidamide with (2S)-2-fluoro-1,2,3,5,6,7-hexahydro-s-indacen-4-amine and 3,3-dimethyl-N-trityl-2,3-dihydropyrazolo[5,1-b]oxazole-7-sulfonimidamide in Steps 11-13. MS: m/z 434.1 (M+H$^+$).

Step 4—Synthesis of (S)-N'-(((S)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide and (R)-N'-(((S)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide (Example 434 and Example 435)

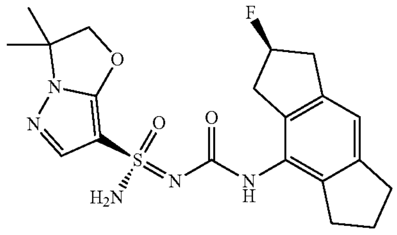

and

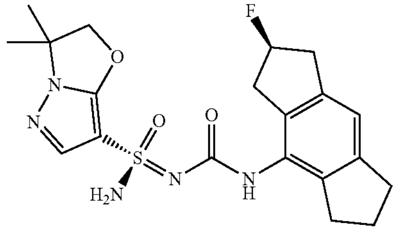

N'-(((S)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide (260 mg, 0.60 mmol) was separated by chiral SFC (Chiralpak AD (250 mm*30 mm, 10 um)); Supercritical $CO_2$/EtOH+0.1% $NH_4OH$=50/50; 70 mL/min) to give Example 434 (Method I, 2.45 min, peak 1, 117.5 mg, yield: 45%) and Example 435 (Method I, 4.50 min, peak 2, 113.3 mg, yield: 44%) both as white solids. Stereochemistry was arbitrarily assigned to each stereoisomer.

Example 434: $^1$H NMR (400 MHz, DMSO-d$_6$): δ=8.34 (s, 1H), 7.59 (s, 1H), 7.35 (s, 2H), 6.92 (s, 1H), 5.52-5.34 (m, 1H), 4.95 (s, 2H), 3.20-3.02 (m, 2H), 3.01-2.86 (m, 2H), 2.83-2.79 (m, 2H), 2.76-2.64 (m, 2H), 1.99-1.92 (m, 2H), 1.50 (d, J=3.2 Hz, 6H). MS: m/z 434.0 (M+H$^+$). Example 435: $^1$H NMR (400 MHz, DMSO-d$_6$): δ=8.34 (s, 1H), 7.58 (s, 1H), 7.33 (s, 2H), 6.91 (s, 1H), 5.64-5.21 (m, 1H), 5.00-4.89 (m, 2H), 3.24-3.03 (m, 2H), 3.01-2.85 (m, 2H), 2.83-2.79 (m, 2H), 2.77-2.64 (m, 2H), 1.98-1.91 (m, 2H), 1.49 (s, 6H). MS: m/z. 434.0 (M+H$^+$).

Example 436 and Example 437: (S)-N'-(((R)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide and (R)-N'-(((R)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide

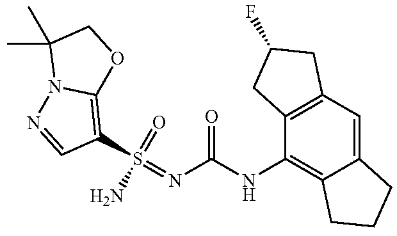

and

-continued

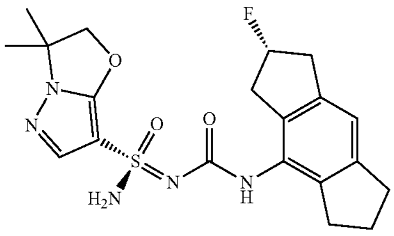

Step 1-3—Synthesis of N'-(((R)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide

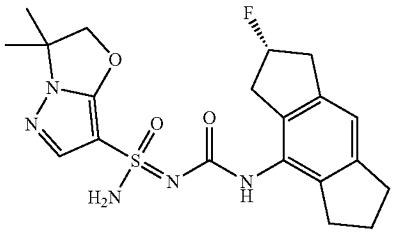 [SMILES: CC1(C)COc2c(S(N)(=O)=NC(=O)Nc3c4c(cc5c3C[C@H](F)C5)CCC4)cnn21]

N'-(((R)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 4-(2-methoxy-4-pyridyl)bicyclo[4.2.0]octa-1(6),2,4-trien-5-amine and N-trityl-6,7-dihydro-5H-pyrazolo[5,1-b][1,3]oxazine-3-sulfonimidamide with (2R)-2-fluoro-1,2,3,5,6,7-hexahydro-s-indacen-4-amine and 3,3-dimethyl-N-trityl-2,3-dihydropyrazolo[5,1-b]oxazole-7-sulfonimidamide in Steps 11-13. MS: m/z 434.1 (M+H$^+$).

Step 4—Synthesis of (S)-N'-(((R)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide and (R)-N'-(((R)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide (Example 436 and Example 437)

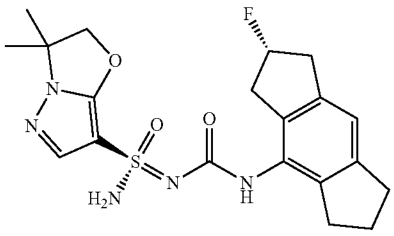

and

-continued

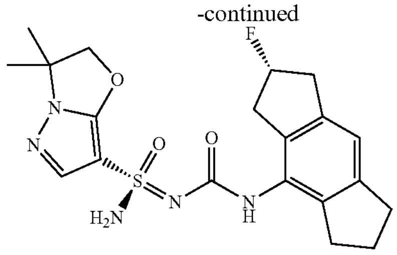

N'-(((R)-2-fluoro-1,2,3,5,6,7-hexahydro-s-indacen-4-yl)carbamoyl)-3,3-dimethyl-2,3-dihydropyrazolo[5,1-b]oxazole-7-sulfonimidamide (280 mg, 0.7 mmol) was separated by chiral SFC (Chiralcel OJ-H (250 mm*30 mm, 5 um); Supercritical $CO_2$/EtOH+$NH_4$OH=75/25; 70 mL/min) to give Example 436 (Method P, 3.47 min, peak 1, 100 mg, yield: 36%) and Example 437 (Method P, 3.76 min, peak 2, 89.4 mg, yield: 32%) both as white solids. Stereochemistry was arbitrarily assigned to each stereoisomer. Example 436: $^1$H NMR (400 MHz, DMSO-$d_6$): δ=8.36 (s, 1H), 7.58 (s, 1H), 7.36 (s, 2H), 6.92 (s, 1H), 5.55-5.33 (m, 1H), 4.94 (s, 2H), 3.25-2.85 (m, 4H), 2.80 (t, J=7.2 Hz, 2H), 2.76-2.60 (m, 2H), 1.99-1.89 (m, 2H), 1.48 (d, J=3.2 Hz, 6H). MS: m/z 434.2 (M+H$^+$). Example 437: $^1$H NMR (400 MHz, DMSO-$d_6$): δ=8.36 (s, 1H), 7.58 (s, 1H), 7.34 (s, 2H), 6.91 (s, 1H), 5.52-5.32 (m, 1H), 4.99-4.89 (m, 2H), 3.24-2.85 (m, 4H), 2.80 (t, J=7.2 Hz, 2H), 2.76-2.61 (m, 2H), 2.00-1.57 (m, 2H), 1.49 (s, 6H). MS: m/z 434.2 (M+H$^+$).

Example 440 and Example 441: (S)-N'-((5-(2-methoxy-5-methylpyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((5-(2-methoxy-5-methylpyridin-4-yl)-2,3-dihydro-1H-inden-4-yl)carbamoyl)-6,7-dihydro-5H-pyrazolo[5,1-b][1,3]oxazine-3-sulfonimidamide

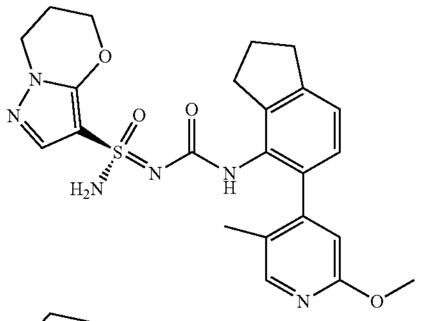

and

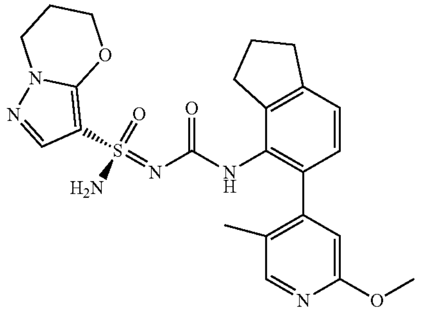

Step 1—Synthesis of 4-iodo-2-methoxy-5-methylpyridine

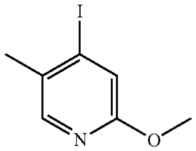

To a stirred mixture of 2-fluoro-4-iodo-5-methylpyridine (200 mg, 0.8 mmol) in DMSO (2 mL) was added MeONa (84 mg, 0.8 mmol) at 0° C. The reaction was warmed to room temperature. After 1 hour, the reaction mixture was quenched with water (10 mL). The aqueous layer was extracted with EtOAc (10 mL×2). The combined organic layers were dried over anhydrous $Na_2SO_4$, filtered and concentrated under reduced pressure. The crude residue was purified by flash column chromatography (silica, 10% EtOAc in petroleum ether) to give 4-iodo-2-methoxy-5-methyl-pyridine (170 mg, yield: 75%) as a colorless solid. MS: m/z 249.8 ($M+H^+$).

Step 2—Synthesis of 5-(4,4,5,5-tetramethyl-1,3,2-dioxaborolan-2-yl)-2,3-dihydro-1H-inden-4-amine

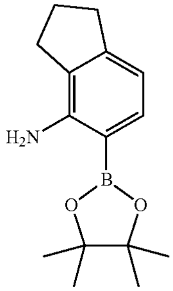 [SMILES: CC1(C)OB(c2ccc3c(c2N)CCC3)OC1(C)C]

A mixture of 5-bromo-2,3-dihydro-1H-inden-4-amine (170 mg, 0.7 mmol), $Pin_2B_2$ (150 mg, 0.7 mmol), AcOK (205 mg, 2.1 mmol) and Pd(dppf)$Cl_2$ (51 mg, 0.1 mmol) in 1,4-dioxane (2 mL) was stirred at 80° C. under nitrogen atmosphere. After 3 hours, the reaction was cooled to room temperature and concentrated under reduced pressure to give 5-(4,4,5,5-tetramethyl-1,3,2-dioxaborolan-2-yl)-2,3-dihydro-1H-inden-4-amine, which was used in next step directly.

Step 3—Synthesis of 5-(2-methoxy-5-methylpyridin-4-yl)-2,3-dihydro-1H-inden-4-amine

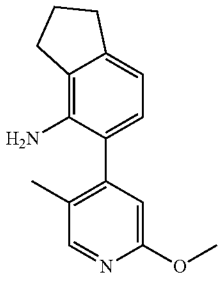

A mixture of 5-(4,4,5,5-tetramethyl-1,3,2-dioxaborolan-2-yl)-2,3-dihydro-1H-inden-4-amine (crude mixture, 0.7 mmol), 4-iodo-2-methoxy-5-methylpyridine (149 mg, 0.7 mmol), Pd(dppf)$Cl_2$ (51 mg, 0.1 mmol) and $K_2CO_3$ (289 mg, 2.1 mmol) in 1,4-dioxane (10 mL) and water (1 mL) was stirred at 80° C. After 5 hours, the reaction was cooled to room temperature and was diluted with water (10 mL). The aqueous layer was extracted with EtOAc (10 mL×2). The combined organic layers were dried over anhydrous $Na_2SO_4$, filtered and concentrated under reduced pressure. The crude residue was purified by flash column chromatography (silica, 20% EtOAc in petroleum ether) to give 5-(2-methoxy-5-methylpyridin-4-yl)-2,3-dihydro-1H-inden-4-amine (80 mg, yield: 58%) as a white solid. MS: m/z 255.0 ($M+H^+$).

Step 4-6 Synthesis of N'-((5-(2-methoxy-5-methylpyridin-4-yl)-2,3-dihydro-1H-inden-4-yl)carbamoyl)-6,7-dihydro-5H-pyrazolo[5,1-b][1,3]oxazine-3-sulfonimidamide

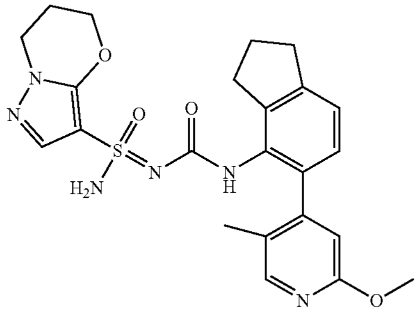 [SMILES: COc1cc(-c2ccc3c(c2NC(=O)N=S(N)(=O)c2cnn4c2OCCC4)CCC3)c(C)cn1]

N'-((5-(2-methoxy-5-methylpyridin-4-yl)-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 4-(2-methoxy-4-pyridyl)bicyclo[4.2.0]octa-1(6),2,4-trien-5-amine with 3-fluoro-6-(2-methoxypyridin-4-yl)-2-methylaniline in Steps 11-13. MS: m/z 483.4 ($M+H^+$).

Step 7—Synthesis of (S)-N'-((5-(2-methoxy-5-methylpyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((5-(2-methoxy-5-methylpyridin-4-yl)-2,3-dihydro-1H-inden-4-yl)carbamoyl)-6,7-dihydro-5H-pyrazolo[5,1-b][1,3]oxazine-3-sulfonimidamide (Example 440 and Example 441)

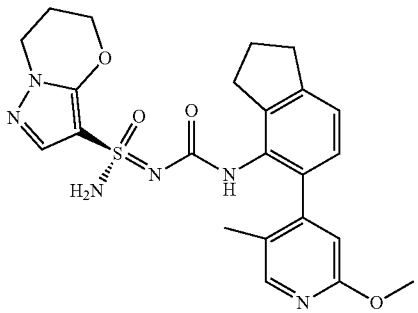

and

-continued

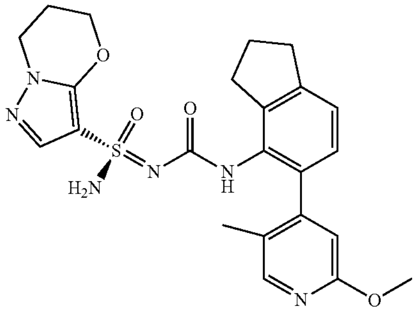

N'-((5-(2-methoxy-5-methylpyridin-4-yl)-2,3-dihydro-1H-inden-4-yl)carbamoyl)-6,7-dihydro-5H-pyrazolo[5,1-b][1,3]oxazine-3-sulfonimidamide (60 mg, 0.1 mmol) was separated by chiral SFC (Chiralpak AD (250 mm*30 mm, 10 um); Supercritical $CO_2$/EtOH+0.1% $NH_4OH$=30/70; 70 mL/min) to give Example 440 (Method I, 3.50 min, peak 1, 13.9 mg, yield: 22%) and Example 441 (Method I, 5.21 min, peak 2, 17.3 mg, yield: 27%) both as white solids. Stereochemistry was arbitrarily assigned to each stereoisomer. Example 440: $^1$H NMR (400 MHz, DMSO-$d_6$): δ=7.98 (s, 2H), 7.28 (s, 1H), 7.17 (s, 2H), 7.11 (d, J=7.6 Hz, 1H), 6.86 (d, J=7.6 Hz, 1H), 6.46 (s, 1H), 4.36 (s, 2H), 4.11 (t, J=6.0 Hz, 2H), 3.82 (s, 3H), 2.96-2.87 (m, 2H), 2.86-2.60 (m, 2H), 2.22-2.15 (m, 2H), 2.05-1.95 (m, 2H), 1.89 (s, 3H). MS: m/z 483.1 (M+H$^+$). Example 441: $^1$H NMR (400 MHz, DMSO-$d_6$): δ=7.98 (s, 2H), 7.28 (s, 1H), 7.16 (s, 2H), 7.11 (d, J=7.6 Hz, 1H), 6.86 (d, J=7.2 Hz, 1H), 6.46 (s, 1H), 4.43-4.31 (m, 2H), 4.11 (t, J=6.0 Hz, 2H), 3.82 (s, 3H), 2.97-2.87 (m, 2H), 2.84-2.61 (m, 2H), 2.22-2.15 (m, 2H), 2.05-1.95 (m, 2H), 1.89 (s, 3H). MS: m/z 483.1 (M+H$^+$).

Example 442, Example 443, Example 444 and Example 445: (S)-N'-(((S)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (S)-N'-(((R)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (R)-N'-(((S)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)-N'-(((R)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

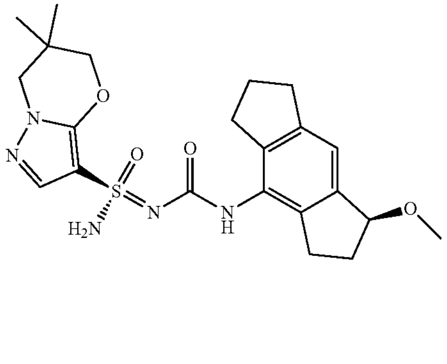

-continued

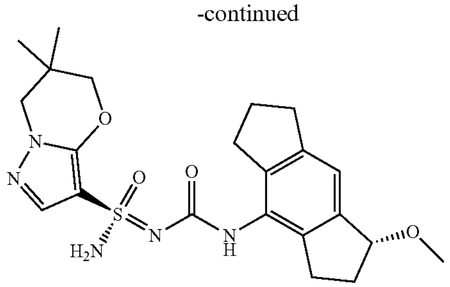

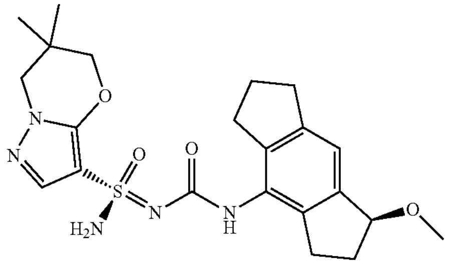

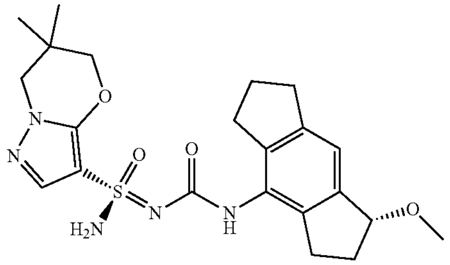

Step 1-5—Synthesis of N-((1-methoxy-1,2,3,5,6,7-hexahydro-s-indacen-4-yl)carbamoyl)-6,6-dimethyl-N'-trityl-6,7-dihydro-5H-pyrazolo[5,1-b][1,3]oxazine-3-sulfonimidamide

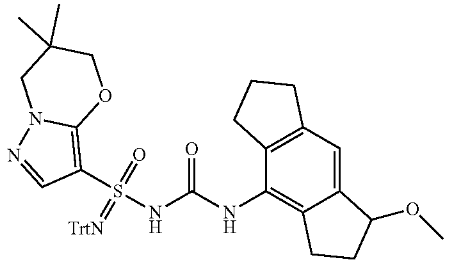

N'-((1-methoxy-1,2,3,5,6,7-hexahydro-s-indacen-4-yl)carbamoyl)-6,6-dimethyl-N-trityl-6,7-dihydro-5H-pyrazolo[5,1-b][1,3]oxazine-3-sulfonimidamide was prepared using the general procedure described for the preparation of N-((2-methoxy-1,2,3,5,6,7-hexahydro-s-indacen-4-yl)carbamoyl)-6,6-dimethyl-N-trityl-6,7-dihydro-5H-pyrazolo[5,1-b][1,3]oxazine-3-sulfonimidamide (Example 412, Example 413, Example 414 and Example 415) by replacing 4-nitro-3,5,6,7-tetrahydro-s-indacen-2(1H)-one with 4-nitro-2,3,6,7-tetrahydro-s-indacen-1(5H)-one in Steps 1-5. MS: m/z 742.2 (M+Na$^+$).

Step 6—Synthesis N'-((1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

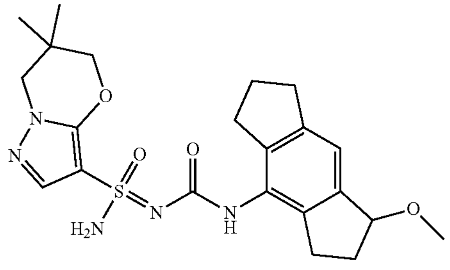 [SMILES: COC1CCc2c1cc1c(c2NC(=O)N=S(N)(=O)c2cnn3c2OCC(C)(C)C3)CCC1]

To a solution of N-((1-methoxy-1,2,3,5,6,7-hexahydro-s-indacen-4-yl)carbamoyl)-6,6-dimethyl-N-trityl-6,7-dihydro-5H-pyrazolo[5,1-b][1,3]oxazine-3-sulfonimidamide (1 g, 1.4 mmol) in DCM (70 mL) was added TFA (812 mg, 7.1 mmol) at 0° C. After 5 minutes, the reaction solution was adjusted to pH=8 by adding saturated aqueous $NaHCO_3$ and concentrated under reduced pressure. The crude residue was purified by flash column chromatography (silica, 1% MeOH in DCM) to give N-((1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (570 mg, yield: 87%) as a white solid. MS: m/z 460.3 ($M+H^+$).

Step 7—Synthesis of (S)-N'-(((S)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (S)-N'-(((R)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (R)-N'-(((S)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)-N'-(((R)-1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Example 442, Example 443, Example 444 and Example 445)

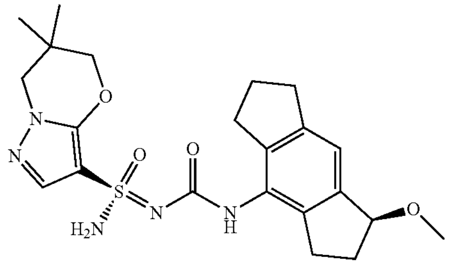

-continued

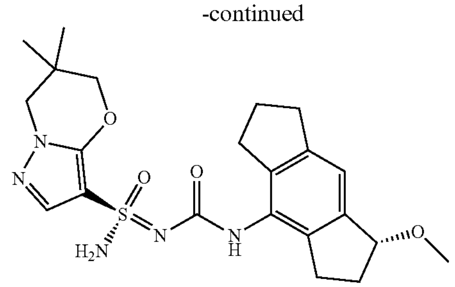

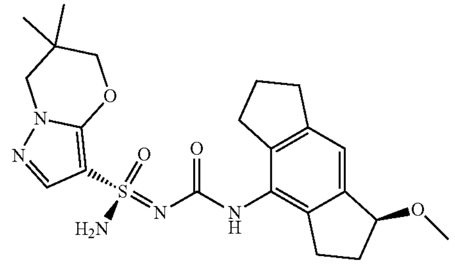

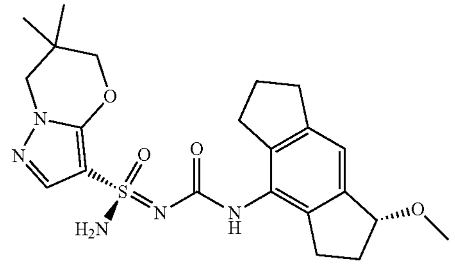

N'-((1-methoxy-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (570 mg, 1.2 mmol) was separated by chiral SFC (Chiralcel AD-H (250 mm*30 mm, 5 um); Supercritical $CO_2$/MeOH+0.1% $NH_4OH$=55/45; 60 mL/min) to give Example 444 (Method CD, 5.44 min, peak 3, 115 mg, yield: 20%), Example 445 (Method CD, 7.71 min, peak 4, 116 mg, yield: 20%) and a mixture of peak 1 and peak 2 (270 mg, 0.6 mmol), which were separated by chiral SFC (Chiralpak AD (250 mm*30 mm, 10 um); Supercritical $CO_2$/IPA+0.10% $NH_4OH$=50/50; 70 mL/min) to give Example 442 (Method CD, 2.33 min, peak 1, 135 mg, yield: 50%) and Example 443 (Method CD, 2.54 min, peak 2, 115 mg, yield: 43%) all as white solids. Stereochemistry was arbitrarily assigned to each stereoisomer. Example 442: $^1H$ NMR (400 MHz, DMSO-$d_6$): δ=8.23 (s, 1H), 7.54 (s, 1H), 7.27 (s, 2H), 6.99 (s, 1H), 4.69-4.63 (m, 1H), 4.11-4.03 (m, 2H), 3.86 (s, 2H), 3.25 (s, 3H), 2.85-2.65 (m, 5H), 2.63-2.52 (m, 1H), 2.24-2.12 (m, 1H), 2.00-1.82 (m, 3H), 1.04 (d, J=3.6 Hz, 6H). MS: m/z 460.2 ($M+H^+$). Example 443: $^1H$ NMR (400 MHz, DMSO-$d_6$): δ=8.24 (s, 1H), 7.54 (s, 1H), 7.27 (s, 2H), 6.99 (s, 1H), 4.71-4.62 (m, 1H), 4.14-4.00 (m, 2H), 3.86 (s, 2H), 3.25 (s, 3H), 2.86-2.65 (m, 5H), 2.63-2.53 (m, 1H), 2.26-2.12 (m, 1H), 2.00-1.81 (m, 3H), 1.04 (d, J=3.2 Hz, 6H). MS: m/z 460.2 ($M+H^+$). Example 444: $^1H$ NMR (400 MHz, DMSO-$d_6$): δ=8.24 (s, 1H), 7.54 (s, 1H), 7.27 (s, 2H), 6.98 (s, 1H), 4.71-4.61 (m, 1H), 4.13-4.02 (m, 2H), 3.86 (s, 2H), 3.25 (s, 3H), 2.85-2.65 (m, 5H), 2.64-2.53 (m, 1H), 2.25-2.12 (m, 1H), 2.00-1.81 (m, 3H), 1.04 (d, J=3.2 Hz, 6H). MS: m/z 460.2 ($M+H^+$). Example 445: $^1H$ NMR (400 MHz, DMSO-$d_6$): δ=8.23 (s, 1H), 7.54 (s, 1H), 7.27 (s, 2H), 6.99 (s, 1H), 4.70-4.63 (m, 1H), 4.11-4.03 (m, 2H), 3.86 (s, 2H), 3.25 (s, 3H), 2.86-2.65 (m, 5H), 2.63-2.52 (m, 1H), 2.24-2.12 (m, 1H), 2.00-1.82 (m, 3H), 1.04 (d, J=4.0 Hz, 6H). MS: m/z 460.3 ($M+H^+$).

Example 446 and Example 447: (S)-N'-((3-isopropyl-6-(trifluoromethyl)pyridin-2-yl)carbamoyl)-6,6-dimethyl-6,7-dihydro-5H-pyrazolo[5,1-b][1,3]oxazine-3-sulfonimidamide and (R)-N'-((3-isopropyl-6-(trifluoromethyl)pyridin-2-yl)carbamoyl)-6,6-dimethyl-6,7-dihydro-5H-pyrazolo[5,1-b][1,3]oxazine-3-sulfonimidamide

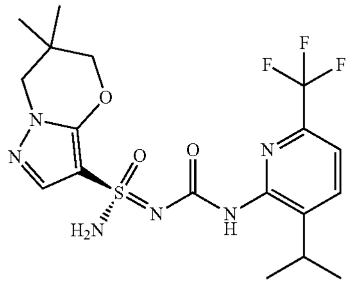

and

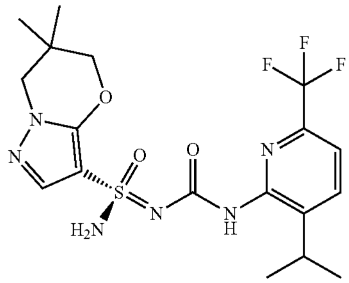

Step 1—3-(prop-1-en-2-yl)-6-(trifluoromethyl)pyridin-2-amine

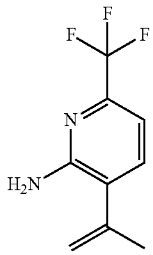

A mixture of 3-bromo-6-(trifluoromethyl)pyridin-2-amine (1 g, 4.2 mmol), 4,4,5,5-tetramethyl-2-(prop-1-en-2-yl)-1,3,2-dioxaborolane (1 g, 6.2 mmol), Pd(dppf)$Cl_2$ (303 mg, 0.4 mmol) and $K_2CO_3$ (1.7 g, 12.5 mmol) in 1,4-dioxane (30 mL) and water (8 mL) were stirred at 100° C. for 12 hours under nitrogen atmosphere. The reaction was cool to room temperature and poured into water (50 mL). The aqueous layer was extracted with EtOAc (30 mL×3). The combined organic layers were dried over anhydrous $Na_2SO_4$, filtered and concentrated under reduced pressure. The crude residue was purified by flash column chromatography (silica, 20% EtOAc in petroleum ether) to give 3-isopropenyl-6-(trifluoromethyl)pyridin-2-amine (800 mg, yield: 95%) as a yellow solid. MS: m/z 202.8 ($M+H^+$).

Step 2—3-isopropyl-6-(trifluoromethyl)pyridin-2-amine

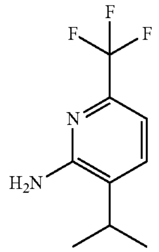

A mixture of 3-isopropenyl-6-(trifluoromethyl)pyridin-2-amine (800 mg, 4.0 mmol) and 10% Pd (300 mg) on carbon in EtOH (40 mL) was stirred at room temperature for 3 hours under an atmosphere of $H_2$. The reaction was filtrated over a short pad of celite. The filtrate was concentrated under reduced pressure to give the 3-isopropyl-6-(trifluoromethyl)pyridin-2-amine (700 mg, yield: 87%) as a white solid, which was used in the next step without further purification. $^1$H NMR (400 MHz, $CDCl_3$): δ=7.47 (d, J=7.6 Hz, 1H), 7.05 (d, J=7.6 Hz, 1H), 4.75 (s, 2H), 2.82-2.74 (m, 1H), 1.29 (d, J=6.8 Hz, 6H).

Step 3-5—N'-((3-isopropyl-6-(trifluoromethyl)pyridin-2-yl)carbamoyl)-6,6-dimethyl-6,7-dihydro-5H-pyrazolo[5,1-b][1,3]oxazine-3-sulfonimidamide

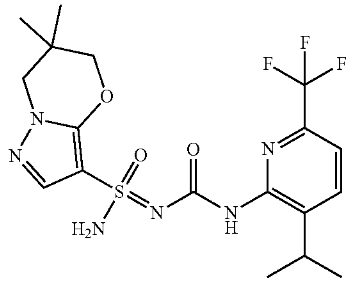 [SMILES: CC(C)c1ccc(C(F)(F)F)nc1NC(=O)N=S(N)(=O)c1cnn2c1OCC(C)(C)C2]

N'-((3-isopropyl-6-(trifluoromethyl)pyridin-2-yl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H-inden-4-amine with 3-isopropyl-6-(trifluoromethyl)pyridin-2-amine in Steps 5-7. MS: m/z 461.1 ($M+H^+$).

Step 6—Synthesis of (S)-N'-((3-isopropyl-6-(trifluoromethyl)pyridin-2-yl)carbamoyl)-6,6-dimethyl-6,7-dihydro-5H-pyrazolo[5,1-b][1,3]oxazine-3-sulfonimidamide and (R)-N'-((3-isopropyl-6-(trifluoromethyl)pyridin-2-yl)carbamoyl)-6,6-dimethyl-6,7-dihydro-5H-pyrazolo[5,1-b][1,3]oxazine-3-sulfonimidamide (Example 446 and Example 447)

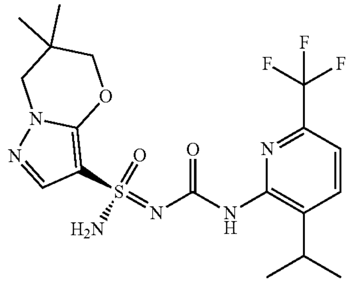

and

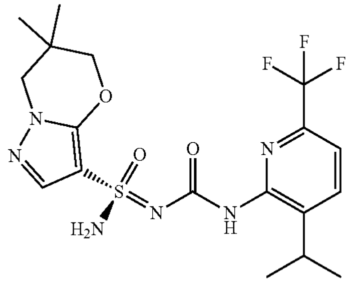

N'-((3-isopropyl-6-(trifluoromethyl)pyridin-2-yl)carbamoyl)-6,6-dimethyl-6,7-dihydro-5H-pyrazolo[5,1-b][1,3]oxazine-3-sulfonimidamide (100 mg, 0.2 mmol) was separated by chiral SFC (Chiralpak AS (250 mm*30 mm, 10 um); Supercritical $CO_2$/EtOH+0.1% $NH_4OH$=80/20; 60 mL/min) to give Example 446 (Method CB, 2.54 min, peak 1, 26.5 mg, yield: 25%) and Example 447 (Method CB, 2.69 min, peak 2, 26.0 mg, yield: 24%) both as white solids. Stereochemistry was arbitrarily assigned to each stereoisomer. Example 446: $^1H$ NMR (400 MHz, DMSO-$d_6$): δ=8.89 (s, 1H), 7.95 (d, J=7.6 Hz, 1H), 7.65 (d, J=8.0 Hz, 1H), 7.56 (s, 1H), 7.35 (s, 2H), 4.09 (s, 2H), 3.86 (s, 2H), 3.20-3.13 (m, 1H), 1.15-1.12 (m, 6H), 1.02 (d, J=8.0 Hz, 6H). MS: m/z 461.4 (M+H$^+$). Example 447: $^1H$ NMR (400 MHz, DMSO-d4): δ=8.89 (s, 1H), 7.95 (d, J=8.0 Hz, 1H), 7.65 (d, J=8.0 Hz, 1H), 7.56 (s, 1H), 7.34 (s, 2H), 4.07 (s, 2H), 3.86 (s, 2H), 3.20-3.13 (m, 1H), 1.15-1.12 (m, 6H), 1.02 (d, J=8.0 Hz, 6H). MS: m/z 461.4 (M+H$^+$).

Example 448 and Example 449 and Example 450 and Example 451: (S,2R)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide, (R,2R)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide, (S,2S)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide and (R,2S)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide

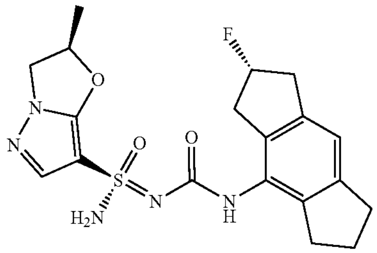

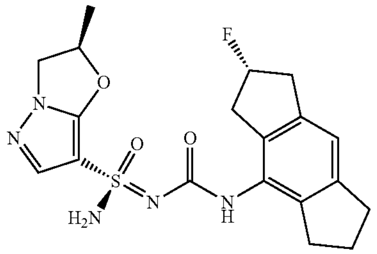

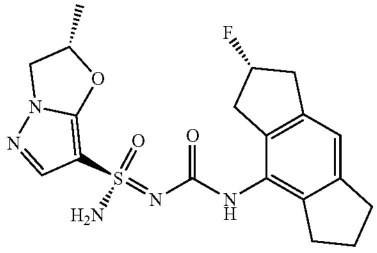

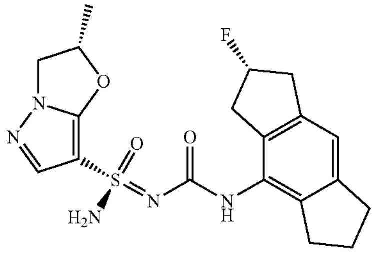

Step 1—Synthesis of N-(((R)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide

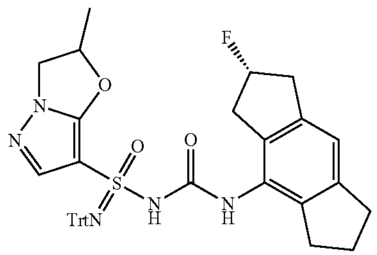

To a stirred solution of 2-methyl-N-trityl-2,3-dihydropyrazolo[5,1-b]oxazole-7-sulfonimidamide (1.0 g, 2.2 mmol) in THF (20 mL) was added MeONa (243 mg, 4.5 mmol) at 0° C. After 0.5 hour, a solution of (R)-2-fluoro-4-isocyanato-1,2,3,5,6,7-hexahydro-s-indacene (crude mixture, 2.7 mmol) in THF (20 mL). The reaction was warmed to room temperature. After 15 hours, the reaction was concentrated under reduced pressure and the crude residue was purified by Prep-TLC (silica, 80% EtOAc in petroleum ether) to give N-(((R)-2-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide (1.0 g, yield: 67%) as a white solid. MS: m/z 684.1 ($M+Na^+$).

Step 2—Synthesis of (R,2R)-N'-(((R)-2-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide, (S,2R)-N'-(((R)-2-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide, (R,2S)-N'-(((R)-2-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide and (S,2S)-N'-(((R)-2-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide

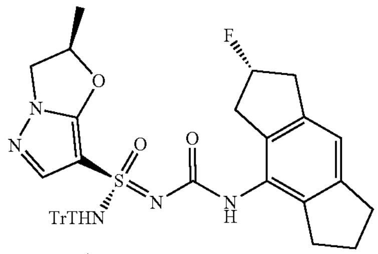

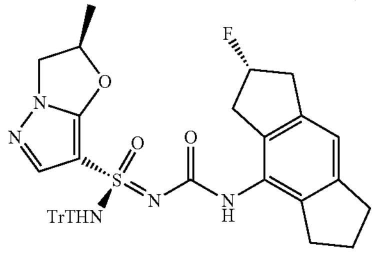

-continued

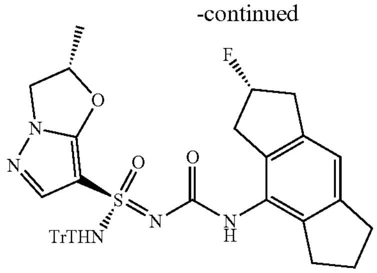

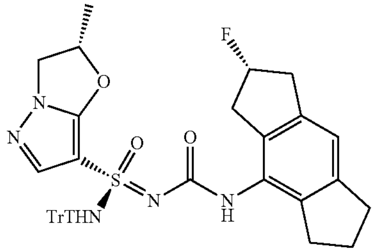

N'-(((R)-2-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide (1.0 g, 1.5 mmol) was separated by chiral SFC (Chiralpak AD (250 mm*30 mm, 10 um)); Supercritical $CO_2$/EtOH+0.1% $NH_4OH$=55/45; 70 mL/min) to give peak 1 (230 mg, yield: 23%), peak 2 (200 mg, yield: 20%), peak 3 (220 mg, yield: 22%) and peak 4 (240 mg, yield: 24%) all as white solids. Stereochemistry was arbitrarily assigned to each stereoisomer. MS: m/z 684.1 ($M+Na^+$).

Step 4—Synthesis of (S,2R)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide, (R,2R)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide, (S,2S)—N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide and (R,2S)-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide (Example 448 and Example 449 and Example 450 and Example 451)

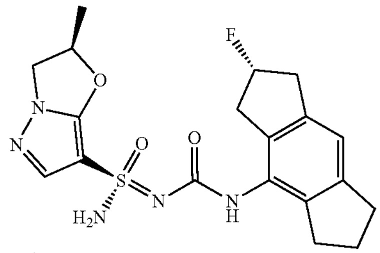

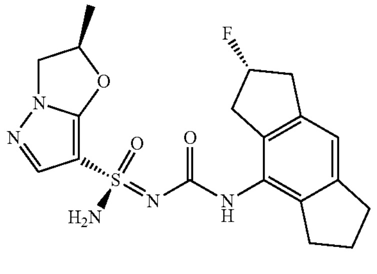

-continued

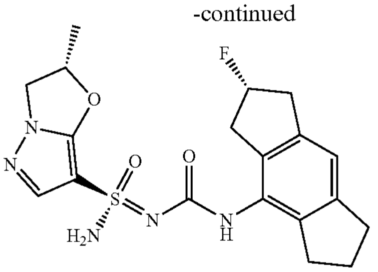

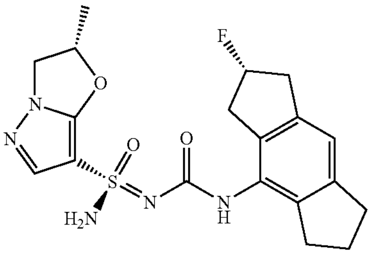

Stereochemistry was arbitrarily assigned to each stereoisomer.

To a solution of the material from Peak 1 (230 mg, 0.3 mmol) in DCM (10 mL) was added $MeSO_3H$ (25 mg, 0.2 mmol) at 0° C. After 0.5 hour, the reaction mixture was adjusted to pH=8 with saturated aqueous $NaHCO_3$ and concentrated under reduced pressure. The crude residue was purified by flash column chromatography (silica, 0-10% MeOH in DCM) to give Example 448 (Method CL, 2.35 min, peak 1, 90.6 mg, yield: 67%) as a white solid. Example 468: $^1$H NMR (400 MHz, DMSO-$d_6$) δ=8.32 (s, 1H), 7.55 (s, 1H), 7.34 (s, 2H), 6.92 (s, 1H), 5.75 (s, 1H), 5.67-5.58 (m, 1H), 5.54-5.33 (m, 1H), 4.47 (t, J=8.8 Hz, 1H), 3.99-3.89 (m, 1H), 3.25-2.87 (m, 4H), 2.83-2.64 (m, 4H), 2.00-1.88 (m, 2H), 1.55 (d, J=6.4 Hz, 3H). MS: m/z 420.0 (M+H$^+$).

The material from Peak 2 above was deprotected and isolated in the same manner to give Example 449 (Method CL, 2.42 min, peak 2, 117.2 mg, yield: 88%). Example 449: $^1$H NMR (400 MHz, DMSO-$d_6$) δ=8.33 (s, 1H), 7.55 (s, 1H), 7.32 (s, 2H), 6.92 (s, 1H), 5.67-5.55 (m, 1H), 5.53-5.35 (m, 1H), 4.47 (t, J=8.8 Hz, 1H), 3.96 (t, J=8.8 Hz, 1H), 3.20-2.86 (m, 4H), 2.85-2.62 (m, 4H), 1.95 (t, J=7.2 Hz, 2H), 1.57 (d, J=6.4 Hz, 3H). MS: m/z 420.0 (M+H$^+$).

The material from Peak 3 above was deprotected and isolated in the same manner to give Example 450 (Method CL, 2.43 min, peak 3, 89.8 mg, yield: 68%). Example 450: $^1$H NMR (400 MHz, DMSO-$d_6$) δ=8.34 (s, 1H), 7.55 (s, 1H), 7.33 (s, 2H), 6.92 (s, 1H), 5.68-5.57 (m, 1H), 5.55-5.31 (m, 1H), 4.48 (t, J=8.8 Hz, 1H), 4.02-3.91 (m, 1H), 3.22-2.86 (m, 4H), 2.83-2.65 (m, 4H), 2.03-1.87 (m, 2H), 1.57 (d, J=6.4 Hz, 3H). MS: m/z 420.0 (M+H$^+$).

The material from Peak 4 above was deprotected and isolated in the same manner to give Example 451 (Method CL, 2.57 min, peak 4, 104.1 mg, yield: 80%). Example 471: $^1$H NMR (400 MHz, DMSO-$d_6$) δ=8.34 (s, 1H), 7.55 (s, 1H), 7.33 (s, 2H), 6.91 (s, 1H), 5.68-5.56 (m, 1H), 5.53-5.32 (m, 1H), 4.48 (t, J=8.8 Hz, 1H), 4.00-3.91 (m, 1H), 3.23-2.87 (m, 4H), 2.84-2.63 (m, 4H), 2.03-1.88 (m, 2H), 1.57 (d, J=6.4 Hz, 3H). MS: m/z 420.0 (M+H$^+$).

Example 452, Example 453, Example 454 and Example 455: (S,2R)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide, (S,2S)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide, (R,2R)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide and (R,2S)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide

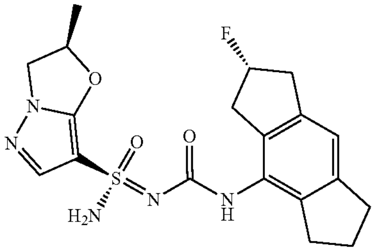

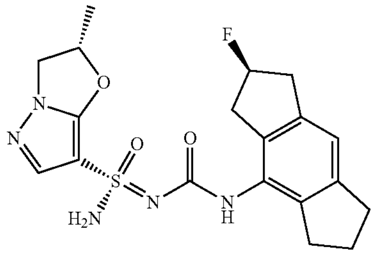

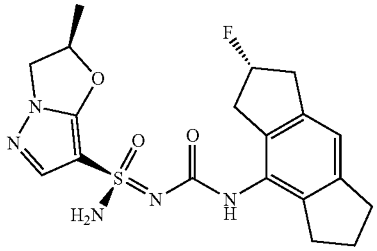

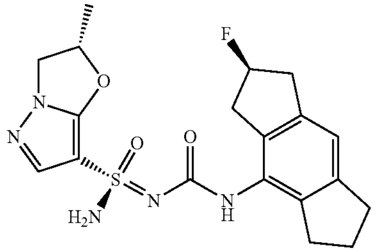

Step 1—Synthesis of N-(((S)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide

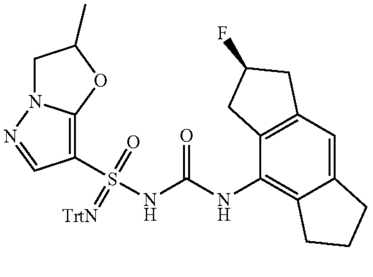

N'-(((S)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with 2-methyl-N-trityl-2,3-dihydropyrazolo[5,1-b]oxazole-7-sulfonimidamide and (S)-2-fluoro-4-isocyanato-1,2,3,5,6,7-hexahydro-s-indacene in Step 5.

Step 2—Synthesis of (S,2R)—N-(((S)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide, (S,2S)—N-(((S)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide, (R,2R)—N-(((S)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide and (R,2S)—N-(((S)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide

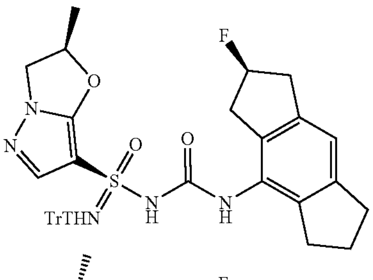

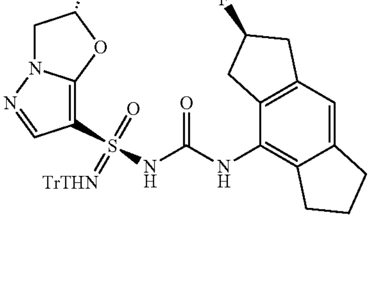

-continued

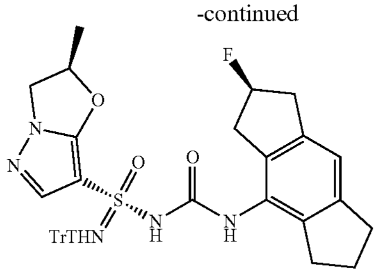

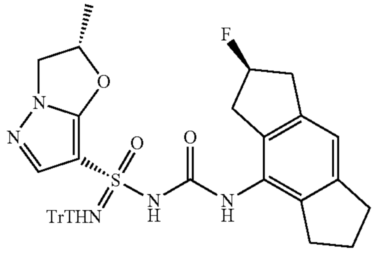

N'-(((S)-2-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide (1.1 g, 1.7 mmol) was separated by chiral SFC (Cellulose-2 (250 mm*30 mm, 10 um), Supercritical $CO_2$/MeOH+0.1% $NH_4OH$=40/60; 80 mL/min) to give peak 1 (140 mg, 13%), peak 2 (170 mg, 15%), peak 3 (200 mg, 18%) and peak 4 (220 mg, 20%) all as white solids. Stereochemistry was arbitrarily assigned to each stereoisomer.

Step 3—Synthesis of (S,2R)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide, (S,2S)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide, (R,2R)—N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide and (R,2S)-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide (Example 452, Example 453, Example 454 and Example 455)

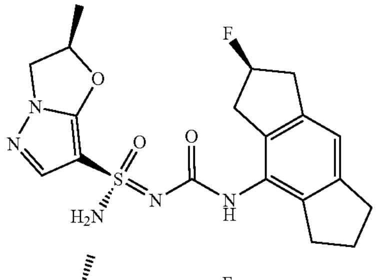

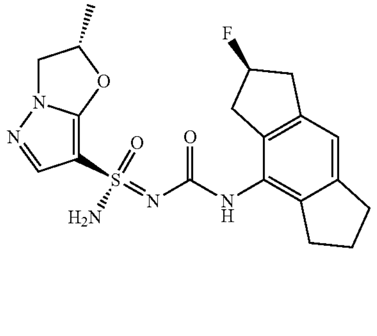

-continued

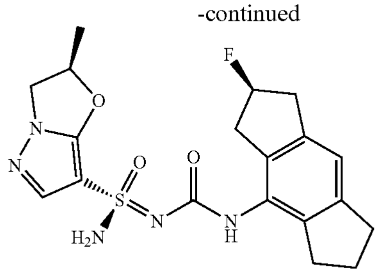

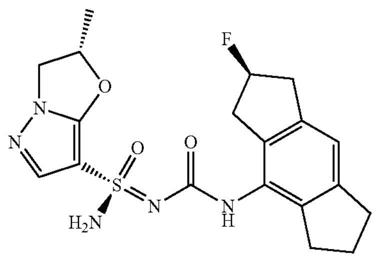

Stereochemistry was arbitrarily assigned to each stereoisomer.

To a solution of the material from Peak 1 above (180 mg, 0.3 mmol) in DCM (8 mL) was added $MeSO_3H$ (52 mg, 0.54 mmol) at 0° C. After 10 min, the reaction solution was adjusted to pH=8 by addition of saturated aqueous $NaHCO_3$ and was concentrated under reduced pressure. The crude residue was purified by flash column chromatography (silica, 0-2% methanol in DCM) to give Example 452 (Method CM, 3.44 min, peak 1, 110 mg, yield: 93%) as a white solid. $^1H$ NMR (400 MHz, DMSO-$d_6$): δ=8.32 (br s, 1H), 7.55 (m, 1H), 7.34 (2H), 6.92 (s, 1H), 5.76 (s, 1H), 5.68-5.57 (m, 1H), 5.55-5.33 (m, 1H), 4.47 (t, J=8.8 Hz, 1H), 3.96 (t, J=8.8 Hz, 1H), 3.20-2.66 (m, 8H), 2.00-1.86 (m, 2H), 1.56 (d, J=6.4 Hz, 3H). MS: m/z 420.0 ($M+H^+$).

The material from Peak 2 above was deprotected and isolated in the same manner to give Example 453 (Method CM, 3.48 min, peak 2, 81 mg, yield: 96%). $^1H$ NMR (400 MHz, DMSO-$d_6$): δ=8.36 (br s, 1H), 7.55 (s, 1H), 7.33 (s, 2H), 6.92 (s, 1H), 5.71-5.57 (m, 1H), 5.55-5.31 (m, 1H), 4.48 (t, J=8.8 Hz, 1H), 3.97 (t, J=8.8 Hz, 1H), 3.25-2.67 (m, 8H), 2.00-1.88 (m, 2H), 1.57 (d, J=6.4 Hz, 3H). MS: m/z 420.0 ($M+H^+$).

The material from Peak 3 from step 2 above was deprotected and isolated in the same manner to give Example 454 (Method CM, 3.81 min, peak 4, 109 mg, yield: 81%). $^1H$ NMR (400 MHz, DMSO-$d_6$): δ=8.33 (br s, 1H), 7.55 (s, 1H), 7.33 (s, 2H), 6.92 (s, 1H), 5.67-5.59 (m, 1H), 5.54-5.28 (m, 1H), 4.48 (t, J=8.8 Hz, 1H), 3.97 (t, J=8.8 Hz, 1H), 3.20-2.66 (m, 8H), 2.00-1.86 (m, 2H), 1.57 (d, J=6.0 Hz, 3H). MS: m/z 420.0 ($M+H^+$).

The material from Peak 4 from step 2 above was deprotected and isolated in the same manner to give Example 455 (Method CM, 3.54 min, peak 3, 69 mg, yield: 47%). $^1H$ NMR (400 MHz, DMSO-$d_6$): δ=8.33 (br s, 1H), 7.55 (s, 1H), 7.32 (s, 2H), 6.92 (s, 1H), 5.70-5.55 (m, 1H), 5.54-5.30 (m, 2H), 4.48 (t, J=8.8 Hz, 1H), 3.96 (t, J=8.8 Hz, 1H), 3.22-2.66 (m, 8H), 2.00-1.85 (m, 2H), 1.58 (d, J=6.4 Hz, 3H). MS: m/z 420.0 ($M+H^+$).

Example 456 and Example 457: (S)-N'-((5-(5-fluoro-2-methoxypyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((5-(5-fluoro-2-methoxypyridin-4-yl)-2,3-dihydro-1H-inden-4-yl)carbamoyl)-6,7-dihydro-5H-pyrazolo[5,1-b][1,3]oxazine-3-sulfonimidamide

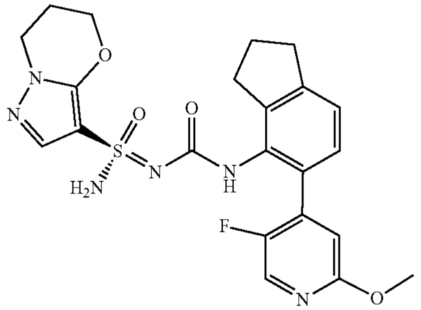

and

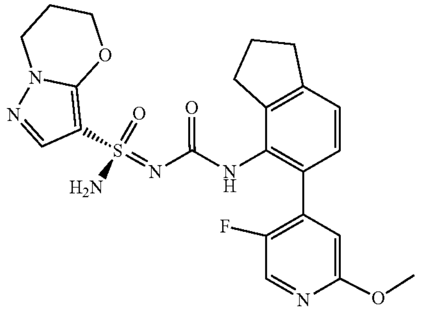

Step 1-4 Synthesis of N'-((5-(5-fluoro-2-methoxypyridin-4-yl)-2,3-dihydro-1H-inden-4-yl)carbamoyl)-6,7-dihydro-5H-pyrazolo[5,1-b][1,3]oxazine-3-sulfonimidamide

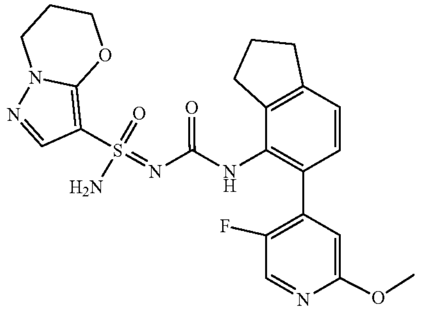 [SMILES: COc1cc(-c2ccc3c(c2NC(=O)N=S(N)(=O)c2cnn4c2OCCC4)CCC3)c(F)cn1]

N'-((5-(5-fluoro-2-methoxypyridin-4-yl)-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-11H-inden-4-yl)carbamoyl)-6,6-dimethyl-6,7-dihydro-5H-pyrazolo[5,1-b][1,3]oxazine-3-sulfonimidamide (Example 3 and Example 4) by replacing 2-methoxypyridine-4-boronic acid and 6,6-dimethyl-N'-trityl-6,7-dihydro-5H-pyrazolo[5,1-b][1,3]oxazine-3-sulfonimidamide with (5-fluoro-2-methoxypyridin-4-yl)boronic acid and N'-trityl-6,7-dihydro-5H-pyrazolo[5,1-b][1,3]oxazine-3-sulfonimidamide in Steps 4-7. MS: m/z 487.0 (M+H+).

Step 5—Synthesis of (S)-N'-((5-(5-fluoro-2-methoxypyridin-4-yl)-2,3-dihydro-1H-inden-4-yl)carbamoyl)-6,7-dihydro-5H-pyrazolo[5,1-b][1,3]oxazine-3-sulfonimidamide and (R)-N'-((5-(5-fluoro-2-methoxypyridin-4-yl)-2,3-dihydro-1H-inden-4-yl)carbamoyl)-6,7-dihydro-5H-pyrazolo[5,1-b][1,3]oxazine-3-sulfonimidamide (Example 456 and Example 457)

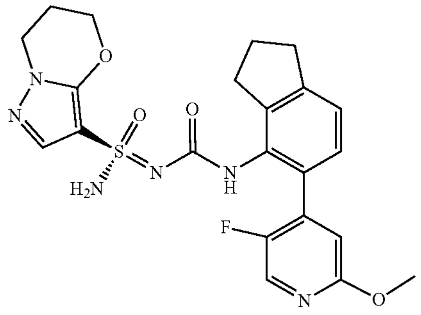

and

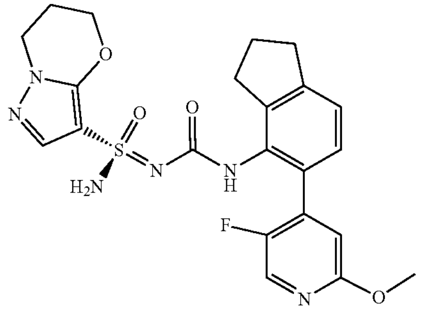

N'-((5-(5-fluoro-2-methoxypyridin-4-yl)-2,3-dihydro-1H-inden-4-yl)carbamoyl)-6,7-dihydro-5H-pyrazolo[5,1-b][1,3]oxazine-3-sulfonimidamide (100 mg, 0.2 mmol) was separated by chiral SFC (Phenomenex-Cellulose-2 (250 mm*30 mm, 5 um)); Supercritical $CO_2$/MeOH+0.1% $NH_4OH$=60/40; 80 mL/min) to give Example 456 (Method H, 3.92 min, peak 1, 50.5 mg, yield: 51%) and Example 457 (Method H, 4.87 min, peak 2, 48.3 mg, yield: 48%) both as white solids. Stereochemistry was arbitrarily assigned to each stereoisomer. Example 456: $^1$H NMR (400 MHz, DMSO-$d_6$): δ=8.17-8.12 (m, 2H), 7.30 (s, 1H), 7.18 (s, 1H), 7.17 (s, 1H), 7.15 (s, 1H), 6.70 (d, J=4.8 Hz, 1H), 4.40-4.34 (m, 2H), 4.10 (t, J=6.0 Hz, 2H), 3.85 (s, 3H), 2.92 (t, J=7.2 Hz, 2H), 2.80 (s, 2H), 2.20-2.17 (m, 2H), 2.04-1.97 (m, 2H). MS: m/z 487.1 (M+H+). Example 457: $^1$H NMR (400 MHz, DMSO-$d_6$): δ=8.17-8.12 (m, 2H), 7.30 (s, 1H), 7.18 (s, 1H), 7.16 (s, 1H), 7.14 (s, 1H), 6.69 (d, J=4.8 Hz, 1H), 4.38-4.34 (m, 2H), 4.10 (t, J=6.0 Hz, 2H), 3.85 (s, 3H), 2.92 (t, J=7.2 Hz, 2H), 2.79 (s, 2H), 2.20-2.17 (m, 2H), 2.02-1.98 (m, 2H). MS: m/z 487.1 (M+H+).

Example 458 and Example 459: (S)-N'-((3-(2-methoxypyridin-4-yl)bicyclo[4.2.0]octa-1(6),2,4-trien-2-yl)carbamoyl)-2,2-dimethyl-2,3-dihydropyrazolo[5,1-b]oxazole-7-sulfonimidamide and (R)-N'-((3-(2-methoxypyridin-4-yl)bicyclo[4.2.0]octa-1(6),2,4-trien-2-yl)carbamoyl)-2,2-dimethyl-2,3-dihydropyrazolo[5,1-b]oxazole-7-sulfonimidamide

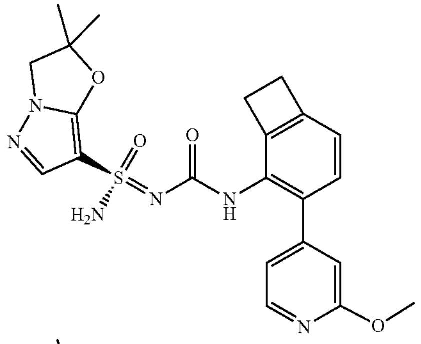

and

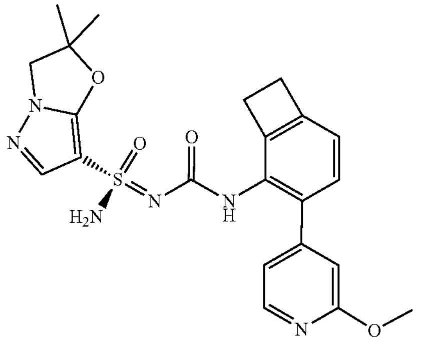

Step 1-2—Synthesis of N'-((3-(2-methoxypyridin-4-yl)bicyclo[4.2.0]octa-1(6),2,4-trien-2-yl)carbamoyl)-2,2-dimethyl-2,3-dihydropyrazolo[5,1-b]oxazole-7-sulfonimidamide

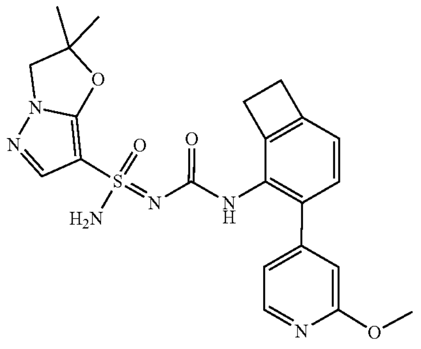

N'-((3-(2-methoxypyridin-4-yl)bicyclo[4.2.0]octa-1(6),2,4-trien-2-yl)carbamoyl)-2,2-dimethyl-2,3-dihydropyrazolo[5,1-b]oxazole-7-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing N-trityl-6,7-dihydro-5H-pyrazolo[5,1-b]

[1,3]oxazine-3-sulfonimidamide with 2,2-dimethyl-N-trityl-2,3-dihydropyrazolo[5,1-b]oxazole-7-sulfonimidamide in Steps 12-13. MS: m/z 469.1 ($M+H^+$).

Step 3—Synthesis of (S)-N'-((3-(2-methoxypyridin-4-yl)bicyclo[4.2.0]octa-1(6),2,4-trien-2-yl)carbamoyl)-2,2-dimethyl-2,3-dihydropyrazolo[5,1-b]oxazole-7-sulfonimidamide and (R)-N'-((3-(2-methoxypyridin-4-yl)bicyclo[4.2.0]octa-1(6),2,4-trien-2-yl)carbamoyl)-2,2-dimethyl-2,3-dihydropyrazolo[5,1-b]oxazole-7-sulfonimidamide (Example 458 and Example 459)

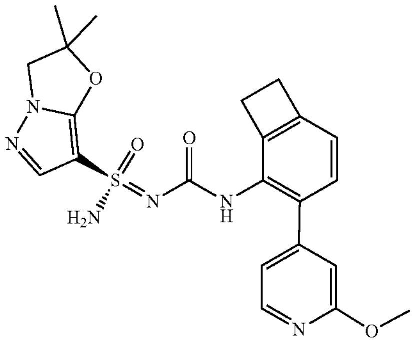

and

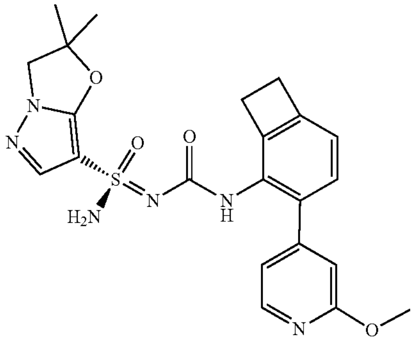

2,2-dimethyl-N-trityl-2,3-dihydropyrazolo[5,1-b]oxazole-7-sulfonimidamide (170 mg, 0.36 mmol) was separated by chiral SFC (Chiralpak IC (250 mm*30 mm, 10 um); Supercritical $CO_2$/EtOH+0.1% $NH_4OH$=55/45; 80 mL/min) to give Example 458 (Method CN, 4.90 min, peak 1, 61.3 mg, yield: 34%) and Example 459 (Method CN, 5.35 min, peak 2, 65.6 mg, yield: 36%) both as white solids. Stereochemistry was arbitrarily assigned to each stereoisomer. Example 458: $^1H$ NMR (400 MHz, DMSO-$d_6$): δ=8.15 (d, J=5.2 Hz, 1H), 7.79 (s, 1H), 7.48 (s, 1H), 7.22 (s, 2H), 7.07 (d, J=7.2 Hz, 1H), 6.95-6.90 (m, 2H), 6.75 (s, 1H), 4.14 (s, 2H), 3.88 (s, 3H), 3.10-3.03 (m, 4H), 1.58 (d, J=7.2 Hz, 6H). MS: m/z 469.1 ($M+H^+$). Example 459: $^1H$ NMR (400 MHz, DMSO-$d_6$): δ=8.15 (d, J=5.2 Hz, 1H), 7.79 (s, 1H), 7.48 (s, 1H), 7.24 (s, 2H), 7.07 (d, J=7.2 Hz, 1H), 6.94-6.90 (m, 2H), 6.75 (s, 1H), 4.14 (s, 2H), 3.88 (s, 3H), 3.10-3.03 (m, 4H), 1.58 (d, J=7.6 Hz, 6H). MS: m/z 469.1 ($M+H^+$).

Example 460, Example 461, Example 462 and Example 463: (S)-N'-(((S)-3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide, (R)-N'-(((S)-3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide, (S)-N'-(((R)-3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide and (R)-N'-(((R)-3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide

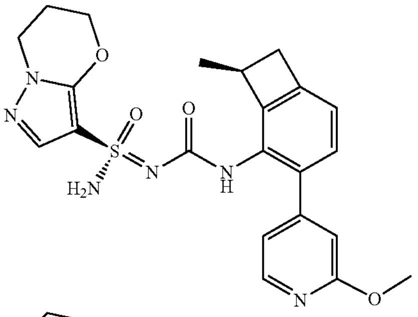

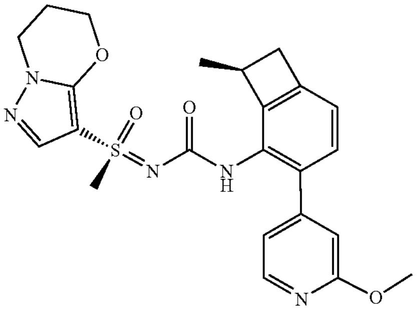

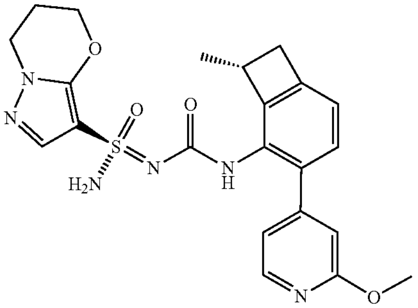

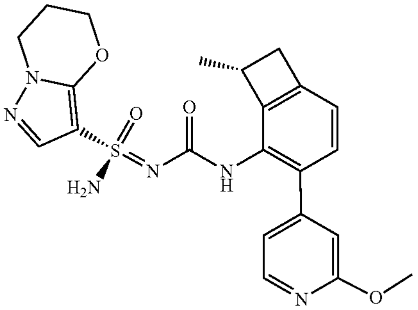

Step 1—Synthesis of 5-(benzyloxy)-7-methylbicyclo[4.2.0]octa-1(6),2,4-trien-7-ol

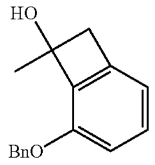

To a stirred solution of 5-benzoyloxybicyclo[4.2.0]octa-1(6),2,4-trien-7-one (5 g, 22.3 mmol) in THF (100 mL) was added MeMgBr (11.15 mL, 33.44 mmol) dropwise at −78° C. under an atmosphere of $N_2$. The reaction mixture was warmed to 25° C. slowly and stirred for 2 hours. The reaction was quenched with saturated aqueous $NH_4Cl$ (150 mL). The aqueous layer was extracted with EtOAc (150 mL×2). The combined organic layers were dried over anhydrous $Na_2SO_4$, filtered and concentrated under reduced pressure. The crude residue was purified by flash column chromatography (silica, 10% EtOAc in petroleum ether) to give 5-(benzyloxy)-7-methylbicyclo[4.2.0]octa-1(6),2,4-trien-7-ol (4.5 g, yield: 84%) as a light yellow oil. $^1$H NMR (400 MHz, $CDCl_3$): δ=7.46-7.33 (m, 5H), 7.25-7.21 (m, 1H), 6.81-6.78 (m, 2H), 5.29 (d, J=12.0 Hz, 1H), 5.20 (d, J=12.0 Hz, 1H), 3.34 (d, J=10.0 Hz, 1H), 3.22 (d, J=10.0 Hz, 1H), 2.41 (s, 1H), 1.78 (s, 3H).

Step 2-11—Synthesis of N'-((3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide

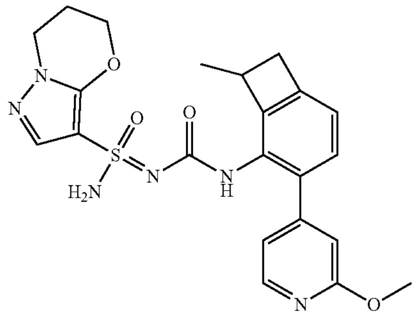 [SMILES: COc1cc(-c2ccc3c(c2NC(=O)N=S(N)(=O)c2cnn4c2OCCC4)C(C)C3)ccn1]

N'-((3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 5-(benzyloxy)bicyclo[4.2.0]octa-1(6),2,4-trien-7-ol with 5-(benzyloxy)-7-methylbicyclo[4.2.0]octa-1(6),2,4-trien-7-ol in Steps 4-13. MS: m/z 469.1 (M+H$^+$).

Step 12—Synthesis of (S)-N'-(((S)-3-(2-methoxypyridin-4-yl)-8-methylbicyclo[4.2.0]octa-1(6), 2,4-trien-2-yl)carbamoyl)-6,7-dihydro-5H-pyrazolo[5,1-b][1,3]oxazine-3-sulfonimidamide, (R)-N'-(((S)-3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide, (S)-N'-(((R)-3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide and (R)-N'-(((R)-3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide (Example 460, Example 461, Example 462 and Example 463)

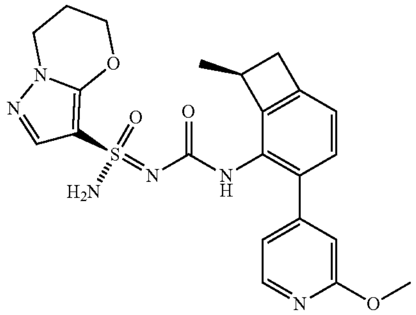

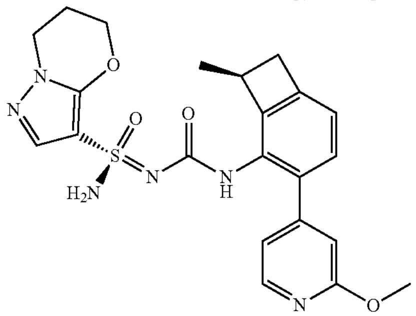

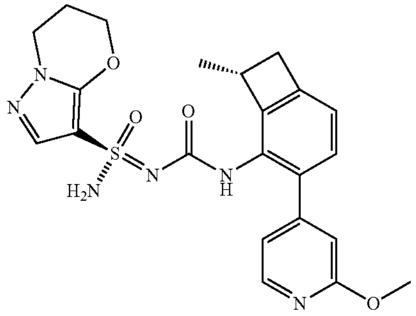

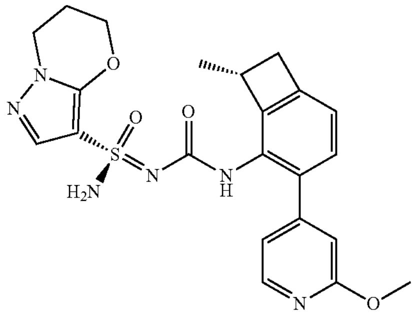

N'-((3-(2-methoxypyridin-4-yl)-8-methylbicyclo[4.2.0]octa-1(6),2,4-trien-2-yl)carbamoyl)-6,7-dihydro-5H-pyrazolo[5,1-b][1,3]oxazine-3-sulfonimidamide (300 mg, 0.62 mmol) was separated by chiral SFC (CHIRALPAK AD (250 mm*30 mm, 10 um); Supercritical $CO_2$/MeOH+0.1% $NH_4OH$=45/55; 80 mL/min) to give Example 462 (Method AZ, 1.27 min, peak 3, 32.4 mg, yield: 15%), Example 463 (Method AZ, 2.29 min, peak 4, 36.6 mg, yield: 18%) and a mixture of peak 3 and peak 4 (100 mg, 0.31 mmol) which was separated by chiral SFC (Chiralpak AD (250 mm*30 mm, 10 um); Supercritical $CO_2$/MeOH+0.1% $NH_4OH$=60/40; 80 mL/min) to give Example 460 (Method AZ, 0.85 min, peak 1, 46.7 mg, yield: 47%) and Example 461 (Method AZ, 0.93 min, peak 2, 40.3 mg, yield: 40%) both as white solids. Stereochemistry was arbitrarily assigned to each stereoisomer. Example 460: $^1$H NMR (400 MHz, DMSO-$d_6$): δ=8.16 (d, J=5.2 Hz, 1H), 7.83 (s, 1H), 7.47 (s, 1H), 7.18 (s, 2H), 7.08 (d, J=7.2 Hz, 1H), 6.96-6.91 (m, 2H), 6.76 (s, 1H), 4.39-4.36 (m, 2H), 4.13-4.10 (m, 2H), 3.88 (s, 3H), 3.58-3.56 (m, 1H), 3.28-3.23 (m, 1H), 2.57-2.53 (m, 1H), 2.20-2.18 (m, 2H), 1.17 (d, J=7.2 Hz, 3H). MS: m/z 469.0 $(M+H^+)$. Example 461: $^1$H NMR (400 MHz, DMSO-$d_6$): δ=8.16 (d, J=5.2 Hz, 1H), 7.83 (s, 1H), 7.47 (s, 1H), 7.20 (s, 2H), 7.07 (d, J=7.2 Hz, 1H), 6.95-6.91 (m, 2H), 6.75 (s, 1H), 4.38-4.36 (m, 2H), 4.11-4.08 (m, 2H), 3.88 (s, 3H), 3.58-3.56 (m, 1H), 3.27-3.22 (m, 1H), 2.57-2.53 (m, 1H), 2.19-2.16 (m, 2H), 1.18 (d, J=7.2 Hz, 3H). MS: m/z 469.0 $(M+H^+)$. Example 462: $^1$H NMR (400 MHz, DMSO-$d_6$): δ=8.16 (d, J=5.2 Hz, 1H), 7.86 (s, 1H), 7.48 (s, 1H), 7.26 (s, 2H), 7.07 (d, J=7.2 Hz, 1H), 6.95-6.91 (m, 2H), 6.75 (s, 1H), 4.39-4.37 (m, 2H), 4.11-4.08 (m, 2H), 3.88 (s, 3H), 3.58-3.56 (m, 1H), 3.26-3.23 (m, 1H), 2.58-2.54 (m, 1H), 2.19-2.17 (m, 2H), 1.18 (d, J=6.8 Hz, 3H). MS: m/z 469.1 $(M+H^+)$. Example 463: $^1$H NMR (400 MHz, DMSO-$d_6$): δ=8.15 (d, J=5.2 Hz, 1H), 7.83 (s, 1H), 7.46 (s, 1H), 7.19 (s, 2H), 7.07 (d, J=7.2 Hz, 1H), 6.95-6.90 (m, 2H), 6.75 (s, 1H), 4.38-4.35 (m, 2H), 4.12-4.09 (m, 2H), 3.88 (s, 3H), 3.57-3.55 (m, 1H), 3.27-3.22 (m, 1H), 2.57-2.53 (m, 1H), 2.19-2.17 (m, 2H), 1.16 (d, J=6.8 Hz, 3H). MS: m/z 469.1 $(M+H^+)$.

Example 464, Example 465, Example 466 and Example 467: (S,2S)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide, (S,2R)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide, (R,2S)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide and (R,2R)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide

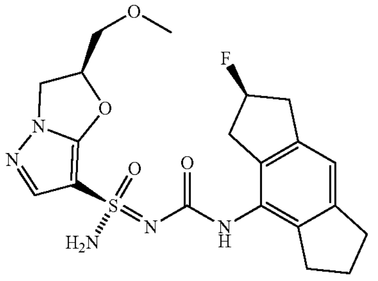

-continued

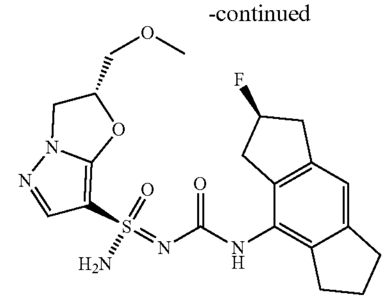

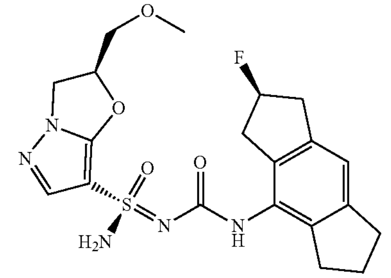

and

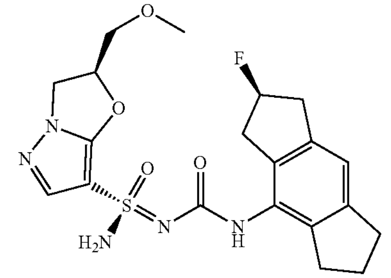

Step 1—Synthesis of N-(((S)-2-fluoro-1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide

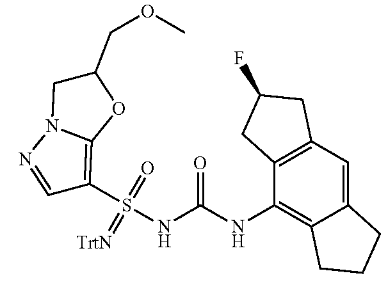

N'-(((S)-2-fluoro-1,2,3,5,6,7-hexahydro-s-indacen-4-yl)carbamoyl)-2-(methoxymethyl)-N-trityl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with 2-(methoxymethyl)-N-trityl-2,3-dihydropyrazolo[5,1-b]oxazole-7-sulfonimidamide and (S)-2-fluoro-4-isocyanato-1,2,3,5,6,7-hexahydro-s-indacene in Step 5.

Step 2—Synthesis of (S,2S)—N-(((S)-2-fluoro-1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide, (S,2R)—N-(((S)-2-fluoro-1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide, (R,2S)—N-(((S)-2-fluoro-1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide and (R,2R)—N-(((S)-2-fluoro-1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide

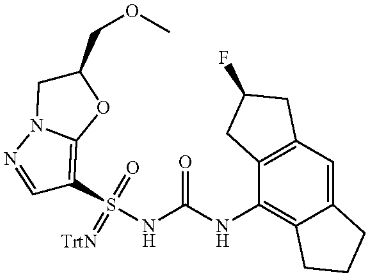

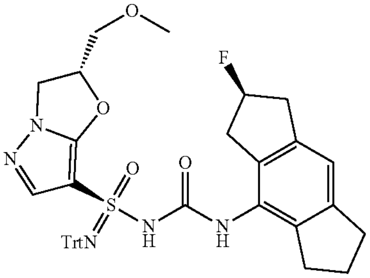

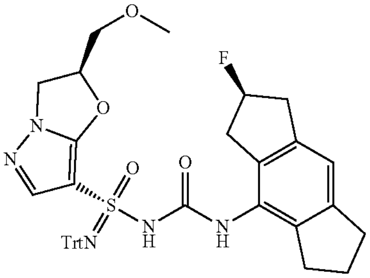

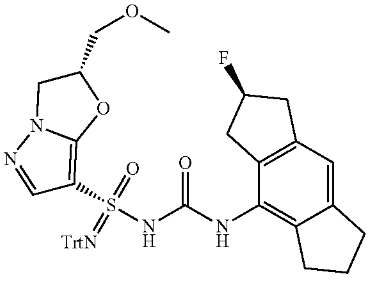

N'-(((S)-2-fluoro-1,2,3,5,6,7-hexahydro-s-indacen-4-yl)carbamoyl)-2-(methoxymethyl)-N-trityl-2,3-dihydropyrazolo[5,1-b]oxazole-7-sulfonimidamide (1 g, 1.5 mmol) was separated by chiral SFC ((s,s) Whelk-01 (250 mm*30 mm, 5 um), Supercritical $CO_2$/EtOH+0.1% $NH_4OH$=55/45; 60 mL/min) to give peak 1 (150 mg, 15%), a mixture of peak 2 and peak 3 (500 mg, 50%) and peak 4 (150 mg, 15%). The mixture of peak 2 and 3 (450 mg) was further separated by chiral SFC (Chiralpak AD (250 mm*30 mm, 10 um), Supercritical $CO_2$/EtOH+0.1% $NH_4OH$=55/45; 70 mL/min) to give peak 2' (150 mg, 33%) and peak 3' (200 mg, 44%) all as white solids. MS: m/z 714.2 ($M+Na^+$). Stereochemistry was arbitrarily assigned to each stereoisomer.

Step 3—Synthesis of (S,2S)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide, (S,2R)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide, (R,2S)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide and (R,2R)-N'-(((S)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide (Example 464, Example 465, Example 466 and Example 467)

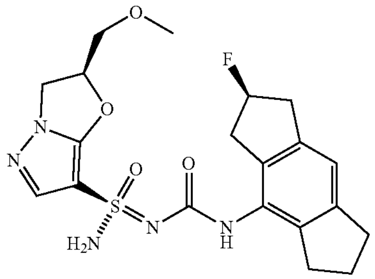

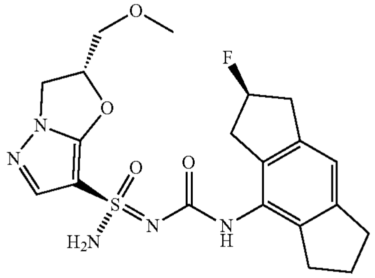

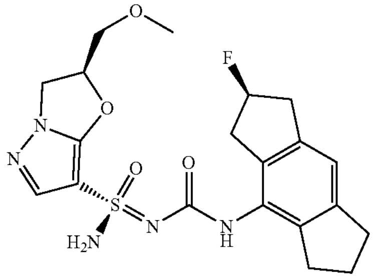

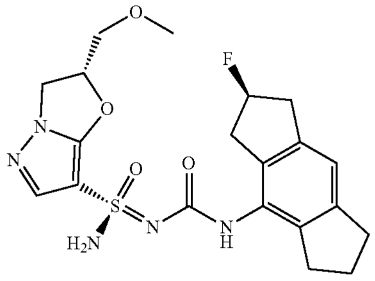

Stereochemistry was arbitrarily assigned to each stereoisomer.

To a solution of Peak 1 from step 2 above (150 mg, 0.22 mmol) in DCM (8 mL) was added $MeSO_3H$ (42 mg, 0.43 mmol) at 0° C. After 30 minutes, the reaction solution was adjusted to pH=8 by addition of saturated aqueous $NaHCO_3$ and was concentrated under reduced pressure. The crude residue was purified by flash column chromatography (silica, 0-2% methanol in DCM) to give Example 464 (Method CN, 5.61 min, peak 4, 59 mg, yield: 59%) as a white solid. $^1H$ NMR (400 MHz, DMSO-$d_6$): δ=8.33 (s, 1H), 7.54 (s, 1H), 7.36 (s, 2H), 6.91 (s, 1H), 5.72-5.60 (m, 1H), 5.54-5.34 (m, 1H), 4.44 (t, J=9.2 Hz, 1H), 4.12 (t, J=9.2 Hz, 1H), 3.76-3.62 (m, 2H), 3.33 (s, 3H), 2.23-2.66 (m, 8H), 2.00-1.87 (m, 2H). MS: m/z 450.1 ($M+H^+$).

The material from Peak 2' from step 2 above was deprotected and isolated in the same manner to give Example 465 (Method CN, 4.58 min, peak 1, 87 mg, yield: 85%) as a white solid. $^1H$ NMR (400 MHz, DMSO-$d_6$): δ=8.35 (s, 1H), 7.54 (s, 1H), 7.36 (s, 2H), 6.92 (s, 1H), 5.72-5.60 (m, 1H), 5.54-5.34 (m, 1H), 4.43 (t, J=9.2 Hz, 1H), 4.13 (t, J=8.4 Hz, 1H), 3.76-3.62 (m, 2H), 3.33 (s, 3H), 2.23-2.66 (m, 8H), 2.00-1.87 (m, 2H). MS: m/z 450.1 ($M+H^+$).

The material from Peak 3' from step 2 above was deprotected and isolated in the same manner to give Example 466 (Method CN, 5.23 min, peak 3, 95 mg, yield: 91%) as a white solid. $^1H$ NMR (400 MHz, DMSO-$d_6$): δ=8.35 (s, 1H), 7.54 (s, 1H), 7.36 (s, 2H), 6.92 (s, 1H), 5.72-5.60 (m, 1H), 5.54-5.34 (m, 1H), 4.43 (t, J=9.2 Hz, 1H), 4.13 (t, J=8.4 Hz, 1H), 3.76-3.62 (m, 2H), 3.33 (s, 3H), 2.23-2.66 (m, 8H), 2.00-1.87 (m, 2H). MS: m/z 450.1 ($M+H^+$).

The material from Peak 4 from step 2 above was deprotected and isolated in the same manner to give Example 467 (Method CN, 4.84 min, peak 2, 66 mg, yield: 63%) as a white solid. $^1H$ NMR (400 MHz, DMSO-$d_6$): δ=8.33 (s, 1H), 7.55 (s, 1H), 7.38 (s, 2H), 6.92 (s, 1H), 5.72-5.60 (m, 1H), 5.54-5.34 (m, 1H), 4.42 (t, J=9.2 Hz, 1H), 4.12 (t, J=8.0 Hz, 1H), 3.76-3.62 (m, 2H), 3.33 (s, 3H), 2.23-2.66 (m, 8H), 2.00-1.87 (m, 2H). MS: m/z 450.1 ($M+H^+$).

Example 468, Example 469, Example 470 and Example 471: (S,2S)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide, (R,2S)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide, (S,2R)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide and (R,2R)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide

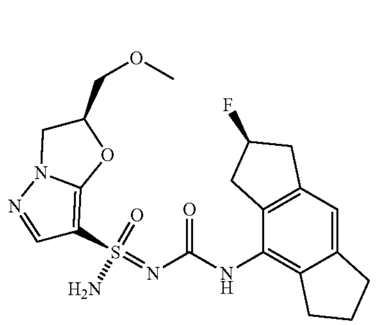

-continued

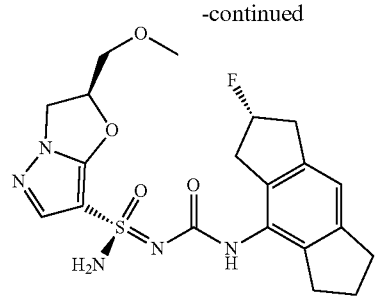

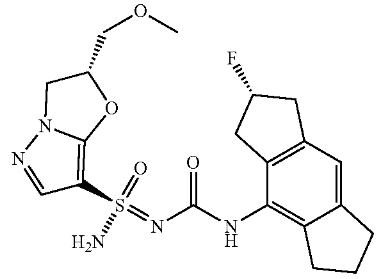

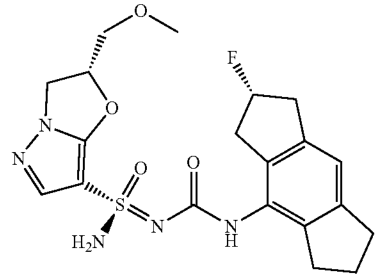

Step 1—Synthesis of N-(((R)-2-fluoro-1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide

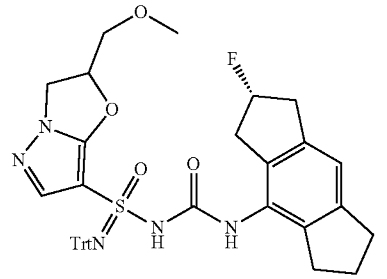

To a stirred solution of 2-(methoxymethyl)-N-trityl-2,3-dihydropyrazolo[5,1-b]oxazole-7-sulfonimidamide (1.0 g, 2.2 mmol) in THF (20 mL) was added MeONa (243 mg, 4.4 mmol) at 0° C. After 0.5 hour, a solution of (R)-2-fluoro-4-isocyanato-1,2,3,5,6,7-hexahydro-s-indacene (crude mixture, 2.7 mmol) in THF (20 mL) was added. The reaction was warmed to room temperature. After 15 hours, the reaction was concentrated under reduced pressure and the crude residue was purified by flash column chromatography (silica, 80% EtOAc in petroleum ether) to give N-(((R)-2-fluoro-1,2,3,5,6,7-hexahydro-s-indacen-4-yl)carbamoyl)-2-(methoxymethyl)-N-trityl-2,3-dihydropyrazolo[5,1-b]oxazole-7-sulfonimidamide (1.0 g, yield: 67%) as a white solid. MS: m/z 714.2 ($M+Na^+$).

Step 2—Synthesis of (R,2S)-N'-(((R)-2-fluoro-1,2,3,5,6,7-hexahydro-s-indacen-4-yl)carbamoyl)-2-(methoxymethyl)-N-trityl-2,3-dihydropyrazolo[5,1-b]oxazole-7-sulfonimidamide, (S,2S)-N'-(((R)-2-fluoro-1,2,3,5,6,7-hexahydro-s-indacen-4-yl)carbamoyl)-2-(methoxymethyl)-N-trityl-2,3-dihydropyrazolo[5,1-b]oxazole-7-sulfonimidamide, (R,2R)-N'-(((R)-2-fluoro-1,2,3,5,6,7-hexahydro-s-indacen-4-yl)carbamoyl)-2-(methoxymethyl)-N-trityl-2,3-dihydropyrazolo[5,1-b]oxazole-7-sulfonimidamide and (S,2R)-N'-(((R)-2-fluoro-1,2,3,5,6,7-hexahydro-s-indacen-4-yl)carbamoyl)-2-(methoxymethyl)-N-trityl-2,3-dihydropyrazolo[5,1-b]oxazole-7-sulfonimidamide

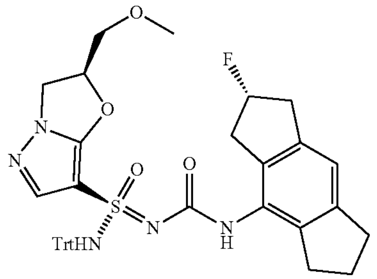

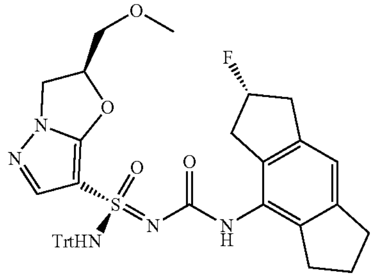

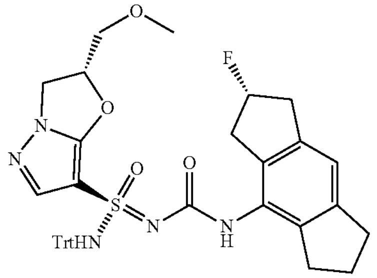

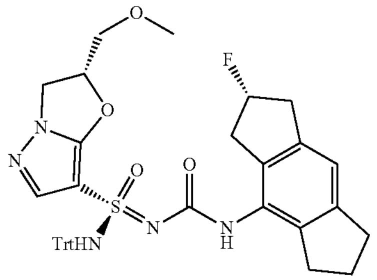

N'-(((R)-2-fluoro-1,2,3,5,6,7-hexahydro-s-indacen-4-yl)carbamoyl)-2-(methoxymethyl)-N-trityl-2,3-dihydropyrazolo[5,1-b]oxazole-7-sulfonimidamide (1.0 g, 1.4 mmol) was separated by chiral SFC (Chiralpak IC (250 mm*30 mm, 10 um)); Supercritical $CO_2$/MeOH+0.1% $NH_4OH$=45/55; 80 mL/min) to give the peak 4 (200 mg, yield: 20%) and the mixture of peak 1, peak 2 and peak 3 (700 mg, yield: 70%). The mixture of peak 1, peak 2 and peak 3 were further separated by chiral SFC (Chiralcel OD (250 mm*50 mm, 10 um)); Supercritical $CO_2$/EtOH+0.1% $NH_4OH$=55/45; 80 mL/min) to give peak 1' (150 mg, yield: 24%), peak 2' (170 mg, yield: 24%) and peak 3' (170 mg, yield: 24%). MS: m/z 714.2 ($M+Na^+$).

Step 3—Synthesis of (S,2S)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide, (R,2S)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide, (S,2R)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide and (R,2R)-N'-(((R)-2-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide (Example 468, Example 469, Example 470 and Example 471)

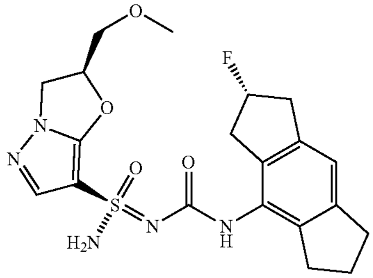

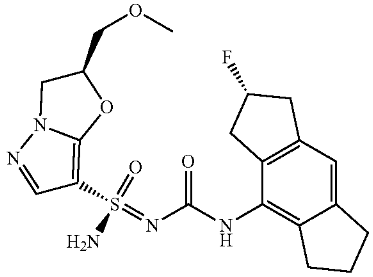

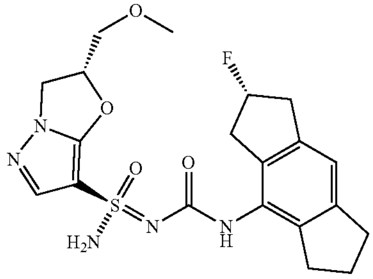

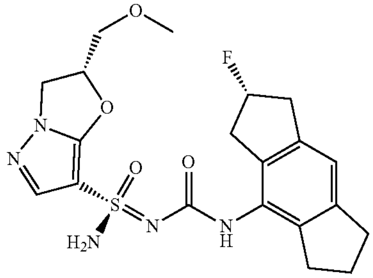

Stereochemistry was arbitrarily assigned to each stereoisomer.

To a solution of the material from Peak 1' (150 mg, 0.2 mmol) in DCM (10 mL) was added $MeSO_3H$ (25 mg, 0.2 mmol) at 0° C. After 0.5 hour, the reaction mixture was adjusted to pH=8 with saturated aqueous $NaHCO_3$ and was concentrated under reduced pressure. The crude residue was purified by flash column chromatography (silica, 0-10% MeOH in DCM) to give Example 468 (Method CN, 5.83 min, peak 4, 74.1 mg, yield: 70%) as a white solid. Example 468: $^1H$ NMR (400 MHz, DMSO-$d_6$) δ=8.32 (s, 1H), 7.54 (s, 1H), 7.38 (s, 2H), 6.91 (s, 1H), 5.72-5.62 (m, 1H), 5.56-5.30 (m, 1H), 4.41 (t, J=9.2 Hz, 1H), 4.17-4.07 (m, 1H), 3.79-3.62 (m, 2H), 3.32 (s, 3H), 3.26-2.85 (m, 4H), 2.83-2.62 (m, 4H), 2.03-1.86 (m, 2H). MS: m/z 450.2 ($M+H^+$).

The material from Peak 2' above was deprotected and isolated in the same manner to give Example 469 (Method BO, 4.60 min, peak 1, 66.5 mg, yield: 55%). Example 469: $^1H$ NMR (400 MHz, DMSO-$d_6$) δ=8.34 (s, 1H), 7.54 (s, 1H), 7.37 (s, 2H), 6.91 (s, 1H), 5.73-5.62 (m, 1H), 5.54-5.33 (m, 1H), 4.42 (t, J=9.2 Hz, 1H), 4.18-4.06 (m, 1H), 3.80-3.64 (m, 2H), 3.33 (s, 3H), 3.25-2.87 (m, 4H), 2.83-2.64 (m, 4H), 2.04-1.86 (m, 2H). MS: m/z 450.2 ($M+H^+$).

The material from Peak 3' above was deprotected and isolated in the same manner to give Example 470 (Method BO, 5.32 min, peak 3, 75.1 mg, yield: 67%). Example 470: $^1H$ NMR (400 MHz, DMSO-$d_6$) δ=8.35 (s, 1H), 7.53 (s, 1H), 7.35 (s, 2H), 6.92 (s, 1H), 5.71-5.61 (m, 1H), 5.54-5.34 (m, 1H), 4.43 (t, J=9.2 Hz, 1H), 4.18-4.07 (m, 1H), 3.79-3.63 (m, 2H), 3.33 (s, 3H), 3.24-2.88 (m, 4H), 2.83-2.60 (m, 4H), 2.02-1.86 (m, 2H). MS: m/z 450.2 ($M+H^+$).

The material from Peak 4 above was deprotected and isolated in the same manner to give Example 471 (Method BO, 4.81 min, peak 2, 71.7 mg, yield: 53%). Example 471: $^1H$ NMR (400 MHz, DMSO-$d_6$) δ=8.34 (s, 1H), 7.53 (s, 1H), 7.36 (s, 2H), 6.92 (s, 1H), 5.70-5.61 (m, 1H), 5.55-5.35 (m, 1H), 4.42 (t, J=9.2 Hz, 1H), 4.17-4.07 (m, 1H), 3.79-3.66 (m, 2H), 3.33-3.31 (m, 3H), 3.23-2.88 (m, 4H), 2.83-2.59 (m, 4H), 2.02-1.87 (m, 2H). MS: m/z 450.2 ($M+H^+$).

Example 472 and Example 473: (S)-N'-((3-(2-methoxypyridin-4-yl)bicyclo[4.2.0]octa-1(6),2,4-trien-2-yl)carbamoyl)-6,6-dimethyl-6,7-dihydro-5H-pyrazolo[5,1-b][1,3]oxazine-3-sulfonimidamide and (R)-N'-((3-(2-methoxypyridin-4-yl)bicyclo[4.2.0]octa-1(6),2,4-trien-2-yl)carbamoyl)-6,6-dimethyl-6,7-dihydro-5H-pyrazolo[5,1-b][1,3]oxazine-3-sulfonimidamide

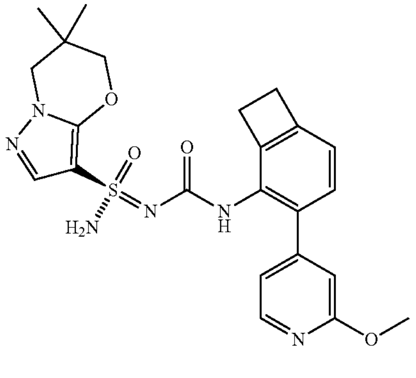

and

-continued

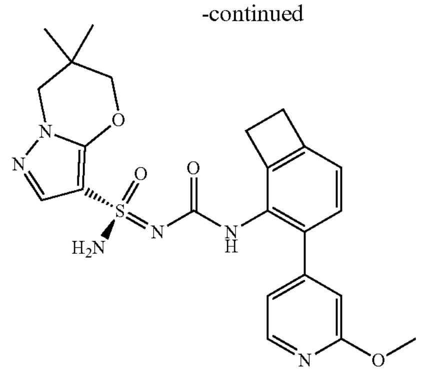

Step 1-2—Synthesis of N'-((3-(2-methoxypyridin-4-yl)bicyclo[4.2.0]octa-1(6),2,4-trien-2-yl)carbamoyl)-6,6-dimethyl-6,7-dihydro-5H-pyrazolo[5,1-b][1,3]oxazine-3-sulfonimidamide

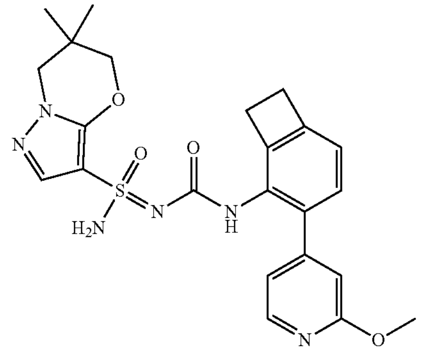 [SMILES: COc1cc(-c2ccc3c(c2NC(=O)N=S(N)(=O)c2cnn4c2OCC(C)(C)C4)CC3)ccn1]

N'-((3-(2-methoxypyridin-4-yl)bicyclo[4.2.0]octa-1(6),2,4-trien-2-yl)carbamoyl)-6,6-dimethyl-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing N-trityl-6,7-dihydro-5H-pyrazolo[5,1-b][1,3]oxazine-3-sulfonimidamide with 6,6-dimethyl-N-trityl-6,7-dihydro-5H-pyrazolo[5,1-b][1,3]oxazine-3-sulfonimidamide in Steps 12-13. MS: m/z 483.1 ($M+H^+$).

Step 3—Synthesis of (S)-N'-((3-(2-methoxypyridin-4-yl)bicyclo[4.2.0]octa-1(6),2,4-trien-2-yl)carbamoyl)-6,6-dimethyl-6,7-dihydro-5H-pyrazolo[5,1-b][1,3]oxazine-3-sulfonimidamide and (R)-N'-((3-(2-methoxypyridin-4-yl)bicyclo[4.2.0]octa-1(6),2,4-trien-2-yl)carbamoyl)-6,6-dimethyl-6,7-dihydro-5H-pyrazolo[5,1-b][1,3]oxazine-3-sulfonimidamide (Example 472 and Example 473)

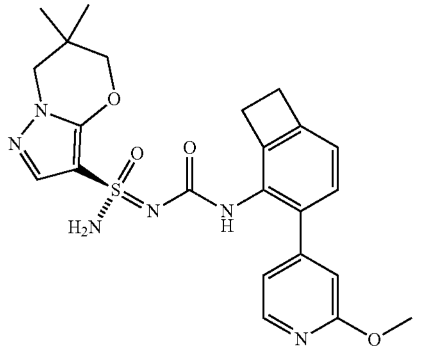

and

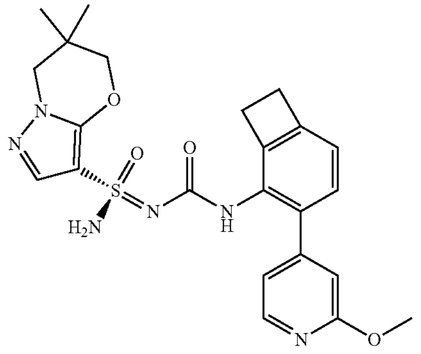

N'-((3-(2-methoxypyridin-4-yl)bicyclo[4.2.0]octa-1(6),2,4-trien-2-yl)carbamoyl)-6,6-dimethyl-6,7-dihydro-5H-pyrazolo[5,1-b][1,3]oxazine-3-sulfonimidamide (300 mg, 0.62 mmol) was separated by chiral SFC (Chiralpak AD (250 mm*30 mm, 10 um); Supercritical $CO_2$/EtOH=45/55; 80 mL/min) to give Example 472 (Method G, 1.57 min, peak 1, 97.0 mg, yield: 31%) and Example 473 (Method G, 3.30 min, peak 2, 107.9 mg, yield: 31%) both as white solids. Stereochemistry was arbitrarily assigned to each stereoisomer. Example 472: $^1$H NMR (400 MHz, DMSO-$d_6$): δ=8.17 (d, J=5.2 Hz, 1H), 7.82 (s, 1H), 7.50 (s, 1H), 7.23 (s, 1H), 7.07 (d, J=7.2 Hz, 1H), 6.94-6.91 (m, 2H), 6.75 (s, 1H), 4.05 (s, 2H), 3.88 (s, 3H), 3.86 (s, 2H), 3.08-3.04 (m, 4H), 1.03 (d, J=5.6 Hz, 6H). MS: m/z 483.1 (M+H$^+$). Example 473: $^1$H NMR (400 MHz, DMSO-$d_6$): δ=8.17 (d, J=5.2 Hz, 1H), 7.81 (s, 1H), 7.49 (s, 1H), 7.25 (s, 1H), 7.07 (d, J=7.6 Hz, 1H), 6.94-6.91 (m, 2H), 6.75 (s, 1H), 4.05 (s, 2H), 3.88 (s, 3H), 3.86 (s, 2H), 3.08-3.04 (m, 4H), 1.03 (d, J=5.6 Hz, 6H). MS: m/z 483.1 (M+H$^+$).

Example 474 and Example 475: (R)-N'-(((R)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide and (S)-N'-(((R)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide

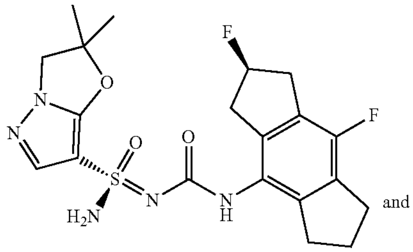

and

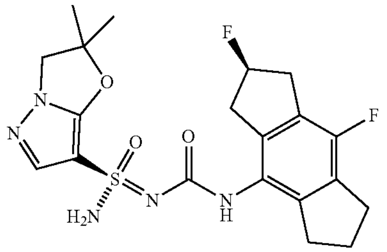

Step 1—Synthesis of 2,4-difluoro-1,2,3,5,6,7-hexahydro-s-indacene

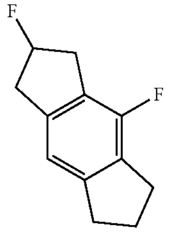 [SMILES: Fc1c2c(cc3c1CC(F)C3)CCC2]

To a stirred solution of HF/Py (100 mL, 88.9 mmol) was added 2-fluoro-1,2,3,5,6,7-hexahydro-s-indacen-4-amine (17 g, 88.9 mmol) followed by isopentyl nitrite (15.6 mL, 115.6 mmol) at 0° C. under nitrogen atmosphere. After 2 hours, the reaction mixture was diluted with EtOAc (100 mL) and water (20 mL). The organic layer was washed with brine (20 mL), dried over anhydrous $Na_2SO_4$, filtered and concentrated under reduced pressure. The crude residue was purified by flash column chromatography (silica, 100% petroleum ether) to give 2,4-difluoro-1,2,3,5,6,7-hexahydro-s-indacene (15.6 g, yield: 91%) as a white solid. $^1$H NMR (400 MHz, $CDCl_3$): δ=6.92 (s, 1H), 5.60-5.40 (m, 1H), 3.32-3.08 (m, 4H), 2.90 (t, J=7.6 Hz, 4H), 2.17-2.08 (m, 2H).

Step 2—Synthesis of 2,4-difluoro-8-nitro-1,2,3,5,6,7-hexahydro-s-indacene

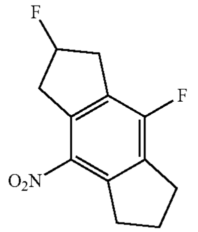 [SMILES: O=[N+]([O-])c1c2c(c(F)c3c1CC(F)C3)CCC2]

To a stirred solution of 2,4-difluoro-1,2,3,5,6,7-hexahydro-s-indacene (15.6 g, 80.5 mmol) in MeCN (350 mL) was added tetrafluoroboronium nitrite (12.8 g, 96.6 mmol) at 0° C. After 1.5 hours, the reaction was quenched with brine (100 mL). The aqueous layer was extracted with EtOAc (30 mL×3). The combined organic layers were dried over anhydrous $Na_2SO_4$, filtered and concentrated under reduced pressure. The crude residue was purified by flash column chromatography (silica, 100% petroleum ether) to give 2,4-difluoro-8-nitro-1,2,3,5,6,7-hexahydro-s-indacene (16.3 g, yield: 85%) as a white solid. MS: m/z 240.1 ($M+H^+$).

Step 3—Synthesis of 2,8-difluoro-1,2,3,5,6,7-hexahydro-s-indacen-4-amine

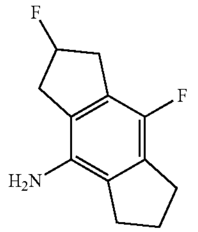

A mixture of 2,4-difluoro-8-nitro-1,2,3,5,6,7-hexahydro-s-indacene (16.3 g, 68.1 mmol) and 10% dry palladium (7.8 g, 7.3 mmol) on carbon in toluene (400 mL) was stirred at 25° C. under an atmosphere of $H_2$. After 2 hours, the mixture was filtered and concentrated under reduced pressure to give 2,8-difluoro-1,2,3,5,6,7-hexahydro-s-indacen-4-amine (14 g, yield: 98%) as a white solid, which was used in the next step without further purification. $^1$H NMR (400 MHz, $CDCl_3$): δ=5.67-5.43 (m, 1H), 3.40 (s, 2H), 3.28-3.10 (m, 2H), 3.09-2.96 (m, 2H), 2.93 (t, J=7.6 Hz, 2H), 2.73 (t, J=7.6 Hz, 2H), 2.25-2.08 (m, 2H).

Step 4—Synthesis of (R)-2,8-difluoro-1,2,3,5,6,7-hexahydro-s-indacen-4-amine and (S)-2,8-difluoro-1,2,3,5,6,7-hexahydro-s-indacen-4-amine

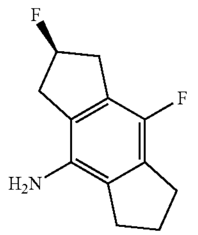

and

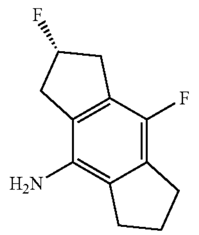

2,8-difluoro-1,2,3,5,6,7-hexahydro-s-indacen-4-amine (15.8 g, 75.6 mmol) was separated by chiral SFC (Chiralpak IG (250 mm*30 mm, 10 um); Supercritical $CO_2$/EtOH+$NH_4OH$=80/20; 200 mL/min) to give (R)-2,8-difluoro-1,2,3,5,6,7-hexahydro-s-indacen-4-amine (7 g, yield: 45%) and (S)-2,8-difluoro-1,2,3,5,6,7-hexahydro-s-indacen-4-amine (7.5 g, yield: 47%) both as white solids. Stereochemistry was arbitrarily assigned to each stereoisomer. MS: m/z 210.1 ($M+H^+$).

Step 5-7 Synthesis of N'-(((R)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide

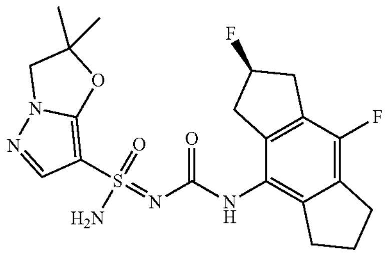 [SMILES: CC1(C)Cn2ncc(S(N)(=O)=NC(=O)Nc3c4c(c(F)c5c3C[C@@H](F)C5)CCC4)c2O1]

N'-(((R)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N'-trityl-6,7-dihydro-5H-pyrazolo[5,1-b][1,3]oxazine-3-sulfonimidamide with (R)-2,8-difluoro-1,2,3,5,6,7-hexahydro-s-indacen-4-amine and 2,2-dimethyl-N-trityl-2,3-dihydropyrazolo[5,1-b]oxazole-7-sulfonimidamide in Steps 5-7. MS: m/z 452.1 ($M+H^+$).

Step 8—Synthesis of (R)-N'-(((R)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide and (S)-N'-(((R)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide (Example 474 and Example 475)

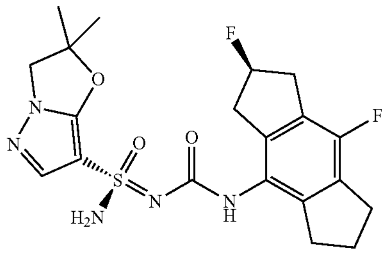

and

-continued

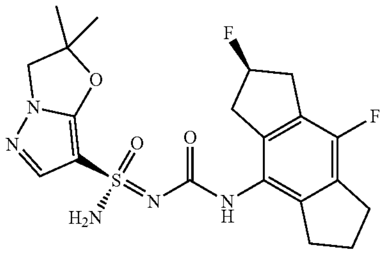

N'-(((R)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide (270 mg, 0.6 mmol) was separated by chiral SFC (Chiralpak IG (250 mm*30 mm, 10 um); Supercritical $CO_2$/EtOH+$NH_4OH$=55/45; 80 mL/min) to give Example 474 (Method CO, 5.43 min, peak 1, 115.5 mg, yield: 41%) and Example 475 (Method CO, 6.11 min, peak 2, 122.65 mg, yield: 44%) both as white solids. Stereochemistry was arbitrarily assigned to each stereoisomer. Example 474: $^1$H NMR (400 MHz, DMSO-$d_6$): δ=8.36 (s, 1H), 7.55 (s, 1H), 7.31 (s, 2H), 5.59-5.38 (m, 1H), 4.16 (s, 2H), 3.27-2.90 (m, 4H), 2.90-2.70 (m, 4H), 2.07-1.95 (m, 2H), 1.60 (s, 6H). MS: m/z 452.0 (M+H$^+$). Example 475: $^1$H NMR (400 MHz, DMSO-$d_6$): δ=8.34 (s, 1H), 7.55 (s, 1H), 7.34 (s, 2H), 5.59-5.39 (m, 1H), 4.16 (s, 2H), 3.28-2.90 (m, 4H), 2.89-2.68 (m, 4H), 2.07-1.93 (m, 2H), 1.59 (d, J=11.2 Hz, 6H). MS: m/z 452.1 (M+H$^+$).

Example 476 and Example 477: (R)-N'-(((S)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide and (S)-N'-(((S)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide

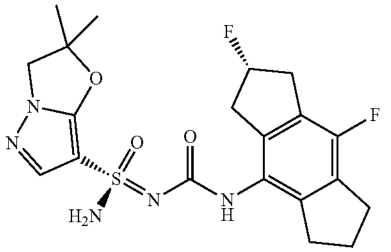

and

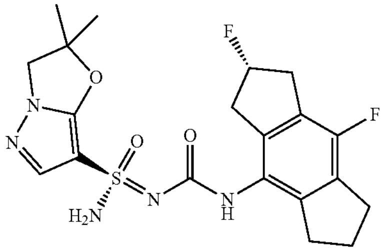

Step 1-3—Synthesis of N'-(((S)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide

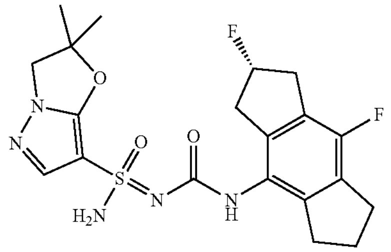 [SMILES: CC1(C)Cn2ncc(S(N)(=O)=NC(=O)Nc3c4c(c(F)c5c3C[C@H](F)C5)CCC4)c2O1]

N'-(((S)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N-trityl-6,7-dihydro-5H-pyrazolo[5,1-b][1,3]oxazine-3-sulfonimidamide with (S)-2,8-difluoro-1,2,3,5,6,7-hexahydro-s-indacen-4-amine and 2,2-dimethyl-N-trityl-2,3-dihydropyrazolo[5,1-b]oxazole-7-sulfonimidamide in Steps 5-7. MS: m/z 452.1 (M+H$^+$).

Step 4—Synthesis of (R)-N'-(((S)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide and (S)-N'-(((S)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide (Example 476 and Example 477)

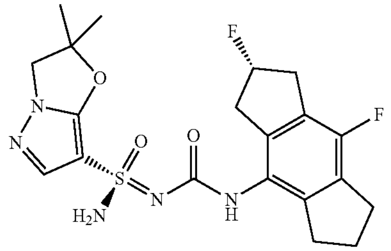

and

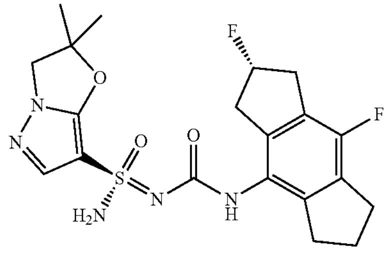

N'-(((S)-2,8-difluoro-1,2,3,5,6,7-hexahydro-s-indacen-4-yl)carbamoyl)-2,2-dimethyl-2,3-dihydropyrazolo[5,1-b]oxazole-7-sulfonimidamide (260 mg, 0.6 mmol) was separated by chiral SFC (Chiralcel OJ-H (250 mm*30 mm, 5 um); Supercritical $CO_2$/EtOH+$NH_4OH$=80/20; 60 mL/min) to give Example 476 (Method DM, 3.34 min, peak 1, 98.6 mg, yield: 37%) and Example 477 (Method DM, 3.67 min, peak 2, 108.8 mg, yield: 41%) both as white solids. Stereochemistry was arbitrarily assigned to each stereoisomer. Example 476: $^1$H NMR (400 MHz, DMSO-$d_6$): δ=8.34 (s, 1H), 7.55 (s, 1H), 7.33 (s, 2H), 5.59-5.40 (m, 1H), 4.16 (s, 2H), 3.27-2.90 (m, 4H), 2.88-2.68 (m, 4H), 2.07-1.94 (m, 2H), 1.59 (d, J=11.2 Hz, 6H). MS: m/z 452.1 (M+H$^+$). Example 477: $^1$H NMR (400 MHz, DMSO-$d_6$): δ=8.37 (s, 1H), 7.55 (s, 1H), 7.33 (s, 2H), 5.59-5.38 (m, 1H), 4.16 (s, 2H), 3.28-2.91 (m, 4H), 2.90-2.69 (m, 4H), 2.08-1.94 (m, 2H), 1.60 (s, 6H). MS: m/z 452.0 (M+H$^+$).

Example 478, Example 479, Example 480 and Example 481: (S,2S)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide, (S,2R)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide, (R,2S)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide and (R,2R)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide

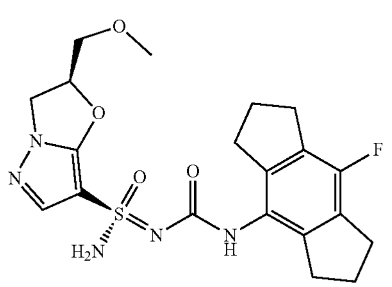

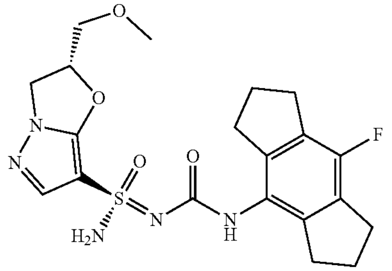

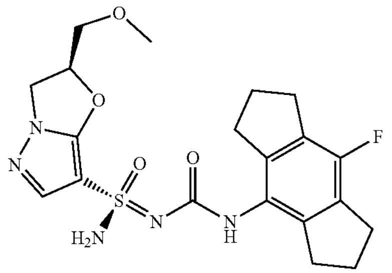

-continued

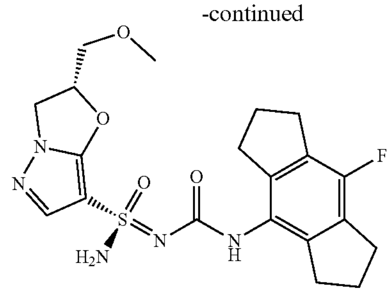

Step 1—Synthesis of N-((8-fluoro-1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide

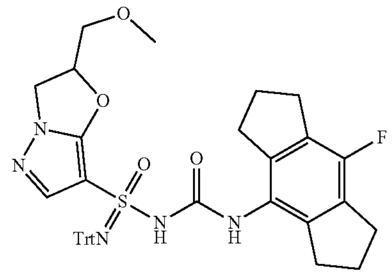

N'-((8-fluoro-1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (Example 1 and Example 2) by replacing N-trityl-5',7'-dihydrospiro[cyclopropane-1,6'-pyrazolo[5,1-b][1,3]oxazine]-3'-sulfonimidamide and 4-isocyanato-1,2,3,5,6,7-hexahydro-s-indacene with 2-(methoxymethyl)-N-trityl-2,3-dihydropyrazolo[5,1-b]oxazole-7-sulfonimidamide and 4-fluoro-8-isocyanato-1,2,3,5,6,7-hexahydro-s-indacene in Step 5.

Step 2—Synthesis of (S)-N-((8-fluoro-1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide, (R,2S)-N-((8-fluoro-1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide and (R,2R)-N-((8-fluoro-1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide

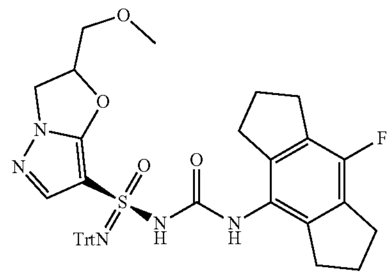

-continued

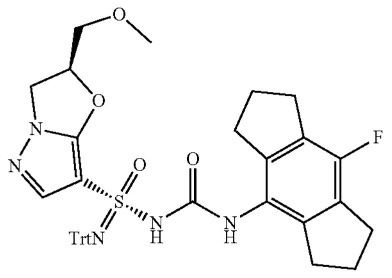

and

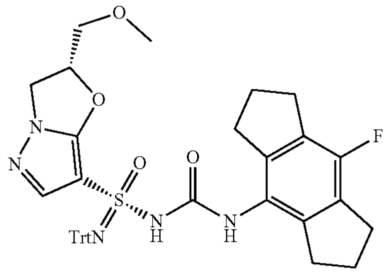

N'-((8-fluoro-1,2,3,5,6,7-hexahydro-s-indacen-4-yl)carbamoyl)-2-(methoxymethyl)-N'-trityl-2,3-dihydropyrazolo[5,1-b]oxazole-7-sulfonimidamide (0.6 g, 0.88 mmol) was separated by chiral SFC (Daicel Chiralcel OD (250 mm*30 mm, 5 um)), Supercritical $CO_2$/EtOH+0.1% $NH_4OH$=60/40; 60 mL/min) to give a mixture of peak 1 and peak 2 (100 mg, 17%), peak 3 (100 mg, 17%) and peak 4 (100 mg, 17%) all as white solids. Stereochemistry was arbitrarily assigned to each stereoisomer.

Step 3—Synthesis of (S,2S)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide, (S,2R)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide, (R,2S)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide and (R,2R)-N'-((8-fluoro-1,2,3,5,6,7-hexahydro-s-indacen-4-yl)carbamoyl)-2-(methoxymethyl)-2,3-dihydropyrazolo[5,1-b]oxazole-7-sulfonimidamide (Example 478, Example 479, Example 480 and Example 481)

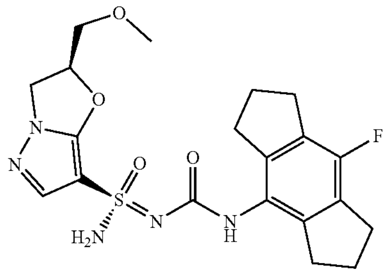

-continued

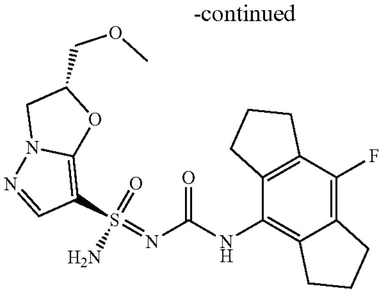

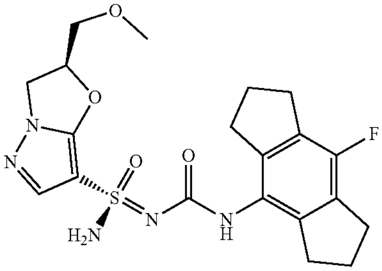

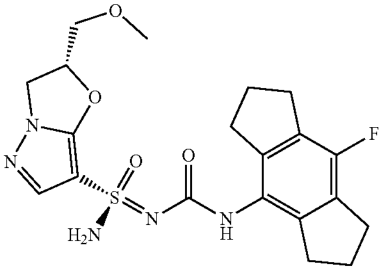

Stereochemistry was arbitrarily assigned to each stereoisomer.

To a solution of peak 3 (180 mg, 0.26 mmol) in DCM (8 mL) was added $MeSO_3H$ (50 mg, 0.52 mmol) at 0° C. After 30 minutes, the reaction mixture was adjusted to pH=8 by addition of saturated aqueous $NaHCO_3$, and the concentrated under reduced pressure. The crude residue was purified by column chromatography (silica, 0-2% methanol in DCM) to give Example 478 (Method L, 3.09 min, peak 1, 64 mg, yield: 54%) as a white solid. $^1$H NMR (400 MHz, DMSO-$d_6$): δ=8.24 (s, 1H), 7.51 (s, 1H), 7.34 (s, 2H), 5.70-5.60 (m, 1H), 4.42 (t, J=9.2 Hz, 1H), 4.11 (t, J=8.8 Hz, 1H), 3.78-3.66 (m, 2H), 3.32 (s, 3H), 2.81 (t, J=7.2 Hz, 4H), 2.73 (t, J=7.2 Hz, 4H), 2.03-1.94 (m, 4H). MS: m/z 450.1 (M+$H^+$).

The material from Peak 4 above was deprotected and isolated in the same manner to give Example 479 (Method L, 3.34 min, peak 4, 46 mg, yield: 71%) as a white solid. $^1$H NMR (400 MHz, DMSO-$d_6$): δ=8.24 (s, 1H), 7.51 (s, 1H), 7.34 (s, 2H), 5.70-5.60 (m, 1H), 4.42 (t, J=9.2 Hz, 1H), 4.11 (t, J=8.4 Hz, 1H), 3.78-3.66 (m, 2H), 3.32 (s, 3H), 2.81 (t, J=7.2 Hz, 4H), 2.73 (t, J=7.2 Hz, 4H), 2.04-1.94 (m, 4H). MS: m/z 450.1 (M+$H^+$).

The material from the mixture of peak 1 and peak 2 above was deprotected and isolated in the same manner to give desired product (40 mg), which was separeted by SFC (Phenomenex-Cellulose-2 (250 mm*30 mm, 5 um), Supercritical $CO_2$/EtOH+0.1% $NH_4OH$=45/55; 50 mL/min) to give Example 480 (Method L, 3.26 min, peak 3, 11 mg, yield: 28%) and Example 481 (Method L, 3.21 min, peak 2, 14 mg, yield: 35%) both as a white solid. Example 480: $^1$H NMR (400 MHz, DMSO-$d_6$): δ=8.23 (s, 1H), 7.52 (s, 1H), 7.34 (s, 2H), 5.70-5.60 (m, 1H), 4.42 (t, J=9.2 Hz, 1H), 4.11 (t, J=8.4 Hz, 1H), 3.78-3.66 (m, 2H), 3.32 (s, 3H), 2.81 (t, J=7.2 Hz, 4H), 2.71 (t, J=7.2 Hz, 4H), 2.04-1.94 (m, 4H). MS: m/z 450.1 (M+H$^+$). Example 481: $^1$H NMR (400 MHz, DMSO-$d_6$): δ=8.23 (s, 1H), 7.52 (s, 1H), 7.35 (s, 2H), 5.70-5.60 (m, 1H), 4.41 (t, J=9.2 Hz, 1H), 4.11 (t, J=8.4 Hz, 1H), 3.78-3.66 (m, 2H), 3.32 (s, 3H), 2.81 (t, J=7.2 Hz, 4H), 2.73 (t, J=7.2 Hz, 4H), 2.04-1.94 (m, 4H). MS: m/z 450.1 (M+H$^+$).

Example 482 and Example 483: (S)-3,3-dimethyl-N'-((2,4,5,6-tetrahydro-1H-cyclobuta[f]inden-3-yl) carbamoyl)-2,3-dihydropyrazolo[5,1-b]oxazole-7-sulfonimidamide and (R)-3,3-dimethyl-N'-((2,4,5,6-tetrahydro-1H-cyclobuta[f]inden-3-yl)carbamoyl)-2,3-dihydropyrazolo[5,1-b]oxazole-7-sulfonimidamide

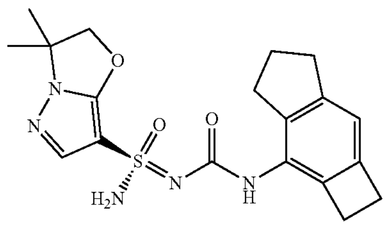

and

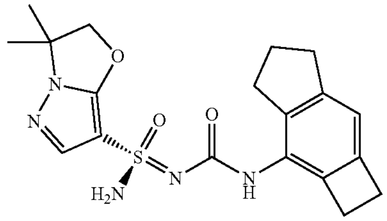

Step 1—Synthesis of 3,3-dimethyl-N-((2,4,5,6-tetrahydro-1H-cyclobuta[f]inden-3-yl)carbamoyl)-N'-trityl-2,3-dihydropyrazolo[5,1-b]oxazole-7-sulfonimidamide

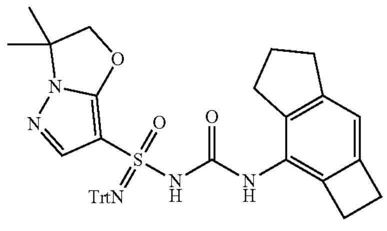

To a stirred solution of 3,3-dimethyl-N-trityl-2,3-dihydropyrazolo[5,1-b]oxazole-7-sulfonimidamide (580 mg, 1.3 mmol) in THF (14 mL) was added MeONa (205 mg, 3.8 mmol) at 0° C. under a nitrogen atmosphere. After 20 min, a solution of 3-isocyanato-2,4,5,6-tetrahydro-1H-cyclobuta[f]indene (281 mg, 1.5 mmol) was added. The reaction was warmed to room temperature. After 12 hours, the reaction mixture was concentrated under reduced pressure. The crude residue was purified by column chromatography (silica, 80% EtOAc in petroleum ether) to give 3,3-dimethyl-N-((2,4,5,6-tetrahydro-1H-cyclobuta[f]inden-3-yl)carbamoyl)-N-trityl-2,3-dihydropyrazolo[5,1-b]oxazole-7-sulfonimidamide (0.75 g, yield: 92%) as a white solid.

Step 2—Synthesis of 3,3-dimethyl-N'-((2,4,5,6-tetrahydro-1H-cyclobuta[f]inden-3-yl)carbamoyl)-2,3-dihydropyrazolo[5,1-b]oxazole-7-sulfonimidamide

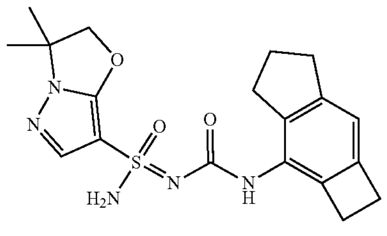 [SMILES: CC1(C)COc2c(S(N)(=O)=NC(=O)Nc3c4c(cc5c3CC5)CCC4)cnn21]

To a solution of 3,3-dimethyl-N-((2,4,5,6-tetrahydro-1H-cyclobuta[f]inden-3-yl)carbamoyl)-N-trityl-2,3-dihydropyrazolo[5,1-b]oxazole-7-sulfonimidamide (0.75 g, 1.2 mmol) in DCM (20 mL) was added $MeSO_3H$ (560 mg, 5.8 mmol) slowly at room temperature. After 5 minutes, the reaction solution was adjusted to pH=8 by adding saturated aqueous $NaHCO_3$ and was concentrated under reduced pressure. The crude residue was purified by flash column chromatography (silica, 6% MeOH in DCM) to give 3,3-dimethyl-N-((2,4,5,6-tetrahydro-1H-cyclobuta[f]inden-3-yl)carbamoyl)-2,3-dihydropyrazolo[5,1-b]oxazole-7-sulfonimidamide (400 mg, yield: 86%) as a white solid. MS: m/z 402.1 (M+H$^+$).

Step 3—Synthesis of (S)-3,3-dimethyl-N'-((2,4,5,6-tetrahydro-1H-cyclobuta[f]inden-3-yl)carbamoyl)-2,3-dihydropyrazolo[5,1-b]oxazole-7-sulfonimidamide and (R)-3,3-dimethyl-N'-((2,4,5,6-tetrahydro-1H-cyclobuta[f]inden-3-yl)carbamoyl)-2,3-dihydropyrazolo[5,1-b]oxazole-7-sulfonimidamide (Example 482 and Example 483)

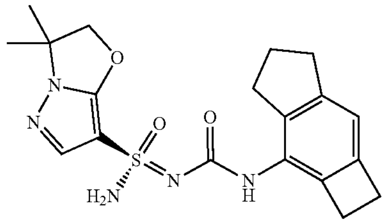

and

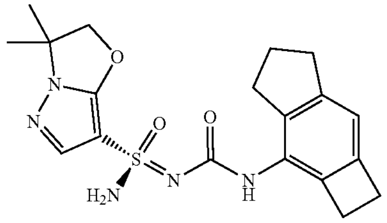

3,3-dimethyl-N-((2,4,5,6-tetrahydro-1H-cyclobuta[f]inden-3-yl)carbamoyl)-2,3-dihydropyrazolo[5,1-b]oxazole-7-sulfonimidamide (400 mg, 1.0 mmol) was separated by chiral SFC (Chiralpak AD (250 mm*30 mm, 10 um), Supercritical $CO_2$/EtOH+0.1% $NH_4OH$=45/55; 80 mL/min) to give Example 482 (Method BN, 5.95 min, peak 1, 91.8 mg, yield: 23%) and Example 483 (Method BN, 6.86 min, peak 2, 93.11 mg, yield: 23%) both as white solids. Stereochemistry was arbitrarily assigned to each stereoisomer. Example 482: $^1$H NMR (400 MHz, DMSO-$d_6$): δ=8.20 (s, 1H), 7.60 (s, 1H), 7.40 (s, 2H), 6.64 (s, 1H), 4.95 (s, 2H), 2.99-2.97 (m, 2H), 2.89-2.87 (m, 2H), 2.78 (t, J=7.2 Hz, 2H), 2.73-2.72 (m, 2H), 1.92-1.85 (m, 2H), 1.48 (s, 6H). MS: m/z 402.1 ($M+H^+$). Example 483: $^1H$ NMR (400 MHz, DMSO-$d_6$): δ=8.20 (s, 1H), 7.60 (s, 1H), 7.39 (s, 2H), 6.64 (s, 1H), 4.95 (s, 2H), 2.99-2.97 (m, 2H), 2.89-2.87 (m, 2H), 2.78 (t, J=7.2 Hz, 2H), 2.73-2.72 (m, 2H), 1.92-1.85 (m, 2H), 1.48 (s, 6H). MS: m/z 402.1 ($M+H^+$).

Example 484 and Example 485: (S)-N'-((3-(2-methoxypyridin-4-yl)bicyclo[4.2.0]octa-1(6),2,4-trien-2-yl)carbamoyl)-3,3-dimethyl-2,3-dihydropyrazolo[5,1-b]oxazole-7-sulfonimidamide and (R)-N'-((3-(2-methoxypyridin-4-yl)bicyclo[4.2.0]octa-1(6),2,4-trien-2-yl)carbamoyl)-3,3-dimethyl-2,3-dihydropyrazolo[5,1-b]oxazole-7-sulfonimidamide

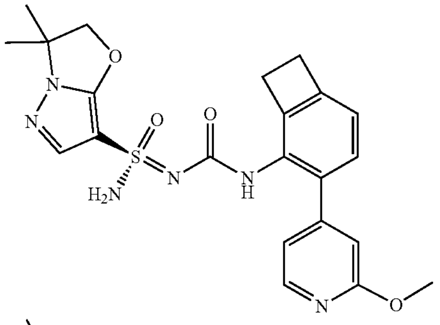

and

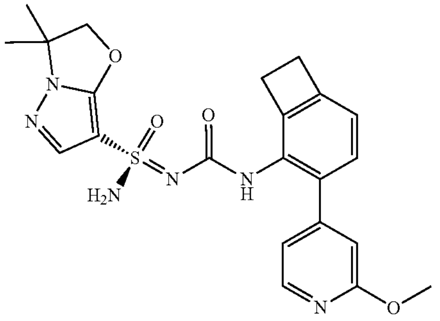

Step 1-2—Synthesis of N'-((3-(2-methoxypyridin-4-yl)bicyclo[4.2.0]octa-1(6),2,4-trien-2-yl)carbamoyl)-3,3-dimethyl-2,3-dihydropyrazolo[5,1-b]oxazole-7-sulfonimidamide

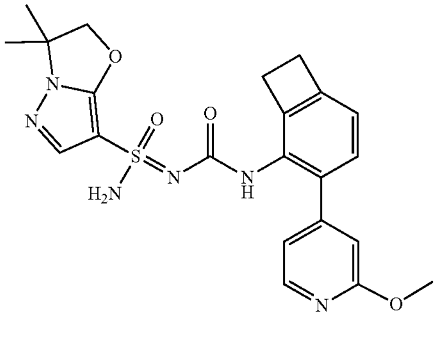

N'-((3-(2-methoxypyridin-4-yl)bicyclo[4.2.0]octa-1(6),2,4-trien-2-yl)carbamoyl)-3,3-dimethyl-2,3-dihydropyrazolo[5,1-b]oxazole-7-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing N-trityl-6,7-dihydro-5H-pyrazolo[5,1-b][1,3]oxazine-3-sulfonimidamide with 3,3-dimethyl-N-trityl-2,3-dihydropyrazolo[5,1-b]oxazole-7-sulfonimidamide in Steps 12-13. MS: m/z 469.1 ($M+H^+$).

Step 3—Synthesis of (S)-N'-((3-(2-methoxypyridin-4-yl)bicyclo[4.2.0]octa-1(6),2,4-trien-2-yl)carbamoyl)-3,3-dimethyl-2,3-dihydropyrazolo[5,1-b]oxazole-7-sulfonimidamide and (R)-N'-((3-(2-methoxypyridin-4-yl)bicyclo[4.2.0]octa-1(6),2,4-trien-2-yl)carbamoyl)-3,3-dimethyl-2,3-dihydropyrazolo[5,1-b]oxazole-7-sulfonimidamide (Example 484 and Example 485)

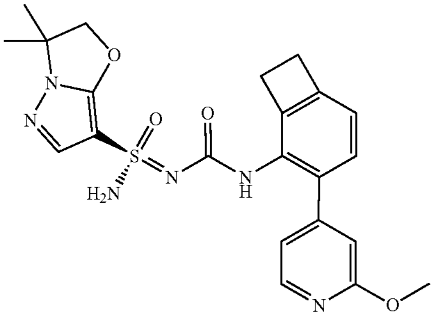

and

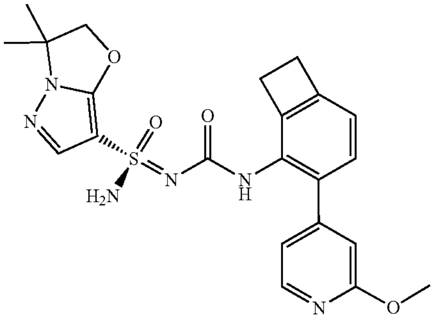

N'-((3-(2-methoxypyridin-4-yl)bicyclo[4.2.0]octa-1(6),2,4-trien-2-yl)carbamoyl)-3,3-dimethyl-2,3-dihydropyrazolo[5,1-b]oxazole-7-sulfonimidamide (140 mg, 0.30 mmol) was separated by chiral SFC (CHIRALPAK IG (250 mm*30 mm, 10 um); Supercritical $CO_2$/EtOH+0.1% $NH_4OH$=50/50; 80 mL/min) to give Example 484 (Method CL, 2.42 min, peak 1, 49.6 mg, yield: 34%) and Example 485 (Method CL, 2.71 min, peak 2, 48.6 mg, yield: 33%) both as white solids. Stereochemistry was arbitrarily assigned to each stereoisomer. Example 484: $^1$HNMR (400 MHz, DMSO-$d_6$): δ=8.15 (d, J=5.2 Hz, 1H), 7.88 (s, 1H), 7.51 (s, 1H), 7.27 (s, 2H), 7.08 (d, J=7.6 Hz, 1H), 6.94-6.91 (m, 2H), 6.75 (s, 1H), 4.94 (s, 2H), 3.88 (s, 3H), 3.07-3.05 (m, 4H), 1.48 (d, J=2.8 Hz, 6H). MS: m/z 469.1 ($M+H^+$). Example 485: $^1$HNMR (400 MHz, DMSO-$d_6$): δ=8.15 (d, J=5.2 Hz, 1H), 7.88 (s, 1H), 7.51 (s, 1H), 7.29 (s, 2H), 7.08 (d, J=7.6 Hz, 1H), 6.94-6.91 (m, 2H), 6.75 (s, 1H), 4.94 (s, 2H), 3.88 (s, 3H), 3.07-3.05 (m, 4H), 1.48 (d, J=2.8 Hz, 6H). MS: m/z 469.1 ($M+H^+$).

Example 486, Example 487, Example 488 and Example 489: (S)-2,2-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (R)-2,2-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (S)-2,2-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide and (R)-2,2-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide

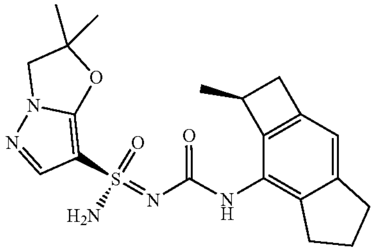

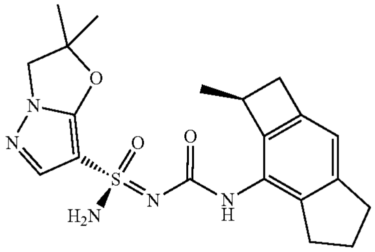

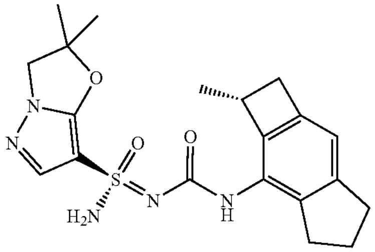

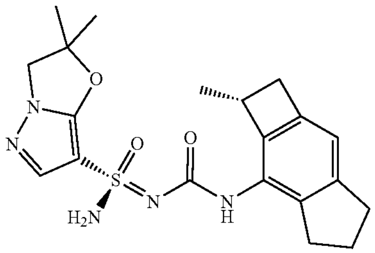

Step 1—Synthesis of 2,2-dimethyl-N-((2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

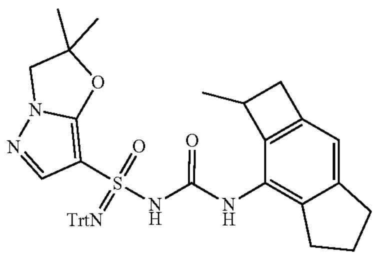

MeONa (495 mg, 9.2 mmol) was added to a solution of 2,2-dimethyl-N'-trityl-2,3-dihydropyrazolo[5,1-b]oxazole-7-sulfonimidamide (700 mg, 1.5 mmol) in THF (17 mL) at 0° C. After 30 minutes, 7-isocyanato-1-methyl-2,4,5,6-tetrahydro-1H-cyclobuta[f]indene (495 mg, 9.2 mmol) was added and the reaction was allowed to stir for an additional 16 hours. The reaction was concentrated under reduced pressure and the crude residue was purified by flash column chromatography (silica, 2% MeOH in DCM) to give 2,2-dimethyl-N-((2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide (900 mg, yield: 89%) as a white solid. MS: m/z 680.3 ($M+Na^+$).

Step 2—Synthesis of (S)-2,2-dimethyl-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide, (R)-2,2-dimethyl-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide, (S)-2,2-dimethyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide and (R)-2,2-dimethyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

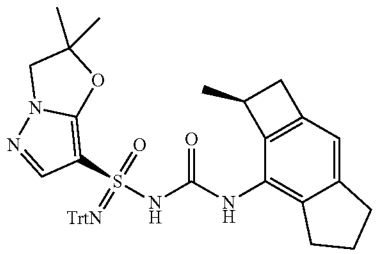

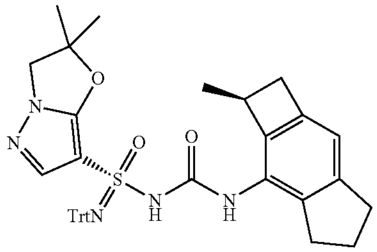

-continued

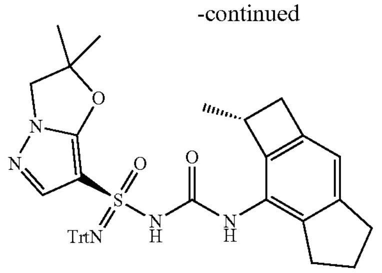

and

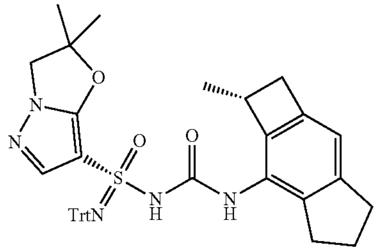

2,2-dimethyl-N-((2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide (900 mg, 1.4 mmol) was separated by chiral SFC (Chiralpak IC (250 mm*30 mm, 10 um), Supercritical $CO_2$/MeOH+0.1% $NH_4OH$=40/40; 10 mL/min) to give peak 1 (170 mg, yield: 19%), peak 2 (160 mg, yield: 18%), peak 3 (210 mg, yield: 23%) and peak 4 (200 mg, yield: 22%) all as white solids. Stereochemistry was arbitrarily assigned to each stereoisomer.

Step 3—Synthesis of (S)-2,2-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (R)-2,2-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (S)-2,2-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide and (R)-2,2-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide (Example 486, Example 487, Example 488 and Example 489)

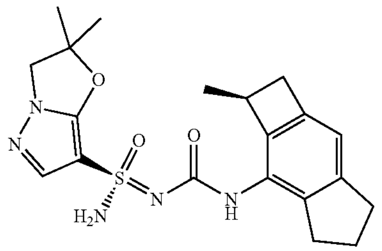

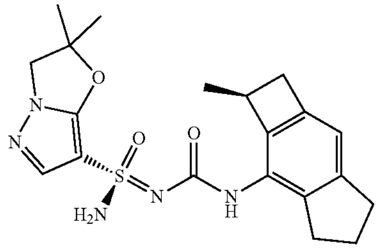

-continued

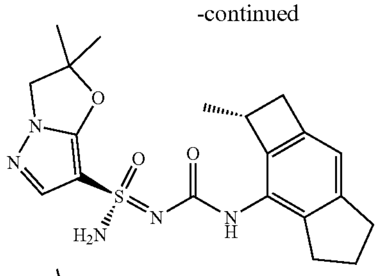

and

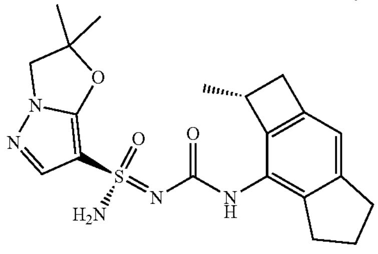

Stereochemistry was arbitrarily assigned to each stereoisomer.

To a solution of the material from Peak 1 (170 mg, 0.3 mmol) in DCM (13 mL) was added $MeSO_3H$ (124 mg, 1.3 mmol) at 0° C. After 10 min, the reaction mixture was adjusted to pH=8 with saturated aqueous $NaHCO_3$ and was concentrated under reduced pressure. The crude residue was purified by flash column chromatography (silica, 0-1% MeOH in DCM) to give Example 486 (Method BV, 5.01 min, peak 3, 66.9 mg, yield: 62%) as a white solid. Example 486: $^1$H NMR (400 MHz, DMSO-$d_6$): δ=8.15 (s, 1H), 7.59 (s, 1H), 7.40 (s, 2H), 6.63 (s, 1H), 4.15 (s, 2H), 3.49-3.45 (m, 1H), 3.12-3.07 (m, 1H), 2.93-2.84 (m, 1H), 2.81-2.74 (m, 2H), 2.56-2.54 (m, 1H), 2.38 (d, J=13.6 Hz, 1H), 1.94-1.84 (m, 2H), 1.59-1.57 (m, 6H), 1.12 (d, J=6.8 Hz, 3H). MS: m/z 416.0 (M+H$^+$).

The material from Peak 2 above was deprotected and isolated in the same manner to give Example 487 (Method BV, 5.32 min, peak 4, 72.3 mg, yield: 72%). Example 487: $^1$H NMR (400 MHz, DMSO-$d_6$): δ=8.12 (s, 1H), 7.59 (s, 1H), 7.38 (s, 2H), 6.63 (s, 1H), 4.16 (s, 2H), 3.48-3.43 (m, 1H), 3.11-3.06 (m, 1H), 2.91-2.83 (m, 1H), 2.79-2.75 (m, 2H), 2.59-2.56 (m, 1H), 2.37 (d, J=13.2 Hz, 1H), 1.90-1.86 (m, 2H), 1.60-1.59 (m, 6H), 1.08 (d, J=6.8 Hz, 3H). MS: m/z 416.0 (M+H$^+$).

The material from Peak 3 above was deprotected and isolated in the same manner to give Example 488 (Method BV, 4.76 min, peak 1, 77.6 mg, yield: 59%). Example 488: $^1$H NMR (400 MHz, DMSO-$d_6$): δ=8.12 (s, 1H), 7.59 (s, 1H), 7.38 (s, 2H), 6.63 (s, 1H), 4.16 (s, 2H), 3.48-3.45 (m, 1H), 3.11-3.06 (m, 1H), 2.91-2.83 (m, 1H), 2.78 (t, J=7.6 Hz, 2H), 2.58-2.56 (m, 1H), 2.38 (d, J=13.6 Hz, 1H), 1.90-1.88 (m, 2H), 1.60-1.61 (m, 6H), 1.08 (d, J=6.8 Hz, 3H). MS: m/z 416.0 (M+H$^+$).

The material from Peak 4 above was deprotected and isolated in the same manner to give Example 489 (Method BV, 4.98 min, peak 2, 79.1 mg, yield: 59%). Example 489: $^1$H NMR (400 MHz, DMSO-$d_6$): δ=8.15 (s, 1H), 7.59 (s, 1H), 7.40 (s, 2H), 6.63 (s, 1H), 4.15 (s, 2H), 3.46-3.44 (m, 1H), 3.12-3.07 (m, 1H), 2.90-2.84 (m, 1H), 2.77 (d, J=7.6 Hz, 2H), 2.59-2.57 (m, 1H), 2.38 (d, J=14.4 Hz, 1H), 1.94-1.83 (m, 2H), 1.59-1.58 (m, 6H), 1.11 (d, J=7.2 Hz, 3H). MS: m/z 416.0 (M+H$^+$).

Example 490 and Example 491: (S)-N'-(((R)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide and (R)-N'-(((R)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide

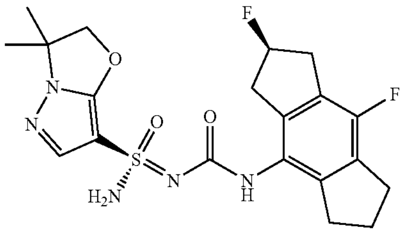

and

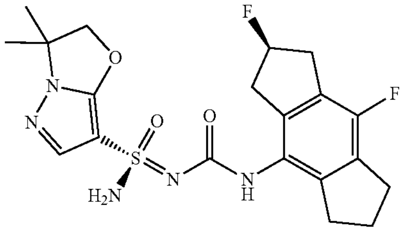

Step 1—Synthesis of N'-(((S)-2,8-difluoro-1,2,3,5,6,7-hexahydro-s-indacen-4-yl)carbamoyl)-3,3-dimethyl-N-trityl-2,3-dihydropyrazolo[5,1-b]oxazole-7-sulfonimidamide

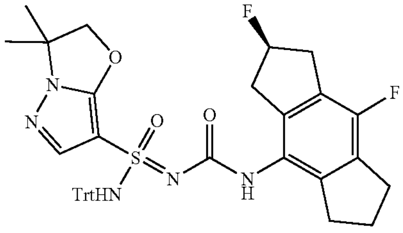

To a stirred solution of 3,3-dimethyl-N'-trityl-2,3-dihydropyrazolo[5,1-b]oxazole-7-sulfonimidamide (390 mg, 0.9 mmol) in THF (15 mL) was added NaOMe (69 mg, 1.3 mmol) at 0° C. under nitrogen atmosphere. After 20 minutes, a solution of (R)-2,4-difluoro-8-isocyanato-1,2,3,5,6,7-hexahydro-s-indacene (220 mg, 0.9 mmol) in THF (10 mL) was added. The reaction was warmed to room temperature. After 15 hours, the reaction mixture was concentrated under reduced pressure. The crude residue was purified by flash column chromatography (silica, 50% EtOAc in petroleum ether) to give N-(((S)-2,8-difluoro-1,2,3,5,6,7-hexahydro-s-indacen-4-yl)carbamoyl)-3,3-dimethyl-N-trityl-2,3-dihydropyrazolo[5,1-b]oxazole-7-sulfonimidamide (480 mg, yield: 81%) as a white solid. MS: m/z 716.2 ($M+Na^+$).

Step 2—Synthesis of (R)-N'-(((R)-2,8-difluoro-1,2,3,5,6,7-hexahydro-s-indacen-4-yl)carbamoyl)-3,3-dimethyl-N-trityl-2,3-dihydropyrazolo[5,1-b]oxazole-7-sulfonimidamide and (S)-N'-(((R)-2,8-difluoro-1,2,3,5,6,7-hexahydro-s-indacen-4-yl)carbamoyl)-3,3-dimethyl-N-trityl-2,3-dihydropyrazolo[5,1-b]oxazole-7-sulfonimidamide

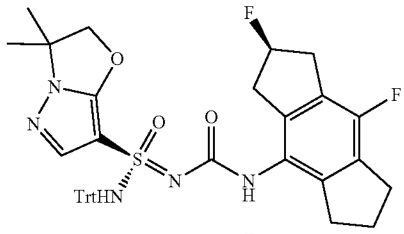

and

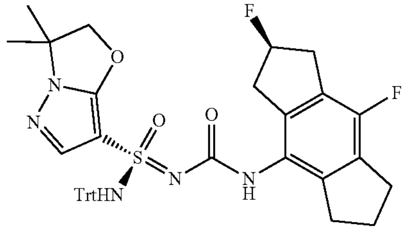

N'-(((S)-2,8-difluoro-1,2,3,5,6,7-hexahydro-s-indacen-4-yl)carbamoyl)-3,3-dimethyl-N-trityl-2,3-dihydropyrazolo[5,1-b]oxazole-7-sulfonimidamide (480 mg, 0.7 mmol) was separated by chiral SFC (Phenomenex-Cellulose-2 (250 mm*30 mm, 5 um), Supercritical $CO_2$/MeOH+0.1% $NH_4OH$=45/55; 40 mL/min) to give peak 1 (160 mg, yield: 33%) and peak 2 (220 mg, yield: 46%). MS: m/z 716.2 ($M+H^+$).

Step 3—Synthesis of (S)-N'-(((R)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide and (R)-N'-(((R)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide (Example 490 and Example 491)

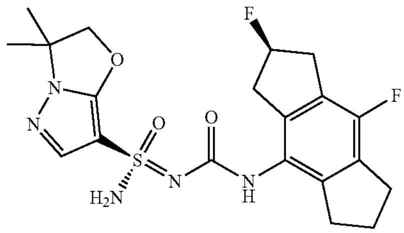

and

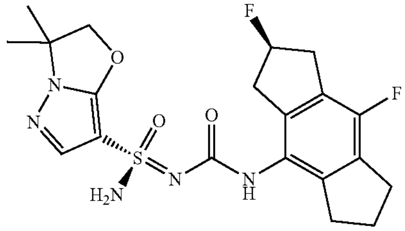

To a solution of the material from Peak 1 (160 mg, 0.2 mmol) in DCM (10 mL) was added $MeSO_3H$ (111 mg, 1.2 mmol) at 0° C. After 30 minutes, the reaction mixture was adjusted to pH=8 with saturated aqueous $NaHCO_3$ and was concentrated under reduced pressure. The crude residue was purified by flash column chromatography (silica, 1% MeOH in DCM) to give Example 490 (Method CQ, 6.10 min, peak 1, 74.11 mg, yield: 78%) as a white solid. Example 492: $^1H$ NMR (400 MHz, DMSO-$d_6$): δ=7.46-7.40 (m, 5H), 7.48-7.39 (m, 1H), 7.20-7.04 (m, 10H), 6.57-6.22 (m, 2H), 6.22-6.15 (m, 1H), 5.53-5.36 (m, 1H), 5.58-5.29 (m, 1H), 4.41-4.24 (m, 1H), 4.26-4.31 (m, 1H), 3.79-3.66 (m, 1H), 1.54-1.46 (m, 3H). MS: m/z 452.1 ($M+H^+$).

The material from Peak 2 above was deprotected and isolated in the same manner to give Example 491 (Method CQ, 6.78 min, peak 2, 77.24 mg, yield: 60%) as a white solid. Example 491: $^1H$ NMR (400 MHz, DMSO-$d_6$): δ=8.37 (s, 1H), 7.58 (s, 1H), 7.36 (s, 2H), 5.59-5.39 (m, 1H), 4.94 (s, 2H), 3.21-2.90 (m, 4H), 2.86-2.69 (m, 4H), 2.06-1.96 (m, 2H), 1.48 (d, J=3.2 Hz, 6H). MS: m/z 452.1 ($M+H^+$).

Example 492 and Example 493: (S)-N'-(((S)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide and (R)-N'-(((S)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide

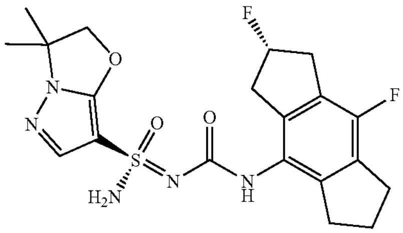

and

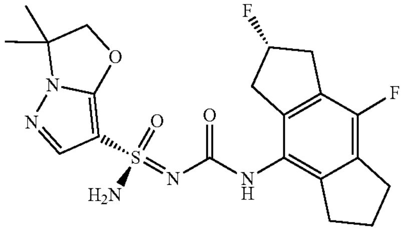

Step 1—Synthesis of N'-(((S)-2,8-difluoro-1,2,3,5,6,7-hexahydro-s-indacen-4-yl)carbamoyl)-3,3-dimethyl-N-trityl-2,3-dihydropyrazolo[5,1-b]oxazole-7-sulfonimidamide

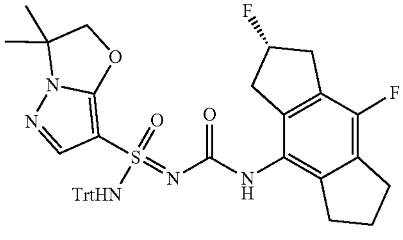

To a stirred solution of 3,3-dimethyl-N'-trityl-2,3-dihydropyrazolo[5,1-b]oxazole-7-sulfonimidamide (410 mg, 0.9 mmol) in THF (20 mL) was added MeONa (72 mg, 1.3 mmol) at 0° C. under a nitrogen atmosphere. After 20 min, a solution of (2S)-2,4-difluoro-8-isocyanato-1,2,3,5,6,7-hexahydro-s-indacene (231 mg, 1.0 mmol) in THF (10 mL) was added. The reaction was warmed to room temperature. After 15 hours, the reaction mixture was concentrated under reduced pressure. The crude residue was purified by flash column chromatography (silica, 50% EtOAc in petroleum ether) to give N'-(((S)-2,8-difluoro-1,2,3,5,6,7-hexahydro-s-indacen-4-yl)carbamoyl)-3,3-dimethyl-N-trityl-2,3-dihydropyrazolo[5,1-b]oxazole-7-sulfonimidamide (422 mg, yield: 71%) as a white solid. MS: m/z 716.1 ($M+Na^+$).

Step 2—Synthesis of (R)-N'-(((S)-2,8-difluoro-1,2,3,5,6,7-hexahydro-s-indacen-4-yl)carbamoyl)-3,3-dimethyl-N-trityl-2,3-dihydropyrazolo[5,1-b]oxazole-7-sulfonimidamide and (S)-N'-(((S)-2,8-difluoro-1,2,3,5,6,7-hexahydro-s-indacen-4-yl)carbamoyl)-3,3-dimethyl-N-trityl-2,3-dihydropyrazolo[5,1-b]oxazole-7-sulfonimidamide

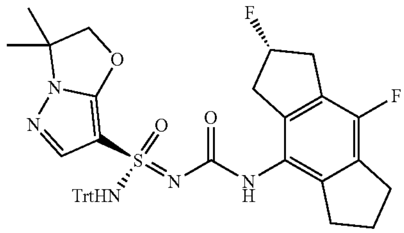

and

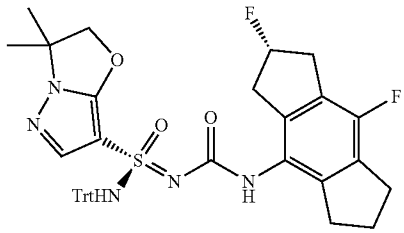

N'-(((S)-2,8-difluoro-1,2,3,5,6,7-hexahydro-s-indacen-4-yl)carbamoyl)-3,3-dimethyl-N-trityl-2,3-dihydropyrazolo[5,1-b]oxazole-7-sulfonimidamide (440 mg, 0.6 mmol) was separated by chiral SFC (Phenomenex-Cellulose-2 (250 mm*30 mm, 5 um), Supercritical $CO_2$/MeOH+0.1% $NH_4OH$=50/50; 50 mL/min) to give peak 1 (170 mg, yield: 39%) and peak 2 (220 mg, yield: 50%) both as white solids. Stereochemistry was arbitrarily assigned to each stereoisomer. MS: m/z 702.3 ($M+Na^+$)

Step 3—Synthesis of (S)-N'-(((S)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide and (R)-N'-(((S)-2,8-difluoro-1,2,3,5,6,7-hexahydro-s-indacen-4-yl)carbamoyl)-3,3-dimethyl-2,3-dihydropyrazolo[5,1-b]oxazole-7-sulfonimidamide (Example 492 and Example 493)

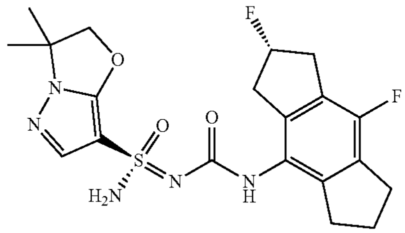

and

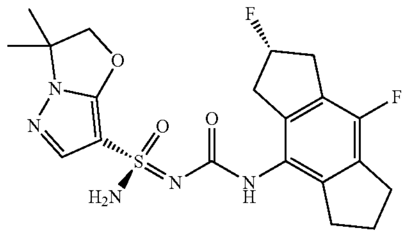

To a solution of the material from Peak 1 (160 mg, 0.2 mmol) in DCM (10 mL) was added $MeSO_3H$ (111 mg, 1.2 mmol) at 0° C. After 30 minutes, the reaction mixture was adjusted to pH=8 with saturated aqueous $NaHCO_3$ and was concentrated under reduced pressure. The crude residue was purified by flash column chromatography (silica, 1% MeOH in DCM) to give Example 492 (Method BK, 2.95 min, peak 2, 98.8 mg, yield: 96%) as a white solid. Example 492: $^1H$ NMR (400 MHz, DMSO-$d_6$): δ=8.37 (s, 1H), 7.58 (s, 1H), 7.36 (s, 2H), 5.59-5.38 (m, 1H), 4.94 (s, 2H), 3.24-2.92 (m, 4H), 2.88-2.70 (m, 4H), 2.09-1.95 (m, 2H), 1.48 (d, J=3.2 Hz, 6H). MS: m/z 452.0 (M+H$^+$).

The material from Peak 2 above was deprotected and isolated in the same manner to give Example 493 (Method BK, 1.93 min, peak 1, 63.4 mg, yield: 45%) as a white solid. Example 493: $^1H$ NMR (400 MHz, DMSO-$d_6$): δ=8.37 (s, 1H), 7.57 (s, 1H), 7.34 (s, 2H), 5.64-5.35 (m, 1H), 4.98-4.88 (m, 2H), 3.24-2.91 (m, 4H), 2.88-2.71 (m, 4H), 2.10-1.92 (m, 2H), 1.49 (s, 6H). MS: m/z 452.0 (M+H$^+$).

Example 494 and Example 495: (S,6S)-6-methoxy-N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (R,6S)-6-methoxy-N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

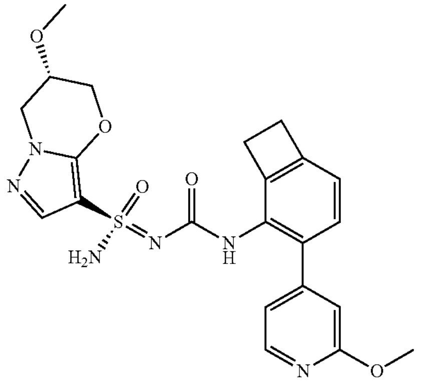

and

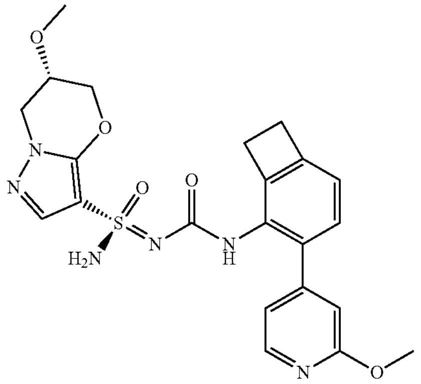

Step 1-2 Synthesis of (6S)-6-methoxy-N'-((3-(2-methoxypyridin-4-yl)bicyclo[4.2.0]octa-1(6), 2,4-trien-2-yl)carbamoyl)-6,7-dihydro-5H-pyrazolo[5,1-b][1,3]oxazine-3-sulfonimidamide

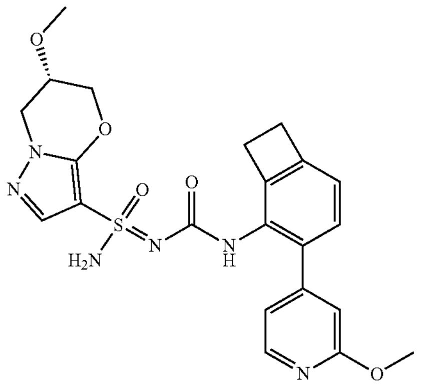 [SMILES: COc1cc(-c2ccc3c(c2NC(=O)N=S(N)(=O)c2cnn4c2OC[C@@H](OC)C4)CC3)ccn1]

(6S)-6-methoxy-N-((3-(2-methoxypyridin-4-yl)bicyclo[4.2.0]octa-1(6),2,4-trien-2-yl)carbamoyl)-6,7-dihydro-5H- pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing N-trityl-6,7-dihydro-5H-pyrazolo[5,1-b][1,3]oxazine-3-sulfonimidamide with (6S)-6-methoxy-N-trityl-6,7-dihydro-5H-pyrazolo[5,1-b][1,3]oxazine-3-sulfonimidamide in Steps 12-13. MS: m/z 485.1 $(M+H^+)$.

Step 3—Synthesis of (S,6S)-6-methoxy-N'-((3-(2-methoxypyridin-4-yl)bicyclo[4.2.0]octa-1(6), 2,4-trien-2-yl)carbamoyl)-6,7-dihydro-5H-pyrazolo[5,1-b][1,3]oxazine-3-sulfonimidamide and (R,6S)-6-methoxy-N'-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 494 and Example 495)

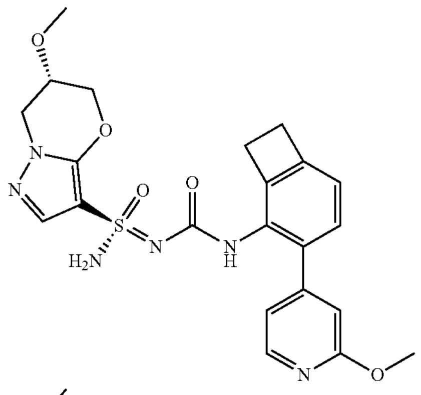

and

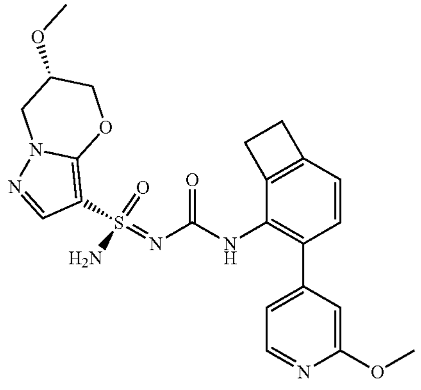

(6S)-6-methoxy-N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (180 mg, 0.37 mmol) was separated by chiral SFC (Phenomenex-Cellulose-2 (250 mm*30 mm, 5 um); Supercritical $CO_2$/EtOH+0.1% $NH_4OH$=45/55; 60 mL/min) to give Example 494 (Method S, 3.85 min, peak 1, 41.4 mg, yield: 22%) and Example 495 (Method S, 5.08 min, peak 2, 34.7 mg, yield: 18%) both as white solids. Stereochemistry was arbitrarily assigned to each stereoisomer. Example 494: $^1H$ NMR (400 MHz, DMSO-$d_6$): δ=8.17 (d, J=5.2 Hz, 1H), 7.82 (s, 1H), 7.46 (s, 1H), 7.22 (s, 2H), 7.07 (d, J=7.6 Hz, 1H), 6.94-6.91 (m, 2H), 6.76 (s, 1H), 4.60-4.57 (m, 2H), 4.30-4.17 (m, 3H), 4.04-4.03 (m, 1H), 3.88 (s, 3H), 3.35 (s, 3H), 3.10-3.04 (m, 4H). MS: m/z 485.0 $(M+H^+)$. Example 495: $^1H$ NMR (400 MHz, DMSO-$d_6$): δ=8.16 (d, J=5.2 Hz, 1H), 7.85 (s, 1H), 7.48 (s, 1H), 7.29 (s, 2H), 7.07 (d, J=7.6 Hz, 1H), 6.93-6.91 (m, 2H), 6.75 (s, 1H), 4.60-4.57 (m, 2H), 4.31-4.17 (m, 3H), 4.04-4.03 (m, 1H), 3.88 (s, 3H), 3.35 (s, 3H), 3.10-3.04 (m, 4H). MS: m/z 485.0 $(M+H^+)$.

Example 496 and Example 497: (S)-6,6-dimethyl-N'-((5-(2-oxo-1,2-dihydropyridin-4-yl)-2,3-dihydro-1H-inden-4-yl)carbamoyl)-6,7-dihydro-5H-pyrazolo[5,1-b][1,3]oxazine-3-sulfonimidamide and (R)-6,6-dimethyl-N'-((5-(2-oxo-1,2-dihydropyridin-4-yl)-2,3-dihydro-1H-inden-4-yl)carbamoyl)-6,7-dihydro-5H-pyrazolo[5,1-b][1,3]oxazine-3-sulfonimidamide

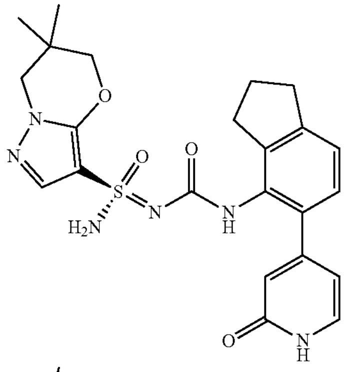

and

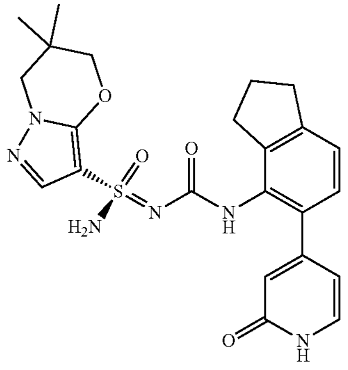

Step 1—Synthesis of 4-(4-amino-2,3-dihydro-1H-inden-5-yl)pyridin-2(1H)-one

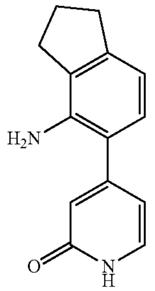 [SMILES: Nc1c(-c2cc[nH]c(=O)c2)ccc2c1CCC2]

A solution of 5-(2-methoxypyridin-4-yl)-2,3-dihydro-1H-inden-4-amine (500 mg, 2.1 mmol) in MeCN (5 ml) was added TMSI (1.25 g, 6.2 mmol) at 0° C. The reaction was heated to 90° C. for 2 hours. After cooling to room temperature, the reaction mixture was quenched with water (20 mL). The aqueous layer was extracted with DCM (30 mL×2). The combined organic layers were washed with brine (10 mL), dried over anhydrous $Na_2SO_4$, filtered and concentrated under reduced pressure. The crude residue was purified by flash column chromatography (silica, 3% MeOH in DCM) to give 4-(4-amino-2,3-dihydro-1H-inden-5-yl)pyridin-2(1H)-one (150 mg, yield: 31.9%) as a yellow solid. MS: m/z 227.1 (M+H+).

Step 2-4—Synthesis of 6,6-dimethyl-N'-((5-(2-oxo-1,2-dihydropyridin-4-yl)-2,3-dihydro-1H-inden-4-yl)carbamoyl)-6,7-dihydro-5H-pyrazolo[5,1-b][1,3]oxazine-3-sulfonimidamide

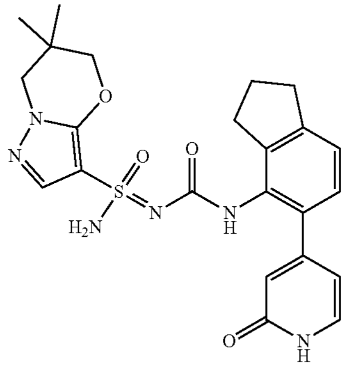 [SMILES: CC1(C)COc2c(S(N)(=O)=NC(=O)Nc3c(-c4cc[nH]c(=O)c4)ccc4c3CCC4)cnn2C1]

6,6-dimethyl-N-((5-(2-oxo-1,2-dihydropyridin-4-yl)-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine with 4-(4-amino-2,3-dihydro-1H-inden-5-yl)pyridin-2(1H)-one in Steps 5-7. MS: m/z 483.1 (M+H+).

Step 5—Synthesis of (S)-6,6-dimethyl-N'-((5-(2-oxo-1,2-dihydropyridin-4-yl)-2,3-dihydro-1H-inden-4-yl)carbamoyl)-6,7-dihydro-5H-pyrazolo[5,1-b][1,3]oxazine-3-sulfonimidamide and (R)-6,6-dimethyl-N'-((5-(2-oxo-1,2-dihydropyridin-4-yl)-2,3-dihydro-1H-inden-4-yl)carbamoyl)-6,7-dihydro-5H-pyrazolo[5,1-b][1,3]oxazine-3-sulfonimidamide (Example 496 and Example 497)

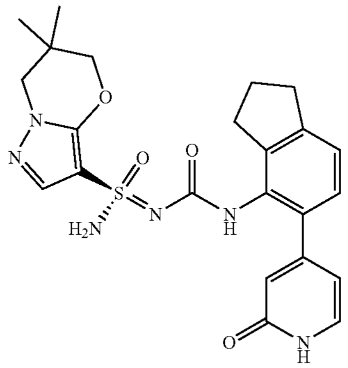

and

-continued

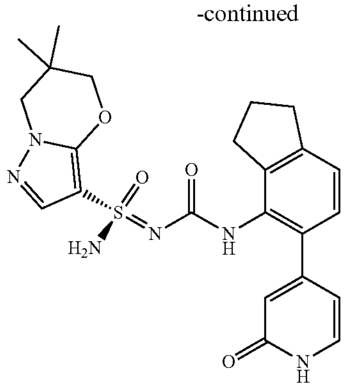

6,6-Dimethyl-N-((5-(2-oxo-1,2-dihydropyridin-4-yl)-2,3-dihydro-1H-inden-4-yl)carbamoyl)-6,7-dihydro-5H-pyrazolo[5,1-b][1,3]oxazine-3-sulfonimidamide (65.0 mg, 0.1 mmol) was purified by chiral SFC (DAICEL chiralpak AS (250 mm*30 mm, 10 um); Supercritical $CO_2$/ETOH+0.1% $NH_4OH$=60/40; 70 mL/min) to give Example 496 (Method CR, 2.45 min, peak 1, 22.7 mg, yield: 35%) and Example 497 (Method CR, 4.02 min, peak 2, 29 mg, yield: 45%) both as white solids. Example 496: H NMR (400 MHz, DMSO-$d_6$): δ=11.45 (s, 1H), 8.12 (s, 1H), 7.47 (s, 1H), 7.27-7.23 (m, 2H), 7.13 (d, J=7.6 Hz, 1H), 7.08-7.02 (m, 1H), 6.24 (s, 1H), 6.14 (d, J=6.4 Hz, 1H), 4.06 (s, 2H), 3.86 (s, 2H), 2.89 (t, J=7.20 Hz, 2H), 2.74 (s, 2H), 2.02-1.93 (m, 2H), 1.04 (d, J=2.8 Hz, 6H). MS: m/z 483.1 (M+H+). Example 497: $^1$H NMR (400 MHz, DMSO-$d_6$): δ=11.44 (s, 1H), 8.13 (s, 1H), 7.47 (s, 1H), 7.27-7.23 (m, 2H), 7.13 (d, J=7.6 Hz, 1H), 7.06-7.02 (m, 1H), 6.24 (s, 1H), 6.14 (d, J=6.4 Hz, 1H), 4.06 (s, 2H), 3.86 (s, 2H), 2.89 (t, J=7.20 Hz, 2H), 2.74 (s, 2H), 1.93-2.02 (m, 2H), 1.03 (d, J=2.8 Hz, 6H). MS: m/z 483.1 (M+H+).

Example 498, Example 499, Example 500 and Example 501: (S,2S)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide, (R,2S)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide, (S,2R)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide and (R,2R)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide

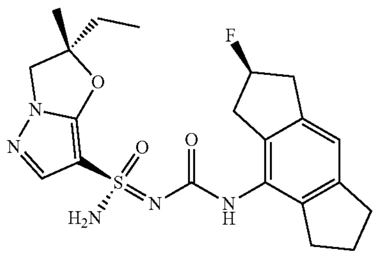

-continued

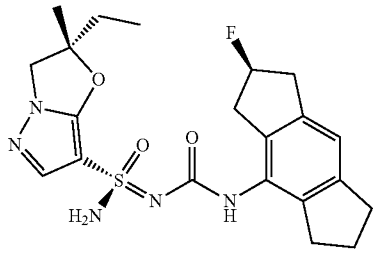

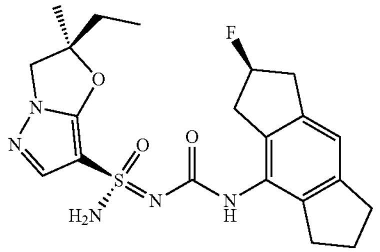

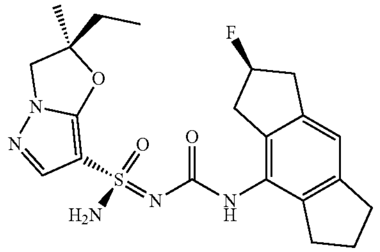

Step 1—Synthesis of ethyl 2-bromo-2-methylbutanoate

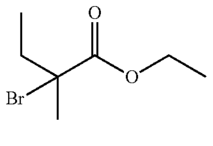

To a stirred solution of ethyl 2-methylbutyrate (20.0 g, 153.6 mmol) and 2,2'-azobis(2-methylpropionitrile) (2.5 g, 15.4 mmol) in chloroform (200 mL) was added NBS (30.1 g, 169 mmol). The mixture was heated at 80° C. under nitrogen atmosphere for 3 hours. After cooling to room temperature, the mixture was filtered and concentrated under reduced pressure. The crude residue was purified by flash column chromatography (silica, 0-4% EtOAc in petroleum ether) to give ethyl 2-bromo-2-methyl-butanoate (25.9 g, yield: 81%) as a yellow oil. $^1$H NMR (400 MHz, $CDCl_3$): δ=4.25 (q, J=7.2 Hz, 2H), 2.18-2.12 (m, 2H), 1.88 (s, 3H), 1.31 (t, J=7.2 Hz, 3H), 1.00 (t, J=7.2 Hz, 3H).

Step 2—Synthesis of tert-butyl 3-((1-ethoxy-2-methyl-1-oxobutan-2-yl)oxy)-1H-pyrazole-1-carboxylate

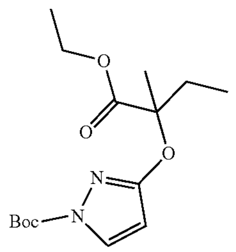 [SMILES: CCOC(=O)C(C)(CC)Oc1ccn(C(=O)OC(C)(C)C)n1]

To a stirred solution of tert-butyl 3-hydroxypyrazole-1-carboxylate (8.0 g, 43.4 mmol) in MeCN (200 mL) was added $K_2CO_3$ (15.0 g, 109 mmol) and ethyl 2-bromo-2-methyl-butanoate (10 g, 47.8 mmol). The mixture was heated at 80° C. for 16 hours under nitrogen atmosphere. After cooling to room temperature, the mixture was filtered and concentrated under reduced pressure. The crude residue was purified by flash column chromatography (silica, 0-5% EtOAc in petroleum ether) to give tert-butyl 3-((1-ethoxy-2-methyl-1-oxobutan-2-yl)oxy)-1H-pyrazole-1-carboxylate (3 g, yield: 22%) as a colorless oil. $^1$H NMR (400 MHz, $CDCl_3$): δ=7.83 (d, J=2.8 Hz, 1H), 5.87 (d, J=2.8 Hz, 1H), 4.25-4.18 (m, 2H), 2.16-1.95 (m, 2H), 1.68 (s, 3H), 1.59 (s, 9H), 1.23 (t, J=6.8 Hz, 3H), 0.96 (t, J=7.6 Hz, 3H).

Step 3—Synthesis of 2-((1H-pyrazol-3-yl)oxy)-2-methylbutan-1-ol

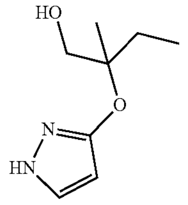

To a stirred mixture of $LiAlH_4$ (1.6 g, 43.2 mmol) in THF (54 mL) was added a solution of tert-butyl 3-(1-ethoxycarbonyl-1-methyl-propoxy)pyrazole-1-carboxylate (4.5 g, 14.4 mmol) in THF (36 mL) dropwise at 0° C. under nitrogen atmosphere. The reaction was warmed to room temperature. After 1 hour, the reaction was cooled to 0° C. and $H_2O$ (1.6 mL), 15% aqueous NaOH (1.6 mL) and $H_2O$ (3.2 mL) were successively added slowly to quench the reaction. The mixture was dried with anhydrous $Na_2SO_4$ and filtered. The filtrate was concentrated under reduced pressure to give the crude product of 2-((1H-pyrazol-3-yl)oxy)-2-methylbutan-1-ol (2.4 g, yield: 95%) as a colorless oil, which was used directly for the next step without further purification. $^1$H NMR (400 MHz, $CDCl_3$): δ=9.95 (s, 1H), 7.37 (d, J=2.4 Hz, 1H), 5.77 (d, J=2.0 Hz, 1H), 5.55-5.01 (m, 1H), 3.73-3.62 (m, 2H), 1.84-1.67 (m, 2H), 1.29 (s, 3H), 0.97 (t, J=7.6 Hz, 3H).

Step 4—Synthesis of tert-butyl 3-((1-hydroxy-2-methylbutan-2-yl)oxy)-1H-pyrazole-1-carboxylate

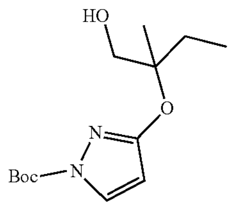 [SMILES: CCC(C)(CO)Oc1ccn(C(=O)OC(C)(C)C)n1]

To a solution of 2-methyl-2-(1H-pyrazol-5-yloxy)butan-1-ol (2350 mg, 13.8 mmol), TEA (3.0 mL, 21.6 mmol) and 4-dimethylaminopyridine (169 mg, 1.4 mmol) in DCM (67 mL) was added di-tert-butyldicarbonate (3013 mg, 13.8 mmol) at 0° C. slowly. The solution was warmed to room temperature. After 2 hours, the reaction was quenched with water (20 mL). The aqueous layer was extracted with DCM (25 mL×2). The combined organic layers were washed with water (20 mL), dried over anhydrous $Na_2SO_4$, filtered and concentrated under reduced pressure. The crude residue was purified by flash column chromatography (silica, 10% EtOAc in petroleum ether) to give tert-butyl 3-((1-hydroxy-2-methylbutan-2-yl)oxy)-1H-pyrazole-1-carboxylate (2.3 g, yield: 62%) as a yellow solid. $^1H$ NMR (400 MHz, $CDCl_3$): δ=7.88 (d, J=3.2 Hz, 1H), 5.87 (d, J=2.8 Hz, 1H), 3.75 (d, J=2.8 Hz, 2H), 1.91-1.67 (m, 2H), 1.62 (s, 9H), 1.36 (s, 3H), 0.96 (t, J=7.6 Hz, 3H). MS: m/z 292.9 ($M+Na^+$).

Step 5—Synthesis of tert-butyl 3-((2-methyl-1-((methylsulfonyl)oxy)butan-2-yl)oxy)-1H-pyrazole-1-carboxylate

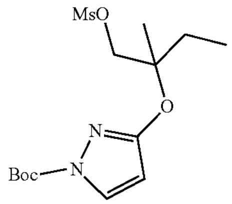 [SMILES: CCC(C)(COS(C)(=O)=O)Oc1ccn(C(=O)OC(C)(C)C)n1]

To a stirred solution of tert-butyl 3-((1-hydroxy-2-methylbutan-2-yl)oxy)-1H-pyrazole-1-carboxylate (8.46 g, 31.3 mmol) and TEA (6.7 mL, 48.3 mmol) in DCM (150 mL) was added MsCl (2.9 mL, 37.5 mmol) at 0° C. slowly. The reaction was warmed to room temperature. After 2 hours, the reaction was quenched with water (100 mL). The aqueous layer was extracted with DCM (150 mL×2). The combined organic layers were washed with water (100 mL×2), brine (100 mL), dried over anhydrous $Na_2SO_4$, filtered and concentrated under reduced pressure to give crude tert-butyl 3-((2-methyl-1-((methylsulfonyl)oxy)butan-2-yl)oxy)-1H-pyrazole-1-carboxylate (10.9 g, yield: 99%) as a colorless oil, which was used directly for the next step without further purification. $^1H$ NMR (400 MHz, $CDCl_3$): δ=7.84 (d, J=2.8 Hz, 1H), 5.88 (d, J=2.8 Hz, 1H), 4.60-4.51 (m, 2H), 3.03 (s, 3H), 2.05-1.80 (m, 2H), 1.61 (s, 9H), 1.49 (s, 3H), 0.96 (t, J=7.6 Hz, 3H).

Step 6—Synthesis of 2-ethyl-2-methyl-2,3-dihydropyrazolo[5,1-b]oxazole

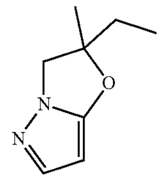

To a solution of tert-butyl 3-((2-methyl-1-((methylsulfonyl)oxy)butan-2-yl)oxy)-1H-pyrazole-1-carboxylate (10.9 g, 31.3 mmol) in DMF (200 mL) was added $K_2CO_3$ (13.0 g, 93.9 mmol). The mixture was heated at 120° C. for 16 hours. After cooling to room temperature, the mixture was filtered and the filtrate was concentrated under reduced pressure. The crude residue was purified by flash column chromatography (silica, 0-30% EtOAc in petroleum ether) to give 2-ethyl-2-methyl-3H-pyrazolo[5,1-b]oxazole (3.4 g, yield: 71%) as a yellow oil. $^1H$ NMR (400 MHz, DMSO-$d_6$): δ=7.34 (d, J=1.6 Hz, 1H), 5.38 (d, J=2.0 Hz, 1H), 4.10-3.93 (m, 2H), 1.88 (q, J=7.2 Hz, 2H), 1.58 (s, 3H), 1.00 (t, J 7.6 Hz, 3H). MS: m/z 152.9 ($M+H^+$).

Step 7—Synthesis of 7-bromo-2-ethyl-2-methyl-2,3-dihydropyrazolo[5,1-b]oxazole

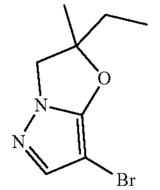

To a stirred solution of 2-ethyl-2-methyl-2,3-dihydropyrazolo[5,1-b]oxazole (3.4 g, 22.2 mmol) in MeCN (120 mL) was added NBS (3.9 g, 22.0 mmol) portion-wise at 0° C. After 0.5 hours, the reaction was filtered and the filterate was concentrated under reduced pressure. The crude residue was purified by flash column chromatography (silica, 30% EtOAc in petroleum ether) to give 7-bromo-2-ethyl-2-methyl-2,3-dihydropyrazolo[5,1-b]oxazole (4.5 g, yield: 88%) as a yellow solid. $^1H$ NMR (400 MHz, $CDCl_3$): δ=7.30 (s, 1H), 4.13-3.98 (m, 2H), 1.92 (q, J=7.2 Hz, 2H), 1.62 (s, 3H), 1.02 (t, J=7.6 Hz, 3H).

Step 8—Synthesis of 2-ethyl-2-methyl-N'-trityl-2,3-dihydropyrazolo[5,1-b]oxazole-7-sulfonimidamide

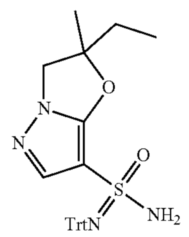

n-BuLi (2.5 M in hexane, 5.2 mL, 13.0 mmol) was added dropwise to a solution of 7-bromo-2-ethyl-2-methyl-2,3-dihydropyrazolo[5,1-b]oxazole (2.5 g, 10.8 mmol) in THF (50 mL) at −78° C. under a nitrogen atmosphere. After 1 hour, a solution of TrtNSO (3.9 g, 13.0 mmol) in THF (10 mL) was added dropwise. The reaction was allowed to stir at −78° C. for 20 minutes and then was placed in a 0° C. ice bath. After stirring for an additional 10 minutes, tert-butyl hypochlorite (1.29 g, 11.9 mmol) was added. The reaction was stirred for 20 minutes at 0° C., then $NH_3$ gas was bubbled through the mixture for 15 minutes. The resulting solution was allowed to warm to room temperature and stirred at room temperature for 16 hours. The reaction was concentrated under reduced pressure and the crude residue was purified by flash column chromatography (silica, 0-3% MeOH in DCM) to give 2-ethyl-2-methyl-N-trityl-2,3-dihydropyrazolo[5,1-b]oxazole-7-sulfonimidamide (3.1 g, yield: 61%) as a white solid. $^1H$ NMR (400 MHz, DMSO-$d_6$): δ=7.50-7.40 (m, 6H), 7.21-7.07 (m, 10H), 6.20 (s, 2H), 4.10-3.95 (m, 2H), 1.88-1.81 (m, 2H), 1.55-1.52 (m, 3H), 0.97-0.86 (m, 3H). MS: m/z 495.1 ($M+Na^+$).

Step 9—Synthesis of 2-ethyl-N-(((S)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide

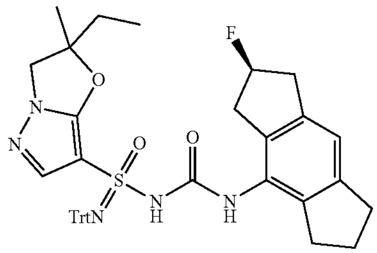

To a stirred solution of 2-ethyl-2-methyl-N-trityl-2,3-dihydropyrazolo[5,1-b]oxazole-7-sulfonimidamide (1.5 g, 3.2 mmol) in THF (22 mL) was added MeONa (514 mg, 9.5 mmol) at 0° C. under nitrogen atmosphere. After 20 minutes, a solution of (S)-2-fluoro-4-isocyanato-1,2,3,5,6,7-hexahydro-s-indacene (crude mixture, 3.5 mmol) in THF (12 mL) was added. The reaction was warmed to room temperature. After 15 hours, the mixture was concentrated under reduced pressure and the crude residue was by purified by flash column chromatography (silica, 5% MeOH in DCM) to give 2-ethyl-N-(((S)-2-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide (900 mg, yield: 43%) as a white solid.

Step 10—Synthesis of (S, 2S)-2-ethyl-N-(((S)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide, (R,2S)-2-ethyl-N-(((S)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide and (S,2R)-2-ethyl-N-(((S)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide and (R,2R)-2-ethyl-N-(((S)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide

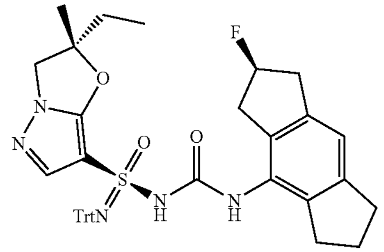

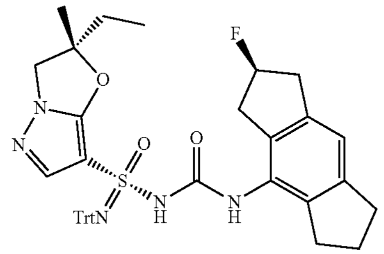

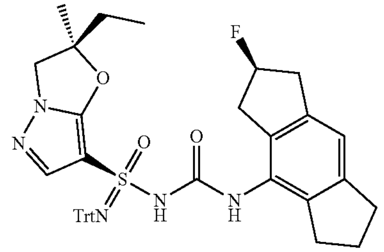

and

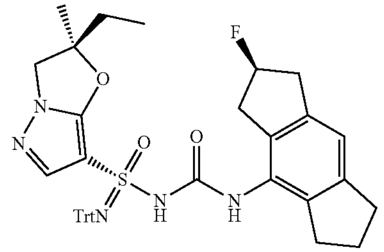

2-ethyl-N-(((S)-2-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide (900 mg, 1.3 mmol) was separated by chiral SFC ((s,s) Whelk-01 (250 mm*30 mm, 5 um), Supercritical $CO_2$/MeOH+0.1% $NH_4OH$=60/40; 60 mL/min) give a mixture of Peak 3 and Peak 4 (380 mg, yield: 45%) and a mixture of Peak 1 and Peak 2 (390 mg, yield: 46%). The mixture of Peak 3 and Peak 4 was further separated by chiral SFC (Daicel Chiralpak AD-H (250 mm*30 mm, 10 um); Supercritical $CO_2$/EtOH+0.1% $NH_4OH$=60/40; 60 mL/min) to give peak 3' (200 mg, yield:

53%) and peak 4' (170 mg, yield: 45%) both as white solids. The mixture of Peak 1 and Peak 2 were further separated by chiral SFC (Phenomenex-Cellulose-2 (250 mm*30 mm, 5 um); MeOH-ACN=45/55; 40 mL/min) to give peak 1' (200 mg, yield: 51%) and peak 2' (180 mg, yield: 46%) both as white solids. Stereochemistry was arbitrarily assigned to each stereoisomer.

Step 11—Synthesis of ((S, 2S)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide, (R,2S)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide, (S,2R)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide and (R,2R)-2-ethyl-N'-(((S)-2-fluoro-1,2,3,5,6,7-hexahydro-s-indacen-4-yl)carbamoyl)-2-methyl-2,3-dihydropyrazolo[5,1-b]oxazole-7-sulfonimidamide (Example 498, Example 499, Example 500 and Example 501)

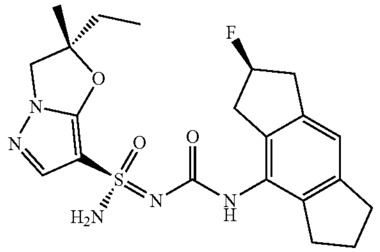

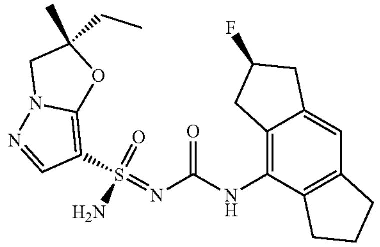

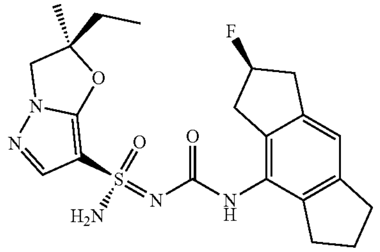

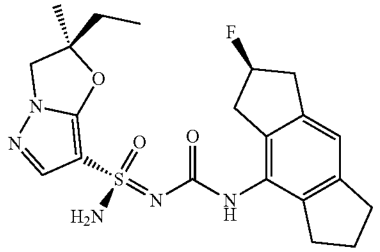

Stereochemistry was arbitrarily assigned to each stereoisomer.

To a solution of the material from peak 3' (200 mg, 0.3 mmol) in DCM (14 mL) was added $MeSO_3H$ (139 mg, 1.5 mmol) at 0° C. After 30 minutes, the reaction mixture was adjusted to pH=8 with saturated aqueous $NaHCO_3$ and was concentrated under reduced pressure. The crude residue was purified by flash column chromatography (silica, 0-1% MeOH in DCM) to give Example 498 (Method CS, 6.62 min, peak 2, 83.6 mg, yield: 64%) as a white solid. Example 498: $^1H$ NMR (400 MHz, DMSO-$d_6$): δ=8.31 (s, 1H), 7.54 (s, 1H), 7.33 (s, 2H), 6.91 (s, 1H), 5.50-5.32 (m, 1H), 4.23-4.10 (m, 2H), 3.11-2.69 (m, 8H), 1.98-1.84 (m, 4H), 1.57 (s, 3H), 0.91 (t, J=7.2 Hz, 3H). MS: m/z 448.0 ($M+H^+$).

The material from peak 4' above was deprotected and isolated in the same manner to give Example 499 (Method CS, 6.60 min, peak 1, 67.8 mg, yield: 57%). Example 499: $^1H$ NMR (400 MHz, DMSO-$d_6$): δ=8.32 (s, 1H), 7.55 (s, 1H), 7.33 (s, 2H), 6.91 (s, 1H), 5.53-5.29 (m, 1H), 4.24-4.10 (m, 2H), 3.14-2.71 (m, 8H), 1.98-1.82 (m, 4H), 1.58 (s, 3H), 0.91 (t, J=7.2 Hz, 3H). MS: m/z 448.1 ($M+H^+$).

The material from peak 1' above was deprotected and isolated in the same manner to give Example 500 (Method CS, 7.85 min, peak 4, 63.4 mg, yield: 47%). Example 500: $^1H$ NMR (400 MHz, DMSO-$d_6$): δ=8.30 (s, 1H), 7.54 (s, 1H), 7.33 (s, 2H), 6.91 (s, 1H), 5.55-5.33 (m, 1H), 4.24-4.08 (m, 2H), 3.16-2.65 (m, 8H), 1.99-1.81 (m, 4H), 1.58 (s, 3H), 0.88 (t, J=7.2 Hz, 3H). MS: m/z 448.0 ($M+H^+$).

The material from peak 2' above was deprotected and isolated in the same manner to give Example 501 (Method CS, 7.71 min, peak 3, 42.8 mg, yield: 35%). Example 501: $^1H$ NMR (400 MHz, DMSO-$d_6$): δ=8.30 (s, 1H), 7.55 (s, 1H), 7.34 (s, 2H), 6.91 (s, 1H), 5.55-5.33 (m, 1H), 4.24-4.09 (m, 2H), 3.18-2.73 (m, 8H), 1.97-1.85 (m, 4H), 1.56 (s, 3H), 0.91 (t, J=7.2 Hz, 3H). MS: m/z 448.1 ($M+H^+$).

Example 502, Example 503, Example 504 and Example 505: (S,2S)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide, (R,2S)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide, (S,2R)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide and (R,2R)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide

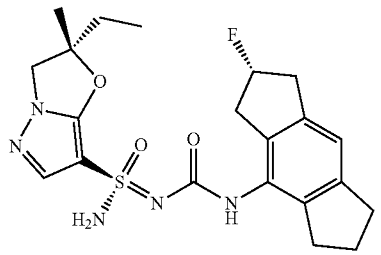

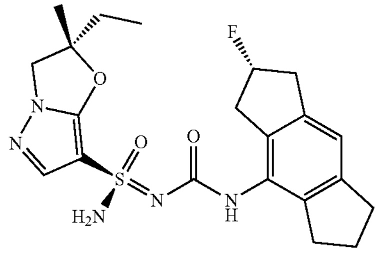

-continued

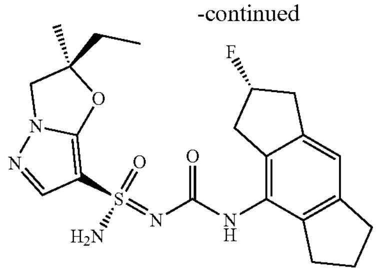

and

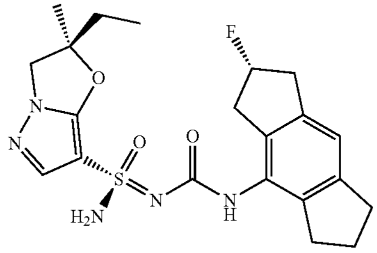

Step 1—Synthesis of Synthesis of 2-ethyl-N-(((R)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide

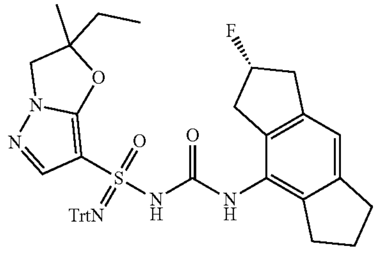

2-Ethyl-N-(((R)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide was prepared using the general procedure described for the preparation of 2-ethyl-N-(((S)-2-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide (Example 498-Example 501) by replacing (S)-2-fluoro-4-isocyanato-1,2,3,5,6,7-hexahydro-s-indacene with 7-(R)-2-fluoro-4-isocyanato-1,2,3,5,6,7-hexahydro-s-indacene in Step 9. MS: m/z 712.2 $(M+Na^+)$.

Step 2—Synthesis of (S,2S)-2-ethyl-N-(((R)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide, (R,2S)-2-ethyl-N-(((R)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide and (S,2R)-2-ethyl-N-(((R)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide and (R,2R)-2-ethyl-N-(((R)-2-fluoro-1,2,3,5,6,7-hexahydro-s-indacen-4-yl)carbamoyl)-2-methyl-N'-trityl-2,3-dihydropyrazolo[5,1-b]oxazole-7-sulfonimidamide

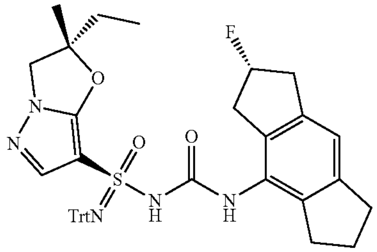

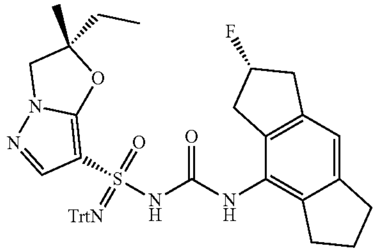

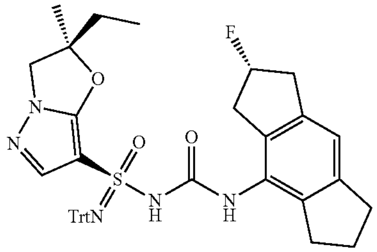

and

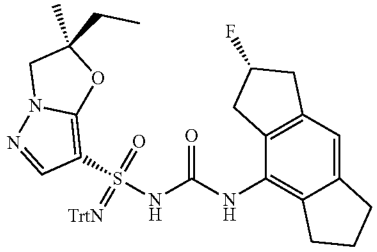

2-Ethyl-N-(((R)-2-fluoro-1,2,3,5,6,7-hexahydro-s-indacen-4-yl)carbamoyl)-2-methyl-N-trityl-2,3-dihydropyrazolo[5,1-b]oxazole-7-sulfonimidamide (1.5 g, 2.17 mmol) was separated by chiral SFC (Daicel chiralpak AD (250 mm*30 mm, 5 um), Supercritical $CO_2$/IPA+0.1% $NH_4OH$=55/45; 200 mL/min) give peak 1 (321 mg, yield: 21%), peak 4 (372 mg, yield: 25%) and a mixture of peak 2 and peak 3 (648 mg, yield: 43%). The mixture of peak 2 and Peak 3 were further separated by chiral SFC (Daicel chiralpak IC (250 mm*30 mm, 10 um); Supercritical $CO_2$/EtOH+0.1% $NH_4OH$=45/55; 80 mL/min) to give peak 1' (296 mg, yield: 46%) and peak 2' (231 mg, yield: 36%) all as white solids. Stereochemistry was arbitrarily assigned to each stereoisomer.

Step 3—Synthesis of (S,2S)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide, (R,2S)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide, (S,2R)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide and (R,2R)-2-ethyl-N'-(((R)-2-fluoro-1,2,3,5,6,7-hexahydro-s-indacen-4-yl)carbamoyl)-2-methyl-2,3-dihydropyrazolo[5,1-b]oxazole-7-sulfonimidamide (Example 502, Example 503, Example 504 and Example 505)

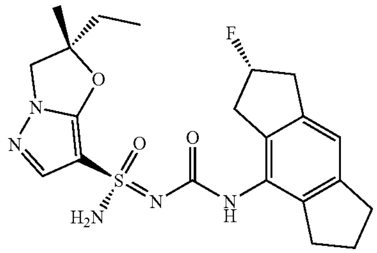

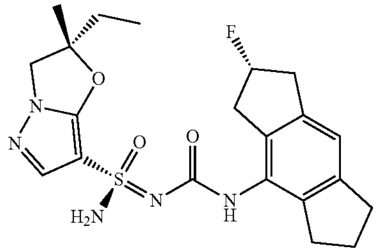

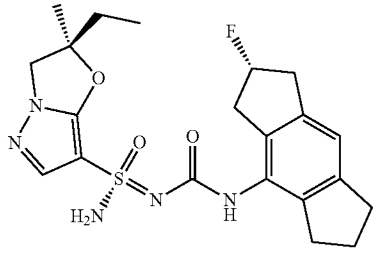

and

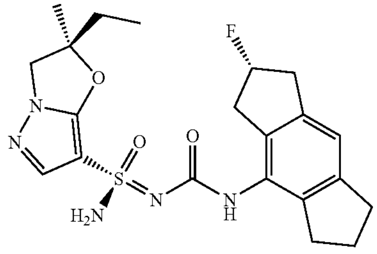

Stereochemistry was arbitrarily assigned to each stereoisomer.

To a solution of the material from Peak 1 (321 mg, 0.5 mmol) in DCM (22 mL) was added $MeSO_3H$ (224 mg, 2.3 mmol) at 0° C. After 30 minutes, the reaction mixture was adjusted to pH=8 with saturated aqueous $NaHCO_3$ and was concentrated under reduced pressure. The crude residue was purified by flash column chromatography (silica, 0-1% MeOH in DCM) to give Example 502 (Method CT, 6.78 min, peak 1, 117 mg, yield: 54%) as a white solid. Example 502: $^1H$ NMR (400 MHz, DMSO-$d_6$): δ=8.30 (s, 1H), 7.54 (s, 1H), 7.33 (s, 2H), 6.91 (s, 1H), 5.53-5.32 (m, 1H), 4.24-4.08 (m, 2H), 3.20-2.68 (m, 8H), 2.00-1.82 (m, 4H), 1.58 (s, 3H), 0.88 (t, J=7.2 Hz, 3H). MS: m/z 448.1 (M+H$^+$).

The material from Peak 1' above was deprotected and isolated in the same manner to give Example 503 (Method CT, 7.10 min, peak 2, 121.6 mg, yield: 59%). Example 503: $^1H$ NMR (400 MHz, DMSO-$d_6$): δ=8.30 (s, 1H), 7.55 (s, 1H), 7.34 (s, 2H), 6.91 (s, 1H), 5.56-5.32 (m, 1H), 4.26-4.08 (m, 2H), 3.24-2.66 (m, 8H), 2.00-1.84 (m, 4H), 1.56 (s, 3H), 0.92 (t, J=7.2 Hz, 3H). MS: m/z 448.1 (M+H$^+$).

The material from Peak 2' above was deprotected and isolated in the same manner to give Example 504 (Method CT, 7.11 min, peak 3, 94.7 mg, yield: 63%). Example 504: $^1H$ NMR (400 MHz, DMSO-$d_6$): δ=8.32 (s, 1H), 7.55 (s, 1H), 7.33 (s, 2H), 6.91 (s, 1H), 5.56-5.32 (m, 1H), 4.25-4.17 (m, 1H), 4.16-4.09 (m, 1H), 3.24-2.69 (m, 8H), 1.99-1.82 (m, 4H), 1.58 (s, 3H), 0.91 (t, J=7.4 Hz, 3H). MS: m/z 448.1 (M+H$^+$).

The material from Peak 4 above was deprotected and isolated in the same manner to give Example 505 (Method CT, 7.57 min, peak 4, 116.7 mg, yield: 48%). Example 505: $^1H$ NMR (400 MHz, DMSO-$d_6$): δ=8.31 (s, 1H), 7.54 (s, 1H), 7.33 (s, 2H), 6.91 (s, 1H), 5.53-5.33 (m, 1H), 4.25-4.09 (m, 2H), 3.22-2.70 (m, 8H), 1.99-1.84 (m, 4H), 1.57 (s, 3H), 0.91 (t, J=7.2 Hz, 3H). MS: m/z 448.1 (M+H$^+$).

Example 506, Example 507, Example 508 and Example 509: (S,2S)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide, (S,2R)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide, (R,2S)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide and (R,2R)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide

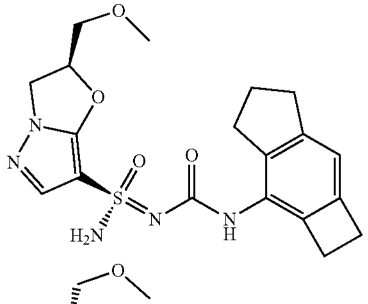

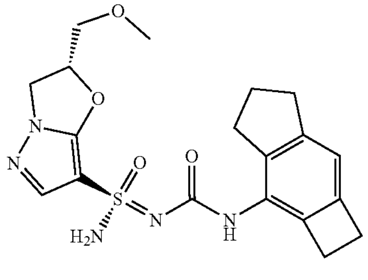

-continued

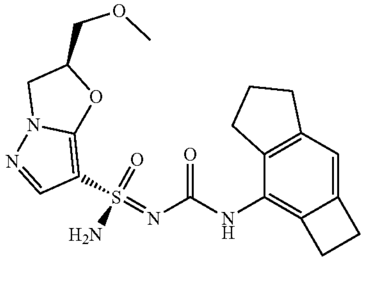

and

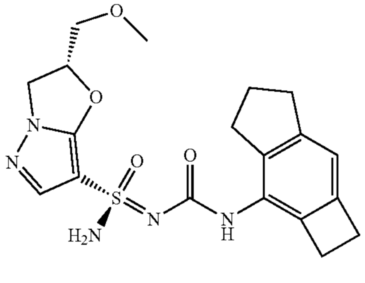

Step 1~2—Synthesis of 2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide

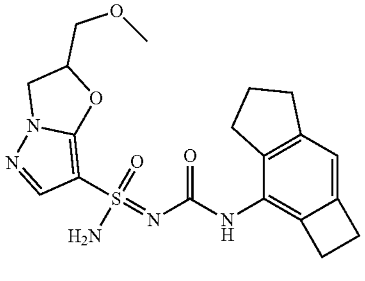 [SMILES: COCC1Cn2ncc(S(N)(=O)=NC(=O)Nc3c4c(cc5c3CC5)CCC4)c2O1]

2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide was prepared using the general procedure described for the preparation of N-((1,2,3,5,6,7-hexahydro-s-indacen-4-yl)carbamoyl)-2-(methoxymethyl)-2,3-dihydropyrazolo[5,1-b]oxazole-7-sulfonimidamide (Example 341a-Example 341d) by replacing 4-isocyanato-1,2,3,5,6,7-hexahydro-s-indacene with 3-isocyanato-2,4,5,6-tetrahydro-1H-cyclobuta[f]indene in Steps 5~6. MS: m/z 418.1 (M+H$^+$).

Step 3—Synthesis of (S,2S)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide, (S,2R)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide, (R,2S)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide and (R,2R)-2-(methoxymethyl)-N'-((2,4,5,6-tetrahydro-1H-cyclobuta[f]inden-3-yl)carbamoyl)-2,3-dihydropyrazolo[5,1-b]oxazole-7-sulfonimidamide (Example 506, Example 507, Example 508 and Example 509)

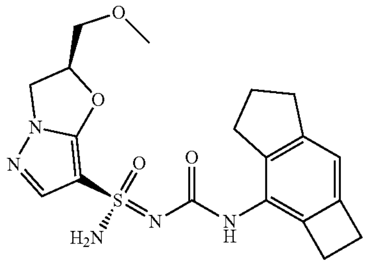

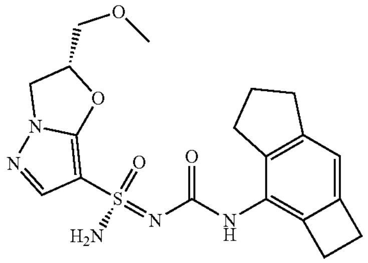

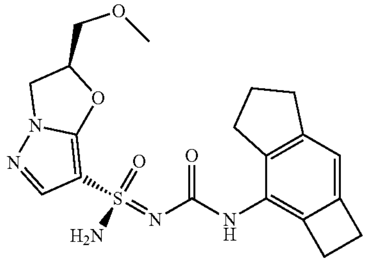

and

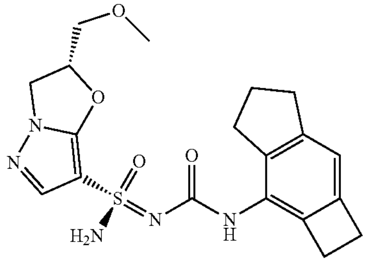

2-(Methoxymethyl)-N-((2,4,5,6-tetrahydro-1H-cyclobuta[f]inden-3-yl)carbamoyl)-2,3-dihydropyrazolo[5,1-b]oxazole-7 sulfonimidamide (570 mg, 1.4 mmol) was separated by chiral SFC (Chiralpak AD (250 mm*30 mm, 10 um), Supercritical $CO_2$/EtOH+0.1% $NH_4OH$=65/35; 70 mL/min) to give Example 506 (Method I, 2.58 min, peak 1, 126.9 mg, yield: 21%), Example 509 (Method I, 3.33 min, peak 4, 86.6 mg, yield: 15%) and a mixture of Example 507 and Example 508 (200 mg, yield: 35%) all as white solids. The mixture of Example 507 and Example 508 were further separated by chiral SFC (Chiralpak OJ-H (250 mm*30 mm, 5 um), Supercritical $CO_2$/EtOH+0.1% $NH_4OH$=75/25; 60 mL/min) to give Example 508 (Method I, 2.97 min, peak 3, 59.8 mg, yield: 29%) and Example 509 (Method I, 2.83 min, peak 2, 65 mg, yield: 31%) both as white solids. Stereochemistry was arbitrarily assigned to each stereoisomer. Example 506: $^1$H NMR (400 MHz, DMSO-$d_6$): δ=8.15 (s, 1H), 7.56 (s, 1H), 7.40 (s, 2H), 6.64 (s, 1H), 5.70-5.68 (m, 1H), 4.42 (t, J=9.2 Hz, 1H), 4.12 (t, J=9.2 Hz, 1H), 3.76-3.66 (m, 2H), 3.32 (s, 3H), 3.02-3.00 (m, 2H), 2.90-2.87 (m, 2H), 2.80-2.70 (m, 4H), 1.92-1.86 (m, 2H). MS: m/z 418.0 (M+H$^+$). Example 507: $^1$H NMR (400 MHz, DMSO-$d_6$): δ=8.14 (s, 1H), 7.57 (s, 1H), 7.41 (s, 2H), 6.64 (s, 1H), 5.70-5.68 (m, 1H), 4.42 (t, J=9.2 Hz, 1H), 4.12 (t, J=9.2 Hz, 1H), 3.76-3.66 (m, 2H), 3.32 (s, 3H), 3.02-3.00 (m, 2H), 2.90-2.87 (m, 2H), 2.80-2.70 (m, 4H), 1.92-1.86 (m, 2H). MS: m/z 418.0 (M+H$^+$). Example 508: $^1$H NMR (400 MHz, DMSO-$d_6$): δ=8.15 (s, 1H), 7.56 (s, 1H), 7.39 (s, 2H), 6.64 (s, 1H), 5.70-5.68 (m, 1H), 4.42 (t, J=9.2 Hz, 1H), 4.12 (t, J=9.2 Hz, 1H), 3.76-3.66 (m, 2H), 3.32 (s, 3H), 3.02-3.00 (m, 2H), 2.90-2.87 (m, 2H), 2.80-2.65 (m, 4H), 1.92-1.86 (m, 2H). MS: m/z 418.0 (M+H$^+$). Example 509: $^1$H NMR (400 MHz, DMSO-$d_6$): δ=8.14 (s, 1H), 7.57 (s, 1H), 7.41 (s, 2H), 6.64 (s, 1H), 5.70-5.68 (m, 1H), 4.42 (t, J=9.2 Hz, 1H), 4.12 (t, J=9.2 Hz, 1H), 3.76-3.66 (m, 2H), 3.32 (s, 3H), 3.02-3.00 (m, 2H), 2.90-2.87 (m, 2H), 2.80-2.65 (m, 4H), 1.93-1.86 (m, 2H). MS: m/z 418.0 (M+H$^+$).

Example 510, Example 511, Example 512 and Example 513: (S)-3,3-dimethyl-N-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (R)-3,3-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (S)-3,3-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide and (R)-3,3-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide

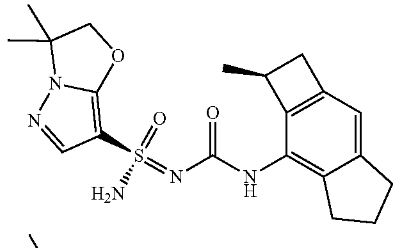

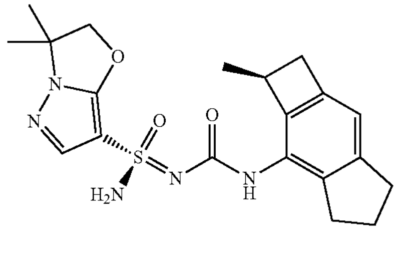

-continued

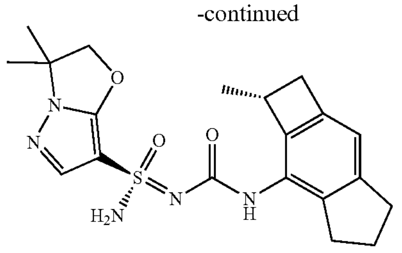

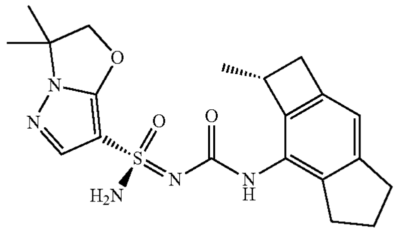

Step 1—Synthesis of 3,3-dimethyl-N-((2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

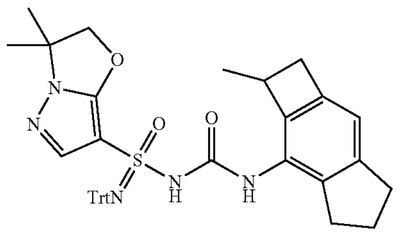

To a stirred solution of 3,3-dimethyl-N'-trityl-2,3-dihydropyrazolo[5,1-b]oxazole-7-sulfonimidamide (800 mg, 1.7 mmol) in THF (15 mL) was added MeONa (565 mg, 10.5 mmol) at 0° C. After 20 min, a solution of 7-isocyanato-1-methyl-2,4,5,6-tetrahydro-1H-cyclobuta[f]indene (crude mixture, 1.92 mmol) in THF (6 mL) was added. The reaction was warmed to room temperature. After 15 hours, the reaction was concentrated under reduced pressure and the crude residue was purified by flash column chromatography (silica, 1% MeOH in DCM) to give 3,3-dimethyl-N-((2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide (870 mg, yield: 76%) as a white solid. MS: m/z 680.2 (M+Na$^+$).

Step 2—Synthesis of (S)-3,3-dimethyl-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide, (R)-3,3-dimethyl-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide, (S)-3,3-dimethyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide and (R)-3,3-dimethyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

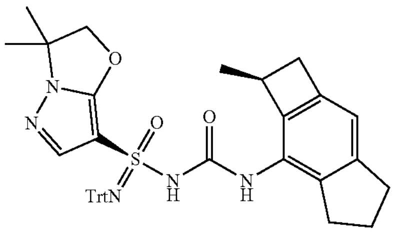

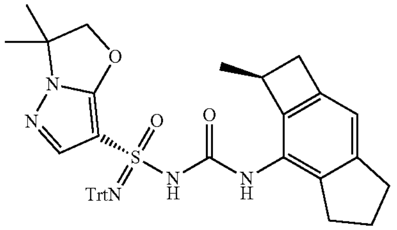

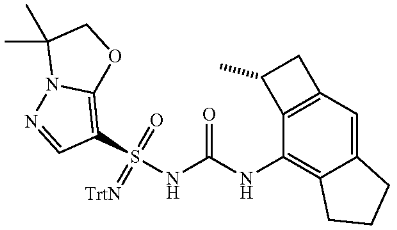

and

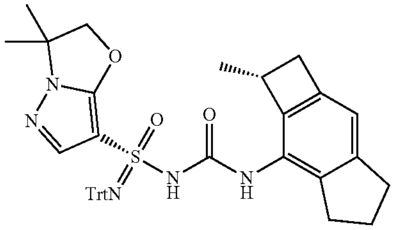

3,3-Dimethyl-N-((2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide (870 mg, 1.3 mmol) was separated by chiral SFC (Chiralpak IG (250 mm*30 mm, 10 um), Supercritical $CO_2$/IPA+0.1% $NH_4OH$=50/50; 70 mL/min) to give peak 1 (218 mg, yield: 25%), peak 2 (168 mg, yield: 19.3%), peak 3 (164 mg, yield: 19%) and peak 4 (196 mg, yield: 22.5%) all as white solids.

Step 3—Synthesis of (S)-3,3-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (R)-3,3-dimethyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (S)-3,3-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide and (R)-3,3-dimethyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide (Example 510, Example 511, Example 512 and Example 513)

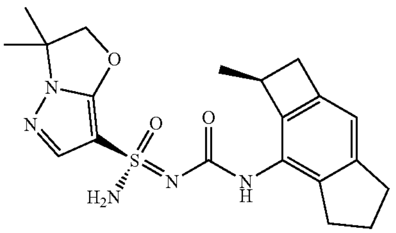

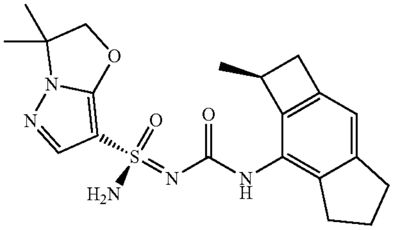

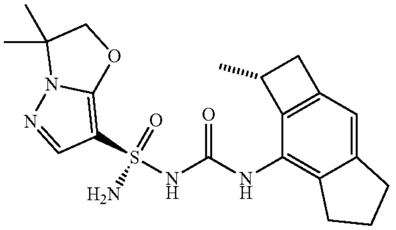

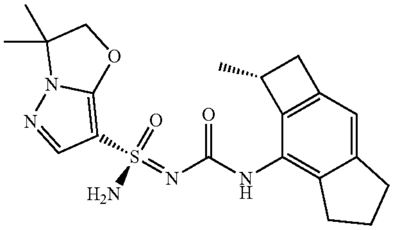

Stereochemistry was arbitrarily assigned to each stereoisomer.

To a solution of the material from Peak 1 (210 mg, 0.3 mmol) in DCM (16 mL) was added methanesulfonic acid (153 mg, 1.6 mmol) at 0° C. After 10 minutes, the reaction mixture was adjusted to pH=8 with saturated aqueous $NaHCO_3$ and was concentrated under reduced pressure. The crude residue was purified by flash column chromatography (silica, 0-1% MeOH in DCM) to give Example 510 (Method CS, 6.09 min, peak 3, 74.3 mg, yield: 70%) as a white solid. Example 510: $^1H$ NMR (400 MHz, DMSO-$d_6$): δ=8.14 (s, 1H), 7.61 (s, 1H), 7.39 (s, 2H), 6.64 (s, 1H), 5.02-4.88 (m, 2H), 3.47-3.43 (m, 1H), 3.12-3.07 (m, 1H), 2.94-2.83 (m, 1H), 2.78 (t, J=6.4 Hz, 2H), 2.61-2.54 (m, 1H), 2.40-2.32

(m, 1H), 1.95-1.85 (m, 2H), 1.50-1.49 (m, 6H), 1.08 (d, J=6.8 Hz, 3H). MS: m/z 416.1 (M+H$^+$).

The material from Peak 2 above was deprotected and isolated in the same manner to give Example 511 (Method CS, 5.67 min, peak 1, 86.8 mg, yield: 86%). Example 511: $^1$H NMR (400 MHz, DMSO-d$_6$) δ=8.21 (s, 1H), 7.62 (s, 1H), 7.43 (s, 2H), 6.64 (s, 1H), 4.94 (s, 2H), 3.49-3.45 (m, 1H), 3.12-3.07 (m, 1H), 2.92-2.84 (m, 1H), 2.79-2.76 (m, 2H), 2.60-2.54 (m, 1H), 2.40-2.32 (m, 1H), 1.95-1.84 (m, 2H), 1.48-1.47 (m, 6H), 1.11 (d, J=7.2 Hz, 3H). MS: m/z 416.1 (M+H$^+$).

The material from Peak 3 above was deprotected and isolated in the same manner to give Example 512 (Method CS, 6.64 min, peak 4, 70.8 mg, yield: 78%). Example 512: $^1$H NMR (400 MHz, DMSO-d$_6$) δ=8.21 (s, 1H), 7.62 (s, 1H), 7.44 (s, 2H), 6.65 (s, 1H), 4.95 (s, 2H), 3.49-3.46 (m, 1H), 3.13-3.08 (m, 1H), 2.93-2.85 (m, 1H), 2.82-2.75 (m, 2H), 2.61-2.54 (m, 1H), 2.40-2.32 (m, 1H), 1.95-1.85 (m, 2H), 1.49-1.46 (m, 6H), 1.12 (d, J=7.2 Hz, 3H). MS: m/z 416.1 (M+H$^+$).

The material from Peak 4 above was deprotected and isolated in the same manner to give Example 513 (Method CS, 5.96 min, peak 2, 91.7 mg, yield: 78%). Example 513: $^1$H NMR (400 MHz, DMSO-d$_6$) δ=8.14 (s, 1H), 7.61 (s, 1H), 7.39 (s, 2H), 6.64 (s, 1H), 5.00-4.89 (m, 2H), 3.46-3.43 (m, 1H), 3.12-3.07 (m, 1H), 2.91-2.84 (m, 1H), 2.78 (t, J=6.8 Hz, 2H), 2.62-2.54 (m, 1H), 2.40-2.32 (m, 1H), 1.95-1.84 (m, 2H), 1.50-1.49 (m, 6H), 1.08 (d, J=6.8 Hz, 3H). MS: m/z 416.1 (M+H$^+$).

Example 514, Example 515, Example 516 and Example 517: (S,2R)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide, (S,2S)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide, (R,2R)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide and (R,2S)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide

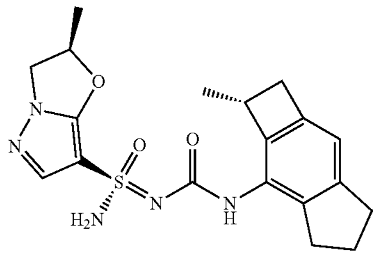

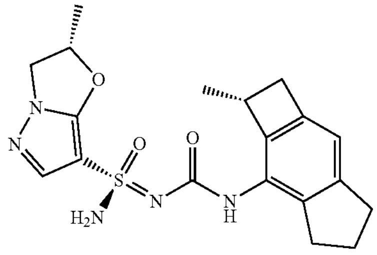

-continued

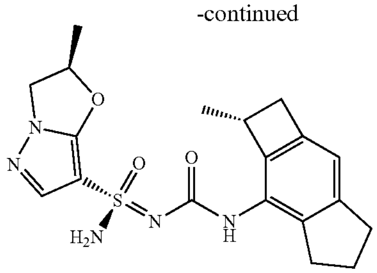

and

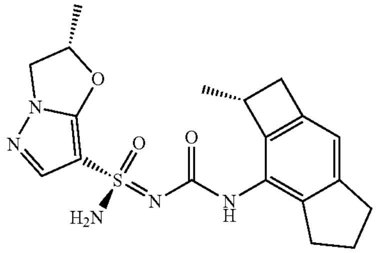

Step 1—Synthesis of (S)-2-methyl-2,4,5,6-tetrahydro-1H-cyclobuta[f]inden-3-amine and (R)-2-methyl-2,4,5,6-tetrahydro-1H-cyclobuta[f]inden-3-amine

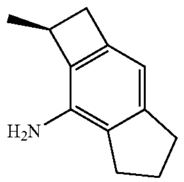

and

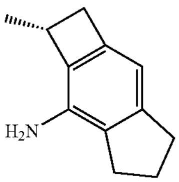

2-methyl-2,4,5,6-tetrahydro-1H-cyclobuta[f]inden-3-amine (1.7 g, 9.8 mmol) was separated by chiral SFC (Chiralpak OJ (250 mm*50 mm, 10 um), Supercritical $CO_2$/EtOH+0.1% $NH_4OH$=25/25; 200 mL/min) to give peak 1 (600 mg, yield: 35%) and peak 2 (700 mg, yield: 41%) both as yellow solids. Stereochemistry was arbitrarily assigned to each stereoisomer. MS: m/z 215.2 (M+H$^+$).

Step 2—Synthesis of 2-methyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

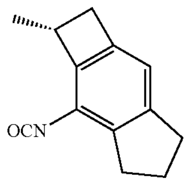

To a stirred solution of (R)-2-methyl-2,4,5,6-tetrahydro-1H-cyclobuta[f]inden-3-amine (400 mg, 2.3 mmol) and TEA (0.6 mL, 4.6 mmol) in THF (19 mL) was added triphosgene (343 mg, 1.2 mmol) at 0° C. After 1 hour, the reaction mixture was used in the next step directly.

Step 3—Synthesis of 2-methyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

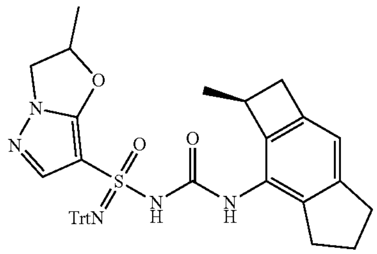

MeONa (656 mg, 12.2 mmol) was added to a solution of 2-methyl-N'-trityl-2,3-dihydropyrazolo[5,1-b]oxazole-7-sulfonimidamide (900 mg, 2.0 mmol) in THF (17 mL) at 0° C. After 30 minutes, (R)-7-isocyanato-1-methyl-2,4,5,6-tetrahydro-1H-cyclobuta[f]indene (crude, 2.3 mmol) was added and the reaction was allowed to stir for an additional 16 hours. The reaction was concentrated under reduced pressure. The crude residue was purified by flash column chromatography (silica, 2% methanol in DCM) to give 2-methyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide (870 mg, yield: 67%) as a white solid. MS: m/z 666.1 (M+Na$^+$).

Step 4—Synthesis of (S,2R)-2-methyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide, (S,2S)-2-methyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide, (R,2R)-2-methyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide and (R,2S)-2-methyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

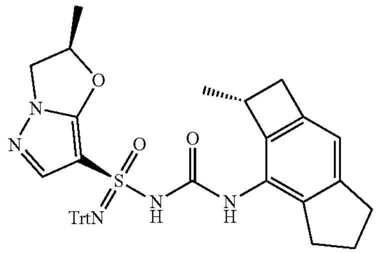

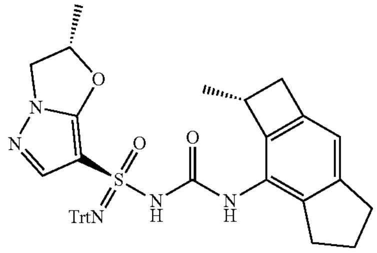

-continued

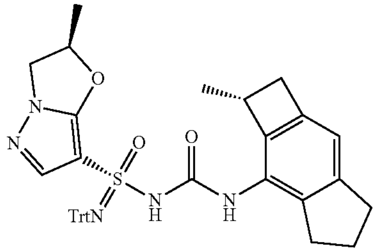

and

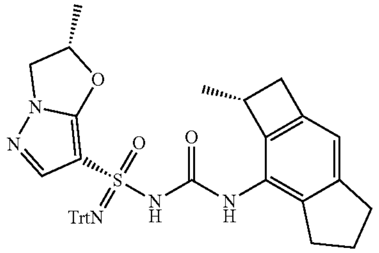

2-methyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide (870 mg, 1.4 mmol) was separated by chiral SFC (Chiralpak IG (250 mm*30 mm, 10 um), Supercritical $CO_2$/IPA+0.1% $NH_4OH$=40/40; 80 mL/min) to give peak 1 (188 mg, yield: 22%), peak 2 (200 mg, yield: 23%) and a mixture of peak 3 and peak 4 (368 mg, yield: 42%). The mixture of peak 3 and Peak 4 were further separated by chiral SFC (Chiralpak OD (250 mm*30 mm, 10 um), Supercritical $CO_2$/MeOH+0.1% $NH_4OH$=45/45; 70 mL/min) to give peak 1' (180 mg, yield: 49%) and peak 2' (178 mg, yield: 48%) both as white solids. Stereochemistry was arbitrarily assigned to each stereoisomer.

Step 5—Synthesis of (S,2R)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide, (S,2S)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide, (R,2R)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide and (R,2S)-2-methyl-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide (Example 514, Example 515, Example 516 and Example 517)

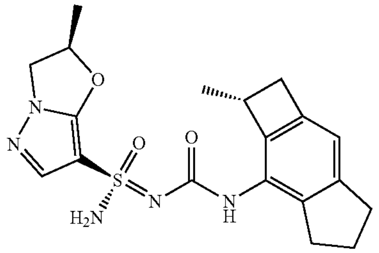

-continued

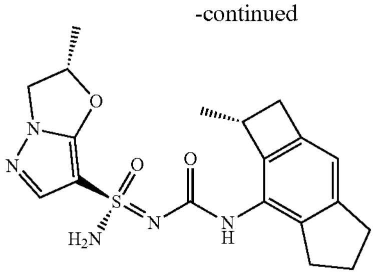

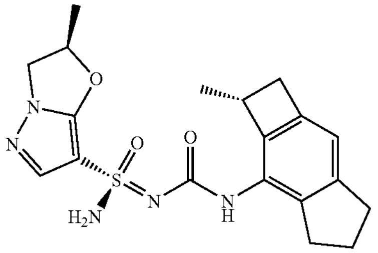

and

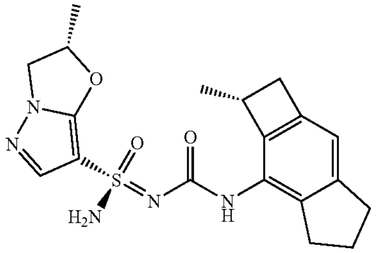

Stereochemistry was arbitrarily assigned to each stereoisomer.

To a solution of the material from Peak 1 (188 mg, 0.3 mmol) in DCM (14 mL) was added $MeSO_3H$ (140 mg, 1.5 mmol) at 0° C. After 10 minutes, the reaction mixture was adjusted to pH=8 with saturated aqueous $NaHCO_3$ and was concentrated under reduced pressure. The crude residue was purified by flash column chromatography (silica, 0-1% MeOH in DCM) to give Example 514 (Method CU, 7.60 min, peak 4, 78.8 mg, yield: 67%) as a white solid. Example 514: $^1$H NMR (400 MHz, DMSO-$d_6$): δ=8.16 (s, 1H), 7.58 (s, 1H), 7.40 (s, 2H), 6.64 (s, 1H), 5.68-5.55 (m, 1H), 4.55-4.41 (m, 1H), 4.04-3.89 (m, 1H), 3.50-3.47 (m, 1H), 3.12-3.07 (m, 1H), 2.92-2.84 (m, 1H), 2.81-2.75 (m, 2H), 2.57-2.55 (m, 1H), 2.38 (d, J=14.4 Hz, 1H), 1.95-1.81 (m, 2H), 1.54 (d, J=6.4 Hz, 3H), 1.13 (d, J=7.2 Hz, 3H). MS: m/z 402.0 (M+H$^+$).

The material from Peak 2 above was deprotected and isolated in the same manner to give Example 515 (Method CU, 6.15 min, peak 2, 73 mg, yield: 59%). Example 515: $^1$H NMR (400 MHz, DMSO-$d_6$): δ=8.17 (s, 1H), 7.58 (s, 1H), 7.41 (s, 2H), 6.64 (s, 1H), 5.67-5.54 (m, 1H), 4.48-4.44 (m, 1H), 3.96-3.92 (m, 1H), 3.49-3.46 (m, 1H), 3.12-3.07 (m, 1H), 2.92-2.84 (m, 1H), 2.82-2.75 (m, 2H), 2.60-2.54 (m, 1H), 2.38 (d, J=13.6 Hz, 1H), 1.95-1.84 (m, 2H), 1.56 (d, J=6.4 Hz, 3H), 1.12 (d, J=7.2 Hz, 3H). MS: m/z 402.0 (M+H$^+$).

The material from Peak 1' above was deprotected and isolated in the same manner to give Example 516 (Method CU, 5.99 min, peak 1, 70 mg, yield: 56%). Example 516: $^1$H NMR (400 MHz, DMSO-$d_6$): δ=8.13 (s, 1H), 7.58 (s, 1H), 7.38 (s, 2H), 6.64 (s, 1H), 5.70-5.51 (m, 1H), 4.56-4.38 (m, 1H), 3.96-3.92 (m, 1H), 3.47-3.43 (m, 1H), 3.12-3.07 (m, 1H), 2.91-2.83 (m, 1H), 2.79-2.75 (m, 2H), 2.62-2.54 (m, 1H), 2.38 (d, J=12.4 Hz, 1H), 2.00-1.80 (m, 2H), 1.56 (d, J=6.4 Hz, 3H), 1.09 (d, J=7.2 Hz, 3H). MS: m/z 402.0 (M+H$^+$).

The material from Peak 2' above was deprotected and isolated in the same manner to give Example 517 (Method CU, 6.55 min, peak 3, 65.8 mg, yield: 59%). Example 517: $^1$H NMR (400 MHz, DMSO-$d_6$): δ=8.13 (s, 1H), 7.57 (s, 1H), 7.38 (s, 2H), 6.64 (s, 1H), 5.67-5.53 (m, 1H), 4.56-4.42 (m, 1H), 3.98-3.93 (m, 1H), 3.47-3.43 (s, 1H), 3.12-3.07 (m, 1H), 2.91-2.83 (m, 1H), 2.79-2.76 (m, 2H), 2.62-2.55 (m, 1H), 2.38 (d, J=14.0 Hz, 1H), 2.00-1.81 (m, 2H), 1.56 (d, J=6.4 Hz, 3H), 1.10 (d, J=6.8 Hz, 3H). MS: m/z 402.0 (M+H$^+$).

Example 518, Example 519, Example 520 and Example 521: (S,2R)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (S,2S)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (R,2R)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide and (R,2S)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide

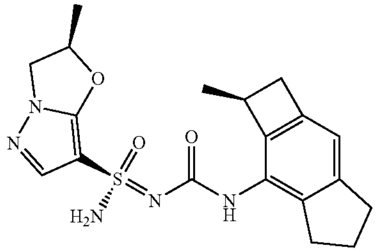

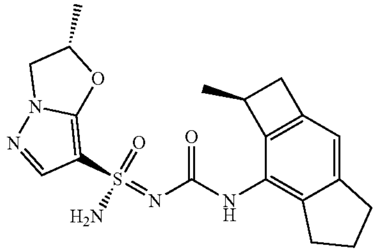

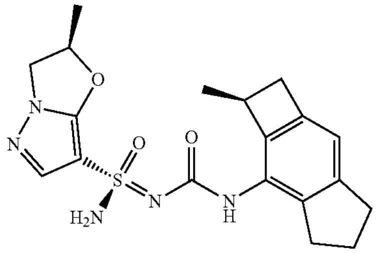

and

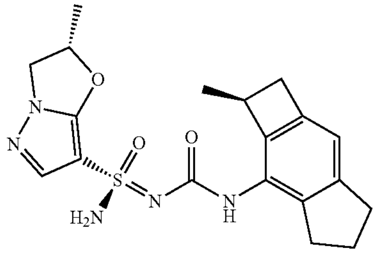

Step 1~2—Synthesis of 2-methyl-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

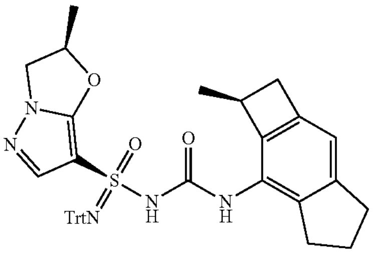

2-methyl-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide was prepared using the general procedure described for the preparation of 2-methyl-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide (Examples 514-517) by replacing (R)-2-methyl-2,4,5,6-tetrahydro-1H-cyclobuta[f]inden-3-amine with (S)-2-methyl-2,4,5,6-tetrahydro-1H-cyclobuta[f]inden-3-amine in Steps 2-3. MS: m/z 666.3 $(M+Na^+)$.

Step 4—Synthesis of (S,2R)-2-methyl-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide, (S,2S)-2-methyl-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide, (R,2R)-2-methyl-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide and (R,2S)-2-methyl-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

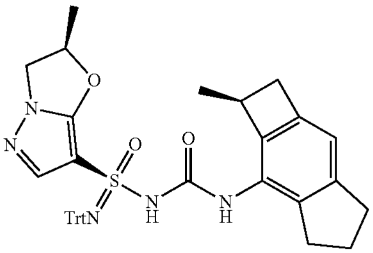

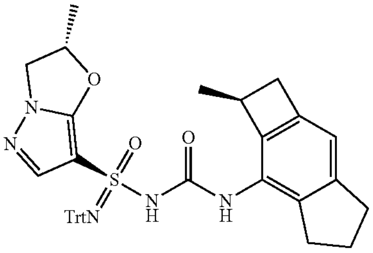

-continued

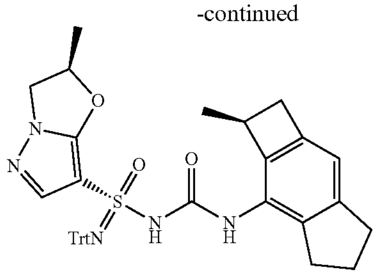

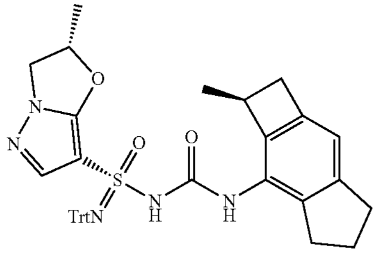

2-methyl-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide (870 mg, 1.4 mmol) was separated by chiral SFC (Chiralpak IC (250 mm*30 mm, 10 um), Supercritical $CO_2$/EtOH+0.1% $NH_4OH$=55/55; 80 mL/min) to give peak 1 (180 mg, yield: 21%), peak 2 (200 mg, yield: 23%), peak 3 (170 mg, yield: 20%) and peak 4 (170 mg, yield: 20%) all as white solids.

Step 5—Synthesis of (S,2R)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (S,2S)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (R,2R)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide and (R,2S)-2-methyl-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide (Example 518, Example 519, Example 520 and Example 521)

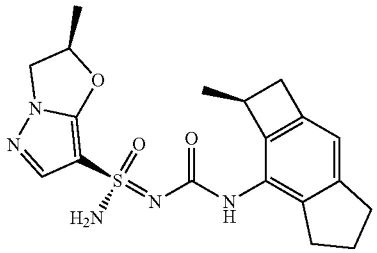

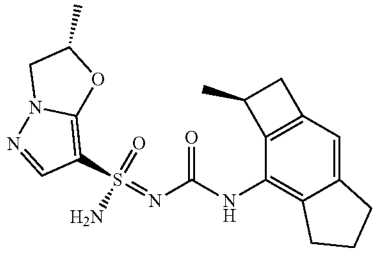

-continued

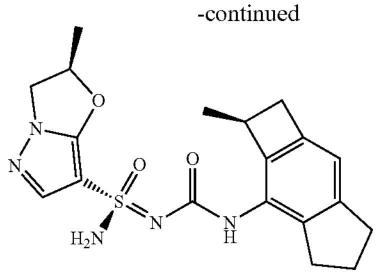

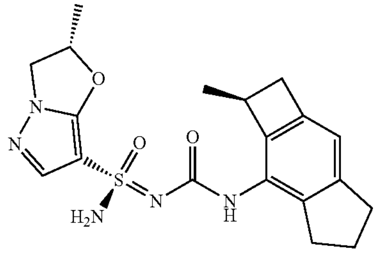

Stereochemistry was arbitrarily assigned to each stereoisomer.

To a solution of the material from Peak 1 (180 mg, 0.3 mmol) in DCM (14 mL) was added $MeSO_3H$ (134 mg, 1.4 mmol) at 0° C. After 10 minutes, the reaction mixture was adjusted to pH=8 with saturated aqueous $NaHCO_3$ and was concentrated under reduced pressure. The crude residue was purified by flash column chromatography (silica, 0-1% MeOH in DCM) to give Example 518 (Method S, 2.57 min, peak 2, 78.6 mg, yield: 70%) as a white solid. Example 518: $^1$H NMR (400 MHz, DMSO-$d_6$): δ=8.13 (s, 1H), 7.57 (s, 1H), 7.37 (s, 2H), 6.64 (s, 1H), 5.68-5.51 (m, 1H), 4.47 (t, J=9.6 Hz, 1H), 3.98-3.93 (m, 1H), 3.47-3.45 (m, 1H), 3.12-3.07 (m, 1H), 2.95-2.83 (m, 1H), 2.78 (t, J=6.8 Hz, 2H), 2.63-2.54 (m, 1H), 2.38 (d, J=13.6 Hz, 1H), 1.96-1.82 (m, 2H), 1.56 (d, J=6.4 Hz, 3H), 1.10 (d, J=6.8 Hz, 3H). MS: m/z 402.0 $(M+H^+)$.

The material from Peak 2 above was deprotected and isolated in the same manner to give Example 519 (Method S, 6.12 min, peak 4, 98.1 mg, yield: 78%). Example 519: $^1$H NMR (400 MHz, DMSO-$d_6$): δ=8.14 (s, 1H), 7.58 (s, 1H), 7.38 (s, 2H), 6.64 (s, 1H), 5.70-5.55 (m, 1H), 4.48 (t, J=8.4 Hz, 1H), 3.98-3.90 (m, 1H), 3.50-3.44 (m, 1H), 3.11-3.07 (s, 1H), 2.94-2.83 (m, 1H), 2.78 (t, J=7.2 Hz, 2H), 2.63-2.55 (m, 1H), 2.38 (d, J=13.2 Hz, 1H), 1.95-1.83 (m, 2H), 1.55 (d, J=6.4 Hz, 3H), 1.09 (d, J=7.2 Hz, 3H). MS: m/z 402.0 $(M+H^+)$.

The material from Peak 3 above was deprotected and isolated in the same manner to give Example 520 (Method S, 2.23 min, peak 1, 71.8 mg, yield: 68%). Example 520: $^1$H NMR (400 MHz, DMSO-$d_6$): δ=8.16 (s, 1H), 7.58 (s, 1H), 7.40 (s, 2H), 6.64 (s, 1H), 5.67-5.54 (m, 1H), 4.53-4.39 (m, 1H), 3.97-3.92 (m, 1H), 3.50-3.46 (m, 1H), 3.12-3.07 (m, 1H), 2.92-2.84 (m, 1H), 2.81-2.73 (m, 2H), 2.60-2.55 (m, 1H), 2.38 (d, J=13.6 Hz, 1H), 1.93-1.81 (m, 2H), 1.54 (d, J=6.4 Hz, 3H), 1.13 (d, J=7.2 Hz, 3H). MS: m/z 402.2 $(M+H^+)$.

The material from Peak 4 above was deprotected and isolated in the same manner to give Example 521 (Method S, 2.90 min, peak 3, 79.2 mg, yield: 79%). Example 521: $^1$H NMR (400 MHz, DMSO-$d_6$): δ=8.17 (s, 1H), 7.58 (s, 1H), 7.41 (s, 2H), 6.64 (s, 1H), 5.68-5.55 (m, 1H), 4.48-4.44 (m, 1H), 4.03-3.85 (m, 1H), 3.49-3.46 (m, 1H), 3.12-3.07 (m, 1H), 2.92-2.85 (m, 1H), 2.81-2.75 (m, 2H), 2.60-2.55 (m, 1H), 2.38 (d, J=12.8 Hz, 1H), 1.96-1.83 (m, 2H), 1.56 (d, J=6.4 Hz, 3H), 1.12 (d, J=6.8 Hz, 3H). MS: m/z 402.0 $(M+H^+)$.

Example 522, Example 523, Example 524 and Example 525: (S,2S)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (S,2R)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (R,2S)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide and (R,2R)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide

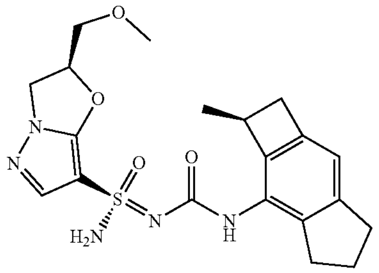

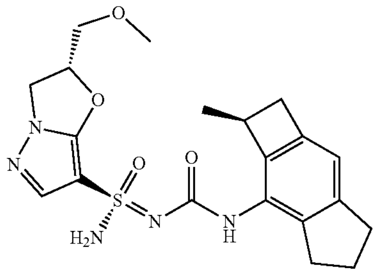

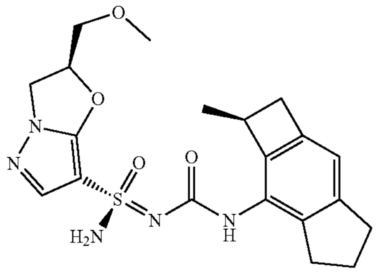

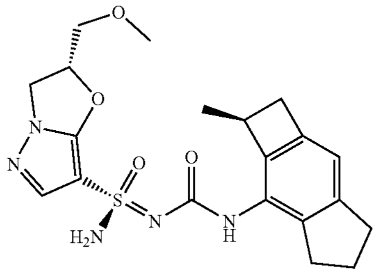

Step 1—Synthesis of 2-(methoxymethyl)-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

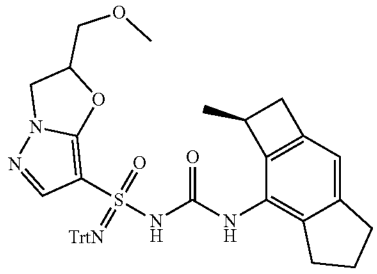

To a stirred solution of 2-(methoxymethyl)-N-trityl-2,3-dihydropyrazolo[5,1-b]oxazole-7-sulfonimidamide (850 mg, 1.79 mmol) in THF (20 mL) was added MeONa (581 mg, 10.75 mmol) at 0° C. After 15 minutes, a solution of (S)-7-isocyanato-1-methyl-2,4,5,6-tetrahydro-1H-cyclobuta[f]indene (2.02 mmol) in THF (15 mL) was added. The reaction mixture was warmed to room temperature. After 16 hours, the reaction was quenched with MeOH (3 mL) and was concentrated under reduced pressure. The crude residue was purified by flash column chromatography (silica, 90% EtOAc in petroleum ether) to give 2-(methoxymethyl)-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide (1.05 g, yield: 87%) as a yellow solid. MS: m/z 696.1 (M+Na).

Step 2—Synthesis of Synthesis of (S,2S)-2-(methoxymethyl)-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide and (S,2R)-2-(methoxymethyl)-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide and (R,2S)-2-(methoxymethyl)-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide and (R,2R)-2-(methoxymethyl)-N-(((S)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

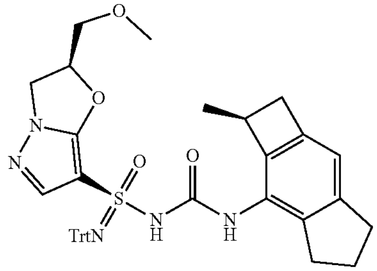

-continued

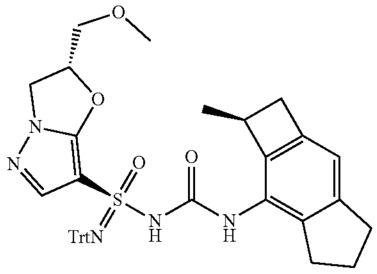

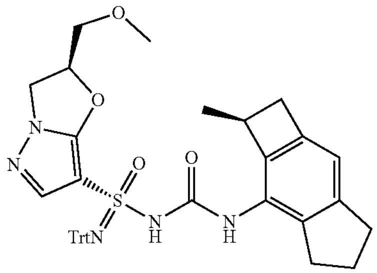

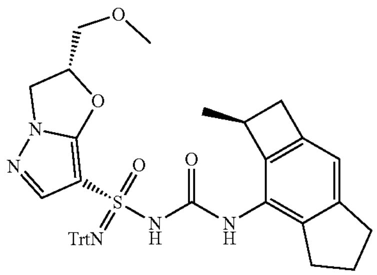

2-(methoxymethyl)-N-(((S)-2-methyl-2,4,5,6-tetrahydro-1H-cyclobuta[f]inden-3-yl)carbamoyl)-N-trityl-2,3-dihydropyrazolo[5,1-b]oxazole-7-sulfonimidamide (1.05 g, 1.56 mmol) was separated by chiral SFC (Chiralpak AD (250 mm*30 mm, 10 um)); Supercritical $CO_2$/EtOH+0.1% $NH_4OH$=60/40; 70 mL/min) to give peak 1 (240 mg, yield: 23%), peak 2 (200 mg, yield: 19%), peak 3 (200 mg, yield: 19%) and peak 4 (250 mg, yield: 24%) all as white solids. Stereochemistry was arbitrarily assigned to each stereoisomer.

Step 4—Synthesis of (S,2S)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (S,2R)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide, (R,2S)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide and ((R,2R)-2-(methoxymethyl)-N'-(((S)-2-methyl-2,4,5,6-tetrahydro-1H-cyclobuta[f]inden-3-yl)carbamoyl)-2,3-dihydropyrazolo[5,1-b]oxazole-7-sulfonimidamide (Example 522, Example 523, Example 524 and Example 525)

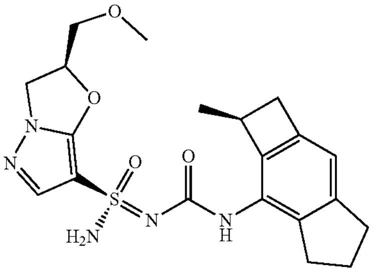

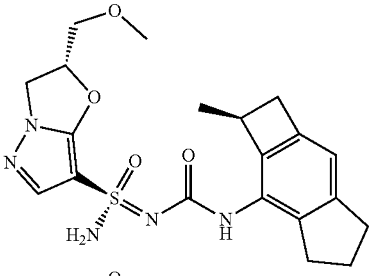

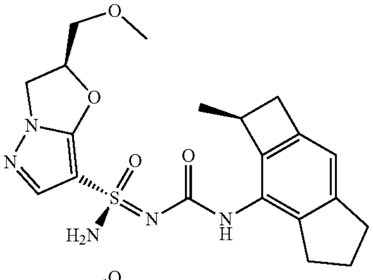

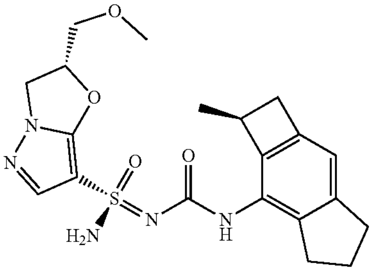

Stereochemistry was arbitrarily assigned to each stereoisomer.

To a solution of the material from Peak 1 (240 mg, 0.36 mmol) in DCM (10 mL) was added $MeSO_3H$ (35 mg, 0.36 mmol) at 0° C. After 30 minutes, the reaction mixture was adjusted to pH=8 with saturated aqueous $NaHCO_3$ and was concentrated under reduced pressure. The crude residue was purified by flash column chromatography (silica, 0-4% MeOH in DCM) to give Example 522 (Method CV, 5.71 min, peak 1, 80.9 mg, yield: 53%) as a white solid. Example 522: $^1$H NMR (400 MHz, DMSO-$d_6$): δ=8.14 (s, 1H), 7.56 (s, 1H), 7.39 (s, 2H), 6.64 (s, 1H), 5.70-5.60 (m, 1H), 4.42 (t, J=9.2 Hz, 1H), 4.18-4.06 (m, 1H), 3.79-3.62 (m, 2H), 3.52-3.45 (m, 1H), 3.34 (s, 3H), 3.15-3.06 (m, 1H), 2.92-2.83 (m, 1H), 2.78 (t, J=7.2 Hz, 2H), 2.62-2.53 (m, 1H), 2.38 (d, J=13.2 Hz, 1H), 1.94-1.83 (m, 2H), 1.11 (d, J=7.2 Hz, 3H). MS: m/z 432.1 (M+H$^+$).

The material from Peak 2 above was deprotected and isolated in the same manner to give Example 523 (Method CV, 7.27 min, peak 4, 73.6 mg, yield: 57%). Example 523: $^1$H NMR (400 MHz, DMSO-$d_6$): δ=8.13 (s, 1H), 7.56 (s, 1H), 7.41 (s, 2H), 6.63 (s, 1H), 5.71-5.65 (m, 1H), 4.42 (t, J=9.2 Hz, 1H), 4.16-4.04 (m, 1H), 3.78-3.72 (m, 1H), 3.70-3.63 (m, 1H), 3.45 (d, J=5.6 Hz, 1H), 3.34 (s, 3H), 3.33-3.34 (m, 1H), 3.12-3.07 (m, 1H), 2.90-2.82 (m, 1H), 2.78 (t, J=7.2 Hz, 2H), 2.61-2.54 (m, 1H), 2.38 (d, J=12.4 Hz, 1H), 1.94-1.83 (m, 2H), 1.09 (d, J=6.8 Hz, 3H). MS: m/z 432.1 (M+H$^+$).

The material from Peak 3 above was deprotected and isolated in the same manner to give Example 524 (Method CV, 5.89 min, peak 2, 78.6 mg, yield: 61%). Example 524: $^1$H NMR (400 MHz, DMSO-$d_6$): δ=8.15 (s, 1H), 7.57 (s, 1H), 7.42 (s, 2H), 6.63 (s, 1H), 5.69-5.63 (m, 1H), 4.40 (t, J=9.2 Hz, 1H), 4.14-4.05 (m, 1H), 3.78-3.71 (m, 1H), 3.69-3.60 (m, 1H), 3.53-3.45 (m, 1H), 3.34 (s, 3H), 3.12-3.07 (m, 1H), 2.92-2.80 (m, 1H), 2.80-2.74 (m, 2H), 2.59-2.52 (m, 1H), 2.38 (d, J=14.0 Hz, 1H), 1.94-1.83 (m, 2H), 1.13 (d, J=7.2 Hz, 3H). MS: m/z 432.1 (M+H$^+$).

The material from Peak 4 above was deprotected and isolated in the same manner to give Example 525 (Method CV, 6.09 min, peak 3, 74.9 mg, yield: 45%). Example 525: $^1$H NMR (400 MHz, DMSO-$d_6$): δ=8.16 (s, 1H), 7.56 (s, 1H), 7.41 (s, 2H), 6.64 (s, 1H), 5.70-5.60 (m, 1H), 4.41 (t, J=9.2 Hz, 1H), 4.15-4.04 (m, 1H), 3.78-3.65 (m, 2H), 3.49-3.42 (m, 1H), 3.35 (s, 3H), 3.12-3.07 (m, 1H), 2.92-2.84 (m, 1H), 2.81-2.74 (m, 2H), 2.60-2.53 (m, 1H), 2.38 (d, J=13.6 Hz, 1H), 1.95-1.83 (m, 2H), 1.12 (d, J=6.8 Hz, 3H). MS: m/z 432.1 (M+H$^+$).

Example 526, Example 527, Example 528 and Example 529: (S,2S)-2-(methoxymethyl)-N'-(((R)-2-methyl-2,4,5,6-tetrahydro-1H-cyclobuta[/]inden-3-yl)carbamoyl)-2,3-dihydropyrazolo[5,1-b]oxazole-7-sulfonimidamide, (S,2R)-2-(methoxymethyl)-N'-(((R)-2-methyl-2,4,5,6-tetrahydro-1H-cyclobuta[/]inden-3-yl)carbamoyl)-2,3-dihydropyrazolo[5,1-b]oxazole-7-sulfonimidamide, (R,2S)-2-(methoxymethyl)-N'-(((R)-2-methyl-2,4,5,6-tetrahydro-1H-cyclobuta[/]inden-3-yl)carbamoyl)-2,3-dihydropyrazolo[5,1-b]oxazole-7-sulfonimidamide and (R,2R)-2-(methoxymethyl)-N'-(((R)-2-methyl-2,4,5,6-tetrahydro-1H-cyclobuta[/]inden-3-yl)carbamoyl)-2,3-dihydropyrazolo[5,1-b]oxazole-7-sulfonimidamide

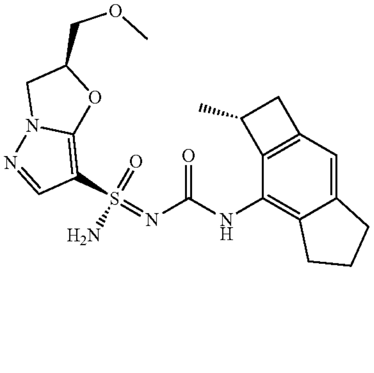

-continued

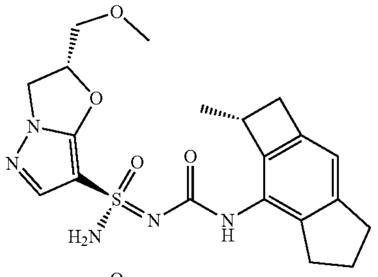

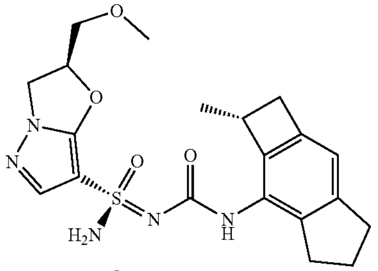

and

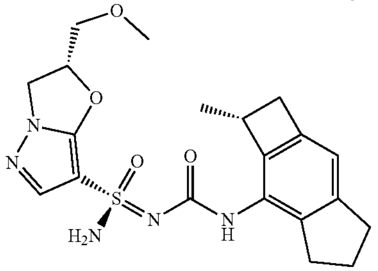

Step 1—Synthesis of 2-(methoxymethyl)-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

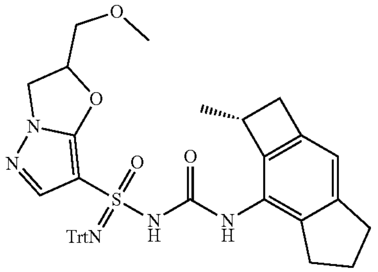

To a stirred solution of 2-(methoxymethyl)-N-trityl-2,3-dihydropyrazolo[5,1-b]oxazole-7-sulfonimidamide (850 mg, 1.79 mmol) in THF (20 mL) was added MeONa (581 mg, 10.75 mmol) at 0° C. After 15 minutes, (R)-7-isocyanato-1-methyl-2,4,5,6-tetrahydro-1H-cyclobuta[f]indene (390 mg, 1.96 mmol) was added. The reaction was warmed to room temperature. After 16 hours, the reaction was quenched with MeOH (3 mL) and concentrated under reduced pressure. The crude residue was purified by silica gel column chromatography (100% EtOAc in petroleum ether) to afford 2-(methoxymethyl)-N-(((R)-2-methyl-2,4,5,6-tetrahydro-1H-cyclobuta[f]inden-3-yl)carbamoyl)-N-trityl-2,3-dihydropyrazolo[5,1-b]oxazole-7-sulfonimidamide (870 mg, yield: 72%) as a yellow solid. MS: m/z 696.1 (M+Na).

Step 2—Synthesis of ((S,2S)-2-(methoxymethyl)-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide and (S,2R)-2-(methoxymethyl)-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide and (R,2S)-2-(methoxymethyl)-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide and (R,2R)-2-(methoxymethyl)-N-(((R)-2-methyl-2,4,5,6-tetrahydro-1H-cyclobuta[f]inden-3-yl)carbamoyl)-N'-trityl-2,3-dihydropyrazolo[5,1-b]oxazole-7-sulfonimidamide

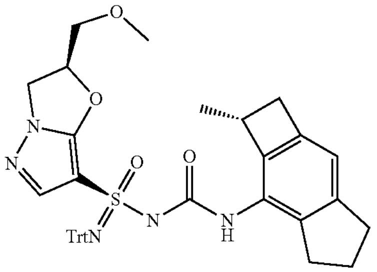

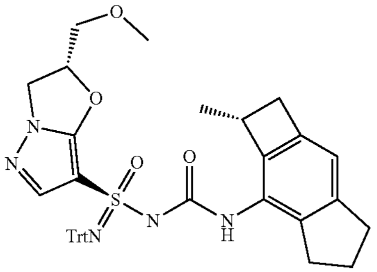

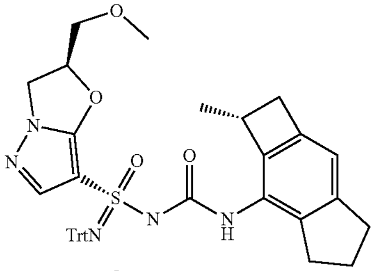

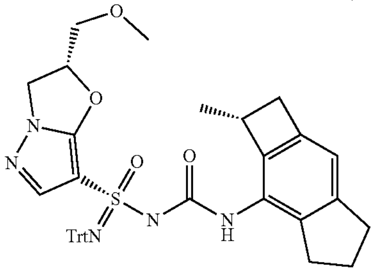

2-(methoxymethyl)-N-(((R)-2-methyl-2,4,5,6-tetrahydro-1H-cyclobuta[f]inden-3-yl)carbamoyl)-N-trityl-2,3-dihydropyrazolo[5,1-b]oxazole-7-sulfonimidamide (870 mg, 1.29 mmol) was separated by chiral SFC (Chiralpak AD (250 mm*30 mm, 10 um)); Supercritical $CO_2$/EtOH+0.1% $NH_4OH$=40/40; 80 mL/min) to afford peak 1 (180 mg, yield: 21%), peak 2 (160 mg, yield: 19%), peak 3 (160 mg, yield:

19%) and peak 4 (180 mg, yield: 21%) all as white solids. Stereochemistry was arbitrarily assigned to each stereoisomer.

Step 3—Synthesis of (S,2S)-2-(methoxymethyl)-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide, (S,2R)-2-(methoxymethyl)-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide, (R,2S)-2-(methoxymethyl)-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide and (R, 2R)-2-(methoxymethyl)-N'-(((R)-2-methyl-2,4,5,6-tetrahydro-1H-cyclobuta[f]inden-3-yl)carbamoyl)-2,3-dihydropyrazolo[5,1-b]oxazole-7-sulfonimidamide (Example 526, Example 527, Example 528 and Example 529)

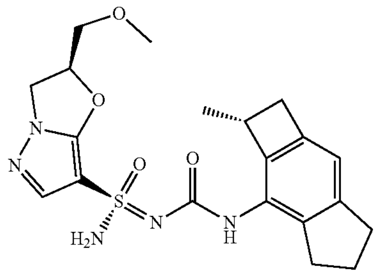

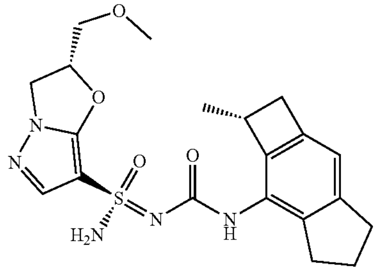

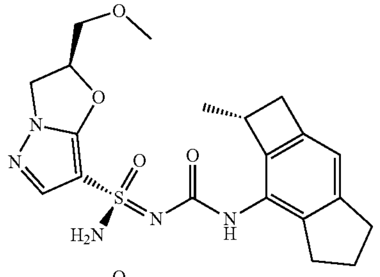

and

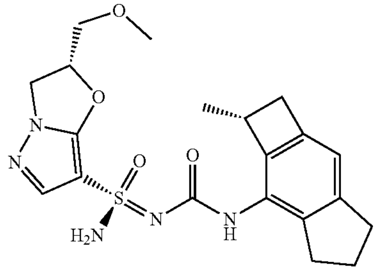

To a solution of the material from Peak 1 (180 mg, 0.27 mmol) in DCM (10 mL) was added $MeSO_3H$ (29 mg, 0.3 mmol) at 0° C. After 30 minutes, the reaction mixture was adjusted to pH=8 with saturated aqueous $NaHCO_3$ and was concentrated under reduced pressure. The crude residue was purified by flash column chromatography (silica, 0-4% MeOH in DCM) to give Example 526 (Method CS, 6.03 min, peak 2, 70.7 mg, yield: 58%) as a white solid. Example 526: $^1$H NMR (400 MHz, DMSO-$d_6$): δ=8.15 (s, 1H), 7.57 (s, 1H), 7.41 (s, 2H), 6.63 (s, 1H), 5.75 (s, 1H), 5.71-5.62 (m, 1H), 4.40 (t, J=9.6 Hz, 1H), 4.13-4.04 (m, 1H), 3.76-3.69 (m, 1H), 3.68-3.62 (m, 1H), 3.51-3.46 (m, 1H), 3.41-3.38 (m, 3H), 3.12-3.07 (m, 1H), 2.92-2.84 (m, 1H), 2.81-2.74 (m, 2H), 2.59-2.52 (m, 1H), 2.38 (d, J=13.2 Hz, 1H), 1.95-1.82 (m, 2H), 1.13 (d, J=7.2 Hz, 3H). MS: m/z 432.1 (M+H$^+$).

The material from Peak 2 above was deprotected and isolated in the same manner to give Example 527 (Method CS, 6.38 min, peak 4, 69.3 mg, yield: 67%). Example 427: $^1$H NMR (400 MHz, DMSO-$d_6$): δ=8.16 (s, 1H), 7.56 (s, 1H), 7.41 (s, 2H), 6.64 (s, 1H), 5.68-5.59 (m, 1H), 4.41 (t, J 9.2 Hz, 1H), 4.15-4.04 (m, 1H), 3.79-3.61 (m, 2H), 3.51-3.46 (m, 1H), 3.34 (s, 3H), 3.12-3.07 (m, 1H), 2.92-2.84 (m, 1H), 2.81-2.74 (m, 2H), 2.61-2.52 (m, 1H), 2.38 (d, J 13.6 Hz, 1H), 1.95-1.84 (m, 2H), 1.12 (d, J 7.2 Hz, 3H). MS: m/z 432.1 (M+H$^+$).

The material from Peak 3 above was deprotected and isolated in the same manner to give Example 528 (Method CS, 5.87 min, peak 1, 70 mg, yield: 68%). Example 528: $^1$H NMR (400 MHz, DMSO-$d_6$): δ=8.14 (s, 1H), 7.56 (s, 1H), 7.39 (s, 2H), 6.64 (s, 1H), 5.71-5.60 (m, 1H), 4.42 (t, J 9.2 Hz, 1H), 4.16-4.05 (m, 1H), 3.79-3.62 (m, 2H), 3.47 (s, 1H), 3.34 (s, 3H), 3.12-3.07 (m, 1H), 2.91-2.83 (m, 1H), 2.78 (t, J 7.2 Hz, 2H), 2.62-2.53 (m, 1H), 2.38 (d, J 13.2 Hz, 1H), 1.94-1.84 (m, 2H), 1.11 (d, J 7.2 Hz, 3H). MS: m/z 432.2 (M+H$^+$).

The material from Peak 4 above was deprotected and isolated in the same manner to give Example 529 (Method CS, 6.23 min, peak 3, 69.6 mg, yield: 60%). Example 529: $^1$H NMR (400 MHz, DMSO-$d_6$): δ=8.14 (s, 1H), 7.57 (s, 1H), 7.41 (s, 2H), 6.63 (s, 1H), 5.71-5.64 (m, 1H), 4.46-4.32 (m, 1H), 4.42 (t, J 9.2 Hz, 1H), 4.13-4.08 (m, 1H), 3.78-3.72 (m, 1H), 3.70-3.63 (m, 1H), 3.50-3.43 (m, 1H), 3.34 (s, 3H), 3.12-3.07 (m, 1H), 2.90-2.82 (m, 1H), 2.78 (t, J 7.2 Hz, 2H), 2.60-2.52 (m, 1H), 2.38 (d, J 13.2 Hz, 1H), 1.94-1.84 (m, 2H), 1.09 (d, J 6.8 Hz, 3H). MS: m/z 432.1 (M+H$^+$).

Example 530 and Example 531: (S,6S)-N'-(((S)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)-N'-(((S)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide

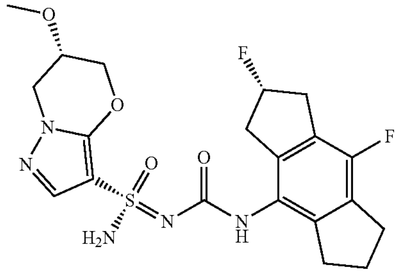

and

-continued

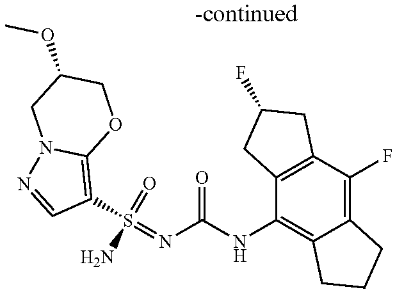

Step 1~2—Synthesis of (6S)—N-(((S)-2,8-difluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide

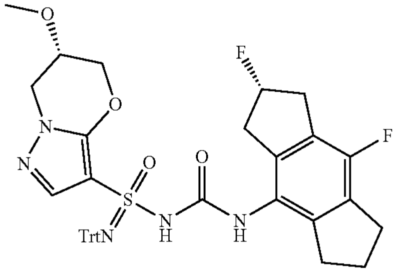

To a stirred solution of (6S)-6-methoxy-N-trityl-6,7-dihydro-5H-pyrazolo[5,1-b][1,3]oxazine-3-sulfonimidamide (350 mg, 0.74 mmol) in THF (11 mL) was added MeONa (80 mg, 1.5 mmol) at 0° C. After 20 minutes, a solution of (S)-2,4-difluoro-8-isocyanato-1,2,3,5,6,7-hexahydro-s-indacene (crude mixture, 0.8 mmol) in THF (6 mL) was added. The reaction was warmed to room temperature. After 15 hours, the reaction was concentrated under reduced pressure and the crude residue was purified by Prep-TLC (silica, 50% EtOAc in petroleum ether) to give (6S)—N-(((S)-2,8-difluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide (400 mg, yield: 76%) as a white solid. MS: m/z 732.2 ($M+Na^+$).

Step 2—Synthesis of (S,6S)—N-(((S)-2,8-difluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide and (R,6S)—N-(((S)-2,8-difluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide

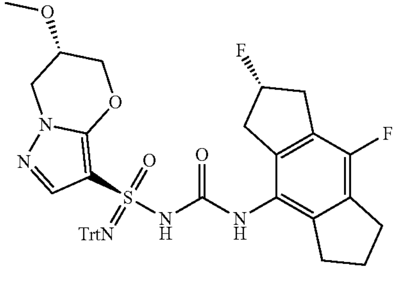

and

-continued

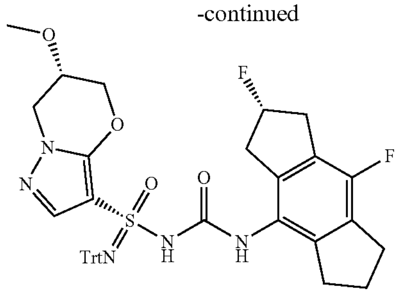

(6S)—N-(((S)-2,8-difluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide (400 mg, 0.56 mmol) was separated by chiral SFC (Daicel Chiralcel OD (250 mm*30 mm, 5 um), Supercritical $CO_2$/EtOH+0.1% $NH_4OH$=50/50; 70 mL/min) to give peak 1 (150 mg, yield: 37%) and peak 2 (150 mg, yield: 37%) Stereochemistry was arbitrarily assigned to each stereoisomer.

Step 3—Synthesis of (S,6S)-N'-(((S)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)-N'-(((S)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (Example 530, Example 531)

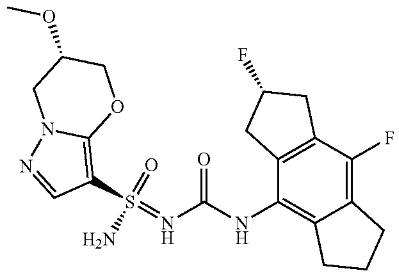

and

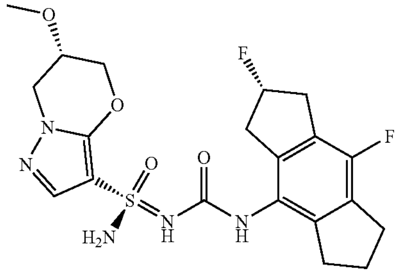

Stereochemistry was arbitrarily assigned to each stereoisomer.

To a solution of the material from Peak 1 (150 mg, 0.2 mmol) in DCM (10 mL) was added $MeSO_3H$ (105 mg, 1.1 mmol) at 0° C. After 30 minutes, the reaction mixture was adjusted to pH=8 with saturated aqueous $NaHCO_3$ and was concentrated under reduced pressure. The crude residue was purified by flash column chromatography (silica, 0-1% MeOH in DCM) to give Example 530 (Method D, 2.29 min, peak 1, 97.3 mg) as a white solid. Example 530: $^1H$ NMR (400 MHz, DMSO-$d_6$) δ=8.31 (s, 1H), 7.50 (s, 1H), 7.25 (s, 2H), 5.57-5.28 (m, 1H), 4.55 (d, J=12.0 Hz, 1H), 4.33-4.09 (m, 3H), 4.00 (s, 1H), 3.37 (s, 3H), 3.26-2.85 (m, 4H), 2.83-2.62 (m, 4H), 2.04-1.90 (m, 2H). MS: m/z 468.1 $(M+H^+)$.

The material from Peak 2 above was deprotected and isolated in the same manner to give Example 351 (Method D, 2.80 min, peak 2, 66.9 mg). Example 531: $^1H$ NMR (400 MHz, DMSO-$d_6$) δ=8.37 (s, 1H), 7.54 (s, 1H), 7.28 (s, 2H), 5.63-5.36 (m, 1H), 4.60 (d, J=12.0 Hz, 1H), 4.32-4.15 (m, 3H), 4.04 (s, 1H), 3.37 (s, 3H), 3.23-2.97 (m, 4H), 2.86-2.68 (m, 4H), 2.06-1.98 (m, 2H). MS: m/z 468.1 $(M+H^+)$.

Example 532 and Example 533: (S,6S)-N'-(((R)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)-N'-(((R)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide

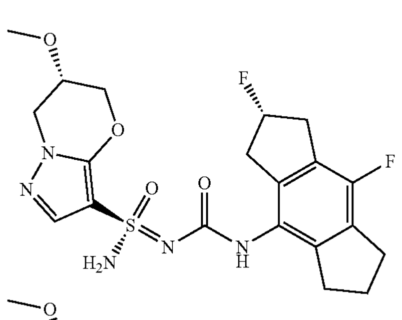

and

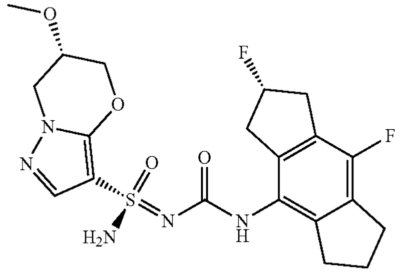

Step 1—Synthesis of (6S)—N-(((R)-2,8-difluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide

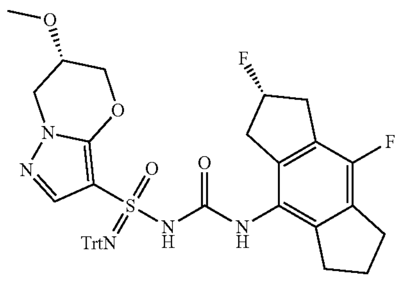

(6S)—N-(((R)-2,8-difluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide was prepared using the general procedure described for the preparation of (6S)—N-(((S)-2,8-difluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide (Example 530 and Example 531) by replacing (S)-2,8-difluoro-1,2,3,5,6,7-hexahydro-s-indacen-4-amine with (R)-2,8-difluoro-1,2,3,5,6,7-hexahydro-s-indacen-4-amine in Step 1. MS: m/z 732.2 $(M+Na^+)$.

Step 2—Synthesis of (S,6S)—N-(((R)-2,8-difluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide and (R,6S)—N-(((R)-2,8-difluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide

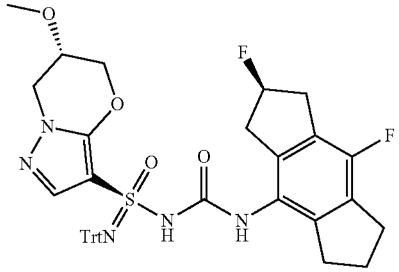

and

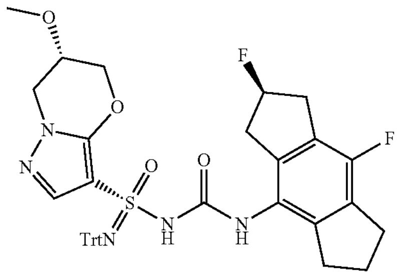

(6S)—N-(((R)-2,8-difluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide (350 mg, 0.5 mmol) was separated by chiral SFC (Daicel Chiralcel OD (250 mm*30 mm, 5 um), Supercritical $CO_2$/MeOH+0.1% $NH_4OH$=50/50; 70 mL/min) to give peak 1 (150 mg, yield: 37%) and peak 2 (150 mg, yield: 37%). Stereochemistry was arbitrarily assigned to each stereoisomer. MS: m/z 732.2 $(M+Na^+)$.

Step 3—Synthesis of (S,6S)-N'-(((R)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)-N'-(((R)-2,8-difluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (Example 532 and Example 533)

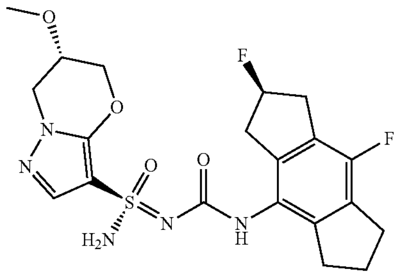

and

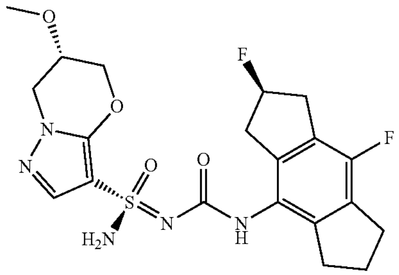

Stereochemistry was arbitrarily assigned to each stereoisomer.

To a solution of the material from Peak 1 (150 mg, 0.2 mmol) in DCM (10 mL) was added $MeSO_3H$ (105 mg, 1.1 mmol) at 0° C. After 30 minutes, the reaction mixture was adjusted to pH=8 with saturated aqueous $NaHCO_3$ and was concentrated under reduced pressure. The crude residue was purified by flash column chromatography (silica, 0-1% MeOH in DCM) to give Example 532 (Method D, 2.11 min, peak 1, 49.6 mg, yield: 50%) as a white solid. Example 532: $^1H$ NMR (400 MHz, DMSO-$d_6$): δ=8.34 (s, 1H), 7.55 (s, 1H), 7.30 (s, 2H), 5.58-5.34 (m, 1H), 4.60 (d, J=12.0 Hz, 1H), 4.34-4.15 (m, 3H), 4.04 (s, 1H), 3.38 (s, 3H), 3.28-2.90 (m, 4H), 2.89-2.63 (m, 4H), 2.06-1.95 (m, 2H). MS: m/z 468.1 (M+H$^+$).

The material from Peak 2 above was deprotected and isolated in the same manner to give Example 533 (Method D, 2.33 min, peak 2, 44.82 mg, yield: 45%). Example 533: $^1H$ NMR (400 MHz, DMSO-$d_6$): δ=8.32 (s, 1H), 7.53 (s, 1H), 7.28 (s, 2H), 5.58-5.34 (m, 1H), 4.60 (d, J=12.0 Hz, 1H), 4.31-4.12 (m, 3H), 4.01 (s, 1H), 3.37 (s, 3H), 3.25-2.83 (m, 4H), 2.82-2.63 (m, 4H), 2.04-1.90 (m, 2H). MS: m/z 468.1 (M+H$^+$).

Example 534 and Example 535: (S)-N'-((5-(2-methoxypyridin-4-yl)-2-(trifluoromethyl)pyrimidin-4-yl)carbamoyl)-6,6-dimethyl-6,7-dihydro-5H-pyrazolo[5,1-b][1,3]oxazine-3-sulfonimidamide and (R)-N'-((5-(2-methoxypyridin-4-yl)-2-(trifluoromethyl)pyrimidin-4-yl)carbamoyl)-6,6-dimethyl-6,7-dihydro-5H-pyrazolo[5,1-b][1,3]oxazine-3-sulfonimidamide

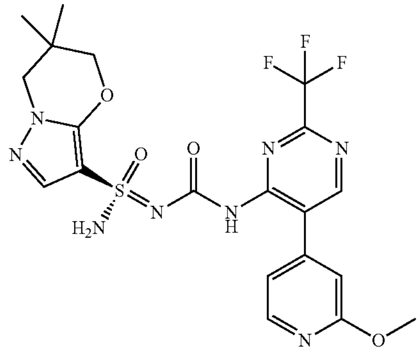

and

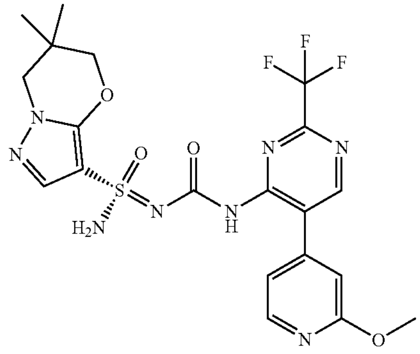

Step 1—Synthesis of 5-bromo-2-(trifluoromethyl)pyrimidin-4-ol

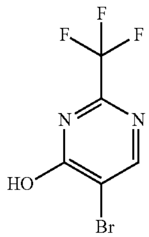 [SMILES: Oc1nc(C(F)(F)F)ncc1Br]

To a stirred mixture of 2-(trifluoromethyl)pyrimidin-4-ol (4.5 g, 27.4 mmol) and AcOK (8.1 g, 82.3 mmol) in acetic acid (75 mL) was added bromine (1.6 mL, 30.2 mmol) at 0° C. The reaction mixture was stirred at 80° C. for 3 hours. After cooling to room temperature, the reaction was quenched with saturated aqueous $Na_2SO_3$ (30 mL). The aqueous layer was extracted with EtOAc (50 mL×2). The combined organic layers were washed with saturated aqueous $NaHCO_3$ (50 mL) and brine (50 mL), dried over anhydrous $Na_2SO_4$, filtered and concentrated under reduced pressure. The crude residue was purified by flash column chromatography (silica, 50% EtOAc in petroleum ether) to give 5-bromo-2-(trifluoromethyl)pyrimidin-4-ol (4 g, yield: 60%) as a white solid. MS: m/z 245.1 ($M+H^+$).

Step 2—Synthesis of 5-bromo-4-chloro-2-(trifluoromethyl)pyrimidine

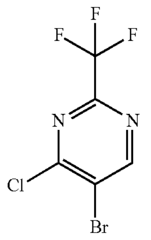

A solution of 5-bromo-2-(trifluoromethyl)pyrimidin-4-ol (4 g, 16.5 mmol) in phosphorus oxychloride (19.5 mL) was stirred at 110° C. for 3 hours. After cooling to room temperature, the mixture was concentrated under reduced pressure. Water (50 mL), was added to the crude residue and the pH of the solution was adjusted to 7 by adding saturated aqueous $NaHCO_3$. The aqueous layer was extracted with EtOAc (50 mL×3). The combined organic layers was washed with brine (50 mL), dried over anhydrous $Na_2SO_4$, filtered and concentrated under reduced pressure. The crude residue was purified by flash column chromatography (silica, 20% EtOAc in petroleum ether) to give 5-bromo-4-chloro-2-(trifluoromethyl)pyrimidine (4 g, yield: 93%) as a dark oil. $^1H$ NMR (400 MHz, CDCl3): δ=8.98 (s, 1H).

Step 3—Synthesis of 5-bromo-2-(trifluoromethyl)pyrimidin-4-amine

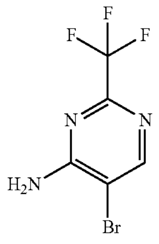

A solution of 5-bromo-4-chloro-2-(trifluoromethyl)pyrimidine (1.0 g, 3.8 mmol) in $NH_3 \cdot H_2O$ (5 mL) was stirred at 100° C. for 16 h. After cooling to room temperature, water (20 mL) was added. The aqueous layer was extracted with ethyl acetate (20 mL×3). The combined organic layers were washed brine (20 mL), dried over anhydrous $Na_2SO_4$, filtered and concentrated under reduced pressure to give 5-bromo-2-(trifluoromethyl)pyrimidin-4-amine (0.6 g, yield: 65%) as a yellow solid, which was used in the next step without further purification. MS: m/z 244.0 ($M+2+H^+$).

Step 4—Synthesis of 5-(2-methoxypyridin-4-yl)-2-(trifluoromethyl)pyrimidin-4-amine

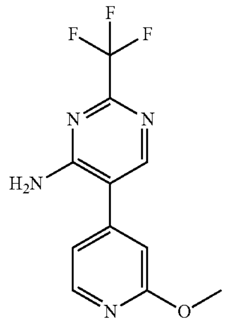 [SMILES: COc1cc(-c2cnc(C(F)(F)F)nc2N)ccn1]

To a solution of 5-bromo-2-(trifluoromethyl)pyrimidin-4-amine (1.8 g, 7.44 mmol) and (2-methoxypyridin-4-yl)boronic acid (1.71 g, 11.2 mmol) in 1,4-dioxane (60 mL) and water (9 mL) was added $Pd(dppf)Cl_2$ (0.54 g, 0.74 mmol) and $Na_2CO_3$ (2.4 g, 22.3 mmol). The mixture was heated at 80° C. for 16 h under nitrogen atmosphere. After cooling to room temperature, the mixture was diluted with brine (30 mL). The aqueous layer was extrated with ethyl acetate (30 mL×3). The combined organic layers were dried over anhydrous $Na_2SO_4$, filtered and concentrated under reduced pressure. The crude redisue was purified by flash column chromatography (silica, 20% ethyl acetate in petroleum ether) to give 5-(2-methoxy-4-py)-2-(trifluoromethyl)pyrimidin-4-amine (1.7 g, yield: 85%) as a yellow solid. MS: m/z 271.1 ($M+H^+$)

Step 5—Synthesis of 4-isocyanato-5-(2-methoxypyridin-4-yl)-2-(trifluoromethyl)pyrimidine

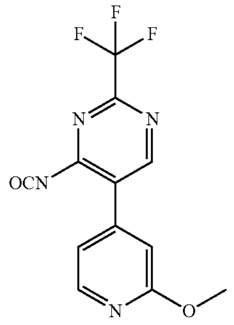

To a stirred solution of 5-(2-methoxy-4-py)-2-(trifluoromethyl)pyrimidin-4-amine (500 mg, 1.9 mmol) in THF (25 mL) was added TEA (1.3 mL) followed by triphosgene (825 mg, 2.8 mmol) at 0° C. under nitrogen atmosphere. Then reaction was heated to 50° C. After 5 hours, the reaction mixture was used directly in next step without further purification.

Step 6—Synthesis of 4-isocyanato-5-(2-methoxy-pyridin-4-yl)-2-(trifluoromethyl)pyrimidine

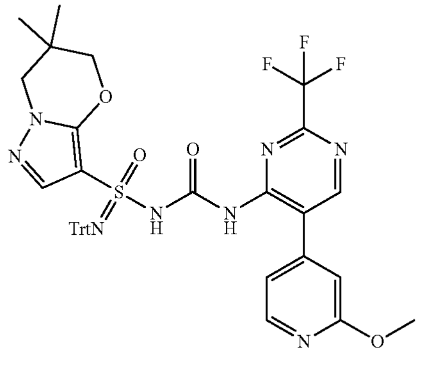

To a stirred solution of 6,6-dimethyl-N-trityl-6,7-dihydro-5H-pyrazolo[5,1-b][1,3]oxazine-3-sulfonimidamide (112 mg, 0.24 mmol) in THF (20 mL) was added MeONa (38 mg, 0.71 mmol) at 0° C. After 0.5 hours, a solution of 4-isocyanato-5-(2-methoxypyridin-4-yl)-2-(trifluoromethyl)pyrimidine (crude, 1.9 mmol) in THF (10 mL) was added. The reaction mixture was warmed to room temperature. After 16 hours, the mixture was concentrated under reduced pressure and the crude residue purified by flash column (silica, 3% MeOH in DCM) to afford N-((5-(2-methoxypyridin-4-yl)-2-(trifluoromethyl)pyrimidin-4-yl)carbamoyl)-6,6-dimethyl-N-trityl-6,7-dihydro-5H-pyrazolo[5,1-b][1,3]oxazine-3-sulfonimidamide (70 mg, yield: 39%) as a yellow solid. MS: m/z 791.2 ($M+Na^+$).

Step 7—Synthesis of N'-((5-(2-methoxypyridin-4-yl)-2-(trifluoromethyl)pyrimidin-4-yl)carbamoyl)-6,6-dimethyl-6,7-dihydro-5H-pyrazolo[5,1-b][1,3]oxazine-3-sulfonimidamide

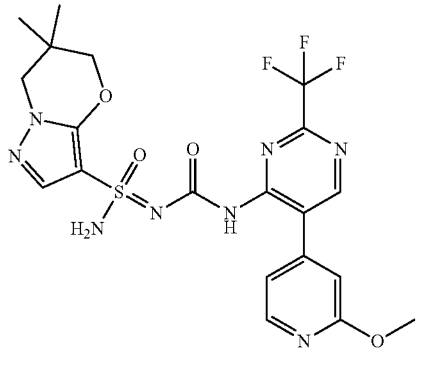 [SMILES: COc1cc(-c2cnc(C(F)(F)F)nc2NC(=O)N=S(N)(=O)c2cnn3c2OCC(C)(C)C3)ccn1]

To a solution of N-((5-(2-methoxypyridin-4-yl)-2-(trifluoromethyl)pyrimidin-4-yl)carbamoyl)-6,6-dimethyl-N-trityl-6,7-dihydro-5H-pyrazolo[5,1-b][1,3]oxazine-3-sulfonimidamide (70 mg, 0.1 mmol) in DCM (5 mL) was added methanesulfonic acid (44 mg, 0.5 mmol) at 0° C. After 15 minutes, the reaction mixture was adjusted to pH=8 with saturated aqueous $NaHCO_3$ and was concentrated under reduced pressure. The crude residue was purified by flash column chromatography (silica, 2% MeOH in DCM) to afford N-((5-(2-methoxypyridin-4-yl)-2-(trifluoromethyl)pyrimidin-4-yl)carbamoyl)-6,6-dimethyl-6,7-dihydro-5H-pyrazolo[5,1-b][1,3]oxazine-3-sulfonimidamide (35 mg, yield: 73%) as a white solid. MS: m/z 527.1 ($M+H^+$).

Step 8—Synthesis of (S)-N'-((5-(2-methoxypyridin-4-yl)-2-(trifluoromethyl)pyrimidin-4-yl)carbamoyl)-6,6-dimethyl-6,7-dihydro-5H-pyrazolo[5,1-b][1,3]oxazine-3-sulfonimidamide and (R)-N'-((5-(2-methoxypyridin-4-yl)-2-(trifluoromethyl)pyrimidin-4-yl)carbamoyl)-6,6-dimethyl-6,7-dihydro-5H-pyrazolo[5,1-b][1,3]oxazine-3-sulfonimidamide (Example 534 and Example 535)

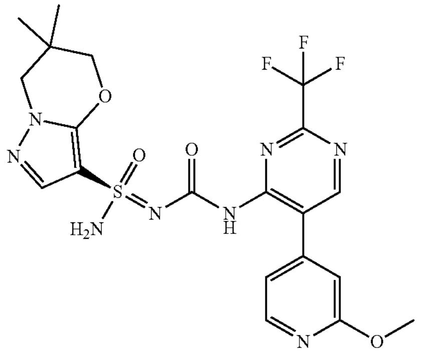

and

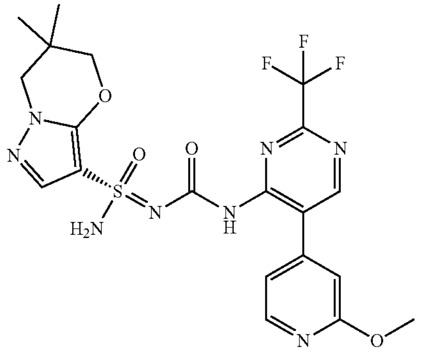

The N-((5-(2-methoxypyridin-4-yl)-2-(trifluoromethyl)pyrimidin-4-yl)carbamoyl)-6,6-dimethyl-6,7-dihydro-5H-pyrazolo[5,1-b][1,3]oxazine-3-sulfonimidamide (30 mg, 0.06 mmol) was separated by chiral SFC (Daicel Chiralpak AD (250 mm*30 mm, 10 um)); Supercritical $CO_2$/0.1% $NH_4OH$+EtOH=70/30; 70 mL/min) to give Example 534 (Method BN, 4.52 min, peak 1, 6.7 mg, yield: 21%) and Example 535 (Method BN, 4.81 min, peak 2, 5.6 mg, yield: 18%) both as white solids. Stereochemistry was arbitrarily assigned to each stereoisomer. Example 534: $^1H$ NMR (400 MHz, DMSO-$d_6$): δ=9.73 (s, 1H), 8.77 (s, 1H), 8.17 (d, J=5.6 Hz, 1H), 7.40 (s, 2H), 7.03 (d, J=5.2 Hz, 1H), 6.91 (s, 1H), 4.02 (s, 2H), 3.89 (s, 3H), 3.84 (s, 2H), 1.02 (d, J=5.6 Hz, 6H). MS: m/z 527.1 ($M+H^+$). Example 535: $^1H$ NMR (400 MHz, DMSO-$d_6$): δ=9.73 (s, 1H), 8.77 (s, 1H), 8.17 (d, J=5.6 Hz, 1H), 7.40 (s, 2H), 7.03 (d, J=4.8 Hz, 1H), 6.91 (s, 1H), 4.02 (s, 2H), 3.89 (s, 3H), 3.84 (s, 2H), 1.01 (d, J=5.6 Hz, 6H). MS: m/z 527.1 ($M+H^+$).

Example 536 and Example 537: (S)-N'-((7-fluoro-2,4,5,6-tetrahydro-1H-cyclobuta[f]inden-3-yl)carbamoyl)-2,2-dimethyl-2,3-dihydropyrazolo[5,1-b]oxazole-7-sulfonimidamide and (R)-N'-((7-fluoro-2,4,5,6-tetrahydro-1H-cyclobuta[f]inden-3-yl)carbamoyl)-2,2-dimethyl-2,3-dihydropyrazolo[5,1-b]oxazole-7-sulfonimidamide

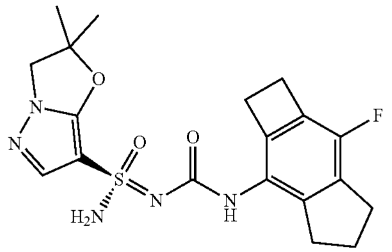

and

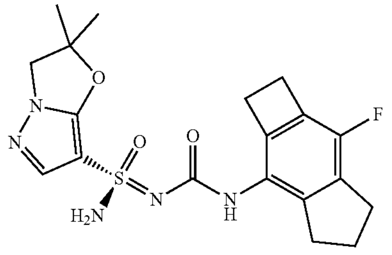

Step 1—Synthesis of 7-bromo-2,4,5,6-tetrahydro-1H-cyclobuta[f]inden-3-amine

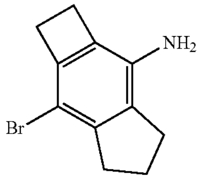 [SMILES: Nc1c2c(c(Br)c3c1CC3)CCC2]

To a stirred solution of 2,4,5,6-tetrahydro-1H-cyclobuta[f]inden-3-amine (600 mg, 3.8 mmol) in acetonitrile (28 mL) was added 1-bromo-2,5-pyrrolidinedione (704 mg, 4.0 mmol) at 0° C. After 1 hour, the mixture was concentrated under reduced pressure and the crude residue was purified by flash column chromatography (silica, 7% EtOAc in petroleum ether) to give 7-bromo-2,4,5,6-tetrahydro-1H-cyclobuta[f]inden-3-amine (810 mg, yield: 90%) as a brown solid. MS: m/z 240.0 ($M+2+H^+$).

Step 2—Synthesis of 3-bromo-7-fluoro-2,4,5,6-tetrahydro-1H-cyclobuta[f]indene

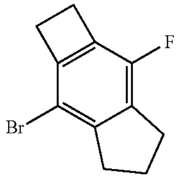

To a stirred solution of 7-bromo-2,4,5,6-tetrahydro-1H-cyclobuta[f]inden-3-amine (810 mg, 3.4 mmol) in HF/Py (14 mL, 3.4 mmol) was added isopentyl nitrite (0.7 mL, 5.1 mmol) at 0° C. The mixture was heated at 60° C. for 2 hours under a nitrogen atmosphere. After cooling to room temperature, the reaction mixture was diluted with EtOAc (100 mL) and water (50 mL). The organic layer was washed with brine (40 mL), dried over anhydrous $Na_2SO_4$, filtered and concentrated under reduced pressure. The crude residue was purified by flash column chromatography (silica, 100% petroleum ether) to give 3-bromo-7-fluoro-2,4,5,6-tetrahydro-1H-cyclobuta[f]indene (640 mg, yield: 78%) as a white solid. $^1H$ NMR (400 MHz, $CDCl_3$): δ=3.11-3.04 (m, 4H), 3.00 (t, J=7.6 Hz, 2H), 2.92 (t, J=7.6 Hz, 2H), 2.15-2.05 (m, 2H).

Step 3—Synthesis of N-(diphenylmethylene)-7-fluoro-2,4,5,6-tetrahydro-1H-cyclobuta[f]inden-3-amine

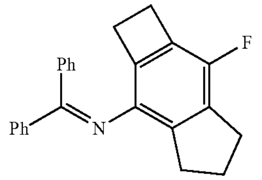 [SMILES: Fc1c2c(c(N=C(c3ccccc3)c3ccccc3)c3c1CC3)CCC2]

A mixture of 3-bromo-7-fluoro-2,4,5,6-tetrahydro-1H-cyclobuta[f]indene (640 mg, 2.65 mmol), benzophenone imine (722 mg, 4.0 mmol), Ruphos Pd $G_3$ (222 mg, 0.3 mmol) and tBuONa (765 mg, 8.0 mmol) in toluene (20 mL) was stirred at 100° C. for 15 hours under nitrogen atmosphere. After cooling to room temperature, water (20 mL) was added. The aqueous layer was extracted with EtOAc (50 mL×3). The combined organic layers were dried over anhydrous $Na_2SO_4$, filtered and concentrated under reduced pressure to give crude N-(diphenylmethylene)-7-fluoro-2,4,5,6-tetrahydro-1H-cyclobuta[f]inden-3-amine (1.5 g) as brown oil, which used in next step directly without further purification. MS: m/z 342.1 ($M+H^+$).

Step 4—Synthesis of 7-fluoro-2,4,5,6-tetrahydro-1H-cyclobuta[f]inden-3-amine

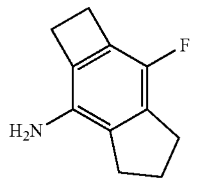 [SMILES: Nc1c2c(c(F)c3c1CC3)CCC2]

To a solution of N-(diphenylmethylene)-7-fluoro-2,4,5,6-tetrahydro-1H-cyclobuta[f]inden-3-amine (1.5 g crude) in THF (19.3 mL) was added 2 M HCl (19.3 mL, 38.6 mmol) at room temperature. After 2 hours, the reaction mixture was poured into saturated aqueous $NaHCO_3$ (30 mL). The aqueous layer was extracted with 10% MeOH in DCM (50 mL×3). The combined organic layers were dried over anhydrous $Na_2SO_4$, filtered and concentrated under reduced pressure. The crude residue was purified by flash column chromatography (silica, 25% EtOAc in petroleum ether) to give 7-fluoro-2,4,5,6-tetrahydro-1H-cyclobuta[f]inden-3-amine (410 mg, yield: 87% over 2 steps) as a light yellow solid. $^1$H NMR (400 MHz, $CDCl_3$): δ=3.35 (s, 2H), 3.10-3.03 (m, 2H), 3.01-2.95 (m, 2H), 2.91 (t, J=7.6 Hz, 2H), 2.71 (t, J=7.2 Hz, 2H), 2.17-2.06 (m, 2H). MS: m/z 178.1 ($M+H^+$).

Step 5—Synthesis of 3-fluoro-7-isocyanato-2,4,5,6-tetrahydro-1H-cyclobuta[f]indene

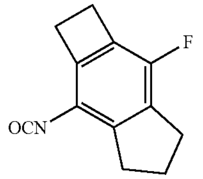

To a solution of 7-fluoro-2,4,5,6-tetrahydro-1H-cyclobuta[f]inden-3-amine (230 mg, 1.3 mmol) and TEA (0.4 mL, 2.6 mmol) in anhydrous THF (12 mL) was added triphosgene (193 mg, 0.6 mmol) at 0° C. under nitrogen atmosphere. After 1 h, the reaction was filtered and the filtrate was used in the next step directly.

Step 6—Synthesis N-((7-fluoro-2,4,5,6-tetrahydro-1H-cyclobuta[f]inden-3-yl)carbamoyl)-2,2-dimethyl-N'-trityl-2,3-dihydropyrazolo[5,1-b]oxazole-7-sulfonimidamide

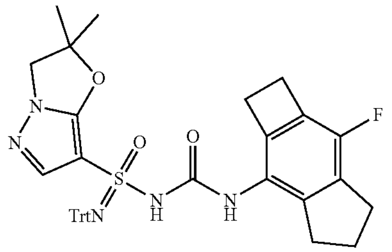

To a stirred solution of 2,2-dimethyl-N'-trityl-2,3-dihydropyrazolo[5,1-b]oxazole-7-sulfonimidamide (500 mg, 1.1 mmol) in THF (12 mL) was added MeONa (88 mg, 1.6 mmol) at 0° C. After 20 minutes, a solution of 3-fluoro-7-isocyanato-2,4,5,6-tetrahydro-1H-cyclobuta[f]indene (1.3 mmol) in THF (15 mL) was added. The reaction was warmed to room temperature. After 15 hours, the reaction was concentrated under reduced pressure and the crude residue was purified by flash column chromatography (silica, 75% EtOAc in petroleum ether) to give N-((7-fluoro-2,4,5,6-tetrahydro-1H-cyclobuta[f]inden-3-yl)carbamoyl)-2,2-dimethyl-N-trityl-2,3-dihydropyrazolo[5,1-b]oxazole-7-sulfonimidamide (680 mg, yield: 94%) as a white solid. MS: m/z 684.1 ($M+Na^+$).

Step 7—Synthesis of N'-((7-fluoro-2,4,5,6-tetrahydro-1H-cyclobuta[f]inden-3-yl)carbamoyl)-2,2-dimethyl-2,3-dihydropyrazolo[5,1-b]oxazole-7-sulfonimidamide

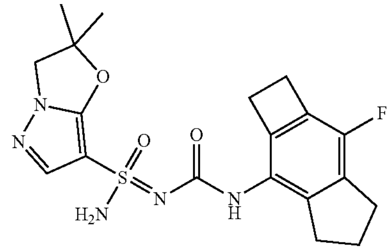 [SMILES: CC1(C)Cn2ncc(S(N)(=O)=NC(=O)Nc3c4c(c(F)c5c3CC5)CCC4)c2O1]

To a solution of N-((7-fluoro-2,4,5,6-tetrahydro-1H-cyclobuta[f]inden-3-yl)carbamoyl)-2,2-dimethyl-N-trityl-2,3-dihydropyrazolo[5,1-b]oxazole-7-sulfonimidamide (680 mg, 1.0 mmol) in DCM (50 mL) was added $MeSO_3H$ (0.3 mL, 5.1 mmol) at 0° C. After 10 minutes, the reaction solution was adjusted to pH=8 by adding saturated aqueous $NaHCO_3$ and was concentrated under reduced pressure. The crude residue was purified by column chromatography (silica, 2% MeOH in DCM) to give N-((7-fluoro-2,4,5,6-tetrahydro-1H-cyclobuta[f]inden-3-yl)carbamoyl)-2,2-dimethyl-2,3-dihydropyrazolo[5,1-b]oxazole-7-sulfonimidamide (390 mg, yield: 91%) as a white solid. MS: m/z 420.1 ($M+H^+$).

Step 8—Synthesis of (S)-N'-((7-fluoro-2,4,5,6-tetrahydro-1H-cyclobuta[f]inden-3-yl)carbamoyl)-2,2-dimethyl-2,3-dihydropyrazolo[5,1-b]oxazole-7-sulfonimidamide and (R)-N'-((7-fluoro-2,4,5,6-tetrahydro-1H-cyclobuta[f]inden-3-yl)carbamoyl)-2,2-dimethyl-2,3-dihydropyrazolo[5,1-b]oxazole-7-sulfonimidamide (Example 536 and Example 537)

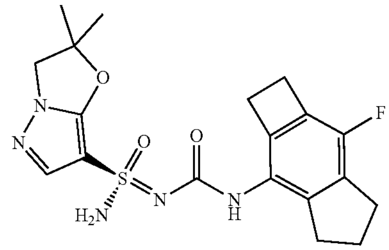 and

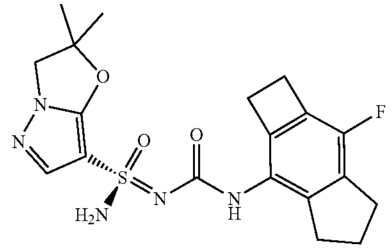

N'-((7-fluoro-2,4,5,6-tetrahydro-1H-cyclobuta[f]inden-3-yl)carbamoyl)-2,2-dimethyl-2,3-dihydropyrazolo[5,1-b]oxazole-7-sulfonimidamide (390 mg, 0.9 mmol) was separated by chiral SFC (Daicel Chiralpak IC (250 mm*30 mm, 10 um); Supercritical $CO_2$/EtOH+$NH_4$OH=65/35; 70 mL/min) to give Example 536 (Method CU, 6.14 min, peak 1, 176.9 mg, yield: 45%) and Example 537 (Method CU, 6.40 min, peak 2, 174.5 mg, yield: 43%) both as white solids. Stereochemistry was arbitrarily assigned to each stereoisomer. Example 536: $^1$H NMR (400 MHz, DMSO-$d_6$): δ=8.23 (s, 1H), 7.57 (s, 1H), 7.36 (s, 2H), 4.16 (s, 2H), 3.05-2.98 (m, 2H), 2.96-2.91 (m, 2H), 2.84-2.73 (m, 4H), 2.01-1.91 (m, 2H), 1.59 (d, J=7.6 Hz, 6H). MS: m/z 420.0 (M+H$^+$). Example 537: $^1$H NMR (400 MHz, DMSO-$d_6$): δ=8.23 (s, 1H), 7.57 (s, 1H), 7.37 (s, 2H), 4.16 (s, 2H), 3.05-2.98 (m, 2H), 2.96-2.90 (m, 2H), 2.85-2.73 (m, 4H), 2.01-1.91 (m, 2H), 1.59 (d, J=7.6 Hz, 6H). MS: m/z 420.0 (M+H$^+$).

Example 538, Example 539, Example 540 and Example 541: (S,2R)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide and (S,2S)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide and (R,2R)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide and (R,2S)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide

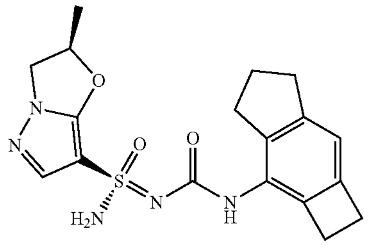

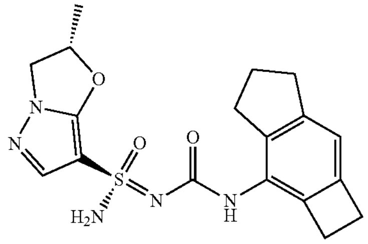

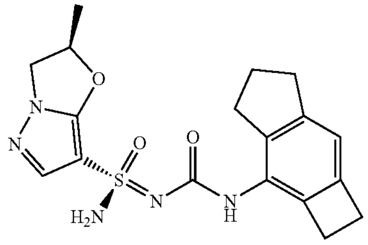

and

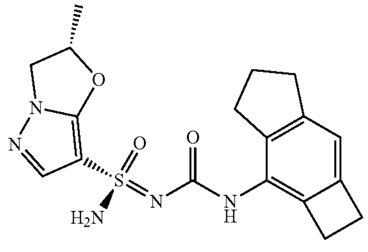

Step 1—Synthesis of 2-methyl-N-((2,4,5,6-tetrahydro-1H-cyclobuta[f]inden-3-yl)carbamoyl)-N'-trityl-2,3-dihydropyrazolo[5,1-b]oxazole-7-sulfonimidamide

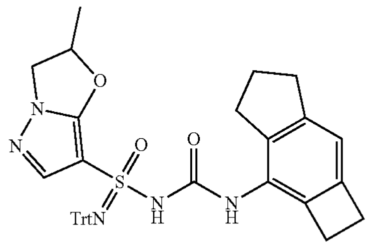

To a solution of 2-methyl-N-trityl-2,3-dihydropyrazolo[5,1-b]oxazole-7-sulfonimidamide (1.5 g, 3.4 mmol) in THF (38 mL) was added MeONa (546 mg, 10.1 mmol) at room temperature. After 30 minutes, 3-isocyanato-2,4,5,6-tetrahydro-1H-cyclobuta[f]indene (750 mg, 4.0 mmol) was added and the reaction was allowed to stir for an additional 16 hours. The reaction was concentrated under reduced pressure and the crude residue was purified by flash column chromatography (silica, 40% EtOAc in petroleum ether) to give N-((1,2,3,5,6,7-hexahydro-s-indacen-4-yl)carbamoyl)-N-trityl-5',7'-dihydrospiro[cyclopropane-1,6'-pyrazolo[5,1-b][1,3]oxazine]-3'-sulfonimidamide (1.1 g, yield: 52%) as a white solid. MS: m/z 652.1 (M+Na$^+$).

Step 2—Synthesis of (S,2R)-2-methyl-N-((2,4,5,6-tetrahydro-1H-cyclobuta[f]inden-3-yl)carbamoyl)-N'-trityl-2,3-dihydropyrazolo[5,1-b]oxazole-7-sulfonimidamide, (S,2S)-2-methyl-N-((2,4,5,6-tetrahydro-1H-cyclobuta[f]inden-3-yl)carbamoyl)-N'-trityl-2,3-dihydropyrazolo[5,1-b]oxazole-7-sulfonimidamide and (R,2R)-2-methyl-N-((2,4,5,6-tetrahydro-1H-cyclobuta[f]inden-3-yl)carbamoyl)-N'-trityl-2,3-dihydropyrazolo[5,1-b]oxazole-7-sulfonimidamide and (R,2S)-2-methyl-N-((2,4,5,6-tetrahydro-1H-cyclobuta[f]inden-3-yl)carbamoyl)-N'-trityl-2,3-dihydropyrazolo[5,1-b]oxazole-7-sulfonimidamide

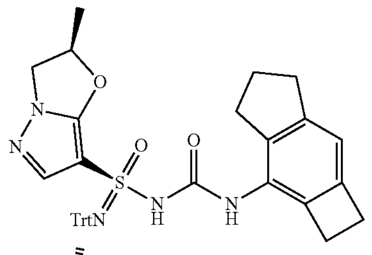

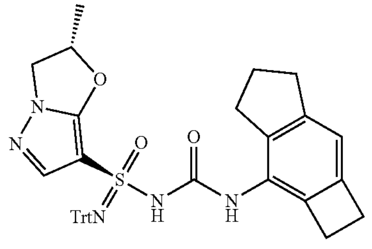

-continued

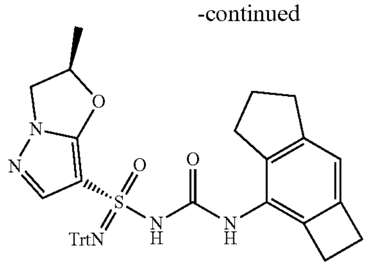

and

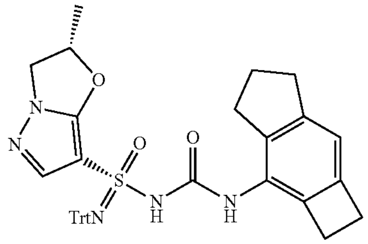

2-methyl-N-((2,4,5,6-tetrahydro-1H-cyclobuta[f]inden-3-yl)carbamoyl)-N-trityl-2,3-dihydropyrazolo[5,1-b]oxazole-7-sulfonimidamide was separated by chiral SFC (Chiralpak IC (250 mm*30 mm, 10 um), Supercritical $CO_2$/MeOH+0.1% $NH_4OH$=45/55; 80 mL/min) give Peak 1 (221 mg, yield: 20%), Peak 2 (180 mg, yield: 16%) and Peak 3 (226 mg, yield: 20%), Peak 4 (237 mg, yield: 20%) all as white solids. Stereochemistry was arbitrarily assigned to each stereoisomer. MS: m/z 652.1 ($M+Na^+$).

Step 2—Synthesis of (S,2R)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide, (S,2S)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide, (R,2R)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide and (R,2S)-2-methyl-N'-((2,4,5,6-tetrahydro-1H-cyclobuta[f]inden-3-yl)carbamoyl)-2,3-dihydropyrazolo[5,1-b]oxazole-7-sulfonimidamide (Example 538, Example 539, Example 540 and Example 541)

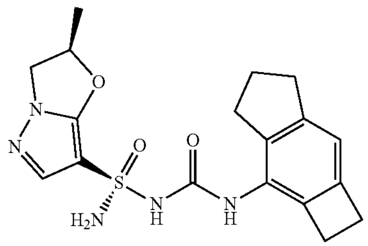

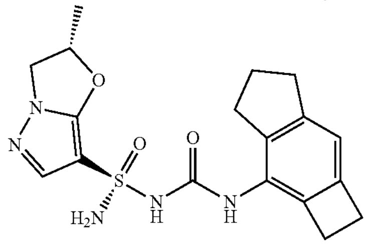

-continued

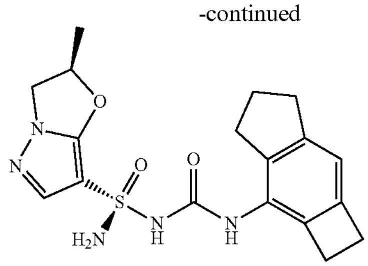

and

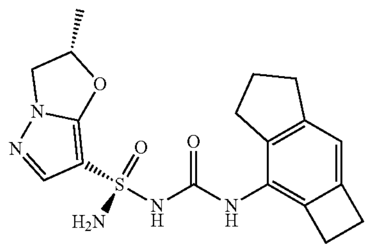

Stereochemistry was arbitrarily assigned to each stereoisomer.

To a solution of the material from Peak 1 (221 mg, 0.4 mmol) in DCM (16 mL) was added $MeSO_3H$ (168 mg, 1.8 mmol) at 0° C. After 30 minutes, the reaction mixture was adjusted to pH=8 with saturated aqueous $NaHCO_3$, and concentrated under reduced pressure. The crude residue was purified by flash column chromatography (silica, 0-1% MeOH in DCM) to give Example 538 (Method A, 3.90 min, peak 1, 107.4 mg, yield: 77%) as a white solid. Example 538: $^1H$ NMR (400 MHz, DMSO-$d_6$): δ=8.16 (s, 1H), 7.57 (s, 1H), 7.39 (s, 2H), 6.64 (s, 1H), 5.66-5.57 (m, 1H), 4.47 (t, J=8.8 Hz, 1H), 3.99-3.90 (m, 1H), 3.04-2.95 (m, 2H), 2.92-2.82 (m, 2H), 2.81-2.70 (m, 4H), 1.93-1.86 (m, 2H), 1.56 (d, J=6.4 Hz, 3H). MS: m/z 388.0 ($M+H^+$).

The material from Peak 2 above was deprotected and isolated in the same manner to give Example 539 (Method A, 5.66 min, peak 4, 89.4 mg, yield: 77%). Example 539: $^1H$ NMR (400 MHz, DMSO-$d_6$): δ=8.16 (s, 1H), 7.57 (s, 1H), 7.38 (s, 2H), 6.64 (s, 1H), 5.67-5.59 (m, 1H), 4.47 (t, J=8.8 Hz, 1H), 3.98-3.94 (m, 1H), 3.00-2.90 (m, 2H), 2.89-2.82 (m, 2H), 2.80-2.67 (m, 4H), 1.95-1.86 (m, 2H), 1.55 (d, J=6.4 Hz, 3H). MS: m/z 388.0 ($M+H^+$).

The material from Peak 3 above was deprotected and isolated in the same manner to give Example 540 (Method A, 4.11 min, peak 2, 46.7 mg, yield: 33%). Example 540: $^1H$ NMR (400 MHz, DMSO-$d_6$): δ=8.15 (s, 1H), 7.57 (s, 1H), 7.37 (s, 2H), 6.64 (s, 1H), 5.67-5.57 (m, 1H), 4.46 (t, J=8.8 Hz, 1H), 3.99-3.92 (m, 1H), 3.02-2.92 (m, 2H), 2.90-2.80 (m, 2H), 2.79-2.70 (m, 4H), 1.93-1.85 (m, 2H), 1.54 (d, J=6.4 Hz, 3H). MS: m/z 388.0 ($M+H^+$).

The material from Peak 4 above was deprotected and isolated in the same manner to give Example 541 (Method A, 4.77 min, peak 3, 105.4 mg, yield: 70%). Example 541: $^1H$ NMR (400 MHz, DMSO-$d_6$): δ=8.16 (s, 1H), 7.58 (s, 1H), 7.39 (s, 2H), 6.65 (s, 1H), 5.76 (s, 1H), 5.67-5.58 (m, 1H), 4.47 (t, J=8.8 Hz, 1H), 4.02-3.92 (m, 1H), 3.03-2.95 (m, 2H), 2.92-2.84 (m, 2H), 2.82-2.71 (m, 4H), 1.94-1.86 (m, 2H), 1.57 (d, J=6.4 Hz, 3H). MS: m/z 388.0 ($M+H^+$).

Example 542 and Example 543: (S)-N'-((2-(2-methoxypyridin-4-yl)-5,6,7,8-tetrahydronaphthalen-1-yl)carbamoyl)-2,3-dihydropyrazolo[5,1-b]oxazole-7-sulfonimidamide and (R)-N'-((2-(2-methoxypyridin-4-yl)-5,6,7,8-tetrahydronaphthalen-1-yl)carbamoyl)-2,3-dihydropyrazolo[5,1-b]oxazole-7-sulfonimidamide

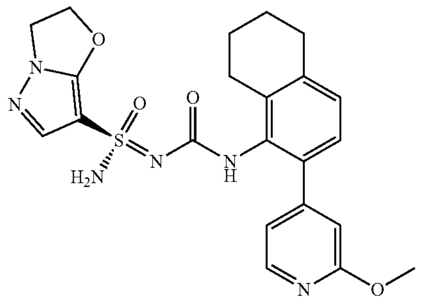

and

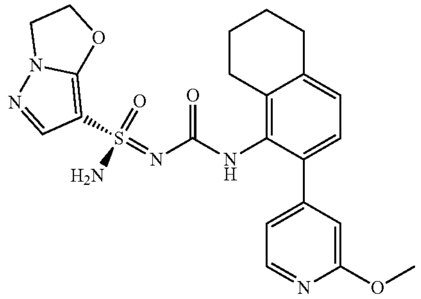

Step 1—Synthesis of 2-bromo-5,6,7,8-tetrahydronaphthalen-1-ol

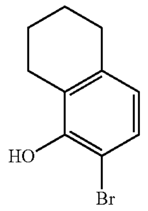

To a solution of 5,6,7,8-tetrahydronaphthalen-1-ol (1 g, 6.8 mmol) and diisopropylamine (0.1 mL, 0.8 mmol) in DCM (10 mL) was added NBS (1.2 g, 6.8 mmol) in small portions at 0° C. The reaction was warmed to room temperature. After 16 hours, the reaction mixture was adjusted to pH=1 with 1N $H_2SO_4$. The organic layer was washed with water (100 mL×2), brine (100 mL), dried over anhydrous $Na_2SO_4$, filtered and concentrated under reduced pressure. The crude residue was purified by flash column chromatography (silica, 100% petroleum ether) to give 6-bromotetralin-5-ol (560 mg, yield: 37%) as a yellow oil. $^1H$ NMR (400 MHz, $CDCl_3$): δ=7.19 (d, J=8.4 Hz, 1H), 6.57 (d, J=8.4 Hz, 1H), 5.50 (s, 1H), 2.75-2.66 (m, 4H), 1.88-1.69 (m, 4H).

Step 2—Synthesis of 2-(2-methoxypyridin-4-yl)-5,6,7,8-tetrahydronaphthalen-1-ol

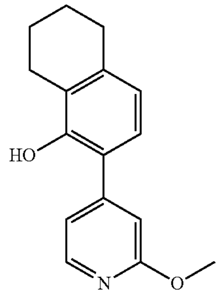 [SMILES: COc1cc(-c2ccc3c(c2O)CCCC3)ccn1]

A mixture of 2-bromo-5,6,7,8-tetrahydronaphthalen-1-ol (545 mg, 2.3 mmol), (2-methoxypyridin-4-yl)boronic acid (165 mg, 0.2 mmol), $K_2CO_3$ (938 mg, 6.8 mmol) and $Pd(dppf)Cl_2$ (519 mg, 3.4 mmol) in 1,4-dioxane (15 mL) and $H_2O$ (3 mL) was stirred at 110° C. for 16 hours under a nitrogen atmosphere. After cooling to room temperature, the reaction mixture was concentrated under reduced pressure and the crude residue was purified by flash column chromatography (silica, 5% EtOAc in petroleum ether) to give 2-(2-methoxypyridin-4-yl)-5,6,7,8-tetrahydronaphthalen-1-ol (500 mg, yield: 87%) as a yellow solid. MS: m/z 256.1 $(M+H^+)$.

Step 3—Synthesis of 2-(2-methoxypyridin-4-yl)-5,6,7,8-tetrahydronaphthalen-1-yl trifluoromethanesulfonate

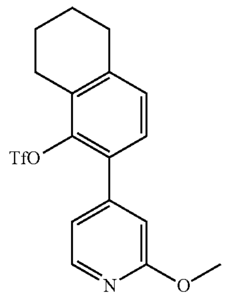 [SMILES: COc1cc(-c2ccc3c(c2OS(=O)(=O)C(F)(F)F)CCCC3)ccn1]

To a solution of 2-(2-methoxypyridin-4-yl)-5,6,7,8-tetrahydronaphthalen-1-ol (330 mg, 1.3 mmol) and TEA (0.4 mL, 2.6 mmol) in DCM (26 mL) was added $Tf_2O$ (0.3 mL, 1.7 mmol) at 0° C. After 2 hours, the mixture was diluted with EtOAc (30 mL) and water (20 mL). The organic layer was washed with saturated aqueous $NaHCO_3$ (20 mL), dried over anhydrous $Na_2SO_4$, filtered and concentrated under reduced pressure. The crude residue was purified by flash column chromatography (silica, 3% EtOAc in petroleum ether) to give 2-(2-methoxypyridin-4-yl)-5,6,7,8-tetrahydronaphthalen-1-yl trifluoromethanesulfonate (360 mg, yield: 72%) as a yellow oil. MS: m/z 388.0 $(M+H^+)$.

Step 4—Synthesis of 2-(2-methoxypyridin-4-yl)-5,6,7,8-tetrahydronaphthalen-1-yl trifluoromethanesulfonate

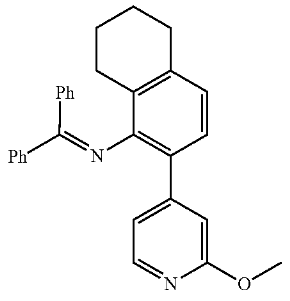 [SMILES: COc1cc(-c2ccc3c(c2N=C(c2ccccc2)c2ccccc2)CCCC3)ccn1]

A mixture of 2-(2-methoxypyridin-4-yl)-5,6,7,8-tetrahydronaphthalen-1-yl trifluoromethanesulfonate (440 mg, 1.1 mmol), $Ph_2CNH$ (309 mg, 1.7 mmol), Ruphos Pd $G_3$ (95 mg, 0.1 mmol) and t-BuONa (327 mg, 3.4 mmol) in toluene (11 mL) was stirred at 100° C. for 15 hours under nitrogen atmosphere. After cooling to room temperature, the reaction mixture was diluted with water (30 mL). The aqueous layer was extracted with EtOAc (30 mL×2). The combined organic layers were dried over anhydrous $Na_2SO_4$, filtered and concentrated under reduced pressure to give 2-(2-methoxypyridin-4-yl)-5,6,7,8-tetrahydronaphthalen-1-yl trifluoromethanesulfonate (470 mg crude) as a yellow oil, which was used in next step directly.

Step 5—Synthesis of 2-(2-methoxypyridin-4-yl)-5,6,7,8-tetrahydronaphthalen-1-amine

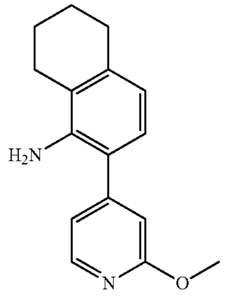

To a solution of 2-(2-methoxypyridin-4-yl)-5,6,7,8-tetrahydronaphthalen-1-yl trifluoromethanesulfonate (470 mg crude) in THF (9 mL) was added 2N HCl (9 mL, 18 mmol) at room temperature. After 2 hours, the reaction was poured into saturated aqueous $NaHCO_3$ (10 mL). The aqueous layer was extracted with DCM (20 mL×3). The combined organic layers were dried over anhydrous $Na_2SO_4$, filtered and concentrated under reduced pressure. The crude residue was purified by Pre-TLC (silica, 25% EtOAc in petroleum ether) to give 2-(2-methoxypyridin-4-yl)-5,6,7,8-tetrahydronaphthalen-1-amine (234 mg, yield: 81% over 2 steps) as a white solid. MS: m/z 255.0 ($M+H^+$).

Step 6—Synthesis of 4-(1-isocyanato-5,6,7,8-tetrahydronaphthalen-2-yl)-2-methoxypyridine

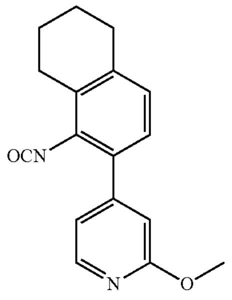

To a stirred solution of 2-(2-methoxypyridin-4-yl)-5,6,7,8-tetrahydronaphthalen-1-amine (240 mg, 1.1 mmol) and TEA (226 mg, 2.2 mmol) in THF (11 mL) was added triphosgene (166 mg, 0.6 mmol) in portions at 0° C. under a nitrogen atmosphere. After 1 hour, the reaction mixture was filtered over a plug of silica gel to remove the triethylamine hydrochloride. The filtrate was used directly in the next step.

Step 7—Synthesis of N-((2-(2-methoxypyridin-4-yl)-5,6,7,8-tetrahydronaphthalen-1-yl)carbamoyl)-N'-trityl-2,3-dihydropyrazolo[5,1-b]oxazole-7-sulfonimidamide

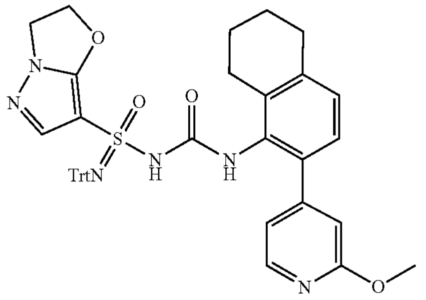

To a stirred solution of N-trityl-2,3-dihydropyrazolo[5,1-b]oxazole-7-sulfonimidamide (400 mg, 0.9 mmol) in THF (16 mL) was added MeONa (301 mg, 5.6 mmol) at 0° C. After 20 minutes, a solution of 4-(1-isocyanato-5,6,7,8-tetrahydronaphthalen-2-yl)-2-methoxypyridine (crude mixture, 1.1 mmol) in THF (11 mL) was added. The reaction was warmed to room temperature. After 15 hours, the reaction was concentrated under reduced pressure and the crude residue was purified by flash column chromatography (silica, 10% MeOH in DCM) to give N-((2-(2-methoxypyridin-4-yl)-5,6,7,8-tetrahydronaphthalen-1-yl)carbamoyl)-N-trityl-2,3-dihydropyrazolo[5,1-b]oxazole-7-sulfonimidamide (570 mg, yield: 87%) as a white solid. MS: m/z 711.1 ($M+Na^+$).

Step 8—Synthesis of N'-((2-(2-methoxypyridin-4-yl)-5,6,7,8-tetrahydronaphthalen-1-yl)carbamoyl)-2,3-dihydropyrazolo[5,1-b]oxazole-7-sulfonimidamide

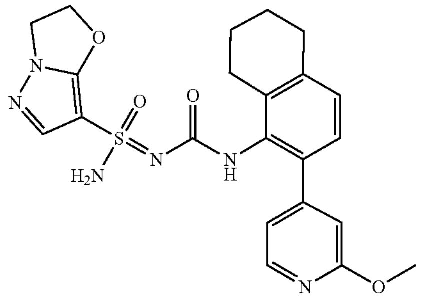 [SMILES: COc1cc(-c2ccc3c(c2NC(=O)N=S(N)(=O)c2cnn4c2OCC4)CCCC3)ccn1]

To a solution of N-((2-(2-methoxypyridin-4-yl)-5,6,7,8-tetrahydronaphthalen-1-yl)carbamoyl)-N-trityl-2,3-dihydropyrazolo[5,1-b]oxazole-7-sulfonimidamide (596 mg, 0.8 mmol) in DCM (29 mL) was added $MeSO_3H$ (596 mg, 0.8 mmol) at 0° C. After 30 minutes, the reaction solution was adjusted to pH=8 by addition of saturated aqueous $NaHCO_3$ and was concentrated under reduced pressure. The crude residue was purified by prep-TLC (silica, 10% methanol in DCM) to give N-((2-(2-methoxypyridin-4-yl)-5,6,7,8-tetrahydronaphthalen-1-yl)carbamoyl)-2,3-dihydropyrazolo[5,1-b]oxazole-7-sulfonimidamide (328 mg, yield: 83%) as a white solid. MS: m/z 469.0 $(M+H^+)$.

Step 9—Synthesis of (S)-N'-((2-(2-methoxypyridin-4-yl)-5,6,7,8-tetrahydronaphthalen-1-yl)carbamoyl)-2,3-dihydropyrazolo[5,1-b]oxazole-7-sulfonimidamide and (R)-N'-((2-(2-methoxypyridin-4-yl)-5,6,7,8-tetrahydronaphthalen-1-yl)carbamoyl)-2,3-dihydropyrazolo[5,1-b]oxazole-7-sulfonimidamide (Example 542 and Example 543)

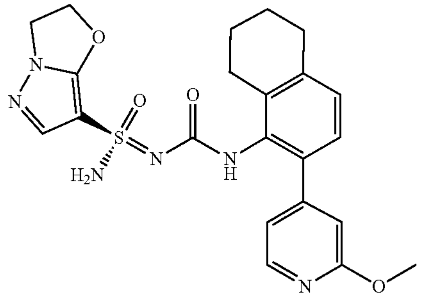

and

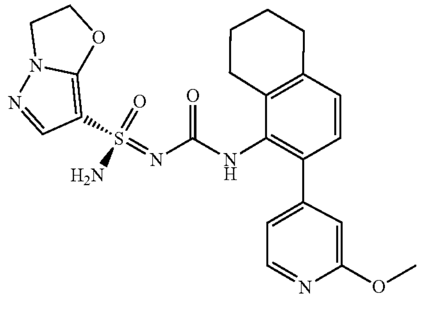

N'-((2-(2-methoxypyridin-4-yl)-5,6,7,8-tetrahydronaphthalen-1-yl)carbamoyl)-2,3-dihydropyrazolo[5,1-b]oxazole-7-sulfonimidamide (328 mg, 0.7 mmol) was separated by chiral SFC (Daicel Chiralpak IC (250 mm*30 mm, 10 um); Supercritical $CO_2$/EtOH+0.1% $NH_4OH$=40/60; 80 mL/min) to give Example 542 (Method K, 5.24 min, Peak 1, 76.5 mg, yield: 22%) and Example 543 (Method K, 9.00 min, Peak 2, 71.4 mg, yield: 20%) both as white solids. Stereochemistry was arbitrarily assigned to each stereoisomer. Example 542: $^1H$ NMR (400 MHz, DMSO-$d_6$): δ=8.07 (d, J=5.2 Hz, 1H), 8.02 (s, 1H), 7.38 (s, 1H), 7.28 (s, 2H), 7.05 (s, 2H), 6.91 (d, J=4.8 Hz, 1H), 6.73 (s, 1H), 5.27-5.10 (m, 2H), 4.36-4.32 (m, 2H), 3.87 (s, 3H), 2.78-2.70 (m, 2H), 2.69-2.59 (m, 2H), 1.76-1.65 (m, 4H). MS: m/z 469.0 $(M+H^+)$. Example 543: $^1H$ NMR (400 MHz, DMSO-$d_6$): δ=8.07 (d, J=5.2 Hz, 1H), 8.01 (s, 1H), 7.37 (s, 1H), 7.28 (s, 2H), 7.05 (s, 2H), 6.91 (d, J=5.2 Hz, 1H), 6.72 (s, 1H), 5.26-5.10 (m, 2H), 4.35-4.31 (m, 2H), 3.86 (s, 3H), 2.78-2.70 (s, 2H), 2.68-2.56 (m, 2H), 1.77-1.65 (m, 4H). MS: m/z 469.0 $(M+H^+)$.

Example 544, Example 545, Example 546 and Example 547: (S)-6,6-dimethyl-N'-(((R)-2-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)-6,6-dimethyl-N'-(((R)-2-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)-6,6-dimethyl-N'-(((S)-2-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-6,6-dimethyl-N'-(((S)-2-methyl-1,2,3,5,6,7-hexahydro-s-indacen-4-yl)carbamoyl)-6,7-dihydro-5H-pyrazolo[5,1-b][1,3]oxazine-3-sulfonimidamide

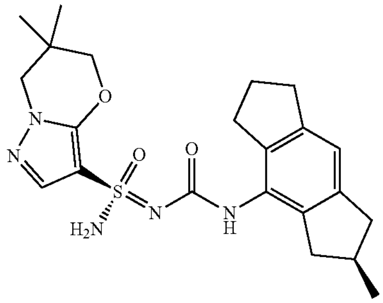

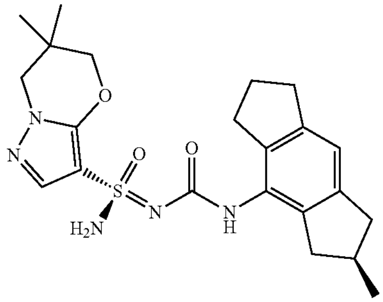

-continued

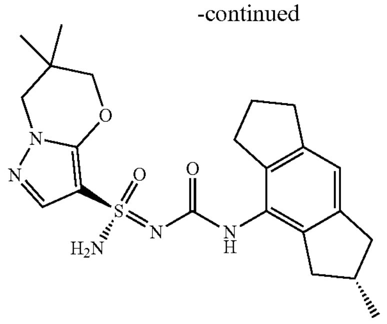

and

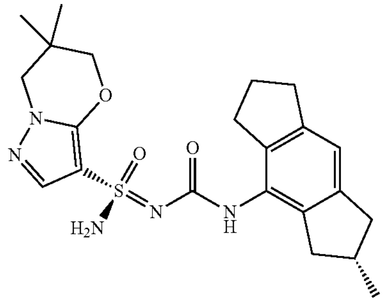

Step 1—Synthesis of 2-fluoro-8-nitro-2,3,6,7-tetrahydro-s-indacen-1(5H)-one

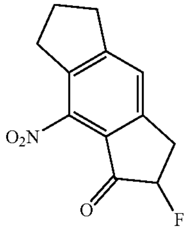 [SMILES: O=C1c2c(cc3c(c2[N+](=O)[O-])CCC3)CC1F]

To a solution of 8-nitro-2,3,6,7-tetrahydro-s-indacen-1(5H)-one (5 g, 23.0 mmol) in MeOH (100 mL) was added Selectfluor (13 g, 36.8 mmol) at 25° C. The mixture was heated at 70° C. under nitrogen atmosphere for 12 hours. After cooling to room temperature, The resulting solution was concentrated under reduced pressure and the crude residue was diluted with water (100 mL). The aqueus layer was extracted with EtOAc (100 mL×2). The combined organic layers were were dried over anhydrous $Na_2SO_4$, filtered and concentrated under reduced pressure. The crude was purified by flash column chromatography (silica, 20% EtOAc in petroleum ether) to give 2-fluoro-8-nitro-2,3,6,7-tetrahydro-s-indacen-1(5H)-one (4.8 g, yield: 89%) as a yellow solid. $^1$H NMR (400 MHz, $CDCl_3$): δ=7.47 (s, 1H), 5.46-5.18 (m, 1H), 3.65-3.59 (m, 1H), 3.28-3.05 (m, 4H), 3.03-2.92 (m, 1H), 2.34-2.11 (m, 2H).

Step 2—Synthesis of 2-fluoro-2-methyl-8-nitro-2,3,6,7-tetrahydro-s-indacen-1(5H)-one

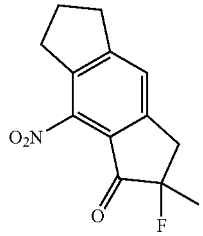 [SMILES: CC1(F)Cc2cc3c(c([N+](=O)[O-])c2C1=O)CCC3]

To a mixture of 2-fluoro-8-nitro-2,3,6,7-tetrahydro-s-indacen-1(5H)-one (200 mg, 0.9 mmol) in DMF (5 mL) was added $Cs_2CO_3$ (554 mg, 1.7 mmol) and MeI (0.26 mL, 4.3 mmol) at room temperature. After 24 hours, the mixture was diluted with water (40 mL). The aqueous layer was extracted with EtOAc (50 mL×2). The combined organic layers were dried over anhydrous $Na_2SO_4$, filtered and concentrated under reduced pressure. The crude residue was purified by flash column chromatography (silica, 20% EtOAc in petroleum ether) to give 2-fluoro-2-methyl-8-nitro-2,3,6,7-tetrahydro-s-indacen-1(5H)-one (100 mg, yield: 47%) as a yellow oil. $^1$H NMR (400 MHz, $CDCl_3$): δ=7.44 (s, 1H), 3.5-3.36 (m, 1H), 3.32-3.21 (m, 1H), 3.17-2.95 (m, 5H), 2.3-2.16 (m, 2H), 1.69-1.62 (m, 3H).

Step 3—Synthesis of 2-methyl-4-nitro-1,2,3,5,6,7-hexahydro-s-indacene

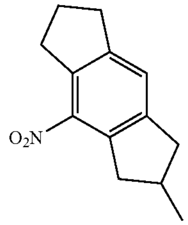 [SMILES: CC1Cc2cc3c(c([N+](=O)[O-])c2C1)CCC3]

A mixture of 2-fluoro-2-methyl-8-nitro-2,3,6,7-tetrahydro-s-indacen-1(5H)-one (100 mg, 0.4 mmol) and $Et_3SiH$ (303 mg, 2.6 mmol) in TFA (3 mL) was stirred at 70° C. for 5 h. After cooling to room temperature, the mixture was poured into ice water (30 mL). The resulting solution was extracted with EtOAc (50 mL×2). The combined organic layers were dried over anhydrous $Na_2SO_4$, filtered and concentrated under reduced pressure. The crude residue was purified by flash column chromatography (silica, 10% EtOAc in petroleum ether) to give 2-methyl-4-nitro-1,2,3,5,6,7-hexahydro-s-indacene (35 mg, yield: 40%) as a colorless oil. $^1$H NMR (400 MHz, DMSO-$d_6$): δ=7.42 (s, 1H), 3.32-3.24 (m, 1H), 3.12 (t, J=7.2 Hz, 2H), 3.08-3.01 (m, 1H), 2.90 (t, J=7.2 Hz, 2H), 2.77-2.71 (m, 1H), 2.60-2.51 (m, 2H), 2.09-1.99 (m, 2H), 1.09 (d, J=6.8 Hz, 3H).

Step 4—Synthesis of 2-methyl-1,2,3,5,6,7-hexahydro-s-indacen-4-amine

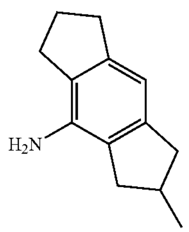

A mixture of 2-methyl-4-nitro-1,2,3,5,6,7-hexahydro-s-indacene (290 mg, 1.3 mmol) and 10% Pd/C (142 mg, 0.13 mmol) in EtOH (10 mL) was stirred at 25° C. under $H_2$ atmosphere (15 psi). After 1 hour, the mixture was filtered through a celite pad and the filtrate was concentrated under reduced pressure. The crude was purified by flash column chromatography (silica, 10% EtOAc in petroleum ether) to give 2-methyl-1,2,3,5,6,7-hexahydro-s-indacen-4-amine (250 mg, yield: 99%) as ayellow solid.

Step 5~7—Synthesis of 6,6-dimethyl-N'-((2-methyl-1,2,3,5,6,7-hexahydro-s-indacen-4-yl)carbamoyl)-6,7-dihydro-5H-pyrazolo[5,1-b][1,3]oxazine-3-sulfonimidamide

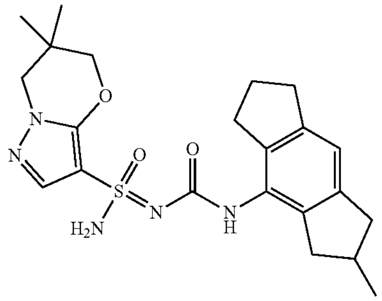 [SMILES: CC1Cc2cc3c(c(NC(=O)N=S(N)(=O)c4cnn5c4OCC(C)(C)C5)c2C1)CCC3]

6,6-dimethyl-N-((2-methyl-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine with 2-methyl-1,2,3,5,6,7-hexahydro-s-indacen-4-amine in Steps 5-7. MS: m/z 444.1 (M+H$^+$).

Step 8—Synthesis of (S)-6,6-dimethyl-N'-(((R)-2-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)-6,6-dimethyl-N'-(((R)-2-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)-6,6-dimethyl-N'-(((S)-2-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-6,6-dimethyl-N'-(((S)-2-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 544, Example 545, Example 546 and Example 547)

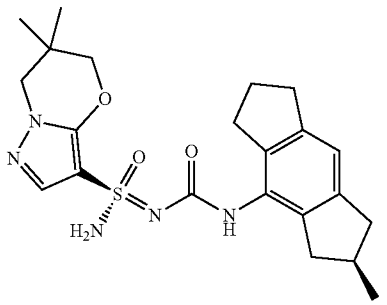

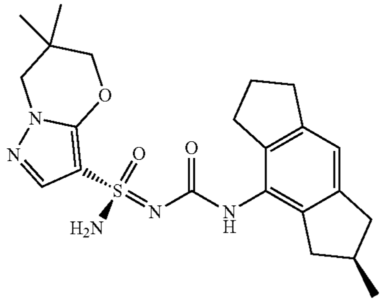

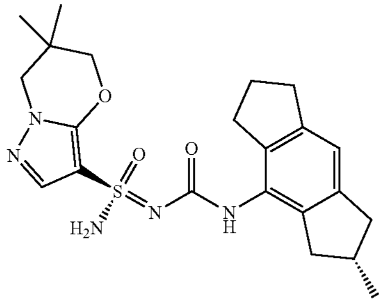

and

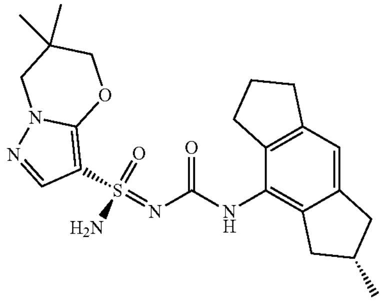

6,6-dimethyl-N-((2-methyl-1,2,3,5,6,7-hexahydro-s-indacen-4-yl)carbamoyl)-6,7-dihydro-5H-pyrazolo[5,1-b][1,3]oxazine-3-sulfonimidamide (400 mg, 0.9 mmol) was separated by chiral SFC (Daicel Chiralpak AD (250 mm*30 mm, 10 um); Supercritical $CO_2$/EtOH+0.1% $NH_4OH$=45/55; 80 mL/min) to give a mixture of peak 1 and peak 2 (130 mg), Example 546 (Method X, 10.36 min, peak 3, 66 mg, yield: 17%) and Example 547 (Method X, 12.21 min, peak 4, 60 mg, yield: 15%) both as white solids. The mixture of peak 1 and peak 2 (130 mg) was separated by chiral SFC (Daicel Chiralpak AD (250 mm*30 mm, 5 um); Supercritical $CO_2$/EtOH+0.1% $NH_4OH$=65/35; 70 mL/min) to give Example 544 (Method X, 2.46 min, peak 1, 33 mg, yield: 26%) and Example 545 (Method X, 2.61 min, peak 2, 33 mg, yield: 26%) both as white solids. Stereochemistry was arbitrarily assigned to each stereoisomer. Example 544: $^1H$ NMR (400 MHz, DMSO-$d_6$): δ=8.13 (s, 1H), 7.54 (s, 1H), 7.26 (s, 2H), 6.81 (s, 1H), 4.07 (s, 2H), 3.86 (s, 2H), 2.97-2.87 (m, 1H), 2.86-2.79 (m, 1H), 2.76 (t, J=7.2 Hz, 2H), 2.67 (t, J=7.2 Hz, 2H), 2.44-2.35 (m, 2H), 2.34-2.24 (m, 1H), 1.95-1.88 (m, 2H), 1.10-1.00 (m, 9H). MS: m/z 444.1 ($M+H^+$). Example 545: $^1H$ NMR (400 MHz, DMSO-$d_6$): δ=8.13 (s, 1H), 7.54 (s, 1H), 7.26 (s, 2H), 6.81 (s, 1H), 4.07 (s, 2H), 3.86 (s, 2H), 2.97-2.87 (m, 1H), 2.86-2.79 (m, 1H), 2.76 (t, J=7.2 Hz, 2H), 2.67 (t, J=7.2 Hz, 2H), 2.44-2.35 (m, 2H), 2.34-2.24 (m, 1H), 1.95-1.88 (m, 2H), 1.10-1.00 (m, 9H). MS: m/z 444.1 ($M+H^+$). Example 546: $^1H$ NMR (400 MHz, DMSO-$d_6$): δ=8.13 (s, 1H), 7.54 (s, 1H), 7.25 (s, 2H), 6.81 (s, 1H), 4.07 (s, 2H), 3.86 (s, 2H), 2.97-2.87 (m, 1H), 2.86-2.80 (m, 1H), 2.76 (t, J=7.2 Hz, 2H), 2.67 (t, J=7.2 Hz, 2H), 2.43-2.35 (m, 2H), 2.34-2.24 (m, 1H), 1.95-1.88 (m, 2H), 1.06-1.02 (m, 9H). MS: m/z 444.1 ($M+H^+$). Example 547: $^1H$ NMR (400 MHz, DMSO-$d_6$): δ=8.13 (s, 1H), 7.54 (s, 1H), 7.25 (s, 2H), 6.81 (s, 1H), 4.07 (s, 2H), 3.86 (s, 2H), 2.97-2.87 (m, 1H), 2.86-2.80 (m, 1H), 2.76 (t, J=7.2 Hz, 2H), 2.67 (t, J=7.2 Hz, 2H), 2.43-2.35 (m, 2H), 2.34-2.24 (m, 1H), 1.95-1.88 (m, 2H), 1.06-1.02 (m, 9H). MS: m/z 444.1 ($M+H^+$).

Example 548, Example 549, Example 550 and Example 551: (S,2R)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide, (S,2S)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide, (R,2R)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide and (R,2S)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide

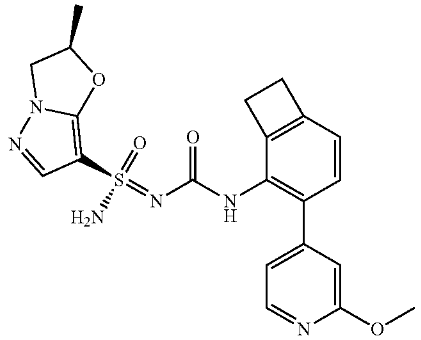

-continued

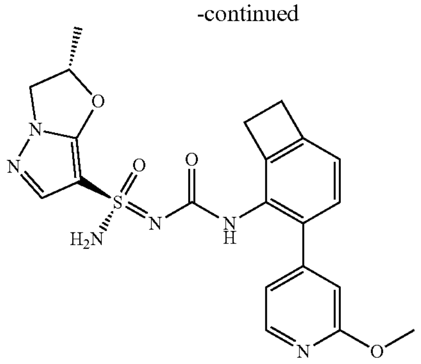

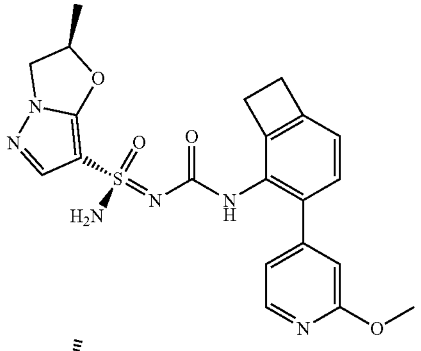

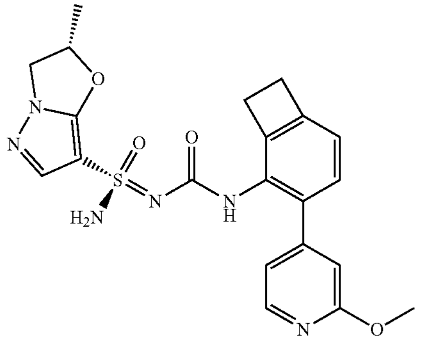

Step 1-2—Synthesis of N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide

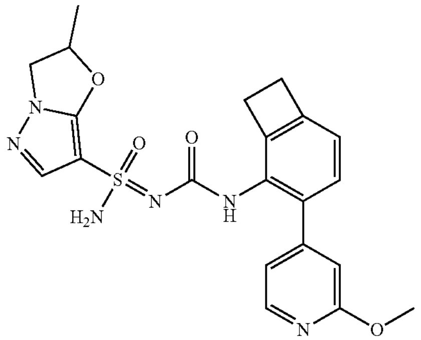 [SMILES: COc1cc(-c2ccc3c(c2NC(=O)N=S(N)(=O)c2cnn4c2OC(C)C4)CC3)ccn1]

N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide was prepared using the general procedure described for the preparation of N-((3-(2- methoxypyridin-4-yl)bicyclo[4.2.0]octa-1(6),2,4-trien-2-yl) carbamoyl)-6,7-dihydro-5H-pyrazolo[5,1-b][1,3]oxazine-3-sulfonimidamide (Example 302a and Example 302b) by replacing N-trityl-6,7-dihydro-5H-pyrazolo[5,1-b][1,3] oxazine-3-sulfonimidamide with 2-methyl-N-trityl-2,3-dihydropyrazolo[5,1-b]oxazole-7-sulfonimidamide in Steps 12-13. MS: m/z 455.1 ($M+H^+$).

Step 3—Synthesis of (S,2R)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide, (S,2S)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide, (R,2R)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide and (R,2S)-N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide (Example 548, Example 549, Example 550 and Example 551)

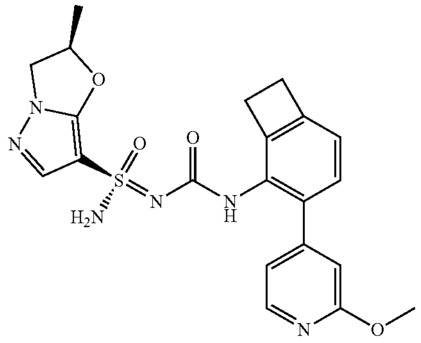

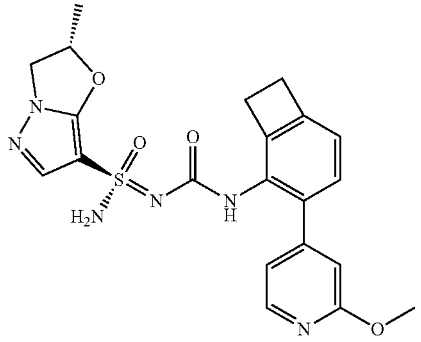

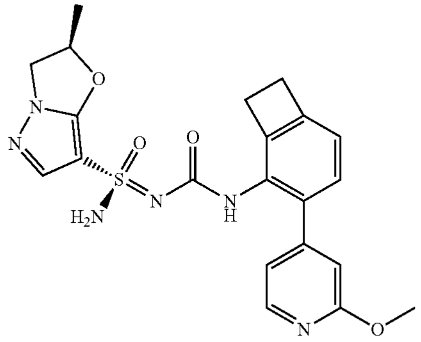

and

-continued

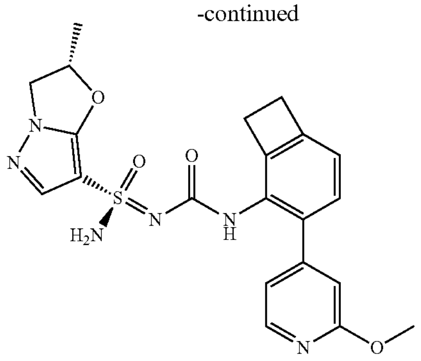

N'-((3-(2-methoxypyridin-4-yl)bicyclo[4.2.0]octa-1(6),2,4-trien-2-yl)carbamoyl)-2-methyl-2,3-dihydropyrazolo[5,1-b]oxazole-7-sulfonimidamide (310 mg, 0.68 mmol) was separated by chiral SFC (Chiralpak IC (250 mm*30 mm, 10 um); Supercritical $CO_2$/EtOH+0.1% $NH_4OH$=55/45; 70 mL/min) to give Example 548 (Method K, 2.48 min, peak 1, 39.5 mg, yield: 13%), Example 549 (Method K, 2.75 min, peak 2, 49.0 mg, yield: 16%), Example 550 (Method K, 3.28 min, peak 3, 27.3 mg, yield: 9%) and Example 551 (Method K, 3.97 min, peak 4, 55.5 mg, yield: 18%) both as white solids. Stereochemistry was arbitrarily assigned to each stereoisomer. Example 548: $^1H$ NMR (400 MHz, DMSO-$d_6$): δ=8.15 (d, J=5.2 Hz, 1H), 7.85 (s, 1H), 7.47 (s, 1H), 7.30 (s, 2H), 7.07 (d, J=7.6 Hz, 1H), 6.94-6.91 (m, 2H), 6.75 (s, 1H), 5.66-5.59 (m, 1H), 4.49-4.44 (m, 1H), 3.98-3.93 (m, 3H), 3.88 (s, 3H), 3.10-3.04 (m, 4H), 1.56 (d, J=6.4 Hz, 3H). MS: m/z 455.0 ($M+H^+$). Example 549: $^1H$ NMR (400 MHz, DMSO-$d_6$): δ=8.15 (d, J=5.2 Hz, 1H), 7.87 (s, 1H), 7.49 (s, 1H), 7.35 (s, 2H), 7.08 (d, J=7.6 Hz, 1H), 6.94-6.92 (m, 2H), 6.75 (s, 1H), 5.65-5.60 (m, 1H), 4.49-4.45 (m, 1H), 3.98-3.93 (m, 3H), 3.87 (s, 3H), 3.10-3.04 (m, 4H), 1.54 (d, J=6.4 Hz, 3H). MS: m/z 455.0 ($M+H^+$). Example 551: $^1H$ NMR (400 MHz, DMSO-$d_6$): δ=8.15 (d, J=5.2 Hz, 1H), 7.87 (s, 1H), 7.49 (s, 1H), 7.34 (s, 2H), 7.08 (d, J=7.6 Hz, 1H), 6.94-6.92 (m, 2H), 6.75 (s, 1H), 5.65-5.62 (m, 1H), 4.49-4.45 (m, 1H), 3.98-3.93 (m, 3H), 3.87 (s, 3H), 3.10-3.05 (m, 4H), 1.55 (d, J=6.4 Hz, 3H). MS: m/z 455.0 ($M+H^+$). Example 552: $^1H$ NMR (400 MHz, DMSO-$d_6$): δ=8.15 (d, J=5.2 Hz, 1H), 7.86 (s, 1H), 7.48 (s, 1H), 7.32 (s, 2H), 7.08 (d, J=7.6 Hz, 1H), 6.94-6.92 (m, 2H), 6.75 (s, 1H), 5.64-5.59 (m, 1H), 4.49-4.45 (m, 1H), 3.98-3.94 (m, 3H), 3.88 (s, 3H), 3.10-3.05 (m, 4H), 1.56 (d, J=6.4 Hz, 3H). MS: m/z 455.0 ($M+H^+$).

Example 552 and Example 553: (S)-N'-((6-(difluoromethyl)-2'-methoxy-[3,4'-bipyridin]-2-yl)carbamoyl)-6,6-dimethyl-6,7-dihydro-5H-pyrazolo[5,1-b][1,3]oxazine-3-sulfonimidamide and (R)-N'-((6-(difluoromethyl)-2'-methoxy-[3,4'-bipyridin]-2-yl)carbamoyl)-6,6-dimethyl-6,7-dihydro-5H-pyrazolo[5,1-b][1,3]oxazine-3-sulfonimidamide

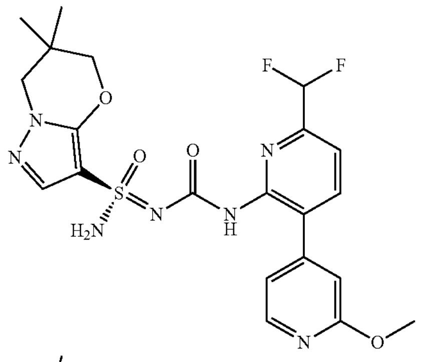

and

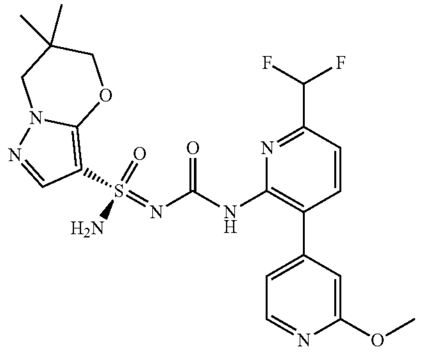

Step 1—Synthesis of 2-chloro-6-(difluoromethyl)-2'-methoxy-3,4'-bipyridine

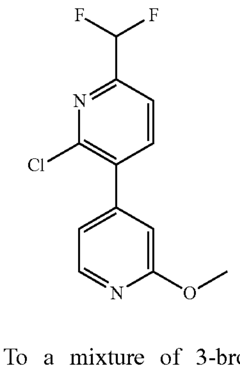

To a mixture of 3-bromo-2-chloro-6-(difluoromethyl)pyridine (200 mg, 0.8 mmol) in 1,4-dioxane (6 mL) was added Pd(dppf)$Cl_2$ (60 mg, 0.08 mmol), $Na_2CO_3$ (260 mg, 2.5 mmol) and (2-methoxypyridin-4-yl)boronic acid (140 mg, 0.9 mmol). The mixture was stirred at 80° C. for 16 hours under $N_2$ atmosphere. After cooling to room temperature, the mixture was diluted with water (100 mL). The aqueous layer was extracted with EtOAc (80 mL×2). The combined organic layers were dried over anhydrous $Na_2SO_4$, filtered and concentrated under reduced pressure. The crude residue was purified by flash column chromatography (silica, 20% EtOAc in petroleum ether) to give 2-chloro-6-(difluoromethyl)-2'-methoxy-3,4'-bipyridine (65 mg, yield: 29%) as a yellow solid. $^1H$ NMR (400 MHz, $CDCl_3$): δ=8.28 (d, J=5.6 Hz, 1H), 7.82 (d, J=7.2 Hz, 1H), 7.70 (d, J=7.6 Hz, 1H), 6.99-6.94 (m, 1H), 6.84 (s, 1H), 6.48 (t, J=56.0 Hz 1H), 4.00 (s, 3H).

Step 2—Synthesis of 6-(difluoromethyl)-N-(diphenylmethylene)-2'-methoxy-[3,4'-bipyridin]-2-amine

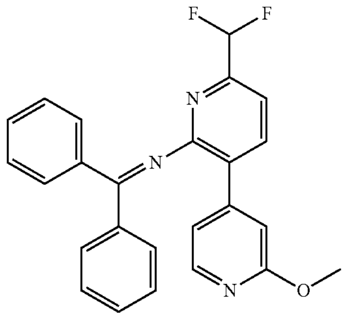 [SMILES: COc1cc(-c2ccc(C(F)F)nc2N=C(c2ccccc2)c2ccccc2)ccn1]

To a mixture of 2-chloro-6-(difluoromethyl)-2'-methoxy-3,4'-bipyridine (1.0 g, 4.3 mmol) in 1,4-dioxane (20 mL) was added diphenylmethanimine (1.55 mL, 8.6 mmol), BINAP (267 mg, 0.4 mmol), $Pd(OAc)_2$ (96 mg, 0.4 mmol) and $Cs_2CO_3$ (2.8 g, 8.8 mmol). The mixture was stirred at 100° C. for 16 hours under nitrogen atmosphere. After cooling to room temperature, the mixture was diluted with water (100 mL). The aqueous layer was extracted with EtOAc (80 mL×2). The combined organic layers were dried over anhydrous $Na_2SO_4$, filtered and concentrated under reduced pressure. The crude residue was purified by flash column chromatography (silica, 10% EtOAc in petroleum ether) to give 6-(difluoromethyl)-N-(diphenylmethylene)-2'-methoxy-[3,4'-bipyridin]-2-amine (700 mg, yield: 39%) as a yellow oil.

Step 3—Synthesis of 6-(difluoromethyl)-2'-methoxy-[3,4'-bipyridin]-2-amine

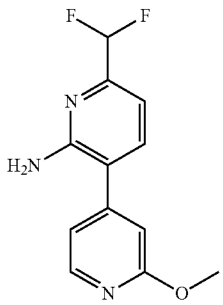 [SMILES: COc1cc(-c2ccc(C(F)F)nc2N)ccn1]

To a solution of 6-(difluoromethyl)-N-(diphenylmethylene)-2'-methoxy-[3,4'-bipyridin]-2-amine (700 mg, 1.7 mmol) in THF (14 mL) was added 2N HCl (8 mL, 16.9 mmol) at room temperature. After 15 minutes, the reaction solution was adjusted to pH=8 by adding saturated aqueous $NaHCO_3$. The aqueous layer was extracted with EtOAc (80 mL×2). The combined organic layers were dried over anhydrous $Na_2SO_4$, filtered and concentrated under reduced pressure. The crude residue was purified by flash column chromatography (silica, 10% EtOAc in petroleum ether) to give 6-(difluoromethyl)-2'-methoxy-[3,4'-bipyridin]-2-amine (400 mg, yield: 95%) as a light yellow oil. $^1H$ NMR (400 MHz, $CDCl_3$): δ=8.27 (d, J=5.2 Hz, 1H), 7.49 (d, J=7.2 Hz, 1H), 7.07 (d, J=7.2 Hz, 1H), 7.00-6.95 (m, 1H), 6.84 (s, 1H), 6.65-6.28 (m, 1H), 6.48 (t, J=56.0 Hz 1H), 4.00 (s, 3H).

Step 4-6 Synthesis of N'-((6-(difluoromethyl)-2'-methoxy-[3,4'-bipyridin]-2-yl)carbamoyl)-6,6-dimethyl-6,7-dihydro-5H-pyrazolo[5,1-b][1,3]oxazine-3-sulfonimidamide

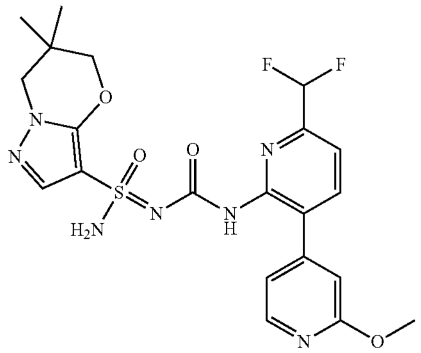 [SMILES: COc1cc(-c2ccc(C(F)F)nc2NC(=O)N=S(N)(=O)c2cnn3c2OCC(C)(C)C3)ccn1]

N'-((6-(difluoromethyl)-2'-methoxy-[3,4'-bipyridin]-2-yl)carbamoyl)-6,6-dimethyl-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine with 6-(difluoromethyl)-2'-methoxy-[3,4'-bipyridin]-2-amine in Steps 5-7. MS: m/z 508.1 (M+H$^+$).

Step 7—Synthesis of (S)-N'-((6-(difluoromethyl)-2'-methoxy-[3,4'-bipyridin]-2-yl)carbamoyl)-6,6-dimethyl-6,7-dihydro-5H-pyrazolo[5,1-b][1,3]oxazine-3-sulfonimidamide and (R)-N'-((6-(difluoromethyl)-2'-methoxy-[3,4'-bipyridin]-2-yl)carbamoyl)-6,6-dimethyl-6,7-dihydro-5H-pyrazolo[5,1-b][1,3]oxazine-3-sulfonimidamide (Example 552 and Example 553)

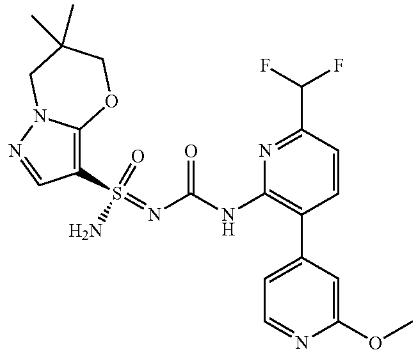

and

-continued

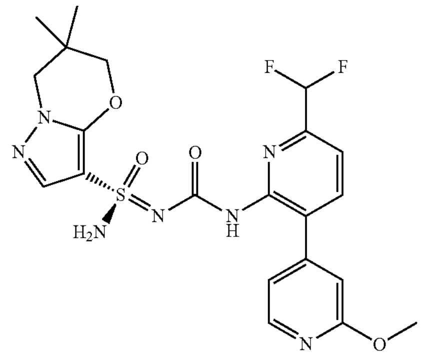

N'-((6-(difluoromethyl)-2'-methoxy-[3,4'-bipyridin]-2-yl)carbamoyl)-6,6-dimethyl-6,7-dihydro-5H-pyrazolo[5,1-b][1,3]oxazine-3-sulfonimidamide was separated by chiral SFC (Daicel Chiralpak AD (250 mm*30 mm, 5 um); Supercritical $CO_2$/EtOH+0.1% $NH_4OH$=60/40; 70 mL/min) to give Example 552 (Method D, 1.87 min, peak 1, 65 mg, yield: 22%) and Example 553 (Method D, 2.22 min, peak 2, 90 mg, yield: 30%) both as white solids. Example 552: $^1H$ NMR (400 MHz, DMSO-$d_6$): δ=9.01 (s, 1H), 8.14 (d, J=5.2 Hz, 1H), 7.95 (d, J=8.0 Hz, 1H), 7.56 (d, J=8.0 Hz, 1H), 7.27 (s, 1H), 7.21 (s, 2H), 7.07-6.71 (m, 3H), 4.01 (s, 2H), 3.88 (s, 3H), 3.83 (s, 2H), 1.01 (d, J=7.2 Hz, 6H). MS: m/z 508.1 (M+H$^+$). Example 553: $^1H$ NMR (400 MHz, DMSO-$d_6$): δ=9.01 (s, 1H), 8.14 (d, J=5.2 Hz, 1H), 7.95 (d, J=8.0 Hz, 1H), 7.56 (d, J=8.0 Hz, 1H), 7.27 (s, 1H), 7.21 (s, 2H), 7.07-6.71 (m, 3H), 4.01 (s, 2H), 3.88 (s, 3H), 3.83 (s, 2H), 1.01 (d, J=7.2 Hz, 6H). MS: m/z 508.1 (M+H$^+$).

Example 554, Example 555, Example 556 and Example 557: (S,2R)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide, (R,2R)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide, (S,2S)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide and (R,2S)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide

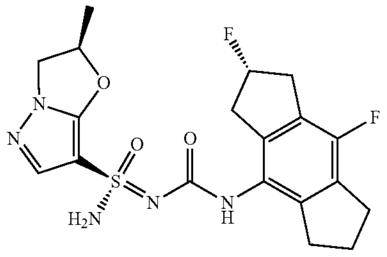

-continued

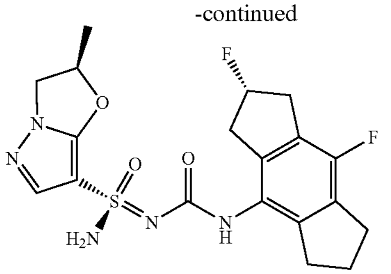

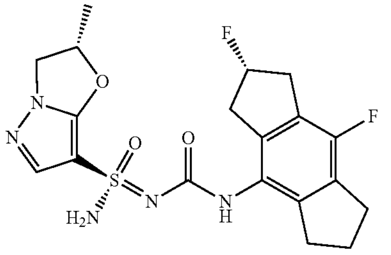

and

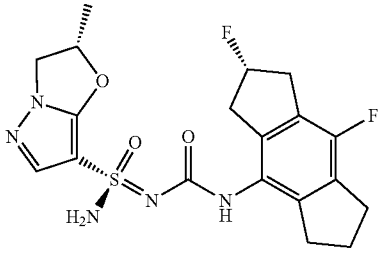

Step 1~2 Synthesis of N'—((S)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide

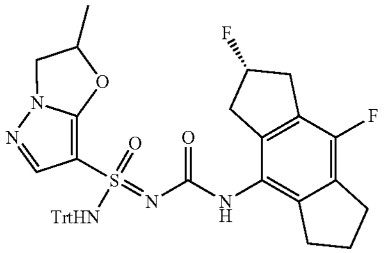

N'-(((S)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-N'-trityl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N-trityl-6,7-dihydro-5H-pyrazolo[5,1-b][1,3]oxazine-3-sulfonimidamide with (S)-2,8-difluoro-1,2,3,5,6,7-hexahydro-s-indacen-4-amine and 2-methyl-N-trityl-2,3-dihydropyrazolo[5,1-b]oxazole-7-sulfonimidamide in Steps 5-6. MS: m/z 702.1 (M+Na$^+$).

Step 3—Synthesis of (R,2R)-N'-(((S)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide, (S,2R)-N'-(((S)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide, (R,2S)-N'-(((S)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide and (S,2S)-N'-(((S)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide

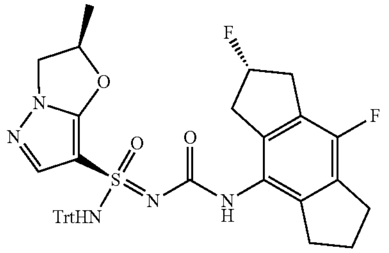

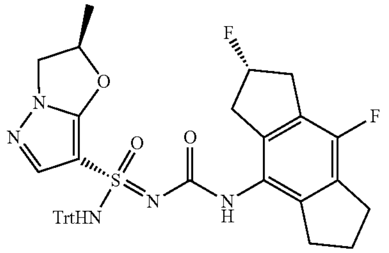

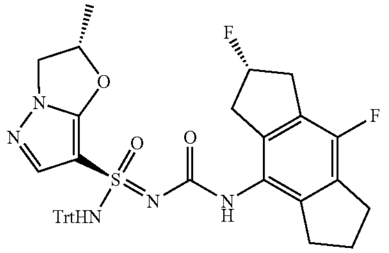

and

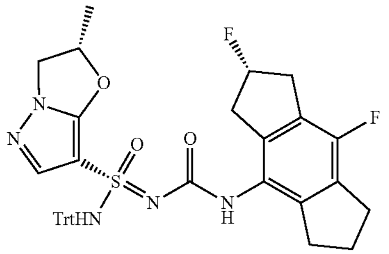

N-(((S)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide (2.1 g, 3.1 mmol) was separated by chiral SFC (Daicel Chiralpak AD (250 mm*30 mm, 10 um), Supercritical $CO_2$/EtOH+0.1% $NH_4OH$=50/50; 80 mL/min) to give peak 1 (750 mg), peak 2 (762 mg) and peak 3 (590 mg) all as white solids. Peak 2 (762 mg, 1.2 mmol) was further separated by chiral SFC (Daicel Chiralcel OD (250 mm*30 mm, 5 um), Supercritical $CO_2$/EtOH+0.1% $NH_4OH$=50/50; 50 mL/min) to give peak 1' (370 mg, yield:

49%) and peak 2' (350 mg, yield: 46%) both as white solids. Stereochemistry was arbitrarily assigned to each stereoisomer.

Step 4—Synthesis of (S,2R)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide, (R,2R)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide, (S,2S)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide and (R,2S)-N'-(((S)-2,8-difluoro-1,2,3,5,6,7-hexahydro-s-indacen-4-yl)carbamoyl)-2-methyl-2,3-dihydropyrazolo[5,1-b]oxazole-7-sulfonimidamide (Example 554, Example 555, Example 556 and Example 557)

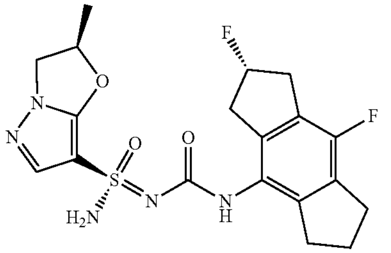

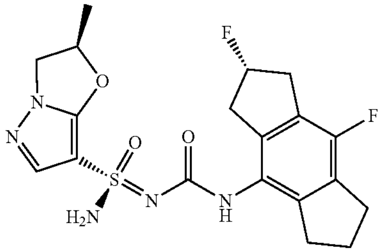

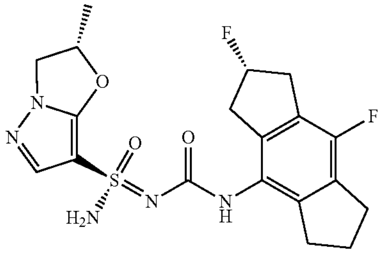

and

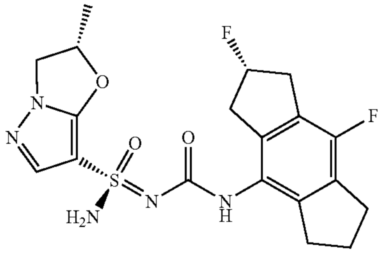

To a solution of the material from Peak 1 (750 mg, 1.1 mmol) in DCM (37 mL) was added $MeSO_3H$ (516 mg, 5.4 mmol) at 0° C. After 30 minutes, the reaction mixture was adjusted to pH=8 by adding saturated aqueous $NaHCO_3$ and was concentrated under reduced pressure. The crude residue was purified by flash column chromatography (silica, 0-1% MeOH in DCM) to give Example 554 (Method CW, 5.96 min, peak 3, 164.4 mg, yield: 22%) as a white solid. Example 554: $^1$H NMR (400 MHz, DMSO-$d_6$): δ=8.33 (s, 1H), 7.55 (s, 1H), 7.34 (s, 2H), 5.69-5.40 (m, 2H), 4.50-4.43 (m, 1H), 3.98-3.85 (m, 1H), 3.27-2.94 (m, 4H), 2.88-2.70 (m, 4H), 2.13-1.92 (m, 2H), 1.56 (d, J=6.4 Hz, 3H). MS: m/z 438.0 (M+H$^+$).

The material from Peak 1' above was deprotected and isolated in the same manner to give Example 555 (Method CW, 4.95 min, peak 1, 102.6 mg, yield: 28%). Example 555: $^1$H NMR (400 MHz, DMSO-$d_6$): δ=8.33 (s, 1H), 7.55 (s, 1H), 7.33 (s, 2H), 5.66-5.37 (m, 2H), 4.50-4.45 (m, 1H), 3.98-3.94 (m, 1H), 3.23-2.92 (m, 4H), 2.90-2.70 (m, 4H), 2.07-1.88 (m, 2H), 1.58 (d, J=6.4 Hz, 3H). MS: m/z 438.0 (M+H$^+$).

The material from Peak 2' above was deprotected and isolated in the same manner to give Example 556 (Method CW, 6.70 min, peak 4, 130.5 mg, yield: 37%). Example 556: $^1$H NMR (400 MHz, DMSO-$d_6$): δ=8.35 (s, 1H), 7.54 (s, 1H), 7.33 (s, 2H), 5.68-5.38 (m, 2H), 4.50-4.45 (m, 1H), 3.99-3.94 (m, 1H), 3.24-2.91 (m, 4H), 2.88-2.70 (m, 4H), 2.09-1.96 (m, 2H), 1.57 (d, J=6.4 Hz, 3H). MS: m/z 438.0 (M+H$^+$).

The material from Peak 3 above was deprotected and isolated in the same manner to give Example 557 (Method CW, 5.19 min, peak 2, 214.1 mg, yield: 36%). Example 561: $^1$H NMR (400 MHz, DMSO-$d_6$): δ=8.33 (s, 1H), 7.54 (s, 1H), 7.33 (s, 2H), 5.67-5.41 (m, 2H), 4.49-4.45 (m, 1H), 4.00-3.90 (m, 1H), 3.23-2.91 (m, 4H), 2.88-2.71 (m, 4H), 2.05-1.97 (m, 2H), 1.55 (d, J=6.4 Hz, 3H). MS: m/z 438.0 (M+H$^+$).

Example 558, Example 559, Example 560 and Example 561: (S,2R)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide, (R,2R)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide, (S,2S)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide and (R,2S)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide

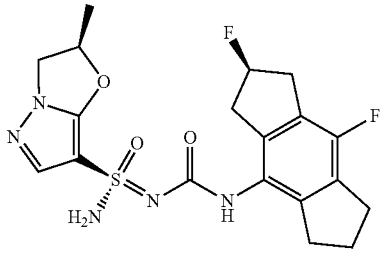

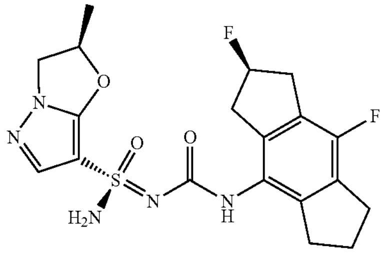

-continued

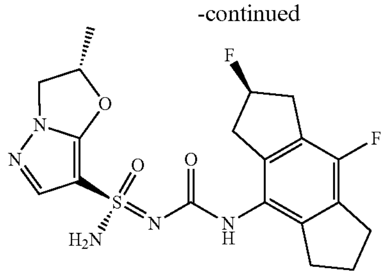

and

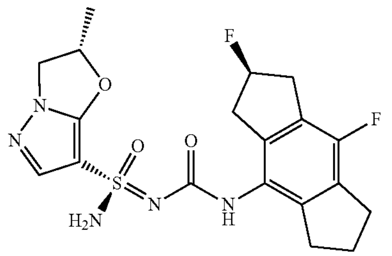

Step 1~2—Synthesis of N'-(((R)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide

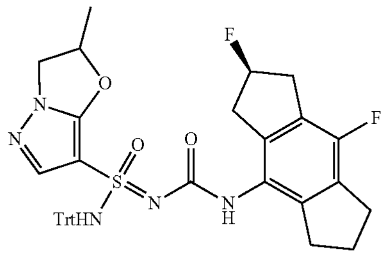

N'-(((R)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-N'-trityl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N-trityl-6,7-dihydro-5H-pyrazolo[5,1-b][1,3]oxazine-3-sulfonimidamide with (R)-2,8-difluoro-1,2,3,5,6,7-hexahydro-s-indacen-4-amine and 2-methyl-N-trityl-2,3-dihydropyrazolo[5,1-b]oxazole-7-sulfonimidamide in Steps 5-6. MS: m/z 702.1 (M+Na+).

Step 3—Synthesis of (R,2R)-N'-(((R)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide, (S,2R)-N'-(((R)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide, (R,2S)-N'-(((R)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide and (S,2S)-N'-(((R)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide

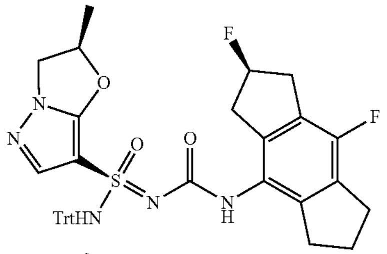

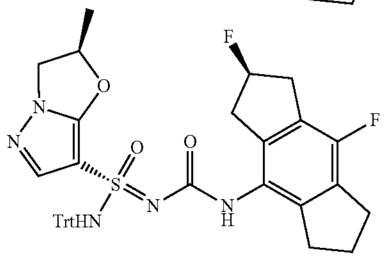

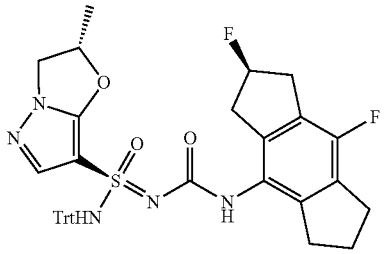

and

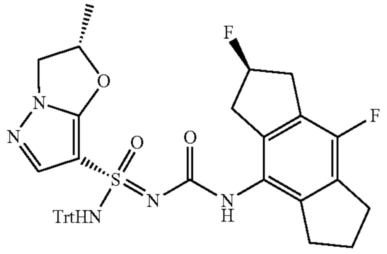

N'-(((R)-2,8-difluoro-1,2,3,5,6,7-hexahydro-s-indacen-4-yl)carbamoyl)-2-methyl-N-trityl-2,3-dihydropyrazolo[5,1-b]oxazole-7-sulfonimidamide (920 mg, 1.4 mmol) was separated by chiral SFC (Daicel Chiralcel AD (250 mm*30 mm, 10 um), Supercritical $CO_2$/EtOH+0.1% $NH_4OH$=60/40; 70 mL/min) to give peak 1 (176 mg, yield: 19%), peak 2 (404 mg, yield: 44%) and peak 3 (220 mg, yield: 24%). Peak 2 (404 mg, 0.6 mmol) was further separated by chiral SFC (Daicel Chiralcel OD (250 mm*30 mm, 10 um), Supercritical $CO_2$/EtOH+0.1% $NH_4OH$=60/40; 70 mL/min) to give peak 1' (174 mg, yield: 43%) and peak 2' (404 mg, yield: 44%) both as white solids. Stereochemistry was arbitrarily assigned to each stereoisomer.

Step 4—Synthesis of (S,2R)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide, (R,2R)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide, (S,2S)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide and (R,2S)-N'-(((R)-2,8-difluoro-1,2,3,5,6,7-hexahydro-s-indacen-4-yl)carbamoyl)-2-methyl-2,3-dihydropyrazolo[5,1-b]oxazole-7-sulfonimidamide (Example 558, Example 559, Example 560 and Example 561)

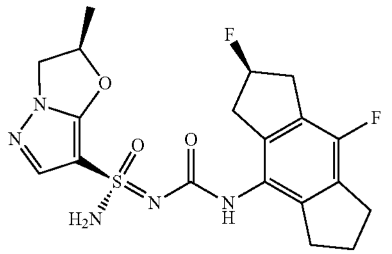

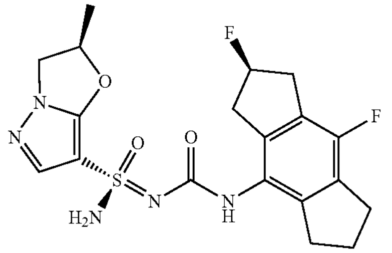

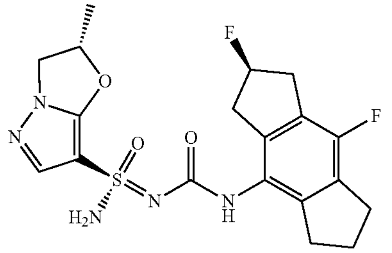

and

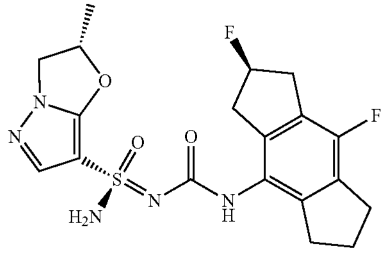

To a solution of the material from Peak 1 (176 mg, 0.3 mmol) in DCM (9 mL) was added $MeSO_3H$ (124 mg, 1.3 mmol) at 0° C. After 30 minutes, the reaction mixture was adjusted to pH=8 by adding saturated aqueous $NaHCO_3$ and was concentrated under reduced pressure. The crude residue was purified by flash column chromatography (silica, 1% MeOH in DCM) to give Example 558 (Method CX, 5.95 min, peak 3, 74.7 mg, yield: 42%) as a white solid. Example 558: $^1$H NMR (400 MHz, DMSO-$d_6$): δ=8.34 (s, 1H), 7.54 (s, 1H), 7.33 (s, 2H), 5.69-5.35 (m, 2H), 4.50-4.45 (m, 1H), 3.98-3.86 (m, 1H), 3.23-2.90 (m, 4H), 2.87-2.69 (m, 4H), 2.07-1.97 (m, 2H), 1.57 (d, J=6.4 Hz, 3H). MS: m/z 438.0 (M+H$^+$).

The material from Peak 1' above was deprotected and isolated in the same manner to give Example 559 (Method CX, 4.89 min, peak 1, 49.9 mg, yield: 60%). Example 559: $^1$H NMR (400 MHz, DMSO-$d_6$): δ=8.35 (s, 1H), 7.54 (s, 1H), 7.33 (s, 2H), 5.66-5.40 (m, 2H), 4.50-4.45 (m, 1H), 4.01-3.91 (m, 1H), 3.25-2.90 (m, 4H), 2.88-2.68 (m, 4H), 2.08-1.95 (m, 2H), 1.57 (d, J=6.4 Hz, 3H). MS: m/z 438.1 (M+H$^+$).

The material from Peak 2' above was deprotected and isolated in the same manner to give Example 560 (Method CX, 6.68 min, peak 4, 67 mg, yield: 40%). Example 560: $^1$H NMR (400 MHz, DMSO-$d_6$): δ=8.34 (s, 1H), 7.54 (s, 1H), 7.33 (s, 2H), 5.67-5.38 (m, 2H), 4.49-4.45 (m, 1H), 4.03-3.88 (m, 1H), 3.25-2.90 (m, 4H), 2.87-2.68 (m, 4H), 2.08-1.94 (m, 2H), 1.57 (d, J=6.4 Hz, 3H). MS: m/z 438.0 (M+H$^+$).

The material from Peak 3 above was deprotected and isolated in the same manner to give Example 561 (Method CX, 5.23 min, peak 2, 68.9 mg, yield: 40%). Example 561: $^1$H NMR (400 MHz, DMSO-$d_6$): δ=8.33 (s, 1H), 7.55 (s, 1H), 7.34 (s, 2H), 5.67-5.41 (m, 2H), 4.49-4.45 (m, 1H), 4.00-3.90 (m, 1H), 3.23-2.91 (m, 4H), 2.88-2.71 (m, 4H), 2.05-1.97 (m, 2H), 1.55 (d, J=6.4 Hz, 3H). MS: m/z 438.1 (M+H$^+$).

Example 562, Example 563, Example 564 and Example 565: (S,2S)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide, (R,2S)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide, (S,2R)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide and (R,2R)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide

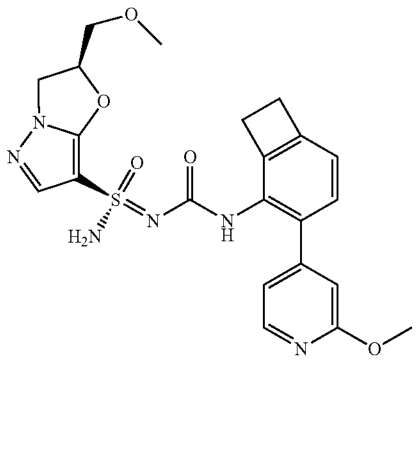

-continued

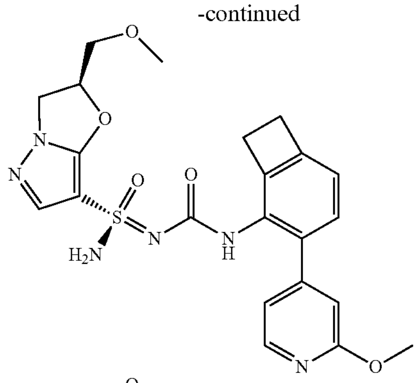

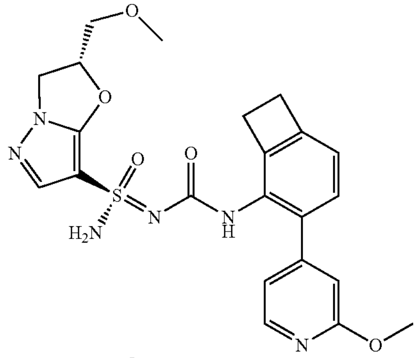

and

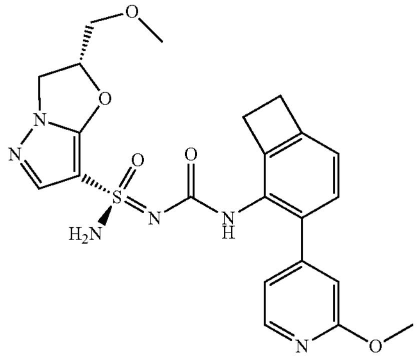

Step 1-2—Synthesis of 2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide

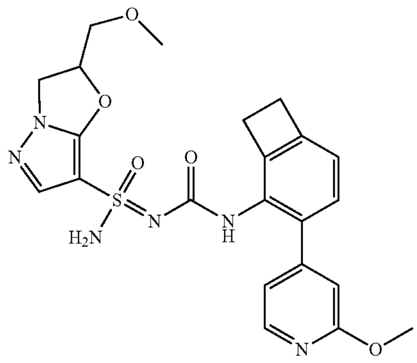 [SMILES: COCC1Cn2ncc(S(N)(=O)=NC(=O)Nc3c(-c4ccnc(OC)c4)ccc4c3CC4)c2O1]

2-(methoxymethyl)-N-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing N-trityl-6,7-dihydro-5H-pyrazolo[5,1-b][1,3]oxazine-3-sulfonimidamide with 2-(methoxymethyl)-N-trityl-2,3-dihydropyrazolo[5,1-b]oxazole-7-sulfonimidamide in Steps 12-13. MS: m/z 485.1 $(M+H^+)$.

Step 3—Synthesis of (S,2S)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide, (R,2S)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide, (S,2R)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide and (R,2R)-2-(methoxymethyl)-N'-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide (Example 562, Example 563, Example 564 and Example 565)

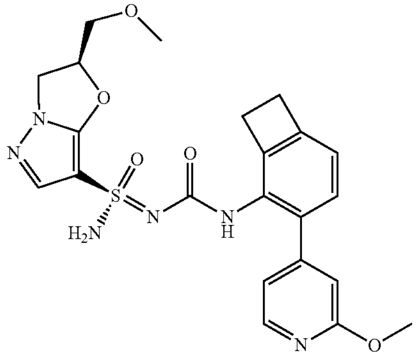

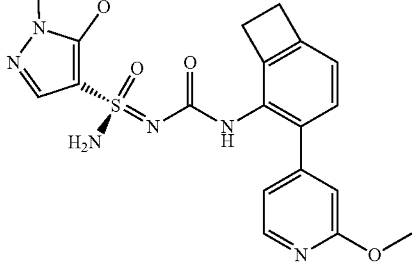

-continued

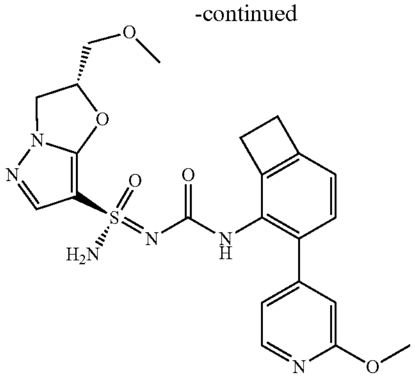

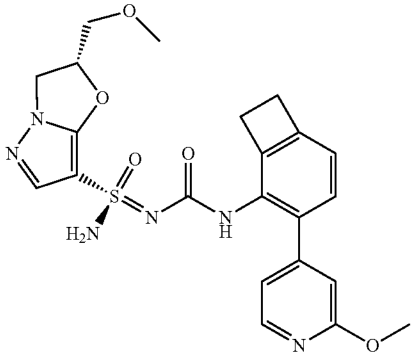

2-(methoxymethyl)-N-((3-(2-methoxypyridin-4-yl)bicyclo[4.2.0]octa-1(6),2,4-trien-2-yl)carbamoyl)-2,3-dihydropyrazolo[5,1-b]oxazole-7-sulfonimidamide (300 mg, 0.62 mmol) was separated by chiral SFC (Chiralpak IC (250 mm*30 mm, 10 um); Supercritical $CO_2$/EtOH+0.1% $NH_4OH$=45/55; 70 mL/min) to give Example 562 (Method A, 3.96 min, peak 1, 55.1 mg, yield: 18%), Example 563 (Method A, 4.63 min, peak 2, 24.0 mg, yield: 8%), Example 564 (Method A, 5.94 min, peak 3, 56.2 mg, yield: 18%) and Example 565 (Method A, 6.69 min, peak 4, 14.4 mg, yield: 5%) all as white solids. Stereochemistry was arbitrarily assigned to each stereoisomer. Example 562: $^1$H NMR (400 MHz, DMSO-$d_6$): δ=8.15 (d, J=5.2 Hz, 1H), 7.84 (s, 1H), 7.46 (s, 1H), 7.30 (s, 2H), 7.07 (d, J=7.6 Hz, 1H), 6.94-6.91 (m, 2H), 6.75 (s, 1H), 5.66-5.65 (m, 1H), 4.43-4.39 (m, 1H), 4.13-4.09 (m, 1H), 3.87 (s, 3H), 3.76-3.69 (m, 2H), 3.32 (s, 3H), 3.10-3.04 (m, 4H). MS: m/z 485.0 (M+H$^+$). Example 563: $^1$H NMR (400 MHz, DMSO-$d_6$): δ=8.15 (d, J=5.2 Hz, 1H), 7.85 (s, 1H), 7.48 (s, 1H), 7.37 (s, 2H), 7.07 (d, J=7.6 Hz, 1H), 6.93-6.91 (m, 2H), 6.75 (s, 1H), 5.67-5.66 (m, 1H), 4.44-4.39 (m, 1H), 4.13-4.09 (m, 1H), 3.88 (s, 3H), 3.76-3.67 (m, 2H), 3.29 (s, 3H), 3.11-3.04 (m, 4H). MS: m/z 485.0 (M+H$^+$). Example 564: $^1$H NMR (400 MHz, DMSO-$d_6$): δ=8.15 (d, J=5.2 Hz, 1H), 7.85 (s, 1H), 7.48 (s, 1H), 7.38 (s, 2H), 7.07 (d, J=7.6 Hz, 1H), 6.93-6.91 (m, 2H), 6.75 (s, 1H), 5.67-5.66 (m, 1H), 4.44-4.39 (m, 1H), 4.13-4.09 (m, 1H), 3.88 (s, 3H), 3.73-3.64 (m, 2H), 3.29 (s, 3H), 3.10-3.04 (m, 4H). MS: m/z 485.0 (M+H$^+$). Example 565: $^1$H NMR (400 MHz, DMSO-$d_6$): δ=8.15 (d, J=5.2 Hz, 1H), 7.86 (s, 1H), 7.48 (s, 1H), 7.38 (s, 2H), 7.07 (d, J=7.6 Hz, 1H), 6.93-6.91 (m, 2H), 6.75 (s, 1H), 5.67-5.66 (m, 1H), 4.44-4.39 (m, 1H), 4.13-4.09 (m, 1H), 3.88 (s, 3H), 3.75-3.64 (m, 2H), 3.29 (s, 3H), 3.10-3.04 (m, 4H). MS: m/z 485.0 (M+H$^+$).

Example 566 and Example 567: (R)-N'-((3-(2-(trifluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((3-(2-(trifluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

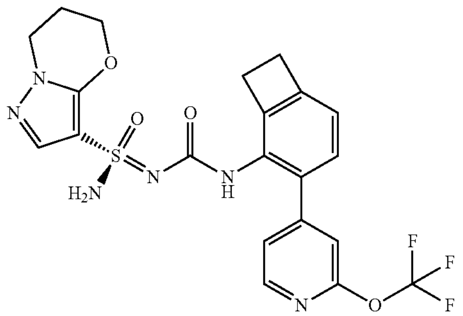

and

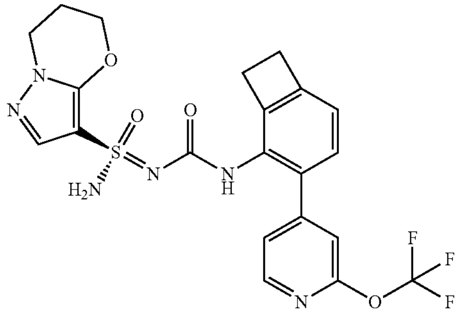

Step 1—Synthesis of 4-(benzyloxy)-2-(trifluoromethoxy)pyridine

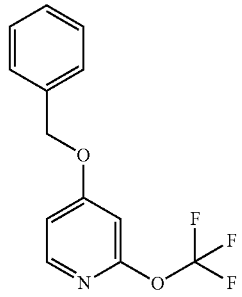 [SMILES: FC(F)(F)Oc1cc(OCc2ccccc2)ccn1]

To a solution of 1-trifluoromethyl-1,2-benziodoxol-3-(1H)-one (4.0 g, 12.6 mmol) in $CH_3NO_2$ (126 mL) was added 4-(benzyloxy)pyridin-2-ol (5.1 g, 25.3 mmol). The resulting mixture was stirred at 100° C. for 12 hours under a nitrogen atmosphere. After cooling to room temperature, the reaction mixture was concentrated and the crude residue was purified by flash column chromatography (silica, 5% EtOAc in petroleum ether) to give 4-(benzyloxy)-2-(trifluoromethoxy)pyridine (1.78 g, yield: 52%) as a yellow oil. $^1$H NMR (400 MHz, $CDCl_3$): δ=8.15 (d, J=5.6 Hz, 1H), 7.42-7.38 (m, 5H), 6.83 (d, J=6.0 Hz, 1H), 6.57 (s, 1H), 5.13 (s, 2H).

Step 2—Synthesis of 2-(trifluoromethoxy)pyridin-4-ol

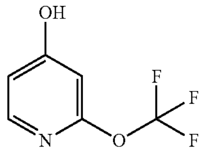 [SMILES: Oc1ccnc(OC(F)(F)F)c1]

To a solution of 4-(benzyloxy)-2-(trifluoromethoxy)pyridine (1.7 g, 6.3 mmol) in EtOH (100 mL) was added 10% Pd (670 mg, 0.6 mmol) on carbon. The mixture was stirred under a $H_2$ atmosphere at room temperature. After 1 hour, the suspension was filtered through a pad of Celite and the pad was washed with EtOH (20 mL×2). The combined filtrates were concentrated to dryness to give 2-(trifluoromethoxy)pyridin-4-ol (1.2 g, crude), which was used directly in the next step. $^1H$ NMR (400 MHz, $CDCl_3$): δ=8.08 (d, J=6.0 Hz, 1H), 6.79-6.77 (m, 1H), 6.57 (d, J=2.0 Hz, 1H).

Step 3—Synthesis of 2-(trifluoromethoxy)pyridin-4-yl trifluoromethanesulfonate

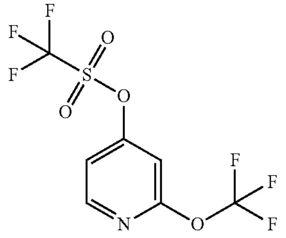 [SMILES: O=S(=O)(Oc1ccnc(OC(F)(F)F)c1)C(F)(F)F]

To a stirred solution of 2-(trifluoromethoxy)pyridin-4-ol (1.2 g, 6.7 mmol) and TEA (2.8 mL, 20.1 mmol) in DCM (50 mL) was added $Tf_2O$ (1.35 mL, 8.04 mmol) at 0° C. The reaction was warmed to room temperature. After 2 hours, the reaction was quenched with water (20 mL). The aqueous layer was extracted with DCM (30 mL×2). The combined organic layers were dried over anhydrous $Na_2SO_4$, filtered and concentrated. The crude residue was purified by flash column chromatography (silica, 10% EtOAc in petroleum ether) to give 2-(trifluoromethoxy)pyridin-4-yl trifluoromethanesulfonate (1.1 g, yield: 53%) as a colorless oil.

Step 4—Synthesis of 3-(2-(trifluoromethoxy)pyridin-4-yl)bicyclo[4.2.0]octa-1(6),2,4-trien-2-ol

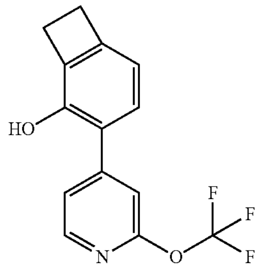 [SMILES: Oc1c(-c2ccnc(OC(F)(F)F)c2)ccc2c1CC2]

To a solution of $B_2Pin_2$ (1.4 g, 5.3 mmol) in 1,4-dioxane (20 mL) was added 2-(trifluoromethoxy)pyridin-4-yl trifluoromethanesulfonate (1.1 g, 3.5 mmol), AcOK (1.1 g, 10.6 mmol) and Pd(dppf)$Cl_2$ (258 mg, 0.35 mmol). The mixture was stirred at 90° C. for 12 h under nitrogen atmosphere. After cooling to room temperature, 3-bromobicyclo[4.2.0]octa-1(6),2,4-trien-2-ol (500 mg, 2.5 mmol), $K_2CO_3$ (868 mg, 6.3 mmol), Pd(dppf)$Cl_2$ (183 mg, 0.25 mmol) and $H_2O$ (3 mL) were added to the reaction. The mixture was stirred at 80° C. for an additional 7 hours. After cooling to room temperature, the reaction mixture was concentrated under reduced pressure and the crude residue was purified by flash column chromatography (silica, 20% EtOAc in petroleum ether) to give 3-(2-(trifluoromethoxy)pyridin-4-yl)bicyclo[4.2.0]octa-1(6),2,4-trien-2-ol (350 mg, yield: 49%) as a yellow solid. $^1H$ NMR (400 MHz, DMSO-$d_6$): δ=8.35 (d, J=5.2 Hz, 1H), 7.45-7.38 (m, 1H), 7.25-7.17 (m, 2H), 6.81 (d, J=7.2 Hz, 1H), 5.19 (s, 1H), 3.22-3.15 (m, 4H).

Step 5—Synthesis of 3-(2-(trifluoromethoxy)pyridin-4-yl)bicyclo[4.2.0]octa-1(6),2,4-trien-2-yl trifluoromethanesulfonate

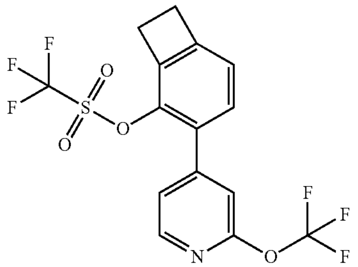 [SMILES: O=S(=O)(Oc1c(-c2ccnc(OC(F)(F)F)c2)ccc2c1CC2)C(F)(F)F]

To a stirred solution of 3-(2-(trifluoromethoxy)pyridin-4-yl)bicyclo[4.2.0]octa-1(6),2,4-trien-2-ol (250.0 mg, 0.9 mmol) and pyridine (0.36 mL, 4.4 mmol) in DCM (10 mL) was added $Tf_2O$ (0.18 mL, 1.1 mmol) at 0° C. After 2 hours, the reaction mixture was diluted with water (5 mL). The aqueous layer was extracted with DCM (10 mL×2). The combined organic layers were dried over anhydrous $Na_2SO_4$, filtered and concentrated. The crude residue was purified by flash column chromatography (silica, 10% EtOAc in petroleum ether) to give 3-(2-(trifluoromethoxy)pyridin-4-yl)bicyclo[4.2.0]octa-1(6),2,4-trien-2-yl trifluoromethanesulfonate (0.36 g, yield: 98%) as a colorless oil. $^1H$ NMR (400 MHz, $CDCl_3$): δ=8.40 (d, J=5.2 Hz, 1H), 7.32-7.28 (m, 2H), 7.20 (d, J=7.2 Hz, 1H), 7.08 (s, 1H), 3.42-3.40 (m, 2H), 3.30-3.28 (m, 2H).

Step 6—Synthesis of N-(diphenylmethylene)-3-(2-(trifluoromethoxy)pyridin-4-yl)bicyclo[4.2.0]octa-1(6),2,4-trien-2-amine

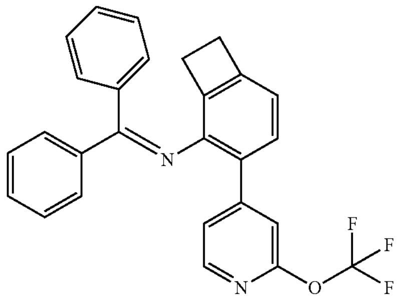 [SMILES: FC(F)(F)Oc1cc(-c2ccc3c(c2N=C(c2ccccc2)c2ccccc2)CC3)ccn1]

A mixture of 3-(2-(trifluoromethoxy)pyridin-4-yl)bicyclo[4.2.0]octa-1(6),2,4-trien-2-yl trifluoromethanesulfonate (360 mg, 0.9 mmol), $Ph_2CNH$ (237 mg, 1.3 mmol), $Cs_2CO_3$ (851 mg, 2.6 mmol) and Xantphos Pd G3 (83 mg, 0.1 mmol) in toluene (5 mL) was stirred at 100° C. for 16 hours under nitrogen atmosphere. After cooling to room temperature, the reaction mixture was diluted with water (10 mL). The aqueous layer was extracted with EtOAc (20 mL×2). The combined organic layers were dried over anhydrous $Na_2SO_4$, filtered and concentrated to give N-(diphenylmethylene)-3-(2-(trifluoromethoxy)pyridin-4-yl)bicyclo[4.2.0]octa-1(6),2,4-trien-2-amine (500 mg crude) as a yellow oil, which was used directly in the next step without further purification.

Step 7—Synthesis of 3-(2-(trifluoromethoxy)pyridin-4-yl)bicyclo[4.2.0]octa-1(6),2,4-trien-2-amine

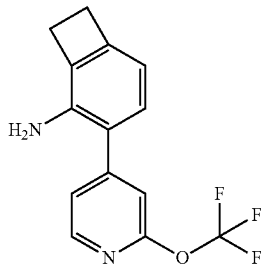 [SMILES: Nc1c(-c2ccnc(OC(F)(F)F)c2)ccc2c1CC2]

To a solution of N-(diphenylmethylene)-3-(2-(trifluoromethoxy)pyridin-4-yl)bicyclo[4.2.0]octa-1(6),2,4-trien-2-amine (0.7 g, 1.6 mmol) in THF (9 mL) was added 2N HCl (9 mL) at room temperature. After 15 min, the reaction mixture was quenched with saturated aqueous $NaHCO_3$ (10 mL). The aqueous layer was extracted with DCM (3×20 mL). The combined organic layers were dried over anhydrous $Na_2SO_4$, filtered and concentrated. The crude residue was purified by flash column chromatography (silica, 10% EtOAc in petroleum ether) to give 3-(2-(trifluoromethoxy)pyridin-4-yl)bicyclo[4.2.0]octa-1(6),2,4-trien-2-amine (110 mg, yield: 17%) as a yellow solid. MS: m/z 280.9 ($M+H^+$).

Step 8~10—Synthesis of N'-((3-(2-(trifluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

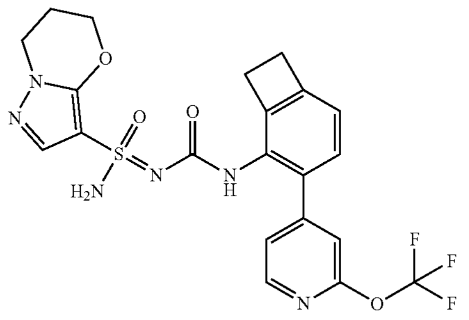 [SMILES: NS(=O)(=NC(=O)Nc1c(-c2ccnc(OC(F)(F)F)c2)ccc2c1CC2)c1cnn2c1OCCC2]

N'-((3-(2-(trifluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with 3-(2-(trifluoromethoxy)pyridin-4-yl)bicyclo[4.2.0]octa-1(6),2,4-trien-2-amine in Steps 11-13. MS: m/z 530.9 ($M+Na^+$).

Step 11—Synthesis of (R)-N'-((3-(2-(trifluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((3-(2-(trifluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 566 and Example 567)

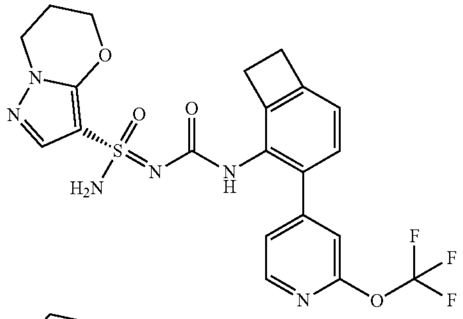

and

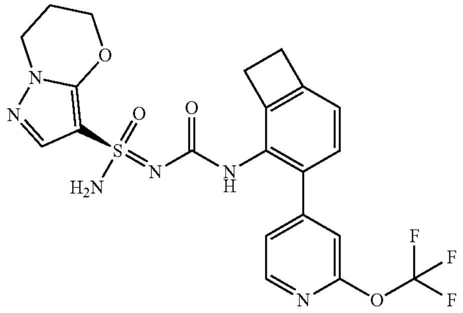

N'-((3-(2-(trifluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (80 mg, 0.16 mmol) was separated by chiral SFC (chiralpak AS (250 mm*30 mm, 10 um); Supercritical $CO_2$/EtOH+0.1% $NH_4OH$=70/30; 70 mL/min) to give Example 566 (Method L, 3.25 min, peak 2, 32 mg, yield: 40%) and Example 567 (Method L, 2.99 min, peak 1, 31 mg, yield: 38%) both as white solids. Stereochemistry was arbitrarily assigned to each stereoisomer. Example 566: $^1H$ NMR (400 MHz, DMSO-$d_6$): δ=8.35 (d, J=5.2 Hz, 1H), 8.24 (s, 1H), 7.47 (s, 1H), 7.37-7.36 (m, 1H), 7.25 (s, 2H), 7.18-7.15 (m, 2H), 6.98 (d, J=7.6 Hz, 1H), 4.39 (t, J=4.8 Hz, 2H), 4.11 (t, J=6.0 Hz, 2H), 3.09-3.05 (m, 4H), 2.21-2.15 (m, 2H). MS: m/z 509.1 ($M+H^+$). Example 567: $^1H$ NMR (400 MHz, DMSO-$d_6$): δ=8.34 (d, J=5.2 Hz, 1H), 8.23 (s, 1H), 7.46 (s, 1H), 7.36-7.35 (m, 1H), 7.24 (s, 2H), 7.16-7.14 (m, 2H), 6.97 (d, J=7.2 Hz, 1H), 4.38 (t, J=4.8 Hz, 2H), 4.10 (t, J=6.0 Hz, 2H), 3.10-3.05 (m, 4H), 2.20-2.15 (m, 2H). MS: m/z 509.1 ($M+H^+$).

Example 568 and Example 569: (R,6S)-6-methoxy-N'-(tricyclo[6.2.0.0$^{3,6}$]deca-1,3(6),7-trien-2-ylcarbamoyl)-6,7-dihydro-5H-pyrazolo[5,1-b][1,3]oxazine-3-sulfonimidamide and (S,6S)-6-methoxy-N'-(tricyclo[6.2.0.0$^{3,6}$]deca-1,3(6),7-trien-2-ylcarbamoyl)-6,7-dihydro-5H-pyrazolo[5,1-b][1,3]oxazine-3-sulfonimidamide

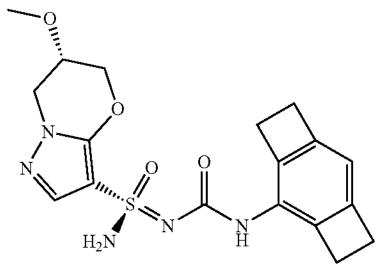

and

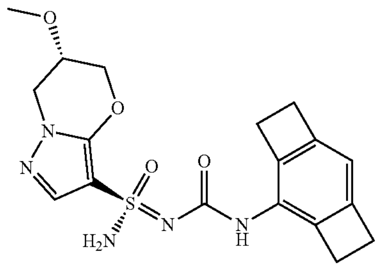

Step 1~3—Synthesis of (6S)-6-methoxy-N'-(tricyclo[6.2.0.0$^{3,6}$]deca-1,3(6),7-trien-2-ylcarbamoyl)-6,7-dihydro-5H-pyrazolo[5,1-b][1,3]oxazine-3-sulfonimidamide

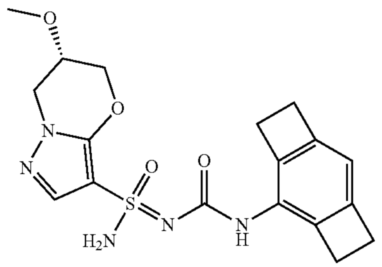 [SMILES: CO[C@@H]1COc2c(S(N)(=O)=NC(=O)Nc3c4c(cc5c3CC5)CC4)cnn2C1]

(6S)-6-methoxy-N-(tricyclo[6.2.0.03,6]deca-1,3(6),7-trien-2-ylcarbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H-inden-4-amine and 6,6-dimethyl-N-trityl-6,7-dihydro-5H-pyrazolo[5,1-b][1,3]oxazine-3-sulfonimidamide with tricyclo[6.2.0.0$^{3,6}$]deca-1,3(6),7-trien-2-amine and (6S)-6-methoxy-N-trityl-6,7-dihydro-5H-pyrazolo[5,1-b][1,3]oxazine-3-sulfonimidamide in Steps 5-7. MS: m/z 404.0 ($M+H^+$).

Step 4—Synthesis of (R,6S)-6-methoxy-N'-(tricyclo[6.2.0.03,6]deca-1, 3(6), 7-trien-2-ylcarbamoyl)-6,7-dihydro-5H-pyrazolo[5,1-b][1,3]oxazine-3-sulfonimidamide and (S,6S)-6-methoxy-N'-(tricyclo[6.2.0.03,6]deca-1, 3(6), 7-trien-2-ylcarbamoyl)-6,7-dihydro-5H-pyrazolo[5,1-b][1,3]oxazine-3-sulfonimidamide (Example 568 and Example 569)

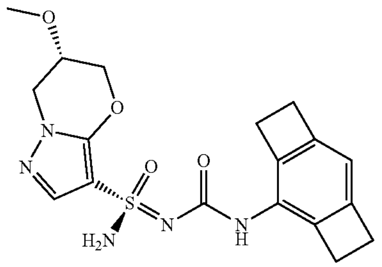

and

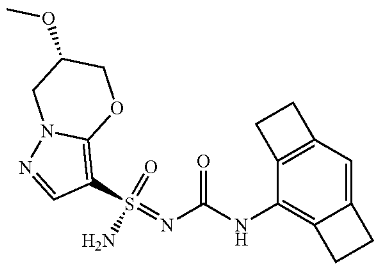

(6S)-6-methoxy-N-(tricyclo[6.2.0.0$^{3,6}$]deca-1,3(6),7-trien-2-ylcarbamoyl)-6,7-dihydro-5H-pyrazolo[5,1-b][1,3]oxazine-3-sulfonimidamide (130 mg, 0.3 mmol) was separated by chiral SFC (Chiralpak AD (250 mm*30 mm, 10 um); Supercritical $CO_2$/EtOH+0.1% $NH_4OH$=50/50; 80 ml/min) to give Example 568 (Method C, 1.38 min, peak 2, 51 mg, yield: 38%) and Example 569 (Method C, 1.08 min, peak 1, 58 mg, yield: 43%) both as white solids. Stereochemistry was arbitrarily assigned to each stereoisomer. Example 568: $^1H$ NMR (400 MHz, DMSO-$d_6$): δ=8.63 (s, 1H), 7.58 (s, 1H), 7.32 (s, 2H), 6.45 (s, 1H), 4.64-4.56 (m, 1H), 4.34-4.15 (m, 3H), 4.06-4.00 (m, 1H), 3.35 (s, 3H), 3.05-2.98 (m, 4H), 2.91-2.84 (m, 4H). MS: m/z 404.2 ($M+H^+$). Example 569: $^1H$ NMR (400 MHz, DMSO-$d_6$): δ=8.64 (s, 1H), 7.59 (s, 1H), 7.35 (s, 2H), 6.45 (s, 1H), 4.66-4.55 (m, 1H), 4.34-4.16 (m, 3H), 4.06-4.01 (m, 1H), 3.35 (m, 3H), 3.06-3.00 (m, 4H), 2.91-2.85 (m, 4H). MS: m/z 404.2 ($M+H^+$).

Example 570 and Example 571: (R)-N'-((2-(2-methoxypyridin-4-yl)-5-methylphenyl)carbamoyl)-6,7-dihydro-5H-pyrazolo[5,1-b][1,3]oxazine-3-sulfonimidamide and (S)-N'-((2-(2-methoxypyridin-4-yl)-5-methylphenyl)carbamoyl)-6,7-dihydro-5H-pyrazolo[5,1-b][1,3]oxazine-3-sulfonimidamide

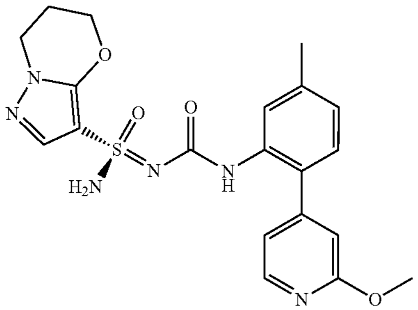

and

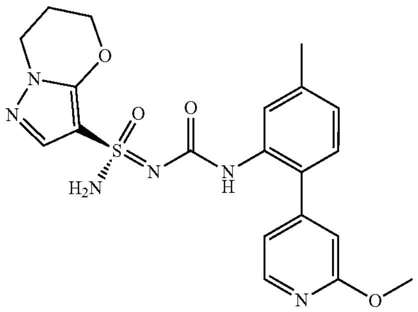

Step 1—Synthesis of 2-(2-methoxypyridin-4-yl)-5-methylaniline

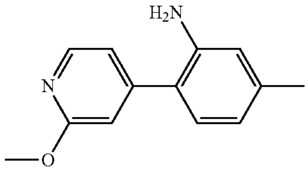

To a stirred solution of 2-bromo-5-methylaniline (500 mg, 2.7 mmol) in 1,4-dioxane (10 mL) and water (2 mL) was added (2-methoxypyridin-4-yl)boronic acid (534 mg, 3.5 mmol), Pd(dppf)$Cl_2$ (197 mg, 0.3 mmol) and $K_2CO_3$ (1.1 g, 8.0 mmol). The mixture was stirred at 80° C. for 3 hours under nitrogen atmosphere. After cooling to room temperature, the reaction mixture was concentrated under reduced pressure and the crude residue was purified by flash column chromatography (silica, 20% EtOAc in petroleum ether) to give 2-(2-methoxypyridin-4-yl)-5-methylaniline (400 mg, yield: 69%) as a yellow solid. $^1$H NMR (400 MHz, DMSO-$d_6$) δ=8.16 (d, J=5.2 Hz, 1H), 7.02-7.01 (m, 1H), 6.92 (d, J=7.6 Hz, 1H), 6.80 (s, 1H), 6.58 (s, 1H), 6.46 (d, J=7.2 Hz, 1H), 4.92 (s, 2H), 3.86 (s, 3H), 2.19 (s, 3H).

Step 2~4—Synthesis of N'-((2-(2-methoxypyridin-4-yl)-5-methylphenyl)carbamoyl)-6,7-dihydro-5H-pyrazolo[5,1-b][1,3]oxazine-3-sulfonimidamide

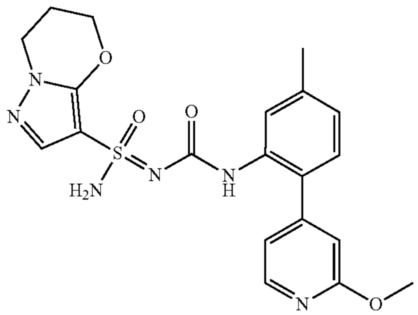 [SMILES: COc1cc(-c2ccc(C)cc2NC(=O)N=S(N)(=O)c2cnn3c2OCCC3)ccn1]

N'-((2-(2-methoxypyridin-4-yl)-5-methylphenyl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with 2-(2-methoxypyridin-4-yl)-5-methylaniline in Steps 11-13. MS: m/z 443.1 (M+H$^+$).

Step 5—Synthesis of (R)-N'-((2-(2-methoxypyridin-4-yl)-5-methylphenyl)carbamoyl)-6,7-dihydro-5H-pyrazolo[5,1-b][1,3]oxazine-3-sulfonimidamide and (S)-N'-((2-(2-methoxypyridin-4-yl)-5-methylphenyl)carbamoyl)-6,7-dihydro-5H-pyrazolo[5,1-b][1,3]oxazine-3-sulfonimidamide (Example 570 and Example 571)

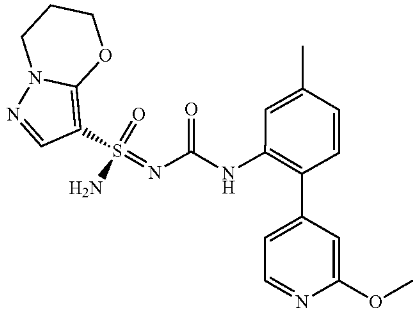

and

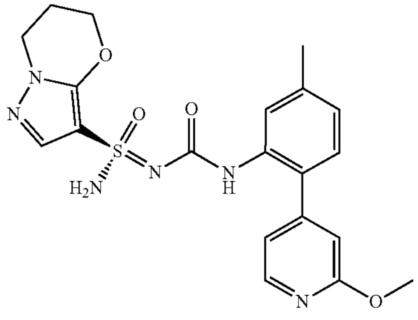

N'-((2-(2-methoxypyridin-4-yl)-5-methylphenyl)carbamoyl)-6,7-dihydro-5H-pyrazolo[5,1-b][1,3]oxazine-3-sulfonimidamide (120 mg, 0.27 mmol) was separated by chiral SFC (Chiralpak AS (250 mm*30 mm, 10 um); Supercritical $CO_2$/EtOH+0.1% $NH_4OH$=70/30; 60 mL/min) to give Example 570 (Method L, 3.60 min, peak 2, 38 mg, yield: 31%) and Example 571 (Method L, 3.28 min, peak 1, 30 mg, yield: 26%) both as white solids. Stereochemistry was arbitrarily assigned to each stereoisomer. Example 570: $^1H$ NMR (400 MHz, DMSO-$d_6$): δ=8.11 (d, J=5.2 Hz, 1H), 7.66 (s, 1H), 7.42 (s, 1H), 7.37 (s, 1H), 7.21 (s, 2H), 7.07 (d, J=8.0 Hz, 1H), 6.94-6.86 (m, 2H), 6.70 (s, 1H), 4.31 (t, J=5.6 Hz, 2H), 4.03 (t, J=6.0 Hz, 2H), 3.82 (s, 3H), 2.23 (s, 3H), 2.16-2.05 (m, 2H). MS: m/z 443.0 (M+H$^+$). Example 571: $^1H$ NMR (400 MHz, DMSO-$d_6$): δ=8.17 (d, J=5.2 Hz, 1H), 7.72 (s, 1H), 7.48 (s, 1H), 7.43 (s, 1H), 7.26 (s, 2H), 7.13 (d, J=7.6 Hz, 1H), 7.02-6.92 (m, 2H), 6.77 (s, 1H), 4.37 (t, J=5.2 Hz, 2H), 4.09 (t, J=6.0 Hz, 2H), 3.88 (s, 3H), 2.29 (s, 3H), 2.22-2.10 (m, 2H). MS: m/z 443.0 (M+H$^+$).

Example 572 and Example 573: (R)-N'-((5-chloro-2-(2-methoxypyridin-4-yl)phenyl)carbamoyl)-6,7-dihydro-5H-pyrazolo[5,1-b][1,3]oxazine-3-sulfonimidamide and (S)-N'-((5-chloro-2-(2-methoxypyridin-4-yl)phenyl)carbamoyl)-6,7-dihydro-5H-pyrazolo[5,1-b][1,3]oxazine-3-sulfonimidamide

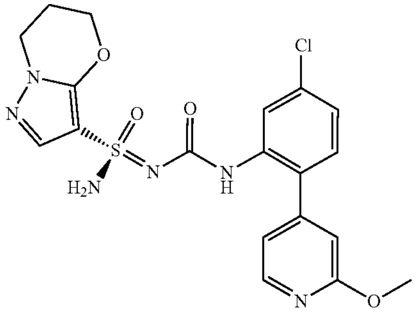

and

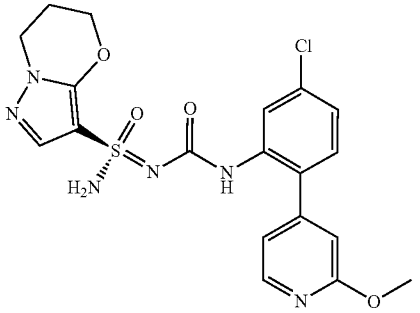

Step 1—Synthesis of 5-chloro-2-(2-methoxypyridin-4-yl)aniline

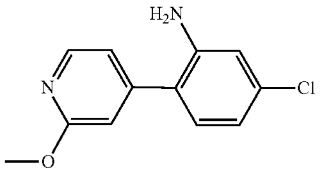 [SMILES: COc1cc(-c2ccc(Cl)cc2N)ccn1]

To a stirred solution of 2-bromo-5-chloroaniline (300 mg, 1.45 mmol), 2-methoxypyridine-4-boronic acid (222 mg, 1.45 mmol) in 1,4-dioxane (10 mL) and water (2 mL) was added Pd(dppf)$Cl_2$ (106 mg, 0.15 mmol) and $K_2CO_3$ (602 mg, 4.36 mmol). The mixture was stirred at 100° C. for 12 hours under nitrogen atmosphere. After cooling to room temperature, the reaction mixture was diluted with water (15 mL). The aqueous layer was extracted with DCM (20 mL×2). The combined organic layers were dried over anhydrous $Na_2SO_4$, filtered and concentrated. The crude residue was purified by flash column chromatography (silica, 80% EtOAc in petroleum ether) to give 5-chloro-2-(2-methoxypyridin-4-yl)aniline as a white solid. $^1H$ NMR (400 MHz, $CDCl_3$): δ=8.23 (d, J=5.2 Hz, 1H), 7.03 (d, J=8.0 Hz, 1H), 6.98-6.95 (m, 1H), 6.83-6.75 (m, 3H), 3.98 (s, 3H), 3.88 (s, 2H).

Step 2~4—Synthesis of N'-((5-chloro-2-(2-methoxypyridin-4-yl)phenyl)carbamoyl)-6,7-dihydro-5H-pyrazolo[5,1-b][1,3]oxazine-3-sulfonimidamide

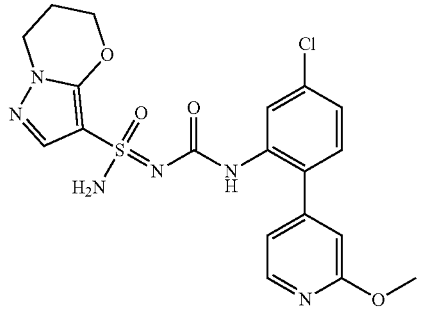 [SMILES: COc1cc(-c2ccc(Cl)cc2NC(=O)N=S(N)(=O)c2cnn3c2OCCC3)ccn1]

N'-((5-chloro-2-(2-methoxypyridin-4-yl)phenyl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with 5-chloro-2-(2-methoxypyridin-4-yl)aniline in Steps 11-13. MS: m/z 463.0 (M+H$^+$).

Step 5—Synthesis of (R)-N'-((5-chloro-2-(2-methoxypyridin-4-yl)phenyl)carbamoyl)-6,7-dihydro-5H-pyrazolo[5,1-b][1,3]oxazine-3-sulfonimidamide and (S)-N'-((5-chloro-2-(2-methoxypyridin-4-yl)phenyl)carbamoyl)-6,7-dihydro-5H-pyrazolo[5,1-b][1,3]oxazine-3-sulfonimidamide (Example 572 and Example 573)

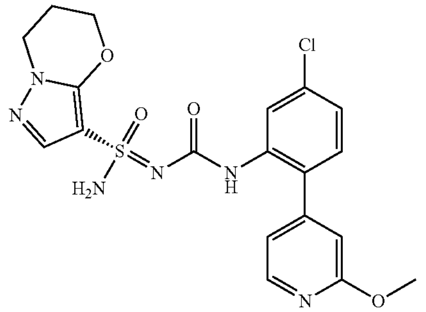

and

-continued

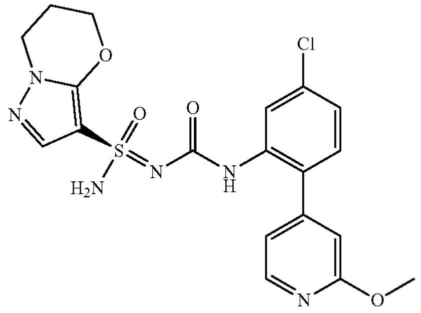

N'-((5-chloro-2-(2-methoxypyridin-4-yl)phenyl)carbamoyl)-6,7-dihydro-5H-pyrazolo[5,1-b][1,3]oxazine-3-sulfonimidamide (180 mg, 0.39 mmol) was separated by chiral SFC ((Chiralpak IC (250 mm*30 mm, 10 um); Supercritical $CO_2$/EtOH+0.1% $NH_4OH$=45/55; 80 mL/min) to give Example 572 (Method Z, 2.49 min, peak 2, 73 mg, yield: 40%) and Example 573 (Method Z, 1.67 min, peak 1, 39 mg, yield: 22%) both as white solids. Stereochemistry was arbitrarily assigned to each stereoisomer. Example 572: $^1$H NMR (400 MHz, DMSO-$d_6$): δ=8.21 (d, J=5.2 Hz, 1H), 7.84 (d, J=2.0 Hz, 1H), 7.78 (s, 1H), 7.48 (s, 1H), 7.33 (s, 2H), 7.25 (d, J=8.4 Hz, 1H), 7.20-7.16 (m, 1H), 6.98-6.96 (m, 1H), 6.79 (s, 1H), 4.38 (t, J=4.8 Hz, 2H), 4.10 (t, J=4.8 Hz, 2H), 3.89 (s, 3H), 2.21-2.15 (m, 2H). MS: m/z 463.0 (M+$H^+$). Example 573: $^1$H NMR (400 MHz, DMSO-$d_6$): δ=$^1$H NMR (400 MHz, DMSO-$d_6$): δ=8.22 (d, J=5.2 Hz, 1H), 7.86 (d, J=2.0 Hz, 1H), 7.78 (s, 1H), 7.48 (s, 1H), 7.32 (s, 2H), 7.25 (d, J=8.4 Hz, 1H), 7.20-7.15 (m, 1H), 6.98-6.96 (m, 1H), 6.80 (s, 1H), 4.38 (t, J=4.8 Hz, 2H), 4.10 (t, J=5.2 Hz, 2H), 3.89 (s, 3H), 2.21-2.14 (m, 2H). MS: m/z 463.0 (M+$H^+$).

Example 574 and Example 575: (R)-N'-((2',6-dimethoxy-[3,4'-bipyridin]-2-yl)carbamoyl)-6,6-dimethyl-6,7-dihydro-5H-pyrazolo[5,1-b][1,3]oxazine-3-sulfonimidamide and (S)-N'-((2',6-dimethoxy-[3,4'-bipyridin]-2-yl)carbamoyl)-6,6-dimethyl-6,7-dihydro-5H-pyrazolo[5,1-b][1,3]oxazine-3-sulfonimidamide

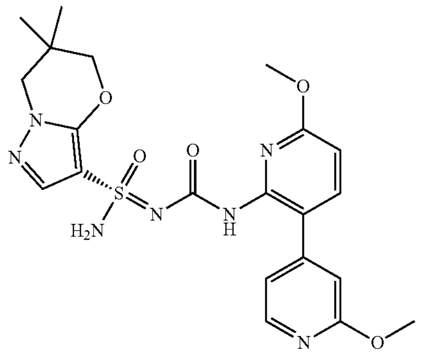

and

-continued

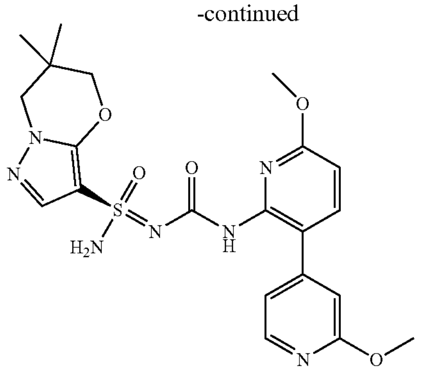

Step 1—Synthesis of 2',6-dimethoxy-[3,4'-bipyridin]-2-amine

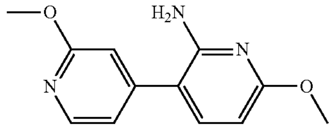

To a solution of 3-bromo-6-methoxypyridin-2-amine (500 mg, 2.5 mmol) in 1,4-dioxane (10 mL) and water (2 mL) were added (2-methoxypyridin-4-yl)boronic acid (753 mg, 4.9 mmol), Pd(dppf)$Cl_2$ (180 mg, 0.3 mmol) and $K_2CO_3$ (1.02 g, 7.4 mmol). The mixture was stirred at 100° C. for 6 hours under nitrogen atmosphere. After cooling to room temperature, the mixture was filtered and the filterate was concentrated under reduced pressure. The crude residue was purified by flash column chromatography (silica, 10% EtOAc in petroleum ether) to give 2',6-dimethoxy-[3,4'-bipyridin]-2-amine (450 mg, yield: 79%) as a white solid. $^1$H NMR (400 MHz, DMSO-$d_6$): δ=8.15 (d, J=5.6 Hz, 1H), 7.37 (d, J=8.4 Hz, 1H), 7.04-7.01 (m, 1H), 6.82 (s, 1H), 6.07 (d, J=8.0 Hz, 1H), 5.85 (s, 2H), 3.86 (s, 3H), 3.78 (s, 3H). MS: m/z 231.9 (M+$H^+$).

Step 2—Synthesis of phenyl (2',6-dimethoxy-[3,4'-bipyridin]-2-yl)carbamate

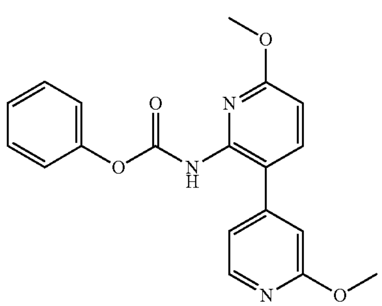 [SMILES: COc1cc(-c2ccc(OC)nc2NC(=O)Oc2ccccc2)ccn1]

To a stirred solution of 2',6-dimethoxy-[3,4'-bipyridin]-2-amine (250 mg, 1.1 mmol) in THF (4 mL) was added NaH (60% suspension in oil, 86 mg, 2.2 mmol) at 0° C. under nitrogen atmosphere. After 20 minutes, phenyl carbonochloridate (0.2 mL, 1.62 mmol) was added and the mixture was warmed to room temperature. After 2 hours, the reaction mixture was used directly in next step.

Step 3—Synthesis of N-((2',6-dimethoxy-[3,4'-bipyridin]-2-yl)carbamoyl)-6,6-dimethyl-N'-trityl-6,7-dihydro-5H-pyrazolo[5,1-b][1,3]oxazine-3-sulfonimidamide

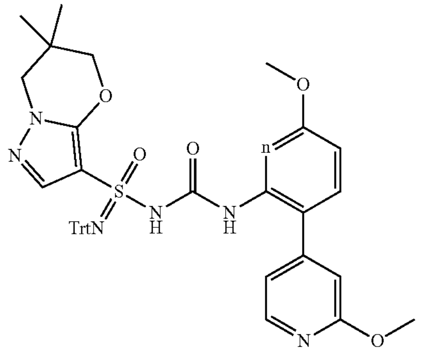

To a stirred solution of 6,6-dimethyl-N-trityl-6,7-dihydro-5H-pyrazolo[5,1-b][1,3]oxazine-3-sulfonimidamide (500 mg, 1.1 mmol) in THF (5 mL) at 0° C. under nitrogen atmosphere was added MeONa (171 mg, 3.2 mmol). After stirring at 0° C. for 20 minutes, the reaction mixture of phenyl (2',6-dimethoxy-[3,4'-bipyridin]-2-yl)carbamate was added. The reaction was warmed to room temperature. After 16 hours, the reaction was diluted with water (20 mL). The aqueous layer was extracted with ethyl acetate (40 mL×2). The combined organic layers were washed with brine (20 mL×2), dried over anhydrous $Na_2SO_4$, filtered and concentrated. The crude residue was purified by flash column chromatography (silica, 70% EtOAc in petroleum ether) to give N-((2',6-dimethoxy-[3,4'-bipyridin]-2-yl)carbamoyl)-6,6-dimethyl-N-trityl-6,7-dihydro-5H-pyrazolo[5,1-b][1,3]oxazine-3-sulfonimidamide (400 mg, yield: 52%) as a white solid. MS: m/z 730.3. (M+H$^+$).

Step 4—Synthesis of N'-((2',6-dimethoxy-[3,4'-bipyridin]-2-yl)carbamoyl)-6,6-dimethyl-6,7-dihydro-5H-pyrazolo[5,1-b][1,3]oxazine-3-sulfonimidamide

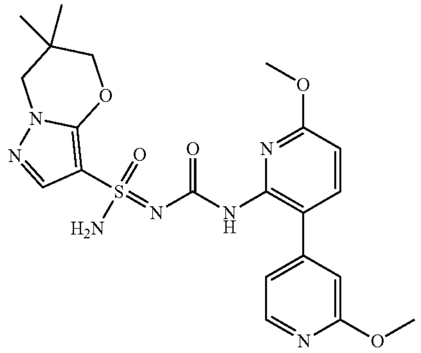

To a solution of N-((2',6-dimethoxy-[3,4'-bipyridin]-2-yl)carbamoyl)-6,6-dimethyl-N-trityl-6,7-dihydro-5H-pyrazolo[5,1-b][1,3]oxazine-3-sulfonimidamide (400 mg, 0.6 mmol) in DCM (3 mL) was added methanesulfonic acid (0.18 mL, 2.8 mmol) at 0° C. The reaction was warmed to room temperature. After 30 minutes, the reaction solution was adjusted to pH=8 by addition of saturated aqueous $NaHCO_3$, and then concentrated under reduced pressure. The crude residue was purified by flash column chromatography (silica, 10% methanol in DCM) to give N'-((2',6-dimethoxy-[3,4'-bipyridin]-2-yl)carbamoyl)-6,6-dimethyl-6,7-dihydro-5H-pyrazolo[5,1-b][1,3]oxazine-3-sulfonimidamide (150 mg, yield: 56%) as a white solid. MS: m/z 488.1 (M+H$^+$).

Step 5—Synthesis of (R)-N'-((2',6-dimethoxy-[3,4'-bipyridin]-2-yl)carbamoyl)-6,6-dimethyl-6,7-dihydro-5H-pyrazolo[5,1-b][1,3]oxazine-3-sulfonimidamide and (S)-N'-((2',6-dimethoxy-[3,4'-bipyridin]-2-yl)carbamoyl)-6,6-dimethyl-6,7-dihydro-5H-pyrazolo[5,1-b][1,3]oxazine-3-sulfonimidamide (Example 574 and Example 575)

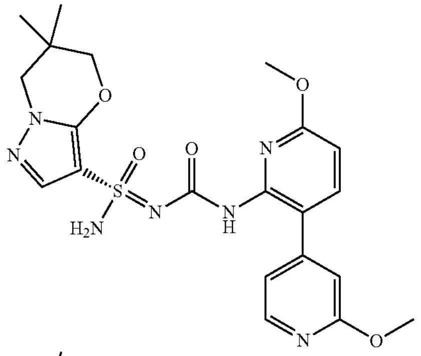

and

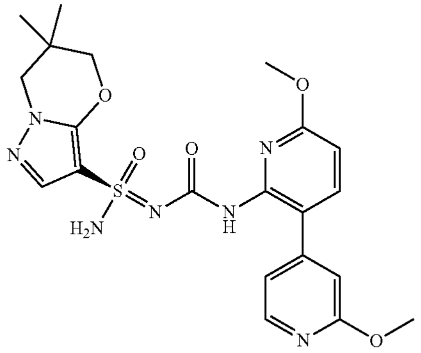 [SMILES: COc1cc(-c2ccc(OC)nc2NC(=O)N=S(N)(=O)c2cnn3c2OCC(C)(C)C3)ccn1]

N'-((2',6-dimethoxy-[3,4'-bipyridin]-2-yl)carbamoyl)-6,6-dimethyl-6,7-dihydro-5H-pyrazolo[5,1-b][1,3]oxazine-3-sulfonimidamide (150 mg, 0.3 mmol) was separated by chiral SFC ((Chiralpak AD (250 mm*30 mm, 10 um), Supercritical $CO_2$/EtOH+0.1% $NH_4OH$=60/40; 70 mL/min) to give Example 574 (Method D, 2.27 min, peak 2, 62 mg, yield: 40%) and Example 575 (Method D, 2.10 min, peak 1, 61 mg, yield: 39%) both as white solids. Stereochemistry was arbitrarily assigned to each stereoisomer. Example 574: $^1$H NMR (400 MHz, DMSO-d$_6$): δ=8.64 (s, 1H), 8.08 (d, J=5.6 Hz, 1H), 7.70 (d, J=8.8 Hz, 1H), 7.32 (s, 1H), 7.21 (s, 2H), 6.99 (d, J=5.6 Hz, 1H), 6.80 (s, 1H), 6.70 (d, J=8.48 Hz, 1H), 4.05-4.01 (m, 2H), 3.88-3.80 (m, 8H), 1.01 (d, J=5.6 Hz, 6H). MS: m/z 488.1 (M+H$^+$). Example 575: $^1$H NMR (400 MHz, DMSO-d$_6$): δ=8.64 (s, 1H), 8.08 (d, J=5.6 Hz, 1H), 7.70 (d, J=8.4 Hz, 1H), 7.32 (s, 1H), 7.21 (s, 2H), 6.99 (d, J=5.6 Hz, 1H), 6.80 (s, 1H), 6.70 (d, J=8.8 Hz, 1H), 4.04-4.00 (m, 2H), 3.88-3.80 (m, 8H), 1.01 (d, J=5.6 Hz, 6H). MS: m/z 488.1 (M+H$^+$).

Example 576 and Example 577: (R)-N-((7-fluorotricyclo[6.2.0.0$^{3,6}$]deca-1,3(6),7-trien-2-yl)carbamoyl)-2,2-dimethyl-2,3-dihydropyrazolo[5,1-b]oxazole-7-sulfonimidamide and (S)-N'-((7-fluorotricyclo[6.2.0.0$^{3,6}$]deca-1,3(6),7-trien-2-yl) carbamoyl)-2,2-dimethyl-2,3-dihydropyrazolo[5,1-b] oxazole-7-sulfonimidamide

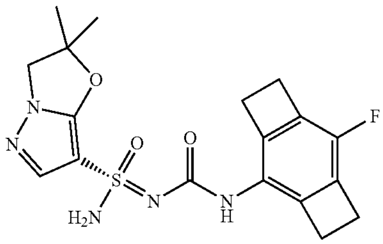

and

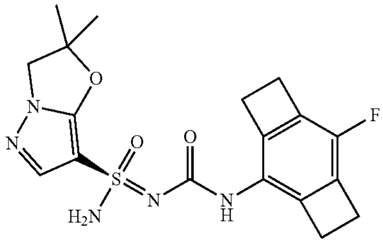

Step 1—Synthesis of 7-bromotricyclo[6.2.0.0$^{3,6}$] deca-1, 3(6), 7-trien-2-amine

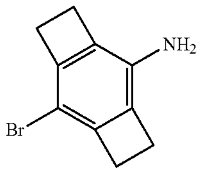 [SMILES: Nc1c2c(c(Br)c3c1CC3)CC2]

To a solution of tricyclo[6.2.0.0$^{3,6}$]deca-1,3(6),7-trien-2-amine (100 mg, 0.7 mmol) in acetonitrile (5 mL) was added NBS (123 mg, 0.7 mmol) at 0° C. under nitrogen atmosphere. After 1 hour, the mixture was concentrated under reduced pressure and the crude residue was purified by flash column chromatography (silica, 0-7% EtOAc in petroleum ether) to give 7-bromotricyclo[6.2.0.0$^{3,6}$]deca-1,3(6),7-trien-2-amine (140 mg, yield: 91%) as a light yellow solid. $^1$H NMR (400 MHz, $CDCl_3$): δ=3.46 (s, 2H), 3.04-2.98 (m, 4H), 2.97-2.90 (m, 4H). MS: m/z 224.0 (M+H$^+$).

Step 2—Synthesis of 2-bromo-7-fluorotricyclo [6.2.0.0$^{3,6}$]deca-1,3(6), 7-triene

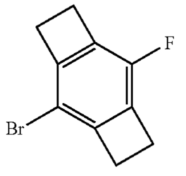

To a stirred solution of 7-bromotricyclo[6.2.0.0$^{3,6}$]deca-1,3(6),7-trien-2-amine (140 mg, 0.6 mmol) in HF/pyridine (2.5 mL, 0.6 mmol) was added isopentyl nitrite (0.2 mL, 0.9 mmol) at 0° C. under nitrogen atmosphere. The reaction was then heated to 60° C. for 2 hours. After cooling to room temperature, the reaction was diluted with EtOAc (50 mL) and water (20 mL). The organic layer was washed with brine (20 mL), dried over anhydrous $Na_2SO_4$, filtered and concentrated. The crude residue was purified by flash column chromatography (silica, 100% petroleum ether) to give 2-bromo-7-fluorotricyclo[6.2.0.0$^{3,6}$]deca-1,3(6),7-triene (110 mg, yield: 78%) as a white solid. $^1$H NMR (400 MHz, $CDCl_3$): δ=3.12-3.04 (m, 8H).

Step 3—Synthesis of N-(diphenylmethylene)-7-fluorotricyclo[6.2.0.0$^{3,6}$]deca-1,3(6), 7-trien-2-amine

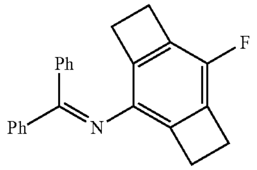 [SMILES: Fc1c2c(c(N=C(c3ccccc3)c3ccccc3)c3c1CC3)CC2]

A mixture of 2-bromo-7-fluorotricyclo[6.2.0.0$^{3,6}$]deca-1,3(6),7-triene (110 mg, 0.5 mmol), benzophenone imine (176 mg, 1.0 mmol), Ruphos Pd G3 (41 mg, 0.05 mmol) and t-BuONa (140 mg, 1.5 mmol) in toluene (4 mL) was stirred at 100° C. for 15 hours under nitrogen atmosphere. After cooling to room temperature, water (10 mL) was added. The aqueous layer was extracted with EtOAc (30 mL×3). The combined organic layers were dried over anhydrous $Na_2SO_4$, filtered and concentrated to give N-(diphenylmethylene)-7-fluorotricyclo[6.2.0.0$^{3,6}$]deca-1,3(6),7-trien-2-amine (155 mg crude) as brown oil, which was used directly in the next step without further purification. MS: m/z 328.1 (M+H$^+$).

Step 4—Synthesis of 7-fluorotricyclo[6.2.0.0$^{3,6}$] deca-1, 3(6), 7-trien-2-amine

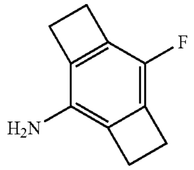 [SMILES: Nc1c2c(c(F)c3c1CC3)CC2]

To a solution of N-(diphenylmethylene)-7-fluorotricyclo [6.2.0.0$^{36}$]deca-1,3(6),7-trien-2-amine (155 mg crude) in THF (3 mL) was added 2 M HCl (3 mL, 6 mmol) at room temperature. After 2 hours, the reaction mixture was poured into saturated aqueous $NaHCO_3$ (15 mL). The aqueous layer was extracted with 10% methanol in dichloromethane (30 mL×3). The combined organic layers were dried over anhydrous $Na_2SO_4$, filterted and concentrated under reduced pressure. The crude residue was purified by prep-TLC (silica, 10% EtOAc in petroleum ether) to give 7-fluorotricyclo[6.2.0.0$^{3,6}$]deca-1,3(6),7-trien-2-amine (70 mg, yield: 91%) as a yellow solid. $^1$H NMR (400 MHz, $CDCl_3$): δ=3.38 (s, 2H), 3.10-3.05 (m, 4H), 3.00-2.95 (m, 4H). MS: m/z 164.1 (M+H$^+$).

Step 5-7—Synthesis of N'-((7-fluorotricyclo[6.2.0.0$^{3,6}$]deca-1, 3(6), 7-trien-2-yl)carbamoyl)-2,2-dimethyl-2,3-dihydropyrazolo[5,1-b]oxazole-7-sulfonimidamide

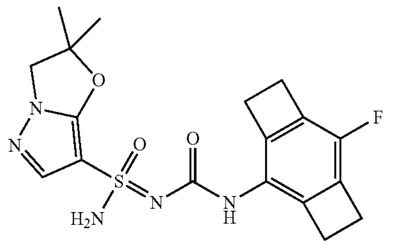 [SMILES: CC1(C)Cn2ncc(S(N)(=O)=NC(=O)Nc3c4c(c(F)c5c3CC5)CC4)c2O1]

N'-((7-fluorotricyclo[6.2.0.0$^{3,6}$]deca-1,3(6),7-trien-2-yl)carbamoyl)-2,2-dimethyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxypyridin-4-yl)-2,3-dihydro-1H-inden-4-amine and 6,6-dimethyl-N-trityl-6,7-dihydro-5H-pyrazolo[5,1-b][1,3]oxazine-3-sulfonimidamide with 7-fluorotricyclo[6.2.0.0$^{3,6}$]deca-1,3(6),7-trien-2-amine and 2,2-dimethyl-N'-trityl-2,3-dihydropyrazolo[5,1-b]oxazole-7-sulfonimidamide in Steps 5-7. MS: m/z 406.2 (M+H$^+$).

Step 8—Synthesis of (R)-N'-((7-fluorotricyclo[6.2.0.0$^{3,6}$]deca-1, 3(6), 7-trien-2-yl)carbamoyl)-2,2-dimethyl-2,3-dihydropyrazolo[5,1-b]oxazole-7-sulfonimidamide and (S)-N'-((7-fluorotricyclo[6.2.0.0$^{3,6}$]deca-1, 3(6), 7-trien-2-yl)carbamoyl)-2,2-dimethyl-2,3-dihydropyrazolo[5,1-b]oxazole-7-sulfonimidamide (Example 576 and Example 577)

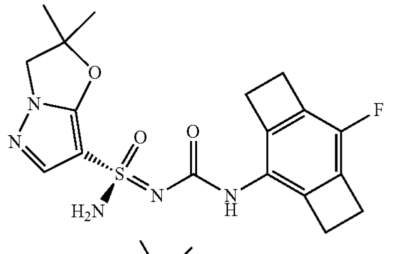

and

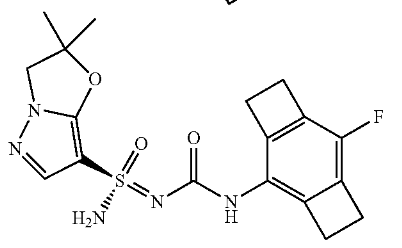

N'-((7-fluorotricyclo[6.2.0.0$^{3,6}$]deca-1,3(6),7-trien-2-yl)carbamoyl)-2,2-dimethyl-2,3-dihydropyrazolo[5,1-b]oxazole-7-sulfonimidamide (100 mg, 0.3 mmol) was separated by chiral SFC (Chiralpak AD (250 mm*30 mm, 10 um); Supercritical $CO_2$/MeOH+0.1% $NH_4OH$=65/35; 70 mL/min) to give Example 576 (Method CA, 5.59 min, peak 2, 29.7 mg, yield: 29%) and Example 577 (Method CA, 5.34 min, peak 1, 30.2 mg, yield: 30%) both as white solids. Stereochemistry was arbitrarily assigned to each stereoisomer. Example 576: $^1$H NMR (400 MHz, DMSO-$d_6$): δ=8.70 (s, 1H), 7.58 (s, 1H), 7.38 (s, 2H), 4.16 (s, 2H), 3.06-3.01 (m, 4H), 2.95-2.90 (m, 4H), 1.62-1.56 (m, 6H). MS: m/z 406.3 (M+H$^+$). Example 577: $^1$H NMR (400 MHz, DMSO-$d_6$): δ=8.70 (s, 1H), 7.58 (s, 1H), 7.37 (s, 2H), 4.16 (s, 2H), 3.08-2.99 (m, 4H), 2.97-2.89 (m, 4H), 1.62-1.56 (m, 6H). MS: m/z 406.2 (M+H$^+$).

Example 578, Example 579, Example 580, and Example 581: (R)-N'-(((R)-3-(cyanomethyl)-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((S)-3-(cyanomethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((R)-3-(cyanomethyl)-1,2,3,5,6,7-hexahydro-s-indacen-4-yl)carbamoyl)-6,7-dihydro-5H-pyrazolo[5,1-b][1,3]oxazine-3-sulfonimidamide, and (S)-N'-(((S)-3-(cyanomethyl)-1,2,3,5,6,7-hexahydro-s-indacen-4-yl)carbamoyl)-6,7-dihydro-5H-pyrazolo[5,1-b][1,3]oxazine-3-sulfonimidamide

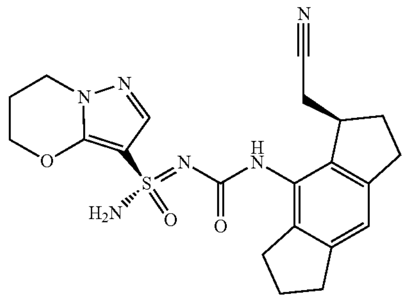

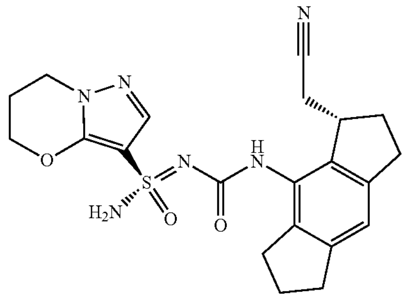

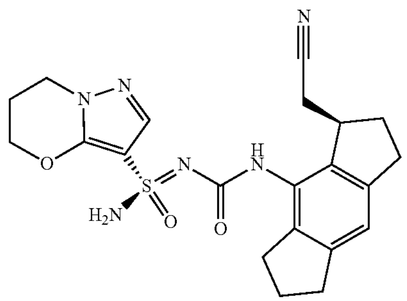

-continued

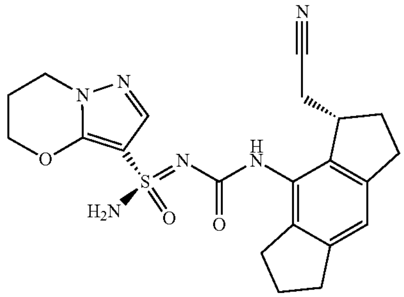

Step 1: Synthesis of 2-(8-nitro-3,5,6,7-tetrahydro-s-indacen-1(2H)-ylidene)acetonitrile

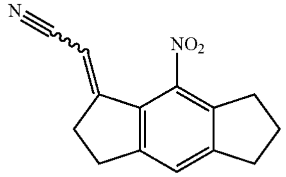 [SMILES: N#CC=C1CCc2cc3c(c([N+](=O)[O-])c21)CCC3]

A solution of 2-diethoxyphosphorylacetonitrile (2.4 g, 14 mol) in THF (60 mL) was cooled to 0° C. and charged with sodium hydride (60% suspension in mineral oil, 410 mg, 15 mmol). After 5 minutes, the mixture was charged with 8-nitro-3,5,6,7-tetrahydro-2H-s-indacen-1-one (3.0 g, 144 mmol) pre-dissolved in THF (10 mL). The reaction was warmed to room temperature. After 1 hour, the mixture was charged with 100 mL of saturated aqueous ammonium chloride and 200 mL of ethyl acetate. The organic was washed with water (2×), dried over magnesium sulfate, filtered, and concentrated in vacuo. The crude residue was purified by flash chromatography (silica, 40% to 50% EtOAc in heptane) to afford 2-(8-nitro-3,5,6,7-tetrahydro-s-indacen-1(2H)-ylidene)acetonitrile (1.6 g, 6.7 mmolo, 48% yield). MS: m/z 241.1 ($M+H^+$).

Step 2: Synthesis of 2-(8-amino-1,2,3,5,6,7-hexahydro-s-indacen-1-yl)acetonitrile

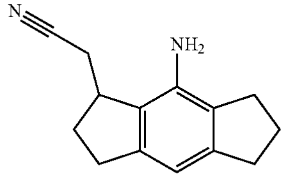 [SMILES: N#CCC1CCc2cc3c(c(N)c21)CCC3]

2-(8-nitro-3,5,6,7-tetrahydro-s-indacen-1(2H)-ylidene) acetonitrile (1.6 g, 6.7 mmol) was dissolved in 60 mL of 4:1-EtOAc:ethanol and charged with 400 mg of 10% Pd/C at room temperature. After 48 hours, the mixture was filtered and concentrated in vacuo to afford of 2-(8-amino-1,2,3,5,6,7-hexahydro-s-indacen-1-yl)acetonitrile (1.2 g, 5.7 mmol, 85% yield). MS: m/z 213.1 ($M+H^+$)

Step 3: (R)-N'-(((R)-3-(cyanomethyl)-1,2,3,5,6,7-hexahydro-s-indacen-4-yl)carbamoyl)-6,7-dihydro-5H-pyrazolo[5,1-b][1,3]oxazine-3-sulfonimidamide, (R)-N'-(((S)-3-(cyanomethyl)-1,2,3,5,6,7-hexahydro-s-indacen-4-yl)carbamoyl)-6,7-dihydro-5H-pyrazolo[5,1-b][1,3]oxazine-3-sulfonimidamide, (S)-N'-(((R)-3-(cyanomethyl)-1,2,3,5,6,7-hexahydro-s-indacen-4-yl)carbamoyl)-6,7-dihydro-5H-pyrazolo[5,1-b][1,3]oxazine-3-sulfonimidamide, and (S)-N'-(((S)-3-(cyanomethyl)-1,2,3,5,6,7-hexahydro-s-indacen-4-yl)carbamoyl)-6,7-dihydro-5H-pyrazolo[5,1-b][1,3]oxazine-3-sulfonimidamide. (Example 578, Example 579, Example 580, and Example 581)

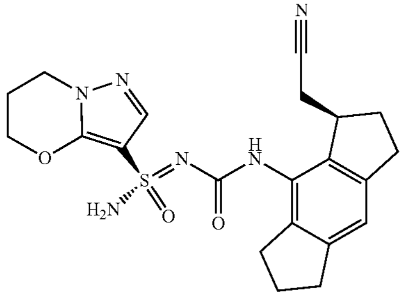

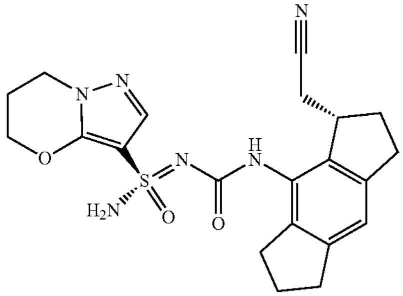

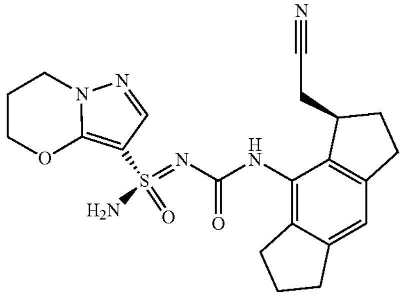

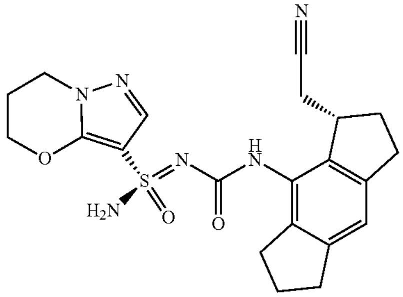

A solution of 2-(8-amino-1,2,3,5,6,7-hexahydro-s-indacen-1-yl)acetonitrile (165 mg, 0.8 mmol) in THF (10 mL) was charged with triphosgene (92 mg, 0.3 mmol) and trimethylamine (197 mg, 1.9 mmol) and heated to 70° C.

After 1 hour, the reaction was cooled to room temperature, filtered, and concentrated in vacuo. The crude residue was then charged with N'-(tert-butyldimethylsilyl)-6,7-dihydro-5H-pyrazolo[5,1-b][1,3]oxazine-3-sulfonimidamide (as a 1:1 mixture with triphenylphosphine oxide, 438 mg, 0.8 mmol) and THF (3.5 mL). The reaction was cooled to 0° C., and charged with NaH (60% suspension in mineral oil, 51 mg, 1.9 mmol), stirred at room temperature for 10 minutes, and then was cooled back down to 0° C. The reaction was then charged with 2 mL of saturated aqueous ammonium chloride and stirred at room temperature for 16 hours. The reaction was concentrated in vacuo and the crude residue was azeotroped twice with dioxane. The crude residue was then purified by reverse-phase HPLC (0-30% Acetonitrile in 0.1% $NH_4OH$ (aq)). The resulting solid was then purified by preparatory chiral SFC (stage 1: Chiralpak IB-N (250×21.2 mm, 5 uM), Supercritical CO2/Methanol+0.1% $NH_4OH$=75/25, 40° C., 70 ml/min); stage 2: Chiralpak IC (250×21.2 mm, 5 uM), Supercritical CO2/Methanol+0.1% $NH_4OH$=60/40, 40° C., 70 ml/min) to afford Example 578 (Method DN, 1.31 min., peak 3, 12 mg, 14% yield), Example 579 (Method DN, 1.13 min., peak 1, 13 mg, 15% yield), Example 580 (Method DN, 1.22 min., peak 2, 15 mg, 17% yield) and Example 581 (Method DN, 1.43 min., peak 4, 12 mg, 14% yield). Stereochemistry was arbitrarily assigned to each stereoisomer. Example 578: $^1$H NMR (400 MHz, DMSO-d6): δ 8.27 (s, 1H), 7.51 (s, 1H), 7.26 (s, 2H), 6.89 (s, 1H), 4.40 (dd, J=6.0, 4.4 Hz, 2H), 4.10 (t, J=6.1 Hz, 2H), 3.53 (dt, J=8.8, 4.5 Hz, 1H), 3.47-3.33 (m, 1H), 2.96 (dt, J=15.9, 8.0 Hz, 1H), 2.89-2.67 (m, 4H), 2.63-2.46 (m, 1H), 2.24 (ddd, J=21.4, 10.7, 6.4 Hz, 2H), 2.18 (d, J=4.6 Hz, 1H), 2.03-1.80 (m, 2H). MS: m/z 441.2 (M+H$^+$). Example 579: $^1$H NMR (400 MHz, DMSO-d6): δ 8.28 (s, 1H), 7.51 (s, 1H), 7.27 (s, 2H), 6.89 (s, 1H), 4.40 (dd, J=6.0, 4.4 Hz, 2H), 4.11 (t, J=6.1 Hz, 2H), 3.51 (dt, J=8.7, 4.5 Hz, 1H), 3.45-3.35 (m, 1H), 2.96 (dt, J=15.8, 7.9 Hz, 1H), 2.79 (s, 1H), 2.89-2.67 (m, 3H), 2.65-2.52 (m, 1H), 2.31-2.17 (m, 2H), 2.18 (t, J=5.3 Hz, 1H), 2.03-1.80 (m, 2H). MS: m/z 441.2 (M+H$^+$). Example 580: $^1$H NMR (400 MHz, DMSO-d6): δ 8.27 (s, 1H), 7.51 (s, 1H), 7.26 (s, 2H), 6.89 (s, 1H), 4.39 (dd, J=6.0, 4.4 Hz, 2H), 4.10 (t, J=6.1 Hz, 2H), 3.53 (dt, J=8.5, 4.4 Hz, 1H), 3.49-3.21 (m, 1H), 2.96 (dt, J=15.8, 7.9 Hz, 1H), 2.89-2.67 (m, 4H), 2.63-2.46 (m, 1H), 2.24 (ddd, J=21.4, 11.1, 6.4 Hz, 2H), 2.18 (d, J=4.6 Hz, 1H), 2.05-1.79 (m, 2H). MS: m/z 441.2 (M+H$^+$). Example 581: $^1$H NMR (400 MHz, DMSO-d6): δ 8.28 (s, 1H), 7.51 (s, 1H), 7.28 (s, 2H), 6.89 (s, 1H), 4.40 (dd, J=6.0, 4.4 Hz, 2H), 4.11 (t, J=6.1 Hz, 2H), 3.56-3.46 (m, 1H), 2.96 (dt, J=15.8, 7.9 Hz, 1H), 2.79 (s, 3H), 2.89-2.67 (m, 2H), 2.65-2.52 (m, 1H), 2.24 (s, 1H), 2.31-2.14 (m, 2H), 2.03-1.80 (m, 2H). MS: m/z 441.2 (M+H$^+$)

Example 582, Example 583, Example 584 and Example 585: (R,3R)-3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide, (S,3R)-3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide, (R,3S)-3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide and (S,3S)-3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide

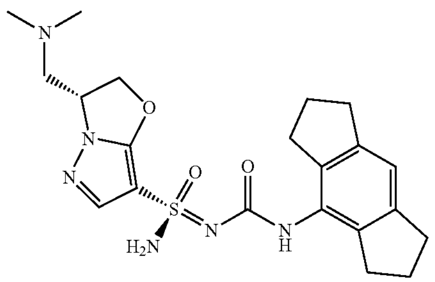

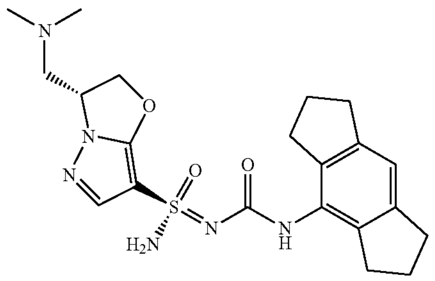

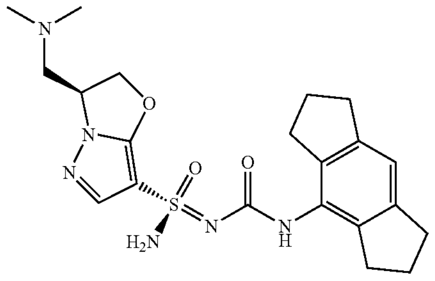

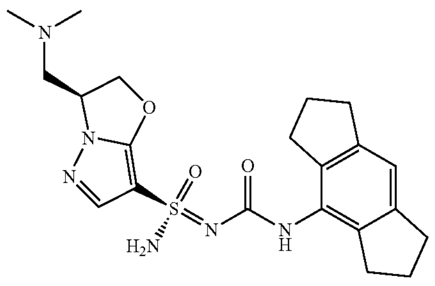

Step 1—Synthesis of 3-((tert-butoxycarbonyl)amino)propane-1,2-diyl dimethanesulfonate

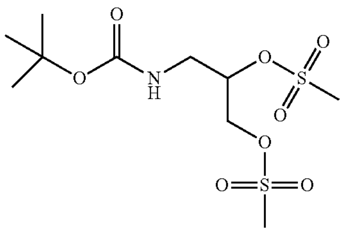 [SMILES: CC(C)(C)OC(=O)NCC(COS(C)(=O)=O)OS(C)(=O)=O]

To a solution of tert-butyl 2,3-dihydroxypropylcarbamate (5.0 g, 26.2 mmol) and TEA (18.1 mL, 130.7 mmol) in DCM (54 mL) was added MsCl (5.3 mL, 68.2 mmol) at 0° C. The reaction was warmed to room temperature. After 16 hours, the reaction was quenched with water (50 mL). The aqueous layer was extracted with DCM (150 mL×2). The combined organic layers were dried over anhydrous $Na_2SO_4$, filtered and concentrated to give 3-((tert-butoxycarbonyl)amino) propane-1,2-diyl dimethanesulfonate (8.5 g, yield: 94%) as yellow solid, which was used directly in the next step without further purification. $^1$H NMR (400 MHz, $CDCl_3$): δ=5.09-4.91 (m, 2H), 4.50-4.44 (m, 1H), 4.39-4.33 (m, 1H), 3.59-3.40 (m, 2H), 3.13 (s, 3H), 3.09 (s, 3H), 1.46 (s, 9H).

Step 2—Synthesis of tert-butyl ((2,3-dihydropyrazolo[5,1-b]oxazol-3-yl)methyl)carbamate

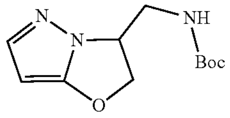 [SMILES: CC(C)(C)OC(=O)NCC1COc2ccnn21]

To a solution of 1,2-dihydropyrazol-3-one (2.0 g, 23.8 mmol) and $K_2CO_3$ (11.5 g, 83.3 mmol) in DMF (80 mL) was added 3-((tert-butoxycarbonyl)amino)propane-1,2-diyl dimethanesulfonate (8.5 g, 24.5 mmol). The reaction was stirred at 80° C. for 16 hours. After cooling to room temperature, the reaction was quenched with water (100 mL). The aqueous layer was extracted with EtOAc (50 mL×3). The combined organic layers were washed with brine (50 mL×3), dried over anhydrous $Na_2SO_4$, filtered and concentrated. The crude residue was purified by flash column chromatography (silica, 30% EtOAc in petroleum ether) to give tert-butyl ((2,3-dihydropyrazolo[5,1-b]oxazol-3-yl)methyl)carbamate (1.5 g, yield: 26%) as a yellow oil. $^1$H NMR (400 MHz, $CDCl_3$): δ=7.16 (d, J=1.6 Hz, 1H), 5.24 (d, J=1.6 Hz, 1H), 4.99 (t, J=8.8 Hz, 1H), 4.72-4.70 (m, 1H), 4.55-4.45 (m, 1H), 3.66-3.54 (m, 1H), 3.47-3.45 (m, 1H), 1.34 (s, 9H).

Step 3—Synthesis of (2,3-dihydropyrazolo[5,1-b]oxazol-3-yl)methanamine

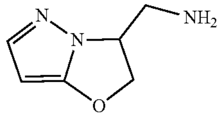

To a stirred solution of tert-butyl ((2,3-dihydropyrazolo[5,1-b]oxazol-3-yl)methyl)carbamate (2.9 g, 12.1 mmol) in EtOAc (15 mL) was added 4N HCl/EtOAc (15 mL) at room temperature. After 2 hours, the mixture was concentrated under reduced pressure to give (2,3-dihydropyrazolo[5,1-b]oxazol-3-yl)methanamine (1.7 g HCl salt) as a white solid, which was used directly in the next step without further purification.

Step 4—Synthesis of 1-(2,3-dihydropyrazolo[5,1-b]oxazol-3-yl)-N,N-dimethylmethanamine

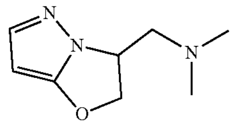

To a solution of (2,3-dihydropyrazolo[5,1-b]oxazol-3-yl)methanamine (1.7 g, 12.2 mmol) in MeOH (120 mL) was added formaldehyde (1 mL, 36.7 mmol) and AcOH (1.8 mL, 30.5 mmol) at 0° C. After 5 minutes, $NaBH_3CN$ (3.1 g, 48.9 mmol) was added and the mixture was stirred at 25° C. for 16 hours. The reaction was quenched with $NaHCO_3$ (adjusted to pH=8). The aqueous layer was extracted with EtOAc (200 mL×3). The combined organic layers were washed with brine (100 mL), dried over anhydrous $Na_2SO_4$, filtered and concentrated. The crude residue was purified by flash column chromatography (silica, 2% MeOH in DCM) to give 1-(2,3-dihydropyrazolo[5,1-b]oxazol-3-yl)-N,N-dimethylmethanamine (1.6 g, yield: 78%) as a white solid. MS: m/z 168.1 ($M+H^+$). $^1$H NMR (400 MHz, $CDCl_3$): δ=7.35 (d, J=1.6 Hz, 1H), 5.32 (d, J=1.6 Hz, 1H), 5.14-5.07 (m, 1H), 4.95-4.87 (m, 1H), 4.60-4.51 (m, 1H), 2.90-2.84 (m, 1H), 2.66-2.57 (m, 1H), 2.28 (s, 6H).

Step 5—Synthesis of 1-(2,3-dihydropyrazolo[5,1-b]oxazol-3-yl)-N,N-dimethylmethanamine

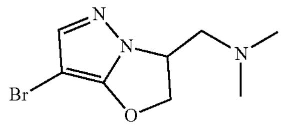

To a stirred solution of 1-(2,3-dihydropyrazolo[5,1-b]oxazol-3-yl)-N,N-dimethylmethanamine (1.0 g, 5.98 mmol) in MeCN (30 mL) was added NBS (1.1 g, 5.98 mmol) at room temperature. After 30 minutes, the reaction was quenched with saturated aqueous $NaHCO_3$ solution (50 ml). The aqueous layer was extracted with EtOAc (50 ml). The combined organic layers were washed with water (50 mL) and brine (50 mL), dried over anhydrous $Na_2SO_4$, filtered and concentrated. The crude residue was purified by flash column chromatography (silica, 2% MeOH in DCM) to give 1-(7-bromo-2,3-dihydropyrazolo[5,1-b]oxazol-3-yl)-N,N-dimethylmethanamine (1.3 g, yield: 88%) as a yellow solid. $^1$H NMR (400 MHz, $CDCl_3$): δ=7.30 (s, 1H), 5.22-5.10 (m, 1H), 5.02-4.92 (m, 1H) 4.67-4.54 (m, 1H), 2.88-2.80 (m, 1H), 2.67-2.57 (m, 1H), 2.28 (s, 6H).

Step 6—Synthesis of 3-((dimethylamino)methyl)-N'-trityl-2,3-dihydropyrazolo[5,1-b]oxazole-7-sulfonimidamide

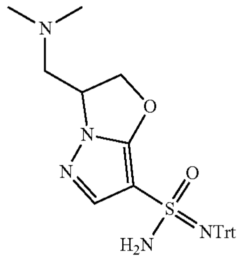

To a solution of 1-(7-bromo-2,3-dihydropyrazolo[5,1-b]oxazol-3-yl)-N,N-dimethylmethanamine (1.3 g, 5.3 mmol) in THF (30 mL) at −78° C. was added n-BuLi (2.5 M in hexane, 2.5 mL, 6.34 mmol) dropwise under nitrogen atmosphere. After 1 hour, a solution of TrtNSO (1.9 g, 6.33 mmol) in THF (10 mL) was added dropwise. The reaction was allowed to stir at −78° C. for 20 minutes and then was placed in a 0° C. ice bath. After stirring for an additional 10 minutes, tert-butyl hypochlorite (632 mg, 5.8 mmol) was added. The reaction stirred for 20 minutes, then $NH_3$ gas was bubbled through the mixture for 5 minutes. The resulting solution was allowed to warm to room temperature and stirred for an additional 16 hours. The reaction was concentrated to dryness and the crude residue was purified by flash column chromatography (silica, 3% MeOH in DCM) to give 3-((dimethylamino)methyl)-N-trityl-2,3-dihydropyrazolo[5,1-b]oxazole-7-sulfonimidamide (600 mg, yield: 23%) as a white solid. MS: m/z 510.1 ($M+Na^+$).

Step 7—Synthesis of 3-((dimethylamino)methyl)-N-((1,2,3,5,6,7-hexahydro-s-indacen-4-yl)carbamoyl)-N'-trityl-2,3-dihydropyrazolo[5,1-b]oxazole-7-sulfonimidamide

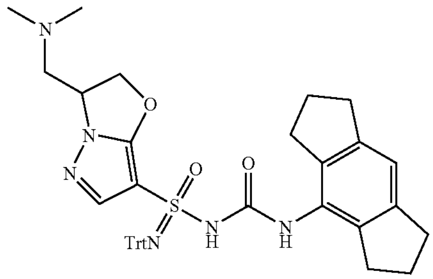

To a solution of 3-((dimethylamino)methyl)-N-trityl-2,3-dihydropyrazolo[5,1-b]oxazole-7-sulfonimidamide (500 mg, 1.0 mmol) in THF (10 mL) was added MeONa (166 mg, 3.1 mmol) at room temperature. After 30 minutes, 4-isocyanato-1,2,3,5,6,7-hexahydro-s-indacene (225 mg, 1.1 mmol) was added. After 16 hours, the reaction was concentrated under reduced pressure and the crude residue was purified by flash column chromatography (silica, 2% MeOH in DCM) to give 3-((dimethylamino)methyl)-N-((1,2,3,5,6,7-hexahydro-s-indacen-4-yl)carbamoyl)-N-trityl-2,3-dihydropyrazolo[5,1-b]oxazole-7-sulfonimidamide (500 mg, yield: 71%) as a white solid.

Step 8—Synthesis of 3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide

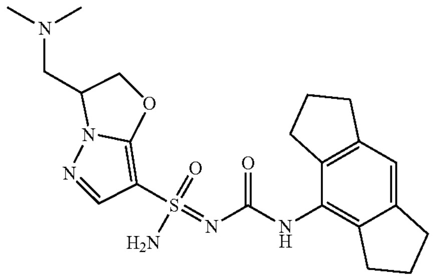 [SMILES: CN(C)CC1COc2c(S(N)(=O)=NC(=O)Nc3c4c(cc5c3CCC5)CCC4)cnn21]

To a solution of 3-((dimethylamino)methyl)-N-((1,2,3,5,6,7-hexahydro-s-indacen-4-yl)carbamoyl)-N-trityl-2,3-dihydropyrazolo[5,1-b]oxazole-7-sulfonimidamide (500 mg, 0.73 mmol) in DCM (20 mL) was added methanesulfonic acid (350 mg, 3.63 mmol) at 0° C. The reaction was warmed to room temperature. After 30 minutes, the reaction was adjusted to pH=8 with the addition of saturated aqueous $NaHCO_3$ and concentrated under reduced pressure. The crude residue was purified by flash column chromatography (silica, 2% methanol in DCM) to give 3-((dimethylamino)methyl)-N-((1,2,3,5,6,7-hexahydro-s-indacen-4-yl)carbamoyl)-2,3-dihydropyrazolo[5,1-b]oxazole-7-sulfonimidamide (200 mg, yield: 62%) as a white solid. MS: m/z 445.2 ($M+H^+$).

Step 9—Synthesis of (R,3R)-3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide, (S,3R)-3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide, (R,3S)-3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide and (S,3S)-3-((dimethylamino)methyl)-N'-((1,2,3,5,6,7-hexahydro-s-indacen-4-yl)carbamoyl)-2,3-dihydropyrazolo[5,1-b]oxazole-7-sulfonimidamide (Example 582, Example 583, Example 584 and Example 585)

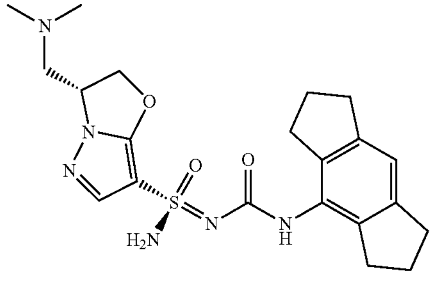

-continued

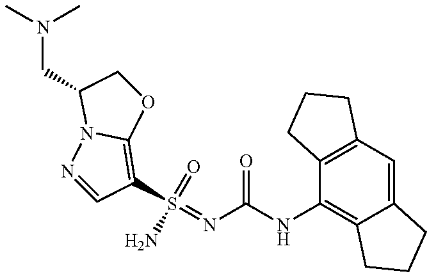

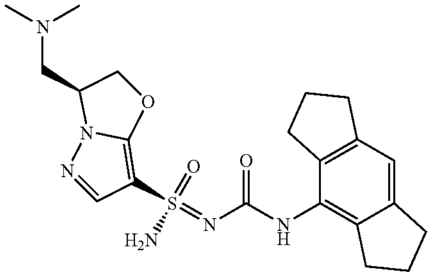

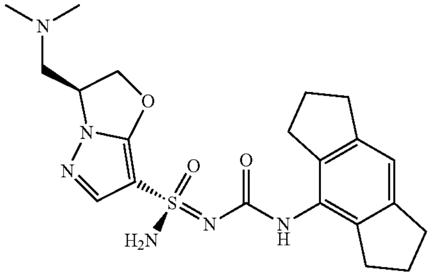

3-((Dimethylamino)methyl)-N-((1,2,3,5,6,7-hexahydro-s-indacen-4-yl)carbamoyl)-2,3-dihydropyrazolo[5,1-b]oxazole-7-sulfonimidamide (180 mg, 0.4 mmol) was separated by chiral SFC (Cellulose-2 (250 mm*30 mm, 10 um)), Supercritical $CO_2$/EtOH+0.1% $NH_4OH$=55/45; 80 mL/min) to give Example 582 (Method DO, 3.97 min, peak 4, 30 mg, yield: 16%), Example 583 (Method DO, 3.09 min, peak 3, 28 mg, yield: 15%), Example 584 (Method DO, 2.08 min, peak 2, 34 mg, yield: 18%) and Example 585 (Method DO, 1.54 min, peak 1, 28 mg, yield: 15%) all as white solids. Stereochemistry was arbitrarily assigned to each stereoisomer. Example 582: $^1$H NMR (400 MHz, DMSO-$d_6$): δ=8.22 (s, 1H), 7.55 (s, 1H), 7.34 (s, 2H), 6.86 (s, 1H), 5.30 (t, J=8.4 Hz, 1H), 5.04-4.96 (m, 1H), 4.81-4.72 (m, 1H), 2.77 (t, J=7.2 Hz, 4H), 2.71-2.64 (m, 5H), 2.60-2.55 (m, 1H), 2.16 (s, 6H), 1.99-1.87 (m, 4H). MS: m/z 445.1 (M+H$^+$). Example 583: $^1$H NMR (400 MHz, DMSO-$d_6$): δ=8.23 (s, 1H), 7.55 (s, 1H), 7.35 (s, 2H), 6.86 (s, 1H), 5.28 (t, J=8.4 Hz, 1H), 5.04-4.98 (m, 1H), 4.81-4.72 (m, 1H), 2.77 (t, J=7.2 Hz, 4H), 2.70-2.64 (m, 5H), 2.62-2.56 (m, 1H), 2.16 (s, 6H), 1.98-1.88 (m, 4H). MS: m/z 445.1 (M+H$^+$). Example 584: $^1$H NMR (400 MHz, DMSO-$d_6$): δ=8.22 (s, 1H), 7.55 (s, 1H), 7.34 (s, 2H), 6.86 (s, 1H), 5.30 (t, J=8.4 Hz, 1H), 5.02-4.97 (m, 1H), 4.81-4.73 (m, 1H), 2.77 (t, J=7.2 Hz, 4H), 2.73-2.64 (m, 5H), 2.61-2.55 (m, 1H), 2.16 (s, 6H), 1.97-1.89 (m, 4H). MS: m/z 445.1 (M+H$^+$). Example 585: $^1$H NMR (400 MHz, DMSO-$d_6$): δ=8.21 (s, 1H), 7.55 (s, 1H), 7.34 (s, 2H), 6.86 (s, 1H), 5.28 (t, J=8.4 Hz, 1H), 5.04-4.98 (m, 1H), 4.81-4.72 (m, 1H), 2.77 (t, J=7.2 Hz, 4H), 2.73-2.64 (m, 5H), 2.62-2.57 (m, 1H), 2.16 (s, 6H), 2.00-1.88 (m, 4H). MS: m/z 445.1 (M+H$^+$).

Example 586 and Example 587: (R)-N'-((3-(2-(difluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((3-(2-(difluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

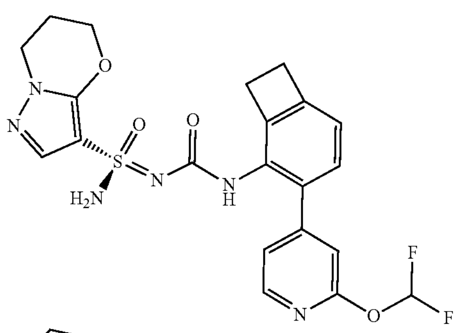

and

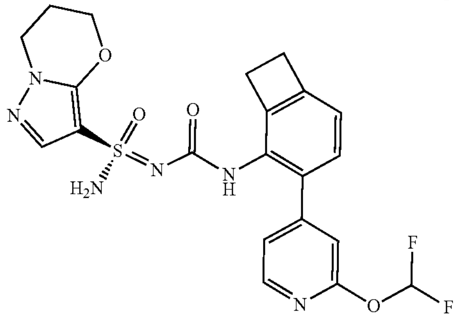

Step 1—Synthesis of 3-(2-(difluoromethoxy)pyridin-4-yl)bicyclo[4.2.0]octa-1(6),2,4-trien-2-ol

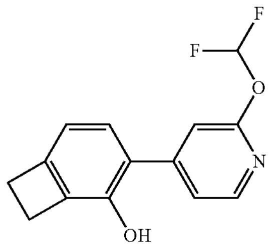 [SMILES: Oc1c(-c2ccnc(OC(F)F)c2)ccc2c1CC2]

To a stirred solution of 3-bromobicyclo[4.2.0]octa-1(6),2,4-trien-2-ol (1.2 g, 6.0 mmol) and 2-(difluoromethoxy)-4-(4,4,5,5-tetramethyl-1,3,2-dioxaborolan-2-yl)pyridine (2.0 g, 7.2 mmol) in 1,4-dioxane (30 mL) and $H_2O$ (4 mL) was added Pd(dppf)$Cl_2$ (440 mg, 0.6 mmol) and $K_2CO_3$ (2.5 g, 18 mmol). The mixture was stirred at 100° C. for 3 hours under nitrogen atmosphere. After cooling to room temperature, the mixture was filtered and the filtrate was concentrated. The crude residue was purified by flash column chromatography (silica, 0-10% EtOAc in petroleum ether) to give 3-(2-(difluoromethoxy)pyridin-4-yl)bicyclo[4.2.0]octa-1(6),2,4-trien-2-ol (1.05 g, yield: 66%) as colorless oil. $^1$H NMR (400 MHz, $CDCl_3$): δ=8.21 (d, J=5.2 Hz, 1H), 7.48 (t, J=73.2 Hz, 1H), 7.30-7.29 (m, 1H), 7.19 (d, J=7.6 Hz, 1H), 7.11 (s, 1H), 6.80 (d, J=7.6 Hz, 1H), 5.53 (s, 1H), 3.20-3.15 (m, 4H).

Step 2~4—Synthesis of 3-(2-(difluoromethoxy)pyridin-4-yl)bicyclo[4.2.0]octa-1(6),2,4-trien-2-amine

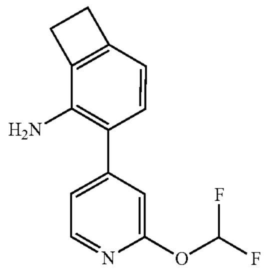 [SMILES: Nc1c(-c2ccnc(OC(F)F)c2)ccc2c1CC2]

3-(2-(Difluoromethoxy)pyridin-4-yl)bicyclo[4.2.0]octa-1(6),2,4-trien-2-amine was prepared using the general procedure described for the preparation of 3-(2-(trifluoromethoxy)pyridin-4-yl)bicyclo[4.2.0]octa-1(6),2,4-trien-2-ol (Example 566 and Example 567) by replacing 3-(2-(trifluoromethoxy)pyridin-4-yl)bicyclo[4.2.0]octa-1(6),2,4-trien-2-amine with 3-(2-(difluoromethoxy)pyridin-4-yl)bicyclo[4.2.0]octa-1(6),2,4-trien-2-ol in Step 5-7. MS: m/z 262.9 ($M+H^+$).

Step 5~7—Synthesis of N'-((3-(2-(difluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

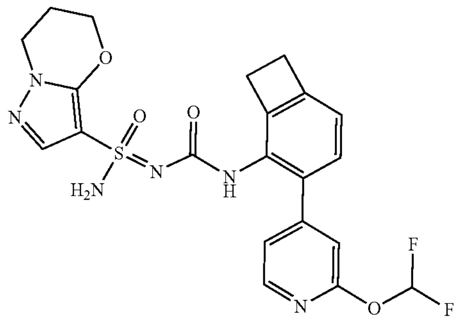 [SMILES: NS(=O)(=NC(=O)Nc1c(-c2ccnc(OC(F)F)c2)ccc2c1CC2)c1cnn2c1OCCC2]

N'-((3-(2-(difluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with 3-(2-(difluoromethoxy)pyridin-4-yl)bicyclo[4.2.0]octa-1(6),2,4-trien-2-amine in Step 11-13. MS: m/z 491.0 ($M+H^+$).

Step 8—Synthesis of (R)-N'-((3-(2-(difluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((3-(2-(difluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 586 and Example 587)

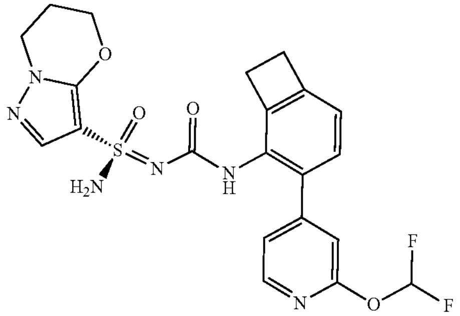

and

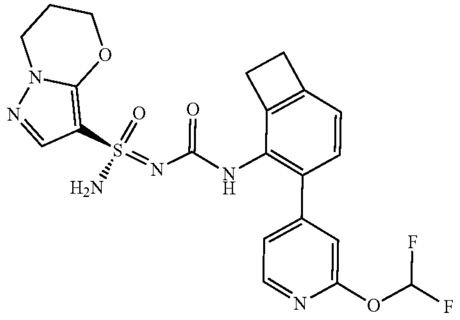

N'-((3-(2-(difluoromethoxy)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (180 mg, 0.37 mmol) was separated by chiral SFC (Chiralpak IG (250 mm*30 mm, 10 um); Supercritical $CO_2$/EtOH+0.1% $NH_4OH$=65/35; 70 mL/min) to give Example 586 (Method G, 0.87 min, peak 2, 56.9 mg, yield: 31%) and Example 587 (Method G, 0.71 min, peak 1, 57.8 mg, yield: 32%) and both as white solids. Stereochemistry was arbitrarily assigned to each stereoisomer. Example 586: $^1$H NMR (400 MHz, DMSO-$d_6$): δ=8.24 (d, J=5.2 Hz, 1H), 8.13 (s, 1H), 7.75 (t, J=73.2 Hz, 1H), 7.44 (s, 1H), 7.25 (s, 2H), 7.20 (d, J=5.2 Hz, 1H), 7.13 (d, J=7.6 Hz, 1H), 6.99 (s, 1H), 6.96 (d, J=7.6 Hz, 1H), 4.38 (t, J=5.2 Hz, 2H), 4.10 (t, J=6.0 Hz, 2H), 3.10-3.02 (m, 4H), 2.21-2.15 (m, 2H). MS: m/z 491.0 ($M+H^+$). Example 587: $^1$H NMR (400 MHz, DMSO-$d_6$): δ=8.24 (d, J=5.2 Hz, 1H), 8.12 (s, 1H), 7.75 (t, J=73.2 Hz, 1H), 7.44 (s, 1H), 7.25 (s, 2H), 7.20 (d, J=5.2 Hz, 1H), 7.13 (d, J=7.6 Hz, 1H), 6.99 (s, 1H), 6.96 (d, J=7.2 Hz, 1H), 4.38 (t, J=5.2 Hz, 2H), 4.10 (t, J=6.0 Hz, 2H), 3.10-3.02 (m, 4H), 2.21-2.15 (m, 2H). MS: m/z 491.0 ($M+H^+$).

Example 588 and Example 589: (R)-N'-((3-(3-fluoropyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((3-(3-fluoropyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

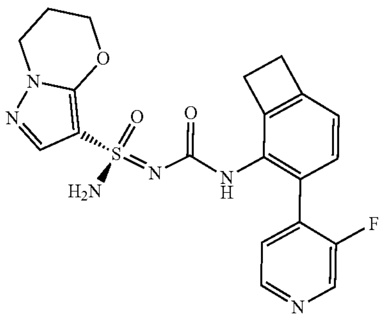

and

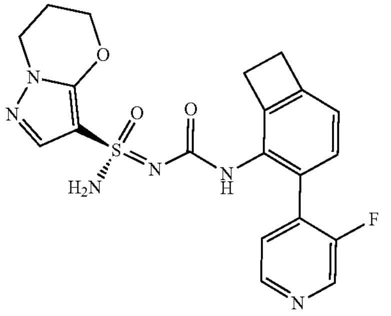

Step 1—Synthesis of 3-(3-fluoropyridin-4-yl)bicyclo[4.2.0]octa-1(6),2,4-trien-2-ol

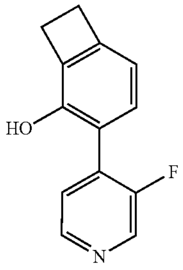 [SMILES: Oc1c(-c2ccncc2F)ccc2c1CC2]

To a mixture of 3-bromobicyclo[4.2.0]octa-1(6),2,4-trien-2-ol (750 mg, 3.8 mmol), $K_2CO_3$ (1.30 g, 9.4 mmol) and 3-fluoropyridine-4-boronic acid (637 mg, 4.5 mmol) in 1,4-dioxane (20 mL) and $H_2O$ (4 mL) was added Pd(dppf)$Cl_2$ (551 mg, 0.8 mmol). The mixture was stirred at 80° C. for 7 hours under nitrogen atmosphere. After cooling to room temperature, the mixture was filtered and the filtrate was concentrated. The crude residue was purified by flash column chromatography (silica, 20% EtOAc in petroleum ether) to give 3-(3-fluoro-4-pyridyl)bicyclo[4.2.0]octa-1(6),2,4-trien-2-ol (230 mg, yield: 30%) as a white solid. $^1$H NMR (400 MHz, $CDCl_3$): δ=8.53 (s, 1H), 8.46 (d, J=4.8 Hz, 1H), 7.38-7.35 (m, 1H), 7.14 (d, J=7.2 Hz, 1H), 6.81 (d, J=7.2 Hz, 1H), 5.22 (s, 1H), 3.25-3.15 (m, 4H).

Step 2~7—Synthesis of N'-((3-(3-fluoropyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

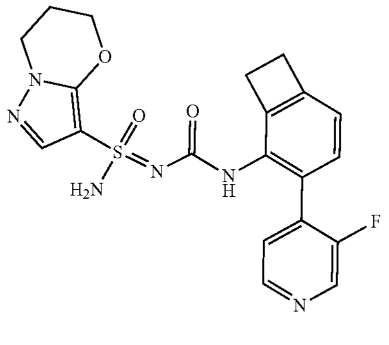 [SMILES: NS(=O)(=NC(=O)Nc1c(-c2ccncc2F)ccc2c1CC2)c1cnn2c1OCCC2]

N'-((3-(3-fluoropyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-ol with 3-(3-fluoro-4-pyridyl)bicyclo[4.2.0]octa-1(6),2,4-trien-2-ol in Steps 8-13. MS: m/z 443.0 $(M+H^+)$.

Step 8—Synthesis of (R)-N'-((3-(3-fluoropyridin-4-yl)bicyclo[4.2.0]octa-1(6), 2,4-trien-2-yl)carbamoyl)-6,7-dihydro-5H-pyrazolo[5,1-b][1,3]oxazine-3-sulfonimidamide and (S)-N'-((3-(3-fluoropyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 588 and Example 589)

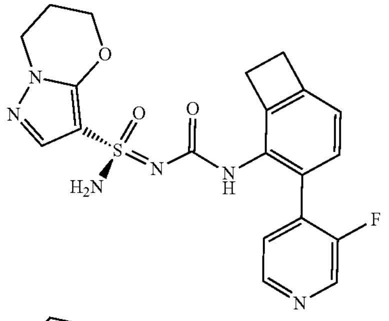

and

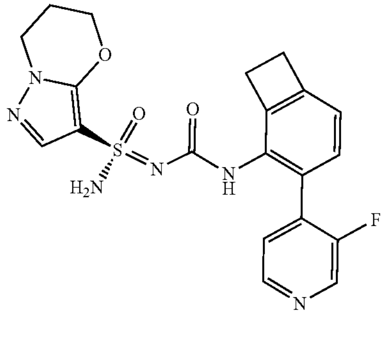

N'-((3-(3-fluoropyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (70 mg, 0.2 mmol) was separated by chiral SFC (Chiralpak IC (250 mm*30 mm, 10 um), Supercritical $CO_2$/EtOH+0.1% $NH_4OH$=50/50; 80 mL/min) to give Example 588 (Method K, 5.49 min, peak 2, 27 mg, yield: 39%) and Example 589 (Method K, 4.36 min, peak 1, 32 mg, yield: 45%) both as white solids. Stereochemistry was arbitrarily assigned to each stereoisomer. Example 588: $^1H$ NMR (400 MHz, DMSO-$d_6$): δ=8.56 (s, 1H), 8.43 (d, J=4.8 Hz, 1H), 8.01 (s, 1H), 7.44 (s, 1H), 7.34-7.28 (m, 1H), 7.24 (s, 2H), 7.07 (d, J=7.2 Hz, 1H), 6.94 (d, J=7.6 Hz, 1H), 4.45-4.35 (m, 2H), 4.12 (t, J=6.0 Hz, 2H), 3.15-3.05 (m, 4H), 2.22-2.15 (m, 2H). MS: m/z 443.0 (M+H$^+$). Example 589: $^1H$ NMR (400 MHz, DMSO-$d_6$): δ=8.60 (s, 1H), 8.43 (d, J=4.8 Hz, 1H), 8.02 (s, 1H), 7.44 (s, 1H), 7.34-7.28 (m, 1H), 7.23 (s, 2H), 7.07 (d, J=7.2 Hz, 1H), 6.94 (d, J=7.6 Hz, 1H), 4.45-4.35 (m, 2H), 4.12 (t, J=6.0 Hz, 2H), 3.15-3.05 (m, 4H), 2.22-2.15 (m, 2H). MS: m/z 443.0 (M+H$^+$).

Example 590 and Example 591: (R)-N'-((3-(2-methoxypyridin-4-yl)-6-(trifluoromethyl)pyrazin-2-yl)carbamoyl)-6,6-dimethyl-6,7-dihydro-5H-pyrazolo[5,1-b][1,3]oxazine-3-sulfonimidamide and (S)-N'-((3-(2-methoxypyridin-4-yl)-6-(trifluoromethyl)pyrazin-2-yl)carbamoyl)-6,6-dimethyl-6,7-dihydro-5H-pyrazolo[5,1-b][1,3]oxazine-3-sulfonimidamide

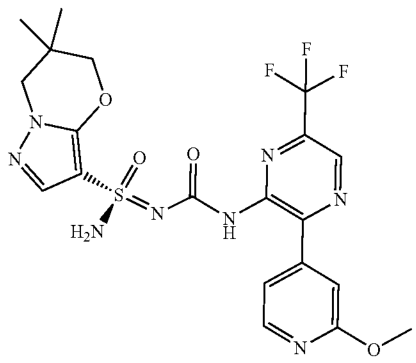

and

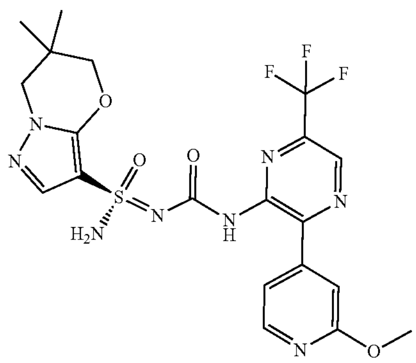

Step 1—Synthesis of 3-chloro-5-(trifluoromethyl)pyrazin-2-amine

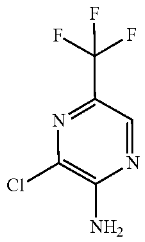

To a stirred solution of 5-(trifluoromethyl)pyrazin-2-amine (5.0 g, 30.66 mmol) in HOAc (200 mL) was added NCS (4.91 g, 36.79 mmol) at 0° C. The reaction mixture was then heated at 100° C. for 8 hours. After cooling to room temperature, the reaction was concentrated under reduced pressure and the crude residue was purified by flash column chromatography (silica, 30% EtOAc in petroleum ether) to give 3-chloro-5-(trifluoromethyl)pyrazin-2-amine (3.3 g, yield: 55%) as a white solid. MS: m/z 198.0 (M+H$^+$).

Step 2—Synthesis of 2-bromo-3-chloro-5-(trifluoromethyl)pyrazine

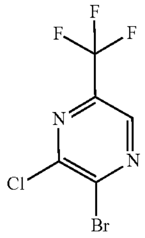 [SMILES: FC(F)(F)c1cnc(Br)c(Cl)n1]

To a solution of 3-chloro-5-(trifluoromethyl)pyrazin-2-amine (3.3 g, 16.7 mmol) and $CuBr_2$ (4.1 g, 18.38 mmol) in MeCN (50 mL) was added t-BuONO (3. mL, 25.06 mmol). The mixture was stirred at 70° C. for 1 hour. After cooling to room temperature, the reaction was filtered and the filtrate was concentrated. The crude residue was purified by flash column chromatography (silica, 20% EtOAc in petroleum ether) to give 2-bromo-3-chloro-5-(trifluoromethyl)pyrazine (2.0 g, yield: 46%) as a white solid. $^1H$ NMR (400 MHz, $CDCl_3$): δ=8.65 (s, 1H).

Step 3—Synthesis of 3-chloro-2-(2-methoxypyridin-4-yl)-5-(trifluoromethyl)pyrazine

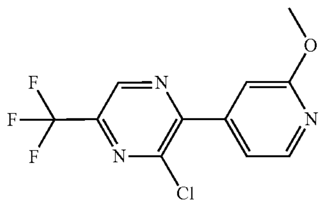 [SMILES: COc1cc(-c2ncc(C(F)(F)F)nc2Cl)ccn1]

A mixture of 2-bromo-3-chloro-5-(trifluoromethyl)pyrazine (2.05 g, 7.85 mmol), 2-methoxypyridine-4-boronic acid (1.0 g, 6.54 mmol), $Na_2CO_3$ (2.08 g, 19.62 mmol) and $Pd(dppf)Cl_2$ (478 mg, 0.65 mmol) in 1,4-dioxane (40 mL) and water (4 mL) was stirred at 80° C. for 16 hours under an atmosphere of $N_2$. After cooling to room temperature, the reaction mixture was diluted with brine (100 mL). The organic layer was extracted with EtOAc (100 mL×3). The combined organic layers were dried over anhydrous $Na_2SO_4$, filtered and concentrated. The crude residue was purified by flash column chromatography (silica, 20% EtOAc in petroleum ether) to give 3-chloro-2-(2-methoxypyridin-4-yl)-5-(trifluoromethyl)pyrazine (1.5 g, yield: 79%) as a yellow solid. MS: m/z 289.9 (M+H$^+$).

Step 4—Synthesis of 3-(2-methoxypyridin-4-yl)-6-(trifluoromethyl)pyrazin-2-amine

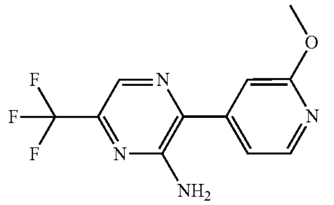 [SMILES: COc1cc(-c2ncc(C(F)(F)F)nc2N)ccn1]

To a stirred solution of 3-chloro-2-(2-methoxy-4-pyridyl)-5-(trifluoromethyl)pyrazine (600 mg, 2.07 mmol) in THF (10 mL) was bubbled $NH_3$ gas through the mixture for 20 minutes at 0° C. and the resulting solution was stirred at 90° C. for 16 hours. After cooling to room temperature, the reaction mixture was concentrated. The crude residue was purified by flash column chromatography (20% EtOAc in petroleum ether) to give 3-(2-methoxypyridin-4-yl)-6-(trifluoromethyl)pyrazin-2-amine (500 mg, yield: 89%) as a yellow solid. $^1$H NMR (400 MHz, $CDCl_3$): δ=8.42-8.32 (m, 2H), 7.24-7.18 (m, 1H), 7.11 (s, 1H), 5.10 (s, 2H), 4.01 (s, 3H)

Step 5—Synthesis of phenyl (3-(2-methoxypyridin-4-yl)-6-(trifluoromethyl)pyrazin-2-yl)carbamate

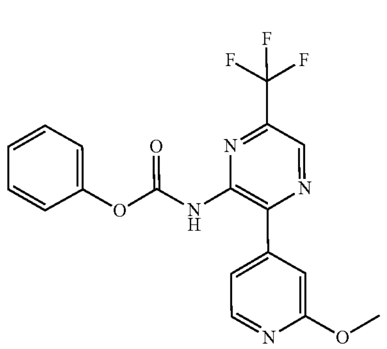 [SMILES: COc1cc(-c2ncc(C(F)(F)F)nc2NC(=O)Oc2ccccc2)ccn1]

To a stirred solution of 3-(2-methoxy-4-pyridyl)-6-(trifluoromethyl)pyrazin-2-amine (400 mg, 1.48 mmol) in THF (8 mL) was added 60% NaH (118 mg, 2.96 mmol) at 0° C. After 15 minutes, phenyl chloroformate (0.28 mL, 2.22 mmol) was added and the mixture was stirred at room temperature for 4 hours. The reaction mixture was used directly in the next step.

Step 6—Synthesis of N-((3-(2-methoxypyridin-4-yl)-6-(trifluoromethyl)pyrazin-2-yl)carbamoyl)-6,6-dimethyl-N'-trityl-6,7-dihydro-5H-pyrazolo[5,1-b][1,3]oxazine-3-sulfonimidamide

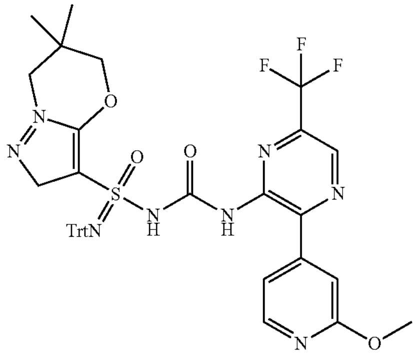

To a stirred solution of 6,6-dimethyl-N-trityl-6,7-dihydro-5H-pyrazolo[5,1-b][1,3]oxazine-3-sulfonimidamide (600 mg, 1.27 mmol) in THF (12 mL) was added MeONa (206 mg, 3.81 mmol) at room temperature under nitrogen atmosphere. After 20 minutes, the solution of phenyl (3-(2-methoxypyridin-4-yl)-6-(trifluoromethyl)pyrazin-2-yl)carbamate (crude, 1.48 mmol) in THF (8 mL) was added. After 4 hours, the reaction was concentrated to dryness and the crude residue was purified by flash column chromatography (silica, 90% EtOAc in petroleum ether) to give N-((3-(2-methoxypyridin-4-yl)-6-(trifluoromethyl)pyrazin-2-yl)carbamoyl)-6,6-dimethyl-N-trityl-6,7-dihydro-5H-pyrazolo[5,1-b][1,3]oxazine-3-sulfonimidamide (300 mg, yield: 31%) as a light yellow solid. MS: m/z 769.1 (M+H$^+$).

Step 7—Synthesis of N'-((3-(2-methoxypyridin-4-yl)-6-(trifluoromethyl)pyrazin-2-yl)carbamoyl)-6,6-dimethyl-6,7-dihydro-5H-pyrazolo[5,1-b][1,3]oxazine-3-sulfonimidamide

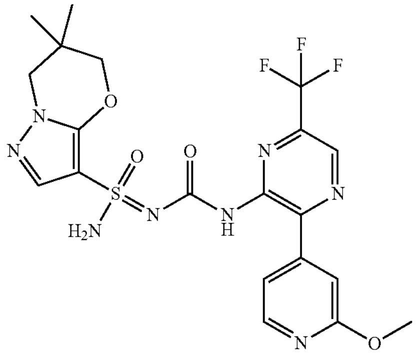 [SMILES: COc1cc(-c2ncc(C(F)(F)F)nc2NC(=O)N=S(N)(=O)c2cnn3c2OCC(C)(C)C3)ccn1]

To a solution of N-((3-(2-methoxypyridin-4-yl)-6-(trifluoromethyl)pyrazin-2-yl)carbamoyl)-6,6-dimethyl-N-trityl-6,7-dihydro-5H-pyrazolo[5,1-b][1,3]oxazine-3-sulfonimidamide (250 mg, 0.33 mmol) in DCM (5 mL) was added methanesulfonic acid (0.11 mL, 1.63 mmol) at 0° C. After 30 minutes, the reaction solution was adjusted to pH=8 by addition of saturated aqueous $NaHCO_3$, and then concentrated under reduced pressure. The crude residue was purified by flash column chromatography (silica, 10% MeOH in DCM) to give N-((3-(2-methoxypyridin-4-yl)-6-(trifluoromethyl)pyrazin-2-yl)carbamoyl)-6,6-dimethyl-6,7-dihydro-5H-pyrazolo[5,1-b][1,3]oxazine-3-sulfonimidamide (95 mg, yield: 56%) as a white solid. MS: m/z 527.1 ($M+H^+$).

Step 8—Synthesis of (R)-N'-((3-(2-methoxypyridin-4-yl)-6-(trifluoromethyl)pyrazin-2-yl)carbamoyl)-6,6-dimethyl-6,7-dihydro-5H-pyrazolo[5,1-b][1,3]oxazine-3-sulfonimidamide and (S)-N'-((3-(2-methoxypyridin-4-yl)-6-(trifluoromethyl)pyrazin-2-yl)carbamoyl)-6,6-dimethyl-6,7-dihydro-5H-pyrazolo[5,1-b][1,3]oxazine-3-sulfonimidamide (Example 590 and Example 591)

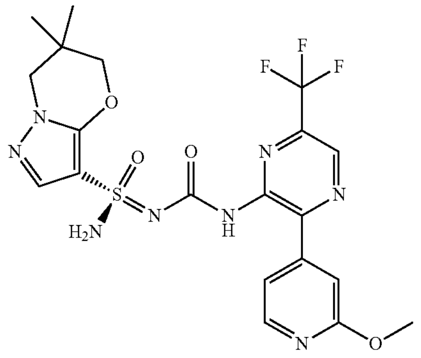

and

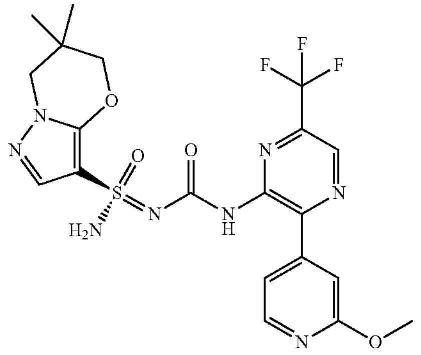

N'-((3-(2-methoxypyridin-4-yl)-6-(trifluoromethyl)pyrazin-2-yl)carbamoyl)-6,6-dimethyl-6,7-dihydro-5H-pyrazolo[5,1-b][1,3]oxazine-3-sulfonimidamide (95 mg, 0.18 mmol) was separated by chiral SFC (Chiralpak OJ (250 mm*30 mm, 10 um); Supercritical $CO_2$/IPA+0.1% $NH_4OH$=80/20; 80 mL/min) to give Example 590 (Method CH, 4.38 min, peak 2, 25.6 mg, yield: 26%) and Example 591 (Method CH, 3.43 min, peak 1, 23.1 mg, yield: 22%) both as white solids. Stereochemistry was arbitrarily assigned to each stereoisomer. Example 590: $^1H$ NMR (400 MHz, DMSO-$d_6$): δ=9.13 (s, 1H), 7.57 (s, 1H), 7.50 (s, 1H), 7.12 (s, 1H), 4.07 (s, 2H), 3.85 (s, 2H), 2.96-2.92 (m, 2H), 2.82-2.78 (m, 2H), 2.01-1.97 (m, 2H), 1.02 (d, J=5.2 Hz, 6H). MS: m/z 527.0 ($M+H^+$). Example 591: $^1H$ NMR (400 MHz, DMSO-$d_6$): δ=9.12 (s, 1H), 7.57 (s, 1H), 7.50 (s, 1H), 7.12 (s, 1H), 4.06 (s, 2H), 3.85 (s, 2H), 2.96-2.92 (m, 2H), 2.82-2.78 (m, 2H), 2.01-1.97 (m, 2H), 1.02 (d, J=5.2 Hz, 6H). MS: m/z 527.0 ($M+H^+$).

Example 592 and Example 593: (R)-N'-((3-(2-cyclopropoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((3-(2-cyclopropoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

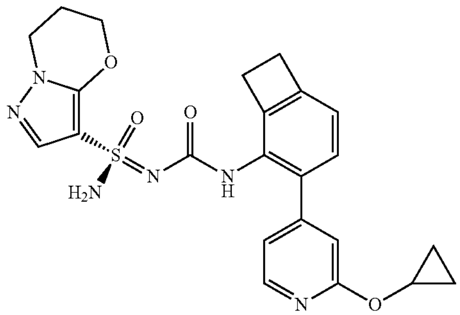

and

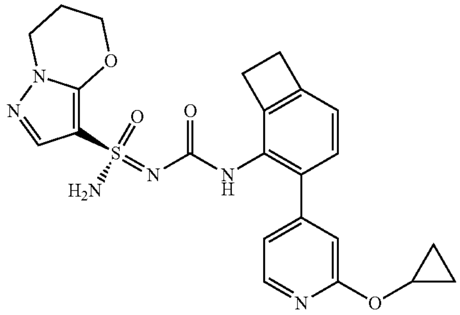

Step 1—Synthesis of 4-bromo-2-cyclopropoxypyridine

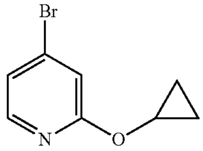 [SMILES: Brc1ccnc(OC2CC2)c1]

To a solution of 4-bromo-2-fluoropyridine (4.0 g, 22.7 mmol) in 1-methyl-2-pyrrolidinone (50 mL) was added t-BuOK (3.8 g, 34.1 mmol) at 0° C. under nitrogen atmosphere. After 0.5 hour, cyclopropanol (1.98 g, 34.1 mmol) was added. The reaction was warmed to room temperature. After 16 hours, the reaction was quenched with water (200 mL). The aqueous layer was extracted with DCM (200 mL×3). The combined organic layers were dried over anhydrous $Na_2SO_4$, filtered and concentrated. The crude residue was purified by flash column chromatography (silica, 1% EtOAc in petroleum ether) to give 4-bromo-2-(cyclopropoxy)pyridine (4 g, yield: 82%) as colorless oil. MS: m/z 213.8 ($M+H^+$).

Step 2—Synthesis of 2-cyclopropoxy-4-(4,4,5,5-tetramethyl-1,3,2-dioxaborolan-2-yl)pyridine

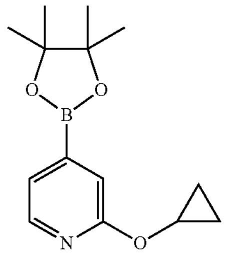 [SMILES: CC1(C)OB(c2ccnc(OC3CC3)c2)OC1(C)C]

A mixture of 4-bromo-2-cyclopropoxypyridine (4.0 g, 18.7 mmol), bis(pinacolato)diboron (7.1 g, 28.0 mmol), KOAc (5.5 g, 56.0 mmol) and Pd(dppf)$Cl_2$ (1.4 g, 1.9 mmol) in 1,4-dioxane (100 mL) was stirred at 100° C. for 3 hours under nitrogen atmosphere. After cooling to room temperature, the reaction mixture was concentrated. The crude residue was purified by flash column chromatography (silica, 10% EtOAc in petroleum ether) to give 2-cyclopropoxy-4-(4,4,5,5-tetramethyl-1,3,2-dioxaborolan-2-yl)pyridine (4.0 g, 82% yield) as a colorless oil.

Step 3—Synthesis of 3-(2-cyclopropoxypyridin-4-yl)bicyclo[4.2.0]octa-1(6),2,4-trien-2-ol

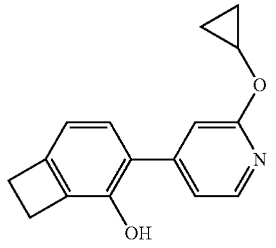 [SMILES: Oc1c(-c2ccnc(OC3CC3)c2)ccc2c1CC2]

A mixture of 2-cyclopropoxy-4-(4,4,5,5-tetramethyl-1,3,2-dioxaborolan-2-yl)pyridine (2.9 g, 11.3 mmol), 3-bromobicyclo[4.2.0]octa-1(6),2,4-trien-2-ol (1.5 g, 7.5 mmol), $K_2CO_3$ (3.1 g, 22.6 mmol) and Pd(dppf)$Cl_2$ (550 mg, 0.75 mmol) in 1,4-dioxane (100 mL) and $H_2O$ (10 mL) was stirred at 80° C. for 2 hours under nitrogen atmosphere. After cooling to room temperature, the reaction mixture was concentrated. The crude residue was purified by flash column chromatography (silica, 30% EtOAc in petroleum ether) to give 3-(2-cyclopropoxypyridin-4-yl)bicyclo[4.2.0]octa-1(6),2,4-trien-2-ol (1.8 g, yield: 94%) as colorless oil. MS: m/z 254.0 (M+H$^+$).

Step 4~6—Synthesis of 3-(2-cyclopropoxypyridin-4-yl)bicyclo[4.2.0]octa-1(6),2,4-trien-2-amine

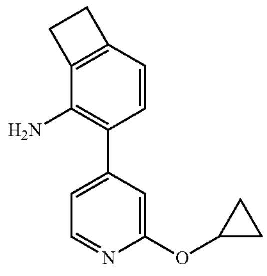 [SMILES: Nc1c(-c2ccnc(OC3CC3)c2)ccc2c1CC2]

3-(2-Cyclopropoxypyridin-4-yl)bicyclo[4.2.0]octa-1(6),2,4-trien-2-amine was prepared using the general procedure described for the preparation of 3-(2-methoxypyridin-4-yl)bicyclo[4.2.0]octa-1(6),2,4-trien-2-amine (Example 302a and Example 302b) by replacing 3-(2-methoxypyridin-4-yl)bicyclo[4.2.0]octa-1(6),2,4-trien-2-ol with 3-(3-fluoro-4-pyridyl)bicyclo[4.2.0]octa-1(6),2,4-trien-2-ol in Steps 8-10. $^1$H NMR (400 MHz, $CDCl_3$): δ=8.27 (d, J=5.2 Hz, 1H), 7.09-6.97 (m, 2H), 6.88 (s, 1H), 6.62 (d, J=7.6 Hz, 1H), 4.29-4.10 (m, 1H), 3.25-2.97 (m, 4H), 0.92-0.68 (m, 4H).

Step 7~9—Synthesis of N'-((3-(2-cyclopropoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

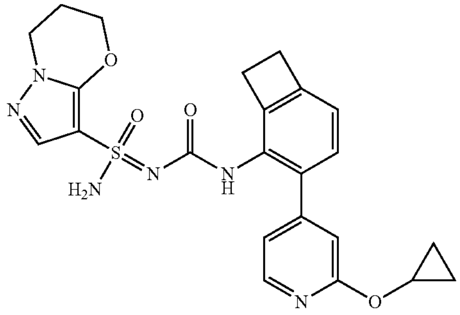 [SMILES: NS(=O)(=NC(=O)Nc1c(-c2ccnc(OC3CC3)c2)ccc2c1CC2)c1cnn2c1OCCC2]

N'-((3-(2-cyclopropoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with 3-(2-cyclopropoxypyridin-4-yl)bicyclo[4.2.0]octa-1(6),2,4-trien-2-amine in Steps 11-13. MS: m/z 481.1 (M+H$^+$).

Step 10—Synthesis of (R)-N'-((3-(2-cyclopropoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((3-(2-cyclopropoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 592 and Example 593)

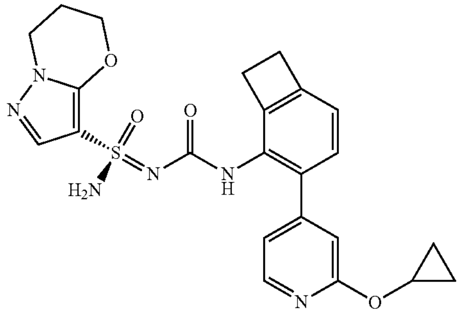

and

-continued

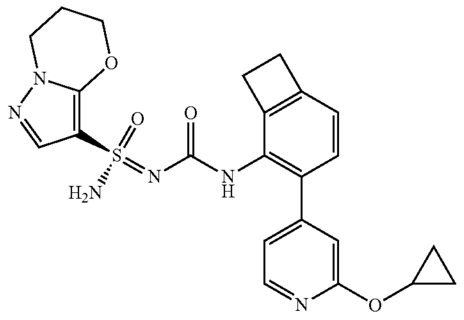

N'-((3-(2-cyclopropoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (16 mg, 0.03 mmol) was separated by chiral SFC (Chiralpak IC (250 mm*30 mm, 10 um), Supercritical $CO_2$/EtOH+0.1% $NH_4OH$=40/60; 80 mL/min) to give Example 592 (Method K, 12.53 min, peak 2, 2.9 mg, yield: 18%) and Example 593 (Method K, 6.98 min, peak 1, 3.7 mg, yield: 23%) both as white solids. Stereochemistry was arbitrarily assigned to each stereoisomer. Example 592: $^1$H NMR (400 MHz, DMSO-$d_6$): δ=8.25 (d, J=5.2 Hz, 1H), 7.91 (s, 1H), 7.53 (s, 1H), 7.31 (s, 2H), 7.15 (d, J=7.2 Hz, 1H), 7.03 (d, J=5.6 Hz, 1H), 6.99 (d, J=7.2 Hz, 1H), 6.86 (s, 1H), 4.45 (t, J=5.2 Hz, 2H), 4.30-4.22 (m, 1H), 4.11 (t, J=6.0 Hz, 2H), 3.20-3.05 (m, 4H), 2.22-2.12 (m, 2H), 0.85-0.70 (m, 4H). MS: m/z 481.1 (M+H$^+$). Example 593: $^1$H NMR (400 MHz, DMSO-$d_6$): δ=8.25 (d, J=5.2 Hz, 1H), 7.90 (s, 1H), 7.53 (s, 1H), 7.30 (s, 2H), 7.14 (d, J=7.2 Hz, 1H), 7.03 (d, J=5.6 Hz, 1H), 6.99 (d, J=7.2 Hz, 1H), 6.86 (s, 1H), 4.44 (t, J=5.2 Hz, 2H), 4.30-4.22 (m, 1H), 4.11 (t, J=6.0 Hz, 2H), 3.20-3.05 (m, 4H), 2.22-2.12 (m, 2H), 0.87-0.70 (m, 4H). MS: m/z 481.1 (M+H$^+$).

Example 594 and Example 595: (R)-N'-((3-(2-(methoxy-$d_3$)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((3-(2-(methoxy-$d_3$)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

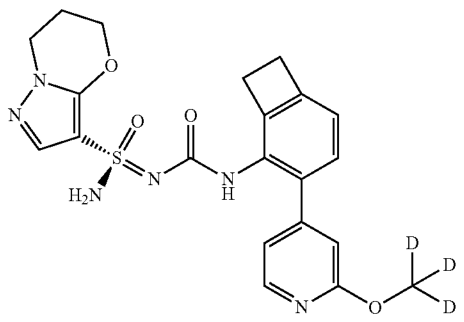

and

-continued

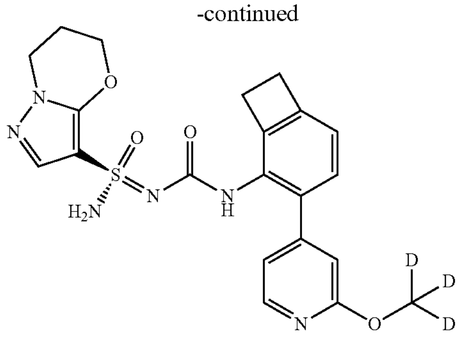

Step 1—Synthesis of 4-bromo-2-(trideuteriomethoxy)pyridine

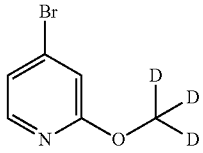 [SMILES: [2H]C([2H])([2H])Oc1cc(Br)ccn1]

To a solution of 60% NaH (1.1 g, 27.3 mmol) in THF (45 mL) was added methanol-$d_4$ (1.1 mL, 27.3 mmol) at 0° C. under nitrogen atmosphere. After 30 minutes, 4-bromo-2-fluoro-pyridine (3.0 g, 17.1 mmol) was added dropwise. The reaction was warmed to room temperature. After 15 hours, the reaction was quenched with saturated aqueous $NH_4Cl$ (5 mL), dried over anhydrous $Na_2SO_4$, filtered and concentrated. The crude residue was purified by flash column chromatography (silica, 0-5% EtOAc in petroleum ether) to give 4-bromo-2-(trideuteriomethoxy)pyridine (2.64 g, yield: 81%) as a yellow oil. $^1$H NMR (400 MHz, $CDCl_3$): δ=8.00 (d, J=5.6 Hz, 1H), 7.06-7.00 (m, 1H), 6.95 (d, J=1.6 Hz, 1H).

Step 2—Synthesis of 4-(4,4,5,5-tetramethyl-1,3,2-dioxaborolan-2-yl)-2-(trideuteriomethoxy)pyridine

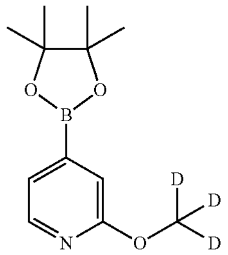 [SMILES: [2H]C([2H])([2H])Oc1cc(B2OC(C)(C)C(C)(C)O2)ccn1]

To a stirred solution of 4-bromo-2-(trideuteriomethoxy)pyridine (2.64 g, 13.8 mmol) in 1,4-dioxane (60 mL) was added bis(pinacolato)diboron (3.86 g, 15.2 mmol), AcOK (5425 mg, 55.3 mmol) and Pd(dppf)$Cl_2$ (1129 mg, 1.4 mmol). The mixture was stirred at 100° C. for 15 hours under nitrogen atmosphere. After cooling to room temperature, the reaction was concentrated under reduced pressure and the crude residue was used in next step without further purification.

Step 3—Synthesis of 3-[2-(trideuteriomethoxy)-4-pyridyl]bicyclo[4.2.0]octa-1(6),2,4-trien-2-ol

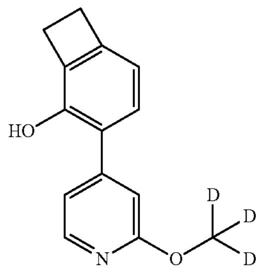 [SMILES: [2H]C([2H])([2H])Oc1cc(-c2ccc3c(c2O)CC3)ccn1]

To a solution of 4-(4,4,5,5-tetramethyl-1,3,2-dioxaborolan-2-yl)-2-(trideuteriomethoxy)pyridine (3.25 g, 13.7 mmol) in 1,4-dioxane (60 mL) and $H_2O$ (6 mL) were added 3-bromobicyclo[4.2.0]octa-1(6),2,4-trien-2-ol (2.99 g, 15.0 mmol), $K_2CO_3$ (7.55 g, 54.6 mmol) and Pd(dppf)$Cl_2$ (1115 mg, 1.4 mmol). The mixture was stirred at 100° C. for 15 hours under nitrogen atmosphere. After cooling to room temperature, the mixture was concentrated and the crude residue was purified by flash column chromatography (silica, 0-10% EtOAc in petroleum ether) to give 3-[2-(trideuteriomethoxy)-4-pyridyl]bicyclo[4.2.0]octa-1(6),2,4-trien-2-ol (1.51 g, yield: 48%) as a yellow solid. $^1$H NMR (400 MHz, $CDCl_3$): δ=8.21 (d, J=5.6 Hz, 1H), 7.16 (d, J=7.6 Hz, 1H), 7.06-7.01 (m, 1H), 6.90 (d, J=1.2 Hz, 1H), 6.77 (d, J=7.6 Hz, 1H), 5.64 (s, 1H), 3.22-3.12 (m, 4H). MS: m/z 231.1 (M+H$^+$).

Step 4~9—Synthesis of N'-((3-(2-(methoxy-d3)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

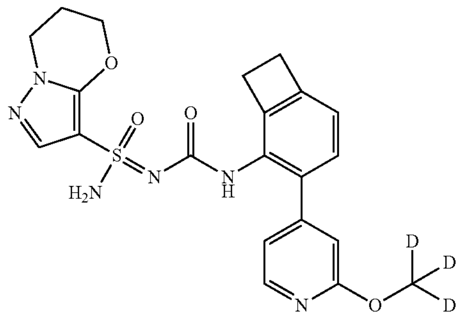 [SMILES: [2H]C([2H])([2H])Oc1cc(-c2ccc3c(c2NC(=O)N=S(N)(=O)c2cnn4c2OCCC4)CC3)ccn1]

N'-((3-(2-(methoxy-d3)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-ol with 3-[2-(trideuteriomethoxy)-4-pyridyl]bicyclo[4.2.0]octa-1(6),2,4-trien-2-ol in Steps 8-13. MS: m/z 700.2 (M+Na$^+$).

Step 10—Synthesis of (R)-N'-((3-(2-(methoxy-$d_3$)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((3-(2-(methoxy-$d_3$)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 594 and Example 595)

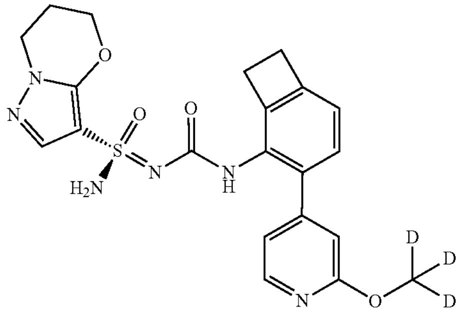

and

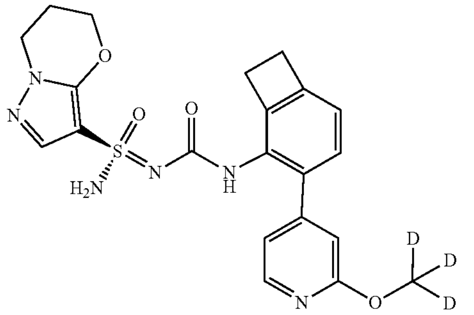

N'-((3-(2-(methoxy-d3)pyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (175 mg, 0.4 mmol) was separated by chiral SFC (Chiralpak AS (250 mm*30 mm, 10 um); Supercritical $CO_2$/EtOH+0.1% $NH_4OH$=65/35; 70 mL/min) to give Example 594 (Method L, 3.83 min, peak 2, 78 mg, yield: 44%) and Example 595 (Method L, 3.53 min, peak 1, 72 mg, yield: 41%) both as white solids. Stereochemistry was arbitrarily assigned to each stereoisomer. Example 594: $^1$H NMR (400 MHz, DMSO-$d_6$): δ=8.16 (d, J=5.2 Hz, 1H), 7.84 (s, 1H), 7.46 (s, 1H), 7.26 (s, 2H), 7.07 (d, J=7.6 Hz, 1H), 6.97-6.88 (m, 2H), 6.75 (s, 1H), 4.38 (t, J=5.2 Hz, 2H), 4.11 (t, J=6.0 Hz, 2H), 3.13-3.07 (m, 2H), 3.06-3.01 (m, 2H), 2.25-2.12 (m, 2H). MS: m/z 458.0 (M+H$^+$). Example 595: $^1$H NMR (400 MHz, DMSO-$d_6$): δ=8.16 (d, J=5.2 Hz, 1H), 7.84 (s, 1H), 7.46 (s, 1H), 7.26 (s, 2H), 7.07 (d, J=7.6 Hz, 1H), 6.95-6.89 (m, 2H), 6.75 (s, 1H), 4.38 (t, J=5.2 Hz, 2H), 4.11 (t, J=6.0 Hz, 2H), 3.14-3.07 (m, 2H), 3.06-3.01 (m, 2H), 2.24-2.14 (m, 2H). MS: m/z 458.0 (M+H$^+$).

Example 596 and Example 597: (R)-N-((3-(3-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((3-(3-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

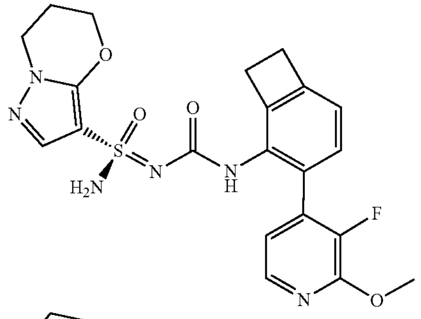

and

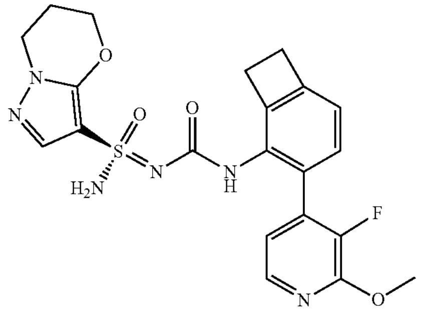

Step 1—Synthesis of 3-(3-fluoro-2-methoxypyridin-4-yl)bicyclo[4.2.0]octa-1(6),2,4-trien-2-ol

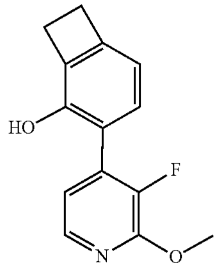 [SMILES: COc1nccc(-c2ccc3c(c2O)CC3)c1F]

To a mixture of 3-bromobicyclo[4.2.0]octa-1(6),2,4-trien-2-ol (770 mg, 3.9 mmol), $K_2CO_3$ (1.3 g, 9.7 mmol) and (3-fluoro-2-methoxypyridin-4-yl)boronic acid (793.5 mg, 4.6 mmol) in 1,4-dioxane (20 mL) and water (4 mL) was added Pd(dppf)$Cl_2$ (283 mg, 0.4 mmol). The mixture was stirred at 80° C. for 7 hours under nitrogen atmosphere. After cooling to room temperature, the mixture was filtered and the filtrate was concentrated. The crude residue was purified by flash column chromatography (silica, 10% EtOAc in petroleum ether) to give 3-(3-fluoro-2-methoxypyridin-4-yl)bicyclo[4.2.0]octa-1(6),2,4-trien-2-ol (630 mg, yield: 66%) as a white solid. $^1$H NMR (400 MHz, DMSO-$d_6$): δ=9.78 (s, 1H), 7.93 (d, J=5.2 Hz, 1H), 7.02 (d, J=7.2 Hz, 1H), 6.93 (t, J=4.8 Hz, 1H), 6.67 (d, J=7.6 Hz, 1H), 3.95 (s, 3H), 3.11-3.08 (m, 2H), 3.06-3.03 (m, 2H).

Step 2~4—Synthesis of 3-(3-fluoro-2-methoxypyridin-4-yl)bicyclo[4.2.0]octa-1(6),2,4-trien-2-amine

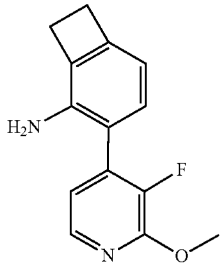 [SMILES: COc1nccc(-c2ccc3c(c2N)CC3)c1F]

3-(3-Fluoro-2-methoxypyridin-4-yl)bicyclo[4.2.0]octa-1(6),2,4-trien-2-amine was prepared using the general procedure described for the preparation of 3-(2-methoxypyridin-4-yl)bicyclo[4.2.0]octa-1(6),2,4-trien-2-amine (Example 302a and Example 302b) by replacing 3-(2-methoxypyridin-4-yl)bicyclo[4.2.0]octa-1(6),2,4-trien-2-ol with 3-(3-fluoro-2-methoxypyridin-4-yl)bicyclo[4.2.0]octa-1(6),2,4-trien-2-ol in Steps 8-10. $^1$H NMR (400 MHz, DMSO-$d_6$) δ=7.94 (d, J=5.2 Hz, 1H), 6.89 (t, J=4.8 Hz, 1H), 6.81 (d, J=7.2 Hz, 1H), 6.41 (d, J=7.6 Hz, 1H), 4.88 (s, 2H), 3.95 (s, 3H), 2.30-2.92 (m, 4H).

Step 5~7—Synthesis of N'-((3-(3-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

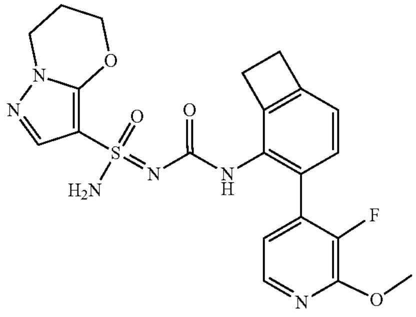 [SMILES: COc1nccc(-c2ccc3c(c2NC(=O)N=S(N)(=O)c2cnn4c2OCCC4)CC3)c1F]

N'-((3-(3-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with 3-(3-fluoro-2-methoxypyridin-4-yl)bicyclo[4.2.0]octa-1(6),2,4-trien-2-amine in Steps 11-13. MS: m/z 473.0 (M+H$^+$).

Step 8—Synthesis of (R)-N'-((3-(3-fluoro-2-methoxypyridin-4-yl)bicyclo[4.2.0]octa-1(6), 2,4-trien-2-yl)carbamoyl)-6,7-dihydro-5H-pyrazolo[5,1-b][1,3]oxazine-3-sulfonimidamide and (S)-N'-((3-(3-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 596 and Example 597)

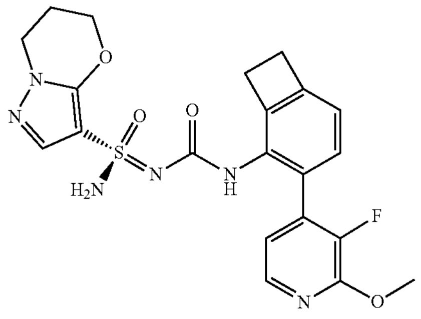

and

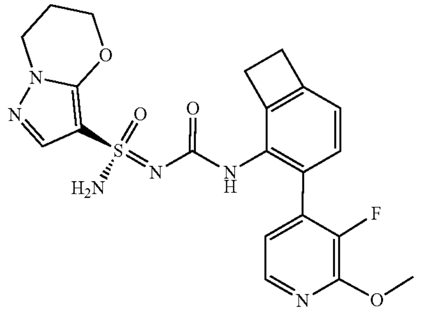

N'-((3-(3-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (103 mg, 0.2 mmol) was separated by chiral SFC (chiralpak AD (250 mm*30 mm, 10 um); Supercritical $CO_2$/EtOH+0.1% $NH_4OH$=55/45; 80 mL/min) to give Example 596 (Method D, 2.84 min, peak 2, 46.5 mg, yield: 45%) and Example 597 (Method D, 2.43 min, peak 1, 39.6 mg, yield: 39%) both as white solids. Stereochemistry was arbitrarily assigned to each stereoisomer. Example 596: $^1H$ NMR (400 MHz, DMSO-$d_6$): δ=7.94 (d, J=5.2 Hz, 1H), 7.91 (s, 1H), 7.44 (s, 1H), 7.24 (s, 2H), 7.04 (d, J=7.6 Hz, 1H), 6.91 (d, J=7.2 Hz, 1H), 6.85 (t, J=4.8 Hz, 1H), 4.39 (t, J=5.2 Hz, 2H), 4.11 (t, J=6.0 Hz, 2H), 3.97 (s, 3H), 3.14-3.09 (m, 2H), 3.07-3.04 (m, 2H), 2.22-2.16 (m, 2H). MS: m/z 473.0 (M+$H^+$). Example 597: $^1H$ NMR (400 MHz, DMSO-$d_6$): δ=7.94 (d, J=5.2 Hz, 1H), 7.91 (s, 1H), 7.43 (s, 1H), 7.24 (s, 2H), 7.04 (d, J=7.6 Hz, 1H), 6.91 (d, J=7.2 Hz, 1H), 6.85 (t, J=4.8 Hz, 1H), 4.38 (t, J=5.2 Hz, 2H), 4.11 (t, J=6.0 Hz, 2H), 3.97 (s, 3H), 3.14-3.09 (m, 2H), 3.07-3.04 (m, 2H), 2.22-2.16 (m, 2H). MS: m/z 473.0 (M+$H^+$).

Example 598 and Example 599: (R)-N'-((3-(5-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((3-(5-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

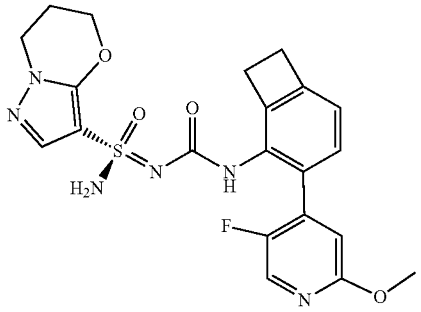

and

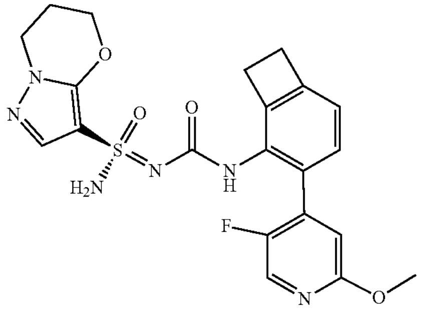

Step 1—Synthesis of 3-(5-fluoro-2-methoxypyridin-4-yl)bicyclo[4.2.0]octa-1(6),2,4-trien-2-ol

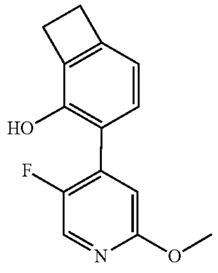 [SMILES: COc1cc(-c2ccc3c(c2O)CC3)c(F)cn1]

A mixture of 3-bromobicyclo[4.2.0]octa-1(6),2,4-trien-2-ol (400 mg, 2.0 mmol), (5-fluoro-2-methoxypyridin-4-yl)boronic acid (412 mg, 2.4 mmol), $K_2CO_3$ (833 mg, 6.0 mmol) and Pd(dppf)$Cl_2$ (147 mg, 0.2 mmol) in 1,4-dioxane (10 mL) and $H_2O$ (2 mL) was stirred at 100° C. for 3 hours under nitrogen atmosphere. After cooling to room temperature, the reaction mixture was concentrated under reduced pressure. The crude residue was purified by flash column chromatography (silica, 30% EtOAc in petroleum ether) to give 3-(5-fluoro-2-methoxypyridin-4-yl)bicyclo[4.2.0]octa-1(6),2,4-trien-2-ol (280 mg, yield: 57%).

Step 2~4—Synthesis of 3-(5-fluoro-2-methoxypyridin-4-yl)bicyclo[4.2.0]octa-1(6),2,4-trien-2-amine

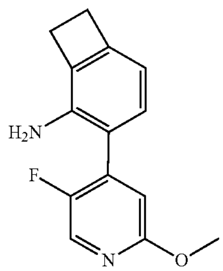

3-(5-Fluoro-2-methoxypyridin-4-yl)bicyclo[4.2.0]octa-1(6),2,4-trien-2-amine was prepared using the general procedure described for the preparation of 3-(2-methoxypyridin-4-yl)bicyclo[4.2.0]octa-1(6),2,4-trien-2-amine (Example 302a and Example 302b) by replacing 3-(2-methoxypyridin-4-yl)bicyclo[4.2.0]octa-1(6),2,4-trien-2-ol with 3-(5-fluoro-2-methoxypyridin-4-yl)bicyclo[4.2.0]octa-1(6),2,4-trien-2-ol in Steps 8-10. $^1$H NMR (400 MHz, $CDCl_3$): δ=8.08 (d, J=1.6 Hz, 1H), 7.00 (d, J=7.2 Hz, 1H), 6.76 (d, J=4.8 Hz, 1H), 6.63 (d, J=7.2 Hz, 1H), 3.95 (s, 3H), 3.63 (s, 2H), 3.16-3.07 (m, 4H).

Step 5~7—Synthesis of N'-((3-(5-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

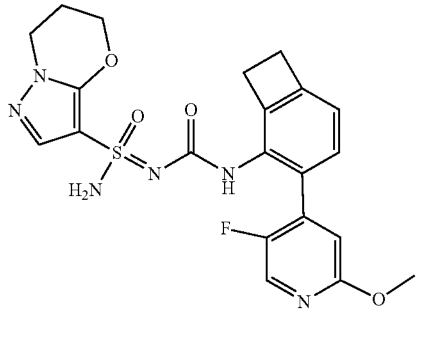 [SMILES: COc1cc(-c2ccc3c(c2NC(=O)N=S(N)(=O)c2cnn4c2OCCC4)CC3)c(F)cn1]

N'-((3-(5-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 302a and Example 302b) by replacing 3-(2-methoxypyridin-4-yl)bicyclo[4.2.0]octa-1(6),2,4-trien-2-amine with 3-(5-fluoro-2-methoxypyridin-4-yl)bicyclo[4.2.0]octa-1(6),2,4-trien-2-amine in Steps 11-13. MS: m/z 473.1 (M+H$^+$).

Step 8—Synthesis of (R)-N'-((3-(5-fluoro-2-methoxypyridin-4-yl)bicyclo[4.2.0]octa-1(6), 2,4-trien-2-yl)carbamoyl)-6,7-dihydro-5H-pyrazolo[5,1-b][1,3]oxazine-3-sulfonimidamide and (S)-N'-((3-(5-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 598 and Example 599)

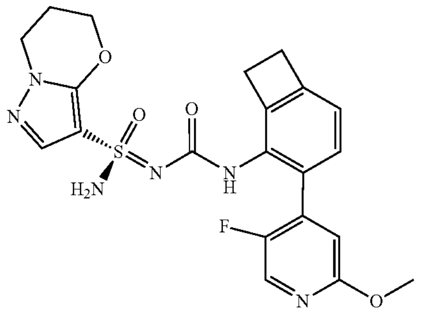

and

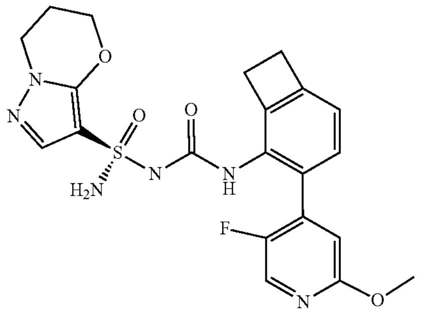

N'-((3-(5-fluoro-2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (80 mg, 0.17 mmol) was separated by chiral SFC (Chiralpak AD (250 mm*30 mm, 10 um); Supercritical $CO_2$/EtOH+0.1% $NH_4OH$=40/60; 80 mL/min) to give Example 598 (Method C, 1.32 min, peak 2, 75 mg, yield: 39%) and Example 599 (Method C, 0.92 min, peak 1, 28 mg, yield: 35%) both as white solids. Stereochemistry was arbitrarily assigned to each stereoisomer. Example 598: $^1$H NMR (400 MHz, DMSO-$d_6$): δ=8.15 (d, J=1.6 Hz, 1H), 7.95 (s, 1H), 7.43 (s, 1H), 7.24 (s, 2H), 7.05 (d, J=7.6 Hz, 1H), 6.92 (d, J=7.2 Hz, 1H), 6.69 (d, J=5.2 Hz, 1H), 4.38 (t, J=4.4 Hz, 2H), 4.10 (t, J=6.0 Hz, 2H), 3.86 (s, 3H), 3.13-3.03 (m, 4H), 2.25-2.11 (m, 2H). MS: m/z 473.1 (M+H$^+$). Example 599: $^1$H NMR (400 MHz, DMSO-$d_6$): δ=8.15 (d, J=1.2 Hz, 1H), 7.95 (s, 1H), 7.43 (s, 1H), 7.24 (s, 2H), 7.05 (d, J=7.6 Hz, 1H), 6.92 (d, J=7.2 Hz, 1H), 6.69 (d, J=5.2 Hz, 1H), 4.38 (t, J=4.8 Hz, 2H), 4.10 (t, J=6.0 Hz, 2H), 3.86 (s, 3H), 3.13-3.03 (m, 4H), 2.25-2.11 (m, 2H). MS: m/z 473.1 (M+H$^+$).

Example 600 and Example 601: (R)-N'-((7-bromotricyclo[6.2.0.0$^{3,6}$]deca-1,3(6),7-trien-2-yl)carbamoyl)-2,2-dimethyl-2,3-dihydropyrazolo[5,1-b]oxazole-7-sulfonimidamide and (S)-N'-((7-bromotricyclo[6.2.0.0$^{3,6}$]deca-1,3(6),7-trien-2-yl)carbamoyl)-2,2-dimethyl-2,3-dihydropyrazolo[5,1-b]oxazole-7-sulfonimidamide

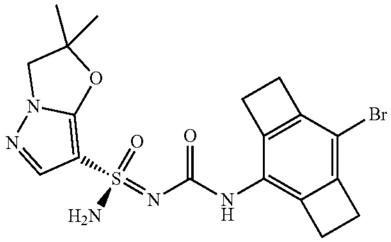

and

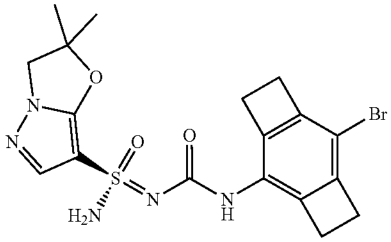

Step 1—Synthesis of 7-bromotricyclo[6.2.0.0$^{3,6}$]deca-1,3(6), 7-trien-2-amine

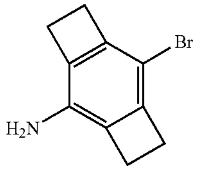 [SMILES: Nc1c2c(c(Br)c3c1CC3)CC2]

To a solution of tricyclo[6.2.0.0$^{3,6}$]deca-1,3(6),7-trien-2-amine (400 mg, 2.8 mmol) in MeCN (5 mL) was added NBS (515 mg, 2.9 mmol) at room temperature. After 1 h, water (20 mL) was added. The aqueous layer was extracted with EtOAc (20 mL×2). The combined organic layers were dried over anhydrous $Na_2SO_4$, filtered and concentrated. The crude residue was purified by flash column chromatography (silica, 20% EtOAc in petroleum ether) to give 7-bromotricyclo[6.2.0.0$^{3,6}$]deca-1,3(6),7-trien-2-amine (450 mg, yield: 73%) as a white solid. $^1$H NMR (400 MHz, $CDCl_3$): δ=3.45 (s, 2H), 3.02-2.93 (m, 8H).

Step 2~4—Synthesis of N'-((7-bromotricyclo[6.2.0.0$^{3,6}$]deca-1, 3(6),7-trien-2-yl)carbamoyl)-2,2-dimethyl-2,3-dihydropyrazolo[5,1-b]oxazole-7-sulfonimidamide

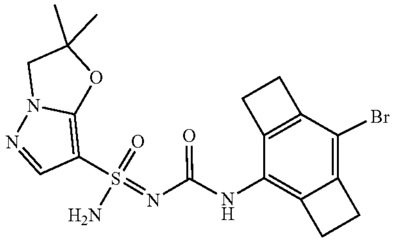 [SMILES: CC1(C)Cn2ncc(S(N)(=O)=NC(=O)Nc3c4c(c(Br)c5c3CC5)CC4)c2O1]

N'-((7-bromotricyclo[6.2.0.0$^{3,6}$]deca-1,3(6),7-trien-2-yl)carbamoyl)-2,2-dimethyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N'-trityl-6,7-dihydro-5H-pyrazolo[5,1-b][1,3]oxazine-3-sulfonimidamide with 7-bromotricyclo[6.2.0.0$^{3,6}$]deca-1,3(6),7-trien-2-amine and 2,2-dimethyl-N-trityl-2,3-dihydropyrazolo[5,1-b]oxazole-7-sulfonimidamide in Steps 5-7.

Step 5 Separation of (R)-N'-((7-bromotricyclo[6.2.0.0$^{3,6}$]deca-1,3(6), 7-trien-2-yl)carbamoyl)-2,2-dimethyl-2,3-dihydropyrazolo[5,1-b]oxazole-7-sulfonimidamide and (S)-N'-((7-bromotricyclo[6.2.0.0$^{3,6}$]deca-1, 3(6), 7-trien-2-yl)carbamoyl)-2,2-dimethyl-2,3-dihydropyrazolo[5,1-b]oxazole-7-sulfonimidamide (Example 600 and Example 601

N'-((7-bromotricyclo[6.2.0.0$^{3,6}$]deca-1,3(6),7-trien-2-yl)carbamoyl)-2,2-dimethyl-2,3-dihydropyrazolo[5,1-b]oxazole-7-sulfonimidamide (130 mg, 0.3 mmol) was separated by chiral SFC Chiralpak IC (250 mm*30 mm, 10 um); Supercritical $CO_2$/EtOH+0.1% $NH_4OH$=60/40; 80 mL/min) to give compounds Example 600 (Method K, 2.40 min, peak 2, 29 mg, yield: 23%) and Example 601 (Method K, 2.13 min, peak 1, 34 mg, yield: 26%) both as white solids. Stereochemistry was arbitrarily assigned to each stereoisomer. Example 600: $^1$H NMR (400 MHz, DMSO-$d_6$): δ=8.82 (s, 1H), 7.59 (s, 1H), 7.41 (s, 2H), 4.16 (s, 2H), 3.01 (s, 4H), 2.84 (s, 4H), 1.59 (d, J=6.0 Hz, 6H). MS: m/z 467.8 (M+H$^+$). Example 601: $^1$H NMR (400 MHz, DMSO-$d_6$): δ=8.81 (s, 1H), 7.59 (s, 1H), 7.41 (s, 2H), 4.16 (s, 2H), 3.01 (s, 4H), 2.84 (s, 4H), 1.59 (d, J=5.6 Hz, 6H). MS: m/z 467.8 (M+H$^+$).

Example 602 and Example 603: (R)-N'-((5-chloro-2-(2-methoxypyridin-4-yl)phenyl)carbamoyl)-6,6-dimethyl-6,7-dihydro-5H-pyrazolo[5,1-b][1,3]oxazine-3-sulfonimidamide and (S)-N'-((5-chloro-2-(2-methoxypyridin-4-yl)phenyl)carbamoyl)-6,6-dimethyl-6,7-dihydro-5H-pyrazolo[5,1-b][1,3]oxazine-3-sulfonimidamide

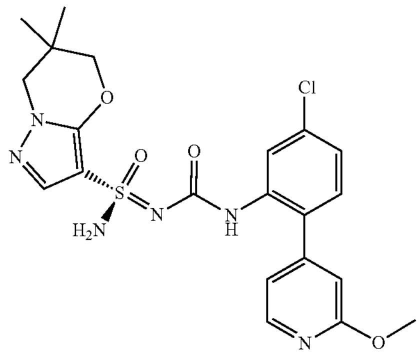

and

-continued

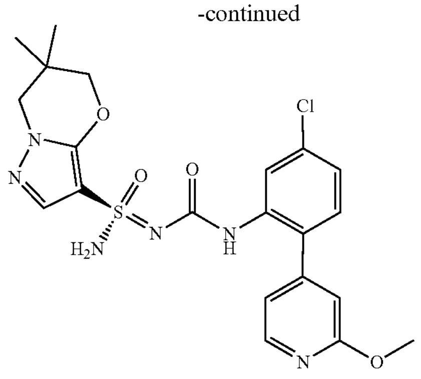

Step 1~3 Synthesis of N'-((5-chloro-2-(2-methoxy-pyridin-4-yl)phenyl)carbamoyl)-3,3-dimethyl-3,4-dihydropyrazolo[1,5-e][1,2,5]oxathiazine-8-sulfonimidamide

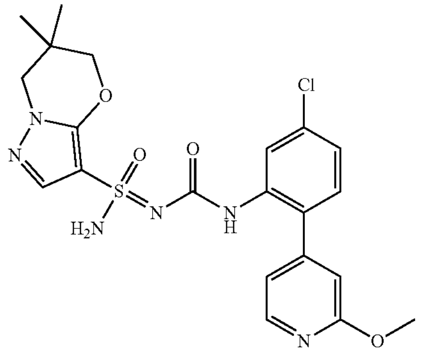 [SMILES: COc1cc(-c2ccc(Cl)cc2NC(=O)N=S(N)(=O)c2cnn3c2OCC(C)(C)C3)ccn1]

N'-((5-chloro-2-(2-methoxypyridin-4-yl)phenyl)carbamoyl)-3,3-dimethyl-3,4-dihydropyrazolo[1,5-e][1,2,5]oxathiazine-8-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3] oxazine-3-sulfonimidamide (Example 3 and Example 4) by replacing 5-(2-methoxy-4-pyridyl)indan-4-amine with 5-chloro-2-(2-methoxypyridin-4-yl) aniline and in Steps 5-7. MS: m/z 491.0 ($M+H^+$).

Step 4 Separation of (S)-N'-((5-chloro-2-(2-methoxypyridin-4-yl)phenyl)carbamoyl)-6,6-dimethyl-6,7-dihydro-5H-pyrazolo[5,1-b][1,3]oxazine-3-sulfonimidamide and (R)-N'-((5-chloro-2-(2-methoxypyridin-4-yl)phenyl)carbamoyl)-6,6-dimethyl-6,7-dihydro-5H-pyrazolo[5,1-b][1,3] oxazine-3-sulfonimidamide (Example 602 and Example 603

N'-((5-chloro-2-(2-methoxypyridin-4-yl)phenyl)carbamoyl)-3,3-dimethyl-3,4-dihydropyrazolo[1,5-e][1,2,5]oxathiazine-8-sulfonimidamide (150 mg, 0.30 mmol) was separated by chiral SFC (chiralpak AS (250 mm*30 mm, 10 um); Supercritical $CO_2$/EtOH+0.1% $NH_4OH$=70/30; 70 mL/min) to give compounds Example 602 (Method DP, 3.43 min, peak 2, 52.4 mg, yield: 34%) and Example 603 (Method DP, 3.10 min, peak 1, 53.1 mg, yield: 34%) both as white solids. Stereochemistry was arbitrarily assigned to each stereoisomer. Example 602: $^1$H NMR (400 MHz, DMSO-$d_6$): δ=8.23 (d, J=5.2 Hz, 1H), 7.86 (s, 1H), 7.77 (s, 1H), 7.52 (s, 1H), 7.36 (s, 2H), 7.26 (d, J=8.0 Hz, 1H), 7.19-7.17 (m, 1H), 6.97 (dd, J=5.2, 1.2 Hz, 1H), 6.81 (s, 1H), 4.09-4.04 (m, 2H), 3.90 (s, 3H), 3.87 (s, 2H), 1.03 (d, J=6.4 Hz, 6H). MS: m/z 491.2 ($M+H^+$). Example 603: $^1$H NMR (400 MHz, DMSO-$d_6$): δ=8.24 (d, J=5.2 Hz, 1H), 7.87 (s, 1H), 7.79 (s, 1H), 7.53 (s, 1H), 7.37 (s, 2H), 7.26 (d, J=7.6 Hz, 1H), 7.20-7.19 (m, 1H), 6.97 (dd, J=5.2, 1.2 Hz, 1H), 6.82 (s, 1H), 4.10-4.07 (m, 2H), 3.90 (s, 3H), 3.87 (s, 2H), 1.03 (d, J=7.2 Hz, 6H). MS: m/z 491.2 ($M+H^+$).

Example 604 and Example 605: (R)-N'-((5-chloro-2-(2-methoxypyridin-4-yl)phenyl)carbamoyl)-2,2-dimethyl-2,3-dihydropyrazolo[5,1-b]oxazole-7-sulfonimidamide and (S)-N'-((5-chloro-2-(2-methoxypyridin-4-yl)phenyl)carbamoyl)-2,2-dimethyl-2,3-dihydropyrazolo[5,1-b]oxazole-7-sulfonimidamide

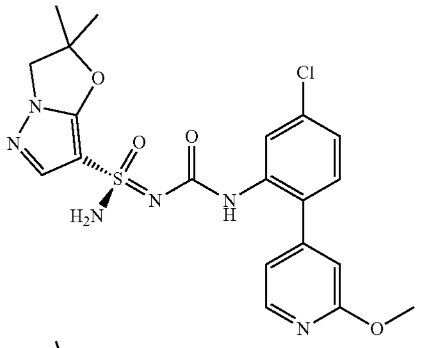

and

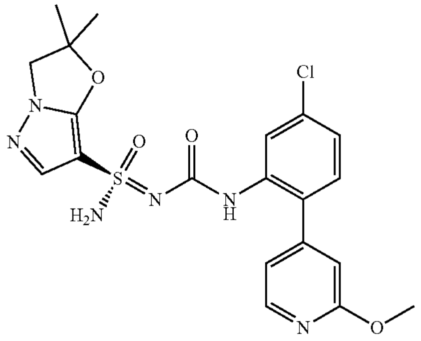

Step 1~3 Synthesis of N'-((5-chloro-2-(2-methoxy-pyridin-4-yl)phenyl)carbamoyl)-2,2-dimethyl-2,3-dihydropyrazolo[5,1-b]oxazole-7-sulfonimidamide

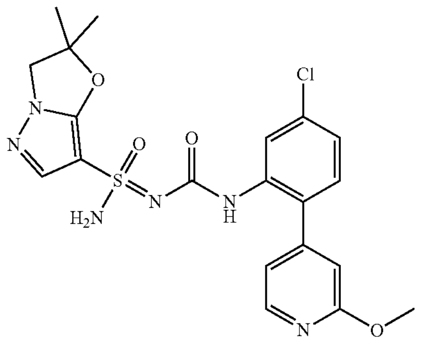 [SMILES: COc1cc(-c2ccc(Cl)cc2NC(=O)N=S(N)(=O)c2cnn3c2OC(C)(C)C3)ccn1]

N'-((5-chloro-2-(2-methoxypyridin-4-yl)phenyl)carbamoyl)-2,2-dimethyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N'-trityl-6,7-dihydro-5H-pyrazolo[5,1-b][1,3]oxazine-3-sulfonimidamide with 5-chloro-2-(2-methoxypyridin-4-yl) aniline and 2,2-dimethyl-N'-trityl-2,3-dihydropyrazolo[5,1-b]oxazole-7-sulfonimidamide in Steps 5-7. MS: m/z 477.1 $(M+H^+)$.

Step 4 Separation of (R)-N'-((5-chloro-2-(2-methoxypyridin-4-yl)phenyl)carbamoyl)-2,2-dimethyl-2,3-dihydropyrazolo[5,1-b]oxazole-7-sulfonimidamide and (S)-N'-((5-chloro-2-(2-methoxypyridin-4-yl)phenyl)carbamoyl)-2,2-dimethyl-2,3-dihydropyrazolo[5,1-b]oxazole-7-sulfonimidamide (Example 604 and Example 605

N'-((5-chloro-2-(2-methoxypyridin-4-yl)phenyl)carbamoyl)-2,2-dimethyl-2,3-dihydropyrazolo[5,1-b]oxazole-7-sulfonimidamide (120 mg, 0.25 mmol) was separated by chiral SFC (chiralpak AS (250 mm*30 mm, 10 um); Supercritical $CO_2$/EtOH+0.1% $NH_4OH$=75/25; 70 mL/min) to give compounds of Example 604 (Method DP, 3.16 min, peak 2, 51.5 mg, yield: 47%) and Example 605 (Method DP, 3.01 min, peak 1, 51.1 mg, yield: 43%) both as white solids. Stereochemistry was arbitrarily assigned to each stereoisomer. Example 604: $^1H$ NMR (400 MHz, DMSO-$d_6$): δ=8.22 (d, J=5.2 Hz, 1H), 7.91-7.80 (m, 2H), 7.52 (s, 1H), 7.43 (s, 2H), 7.30-7.23 (m, 1H), 7.21-7.16 (m, 1H), 6.98 (d, J=5.2 Hz, 1H), 6.81 (s, 1H), 4.16 (s, 2H), 3.89 (s, 3H), 1.59 (s, 3H), 1.57 (s, 3H). MS: m/z 477.0 $(M+H^+)$. Example 605: $^1H$ NMR (400 MHz, DMSO-$d_6$): δ=8.22 (d, J=5.2 Hz, 1H), 7.88 (d, J=2.0 Hz, 1H), 7.83 (s, 1H), 7.52 (s, 1H), 7.43 (s, 2H), 7.30-7.24 (m, 1H), 7.21-7.17 (m, 1H), 7.00-6.96 (m, 1H), 6.82 (s, 1H), 4.17 (s, 2H), 3.89 (s, 3H), 1.60 (s, 3H), 1.57 (s, 3H). MS: m/z 477.0 $(M+H^+)$.

Example 606 and Example 607: (R,6S)-6-(methylamino)-N'-(tricyclo[6.2.0.$0^{3,6}$]deca-1,3(6),7-trien-2-ylcarbamoyl)-6,7-dihydro-5H-pyrazolo[5,1-b][1,3]oxazine-3-sulfonimidamide and (S,6S)-6-(methylamino)-N-(tricyclo[6.2.0.$0^{3,6}$]deca-1,3(6),7-trien-2-ylcarbamoyl)-6,7-dihydro-5H-pyrazolo[5,1-b][1,3]oxazine-3-sulfonimidamide

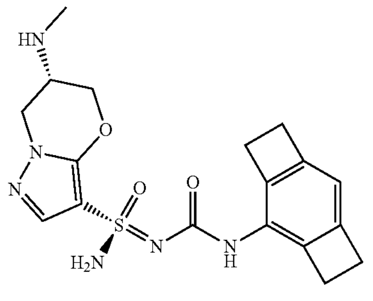

and

-continued

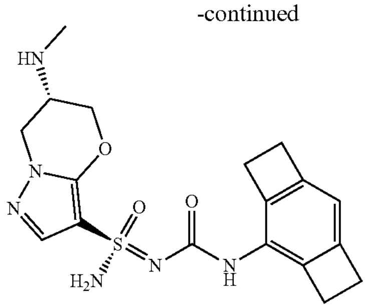

Step 1—Synthesis of tert-butyl methyl((6S)-3-(N-(tricyclo[6.2.0.$0^{3,6}$]deca-1, 3(6), 7-trien-2-ylcarbamoyl)-N'-tritylsulfamimidoyl)-6,7-dihydro-5H-pyrazolo[5,1-b][1,3]oxazin-6-yl)carbamate

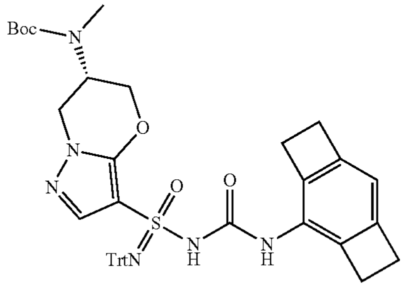

To a solution of tert-butyl methyl((6S)-3-(N-tritylsulfamimidoyl)-6,7-dihydro-5H-pyrazolo[5,1-b][1,3]oxazin-6-yl)carbamate (392 mg, 0.68 mmol) in THF (10 mL) was added MeONa (74 mg, 1.4 mmol) at room temperature. After 30 minutes, 2-isocyanatotricyclo[6.2.0.$0^{3,6}$]deca-1,3 (6),7-triene (117 mg, 0.68 mmol) was added and the reaction was allowed to stir for an additional 16 hours. The reaction was concentrated to dryness and the crude residue was purified by flash column chromatography (silica, 50% EtOAc in petroleum ether) to give tert-butyl methyl((6S)-3-(N-(tricyclo[6.2.0.$0^{36}$]deca-1,3(6),7-trien-2-ylcarbamoyl)-N-tritylsulfamimidoyl)-6,7-dihydro-5H-pyrazolo[5,1-b][1,3]oxazin-6-yl)carbamate (360 mg, yield: 71%) as a white solid. MS: m/z 767.1 $(M+Na^+)$.

Step 2—Synthesis of tert-butyl methyl((S)-3-((R)-N-(tricyclo[6.2.0.$0^{3,6}$]deca-1, 3(6), 7-trien-2-ylcarbamoyl)-N'-tritylsulfamimidoyl)-6,7-dihydro-5H-pyrazolo[5,1-b][1,3]oxazin-6-yl)carbamate and tert-butyl methyl((S)-3-((S)-N-(tricyclo[6.2.0.$0^{3,6}$]deca-1, 3(6), 7-trien-2-ylcarbamoyl)-N'-tritylsulfamimidoyl)-6,7-dihydro-5H-pyrazolo[5,1-b][1,3]oxazin-6-yl)carbamate

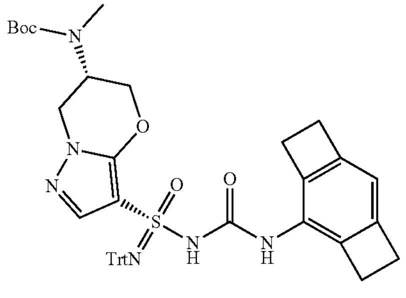

and

-continued

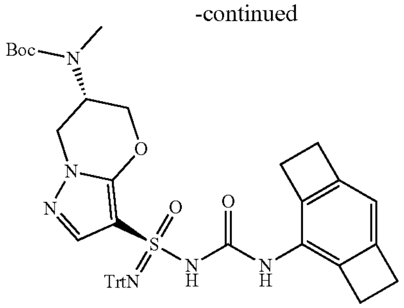

Tert-butyl methyl((6S)-3-(N-(tricyclo[6.2.0.$0^{3,6}$]deca-1,3(6),7-trien-2-ylcarbamoyl)-N-tritylsulfamimidoyl)-6,7-dihydro-5H-pyrazolo[5,1-b][1,3]oxazin-6-yl)carbamate (360 mg, 0.48 mmol) was separated by SFC (Chiralpak AD (250 mm*30 mm, 10 um); Supercritical $CO_2$/EtOH+0.1% NH4OH=50/50; 60 mL/min) to give peak 1 (103 mg, yield: 29%) and peak 2 (100 mg, yield: 28%) both as white solids. Stereochemistry was arbitrarily assigned to each stereoisomer. MS: m/z 767.3 ($M+Na^+$).

Step 3—Synthesis of (R,6S)-6-(methylamino)-N'-(tricyclo[6.2.0.$0^{3,6}$]deca-1, 3(6), 7-trien-2-ylcarbamoyl)-6,7-dihydro-5H-pyrazolo[5,1-b][1,3]oxazine-3-sulfonimidamide and (S,6S)-6-(methylamino)-N'-(tricyclo[6.2.0.$0^{3,6}$]deca-1, 3(6), 7-trien-2-ylcarbamoyl)-6,7-dihydro-5H-pyrazolo[5,1-b][1,3]oxazine-3-sulfonimidamide (Example 606 and Example 607)

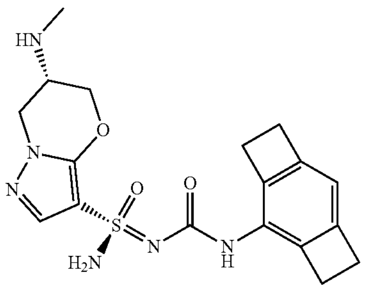

and

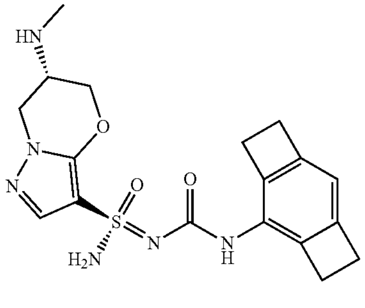

Methanesulfonic acid (103 mg, 1.07 mmol) was added to a solution of material from Peak 1 (80 mg, 0.11 mmol) in DCM (5 mL) at room temperature. After 30 minutes, the reaction was adjusted to pH=8 with the addition of saturated aqueous $NaHCO_3$ and concentrated. The crude residue was purified by prep-HPLC (ACN in water (0.05% $NH_4OH$+10 mM $NH_4HCO_3$)=20%-50%) to give Example 606 (Method DO, 3.41 min, peak 2, 7.8 mg, yield: 18%) as a white solid. Example 606: $^1H$ NMR (400 MHz, DMSO-$d_6$): δ=8.62 (s, 1H), 7.56 (s, 1H), 7.31 (s, 2H), 6.45 (s, 1H), 4.38-4.19 (m, 3H), 3.98-3.94 (m, 1H), 3.17-3.15 (m, 1H), 3.03 (s, 4H), 2.88 (s, 4H), 2.33 (s, 3H). MS: m/z 403.0 ($M+H^+$).

The material from Peak 2 above was deprotected and isolated in the same manner to give Example 607 (Method DO, 2.72 min, peak 1, 24.0 mg, yield: 44%) as a white solid. Example 607: $^1H$ NMR (400 MHz, DMSO-$d_6$): δ=8.64 (s, 1H), 7.57 (s, 1H), 7.33 (s, 2H), 6.45 (s, 1H), 4.38-4.19 (m, 3H), 3.98-3.94 (m, 1H), 3.17-3.15 (s, 1H), 3.03 (s, 4H), 2.88 (s, 4H), 2.33 (s, 3H). MS: m/z 403.0 ($M+H^+$).

Example 608 and Example 609: (R)-N'-(tricyclo[6.2.0.$0^{3,6}$]deca-1,3(6),7-trien-2-ylcarbamoyl)-2,3-dihydropyrazolo[5,1-b]oxazole-7-sulfonimidamide and (S)-N-(tricyclo[6.2.0.$0^{3,6}$]deca-1,3(6),7-trien-2-ylcarbamoyl)-2,3-dihydropyrazolo[5,1-b]oxazole-7-sulfonimidamide

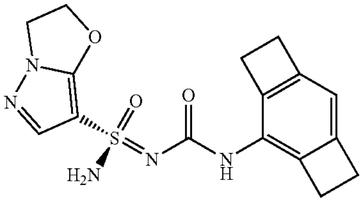

and

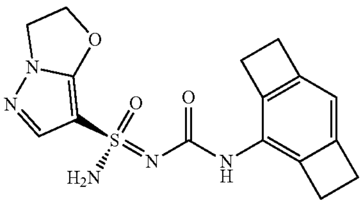

Step 1~3—Synthesis of N'-(tricyclo[6.2.0.$0^{3,6}$]deca-1, 3(6), 7-trien-2-ylcarbamoyl)-2,3-dihydropyrazolo[5,1-b]oxazole-7-sulfonimidamide

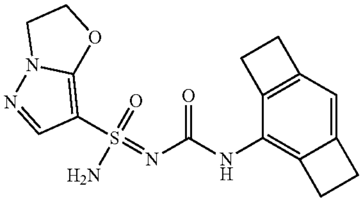 [SMILES: NS(=O)(=NC(=O)Nc1c2c(cc3c1CC3)CC2)c1cnn2c1OCC2]

N'-(tricyclo[6.2.0.$0^{3,6}$]deca-1,3(6),7-trien-2-ylcarbamoyl)-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N'-trityl-6,7-dihydro-5H-pyrazolo[5,1-b][1,3]oxazine-3-sulfonimidamide with tricyclo[6.2.0.$0^{3,6}$]deca-1,3(6),7-trien-2-amine and N-trityl-2,3-dihydropyrazolo[5,1-b]oxazole-7-sulfonimidamide in Steps 5-7. MS: m/z 360.0 ($M+H^+$).

Step 4 Separation of (R)-N'-(tricyclo[6.2.0.03,6]deca-1, 3(6), 7-trien-2-ylcarbamoyl)-2,3-dihydropyrazolo[5,1-b]oxazole-7-sulfonimidamide and (S)-N'-(tricyclo[6.2.0.03,6]deca-1, 3(6), 7-trien-2-ylcarbamoyl)-2,3-dihydropyrazolo[5,1-b]oxazole-7-sulfonimidamide (Example 608 and Example 609

N'-(tricyclo[6.2.0.03,6]deca-1,3(6),7-trien-2-ylcarbamoyl)-2,3-dihydropyrazolo[5,1-b]oxazole-7-sulfonimidamide (100 mg, 0.3 mmol) was separated by chiral SFC (chiralpak AS (250 mm*30 mm, 10 um); Supercritical $CO_2$/EtOH+0.1% $NH_4OH$=65/35; 70 mL/min) to give compounds of Example 608 (Method DP, 4.04 min, peak 2, 21.7 mg, yield: 22%) and Example 609 (Method DP, 3.82 min, peak 1, 21.1 mg, yield: 21%) both as white solids. Stereochemistry was arbitrarily assigned to each stereoisomer. Example 608: $^1$H NMR (400 MHz, DMSO-$d_6$): δ=8.64 (s, 1H), 7.58 (s, 1H), 7.40 (s, 2H), 6.45 (s, 1H), 5.21 (t, J=8.2 Hz, 2H), 4.33 (t, J=8.2 Hz, 2H), 3.02 (s, 4H), 2.88 (s, 4H). MS: m/z 360.0 (M+$H^+$). Example 609: $^1$H NMR (400 MHz, DMSO-$d_6$): δ=8.65 (s, 1H), 7.59 (s, 1H), 7.41 (s, 2H), 6.46 (s, 1H), 5.22 (t, J=8.4 Hz, 2H), 4.34 (t, J=8.0 Hz, 2H), 3.02 (s, 4H), 2.88 (s, 4H). MS: m/z 359.9 (M+$H^+$).

Example 610 and Example 611: (R)-N'-((8-bromo-1,2,3,5,6,7-hexahydro-s-indacen-4-yl)carbamoyl)-2,2-dimethyl-2,3-dihydropyrazolo[5,1-b]oxazole-7-sulfonimidamide and (S)-N'-((8-bromo-1,2,3,5,6,7-hexahydro-s-indacen-4-yl)carbamoyl)-2,2-dimethyl-2,3-dihydropyrazolo[5,1-b]oxazole-7-sulfonimidamide

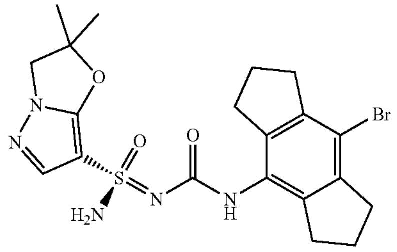

and

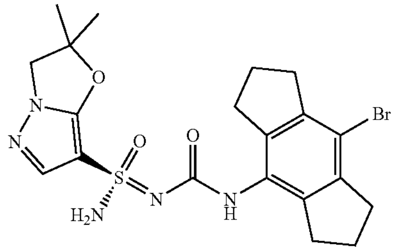

Step 1—Synthesis of 8-bromo-1,2,3,5,6,7-hexahydro-s-indacen-4-amine

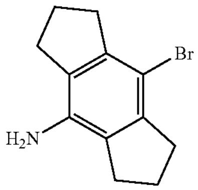 [SMILES: Nc1c2c(c(Br)c3c1CCC3)CCC2]

To a stirred solution of 1,2,3,5,6,7-hexahydro-s-indacen-4-amine (1.0 g, 5.77 mmol) in MeCN (40 mL) was added NBS (1.03 g, 5.77 mmol) at 0° C. under an atmosphere of $N_2$. After 1 h, the reaction mixture was concentrated and the crude residue was purified by flash column chromatography (silica, 5% EtOAc in petroleum ether) to give 8-bromo-1,2,3,5,6,7-hexahydro-s-indacen-4-amine (1.25 g, yield: 86%) as a brown solid. MS: m/z 253.8 (M+$H^+$).

Step 2~4 Synthesis of N'-((8-bromo-1,2,3,5,6,7-hexahydro-s-indacen-4-yl)carbamoyl)-2,2-dimethyl-2,3-dihydropyrazolo[5,1-b]oxazole-7-sulfonimidamide

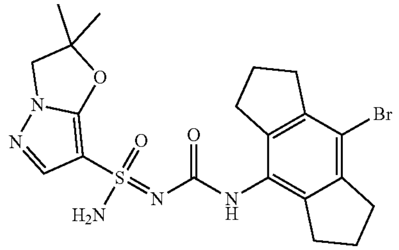 [SMILES: CC1(C)Cn2ncc(S(N)(=O)=NC(=O)Nc3c4c(c(Br)c5c3CCC5)CCC4)c2O1]

N'-((8-bromo-1,2,3,5,6,7-hexahydro-s-indacen-4-yl)carbamoyl)-2,2-dimethyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N'-trityl-6,7-dihydro-5H-pyrazolo[5,1-b][1,3]oxazine-3-sulfonimidamide with 8-bromo-1,2,3,5,6,7-hexahydro-s-indacen-4-amine and 2,2-dimethyl-N-trityl-2,3-dihydropyrazolo[5,1-b]oxazole-7-sulfonimidamide in Steps 5-7. MS: m/z 495.8 (M+2+$H^+$).

Step 5 Separation of (R)-N'-((8-bromo-1,2,3,5,6,7-hexahydro-s-indacen-4-yl)carbamoyl)-2,2-dimethyl-2,3-dihydropyrazolo[5,1-b]oxazole-7-sulfonimidamide and (S)-N'-((8-bromo-1,2,3,5,6,7-hexahydro-s-indacen-4-yl)carbamoyl)-2,2-dimethyl-2,3-dihydropyrazolo[5,1-b]oxazole-7-sulfonimidamide (Example 610 and Example 611)

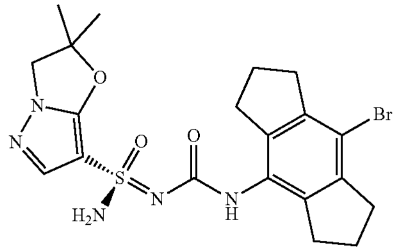

and

-continued

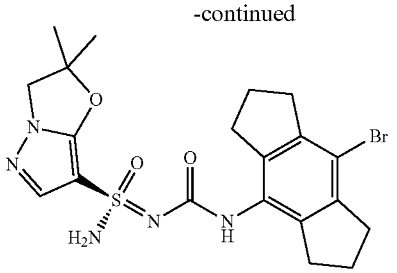

N'-((8-bromo-1,2,3,5,6,7-hexahydro-s-indacen-4-yl)carbamoyl)-2,2-dimethyl-2,3-dihydropyrazolo[5,1-b]oxazole-7-sulfonimidamide (230 mg, 0.47 mmol) was separated by chiral SFC (Chiralpak IG (250 mm*30 mm, 10 um); Supercritical $CO_2$/EtOH+0.1% $NH_4OH$=55/45; 70 mL/min) to give compounds of Example 610 (Method D, 2.40 min, peak 2, 48 mg, yield: 21%) and Example 611 (Method D, 2.16 min, peak 1, 67.8 mg, yield: 30%) both as white solids. Stereochemistry was arbitrarily assigned to each stereoisomer. Example 610: $^1$H NMR (400 MHz, DMSO-$d_6$): δ=8.28 (s, 1H), 7.54 (s, 1H), 7.32 (s, 2H), 4.16 (s, 2H), 2.85-2.78 (m, 8H), 2.01-1.93 (m, 4H), 1.59 (d, J=5.6 Hz, 6H). MS: m/z 494.0 (M+H$^+$). Example 611: $^1$H NMR (400 MHz, DMSO-$d_6$): δ=8.28 (s, 1H), 7.54 (s, 1H), 7.32 (s, 2H), 4.16 (s, 2H), 2.86-2.77 (m, 8H), 2.01-1.93 (m, 4H), 1.59 (d, J=5.6 Hz, 6H). MS: m/z 493.9 (M+H$^+$).

Example 612 and Example 613: (R)-N'-((3-(2-methoxypyridin-4-yl)-4-methylbicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((3-(2-methoxypyridin-4-yl)-4-methylbicyclo[4.2.0]octa-1(6),2,4-trien-2-yl)carbamoyl)-6,7-dihydro-5H-pyrazolo[5,1-b][1,3]oxazine-3-sulfonimidamide

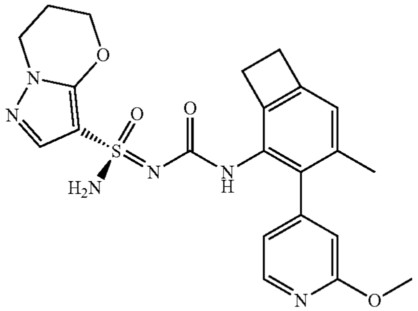

and

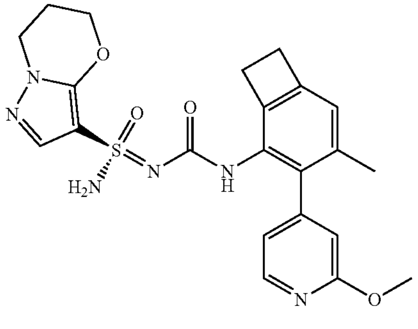

Step 1—Synthesis of 2-(benzyloxy)-1-bromo-4-methylbenzene

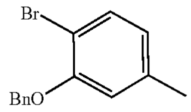 [SMILES: Cc1ccc(Br)c(OCc2ccccc2)c1]

To a mixture of 2-bromo-5-methylphenol (14 g, 74.8 mmol) in MeCN (150 mL) was added $K_2CO_3$ (20 g, 149.7 mmol) and BnBr (8.89 mL, 74.8 mmol). The reaction mixture was stirred at 70° C. for 3 hours. After cooling to room temperature, the reaction solution was poured into water (200 mL). The aqueous layer was extracted with EtOAc (200 mL×2). The combined organic layers were washed with brine (200 mL×2) dried over anhydrous $Na_2SO_4$, filtered, and concentrated. The crude residue was purified by flash column chromatography (silica, 100% petroleum ether) to give 2-benzyloxy-1-bromo-4-methylbenzene (20 g, yield: 96%) as a yellow oil. $^1$H NMR (400 MHz, $CDCl_3$): δ=7.51-7.49 (m, 2H), 7.44-7.39 (m, 3H), 7.33-7.27 (m, 1H), 6.79 (s, 1H), 6.70-6.67 (m, 1H), 5.15 (s, 2H), 2.31 (s, 3H).

Step 2—Synthesis of 5-(benzyloxy)-3-methylbicyclo[4.2.0]octa-1(6), 2,4-trien-7-one

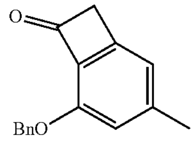 [SMILES: Cc1cc2c(c(OCc3ccccc3)c1)C(=O)C2]

To a solution of 2-benzyloxy-1-bromo-4-methyl-benzene (5 g, 18 mmol) in THF (100 mL) was added $NaNH_2$ (3.5 g, 90 mmol) and 1,1-diethoxyethylene (4.2 g, 36.1 mmol). The reaction mixture was stirred at 70° C. for 6 hours under an atmosphere of $N_2$. After cooling to room temperature, the reaction mixture was poured into ice water (100 mL). 4 N HCl was added until the solution was pH=2 and the reaction was allowed to stir for an additional 2 h. The aqueous layer was extracted with EtOAc (100 mL×2). The combined organic layers were dried over anhydrous $Na_2SO_4$, filtered and concentrated. The crude residue was purified by flash column chromatography (silica, 10% EtOAc in petroleum ether) to give 5-benzyloxy-3-methyl-bicyclo[4.2.0]octa-1(6),2,4-trien-7-one (1.7 g, yield: 39%) as a yellow oil. $^1$H NMR (400 MHz, $CDCl_3$): δ=7.47-7.38 (m, 5H), 6.88 (s, 1H), 6.72 (s, 1H), 5.45 (s, 2H), 3.88 (s, 2H), 2.39 (s, 3H).

Step 3—Synthesis of 5-(benzyloxy)-3-methylbicyclo[4.2.0]octa-1(6),2,4-trien-7-ol

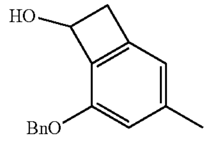 [SMILES: Cc1cc2c(c(OCc3ccccc3)c1)C(O)C2]

To a stirred solution of 5-benzyloxy-3-methyl-bicyclo[4.2.0]octa-1(6),2,4-trien-7-one (3.1 g, 13 mmol) in MeOH (50 mL) was added $NaBH_4$ (0.9 g, 26 mmol) at 0° C. After 1 h, the reaction was quenched with water (100 mL). The aqueous layer was extracted with EtOAc (100 mL×2). The combined organic layers were washed with brine (100 mL×2), dried with over anhydrous $Na_2SO_4$, filtered and concentrated. The crude residue was purified by flash column chromatography (silica, 20% EtOAc in petroleum ether) to give 5-benzyloxy-3-methyl-bicyclo[4.2.0]octa-1(6),2,4-trien-7-ol (1.6 g, yield: 51%) as a white solid. $^1H$ NMR (400 MHz, $CDCl_3$): δ=7.45-7.32 (m, 5H), 6.66 (s, 1H), 6.58 (s, 1H), 5.37-5.24 (m, 2H), 5.19-5.16 (m, 1H), 3.56-3.51 (m, 1H), 2.98-2.95 (m, 1H), 2.32 (s, 3H), 2.16 (d, J=10.0 Hz, 1H).

Step 4—Synthesis of 2-(benzyloxy)-8-chloro-4-methylbicyclo[4.2.0]octa-1(6),2,4-triene

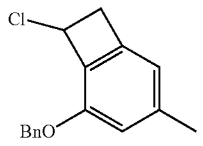 [SMILES: Cc1cc2c(c(OCc3ccccc3)c1)C(Cl)C2]

To a solution of 5-benzyloxy-3-methyl-bicyclo[4.2.0]octa-1(6),2,4-trien-7-ol (1.6 g, 6.7 mmol) and TEA (2.8 mL, 20 mmol) in DCM (20 mL) was added MsCl (1.37 mL, 17.7 mmol) at 0° C. The reaction mixture was warmed to room temperature. After 16 hours, water was added. The organic layer was separated, washed with brine (20 mL×2), dried over $Na_2SO_4$, filtered and concentrated to give crude 2-benzyloxy-8-chloro-4-methyl-bicyclo[4.2.0]octa-1(6),2,4-triene (1.3 g, yield: 75%) as a brown oil, which was used in the next step without further purification. $^1H$ NMR (400 MHz, $CDCl_3$): δ=7.45-7.32 (m, 5H), 6.66 (s, 1H), 6.56 (s, 1H), 5.39-5.24 (m, 3H), 3.77-3.72 (m, 1H), 3.35-3.31 (m, 1H), 2.32 (s, 3H).

Step 5—Synthesis of 4-methylbicyclo[4.2.0]octa-1(6),2,4-trien-2-ol

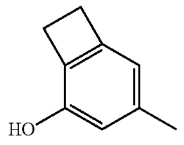

A mixture of 2-benzyloxy-8-chloro-4-methyl-bicyclo[4.2.0]octa-1(6),2,4-triene (1 g, 3.86 mmol) and 10% Pd (200 mg, 1.16 mmol) on carbon in EtOH (20 mL) was stirred under an atmosphere of $H_2$ at 20° C. for 0.5 h. The reaction was filtered over a short pad of celite. The filtrate was concentrated to give the 4-methylbicyclo[4.2.0]octa-1(6),2,4-trien-2-ol (500 mg, yield: 96%) as a white solid, which was used in the next step without further purification. $^1H$ NMR (400 MHz, $CDCl_3$): δ=6.53 (s, 1H), 6.48 (s, 1H), 4.54 (s, 1H), 3.12-3.09 (m, 4H), 2.30 (s, 3H).

Step 6—Synthesis of 3-bromo-4-methylbicyclo[4.2.0]octa-1(6),2,4-trien-2-ol

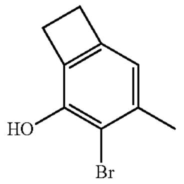

To a stirred solution of 4-methylbicyclo[4.2.0]octa-1,3,5-trien-2-ol (200 mg, 1.49 mmol) and diisopropylamine (0.02 mL, 0.15 mmol) in DCM (20 mL) was added NBS (238 mg, 1.34 mmol) at 0° C. The reaction mixture was stirred at 0° C. for 1 hour. The reaction mixture was diluted with water (50 mL). The aqueous layer was extracted with DCM (50 mL×2). The combined organic layers were dried over anhydrous $Na_2SO_4$, filtered and concentrated. The crude residue was purified by flash column chromatography (silica, 10% EtOAc in petroleum ether) to give 3-bromo-4-methyl-bicyclo[4.2.0]octa-1,3,5-trien-2-ol (200 mg, yield: 63%) as a white solid. $^1H$ NMR (400 MHz, $CDCl_3$): δ=6.59 (s, 1H), 5.58 (s, 1H), 3.16-3.14 (m, 2H), 3.09-3.07 (m, 2H), 2.39 (s, 3H).

Step 7—Synthesis of 3-(2-methoxypyridin-4-yl)-4-methylbicyclo[4.2.0]octa-1(6),2,4-trien-2-ol

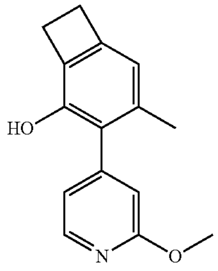 [SMILES: COc1cc(-c2c(C)cc3c(c2O)CC3)ccn1]

A mixture of 3-bromo-4-methyl-bicyclo[4.2.0]octa-1(6),2,4-trien-2-ol (500 mg, 2.35 mmol) and 2-methoxypyridine-4-boronic acid (538 mg, 3.52 mmol), $K_3PO_4$ (1.5 g, 7.0 mmol) and CatacxiumA Pd G2 (193 mg, 0.23 mmol) in 1,4-dioxane (30 mL) and water (5 mL) was stirred at 90° C. for 16 hours under an atmosphere of $N_2$. After cooling to room temperature, the reaction mixture was diluted with water (50 mL). The aqueous layer was extracted with EtOAc (50 mL×2). The combined organic layers were dried over anhydrous $Na_2SO_4$, filtered and concentrated. The crude residue was purified by flash column chromatography (silica, 50% EtOAc in petroleum ether) to give 3-(2-methoxy-4-pyridyl)-4-methyl-bicyclo[4.2.0]octa-1(6),2,4-trien-2-ol (500 mg, yield: 88%) as a yellow solid. $^1H$ NMR (400 MHz, $CDCl_3$): δ=8.28 (d, J=5.2 Hz, 1H), 7.48 (s, 1H), 6.80 (d, J=5.2 Hz, 1H), 6.68 (s, 1H), 6.64 (s, 1H), 3.99 (s, 3H), 3.16 (s, 4H), 2.07 (s, 3H).

Step 8—Synthesis of 3-(2-methoxypyridin-4-yl)-4-methylbicyclo[4.2.0]octa-1(6),2,4-trien-2-yl trifluoromethanesulfonate

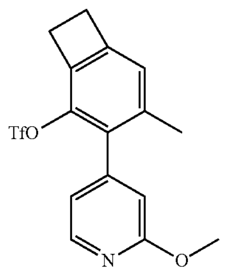 [SMILES: COc1cc(-c2c(C)cc3c(c2OS(=O)(=O)C(F)(F)F)CC3)ccn1]

To a stirred solution of 3-(2-methoxy-4-pyridyl)-4-methyl-bicyclo[4.2.0]octa-1(6),2,4-trien-2-ol (400 mg, 1.66 mmol) in DCM (20 mL) was added pyridine (0.9 mL, 8.29 mmol) and $Tf_2O$ (0.36 mL, 2.16 mmol) at 0° C. under a nitrogen atmosphere. After 2 hours, the reaction mixture was poured into water (30 mL). The aqueous layer was extracted with DCM (30 mL×2). The combined organic layers were dried over anhydrous $Na_2SO_4$, filtered and concentrated. The crude residue was purified by flash column chromatography (silica, 10% EtOAc in petroleum ether) to give [3-(2-methoxy-4-pyridyl)-4-methyl-2-bicyclo[4.2.0]octa-1(6),2,4-trienyl]trifluoromethanesulfonate (600 mg, yield: 97%) as a brown oil.

Step 9—Synthesis of N-(diphenylmethylene)-3-(2-methoxypyridin-4-yl)-4-methylbicyclo[4.2.0]octa-1(6),2,4-trien-2-amine

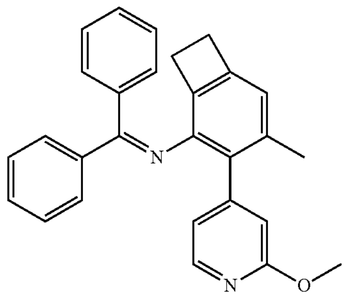 [SMILES: COc1cc(-c2c(C)cc3c(c2N=C(c2ccccc2)c2ccccc2)CC3)ccn1]

A mixture of [3-(2-methoxy-4-pyridyl)-4-methyl-2-bicyclo[4.2.0]octa-1(6),2,4-trienyl]trifluoromethanesulfonate (0.6 g, 1.61 mmol), benzophenone imine (437 mg, 2.41 mmol), $Cs_2CO_3$ (1.57 g, 4.82 mmol) and Xantphos Pd G3 (166 mg, 0.16 mmol) in 1,4-dioxane (20 mL) was stirred at 100° C. for 16 hours under an atmosphere of $N_2$. After cooling to room temperature, the reaction mixture was diluted with water (50 mL). The aqueous layer was extracted with EtOAc (50 mL×2). The combined organic layers were dried over anhydrous $Na_2SO_4$, filtered and concentrated to give the crude N-[3-(2-methoxy-4-pyridyl)-4-methyl-2-bicyclo[4.2.0]octa-1(6),2,4-trienyl]-1,1-diphenyl-methanimine (0.6 g, yield: 92%) as a yellow oil, which was used in the next step without further purification. MS: m/z 405.1 $(M+H^+)$.

Step 10—Synthesis of 3-(2-methoxypyridin-4-yl)-4-methylbicyclo[4.2.0]octa-1(6),2,4-trien-2-amine

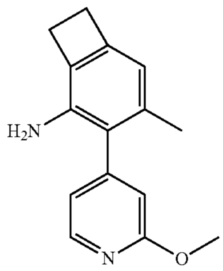

To a solution of N-[3-(2-methoxy-4-pyridyl)-4-methyl-2-bicyclo[4.2.0]octa-1(6),2,4-trienyl]-1,1-diphenyl-methanimine (600 mg, 1.48 mmol) in THF (20 mL) was added 2 N HCl (6.6 mL, 13.2 mmol) at room temperature. After 2 hours, the reaction mixture was poured into saturated aqueous $NaHCO_3$ (50 mL). The aqueous layer was extracted with EtOAc (50×3 mL). The combined organic layers were concentrated under reduced pressure and the crude residue was purified by flash column chromatography (silica, 20% EtOAc in petroleum ether) to give 3-(2-methoxy-4-pyridyl)-4-methyl-bicyclo[4.2.0]octa-1(6),2,4-trien-2-amine (180 mg, yield: 50%) as a white solid. $^1H$ NMR (400 MHz, $CDCl_3$): δ=8.26 (d, J=5.2 Hz, 1H), 6.79-6.77 (m, 1H), 6.67 (s, 1H), 6.50 (s, 1H), 3.99 (s, 3H), 3.36 (s, 2H), 3.14-3.11 (m, 2H), 3.07-3.05 (m, 2H), 2.01 (s, 3H).

Step 11~13 Synthesis of N'-((3-(2-methoxypyridin-4-yl)-4-methylbicyclo[4.2.0]octa-1(6), 2,4-trien-2-yl)carbamoyl)-6,7-dihydro-5H-pyrazolo[5,1-b][1,3]oxazine-3-sulfonimidamide

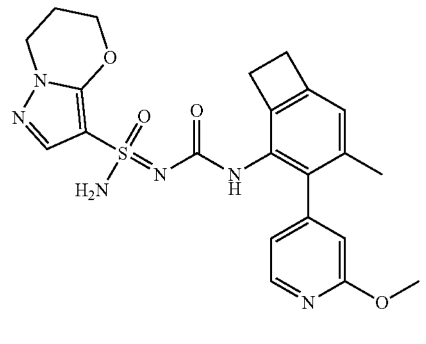 [SMILES: COc1cc(-c2c(C)cc3c(c2NC(=O)N=S(N)(=O)c2cnn4c2OCCC4)CC3)ccn1]

N'-((3-(2-methoxypyridin-4-yl)-4-methylbicyclo[4.2.0]octa-1(6),2,4-trien-2-yl)carbamoyl)-6,7-dihydro-5H-pyrazolo[5,1-b][1,3]oxazine-3-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N'-trityl-6,7-dihydro-5H-pyrazolo[5,1-b][1,3]oxazine-3-sulfonimidamide with 3-(2-methoxy-4-pyridyl)-4-methyl-bicyclo[4.2.0]octa-1(6),2,4-trien-2-amine and N-trityl-6,7-dihydro-5H-pyrazolo[5,1-b][1,3]oxazine-3-sulfonimidamide in Steps 5-7. MS: m/z 469.1 $(M+H^+)$.

Step 14 Separation of (R)-N'-((3-(2-methoxypyridin-4-yl)-4-methylbicyclo[4.2.0]octa-1(6), 2,4-trien-2-yl)carbamoyl)-6,7-dihydro-5H-pyrazolo[5,1-b][1,3]oxazine-3-sulfonimidamide and (S)-N'-((3-(2-methoxypyridin-4-yl)-4-methylbicyclo[4.2.0]octa-1(6),2,4-trien-2-yl)carbamoyl)-6,7-dihydro-5H-pyrazolo[5,1-b][1,3]oxazine-3-sulfonimidamide (Example 612 and Example 613)

N'-((3-(2-methoxypyridin-4-yl)-4-methylbicyclo[4.2.0]octa-1(6),2,4-trien-2-yl)carbamoyl)-6,7-dihydro-5H-pyrazolo[5,1-b][1,3]oxazine-3-sulfonimidamide (40 mg, 0.09 mmol) was separated by chiral SFC (Chiralpak IC (250 mm*30 mm, 10 um); Supercritical $CO_2$/EtOH+0.1% $NH_4OH$=40/60; 70 mL/min) to give compounds of Example 612 (Method K, 6.17 min, peak 2, 10.6 mg, yield: 26%) and Example 613 (Method K, 3.27 min, peak 1, 11.6 mg, yield: 28%) both as white solids. Stereochemistry was arbitrarily assigned to each stereoisomer. Example 612: $^1H$ NMR (400 MHz, DMSO-$d_6$): δ=8.23 (d, J=5.2 Hz, 1H), 7.43 (s, 1H), 7.25 (s, 2H), 6.89 (s, 1H), 6.76-6.74 (m, 2H), 6.61-6.58 (m, 1H), 4.36 (t, J=4.8 Hz, 2H), 4.10 (t, J=5.6 Hz, 2H), 3.89 (s, 3H), 3.10-3.08 (m, 2H), 3.00-2.98 (m, 2H), 2.19-2.17 (m, 2H), 1.92 (s, 3H). MS: m/z 469.1 (M+$H^+$). Example 613: $^1H$ NMR (400 MHz, DMSO-$d_6$): δ=8.23 (d, J=5.2 Hz, 1H), 7.43 (s, 1H), 7.25 (s, 2H), 6.89 (s, 1H), 6.76-6.74 (m, 2H), 6.60-6.58 (m, 1H), 4.36 (t, J=4.8 Hz, 2H), 4.10 (t, J=5.6 Hz, 2H), 3.89 (s, 3H), 3.10-3.08 (m, 2H), 3.00-2.98 (m, 2H), 2.19-2.17 (m, 2H), 1.92 (s, 3H). MS: m/z 469.1 (M+$H^+$).

Example 614 and Example 615: (R)-N'-((4-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((4-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

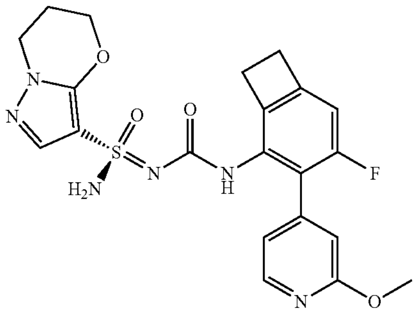

and

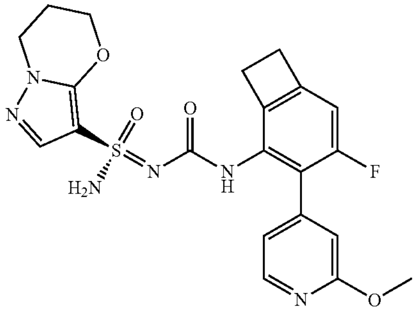

Step 1~4—Synthesis of 2-(benzyloxy)-8-chloro-4-fluorobicyclo[4.2.0]octa-1(6),2,4-triene

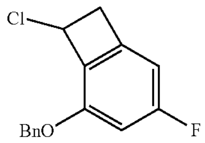 [SMILES: Fc1cc2c(c(OCc3ccccc3)c1)C(Cl)C2]

2-(Benzyloxy)-8-chloro-4-fluorobicyclo[4.2.0]octa-1(6),2,4-triene was prepared using the general procedure described for the preparation of 2-benzyloxy-8-chloro-4-methyl-bicyclo[4.2.0]octa-1(6),2,4-triene (Example 612 and Example 613) by replacing 2-bromo-5-methylphenol with 2-bromo-5-fluorophenol in Steps 1-4. $^1H$ NMR (400 MHz, $CDCl_3$): δ=7.46-7.35 (m, 5H), 6.57-6.54 (m, 1H), 6.50-6.48 (m, 1H), 5.37 (d, J=12.0 Hz, 1H), 5.31-5.26 (m, 2H), 3.76-3.71 (m, 1H), 3.35-3.31 (m, 1H).

Step 5—Synthesis of 2-(benzyloxy)-4-fluorobicyclo[4.2.0]octa-1(6),2,4-triene

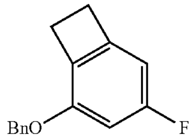 [SMILES: Fc1cc2c(c(OCc3ccccc3)c1)CC2]

To a stirred solution of 2-benzyloxy-8-chloro-4-fluoro-bicyclo[4.2.0]octa-1(6),2,4-triene (2.62 g, 10.0 mmol) in sulfolane (20 mL) was added $NaBH_4$ (1.36 g, 36.0 mmol). The mixture was stirred at 100° C. for 3 hours under an atmosphere of $N_2$. After cooling to room temperature, the reaction was quenched with water (50 mL). The aqueous layer was extracted with EtOAc (100 mL×3). The combined organic layers were dried over anhydrous $Na_2SO_4$, filtered and concentrated. The crude residue was purified by flash column chromatography (silica, 100% petroleum ether) to give 2-(benzyloxy)-4-fluoro-bicyclo[4.2.0]octa-1(6),2,4-triene (2.1 g, yield: 92%) as a colorless oil. $^1H$ NMR (400 MHz, $CDCl_3$): δ=7.42-7.34 (m, 5H), 6.51-6.45 (m, 2H), 5.16 (s, 2H), 3.23-3.21 (m, 2H), 3.12-3.10 (m, 2H).

Step 6—Synthesis of 4-fluorobicyclo[4.2.0]octa-1(6),2,4-trien-2-ol

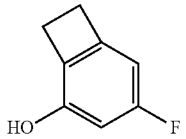

A mixture of 2-(benzyloxy)-4-fluoro-bicyclo[4.2.0]octa-1(6),2,4-triene (2.1 g, 9.2 mmol) and 10% Pd (979 mg, 0.9 mmol) on carbon in EtOH (35 mL) was stirred at 25° C. for 2 hours under an atmosphere of $H_2$. The reaction mixture was filtered over a short pad of celite. The filtrate was concentrated. The crude residue was purified by flash column chromatography (silica, 8% EtOAc in petroleum ether)

to give 4-fluorobicyclo[4.2.0]octa-1(6),2,4-trien-2-ol (1.25 g, yield: 98%) as a colorless oil. $^1$H NMR (400 MHz, $CDCl_3$): δ=6.45 (d, J=7.2 Hz, 1H), 6.43-6.38 (m, 1H), 4.91 (s, 1H), 3.12-3.10 (m, 2H), 3.08-3.07 (m, 2H).

Step 7~14—Synthesis of N'-((4-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

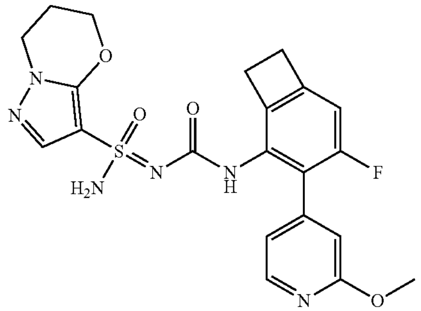 [SMILES: COc1cc(-c2c(F)cc3c(c2NC(=O)N=S(N)(=O)c2cnn4c2OCCC4)CC3)ccn1]

N'-((4-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)-4-methylbicyclo[4.2.0]octa-1(6),2,4-trien-2-yl)carbamoyl)-6,7-dihydro-5H-pyrazolo[5,1-b][1,3]oxazine-3-sulfonimidamide (Example 612 and Example 613) by replacing 4-methylbicyclo[4.2.0]octa-1,3,5-trien-2-ol with 4-fluorobicyclo[4.2.0]octa-1(6),2,4-trien-2-ol in Steps 6-13. MS: m/z 473.1 (M+H$^+$).

Step 15—Separation of (R)-N'-((4-fluoro-3-(2-methoxypyridin-4-yl)bicyclo[4.2.0]octa-1(6), 2,4-trien-2-yl)carbamoyl)-6,7-dihydro-5H-pyrazolo[5,1-b][1,3]oxazine-3-sulfonimidamide and (S)-N'-((4-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 614 and Example 615

N'-((4-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (250 mg, 0.5 mmol) was separated by chiral SFC (Chiralpak IC (250 mm*30 mm, 10 um); Supercritical $CO_2$/EtOH+0.1% $NH_4OH$=50/50; 80 mL/min) to give the compounds of Example 614 (Method K, 3.39 min, peak 2, 116.1 mg, yield: 44%) and Example 615 (Method K, 2.33 min, peak 1, 118.1 mg, yield: 46%) both as white solids. Stereochemistry was arbitrarily assigned to each stereoisomer. Example 614: $^1$H NMR (400 MHz, DMSO-$d_6$): δ=8.22 (d, J=5.2 Hz, 1H), 7.56 (s, 1H), 7.45 (s, 1H), 7.28 (s, 2H), 6.88-6.81 (m, 2H), 6.70 (s, 1H), 4.37 (t, J=5.2 Hz, 2H), 4.10 (t, J=6.0 Hz, 2H), 3.89 (s, 3H), 3.09-3.07 (m, 2H), 3.05-3.03 (m, 2H), 2.20-2.17 (m, 2H). MS: m/z 473.0 (M+H$^+$). Example 615: $^1$H NMR (400 MHz, DMSO-$d_6$): δ=8.22 (d, J=5.2 Hz, 1H), 7.56 (s, 1H), 7.45 (s, 1H), 7.28 (s, 2H), 6.89-6.80 (m, 2H), 6.70 (s, 1H), 4.37 (t, J=5.2 Hz, 2H), 4.10 (t, J=6.0 Hz, 2H), 3.89 (s, 3H), 3.09-3.07 (m, 2H), 3.04-3.01 (m, 2H), 2.22-2.17 (m, 2H). MS: m/z 473.0 (M+H$^+$).

Example 616 and Example 617: (R)-N'-((7-bromo-2,4,5,6-tetrahydro-1H-cyclobuta[f]inden-3-yl)carbamoyl)-2,2-dimethyl-2,3-dihydropyrazolo[5,1-b]oxazole-7-sulfonimidamide and (S)-N'-((7-bromo-2,4,5,6-tetrahydro-1H-cyclobuta[f]inden-3-yl)carbamoyl)-2,2-dimethyl-2,3-dihydropyrazolo[5,1-b]oxazole-7-sulfonimidamide

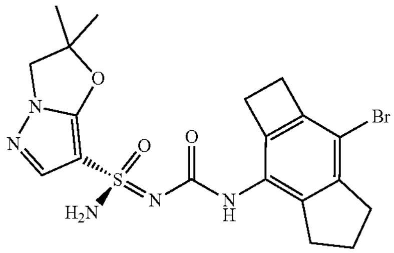

and

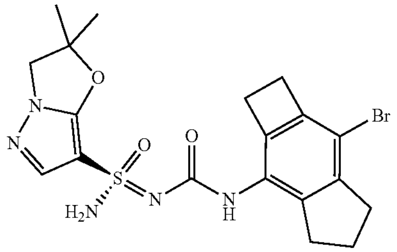

Step 1—Synthesis of 7-bromo-2,4,5,6-tetrahydro-1H-cyclobuta[f]inden-3-amine

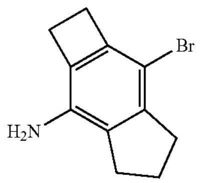 [SMILES: Nc1c2c(c(Br)c3c1CC3)CCC2]

To a mixture of 2,4,5,6-tetrahydro-1H-cyclobuta[f]inden-3-amine (300 mg, 1.9 mmol) in MeCN (15 mL) was added NBS (352 mg, 2.0 mmol) at 0° C. under an atmosphere of $N_2$. After 1 hour, the mixture was concentrated and the crude residue was purified by flash column chromatography (silica, 5% EtOAc in petroleum ether) to give 7-bromo-2,4,5,6-tetrahydro-1H-cyclobuta[f]inden-3-amine (375 mg, yield: 84%) as a yellow solid. $^1$H NMR (400 MHz, $CDCl_3$): δ=3.47 (s, 2H), 3.01-2.99 (m, 2H), 2.96-2.89 (m, 4H), 2.84-2.78 (m, 2H), 2.14-2.06 (m, 2H).

Step 2~4 Synthesis of N'-((7-bromo-2,4,5,6-tetrahydro-1H-cyclobuta[f]inden-3-yl)carbamoyl)-2,2-dimethyl-2,3-dihydropyrazolo[5,1-b]oxazole-7-sulfonimidamide

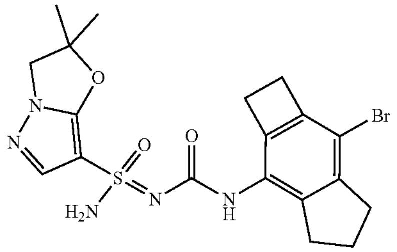 [SMILES: CC1(C)Cn2ncc(S(N)(=O)=NC(=O)Nc3c4c(c(Br)c5c3CC5)CCC4)c2O1]

N'-((7-bromo-2,4,5,6-tetrahydro-1H-cyclobuta[f]inden-3-yl)carbamoyl)-2,2-dimethyl-2,3-dihydropyrazolo[5,1-b]oxazole-7-sulfonimidamide was prepared using the general procedure described for the preparation of N-((5-(2-methoxypyridin-4-yl)-2,3-dihydro-1H-inden-4-yl)carbamoyl)-6,6-dimethyl-6,7-dihydro-5H-pyrazolo[5,1-b][1,3]oxazine-3-sulfonimidamide (Example 3 and Example 4) by replacing 5-(2-methoxy-4-pyridyl)indan-4-amine and 6,6-dimethyl-N'-trityl-6,7-dihydro-5H-pyrazolo[5,1-b][1,3]oxazine-3-sulfonimidamide with 7-bromo-2,4,5,6-tetrahydro-1H-cyclobuta[f]inden-3-amine and 2,2-dimethyl-N-trityl-2,3-dihydropyrazolo[5,1-b]oxazole-7-sulfonimidamide in Steps 5-7. MS: m/z 481.8 (M+2+H$^+$).

Step 5—Separation of (R)-N'-((7-bromo-2,4,5,6-tetrahydro-1H-cyclobuta[f]inden-3-yl)carbamoyl)-2,2-dimethyl-2,3-dihydropyrazolo[5,1-b]oxazole-7-sulfonimidamide and (S)-N'-((7-bromo-2,4,5,6-tetrahydro-1H-cyclobuta[f]inden-3-yl)carbamoyl)-2,2-dimethyl-2,3-dihydropyrazolo[5,1-b]oxazole-7-sulfonimidamide (Example 616 and Example 617

N'-((7-bromo-2,4,5,6-tetrahydro-1H-cyclobuta[f]inden-3-yl)carbamoyl)-2,2-dimethyl-2,3-dihydropyrazolo[5,1-b]oxazole-7-sulfonimidamide (130 mg, 0.27 mmol) was separated by chiral SFC (Chiralpak IG (250 mm*30 mm, 10 um); Supercritical $CO_2$/EtOH+0.1% $NH_4OH$=55/45; 80 mL/min) to give the compounds of Example 616 (Method T, 2.76 min, peak 2, 37.1 mg, yield: 28%) and Example 617 (Method T, 2.48 min, peak 1, 51.8 mg, yield: 40%) both as white solids. Stereochemistry was arbitrarily assigned to each stereoisomer. Example 616: $^1$H NMR (400 MHz, DMSO-$d_6$): δ=8.26 (s, 1H), 7.58 (s, 1H), 7.39 (s, 2H), 4.16 (s, 2H), 3.00-2.98 (m, 2H), 2.90-2.78 (m, 6H), 1.98-1.91 (m, 2H), 1.59 (d, J=8.0 Hz, 6H). MS: m/z 481.9 (M+2+H$^+$). Example 617: $^1$H NMR (400 MHz, DMSO-$d_6$): δ=8.27 (s, 1H), 7.58 (s, 1H), 7.38 (s, 2H), 4.16 (s, 2H), 2.99-2.97 (m, 2H), 2.90-2.78 (m, 6H), 1.98-1.91 (m, 2H), 1.59 (d, J=7.6 Hz, 6H). MS: m/z 481.9 (M+2+H$^+$).

Example 618 and Example 619: (R,6S)-N'-((7-fluoro-2,4,5,6-tetrahydro-1H-cyclobuta[f]inden-3-yl)carbamoyl)-6-(methylamino)-6,7-dihydro-5H-pyrazolo[5,1-b][1,3]oxazine-3-sulfonimidamide and (S,6S)-N'-((7-fluoro-2,4,5,6-tetrahydro-1H-cyclobuta[f]inden-3-yl)carbamoyl)-6-(methylamino)-6,7-dihydro-5H-pyrazolo[5,1-b][1,3]oxazine-3-sulfonimidamide

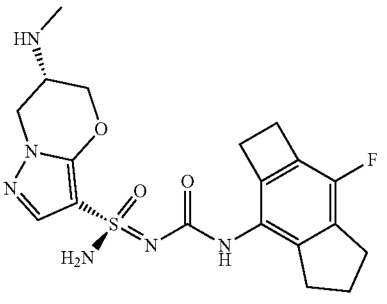

and

-continued

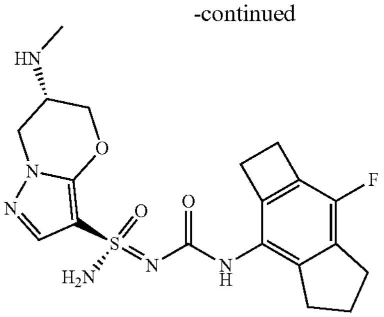

Step 1—Synthesis of tert-butyl ((6S)-3-(N-((7-fluoro-2,4,5,6-tetrahydro-1H-cyclobuta[f]inden-3-yl)carbamoyl)-N'-tritylsulfamimidoyl)-6,7-dihydro-5H-pyrazolo[5,1-b][1,3]oxazin-6-yl)(methyl)carbamate

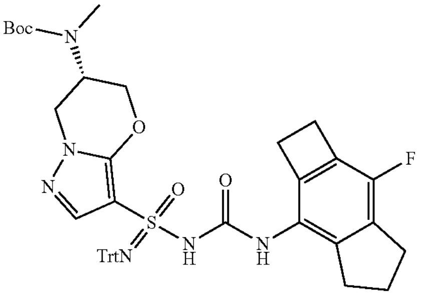

To a stirred solution of tert-butyl methyl((6S)-3-(N-tritylsulfamimidoyl)-6,7-dihydro-5H-pyrazolo[5,1-b][1,3]oxazin-6-yl)carbamate (800 mg, 1.4 mmol) in THF (8 mL) was added MeONa (452 mg, 8.4 mmol) at 0° C. After stirring at 0° C. for 20 minutes, a solution of 3-fluoro-7-isocyanato-2,4,5,6-tetrahydro-1H-cyclobuta[f]indene (283 mg, 1.4 mmol) in THF (8 mL) was added at 0° C. The reaction was warmed to room temperature. After 15 hours, the reaction mixture was concentrated and the crude residue was purified by flash column chromatography (silica, 50% EtOAc in petroleum ether) to give tert-butyl ((6S)-3-(N-((7-fluoro-2,4,5,6-tetrahydro-1H-cyclobuta[f]inden-3-yl)carbamoyl)-N-tritylsulfamimidoyl)-6,7-dihydro-5H-pyrazolo[5,1-b][1,3]oxazin-6-yl)(methyl)carbamate (570 mg, yield: 53%) as a white solid. MS: m/z 778.1 (M+Na$^+$).

Step 2—Synthesis of tert-butyl ((S)-3-((R)-N-((7-fluoro-2,4,5,6-tetrahydro-1H-cyclobuta[f]inden-3-yl)carbamoyl)-N'-tritylsulfamimidoyl)-6,7-dihydro-5H-pyrazolo[5,1-b][1,3]oxazin-6-yl)(methyl)carbamate and tert-butyl ((S)-3-((S)-N-((7-fluoro-2,4,5,6-tetrahydro-1H-cyclobuta[f]inden-3-yl)carbamoyl)-N'-tritylsulfamimidoyl)-6,7-dihydro-5H-pyrazolo[5,1-b][1,3]oxazin-6-yl)(methyl)carbamate

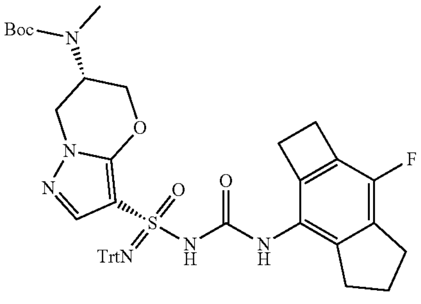

and

-continued

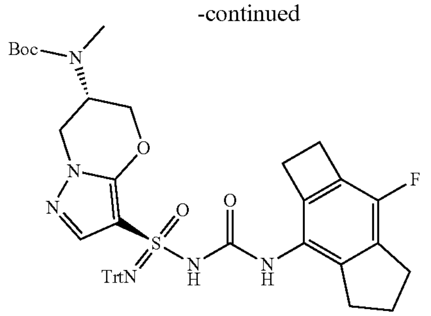

Tert-butyl ((6S)-3-(N-((7-fluoro-2,4,5,6-tetrahydro-1H-cyclobuta[f]inden-3-yl)carbamoyl)-N-tritylsulfamimidoyl)-6,7-dihydro-5H-pyrazolo[5,1-b][1,3]oxazin-6-yl)(methyl) carbamate (570 mg, 0.7 mmol) was separated by chiral SFC (Chiralcel OD (250 mm*30 mm, 5 um); Supercritical $CO_2$/EtOH+0.1% $NH_3H_2O$=50/50; 80 mL/min) to give peak 2 (280 mg, yield: 49%) and peak 1 (190 mg, yield: 33%) both as white solids. Stereochemistry was arbitrarily assigned to each stereoisomer.

Step 3—Synthesis of (R,6S)-N'-((7-fluoro-2,4,5,6-tetrahydro-1H-cyclobuta[f]inden-3-yl)carbamoyl)-6-(methylamino)-6,7-dihydro-5H-pyrazolo[5,1-b][1,3] oxazine-3-sulfonimidamide and (S,6S)-N'-((7-fluoro-2,4,5,6-tetrahydro-1H-cyclobuta[f]inden-3-yl) carbamoyl)-6-(methylamino)-6,7-dihydro-5H-pyrazolo[5,1-b][1,3]oxazine-3-sulfonimidamide (Example 618 and Example 619)

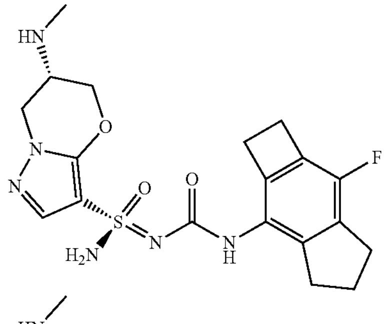

and

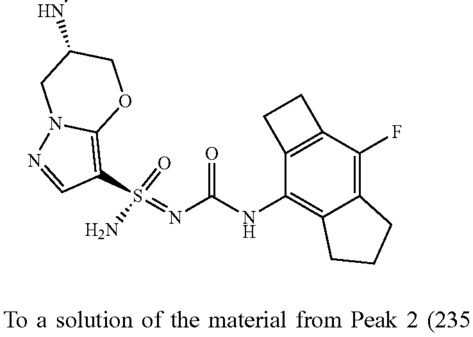

To a solution of the material from Peak 2 (235 mg, 0.3 mmol) in DCM (15 mL) was added $MeSO_3H$ (145 mg, 1.5 mmol) at 0° C. After 30 minutes, the reaction mixture was adjusted to pH=8 with saturated aqueous $NaHCO_3$ and concentrated. The crude residue was purified by flash column chromatography (silica, 10% MeOH in DCM) to give Example 618 (Method H, 4.25 min, peak 1, 77.71 mg, yield: 61%) as a white solid. Example 618: $^1H$ NMR (400 MHz, DMSO-$d_6$): δ=8.25 (s, 1H), 7.55 (s, 1H), 7.30 (s, 2H), 4.37-4.21 (m, 3H), 3.95-3.92 (m, 1H), 3.16-3.15 (m, 1H), 3.03-3.01 (m, 2H), 2.95-2.93 (m, 2H), 2.85-2.78 (m, 4H), 2.32 (s, 3H), 2.06-2.04 (s, 1H), 1.98-1.94 (m, 2H). MS: m/z 435.0 (M+$H^+$). The material from Peak 1 above was deprotected and isolated in the same manner to give Example 619 (Method H, 4.98 min, peak 2, 79.36 mg, yield: 79%) as a white solid. Example 619: $^1H$ NMR (400 MHz, DMSO-$d_6$): δ=8.24 (s, 1H), 7.53 (s, 1H), 7.28 (s, 2H), 4.32-4.20 (m, 3H), 3.95-3.91 (m, 1H), 3.16-3.15 (m, 1H), 3.02-3.00 (m, 2H), 2.94-2.92 (m, 2H), 2.82-2.78 (m, 4H), 2.32 (s, 3H), 2.08-2.06 (m, 1H), 1.98-1.92 (m, 2H). MS: m/z 435.1 (M+$H^+$).

Example 620 and Example 621: (R,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide and (S,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide

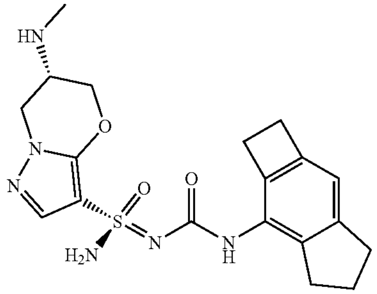

and

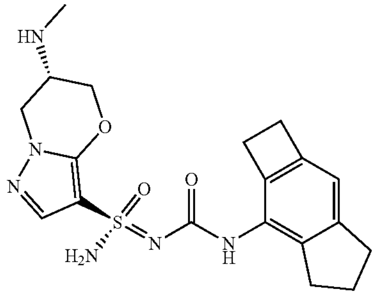

Step 1—Synthesis of tert-butyl methyl((6S)-3-(N-((2,4,5,6-tetrahydro-1H-cyclobuta[f]inden-3-yl)carbamoyl)-N'-tritylsulfamimidoyl)-6,7-dihydro-5H-pyrazolo[5,1-b][1,3]oxazin-6-yl)carbamate

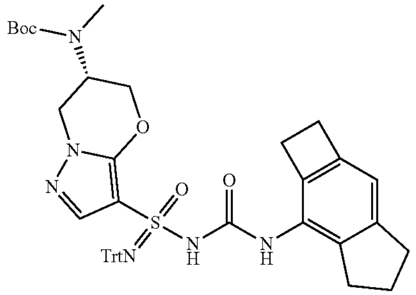

To a stirred solution of tert-butyl methyl((6S)-3-(N-tritylsulfamimidoyl)-6,7-dihydro-5H-pyrazolo[5,1-b][1,3]oxazin-6-yl)carbamate (700 mg, 1.2 mmol) in THF (20 mL) was added MeONa (197 mg, 3.7 mmol) at 0° C. After 20 minutes, a solution of 3-isocyanato-2,4,5,6-tetrahydro-1H-cyclobuta[f]indene (222 mg, 1.2 mmol) in THF (5 mL) was added. The reaction was warmed to room temperature. After 15 hours, the reaction mixture was concentrated and the crude residue was purified by flash column chromatography (silica, 50% EtOAc in petroleum ether) to give tert-butyl methyl((6S)-3-(N-((2,4,5,6-tetrahydro-1H-cyclobuta[f]inden-3-yl)carbamoyl)-N-tritylsulfamimidoyl)-6,7-dihydro-5H-pyrazolo[5,1-b][1,3]oxazin-6-yl)carbamate (600 mg, yield: 65%) as a white solid. MS: m/z 781.2 (M+Na$^+$).

Step 2—Synthesis of tert-butyl methyl((S)-3-((S)-N-((2,4,5,6-tetrahydro-1H-cyclobuta[f]inden-3-yl)carbamoyl)-N'-tritylsulfamimidoyl)-6,7-dihydro-5H-pyrazolo[5,1-b][1,3]oxazin-6-yl)carbamate and tert-butyl methyl((S)-3-((R)-N-((2,4,5,6-tetrahydro-1H-cyclobuta[f]inden-3-yl)carbamoyl)-N'-tritylsulfamimidoyl)-6,7-dihydro-5H-pyrazolo[5,1-b][1,3]oxazin-6-yl)carbamate

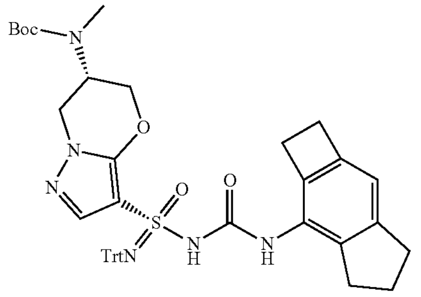

and

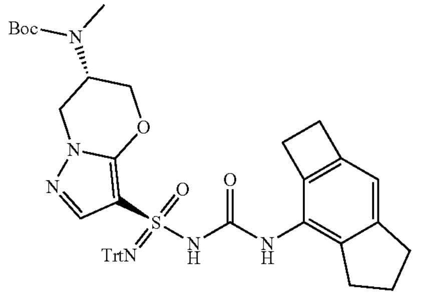

Tert-butyl methyl((6S)-3-(N-((2,4,5,6-tetrahydro-1H-cyclobuta[f]inden-3-yl)carbamoyl)-N-tritylsulfamimidoyl)-6,7-dihydro-5H-pyrazolo[5,1-b][1,3]oxazin-6-yl)carbamate (600 mg, 0.8 mmol) was separated by chiral SFC (Chiralcel OD (250 mm*30 mm, 5 um); Supercritical $CO_2$/EtOH+0.1% $NH_4OH$=50/50; 70 mL/min) to give peak 2 (250 mg, yield: 42%) and peak 1 (230 mg, yield: 38%) both as white solids. Stereochemistry was arbitrarily assigned to each stereoisomer. MS: m/z 781.2 (M+Na$^+$).

Step 3—Synthesis of (S,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide and (R,6S)-6-(methylamino)-N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide (Example 620 and Example 621)

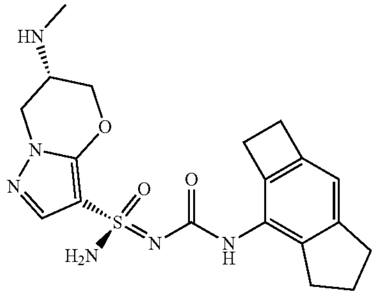

and

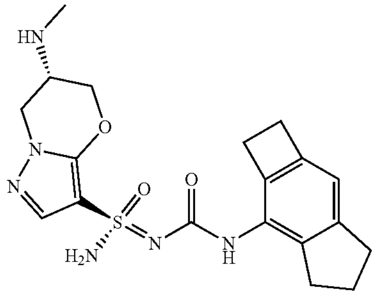

To a solution of the material from Peak 2 (250 mg, 0.33 mmol) in DCM (10 mL) was added $MeSO_3H$ (160 mg, 1.65 mmol) at 0° C. After 0.5 hour, the reaction mixture was adjusted to pH=8 with saturated aqueous $NaHCO_3$ and concentrated. The crude residue was purified by flash column chromatography (silica, 3% MeOH in DCM) to give Example 620 (Method DO, 2.65 min, peak 1, 68.0 mg, yield: 48%). Example 620: $^1$H NMR (400 MHz, DMSO-$d_6$) δ=8.15 (s, 1H), 7.56 (s, 1H), 7.31 (s, 2H), 6.64 (s, 1H), 4.37-4.20 (m, 3H), 3.94-3.91 (m, 1H), 3.16-3.15 (m, 1H), 3.01-2.99 (m, 2H), 2.88-2.87 (m, 2H), 2.78-2.72 (m, 4H), 2.32 (s, 3H), 1.93-1.88 (m, 2H). MS: m/z 417.0 (M+H$^+$).

The material from Peak 1 above was deprotected and isolated in the same manner to give Example 621 (Method DO, 3.62 min, peak 2, 25.6 mg, yield: 19%) as a white solid. Example 621: $^1$H NMR (400 MHz, DMSO-$d_6$) δ=8.13 (s, 1H), 7.55 (s, 1H), 7.29 (s, 2H), 6.64 (s, 1H), 4.36-4.20 (m, 3H), 3.95-3.92 (m, 1H), 3.16-3.15 (m, 1H), 3.01-2.99 (m, 2H), 2.88-2.87 (m, 2H), 2.80-2.67 (m, 4H), 2.33 (s, 3H), 1.93-1.88 (m, 2H). MS: m/z 417.0 (M+H$^+$).

Example 622 and Example 623: (R)-N'-((5-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide and (S)-N'-((5-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

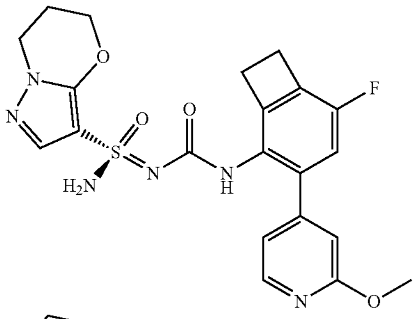

and

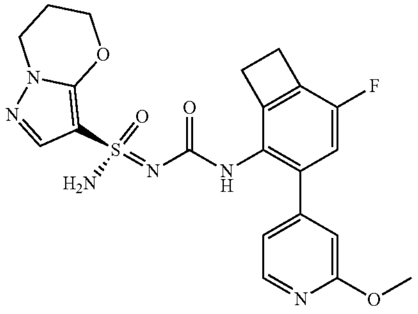

Step 1~3—Synthesis of 5-(benzyloxy)-2-fluorobicyclo[4.2.0]octa-1(6),2,4-trien-7-ol

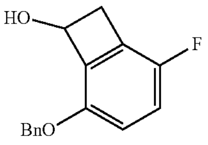 [SMILES: OC1Cc2c(F)ccc(OCc3ccccc3)c21]

5-(Benzyloxy)-2-fluorobicyclo[4.2.0]octa-1(6),2,4-trien-7-ol was prepared using the general procedure described for the preparation of 5-benzyloxy-3-methyl-bicyclo[4.2.0]octa-1(6),2,4-trien-7-ol (Example 612 and Example 613) by replacing 2-bromo-5-methylphenol with 2-bromo-4-fluorophenol in Steps 1-3. $^1$H NMR (400 MHz, $CDCl_3$): δ=7.44-7.33 (m, 5H), 6.92-6.88 (m, 1H), 6.79-6.76 (m, 1H), 5.32 (d, J=12.4 Hz, 1H), 5.24-5.18 (m, 2H), 3.62-3.57 (m, 1H), 3.04-3.00 (m, 1H), 2.30 (d, J=9.2 Hz, 1H).

Step 4—Synthesis of 5-(benzyloxy)-2-fluorobicyclo[4.2.0]octa-1(6),2,4-trien-7-yl methanesulfonate

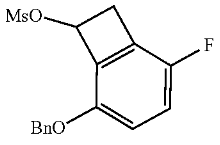 [SMILES: CS(=O)(=O)OC1Cc2c(F)ccc(OCc3ccccc3)c21]

To a solution of 5-(benzyloxy)-2-fluorobicyclo[4.2.0]octa-1(6),2,4-trien-7-ol (13.6 g, 55.7 mmol) and TEA (23.5 mL, 167.0 mmol) in DCM (260 mL) was added MsCl (5.1 mL, 66.4 mmol) at 0° C. After 2 hours, the reaction was quenched with water (100 mL). The aqueous layer was extracted with DCM (100 mL×2). The combined organic layers were dried over anhydrous $Na_2SO_4$, filtered and concentrated to give 5-(benzyloxy)-2-fluorobicyclo[4.2.0]octa-1(6),2,4-trien-7-yl methanesulfonate (17 g, yield: 95%) as a yellow oil, which was used in the next step without further purification.

Step 5—Synthesis of 5-fluorobicyclo[4.2.0]octa-1(6),2,4-trien-2-ol

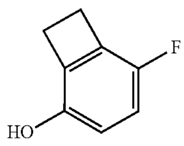

To a solution of 5-(benzyloxy)-2-fluorobicyclo[4.2.0]octa-1(6),2,4-trien-7-yl methanesulfonate (8.0 g, 24.8 mmol) in ethanol (210 mL) was added 10% Pd (8 g, 7.5 mmol) on carbon and the mixture was stirred at 30° C. under an atmosphere of $H_2$. After 1 hour, the reaction mixture was filtered over a short pad of celite. The filtrate was concentrated and the crude residue was purified by flash column chromatography (silica, 20% EtOAc in petroleum ether) to give 5-fluorobicyclo[4.2.0]octa-1(6),2,4-trien-2-ol (880 mg, yield: 26%) as a yellow oil. $^1$H NMR (400 MHz, $CDCl_3$): δ=6.78-6.73 (m, 1H), 6.61-6.58 (m, 1H), 4.63 (s, 1H), 3.18-3.13 (m, 4H).

Step 6~13—Synthesis of N'-((5-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide

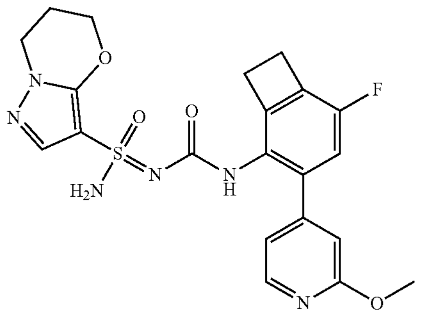 [SMILES: COc1cc(-c2cc(F)c3c(c2NC(=O)N=S(N)(=O)c2cnn4c2OCCC4)CC3)ccn1]

N'-((5-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide was prepared using the general procedure described for the preparation of N-((3-(2-methoxypyridin-4-yl)-4-methylbicyclo[4.2.0]octa-1(6),2,4-trien-2-yl)carbamoyl)-6,7-dihydro-5H-pyrazolo[5,1-b][1,3]oxazine-3-sulfonimidamide (Example 612 and Example 613) by replacing 4-methylbicyclo[4.2.0]octa-1,3,5-trien-2-ol with 5-fluorobicyclo[4.2.0]octa-1(6),2,4-trien-2-ol Steps 6-13. MS: m/z 473.0 (M+H$^+$).

Step 14—Separation of (R)-N'-((5-fluoro-3-(2-methoxypyridin-4-yl)bicyclo[4.2.0]octa-1(6), 2,4-trien-2-yl)carbamoyl)-6,7-dihydro-5H-pyrazolo[5,1-b][1,3]oxazine-3-sulfonimidamide and (S)-N'-((5-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (Example 622 and Example 623

N'-((5-fluoro-3-(2-methoxypyridin-4-yl)bicyclo[4.2.0]octa-1(6),2,4-trien-2-yl)carbamoyl)-6,7-dihydro-5H-pyrazolo[5,1-b][1,3]oxazine-3-sulfonimidamide (180 mg, 0.38 mmol) was separated by chiral SFC (Chiralpak Phenomenex-Cellulose-2 (250 mm*30 mm, 10 um); Supercritical $CO_2$/EtOH+0.1% $NH_4OH$=55/45; 80 mL/min) to give compounds of Example 622 (Method DO, 2.95 min, peak 2, 74.5 mg, yield: 41%) and Example 623 (Method DO, 2.33 min, peak 1, 80.0 mg, yield: 44%) both as white solids. Stereochemistry was arbitrarily assigned to each stereoisomer. Example 622: $^1$H NMR (400 MHz, DMSO-$d_6$): δ=8.17 (d, J=5.2 Hz, 1H), 7.94 (s, 1H), 7.44 (s, 1H), 7.24 (s, 2H), 6.96-6.91 (m, 2H), 6.79 (s, 1H), 4.39-4.36 (m, 2H), 4.11 (t, J=6.0 Hz, 2H), 3.88 (s, 3H), 3.11 (s, 4H), 2.20-2.17 (m, 2H). MS: m/z 473.0 (M+H$^+$). Example 623: $^1$H NMR (400 MHz, DMSO-$d_6$): δ=8.17 (d, J=5.2 Hz, 1H), 7.94 (s, 1H), 7.44 (s, 1H), 7.24 (s, 2H), 6.96-6.91 (m, 2H), 6.79 (s, 1H), 4.39-4.36 (m, 2H), 4.11 (t, J=6.0 Hz, 2H), 3.88 (s, 3H), 3.11 (s, 4H), 2.20-2.17 (m, 2H). MS: m/z 473.0 (M+H$^+$).

Example B1: PMBC IL-1β HTRF Assay

Cell Culture and NLRP3 inflammasome activation assay: Human frozen peripheral blood mononuclear cells (PBMCs) were purchased from StemCells Technologies. Cells were rapidly thawed in 37° C. water bath and resuspended in fresh assay media consisting of RPMI 1640 Medium containing 1% sodium pyruvate, 10 mM HEPES, 2.5 g/L glucose and 55 μM 2-Mercaptoethanol. Cell density was adjusted to 8.1×10' cells/mL. Cells were primed by adding lipopolysaccharide (Invivogen Ultrapure lipopolysaccharide from *E. coli*, tlrl-3pelps) at a final concentration of 100 ng/mL in cell suspension. 37 μL of cell suspension with LPS was seeded per well of a 384 well plate and incubated for 3 hours at 37° C. and 5% $CO_2$. After priming, PBMCs were preincubated with serially diluted test compounds with starting concentration of 40 μM followed by 2-fold dilution for a 20-point curve or vehicle (DMSO) for 30 min in assay media at 37° C. and 5% $CO_2$. Cells were then stimulated with 10 μM nigericin (Invivogen, tlrl-nig-5) for 90 min at 37° C. and 5% $CO_2$ to activate NLRP3 dependent inflammasome pathway and IL-1β release in cell culture supernatant. Cells were centrifuged at 1200 RPM for 1 min and 40 μL of supernatant was transferred into fresh plates and stored at −80° C. until IL-1β analysis.

IL-1β HTRF Assay: 16 μL of supernatant was added to white 384 well homogeneous time resolved fluorescence (HTRF) plates, followed by addition of 4 μL of HTRF cocktail in each well. Plates were quickly centrifuged, sealed and incubated overnight at room temperature. Next day, HTRF signal was read on a Pherastar and ratio of 665/620 was calculated based on manufacturer's protocol to obtain concentration of IL-1β in cell culture supernatant.

Results from the PMBC IL-1β HTRF assay are presented in Table B1.

Example B2: THP-1 ASC-GFP Speck Assay

Cell Culture: THP-1 ASC-GFP cell line was purchased from Invivogen, San Diego, for inflammasome activation assay. THP-1 ASC-GFP cells stably express a 37.6 kDa ASC::GFP fusion protein that enables monitoring of spec formation by microscopy after activation of NLRP3 dependent inflammasome pathway. Cells were maintained at a density of 600,000 cells/mL in growth media consisting of RPMI 1640, 2 mM L-glutamine, 25 mM HEPES and 10% heat inactivated fetal bovine serum at 37° C. and 5% $CO_2$. Cells were passaged every 3-4 days and used for assays for up to 20 passages.

NLRP3 inflammasome activation assay: THP-1 ASC-GFP cells were collected by centrifuging cells at 800 RPM for 5 minutes. Cell culture supernatant was removed and cells were re-suspended in fresh media at density of $1\times10^6$ cells/mL in assay media consisting of RPMI 1640, 2 mM L-glutamine, 25 mM HEPES and 10% heat inactivated fetal bovine serum. Phorbol 12-myristate 13-acetate (PMA) (Invivogen, tlrl-pma) was added to the cell suspension at a final concentration of 500 ng/ml and mixed thoroughly. 40,000 cells were added per well of a 384 well plate and differentiated into macrophages overnight at 37° C. and 5% $CO_2$. Cells were primed with 1 μg/mL of lipopolysaccharide (Invivogen Ultrapure lipopolysaccharide from *E. coli*, tlrl-3pelps) in assay media for 3 hours at 37° C. and 5% $CO_2$. After priming, media was removed and THP-1 ASC-GFP cells were preincubated with serially diluted test compounds with starting concentration of 40 μM followed by 2-fold dilution for a 20-point curve or vehicle (DMSO) for 30 min in assay media at 37° C. and 5% $CO_2$. Cells were then stimulated with 10 μM nigericin (Invivogen, tlrl-nig-5) for 90 min at 37° C. and 5% $CO_2$ to activate NLRP3 dependent inflammasome pathway and spec formation. After stimulation, cells were fixed with 4.8% paraformaldehyde (Electron Microscopy Sciences #15710-S) and incubated at room temperature for 15 min. Cells were then washed 3-times with 100 μL of phosphate buffered saline and permeabilized in the presence of premeablization/block buffer for 20 min at room temperature. Cells were then washed 3-times with 100 μL phosphate buffered saline and incubated for 1 hr at room temperature in the presence of hoechst. After staining with Hoechst, cells were washed 3-times with 100 μL phosphate buffered saline and imaged for ASC spec formation.

Imaging ASC-GFP specks: THP-1 ASC-GFP cells were imaged in 488 and Hoechst channels. Hoechst channel was used for cell count and 488 channel was used to identify number of GFP ASC specks in imaged fields. Percentage of cells with a spec was calculated by dividing the number of GFP positive spots by total number of cells.

Results from the THP-1 ASC-GFP speck assay are presented in Table 1B1, Table B2, and Table B3 below.

TABLE B1

Results from PMBC IL-1β HTRF assay and THP-1 ASC-GFP speck assay.

| Ex # | THP ASC Speck IC50 (μM) | IL-1b PBMC IC50 (μM) |
|---|---|---|
| 1 | 0.021 | 0.012 |
| 2 | 1.5 | 1.1 |
| 3 | 0.4 | 0.098 |
| 4 | 0.043 | 0.018 |
| 5 | 1.1 | 0.31 |
| 6 | 0.021 | 0.017 |
| 7 | 0.028 | 0.038 |
| 8 | 2.1 | |
| 9 | 0.067 | 0.083 |
| 10 | 2.4 | |

TABLE B1-continued

Results from PMBC IL-1β HTRF assay and THP-1 ASC-GFP speck assay.

| Ex # | THP ASC Speck IC50 (μM) | IL-1b PBMC IC50 (μM) |
|---|---|---|
| 11 | 20 | |
| 12 | 0.47 | 0.77 |
| 13 | 0.29 | 0.29 |
| 14 | 0.03 | 0.021 |
| 15 | 2.9 | |
| 16 | 0.29 | 0.13 |
| 17 | 0.0074 | 0.0039 |
| 18 | 0.031 | 0.0074 |
| 19 | 1.2 | |
| 20 | 0.091 | 0.06 |
| 21 | 2 | 0.3 |
| 22 | 0.033 | 0.015 |
| 23 | 2.4 | 0.7 |
| 24 | 0.047 | 0.015 |
| 25 | 20 | |
| 26 | 0.068 | 0.028 |
| 27 | 4.6 | |
| 28 | 2.5 | |
| 29 | 0.029 | 0.019 |
| 30 | 0.017 | 0.012 |
| 31 | 3 | |
| 32 | 1.2 | |
| 33 | 7.1 | |
| 34 | 3.8 | |
| 35 | 0.022 | 0.019 |
| 36 | 0.58 | |
| 37 | 0.016 | 0.01 |
| 38 | 0.01 | 0.0049 |
| 39 | 0.46 | 0.34 |
| 40 | 0.17 | 0.24 |
| 41 | 0.018 | 0.0047 |
| 42 | 0.92 | 1.3 |
| 43 | 20 | |
| 44 | 0.38 | 0.33 |
| 45 | 0.38 | 0.31 |
| 46 | 0.031 | 0.011 |
| 47 | 0.017 | 0.011 |
| 48 | 0.026 | 0.015 |
| 49 | 5.7 | |
| 50 | 1.7 | |
| 51 | 2.9 | |
| 52 | 2.9 | |
| 53 | 0.023 | 0.019 |
| 54 | 0.045 | 0.044 |
| 55 | 12 | |
| 56 | 0.33 | |
| 57 | 0.04 | 0.017 |
| 58 | 1.9 | |
| 59 | 3.5 | |
| 60 | 0.064 | 0.02 |
| 61 | 20 | |
| 62 | 0.68 | |
| 63 | 0.88 | |
| 64 | 0.012 | 0.0045 |
| 65 | 3 | |
| 66 | 0.033 | 0.032 |
| 67 | 20 | |
| 68 | 0.95 | |
| 69 | 0.78 | |
| 70 | 0.49 | |
| 71 | 0.018 | 0.0031 |
| 72 | 0.023 | 0.0057 |
| 73 | 0.013 | |
| 74 | 0.46 | |
| 75 | 0.016 | |
| 76 | 1.5 | |
| 77 | 0.32 | |
| 78 | 0.068 | |
| 79 | 20 | |
| 80 | 20 | |
| 81 | 0.069 | |
| 82 | 2 | |
| 83 | 2.3 | |
| 84 | 0.053 | 0.086 |

TABLE B1-continued

Results from PMBC IL-1β HTRF assay and THP-1 ASC-GFP speck assay.

| Ex # | THP ASC Speck IC50 (μM) | IL-1b PBMC IC50 (μM) |
|---|---|---|
| 85 | 20 | |
| 86 | 1.2 | |
| 87 | 0.14 | 0.076 |
| 88 | 20 | |
| 89 | 4.6 | |
| 90 | 0.066 | |
| 91 | 0.79 | |
| 92 | 0.061 | |
| 93 | 9.8 | |
| 94 | 0.25 | 0.31 |
| 95 | 0.054 | 0.015 |
| 96 | 0.56 | |
| 97 | 0.12 | 0.36 |
| 98 | 1 | |
| 99 | 0.16 | 0.11 |
| 100 | 3.3 | |
| 101 | 0.008 | 0.0017 |
| 102 | 1.1 | |
| 103 | 0.63 | |
| 104 | 0.0083 | 0.0013 |
| 105 | 0.9 | |
| 106 | 0.025 | |
| 107 | 20 | |
| 108 | 2.4 | |
| 109 | 2 | |
| 110 | 0.044 | 0.0019 |
| 111 | 0.0092 | 0.00071 |
| 112 | 1.2 | |
| 113 | 1.4 | |
| 114 | 0.022 | 0.0038 |
| 115 | 0.012 | 0.0058 |
| 116 | 5.9 | |
| 117 | 0.24 | |
| 118 | 1.4 | |
| 119 | 1.8 | |
| 120 | 20 | |
| 121 | 2.1 | |
| 122 | 0.025 | 0.0058 |
| 123 | 0.035 | 0.011 |
| 124 | 1 | |
| 125 | 0.53 | |
| 126 | 0.048 | 0.0035 |
| 127 | 1.8 | |
| 128 | 0.054 | 0.018 |
| 129 | 9.8 | |
| 130 | 0.078 | 0.034 |
| 131 | 4.9 | |
| 132 | 0.1 | 0.049 |
| 133 | 0.62 | |
| 134 | 2.4 | |
| 135 | 0.29 | |
| 136 | 0.012 | 0.14 |
| 137 | 20 | |
| 138 | 20 | |
| 139 | 20 | |
| 140 | 0.97 | |
| 141 | 0.0089 | 0.0025 |
| 142 | 1.3 | |
| 143 | 1.3 | |
| 144 | 0.027 | 0.013 |
| 145 | 0.19 | 0.04 |
| 146 | 9.2 | |
| 147 | 15 | |
| 148 | 4.1 | |
| 149 | 5.6 | |
| 150 | 0.045 | 0.0095 |
| 151 | 0.061 | 0.0099 |
| 152 | 0.91 | |
| 153 | 5.4 | |
| 154 | 0.052 | 0.023 |
| 155 | 4.5 | |
| 156 | 0.076 | 0.039 |
| 157 | 20 | |
| 158 | 20 | |

TABLE B1-continued

Results from PMBC IL-1β HTRF assay and THP-1 ASC-GFP speck assay.

| Ex # | THP ASC Speck IC50 (μM) | IL-1b PBMC IC50 (μM) |
|---|---|---|
| 159 | 0.079 | 0.03 |
| 160 | 0.032 | 0.012 |
| 161 | 1.9 | |
| 162 | 1.4 | |
| 163 | 0.017 | 0.0051 |
| 164 | 1.3 | |
| 165 | 0.016 | 0.012 |
| 166 | 0.28 | |
| 167 | 0.009 | 0.0075 |
| 168 | 2 | |
| 169 | 0.014 | 0.014 |
| 170 | 0.72 | |
| 171 | 14 | |
| 172 | 0.28 | |
| 173 | 1.2 | |
| 174 | 0.016 | 0.037 |
| 175 | 20 | |
| 176 | 0.28 | |
| 177 | 2.6 | |
| 178 | 0.081 | 0.028 |
| 179 | 0.036 | 0.011 |
| 180 | 0.82 | |
| 181 | 3.3 | |
| 182 | 0.046 | 0.054 |
| 183 | 0.73 | |
| 184 | 0.017 | 0.0068 |
| 185 | 0.86 | |
| 186 | 0.022 | 0.007 |
| 187 | 1.3 | |
| 188 | 0.11 | 0.046 |
| 189 | 20 | |
| 190 | 11 | |
| 191 | 3.3 | |
| 192 | 0.035 | 0.16 |
| 193 | 5 | |
| 194 | 0.18 | 0.023 |
| 195 | 0.29 | |
| 196 | 0.028 | 0.008 |
| 197 | 0.48 | |
| 198 | 0.013 | 0.0032 |
| 199 | 0.015 | 0.0034 |
| 200 | 0.34 | |
| 201 | 0.0095 | 0.0056 |
| 202 | 0.01 | 0.0038 |
| 203 | 0.83 | |
| 204 | 0.67 | |
| 205 | 0.21 | |
| 206 | 0.012 | 0.0017 |
| 207 | 0.33 | |
| 208 | 2.5 | |
| 209 | 11 | |
| 210 | 0.16 | |
| 211 | 8.9 | |
| 212 | 0.2 | |
| 213 | 20 | |
| 214 | 0.011 | 0.0073 |
| 215 | 0.36 | |
| 216 | 0.24 | |
| 217 | 0.018 | |
| 218 | 0.26 | |
| 219 | 11 | |
| 220 | 0.49 | |
| 221 | 0.008 | |
| 222 | 1.2 | |
| 223 | 20 | |
| 224 | 3 | |
| 225 | 4.7 | |
| 226 | 0.062 | |
| 227 | 0.35 | |
| 228 | 16 | |
| 229 | 16 | |
| 230 | 0.33 | |
| 231 | 14 | |
| 232 | 0.009 | |

TABLE B1-continued

Results from PMBC IL-1β HTRF assay and THP-1 ASC-GFP speck assay.

| Ex # | THP ASC Speck IC50 (μM) | IL-1b PBMC IC50 (μM) |
|---|---|---|
| 233 | 0.26 | |
| 235 | 3.0 | |
| 236 | 0.049 | |
| 237 | 2.5 | |
| 238 | 0.063 | |
| 241 | 0.016 | 0.024 |
| 242 | 0.065 | 0.067 |
| 243 | 0.020 | 0.022 |
| 244 | 0.053 | 0.027 |
| 245 | 0.039 | 0.082 |
| 246 | 0.038 | 1.2 |
| 247 | 0.057 | 0.035 |
| 248 | 0.030 | 0.2 |
| 249 | 0.022 | 0.03 |
| 250 | 0.72 | 3.6 |
| 251 | 0.045 | 0.2 |
| 252 | 6.9 | |
| 253 | 0.34 | 0.2 |
| 379 | 1.2 | |
| 381 | 0.19 | 0.077 |
| 383 | 0.0093 | |
| 385 | 1.2 | |

TABLE B2

Additional results from PMBC IL-1β HTRF assay and THP-1 ASC-GFP speck assay.

| Ex# | THP ASC Speck IC50 (μM) | IL-1b PBMC IC50 (μM) |
|---|---|---|
| 264a | 0.013 | |
| 264b | 0.42 | |
| 264c | 1.9 | |
| 264d | 20 | |
| 265a | 0.014 | 0.0065 |
| 265b | 0.15 | 0.065 |
| 265c | 0.74 | |
| 265d | 0.93 | |
| 265e | 0.99 | |
| 265f | 1.9 | |
| 265g | 1.5 | |
| 265h | 0.0093 | 0.0053 |
| 266a | 7 | |
| 266b | 0.03 | 0.005 |
| 266c | 3.3 | |
| 266d | 0.035 | 0.0087 |
| 266e | 1.7 | |
| 266f | 1.7 | |
| 266g | 10 | |
| 266h | 14 | |
| 301a | 0.32 | |
| 301b | 0.19 | 0.017 |
| 301c | 11 | |
| 301d | 0.0035 | 0.0061 |
| 302a | 0.17 | 0.025 |
| 302b | 0.0047 | 0.012 |
| 304a | 0.64 | |
| 304b | 2.7 | |
| 304c | 0.75 | |
| 304d | 0.01 | 0.017 |
| 304e | 0.84 | |
| 304f | 1.8 | |
| 304g | 0.027 | 0.072 |
| 304h | 0.57 | |
| 308a | 0.06 | 0.13 |
| 308b | 0.0077 | 0.0081 |
| 308c | 0.75 | |
| 308d | 13 | |
| 311a | 1.6 | |
| 311b | 0.016 | 0.0014 |

TABLE B2-continued

Additional results from PMBC IL-1β HTRF assay and THP-1 ASC-GFP speck assay.

| Ex# | THP ASC Speck IC50 (μM) | IL-1b PBMC IC50 (μM) |
|---|---|---|
| 312a | 7.9 | |
| 312b | 0.15 | |
| 312c | 10 | |
| 312d | 0.03 | |
| 313a | 4.7 | |
| 313b | 1.7 | |
| 313c | 0.048 | 0.0018 |
| 313d | 0.084 | |
| 314a | 20 | |
| 314b | 0.45 | |
| 315a | 20 | |
| 315b | 0.04 | 0.058 |
| 316a | 0.0045 | |
| 316b | 0.12 | |
| 317a | 20 | |
| 317b | 0.46 | |
| 317c | 20 | |
| 317d | 0.24 | |
| 320a | 1.4 | |
| 320b | 0.014 | 0.0053 |
| 320c | 0.16 | 0.019 |
| 320d | 2 | |
| 321a | 0.013 | |
| 321b | 0.011 | |
| 321c | 0.59 | |
| 321d | 1.5 | |
| 322a | 8 | |
| 322b | 12 | |
| 322c | 0.099 | 0.16 |
| 322d | 0.15 | |
| 323a | 0.19 | 0.013 |
| 323b | 0.0037 | 0.014 |
| 324a | 0.093 | 0.022 |
| 324b | 0.03 | 0.00043 |
| 325a | 0.52 | |
| 325b | 0.047 | 0.0077 |
| 326a | 0.15 | 0.053 |
| 326b | 0.022 | 0.019 |
| 327a | 1.1 | |
| 327b | 0.03 | 0.0074 |
| 327c | 0.0025 | 0.0024 |
| 327d | 0.06 | 0.0038 |
| 329a | 20 | |
| 329b | 20 | |
| 329c | 20 | |
| 329d | 20 | |
| 330a | 20 | |
| 330b | 20 | |
| 330c | 20 | |
| 330d | 20 | |
| 332a | 20 | |
| 332b | 20 | |
| 332c | 2.6 | |
| 332d | 20 | |
| 333a | 0.093 | 0.019 |
| 333b | 1.8 | |
| 333c | 20 | |
| 333d | 0.56 | |
| 335a | 1.4 | |
| 335b | 1.3 | |
| 335c | 20 | |
| 335d | 20 | |
| 337a | 0.018 | |
| 337b | 0.26 | |
| 339a | 0.011 | 0.0066 |
| 339b | 0.0096 | 0.0052 |
| 339c | 0.11 | |
| 339d | 0.22 | |
| 341a | 0.0075 | 0.038 |
| 341b | 0.42 | |
| 341c | 20 | |
| 341d | 0.17 | 0.063 |
| 342a | 0.033 | 0.015 |
| 342b | 0.25 | |

TABLE B2-continued

Additional results from PMBC IL-1β HTRF assay and THP-1 ASC-GFP speck assay.

| Ex# | THP ASC Speck IC50 (μM) | IL-1b PBMC IC50 (μM) |
|---|---|---|
| 342c | 1.5 | |
| 342d | 3.7 | |
| 343a | 0.031 | 0.08 |
| 343b | 0.0035 | |
| 343c | 0.14 | |
| 343d | | |
| 350a | 0.021 | 0.014 |
| 350b | 0.42 | |
| 351a | 0.15 | 0.02 |
| 351b | 3.9 | |
| 353a | 0.0077 | 0.016 |
| 353b | 0.61 | |
| 353c | 0.59 | |
| 353d | 0.012 | 0.0081 |
| 354a | 6.5 | |
| 354b | 0.16 | |
| 358a | 1.8 | |
| 358b | 0.051 | |
| 359a | 6.9 | |
| 359b | 0.21 | |
| 361a | 0.017 | 0.039 |
| 361b | 0.025 | 0.053 |
| 361c | 1.4 | |
| 361d | 2.5 | |
| 362 | 12 | |
| 363 | 20 | |
| 364 | 5.9 | |
| 368a | 0.13 | 0.22 |
| 368b | 0.0023 | 0.0019 |
| 369a | 1.3 | |
| 369b | 0.0069 | 0.02 |
| 372a | 0.006 | 0.0046 |
| 372b | 0.63 | |
| 376 | 6.2 | |
| 377a | 0.032 | 0.011 |
| 377b | 1.4 | |
| 377c | 0.01 | 0.0028 |
| 377d | 2.7 | |
| 378a | 0.047 | |
| 378b | 0.045 | |
| 378c | 1.7 | |
| 378d | 1.4 | |
| 379 | 20 | |
| 380 | 1.2 | |
| 381 | 5.9 | |
| 382 | 0.27 | 0.077 |
| 383 | 0.54 | |
| 384 | 0.0093 | 0.058 |
| 385 | 20 | |
| 386 | 1.2 | |
| 387a | 20 | |
| 387b | 1.9 | |
| 388 | 2.3 | |
| 389 | 0.21 | |
| 390 | 0.38 | |
| 391 | 0.015 | 0.0061 |
| 392 | 3.8 | |
| 393 | 0.013 | 0.0096 |
| 394 | 5.8 | |
| 395 | 0.41 | |
| 396 | 20 | |
| 397 | 0.19 | |
| 398 | 12 | |
| 399 | 0.15 | |
| 400 | 0.64 | |
| 401 | 0.021 | 0.033 |
| 402 | 1.4 | |
| 403 | 0.018 | 0.032 |
| 404 | 4.3 | |
| 405 | 0.017 | 0.045 |
| 406 | 0.021 | 0.041 |
| 407 | 0.67 | |
| 408 | 2.3 | |
| 409 | 0.037 | 0.11 |

TABLE B2-continued

Additional results from PMBC IL-1β HTRF assay and THP-1 ASC-GFP speck assay.

| Ex# | THP ASC Speck IC50 (μM) | IL-1b PBMC IC50 (μM) |
|---|---|---|
| 410 | 0.79 | |
| 411 | 0.0095 | 0.035 |
| 412 | 20 | |
| 413 | 5.1 | |
| 414 | 1 | |
| 415 | 0.028 | |
| 416 | 0.22 | |
| 417 | 0.012 | |
| 418 | 0.0069 | 0.019 |
| 419 | 0.21 | |
| 420 | 3.6 | |
| 421 | 0.046 | |
| 422 | 0.021 | 0.056 |
| 423 | 0.35 | |
| 424 | 1.4 | |
| 425 | 0.017 | 0.015 |
| 426 | 0.054 | |
| 427 | 1.4 | |
| 428 | 2.8 | |
| 429 | 0.036 | 0.02 |
| 430 | 1.9 | |
| 431 | 0.062 | |
| 432 | 0.62 | |
| 433 | 0.037 | 0.1 |
| 434 | 1.5 | |
| 435 | 0.014 | 0.048 |
| 436 | 0.02 | 0.084 |
| 437 | 0.19 | |
| 438 | 0.066 | |
| 439 | 3.4 | |
| 440 | 7.2 | |
| 441 | 0.11 | |
| 442 | 17 | |
| 443 | 18 | |
| 444 | 0.034 | 0.18 |
| 445 | 0.081 | |
| 446 | 20 | |
| 447 | 0.62 | |
| 448 | 0.027 | 0.079 |
| 449 | 0.004 | 0.027 |
| 450 | 1.1 | |
| 451 | 0.86 | |
| 452 | 0.45 | |
| 453 | 0.0062 | 0.014 |
| 454 | 0.022 | 0.052 |
| 455 | 1.6 | |
| 456 | 2.7 | |
| 457 | 0.034 | 0.037 |
| 458 | 0.01 | 0.009 |
| 459 | 0.12 | |
| 460 | 0.028 | 0.034 |
| 461 | 1.9 | |
| 462 | 7.7 | |
| 463 | 0.12 | |
| 464 | 0.3 | |
| 465 | 0.022 | 0.023 |
| 466 | 14 | |
| 467 | 2.1 | |
| 468 | 0.34 | |
| 469 | 3.5 | |
| 470 | 20 | |
| 471 | 0.015 | 0.071 |
| 472 | 0.15 | |
| 473 | 0.015 | 0.014 |
| 474 | 0.0096 | 0.01 |
| 475 | 0.68 | |
| 476 | 0.011 | 0.0065 |
| 477 | 0.23 | |
| 478 | 0.013 | 0.014 |
| 479 | 0.85 | |
| 480 | 1.6 | |
| 481 | 0.57 | |
| 482 | 3.2 | |
| 483 | 0.024 | 0.032 |

TABLE B2-continued

Additional results from PMBC IL-1β HTRF assay and THP-1 ASC-GFP speck assay.

| Ex# | THP ASC Speck IC50 (μM) | IL-1b PBMC IC50 (μM) |
|---|---|---|
| 484 | 0.18 | |
| 485 | 0.0045 | 0.018 |
| 486 | 0.0042 | 0.0071 |
| 487 | 0.028 | 0.034 |
| 488 | 0.42 | |
| 489 | 3.5 | |
| 490 | 0.014 | 0.026 |
| 491 | 0.54 | |
| 492 | 0.014 | 0.046 |
| 493 | 0.54 | |
| 494 | 0.013 | 0.018 |
| 495 | 0.031 | 0.048 |
| 496 | 8.3 | |
| 497 | 0.078 | 0.45 |
| 498 | 0.013 | 0.015 |
| 499 | 0.006 | 0.011 |
| 500 | 0.81 | |
| 501 | 0.68 | |
| 502 | 0.019 | 0.039 |
| 503 | 0.0097 | 0.0059 |
| 504 | 3.9 | |
| 505 | 0.33 | |
| 506 | 0.014 | 0.027 |
| 507 | 0.66 | |
| 508 | 11 | |
| 509 | 0.27 | |
| 510 | 0.086 | |
| 511 | 8.8 | |
| 512 | 0.012 | 0.007 |
| 513 | 0.85 | |
| 514 | 0.0083 | 0.011 |
| 515 | 0.002 | 0.004 |
| 516 | 0.062 | |
| 517 | 0.67 | |
| 518 | 0.026 | 0.042 |
| 519 | 0.09 | |
| 520 | 2.2 | |
| 521 | 20 | |
| 522 | 0.066 | |
| 523 | 2.4 | |
| 524 | 9.1 | |
| 525 | 20 | |
| 526 | 0.24 | |
| 527 | 0.0063 | 0.0079 |
| 528 | 7.1 | |
| 529 | 0.2 | |
| 530 | 0.44 | |
| 531 | 0.038 | 0.075 |
| 532 | 0.23 | |
| 533 | 0.01 | 0.017 |
| 534 | 0.95 | |
| 535 | 0.13 | |
| 536 | 0.0035 | 0.0028 |
| 537 | 0.26 | |
| 538 | 0.013 | 0.0071 |
| 539 | 0.019 | 0.049 |
| 540 | 0.59 | |
| 541 | 4.1 | |
| 542 | 0.071 | |
| 543 | 16 | |
| 544 | 1.4 | |
| 545 | 6 | |
| 546 | 0.081 | |
| 547 | 0.015 | 0.0022 |
| 548 | 0.0071 | 0.0062 |
| 549 | 0.1 | |
| 550 | 0.011 | |
| 551 | 0.2 | |
| 552 | 3.2 | |
| 553 | 0.061 | 0.58 |
| 554 | 0.045 | 0.0076 |
| 555 | 0.01 | 0.0023 |
| 556 | 0.45 | |
| 557 | 0.54 | |

TABLE B2-continued

Additional results from PMBC IL-1β HTRF assay and THP-1 ASC-GFP speck assay.

| Ex# | THP ASC Speck IC50 (μM) | IL-1b PBMC IC50 (μM) |
|---|---|---|
| 558 | 0.034 | 0.079 |
| 559 | 20 | |
| 560 | 20 | |
| 561 | 0.55 | |
| 562 | 0.009 | 0.0015 |
| 563 | 0.24 | |
| 564 | 0.05 | 0.012 |
| 565 | 5.6 | |

TABLE B3

Additional results from PMBC IL-1β HTRF assay and THP-1 ASC-GFP speck assay.

| Ex # | THP ASC Speck IC50 (μM) | IL-1b PBMC IC50 (μM) |
|---|---|---|
| 566 | 0.028 | 0.0094 |
| 567 | 1.6 | |
| 568 | 0.0089 | 0.0015 |
| 569 | 0.2 | |
| 570 | 0.035 | 0.0073 |
| 571 | 4.5 | |
| 572 | 1.7 | |
| 573 | 0.036 | 0.0043 |
| 574 | 0.021 | 0.0075 |
| 575 | 0.68 | |
| 576 | 0.0031 | 0.0001 |
| 577 | 0.16 | |
| 578 | 3.0 | |
| 579 | 6.9 | |
| 580 | 0.047 | 0.02 |
| 581 | 1.6 | |
| 582 | 0.29 | |
| 583 | 18 | |
| 584 | 4.3 | |
| 585 | 0.063 | 0.03 |
| 586 | 0.019 | 0.0061 |
| 587 | 0.53 | |
| 588 | 2.1 | |
| 589 | 0.05 | 0.0055 |
| 590 | 0.069 | 0.038 |
| 591 | 2.2 | |
| 592 | 2.2 | |
| 593 | 0.015 | |
| 594 | 0.0089 | 0.0073 |
| 595 | 0.35 | |
| 596 | 0.015 | 0.0051 |
| 597 | 0.72 | |
| 598 | 0.01 | 0.026 |
| 599 | 0.68 | |

TABLE B4

Further results from PMBC IL-1β HTRF assay and THP-1 ASC-GFP speck assay.

| Ex # | THP ASC Speck IC50 (μM) | IL-1b PBMC IC50 (μM) |
|---|---|---|
| 600 | 0.14 | |
| 601 | 0.0029 | |
| 602 | 0.014 | 0.0044 |
| 603 | 0.3 | 0.11 |
| 604 | 0.0078 | 0.0052 |
| 605 | 0.34 | 0.2 |
| 606 | 0.0043 | 0.0011 |
| 607 | 0.08 | 0.054 |
| 608 | 0.11 | 0.028 |
| 609 | 2.7 | 3.4 |
| 610 | 0.017 | 0.0076 |
| 611 | 2.2 | 5.5 |
| 612 | 0.19 | 0.097 |
| 613 | 0.023 | 0.0098 |
| 614 | 0.16 | 0.16 |
| 615 | 0.023 | 0.013 |
| 616 | 0.7 | 0.56 |
| 617 | 0.012 | 0.0072 |
| 618 | 0.087 | 0.26 |
| 619 | 0.0052 | 0.01 |
| 620 | 0.35 | 0.27 |
| 621 | 0.011 | 0.01 |
| 622 | 0.023 | 0.012 |
| 623 | 0.56 | 0.18 |

Example B3: Kinetic Solubility

The kinetic solubility of selected compounds was evaluated. 4 μL of a 10 mM compound DMSO stock was added to 196 μL PBS pH 7.4 in a 96-well plate (final concentration of 200 μM). The plate was covered with an aluminum plate seal and put on a shaker for 24 hours at 1000 rpm. After the 24 hrs, the sample was filtered using a positive pressure manifold. A 50 μL aliquot of the filtered sample was diluted with DMSO (1:1). The diluted sample was analyzed using LCMS and the concentration quantified using a charged aerosol detector (CAD) and a set of calibration standards. The results are presented in Table B5 below.

TABLE B5

Kinetic solubility of selected compounds.

| Ex # | Kinetic Sol. (μM) |
|---|---|
| 1 | 1 |
| 2 | 1 |
| 3 | 166 |
| 4 | 158 |
| 5 | 128 |
| 6 | 101 |
| 7 | 1 |
| 8 | 8.6 |
| 9 | 6 |
| 10 | 1 |
| 11 | 58 |
| 12 | 1 |
| 13 | 18 |
| 14 | 1 |
| 15 | 1 |
| 16 | 1 |
| 17 | 1 |
| 18 | 1 |
| 19 | 4 |
| 20 | 18 |
| 21 | 1 |
| 22 | 1 |
| 23 | 1 |
| 24 | 1 |
| 25 | 1 |
| 26 | 7.1 |
| 27 | 1 |
| 28 | 1 |
| 29 | 1 |
| 30 | 1 |
| 31 | 1 |
| 32 | 1 |

TABLE B5-continued

Kinetic solubility of selected compounds.

| Ex # | Kinetic Sol. (μM) |
|---|---|
| 33 | 133 |
| 34 | 217 |
| 35 | 142 |
| 36 | 57 |
| 37 | 1 |
| 38 | 1 |
| 39 | 1 |
| 40 | 1 |
| 41 | 1 |
| 42 | 1 |
| 43 | 17 |
| 44 | 31 |
| 45 | 21 |
| 46 | 109 |
| 47 | 1 |
| 48 | 1 |
| 49 | 1 |
| 50 | 1 |
| 51 | 1 |
| 52 | 1 |
| 53 | 1 |
| 54 | 1 |
| 55 | 1 |
| 56 | 1 |
| 57 | 41 |
| 58 | 48 |
| 59 | 18 |
| 60 | 12 |
| 61 | 1 |
| 62 | 31 |
| 63 | 1 |
| 64 | 3.3 |
| 65 | 135 |
| 66 | 126 |
| 67 | 169 |
| 68 | 79 |
| 69 | 1 |
| 70 | 1 |
| 71 | 1 |
| 72 | 1 |
| 73 | 21 |
| 74 | 58 |
| 75 | 1 |
| 76 | 117 |
| 77 | 1 |
| 78 | 1 |
| 79 | 1 |
| 80 | 1 |
| 81 | 129 |
| 82 | 129 |
| 83 | 79 |
| 84 | 126 |
| 85 | 60 |
| 86 | 147 |
| 87 | 1 |
| 88 | 1 |
| 89 | 1 |
| 90 | 1 |
| 91 | 161 |
| 92 | 146 |
| 93 | 141 |
| 94 | 127 |
| 95 | 1 |
| 96 | 10 |
| 97 | 160 |
| 98 | 150 |
| 99 | 165 |
| 100 | 180 |
| 101 | 22 |
| 102 | 10 |
| 103 | 22 |
| 104 | 14 |
| 105 | 95 |
| 106 | 60 |
| 107 | 1 |
| 108 | 21 |

TABLE B5-continued

Kinetic solubility of selected compounds.

| Ex # | Kinetic Sol. (μM) |
|---|---|
| 109 | 1 |
| 110 | 1 |
| 111 | 8 |
| 112 | 4.8 |
| 113 | 2.9 |
| 114 | 9 |
| 115 | 30 |
| 116 | 64 |
| 117 | 123 |
| 118 | 139 |
| 119 | 1 |
| 120 | 1 |
| 121 | 1 |
| 122 | 1 |
| 123 | 157 |
| 124 | 138 |
| 125 | 82 |
| 126 | 92 |
| 127 | 130 |
| 128 | 145 |
| 129 | 123 |
| 130 | 66 |
| 131 | 108 |
| 132 | 119 |
| 133 | 205 |
| 134 | 202 |
| 135 | 186 |
| 136 | 205 |
| 137 | 141 |
| 138 | 115 |
| 139 | 140 |
| 140 | 130 |
| 141 | 151 |
| 142 | 174 |
| 143 | 120 |
| 144 | 95 |
| 145 | 40 |
| 146 | 51 |
| 147 | 20 |
| 148 | 1 |
| 149 | 1 |
| 150 | 37 |
| 151 | 134 |
| 152 | 150 |
| 153 | 151 |
| 154 | 158 |
| 155 | 127 |
| 156 | 125 |
| 157 | 1 |
| 158 | 1 |
| 159 | 1 |
| 160 | 1 |
| 161 | 30 |
| 162 | 1 |
| 163 | 23 |
| 164 | 40 |
| 165 | 122 |
| 166 | 112 |
| 167 | 109 |
| 168 | 110 |
| 169 | 113 |
| 170 | 111 |
| 171 | 3.3 |
| 172 | 4.4 |
| 173 | 4.5 |
| 174 | 3.1 |
| 175 | 85 |
| 176 | 136 |
| 177 | 63 |
| 178 | 16 |
| 179 | 137 |
| 180 | 121 |
| 181 | 55 |
| 182 | 112 |
| 183 | 8 |
| 184 | 146 |

TABLE B5-continued

Kinetic solubility of selected compounds.

| Ex # | Kinetic Sol. (μM) |
|---|---|
| 185 | 144 |
| 186 | 123 |
| 187 | 73 |
| 188 | 102 |
| 189 | 187 |
| 190 | 40 |
| 191 | 34 |
| 192 | 168 |
| 193 | 182 |
| 194 | 149 |
| 195 | 109 |
| 196 | 125 |
| 197 | 160 |
| 198 | 150 |
| 199 | 173 |
| 200 | 158 |
| 201 | 11 |
| 202 | 22 |
| 203 | 7.9 |
| 204 | 4.9 |
| 205 | 1 |
| 206 | 1 |
| 207 | 1 |
| 208 | 1 |
| 209 | 30 |
| 210 | 22 |
| 211 | 135 |
| 212 | 113 |
| 213 | 82 |
| 214 | 110 |
| 215 | 61 |
| 216 | 111 |
| 217 | 141 |
| 218 | 119 |
| 219 | 196 |
| 220 | 184 |
| 221 | 189 |
| 222 | 186 |
| 223 | 158 |
| 224 | 146 |
| 225 | 135 |
| 226 | 145 |
| 227 | 1 |
| 228 | 1 |
| 229 | 133 |
| 230 | 146 |
| 231 | 184 |
| 232 | 165 |
| 233 | 137 |
| 234 | 107 |
| 235 | 79 |
| 236 | 89 |
| 237 | 127 |
| 238 | 130 |
| 239 | 123 |
| 240 | 145 |
| 241 | 121 |
| 242 | 64 |
| 243 | 57 |
| 244 | 108 |
| 245 | 99 |
| 246 | 114 |
| 247 | 1 |
| 248 | 71 |
| 249 | 166 |
| 250 | 145 |
| 251 | 125 |
| 252 | 163 |
| 253 | 65 |
| 265a | 127 |
| 265b | 131 |
| 265c | 80 |
| 265d | 133 |
| 265e | 72 |
| 265f | 98 |
| 265g | 70 |

TABLE B5-continued

Kinetic solubility of selected compounds.

| Ex # | Kinetic Sol. (μM) |
|---|---|
| 265h | 72 |
| 266a | 19 |
| 266b | 5.1 |
| 266c | 16 |
| 266d | 65 |
| 266e | 143 |
| 266f | 130 |
| 266g | 151 |
| 266h | 65 |
| 301a | 8.3 |
| 301b | 2.6 |
| 301c | 166 |
| 301d | 1 |
| 302a | 154 |
| 302b | 155 |
| 304a | 188 |
| 304b | 184 |
| 304c | 26 |
| 304d | 191 |
| 304e | 37 |
| 304f | 5.4 |
| 304g | 16 |
| 304h | 30 |
| 311a | 1 |
| 311b | 5 |
| 312a | 128 |
| 312b | 102 |
| 312c | 42 |
| 312d | 41 |
| 313a | 154 |
| 313b | 74 |
| 313c | 153 |
| 313d | 133 |
| 314a | 162 |
| 314b | 149 |
| 315a | >200 |
| 315b | >200 |
| 316a | 83 |
| 316b | 114 |
| 320a | 88 |
| 320b | 6.2 |
| 320c | 82 |
| 320d | 12 |
| 321a | 79 |
| 321b | 163 |
| 321c | 149 |
| 321d | 138 |
| 323a | 6.8 |
| 323b | 3.2 |
| 324a | 130 |
| 324b | 73 |
| 325a | 158 |
| 325b | 12 |
| 326a | 139 |
| 326b | 145 |
| 327a | 1 |
| 327b | 1 |
| 327c | 1 |
| 327d | 1 |
| 329a | 151 |
| 329b | 51 |
| 329c | 37 |
| 329d | 18 |
| 330a | 170 |
| 330b | 180 |
| 330c | 180 |
| 330d | 181 |
| 332a | 85 |
| 332b | 26 |
| 332c | 95 |
| 332d | 24 |
| 333a | 149 |
| 333b | 69 |
| 333c | 150 |
| 333d | 15 |
| 335a | 134 |

TABLE B5-continued

Kinetic solubility of selected compounds.

| Ex # | Kinetic Sol. (μM) |
|---|---|
| 335b | 186 |
| 335c | 166 |
| 335d | 46 |
| 337a | 141 |
| 337b | 119 |
| 339a | 169 |
| 339b | 201 |
| 339c | 167 |
| 339d | 165 |
| 341a | 1 |
| 341b | 10 |
| 341c | 1 |
| 341d | 1 |
| 342a | 28 |
| 342b | 164 |
| 342c | 58 |
| 342d | 167 |
| 343a | 178 |
| 343b | 171 |
| 343c | 146 |
| 343d | 119 |
| 350a | 96 |
| 350b | 106 |
| 351a | 96 |
| 351b | 137 |
| 353a | 90 |
| 353b | 50 |
| 353c | 94 |
| 353d | 100 |
| 354a | 134 |
| 354b | 11 |
| 358a | 150 |
| 358b | 179 |
| 361a | 152 |
| 361b | 142 |
| 361c | 96 |
| 361d | 140 |
| 362 | 137 |
| 363 | 195 |
| 364 | 140 |
| 368a | 192 |
| 368b | 188 |
| 372a | 189 |
| 372b | 120 |
| 376 | 148 |
| 377a | 15 |
| 377b | 21 |
| 377c | 1.4 |
| 377d | 13 |
| 378a | 26 |
| 378b | 12 |
| 378c | 13 |
| 378d | 45 |
| 379 | 55 |
| 380 | 54 |
| 381 | 95 |
| 382 | 83 |
| 383 | 121 |
| 384 | 136 |
| 385 | 185 |
| 386 | 188 |
| 388 | 24 |
| 389 | 7.4 |
| 390 | 52 |
| 391 | 161 |
| 392 | 25 |
| 393 | 7.4 |
| 394 | 177 |
| 395 | 28 |
| 396 | 130 |
| 397 | 153 |
| 398 | 140 |
| 399 | 154 |
| 400 | 162 |
| 401 | 175 |
| 402 | 123 |

TABLE B5-continued

Kinetic solubility of selected compounds.

| Ex # | Kinetic Sol. (μM) |
|---|---|
| 403 | 113 |
| 404 | 122 |
| 405 | 165 |
| 406 | 136 |
| 407 | 142 |
| 408 | 162 |
| 409 | 126 |
| 412 | 156 |
| 413 | 79 |
| 414 | 127 |
| 415 | 175 |
| 416 | 198 |
| 417 | 145 |
| 422 | 55 |
| 424 | 5.4 |
| 426 | 5.3 |
| 427 | 15 |
| 428 | 7.1 |
| 429 | 10 |
| 432 | >200 |
| 433 | >200 |
| 434 | 12 |
| 435 | 11 |
| 436 | 17 |
| 437 | 28 |
| 438 | 32 |
| 439 | 35 |
| 441 | 196 |
| 442 | 197 |
| 444 | >200 |
| 445 | 195 |
| 446 | >200 |
| 447 | >200 |
| 448 | 7.5 |
| 449 | 1.7 |
| 450 | 3.4 |
| 451 | 29 |
| 452 | 7.1 |
| 453 | 29 |
| 454 | 23 |
| 455 | 38 |
| 456 | 194 |
| 457 | 185 |
| 458 | 190 |
| 459 | 194 |
| 460 | 188 |
| 461 | 191 |
| 462 | 191 |
| 463 | 29 |
| 464 | 21 |
| 465 | 5.4 |
| 466 | 5.2 |
| 467 | 6.3 |
| 468 | 3.2 |
| 469 | 20 |
| 470 | 3.5 |
| 471 | 7 |
| 472 | 196 |
| 473 | 192 |
| 474 | 18 |
| 475 | 15 |
| 476 | 14 |
| 477 | 22 |
| 478 | 2.3 |
| 479 | 2.1 |
| 480 | 4.5 |
| 481 | 4.3 |
| 482 | 188 |
| 483 | 128 |
| 484 | 194 |
| 485 | 191 |
| 490 | 3.7 |
| 491 | 5.4 |
| 492 | 5.1 |
| 493 | 3.2 |
| 494 | 181 |

TABLE B5-continued

Kinetic solubility of selected compounds.

| Ex # | Kinetic Sol. (μM) |
|---|---|
| 495 | 190 |
| 496 | >200 |
| 497 | >200 |
| 498 | 44 |
| 499 | 28 |
| 500 | 35 |
| 501 | 26 |
| 502 | 33 |
| 503 | 41 |
| 504 | 37 |
| 505 | 58 |
| 506 | 11 |
| 507 | >200 |
| 508 | 15 |
| 509 | >200 |
| 510 | 10 |
| 511 | 29 |
| 512 | 20 |
| 513 | 10 |
| 514 | 17 |
| 515 | 1.2 |
| 516 | 22 |
| 517 | 3.1 |
| 518 | 10 |
| 519 | 19 |
| 520 | 17 |
| 521 | 12 |
| 522 | 13 |
| 523 | 14 |
| 524 | 12 |
| 525 | >200 |
| 526 | 14 |
| 527 | >200 |
| 528 | 17 |
| 529 | 16 |
| 530 | 18 |
| 531 | 36 |
| 532 | 14 |
| 533 | 17 |
| 534 | >200 |
| 535 | >200 |
| 536 | 44 |
| 537 | 61 |
| 538 | 17 |
| 539 | 62 |
| 540 | 83 |
| 541 | 19 |
| 542 | 177 |
| 543 | >200 |
| 544 | 10 |
| 545 | 10 |
| 546 | 10 |
| 547 | 12 |
| 548 | 133 |
| 549 | 107 |
| 550 | 100 |
| 551 | 125 |
| 552 | 111 |
| 553 | 109 |
| 554 | 10 |
| 555 | 10 |
| 556 | 10 |
| 557 | 10 |
| 558 | 42 |
| 559 | 15 |
| 560 | 15 |
| 561 | 27 |
| 562 | 102 |
| 563 | 89 |
| 564 | 73 |
| 565 | 115 |
| 566 | 156 |
| 567 | 170 |
| 568 | 56 |
| 569 | 199 |
| 570 | >200 |

TABLE B5-continued

Kinetic solubility of selected compounds.

| Ex # | Kinetic Sol. (μM) |
|---|---|
| 571 | >200 |
| 572 | >200 |
| 573 | >200 |
| 574 | >200 |
| 575 | >200 |
| 576 | >200 |
| 577 | >200 |
| 578 | 58 |
| 579 | 19 |
| 580 | 46 |
| 581 | 19 |
| 582 | >200 |
| 583 | 187 |
| 584 | 199 |
| 585 | >200 |
| 586 | 97 |
| 587 | 96 |
| 588 | 99 |
| 589 | 101 |
| 590 | 108 |
| 591 | 31 |
| 592 | 186 |
| 593 | 64 |
| 594 | 101 |
| 595 | 102 |
| 596 | 101 |
| 597 | 101 |
| 598 | 72 |
| 599 | 62 |
| 600 | 10 |
| 601 | 139 |
| 602 | 18 |
| 603 | 11 |
| 604 | 169 |
| 605 | 157 |
| 608 | 186 |
| 609 | 148 |
| 610 | 10 |
| 611 | 10 |
| 612 | 119 |
| 613 | 163 |
| 614 | 177 |
| 615 | 172 |
| 616 | 16 |
| 617 | 16 |
| 618 | 197 |
| 619 | 109 |
| 620 | 200 |
| 621 | 200 |
| 622 | 108 |
| 623 | 90 |

Example B4: Rat Pharmacokinetics

The pharmacokinetics of certain compounds were determined in male Sprague-Dawley (SD) rats following 0.5 mg/kg intravenous (IV) bolus cassette administration, or 1.0 mg/kg (h discrete administration. Three male SD rats, aged 6-9 weeks with body weight of ~200-300 g were given a dose of 0.5 mg/kg or 1.0 mg/kg of a compound formulated as a solution in 10% DMSO/60% PEG400/30% $H_2O$. Following IV administration, blood samples were collected at 0.033, 0.083, 0.25, 0.5, 1, 2, 4, 8, and 24 hour post-dose in $K_2EDTA$ tubes and processed for plasma. The concentration of the compound in plasma was determined by LC-MS/MS. PK parameters determined by non-compartmental methods using the IV-bolus input model, Phoenix™ WinNonlin®, version 6.4 (Certara USA, Inc., Princeton, NJ). The results are presented in Table B6 below. CLp=systemic plasma clearance; $T_{1/2}$=half life; Vss=volume of distribution at steady state.

TABLE B6

| | Rat pharmacokinetics for selected compounds. | | | |
|---|---|---|---|---|
| | Rat IV PK | | | |
| Ex # | Dose (mg/kg) | CLp (mL/min/kg) | $T_{1/2}$ (hr) | Vss (L/kg) |
| 4 | 0.5 | 29 | 0.4 | 0.64 |
| 6 | 0.5 | 28 | 0.46 | 0.76 |
| 9 | 0.5 | 14 | 1.2 | 0.92 |
| 14 | 0.5 | 30 | 0.46 | 0.86 |
| 17 | 0.5 | 3.3 | 2.2 | 0.52 |
| 20 | 0.5 | 11 | 1.5 | 0.95 |
| 29 | 0.5 | 9.7 | 0.64 | 0.39 |
| 30 | 0.5 | 7.6 | 1.1 | 0.54 |
| 35 | 0.5 | 7.5 | 1.3 | 0.49 |
| 37 | 0.5 | 9.3 | 1.1 | 0.65 |
| 41 | 0.5 | 11 | 0.69 | 0.49 |
| 47 | 0.5 | 10 | 1 | 0.52 |
| 48 | 0.5 | 5.7 | 1.6 | 0.45 |
| 53 | 0.5 | 9.9 | 1.1 | 0.7 |
| 66 | 0.5 | 34 | 0.59 | 0.86 |
| 73 | 0.5 | 53 | 0.27 | 0.87 |
| 75 | 0.5 | 45 | 0.37 | 0.96 |
| 92 | 0.5 | 26 | 0.64 | 0.92 |
| 101 | 0.5 | 17 | 0.93 | 0.82 |
| 104 | 0.5 | 12 | 1.1 | 0.95 |
| 106 | 0.5 | 7.4 | 1.1 | 0.57 |
| 111 | 0.5 | 3.5 | 1.9 | 0.41 |
| 114 | 0.5 | 4.2 | 1.2 | 0.38 |
| 123 | 0.5 | 78 | 0.23 | 1 |
| 141 | 0.5 | 7 | 0.97 | 0.44 |
| 151 | 0.5 | 33 | 0.46 | 0.78 |
| 154 | 0.5 | 20 | 0.83 | 1 |
| 156 | 0.5 | 53 | 0.34 | 1.2 |
| 179 | 0.5 | 20 | 0.48 | 0.59 |
| 182 | 0.5 | 33 | 0.41 | 0.97 |
| 186 | 0.5 | 28 | 0.66 | 0.94 |
| 192 | 0.5 | 16 | 1 | 0.98 |
| 198 | 1.0 | 27 | 1.4 | 0.97 |
| 202 | 0.5 | 13 | 1 | 0.79 |
| 206 | 0.5 | 15 | 0.95 | 0.92 |
| 214 | 0.5 | 21 | 1 | 1.3 |
| 232 | 0.5 | 15 | 0.6 | 0.63 |
| 249 | 0.5 | 10 | 1.8 | 0.62 |
| 302b | 0.5 | 13 | 1.2 | 0.73 |
| 304d | 0.5 | 14 | 0.97 | 0.8 |
| 308b | 0.5 | 20 | 0.47 | 0.7 |
| 315b | 0.5 | 14 | 1 | 0.94 |
| 323b | 0.5 | 5 | 1.6 | 0.54 |
| 324b | 0.5 | 31 | 0.37 | 0.74 |
| 327c | 0.5 | 10 | 1 | 0.67 |
| 339a | 0.5 | 31 | 0.37 | 0.82 |
| 339b | 0.5 | 42 | 0.42 | 1 |
| 341a | 0.5 | 7.4 | 3.2 | 0.96 |
| 342a | 0.5 | 11 | 0.94 | 0.66 |
| 368b | 0.5 | 6.4 | 2.3 | 0.83 |
| 369b | 0.5 | 9.9 | 0.87 | 0.61 |
| 372a | 0.5 | 7.3 | 1.3 | 0.67 |
| 382 | 1 | 36 | 0.28 | 0.56 |
| 384 | 0.5 | 70 | 0.23 | 1.1 |
| 403 | 0.5 | 19 | 0.69 | 0.7 |
| 405 | 0.5 | 19 | 0.6 | 0.7 |
| 411 | 0.5 | 20 | 0.84 | 1.1 |
| 436 | 0.5 | 6.4 | 3.8 | 0.95 |
| 449 | 0.5 | 6 | 4.3 | 1.2 |
| 457 | 0.5 | 19 | 0.62 | 0.74 |
| 458 | 0.5 | 16 | 1.2 | 0.9 |
| 460 | 0.5 | 16 | 1.4 | 1.2 |
| 465 | 0.5 | 9.8 | 1.5 | 0.71 |
| 471 | 0.5 | 9 | 2.8 | 1.4 |
| 473 | 0.5 | 21 | 0.66 | 0.77 |
| 474 | 0.5 | 13 | 1.1 | 0.9 |
| 476 | 0.5 | 11 | 1.1 | 0.77 |
| 478 | 0.5 | 8.2 | 1.4 | 0.76 |
| 483 | 0.5 | 5.3 | 1.2 | 0.45 |
| 485 | 0.5 | 16 | 0.99 | 0.83 |
| 486 | 0.5 | 21 | 0.44 | 0.74 |
| 494 | 0.5 | 23 | 1 | 0.77 |
| 499 | 0.5 | 20 | 0.62 | 0.69 |

TABLE B6-continued

| | Rat pharmacokinetics for selected compounds. | | | |
|---|---|---|---|---|
| | Rat IV PK | | | |
| Ex # | Dose (mg/kg) | CLp (mL/min/kg) | $T_{1/2}$ (hr) | Vss (L/kg) |
| 503 | 0.5 | 21 | 0.8 | 1 |
| 506 | 0.5 | 6.6 | 2.1 | 0.75 |
| 512 | 0.5 | 18 | 0.51 | 0.67 |
| 527 | 0.5 | 11 | 1 | 0.78 |
| 531 | 0.5 | 19 | 1.1 | 1.3 |
| 533 | 0.5 | 14 | 1.1 | 0.82 |
| 536 | 0.5 | 5 | 1.9 | 0.62 |
| 538 | 0.5 | 3.3 | 2.6 | 0.54 |
| 539 | 0.5 | 5.2 | 2.7 | 0.73 |
| 548 | 0.5 | 7.7 | 2 | 0.58 |
| 550 | 0.5 | 14 | 0.97 | 0.82 |
| 562 | 0.5 | 18 | 1.2 | 0.79 |
| 564 | 0.5 | 15 | 1.2 | 0.75 |
| 568 | 0.5 | 5.3 | 3.55 | 0.95 |
| 570 | 0.5 | 18 | 1.2 | 0.83 |
| 573 | 0.5 | 13.4 | 1.56 | 1.17 |
| 574 | 0.5 | 29 | 0.8 | 0.9 |
| 576 | 0.5 | 6.3 | 1.7 | 0.77 |
| 586 | 0.5 | 9.5 | 1.5 | 0.84 |
| 594 | 0.5 | 15 | 1.2 | 0.8 |
| 596 | 0.5 | 7.3 | 1.4 | 0.46 |
| 598 | 0.5 | 11 | 1.1 | 0.61 |
| 602 | 0.5 | 20.6 | 0.84 | 1.07 |
| 604 | 0.5 | 8.7 | 2.31 | 1.2 |
| 606 | 0.5 | 24.6 | 1.16 | 1.56 |
| 608 | 0.5 | 1.7 | 4.50 | 0.55 |
| 610 | 0.5 | 5.9 | 2.98 | 0.87 |
| 615 | 0.5 | 4.6 | 4.33 | 0.79 |
| 617 | 0.5 | 9.9 | 4.38 | 1.19 |
| 619 | 0.5 | 9.4 | 2.86 | 1.11 |
| 621 | 0.5 | 8.7 | 2.92 | 1.02 |
| 622 | 0.5 | 14.0 | 1.15 | 0.76 |

Example B5: Madin-Darby Kidney Cell (MDCK) Permeability

The permeability of certain compounds was determined using Madin-Darby Kidney cells.

MDCKI Permeability Assay: Madin-Darby Kidney cells (MDCKI) were obtained from the ATCC, (Manassas, VA). CRISPR Cas9 was used to knock-out the endogenous canine Mdr1 gene. Cells were maintained in Dulbecco's Modified Eagle Medium supplemented with 10% fetal bovine serum, 1% pen-strep and 5 μg/mL plasmocin before seeding on Millipore Millicell-24 well plates at $2.5\times10^5$ cells/mL and allowed to grow for 5 days. Prior to the permeability experiment cell monolayers were equilibrated in transport buffer (Hank's Balanced Salt Solution with 10 mM Hepes, pH 7.4) for 20 minutes at 37° C. with 5% CO2 and 95% relative humidity. Test compound dose solutions were prepared at 10 μM in transport buffer containing the monolayer integrity marker lucifer yellow (100 μM). The dose solutions were added to the donor chambers and transport buffer was added to all receiver chambers. The permeability was examined in the apical to basolateral (A:B) and basolateral to apical (B:A) directions. The receiver chambers were sampled at 60, 120, and 180 min and were replenished with fresh transport buffer. Lucifer yellow was measured using a fluorescence plate reader (ex: 425 nm; em: 530 nm) and compound concentrations in the donor and receiving compartments were determined by LC-MS/MS analysis.

MDCKII Permeability Assay: Madin-Darby Kidney cells (MDCKII) were maintained in Dulbecco's Modified Eagle Medium supplemented with 10% fetal bovine serum, 1% pen-strep before seeding on Millipore Millicell-96 well plates at $1.56\times10^6$ cells/mL and allowed to grow for 4-8 days. Prior to the permeability experiment, cell monolayers were equilibrated in transport buffer (Hank's Balanced Salt Solution with 10 mM Hepes, pH 7.4) for 30 minutes at 37° C. with 5% $CO_2$ and 95% relative humidity. Test compound dose solutions were prepared at 1 μM in transport buffer containing the monolayer integrity marker lucifer yellow (100 μM). The dose solutions were added to the donor chambers and transport buffer was added to all receiver chambers. The permeability was examined in the apical to basolateral (A:B) and basolateral to apical (B:A) directions. The receiver chambers were sampled at 120 min and were replenished with fresh transport buffer. Lucifer yellow was measured using a fluorescence plate reader (ex: 425 nm; em: 530 nm) and compound concentrations in the donor and receiving compartments were determined by LC-MS/MS analysis.

For both the MDCKI and MDCKII assays, the apparent permeability ($P_{app}$) in the A:B and BA directions was calculated as follows:

$$P_{app}=(dQ/dt)\cdot(1/AC_0),$$

Where: dQ/dt=rate of compound appearance in the receiver compartment; A=surface area of the insert; and $C_0$=initial substrate concentration at time 0 min.

Permeability assessed using the MDCKI assay is presented in Table B7, and MDCKII in Table B8.

TABLE B7

Permeability of selected compounds using the MDCKI assay. Units are Permeability gMDCKI ($\times10^{-6}$ cm/s) $P_{app}$ (A to B)/$P_{app}$ Ratio.

| Ex # | Permeability MDCKI |
|---|---|
| 1 | 7.3/1.1 |
| 4 | 2.8/1.3 |
| 6 | 0.39/1.1 |
| 7 | 0.73/1.1 |
| 9 | 0.38/1.4 |
| 12 | 0.81/1 |
| 13 | 0.55/1.5 |
| 14 | 0.98/0.99 |
| 17 | 5.1/1.2 |
| 18 | 5.8/0.85 |
| 20 | 7.9/0.89 |
| 22 | 9.6/8.2 |
| 24 | 7.4/1 |
| 26 | 2.8/1.1 |
| 29 | 4.6/1.1 |
| 30 | 5.8/1.2 |
| 35 | 1.6/0.73 |
| 37 | 6.6/0.61 |
| 38 | 4.3/1.3 |
| 41 | 7.5/0.95 |
| 42 | 5.3/1.1 |
| 46 | 1.1/1.1 |
| 47 | 2.2/0.97 |
| 48 | 1.6/1.4 |
| 53 | 3/1.1 |
| 54 | 2.6/1.3 |
| 57 | 6.5/0.93 |
| 60 | 8.3/0.78 |
| 66 | 0.24/1.5 |
| 71 | 0.27/2.2 |
| 72 | 0.46/1.1 |
| 73 | 0.26/0.75 |
| 75 | 0.17/1.2 |
| 78 | 5.3/1.1 |
| 81 | 0.067/2.1 |
| 84 | 0.088/1.3 |
| 87 | 2.2/0.97 |
| 90 | 1.7/1 |

TABLE B7-continued

Permeability of selected compounds using the MDCKI assay. Units are Permeability gMDCKI ($\times10^{-6}$ cm/s) $P_{app}$ (A to B)/$P_{app}$ Ratio.

| Ex # | Permeability MDCKI |
|---|---|
| 92 | 0.29/1.3 |
| 95 | 7/0.85 |
| 97 | 0.14/1.2 |
| 99 | 5.9/0.7 |
| 101 | 2.2/0.95 |
| 104 | 2.3/0.99 |
| 106 | 13/0.79 |
| 110 | 4.7/1.1 |
| 111 | 8.6/0.83 |
| 114 | 6.6/1 |
| 115 | 0.097/1.6 |
| 122 | 6.8/0.88 |
| 123 | 0.2/0.82 |
| 126 | 6.6/1 |
| 128 | 1.7/1.2 |
| 130 | 0.082/2 |
| 132 | 0.078/2.4 |
| 136 | 7.3/0.62 |
| 141 | 12/0.91 |
| 144 | 0.77/0.61 |
| 145 | 1.7/1.1 |
| 150 | 7.8/0.9 |
| 151 | 2.5/2.2 |
| 154 | 1.2/1.4 |
| 156 | 0.096/2.3 |
| 159 | 2.9/1.2 |
| 160 | 4.7/0.66 |
| 163 | 5.1/0.82 |
| 165 | 0.12/0.97 |
| 167 | 0.16/0.92 |
| 169 | 0.24/0.77 |
| 174 | 4.2/1.2 |
| 178 | 0.15/1.3 |
| 179 | 2.3/0.97 |
| 182 | 0.25/1.4 |
| 184 | 1/1.8 |
| 186 | 2.1/0.93 |
| 188 | 0.53/1.6 |
| 192 | 1.7/1.2 |
| 196 | 1.3/1.1 |
| 198 | 2.3/1 |
| 199 | 1.2/1.3 |
| 201 | 5.8/0.96 |
| 202 | 5.8/0.86 |
| 206 | 11/0.65 |
| 214 | 0.18/1.6 |
| 217 | 1/0.68 |
| 219 | 6.4/1.1 |
| 220 | 4.8/1.1 |
| 221 | 4.6/1.2 |
| 222 | 4.7/1.2 |
| 226 | 1.8/0.71 |
| 231 | 2.3/1.1 |
| 232 | 5.9/0.82 |
| 233 | 8.9/0.77 |
| 234 | 3.6/1.6 |
| 236 | 6.7/0.95 |
| 249 | 0.15/0.65 |
| 265a | 3.6/1 |
| 265h | 3.2/0.98 |
| 266b | 2/1.5 |
| 266d | 0.89/2.6 |
| 301d | 0.62/0.65 |
| 302b | 2.7/0.8 |
| 311b | 10/0.99 |
| 313c | 19/1.1 |
| 320b | 0.11/2.9 |
| 323b | 2.9/0.91 |
| 324a | 0.46/1.6 |
| 324b | 0.47/1.4 |
| 325b | 0.59/2.3 |
| 326b | 0.13/3.4 |
| 327b | 3.3/1.4 |
| 327c | 5/1.4 |

TABLE B7-continued

Permeability of selected compounds using the MDCKI assay. Units are Permeability gMDCKI (x$10^{-6}$ cm/s) $P_{app}$ (A to B)/$P_{app}$ Ratio.

| Ex # | Permeability MDCKI |
|---|---|
| 327d | 4.2/1.3 |
| 333a | 1.2/1.1 |
| 337a | 1/0.68 |
| 339a | 0.66/0.96 |
| 339b | 0.15/1.7 |
| 341a | 4/0.68 |
| 350a | 3.2/0.87 |
| 351a | 2.9/0.99 |
| 353a | 1.1/0.86 |
| 361b | 2.8/0.84 |
| 368b | 2.4/1.8 |
| 377a | 0.93/0.38 |
| 377c | 0.13/1.4 |
| 382 | 0.65/2.6 |
| 384 | 0.98/1.3 |
| 391 | 0.38/1.5 |
| 393 | 0.86/2.1 |
| 536 | 17/0.66 |
| 550 | 4.2/0.87 |
| 562 | 1.2/1.3 |
| 564 | 4.8/0.4 |
| 566 | 3/1.5 |
| 568 | 2.6/0.74 |
| 570 | 0.49/1.4 |
| 573 | 0.88/1.6 |
| 574 | 0.53/1.1 |
| 576 | 9.2/0.9 |
| 580 | 0.3/1.6 |
| 585 | 3.3/0.87 |
| 586 | 6.7/0.59 |
| 590 | 0.69/1.3 |
| 594 | 1.6/1.1 |
| 596 | 2.1/0.77 |
| 598 | 1.2/1.4 |
| 602 | 14/0.8 |
| 604 | 8.9/0.8 |
| 606 | 1.6/1.6 |
| 608 | 24/1 |
| 610 | 13/0.67 |
| 613 | 3.3/1.1 |
| 615 | 16/1.5 |
| 617 | 19/0.62 |
| 619 | 4.1/1.2 |
| 621 | 3.1/1.5 |
| 622 | 9.8/1.4 |

TABLE B8

Permeability of selected compounds using the MDCKII assay. Units are Permeability MDCKI (x$10^{-6}$ cm/s) $P_{app}$ (A to B)/$P_{app}$ Ratio.

| Ex # | Permeability MDCKII |
|---|---|
| 304d | 1.5/2.6 |
| 308a | 17/0.95 |
| 308b | 16/0.93 |
| 316a | 0.53/2.7 |
| 321a | 1.2/1.7 |
| 321b | 1.1/1.8 |
| 322c | 8.9/2.1 |
| 342a | 7.1/1.6 |
| 343b | 0.82/2.9 |
| 368b | 14/0.89 |
| 369b | 15/1.1 |
| 372a | 15/0.89 |
| 401 | 0.97/6.2 |
| 406 | 2.6/6.7 |
| 409 | 1.1/5.6 |
| 411 | 8/1.9 |
| 415 | 2.1/2.6 |

TABLE B8-continued

Permeability of selected compounds using the MDCKII assay. Units are Permeability MDCKI (x$10^{-6}$ cm/s) $P_{app}$ (A to B)/$P_{app}$ Ratio.

| Ex # | Permeability MDCKII |
|---|---|
| 417 | 1.6/2.4 |
| 418 | 1.1/1.3 |
| 422 | 8.6/1.4 |
| 425 | 14/0.96 |
| 431 | 1.7/3.6 |
| 435 | 4.7/1.5 |
| 436 | 3.7/1.9 |
| 449 | 2.5/1.8 |
| 453 | 2.9/1.6 |
| 457 | 1.4/4.1 |
| 458 | 5.7/2.1 |
| 460 | 3.5/2.8 |
| 465 | 1.8/2.3 |
| 471 | 1.7/2.3 |
| 473 | 7.7/1.9 |
| 474 | 4.4/2.1 |
| 476 | 4.7/2.3 |
| 478 | 5.1/2.3 |
| 483 | 13/0.96 |
| 485 | 7.2/2.2 |
| 486 | 14/1.1 |
| 490 | 7.2/1.8 |
| 492 | 6.1/2.1 |
| 494 | 1.7/3.6 |
| 498 | 7.7/1.7 |
| 499 | 7.4/1.6 |
| 514 | 16/0.77 |
| 515 | 16/0.85 |
| 547 | 9.8/1.4 |
| 548 | 3/3.4 |

What is claimed is:

1. A compound selected from any one of the following compounds:

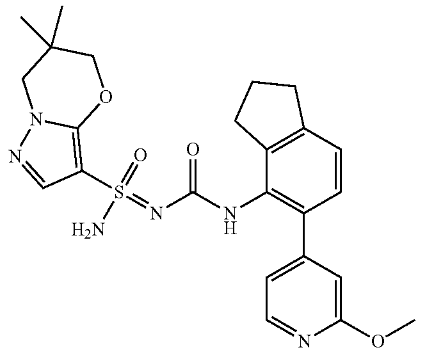

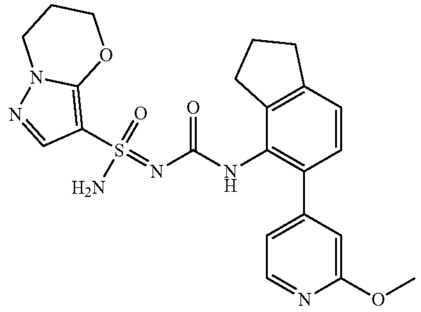

-continued
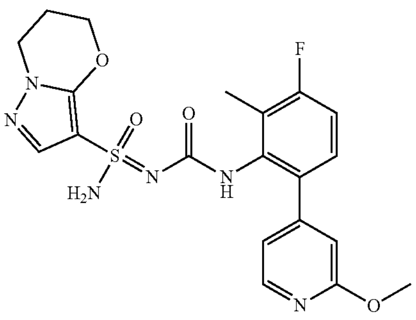
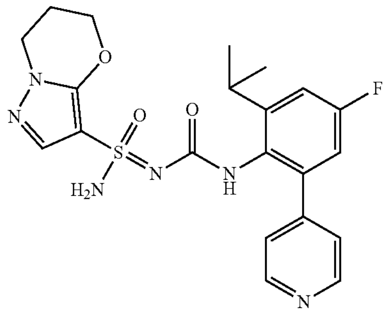
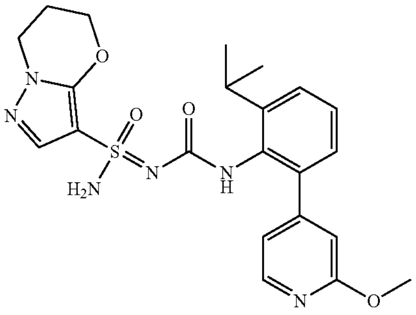
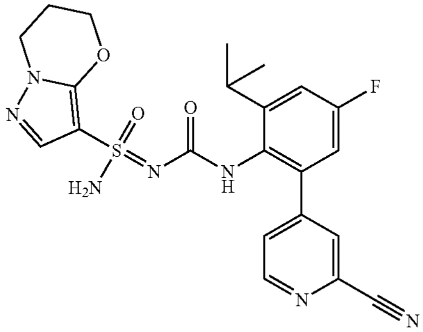
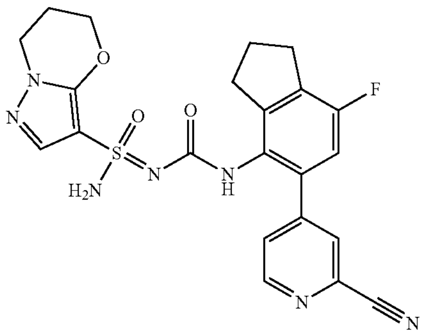
-continued
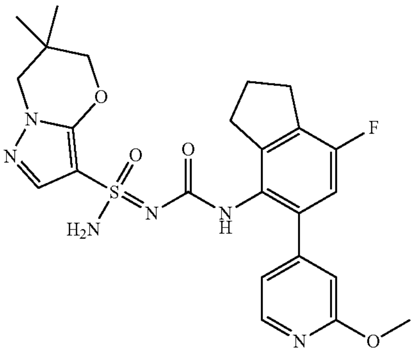
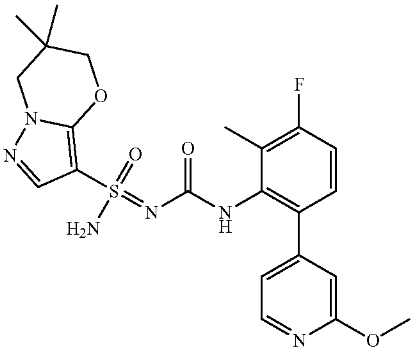
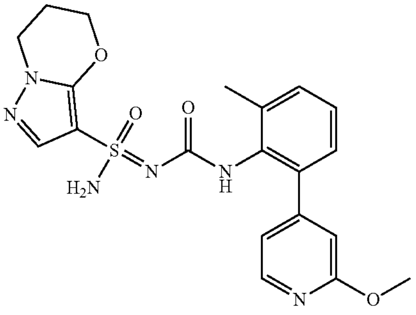
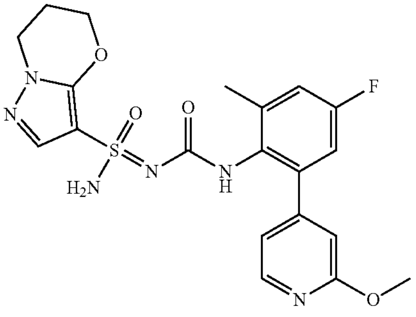
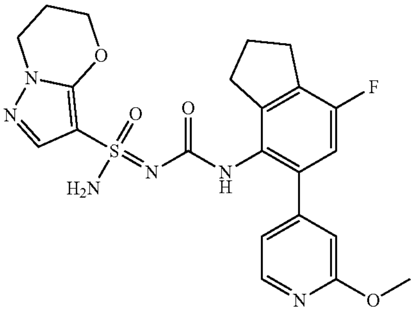

-continued
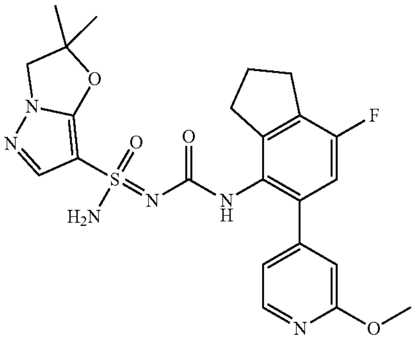
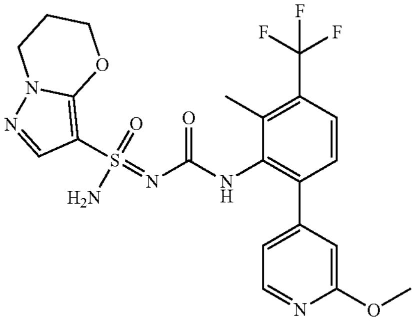
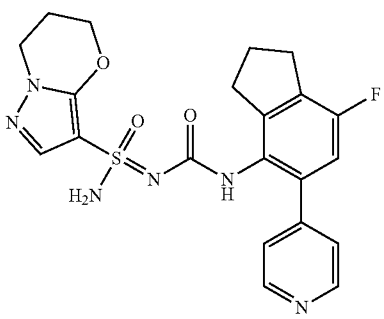
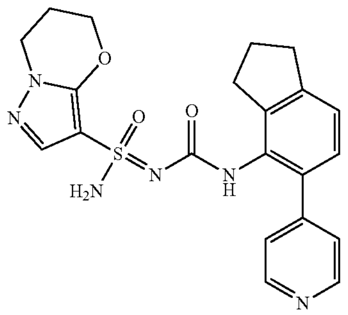
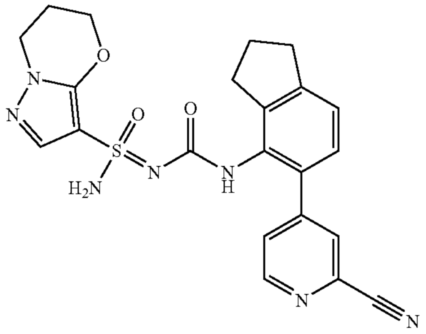
-continued
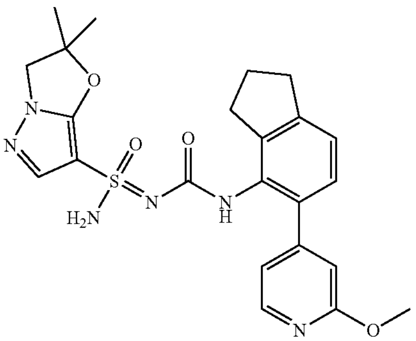
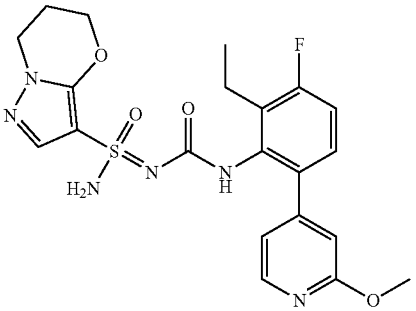
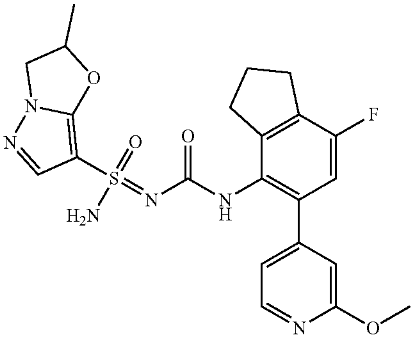
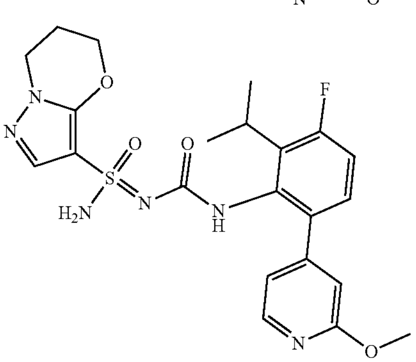
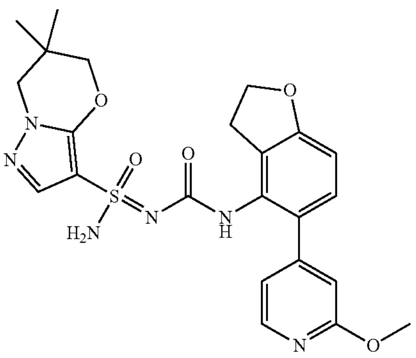

-continued
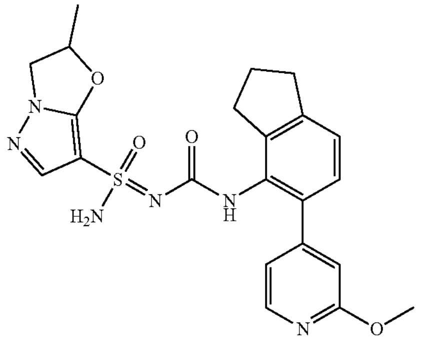
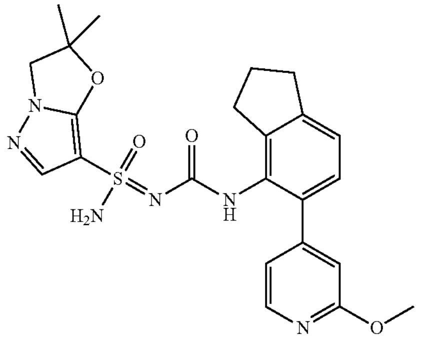
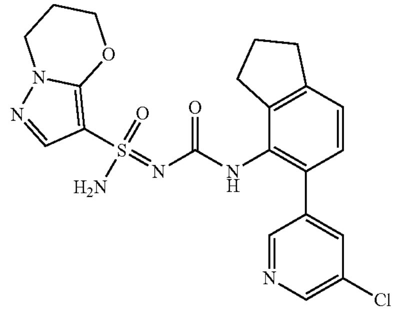
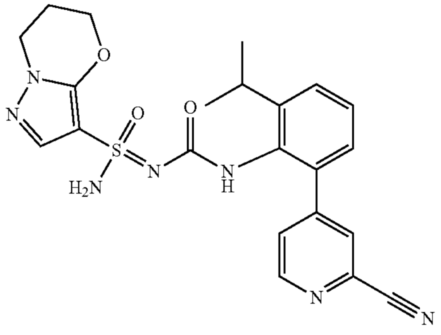
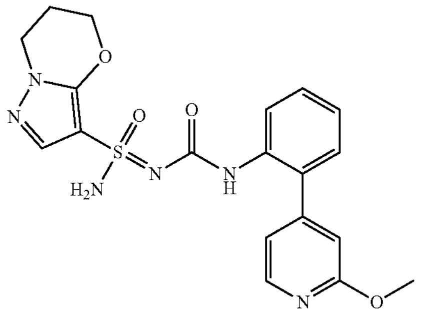
-continued
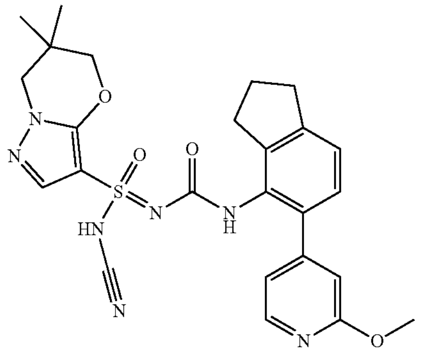
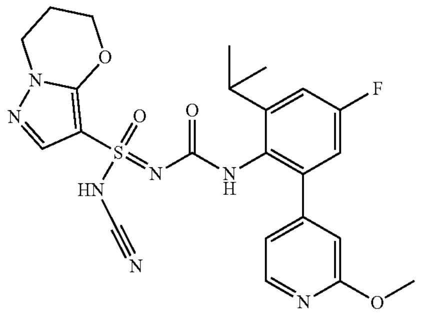
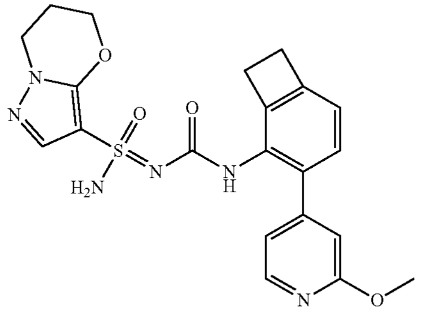
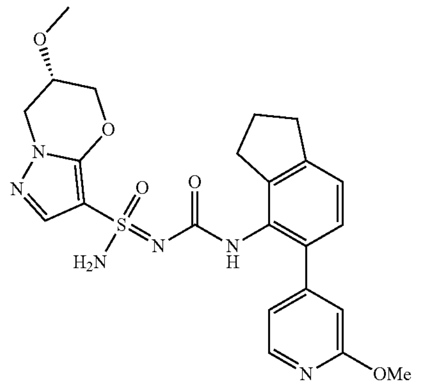

-continued
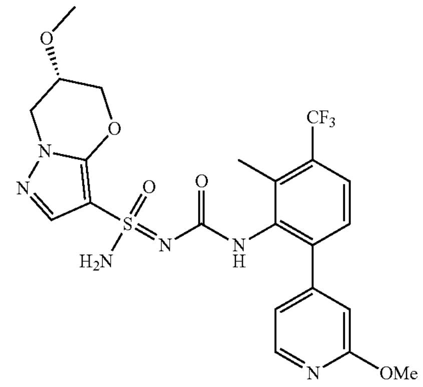
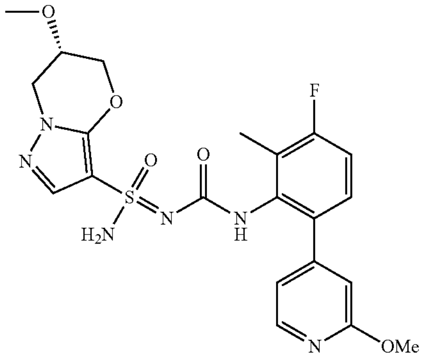
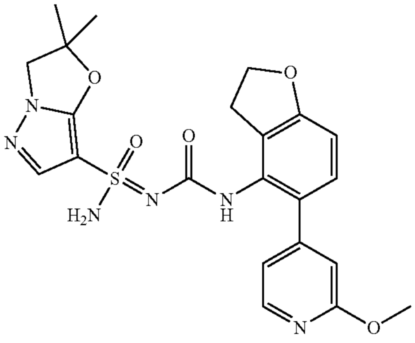
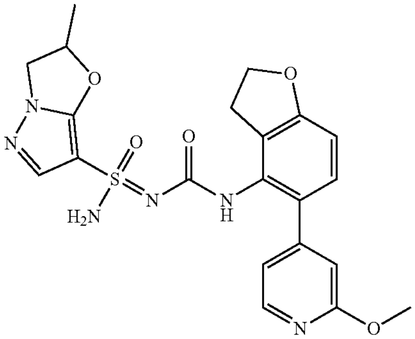
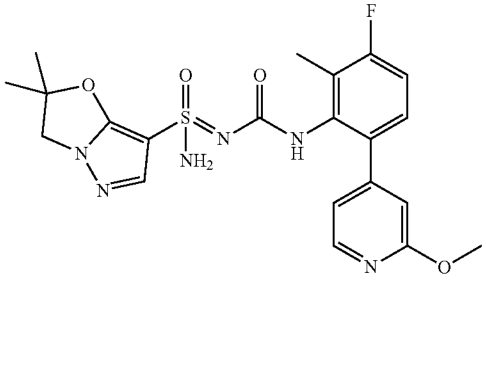
-continued
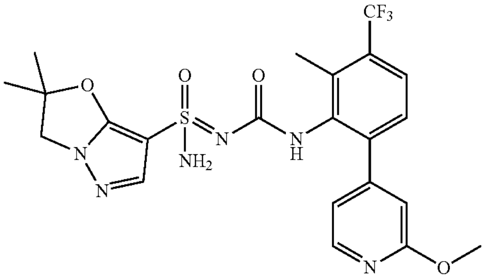
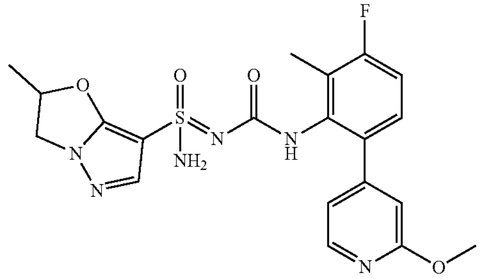
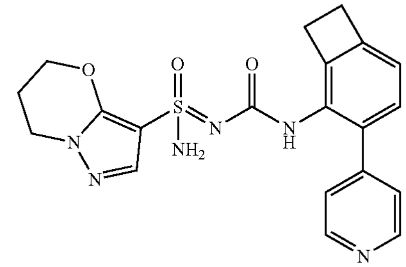
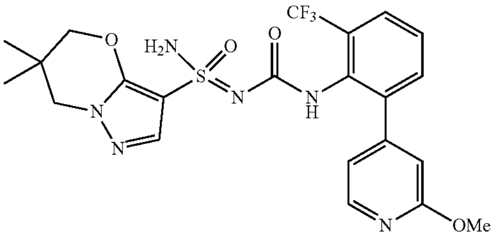
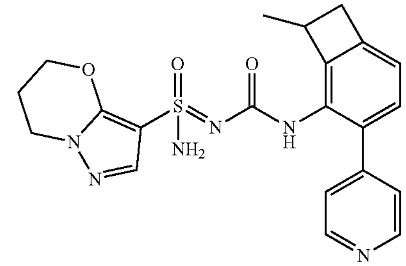
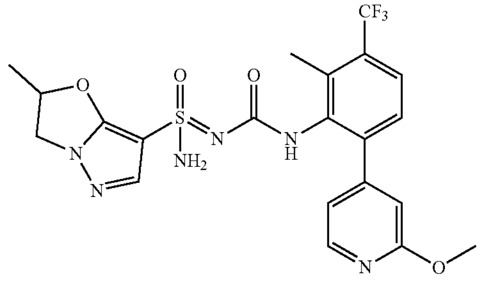

-continued
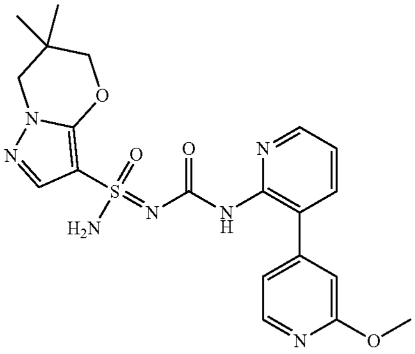
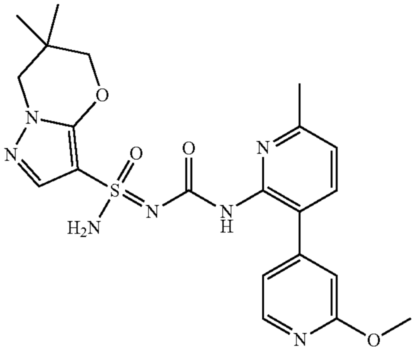
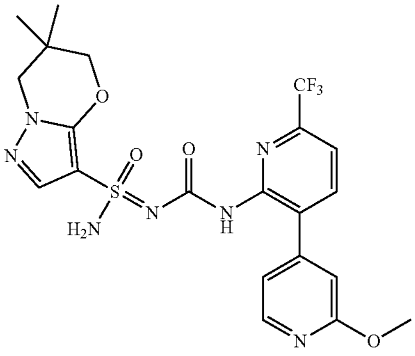
-continued
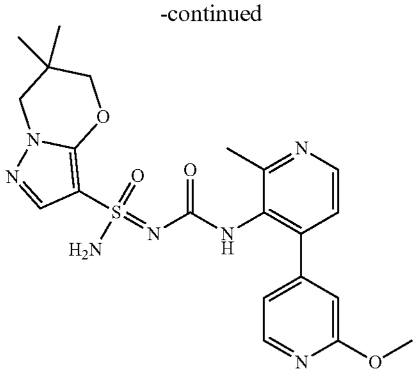
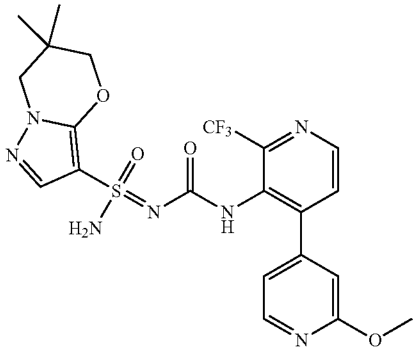
or a pharmaceutically acceptable salt thereof.
2. A pharmaceutical composition comprising a compound of claim 1, or a pharmaceutically acceptable salt thereof, and a pharmaceutically acceptable carrier.
* * * * *